US012790325B2

(12) United States Patent
Schirok et al.

(10) Patent No.: US 12,790,325 B2
(45) Date of Patent: Nov. 10, 2026

(54) SUBSTITUTED 2-AMINO-PYRAZOLYL-[1,2,4]TRIAZOLO[1,5A]PYRIDINE DERIVATIVES AND USE THEREOF

(71) Applicant: The Johns Hopkins University, Baltimore, MD (US)

(72) Inventors: Hartmut Schirok, Langenfeld (DE); William Schubert, Wuppertal (DE); Michael Koch, Berlin (DE); Lionel Nicolas, Berlin (DE); Carsten Terjung, Berlin (DE); Mario Lobell, Berlin (DE); Simon Holton, Berlin (DE); Natalia Jungmann, Berlin (DE); Derek Welsbie, Rancho Sante Fe, CA (US); Donald Zack, Baltimore, MD (US); Cynthia Berlinicke, Baltimore, MD (US); Amit Patel, Baltimore, MD (US); Brendan N. Lilley, Baltimore, MD (US); Byung-Jin Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1275 days.

(21) Appl. No.: 17/603,994

(22) PCT Filed: Apr. 20, 2020

(86) PCT No.: PCT/US2020/029021

§ 371 (c)(1),
(2) Date: Oct. 15, 2021

(87) PCT Pub. No.: WO2020/215094

PCT Pub. Date: Oct. 22, 2020

(65) Prior Publication Data

US 2023/0086702 A1 Mar. 23, 2023

Related U.S. Application Data

(63) Continuation of application No. PCT/US2020/028869, filed on Apr. 17, 2020.

(60) Provisional application No. 62/835,652, filed on Apr. 18, 2019, provisional application No. 62/835,649, filed on Apr. 18, 2019.

(51) Int. Cl.

| | |
|---|---|
| ***C07D 471/04*** | (2006.01) |
| ***A61K 31/437*** | (2006.01) |
| ***A61K 31/444*** | (2006.01) |
| ***A61K 31/4545*** | (2006.01) |
| ***A61K 31/4709*** | (2006.01) |
| ***A61K 31/4725*** | (2006.01) |
| ***A61K 31/5377*** | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/4709* (2013.01); *A61K 31/4725* (2013.01); *A61K 31/5377* (2013.01)

(58) Field of Classification Search
CPC .. C07D 471/04; A61K 31/437; A61K 31/444; A61K 31/4545; A61K 31/4709; A61K 31/4725; A61K 31/5377
USPC ..................................................... 514/210.21
See application file for complete search history.

(56) References Cited

U.S. PATENT DOCUMENTS

2023/0382904 A1 11/2023 Patel et al.

FOREIGN PATENT DOCUMENTS

| | | |
|---|---|---|
| JP | 2010-534206 A | 11/2010 |
| WO | WO 2004072033 | 8/2004 |
| WO | WO 2005044195 | 5/2005 |
| WO | WO 2008025821 | 3/2008 |
| WO | WO 2009017954 | 2/2009 |
| WO | WO 2009027283 | 3/2009 |
| WO | WO 2009064835 | 5/2009 |
| WO | WO 2009068482 | 6/2009 |
| WO | WO 2009155565 | 12/2009 |
| WO | WO 2010007100 | 1/2010 |
| WO | WO 2010020363 | 2/2010 |
| WO | WO 2010057877 | 5/2010 |
| WO | WO 2010141796 | 12/2010 |
| WO | WO 2011064328 | 6/2011 |
| WO | WO 2011092272 | 8/2011 |
| WO | WO 2011100502 | 8/2011 |
| WO | WC 2011154677 | 12/2011 |
| WO | WO 2011157688 | 12/2011 |
| WO | WO 2012143329 | 10/2012 |
| WO | WO 2012175522 | 12/2012 |
| WO | WO 2013031671 | 3/2013 |
| WO | WO 2014109414 | 7/2014 |

(Continued)

OTHER PUBLICATIONS

Healy et al. Adv Drug Deliv Rev., Aug. 1, 2017:117:25-46 (Year: 2017).*

(Continued)

*Primary Examiner* — Kortney L. Klinkel
*Assistant Examiner* — Grace Ching Hsu
(74) *Attorney, Agent, or Firm* — Fish & Richardson P.C.

(57) ABSTRACT

Provided herein are 2-amino-pyrazolyl-[1,2,4]triazolo[1,5a] pyridine derivatives. Such compounds are useful, for example, for the treatment and/or prevention of neurodegenerative diseases or disorders such as ophthalmological neurodegenerative disorders. This disclosure also features compositions containing the same as well as methods of using and making the same.

24 Claims, 13 Drawing Sheets

(56) References Cited

FOREIGN PATENT DOCUMENTS

| | | |
|---|---|---|
| WO | WO 2014111496 | 7/2014 |
| WO | WO 2014141187 | 9/2014 |
| WO | WO 2014195276 | 12/2014 |
| WO | WO 2015013715 | 1/2015 |
| WO | WO 2015134171 A1 | 9/2015 |
| WO | WO 2015161011 | 10/2015 |
| WO | WO 2015188681 | 12/2015 |
| WO | WO 2016000615 | 1/2016 |
| WO | WO 2016/057522 A1 * | 4/2016 |
| WO | WO 2016057522 | 4/2016 |
| WO | WO 2017037573 | 3/2017 |
| WO | WO 2017042114 | 3/2017 |
| WO | WO 2017102091 | 6/2017 |
| WO | WO 2017215506 | 12/2017 |
| WO | WO 2018017633 | 1/2018 |
| WO | WO 2018044808 | 3/2018 |
| WO | WO 2019089442 | 5/2019 |
| WO | WO 2016161160 | 10/2020 |

OTHER PUBLICATIONS

Braun et al. Cryst. Growth Des. 2017, 17, 10, 5349-5365 (Year: 2017).*

Zhang, et. al., ARVO Annual Meeting Abstract, Jul. 2018, vol. 59, Issue 9 (Year: 2018).*

Welsbie et al., "Identification of a retinal neuroprotective kinase inhibitor with preferential activity against DLK compared to LZK," Investigative Ophthalmology & Visual Science, Jul. 2018, 59:2493.

Adib et al., "An axonal stress response pathway: degenerative and regenerative signaling by DLK," Curr. Opin. Neurobiol., 2018, 53:110-119.

Andersen et al., "Direct Access to a,a-Difluoroacylated Arenes by Palladium-Catalyzed Carbonylation of (Hetero)Aryl Boronic Acid Derivatives," Angew. Chem. Int. Ed. 2016, 55, 10396-10400.

Ando et al., "Facile One-Pot Synthesis of N-Difluoromethyl-2-pyridone Derivatives," Org. Lett., 2006, 8:3805-3808.

Augustine et al., "Propylphosphonic anhydride (T3P®): an efficient reagent for the one-pot synthesis of 1,2,4-oxadiazoles, 1,3,4-oxadiazoles, and 1,3,4-thiadiazoles," Tetrahedron, 2009, 65:9989-9996.

Avitia et al., "Single-flask preparation of polyazatriaryl ligands by sequential borylation/Suzuki-Miyaura coupling," Tetrahedron Lett. 2011, 52:1631-1634.

Bertens et al., "Design of the ocular coil, a new device for non-invasive drug delivery," Eur J Pharm Biopharm. Mar. 12, 2020. pii: S0939-6411(20):30074-6.

Billingsley et al., "Palladium-Catalyzed Borylation of Aryl Chlorides: Scope, Applications, and Computational Studies," Angewandte, 2007, 46, 5359-5363.

Blomberg et al., "Synthesis of a β-strand mimetic based on a pyridine scaffold," Tetrahedron, 2006, 62:10937-10944.

Börchers et al., "TNFα-induced DLK activation contributes to apoptosis in the beta-cell line HIT," Naunyn-Schmideberg's Arch. Pharmacol. 2017, 390, 813-825.

Boschelli et al., "Synthesis and Tyrosine Kinase Inhibitory Activity of a Series of 2-Amino-8H-pyrido[2,3-d]pyrimidines: Identification of Potent, Selective Platelet-Derived Growth Factor Receptor Tyrosine Kinase Inhibitors," J. Med. Chem., 1998, 41:4365-4377.

Bouillon et al., "Synthesis of novel halopyridinylboronic acids and esters. Part 3: 2, or 3-Halopyridin-4-yl-boronic acids and esters," Tetrahedron, 2002, 58:4369-4373.

Cao et al., "Syntheses, Antifeedant Activity, and QSAR Analysis of New Oxa(thia)diazolyl 3(2H)-Pyridazinones," J. Agric. Food Chem., 2005, 53:3120-3125.

CAS No. 36953-37-4, dated Nov. 16, 1984; CAS No. 74427-22-8, dated Nov. 16, 1984; CAS No. 1029715-63-6, dated Jun. 22, 2008; CAS No. 1040377-03-4, dated Aug. 12, 2009; CAS No. 1040377-08-9, dated Aug. 12, 2008; CAS No. 10465-78-8, dated Nov. 16, 1984; CAS No. 1049730-40-6, dated Sep. 17, 2008; CAS No. 1049730-42-8, dated Sep. 17, 2008; CAS No. 107496-54-8, dated Apr. 11, 1987; CAS No. 108338-20-1, dated May 30, 1987; CAS No. 1114563-10-8, dated Mar. 2, 2009; CAS No. 1122-58-3, dated Nov. 16, 1984; CAS No. 113118-82-4, dated Feb. 27, 1988; CAS No. 1233526-60-7, dated Jul. 22, 2010,;CAS No. 1256810-49-7, dated Dec. 16, 2010; CAS No. 125700-67-6, dated Mar. 2, 1990; CAS No. 1310584-14-5, dated Jun. 28, 2011; CAS No. 13466-38-1, dated Nov. 16, 1984; CAS No. 1361849-85-5, dated Mar. 23, 2012; CAS No. 137081-41-5, dated Nov. 1, 1991; CAS No. 139484- 32-5, dated Mar. 6, 1992; CAS No. 13965-03-2, dated Nov. 16, 1984; CAS No. 141699-55-0, dated Jun. 5, 1992; CAS No. 148893-10-1, dated Jul. 23, 1993; CAS No. 153077-87-3, dated Feb. 17, 1994; CAS No. 157141-27-0, dated Aug. 19, 1994; CAS No. 175204-90-7, dated Apr. 17, 1996; CAS No. 1766-28-5, dated Nov. 16, 1984; CAS No. 1883816-46-3, dated Mar. 21, 2016; CAS No. 19172-47-5, dated Nov. 16, 1984; CAS No. 194151-99-0, dated Sep. 18, 1997; CAS No.1956306-65-2, dated Jul. 20, 2016; CAS No. 2101930-90-7, dated Jul. 13, 2017; CAS No. 223463-13-6, dated May 21, 1999; CAS No. 2340-22-9, dated Nov. 16, 1984; CAS No. 2446-83-5, dated Nov. 16, 1984; CAS No. 26386-88-9, dated Nov. 16, 1984; CAS No. 26543-06-6, dated Nov. 16, 1984; CAS No. 293294-72-1, dated Oct. 6, 2000; CAS No. 2942-58-7, dated Nov. 16, 1984, CAS No. 31181-88-1, dated Nov. 16, 1984; CAS No. 374063-92-0, dated Dec. 6, 2001; CAS No. 38185-55-6, dated Nov. 16; 1984; CAS No. 386704-12-7, dated Jan. 25; 2002; CAS No. 4397-00-6, dated Nov. 16; 1984; CAS No.4652-27-1, dated Nov. 16, 1984; CAS No. 50675-18-8, dated Nov. 16, 1984; CAS No. 611-69-8, dated Nov. 16, 1984; CAS No. 6246-06-6, dated Nov. 16, 1984; CAS No. 6638-79-5, dated Nov. 16, 1984; CAS No. 6674-22-2, dated Nov. 16, 1984; CAS No. 68957-94-8, dated Nov. 16, 1984; CAS No. 6914-76-7, dated Nov. 16, 1984; CAS No. 7283-96-7, dated Nov. 16, 1984; CAS No. 73183-34-3, dated Nov. 16, 1984; CAS No. 7789-59-5, dated Nov. 16, 1984; CAS No. 845827-13-6, dated Mar. 17, 2005; CAS No. 870-50-8, dated Nov. 16; 1984; CAS No. 877399-74-1, dated Mar. 21, 2006; CAS No. 887583-90-6, dated Jun. 13; 2006; CAS No. 921602-78-0, dated Feb. 16, 2007; CAS No. 946578-32-1, dated Sep. 11, 2007; CAS No. 95464-05-4, dated Mar. 23, 1985; CAS No. 97112-03-3 dated Jul. 6, 1985, 50 pages.

Chen et al., "Intramolecular Reactivity of trans [4+4] Photodimers of 2-Pyridones," Synthesis, 2007, 2351-2359.

Chen et al., "Leucine Zipper-Bearing Kinase Is a Critical Regulator of Astrocyte Reactivity in the Adult Mammalian CNS," Cell Reports, 2018, 22:3587-3597.

Chen et al., "Leucine Zipper-bearing Kinase promotes axon growth in mammalian central nervous system neurons," Scientific Rep., 2016, 6:31482.

Chowdhury et al., "Synthesis of 1-(methanesulfonyl- and aminosulfonylphenyl) acetylenes that possess a 2-(N-difluoromethyl-1,2-dihydropyridin-2-one) pharmacophore: Evaluation as dual inhibitors of cyclooxygenases and 5-lipoxygenase with anti-inflammatory activity," Bioorg. Med. Chem. Lett., 2009, 19:584-588.

Cook et al., "Efficient and chromatography-free methodology for the modular synthesis of oligo-(1H-pyrazol-4-yl)-arenes with controllable size, shape and steric bulk," Tetrahedron Lett., 2016, 57:895-898.

Cornejo et al., "The First Immobilization of Pyridine-bis(oxazoline) Chiral Ligands," Org. Lett. 2002, 4:3927-3930.

De et al., "Synthesis and Rearrangement of Quinone-Embedded Epoxycyclopentenones: A New Avenue to Pyranonaphthoquinones and Indenopyranones," J. Org. Chem. 2009, 74:1598-1604.

Diemer et al., "Synthesis of 4-[N-methyl-4-pyridinio]-phenolate (POMP) and negative solvatochromism of this model molecule in view of nonlinear optical applications," Tetrahedron Lett. 2005, 46:4737-4740.

Dubald et al., "Ophthalmic Drug Delivery Systems for Antibiotherapy—A Review," Pharmaceutics, 2018, 10(1):10.

East et al., "DNA gyrase (GyrB)/topoisomerase IV (ParE) inhibitors: Synthesis and antibacterial activity," Bioorg. Med. Chem. Lett., 2009, 19: 894-899.

Edmondson et al., "(2S,3S)-3-Amino-4-(3,3-difluoropyrrolidin-1-yl)-N,N-dimethyl-4-oxo-2-(4-[1,2,4]triazolo[1,5-a]-pyridin-6-

(56) References Cited

OTHER PUBLICATIONS ylphenyl)butanamide: A Selective α-Amino Amide Dipeptidyl Peptidase IV Inhibitor for the Treatment of Type 2 Diabetes," J. Med. Chem., 2006, 49:3614-3627.

Fernandes et al., "DLK-dependent signaling is important for somal but not axonal degeneration of retinal ganglion cells following axonal injury," Neurobiol. Dis., 2014, 69:108-116.

Ferraris et al., "Dual leucine zipper kinase as a therapeutic target for neurodegenerative conditions," Future Med. Chem., 2013, 5:1923-1934.

Furet et al., "Discovery of NVP-BYL719 a potent and selective phosphatidylinositol-3 kinase alpha inhibitor selected for clinical evaluation," Bioorg. Med. Chem. Lett. 2013, 23:3741-3748.

Gerlach et al., "Discovery of tetrahydroindazoles as a novel class of potent and in vivo efficacious gamma secretase modulators," Bioorg. Med. Chem. 2018, 26, 3227-3241.

Ghosh et al., "DLK induces developmental neuronal degeneration via selective regulation of proapoptotic JNK activity," J. Cell. Biol. 2011, 194:751-764.

Han et al., "A practical and expedient synthesis of 2-heterocycle (C—N bond) substituted 4-oxo-4-arylbutanoates," Tetrahedron Lett, 2007, 48:2845-2849.

Hao et al., "An evolutionarily conserved mechanism for cAMP elicited axonal regeneration involves direct activation of the dual leucine zipper kinase DLK," 2016, 5:e14048.

Holland et al., "Palmitoylation controls DLK localization, interactions and activity to ensure effective axonal injury signaling," PNAS 2016, 113:763-768.

Holland et al., "Roles of Palmitoylation in Axon Growth, Degeneration and Regeneration," J. Neuroscience Res., 2017, 95:1528-1539.

Huntwork-Rodriguez et al., "JNK-mediated phosphorylation of DLK suppresses its ubiquitination to promote neuronal apoptosi," J. Cell Biol.,2013, 202:747-763.

International Preliminary Report on Patentability in Appln. No. PCT/US2020/029021, Sep. 28, 2021, 7 pages.

International Search Report and Written Opinion in Application No. PCT/US2021/054493, dated Jan. 20, 2022, 10 pages.

International Search Report and Written Opinion in Appln. No. PCT/US2020/029021, dated Jun. 11, 2020, 10 pages.

Itoh et al., "ZPK/DLK, a mitogen-activated protein kinase kinase kinase, is a critical mediator of programmed cell death of motoneurons," J. Neurosci, 2011, 31:7223-7228.

Jacksonimmuno.com [online], "Goat Anti-Mouse IgM, μ Chain Specific, Catalog No. 115-001-020," available on and before Jun. 16, 2022, retrieved on Jun. 16, 2022, retrieved from URL<https://www.jacksonimmuno.com/catalog/products/115-001-020>, 3 pages.

Jervis, "A Summary of Recent Advances in Ocular Inserts and Implants," J. of Bioequiv. Availab., 2017, 9:1.

Joost, "The role of dual leucine zipper kinase (DLK) in β-cell apoptosis: a potential target for the prevention and treatment of type 2 diabetes?:Commentary to: Börchers et al., TNF-α induced DLK activation contributes to apoptosis in the β-cell line HIT," Naunyn-Schmiedeberg's Arch. Pharmacol., 2017, 390:767-768.

Kamatsuka et al., "Design and Synthesis of Tunable Ligands with 4,4'-Bipyridyl as an Electron-Accepting Unit and Their Rhenium Complexes," Organometallics 2017, 36:3429-3434.

Kuo et al., "Synthesis and Identification of [1,3,5] Triazine-pyridine Biheteroaryl as a Novel Series of Potent Cyclin-Dependent Kinase Inhibitors," J. Med. Chem, 2005, 48:4535-4546.

Larhammar et al., "Dual leucine zipper kinase-dependent PERK activation contributes to neuronal degeneration following insult," eLife 2017, 6, e20725.

Larhammar et al., "The Ste20 Family Kinases MAP4K4, MINK1, and TNIK Converge to Regulate Stress-Induced JNK Signaling in Neurons," J. Neuroscience, 2017, 37:11074-11084.

Le Pichon et al., "Loss of dual leucine zipper kinase signaling is protective in animal models of neurodegenerative disease," Sci. Transl. Med., 2017, 9:403:eaag0394.

Levy et al., "An Improved Synthesis of the Free Base and Diglycolate Salt of CEP-33779; A Janus Kinase 2 Inhibitor," Org. Process. Res. Dev., 2016, 20:2085-2091.

Li et al., "An Improved Protocol for the Preparation of 3-Pyridyl- and Some Arylboronic Acids," J. Org. Chem., 2002, 67:5394-5397.

Lindsay-Scott et al., "A Flexible Strategy for the Regiocontrolled Synthesis of Pyrazolo[1,5-a]pyrazines," J. Org. Chem., 2017, 82:11295-11303.

Liu et al., "Syntheses, crystal structure and photophysical property of iridium complexes with 1, 3, 4-oxadiazole and 1,3,4-thiadiazole derivatives as ancillary ligands," J. Organomet. Chem., 2015, 785:11-18.

Lu et al., "Preparation and applications of a polymer-supported phosphoryl azide," Tetrahedron Lett. 2003, 44:9267-9269.

Maharvi et al., "Synthesis of a DOTA (Gd3+)-conjugate of proton-pump inhibitor pantoprazole for gastric wall imaging studies," Bioorg. Med. Chem. Lett., 2013, 23:2808-2811.

Mata et al., "Characterization of dual leucine zipper-bearing kinase, a mixed lineage kinase present in synaptic terminals whose phosphorylation state is regulated by membrane depolarization via calcineurin," J. Biol. Chem. Jul. 12, 1996, 271(28):16888-16896.

Menet et al., "Triazolopyridines as Selective JAK1 Inhibitors: From Hit Identification to GLPG0634," J. Med. Chem., 2014, 57:9323-9342.

Mullens et al., "An improved synthesis of 1-methyl-1H-pyrazole-4-boronic acid pinacol ester and its corresponding lithium hydroxy ate complex: application in Suzuki couplings," Tetrahedron Lett. 2009, 50, 6783-6786.

Oetjen et al., "Dual leucine zipper kinase (MAP3K12) modulators: a patent review (2010-2015)," Expert Opin. Ther. Patents 2016, 26:607-616.

Patel et al., "Ocular drug delivery systems: An overview," World J Pharmacol., 2013, 2(2): 47-64.

Patel et al., "Discovery of Dual Leucine Zipper Kinase (DLK, MAP3K12) Inhibitors with Activity in Neurodegeneration Models," J. Med. Chem. 2015, 58:401-418.

Patel et al., "Scaffold-Hopping and Structure-Based Discovery of Potent, Selective, and Brain Penetrant N-(1H-Pyrazol-3-yl)pyridin-2-amine Inhibitors of Dual Leucine Zipper Kinase (DLK, MAP3K12)," J. Med. Chem., 2015, 58, 8182-8199.

Patel et al., "Selective Inhibitors of Dual Leucine Zipper Kinase (DLK, MAP3K12) with Activity in a Model of Alzheimer's Disease," J. Med. Chem., 2017, 60:8083-8102.

Pozniak et al., "Dual leucine zipper kinase is required for excitotoxicity-induced neuronal degeneration," J. Exp. Med., 2013, 210:2553-2567.

Ruchelman et al., "Nitro and amino substitution within the A-ring of 5H-8,9-dimethoxy-5-(2-N,N-dimethylaminoethyl)dibenzo[c,h][1,6]naphthyridin-6-ones: influence on topoisomerase I-targeting activity and cytotoxicity," Bioorg. Med. Chem. 2004, 12, 3731-3742.

Sajitha et al., "Novel Burgess reagent mediated C-to-N aryl migration reaction in nitrones," RSC Adv., 2014, 4:44689-44691.

Sato et al., "CsF in Organic Synthesis. Tuning of N- or O-Alkylation of 2-Pyridone," Synlett, 1995, 1995(8):845-846.

Shin et al., "Dual Leucine Zipper Kinase Is Required for Retrograde Injury Signaling and Axonal Regeneration," Neuron, 2012, 74:1015-1022.

Simard-Bisson et al., "A Role for DLK in Microtubule Rorganization to the Cell Periphery and in the Maintenance of Desmosomal and Tight Junction Integrity," J. Invest. Dermatol., 2017, 137:132-141.

Singh et al., "Promising therapeutic drug delivery systems for glaucoma: a comprehensive review," Ther Adv Ophthalmol., 2020, 12:1-17.

Sirakanyan et al., "New heterocyclic systems derived from pyridine: new substrates for the investigation of the azide/tetrazole equilibrium," Tetrahedron 2014, 70:8648-8656.

Siu et al., "Dual Leucine Zipper Kinase Inhibitors for the Treatment of Neurodegeneration," J. Med. Chem., 2018, 61:8078-8087.

Sivasubramanian et al., "Value of zeolites in asymmetric induction during photocyclization of pyridones, cyclohexadienones and naphthalenones," Org. Biomol. Chem., 2007, 5:1569-1576.

(56) References Cited

OTHER PUBLICATIONS

Spencer et al.,"Breaking Barriers: Bioinspired Strategies for Targeted Neuronal Delivery to the Central Nervous System," Pharmaceutics, 2020, 12(2): 192.
Stewart et al., "Process Development and Large-Scale Synthesis of a c-Met Kinase Inhibitor," Org. Proc. Res. Dev. 2010, 14:849-858.
Tedeschi et al., "The DLK signalling pathway—a double-edged sword in neural development and regeneration," EMBO reports, 2013, 14:605-614.
Valakh et al., "Cytoskeletal disruption activates the DLK/JNK pathway, which promotes axonal regeneration and mimics a preconditioning injury," Neurobiol. Dis. 2015, 77, 13-25. DOI: 10.1016/j.nbd.2015.02.014.
Verheij et al., "Design, Synthesis, and Structure-Activity Relationships of Highly Potent 5-HT3 Receptor Ligands," J. Med. Chem., 2012, 55:8603-8614.
Wallbach et al., "Distinct functions of the dual leucine zipper kinase depending on its subcellular localization," Cell. Signal, 2016, 28:272-283.
Watkins et al., "DLK initiates a transcriptional program that couples apoptotic and regenerative responses to axonal injury," Proc. Natl. Acad. Sci., 2013, 110:4039-4044.
Welsbie et al., "Enhanced Functional Genomic Screening Identifies Novel Mediators of Dual Leucine Zipper Kinase-Dependent Injury Signaling in Neurons," Neuron, 2017, 94:1142-1154.
Welsbie et al., "Functional genomic screening identifies dual leucine zipper kinase as a key mediator of retinal ganglion cell death," PNAS 2013, 110, 4045-4050.
Westaway et al., "Cell Penetrant Inhibitors of the KDM4 and KDM5 Families of Histone Lysine Demethylases. 2. Pyrido[3,4-d]pyrimidin-4(3H)-one Derivatives," J. Med. Chem. 2016, 59:1370-1387.
Wlaschin et al., "Dual leucine zipper kinase is required for mechanical allodynia and microgliosis after nerve injury," eLife, 2018, 7: e33910.
Xi et al., "Structure-based design and synthesis of imidazo [1,2-a]pyridine derivatives as novel and potent Nek2 inhibitors with in vitro and in vivo antitumor activities," J. Med. Chem., 2017, 126:1083-1106.
Xu et al., "Design, synthesis, and evaluation of novel porcupine inhibitors featuring a fused 3-ring system based on the 'reversed' amide scaffold," Bioorg. Med. Chem. 2016, 24, 5861-5872.
Yin et al., "DLK silencing attenuated neuron apoptosis through JIP3/MA2K7/JNK pathway in early brain injury after SAH in rats," Neurobiol. Disease, 2017, 103:133-143.
Yin et al., "Tozasertib attenuates neuronal apoptosis via DLK/JIP3/MA2K7/JNK pathway in early brain injury after SAH in rats," Neuropharmacol., 2016, 108:316-323.
Zhang et al., "Synthesis and biological evaluation of 2-amino-5-aryl-3-benzylthiopyridine scaffold based potent c-Met inhibitors," Bioorg. Med. Chem. 2013, 21:6804-6820.
Extended European Search Report in European Application No. 20792265.9, dated Dec. 19, 2022, 9 pages.
International Preliminary Report on Patentability in Application No. PCT/US2021/054493, dated Apr. 27, 2023, 7 pages.
Extended European Search Report in European Application No. 21880875.6, dated Apr. 17, 2024, 7 pages.
Carlson et al., "Peripheral Neuropathy with Microtubule-Targeting Agents: Occurrence and Management Approach," Clinical Breast Cancer, Apr. 2011, 11(2):73-81.
Chaturvedi et al., "Mitochondrial Diseases of the Brain," Free Radical Biology and Medicine, Apr. 2013, 63:1-29.
Chen et al., "Antiapoptotic and Trophic Effects of Dominant-Negative Forms of Dual Leucine Zipper Kinase in Dopamine Neurons of the Substantia Nigra In Vivo," The Journal of Neuroscience, Jan. 2008, 28(3):672-680.
Craig et al., "Discovery of Potent and Selective Dual Leucine Zipper Kinase/Leucine Zipper-Bearing Kinase Inhibitors with Neuroprotective Properties in In Vitro and In Vivo Models of Amyotrophic Lateral Sclerosis," Journal of Medicinal Chemistry, Dec. 2022, 65(24):16290-16312.
Hur et al., "Microtubule-Targeting Agents Enter the Central Nervous System (CNS): Double-edged Swords for Treating CNS Injury and Disease," International Neurology Journal, Dec. 2014, 18(4):171-178.
Lagiakos et al., "In Silico Enabled Discovery of KAI-11101, a Preclinical DLK Inhibitor for the Treatment of Neurodegenerative Disease and Neuronal Injury," Journal of Medicinal Chemistry, Dec. 2024, 68(3):2720-2741.
Le et al., "Discovery of IACS-52825, a Potent and Selective DLK Inhibitor for Treatment of Chemotherapy-Induced Peripheral Neuropathy," Journal of Medicinal Chemistry, Jul. 2023, 66(14):9954-9971.
Le Pichon et al., "Loss of dual leucine zipper kinase signaling is protective in animal models of neurodegenerative disease," Sci. Transl. Med., 2017, 9:403:eaag0394; Supplementary Materials, 45 pages.
London et al., "The retina as a window to the brain—from eye research to CNS disorders," Nature Reviews Neurology, Jan. 2013, 9(1):44-53.
Ma et al., "Inhibition of dual leucine zipper kinase prevents chemotherapy-induced peripheral neuropathy and cognitive impairments," Pain, Oct. 2021, 162(10):2599-2612.
Millecamps et al., "Axonal transport deficits and neurodegenerative diseases," Nature Reviews Neuroscience, Mar. 2013, 14(3):161-176.
Rojas et al., "Mitochondrial optic neuropathy: In vivo model of neurodegeneration and neuroprotective strategies," Eye and Brain, Mar. 2010, 2:21-37.
Van Bergen et al., "Mitochondrial disorders and the eye," Eye and Brain, Sep. 2011, 3:29-47.

* cited by examiner

PRECIPITATION REMAINING AT HARVEST:

| | 1 hour | 2 hours | 4 hours | 6 hours | 24 hours | 3 days | 5 days | 14 days |
|---|---|---|---|---|---|---|---|---|
| Vehicle | NONE | NONE | NONE | NONE | NONE | NONE | NONE | NONE |
| 0.004 mM | ——— | NONE | NONE | NONE | ——— | ——— | ——— | ——— |
| 0.04 mM | ——— | NONE | NONE | NONE | ——— | ——— | ——— | ——— |
| 0.4 mM | NONE | NONE | NONE | NONE | NONE | ——— | ——— | ——— |
| 4 mM | YES | YES | YES | YES | NONE | ——— | ——— | ——— |
| 8-10 mM | ——— | ——— | ——— | ——— | ——— | LITTLE | NONE | NONE |
| 30 mM | ——— | ——— | ——— | ——— | ——— | YES | YES | NONE |
| 100 mM | ——— | ——— | ——— | ——— | ——— | LOTS | LOTS | YES |
| 300 mM | ——— | ——— | ——— | ——— | ——— | LOTS | LOTS | YES (MORE THAN 100 mM) |

ACTIVITY (JUN PHOSPHORYLATION):

| | 1 hour | 2 hours | 4 hours | 6 hours | 24 hours | 3 days | 5 days | 14 days |
|---|---|---|---|---|---|---|---|---|
| Vehicle | NO | NO | NO | NO | NO | NO | NO | NO |
| 0.004 mM | ——— | NO | NO | NO | ——— | ——— | ——— | ——— |
| 0.04 mM | ——— | NO | NO | PARTIAL | ——— | ——— | ——— | ——— |
| 0.4 mM | NO | NO | MOSTLY | MOSTLY | NONE | ——— | ——— | ——— |
| 4 mM | NO | NO | YES | YES | YES | ——— | ——— | ——— |
| 8-10 mM | ——— | ——— | ——— | ——— | ——— | YES | YES | NO |
| 30 mM | ——— | ——— | ——— | ——— | ——— | YES | YES | PARTIAL |
| 100 mM | ——— | ——— | ——— | ——— | ——— | YES | YES | YES |
| 300 mM | ——— | ——— | ——— | ——— | ——— | YES | YES | YES |

ACTIVITY (SURVIVING RBPMS+ RGCS):

| | 1 hour | 2 hours | 4 hours | 6 hours | 24 hours | 3 days | 5 days | 14 days |
|---|---|---|---|---|---|---|---|---|
| Vehicle | ——— | ——— | ——— | ——— | ——— | ——— | ——— | FEW |
| 0.004 mM | ——— | ——— | ——— | ——— | ——— | ——— | ——— | ——— |
| 0.04 mM | ——— | ——— | ——— | ——— | ——— | ——— | ——— | ——— |
| 0.4 mM | ——— | ——— | ——— | ——— | ——— | ——— | ——— | ——— |
| 4 mM | ——— | ——— | ——— | ——— | ——— | ——— | ——— | ——— |
| 8-10 mM | ——— | ——— | ——— | ——— | ——— | ——— | ——— | MANY |
| 30 mM | ——— | ——— | ——— | ——— | ——— | ——— | ——— | ~ALL |
| 100 mM | ——— | ——— | ——— | ——— | ——— | ——— | ——— | ~ALL |
| 300 mM | ——— | ——— | ——— | ——— | ——— | ——— | ——— | ~ALL |

FIG. 12

SUBSTITUTED 2-AMINO-PYRAZOLYL-[1,2,4]TRIAZOLO[1,5A]PYRIDINE DERIVATIVES AND USE THEREOF

CROSS-REFERENCE TO RELATED APPLICATIONS

This application is a National Stage application under 35 U.S.C. § 371 of International Application No. PCT/US2020/029021 having an International Filing Date of Apr. 20, 2020, which claims the benefit of PCT Application No. PCT/US20/028869, filed on Apr. 17, 2020; and also claims priority to U.S. Provisional Application No. 62/835,649, filed on Apr. 18, 2019; and U.S. Provisional Application No. 62/835,652, filed on Apr. 18, 2019; the contents of each of which are hereby incorporated by reference in their entireties.

TECHNICAL FIELD

The present application relates to 2-amino-pyrazolyl-[1,2,4]triazolo[1,5a]pyridine derivatives, to processes for preparation thereof, to the use thereof alone or in combination for treatment and/or prevention of diseases and to the use thereof for production of medicaments for treatment and/or prevention of neurodegenerative diseases such as ophthalmological neurodegenerative disorders. Such treatments can be effected as monotherapy or else in combination with other medicaments or further therapeutic measures.

BACKGROUND

Neuronal cell death in response to axon injury is a key feature of many neurodegenerative diseases. As one example, the atrophic (dry) form of age-related macular degeneration (AMD) is a potentially blinding form of neurodegeneration which affects millions of people world-wide, and from which there are no proven or licensed treatments available. As another example, glaucoma, a neurodegenerative disease that affects millions and that results in damage to the optic nerve, is a major cause of vision loss and blindness, worldwide. While an important risk factor for glaucomatous injury of retinal ganglion cells (RGCs) and optic nerve damage is elevated intraocular pressure, lowering pressure can be challenging in some patients, and in others, RGC damage continues despite pressure lowering. Thus, the development of effective neuroprotective strategies could complement pressure lowering by mitigating RGC injury, damage, and cell loss. As an additional example of ocular neurodegenerative disease, retinitis pigmentosa (RP) and associated retinal degenerations constitute a group of diseases in which there is degeneration of photoreceptor and retinal pigment epithelial (RPE) cells. Since vision loss from AMD, glaucoma, and the RP-like group of diseases, cannot be reversed once it occurs, it is essential to develop better treatments for these diseases to prevent vision loss before it occurs. There is similarly a need to develop better, and safer, treatments for the many other forms of neurodegenerative diseases for which no or inadequate therapies are currently available.

SUMMARY

In one aspect, herein is disclosed a compound of formula (I)

(I)

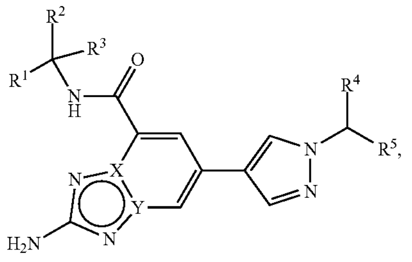

in which

X is nitrogen and Y is carbon, or

X is carbon and Y is nitrogen, $R^1$ and $R^2$ are each independently hydrogen or $(C_1-C_3)$-alkyl, $R^3$ is $(C_1-C_6)$-alkyl, $(C_3-C_7)$-cycloalkyl or $(C_3-C_7)$-cycloalkyl-$(C_1-C_3)$-alkyl wherein the $(C_1-C_6)$-alkyl, $(C_3-C_7)$-cycloalkyl, or $(C_3-C_7)$-cycloalkyl-$(C_1-C_3)$-alkyl may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteroatoms selected from the group consisting of O or N, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is hydrogen, $(C_1-C_6)$-alkyl, $(C_3-C_7)$-cycloalkyl or 4- to 7-membered heterocyclyl wherein the $(C_1-C_6)$-alkyl, $(C_3-C_7)$-cycloalkyl or 4- to 7-membered heterocyclyl may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3-C_7)$-cycloalkyl, phenyl or heteroaryl wherein the $(C_3-C_7)$-cycloalkyl, phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^4$ and $R^5$ are joined to one another and, taken together with the carbon atom to which they are attached, form a 4- to 7-membered ring containing up to two heteroatoms selected from the group consisting of O or N, wherein the ring may be substituted by benzyl, 4- to 7-membered heterocyclyl, $(C_1-C_4)$-alkyl, $(C_1-C_4)$-alkoxy, oxo, cyano, chlorine, bromine or up to three times by fluorine, or may be annellated with phenyl or heteroaryl where $(C_1-C_4)$-alkyl is optionally substituted by 4- to 7-membered heterocyclyl or up to three times by fluorine, and the nitrogen of each of the 4- to 7-membered heterocyclyls may independently be substituted by $C(O)OR^6$ or $C(O)R^6$, $R^6$ is $(C_1-C_4)$-alkyl and the salts, solvates and solvates of the salts thereof.

In a second aspect, herein is disclosed a compound of Formula (II)

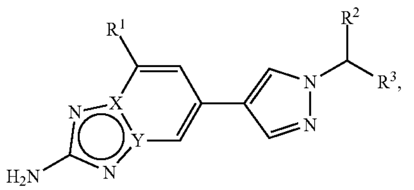

(II)

in which

X is nitrogen and Y is carbon, or

X is carbon and Y is nitrogen, $R^1$ is phenyl or heteroaryl, each of which may be substituted by $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, up to three times by hydroxyl, fluorine, chlorine or bromine, where $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl and $(C_3-C_7)$-cycloalkoxy may be substituted by hydroxyl, cyano and up to three times by fluorine $R^2$ is hydrogen, $(C_1-C_6)$-alkyl, $(C_3-C_7)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine, $R^3$ is $(C_3-C_7)$-cycloalkyl, phenyl or heteroaryl wherein the $(C_3-C_7)$-cycloalkyl, phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^2$ and $R^3$ are joined to one another and, taken together with the carbon atom to which they are attached, form a 4- to 7-membered fused ring containing up to two heteratoms selected from the group consisting of O or N, which fused ring may be substituted by benzyl, 4- to 7-membered heterocyclyl, $(C_1-C_4)$-alkyl, $(C_1-C_4)$-alkoxy, oxo, cyano, chlorine, bromine or up to three times by fluorine, or may be annellated with phenyl or heteroaryl where $(C_1-C_4)$-alkyl is optionally substituted by 4- to 7-membered heterocyclyl or up to three times by fluorine, $R^4$ and $R^5$ are each independently $(C_1-C_4)$-alkyl optionally substituted up to three times by fluorine and the salts, solvates and solvates of the salts thereof.

Also provided herein are pharmaceutical compositions comprising a compound as described herein, or a pharmaceutically acceptable salt thereof, and a pharmaceutically acceptable excipient.

Also provided herein are methods for treating a neurodegenerative disease in a subject, the method comprising administering to the subject an effective amount of a compound as described herein, or a pharmaceutical composition as described herein.

Also provided herein are method for treating an optic neuropathy in a subject, the method comprising administering to the subject an effective amount of a compound as described herein, or a pharmaceutical composition as described herein.

Also provided herein is the sse of a compound as described herein, or a pharmaceutically acceptable salt thereof, for the manufacture of a medicament of treating a neurodegenerative disease in a subject.

Also provided herein is a compound as described herein, or a pharmaceutically acceptable salt thereof, for use in treating a subject identified or diagnosed as having a neurodegenerative disease.

Also provided herein are methods of inhibiting DLK and/or LZK activity in a mammalian cell, the method comprising contacting the mammalian cell with a compound as described herein, or a pharmaceutically acceptable salt thereof.

The details of one or more embodiments of the disclosure are set forth in the accompanying drawings and the description below. Other features, objects, and advantages of the disclosure will be apparent from the description and drawings, and from the claims.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 12 is a summary of observed precipitation of 1-81.

DETAILED DESCRIPTION

Figure 1:
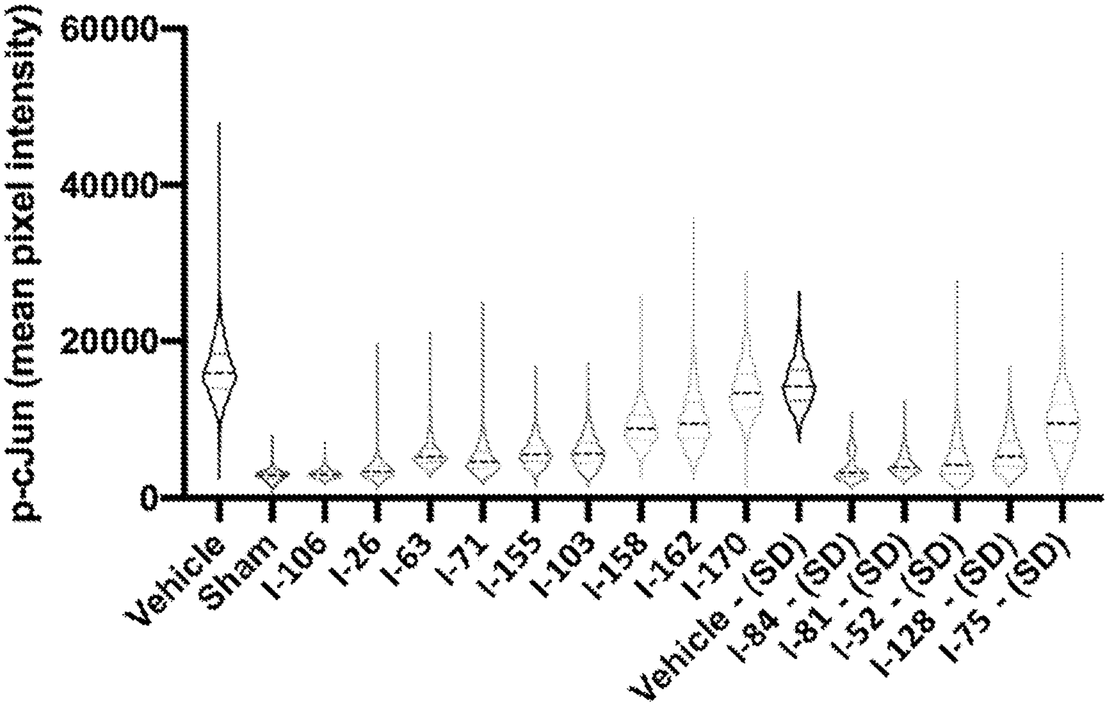
FIG. 1 is a plot showing the results of a target engagement assay with compounds of Formula (I) and (II).

Dual leucine zipper kinase (DLK, MAP3K12) is a key component of the neuronal stress response that regulates neurodegeneration in models of acute neuronal injury and chronic neurodegenerative diseases such as Alzheimer's, Parkinson's, and amyotrophic lateral sclerosis (ALS). The neuronally enriched kinase DLK (dual leucine zipper kinase, also known as mitogen activated protein 3 kinase 12, MAP3K12) represents a putative druggable component of this conserved neuronal degeneration pathway. Pharmacological inhibition or genetic deletion of DLK is sufficient to reduce the neuronal injury response and results in the protection of various neuronal populations from degeneration in response to a wide range of neuronal insults, suggesting that the inhibition of DLK might represent an attractive and potent therapeutic strategy. (Mata, M. et al., *J. Biol. Chem.* 1996, 271, 16888-16896; Watkins, T. A. et al., *Proc. Natd. Acad. Sci.*, 2013, 110, 4039-4044)).

Leucine Zipper-bearing Kinase (LZK/MAP3K13) is a member of the mixed lineage kinase family with high sequence identity to Dual Leucine Zipper Kinase (DLK/MAP3K12) and has been shown to also play a role in neuronal survival. In RGC cell death signaling DLK and LZK appear to be able to compensate for each other, at least partially, likely reflecting their participation in common biochemical complexes. (Welsbie, D. S. et al., *Neuron,* 2017, 94, 1142-1154). Combined inhibition of DLK and LZK is more effective in preventing neuronal cell death than inhibition of either one alone.

Provided herein are compounds of low molecular weight that can inhibit both DLK and LZK. Such compounds can be suitable for treatment and/or prevention of neurodegenerative disorders, such as ophthalmological neurodegenerative disorders.

Amino-triazolopyridines are known from WO 2009/068482, WO 2010/007100, and WO 2010/057877 as PI3K inhibitors for the treatment and prophylaxis of e.g. immunological, inflammatory, autoimmune, or allergic disorders; from WO 2016/057522 as CFTR inhibitors for the treatment of cystic fibrosis; from WO 2009/017954 as JAK2 inhibitors for the treatment of cancer; and from WO 2011/064328, WO 2011/157688, WO 2012/143329, and WO 2014/195276 as MPS-1 inhibitors for the treatment of cancer.

The present disclosure provides compounds of the general formula (A)

(A)

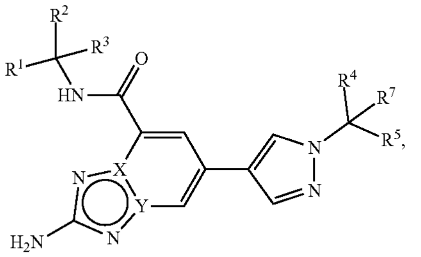

in which

X is nitrogen and Y is carbon, or

X is carbon and Y is nitrogen, $R^1$ and $R^2$ are each independently hydrogen or $(C_1-C_3)$-alkyl, $R^3$ is $(C_1-C_6)$-alkyl, $(C_3-C_7)$-cycloalkyl or $(C_3-C_7)$-cycloalkyl-$(C_1-C_3)$-alkyl wherein the $(C_1-C_6)$-alkyl, $(C_3-C_7)$-cycloalkyl, or $(C_3-C_7)$-cycloalkyl-$(C_1-C_3)$-alkyl may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is hydrogen, $(C_1-C_6)$-alkyl, $(C_3-C_7)$-cycloalkyl or 4- to 7-membered heterocyclyl wherein the $(C_1-C_6)$-alkyl, $(C_3-C_7)$-cycloalkyl or 4- to 7-membered heterocyclyl may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3-C_7)$-cycloalkyl, cyanomethyl, phenyl, or heteroaryl wherein the $(C_3-C_7)$-cycloalkyl, phenyl or heteroaryl may be substituted by one or more $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, $(C_1\text{-}C_4)$-alkyl, $(C_1\text{-}C_4)$-alkoxy, oxo, cyano, chlorine, bromine or up to three times by fluorine, or may be annellated with phenyl or heteroaryl where $(C_1\text{-}C_4)$-alkyl is optionally substituted by 4- to 7-membered heterocyclyl or up to three times by fluorine, and the nitrogen of each of the 4- to 7-membered heterocyclyl may independently be substituted by $C(O)OR^6$ or $C(O)R^6$, $R^6$ is $(C_1\text{-}C_4)$-alkyl, $R^7$ is hydrogen, $(C_1\text{-}C_6)$-alkyl, $(C_3\text{-}C_7)$-cycloalkyl or 4- to 7-membered heterocyclyl wherein the $(C_1\text{-}C_5)$-alkyl, $(C_3\text{-}C_7)$-cycloalkyl or 4- to 7-membered heterocyclyl may be substituted by $(C_1\text{-}C_4)$-alkyl, $(C_1\text{-}C_4)$-alkoxy, oxo, cyano, chlorine, bromine or up to three times by fluorine, where $(C_1\text{-}C_4)$-alkoxy and $(C_1\text{-}C_4)$-alkyl may be substituted up to three times by fluorine, and the nitrogen of a 4- to 7-membered heterocyclyl may be substituted by $C(O)OR^6$ or $C(O)R^6$, and the salts, solvates and solvates of the salts thereof.

The present disclosure provides compounds of the general formula (AI)

(AI)

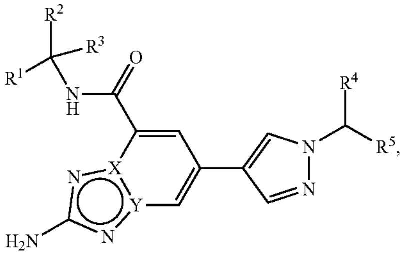

in which

X is nitrogen and Y is carbon, or

X is carbon and Y is nitrogen, $R^1$ and $R^2$ are each independently hydrogen or $(C_1\text{-}C_3)$-alkyl, $R^3$ is $(C_1\text{-}C_6)$-alkyl, $(C_3\text{-}C_7)$-cycloalkyl or $(C_3\text{-}C_7)$-cycloalkyl-$(C_1\text{-}C_3)$-alkyl wherein the $(C_1\text{-}C_6)$-alkyl, $(C_3\text{-}C_7)$-cycloalkyl, or $(C_3\text{-}C_7)$-cycloalkyl-$(C_1\text{-}C_3)$-alkyl may be substituted by hydroxyl, $(C_1\text{-}C_4)$-alkoxy, oxo, cyano, chlorine, bromine, or up to three times by fluorine, where $(C_1\text{-}C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, $(C_1\text{-}C_4)$-alkoxy, $(C_1\text{-}C_4)$-alkyl, oxo, cyano, chlorine, bromine, or fluorine, where $(C_1\text{-}C_4)$-alkoxy and $(C_1\text{-}C_4)$-alkyl may be substituted up to three times by fluorine, $R^4$ is hydrogen, $(C_1\text{-}C_5)$-alkyl, $(C_3\text{-}C_7)$-cycloalkyl or 4- to 7-membered heterocyclyl wherein the $(C_1\text{-}C_6)$-alkyl, $(C_3\text{-}C_7)$-cycloalkyl or 4- to 7-membered heterocyclyl may be substituted by $(C_1\text{-}C_4)$-alkyl, $(C_1\text{-}C_4)$-alkoxy, oxo, cyano, chlorine, bromine or up to three times by fluorine, where $(C_1\text{-}C_4)$-alkoxy and $(C_1\text{-}C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3\text{-}C_7)$-cycloalkyl, cyanomethyl, phenyl, or heteroaryl wherein the $(C_3\text{-}C_7)$-cycloalkyl, phenyl or heteroaryl may be substituted by one or more $(C_1\text{-}C_4)$-alkyl, $(C_1\text{-}C_4)$-alkoxy, cyano, 4- to 7-membered heterocyclyl, chlorine, bromine or up to three times by fluorine where $(C_1\text{-}C_4)$-alkyl and $(C_1\text{-}C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, $(C_1\text{-}C_4)$-alkyl, $(C_1\text{-}C_4)$-alkoxy, oxo, cyano, chlorine, bromine or up to three times by fluorine, or may be annellated with phenyl or heteroaryl where $(C_1\text{-}C_4)$-alkyl is optionally substituted by 4- to 7-membered heterocyclyl or up to three times by fluorine, and the nitrogen of each of the 4- to 7-membered heterocyclyl may independently be substituted by $C(O)OR^6$ or $C(O)R^6$, $R^6$ is $(C_1\text{-}C_4)$-alkyl and the salts, solvates and solvates of the salts thereof.

The present disclosure provides compounds of the general formula (I)

(I)

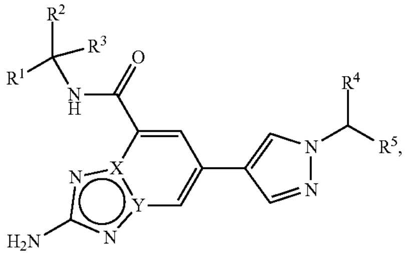

in which

X is nitrogen and Y is carbon, or

X is carbon and Y is nitrogen, $R^1$ and $R^2$ are each independently hydrogen or $(C_1\text{-}C_3)$-alkyl, $R^3$ is $(C_1\text{-}C_6)$-alkyl, $(C_3\text{-}C_7)$-cycloalkyl or $(C_3\text{-}C_7)$-cycloalkyl-$(C_1\text{-}C_3)$-alkyl wherein the $(C_1\text{-}C_6)$-alkyl, $(C_3\text{-}C_7)$-cycloalkyl, or $(C_3\text{-}C_7)$-cycloalkyl-$(C_1\text{-}C_3)$-alkyl may be substituted by hydroxyl, $(C_1\text{-}C_4)$-alkoxy, oxo, cyano, chlorine, bromine, or up to three times by fluorine, where $(C_1\text{-}C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, $(C_1\text{-}C_4)$-alkoxy, $(C_1\text{-}C_4)$-alkyl, oxo, cyano, chlorine, bromine, or fluorine, where ($C_1$-$C_4$)-alkoxy and ($C_1$-$C_4$)-alkyl may be substituted up to three times by fluorine, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by $C(O)OR^6$ or $C(O)R^6$, $R^5$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy—may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, and the nitrogen of each of the 4- to 7-membered heterocyclyl may independently be substituted by $C(O)OR^6$ or $C(O)R^6$, $R^6$ is ($C_1$-$C_4$)-alkyl and the salts, solvates and solvates of the salts thereof.

The present disclosure also provides compounds of the general formula (B)

(B)

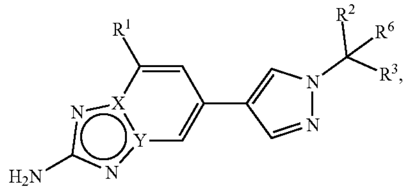

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^5$ are each independently ($C_1$-$C_4$)-alkyl optionally substituted up to three times by fluorine, $R^6$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by $C(O)OR^6$ or $C(O)R^6$, and the salts, solvates and solvates of the salts thereof.

The present disclosure also provides compounds of the general formula (BII)

(BII)

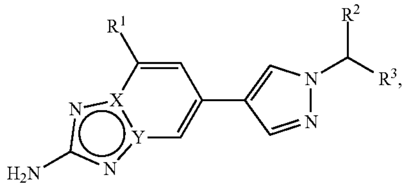

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and R are each independently ($C_1$-$C_4$)-alkyl optionally substituted up to three times by fluorine and the salts, solvates and solvates of the salts thereof.

The present disclosure also provides compounds of the general formula (II)

(II)

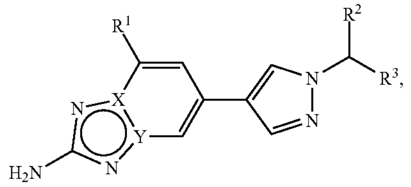

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_4$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered fused ring containing up to two heteratoms selected from the group consisting of O or N, which fused ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^5$ are each independently ($C_1$-$C_4$)-alkyl optionally substituted up to three times by fluorine and the salts, solvates and solvates of the salts thereof.

The compounds provided herein include the compounds of formulae (A), (AI), (I), (B), (BII), (II), and the salts, solvates and solvates of the salts thereof, the compounds of the formulae (I-A), (I-B), (I-C) (I-D), (II-A), (II-B), (II-C), (II-D), (II-E), (II-F), (II-G), and (II-H) below that are encompassed by formulae (A), (AI), (I), (B), (BII), (II), and the salts, solvates and solvates of the salts thereof, and the compounds cited hereinafter as working examples that are encompassed by formulae (A), (AI), (I), (B), (BII), (II), and the salts, solvates and solvates of the salts thereof, if the compounds cited hereinafter that are encompassed by formulae (A), (AI), (I), (B), (BII), (II), are not already salts, solvates and solvates of the salts.

Salts in the context of the present disclosure are physiologically acceptable salts of compounds of Formula (A), (AI), (I), (I-A), (I-B), (I-C), (I-D), (B), (BII), (II), (II-A), (II-B), (II-C), (II-D), (II-E), (II-F), (II-G), and (II-H). Also encompassed are salts which are not themselves suitable for pharmaceutical applications but can be used, for example, for the isolation, purification or storage of compounds of Formulae (A), (AI), (I), (I-A), (I-B), (I-C), (I-D), (B), (BII), (II), (II-A), (II-B), (II-C), (II-D), (II-E), (II-F), (II-G), and (II-H).

Physiologically acceptable salts of compounds of Formulae (A), (AI), (I), (I-A), (I-B), (I-C), (I-D), (B), (BII), (II), (II-A), (II-B), (II-C), (II-D), (II-E), (II-F), (II-G), and (II-H)include acid addition salts of mineral acids, carboxylic acids and sulfonic acids, for example, salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

In addition, physiologically acceptable salts of compounds of Formula (A), (AI), (I), (I-A), (I-B), (I-C), (I-D), (B), (BII), (II), (II-A), (II-B), (II-C), (II-D), (II-E), (II-F), (II-G), or (II-H) also include salts derived from conventional bases, by way of example alkali metal salts (e.g. sodium and potassium salts), alkaline earth metal salts (e.g. calcium and magnesium salts), zinc salts and ammonium salts derived from ammonia or organic amines having 1 to 20 carbon atoms, by way of example ethylamine, diethylamine, triethylamine, N,N-ethyldiisopropylamine, monoethanolamine, diethanolamine, triethanolamine, dimethylaminoethanol, diethylaminoethanol, tris(hydroxymethyl)aminomethane, choline, benzalkonium, procaine, dibenzylamine, dicyclohexylamine, N-methylmorpholine, N-methylpiperidine, arginine, lysine and 1,2-ethylenediamine.

Solvates in the context of the disclosure are described as those forms of a compound of Formula (A), (AI), (I), (I-A), (I-B), (I-C), (I-D), (B), (BII), (II), (II-A), (II-B), (II-C), (II-D), (II-E), (II-F), (II-G), or (II-H) which form a complex in the solid or liquid state by coordination with solvent molecules. Hydrates are a specific form of the solvates in which the coordination is with water. Solvates exemplified in the context of the present disclosure are hydrates.

A compound of Formula (A), (AI), (I), (I-A), (I-B), (I-C), (I-D), (B), (BII), (II), (II-A), (II-B), (II-C), (II-D), (II-E), (II-F), (II-G), or (II-H) may, depending on its structure, exist in different stereoisomeric forms, i.e. in the form of configurational isomers or else, if appropriate, of conformational isomers (enantiomers and/or diastereomers, including those in the case of atropisomers). The present disclosure therefore encompasses the enantiomers and diastereomers, and the respective mixtures thereof. The stereoisomerically homogeneous constituents can be isolated from such mixtures of enantiomers and/or diastereomers in a known manner; chromatography processes can be used for the purpose, especially HPLC chromatography on achiral or chiral separation phases. In the case of carboxylic acids as intermediates or end products, separation is alternatively also possible via diastereomeric salts using chiral amine bases.

If a compound of Formula (A), (AI), (I), (I-A), (I-B), (I-C), (I-D), (B), (BII), (II), (II-A), (II-B), (II-C), (II-D), (II-E), (II-F), (II-G), or (II-H) can occur in tautomeric forms, the present disclosure encompasses all the tautomeric forms.

The present disclosure also encompasses all suitable isotopic variants of a compound of Formula (A), (AI), (I), (I-A), (I-B), (I-C), (I-D), (B), (BII), (II), (II-A), (II-B), (II-C), (II-D), (II-E), (II-F), (II-G), or (II-H). An isotopic variant of a compound of Formula (A), (AI), (I), (I-A), (I-B), (I-C), (I-D), (B), (BII), (II), (II-A), (II-B), (II-C), (II-D), (II-E), (II-F), (II-G), or (II-H) is understood here to mean a compound in which at least one atom within the compound of Formula (A), (AI), (I), (I-A), (I-B), (I-C), (I-D), (B), (BII), (II), (II-A), (II-B), (II-C), (II-D), (II-E), (II-F), (II-G), or (II-H) has been exchanged for another atom of the same atomic number, but with a different atomic mass than the atomic mass which usually or predominantly occurs in nature. Examples of isotopes which can be incorporated into a compound of Formula (A), (AI), (I), (I-A), (I-B), (I-C), (I-D), (B), (BII), (II), (II-A), (II-B), (II-C), (II-D), (II-E), (II-F), (II-G), or (II-H) are those of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}s$, $^{36}S$, $^{18}F$, $^{36}Cl$, $^{82}Br$, $^{123}I$, $^{124}I$ $^{12}91$ and $^{131}I$. Particular isotopic variants of a compound of Formula (A), (AI), (I), (I-A), (I-B), (I-C), (I-D), (B), (BII), (II), (II-A), (II-B), (II-C), (II-D), (II-E), (II-F), (II-G), or (II-H), especially those in which one or more radioactive isotopes have been incorporated, may be beneficial, for example, for the examination of the mechanism of action or of the active ingredient distribution in the body; due to comparatively easy preparability and detectability, particularly compounds labelled with $^{3}H$, $^{14}C$ and/or $^{18}F$ isotopes are suitable for the purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of a compound of Formula (A), (AI), (I), (I-A), (I-B), (I-C), (I-D), (B), (BII), (II), (II-A), (II-B), (II-C), (II-D), (II-E), (II-F), (II-G), or (II-H) may therefore possibly also constitute an exemplified embodiment of the present disclosure. Isotopic variants of a compound of Formula (A), (AI), (I), (I-A), (I-B), (I-C), (I-D), (B), (BII), (II), (II-A), (H-B), (II-C), (II-D), (II-E), (II-F), (II-G), or (II-H) can be prepared by commonly used processes known to those skilled in the art, for example by the methods described further down and the procedures described in the working examples, by using corresponding isotopic modifications of the respective reagents and/or starting compounds.

In addition, the present disclosure also encompasses prodrugs of a compound of Formula (A), (AI), (I), (I-A), (I-B), (I-C), (I-D), (B), (BII), (II), (II-A), (II-B), (II-C), (II-D), (II-E), (II-F), (II-G), or (II-H). The term "prodrugs" refers here to compounds which may themselves be biologically active or inactive, but are converted while present in the body, for example by a metabolic or hydrolytic route, to compounds of Formula (A), (AI), (I), (I-A), (I-B), (I-C), (I-D), (B), (BII), (II), (II-A), (II-B), (II-C), (II-D), (II-E), (II-F), (II-G), or (II-H).

In the context of the present disclosure, unless specified otherwise, the substituents and radicals are defined as follows:

($C_1$-$C_6$)-Alkyl, ($C_1$-$C_4$)-alkyl and ($C_1$-$C_3$)-alkyl in the context of the disclosure represent a straight-chain or branched alkyl radical having 1 to 6, 1 to 4 and 1 to 3 carbon atoms respectively. Examples include: methyl, ethyl, n-propyl, isopropyl, n-butyl, isobutyl, sec-butyl, tert-butyl, n-pentyl, 2-pentyl, 3-pentyl, neopentyl, 3-methylbutyl, n-hexyl, 2-hexyl, 3-hexyl and 4-methylpentyl. Examples include a straight-chain or branched alkyl radical having 1 to 4 carbon atoms, such as methyl, ethyl, n-propyl, isopropyl, n-butyl, isobutyl, sec-butyl and tert-butyl. Examples include a straight-chain or branched alkyl radical having 1 to 3 carbon atoms, such as methyl, ethyl, n-propyl and isopropyl.

($C_1$-$C_4$)-Alkoxy and ($C_1$-$C_3$)-alkoxy in the context of the disclosure represents a straight-chain or branched alkoxy radical having 1 to 4 carbon atoms respectively. Examples include: methoxy, ethoxy, n-propoxy, isopropoxy, n-butoxy, isobutoxy, sec-butoxy and tert-butoxy. Examples include a straight-chain or branched alkoxy radical, such as methoxy, ethoxy, n-propoxy and isopropoxy.

($C_3$-$C_7$)-Cycloalkyl in the context of the disclosure is a monocyclic saturated cycloalkyl group having 3 to 7 ring carbon atoms. Examples include: cyclopropyl, cyclobutyl, cyclopentyl, cyclohexyl and cycloheptyl.

($C_3$-$C_7$)-Cycloalkxoy in the context of the disclosure is a monocyclic saturated cycloalkyl group having 3 to 7 ring carbon atoms bound as via oxygen as an ether to the rest of the molecule. Examples include: cyclopropoxy, cyclobutoxy, cyclopentoxy, cyclohexoxy and cycloheptoxy.

($C_3$-$C_7$)-Cycloalkyl-($C_1$-$C_3$)-alkyl in the context of the disclosure is a ($C_1$-$C_3$)-alkyl substituted by ($C_3$-$C_7$)-cycloalkyl and bound to the rest of the molecule via the ($C_1$-$C_3$)-alkyl group.

4- to 7-Membered heterocyclyl in the context of the disclosure is a monocyclic or optionally bicyclic saturated heterocycle which has a total of 4 to 7 ring atoms, contains one or two identical or different ring heteroatoms from the group of N, O and S and is joined via a ring carbon atom or optionally via a ring nitrogen atom. Examples include: azetidinyl, oxetanyl, thietanyl, pyrrolidinyl, pyrazolidinyl, tetrahydrofuranyl, thiolanyl, 1,2-oxazolidinyl, 1,3-oxazolidinyl, 1,3-thiazolidinyl, piperidinyl, piperazinyl, tetrahydropyranyl, tetrahydrothiopyranyl, 1,3-dioxanyl, 1,4-dioxanyl, 1,2-oxazinanyl, morpholinyl, thiomorpholinyl, azepanyl, 1,4-diazepanyl, 1,4-oxazepanyl and 7-azabicyclo[2.2.1]heptyl. In some embodiments, the heterocyclyl is a 4- to 6 membered heterocyclyl which is a monocyclic saturated heterocycle which has a total of 4 to 6 ring atoms, contains one or two identical or different ring heteroatoms from the group of N and O and is joined via a ring carbon atom or optionally via a ring nitrogen atom, for example azetidinyl, oxetanyl, pyrrolidinyl, pyrazolidinyl, tetrahydrofuranyl, 1,3-oxazolidinyl, piperidinyl, piperazinyl, tetrahydropyranyl, 1,4-dioxanyl, 1,2-oxazinanyl and morpholinyl. In some embodiments, the heterocyclyl is a 5- or 6 membered heterocyclyl which is a monocyclic saturated heterocycle which has a total of 5 or 6 ring atoms, contains one or two identical or different ring heteroatoms from the group of N and O and is joined via a ring carbon atom or optionally via a ring nitrogen atom, for example pyrrolidinyl, pyrazolidinyl, tetrahydrofuranyl, 1,3-oxazolidinyl, piperidinyl, piperazinyl, tetrahydropyranyl, 1,4-dioxanyl, 1,2-oxazinanyl and morpholinyl.

Heteroaryl or 5- to 10-membered heteroaryl in the context of the disclosure is a monocyclic or optionally bicyclic aromatic heterocycle (heteroaromatic) which has a total of 5 to 10 ring atoms, contains up to four identical or different ring heteroatoms from the group of N, O and S and is joined via a ring carbon atom or optionally via a ring nitrogen atom. Examples include: furyl, pyrrolyl, thienyl, pyrazolyl, imidazolyl, 1,2-oxazolyl (isoxazolyl), 1,3-oxazolyl, 1,2-thiazolyl (isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl, 1,3,4-thiadiazolyl, tetrazolyl, pyridyl, pyrimidinyl, pyridazinyl, pyrazinyl, 1,2,4-triazinyl, 1,3,5-triazinyl, benzofuranyl, benzothienyl, benzimidazolyl, benzoxazolyl, benzothiazolyl, benzotriazolyl, indolyl, indolizinyl, indazolyl, quinolinyl, isoquinolinyl, naphthyridinyl, quinazolinyl, quinoxalinyl, cinnolinyl, phthalazinyl, pyrazolo[3,4-b]pyridinyl, purinyl and pteridinyl. In some embodiments, the heteroaryl is a 5-6 membered heteroaryl which is a monocyclic heteroaromatic system which has a total of 5 or 6 ring atoms, contains one or two identical or different ring heteroatoms from the group of N, O and S and is joined via a ring carbon atom or optionally via a ring nitrogen atom, for example furyl, pyrrolyl, thienyl, pyrazolyl, imidazolyl, 1,3-oxazolyl, 1,3-thiazolyl, pyridyl, pyrimidinyl, pyridazinyl and pyrazinyl.

In the definition of $R^2$ and $R^3$ or $R^4$ and $R^5$ radicals that are joined to one another and thus form a ring, the term 4- to 7-membered heterocycle means a monocyclic saturated heterocycle which has a total of 4 to 7 ring atoms and may contain up to two further, identical or different, ring heteroatoms from the group of N and O. Examples include: azetidinyl, pyrrolidinyl, pyrazolidinyl, 1,2-oxazolidinyl, imidazolidinyl, 1,3-oxazolidinyl, piperidinyl, piperazinyl, 1,2-oxazinanyl, morpholinyl, azepanyl, 1,4-diazepanyl, and 1,4-oxazepanyl. In some embodiments, the heterocycle is a 5- to 7-membered heterocycle which is a monocyclic saturated heterocycle which has a total of 5 to 7 ring atoms, contains one ring nitrogen atom, is joined via said atom and may contain one further ring heteroatom from the group of N and O, for example pyrrolidinyl, pyrazolidinyl, imidazolidinyl, 1,3-oxazolidinyl, piperidinyl, piperazinyl, 1,2-oxazinanyl, morpholinyl, azepanyl, 1,4-diazepanyl and 1,4-oxazepanyl.

An oxo substituent in the context of the disclosure is an oxygen atom bonded to a carbon atom via a double bond.

In the context of the present disclosure, all radicals which occur more than once are defined independently of one another. When radicals in a compounds of Formula (A), (AI), (I), (I-A), (I-B), (I-C), (I-D), (B), (BII), (II), (II-A), (II-B), (II-C), (II-D), (II-E), (II-F), (II-G), or (II-H) are substituted, the radicals may be mono- or polysubstituted, unless specified otherwise. Substitution by one or two identical or different substituents (e.g., 1 substituent) is exemplified.

Compounds of Formula (I)

The present disclosure provides compounds of the general formula (A)

(A)

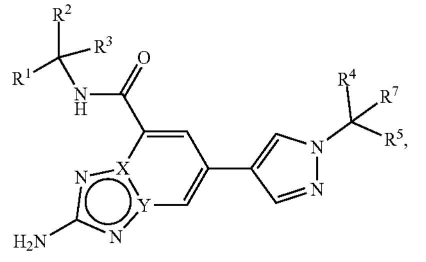

in which

X is nitrogen and Y is carbon, or

X is carbon and Y is nitrogen, $R^1$ and $R^2$ are each independently hydrogen or $(C_1$-$C_3)$-alkyl, $R^3$ is $(C_1$-$C_5)$-alkyl, $(C_3$-$C_7)$-cycloalkyl or $(C_3$-$C_7)$-cycloalkyl-$(C_1$-$C_3)$-alkyl wherein the $(C_1$-$C_6)$-alkyl, $(C_3$-$C_7)$-cycloalkyl, or $(C_3$-$C_7)$-cycloalkyl-$(C_1$-$C_3)$-alkyl may be substituted by hydroxyl, $(C_1$-$C_4)$-alkoxy, oxo, cyano, chlorine, bromine, or up to three times by fluorine, where $(C_1$-$C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, $(C_1$-$C_4)$-alkoxy, $(C_1$-$C_4)$-alkyl, oxo, cyano, chlorine, bromine, or fluorine, where $(C_1$-$C_4)$-alkoxy and $(C_1$-$C_4)$-alkyl may be substituted up to three times by fluorine, $R^4$ is hydrogen, $(C_1$-$C_5)$-alkyl, $(C_3$-$C_7)$-cycloalkyl or 4- to 7-membered heterocyclyl wherein the $(C_1$-$C_6)$-alkyl, $(C_3$-$C_7)$-cycloalkyl or 4- to 7-membered heterocyclyl may be substituted by $(C_1$-$C_4)$-alkyl, $(C_1$-$C_4)$-alkoxy, oxo, cyano, chlorine, bromine or up to three times by fluorine, where $(C_1$-$C_4)$-alkoxy and $(C_1$-$C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3$-$C_7)$-cycloalkyl, cyanomethyl, phenyl, or heteroaryl wherein the $(C_3$-$C_7)$-cycloalkyl, phenyl or heteroaryl may be substituted by one or more $(C_1$-$C_4)$-alkyl, $(C_1$-$C_4)$-alkoxy, cyano, 4- to 7-membered heterocyclyl, chlorine, bromine or up to three times by fluorine where $(C_1$-$C_4)$-alkyl and $(C_1$-$C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, and the nitrogen of each of the 4- to 7-membered heterocyclyl may independently be substituted by C(O)OR$^6$ or C(O)R$^6$, $R^6$ is ($C_1$-$C_4$)-alkyl, $R^7$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, and the salts, solvates and solvates of the salts thereof.

The present disclosure provides compounds of the general formula (AI)

(AI)

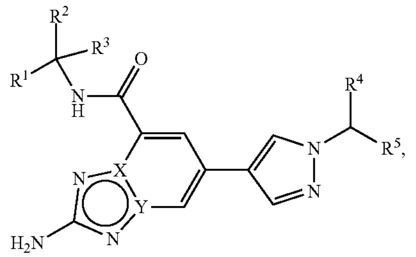

in which

X is nitrogen and Y is carbon, or

X is carbon and Y is nitrogen, $R^1$ and $R^2$ are each independently hydrogen or ($C_1$-$C_3$)-alkyl, $R^3$ is ($C_1$-$C_6$)-alkyl, ($C_3$-$C_7$)-cycloalkyl or ($C_3$-$C_7$)-cycloalkyl-($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl may be substituted by hydroxyl, ($C_1$-$C_4$)-alkoxy, oxo, cyano, chlorine, bromine, or up to three times by fluorine, where ($C_1$-$C_4$)-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, ($C_1$-$C_4$)-alkoxy, ($C_1$-$C_4$)-alkyl, oxo, cyano, chlorine, bromine, or fluorine, where ($C_1$-$C_4$)-alkoxy and ($C_1$-$C_4$)-alkyl may be substituted up to three times by fluorine, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, $R^5$ is ($C_3$-$C_7$)-cycloalkyl, cyanomethyl, phenyl, or heteroaryl wherein the ($C_3$-$C_7$)-cycloalkyl, phenyl or heteroaryl may be substituted by one or more ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, and the nitrogen of each of the 4- to 7-membered heterocyclyl may independently be substituted by C(O)OR$^6$ or C(O)R$^6$, $R^6$ is ($C_1$-$C_4$)-alkyl and the salts, solvates and solvates of the salts thereof.

The present disclosure provides compounds of the general formula (I)

(I)

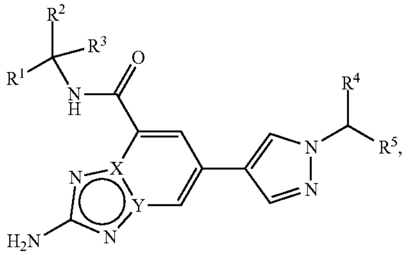

in which

X is nitrogen and Y is carbon, or

X is carbon and Y is nitrogen, $R^1$ and $R^2$ are each independently hydrogen or ($C_1$-$C_3$)-alkyl, $R^3$ is ($C_1$-$C_6$)-alkyl, ($C_3$-$C_7$)-cycloalkyl or ($C_3$-$C_7$)-cycloalkyl-($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl may be substituted by hydroxyl, ($C_1$-$C_4$)-alkoxy, oxo, cyano, chlorine, bromine, or up to three times by fluorine, where ($C_1$-$C_4$)-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, ($C_1$-$C_4$)-alkoxy, ($C_1$-$C_4$)-alkyl, oxo, cyano, chlorine, bromine, or fluorine, where ($C_1$-$C_4$)-alkoxy and ($C_1$-$C_4$)-alkyl may be substituted up to three times by fluorine, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where $(C_1-C_4)$-alkoxy and $(C_1-C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3-C_7)$-cycloalkyl, phenyl or heteroaryl wherein the $(C_3-C_7)$-cycloalkyl, phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, $(C_1-C_4)$-alkyl, $(C_1-C_4)$-alkoxy, oxo, cyano, chlorine, bromine or up to three times by fluorine, or may be annellated with phenyl or heteroaryl where $(C_1-C_4)$-alkyl is optionally substituted by 4- to 7-membered heterocyclyl or up to three times by fluorine, and the nitrogen of each of the 4- to 7-membered heterocyclyl may independently be substituted by $C(O)OR^6$ or $C(O)R^6$, $R^6$ is $(C_1-C_4)$-alkyl and the salts, solvates and solvates of the salts thereof.

In some embodiments,

X is nitrogen and Y is carbon, $R^1$ and $R^2$ are each independently hydrogen or methyl, $R^3$ is $(C_1-C_6)$-alkyl which may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two O atoms, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is $(C_1-C_5)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments,

X is nitrogen and Y is carbon, $R^1$ is hydrogen, $R^2$ is methyl, $R^3$ is $(C_1-C_4)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, wherein the ring may be substituted by hydroxyl, $(C_1-C_4)$-alkoxy, chlorine, bromine, or fluorine where $(C_1-C_4)$-alkoxy may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments, the compound is a compound of formula (I-A) in which (I-A)

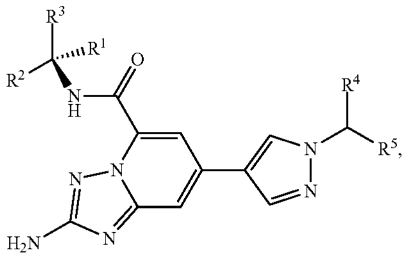

$R^1$ is hydrogen, $R^2$ is methyl, $R^3$ is $(C_1-C_3)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments, the compound is a compound of formula (I-B) in which (I-B)

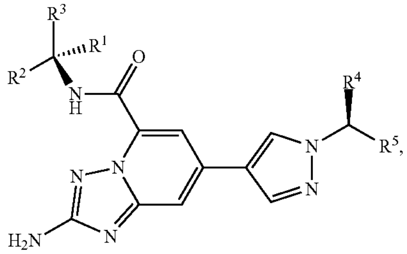

$R^1$ is hydrogen, $R^2$ is methyl, $R^3$ is methyl or ethyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a furanyl ring, $R^4$ is $(C_1-C_6)$-alkyl, cyclopropyl, cyclobutyl, cyclopentyl, 4- to 7-membered heterocyclyl, each of which may be substituted by chlorine, bromine or up to three times by fluorine and the nitrogen of a 4- to 7-membered heterocyclyl may be substituted by $C(O)OR^6$ or $C(O)R^6$, $R^5$ is phenyl, 3-pyridinyl or 4-pyridinyl, each of which may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments,

X is carbon and Y is nitrogen, $R^1$ and $R^2$ are each independently hydrogen or methyl, $R^3$ is $(C_1-C_6)$-alkyl which may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two O atoms, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments,

X is carbon and Y is nitrogen, $R^1$ is hydrogen, $R^2$ is methyl, $R^3$ is $(C_1-C_4)$-alkyl which may be substituted by hydroxyl, $(C_1-C_4)$-alkoxy, chlorine or up to three times by fluorine, where $(C_1-C_4)$-alkoxy may be substituted up to three times by fluorine.

or $R^2$ and $R^3$ are joined to one another and, taken together with the carbon atom to which they are attached, form a 4- to 7-membered ring containing up to one O atom, wherein the ring may be substituted by hydroxyl, $(C_1-C_4)$-alkoxy, chlorine, bromine, or fluorine where $(C_1-C_4)$-alkoxy may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

In some embodiments, the compound is a compound of formula (I-C) in which (I-C)

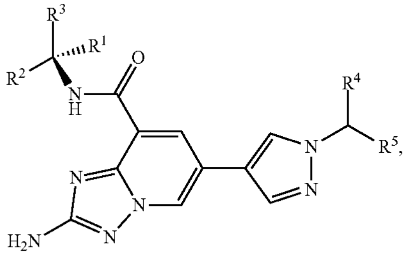

$R^1$ is hydrogen, $R^2$ is methyl, $R^3$ is $(C_1-C_3)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is ($C_1$-$C_4$)-alkyl and the salts, solvates and solvates of the salts thereof.

In some embodiments, the compound is a compound of formula (I-D) in which (I-D)

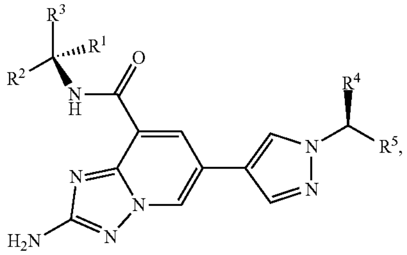

$R^1$ is hydrogen, $R^2$ is methyl, $R^3$ is methyl or ethyl which may be substituted by hydroxyl, ($C_1$-$C_4$)-alkoxy, chlorine or up to three times by fluorine, where ($C_1$-$C_4$)-alkoxy may be substituted up to three times by fluorine, or $R^2$ and $R^3$ are joined to one another and, taken together with the carbon atom to which they are attached, form a furanyl ring, $R^4$ is ($C_1$-$C_5$)-alkyl, cyclopropyl, cyclobutyl, cyclopentyl, 4- to 7-membered heterocyclyl wherein the ($C_1$-$C_6$)-alkyl, ($C_3$-$C_7$)-cycloalkyl, or 4- to 7-membered heterocyclyl may be substituted by chlorine, bromine or up to three times by fluorine and the nitrogen of a 4- to 7-membered heterocyclyl may be substituted by C(O)OR$^6$ or C(O)R$^6$, $R^5$ is phenyl, 3-pyridinyl or 4-pyridinyl, each of which may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl and the salts, solvates and solvates of the salts thereof.

In some embodiments, X is carbon and Y is nitrogen.

$R^1$ and $R^2$ are each independently hydrogen or methyl.

In some embodiments, $R^3$ is ($C_1$-$C_6$)-alkyl, which may be substituted by hydroxyl, ($C_1$-$C_4$)-alkoxy, chlorine or up to three times by fluorine, where ($C_1$-$C_4$)-alkoxy may be substituted up to three times by fluorine. In some embodiments, $R^3$ is methyl or ethyl, each of which may be substituted by hydroxyl, ($C_1$-$C_4$)-alkoxy, chlorine or up to three times by fluorine, where ($C_1$-$C_4$)-alkoxy may be substituted up to three times by fluorine. In some embodiments, $R^3$ is methyl or ethyl, each of which may be substituted by ($C_1$-$C_4$)-alkoxy, chlorine, or up to three times by fluorine, where ($C_1$-$C_4$)-alkoxy may be substituted up to three times by fluorine. In some embodiments, $R^3$ is methyl or ethyl, each of which may be substituted by ($C_1$-$C_4$)-alkoxy or up to three times by fluorine, where ($C_1$-$C_4$)-alkoxy may be substituted up to three times by fluorine. In some embodiments, $R^3$ is methyl or ethyl, each of which may be substituted by up to three times by fluorine. In some embodiments, $R^3$ is ethyl which may be substituted by hydroxyl, ($C_1$-$C_4$)-alkoxy, chlorine, or up to three times by fluorine, where ($C_1$-$C_4$)-alkoxy may be substituted up to three times by fluorine. In some embodiments, $R^3$ is ethyl which may be substituted by ($C_1$-$C_4$)-alkoxy, chlorine, or up to three times by fluorine, where ($C_1$-$C_4$)-alkoxy may be substituted up to three times by fluorine. In some embodiments, $R^3$ is ethyl which may be substituted by ($C_1$-$C_4$)-alkoxy, or up to three times by fluorine, where ($C_1$-$C_4$)-alkoxy may be substituted up to three times by fluorine. In some embodiments, $R^3$ is ethyl which may be substituted up to three times by fluorine. For example, $R^3$ is unsubstituted ethyl.

In some embodiments, the stereochemical configuration of the atom that $R^1$, $R^2$, and $R^3$ are bonded to is (S). In some embodiments, the stereochemical configuration of the atom that $R^1$, $R^2$, and $R^3$ are bonded to is (R).

In some embodiments, $R^4$ is ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine; and the nitrogen of the 4- to 7-membered heterocyclyl may be substituted by C(O)OR$^6$ or C(O)R$^6$. In some embodiments, $R^4$ is ($C_3$-$C_6$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine; and the nitrogen of the 4- to 7-membered heterocyclyl may be substituted by C(O)OR$^6$ or C(O)R$^6$. In some embodiments, $R^4$ is cyclobutyl, cyclopentyl, or 4- to 7-membered heterocyclyl, each of which may be substituted by ($C_1$-$C_4$)-alkyl, ($C_1$-$C_4$)-alkoxy, oxo, or up to three times by fluorine; and the nitrogen of the 4- to 7-membered heterocyclyl may be substituted by C(O)OR$^6$ or C(O)R$^6$. In some embodiments, $R^4$ is cyclobutyl, cyclopentyl, or 4- to 7-membered heterocyclyl, each of which may be substituted by ($C_1$-$C_4$)-alkyl, oxo, or up to three times by fluorine; and the nitrogen of the 4- to 7-membered heterocyclyl may be substituted by C(O)0R$^6$ or C(O)R$^6$. In some embodiments, $R^4$ is cyclobutyl, cyclopentyl, or 4-to 7-membered heterocyclyl, each of which may be substituted by chlorine, bromine, or up to three times by fluorine; and the nitrogen of the 4- to 7-membered heterocyclyl may be substituted by C(O)OR$^6$ or C(O)R$^6$. In some embodiments, $R^4$ is cyclopentyl or 4- to 7-membered heterocyclyl, each of which may be substituted by chlorine, bromine, or up to three times by fluorine; and the nitrogen of the 4- to 7-membered heterocyclyl may be substituted by C(O)OR$^6$ or C(O)R$^6$. In some embodiments, $R^4$ is 4- to 7-membered heterocyclyl which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine; and the nitrogen of the 4- to 7-membered heterocyclyl may be substituted by C(O)OR$^6$ or C(O)R$^6$. In some embodiments, $R^4$ is 4- to 7-membered heterocyclyl which may be substituted by ($C_1$-$C_4$)-alkyl, ($C_1$-$C_4$)-alkoxy, or up to three times by fluorine; and the nitrogen of the 4- to 7-membered heterocyclyl may be substituted by C(O)OR$^6$ or C(O)R$^6$. In some embodiments; $R^4$ is 4- to 7-membered heterocyclyl which may be substituted by chlorine, bromine, or up to three times by fluorine; and the nitrogen of the 4- to 7-membered heterocyclyl may be substituted by C(O)OR$^6$ or C(O)R$^6$. In some embodiments, $R^4$ is 5- to 6-membered heterocyclyl which may be substituted by chlorine, bromine, or up to three times by fluorine and the nitrogen of the 5- to 6-membered heterocyclyl may be substituted by C(O)OR$^6$ or C(O)R$^6$. In some embodiments, $R^4$ is piperidinyl which may be substituted by chlorine, bromine, or up to three times by fluorine and the nitrogen of the piperidinyl may be substituted by C(O)OR$^6$ or C(O)R$^6$. In some embodiments, $R^4$ is piperidinyl and the nitrogen of the piperidinyl may be substituted by C(O)OR$^6$ or C(O)R$^6$. In some embodiments, $R^4$ is 4-piperidinyl and the nitrogen of the 4-piperidinyl may be substituted by $C(O)OR^6$ or $C(O)R^6$. In some embodiments, $R^4$ is 4-piperidinyl and the nitrogen of the piperidinyl may be substituted by C(O)OtBu or C(O)Me. For example, $R^4$ is 4-piperidinyl. For example, $R^4$ is 4-piperidinyl and the nitrogen of the piperidinyl may be substituted by C(O)OtBu. For example, $R^4$ is 4-piperidinyl and the nitrogen of the piperidinyl may be substituted by C(O)Me.

In some embodiments, $R^6$ methyl or t-butyl. For example, $R^6$ is methyl. For example, $R^6$ is t-butyl.

In some embodiments, $R^5$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine. In some embodiments, $R^5$ is phenyl or heteroaryl wherein the phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine. In some embodiments, $R^5$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, 4- to 7-membered heterocyclyl, or up to three times by fluorine. In some embodiments, $R^5$ is phenyl or heteroaryl wherein the phenyl or heteroaryl may be substituted by $(C_1-C_4)$-alkyl, $(C_1-C_4)$-alkoxy, 4- to 7-membered heterocyclyl, or up to three times by fluorine. In some embodiments, $R^5$ is phenyl, 3-pyridinyl, or 4-pyridinyl, each of which may—be substituted by $(C_1-C_4)$-alkyl, $(C_1-C_4)$-alkoxy, cyano, chlorine, bromine, or up to three times by fluorine; where $(C_1-C_4)$-alkyl and $(C_1-C_4)$-alkoxy may be substituted up to three times by fluorine. In some embodiments, $R^5$ is phenyl, 3-pyridinyl, or 4-pyridinyl, each of which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine. In some embodiments, $R^5$ is 3-pyridinyl which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine. In some embodiments, $R^5$ is 3-pyridinyl which may be substituted by $(C_1-C_4)$-alkyl; where $(C_1-C_4)$-alkyl may be substituted up to three times by fluorine. In some embodiments, $R^5$ is 3-pyridinyl which may be substituted by trifluoromethyl. In some embodiments, $R^5$ is 3-pyridinyl which is substituted by trifluoromethyl. In some embodiments, $R^5$ is 6-(trifluoromethyl)pyridin-3-yl.

In some embodiments, the stereochemical configuration of the atom that $R^4$ and $R^5$ are bonded to is (S). In some embodiments, the stereochemical configuration of the atom that $R^4$ and $R^5$ are bonded to is (R).

In some embodiments,

X is carbon and Y is nitrogen;

$R^1$ and $R^2$ are each independently hydrogen or methyl;

$R^3$ is methyl or ethyl, each of which may be substituted by hydroxyl, $(C_1-C_4)$-alkoxy, chlorine or up to three times by fluorine, where $(C_1-C_4)$-alkoxy may be substituted up to three times by fluorine;

$R^4$ is $(C_3-C_7)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine; and the nitrogen of the 4- to 7-membered heterocyclyl may be substituted by $C(O)OR^6$ or $C(O)R^6$;

$R^5$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine; and $R^6$ is methyl or t-butyl.

In some embodiments,

X is carbon and Y is nitrogen;

$R^1$ and $R^2$ are each independently hydrogen or methyl;

$R^3$ is ethyl which may be substituted by hydroxyl, $(C_1-C_4)$-alkoxy, chlorine or up to three times by fluorine;

$R^4$ is $(C_3-C_6)$-cycloalkyl or 4- to 7-membered heterocyclyl, each of which may be substituted by $(C_1-C_4)$-alkyl, $(C_1-C_4)$-alkoxy, oxo, cyano, chlorine, bromine, or up to three times by fluorine; and the nitrogen of the 4- to 7-membered heterocyclyl may be substituted by $C(O)OR^6$ or $C(O)R^6$;

$R^5$ is phenyl or heteroaryl wherein the phenyl, or heteroaryl may be substituted by $(C_1-C_4)$-alkyl, $(C_1-C_4)$-alkoxy, cyano, 4- to 7-membered heterocyclyl, or up to three times by fluorine; and $R^6$ is methyl or t-butyl.

In some embodiments,

X is carbon and Y is nitrogen;

$R^1$ and $R^2$ are each independently hydrogen or methyl;

$R^3$ is methyl or ethyl, each of which may be substituted by hydroxyl, $(C_1-C_4)$-alkoxy, chlorine or up to three times by fluorine, where $(C_1-C_4)$-alkoxy may be substituted up to three times by fluorine;

$R^4$ is 4- to 7-membered heterocyclyl which may be substituted by chlorine, bromine, or up to three times by fluorine; and the nitrogen of the 4- to 7-membered heterocyclyl may be substituted by $C(O)OR^6$ or $C(O)R^6$;

$R^5$ is phenyl, 3-pyridinyl, or 4-pyridinyl, each of which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine; and $R^6$ is methyl or t-butyl.

In some embodiments,

X is carbon and Y is nitrogen;

$R^1$ and $R^2$ are each independently hydrogen or methyl;

$R^3$ is methyl or ethyl, each of which may be substituted by hydroxyl, $(C_1-C_4)$-alkoxy, chlorine or up to three times by fluorine, where $(C_1-C_4)$-alkoxy may be substituted up to three times by fluorine;

the stereochemical configuration of the atom that $R^1$, $R^2$, and $R^3$ are bonded to is (S);

$R^4$ is 4- to 7-membered heterocyclyl which may be substituted by chlorine, bromine, or up to three times by fluorine; and the nitrogen of the 4- to 7-membered heterocyclyl may be substituted by $C(O)OR^6$ or $C(O)R^6$;

$R^5$ is phenyl, 3-pyridinyl, or 4-pyridinyl, each of which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine;

the stereochemical configuration of the atom that $R^4$ and $R^5$ are bonded to is (S); and $R^6$ is methyl or t-butyl.

In some embodiments,

X is carbon and Y is nitrogen;

$R^1$ is hydrogen;

$R^2$ is methyl;

$R^3$ is ethyl;

the stereochemical configuration of the atom that $R^1$, $R^2$, and $R^3$ are bonded to is (S);

$R^4$ is 4-piperidinyl and the nitrogen of the piperidinyl may be substituted by C(O)OtBu or C(O)Me;

$R^5$ is 3-pyridinyl which may be substituted by trifluoromethyl;

the stereochemical configuration of the atom that $R^4$ and $R^5$ are bonded to is (S); and $R^6$ is methyl or t-butyl.

In some embodiments, the compound is selected from the group consisting of:

(I-83)

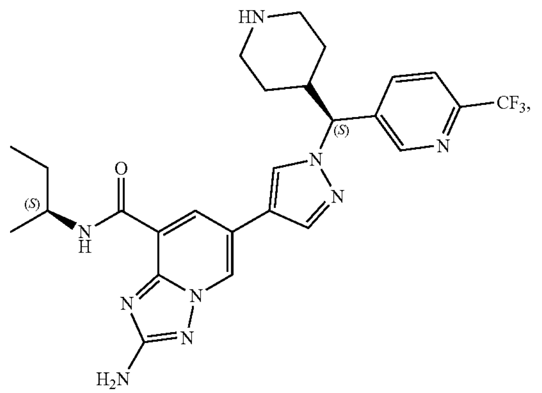

(I-84)

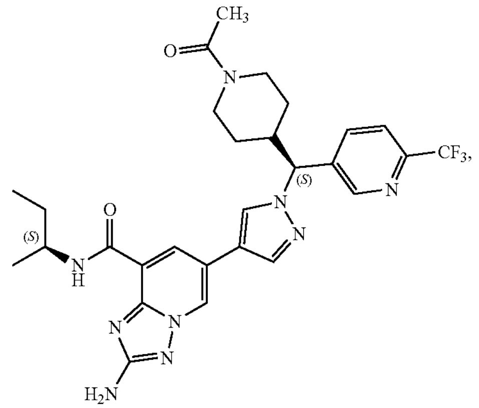

, and

-continued (I-81)

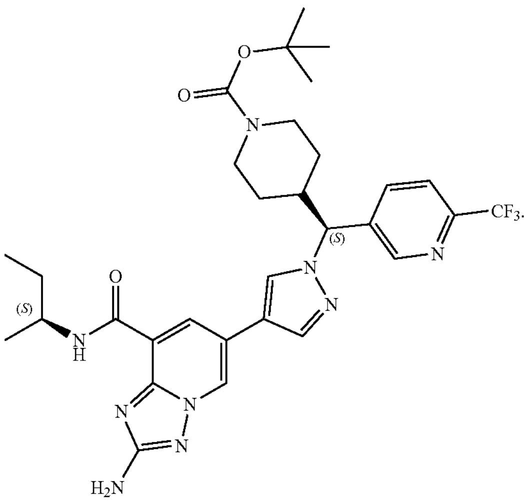

.

In some embodiments, the compound is selected from the group consisting of the compounds disclosed in Table 1A below:

TABLE 1A

| Example Number | Structure |
| --- | --- |
| I-1 | 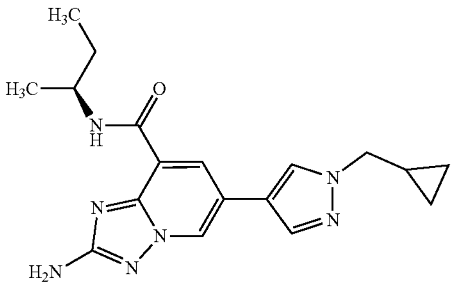 [SMILES: CC[C@H](C)NC(=O)c1cc(-c2cnn(CC3CC3)c2)cn2nc(N)nc12] |

TABLE 1A-continued
| Example Number | Structure |
|---|---|
| I-2 | 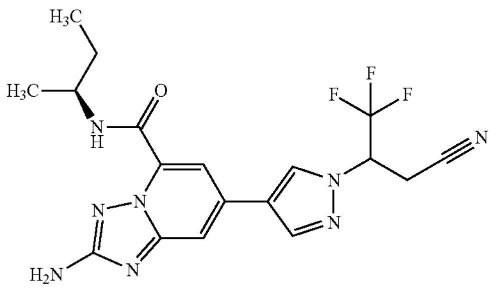 [SMILES: CC[C@H](C)NC(=O)c1cc(-c2cnn(C(CC#N)C(F)(F)F)c2)cc2nc(N)nn12] |
| I-3 | 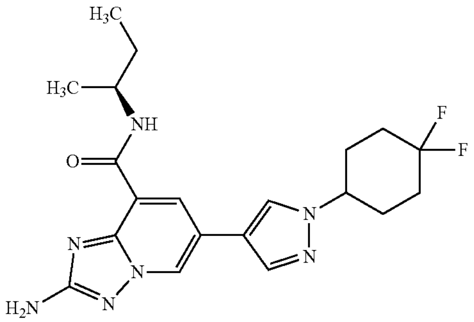 [SMILES: CC[C@H](C)NC(=O)c1cc(-c2cnn(C3CCC(F)(F)CC3)c2)cn2nc(N)nc12] |
| I-4 | 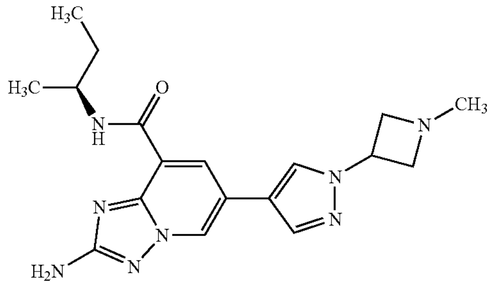 [SMILES: CC[C@H](C)NC(=O)c1cc(-c2cnn(C3CN(C)C3)c2)cn2nc(N)nc12] |
| I-5 | 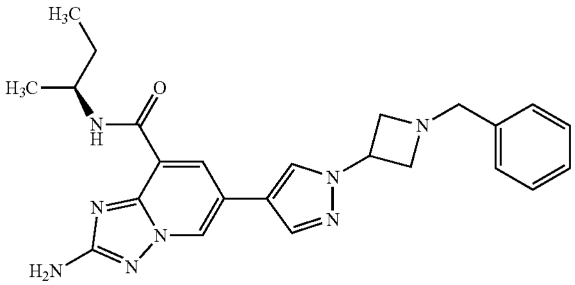 [SMILES: CC[C@H](C)NC(=O)c1cc(-c2cnn(C3CN(Cc4ccccc4)C3)c2)cn2nc(N)nc12] |
| I-6 | 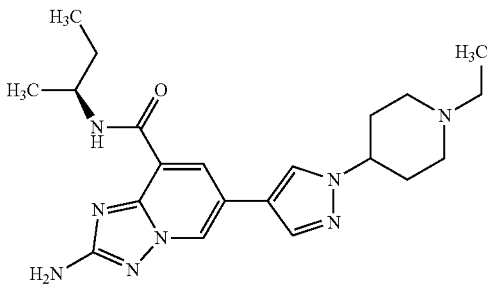 [SMILES: CC[C@H](C)NC(=O)c1cc(-c2cnn(C3CCN(CC)CC3)c2)cn2nc(N)nc12] |

TABLE 1A-continued
| Example Number | Structure |
| --- | --- |
| I-7 | 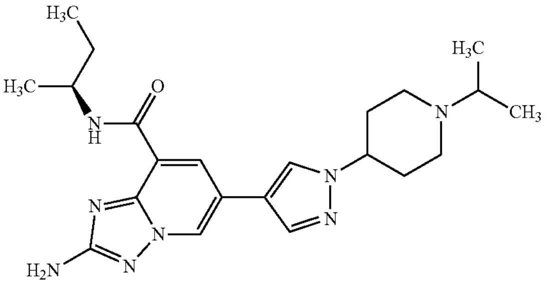 [SMILES: CC[C@H](C)NC(=O)c1cc(-c2cnn(C3CCN(C(C)C)CC3)c2)cn2nc(N)nc12] |
| I-8 | 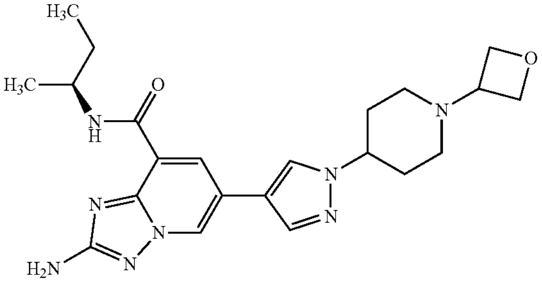 [SMILES: CC[C@H](C)NC(=O)c1cc(-c2cnn(C3CCN(C4COC4)CC3)c2)cn2nc(N)nc12] |
| I-9 | 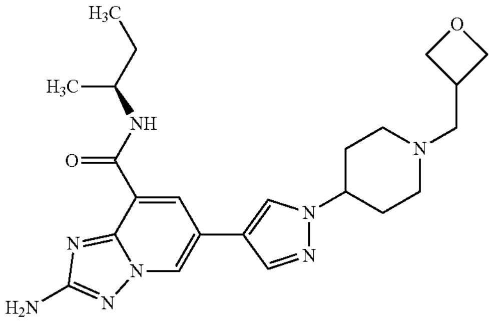 [SMILES: CC[C@H](C)NC(=O)c1cc(-c2cnn(C3CCN(CC4COC4)CC3)c2)cn2nc(N)nc12] |
| I-10 | 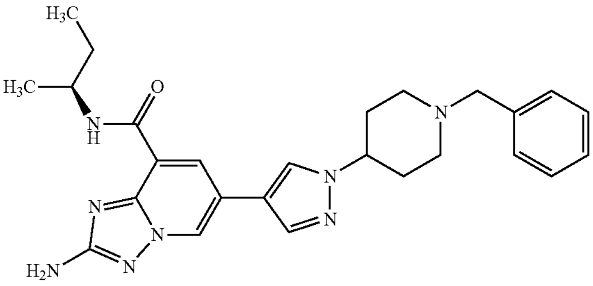 [SMILES: CC[C@H](C)NC(=O)c1cc(-c2cnn(C3CCN(Cc4ccccc4)CC3)c2)cn2nc(N)nc12] |
| I-11 | 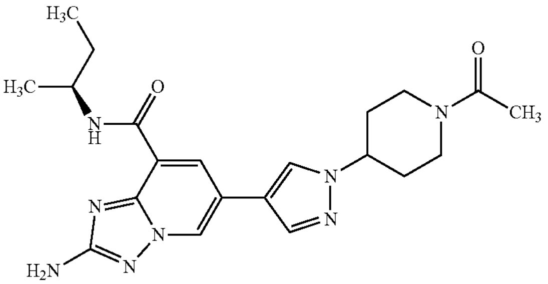 [SMILES: CC[C@H](C)NC(=O)c1cc(-c2cnn(C3CCN(C(C)=O)CC3)c2)cn2nc(N)nc12] |

TABLE 1A-continued
| Example Number | Structure |
|---|---|
| I-12 | 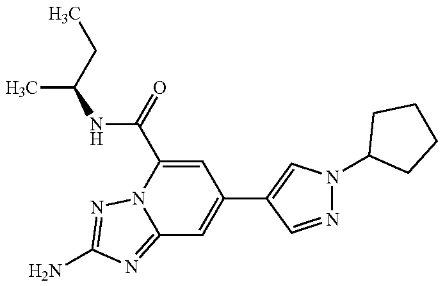 [SMILES: CC[C@H](C)NC(=O)c1cc(-c2cnn(C3CCCC3)c2)cc2nc(N)nn12] |
| I-13 | 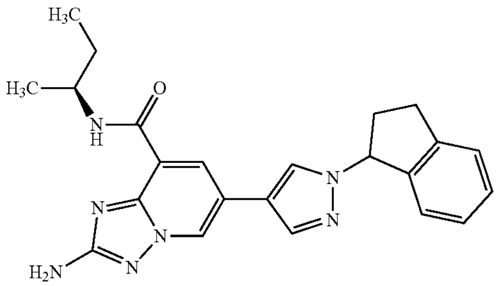 [SMILES: CC[C@H](C)NC(=O)c1cc(-c2cnn(C3CCc4ccccc43)c2)cn2nc(N)nc12] |
| I-16 | 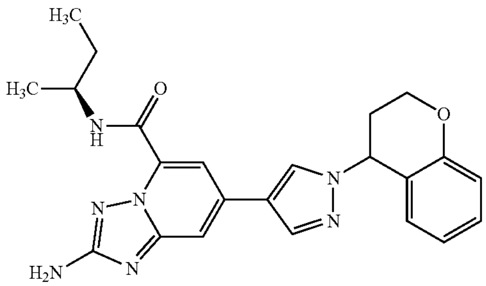 [SMILES: CC[C@H](C)NC(=O)c1cc(-c2cnn(C3CCOc4ccccc43)c2)cc2nc(N)nn12] |
| I-19 | 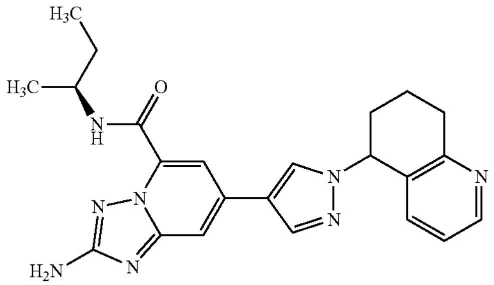 [SMILES: CC[C@H](C)NC(=O)c1cc(-c2cnn(C3CCCc4ncccc43)c2)cc2nc(N)nn12] |
| I-20 | 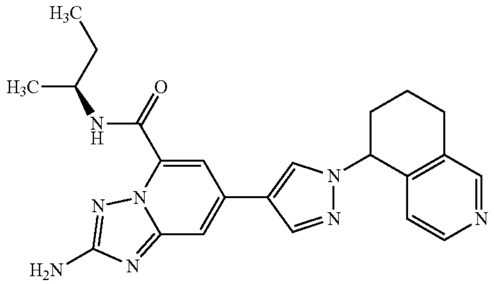 [SMILES: CC[C@H](C)NC(=O)c1cc(-c2cnn(C3CCCc4cnccc43)c2)cc2nc(N)nn12] |

TABLE 1A-continued
| Example Number | Structure |
| --- | --- |
| I-21 | 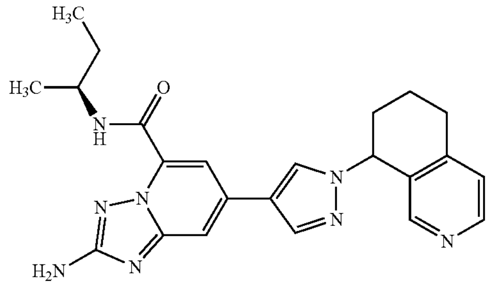 [SMILES: CC[C@H](C)NC(=O)c1cc(-c2cnn(C3CCCc4ccncc43)c2)cc2nc(N)nn12] |
| I-22 | 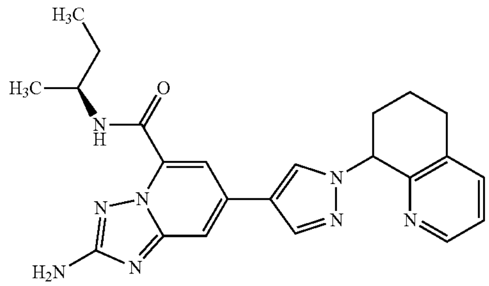 [SMILES: CC[C@H](C)NC(=O)c1cc(-c2cnn(C3CCCc4cccnc43)c2)cc2nc(N)nn12] |
| I-23 | 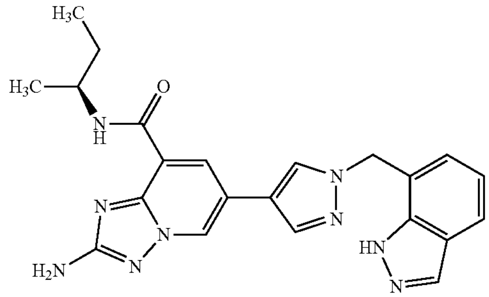 [SMILES: CC[C@H](C)NC(=O)c1cc(-c2cnn(Cc3cccc4cn[nH]c34)c2)cn2nc(N)nc12] |
| I-24 | 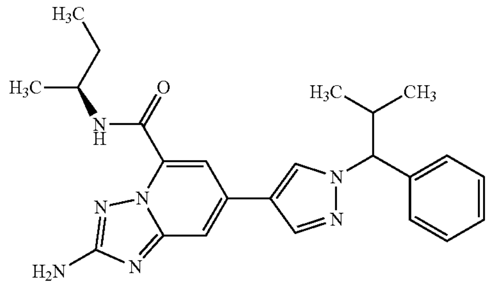 [SMILES: CC[C@H](C)NC(=O)c1cc(-c2cnn(C(c3ccccc3)C(C)C)c2)cc2nc(N)nn12] |
| I-26 | 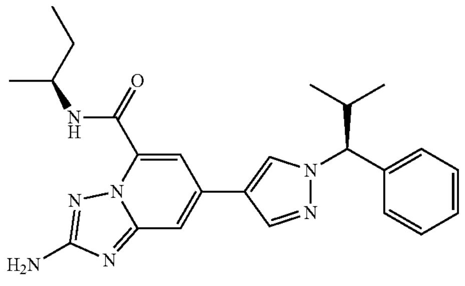 [SMILES: CC[C@H](C)NC(=O)c1cc(-c2cnn([C@H](c3ccccc3)C(C)C)c2)cc2nc(N)nn12] |

TABLE 1A-continued
| Example Number | Structure |
| --- | --- |
| I-27 | 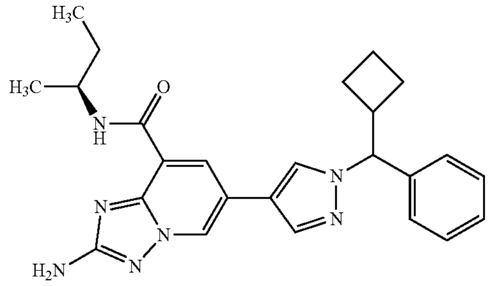 [SMILES: CC[C@H](C)NC(=O)c1cc(-c2cnn(C(c3ccccc3)C3CCC3)c2)cn2nc(N)nc12] |
| I-28 | 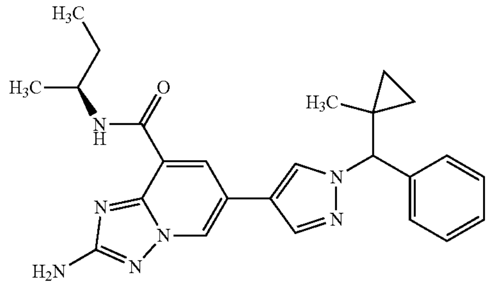 [SMILES: CC[C@H](C)NC(=O)c1cc(-c2cnn(C(c3ccccc3)C3(C)CC3)c2)cn2nc(N)nc12] |
| I-31 | 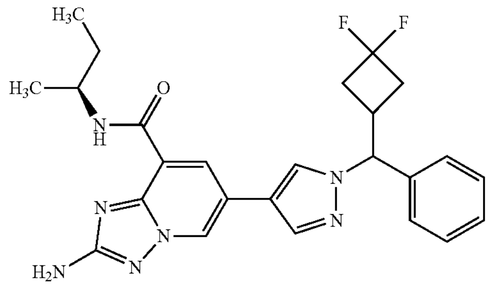 [SMILES: CC[C@H](C)NC(=O)c1cc(-c2cnn(C(c3ccccc3)C3CC(F)(F)C3)c2)cn2nc(N)nc12] |
| I-34 | 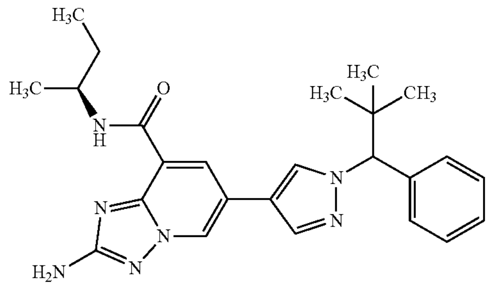 [SMILES: CC[C@H](C)NC(=O)c1cc(-c2cnn(C(c3ccccc3)C(C)(C)C)c2)cn2nc(N)nc12] |
| I-37 | 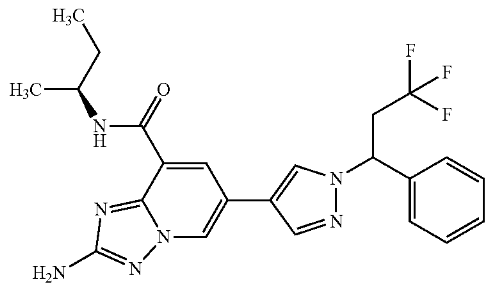 [SMILES: CC[C@H](C)NC(=O)c1cc(-c2cnn(C(CC(F)(F)F)c3ccccc3)c2)cn2nc(N)nc12] |

TABLE 1A-continued
| Example Number | Structure |
|---|---|
| I-40 | 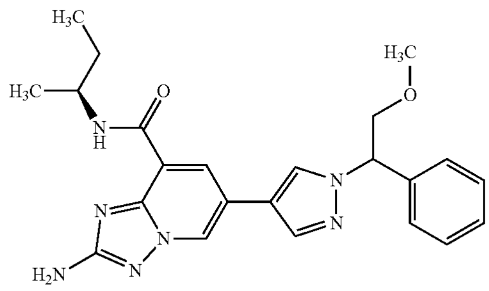 [SMILES: CC[C@H](C)NC(=O)c1cc(-c2cnn(C(COC)c3ccccc3)c2)cn2nc(N)nc12] |
| I-43 | 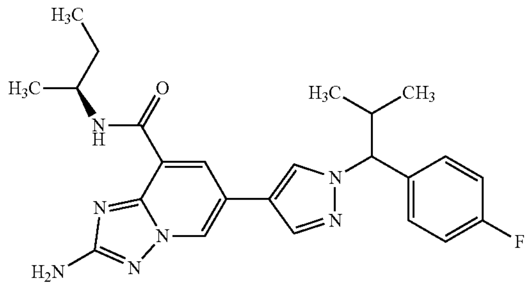 [SMILES: CC[C@H](C)NC(=O)c1cc(-c2cnn(C(c3ccc(F)cc3)C(C)C)c2)cn2nc(N)nc12] |
| I-45 | 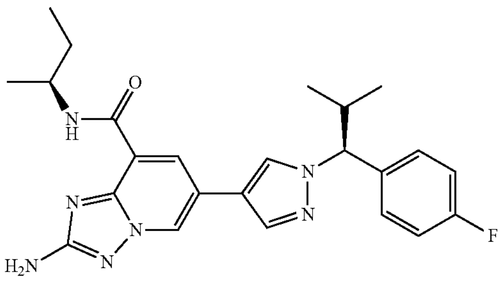 [SMILES: CC[C@H](C)NC(=O)c1cc(-c2cnn([C@H](c3ccc(F)cc3)C(C)C)c2)cn2nc(N)nc12] |
| I-46 | 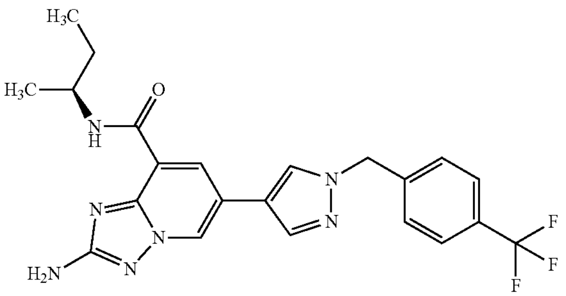 [SMILES: CC[C@H](C)NC(=O)c1cc(-c2cnn(Cc3ccc(C(F)(F)F)cc3)c2)cn2nc(N)nc12] |
| I-47 | 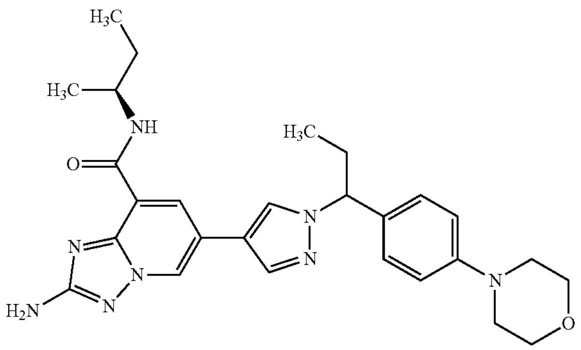 [SMILES: CCC(c1ccc(N2CCOCC2)cc1)n1cc(-c2cc(C(=O)N[C@@H](C)CC)c3nc(N)nn3c2)cn1] |

TABLE 1A-continued
| Example Number | Structure |
| --- | --- |
| I-50 | 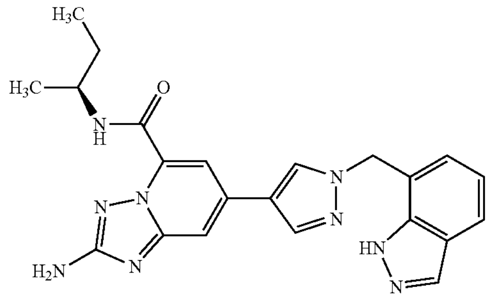 [SMILES: CC[C@H](C)NC(=O)c1cc(-c2cnn(Cc3cccc4cn[nH]c34)c2)cc2nc(N)nn12] |
| I-51 | 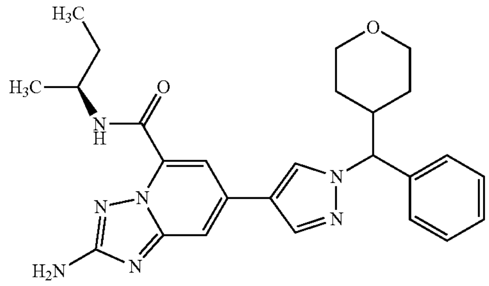 [SMILES: CC[C@H](C)NC(=O)c1cc(-c2cnn(C(c3ccccc3)C3CCOCC3)c2)cc2nc(N)nn12] |
| I-54 | 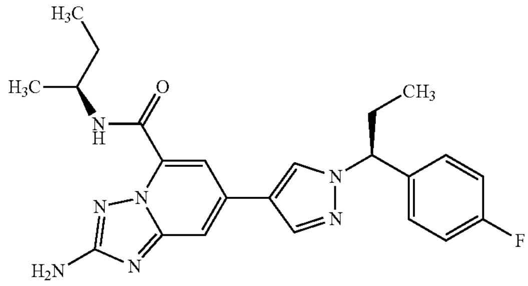 [SMILES: CC[C@H](C)NC(=O)c1cc(-c2cnn([C@@H](CC)c3ccc(F)cc3)c2)cc2nc(N)nn12] |
| I-55 | 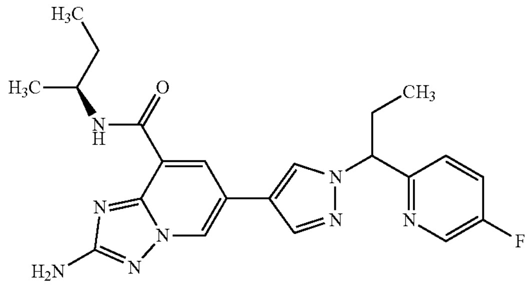 [SMILES: CCC(c1ccc(F)cn1)n1cc(-c2cc(C(=O)N[C@@H](C)CC)c3nc(N)nn3c2)cn1] |
| I-58 | 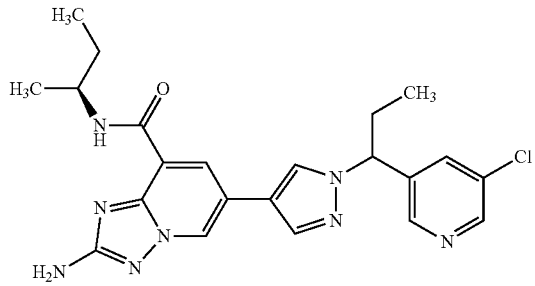 [SMILES: CCC(c1cncc(Cl)c1)n1cc(-c2cc(C(=O)N[C@@H](C)CC)c3nc(N)nn3c2)cn1] |

TABLE 1A-continued
| Example Number | Structure |
|---|---|
| I-60 | 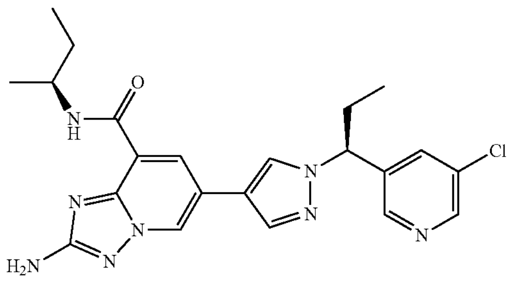 [SMILES: CC[C@H](C)NC(=O)c1cc(-c2cnn([C@@H](CC)c3cncc(Cl)c3)c2)cn2nc(N)nc12] |
| I-61 | 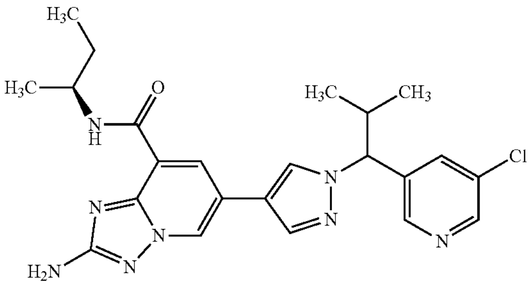 [SMILES: CC[C@H](C)NC(=O)c1cc(-c2cnn(C(c3cncc(Cl)c3)C(C)C)c2)cn2nc(N)nc12] |
| I-63 | 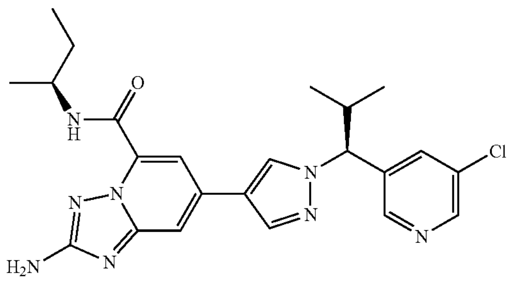 [SMILES: CC[C@H](C)NC(=O)c1cc(-c2cnn([C@H](c3cncc(Cl)c3)C(C)C)c2)cc2nc(N)nn12] |
| I-64 | 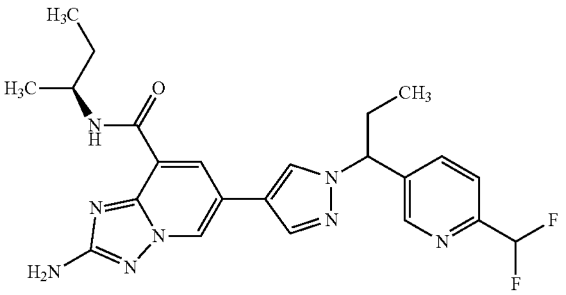 [SMILES: CCC(c1ccc(C(F)F)nc1)n1cc(-c2cc(C(=O)N[C@@H](C)CC)c3nc(N)nn3c2)cn1] |
| I-67 | 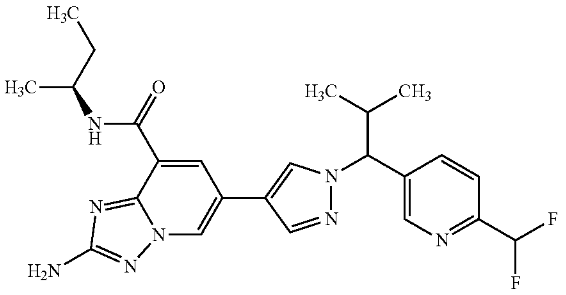 [SMILES: CC[C@H](C)NC(=O)c1cc(-c2cnn(C(c3ccc(C(F)F)nc3)C(C)C)c2)cn2nc(N)nc12] |

TABLE 1A-continued
| Example Number | Structure |
| --- | --- |
| I-70 | 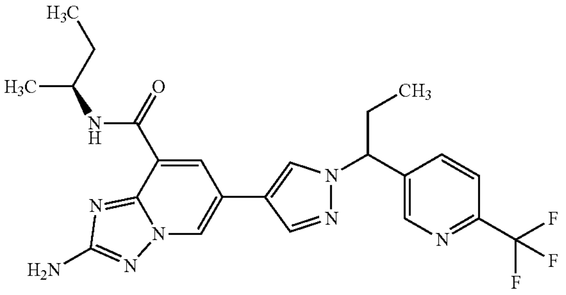 [SMILES: CCC(c1ccc(C(F)(F)F)nc1)n1cc(-c2cc(C(=O)N[C@@H](C)CC)c3nc(N)nn3c2)cn1] |
| I-71 | 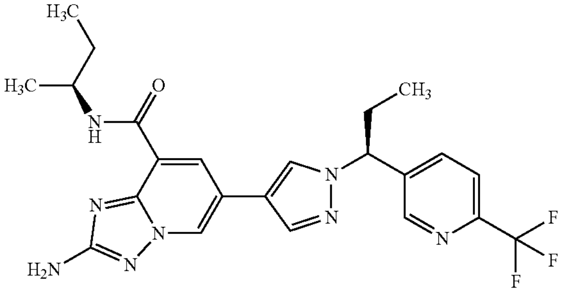 [SMILES: CC[C@H](C)NC(=O)c1cc(-c2cnn([C@@H](CC)c3ccc(C(F)(F)F)nc3)c2)cn2nc(N)nc12] |
| I-72 | 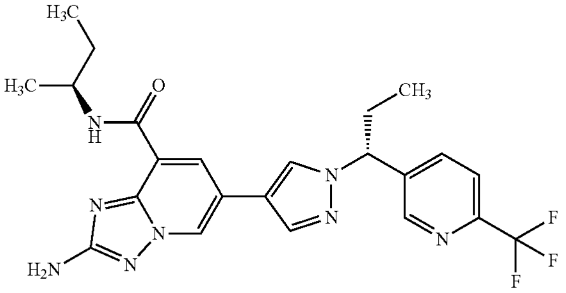 [SMILES: CC[C@H](c1ccc(C(F)(F)F)nc1)n1cc(-c2cc(C(=O)N[C@@H](C)CC)c3nc(N)nn3c2)cn1] |
| I-73 | 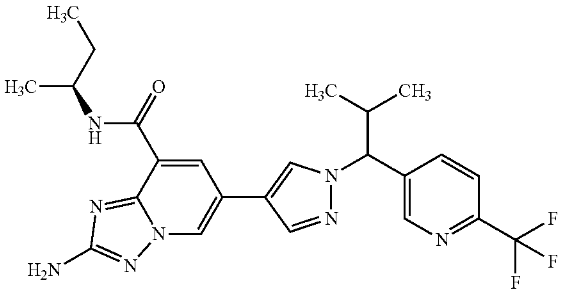 [SMILES: CC[C@H](C)NC(=O)c1cc(-c2cnn(C(c3ccc(C(F)(F)F)nc3)C(C)C)c2)cn2nc(N)nc12] |
| I-75 | 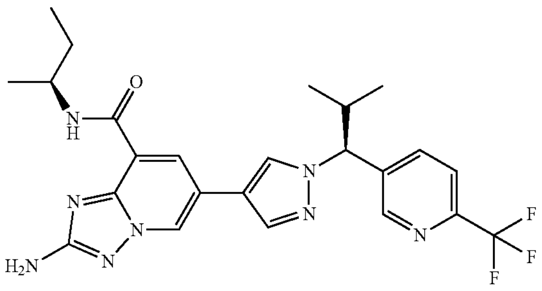 [SMILES: CC[C@H](C)NC(=O)c1cc(-c2cnn([C@H](c3ccc(C(F)(F)F)nc3)C(C)C)c2)cn2nc(N)nc12] |

TABLE 1A-continued
| Example Number | Structure |
|---|---|
| I-76 | 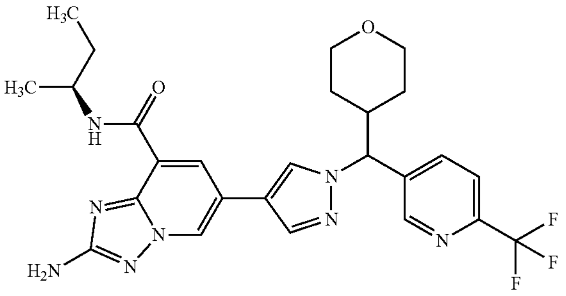 |
| I-79 | 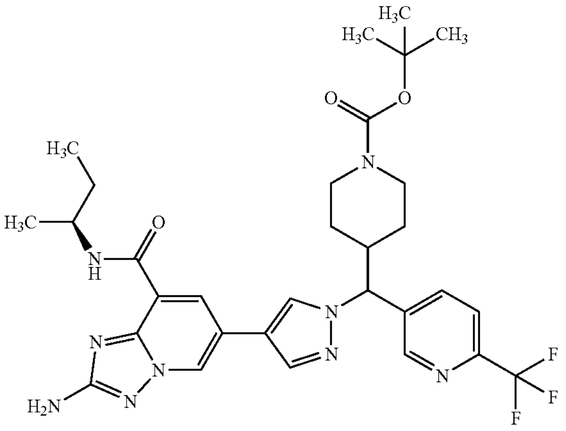 [SMILES: CC[C@H](C)NC(=O)c1cc(-c2cnn(C(c3ccc(C(F)(F)F)nc3)C3CCN(C(=O)OC(C)(C)C)CC3)c2)cn2nc(N)nc12] |
| I-81 | 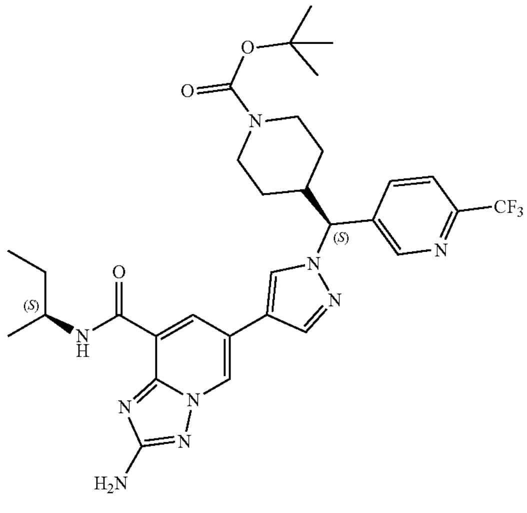 |
| I-82 | 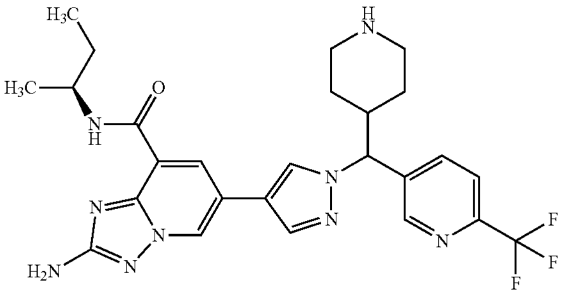 [SMILES: CC[C@H](C)NC(=O)c1cc(-c2cnn(C(c3ccc(C(F)(F)F)nc3)C3CCNCC3)c2)cn2nc(N)nc12] |

TABLE 1A-continued
| Example Number | Structure |
| --- | --- |
| I-83 | 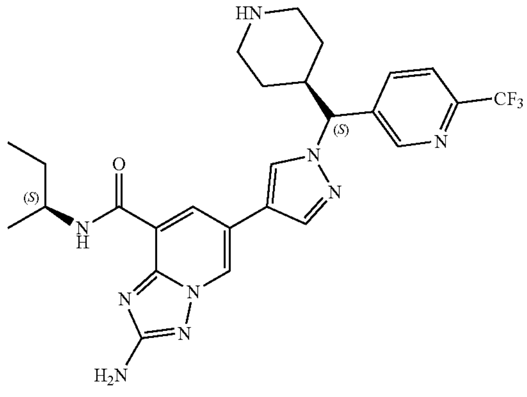 |
| I-84 | 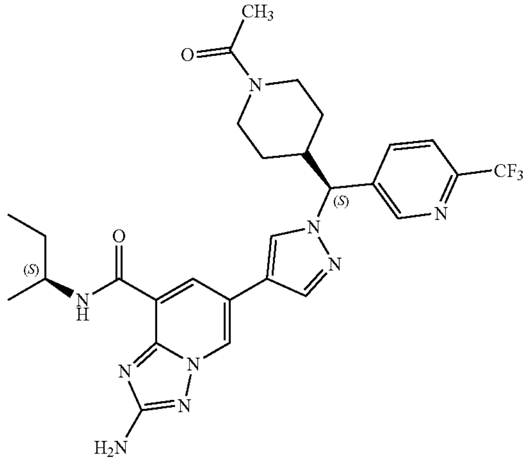 |
| I-85 | 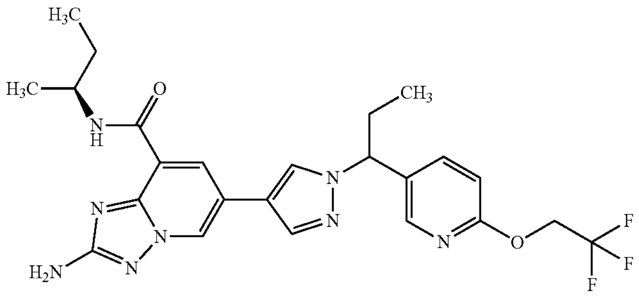 [SMILES: CCC(c1ccc(OCC(F)(F)F)nc1)n1cc(-c2cc(C(=O)N[C@@H](C)CC)c3nc(N)nn3c2)cn1] |
| I-88 | 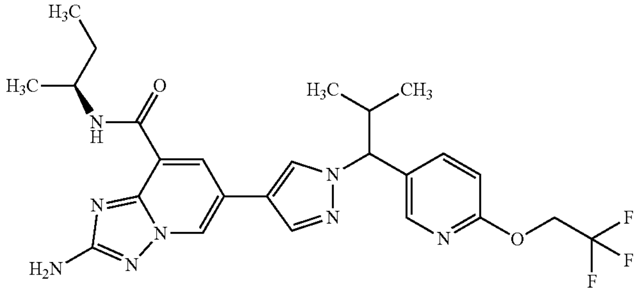 [SMILES: CC[C@H](C)NC(=O)c1cc(-c2cnn(C(c3ccc(OCC(F)(F)F)nc3)C(C)C)c2)cn2nc(N)nc12] |

TABLE 1A-continued
| Example Number | Structure |
| --- | --- |
| I-91 | 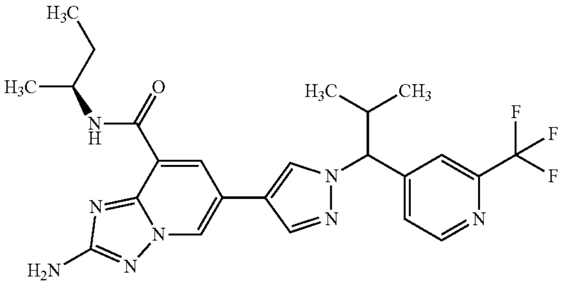 [SMILES: CC[C@H](C)NC(=O)c1cc(-c2cnn(C(c3ccnc(C(F)(F)F)c3)C(C)C)c2)cn2nc(N)nc12] |
| I-92 | 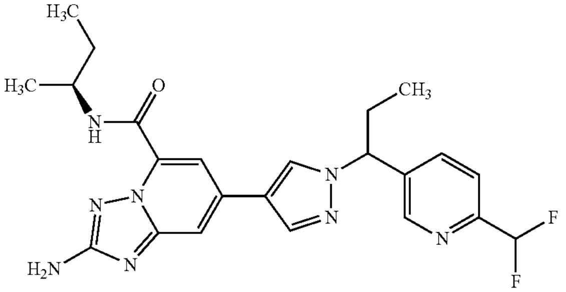 [SMILES: CCC(c1ccc(C(F)F)nc1)n1cc(-c2cc(C(=O)N[C@@H](C)CC)n3nc(N)nc3c2)cn1] |
| I-94 | 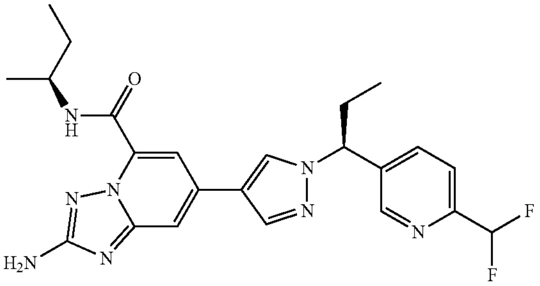 [SMILES: CC[C@H](C)NC(=O)c1cc(-c2cnn([C@@H](CC)c3ccc(C(F)F)nc3)c2)cc2nc(N)nn12] |
| I-95 | 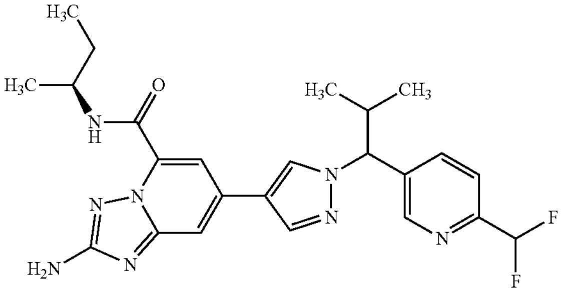 [SMILES: CC[C@H](C)NC(=O)c1cc(-c2cnn(C(c3ccc(C(F)F)nc3)C(C)C)c2)cc2nc(N)nn12] |
| I-97 | 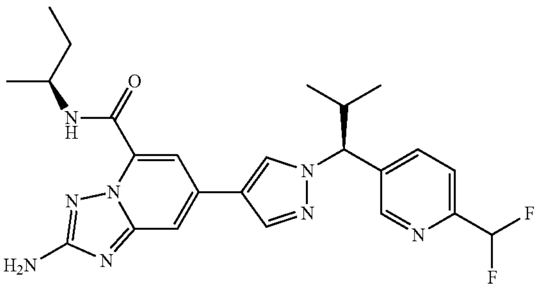 [SMILES: CC[C@H](C)NC(=O)c1cc(-c2cnn([C@H](c3ccc(C(F)F)nc3)C(C)C)c2)cc2nc(N)nn12] |

TABLE 1A-continued
| Example Number | Structure |
| --- | --- |
| I-98 | 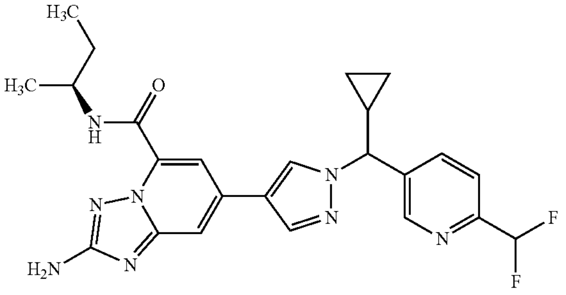 [SMILES: CC[C@H](C)NC(=O)c1cc(-c2cnn(C(c3ccc(C(F)F)nc3)C3CC3)c2)cc2nc(N)nn12] |
| I-101 | 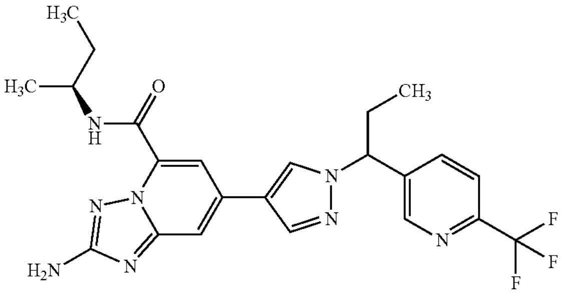 [SMILES: CCC(c1ccc(C(F)(F)F)nc1)n1cc(-c2cc(C(=O)N[C@@H](C)CC)n3nc(N)nc3c2)cn1] |
| I-102 | 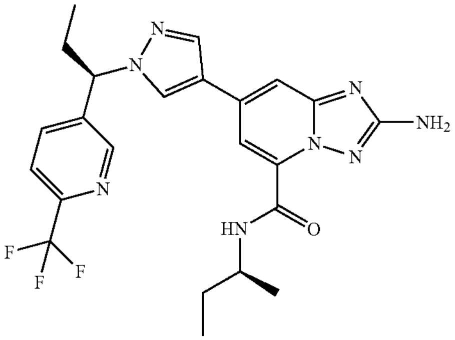 [SMILES: CC[C@H](c1ccc(C(F)(F)F)nc1)n1cc(-c2cc(C(=O)N[C@@H](C)CC)n3nc(N)nc3c2)cn1] |
| I-103 | 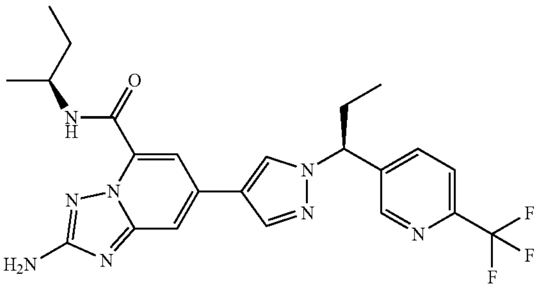 [SMILES: CC[C@H](C)NC(=O)c1cc(-c2cnn([C@@H](CC)c3ccc(C(F)(F)F)nc3)c2)cc2nc(N)nn12] |
| I-104 | 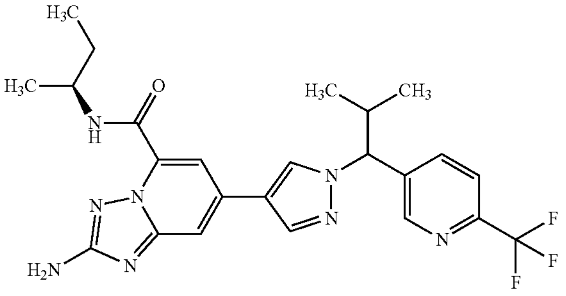 [SMILES: CC[C@H](C)NC(=O)c1cc(-c2cnn(C(c3ccc(C(F)(F)F)nc3)C(C)C)c2)cc2nc(N)nn12] |

TABLE 1A-continued
| Example Number | Structure |
| --- | --- |
| I-106 | 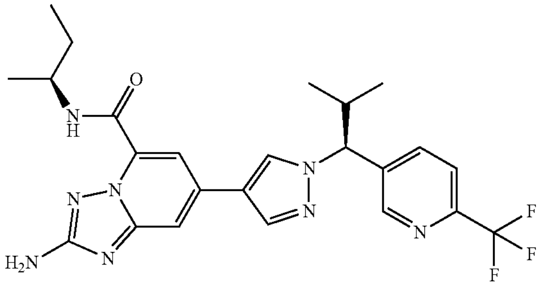 [SMILES: CC[C@H](C)NC(=O)c1cc(-c2cnn([C@H](c3ccc(C(F)(F)F)nc3)C(C)C)c2)cc2nc(N)nn12] |
| I-107 | 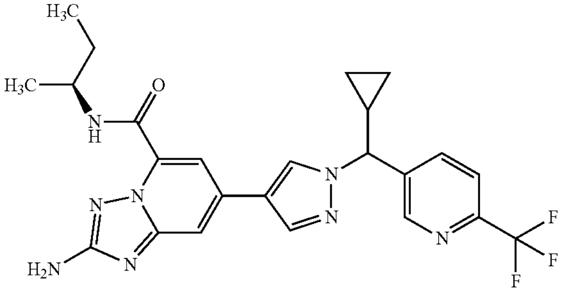 [SMILES: CC[C@H](C)NC(=O)c1cc(-c2cnn(C(c3ccc(C(F)(F)F)nc3)C3CC3)c2)cc2nc(N)nn12] |
| I-109 | 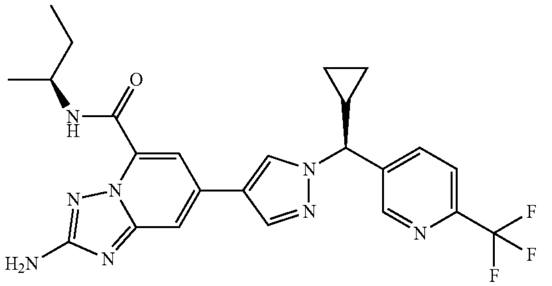 [SMILES: CC[C@H](C)NC(=O)c1cc(-c2cnn([C@H](c3ccc(C(F)(F)F)nc3)C3CC3)c2)cc2nc(N)nn12] |
| I-110 | 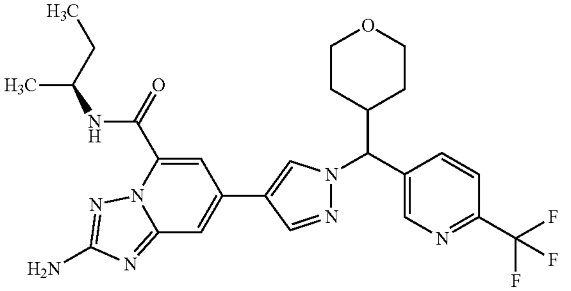 [SMILES: CC[C@H](C)NC(=O)c1cc(-c2cnn(C(c3ccc(C(F)(F)F)nc3)C3CCOCC3)c2)cc2nc(N)nn12] |
| I-113 | 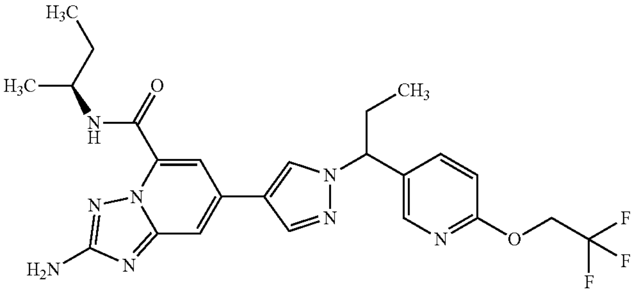 [SMILES: CCC(c1ccc(OCC(F)(F)F)nc1)n1cc(-c2cc(C(=O)N[C@@H](C)CC)n3nc(N)nc3c2)cn1] |

TABLE 1A-continued
| Example Number | Structure |
| --- | --- |
| I-116 | 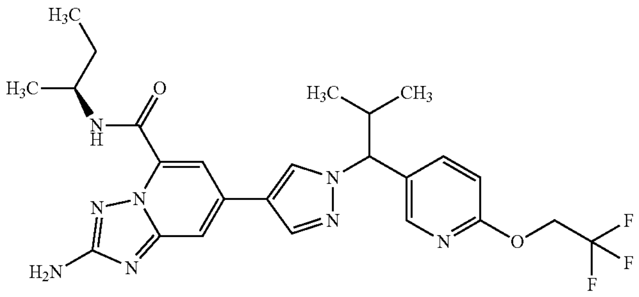 [SMILES: CC[C@H](C)NC(=O)c1cc(-c2cnn(C(c3ccc(OCC(F)(F)F)nc3)C(C)C)c2)cc2nc(N)nn12] |
| I-119 | 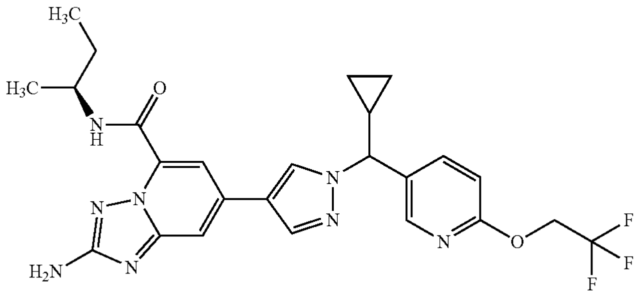 [SMILES: CC[C@H](C)NC(=O)c1cc(-c2cnn(C(c3ccc(OCC(F)(F)F)nc3)C3CC3)c2)cc2nc(N)nn12] |
| I-122 | 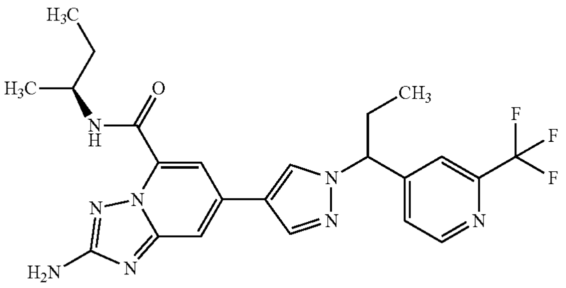 [SMILES: CCC(c1ccnc(C(F)(F)F)c1)n1cc(-c2cc(C(=O)N[C@@H](C)CC)n3nc(N)nc3c2)cn1] |
| I-123 | 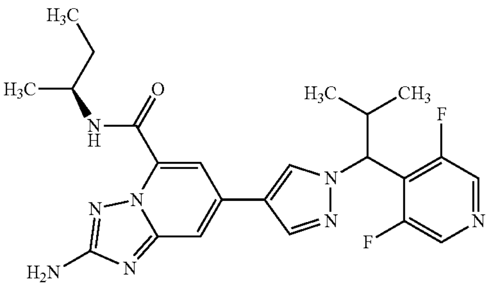 [SMILES: CC[C@H](C)NC(=O)c1cc(-c2cnn(C(c3c(F)cncc3F)C(C)C)c2)cc2nc(N)nn12] |
| I-126 | 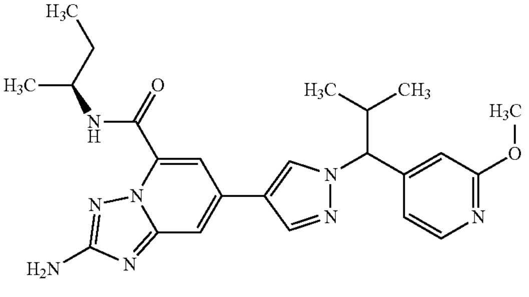 [SMILES: CC[C@H](C)NC(=O)c1cc(-c2cnn(C(c3ccnc(OC)c3)C(C)C)c2)cc2nc(N)nn12] |

TABLE 1A-continued
| Example Number | Structure |
| --- | --- |
| I-128 | 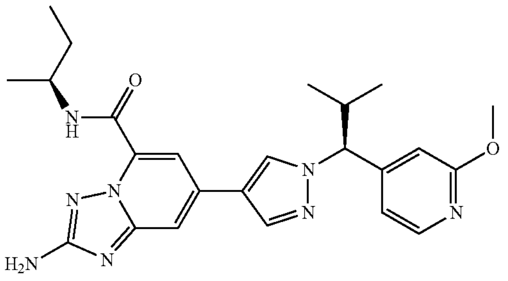 [SMILES: CC[C@H](C)NC(=O)c1cc(-c2cnn([C@H](c3ccnc(OC)c3)C(C)C)c2)cc2nc(N)nn12] |
| I-129 | 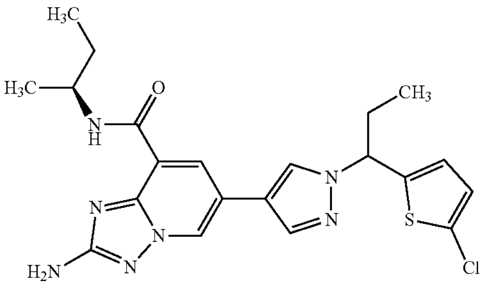 [SMILES: CCC(c1ccc(Cl)s1)n1cc(-c2cc(C(=O)N[C@@H](C)CC)c3nc(N)nn3c2)cn1] |
| I-132 | 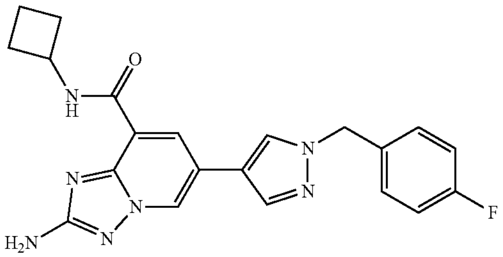 [SMILES: Nc1nc2c(C(=O)NC3CCC3)cc(-c3cnn(Cc4ccc(F)cc4)c3)cn2n1] |
| I-133 | 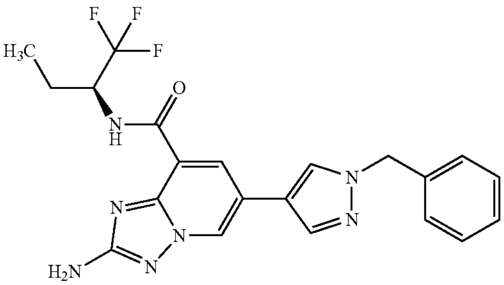 [SMILES: CC[C@H](NC(=O)c1cc(-c2cnn(Cc3ccccc3)c2)cn2nc(N)nc12)C(F)(F)F] |
| I-134 | 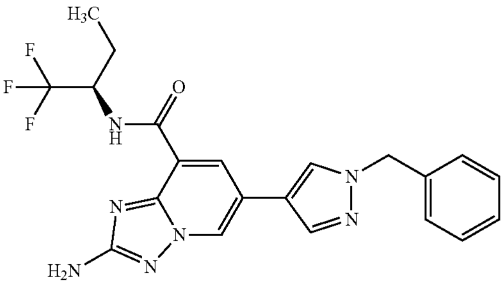 [SMILES: CC[C@@H](NC(=O)c1cc(-c2cnn(Cc3ccccc3)c2)cn2nc(N)nc12)C(F)(F)F] |

TABLE 1A-continued
| Example Number | Structure |
| --- | --- |
| I-135 | 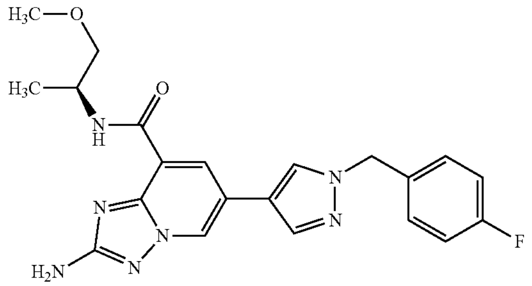 [SMILES: COC[C@H](C)NC(=O)c1cc(-c2cnn(Cc3ccc(F)cc3)c2)cn2nc(N)nc12] |
| I-136 | 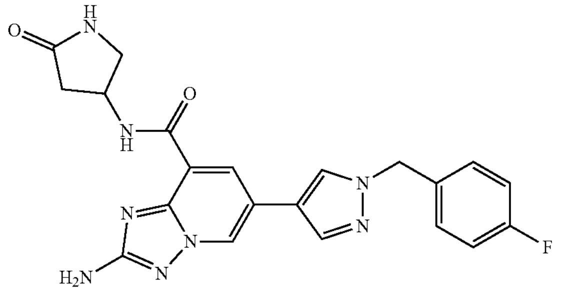 [SMILES: Nc1nc2c(C(=O)NC3CNC(=O)C3)cc(-c3cnn(Cc4ccc(F)cc4)c3)cn2n1] |
| I-137 | 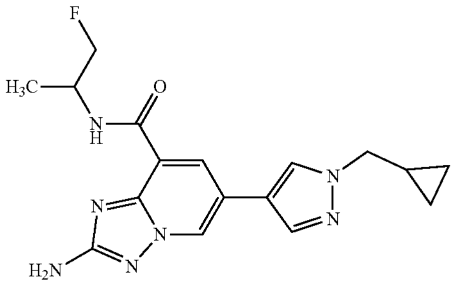 [SMILES: CC(CF)NC(=O)c1cc(-c2cnn(CC3CC3)c2)cn2nc(N)nc12] |
| I-138 | 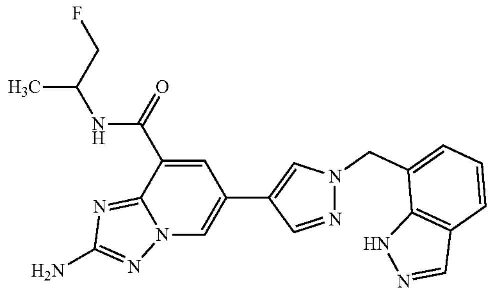 [SMILES: CC(CF)NC(=O)c1cc(-c2cnn(Cc3cccc4cn[nH]c34)c2)cn2nc(N)nc12] |
| I-139 | 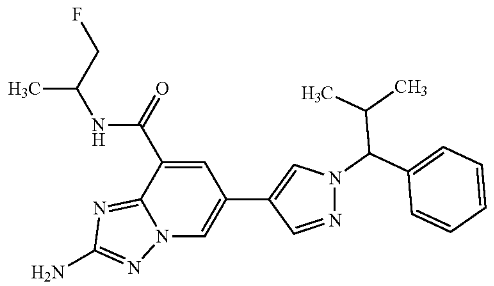 [SMILES: CC(CF)NC(=O)c1cc(-c2cnn(C(c3ccccc3)C(C)C)c2)cn2nc(N)nc12] |

TABLE 1A-continued
| Example Number | Structure |
| --- | --- |
| I-143 | 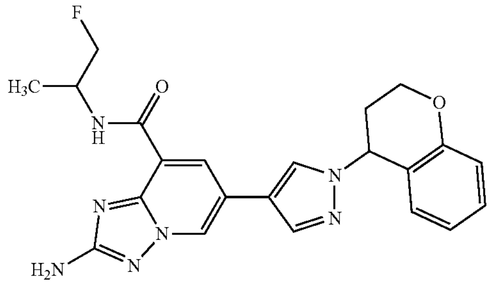 [SMILES: CC(CF)NC(=O)c1cc(-c2cnn(C3CCOc4ccccc43)c2)cn2nc(N)nc12] |
| I-147 | 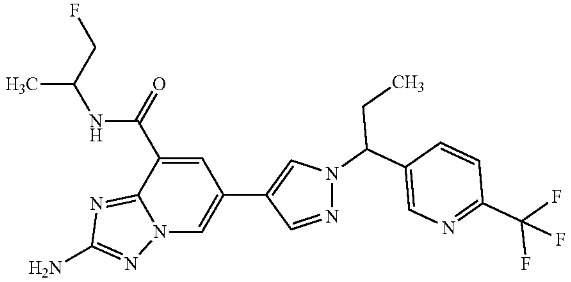 [SMILES: CCC(c1ccc(C(F)(F)F)nc1)n1cc(-c2cc(C(=O)NC(C)CF)c3nc(N)nn3c2)cn1] |
| I-148 | 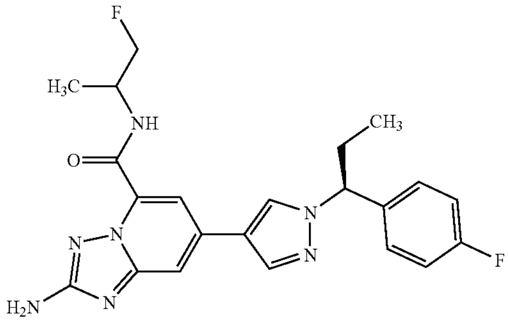 [SMILES: CC[C@@H](c1ccc(F)cc1)n1cc(-c2cc(C(=O)NC(C)CF)n3nc(N)nc3c2)cn1] |
| I-151 | 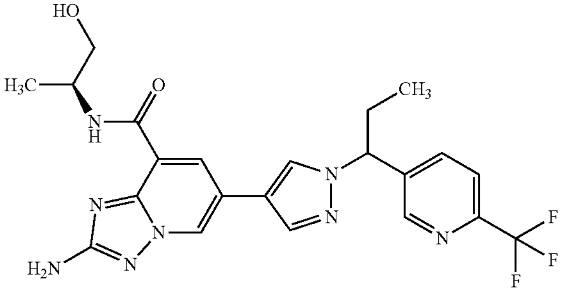 [SMILES: CCC(c1ccc(C(F)(F)F)nc1)n1cc(-c2cc(C(=O)N[C@@H](C)CO)c3nc(N)nn3c2)cn1] |
| I-154 | 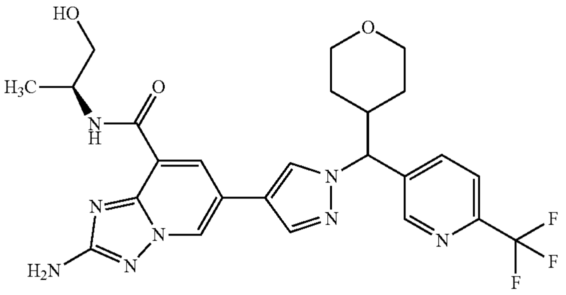 [SMILES: C[C@@H](CO)NC(=O)c1cc(-c2cnn(C(c3ccc(C(F)(F)F)nc3)C3CCOCC3)c2)cn2nc(N)nc12] |

TABLE 1A-continued
| Example Number | Structure |
| --- | --- |
| I-155 | 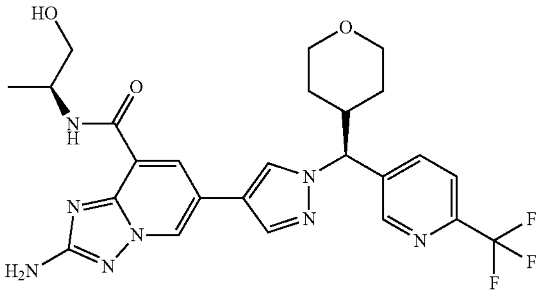 [SMILES: C[C@@H](CO)NC(=O)c1cc(-c2cnn([C@H](c3ccc(C(F)(F)F)nc3)C3CCOCC3)c2)cn2nc(N)nc12] |
| I-157 | 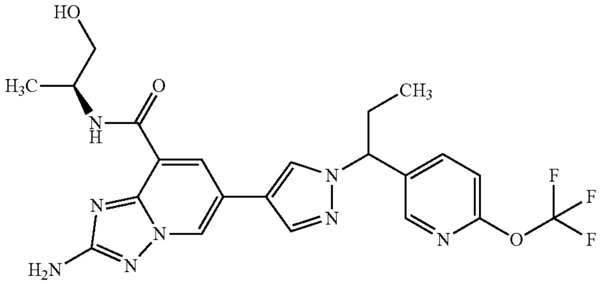 [SMILES: CCC(c1ccc(OC(F)(F)F)nc1)n1cc(-c2cc(C(=O)N[C@@H](C)CO)c3nc(N)nn3c2)cn1] |
| I-158 | 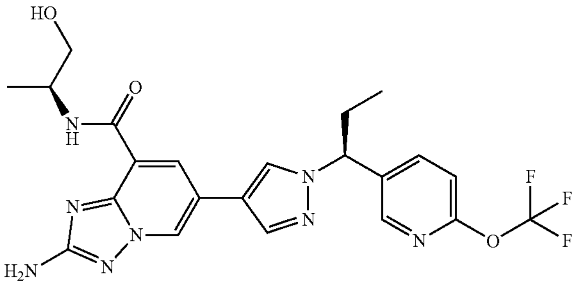 [SMILES: CC[C@@H](c1ccc(OC(F)(F)F)nc1)n1cc(-c2cc(C(=O)N[C@@H](C)CO)c3nc(N)nn3c2)cn1] |
| I-160 | 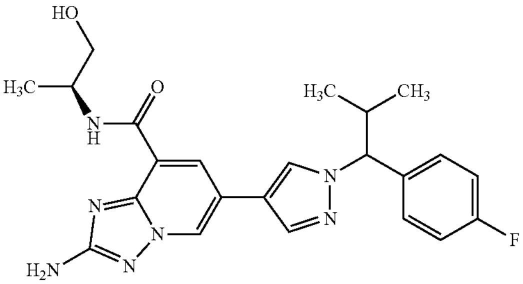 [SMILES: CC(C)C(c1ccc(F)cc1)n1cc(-c2cc(C(=O)N[C@@H](C)CO)c3nc(N)nn3c2)cn1] |
| I-162 | 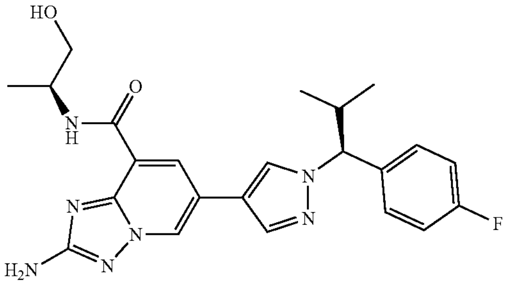 [SMILES: CC(C)[C@@H](c1ccc(F)cc1)n1cc(-c2cc(C(=O)N[C@@H](C)CO)c3nc(N)nn3c2)cn1] |

TABLE 1A-continued
| Example Number | Structure |
|---|---|
| I-163 | 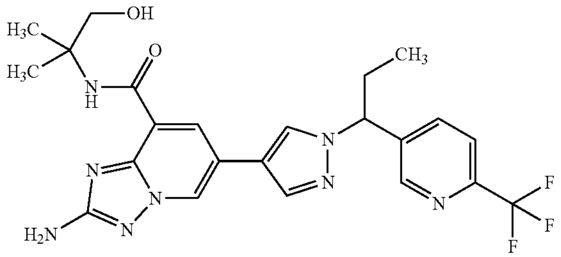 [SMILES: CCC(c1ccc(C(F)(F)F)nc1)n1cc(-c2cc(C(=O)NC(C)(C)CO)c3nc(N)nn3c2)cn1] |
| I-164 | 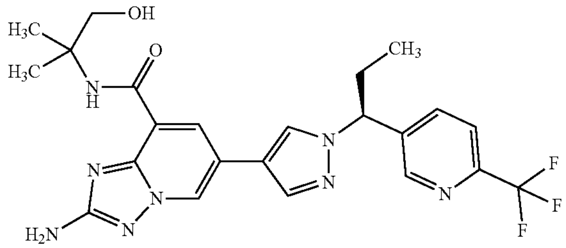 [SMILES: CC[C@@H](c1ccc(C(F)(F)F)nc1)n1cc(-c2cc(C(=O)NC(C)(C)CO)c3nc(N)nn3c2)cn1] |
| I-166 | 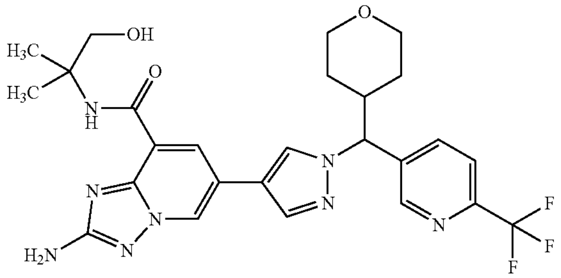 [SMILES: CC(C)(CO)NC(=O)c1cc(-c2cnn(C(c3ccc(C(F)(F)F)nc3)C3CCOCC3)c2)cn2nc(N)nc12] |
| I-169 | 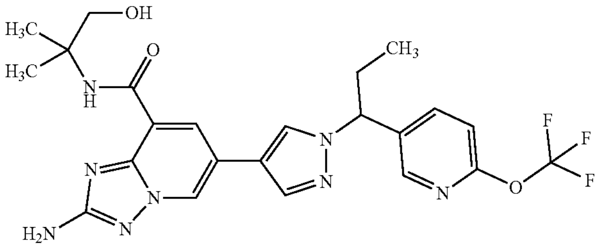 [SMILES: CCC(c1ccc(OC(F)(F)F)nc1)n1cc(-c2cc(C(=O)NC(C)(C)CO)c3nc(N)nn3c2)cn1] |
| I-170 | 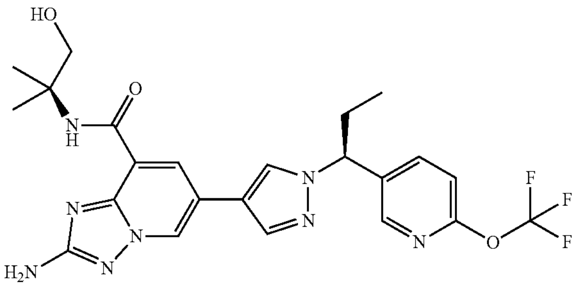 |
| I-172 | 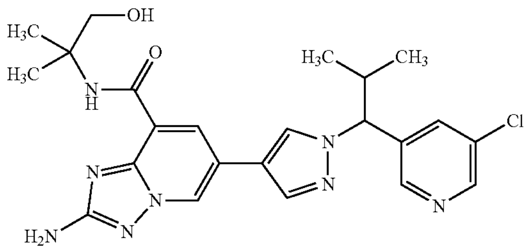 [SMILES: CC(C)C(c1cncc(Cl)c1)n1cc(-c2cc(C(=O)NC(C)(C)CO)c3nc(N)nn3c2)cn1] |

TABLE 1A-continued
| Example Number | Structure |
| --- | --- |
| I-175 | 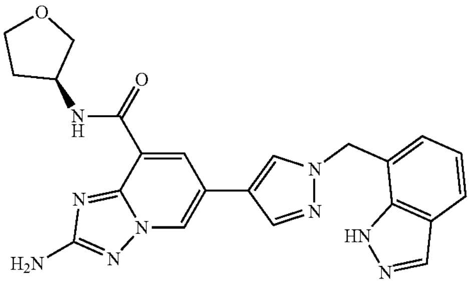 [SMILES: Nc1nc2c(C(=O)N[C@H]3CCOC3)cc(-c3cnn(Cc4cccc5cn[nH]c45)c3)cn2n1] |
| I-176 | 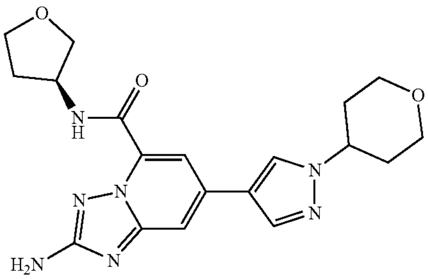 [SMILES: Nc1nc2cc(-c3cnn(C4CCOCC4)c3)cc(C(=O)N[C@H]3CCOC3)n2n1] |
| I-177 | 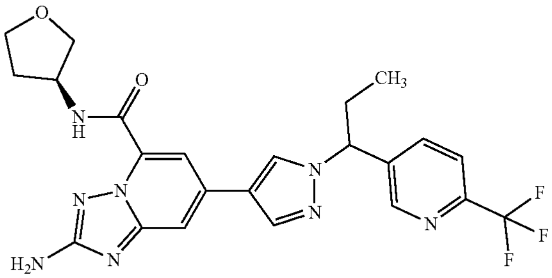 [SMILES: CCC(c1ccc(C(F)(F)F)nc1)n1cc(-c2cc(C(=O)N[C@H]3CCOC3)n3nc(N)nc3c2)cn1] |
| I-180 | 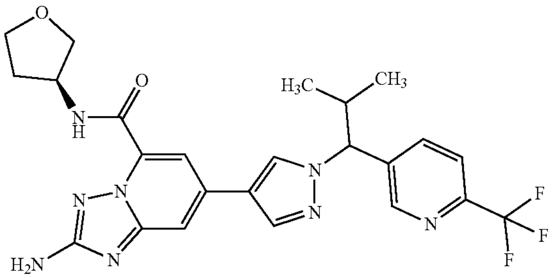 [SMILES: CC(C)C(c1ccc(C(F)(F)F)nc1)n1cc(-c2cc(C(=O)N[C@H]3CCOC3)n3nc(N)nc3c2)cn1] |
| I-183 | 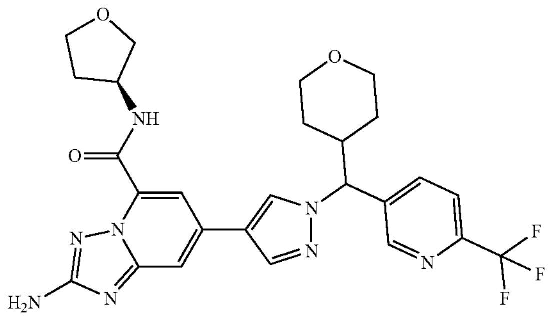 [SMILES: Nc1nc2cc(-c3cnn(C(c4ccc(C(F)(F)F)nc4)C4CCOCC4)c3)cc(C(=O)N[C@H]3CCOC3)n2n1] |

TABLE 1A-continued
| Example Number | Structure |
| --- | --- |
| I-186 | 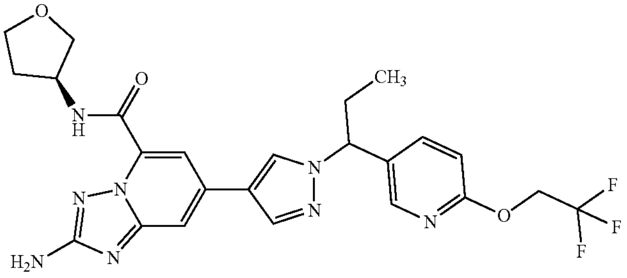 [SMILES: CCC(c1ccc(OCC(F)(F)F)nc1)n1cc(-c2cc(C(=O)N[C@H]3CCOC3)n3nc(N)nc3c2)cn1] |
| I-189 | 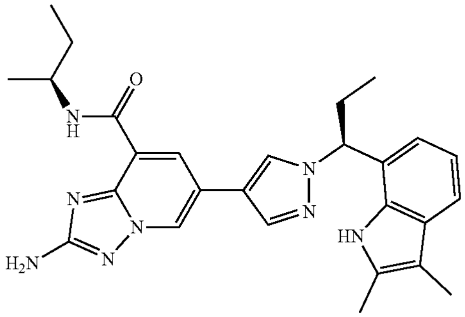 [SMILES: CC[C@H](C)NC(=O)c1cc(-c2cnn([C@@H](CC)c3cccc4c(C)c(C)[nH]c34)c2)cn2nc(N)nc12] |
| I-190 | 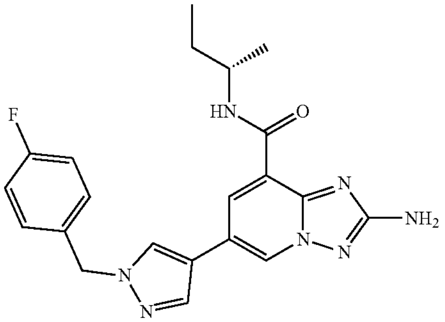 [SMILES: CC[C@H](C)NC(=O)c1cc(-c2cnn(Cc3ccc(F)cc3)c2)cn2nc(N)nc12] |
| I-191 | 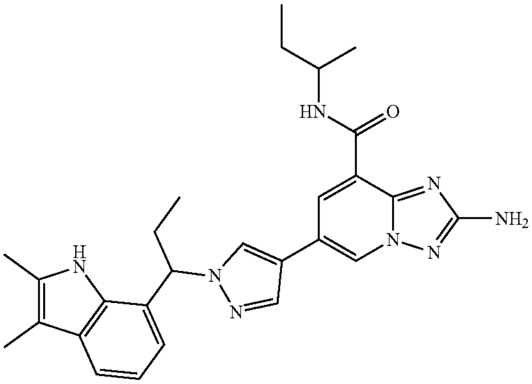 [SMILES: CCC(C)NC(=O)c1cc(-c2cnn(C(CC)c3cccc4c(C)c(C)[nH]c34)c2)cn2nc(N)nc12] |

TABLE 1A-continued
| Example Number | Structure |
|---|---|
| I-192 | 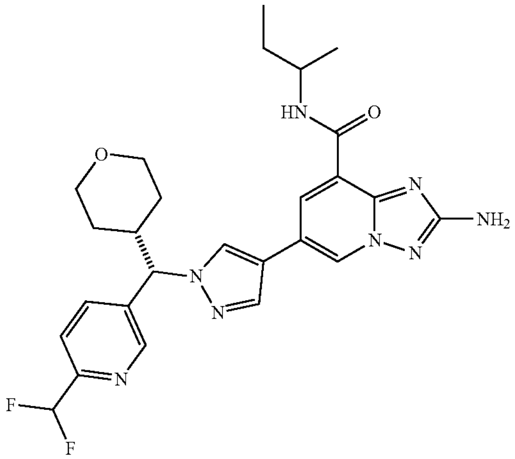 [SMILES: CCC(C)NC(=O)c1cc(-c2cnn([C@H](c3ccc(C(F)F)nc3)C3CCOCC3)c2)cn2nc(N)nc12] |
| I-193 | 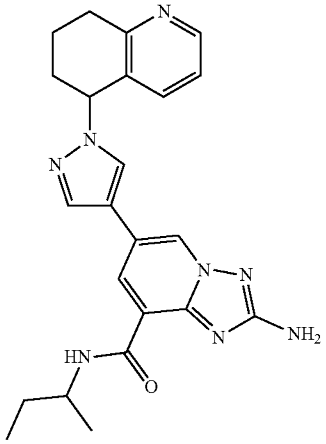 [SMILES: CCC(C)NC(=O)c1cc(-c2cnn(C3CCCc4ncccc43)c2)cn2nc(N)nc12] |
| I-194 | 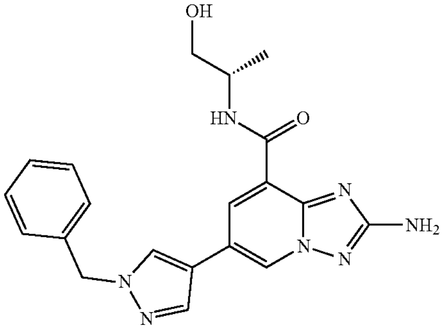 [SMILES: C[C@@H](CO)NC(=O)c1cc(-c2cnn(Cc3ccccc3)c2)cn2nc(N)nc12] |
| I-195 | 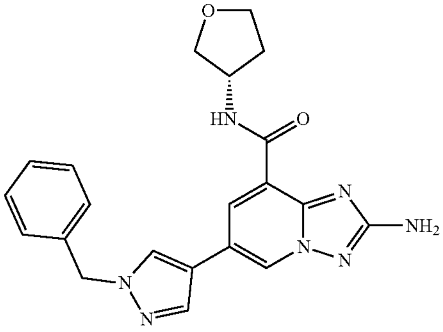 [SMILES: Nc1nc2c(C(=O)N[C@H]3CCOC3)cc(-c3cnn(Cc4ccccc4)c3)cn2n1] |

TABLE 1A-continued
| Example Number | Structure |
| --- | --- |
| I-196 | 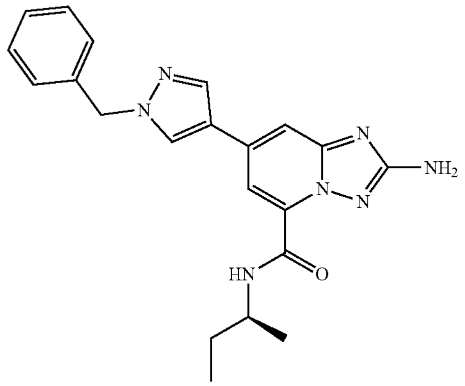 [SMILES: CC[C@H](C)NC(=O)c1cc(-c2cnn(Cc3ccccc3)c2)cc2nc(N)nn12] |
| I-197 | 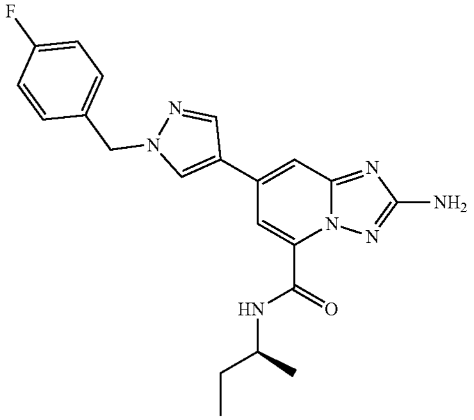 [SMILES: CC[C@H](C)NC(=O)c1cc(-c2cnn(Cc3ccc(F)cc3)c2)cc2nc(N)nn12] |
| I-198 | 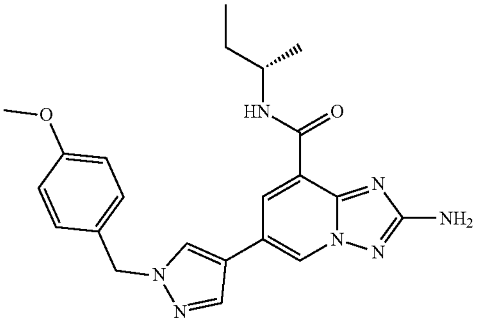 [SMILES: CC[C@H](C)NC(=O)c1cc(-c2cnn(Cc3ccc(OC)cc3)c2)cn2nc(N)nc12] |
| I-199 | 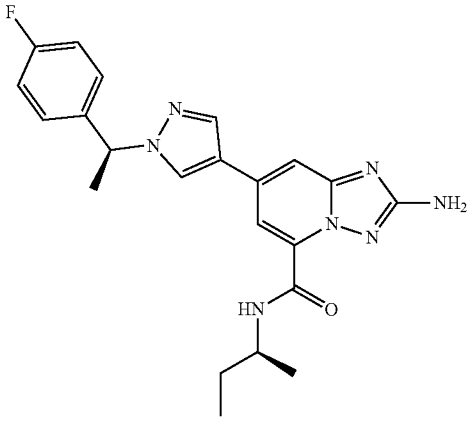 [SMILES: CC[C@H](C)NC(=O)c1cc(-c2cnn([C@@H](C)c3ccc(F)cc3)c2)cc2nc(N)nn12] |

TABLE 1A-continued

| Example Number | Structure |
| --- | --- |
| I-200 | 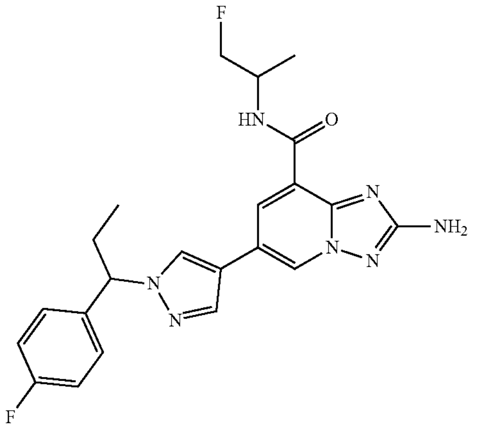 [SMILES: CCC(c1ccc(F)cc1)n1cc(-c2cc(C(=O)NC(C)CF)c3nc(N)nn3c2)cn1] |

and pharmaceutically acceptable salts thereof.

Compounds of Formula (HI)

The present disclosure also provides compounds of the general formula (B)

(B)

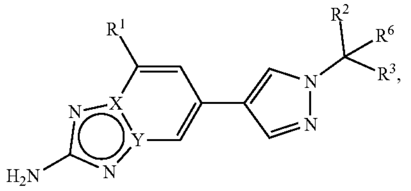

in which

X is nitrogen and Y is carbon, or

X is carbon and Y is nitrogen, $R^1$ is phenyl or heteroaryl, each of which may be substituted by $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, up to three times by hydroxyl, fluorine, chlorine or bromine, where $(C_1-C_4)$-alkyl, $(C_3-C_7)$-cycloalkyl, $(C_1-C_4)$-alkoxy, $(C_3-C_7)$-cycloalkyl-$(C_1-C_3)$-alkyl and $(C_3-C_7)$-cycloalkoxy may be substituted by hydroxyl, cyano and up to three times by fluorine $R^2$ is hydrogen, $(C_1-C_5)$-alkyl, $(C_3-C_7)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine, $R^3$ is $(C_3-C_7)$-cycloalkyl, phenyl or heteroaryl wherein the $(C_3-C_7)$-cycloalkyl, phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, $(C_1-C_4)$-alkyl, $(C_1-C_4)$-alkoxy, oxo, cyano, chlorine, bromine or up to three times by fluorine, or may be annellated with phenyl or heteroaryl where $(C_1-C_4)$-alkyl is optionally substituted by 4- to 7-membered heterocyclyl or up to three times by fluorine, $R^4$ and $R^5$ are each independently $(C_1-C_4)$-alkyl optionally substituted up to three times by fluorine, $R^6$ is hydrogen, $(C_1-C_6)$-alkyl, $(C_3-C_7)$-cycloalkyl or 4- to 7-membered heterocyclyl wherein the $(C_1-C_6)$-alkyl, $(C_3-C_7)$-cycloalkyl or 4- to 7-membered heterocyclyl may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine, and the nitrogen of a 4- to 7-membered heterocyclyl may be substituted by $C(O)OR^6$ or $C(O)R^6$, and the salts, solvates and solvates of the salts thereof.

The present disclosure also provides compounds of the general formula (BII)

(BII)

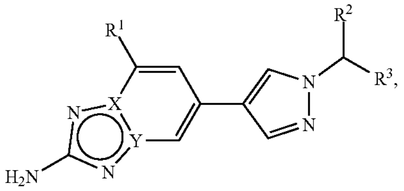

in which

X is nitrogen and Y is carbon, or

X is carbon and Y is nitrogen, $R^1$ is phenyl or heteroaryl, each of which may be substituted by $(C_1-C_4)$-alkyl, $(C_3-C_7)$-cycloalkyl, $(C_3-C_7)$-cycloalkyl-$(C_1-C_3)$-alkyl, 4- to 7-membered heterocyclyl, $(C_1-C_4)$-alkoxy, $(C_3-C_7)$-cycloalkoxy, —$SO_2R^4$, —$NR^4R^5$, cyano, up to three times by hydroxyl, fluorine, chlorine or bromine, where $(C_1-C_4)$-alkyl, $(C_3$-

$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^W$ are each independently ($C_1$-$C_4$)-alkyl optionally substituted up to three times by fluorine and the salts, solvates and solvates of the salts thereof.

The present disclosure also provides compounds of the general formula (II)

(II)

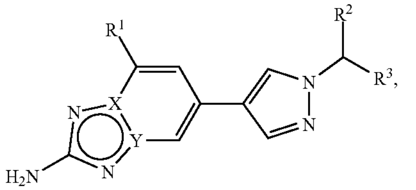

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered fused ring containing up to two heteratoms selected from the group consisting of O or N, which fused ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and R are each independently ($C_1$-$C_4$)-alkyl optionally substituted up to three times by fluorine and the salts, solvates and solvates of the salts thereof.

In some embodiments, X is nitrogen and Y is carbon, $R^1$ is phenyl or heteroaryl, each of which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl, or 4- to 7-membered heterocyclyl may be substituted by chlorine, bromine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

In some embodiments, X is nitrogen and Y is carbon, $R^1$ is phenyl, pyridonyl, pyrimidyl, pyridazinyl, pyrazinyl, pyrazolyl or thiadiazolyl which may be substituted by ($C_1$-$C_4$)-alkyl, ($C_3$-$C_7$)-cycloalkyl, ($C_1$-$C_4$)-alkoxy, —$SO_2W$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl or 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

In some embodiments,

X is nitrogen and Y is carbon, $R^1$ is phenyl, pyridonyl or pyrazolyl which may be substituted by ($C_1$-$C_4$)-alkyl, ($C_3$-$C_7$)-cycloalkyl, ($C_1$-$C_4$)-alkoxy or —$SO_2R^4$ and in addition may be substituted by cyano, fluorine, chlorine or bromine, and where $(C_1-C_4)$-alkyl, $(C_3-C_7)$-cycloalkyl and $(C_1-C_4)$-alkoxy may be substituted by hydroxyl, cyano and up to three times by fluorine $R^2$ is $(C_1-C_6)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^4$ is $(C_1-C_4)$-alkyl optionally substituted up to three times by fluorine and the salts, solvates and solvates of the salts thereof.

In some embodiments, the compound is a compound of formula (II-A) in which (II-A)

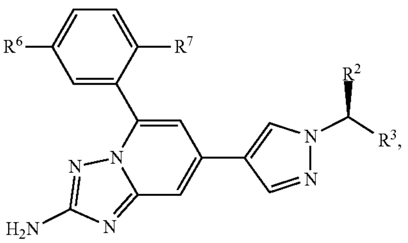

$R^2$ is hydrogen, $(C_1-C_6)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl which is substituted by hydroxyl, cyano or up to three times by fluorine $R^7$ is $(C_1-C_4)$-alkyl, chlorine, bromine or fluorine where $(C_1-C_4)$-alkyl is optionally substituted up to three times by fluorine and the salts, solvates and solvates of the salts thereof.

In some embodiments, the compound is a compound of formula (II-B) in which (II-B)

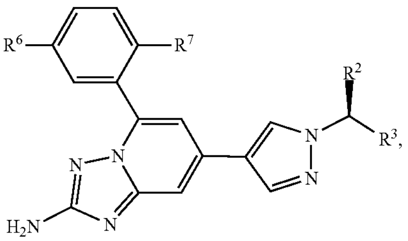

$R^2$ is $(C_1-C_6)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl which is substituted by hydroxyl, cyano or up to three times by fluorine $R^7$ is $(C_1-C_4)$-alkyl, chlorine, bromine or fluorine where $(C_1-C_4)$-alkyl is optionally substituted up to three times by fluorine and the salts, solvates and solvates of the salts thereof.

In some embodiments, the compound is a compound of formula (II-C) in which (II-C)

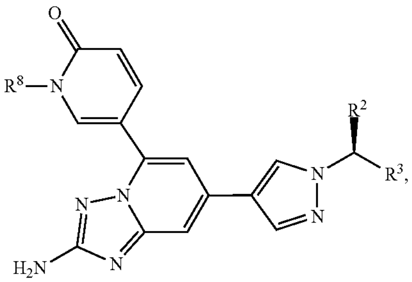

$R^2$ is $(C_1-C_4)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^8$ is $(C_1-C_4)$-alkyl which is optionally substituted by hydroxyl, cyano or up to three times by fluorine and the salts, solvates and solvates of the salts thereof.

In some embodiments, the compound is a compound of formula (II-D) in which (II-D)

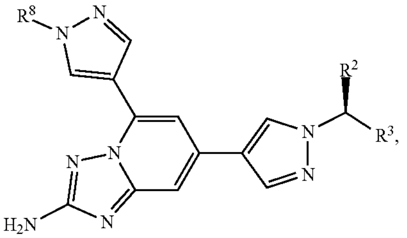

$R^2$ is $(C_1-C_4)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^8$ is $(C_1-C_4)$-alkyl which is optionally substituted by hydroxyl, cyano or up to three times by fluorine and the salts, solvates and solvates of the salts thereof.

In some embodiments,

X is carbon and Y is nitrogen, $R^1$ is phenyl or heteroaryl, each of which may be substituted by $(C_1-C_4)$-alkyl, $(C_3-C_7)$-cycloalkyl, $(C_1-C_4)$-alkoxy, $-SO_2R^4$, $-NR^4R^5$, cyano, up to three times by hydroxyl, fluorine, chlorine or bromine, where $(C_1-C_4)$-alkyl, $(C_3-C_7)$-cycloalkyl, $(C_1-C_4)$-alkoxy and $(C_3-$ $C_7$)-cycloalkoxy may be substituted by hydroxyl, cyano and up to three times by fluorine $R^2$ is ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl, or 4- to 7-membered heterocyclyl may be substituted by chlorine, bromine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl is optionally substituted up to three times by fluorine and the salts, solvates and solvates of the salts thereof.

In some embodiments,

X is carbon and Y is nitrogen, $R^1$ is phenyl, pyridonyl, pyrimidyl, pyridazinyl, pyrazinyl, pyrazolyl or thiadiazolyl which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl or 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and R are each independently ($C_1$-$C_4$)-alkyl optionally substituted up to three times by fluorine and the salts, solvates and solvates of the salts thereof.

In some embodiments,

X is carbon and Y is nitrogen, $R^1$ is phenyl, pyridonyl or pyrazolyl which may be substituted by ($C_1$-$C_4$)-alkyl, ($C_3$-$C_7$)-cycloalkyl, ($C_1$-$C_4$)-alkoxy or —$SO_2R^4$ and in addition may be be substituted by cyano, fluorine, chlorine or bromine, and where ($C_1$-$C_4$)-alkyl, ($C_3$-$C_7$)-cycloalkyl and ($C_1$-$C_4$)-alkoxy may be substituted by hydroxyl, cyano and up to three times by fluorine $R^2$ is ($C_1$-$C_6$)-alkyl, ($C_3$-$C_7$)-cycloalkyl or 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ is ($C_1$-$C_4$)-alkyl optionally substituted up to three times by fluorine and the salts, solvates and solvates of the salts thereof.

In some embodiments, the compound is a compound of formula (II-E) in which (II-E)

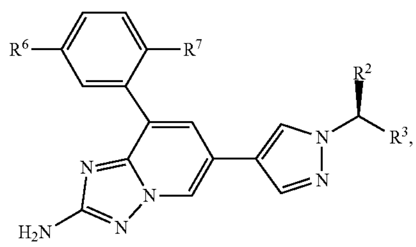

$R^2$ is ($C_1$-$C_6$)-alkyl, ($C_3$-$C_7$)-cycloalkyl or 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl which is substituted by hydroxyl, cyano or up to three times by fluorine $R^7$ is ($C_1$-$C_4$)-alkyl, chlorine, bromine or fluorine where ($C_1$-$C_4$)-alkyl is optionally substituted up to three times by fluorine and the salts, solvates and solvates of the salts thereof.

In some embodiments, the compound is a compound of formula (II-F) in which (II-F)

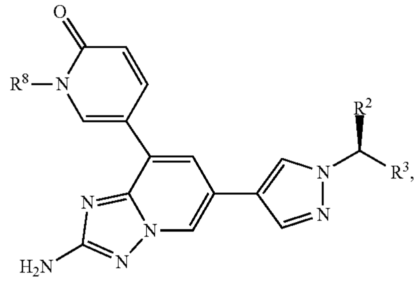

$R^2$ is ($C_1$-$C_6$)-alkyl, ($C_3$-$C_7$)-cycloalkyl or 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^8$ is ($C_1$-$C_4$)-alkyl which is optionally substituted by hydroxyl, cyano or up to three times by fluorine and the salts, solvates and solvates of the salts thereof.

In some embodiments, the compound is a compound of formula (II-G) in which

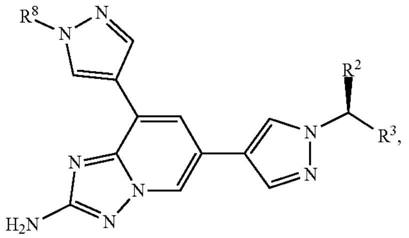

(II-G)

$R^2$ is $(C_1-C_5)$-alkyl, $(C_3-C_7)$-cycloalkyl or 4- to 7-membered heterocyclyl, each of which may be substituted by chlorine or up to three times by fluorine, $R^3$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^8$ is $(C_1-C_4)$-alkyl which is optionally substituted by hydroxyl, cyano or up to three times by fluorine and the salts, solvates and solvates of the salts thereof.

In some embodiments, X is carbon and Y is nitrogen.

In some embodiments, $R^1$ is phenyl or heteroaryl, each of which may be substituted by $(C_1-C_4)$-alkyl, $(C_3-C_7)$-cycloalkyl, 4- to 7-membered heterocyclyl, $(C_1-C_4)$-alkoxy, —$SO_2R^4$, —$NR^4R^5$, cyano, up to three times by hydroxyl, fluorine, chlorine or bromine, where $(C_1-C_4)$-alkyl, $(C_3-C_7)$-cycloalkyl and $(C_1-C_4)$-alkoxy, may be substituted by hydroxyl, cyano and up to three times by fluorine. In some embodiments, $R^1$ is phenyl or heteroaryl, each of which may be substituted by $(C_1-C_4)$-alkyl, —$SO_2R^4$, —$NR^4R^5$, or hydroxyl, where $(C_1-C_4)$-alkyl may be substituted by hydroxyl and up to three times by fluorine. In some embodiments, $R^1$ is phenyl or heteroaryl, each of which may be substituted by $(C_1-C_4)$-alkyl, —$NR^4R^5$, or hydroxyl, where $(C_1-C_4)$-alkyl may be substituted by hydroxyl and up to three times by fluorine. In some embodiments, $R^1$ is phenyl or 5-6-membered heteroaryl, each of which may be substituted by $(C_1-C_4)$-alkyl, —$SO_2R^4$, —$NR^4R^5$, or hydroxyl, where $(C_1-C_4)$-alkyl may be substituted by hydroxyl and up to three times by fluorine. In some embodiments, $R^1$ is phenyl, pyrazolyl, or pyridonyl, each of which may be substituted by $(C_1-C_4)$-alkyl, —$SO_2R^4$, —$NR^4R^5$, or hydroxyl, where $(C_1-C_4)$-alkyl may be substituted up to three times by fluorine. In some embodiments, $R^1$ is phenyl, 4-pyrazolyl, or 5-pyridonyl, each of which may be substituted by trifluoroethyl, —$SO_2Me$, —$SO_2Et$, or —$N(CH_3)_2$.

In some embodiments, $R^2$ is $(C_3-C_7)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine. In some embodiments, $R^2$ is $(C_3-C_6)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine. In some embodiments, $R^2$ is cyclobutyl, cyclopentyl, or 4- to 7-membered heterocyclyl, each of which may be substituted by $(C_1-C_4)$-alkyl, $(C_1-C_4)$-alkoxy, oxo, or up to three times by fluorine. In some embodiments, $R^2$ is cyclobutyl, cyclopentyl, or 4- to 7-membered heterocyclyl, each of which may be substituted by $(C_1-C_4)$-alkyl, oxo, or up to three times by fluorine. In some embodiments, $R^2$ is cyclobutyl, cyclopentyl, or 4- to 7-membered heterocyclyl, each of which may be substituted by chlorine, bromine, or up to three times by fluorine. In some embodiments, $R^2$ is cyclopentyl or 4- to 7-membered heterocyclyl, each of which may be substituted by chlorine, bromine, or up to three times by fluorine. In some embodiments, $R^2$ is 4- to 7-membered heterocyclyl which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine. In some embodiments, $R^2$ is 4-to 7-membered heterocyclyl which may be substituted by $(C_1-C_4)$-alkyl, $(C_1-C_4)$-alkoxy, or up to three times by fluorine. In some embodiments, $R^2$ is 4- to 7-membered heterocyclyl which may be substituted by chlorine, bromine, or up to three times by fluorine. In some embodiments, $R^2$ is 5-to 6-membered heterocyclyl which may be substituted by chlorine, bromine, or up to three times by fluorine. In some embodiments, $R^2$ is piperidinyl which may be substituted by chlorine, bromine, or up to three times by fluorine. In some embodiments, $R^2$ is piperidinyl or tetrahydropyranyl which may be substituted by chlorine, bromine, or up to three times by fluorine. In some embodiments, $R^2$ is tetrahydropyranyl which may be substituted by chlorine, bromine, or up to three times by fluorine. In some embodiments, $R^2$ is piperidinyl. In some embodiments, $R^2$ is tetrahydropyranyl. For example, $R^2$ is 4-piperidinyl. For example, $R^2$ is 4-tetrahydropyranyl.

In some embodiments, $R^3$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine. In some embodiments, $R^3$ is phenyl or heteroaryl wherein the phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine. In some embodiments, $R^3$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, 4- to 7-membered heterocyclyl, or up to three times by fluorine, where $(C_1-C_4)$-alkyl may be substituted up to three times by fluorine. In some embodiments, $R^3$ is phenyl or heteroaryl wherein the phenyl or heteroaryl may be substituted by $(C_1-C_4)$-alkyl, $(C_1-C_4)$-alkoxy, 4- to 7-membered heterocyclyl, or up to three times by fluorine, where $(C_1-C_4)$-alkyl may be substituted up to three times by fluorine. In some embodiments, $R^3$ is phenyl, 3-pyridinyl, or 4-pyridinyl, each of which may be substituted by $(C_1-C_4)$-alkyl, $(C_1-C_4)$-alkoxy, cyano, chlorine, bromine, or up to three times by fluorine; where $(C_1-C_4)$-alkyl and $(C_1-C_4)$-alkoxy may be substituted up to three times by fluorine. In some embodiments, $R^3$ is phenyl, 3-pyridinyl, or 4-pyridinyl, each of which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine. In some embodiments, $R^3$ is 3-pyridinyl which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine. In some embodiments, $R^3$ is 3-pyridinyl which may be substituted by $(C_1-C_4)$-alkyl; where $(C_1-C_4)$-alkyl may be substituted up to three times by fluorine. In some embodiments, $R^3$ is 3-pyridinyl which may be substituted by trifluoromethyl. In some embodiments, $R^3$ is 3-pyridinyl which is substituted by trifluoromethyl. In some embodiments, $R^3$ is 6-(trifluoromethyl)pyridin-3-yl.

In some embodiments, the stereochemical configuration of the atom that $R^2$ and $R^3$ are bonded to is (S). In some embodiments, the stereochemical configuration of the atom that $R^2$ and $R^3$ are bonded to is (R).

In some embodiments,

X is carbon and Y is nitrogen;

$R^1$ is phenyl or heteroaryl, each of which may be substituted by $(C_1-C_4)$-alkyl, $—SO_2R^4$, $—NR^4R^5$, or hydroxyl, where $(C_1-C_4)$-alkyl may be substituted by hydroxyl and up to three times by fluorine;

$R^2$ is $(C_3-C_7)$-cycloalkyl or 4- to 7-membered heterocyclyl, each of which may be substituted by $(C_1-C_4)$-alkyl, $(C_1-C_4)$-alkoxy, oxo, cyano, chlorine, bromine or up to three times by fluorine, where $(C_1-C_4)$-alkoxy and $(C_1-C_4)$-alkyl may be substituted up to three times by fluorine; and $R^3$ is $(C_3-C_7)$-cycloalkyl, phenyl, or heteroaryl wherein the $(C_3-C_7)$-cycloalkyl, phenyl, or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine.

In some embodiments,

X is carbon and Y is nitrogen;

$R^1$ is phenyl or heteroaryl, each of which may be substituted by $(C_1-C_4)$-alkyl, $—NR^4R^5$, or hydroxyl, where $(C_1-C_4)$-alkyl may be substituted by hydroxyl and up to three times by fluorine;

$R^2$ is $(C_3-C_6)$-cycloalkyl or 4- to 7-membered heterocyclyl, each of which may be substituted by $(C_1-C_4)$-alkyl, $(C_1-C_4)$-alkoxy, oxo, cyano, chlorine, bromine, or up to three times by fluorine; and $R^3$ is phenyl or heteroaryl wherein the phenyl, or heteroaryl may be substituted by $(C_1-C_4)$-alkyl, $(C_1-C_4)$-alkoxy, cyano, 4- to 7-membered heterocyclyl, or up to three times by fluorine.

In some embodiments,

X is carbon and Y is nitrogen;

$R^1$ is phenyl, pyrazolyl, or pyridonyl, each of which may be substituted by $(C_1-C_4)$-alkyl, $—SO_2R^4$, $—NR^4R^5$, or hydroxyl, where $(C_1-C_4)$-alkyl may be substituted up to three times by fluorine;

$R^2$ is 4- to 7-membered heterocyclyl which may be substituted by chlorine, bromine, or up to three times by fluorine; and $R^3$ is phenyl, 3-pyridinyl, or 4-pyridinyl, each of which may be substituted by $(C_1-C_4)$-alkyl or $(C_1-C_4)$-alkoxy; where $(C_1-C_4)$-alkyl and $(C_1-C_4)$-alkoxy may be substituted up to three times by fluorine.

In some embodiments,

X is carbon and Y is nitrogen;

$R^1$ is phenyl, 4-pyrazolyl, or 5-pyridonyl, each of which may be substituted by trifluoroethyl, $—SO_2Me$, $—SO_2Et$, or $—N(CH_3)_2$;

$R^2$ is 4-piperidinyl or 4-tetrahydropyranyl; and $R^3$ is 3-pyridinyl which may be substituted by trifluoromethyl.

In some embodiments, the compound is selected from the group consisting of the compounds disclosed in Table 2A below:

TABLE 2A

| Example Number | Structure |
|---|---|
| II-1 | 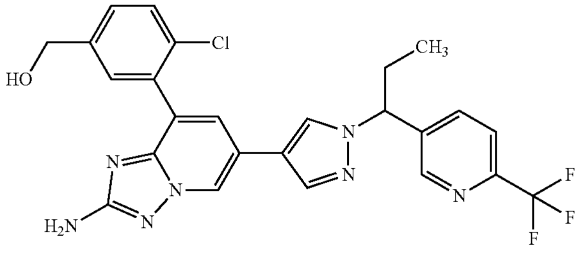 [SMILES: CCC(c1ccc(C(F)(F)F)nc1)n1cc(-c2cc(-c3cc(CO)ccc3Cl)c3nc(N)nn3c2)cn1] |
| II-4 | 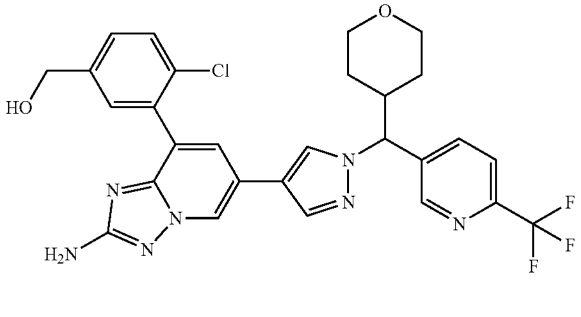 [SMILES: Nc1nc2c(-c3cc(CO)ccc3Cl)cc(-c3cnn(C(c4ccc(C(F)(F)F)nc4)C4CCOCC4)c3)cn2n1] |

TABLE 2A-continued
| Example Number | Structure |
| --- | --- |
| II-7 | 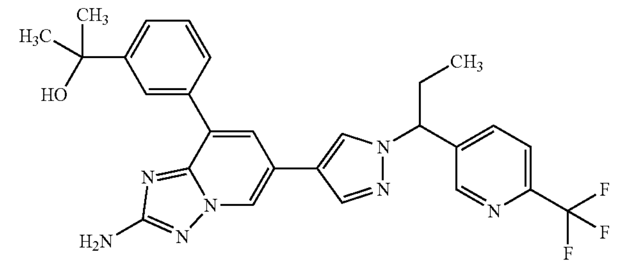 [SMILES: CCC(c1ccc(C(F)(F)F)nc1)n1cc(-c2cc(-c3cccc(C(C)(C)O)c3)c3nc(N)nn3c2)cn1] |
| II-10 | 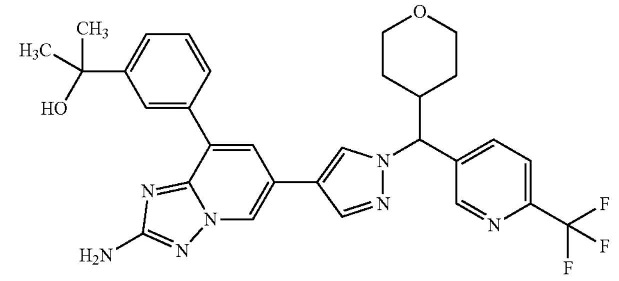 [SMILES: CC(C)(O)c1cccc(-c2cc(-c3cnn(C(c4ccc(C(F)(F)F)nc4)C4CCOCC4)c3)cn3nc(N)nc23)c1] |
| II-13 | 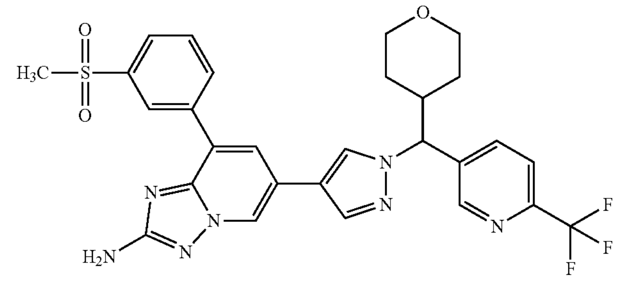 [SMILES: CS(=O)(=O)c1cccc(-c2cc(-c3cnn(C(c4ccc(C(F)(F)F)nc4)C4CCOCC4)c3)cn3nc(N)nc23)c1] |
| II-16 | 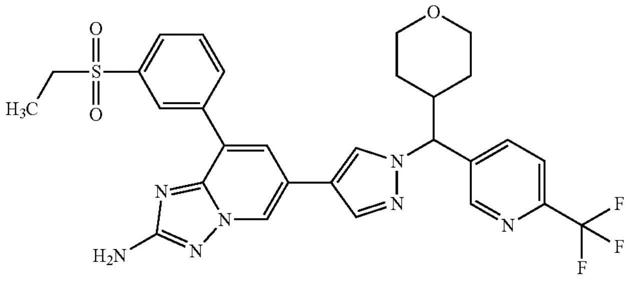 [SMILES: CCS(=O)(=O)c1cccc(-c2cc(-c3cnn(C(c4ccc(C(F)(F)F)nc4)C4CCOCC4)c3)cn3nc(N)nc23)c1] |
| II-19 | 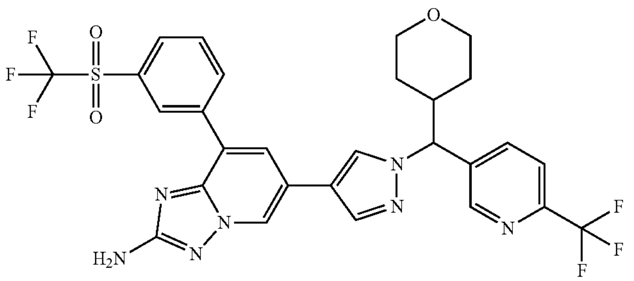 [SMILES: Nc1nc2c(-c3cccc(S(=O)(=O)C(F)(F)F)c3)cc(-c3cnn(C(c4ccc(C(F)(F)F)nc4)C4CCOCC4)c3)cn2n1] |

TABLE 2A-continued
| Example Number | Structure |
|---|---|
| II-22 | 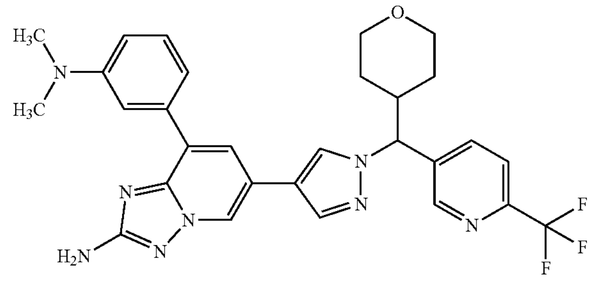 [SMILES: CN(C)c1cccc(-c2cc(-c3cnn(C(c4ccc(C(F)(F)F)nc4)C4CCOCC4)c3)cn3nc(N)nc23)c1] |
| II-25 | 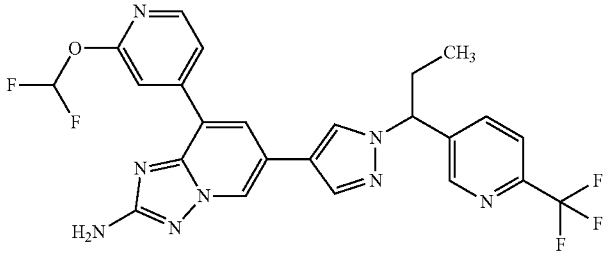 [SMILES: CCC(c1ccc(C(F)(F)F)nc1)n1cc(-c2cc(-c3ccnc(OC(F)F)c3)c3nc(N)nn3c2)cn1] |
| II-28 | 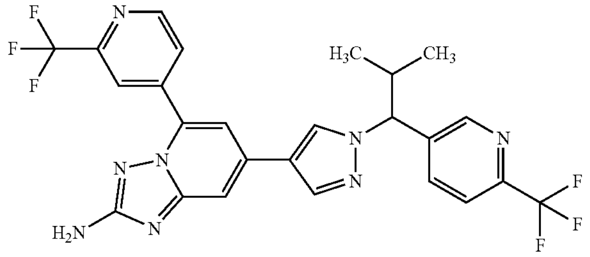 [SMILES: CC(C)C(c1ccc(C(F)(F)F)nc1)n1cc(-c2cc(-c3ccnc(C(F)(F)F)c3)n3nc(N)nc3c2)cn1] |
| II-31 | 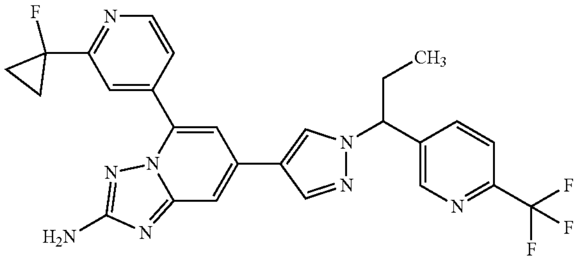 [SMILES: CCC(c1ccc(C(F)(F)F)nc1)n1cc(-c2cc(-c3ccnc(C4(F)CC4)c3)n3nc(N)nc3c2)cn1] |
| II-34 | 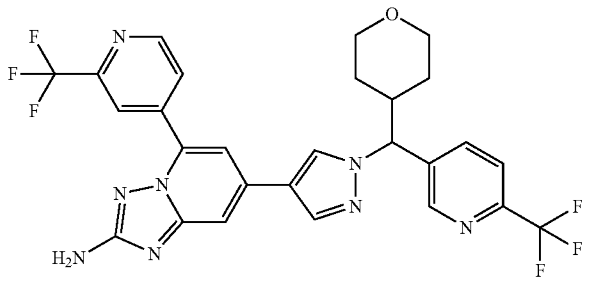 [SMILES: Nc1nc2cc(-c3cnn(C(c4ccc(C(F)(F)F)nc4)C4CCOCC4)c3)cc(-c3ccnc(C(F)(F)F)c3)n2n1] |

TABLE 2A-continued
| Example Number | Structure |
|---|---|
| II-37 | 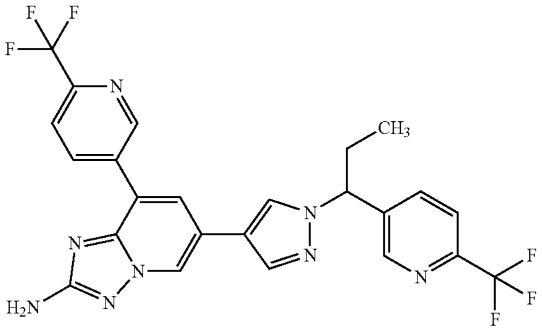 [SMILES: CCC(c1ccc(C(F)(F)F)nc1)n1cc(-c2cc(-c3ccc(C(F)(F)F)nc3)c3nc(N)nn3c2)cn1] |
| II-40 | 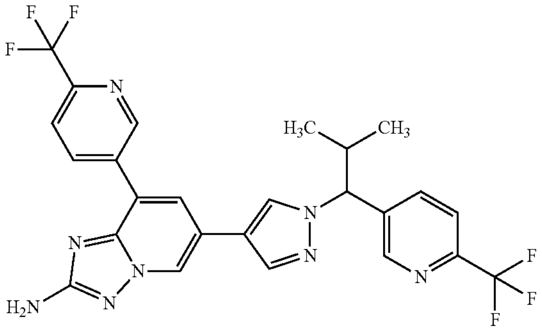 [SMILES: CC(C)C(c1ccc(C(F)(F)F)nc1)n1cc(-c2cc(-c3ccc(C(F)(F)F)nc3)c3nc(N)nn3c2)cn1] |
| II-43 | 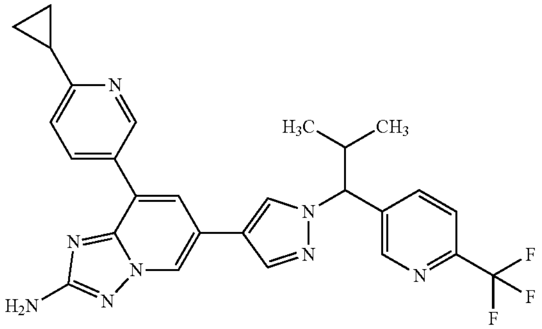 [SMILES: CC(C)C(c1ccc(C(F)(F)F)nc1)n1cc(-c2cc(-c3ccc(C4CC4)nc3)c3nc(N)nn3c2)cn1] |
| II-46 | 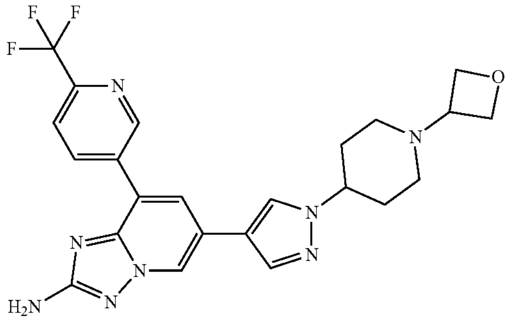 [SMILES: Nc1nc2c(-c3ccc(C(F)(F)F)nc3)cc(-c3cnn(C4CCN(C5COC5)CC4)c3)cn2n1] |

TABLE 2A-continued
| Example Number | Structure |
| --- | --- |
| II-47 | 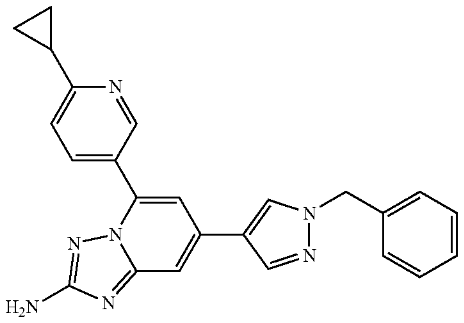 [SMILES: Nc1nc2cc(-c3cnn(Cc4ccccc4)c3)cc(-c3ccc(C4CC4)nc3)n2n1] |
| II-48 | 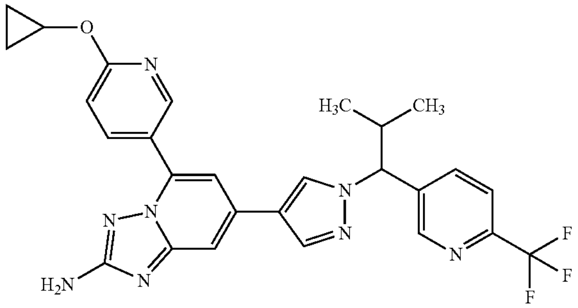 [SMILES: CC(C)C(c1ccc(C(F)(F)F)nc1)n1cc(-c2cc(-c3ccc(OC4CC4)nc3)n3nc(N)nc3c2)cn1] |
| II-49 | 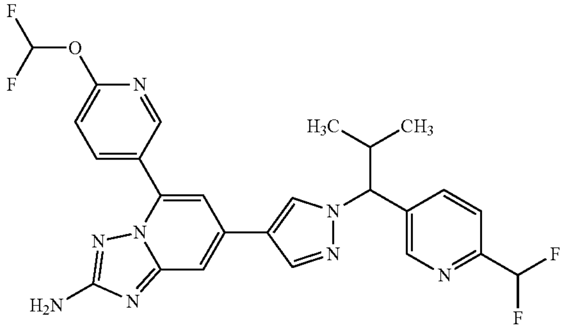 [SMILES: CC(C)C(c1ccc(C(F)F)nc1)n1cc(-c2cc(-c3ccc(OC(F)F)nc3)n3nc(N)nc3c2)cn1] |
| II-52 | 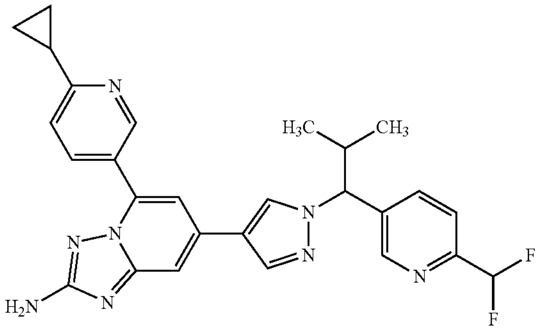 [SMILES: CC(C)C(c1ccc(C(F)F)nc1)n1cc(-c2cc(-c3ccc(C4CC4)nc3)n3nc(N)nc3c2)cn1] |

TABLE 2A-continued
| Example Number | Structure |
|---|---|
| II-55 | 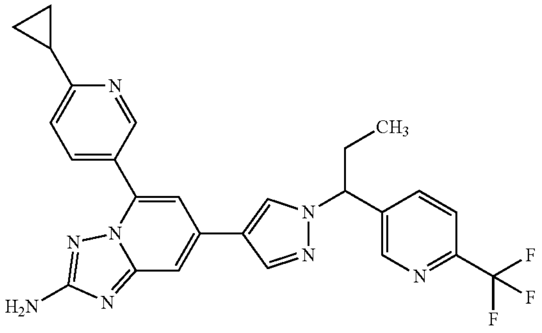 [SMILES: CCC(c1ccc(C(F)(F)F)nc1)n1cc(-c2cc(-c3ccc(C4CC4)nc3)n3nc(N)nc3c2)cn1] |
| II-58 | 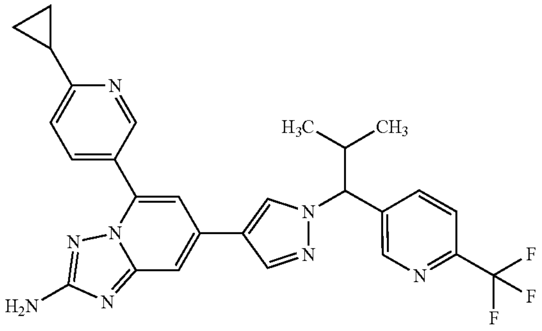 [SMILES: CC(C)C(c1ccc(C(F)(F)F)nc1)n1cc(-c2cc(-c3ccc(C4CC4)nc3)n3nc(N)nc3c2)cn1] |
| II-61 | 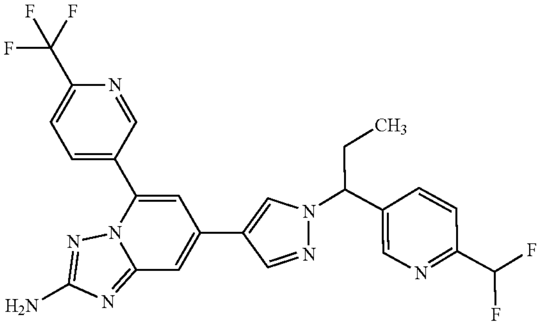 [SMILES: CCC(c1ccc(C(F)F)nc1)n1cc(-c2cc(-c3ccc(C(F)(F)F)nc3)n3nc(N)nc3c2)cn1] |
| II-64 | 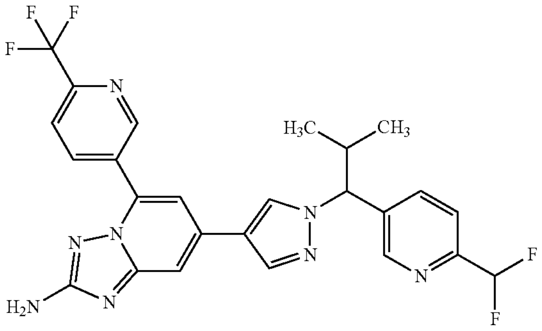 [SMILES: CC(C)C(c1ccc(C(F)F)nc1)n1cc(-c2cc(-c3ccc(C(F)(F)F)nc3)n3nc(N)nc3c2)cn1] |

TABLE 2A-continued
| Example Number | Structure |
| --- | --- |
| II-67 | 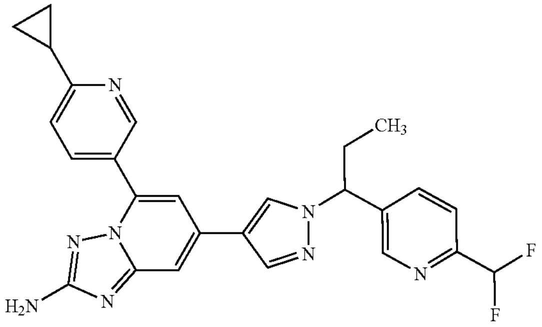 [SMILES: CCC(c1ccc(C(F)F)nc1)n1cc(-c2cc(-c3ccc(C4CC4)nc3)n3nc(N)nc3c2)cn1] |
| II-70 | 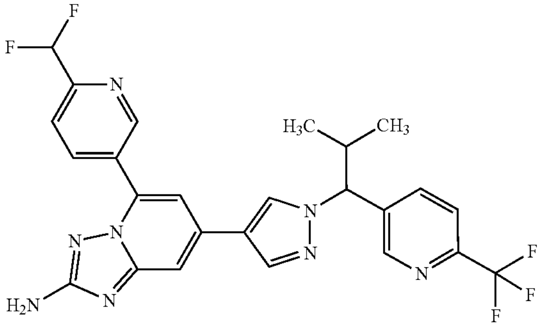 [SMILES: CC(C)C(c1ccc(C(F)(F)F)nc1)n1cc(-c2cc(-c3ccc(C(F)F)nc3)n3nc(N)nc3c2)cn1] |
| II-73 | 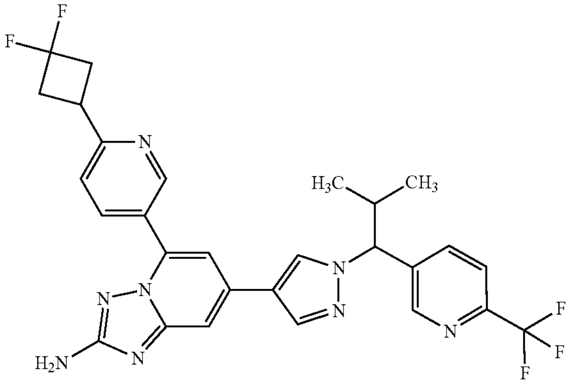 [SMILES: CC(C)C(c1ccc(C(F)(F)F)nc1)n1cc(-c2cc(-c3ccc(C4CC(F)(F)C4)nc3)n3nc(N)nc3c2)cn1] |
| II-76 | 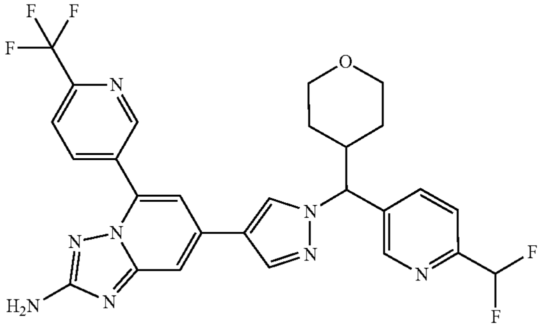 [SMILES: Nc1nc2cc(-c3cnn(C(c4ccc(C(F)F)nc4)C4CCOCC4)c3)cc(-c3ccc(C(F)(F)F)nc3)n2n1] |

TABLE 2A-continued
| Example Number | Structure |
| --- | --- |
| II-79 | 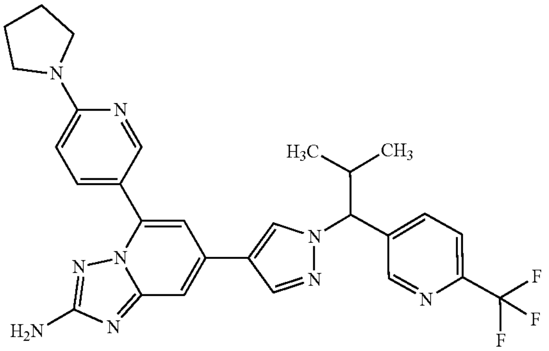 [SMILES: CC(C)C(c1ccc(C(F)(F)F)nc1)n1cc(-c2cc(-c3ccc(N4CCCC4)nc3)n3nc(N)nc3c2)cn1] |
| II-80 | 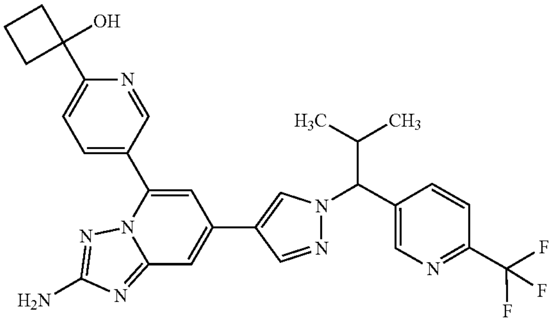 [SMILES: CC(C)C(c1ccc(C(F)(F)F)nc1)n1cc(-c2cc(-c3ccc(C4(O)CCC4)nc3)n3nc(N)nc3c2)cn1] |
| II-83 | 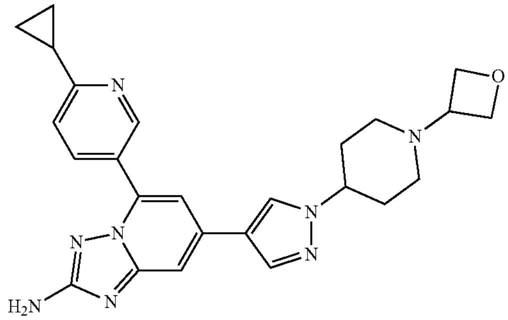 [SMILES: Nc1nc2cc(-c3cnn(C4CCN(C5COC5)CC4)c3)cc(-c3ccc(C4CC4)nc3)n2n1] |
| II-84 | 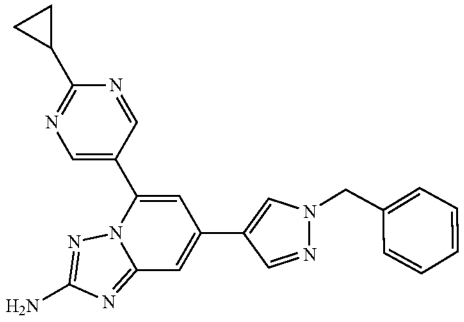 [SMILES: Nc1nc2cc(-c3cnn(Cc4ccccc4)c3)cc(-c3cnc(C4CC4)nc3)n2n1] |

TABLE 2A-continued
| Example Number | Structure |
| --- | --- |
| II-85 | 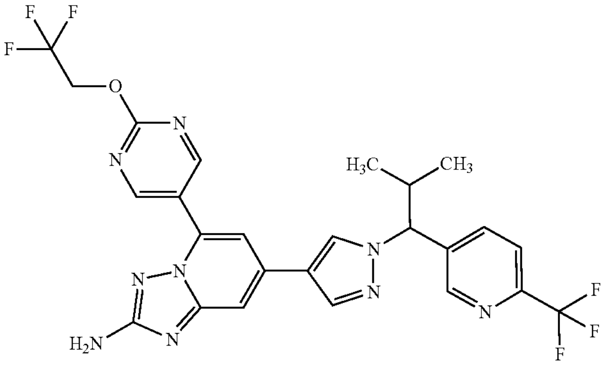 [SMILES: CC(C)C(c1ccc(C(F)(F)F)nc1)n1cc(-c2cc(-c3cnc(OCC(F)(F)F)nc3)n3nc(N)nc3c2)cn1] |
| II-86 | 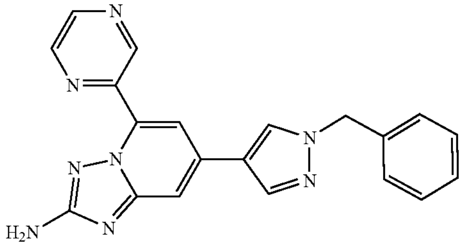 [SMILES: Nc1nc2cc(-c3cnn(Cc4ccccc4)c3)cc(-c3cnccn3)n2n1] |
| II-87 | 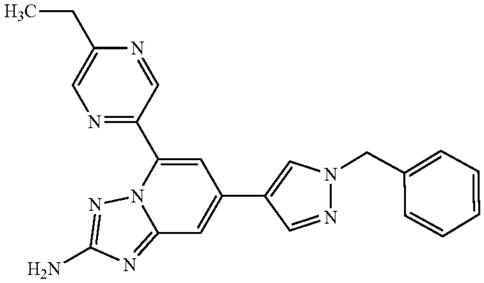 [SMILES: CCc1cnc(-c2cc(-c3cnn(Cc4ccccc4)c3)cc3nc(N)nn23)cn1] |
| II-88 | 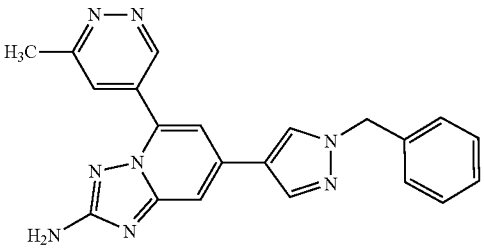 [SMILES: Cc1cc(-c2cc(-c3cnn(Cc4ccccc4)c3)cc3nc(N)nn23)cnn1] |
| II-89 | 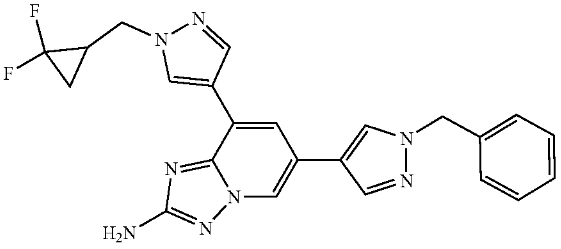 [SMILES: Nc1nc2c(-c3cnn(CC4CC4(F)F)c3)cc(-c3cnn(Cc4ccccc4)c3)cn2n1] |

TABLE 2A-continued
| Example Number | Structure |
| --- | --- |
| II-90 | 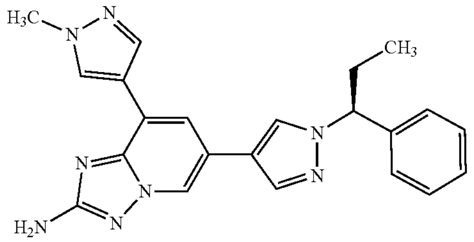 [SMILES: CC[C@@H](c1ccccc1)n1cc(-c2cc(-c3cnn(C)c3)c3nc(N)nn3c2)cn1] |
| II-91 | 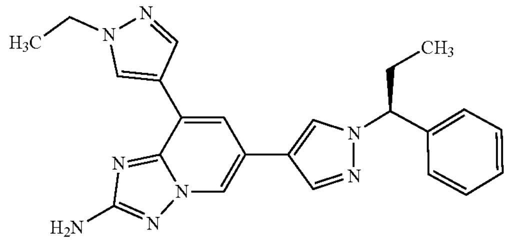 [SMILES: CC[C@@H](c1ccccc1)n1cc(-c2cc(-c3cnn(CC)c3)c3nc(N)nn3c2)cn1] |
| II-92 | 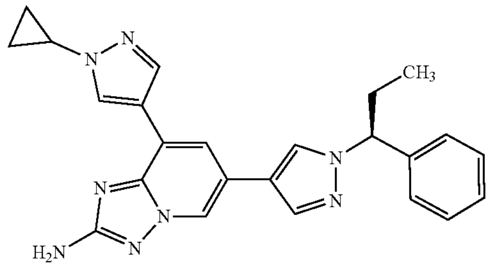 [SMILES: CC[C@@H](c1ccccc1)n1cc(-c2cc(-c3cnn(C4CC4)c3)c3nc(N)nn3c2)cn1] |
| II-93 | 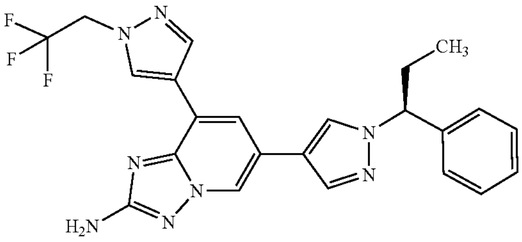 [SMILES: CC[C@@H](c1ccccc1)n1cc(-c2cc(-c3cnn(CC(F)(F)F)c3)c3nc(N)nn3c2)cn1] |
| II-94 | 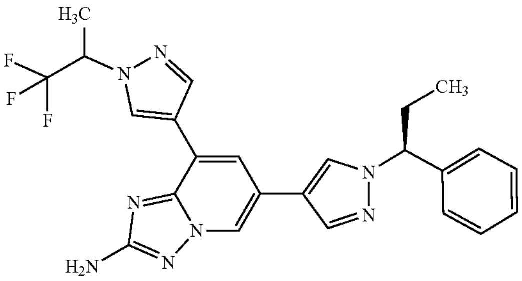 [SMILES: CC[C@@H](c1ccccc1)n1cc(-c2cc(-c3cnn(C(C)C(F)(F)F)c3)c3nc(N)nn3c2)cn1] |
| II-97 | 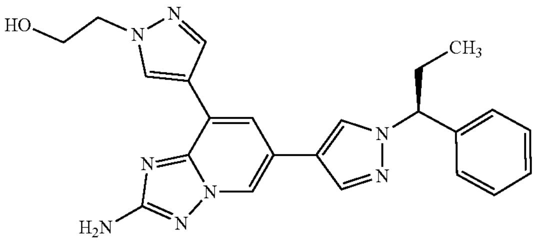 [SMILES: CC[C@@H](c1ccccc1)n1cc(-c2cc(-c3cnn(CCO)c3)c3nc(N)nn3c2)cn1] |

TABLE 2A-continued
| Example Number | Structure |
| --- | --- |
| II-98 | 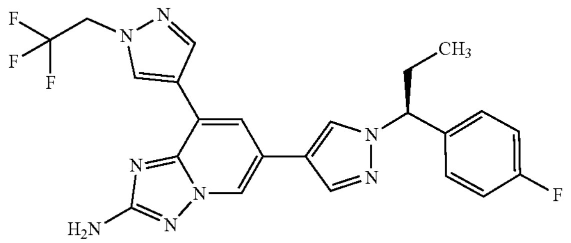 [SMILES: CC[C@@H](c1ccc(F)cc1)n1cc(-c2cc(-c3cnn(CC(F)(F)F)c3)c3nc(N)nn3c2)cn1] |
| II-99 | 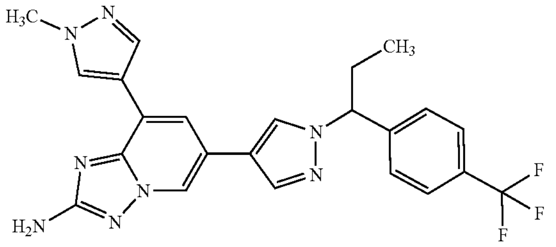 [SMILES: CCC(c1ccc(C(F)(F)F)cc1)n1cc(-c2cc(-c3cnn(C)c3)c3nc(N)nn3c2)cn1] |
| II-102 | 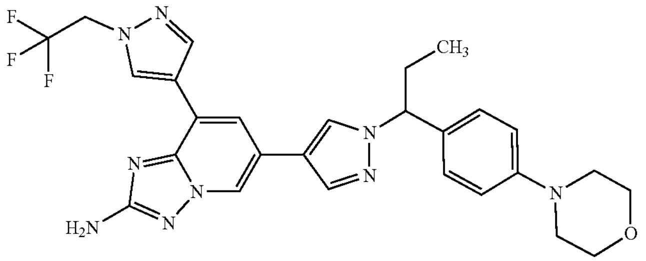 [SMILES: CCC(c1ccc(N2CCOCC2)cc1)n1cc(-c2cc(-c3cnn(CC(F)(F)F)c3)c3nc(N)nn3c2)cn1] |
| II-105 | 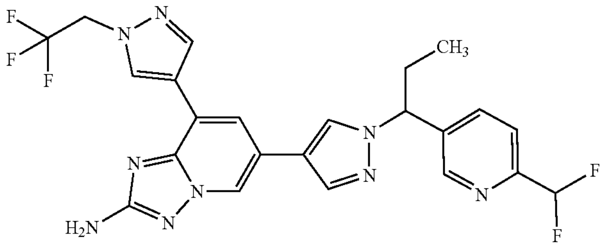 [SMILES: CCC(c1ccc(C(F)F)nc1)n1cc(-c2cc(-c3cnn(CC(F)(F)F)c3)c3nc(N)nn3c2)cn1] |
| II-108 | 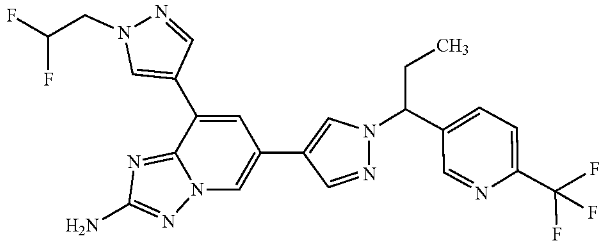 [SMILES: CCC(c1ccc(C(F)(F)F)nc1)n1cc(-c2cc(-c3cnn(CC(F)F)c3)c3nc(N)nn3c2)cn1] |
| II-111 | 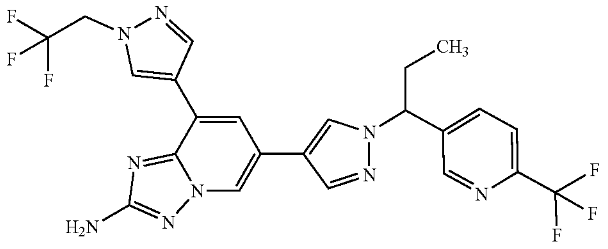 [SMILES: CCC(c1ccc(C(F)(F)F)nc1)n1cc(-c2cc(-c3cnn(CC(F)(F)F)c3)c3nc(N)nn3c2)cn1] |

TABLE 2A-continued
| Example Number | Structure |
| --- | --- |
| II-112 | 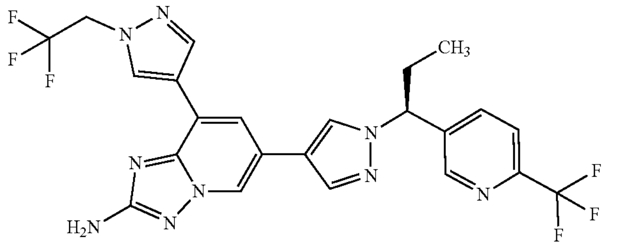 [SMILES: CC[C@@H](c1ccc(C(F)(F)F)nc1)n1cc(-c2cc(-c3cnn(CC(F)(F)F)c3)c3nc(N)nn3c2)cn1] |
| II-114 | 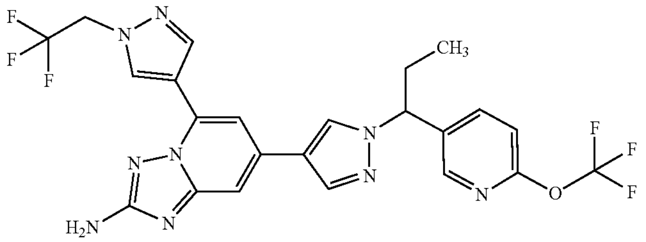 [SMILES: CCC(c1ccc(OC(F)(F)F)nc1)n1cc(-c2cc(-c3cnn(CC(F)(F)F)c3)n3nc(N)nc3c2)cn1] |
| II-116 | 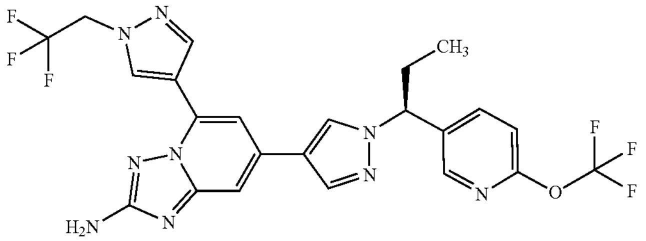 [SMILES: CC[C@@H](c1ccc(OC(F)(F)F)nc1)n1cc(-c2cc(-c3cnn(CC(F)(F)F)c3)n3nc(N)nc3c2)cn1] |
| II-117 | 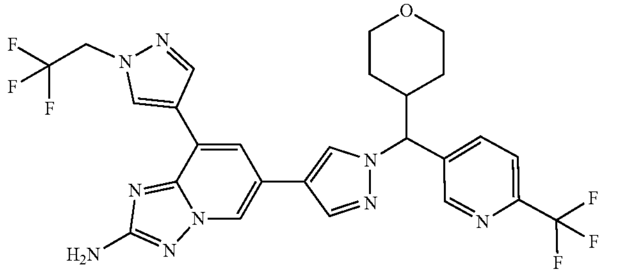 [SMILES: Nc1nc2c(-c3cnn(CC(F)(F)F)c3)cc(-c3cnn(C(c4ccc(C(F)(F)F)nc4)C4CCOCC4)c3)cn2n1] |
| II-120 | 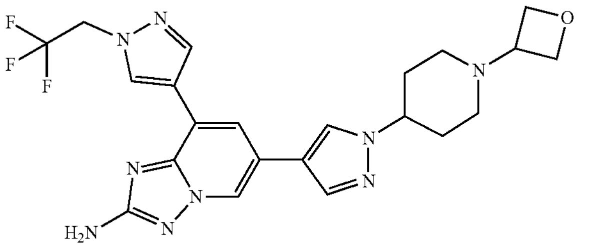 [SMILES: Nc1nc2c(-c3cnn(CC(F)(F)F)c3)cc(-c3cnn(C4CCN(C5COC5)CC4)c3)cn2n1] |
| II-121 | 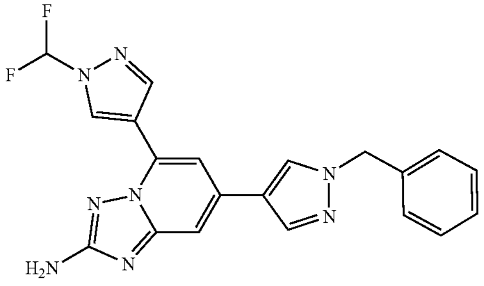 [SMILES: Nc1nc2cc(-c3cnn(Cc4ccccc4)c3)cc(-c3cnn(C(F)F)c3)n2n1] |

TABLE 2A-continued
| Example Number | Structure |
|---|---|
| II-122 | 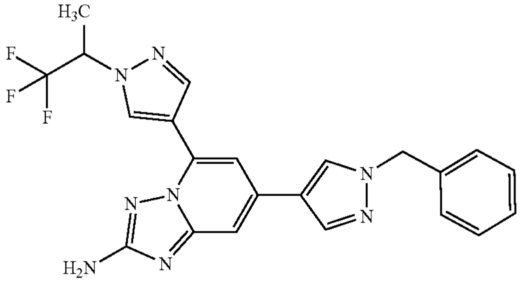 [SMILES: CC(n1cc(-c2cc(-c3cnn(Cc4ccccc4)c3)cc3nc(N)nn23)cn1)C(F)(F)F] |
| II-123 | 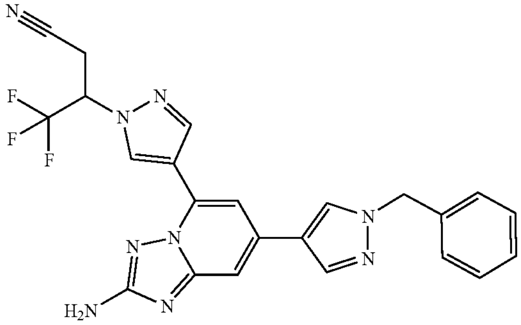 [SMILES: N#CCC(n1cc(-c2cc(-c3cnn(Cc4ccccc4)c3)cc3nc(N)nn23)cn1)C(F)(F)F] |
| II-124 | 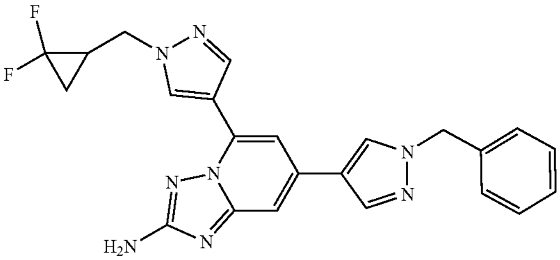 [SMILES: Nc1nc2cc(-c3cnn(Cc4ccccc4)c3)cc(-c3cnn(CC4CC4(F)F)c3)n2n1] |
| II-125 | 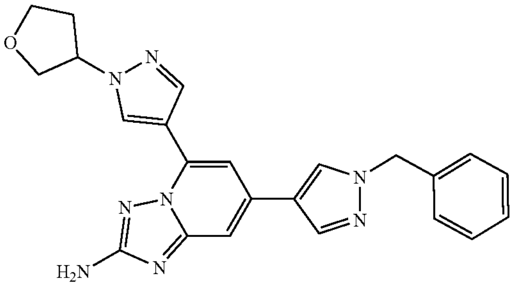 [SMILES: Nc1nc2cc(-c3cnn(Cc4ccccc4)c3)cc(-c3cnn(C4CCOC4)c3)n2n1] |
| II-126 | 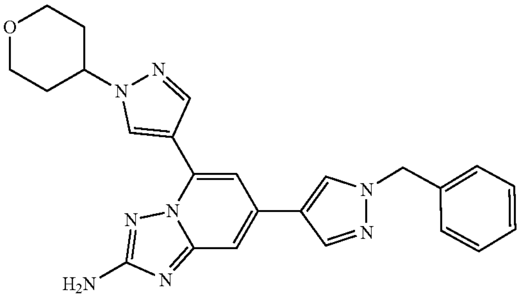 [SMILES: Nc1nc2cc(-c3cnn(Cc4ccccc4)c3)cc(-c3cnn(C4CCOCC4)c3)n2n1] |

TABLE 2A-continued
| Example Number | Structure |
| --- | --- |
| II-127 | 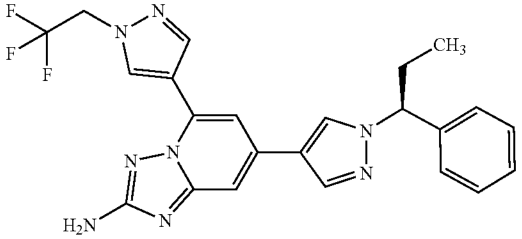 [SMILES: CC[C@@H](c1ccccc1)n1cc(-c2cc(-c3cnn(CC(F)(F)F)c3)n3nc(N)nc3c2)cn1] |
| II-128 | 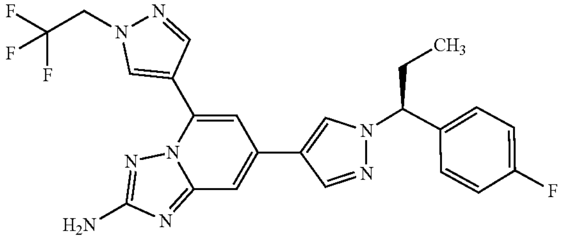 [SMILES: CC[C@@H](c1ccc(F)cc1)n1cc(-c2cc(-c3cnn(CC(F)(F)F)c3)n3nc(N)nc3c2)cn1] |
| II-129 | 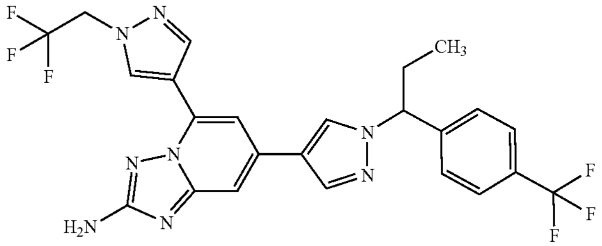 [SMILES: CCC(c1ccc(C(F)(F)F)cc1)n1cc(-c2cc(-c3cnn(CC(F)(F)F)c3)n3nc(N)nc3c2)cn1] |
| II-132 | 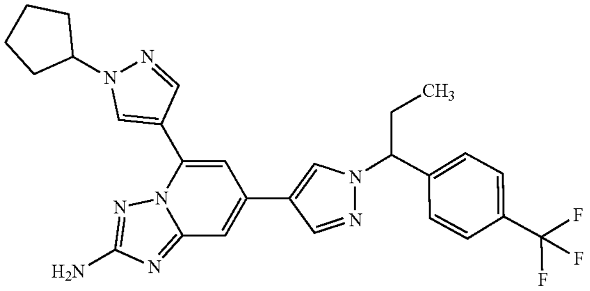 [SMILES: CCC(c1ccc(C(F)(F)F)cc1)n1cc(-c2cc(-c3cnn(C4CCCC4)c3)n3nc(N)nc3c2)cn1] |
| II-135 | 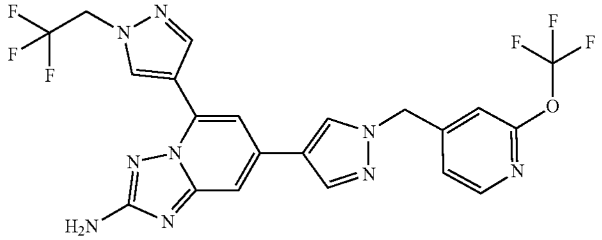 [SMILES: Nc1nc2cc(-c3cnn(Cc4ccnc(OC(F)(F)F)c4)c3)cc(-c3cnn(CC(F)(F)F)c3)n2n1] |
| II-136 | 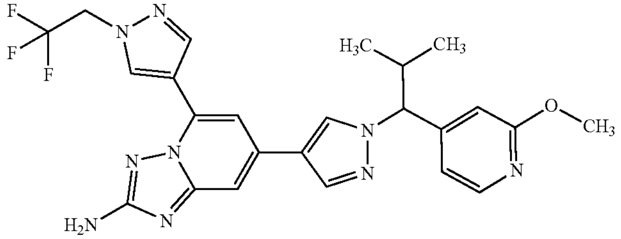 [SMILES: COc1cc(C(C(C)C)n2cc(-c3cc(-c4cnn(CC(F)(F)F)c4)n4nc(N)nc4c3)cn2)ccn1] |

TABLE 2A-continued
| Example Number | Structure |
|---|---|
| II-138 | 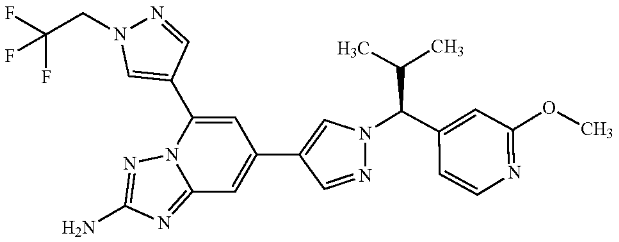 [SMILES: COc1cc([C@H](C(C)C)n2cc(-c3cc(-c4cnn(CC(F)(F)F)c4)n4nc(N)nc4c3)cn2)ccn1] |
| II-139 | 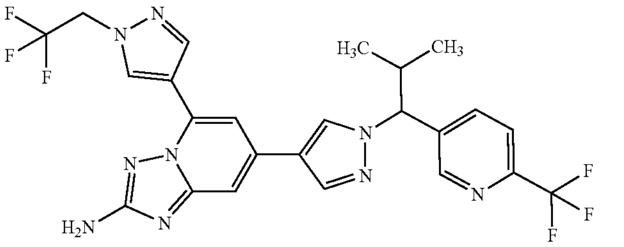 [SMILES: CC(C)C(c1ccc(C(F)(F)F)nc1)n1cc(-c2cc(-c3cnn(CC(F)(F)F)c3)n3nc(N)nc3c2)cn1] |
| II-140 | 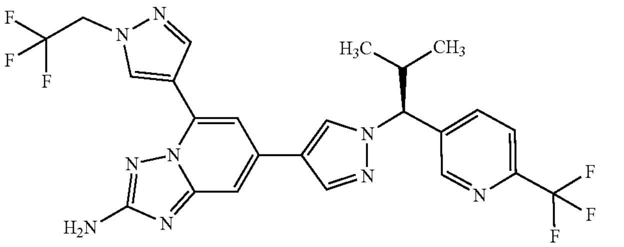 [SMILES: CC(C)[C@@H](c1ccc(C(F)(F)F)nc1)n1cc(-c2cc(-c3cnn(CC(F)(F)F)c3)n3nc(N)nc3c2)cn1] |
| II-142 | 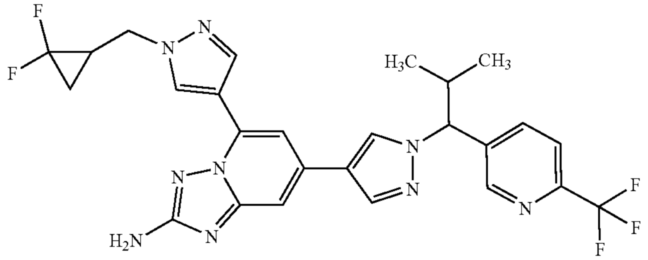 [SMILES: CC(C)C(c1ccc(C(F)(F)F)nc1)n1cc(-c2cc(-c3cnn(CC4CC4(F)F)c3)n3nc(N)nc3c2)cn1] |
| II-143 | 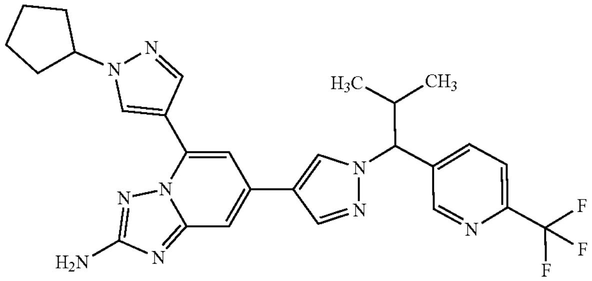 [SMILES: CC(C)C(c1ccc(C(F)(F)F)nc1)n1cc(-c2cc(-c3cnn(C4CCCC4)c3)n3nc(N)nc3c2)cn1] |
| II-145 | 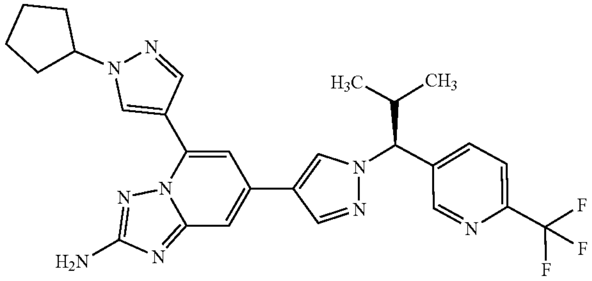 [SMILES: CC(C)[C@@H](c1ccc(C(F)(F)F)nc1)n1cc(-c2cc(-c3cnn(C4CCCC4)c3)n3nc(N)nc3c2)cn1] |

TABLE 2A-continued
| Example Number | Structure |
| --- | --- |
| II-146 | 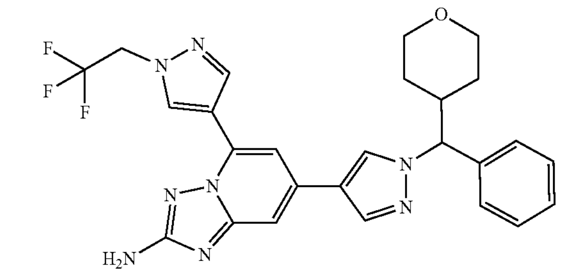 [SMILES: Nc1nc2cc(-c3cnn(C(c4ccccc4)C4CCOCC4)c3)cc(-c3cnn(CC(F)(F)F)c3)n2n1] |
| II-149 | 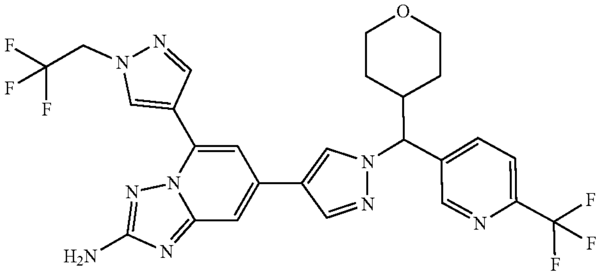 [SMILES: Nc1nc2cc(-c3cnn(C(c4ccc(C(F)(F)F)nc4)C4CCOCC4)c3)cc(-c3cnn(CC(F)(F)F)c3)n2n1] |
| II-152 | 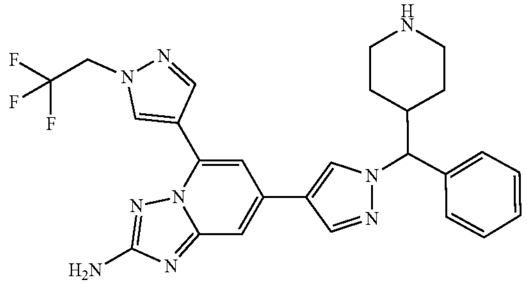 [SMILES: Nc1nc2cc(-c3cnn(C(c4ccccc4)C4CCNCC4)c3)cc(-c3cnn(CC(F)(F)F)c3)n2n1] |
| II-153 | 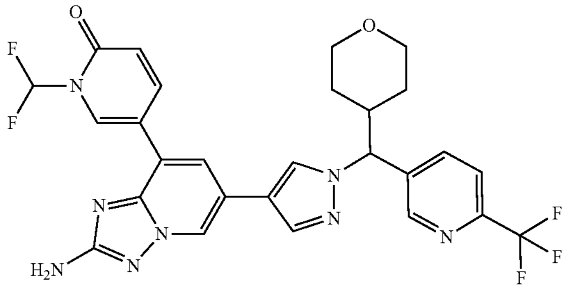 [SMILES: Nc1nc2c(-c3ccc(=O)n(C(F)F)c3)cc(-c3cnn(C(c4ccc(C(F)(F)F)nc4)C4CCOCC4)c3)cn2n1] |
| II-156 | 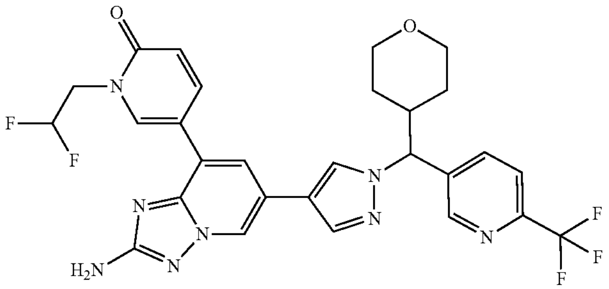 [SMILES: Nc1nc2c(-c3ccc(=O)n(CC(F)F)c3)cc(-c3cnn(C(c4ccc(C(F)(F)F)nc4)C4CCOCC4)c3)cn2n1] |

TABLE 2A-continued
| Example Number | Structure |
| --- | --- |
| II-159 | 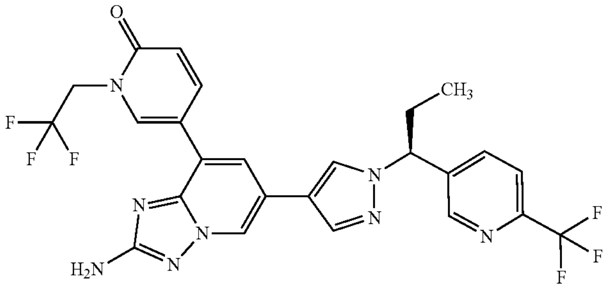 [SMILES: CC[C@@H](c1ccc(C(F)(F)F)nc1)n1cc(-c2cc(-c3ccc(=O)n(CC(F)(F)F)c3)c3nc(N)nn3c2)cn1] |
| II-160 | 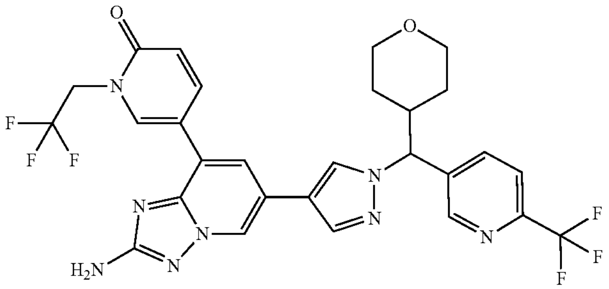 |
| II-162 | 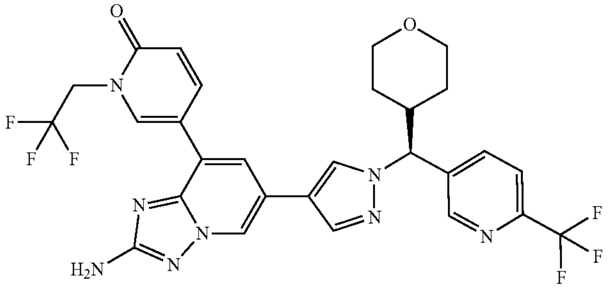 [SMILES: Nc1nc2c(-c3ccc(=O)n(CC(F)(F)F)c3)cc(-c3cnn([C@H](c4ccc(C(F)(F)F)nc4)C4CCOCC4)c3)cn2n1] |
| II-163 | 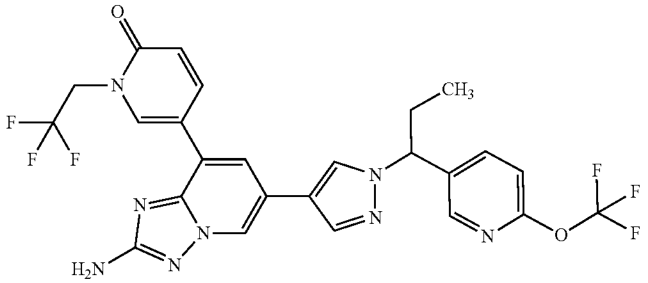 [SMILES: CCC(c1ccc(OC(F)(F)F)nc1)n1cc(-c2cc(-c3ccc(=O)n(CC(F)(F)F)c3)c3nc(N)nn3c2)cn1] |
| II-166 | 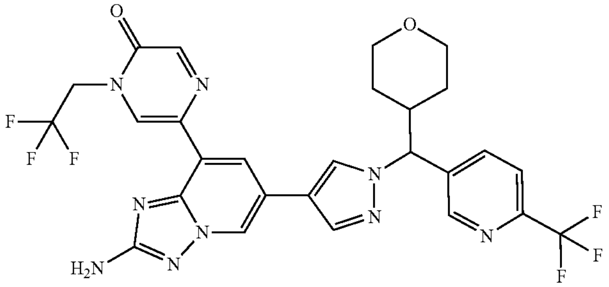 [SMILES: Nc1nc2c(-c3cn(CC(F)(F)F)c(=O)cn3)cc(-c3cnn(C(c4ccc(C(F)(F)F)nc4)C4CCOCC4)c3)cn2n1] |

TABLE 2A-continued
| Example Number | Structure |
| --- | --- |
| II-169 | 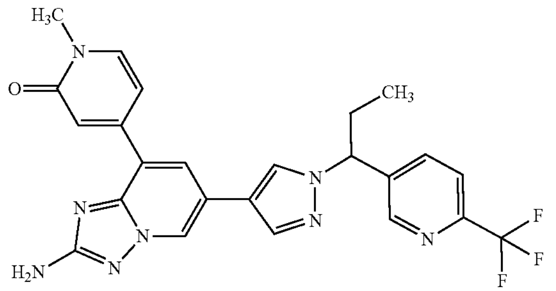 [SMILES: CCC(c1ccc(C(F)(F)F)nc1)n1cc(-c2cc(-c3ccn(C)c(=O)c3)c3nc(N)nn3c2)cn1] |
| II-172 | 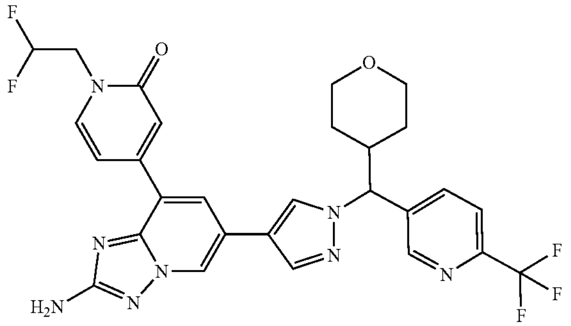 [SMILES: Nc1nc2c(-c3ccn(CC(F)F)c(=O)c3)cc(-c3cnn(C(c4ccc(C(F)(F)F)nc4)C4CCOCC4)c3)cn2n1] |
| II-175 | 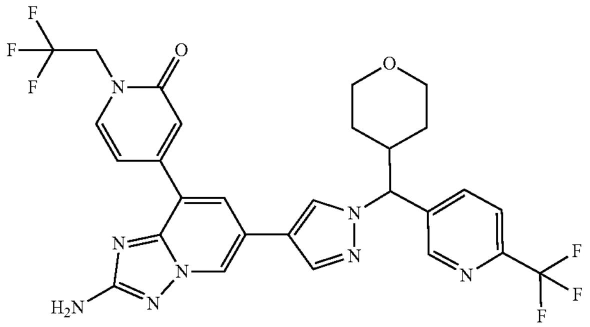 [SMILES: Nc1nc2c(-c3ccn(CC(F)(F)F)c(=O)c3)cc(-c3cnn(C(c4ccc(C(F)(F)F)nc4)C4CCOCC4)c3)cn2n1] |
| II-178 | 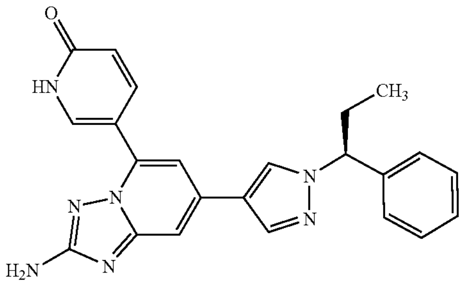 [SMILES: CC[C@@H](c1ccccc1)n1cc(-c2cc(-c3ccc(=O)[nH]c3)n3nc(N)nc3c2)cn1] |
| II-179 | 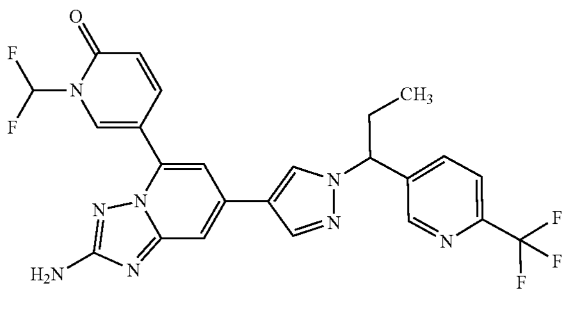 [SMILES: CCC(c1ccc(C(F)(F)F)nc1)n1cc(-c2cc(-c3ccc(=O)n(C(F)F)c3)n3nc(N)nc3c2)cn1] |

TABLE 2A-continued
| Example Number | Structure |
| --- | --- |
| II-182 | 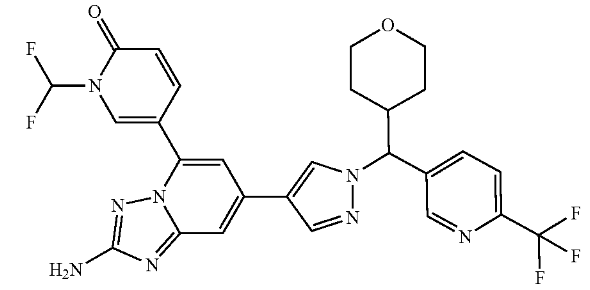 [SMILES: Nc1nc2cc(-c3cnn(C(c4ccc(C(F)(F)F)nc4)C4CCOCC4)c3)cc(-c3ccc(=O)n(C(F)F)c3)n2n1] |
| II-185 | 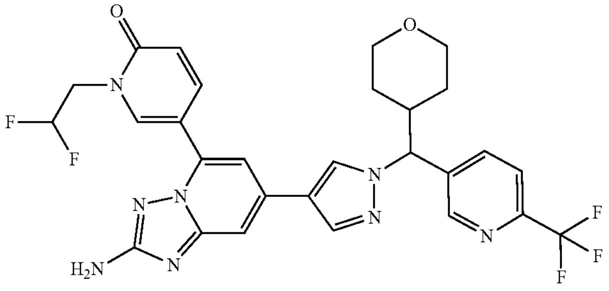 [SMILES: Nc1nc2cc(-c3cnn(C(c4ccc(C(F)(F)F)nc4)C4CCOCC4)c3)cc(-c3ccc(=O)n(CC(F)F)c3)n2n1] |
| II-188 | 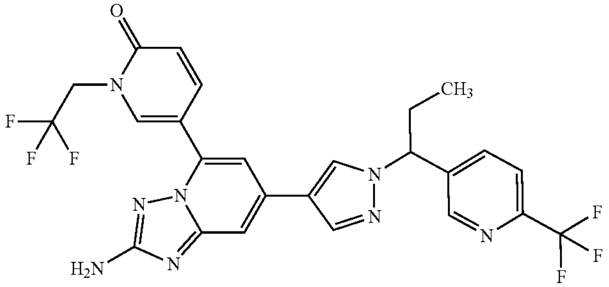 [SMILES: CCC(c1ccc(C(F)(F)F)nc1)n1cc(-c2cc(-c3ccc(=O)n(CC(F)(F)F)c3)n3nc(N)nc3c2)cn1] |
| II-190 | 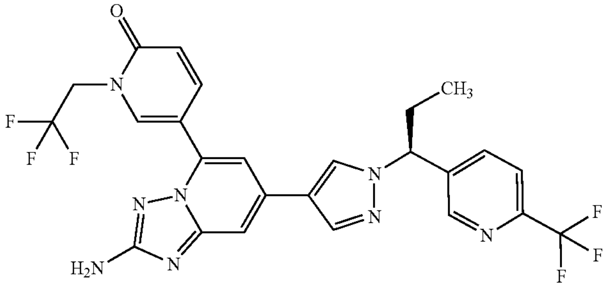 [SMILES: CC[C@@H](c1ccc(C(F)(F)F)nc1)n1cc(-c2cc(-c3ccc(=O)n(CC(F)(F)F)c3)n3nc(N)nc3c2)cn1] |
| II-191 | 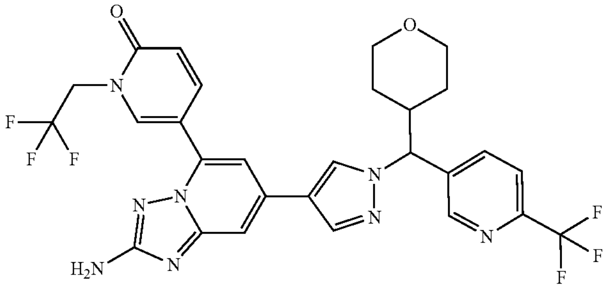 [SMILES: Nc1nc2cc(-c3cnn(C(c4ccc(C(F)(F)F)nc4)C4CCOCC4)c3)cc(-c3ccc(=O)n(CC(F)(F)F)c3)n2n1] |

TABLE 2A-continued

| Example Number | Structure |
| --- | --- |
| II-194 | 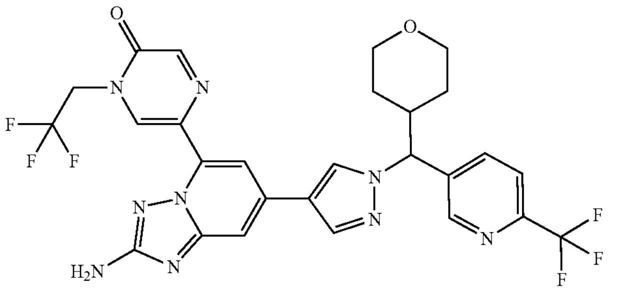 [SMILES: Nc1nc2cc(-c3cnn(C(c4ccc(C(F)(F)F)nc4)C4CCOCC4)c3)cc(-c3cn(CC(F)(F)F)c(=O)cn3)n2n1] |
| II-197 | 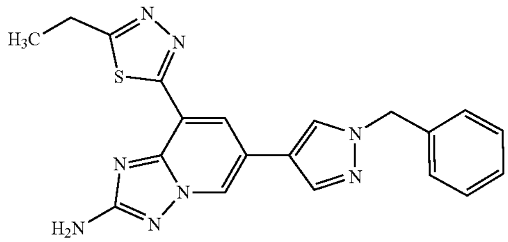 [SMILES: CCc1nnc(-c2cc(-c3cnn(Cc4ccccc4)c3)cn3nc(N)nc23)s1] |
| II-198 | 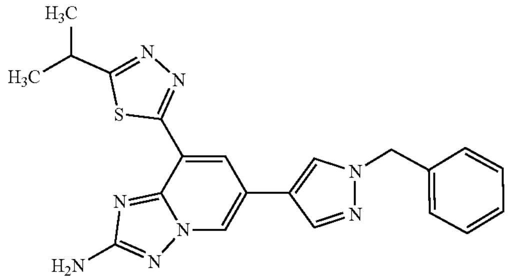 [SMILES: CC(C)c1nnc(-c2cc(-c3cnn(Cc4ccccc4)c3)cn3nc(N)nc23)s1] |
| II-199 | 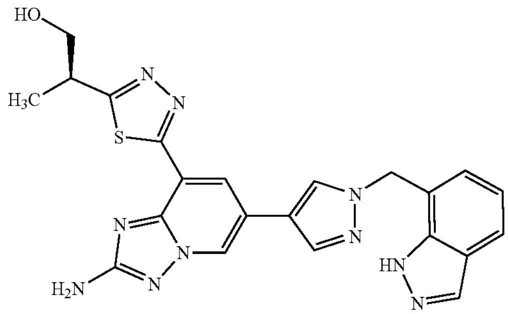 [SMILES: C[C@@H](CO)c1nnc(-c2cc(-c3cnn(Cc4cccc5cn[nH]c45)c3)cn3nc(N)nc23)s1] |

and pharmaceutically acceptable salts thereof.

Irrespective of the particular combinations of the radicals specified, the individual radical definitions specified in the combinations of radicals are also replaced as desired by radical definitions from other combinations.

Processes of Preparing Compounds of Formulae (A), (AI), (I), (I-A), (I-B), (I-C), (I-D), (B), (BII), (II), (II-A), (II-B), (II-C), (II-D), (II-E), (II-F), (II-G), and (IL-H)

The following process schemes include intermediates that are designated using alphanumeric character strings that include a Roman numeral followed by a letter. A number of the strings used to designate intermediates of compounds of Formula (I) are also used to designate intermediates of compounds of Formula (II). For purposes of clarification, in instances where a string used to designate an intermediate of a compound of Formula (I) is the same as a string used to designate an intermediate of a compound of Formula (II), each string applies solely to its respective intermediate.

Processes of Preparing Compounds of Formula (I)

Process Scheme 1

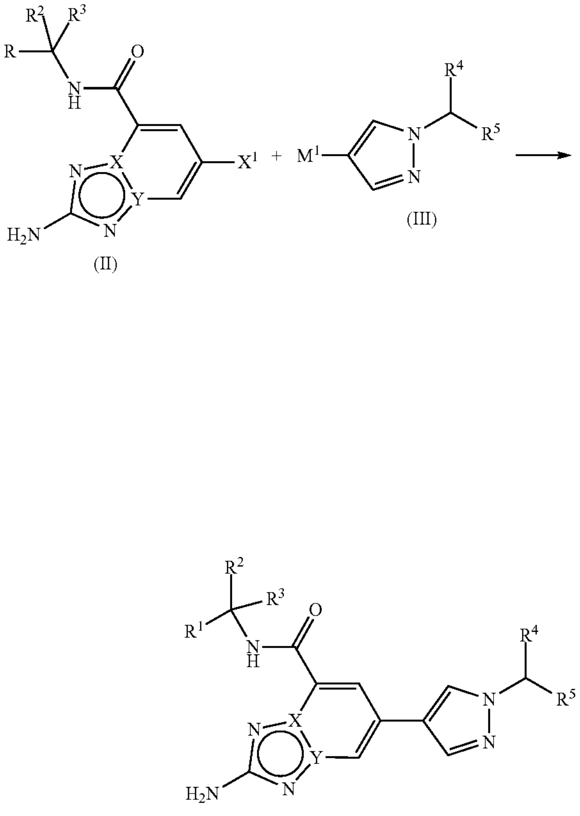

(II) (III) (I)

The processes for preparing compounds of the formula (I) of the disclosure are optionally performed according to Scheme 1 in which $R^1$, $R^2$, $R^3$, $R^4$, $R^5$, X and Y are defined above, $X^1$ is a halogen, for example, chloride or bromide, and $M^1$ is an organometallic coupling partner, for example, a boronic ester or a boronic acid. A compound of the general formula (I) is obtained under metal-catalyzed cross-coupling condition, known to those skilled in the art.

Compound of formula (I) can be prepared under Suzuki conditions by reacting compounds of general formulae (II) and (III), where (III) is a boronic acid or the boronate equivalent, in presence of a base as a tertiary amine base such as triethylamine, NN-diisopropylethylamine, pyridine or 2,6-dimethylpyridine (e.g., trimethylamine); or a carbonate base such as sodium carbonate, potassium carbonate or caesium carbonate (e.g., cesium carbonate); a phosphate base such as potassium orthophosphate, and a palladium catalyst such as but not limited to tetrakis(triphenylphosphine)palladium, dichlorobis(triphenylphosphine)palladium, 1,1'-bis(diphenylphosphino)ferrocene-palladium(II) dichloride dichloromethane complex or XPhos-Pd-G2. The reaction is typically performed within a temperature range of +60° C. to +200° C., for example, at +80° C. to +120° C.; and in an ethereal solvent such as diethyl ether, diisopropyl ether, tert-butyl methyl ether, tetrahydrofuran, 1,4-dioxane or 1,2-dimethoxymethane, for example, 1,4-dioxane, optionally with the addition of N,N-dimethylformamide, toluene or water; see for example WO 2018017633, WO 2004072033 or WO 2017215506. Alternatively, the reaction may be performed in a microwave reactor.

Process Scheme 2

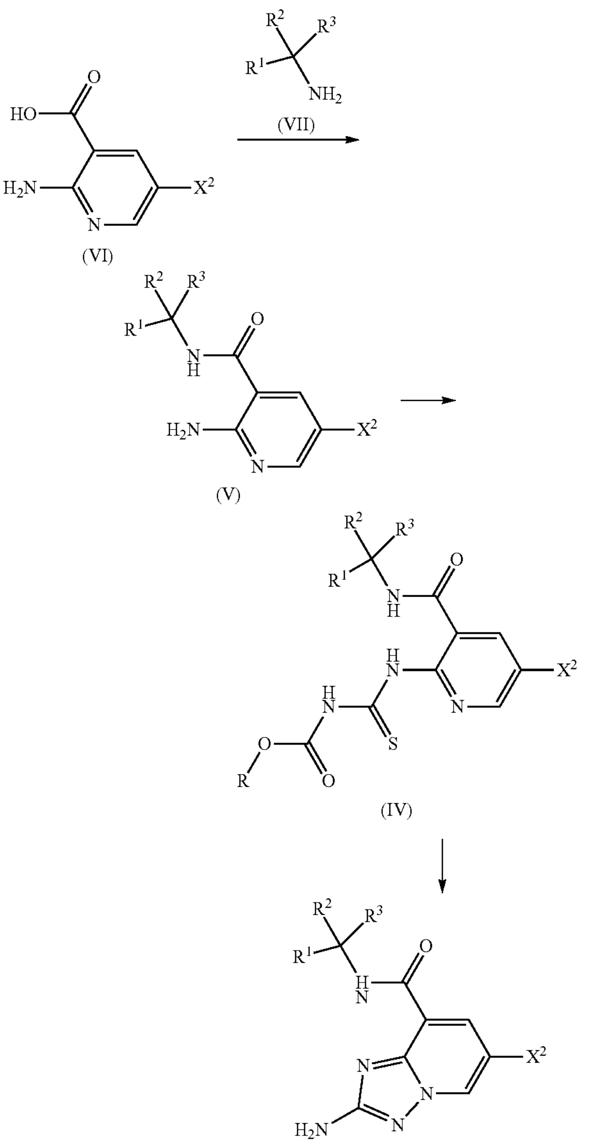

(VI) (VII) (V) (IV) (IIa)

The processes for preparing compounds of the formula (IIa) of the disclosure are optionally performed according to Scheme 2 in which $R^1$ to $R^3$ are defined as above, R is an alkyl or aryl group and $X^2$ is a halogen, for example, chloride or bromide. A compound of general formula (IIa) is obtained from the compound of general formula (IV) by condensation and cyclization with an appropriate hydroxylamine salt and a tertiary amine base such as triethylamine, N,N-diisopropylethylamine, pyridine or 2,6-dimethylpyridine; for example, triethylamine; see for example Bioorg. Med. Chem. Lett. 2009, 19, 894-899, WO 2010020363 or J. Med. Chem. 2014, 57, 9323-9342.

The introduction of the thiourea moiety in compound of general formula (IV) is accomplished by treatment of compound of general formula (V) with a commercially available isothiocyanatocarbonate at room temperature in presence of an ether solvent, for example, tetrahydrofuran or 1,4-dioxane, or a chlorinated solvent such as but not limited to dichloromethane; see for example *Bioorg. Med. Chem.Lett.* 2009, 19, 894-899 or *J. Med. Chem.* 2014, 57, 9323-9342.

The coupling reaction between compounds of general formulae (VI) and (VII) to give (V) can be conducted with the aid of a condensing or activating agent or can be effected via the intermediate of the corresponding carbonyl chloride formed from (VI).

Suitable condensing or activating agents of this kind are, for example, carbodiimides such as N,N-diethyl-, N,N-dipropyl-, N,N-diisopropyl-, N,N-dicyclohexylcarbodiimide (DCC) or N-(3-dimethylaminopropyl)-N-ethylcarbodiimide hydrochloride (EDC), phosgene derivatives such as N,N-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, a-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl) phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N,N-tetramethyluronium tetrafluoroborate (TBTU), O-(benzotriazol-1-yl)-N,N,N,N-tetramethyluronium hexafluorophosphate (HBTU), 2-(2-oxo-1-(2H)-pyridyl)-1,1,3,3-tetramethyluronium tetrafluoroborate (TPTU), 0-(7-azabenzotriazol-1-yl)-N,N,N,N-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine, N,N-diisopropylethylamine, pyridine or 4-N,N-dimethylaminopyridine (DMAP). For example, O-(benzotriazol-1-yl)-N,N,N',N'-tetramethyluronium tetrafluoroborate (TBTU) or O-(7-azabenzotriazol-1-yl)-N,N,N,N-tetramethyluronium hexafluorophosphate (HATU), in each case in combination with N,N-diisopropylethylamine as base.

In the case of a two-stage reaction regime via the carbonyl chloride formed from (VI), the coupling with the amine component (VII) is conducted in the presence of a customary auxiliary base such as sodium carbonate, potassium carbonate, sodium hydride, triethylamine, N-methylmorpholine (NMM), N-methylpiperidine, N,N-diisopropylethylamine, pyridine, 2,6-dimethylpyridine, 4-N,N-dimethylaminopyridine (DMAP), 1,8-diazabicyclo[5.4.0]undec-7-ene (DBU) or 1,5-diazabicyclo[4.3.0]non-5-ene (DBN); for example, N,N-diisopropylethylamine. The preparation of the carbonyl chloride itself is accomplished in a customary manner by treatment of the carboxylic acid (VI) with thionyl chloride, phosphoryl chloride or oxalyl chloride, optionally under the catalytic action of N,N-dimethylformamide (DMF), in an inert solvent such as dichloromethane.

Inert solvents for the coupling reactions mentioned are, for example, ethers such as diethyl ether, diisopropyl ether, tert-butyl methyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, acetonitrile, butyronitrile, ethyl acetate, pyridine, dimethyl sulfoxide (DMSO), N,N-dimethylformamide (DMF), N,N'-dimethylpropyleneurea (DMPU) or N-methylpyrrolidinone (NMP). It is also possible to use mixtures of such solvents. In some embodiments, the solvent is dichloromethane, tetrahydrofuran, N,N-dimethylformamide or mixtures of these solvents. The reactions are generally effected within a temperature range of −20

Process Scheme 3

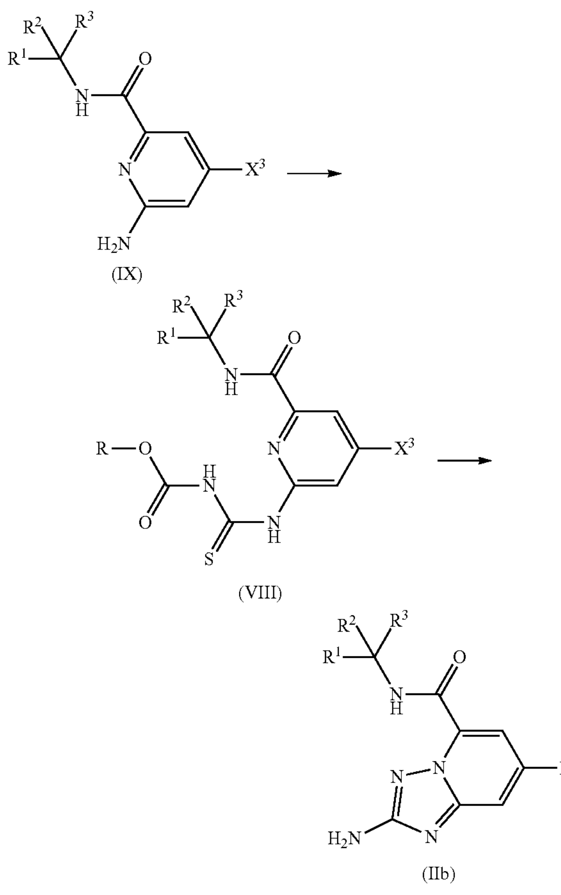

The processes for preparing compounds of the formula (IIb) of the disclosure are optionally performed according to Scheme 3 in which $R^1$ to $R^3$ are defined as above, R is an alkyl or aryl group and $X^3$ is a halogen, for example, chloride or bromide. The preparation of compound of general formula (IIb) is obtained from the compound of general formula (IV) by condensation and cyclization with an appropriate hydroxylamine salt and a tertiary amine base such as triethylamine, N,N-diisopropylethylamine, pyridine or 2,6-dimethylpyridine; for example, triethylamine; see for example *Bioorg. Med. Chem. Lett.* 2009, 19, 894-899, WO 2010020363 or *J. Med. Chem.* 2014, 57, 9323-9342.

The introduction of the thiourea moiety in compound of general formula (VIII) is accomplished by treatment of compound of general formula (IX) with a commercially available isothiocyanatocarbonate at room temperature in presence of an ether solvent, for example, tetrahydrofuran or 1,4-dioxane, or a chlorinated solvent such as but not limited to dichloromethane; see for example *Bioorg. Med. Chem. Lett.* 2009, 19, 894-899 or *J. Med. Chem.* 2014, 57, 9323-9342.

Process Scheme 4

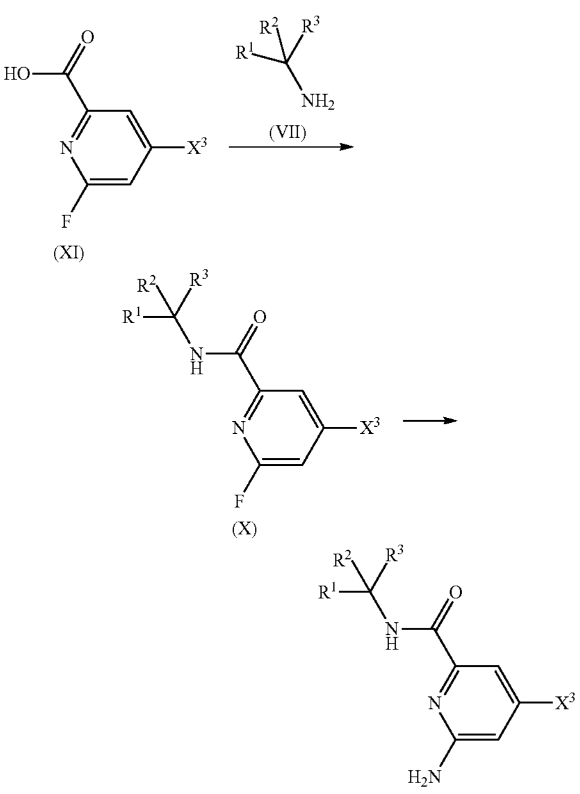

(XI)

(VII)

(X)

(IX)

The processes for preparing compounds of the formula (IX) of the disclosure are optionally performed according to Scheme 4 in which $R^1$ to $R^3$ are defined as above, and $X^3$ is a halogen, for example, chloride or bromide. Compound of general formula (IX) is obtained by condensation of compound of general formula (X) with a source of ammonia, for example, a 30% aqueous solution of ammonia, and advantageously conducted using a microwave apparatus or an autoclave apparatus within a temperature range of +60° C. to +200° C., for example, at +100° C. to +180° C.; see for example WO 2015013715, *Tetrahedron* 2006, 62, 10937-10944 or WO 20110118248.

The amide coupling reaction between compounds of formulae (XI) and (VII) to yield (X) is generally conducted with the aid of a condensing or activating agent. These reactions are conducted under analogous conditions to those described specifically above for the related coupling reaction between (VI) and (VII) to yield (V).

Process Scheme 5

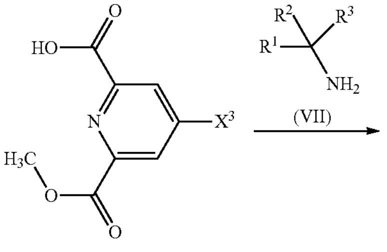

(VII)

(XV)

-continued

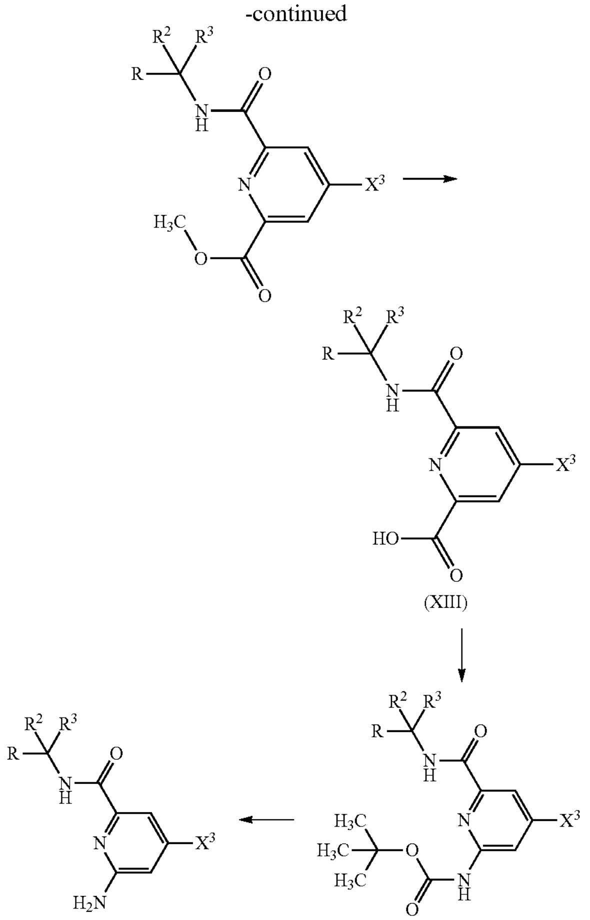

(XIII)

The processes for preparing compounds of the formula (IX) of the disclosure are optionally performed according to Scheme 5 in which $R^1$ to $R^3$ are defined as above, and $X^3$ is a halogen, for example, chloride or bromide. Compound of general formula (IX) is also obtained by removal of tert-butylcarbamate protecting group from compound of formula (XII), and effected by customary methodology by treatment with an acid, for example, hydrochloric acid or trifluoroacetic acid, in an alcohol such as methanol, ethanol or isopropanol or an ether such as diethyl ether, diisopropyl ether, tert-butyl methyl ether, tetrahydrofuran, 1,4-dioxane or 1,2-dimethoxymethane as solvent [cf. T. W. Greene and P. G. M. Wuts, Protective Groups in Organic Synthesis, Wiley, New York, 1999]. The reactions are generally conducted within a temperature range of −20° C. to +40° C.

Curtius rearrangement to provide compound of general formula (XII) is conducted by treatment of carboxylic acid of formula (XIII) with a source of azide, for example, diphenyl phosphoroazidate, in presence of tert-butanol and a tertiary amine base such as triethylamine, N,N-diisopropylethylamine, pyridine or 2,6-dimethylpyridine; for example, triethylamine; in an ether such as diethyl ether, diisopropyl ether, tert-butyl methyl ether, tetrahydrofuran, 1,4-dioxane or 1,2-dimethoxymethane as solvent and within a temperature range of +40° C. to +180° C., for example, at +80° C. to +160° C.; see for example *Tetrahedron Lett.* 2003, 44, 9267-9269; *J. Med. Chem.* 2005, 48, 4535-4546; *J. Med. Chem.* 2006, 49, 3614-3627.

Compound of general formula (XIII) is then obtained in a customary manner by alkaline hydrolysis of the ester of the formula (XIV). The coupling reaction between compounds of formulae (X) and (VII) to yield (X) [amide formation] is generally conducted with the aid of a condensing or activating agent. These reactions are conducted under analogous conditions to those described specifically above for the related coupling reaction between (VI) and (VII) to yield (V).

Process Scheme 6

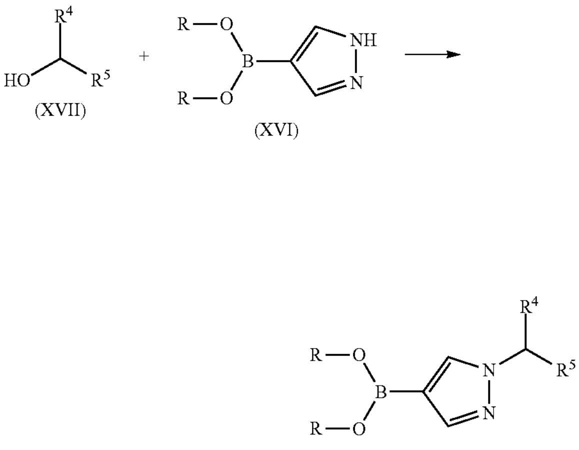

(XVII) (XVI) (III)

The processes for preparing compounds of the formula (III) of the disclosure are optionally performed according to Scheme 6 in which $R^4$ and $R^5$ are defined as above, and R is an alkyl, or two R moieties can form a substituted cycloalkyl together. The Mitsunobu reaction between hydroxyl of formula (XVII) and compound of formula (XVI) to yield compound of formula (III) can be conducted with the aid of a coupling agent such as but not limited to di-tert-butyl azodicarboxylate or diisopropyl azodicarboxylate, with a source of phosphine such as but not limited to triphenylphosphine, or cyanomethylenetributylphosphorane (Tsunoda's reagent) in an ether such as diethyl ether, diisopropyl ether, tert-butyl methyl ether, tetrahydrofuran, 1,4-dioxane or 1,2-dimethoxymethane as solvent, for example, tetrahydrofuran. The reactions are generally effected within a temperature range of −20° C. to +200° C., for example, at rt to +100° C., see for example WO 2017102091 or *J. Med. Chem.* 2016, 59, 1370-1387.

Alternatively a two-stage reaction regime, via an activated form of compound (XVII) with the component (XVI), is conducted in the presence of a customary auxiliary base such as sodium carbonate, potassium carbonate, sodium hydride, triethylamine, N,N-diisopropylethylamine, pyridine; for example, potassium carbonate. The reaction run in a solvent, for example, tetrahydrofuran, dichloromethane or acetonitrile, and generally takes place within a temperature range of 0° C. to +80° C.; see for example WO 2011100502 or WO 2014109414.

The preparation of the activated form of compound (XVII) itself is accomplished in a customary manner by treatment of the hydroxyl group with an activating reagent such as but not limited to methylsulfonyl chloride, in presence of a base such as but not limited to triethylamine. Optionally a catalyst such as 4-(dimethylamino)-pyridine can be added.

Process Scheme 7

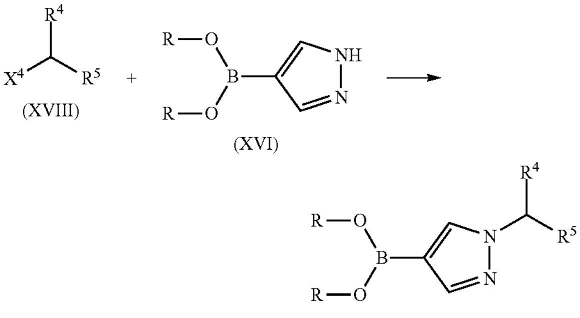

(XVIII) (XVI) (III)

The processes for preparing compounds of the formula (III) of the disclosure are optionally performed according to Scheme 7 in which $R^4$ and $R^5$ are defined as above, R is an alkyl, or two R moieties can form a substituted cycloalkyl together, and $X^4$ is a halide, for example, bromide or iodide. The nucleophilic substitution reaction between alkyl halide of formula (XVIII) and compound of formula (XVI) to yield compound of formula (III) can be conducted with the aid of a base such as but not limited to cesium carbonate or, DBU, in an inert polar aprotic solvent such as acetone, methyl ethyl ketone, acetonitrile, butyronitrile, ethyl acetate, pyridine, dimethyl sulfoxide, N,N-dimethylformamide, N,N-dimethylpropyleneurea or N-methylpyrrolidinone, for example, acetonitrile or N,N-dimethylformamide, and generally takes place within a temperature range of +60° C. to +200° C.; see for example J. Med. Chem. 2011, 54, 6342-6363, WO 2016055028 or WO 2014060395.

Process Scheme 8

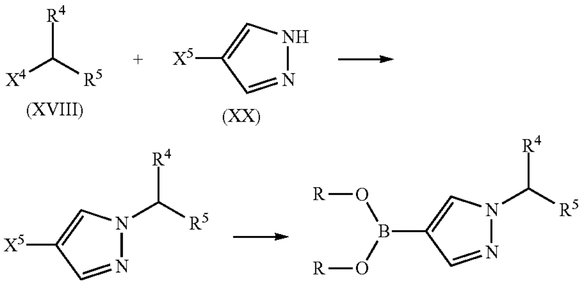

(XVIII) (XX) (XIX) (III)

The processes for preparing compounds of the formula (III) of the disclosure are optionally performed according to Scheme 8 in which $R^4$ and $R^5$ are defined as above, R is a carbonyl group, and $X^4$ and $X^5$ are halides, for example, bromide or iodide. Compound of formula (III) can be obtained by reaction of compound of formula (XIX) with triisopropyl borate, in presence of an organolithium base such as but not limited to n-butyllithium, followed by treatment by pinacol. The additions are typically performed within a temperature range of −78° C. to +25° C., in an inert ether such as diethyl ether, diisopropyl ether, tert-butyl methyl ether, tetrahydrofuran, 1,4-dioxane or 1,2-dimethoxymethane, for example, tetrahydrofuran; or toluene, or hexanes, or mixtures thereof; see for example *Org. Proc. Res. Dev.* 2010, 14, 849-858 or *Tetrahedron Lett.* 2009, 50, 6783-6786.

Alternatively compound of formula (III) can be obtained under Suzuki cross-coupling conditions by reacting compounds of general formula (XIX) and 4,4,4',4',5,5,5',5'-octamethyl-2,2'-bi-1,3,2-dioxaborolane, in presence of a base such as but not limited to potassium acetate, and a palladium catalyst such as but not limited to 1,1'-bis(diphenylphosphino)ferrocene-palladium(II)dichloride dichloromethane complex. The reaction is typically performed within a temperature range of +60° C. to +200° C., for example, at +100° C. to +180° C.; and in a solvent such as but not limited to tetrahydrofuran, 1,4-dioxane, 1,2-dimethoxymethane or N,N-dimethylfonnamide, for example, 1,4-dioxane; see for example *Bioorg. Med. Chem.* 2013, 21, 6804-6820, *Eur. J. Med. Chem.* 2017, 126, 1083-1106 or WO 2016000615. Additionally the reaction may be performed in a microwave reactor.

The nucleophilic substitution reaction between alkyl halide of formula (XVIII) and compound of formula (XX) to yield compound of formula (XIX) can be conducted with the aid of a base such as but not limited to sodium hydride or potassium carbonate, in an inert solvant such as tetrahydrofuran, 1,4-dioxane, 1,2-dimethoxymethane, dimethylsulfoxide or N,N-dimethylformamide, for example, tetrahydrofuran. The reaction is typically performed within a temperature range of +60° C. to +200° C., for example, at +100° C. to +180° C.; see for example *J. Org. Chem.* 2017, 82, 11295-11303 or *Tetrahedron Lett.* 2016, 57, 895-898.

Process Scheme 9

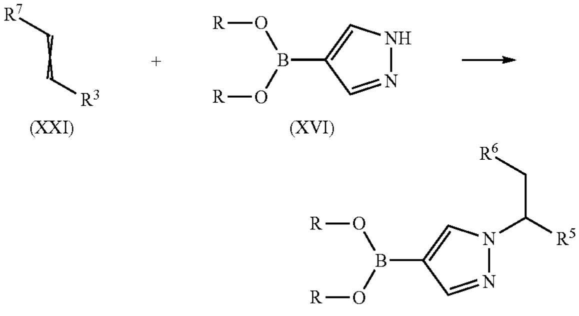

(XXI) (XVI) (III)

The processes for preparing compounds of the formula (III) of the disclosure are optionally performed according to Scheme 9 in which $R^5$ is defined as above, $R^7$ is an electron withdrawing group such as a nitrile or ester group, R is an alkyl, or two R moieties can form a substituted cycloalkyl together. The nucleophilic substitution reaction between compound of formula (XXI) and compound of formula (XVI) to yield compound of formula (III) can be conducted with the aid of a base such as but not limited to cesium carbonate or DBU, in an inert polar aprotic solvent such as acetone, methyl ethyl ketone, acetonitrile, butyronitrile, ethyl acetate, pyridine, dimethyl sulfoxide, N,N-dimethylformamide, N,N-dimethylpropyleneurea or N-methylpyrrolidinone, for example, acetonitrile or N,N-dimethylformamide. The reaction is typically performed within a temperature range of 0° C. to +180° C., for example, at +20° C. to +100° C.; see for example WO 2009064835, *Tetrahedron Lett.* 2007, 48, 2845-2849 or WO 2015188681.

Process Scheme 10

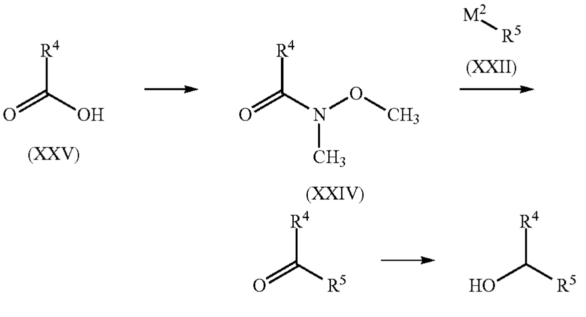

(XXV) (XXIV) (XXII) (XVII)

in which $R^4$ and $R^5$ are defined above and $M^2$ is an organometallic coupling partner, for example, an organomagnesium species. Compound of formula (XVII) can be obtained by reduction of carbonyl of formula (XXII) by a known method with the aid of a reducing agent in a presence of a solvent and generally takes place within a temperature range of −78° C. to +25° C. Suitable reducing agents for the process step for such purposes are customary alkali metal borohydrides such as lithium borohydride, sodium borohydride, potassium borohydride, sodium cyanoborohydride or sodium triacetoxyborohydride; for example, sodium borohydride. Suitable solvents for these reactions are especially alcohols such as methanol, ethanol, n-propanol or isopropanol, ethers such as diisopropyl ether, tert-butyl methyl ether, tetrahydrofuran, 1,4-dioxane or 1,2-dimethoxymethane. For example, ethanol or tetrahydrofuran.

Compound of formula (XXII) can be obtained by addition of organomagnesium reagent of formula (XXIII) onto Weinreb amide of formula (XXIV) in an ether such as diisopropyl ether, tert-butyl methyl ether, tetrahydrofuran, 1,4-dioxane or 1,2-dimethoxymethane; and generally takes place within a temperature range of −78° C. to +25° C.

The coupling between compound of formula (XXV) and N-methoxymethanamine, for example, N-methoxymethanamine hydrochloride, to obtain compound of formula (XXIV) is effected in the same way as described specifically above for the related amide formation between compounds of general formulae (VI) and (VII) to give compound of formula (V). In some embodiments, the transformation is a two-stage reaction variant via the carbonyl chloride formed from (XXV).

Process Scheme 11

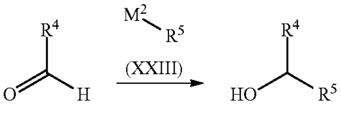

(XXVI) (XVII)

The processes for preparing compounds of the formula (I) of the disclosure are optionally performed according to Scheme 11 in which $R^4$ and $R^5$ are defined above and $M^2$ is an organometallic coupling partner, for example, an organomagnesium species. The addition of compound of formula (XXIII) onto the compound of formula (XXVI) to obtain compound of formula (XVII) is effected in the same way as described specifically above for the related addition between compounds of general formulae (XXIV) and (XXIII) to give compound of formula (XXII).

Useful reaction auxiliaries are, as appropriate, inorganic or organic bases or acid acceptors. These include alkali metal or alkaline earth metal acetates, amides, carbonates, hydrogencarbonates, hydrides, hydroxides or alkoxides, for example sodium acetate, potassium acetate or calcium acetate, lithium amide, sodium amide, potassium amide or calcium amide, sodium carbonate, potassium carbonate or calcium carbonate, sodium hydrogencarbonate, potassium hydrogencarbonate or calcium hydrogencarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; and also basic organic nitrogen compounds, for example trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]-octane (DABCO), 1,5-diazabicyclo [4.3.0]-non-5-ene (DBN) or 1,8-diazabicyclo[5.4.0]-undec-7-ene (DBU).

Useful reaction auxiliaries are, as appropriate, inorganic or organic acids. These include inorganic acids, for example hydrogen fluoride, hydrogen chloride, hydrogen bromide and hydrogen iodide, sulfuric acid, phosphoric acid and nitric acid, and acidic salts such as NaHSO4 and KHSO4, or organic acids, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated C6-C20 fatty acids, alkylsulfuric monoesters, alkylsulfonic acids (sulfonic acids having straight-chain or branched alkyl radicals having 1 to 20 carbon atoms), arylsulfonic acids or aryldisulfonic acids (aromatic radicals, such as phenyl and naphthyl, which bear one or two sulfonic acid groups), alkylphosphonic acids (phosphonic acids having straight-chain or branched alkyl radicals having 1 to 20 carbon atoms), arylphosphonic acids or aryldiphosphonic acids (aromatic radicals, such as phenyl and naphthyl, which bear one or two phosphonic acid radicals), where the alkyl and aryl radicals may bear further substituents, for example p-toluenesulfonic acid, salicylic acid, p-aminosalicylic acid, 2-phenoxybenzoic acid, 2-acetoxybenzoic acid, etc.

The processes according to the disclosure are optionally performed using one or more diluents. Useful diluents are virtually all inert organic solvents. These include aliphatic and aromatic, optionally halogenated hydrocarbons, such as pentane, hexane, heptane, cyclohexane, methyl cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether, tert-butyl methyl ether and dibutyl ether, glycol dimethyl ether and diglycol dimethyl ether, methyltetrahydrofuran, tetrahydrofuran and dioxane, ketones such as acetone, methyl ethyl ketone, methyl isopropyl ketone and methyl isobutyl ketone, esters, such as methyl acetate, ethyl acetate and butyl acetate, nitriles, for example acetonitrile, propionitrile and butyronitrile, alcohols, for example methanol, ethanol, propanol, iso-propanol, butanol, tert-butanol, amides, for example dimethylformamide, dimethylacetamide and N-methylpyrrolidone, and also dimethyl sulfoxide, tetramethylenesulfone and hexamethylphosphoramide and DMPU.

Some exemplary schemes for the synthesis of the core are shown below. The amino substituent in the pyridine ortho position was either installed via Schmitt rearrangement or nucleophilic aromatic substitution of an ortho-fluoro pyridine. The latter required anhydrous conditions in the silver fluoride mediated fluorination step.

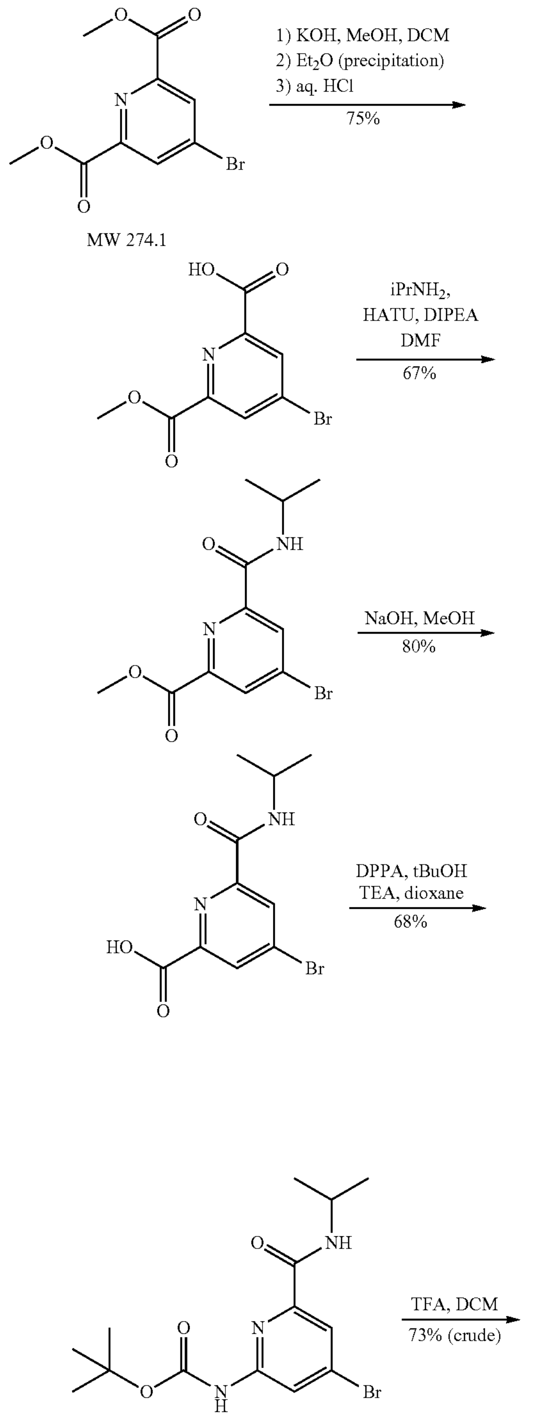

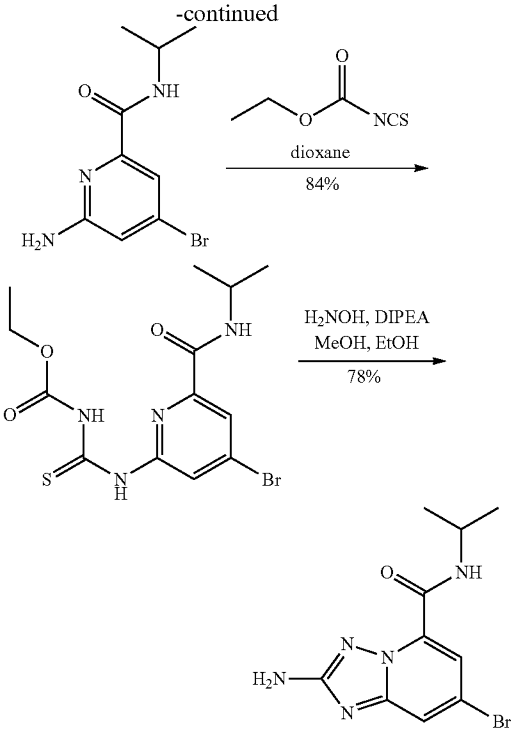
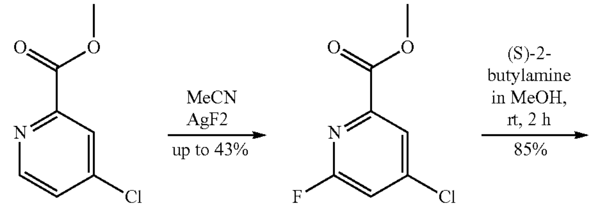
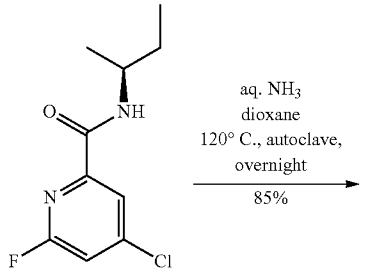
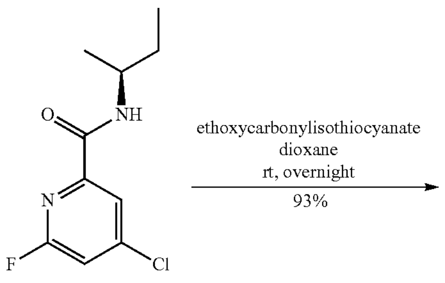
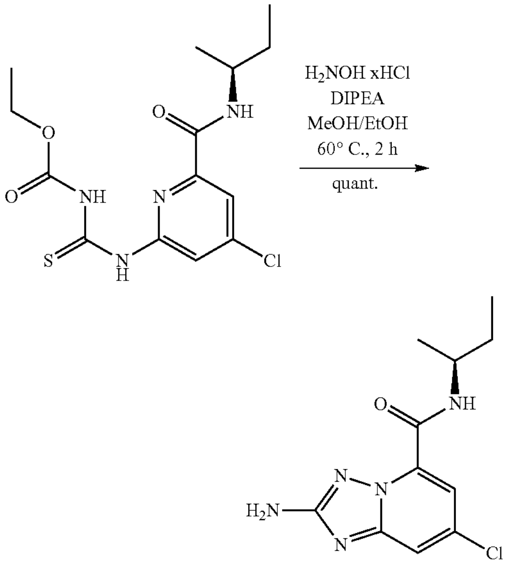
The scheme below depicts a coupling of the triazolo-pyridyl halide (X=halo) with the boronate ester of a pyrazole fragment by means of a Suzuki coupling.
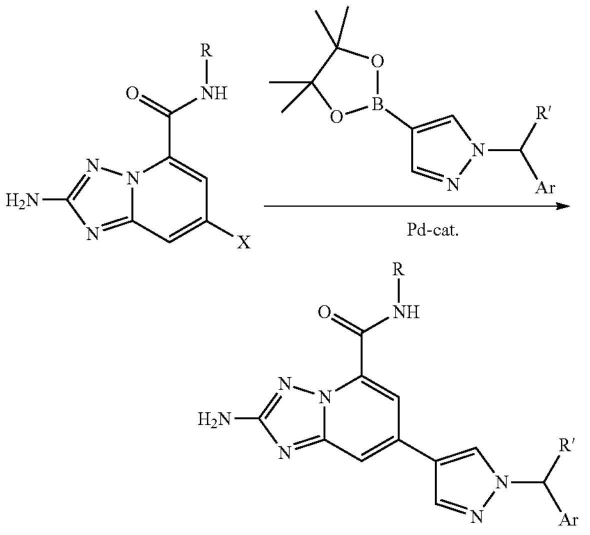
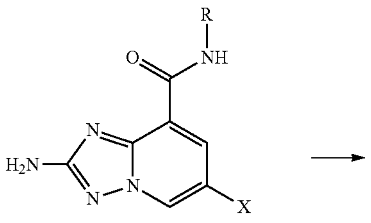

-continued

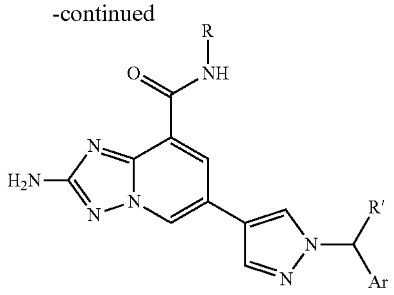

Processes of Preparing Compounds of Formula (II)

Process Scheme 12

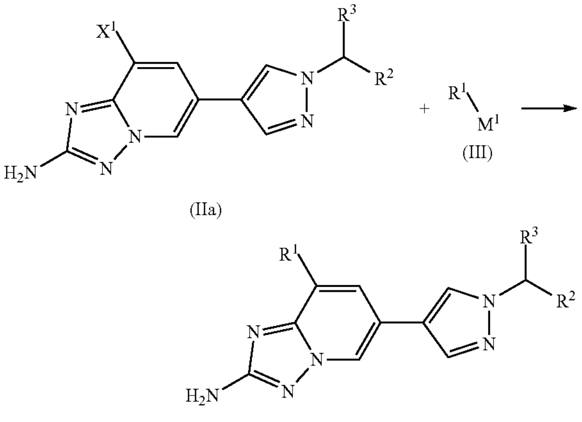

(IIa) (III) (Ia)

The processes for preparing compounds of the formula (Ia) of the disclosure are optionally performed according to Scheme 12 in which $R^1$, $R^2$ and $R^3$ are defined above, $X^1$ is a halogen, for example, chloride or bromide, and $R^1$-$M^1$ is an organometallic coupling partner. A compound of the general formula (Ia) is obtained under metal-catalyzed cross-coupling condition, known to those skilled in the art. Compounds of formula (La) can be prepared under Suzuki conditions by reacting compounds of general formulae (IIa) and (III), where (III) is a boronic acid or the boronate equivalent, in presence of a base as a tertiary amine base such as triethylamine, N,N-diisopropylethylamine, pyridine or 2,6-dimethylpyridine; for example, trimethylamine, or a carbonate base such as sodium carbonate, potassium carbonate or caesium carbonate; for example, caesium carbonate; a phosphate base such as potassium orthophosphate, and a palladium catalyst such as but not limited to tetrakis (triphenylphosphine)palladium, dichlorobis(triphenylphosphine) palladium, 1,1'-bis(diphenylphosphino)ferrocene-palladium(II)dichloride dichloromethane complex or chloro (2-dicyclohexylphosphino-2',4',6'-triisopropyl-1,1'-biphenyl)[2-(2'-amino-1,1'-biphenyl)]palladium(II). The reaction is typically performed within a temperature range of +60° C. to +200° C., for example, at +80° C. to +120° C.; and in an ethereal solvent such as diethyl ether, diisopropyl ether, tert-butyl methyl ether, tetrahydrofuran, 1,4-dioxane or 1,2-dimethoxymethane, for example, 1,4-dioxane, optionally with the addition of N,N-dimethylformamide, toluene or water; see for example WO 2011092272; WO 2010141796; WO 2017042114; *Bioorg. Med. Chem.* 2018, 26, 3227-3241 or *Org. Process. Res. Dev.* 2016, 20, 2085-2091. Additionally the reaction may be performed in a microwave reactor.

Process Scheme 13

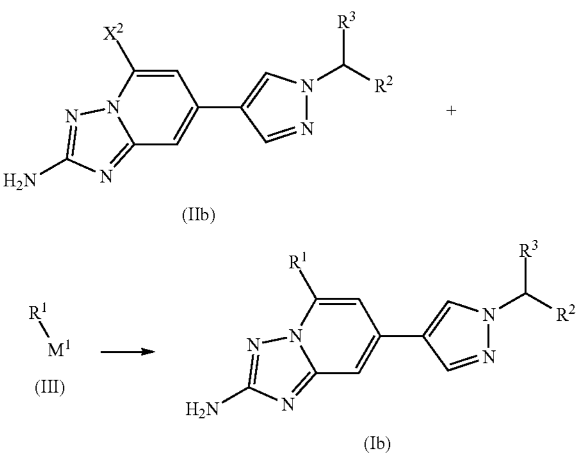

(IIb) (III) (Ib)

The processes for preparing compounds of the formula (Ib) of the disclosure are optionally performed according to Scheme 13 in which $R^1$, $R^2$ and $R^3$ are defined above, $X^2$ is a halogen, for example, chloride, bromide or iodide, and $R^1$-$M^2$ is an organometallic coupling partner. A compound of the general formula (Ib) is obtained under metal-catalyzed cross-coupling condition between compounds of formulae (IIb) and (III). This reaction is conducted under analogous conditions to those described above in Scheme 12.

Process Scheme 14

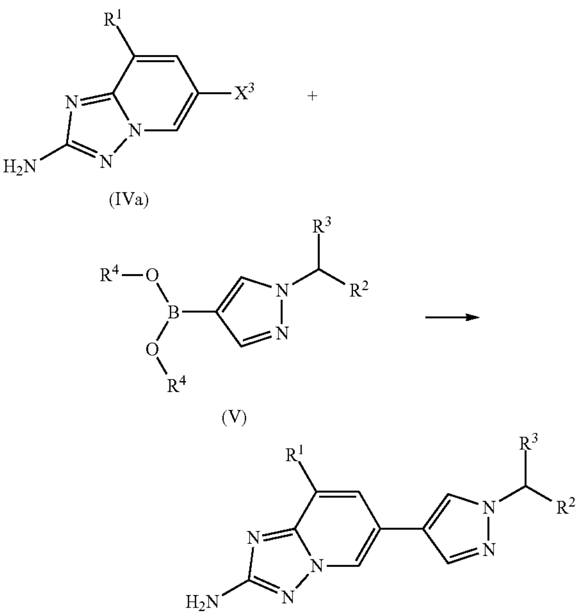

(IVa) (V) (Ia)

The processes for preparing compounds of the formula (Ia) of the disclosure are optionally performed according to Scheme 14 in which $R^1$, $R^2$ and $R^3$ are defined above. $R^4$ is alkyl or two $R^4$ moieties can form a substituted cycloalkyl. $X^3$ is a halogen, for example, bromide. A compound of the general formula (Ia) is obtained under Suzuki cross-coupling conditions between compounds of formulae (IVa) and (V). These reactions are conducted under analogous conditions to those described above.

Process Scheme 15

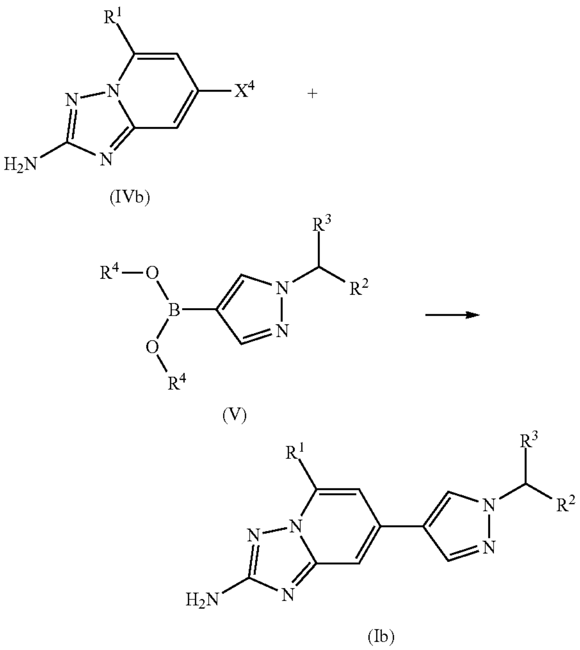

(IVb)

(V)

(Ib)

The processes for preparing compounds of the formula (Ib) of the disclosure are optionally performed according to Scheme 15 in which $R^1$, $R^2$, $R^3$ and $R^4$ are defined above. $X^4$ is a halogen, for example, chloride or bromide. A compound of the general formula (Ib) is obtained under Suzuki cross-coupling conditions between compounds of formulae (IVb) and (V). These reactions are conducted under analogous conditions to those described above.

Process Scheme 16

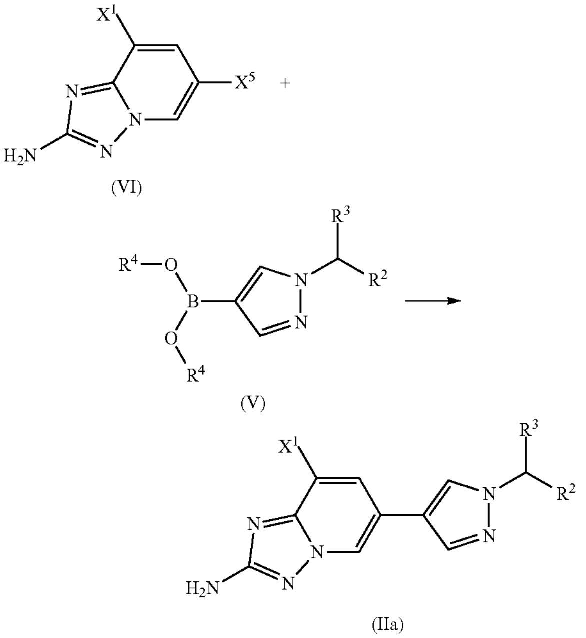

(VI)

(V)

(IIa)

The processes for preparing compounds of the formula (IIa) of the disclosure are optionally performed according to Scheme 16 in which $R^1$, $R^2$, $R^3$ and $R^4$ are defined above. $X^1$ is a halogen, for example, chloride, and $X^5$ is a halogen, for example, bromide. A compound of the general formula (IIa) is obtained under Suzuki cross-coupling conditions as described above between compounds of formulae (V) and (VI).

Process Scheme 17

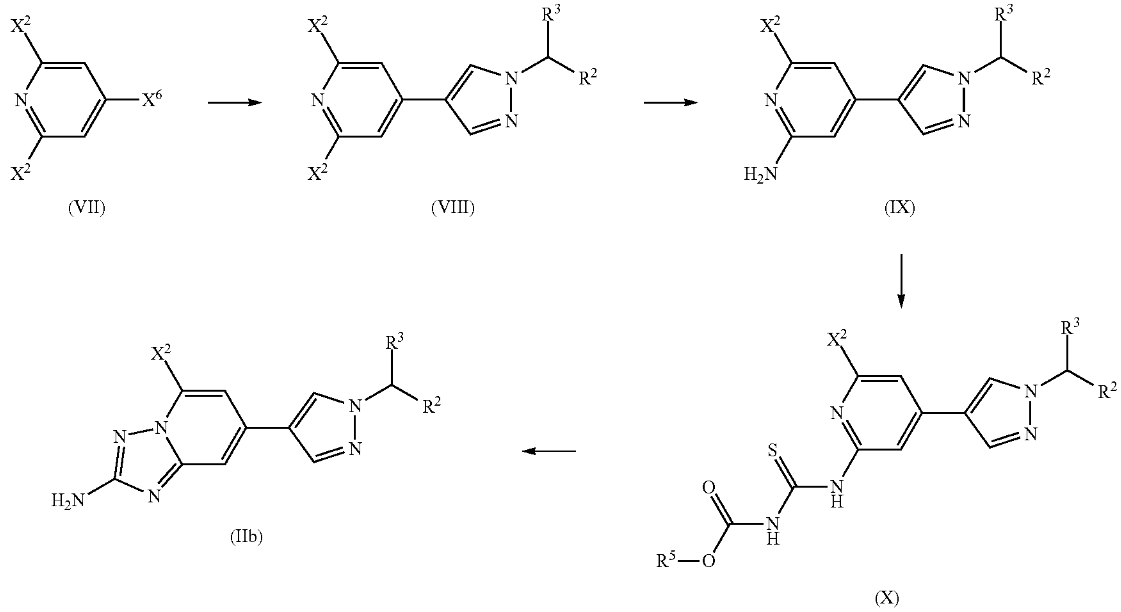

(VII)

(VIII)

(IX)

(X)

(IIb)

The processes for preparing compounds of the formula (IIb) of the disclosure are optionally performed according to Scheme 17 in which $R^2$ and $R^3$ are defined above, $R^5$ is an alkyl or aryl group, $X^2$ is a halogen, for example, chloride, and $X^6$ is also a halogen, for example, iodide. A compound of general formula (IIb) is obtained from the compound of general formula (X) by condensation and cyclization with an appropriate hydroxylamine salt and a tertiary amine base such as triethylamine, N,N-diisopropylethylamine, pyridine or 2,6-dimethylpyridine; for example, triethylamine; see for example *Bioorg. Med. Chem. Lett.* 2009, 19, 894-899, WO 2010020363 or *J. Med. Chem.* 2014, 57, 9323-9342.

The introduction of the thiourea moiety in compound of general formula (X) is accomplished by treatment of compound of general formula (IX) with a commercially available isothiocyanatocarbonate at room temperature in presence of a ether solvent, for example, tetrahydrofuran or 1,4-dioxane, or a chlorinated solvent such as but not limited to dichloromethane; see for example *Bioorg. Med. Chem. Lett.* 2009, 19, 894-899 or *J. Med. Chem.* 2014, 57, 9323-9342.

Compound of general formula (IX) is obtained by condensation of compound of general formula (VIII) with a source of ammonia, for example, a 30% aqueous solution of ammonia, and advantageously conducted using a microwave apparatus or an autoclave apparatus within a temperature range of +60° C. to +220° C., for example, at +100° C. to +200° C.; see for example *Tetrahedron* 2014, 70, 8648-8656; WO 2009027283 or *J. Med. Chem.* 2012, 55, 8603-8614.

A compound of the general formula (VIII) is obtained under Suzuki cross-coupling conditions between compounds of formulae (VII) and (V). These reactions are conducted under Suzuki coupling conditions analogous conditions to those described above.

Process Scheme 18

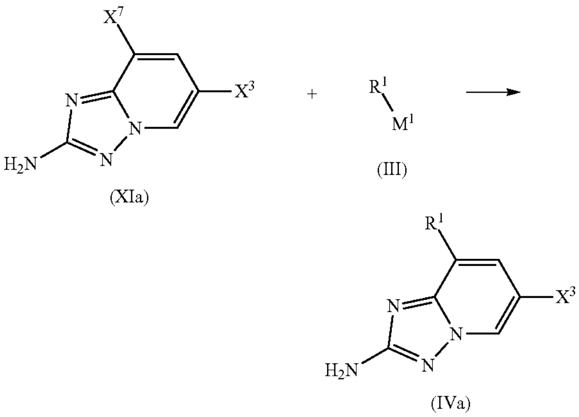

(XIa) (III) (IVa)

The processes for preparing compounds of the formula (IVa) of the disclosure are optionally performed according to Scheme 18 in which $R^1$ is defined above, $X^3$ is a halogen, for example, chloride, $X^7$ is a halogen, for example, bromide or iodide, and $R^1$-$M^1$ is an organometallic coupling partner. A compound of the general formula (IVa) is obtained under Suzuki cross-coupling conditions between compounds of formulae (III) and (XIa). This reaction is conducted under analogous conditions to those described above.

Process Scheme 19

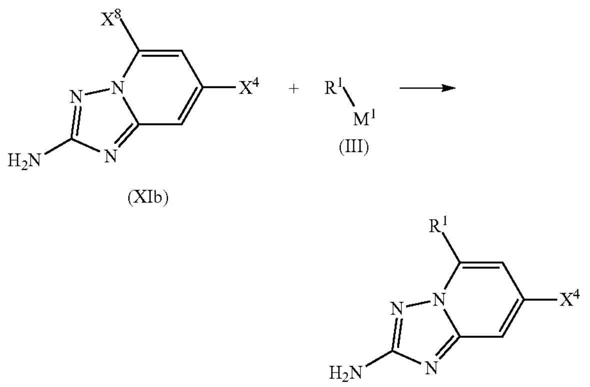

(XIb) (III) (IVb)

The processes for preparing compounds of the formula (IVb) of the disclosure are optionally performed according to Scheme 19 in which $R^1$ is defined above, $X^4$ is a halogen, for example, chloride, $X^8$ is a halogen, for example, chloride, and $R^1$-$M^1$ is an organometallic coupling partner. A compound of the general formula (IVb) is obtained under Suzuki cross-coupling conditions between compounds of formulae (III) and (XIb). This reaction is conducted under analogous conditions to those described above.

Process Scheme 20

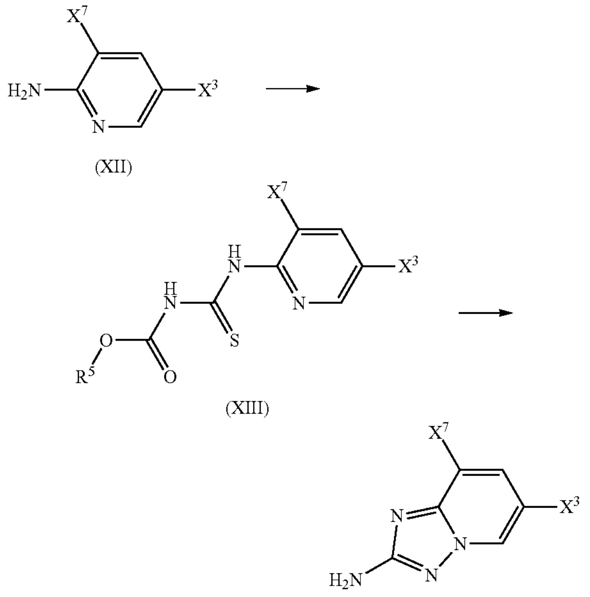

(XII) (XIII) (XIa)

The processes for preparing compounds of the formula (XIa) of the disclosure are optionally performed according to Scheme 20 in which $R^5$ is defined above, $X^3$ is a halogen, for example, chloride, and $X^7$ is also a halogen, for example, bromide or iodide. A compound of general formula (XIa) is obtained from the compound of general formula (XIII) by condensation and cyclization with an appropriate hydroxylamine salt. This reaction is conducted under analogous conditions to those described specifically above for the related cyclization reaction of (X) to yield (IIb).

The introduction of the thiourea moiety in compound of general formula (XII) is accomplished by treatment of compound of general formula (XIII) with a commercially available isothiocyanatocarbonate. This reaction is conducted under analogous conditions to those described specifically above for the transformation of compound of formula (IX) to yield (X).

Process Scheme 21

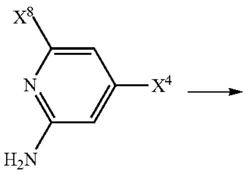

(XIV)

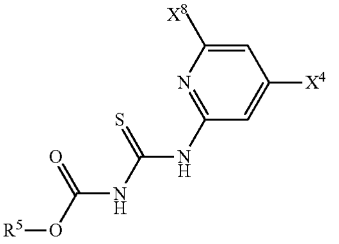

(XV)

-continued

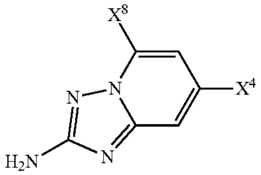

(XIb)

The processes for preparing compounds of the formula (XIb) of the disclosure are optionally performed according to Scheme 21 in which $R^5$ is defined above, $X^4$ is a halogen, for example, chloride, and $X^8$ is also a halogen, for example, chloride. A compound of general formula (XIb) is obtained from the compound of general formula (XIV) via compound of general formula (XV) in analogy to Scheme 20.

Process Scheme 22

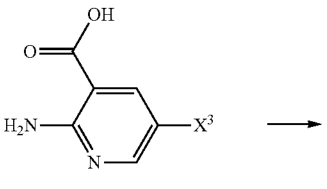

(XVI)

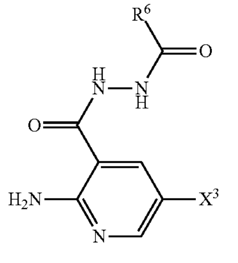

(XVII)

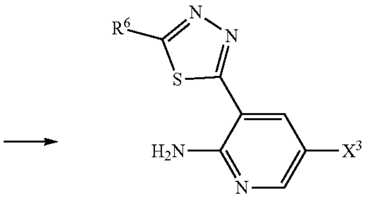

(XVII)

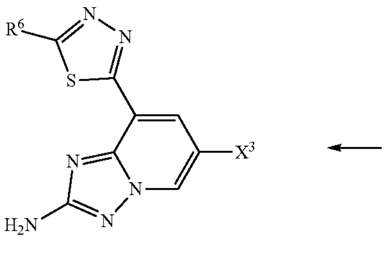

(IVa')

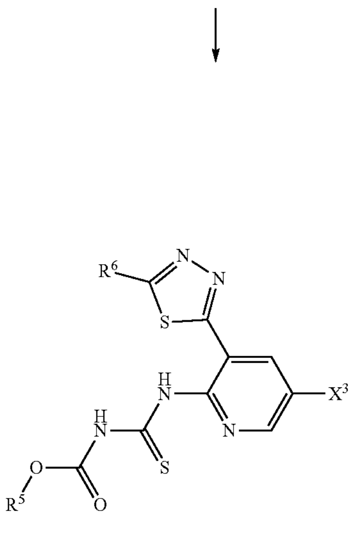

(IXX)

The processes for preparing compounds of the formula (IVa') of the disclosure are optionally performed according to Scheme 22 in which $R^5$ and $R^6$ are defined above and $X^3$ is a halogen, for example, bromide. A compound of general formula (IVa') is obtained from the compound of general formula (IXX) by condensation and cyclization with an appropriate hydroxylamine salt. This reaction is conducted under analogous conditions to those described specifically above for the related cyclization reaction of (X) to yield (IIb).

The introduction of the thiourea moiety in compound of general formula (IXX) is accomplished by treatment of compound of general formula (XVIII) with a commercially available isothiocyanatocarbonate. This reaction is conducted under analogous conditions to those described specifically above for the transformation of compound of formula (IX) to yield (X).

A compound of general formula (XVIII) is obtained by treatment of compound of general formula (XVII) with a source of sulfur such as Lawesson's reagent, Belleau's reagent, diphosphorus pentasulfide or tetraphosphorus decasulfide, for example, is given to Lawesson's reagent or diphosphorus pentasulfide. The reaction is typically performed within a temperature range of +60° C. to +200° C., for example, at +80° C. to +160° C.; and in a solvent such as but not limited to tetrahydrofuran, toluene or xylene; see for example *J. Agric. Food Chem.* 2005, 53, 3120-3125; WO 2015161011; *Tetrahedron* 2009, 65, 9989-9996 or *J. Organomet. Chem.* 2015, 785, 11-18.

The coupling reaction between compounds of general formulae (XVI) and the appropriate hydrazide to give (XVII) can be conducted with the aid of a condensing or activating agent or can be effected via the corresponding carbonyl chloride formed from (XVI). Suitable condensing or activating agents of this kind are, for example, carbodiimides such as N,N-diethyl-, N,N-dipropyl-, N,N'-diisopropyl-, N,N-dicyclohexylcarbodiimide (DCC) or N-(3-dimethylaminopropyl)-N-ethylcarbodiimide hydrochloride (EDC), phosgene derivatives such as N,N-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, a-chloroenamines such as 1-chloro-2-methyl-1-dimethylamino-1-propene, phosphorus compounds such as propanephosphonic anhydride, diethyl cyanophosphonate, bis(2-oxo-3-oxazolidinyl)phosphoryl chloride, benzotriazol-1-yloxytris(dimethylamino)phosphonium hexafluorophosphate or benzotriazol-1-yloxytris(pyrrolidino) phosphonium hexafluorophosphate (PyBOP), or uronium compounds such as O-(benzotriazol-1-yl)-N,N,N,N-tetramethyluronium tetrafluoroborate (TBTU), O-(benzotriazol-1-yl)-N,N,N,N-tetramethyluronium hexafluorophosphate (HBTU), 2-(2-oxo-1-(2H)-pyridyl)-1,1,3,3-tetramethyluronium tetrafluoroborate (TPTU), 0-(7-azabenzotriazol-1-yl)-N,N,N,N-tetramethyluronium hexafluorophosphate (HATU) or O-(1H-6-chlorobenzotriazol-1-yl)-1,1,3,3-tetramethyluronium tetrafluoroborate (TCTU), optionally in combination with further auxiliaries such as 1-hydroxybenzotriazole (HOBt) or N-hydroxysuccinimide (HOSu), and also as bases alkali metal carbonates, for example sodium carbonate or potassium carbonate, or tertiary amine bases such as triethylamine, N-methylmorpholine (NMM), N-methylpiperidine, N,N-diisopropylethylamine, pyridine or 4-N,N-dimethylaminopyridine (DMAP). In some embodiments, O-(benzotriazol-1-yl)-N,N,N,N-tetramethyluronium tetrafluoroborate (TBTU) or O-(7-azabenzotriazol-1-yl)-N,N,N,N-tetramethyluronium hexafluorophosphate (HATU) can be used, in each case in combination with N,N-diisopropylethylamine as base.

In the case of a two-stage reaction regime via the carbonyl chloride formed from (XVI), the coupling with the appropriate hydrazide is conducted in the presence of a customary auxiliary base such as sodium carbonate, potassium carbonate, sodium hydride, triethylamine, N-methylmorpholine (NMM), N-methylpiperidine, N,N-diisopropylethylamine, pyridine, 2,6-dimethylpyridine, 4-N,N-dimethylaminopyridine (DMAP), 1,8-diazabicyclo[5.4.0]undec-7-ene (DBU) or 1,5-diazabicyclo[4.3.0]non-5-ene (DBN); for example, N,N-diisopropylethylamine. The preparation of the carbonyl chloride itself is accomplished in a customary manner by treatment of the carboxylic acid (XX) with thionyl chloride, phosphoryl chloride or oxalyl chloride, optionally under the catalytic action of N,N-dimethylformamide (DMF), in an inert solvent such as dichloromethane.

Inert solvents for the coupling reactions mentioned are, for example, ethers such as diethyl ether, diisopropyl ether, tert-butyl methyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, acetonitrile, butyronitrile, ethyl acetate, pyridine, dimethyl sulfoxide (DMSO), NN-dimethylformamide (DMF), N,N-dimethylpropyleneurea (DMPU) or N-methylpyrrolidinone (NMP). It is also possible to use mixtures of such solvents. In some embodiments, the solvent can be dichloromethane, tetrahydrofuran, N,N-dimethylformamide or mixtures of these solvents. The reactions are generally effected within a temperature range of −20° C. to +40° C., for example, at 0° C. to +30° C.

Process Scheme 23

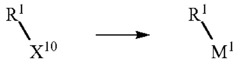

(XX) (III)

The processes for preparing compounds of the formula (III) of the disclosure are optionally performed according to Scheme 23 in which $R^1$ and $M^1$ are defined above, and $X^{10}$ is a halogen, for example, bromide. Compound of formula (III) can be obtained by reaction of compound of formula (XX) with triisopropyl borate, in presence of an organolithium base such as but not limited to n-butyllithium, optionally followed by treatment with pinacol. The additions are typically performed within a temperature range of −78° C. to +25° C., in an inert ether such as diethyl ether, diisopropyl ether, tert-butyl methyl ether, tetrahydrofuran, 1,4-dioxane or 1,2-dimethoxymethane, for example, tetrahydrofuran; or toluene, or hexanes, or mixtures thereof; see for example *Tetrahedron Lett.* 2005, 46, 4737-4740; *Tetrahedron* 2002, 58, 4369-4373; *Angew. Chem. Int. Ed.* 2016, 55, 10396-10400 or *J. Org. Chem.* 2002, 67, 5394-5397.

Alternatively compound of formula (III) can be obtained under Suzuki cross-coupling conditions by reacting compounds of general formula (XX) and 4,4,4',4',5,5,5',5'-octamethyl-2,2'-bi-1,3,2-dioxaborolane, in presence of a base such as but not limited to potassium acetate, and a palladium catalyst such as but not limited to 1,1'-bis(diphenylphosphino)ferrocene-palladium(II)dichloride dichloromethane complex. The reaction is typically performed within a temperature range of +60° C. to +200° C., for example, at +80° C. to +120° C.; and in a solvent such as but not limited to tetrahydrofuran, 1,4-dioxane, 1,2-dimethoxymethane or N,N-dimethylformamide, for example, 1,4-dioxane; see for example Organometallics 2017, 36, 3429-3434; *Bioorg. Med. Chem.* 2016, 24, 5861-5872; *Angew. Chem., Int. Ed.* 2007, 46, 5359-5363 or *Tetrahedron Lett.* 2011, 52, 1631-1634. Additionally the reaction may be performed in a microwave reactor.

carbonyl chloride formed from (XXI). The coupling is conducted in the presence of a customary auxiliary base such as but not limited to lithium hexamethyldisilazane. The preparation of the carbonyl chloride itself is accomplished in a customary manner by treatment of the carboxylic acid (XXI) with thionyl chloride, phosphoryl chloride or oxalyl chloride, optionally under the catalytic action of N,N-dimethylformamide (DMF), in an inert solvent such as dichloromethane.

Inert solvents for the coupling reactions mentioned are, for example, ethers such as diethyl ether, diisopropyl ether, Process Scheme 24

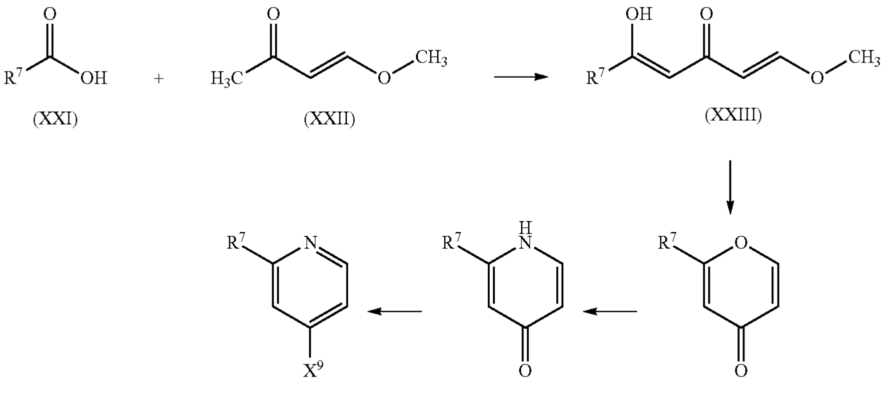

(XXI) (XXII) (XXIII)

(XXVI) (XXV) (XXIV)

The processes for preparing compounds of the formula (XXVI) of the disclosure are optionally performed according to Scheme 24 in which $R^7$ is defined above and $X^9$ is a halogen, for example, bromide. Compound of formula (XXVI) can be obtained under treatment of compound of general formula (XXV) with an excess of halogenating reagent such as phosphorous trichloride, phosphoric trichloride, thionyl chloride, phosphorous tribromide, phosphorus pentabromide, phosphoric tribromide, for example, phosphoric tribromide. The reaction is typically performed neat or in a solvent such as but not limited to N,N-dimethylformamide; and within a temperature range of +60° C. to +200° C., for example, at +100° C. to +180° C.; see for example *Bioorg. Med. Chem.* 2004, 12, 3731-3742; *Bioorg. Med. Chem. Lett.* 2013, 23, 2808-2811; *Org. Lett.* 2002, 4, 3927-3930 or *Bioorg. Med. Chem. Lett.* 2013, 23, 3741-3748.

A compound of general formula (XXV) is obtained by condensation of compound of general formula (XXIV) with a source of ammonia and effected in the same way as described specifically above for the condensation between compound of general formula (VIII) and ammonia to give compound of formula (IX).

Cyclocondensation of compound of general formula (XXIII) to yield compound of general formula (XXIV) is performed under excess of acid such as but not limited to trifluoroacetic acid. The reaction is typically performed in a solvent such as benzene, toluene or dichloromethane, for example, toluene, and within a temperature range of +0° C. to +120° C., for example, at +20° C. to +80° C.; see for example WO 2017037573; WO 2012175522 or WO 2014141187.

Aldol condensation of compounds of general formulae (XXI) and (XXII) to provide compounds of general formula (XXIII) is performed in a two-stage reaction regime via the tert-butyl methyl ether, tetrahydrofuran, 1,4-dioxane, 1,2-dimethoxyethane or bis(2-methoxyethyl) ether, or hydrocarbons such as benzene, toluene, xylene, pentane, hexane or cyclohexane. For example, the solvent is tetrahydrofuran. The reactions are generally effected within a temperature range of −100° C. to +40° C., for example, at −78° C. to +20° C.; see for example WO 20090163469, WO 2014141187 or WO 2016161160.

Process Scheme 25

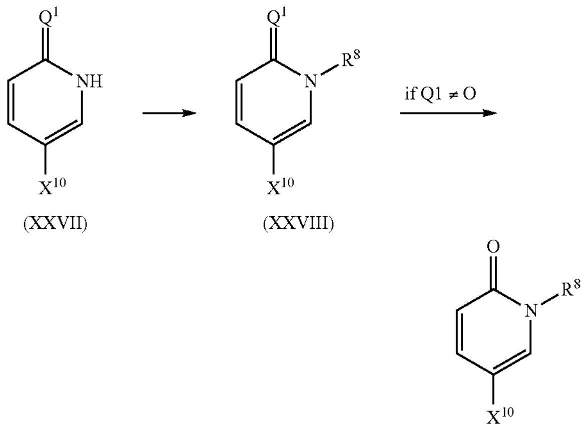

(XXVII) (XXVIII)

(XXIX)

The processes for preparing compounds of the formula (Ia) of the disclosure are optionally performed according to Scheme 23 in which $R^8$ is defined above, $Q^1$ is an oxygen or a substituted nitrogen, and $X^{10}$ is a halogen, for example, bromide. A compound of general formula (XXIX) is obtained by hydrolysis of compound of general formula (XXVIII) in an excess of base such as but not limited to sodium hydroxide or potassium hydroxide. Alternatively hydrolysis can be performed with an excess of acid such as but not limited to potassium bisulfate or hydrochloric acid. Suitable solvents for these reactions are especially alcohols such as methanol, ethanol, n-propanol or 2-propanol, for example, methanol or ethanol, optionally as a mixture with water. The reactions are generally effected within a temperature range of 0° C. to 80° C., see for example *Org. Lett.* 2006, 8, 3805-3808; WO 2011154677; *Bioorg. Med. Chem. Lett.* 2009, 19, 584-588; *$R^5$* C Adv. 2014, 4, 44689-44691 or *J. Med. Chem.* 1998, 41, 4365-4377.

Compound of general formula (XXVIII).is obtained by treatment of compound of general formula (XXVII) with a reagent such as but not limited to a non-substituted or substituted alkyl halide, in presence of a base such as but not limited to sodium carbonate, potassium carbonate, caesium carbonate, sodium hydride, sodium methoxyde, sodium tert-butoxyde, potassium tert-butoxyde, potassium acetate or potassium phosphate, for example, potassium carbonate. Inert solvents for the reaction mentioned are, for example, ethers such as diethyl ether, diisopropyl ether, tert-butyl methyl ether, tetrahydrofuran, 1,4-dioxane, 1,2-dimethoxyethane or bis(2-methoxyethyl), ketones such as acetone, methyl ethyl ketone, methyl isopropyl ketone and methyl isobutyl ketone, esters, such as methyl acetate, ethyl acetate and butyl acetate, nitriles, for example acetonitrile, propionitrile and butyronitrile, amides, for example N,N-dimethylformamide, dimethylacetamide and N-methylpyrrolidone, and also dimethyl sulfoxide, tetramethylenesulfone and hexamethylphosphoramide and DMPU. In some embodiments, the solvent is tetrahydrofuran, acetonitrile or N,N-dimethylformamide. The reactions are generally effected within a temperature range of 0° C. to +200° C., for example, at +20° C. to +140° C.; see for example WO 2013031671; WO 2005044195; *J. Org. Chem.* 2009, 74, 1598-1604; *Synlett* 1995, 845-6; *Org. Biomol. Chem.* 2007, 5, 1569-1576 or Synthesis 2007, 2351-2359.

Process Scheme 26

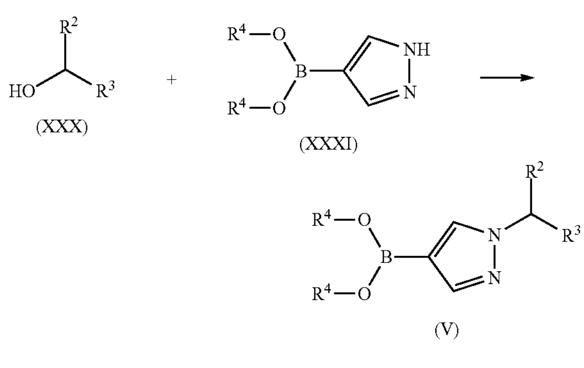

The processes for preparing compounds of the formula (Ia) of the disclosure are optionally performed according to Scheme 12 in which $R^2$ and $R^3$ are defined above, and $R^4$ is an alkyl, or two $R^4$ moieties can form a substituted cycloalkyl. The Mitsunobu reaction between alcohol of formula (XXX) and compound of formula (XXXI) to yield compound of formula (V) can be conducted with the aid of a coupling agent such as but not limited to di-tert-butyl azodicarboxylate or diisopropyl azodicarboxylate, with a source of phosphine such as but not limited to triphenylphosphine, or cyanomethylenetributylphosphorane (Tsunoda's reagent) in an ether such as diethyl ether, diisopropyl ether, tert-butyl methyl ether, tetrahydrofuran, 1,4-dioxane or 1,2-dimethoxymethane as solvent, for example, tetrahydrofuran. The reactions are generally effected within a temperature range of rt to +200° C., for example, at rt to +100° C., see for example WO 2017102091 or *J. Med. Chem.* 2016, 59, 1370-1387. They may also be performed in a microwave oven.

Alternatively a two-stage reaction regime, via an activated form of compound (XXX) with the component (XXXI), is conducted in the presence of a customary auxiliary base such as sodium carbonate, potassium carbonate, sodium hydride, triethylamine, N,N-diisopropylethylamine, pyridine; for example, potassium carbonate. The reaction run in a solvent, for example, tetrahydrofuran, dichloromethane or acetonitrile, and generally takes place within a temperature range of 0° C. to +80° C.; see for example WO 2011100502 or WO 2014109414.

The preparation of the activated form of compound (XXX) itself is accomplished in a customary manner by treatment of the hydroxyl group with an activating reagent such as but not limited to methylsulfonyl chloride, in presence of a base such as but not limited to triethylamine. Optionally a catalyst such as 4-(dimethylamino)-pyridine can be added.

In the processes according to the disclosure, the reaction temperatures can be varied within a relatively wide range. In general, the temperatures employed are between −100° C. and 250° C., for example, between 10° C. and 185° C.

The reaction time varies as a function of the scale of the reaction and of the reaction temperature, but is generally between a few minutes and 48 hours.

The processes according to the disclosure are generally performed under standard pressure. However, it is also possible to work under elevated or reduced pressure.

For performance of the processes according to the disclosure, the starting materials required in each case are generally used in approximately equimolar amounts. However, it is also possible to use one of the components used in each case in a relatively large excess.

Methods of Use

Provided herein are methods for modulating the DLK and/or LZK signalling pathway, for example, the compounds provided herein can modulate DLK and/or LZK. Such compounds can be useful for treating diseases and disorders which can be treated with a modulator of DLK and/or LZK. Compounds of Formula (I) and (II), or pharmaceutically acceptable salts thereof, can have valuable pharmacological properties and can be used for the prevention and/or treatment of diseases in humans and animals. Compounds of Formula (I) and (II), which are low molecular weight, potent and dual-action inhibitors of the DLK and LZK signalling pathway, can be suitable for treatment and/or prevention of neurodegenerative disorders, such as ophthalmological neurodegenerative disorders.

The neurodegenerative ophthalmological disorders which can be treated and/or prevented using a compound of Formula (A), (AI), (I), (I-A), (I-B), (I-C), (I-D), (B), (BII), (II), (II-A), (II-B), (II-C), (II-D), (II-E), (II-F), (II-G), or (II-H), in the context of the disclosure, should be understood, for example, to include the following disorders: age-related macular degeneration (AMD) including dry (non-exudative) and wet (exudative, neovascular) AMD, choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with renal vein occlusion, retinitis pigmentosa and other inherited retinal degenerations (e.g. Stargardt disease), retinopathy of prematurity, glaucoma (including open-angle and narrow/closed-angle glaucoma, primary and secondary glaucoma, normal tension and high-IOP glaucoma), other optic neuropathies including toxic optic neuropathy (e.g. methanol, ethambutol), non-arteritic ischemic optic neuropathy, arteritic ischemic optic neuropathy/giant cell arteritis, traumatic optic neuropathy (including traumatic brain injury), idiopathic intracranial hypertension/pseudotumor cerebri, inflammatory optic neuropathies (e.g. optic neuritis), compressive optic neuropathies (e.g. pituitary adenoma), infiltrative optic neuropathies (e.g. sarcoidosis, lymphoma), autoimmune optic neuropathies, lipid storage diseases (e.g. Tay-Sachs), nutritional optic neuropathies, Leber's hereditary optic neuropathy, dominant optic atrophy, Friedrich's ataxia, radiation-induced optic neuropathy, iatrogenic optic neuropathies, space flight-associated neuro-ocular syndrome (SANS), inflammation disorders of the eye, for example uveitis, scleritis, cataract, refraction anomalies, for example myopia, hyperopia, astigmatism or keratoconus, neurotrophic keratopathy, corneal denneratvation and promoting corneal reinnervation and diabetic keratopathy. Neurodegenerative non-ophthalmological disorders which can be treated and prevented using a compound of Formula (A), (AI), (I), (I-A), (I-B), (I-C), (I-D), (B), (BII), (II), (II-A), (II-B), (II-C), (II-D), (II-E), (II-F), (II-G), or (II-H), in the context of the disclosure, should be understood, for example, to mean but not limited to the following disorders: Amyotrophic lateral sclerosis (ALS), Alzheimer's disease, Parkinson's disease, Parkinson's-plus disease, Huntington's disease, peripheral neuropathies, ischemia, stroke, intracranial haemorrhage, cerebral haemorrhage, nerve damage caused by exposure to toxic compounds selected from the group consisting of heavy metals, industrial solvents, drugs and chemotherapeutic agents, injury to the nervous system caused by physical, mechanical or chemical trauma trigeminal neuralgia, glossopharyngeal neuralgia, Bell's Palsy, myasthenia gravis, muscular dystrophy, progressive muscular atrophy, primary lateral sclerosis (PLS), spinal muscular atrophy, inherited muscular atrophy, invertebrate disk syndromes, cervical spondylosis, plexus disorders, thoracic outlet destruction syndromes, *porphyria*, pseudobulbar palsy, progressive bulbar palsy, multiple system atrophy, progressive supranuclear palsy, corticobasal degeneration, dementia with Lewy bodies, frontotemporal dementia, demyelinating diseases, Guillain-Barra syndrome, multiple sclerosis, Charcot-Marie-Tooth disease, prion disease, Creutzfeldt-Jakob disease, Gerstmann-Striussler-Scheinker syndrome (GSS), fatal familial insomnia (FFI), bovine spongiform encephalopathy, Pick's disease, epilepsy, sensorineural hearing loss, traumatic brain injury, and AIDS demential complex. In some embodiments, the disorder is chemotherapy-induced peripheral neuropathy (CIPN), e.g., nerve damage caused by exposure to chemotherapeutic agents.

Because of their profile of activity, compounds of Formula (I) and (II) can be suitable for treatment and/or prevention of age-related macular degeneration (AMD), choroidal neovascularization (CMV), myopia-associated choroidal neovascularization, diabetic retinopathy, macular oedema, and retinal vein occlusion.

In some embodiments, a compound of Formula (A), (AI), (I), (I-A), (I-B), (I-C), (I-D), (B), (BII), (II), (II-A), (II-B), (II-C), (II-D), (II-E), (II-F), (II-G), or (II-H) can be used to treat and/or prevent optic neuropathies, including glaucoma, inherited retinal degenerations, non-exudative AMD/geographic atrophy, retinal vascular diseases that produce ischemia (diabetes, vein occlusion), retinal detachments and edema-producing diseases (including exudative AMD).

Another aspect of the disclosure are cell transplantation-based regenerative approaches which are being developed for the treatment of ocular and other forms of neurodegeneration. These include photoreceptor and/or RPE transplantation for treatment of macular degeneration and forms of photoreceptor degeneration, and RGC transplantation for the treatment of glaucoma and other forms of optic nerve disease which unfortunately show evidence of significant death of the transplanted cells. Compounds of Formula (A), (AI), (I), (I-A), (I-B), (I-C), (I-D), (B), (BII), (II), (II-A), (II-B), (II-C), (II-D), (II-E), (II-F), (II-G), or (II-H) can be suitable to reduce death and dysfunction of the transplanted cells, for regenerative therapies for both ocular degenerative diseases and other forms of neurodegeneration.

The aforementioned well-characterized diseases in humans can also occur with comparable aetiology in other mammals and can likewise be treated therein with the compounds of the present disclosure.

The present disclosure thus further provides for the use of a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, for the treatment and/or prevention of a disorder, for example, any of the aforementioned disorders, in a subject.

As used herein, the terms "subject," "individual," or "patient," are used interchangeably, refer to any animal, including mammals such as mice, rats, other rodents, rabbits, dogs, cats, swine, cattle, sheep, horses, primates, and humans. In some embodiments, the subject is a human. In some embodiments, the subject has experienced and/or exhibited at least one symptom of the disease or disorder to be treated and/or prevented.

In the context of the present disclosure, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present disclosure and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present disclosure further provides for the use of a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, for the production of a medicament for the treatment and/or prevention of a disorder, for example, any of the aforementioned disorders.

The present disclosure further provides a pharmaceutical composition comprising at least one of the compounds of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, for the treatment and/or prevention of a disorder, for example, any of the aforementioned disorders.

The present disclosure further provides for the use of compounds of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, in a method for the treatment and/or prevention of a disorder, for example, any of the aforementioned disorders, in a subject.

The present disclosure further provides a process for the treatment and/or prevention of a disorder, for example, any of the aforementioned disorders, in a subject using an effective amount of at least one compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof.

The terms “effective amount” or “therapeutically effective amount,” as used herein, refer to a sufficient amount of a chemical entity being administered which will relieve to some extent one or more of the symptoms of the disease or condition being treated. The result includes reduction and/or alleviation of the signs, symptoms, or causes of a disease, or any other desired alteration of a biological system. For example, an “effective amount” for therapeutic uses is the amount of the composition comprising a compound as disclosed herein required to provide a clinically significant decrease in disease symptoms. An appropriate “effective” amount in any individual case is determined using any suitable technique, such as a dose escalation study.

Also provided is a method for modulating DLK and/or LZK activity in a cell, comprising contacting the cell with a compound of Formula (A), (AI), (I), (I-A), (I-B), (I-C), (I-D), (B), (BII), (II), (II-A), (II-B), (II-C), (II-D), (II-E), (II-F), (II-G), or (II-H). In some embodiments, the compounds provided herein inhibit DLK and/or LZK in a cell. In some embodiments, the contacting is in vitro. In some embodiments, the contacting is in vivo. In some embodiments, the contacting is in vivo, wherein the method comprises administering an effective amount of a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, to a subject having a cell having DLK and/or LZK activity. In some embodiments, the cell is a neuronal cell.

As used herein, the term “contacting” refers to the bringing together of indicated moieties in an in vitro system or an in vivo system. For example, “contacting” DLK and/or LZK with a compound provided herein includes the administration of a compound provided herein to an individual or subject, such as a human, having DLK and/or LZK, as well as, for example, introducing a compound provided herein into a sample containing a cellular or purified preparation containing DLK and/or LZK.

In some embodiments, the compound of Formula (A), (AI), (I), (I-A), (I-B), (I-C), (I-D), (B), (BII), (II), (II-A), (II-B), (II-C), (II-D), (II-E), (II-F), (II-G), or (II-H) (or a pharmaceutically acceptable salt thereof) is MNT (micronucleus test) negative. MNT positivity can indicate that a compound is genotoxic. In some embodiments, an in vitro micronucleus test, e.g., a test that evaluates the presence of micronuclei after exposure of cells to a compound of Formula (A), (AI), (I), (I-A), (I-B), (I-C), (I-D), (B), (BII), (II), (II-A), (II-B), (II-C), (II-D), (II-E), (II-F), (II-G), or (II-H), can be used to determine if a compound of Formula (A), (AI), (I), (I-A), (I-B), (I-C), (I-D), (B), (BI), (II), (II-A), (II-B), (II-C), (II-D), (II-E), (II-F), (II-G), or (II-H) is MNT negative.

In some embodiments of any the methods described herein, the compound of Formula (A), (AI), (I), (I-A), (I-B), (I-C), (I-D), (B), (BII), (II), (II-A), (II-B), (II-C), (II-D), (II-E), (II-F), (II-G), or (II-H) (or a pharmaceutically acceptable salt thereof) is administered in combination with a therapeutically effective amount of at least one additional therapeutic agent selected from one or more additional therapies or therapeutic agents. In some embodiments, the compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, can be used in combination with one or more other pharmacologically active substances, provided that this combination does not lead to undesirable and unacceptable side effects. The present disclosure therefore further provides medicaments comprising at least one of a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, and one or more further active ingredients, for example, for the treatment and/or prevention of the aforementioned disorders. In some embodiments, examples of combination active ingredients suitable for the purpose include IOP-lowering/neuroprotective combinations like prostaglandin/neuroprotective (e.g. bimatoprost, tafluprost, latanoprost, travaprost), beta-blocker/neuroprotective (e.g. timolol, levobunolol, carteolol, betaxalol), alpha-agonist/neuroprotective (e.g. brimonidine, apraclonidine), carbonic anhydrase inhibitor/neuroprotective (e.g. dorzolamide, brinzolamide), rho kinase inhibitor/neuroprotective (e.g. netarsudil), cholinergics (e.g. pilocarpine), and anti-inflammatory/neuroprotective combinations like steroid/neuroprotective (e.g. prednisolone, dexamethasone, fluoromethalone, loteprednol, fluocinolone, difluprednate, triamcinolone).

Accordingly, also provided herein is a method for treating a neurodegenerative disorder, comprising administering to a subject in need thereof a pharmaceutical combination for treating a neurodegenerative disorder which comprises (a) a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, (b) an additional therapeutic agent, and (c) optionally at least one pharmaceutically acceptable carrier for simultaneous, separate or sequential use for the treatment of a neurodegenerative disease, wherein the amounts of the compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, and the additional therapeutic agent are together effective in treating the neurodegenerative disease.

These additional therapeutic agents may be administered with one or more doses of the compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, or pharmaceutical composition thereof, as part of the same or separate dosage forms, via the same or different routes of administration, and/or on the same or different administration schedules according to standard pharmaceutical practice known to one skilled in the art.

Pharmaceutical Compositions and Administration

The present disclosure further provides pharmaceutical compositions which comprise at least one compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, typically together with one or more pharmaceutically acceptable excipients.

Compounds of Formula (A), (AI), (I), (I-A), (I-B), (I-C), (I-D), (B), (BII), (II), (II-A), (II-B), (II-C), (II-D), (II-E), (II-F), (II-G), or (II-H), or pharmaceutically acceptable salt thereofs, can act systemically and/or locally. For this purpose, they can be administered in a suitable manner, for example by the oral, parenteral, pulmonal, nasal, sublingual, lingual, buccal, rectal, dermal, transdermal, extraocular, intraocular or otic route, or as an implant or stent.

In some embodiments, a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, or a pharmaceutical composition thereof, is suitable for local and topical administration to the eye (e.g., eye drops, ocular ointments, ocular gels, ocular coil, contact lenses, and other opthalmic inserts). See, e.g., Dubald et al. Pharmaceutics. 2018; 10(1): 10; Bertens et al. Eur J Pharm Biopharm. 2020 Mar 12. pii: S0939-6411(20)30074-6; Singh et al. Ther Adv Ophthalmol. 2020 Mar. 13; 12:2515841420905740; and Patel et al. World J Pharmacol. 2013; 2(2): 47-64. In some embodiments, the administration route is local extraocular or intraocular. More specifically, possible routes of administration include: intravitreal injection, intravitreal impant, periocular injection (e.g. subtenon, subconjunctival), periocular reservoir, retrobulbar injection, subconjunctival injection or depot, intracameral injection, intracameral implant, topical (eye drop or gel), suprachoroidal injection, subconjunctival insert, subretinal delivery, punctal plug, and suprachoroidal implant. Compounds of Formula (A), (AI), (I), (I-A), (I-B), (I-C), (I-D), (B), (BII), (II), (II-A), (II-B), (II-C), (II-D), (II-E), (II-F), (II-G), or (II-H) can be administered in suitable administration forms for these administration routes.

Suitable administration forms for extraocular (topical) administration can include administration forms that release a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, rapidly and/or in a modified or controlled manner and which contain a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, in crystalline and/or amorphized and/or dissolved form, for example eye drops, sprays or lotions (e.g. solutions, suspensions, vesicular/colloidal systems, emulsions, aerosols), powders for eye drops, sprays or lotions (e.g. ground active ingredient, mixtures, lyophilizates, precipitated active ingredient), semisolid eye preparations (e.g. hydrogels, in-situ hydrogels, creams or ointments) or opthalmic inserts (solid or semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable administration forms for intraocular administration include administration forms that release compounds of Formula (A), (AI), (I), (I-A), (I-B), (I-C), (I-D), (B), (BII), (II), (II-A), (II-B), (II-C), (II-D), (II-E), (II-F), (II-G), or (II-H) rapidly and/or in a modified or controlled manner and which contain compounds of Formula (A), (AI), (I), (I-A), (I-B), (I-C), (I-D), (B), (BII), (II), (II-A), (II-B), (II-C), (II-D), (II-E), (II-F), (II-G), or (II-H) in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active ingredient, mixtures, lyophilizates, precipitated active ingredient), gels for injection (semisolid preparations, e.g. hydrogels, in-situ hydrogels) or implants (solid preparations, e.g. biodegradable and nonbiodegradable implants, implantable pumps).

In some embodiments, an injectable composition is implanted at the site of drug release. An injectable composition can include a polymer delivery vehicle. Such polymer delivery vehicles can allow for extended release. In some embodiments, the polymer delivery vehicle can prolong delivery up to a few months in the surrounding tissue. In some embodiments, an injectable composition can form a depot of a compound of Formula (A), (AI), (I), (I-A), (I-B), (I-C), (I-D), (B), (BII), (II), (II-A), (II-B), (II-C), (II-D), (II-E), (II-F), (II-G), or (II-H) at the injection site. In some embodiments, the compound of Formula (A), (AI), (I), (I-A), (I-B), (I-C), (I-D), (B), (BII), (II), (II-A), (II-B), (II-C), (II-D), (II-E), (II-F), (II-G), or (II-H) is released and/or diffuses from the depot over a period of time. For example, a compound of Formula (A), (AI), (I), (I-A), (I-B), (I-C), (I-D), (B), (BII), (II), (II-A), (II-B), (II-C), (II-D), (II-E), (II-F), (II-G), or (II-H) can be released over a few days and up to a few months.

Opthalmic inserts include multi-layered, drug-impregnated devices placed into the eye. In some embodiments, an opthalmic insert is multi-layered. In some embodiments, an opthalmic insert is sterile. In some embodiments, the ophthalmic insert is placed into the cul-de-sac or conjunctival sac or the eye. In some embodiments, the release of the drug from the ophthalmic insert is prolonged. In some embodiments, an opthalmic insert is a soluble ocular drug insert, a poly(vinyl methyl ether-maleic anhydride)anhydride ocular insert, a collagen shield, an ocusert, a minidisc, a new opthalalmic delivery system, or a topical bimatoprost ocular insert. See, e.g., Jervis. J. *Bioequiv. Availab.* 2017, 9:1.

In some embodiments, compositions suitable for ocular delivery include in situ gelling systems, liposomes, nanoparticles (e.g., chitosan-based polymeric nanoparticles, poly (lactic-co-glycolic acid) nanoparticles, gelatin nanoparticles, propoxylated glyceryl triacylate nanoparticles, and PGT-ethylene glycol dimethacrylate nanoparticles), niosomes, nanoemulsions, nanospheres, and microemulsions. In some embodiments, the in situ gelling system is thermosensitive. IN some embodiments, the in situ gelling system comprises triblock polymer PLGA-PEG-PLGA (poly-(DL-lactic acid co-glycolic acid)-polyethylene glycol-poly-(DL-lactic acid co-glycolic acid).

Ocular compositions can include, without limitation, one or more of any of the following: viscogens; stabilizers; preservative; permeation enhancers; and lubricants. Non-limiting examples of viscogens include polyvinylalcohol (PVA), hydroxylmethylcellulose, hydroxylethylcellulose carboxymethylcellulose, glycerin, polyvinylpyrrolidone, and polyethylene glycol. Non-limiting examples of stabilizers include pluronic (triblock copolymers) and cyclodextrins. Non-limiting examples of preservatives include benzalkonium chloride, ETDA, SofZia (boric acid, propylene glycol, sorbitol, and zinc chloride; Alcon Laboratories, Inc.), and purite (stabilized oxychloro complex; Allergan, Inc.)). Non-limiting examples of permeation enhancers include polyoxyethylene glycol ester and ethylenediaminetetra acetic acid sodium salt. In some embodiments, a composition for ocular delivery is isotonic.

In some embodiments, an ocular ointment includes non-aqueous excipients. In some embodiments, an ocular ointment has an oleaginous base, an absorption base, a water-removable base, or a water soluble base. An oleaginous base can be a lipophilic ointment. For example, an oleaginous base can include petrolatum and white ointment. An adsorption base can be used as emollient. For example, an adsorption base can include lanolin, fatty alcohol and petrolatum. A water-soluble base can include only water soluble excipients such as macrogol with high molecular weight. A water removable base includes compositions that are an oil in water emulsion.

In some embodiments, an ocular gel is a hydrogel. For example, a preformed gel or a composition that forms a gel in situ. Hydrogels can include polymers such as methylcellulose, hydroxylethylcellulose, sodium hyaluronate, sodium alginate, povidone, polyvinylalcohol, cellulose acetate and derivatives, carbomer, magrogol, pseudolatex, polymethacrylic acid, alginate sodium, gellan gum (GELRITE®), pluronics, poly(n-isopropyl acrylamide), oly(acrylic acid), polyacrylamide, poloxamer, chitosan, and hydroxyl propyl methyl cellulose.

In some embodiments, a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, or a pharmaceutical composition thereof, is suitable for systemic administration, e.g., through oral or parenteral administration such as intravenous injection, subcutaneous injection, or intramuscular injection.

Suitable administration forms for oral administration include administration forms that release a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, rapidly and/or in a modified manner and which contain a compound of Formula (A), (AI), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, in crystalline and/or amorphized and/or dissolved form, for example, tablets (uncoated or coated tablets, for example with gastric juice-resistant or retarded-dissolution or insoluble coatings which control the release of the compound of Formula (A), (AI), (I), (I-A), (I-B), (I-C), (I-D), (B), (BII), (II), (II-A), (II-B), (II-C), (II-D), (II-E), (II-F), (II-G), or (II-H)), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

In some embodiments, a compound of Formula (A), (Al), (I), (I-A), (I-B), (I-C), (I-D), (B), (BII), (II), (II-A), (II-B), (II-C), (II-D), (II-E), (II-F), (II-G), or (II-H), or a pharmaceutically acceptable salt thereof, or a pharmaceutical composition thereof, is suitable for administration to the central nervous system (CNS). Compounds of Formula (A), (Al), (I), (I-A), (I-B), (I-C), (I-D), (B), (BII), (II), (II-A), (II-B), (II-C), (II-D), (II-E), (II-F), (II-G), or (II-H) can be administered in suitable administration forms for these administration routes. In some embodiments, compositions suitable for CNS delivery include nanoparticles. Non-limiting examples of such nanoparticles include gold nanoparticles, lipid-based nanoparticles (e.g., liposomes), polymeric nanoparticles, and dendrimers. See, e.g., Spencer et al. Pharmaceutics. 2020 February; 12(2): 192.

Parenteral administration can bypass an absorption step (e.g. intravenously, intraarterially, intracardially, intraspinally or intralumbally) or include an absorption (e.g. inhalatively, intramuscularly, subcutaneously, intracutaneously, percutaneously or intraperitoneally).

Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

In some embodiments, treatment of ophthalmological disorders includes extraocular topical or intraocular administration of a compound of Formula (A), (AL), (I), (I-A), (I-B), (I-C), (I-D), (B), (BII), (II), (II-A), (II-B), (II-C), (II-D), (II-E), (II-F), (II-G), or (II-H). In some embodiments, the treatment of other disorders includes oral or intravenous administration of a compound of Formula (A), (Al), (I), (I-A), (I-B), (I-C), (I-D), (B), (BII), (II), (II-A), (II-B), (II-C), (II-D), (II-E), (II-F), (II-G), or (II-H). In some embodiments, the treatment of other disorders includes administration of a compound of Formula (A), (Al), (I), (I-A), (I-B), (I-C), (I-D), (B), (BII), (II), (II-A), (II-B), (II-C), (II-D), (II-E), (II-F), (II-G), or (II-H) to the central nervous system of a subject.

Compounds of Formula (A), (Al), (I), (I-A), (I-B), (I-C), (I-D), (B), (BII), (II), (II-A), (II-B), (II-C), (II-D), (II-E), (II-F), (II-G), or (II-H) can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctants.

In general, it has been found to be advantageous in the case of parenteral administration to administer amounts of about 0.001 to 1 mg/kg, for example, about 0.01 to 0.5 mg/kg, of body weight to achieve effective results. In the case of oral administration the dosage is about 0.01 to 100 mg/kg, for example, about 0.01 to 20 mg/kg or about 0.1 to 10 mg/kg of body weight. In the case of extraocular administration, the dosage is about 1 to 50 mg/ml with an application volume of 10 to 100 pl.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

EXAMPLES

The disclosure will be described in greater detail by way of specific examples. The following examples are offered for illustrative purposes, and to exemplify the oral compositions and methods described herein and are not intended to limit the disclosure in any manner. Many variations will suggest themselves and are within the full-intended scope. Those of skill in the art will readily recognize a variety of non-critical parameters that can be changed or modified to yield essentially the same results.

Abbreviations aq. aqueous
Boc tert-butyloxycarbonyl
br broad (in NMR)
CMBP Cyanomethylene)tributylphosphorane (Tsunoda's reagent) [CAS-RN
d day(s), doublet (in NMR)
DBAD di-tert-butyl azodicarboxylate [CAS-RN 870-50-8]
DBU 1,8-diazabicyclo[5.4.0]undec-7-ene [CAS-RN 6674-22-2]
dd doublet of doublet (in NMR)
ddd doublet of doublet of doublet (in NMR)
DIAD diisopropyl azodicarboxylate [CAS-RN 2446-83-5]
DMAP 4-(dimethylamino)pyridine [CAS-RN 1122-58-3]
DMF N,N-dimethylformamide
DMSO dimethyl sulfoxide
DPPA Diphenyl phosphoryl azide [CAS-RN 26386-88-9]
ESI electrospray ionization (in MS)
h hour(s)
HATU O-(7-azabenzotriazol-1-yl)-N,N,N',N'-tetramethyluronium Hexafluorophosphate [CAS-RN 148893-10-1]
HPLC high-pressure, high-performance liquid chromatography
Lawesson's reagent 2,4-bis(4-methoxyphenyl)-2,4-dithioxo-1,3,2,4-dithiadiphosphetane [CAS-RN 19172-47-5]
LC-MS liquid chromatography-coupled mass spectroscopy
m multiplet (in NMR)
min minute(s)
MS mass spectroscopy
NMR nuclear magnetic resonance spectroscopy
q quartet (in NMR)
Rt retention time (in HPLC)
rt room temperature
s singlet (in NMR)
satd. saturated
SFC supercritical fluid chromatography
t triplet (in NMR)
TBAF tetrabutylammoniumfluoride
TBTU N,N,N',N'-tetramethyl-O-(benzotriazol-1-yl)uronium tetrafluoroborate [CAS-RN 125700-67-6]
TFA trifluoroacetic acid
THF tetrahydrofuran
TMAD N,N,N',N'-tetramethylazodicarboxamide [CAS-RN 10465-78-8]
T3P 2,4,6-tripropyl-1,3,5,2,4,6-trioxatriphosphinane 2,4,6-trioxide [CAS-RN 68957-94-8]
XPhos-Pd-G2 2nd generation XPhos precatalyst, chloro (2-dicyclohexylphosphino-2',4',6'-triisopropyl-1,1'-biphenyl)[2-(2'-amino-1,1'-biphenyl)]palladium(II) [CAS-RN 1310584-14-5]

The following sections include materials, methods, synthetic procedures, and biological data for (1) Compounds of Formula (I), and (2) Compounds of Formula (II). Intermediates and example numbers of Compounds of Formula (I) may be the same as intermediates and example number of Compounds of Formula (II). For purposes of clarification, in instances where the intermediate or example number of a compound of Formula (I) is the same as the intermediate number or example number of a compound of Formula (II), the two structures are distinct and are not to be confused.

Part I. Materials, Methods, Synthetic Procedures, and Biological Data for Compounds of Formula (I)

GC-MS methods

GC-MS method 1: Instrument: Thermo Scientific DSQII, Thermo Scientific Trace GC Ultra; Column: Restek RTX-35MS, 15 m×200 m×0.33 μm; constant flow rate with He: 1.20 ml/min; Oven: 60° C.; Inlet: 220° C.; Gradient: 60° C., 30° C./min to 300° C. (then hold for 3.33 min). GC-MS method 2: Instrument: Waters MS SQ Detector 2, GC Agilent A7890; Column: Restek RTX-35MS, 15 m×200 μm×0.33 μm; constant flow rate with He: 1.20 ml/min; Oven: 60° C.; Inlet: 240° C.; Gradient: 60° C., 30° C./min to 300° C. (then hold for 3.33 min).

LC-MS methods

LC-MS method 1: Instrument MS: Thermo Scientific FT-MS; Instrument UHPLC+: Thermo Scientific UltiMate 3000; Column: Waters, HSS T3, C18 1.8 μm, 2.1×75 mm; Eluent A: water+0.01% formic acid; Eluent B: acetonitrile+0.01% formic acid; Gradient: 0.0 min 10% B to 2.5 min 95% B to 3.5 min 95% B; Oven: 50° C.; Flow rate: 0.90 ml/min; UV-Detection: 210 nm/Optimum Integration Path 210-300 nm LC-MS method 2: Instrument: Waters ACQUITY SQD UPLC System; Column: Waters Acquity UPLC HSS T3, 1.8 μm, 50×1 mm; Eluent A: 1 1 water+0.25 ml formic acid, Eluent B: 1 1 acetonitrile+0.25 ml formic acid; Gradient: 0.0 min 90% A to 1.2 min 5% A to 2.0 min 5% A; Oven: 50° C.; Flow rate: 0.40 ml/min; UV-Detection: 210 nm.

LC-MS method 3: Instrument: Agilent MS Quad 6150; HPLC: Agilent 1290; Column: Waters Acquity UPLC HSS T3, 1.8 μm, 50×2.1 mm; Eluent A: 1 1 water+0.25 ml formic acid, Eluent B: 1 1 acetonitrile+0.25 ml formic acid; Gradient: 0.0 min 90% A to 0.3 min 90% A to 1.7 min 5% A to 3.0 min 5% A; Oven: 50° C.; Flow rate: 1.20 ml/min; UV-Detection: 205-305 nm.

LC-MS method 4: Instrument: Waters Single Quad MS System; Instrument Waters UPLC Acquity; Column: Waters BEH C18, 1.7 μm; 50×2.1 mm; Eluent A: 1 1 water+1.0 ml 25% aq. ammonia; Eluent B: acetonitrile; Gradient: 0.0 min 92% A to 0.1 min 92% A to 1.8 min 5% A to 3.5 min 5% A; Oven: 50° C.; Flow rate: 0.45 ml/min; UV-Detection: 210 nm.

LC-MS method 5: Column: Ascentis Express C18, 2.7 μm, 3.0×50 mm. A linear gradient was applied, starting at 95% A (A: 0.05% TFA in water) and ending at 95% B (B: 0.05% TFA in acetonitrile) over 1.2 min with a total run time of 2.0 min. Oven: 40° C.; Flow rate: 1.5 ml/min.

LC-MS method 6: Column: Ascentis Express C18, 2.7 μm, 3.0×50 mm. A linear gradient was applied, starting at 95% A (A: 0.05% TFA in water) and ending at 95% B (B: 0.05% TFA in acetonitrile) over 1.7 min with a total run time of 3.0 min. Oven: 40° C.; Flow rate: 1.5 ml/min.

LC-MS method 7: Column: Ascentis Express C18, 2.7 μm, 3.0×50 mm. A linear gradient was applied, starting at 95% A (A: 0.05% TFA in water) and ending at 95% B (B: 0.05% TFA in acetonitrile) over 1.7 min with a total run time of 3.0 min. Oven: 40° C.; Flow rate: 1.5 ml/min.

LC-MS method 8: Column: CORTECS C18, 2.7 μm, 2.1×50 mm. A linear gradient was applied, starting at 95% A (A: 0.1% formic acid in water) and ending at 95% B (B: 0.1% formic acid in acetonitrile) over 2.0 min with a total run time of 3.0 min. Oven: 40° C.; Flow rate: 1.0 ml/min.

LC-MS method 9: Column: CORTECS C18, 2.7 m, 2.1×50 mm. A linear gradient was applied, starting at 95% A (A: 0.1% formic acid in water) and ending at 100% B (B: 0.1% formic acid in acetonitrile) over 1.2 min with a total run time of 2.0 min. Oven: 40° C.; Flow rate: 1.0 ml/min.

LC-MS method 10: Column: CORTECS C18, 2.7 μm, 2.1×50 mm. A linear gradient was applied, starting at 90% A (A: 0.1% formic acid in water) and ending at 100% B (B: 0.1% formic acid in acetonitrile) over 1.1 min with a total run time of 2.0 min. Oven: 40° C.; Flow rate: 1.0 ml/min.

LC-MS method 11: Column: Kinetex EVO-C18, 2.6 μm, 3.0×50 mm. A linear gradient was applied, starting at 90% A (A: 5 mM ammonium bicarbonate in water) and ending at 95% B (B: acetonitrile) over 1.2 min with a total run time of 2.0 min. Oven: 40° C.; Flow rate: 1.3 ml/min.

LC-MS method 12: Column: Kinetex EVO-C18, 2.6 μm, 3.0×50 mm. A linear gradient was applied, starting at 90% A (A: 0.2% NH3H2O in water) and ending at 95% B (B: MeOH) over 2.1 min with a total run time of 3.0 min. Oven: 45° C.; Flow rate: 1.0 ml/min.

LC-MS method 13: Column: Kinetex EVO-C18, 2.6 μm, 4.6×50 mm. A linear gradient was applied, starting at 90% A (A: 5 mM ammonium bicarbonate in water)) and ending at 95% B (B: acetonitrile) over 1.45 min with a total run time of 2.0 min. Oven: 40° C.; Flow rate: 1.8 ml/min.

LC-MS method 14: Column: Kinetex EVO-C18, 2.6 μm, 4.6×50 mm. A linear gradient was applied, starting at 90% A (A: 5 mM ammonium bicarbonate in water)) and then to 50% B (B: acetonitrile) over 1.9 min and ending at 95% B (B: acetonitrile) over 2.7 min with a total run time of 3.0 min. Oven: 40° C.; Flow rate: 1.8 ml/min.

LC-MS method 15: Column: Poroshell HPH-C18, 2.7 μm, 3.0×50 mm. A linear gradient was applied, starting at 90% A (A: 0.03% NH3.H2O in water) and ending at 95% B (B: acetonitrile) over 2.0 min with a total run time of 3.0 min. Oven: 40° C.; Flow rate: 1.2 ml/min.

LC-MS method 16: Column: Shim-pack XR-ODS, 2.2 μm, 3.0×50 mm. A linear gradient was applied, starting at 95% A (A: 0.05% TFA in water) and ending at 95% B (B: 0.05% TFA in acetonitrile) over 1.2 min with a total run time of 2.0 min. Oven: 40° C.; Flow rate: 1.5 ml/min.

LC-MS method 17: Column: Shim-pack XR-ODS, 2.2 μm, 3.0×50 mm. A linear gradient was applied, starting at 95% A (A: 0.05% TFA in water) and ending at 95% B (B: 0.05% TFA in acetonitrile) over 3.2 min with a total run time of 4.5 min. Oven: 40° C.; Flow rate: 1.5 ml/min.

LC-MS method 18: Column: IntertSustain, 2.1 μm, 3.0×50 mm. A linear gradient was applied, starting at 90% A (A: 0.03% NH3.H2O in water) and ending at 95% B (B: acetonitrile) over 1.3 min with a total run time of 2.0 min. Oven: 40° C.; Flow rate: 1.2 ml/min.

LC-MS method 19: Column: Luna Omega PS C18 100A, 2.1 m, 3.0×30 mm. A linear gradient was applied, starting at 95% A (A: 0.09% formic acid in water) and ending at 95% B (B: 0.1% formic acid in acetonitrile) over 1.0 min with a total run time of 1.5 min. Oven: 40° C.; Flow rate: 1.2 ml/min.

LC-MS method 20: Column: Ascentis Express C18, 2.7 μm, 3.0×50 mm. A linear gradient was applied, starting at 95% A (A: 0.05% TFA in water) to 60% B (B: 0.05% TFA in acetonitrile) over 3.0 min and ending at 95% B (B: 0.05% TFA in acetonitrile) over 3.3 min with a total run time of 4.5 min. Oven: 40° C.; Flow rate: 1.5 ml/min.

LC-MS method 21: Column: Ascentis Express C18, 2.7 μm, 2.1×50 mm. A linear gradient was applied, starting at 60% A (A: 0.05% TFA in water) and ending at 95% B (B: 0.05% TFA in acetonitrile) over 3.0 min with a total run time of 4.5 min. Oven: 40° C.; Flow rate: 1.5 ml/min.

LC-MS method 22: Column: Kinetex EVO-C18 100A, 2.6 m, 2.1×50 mm. A linear gradient was applied, starting at 90% A (A: 5 mM ammonium bicarbonate in water) and ending at 95% B (B: acetonitrile) over 2.0 min with a total run time of 3.0 min. Oven: 40° C.; Flow rate: 1.2 ml/min.

LC-MS method 23: Column: Ascentis Express C18, 2.7 μm, 2.1×50 mm. A linear gradient was applied, starting at 95% A (A: 0.05% TFA in water) and ending at 100% B (B: 0.05% TFA in acetonitrile) over 1.2 min with a total run time of 2.0 min. Oven: 40° C.; Flow rate: 1.5 ml/min.

LC-MS method 24: Column: Shim-pack XR-ODS, 2.2 μm, 3.0×50 mm. A linear gradient was applied, starting at 95% A (A: 0.05% TFA in water) and ending at 95% B (B: 0.05% TFA in acetonitrile) over 2.0 min with a total run time of 3.0 min. Oven: 40° C.; Flow rate: 1.0 ml/min.

LC-MS method 25: Column: Kinetex EVO-C18, 2.6 m, 3.0×50 mm. A linear gradient was applied, starting at 90% A (A: 5 mM ammonium bicarbonate in water) and ending at 95% B (B: acetonitrile) over 2.1 min with a total run time of 3.0 min. Oven: 40° C.; Flow rate: 1.3 ml/min.

General Materials

Hydrophobic Phase Separation Filter Papers were used from Machery-Nagel™ (MN 617 WA Grade)

General Procedures

General Procedure A:

A mixture of the halogenide, the boronic ester and sodium carbonate (or caesium carbonate where stated) was suspended under argon in a mixture of dioxane and water. The mixture was degassed and purged with argon several times. Then the catalyst was added, and the reaction mixture was stirred for 2.5 h at 90° C. Unless stated otherwise, the reaction mixture was filtered and the solid washed with ethyl acetate. The filtrate was evaporated and the residue was suspended in a minimum of dichloromethane. A solid precipitated, which was filtered off through kieselgur and discarded. The filtrate was concentrated in vacuo and the residue was further purified.

General procedure B:

A mixture of the halogenide, the boronic ester (in general 1.0 to 1-.5 eq.), and sodium carbonate (5.0 eq.) in a mixture of dioxane and water (v/v 3:1, 10 ml per mmol halogenide) was degassed with argon. 1,1'-Bis(diphenylphosphino)ferrocene-palladium(II)dichloride dichloromethane complex [CAS-RN 95464-05-4](0.05 eq. or 0.10 eq.) was added and the mixture was heated to 80° C. (90° C. respectively) for the given time.

General procedure C: A mixture of the halogenide, the boronic ester (in general 1.0 to 1.5 eq.), potassium carbonate (3.0 eq.) and 1,1'-bis(diphenylphosphino)ferrocene-palladium(II)dichloride dichloromethane complex [CAS-RN 95464-05-4](0.10 eq.) in a mixture of dimethoxyethane, water, and dimethylformamide (v/v/v 5.5:4:1, 9.1 ml per mmol halogenide) was degassed with argon. The mixture was heated to 80° C. (90° C. respectively) for the given time.

INTERMEDIATES

Intermediate I-1

2-Amino-5-bromo-N-[(2S)-butan-2-yl]pyridine-3-carboxamide

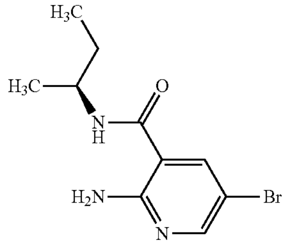

2-Amino-5-bromopyridine-3-carboxylic acid (24.3 g, 112 mmol) was suspended in THF (400 ml) and cooled to 0° C. (2S)-butan-2-amine (9.00 g, 123 mmol) was added leading to a clear solution. Diethylcyanophosphonate [CAS-RN 2942-58-7](21.9 g, 134 mmol) and triethylamine (31 ml, 220 mmol) were added. After 15 min the mixture was warmed to rt and further stirred for 1 h. Subsequently, THF was removed by evaporation under reduced pressure and the residue was triturated with petroleum ether. The precipitate was collected by suction filtration to yield 16.0 g (99% purity, 52% yield) of the title compound.

LC-MS (method 10): Rt=0.78 min; MS (ESIpos): m/z=272, 274 $[M+H]^+$ $^1H$-NMR (400 MHz, DMSO-$d_6$) δ [ppm]: 0.86 (t, 3H), 1.12 (d, 3H), 1.49-1.56 (m, 2H), 3.84-3.91 (m, 1H), 7.21 (s, 2H), 8.10 (s, 1H), 8.14 (s, 1H), 8.23 (d, 1H).

Intermediate I-2

Ethyl [(5-bromo-3-{[(2S)-butan-2-yl]carbamoyl}pyridin-2-yl)carbamothioyl]carbamate

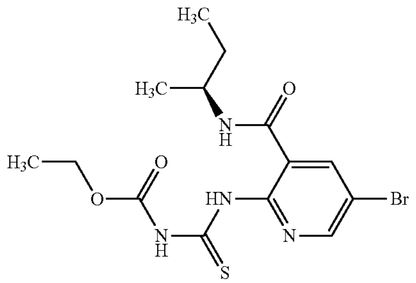 [SMILES: CCOC(=O)NC(=S)Nc1ncc(Br)cc1C(=O)N[C@@H](C)CC]

To a solution of 2-amino-5-bromo-N-[(2S)-butan-2-yl]pyridine-3-carboxamide (16.0 g, 58.8 mmol) in 1,4-dioxane (300 ml) was slowly added ethyl carbonisothiocyanatidate (38.6 g, 294 mmol), and the mixture was stirred at rt for 3 h. The solvent was then evaporated under reduced pressure and the residue was triturated with tert-butyl methyl ether. The precipitate was collected by suction filtration to yield 23.0 g (99% purity, 96% yield) of the title compound.

LC-MS (method 18): Rt=0.67 min; MS (ESIpos): m/z=403, 405 $[M+H]^+$ $^1H$-NMR (300 MHz, DMSO-$d_6$) δ [ppm]: 0.84 (t, 3H), 1.11 (d, 3H), 1.23 (t, 3H), 1.41-1.51 (m, 2H), 3.79-3.88 (m, 1H), 4.19 (q, 2H)), 8.31 (s, 1H), 8.46-8.52 (m, 1H), 8.66 (s, 1H), 12.06-12.13 (m, 2H).

Intermediate I-3

2-Amino-6-bromo-N-[(2S)-butan-2-yl][1,2,4]triazolo[1,5-a]pyridine-8-carboxamide

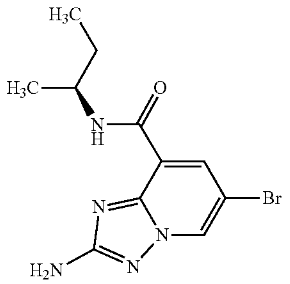 [SMILES: CC[C@H](C)NC(=O)c1cc(Br)cn2nc(N)nc12]

To a solution of hydroxylamine hydrochloride (23.8 g, 342 mmol) in methanol (500 ml) at rt was added N,N-diisopropylethylamine (57 ml, 340 mmol). The mixture was warmed to 60° C. Ethyl [(5-bromo-3-{[(2S)-butan-2-yl]carbamoyl}pyridin-2-yl)carbamothioyl]carbamate (23.0 g, 57.0 mmol) was added and the reaction was further stirred for 1 h at 65° C. After cooling to rt, the solvent was evaporated under reduced pressure. The residue was purified by column chromatography on silica gel (330 g; eluent: petroleum ether/ethyl acetate 1:1) to yield 16.1 g (99% purity, 89% yield) of the title compound.

LC-MS (method 15): Rt=1.23 min; MS (ESIpos): m/z=312, 314 $[M+H]^+$ $^1H$-NMR (300 MHz, DMSO-$d_6$) δ [ppm]: 0.93 (t, 3H), 1.21 (d, 3H), 1.52-1.62 (m, 2H), 3.94-4.04 (m, 1H), 6.56 (s, 2H), 8.06 (s, 1H), 9.16-9.21 (m, 2H).

Intermediate I-4

2-Amino-5-bromo-N-cyclobutylpyridine-3-carboxamide

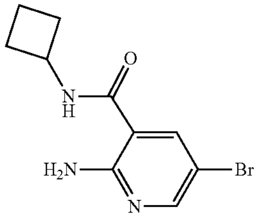 [SMILES: Nc1ncc(Br)cc1C(=O)NC1CCC1]

To a suspension of 2-amino-5-bromopyridine-3-carboxylic acid (1.80 g, 8.29 mmol) in THE (40 ml) cooled to 0° C. were added cyclobutanamine (1.18 g, 16.6 mmol), diethyl cyanophosphonate (2.03 g, 12.4 mmol) and triethylamine (1.68 g, 16.6 mmol). The resulting mixture was stirred at 0° C. for 15 min and then wanned to rt. After stirred for 2 h, the reaction mixture was diluted with 15 water (40 ml) and extracted three times with ethyl acetate (50 ml each). The combined organic layers were washed twice with brine (50 ml each), dried over anhydrous sodium sulfate. The solvent was evaporated under reduced pressure to yield 1.50 g (96% purity, 64% yield) of the title compound.

LC-MS (method 9): Rt=0.90 min; MS (ESIpos): m/z=270 $[M+H]^+$ $^1$H-NMR (300 MHz, DMSO-$d_6$) δ [ppm]: 1.36-1.53 (m, 2H), 1.67-1.89 (m, 4H), 4.32-4.37 (m, 1H), 7.24 (s, 2H), 8.13-8.15 (m, 2H), 8.68 (d, 1H).

Intermediate I-5

Ethyl {[5-bromo-3-(cyclobutylcarbamoyl)pyridin-2-yl]carbamothioyl}carbamate

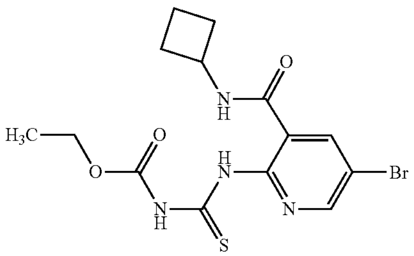 [SMILES: CCOC(=O)NC(=S)Nc1ncc(Br)cc1C(=O)NC1CCC1]

To a solution of 2-amino-5-bromo-N-cyclobutylnicotinamide (1.50 g, 96% purity, 5.33 mmol) in 1,4-dioxane (40 ml) was slowly added ethyl carbonisothiocyanatidate (2.80 g, 21.3 mmol) and the mixture was stirred overnight at rt. The solvent was evaporated and the residue was triturated with hexane. The resulting precipitate was collected by suction filtration and washed with hexane to yield 1.50 g (90% purity, 63% yield) of the title compound.

LC-MS (method 5): $R_t$=1.10 min; MS (ESIpos): m/z=401, 403 $[M+H]^+$ $^1$H-NMR (300 MHz, DMSO-$d_6$) δ [ppm]: 1.27 (t, 3H), 1.66-1.75 (m, 2H), 2.00-2.07 (m, 2H), 2.18-2.26 (m, 2H), 4.21 (q, 2H), 4.31-4.39 (m, 1H), 8.38 (s, 1H), 8.68 (s, 1H), 9.00 (s, 1H), 12.19 (br s, 2H).

Intermediate I-6

2-Amino-6-bromo-N-cyclobutyl[1,2,4]triazolo[1,5-a]pyridine-8-carboxamide

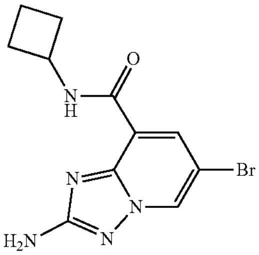 [SMILES: Nc1nc2c(C(=O)NC3CCC3)cc(Br)cn2n1]

To a solution of hydroxylamine hydrochloride (1.40 g, 20.2 mmol) in methanol/ethanol (1:1, 50 ml) at rt was added N,N-diisopropylethylamine (2.60 g, 20.2 mmol) and the mixture was warmed to 60° C. Ethyl {[5-bromo-3-(cyclobutylcarbamoyl)pyridin-2-yl]carbamothioyl}carbamate (1.50 g, 90% purity, 3.36 mmol) was added and the reaction mixture was stirred at 65° C. for 1 h. After cooling to rt, the mixture was diluted with water and the precipitate was collected by suction filtration. After washing with water (50 ml) the residue was dried in vacuo to give 0.95 g (96% purity, 87% yield) of the title compound.

LC-MS (method 8): Rt=1.14 min; MS (ESIpos): m/z=310, 312 $[M+H]^+$ $^1$H-NMR (300 MHz, DMSO-$d_6$) δ [ppm]: 1.69-1.78 (m, 2H), 1.94-2.07 (m, 2H), 2.27-2.39 (m, 2H), 4.39-4.51 (m, 111), 6.56 (s, 2H), 8.02 (s, 1H), 9.16 (s, 1H), 9.50 (d, 1H).

Intermediate I-7

2-Amino-5-bromo-N-(1-fluoropropan-2-yl)pyridine-3-carboxamide (mixture of enantiomers)

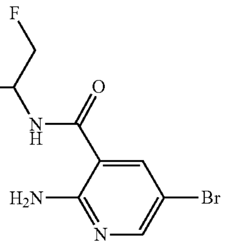

To a suspension of 2-amino-5-bromopyridine-3-carboxylic acid (7.50 g, 34.6 mmol) in THF (220 ml) was added 1-fluoropropan-2-amine-hydrogen chloride (1/1) (5.89 g, 51.8 mmol), TBTU (14.4 g, 44.9 mmol) and triethylamine (19 ml, 140 mmol). The reaction mixture was stirred for 4 h at rt. Subsequently, the mixture was concentrated in vacuo and water was added. It was extracted twice with ethyl acetate and the combined organic layers were washed with brine and dried over anhydrous sodium sulfate and the solvent was evaporated under reduced pressure. The residue was triturated with acetonitrile and the precipitate was collected by suction filtration to yield 7.34 g (100% purity, 77% yield) of the title compound.

LC-MS (method 1): Rt=1.21 min; MS (ESIpos): m/z=276 $[M+H]^+$ $^1$H-NMR (400 MHz, DMSO-$d_6$) δ [ppm]: 1.16 (dd, 3H), 4.19-4.30 (m, 1H), 4.30-4.36 (m, 111), 4.41-4.48 (m, 111), 7.22 (br s, 2H), 8.12 (d, 1H), 8.15 (d, 1H), 8.46 (br d, 1H).

Intermediate I-8

Ethyl [(5-bromo-3-{[1-fluoropropan-2-yl]carbamoyl}pyridin-2-yl)carbamothioyl]carbamate (mixture of enantiomers)

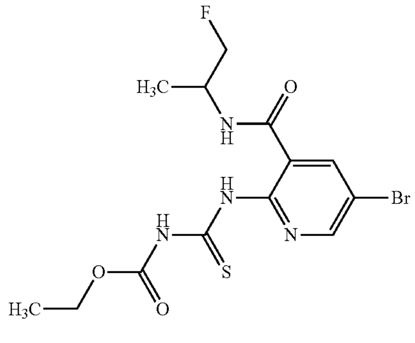 [SMILES: CCOC(=O)NC(=S)Nc1ncc(Br)cc1C(=O)NC(C)CF]

To a solution of 2-amino-5-bromo-N-[1-fluoropropan-2-yl]pyridine-3-carboxamide (7.34 g, 26.6 mmol) in 1,4-dioxane (80 ml) was slowly added ethyl carbonisothiocyanatidate (3.4 ml, 29 mmol), and the mixture was stirred at rt for 12 h. The solvent was then evaporated under reduced pressure and the residue was triturated with tert-butyl methyl ether. The precipitate was collected by suction filtration to yield 9.45 g (96% purity, 84% yield) of the title compound.

LC-MS (method 1): Rt=1.62 min; MS (ESIpos): m/z=407 $[M+H]^+$ $^1$H-NMR (400 MHz, DMSO-$d_6$) δ [ppm]: 1.17 (br d, 3H), 1.26 (t, 3H), 4.21 (q, 3H), 4.33 (d, 1H), 4.45 (d, 1H), 8.33 (d, 1H), 8.69 (d, 1H), 8.75 (br d, 1H), 12.02 (br s, 1H), 12.04 (s, 1H).

Intermediate I-9

2-Amino-6-bromo-N-[1-fluoropropan-2-yl][1,2,4]triazolo[1,5-a]pyridine-8-carboxamide (mixture of enantiomers)

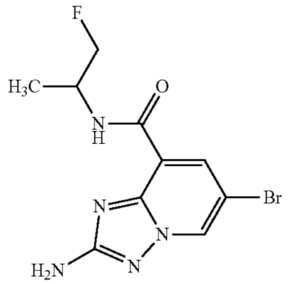 [SMILES: CC(CF)NC(=O)c1cc(Br)cn2nc(N)nc12]

To a solution of hydroxylamine hydrochloride (8.31 g, 120 mmol) in a 1/1 mixture of ethanol and methanol (180 ml) at rt was added N,N-diisopropylethylamine (19 ml, 110 mmol). The mixture was warmed to 60° C. Ethyl [(5-bromo-3-{[1-fluoropropan-2-yl]carbamoyl}pyridin-2-yl)carbamothioyl]carbamate (9.40 g, 96% purity, 22.2 mmol) was added and the reaction was further stirred for 45 minutes at 65° C. After cooling to rt, the mixture was diluted with water, the pH was adjusted with a with saturated solution of sodium bicarbonate to pH 6-7, and the precipitate was collected by suction filtration. After washing with water (50 ml) the residue was dried in vacuo to give 6.15 g (96% purity, 84% yield) of the title compound.

LC-MS (method 1): Rt=1.21 min; MS (ESIpos): m/z=316 $[M+H]^+$ $^1$H-NMR (400 MHz, DMSO-$d_6$) δ [ppm]: 1.28 (d, 3H), 4.22-4.41 (m, 1H), 4.43-4.46 (m, 1H), 4.53-4.60 (m, 1H), 6.57 (s, 2H), 8.08 (d, 1H), 9.18 (d, 1H), 9.38 (d, 1H).

Intermediate I-10a

2-Amino-6-bromo-N-(1-fluoropropan-2-yl)[1,2,4]triazolo[1,5-a]pyridine-8-carboxamide (stereoisomer 1)

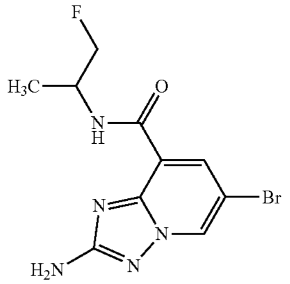 [SMILES: CC(CF)NC(=O)c1cc(Br)cn2nc(N)nc12]

2-Amino-6-bromo-N-(1-fluoropropan-2-yl)[1,2,4]triazolo[1,5-a]pyridine-8-carboxamide (mixture of enantiomers) (1.95 g, 96% purity) was separated by chiral preparative SFC to yield stereoisomer 1 (837 mg, 100% purity) and stereoisomer 2 (719 mg, 100% purity).

Instrument: THAR SFC-Super Chrom Prep 200; Column: Daicel Chiralpak AZ-H, 5 µm, 250×30 mm; Eluent A: $CO_2$; Eluent B: methanol; isocratic: 86% A+14% B; flow: 125 g/min; UV: 210 nm; temperature: 40° C.

Analytical SFC-method: Column: Chiralpak AZ-H, 3 m, 100×4.6 mm; Eluent A: $CO_2$; Eluent B: methanol; isocratic: 80% A+20% B; flow: 3 ml/min; UV: 210 nm; temperature: 40° C.

Stereoisomer 1: $R_t$=2.65 min and

Stereoisomer 2: $R_t$=3.12 (cf. next example)

LC-MS (method 1): $R_t$=1.24 min; MS (ESIpos): m/z=316 $[M+H]^+$ $^1$H-NMR (400 MHz, DMSO-$d_6$) δ [ppm]: 1.28 (d, 3H), 4.27-4.41 (m, 1H), 4.41-4.48 (m, 1H), 4.53-4.60 (m, 1H), 6.57 (s, 2H), 8.08 (d, 1H), 9.18 (d, 1H), 9.38 (br d, 1H).

Intermediate I-10b

2-Amino-6-bromo-N-[1-fluoropropan-2-yl][1,2,4]triazolo[1,5-a]pyridine-8-carboxamide (stereoisomer 2)

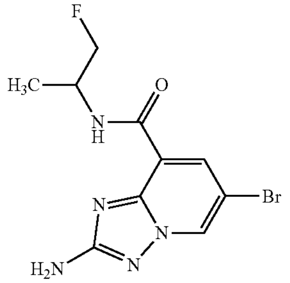 [SMILES: CC(CF)NC(=O)c1cc(Br)cn2nc(N)nc12]

The product was isolated in the previous example as second stereoisomer.

LC-MS (method 1): $R_t$=1.24 min; MS (ESIpos): m/z=316 $[M+H]^+$ $^1$H-NMR (400 MHz, DMSO-$d_6$) δ [ppm]: 1.28 (d, 3H), 4.27-4.40 (m, 1H), 4.40-4.48 (m, 1H), 4.53-4.60 (m, 1H), 6.57 (s, 2H), 8.08 (d, 1H), 9.18 (d, 11H), 9.38 (br d, 1H).

Intermediate I-IIa

2-Amino-5-bromo-N-[(2S)-1,1,1-trifluorobutan-2-yl] pyridine-3-carboxamide

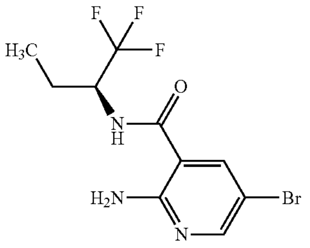 [SMILES: CC[C@H](NC(=O)c1cc(Br)cnc1N)C(F)(F)F]

To a suspension of 2-amino-5-bromonicotinic acid (5.52 g. 25.4 mmol) in N,N-dimethylformamide (100 ml) were added HATU (14.5 g, 38.2 mmol), N,N-diisopropylethylamine (16.4 g. 127 mmol) and (2S)-1,1,1-trifluorobutan-2-amine (3.88 g, 30.5 mmol). After stirring at rt for 1 h, the reaction mixture was diluted with water (200 ml). The precipitate was collected by suction filtration, washed twice with satd. sodium bicarbonate solution (50 ml each) and dried in vacuo to give 7.30 g (99% purity, 87% yield) of the title compound.

LC-MS (method 6): $R_t$=0.96 min; MS (ESIpos): m/z=326, 328 [M+H]$^+$ $^1$H-NMR (300 MHz, DMSO-$d_6$) δ [ppm]: 0.93 (t, 3H), 1.66-1.86 (m, 2H), 4.57-4.68 (m, 1H), 7.28 (s, 2H), 8.21-8.23 (m, 2H), 8.79 (d, 1H);

$^{19}$F-NMR (282 MHz, DMSO-$d_6$) δ [ppm]: −74.29 (s, 3F).

Intermediate I-11b

2-Amino-5-bromo-N-[(2R)-1,1,1-trifluorobutan-2-yl]pyridine-3-carboxamide

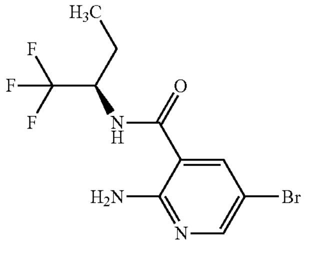 [SMILES: CC[C@@H](NC(=O)c1cc(Br)cnc1N)C(F)(F)F]

2-Amino-5-bromopyridine-3-carboxylic acid (200 mg, 922 μmol) was suspended in THF (2.5 ml) and cooled to 0° C. (2R)-1,1,1-trifluorobutan-2-amine (117 mg, 922 mol), diethylcyanophosphonate (170 pl, 93% purity, 1.0 mmol) and triethylamine (270 pl, 1.9 mmol) were added and stirring was continued for 15 min. The reaction was then warmed to rt and stirred for 1.5 h. Water was added and the mixture was extracted three times with ethyl acetate. The combined organic layers were washed with brine and filtered through a hydrophobic phase separation filter. The solvent was evaporated and the crude product purified by column chromatography (Biotage® SNAP KP-Sil 25 g cartridge, eluent: cyclohexane/ethyl acetate gradient 95: 5 to 40:60) to yield 155 mg (100% purity, 52% yield) of the title compound.

LC-MS (method 1): $R_t$=1.69 min; MS (ESIpos): m/z=326, 328 [M+H]$^+$ $^1$H-NMR (400 MHz, DMSO-$d_6$) δ [ppm]: 0.93 (t, 3H), 1.64-1.87 (m, 2H), 4.55-4.68 (m, 1H), 7.25 (s, 211), 8.21 (s, 2H), 8.76 (d, 1H).

Intermediate I-12a

Ethyl [(5-bromo-3-{[(2S)-1,1,1-trifluorobutan-2-yl] carbamoyl}pyridin-2-yl)carbamothioyl]carbamate

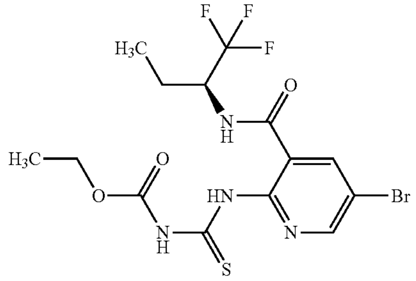 [SMILES: CCOC(=O)NC(=S)Nc1ncc(Br)cc1C(=O)N[C@@H](CC)C(F)(F)F]

To a solution of 2-amino-5-bromo-N-[(2S)-1,1,1-trifluorobutan-2-yl]nicotinamide (7.30 g, 22.4 mmol) in 1,4-dioxane (110 ml) at rt was added dropwise ethyl carbonisothiocyanatidate (14.7 g, 112 mmol). After stirring for 24 h the reaction mixture was concentrated under reduced pressure. The residue was triturated with hexane (150 ml). The precipitate was collected by suction filtration, washed with hexane (50 ml) and dried in vacuo to yield 9.24 g (99% purity, 89% yield) of the title compound.

LC-MS (method 6): $R_t$=1.15 min; MS (ESIpos): m/z=457, 459 [M+H]$^+$ $^1$H-NMR (400 MHz, DMSO-$d_6$) δ [ppm]: 0.92 (t, 3H), 1.24 (t, 3H), 1.54-1.65 (m, 1H), 1.74-1.82 (m, 1H), 4.20 (q, 2H), 4.52-4.59 (m, 1H), 8.27 (d, 1H), 8.73 (d, 1H), 9.00 (d, 1H), 11.82 (s, 2H).

$^{19}$F-NMR (376 MHz, DMSO-$d_6$) δ [ppm]: −74.17 (s, 3F).

Intermediate I-12b

Ethyl [(5-bromo-3-{[(2R)-1,1,1-trifluorobutan-2-yl] carbamoyl}pyridin-2-yl)carbamothioyl]carbamate

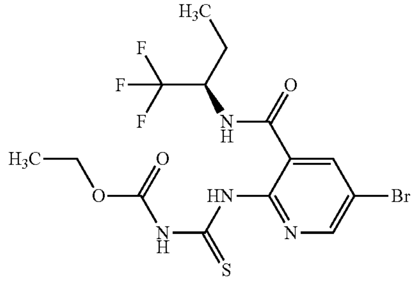 [SMILES: CCOC(=O)NC(=S)Nc1ncc(Br)cc1C(=O)N[C@H](CC)C(F)(F)F]

2-Amino-5-bromo-N-[(2R)-1,1,1-trifluorobutan-2-yl] pyridine-3-carboxamide (2.10 g, 6.44 mmol) was dissolved in 1,4-dioxane (15 ml) and ethyl carbonisothiocyanatidate (840 μl, 7.1 mmol) was slowly added at rt. The mixture was stirred for 3 h, then left stand for 3 days. The reaction mixture was concentrated in vacuo and the residue was triturated with tert-butyl methyl ether/cyclohexane (1:1, 50 ml). The precipitate was collected by suction filtration and washed twice with tert-butyl methyl ether/cyclohexane (1:1, 10 ml each) to yield 1.64 g (100% purity, 56% yield).

LC-MS (method 1): $R_t$=1.90 min; MS (ESIpos): m/z=457, 459 $[M+H]^+$ $^1$H-NMR (400 MHz, DMSO-$d_6$) δ [ppm]: 0.94 (t, 3H), 1.26 (t, 3H), 1.55-1.68 (m, 1H), 1.74-1.87 (m, 1H), 4.21 (q, 2H), 4.50-4.64 (m, 1H), 8.29 (d, 1H), 8.75 (d, 11H), 9.02 (d, 1H), 11.83 (s, 2H).

Intermediate I-13

2-Amino-6-bromo-N-[(2S)-1,1,1-trifluorobutan-2-yl][1,2,4]triazolo[1,5-a]pyridine-8-carboxamide

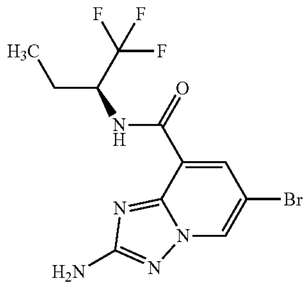 [SMILES: CC[C@H](NC(=O)c1cc(Br)cn2nc(N)nc12)C(F)(F)F]

To a solution of hydroxylamine hydrochloride (7.04 g, 101 mmol) in methanol (100 ml) at rt was added N,N-diisopropylethylamine (13.1 g. 101 mmol). The solution was heated to 60° C. Ethyl [(5-bromo-3-{[(2S)-1,1,1-trifluorobutan-2-yl]carbamoyl}pyridin-2-yl)carbamothioyl]carbamate (9.24 g, 20.3 mmol) was added. The resulting mixture was stirred at 60° C. for 2 h. After cooling to rt, the solvent was evaporated under reduced pressure and the residue was triturated with water (300 ml). The precipitate was collected by suction filtration and stirred for 24 h in satd. sodium bicarbonate solution. The precipitate was collected by suction filtration to yield 6.79 g (98% purity, 89% yield) the title compound.

LC-MS (method 7): $R_t$=1.40 min; MS (ESIpos): m/z=366, 368 $[M+H]^+$ $^1$H-NMR (300 MHz, DMSO-$d_6$) δ [ppm]: 0.94 (t, 3H), 1.64-1.74 (m, 1H), 1.88-2.01 (m, 1H), 4.72-4.88 (m, 1H), 6.65 (s, 2H), 8.12 (d, 1H), 9.23 (d, 1H), 9.61 (d, 1H).

$^{19}$F-NMR (282 MHz, DMSO-$d_6$) δ [ppm]: −74.28 (s, 3F).

Intermediate I-14

2-Amino-6-bromo-N-[(2R)-1,1,1-trifluorobutan-2-yl][1,2,4]triazolo[1,5-a]pyridine-8-carboxamide

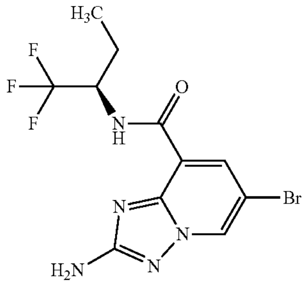 [SMILES: CC[C@@H](NC(=O)c1cc(Br)cn2nc(N)nc12)C(F)(F)F]

Hydroxylamine hydrochloride (1.31 g, 18.9 mmol) und N,N-diisopropylethylamine (3.0 ml, 17 mmol) were dissolved in methanol/ethanol (1:1, 40 ml) and the solution was warmed to 60° C. Ethyl [(5-bromo-3-{[(2R)-1,1,1-trifluorobutan-2-yl]carbamoyl}pyridin-2-yl)carbamothioyl]carbamate (1.60 g, 3.50 mmol) was added (evolving hydrogen sulfide was led into a sodium hydroxide solution). The reaction mixture was stirred at 60° C. for 2 h, then cooled to rt. The pH was adjusted to 6-7 with satd. sodium bicarbonate solution (ca. 15 ml). The mixture was poured into water (100 ml) and then extracted three times with ethyl acetate. The combined organic layers were filtered through a hydrophobic phase separation filter and the solvent was evaporated. The residue was purified by column chromatography (Biotage® SNAP Ultra 25 g cartridge, eluent: cyclohexane/ethyl acetate gradient 85:15 to 49:51) to yield 1.18 g (100% purity, 92% yield) of the title compound.

LC-MS (method 2): $R_t$=0.90 min; MS (ESIpos): m/z=366, 368 $[M+H]^+$ $^1$H-NMR (400 MHz, DMSO-$d_6$) δ [ppm]: 0.99 (t, 3H), 1.60-1.73 (m, 1H), 1.89'-1.99 (m, 1H), 4.72-4.86 (m, 1H), 6.64 (s, 2H), 8.11 (d, 1H), 9.23 (d, 1H), 9.61 (d, 1H).

Intermediate I-15

2-Amino-5-bromo-N-[(2S)-1-methoxypropan-2-yl]pyridine-3-carboxamide

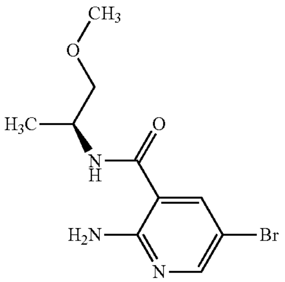 [SMILES: COC[C@H](C)NC(=O)c1cc(Br)cnc1N]

To a suspension of 2-amino-5-bromonicotinic acid (3.00 g, 13.8 mmol) in tetrahydrofuran (40 ml) cooled at 0° C. were added (2S)-1-methoxypropan-2-amine (1.48 g, 16.6 mmol), diethyl cyanophosphonate (2.71 g, 16.6 mmol) and triethylamine (3.9 ml, 28 mmol). The resulting mixture was stirred at 0° C. for 15 min and then warmed to rt. Stirring was continued for 1 h. The reaction mixture was then diluted with water (100 ml) and extracted three times with ethyl acetate (100 ml). The combined organic layers were washed twice with brine (100 ml each) and dried over anhydrous sodium sulfate. The solvent was evaporated under reduced pressure to give 3.80 g (97% purity, 93% yield) of the title compound.

LC-MS (method 13): $R_t$=1.02 min; MS (ESIpos): m/z=288, 290 $[M+H]^+$ $^1$H-NMR (300 MHz, DMSO-$d_6$) δ [ppm]: 1.12 (d, 3H), 3.24-3.41 (m, 5H), 4.07-4.23 (m, 1H), 7.22 (br s, 2H), 8.10 (d, 1H), 8.15 (d, 1H), 8.32 (br d, 1H).

Intermediate I-16

Ethyl [(5-bromo-3-{[(2S)-1-methoxypropan-2-yl] carbamoyl}pyridin-2-yl)carbamothioyl]carbamate

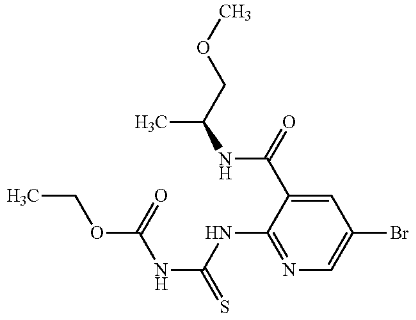 [SMILES: CCOC(=O)NC(=S)Nc1ncc(Br)cc1C(=O)N[C@@H](C)COC]

To a solution of 2-amino-5-bromo-N-[(2S)-1-methoxy-propan-2-yl]nicotinamide (3.80 g, 13.2 mmol) in 1,4-dioxane (50 ml) was added dropwise ethyl carbonisothiocyanatidate (8.65 g, 65.9 mmol) at rt. After stirring for 72 h at rt, the reaction mixture was concentrated under reduced pressure and the residue was triturated with hexane. The residue was purified by flash chromatography (silica gel; eluent: petroleum ether/ethyl acetate 2:1) to yield 4.50 g (95% purity, 77% yield) of the title compound.

LC-MS (method 13): $R_t$=1.14 min; MS (ESIpos): m/z=419, 421 $[M+H]^+$ $^1$H-NMR (300 MHz, DMSO-$d_6$) δ [ppm]: 1.10 (d, 3H), 1.24 (t, 3H), 3.20-3.40 (m, 5H), 4.05-4.25 (m, 3H), 8.30 (d, 1H), 8.56 (br d, 1H), 8.66 (d, 1H), 12.04-12.06 (m, 2H).

Intermediate I-17

2-Amino-6-bromo-N-[(2S)-1-methoxypropan-2-yl] [1,2,4]triazolo[1,5-a]pyridine-8-carboxamide

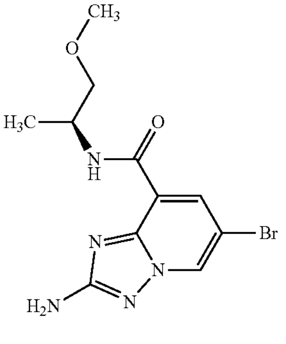 [SMILES: COC[C@H](C)NC(=O)c1cc(Br)cn2nc(N)nc12]

To a solution of hydroxylamine hydrochloride (4.48 g, 64.4 mmol) in methanol/ethanol (1:1, 60 ml) at rt was added N,N-diisopropylethylamine (8.32 g, 64.4 mmol) and the mixture was heated to 60° C. Ethyl [(5-bromo-3-{[(2S)-1-methoxypropan-2-yl]carbamoyl}pyridin-2-yl)carbamothioyl]carbamate (4.50 g, 10.7 mmol) was added and the resulting mixture was stirred at 65° C. for 1 h, then cooled to rt. The reaction mixture was diluted with water (200 ml) and extracted three times with ethyl acetate (100 ml each). The combined organic layers were dried over anhydrous sodium sulfate and the solvent was evaporated under reduced pressure. The residue was purified by flash chromatography (silica gel; eluent: petroleum ether/ethyl acetate, 1:1) to yield 3.19 g (98% purity, 89% yield) of the title compound.

LC-MS (method 14): $R_t$=1.54 min; MS (ESIpos): m/z=328, 330 $[M+H]^+$

Intermediate I-18

2-Amino-5-bromo-N-[(2S)-1-hydroxypropan-2-yl] pyridine-3-carboxamide

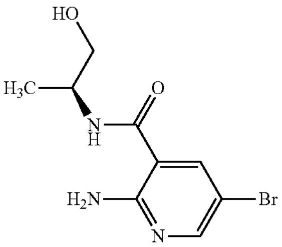

To 2-amino-5-bromopyridine-3-carboxylic acid (20.0 g, 92.2 mmol) and TBTU (38.5 g, 120 mmol) in THF (270 ml) at rt was added (2S)-2-aminopropan-1-ol (8.6 ml, 110 mmol) and the reaction mixture was stirred for 3 h at rt. Subsequently, the mixture was concentrated in vacuo and water was added. It was extracted twice with ethyl acetate and the combined organic layers were washed with brine and dried over anhydrous sodium sulfate and the solvent was evaporated under reduced pressure. The residue was triturated with tert-butyl methyl ether/acetonitrile and the precipitate was collected by suction filtration to yield 17.7 g (100% purity, 70% yield). The mother liquor was concentrated and purified by column chromatography (Biotage® SNAP Ultra 100 g cartridge, eluent: cyclohexane/ethyl acetate gradient 80:26 to 0:100) to yield another 3.00 g (100% purity, 12% yield) of the title compound.

LC-MS (method 1): $R_t$=0.83 min; MS (ESIpos): m/z=274 $[M+H]^+$ $^1$H-NMR (400 MHz, DMSO-$d_6$) δ [ppm]: 1.10 (d, 3H), 3.29-3.37 (m, 1H), 3.38-3.46 (m, 1H), 3.91-4.03 (m, 1H), 4.72 (t, 1H), 7.19 (br s, 2H), 8.08-8.15 (m, 2H), 8.19 (br d, 1H).

Intermediate I-19

Ethyl [(5-bromo-3-{[(2S)-1-hydroxypropan-2-yl] carbamoyl}pyridin-2-yl)carbamothioyl]carbamate

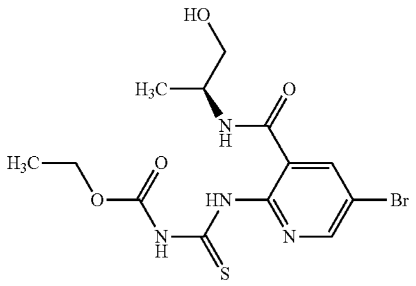

To 2-amino-5-bromo-N-[(2S)-1-hydroxypropan-2-yl] pyridine-3-carboxamide (20.7 g, 75.5 mmol) in 1,4-dioxane (250 ml) at rt was dropwise added ethyl carbonisothiocyanatidate (9.8 ml, 83 mmol) and the reaction mixture was stirred overnight at rt. The solvent was removed under reduced pressure and the residue was triturated with tert-butyl methyl ether (200 ml). The precipitate was collected by suction filtration. It was then triturated with tert-butyl methyl ether (150 ml) and dichloromethane (20 ml) and again collected by suction filtration to yield 29.9 g (93% purity, 90% yield) of the title compound.

LC-MS (method 2): $R_t$=0.71 min; MS (ESIpos): m/z=405 $[M+H]^+$ $^1$H-NMR (400 MHz, DMSO-$d_6$) δ [ppm]: 1.10 (d, 3H), 1.26 (t, 3H), 3.28-3.36 (m, 1H), 3.43 (dt, 1H), 3.89-4.02 (m, 1H), 4.21 (q, 2H), 4.75 (t, 1H), 8.39 (d, 1H), 8.53 (br d, 1H), 8.67 (d, 1H), 12.10-12.21 (m, 2H).

Intermediate I-20

2-Amino-6-bromo-N-[(2S)-1-hydroxypropan-2-yl] [1,2,4]triazolo[1,5-a]pyridine-8-carboxamide

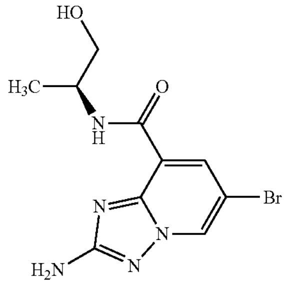

The reaction was performed in two batches of equal size. To a solution of hydroxylamine hydrogen chloride (25.4 g, 365 mmol) in methanol/ethanol (1:1, 400 ml) was added N,N-diisopropylethylamine (59 ml, 340 mmol) and the mixture was heated to 60° C. Ethyl [(5-bromo-3-{[(2S)-1-hydroxypropan-2-yl]carbamoyl}pyridin-2-yl)carbamothioyl]carbamate (29.8 g, 93% purity, 67.6 mmol) was added and the reaction mixture was stirred at 60° C. for 30 min. The two reactions were cooled to rt and combined. The pH was adjusted to 6-7 by addition of satd. sodium bicarbonate solution (ca. 40 ml) and the mixture was poured into water (600 ml). Ethyl acetate was added and the layers were separated. The aqueous layer was extracted twice with ethyl acetate and the combined organic layers were dried over anhydrous sodium sulfate and the solvent was evaporated under reduced pressure to yield 19.5 g (100% purity, 92% yield) of the title compound.

LC-MS (method 1): $R_t$=0.89 min; MS (ESIpos): m/z=314 $[M+H]^+$ $^1$H-NMR (400 MHz, DMSO-$d_6$) δ [ppm]: 1.21 (d, 3H), 3.40-3.54 (m, 2H), 4.01-4.14 (m, 1H), 4.90 (t, 1H), 6.54 (s, 2H), 8.07 (d, 1H), 9.16 (d, 1H), 9.24 (d, 1H).

Intermediate I-21

2-Amino-5-bromo-N-(1-hydroxy-2-methylpropan-2-yl)pyridine-3-carboxamide

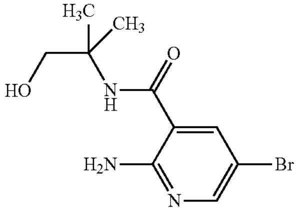 [SMILES: CC(C)(CO)NC(=O)c1cc(Br)cnc1N]

To 2-amino-5-bromopyridine-3-carboxylic acid (5.00 g, 23.0 mmol) and TBTU (9.62 g, 30.0 mmol) in THE (70 ml) at rt were added triethylamine (6.7 ml, 48 mmol) and 2-amino-2-methylpropan-1-ol (2.6 ml, 28 mmol) and the reaction mixture was stirred at rt overnight. The mixture was filtered and water was added. The aqueous layer was extracted twice with ethyl acetate.

The combined organic layers were washed with brine, dried over sodium sulfate, and the solvent was removed in vacuo. The residue was purified by column chromatography (Biotage® SNAP Ultra 100 g cartridge, eluent: cyclohexane/ethyl acetate gradient 80:20 to 0:100) to yield 4.78 g (99% purity, 71% yield) of the title compound.

LC-MS (method 1): $R_t$=1.07 min; MS (ESIpos): m/z=288 $[M+H]^+$ $^1$H-NMR (400 MHz, DMSO-$d_6$) δ [ppm]: 1.28 (s, 6H), 3.50 (d, 2H), 4.79 (t, 1H), 7.00 (s, 2H), 7.68 (s, 1H), 8.01 (d, 1H), 8.10 (d, 1H).

Intermediate I-22

Ethyl ({5-bromo-3-[(1-hydroxy-2-methylpropan-2-yl)carbamoyl]pyridin-2-yl}carbamothioyl)carbamate

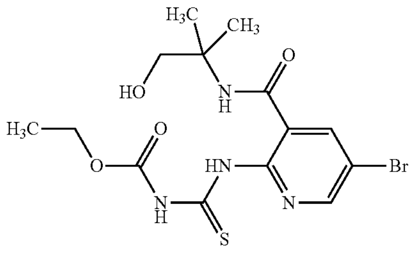 [SMILES: CCOC(=O)NC(=S)Nc1ncc(Br)cc1C(=O)NC(C)(C)CO]

To 2-amino-5-bromo-N-(1-hydroxy-2-methylpropan-2-yl)pyridine-3-carboxamide (4.78 g, 16.6 mmol) in 1,4-dioxane (30 ml) at rt was dropwise added ethyl carbonisothiocyanatidate (2.3 ml, 20 mmol) and the reaction mixture was stirred overnight at rt. The solvent was then removed under reduced pressure and the residue was triturated with tert-butyl methyl ether (60 ml). The precipitate was collected by suction filtration and dried in vacuo to yield 5.87 g (85% purity, 72% yield) of the title compound.

LC-MS (method 1): $R_t$=1.43 min; MS (ESIpos): m/z=419 $[M+H]^+$ $^1$H-NMR (400 MHz, DMSO-$d_6$) δ [ppm]: 1.23-1.28 (m, 9H), 3.48 (d, 2H), 4.21 (q, 2H), 4.74 (t, 1H), 7.98 (s, 1H), 8.26 (d, 1H), 8.66 (d, 1H), 11.83-11.97 (m, 2H).

Intermediate I-23

2-Amino-6-bromo-N-(1-hydroxy-2-methylpropan-2-yl)[1,2,4]triazolo[1,5-a]pyridine-8-carboxamide

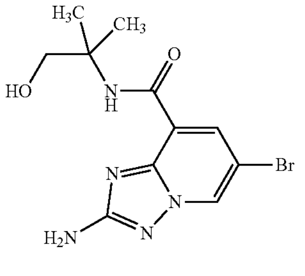 [SMILES: CC(C)(CO)NC(=O)c1cc(Br)cn2nc(N)nc12]

To a solution of hydroxylamine-hydrogen chloride (1/1) (4.47 g, 64.3 mmol) in methanol/ethanol (1:1, 60 ml) was added N,N-diisopropylethylamine-(10 ml, 59 mmol) and the mixture was heated to 60° C. Ethyl ({5-bromo-3-[(1-hydroxy-2-methylpropan-2-yl)carbamoyl]pyridin-2-yl}carbamothioyl)carbamate (5.87 g, 85% purity, 11.9 mmol) was added and the reaction mixture was stirred at 60° C. for 30 min, then cooled to rt. The pH was adjusted to 6-7 by addition of satd. sodium bicarbonate solution (ca. 40 ml) and the mixture was poured into water (300 ml). Ethyl acetate was added and the layers were separated. The aqueous layer was extracted twice with ethyl acetate and the combined organic layers were dried over anhydrous sodium sulfate and the solvent 10 was evaporated under reduced pressure to yield 2.31 g (100% purity, 59% yield) of the title compound.

LC-MS (method 1): $R_t$=1.12 min; MS (ESIpos): m/z=328 $[M+H]^+$ $^1$H-NMR (400 MHz, DMSO-$d_6$) δ [ppm]: 1.35 (s, 6H), 3.55 (d, 2H), 4.91 (t, 1H), 6.49 (s, 2H), 8.03 (d, 1H), 9.14 (d, 1H), 9.27 (s, 1H).

Intermediate I-24

2-Amino-5-bromo-N-[(3S)-tetrahydrofuran-3-yl]nicotinamide

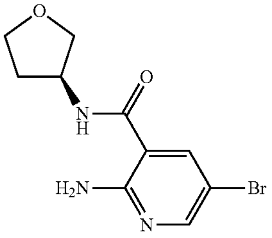 [SMILES: Nc1ncc(Br)cc1C(=O)N[C@H]1CCOC1]

2-Amino-5-bromopyridine-3-carboxylic acid (18.0 g, 82.9 mmol) was suspended in THF (300 ml) and cooled to 0° C. (3S)-Tetrahydrofuran-3-amine (9.39 g, 108 mmol) was added leading to a clear solution. Diethyl cyanophosphonate (16.2 g, 99.5 mmol) and triethylamine (23 ml, 170 mmol) were added. After 15 min, the mixture was warmed to rt and further stirred at this temperature for 2 h. Subsequently, the reaction mixture was diluted with water (1.0 1) and extracted twice with ethyl acetate (1.5 1 each). The combined organic layers were washed with brine, dried over anhydrous sodium sulfate and the solvent was evaporated under reduced pressure to give 23.0 g (92% purity, 89% yield) of the title compound.

LC-MS (method 9): $R_t$=0.88 min; MS (ESIpos): m/z=286, 288 $[M+H]^+$ $^1$H-NMR (300 MHz, DMSO-$d_6$) δ [ppm]: 1.85-1.95 (m, 1H), 2.09-2.20 (m, 1H), 3.56-3.60 (m, 1H), 3.70-3.75 (m, 1H), 3.81-3.89 (m, 2H), 4.36-4.46 (m, 1H), 7.23 (s, 2H), 8.15 (s, 2H), 8.60 (d, 1H).

Intermediate I-25

Ethyl ({5-bromo-3-[(3S)-tetrahydrofuran-3-ylcarbamoyl]pyridin-2-yl}carbamothioyl)carbamate

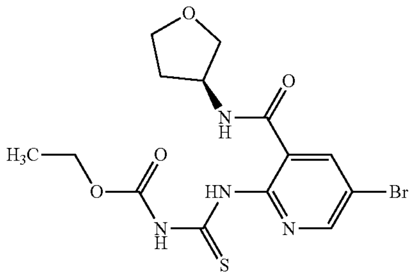 [SMILES: CCOC(=O)NC(=S)Nc1ncc(Br)cc1C(=O)N[C@H]1CCOC1]

To a solution of 2-amino-5-bromo-N-[(3S)-tetrahydrofuran-3-yl]nicotinamide (23.0 g, 92% purity, 74.0 mmol) in 1,4-dioxane (300 ml) was added dropwise ethyl carbonisothiocyanatidate (48.5 g, 370 mmol). The mixture was stirred overnight at rt, then concentrated under reduced pressure. The residue was triturated with hexane (1.0 1). The precipitate was collected by suction filtration, 20 washed twice with hexane (1.0 1 each) and dried in vacuo to yield 30.0 g (99% purity, 96% yield) of the title compound.

LC-MS (method 9): $R_t$=0.86 min; MS (ESIpos): m/z=417, 419 $[M+H]^+$ $^1$H-NMR (300 MHz, DMSO-$d_6$) δ [ppm]: 1.27 (t, 3H), 1.81-1.95 (m, 1H), 2.15 (dq, 1H), 3.56-3.88 (m, 4H), 4.22 (q, 2H), 4.34-4.49 (m, 1H), 8.36 (d, 1H), 8.69 (d, 1H), 8.88 (br d, 1H), 12.04 (s, 2H).

Intermediate I-26

2-Amino-6-bromo-N-[(3S)-tetrahydrofuran-3-yl][1,2,4]triazolo[1,5-a]pyridine-8-carboxamide

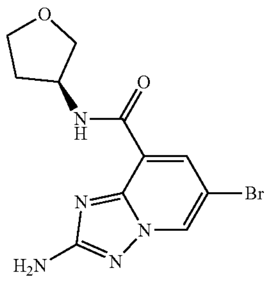 [SMILES: Nc1nc2c(C(=O)N[C@H]3CCOC3)cc(Br)cn2n1]

To a solution of hydroxylamine hydrochloride (29.7 g, 427 mmol) in methanol (450 ml) at rt was added N,N-diisopropylethylamine (55.1 g, 427 mmol) and the mixture was warmed to 60° C. Then ethyl ({5-bromo-3-[(3S)-tetrahydrofuran-3-ylcarbamoyl]pyridin-2-yl}carbamothioyl)carbamate (30.0 g, 71.2 mmol) was added. The reaction mixture was stirred at 60° C. for 2 h. After cooling to rt, the mixture was diluted with water and the precipitate was collected by suction filtration and stirred with sodium bicarbonate solution (1.0 1) overnight. The compound was collected by suction filtration and dried in vacuo to yield 21.0 g (98% purity, 90% yield) of the title compound.

LC-MS (method 8): $R_t$=0.92 min; MS (ESIpos): m/z=326, 328 [M+H]$^+$ $^1$H-NMR (300 MHz, DMSO-$d_6$) δ [ppm]: 1.78-1.93 (m, 1H), 2.22-2.38 (m, 1H), 3.64 (dd, 1H), 3.77 (td, 1H), 3.84-3.97 (m, 2H), 4.50-4.63 (m, 1H), 6.59 (s, 2H), 8.05 (d, 1H), 9.18 (d, 1H), 9.51 (br d, 1H).

Intermediate I-27

2-Amino-5-bromo-N-(5-oxopyrrolidin-3-yl)pyridine-3-carboxamide (mixture of enantiomers)

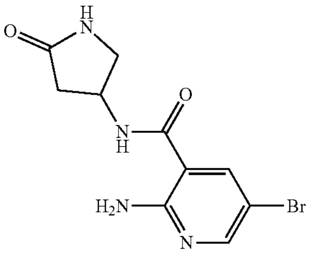 [SMILES: Nc1ncc(Br)cc1C(=O)NC1CNC(=O)C1]

To a solution of racemic 4-aminopyrrolidin-2-one hydrochloride (1.73 g, 12.7 mmol) in N,N-dimethylformamide (50 ml) was added triethylamine (5 ml) dropwise until a pH 10. Then 2-amino-5-bromonicotinic acid (2.50 g, 11.5 mmol) and diethyl cyanophosphonate (2.26 g, 13.8 mmol) were added. The resulting mixture was stirring at rt for 1 h and then poured into water (100 ml). The precipitate was collected by suction filtration and dried in vacio to yield 2.90 g (99% purity, 83% yield) of the title compound.

LC-MS (method 13): $R_t$=0.66 min; MS (ESIpos): m/z=299, 301 [M+H]$^+$ $^1$H-NMR (300 MHz, DMSO-$d_6$) δ [ppm]: 2.22 (dd, 1H), 2.54 (dd, 1H), 3.15 (dd, 1H), 3.58 (dd, 1H), 4.47-4.63 (m, 1H), 7.25 (s, 2H), 7.68 (s, 1H), 8.11-8.21 (m, 2H), 8.81 (br d, 1H).

Intermediate I-28

Ethyl ({5-bromo-3-[(5-oxopyrrolidin-3-yl)carbamoyl]pyridin-2-yl}carbamothioyl)carbamate (mixture of enantiomers)

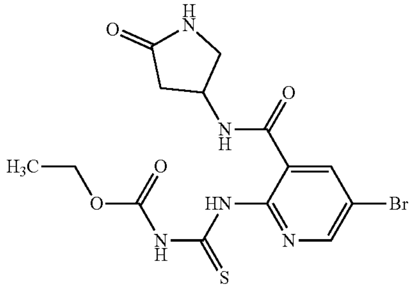 [SMILES: CCOC(=O)NC(=S)Nc1ncc(Br)cc1C(=O)NC1CNC(=O)C1]

To a solution of 2-amino-5-bromo-N-(5-oxopyrrolidin-3-yl)nicotinamide (2.20 g, 7.35 mmol) in 1,4-dioxane (50 ml) was slowly added ethyl carbonisothiocyanatidate (5.79 g, 44.1 mmol). The resulting mixture was stirred at rt for 72 h and was then concentrated under reduced pressure. The residue was triturated with tert-butyl methyl ether and the precipitate was collected by suction filtration and dried in vacuo to yield 2.50 g (97% purity, 76% yield) of the title compound.

LC-MS (method 11): $R_t$=0.68 min; MS (ESIpos): m/z=430, 432 [M+H]$^+$ $^1$H-NMR (300 MHz, DMSO-$d_6$) δ [ppm]: 1.24 (t, 3H), 2.15 (dd, 1H), 2.52 (dd, 1H), 3.14 (dd, 1H), 3.51-3.59 (m, 1H), 4.19 (q, 2H), 4.44-4.58 (m, 1H), 7.64 (s, 1H), 8.36 (d, 1H), 8.66 (d, 1H), 9.08 (br d, 1H), 12.05 (s, 2H).

Intermediate I-29

2-Amino-6-bromo-N-(5-oxopyrrolidin-3-yl)[1,2,4]triazolo[1,5-a]pyridine-8-carboxamide (mixture of enantiomers)

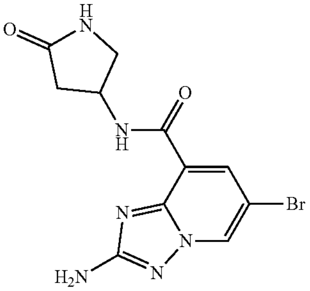 [SMILES: Nc1nc2c(C(=O)NC3CNC(=O)C3)cc(Br)cn2n1]

To a solution of hydroxylamine hydrochloride (2.42 g, 34.9 mmol) in methanol/ethanol (1:1, 60 ml) at rt was added N,N-diisopropylethylamine (4.51 g, 34.9 mmol) and the mixture was heated to 60° C. Ethyl ({5-bromo-3-[(5-oxopyrrolidin-3-yl)carbamoyl]pyridin-2-yl}carbamothioyl)carbamate (2.50 g, 5.81 mmol) was added and the resulting mixture was stirred 15 at 65° C. for 1 h. It was then cooled to rt and water (20 ml) was added. The precipitate was collected by suction filtration and dried in vacuo to give 1.54 g (99% purity, 77% yield) of the title compound.

LC-MS (method 8): $R_t$=0.85 min; MS (ESIpos): m/z=339, 341 $[M+H]^+$ $^1$H-NMR (300 MHz, DMSO-$d_6$) δ [ppm]: 2.20 (dd, 1H), 2.69 (dd, 1H), 3.14-3.26 (m, 1H), 3.69 (dd, 1H), 4.58-4.73 (m, 1H), 6.60 (br s, 2H), 7.77 (br s, 1H), 8.06 (d, 1H), 9.19 (d, 1H), 9.54 (d, 1H).

Intermediate I-30

N-[(2S)-Butan-2-yl]-4-chloro-6-fluoropyridine-2-carboxamide

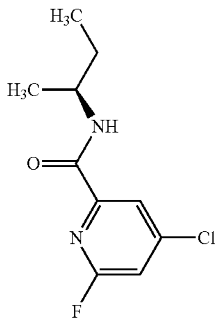

To methyl 4-chloro-6-fluoropyridine-2-carboxylate [CAS-RN 1256810-49-7](600 mg, 3.16 mmol) in methanol (7.1 ml) was added (2S)-butan-2-amine (1.6 ml, 16 mmol) and the mixture was stirred for 2 h at rt in a sealed vessel. The mixture was then evaporated under reduced pressure and the residue was purified by column chromatography (Biotage® SNAP Ultra 25 g cartridge, eluent: cyclohexane/ethyl acetate gradient) to yield 700 mg (95% purity, 91% yield) of the title compound.

LC-MS (method 1): $R_t$=1.81 min; MS (ESIpos): m/z=231 $[M+H]^+$ $^1$H-NMR (400 MHz, DMSO-$d_6$) δ [ppm]: 0.84 (t, 3H), 1.15 (d, 3H), 1.44-1.65 (m, 2H), 3.85-3.97 (m, 1H), 7.74 (t, 1H), 7.96 (s, 1H), 8.44 (br d, 1H).

Intermediate I-31

6-Amino-N-[(2S)-butan-2-yl]-4-chloropyridine-2-carboxamide

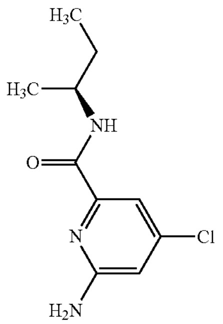

The reaction was performed in four batches of equal size. N-[(2S)-butan-2-yl]-4-chloro-6-fluoropyridine-2-carboxamide (4.50 g, 19.5 mmol) in aq. ammonia (30%, 30 ml) was heated in the microwave oven for 100 min to 120° C. The mixture was then diluted with ethyl acetate and water and the layers were separated. The aqueous phase was extracted twice with ethyl acetate and the combined organic layers were filtered through a hydrophobic phase separation filter. The solvent was removed in vacuo to yield 3.82 g (95% purity, 82% yield) of the title compound.

LC-MS (method 1): $R_t$=1.45 min; MS (ESIpos): m/z=228 $[M+H]^+$ $^1$H-NMR (500 MHz, DMSO-$d_6$) δ [ppm]: 0.86 (t, 3H), 1.14 (d, 3H), 1.51 (quin, 2H), 3.82-3.91 (m, 1H), 6.52 (br s, 2H), 6.68 (d, 1H), 7.11 (d, 1H), 7.91 (br d, 1H).

Intermediate I-32

Ethyl [(6-{[(2S)-butan-2-yl]carbamoyl}-4-chloropyridin-2-yl)carbamothioyl]carbamate

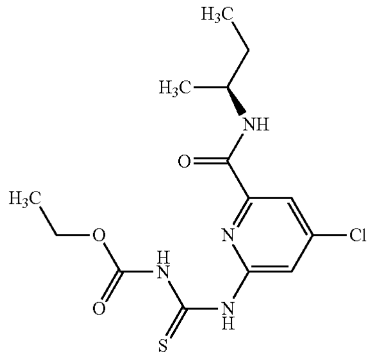 [SMILES: CCOC(=O)NC(=S)Nc1cc(Cl)cc(C(=O)N[C@@H](C)CC)n1]

To 6-amino-N-[(2S)-butan-2-yl]-4-chloropyridine-2-carboxamide (4.47 g, 95% purity, 18.6 mmol) in 1,4-dioxane (40 ml) was added dropwise ethyl carbonisothiocyanatidate (2.4 ml, 21 mmol) and the mixture was stirred at rt overnight. The mixture was concentrated under reduced pressure. The residue was triturated with tert-butyl methyl ether (50 ml) and the precipitate was collected by suction filtration and washed twice with tert-butyl methyl ether (5 ml each) to yield 5.39 g (100% purity, 81% yield) of the title compound.

LC-MS (method 1): $R_t$=2.05 min; MS (ESIpos): m/z=359 $[M+H]^+$ $^1$H-NMR (500 MHz, DMSO-$d_6$) δ [ppm]: 0.86 (t, 3H), 1.17 (d, 3H), 1.28 (t, 3H), 1.47-1.63 (m, 2H), 3.86-3.97 (m, 1H), 4.25 (q, 2H), 7.83 (d, 1H), 8.29 (br d, 1H), 8.80 (br s, 1H), 11.76 (br s, 1H), 12.15 (br s, 1H).

Intermediate I-33

2-Amino-N-[(2S)-butan-2-yl]-7-chloro[1,2,4]triazolo[1,5-a]pyridine-5-carboxamide

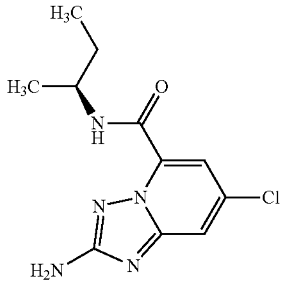 [SMILES: CC[C@H](C)NC(=O)c1cc(Cl)cc2nc(N)nn12]

To hydroxylamine hydrochloride (3.28 g, 47.3 mmol) in methanol/ethanol (1:1, 30 ml) was added N,N-diisopropylethylamine (7.7 ml, 44 mmol), and the mixture was heated to 60° C. Ethyl [(6-{[(2S)-butan-2-yl]carbamoyl}-4-chloropyridin-2-yl)carbamothioyl]carbamate (5.30 g, 14.8 mmol) was added (evolving hydrogen sulfide was led into a sodium hydroxide solution) and heating was continued for 1 h. The mixture was cooled to rt and the pH was adjusted to 6-7 by addition of satd. sodiumbicarbonate solution. The mixture was poured into water (50 ml) and extracted with ethyl acetate. The aqueous layer was extracted twice with ethyl acetate and the combined organic layers filtered through a hydrophobic phase separation filter. The solvent was evaporated and the residue was purified by column chromatography (Biotage® SNAP Ultra 50 g cartridge, eluent: cyclohexane/ethyl acetate gradient) to yield 3.66 g (100% purity, 92% yield) of the title compound.

LC-MS (method 1): $R_t$=1.45 min; MS (ESIpos): m/z=268 $[M+H]^+$ $^1$H-NMR (500 MHz, DMSO-$d_6$) δ [ppm]: 0.94 (t, 3H), 1.22 (d, 3H), 1.59 (quin, 2H), 3.93-4.03 (m, 111), 6.55 (s, 211), 7.48 (d, 1H), 7.76 (d, 1H), 9.94 (br d, 111).

Intermediate I-34

4-Chloro-6-fluoro-N-[(3S)-tetrahydrofuran-3-yl]pyridine-2-carboxamide

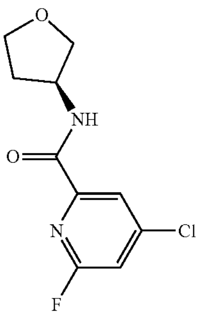 [SMILES: O=C(N[C@H]1CCOC1)c1cc(Cl)cc(F)n1]

Methyl 4-chloro-6-fluoropyridine-2-carboxylate (4.70 g, 24.8 mmol) was dissolved in methanol (10 ml). (3S)-Tetrahydrofuran-3-amine (6.48 g, 74.4 mmol) was added and the reaction mixture was stirred overnight at rt. Volatiles were removed in vacuo. The crude product was purified by column chromatography (silica gel, 220 g; eluent: petroleum ether/ethyl acetate, 5:1) to yield 4.10 g (99% purity, 67% yield) of the title compound.

LC-MS (method 5): $R_t$=0.81 min; MS (ESIpos): m/z=245 $[M+H]^+$

Intermediate I-35

6-Amino-4-chloro-N-[(3S)-tetrahydrofuran-3-yl]pyridine-2-carboxamide

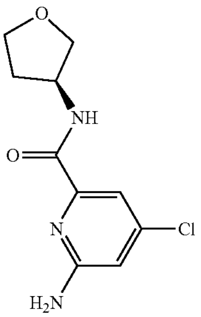 [SMILES: Nc1cc(Cl)cc(C(=O)N[C@H]2CCOC2)n1]

To 4-chloro-6-fluoro-N-[(3S)-tetrahydrofuran-3-yl]pyridine-2-carboxamide (4.00 g, 16.3 mmol) in 1,4-dioxane (30 ml) was added aq. ammonia (30%, 30 ml). The vial was sealed and heated overnight to 120° C. The reaction mixture was then diluted with ethyl acetate (80 ml) and water (80 ml). The layers were separated and the aqueous layer was extracted twice with ethyl acetate (80 ml each). The combined organic layers were dried over anhydrous sodium sulfate and the solvent was evaporated under reduced pressure. The crude product crystallized overnight. It was triturated cyclohexane (20 ml) and tert-butyl methyl ether (1 ml). The precipitate was collected by suction filtration to yield 2.70 g (99% purity, 68% yield) of the title compound.

LC-MS (method 19): $R_t$=0.61 min; MS (ESIpos): m/z=242 $[M+H]^+$

Intermediate I-36

Ethyl ({4-chloro-6-[(3S)-tetrahydrofuran-3-ylcarbamoyl]pyridin-2-yl}carbamothioyl)carbamate

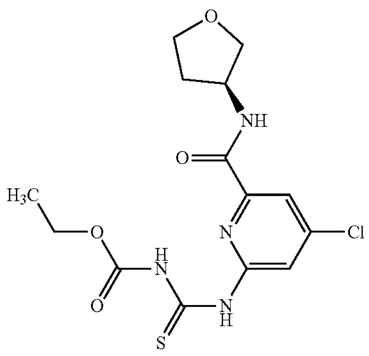 [SMILES: CCOC(=O)NC(=S)Nc1cc(Cl)cc(C(=O)N[C@H]2CCOC2)n1]

To a stirred solution of 6-amino-4-chloro-N-[(3S)-tetrahydrofuran-3-yl]pyridine-2-carboxamide (3.70 g, 15.3 mmol) in 1,4-dioxane (100 ml) at rt was added dropwise ethyl carbonisothiocyanatidate (4.02 g, 30.6 mmol) and stirring was continued overnight. Hexane (200 ml) was added and the precipitate was collected by suction filtration and washed twice with hexane (20 ml each) to yield 5.45 g (98% purity, 94% yield) of the title compound.

LC-MS (method 12): $R_t$=0.89 min; MS (ESIpos): m/z=373 $[M+H]^+$ $^1$H-NMR (300 MHz, DMSO-$d_6$) δ [ppm]: 1.28 (t, 3H), 1.90-2.03 (m, 1H), 2.12-2.26 (m, 1H), 3.63 (dd, 1H), 3.73 (td, 1H), 3.81-3.93 (m, 2H), 4.26 (q, 2H), 4.43-4.56 (m, 1H), 7.84 (d, 1H), 8.68 (d, 1H), 8.79-8.88 (m, 1H), 11.81 (br s, 1H), 12.18 (br s, 1H).

Intermediate I-37

2-Amino-7-chloro-N-[(3S)-tetrahydrofuran-3-yl][1,2,4]triazolo[1,5-a]pyridine-5-carboxamide

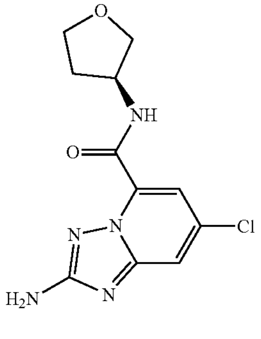 [SMILES: Nc1nc2cc(Cl)cc(C(=O)N[C@H]3CCOC3)n2n1]

To a solution of hydroxylamine hydrochloride (3.65 g, 52.6 mmol) in methanol (80 ml) at rt was added N,N-diisopropylethylamine (11 ml, 66 mmol). The resulting mixture was warmed to 60° C. Ethyl ({4-chloro-6-[(3S)-tetrahydrofuran-3-ylcarbamoyl]pyridin-2-yl}carbamothioyl)carbamate (4.90 g, 13.1 mmol) was added and the reaction mixture was stirred at 65° C. for 1.5 h. It was then cooled to rt and diluted with water (150 ml). The precipitate was collected by suction filtration. The filter cake was triturated with satd. sodium bicarbonate solution (100 ml) and stirred for 4 h. The precipitate was collected by suction filtration, washed with water (20 ml) and dried in vacuo to yield 3.30 g (98% purity, 87% yield) of the title compound.

LC-MS (method 7): $R_t$=0.88 min; MS (ESIpos): m/z=282 $[M+H]^+$ $^1$H-NMR (300 MHz, DMSO-$d_6$) δ [ppm]: 1.86-1.98 (m, 1H), 2.29 (dq, 1H), 3.69 (dd, 1H), 3.77 (td, 1H), 3.85-3.98 (m, 2H), 4.49-4.61 (m, 1H), 6.59 (s, 2H), 7.47 (d, 1H), 7.78 (d, 1H), 10.23 (br d, 1H).

Intermediate I-38

Methyl 4-bromo-6-[(1-fluoropropan-2-yl)carbamoyl]pyridine-2-carboxylate (mixture of enantiomers)

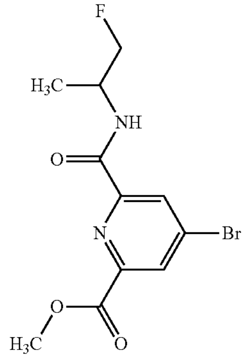

To a solution of 4-bromo-6-(methoxycarbonyl)pyridine-2-carboxylic acid [CAS-RN 293294-72-1](4.3 g, 16.54 mmol) in N,N-dimethylformamide (50 ml) were added HATU (9.43 g, 24.8 mmol), N,N-diisopropylethylamine (6.41 g, 49.6 mmol), racemic 1-fluoropropan-2-amine hydrochloride 5 (1:1) [CAS-RN 921602-78-0](2.25 g, 19.8 mmol). After stirring for 3 h at room temperature, the reaction mixture was diluted with water (150 ml) and extracted three times with ethyl acetate (200 ml each). The combined organic layers were washed three times with brine (200 ml each) and dried over anhydrous sodium sulfate The solvent was evaporated under reduced pressure. The crude product was purified column chromatography (silica gel, 220 g, eluent petroleum ether/ethyl 10 acetate 1:1) to yield 3.80 g (82% purity, 59% yield) of the title compound.

LC-MS (method 16): $R_t$=1.01 min; MS (ESIpos): m/z=319, 321 $[M+H]^+$ $^1$H-NMR (300 MHz, DMSO-$d_6$) δ [ppm]: 1.15-1.23 (m, 3H), 3.94 (s, 3H), 4.31-4.66 (m, 3H), 8.35-8.39 (m, 2H), 8.56 (d, 1H).

Intermediate I-39

4-Bromo-6-[(1-fluoropropan-2-yl)carbamoyl]pyridine-2-carboxylic acid

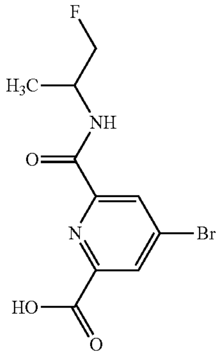 [SMILES: CC(CF)NC(=O)c1cc(Br)cc(C(=O)O)n1]

To a solution of methyl 4-bromo-6-[(1-fluoropropan-2-yl)carbamoyl]pyridine-2-carboxylate (3.8 g, 82% purity, 9.76 mmol) in methanol (50 ml) was added sodium hydroxide (1.56 g, 39.1 mmol). After stirring for 1 h at rt the reaction mixture was concentrated under reduced pressure and diluted with water (40 ml). The pH was adjusted to 5 with 1N hydrochloric acid. The precipitate was collected by suction filtration, washed with water (20 ml) and dried in vacuo to give 2.80 g (99% purity, 93% yield) of the title compound.

LC-MS (method 7): $R_t$=0.77 min; MS (ESIpos): m/z=327, 329 $[M+H]^+$ $^1$H-NMR (300 MHz, DMSO-$d_6$) δ [ppm]: 1.23-1.26 (m, 3H), 4.29-4.42 (m, 2H), 4.56-4.58 (m, 11H), 8.38-8.41 (m, 2H), 9.06 (d, 11H).

Intermediate I-40 tert-Butyl {4-bromo-6-[(1-fluoropropan-2-yl)carbamoyl]pyridin-2-yl}carbamate (mixture of enantiomers)

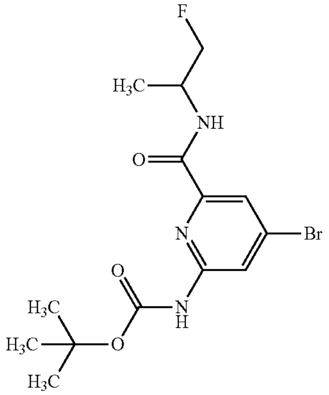 [SMILES: CC(CF)NC(=O)c1cc(Br)cc(NC(=O)OC(C)(C)C)n1]

To a solution of 4-bromo-6-[(1-fluoropropan-2-yl)carbamoyl]pyridine-2-carboxylic acid (2.30 g, 7.54 mmol) in 1,4-dioxane (30 ml) were added triethylamine (1.6 ml, 11 mmol), tert-butanol (12.0 ml, 130 mmol) and diphenyl phosphoroazidate (3.11 g, 11.3 mmol). The resulting mixture was stirred at 100° C. for 4 h. Subsequently, it was cooled to rt and concentrated under reduced pressure. The residue was purified by column chromatography (silica gel 120 g; eluent: petroleum ether/ethyl acetate 5:1) to yield 1.40 g (92% purity, 45% yield) of the title compound.

LC-MS (method 7): $R_t$=1.16 min; MS (ESIpos): m/z=376, 378 $[M+H]^+$)

Intermediate I-41

6-Amino-4-bromo-N-(1-fluoropropan-2-yl)pyridine-2-carboxamide trifluoroacetate (mixture of enantiomers)

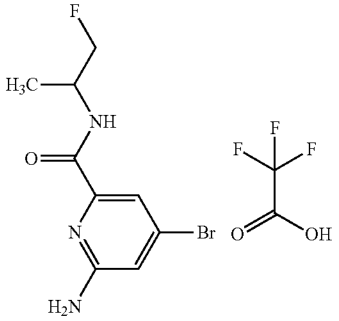

To a solution of tert-butyl {4-bromo-6-[(1-fluoropropan-2-yl)carbamoyl]pyridin-2-yl}carbamate (1.40 g, 92% purity, 3.42 mmol) in dichloromethane (20 ml) was added trifluoroacetic acid (1.3 ml, 17 mmol). After stirring at rt for 3 h, the reaction mixture was concentrated under reduced pressure. The residue was three times coevaporated with dichloromethane (20 ml) to yield 1.00 g (98% purity, 73% yield) of the title compound.

LC-MS (method 16): $R_t$=1.08 min; MS (ESIpos): m/z=276, 278 $[M+H]^+$ $^1$H-NMR (300 MHz, DMSO-$d_6$) δ [ppm]: 1.18 (d, 3H), 4.17-4.39 (m, 2H), 4.48-4.53 (m, 1H), 6.52 (br s, 2H), 6.85 (s, 1H), 7.23 (s, 1H), 8.17 (d, 1H).

Intermediate I-42

Ethyl ({4-bromo-6-[(1-fluoropropan-2-yl)carbamoyl]pyridin-2-yl}carbamothioyl)carbamate (mixture of enantiomers)

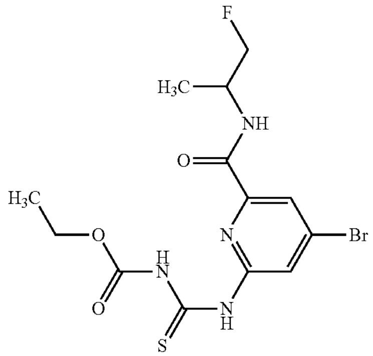 [SMILES: CCOC(=O)NC(=S)Nc1cc(Br)cc(C(=O)NC(C)CF)n1]

To a solution of 6-amino-4-bromo-N-(1-fluoropropan-2-yl)pyridine-2-carboxamide trifluoroacetate (900 mg, 2.31 mmol) in 1,4-dioxane (15 ml) at rt was added dropwise ethyl carbonisothiocyanatidate (908 mg, 6.92 mmol). After stirring overnight at rt, the reaction mixture was diluted with hexane (50 ml). The precipitate was collected by suction filtration, washed with hexane (20 ml) and dried in vacuo to yield 700 mg (96% purity, 71% yield) of the title compound.

LC-MS (method 8): $R_t$=1.47 min; MS (ESIpos): m/z=407, 409 $[M+H]^+$ $^1$H-NMR (300 MHz, DMSO-$d_6$) δ [ppm]: 1.19 (d, 3H), 1.28 (t, 3H), 4.21-4.42 (m, 4H), 4.44-4.60 (m, 1H), 7.98 (s, 1H), 8.58 (d, 1H), 9.00 (s, 1H), 11.79 (s, 1H), 12.18 (s, 1H).

Intermediate I-43

2-Amino-7-bromo-N-(1-fluoropropan-2-yl)[1,2,4]triazolo[1,5-a]pyridine-5-carboxamide (mixture of enantiomers)

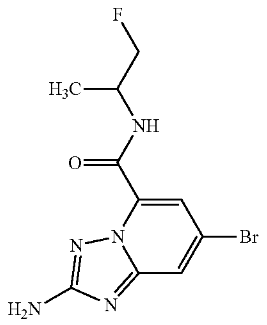 [SMILES: CC(CF)NC(=O)c1cc(Br)cc2nc(N)nn12]

To a solution of hydroxylamine hydrochloride (410 mg, 5.89 mmol) in methanol (15 ml) at rt was added N,N-diisopropylethylamine (1.0 ml, 5.9 mmol). The solution was heated to 65° C. Ethyl ({4-bromo-6-[(1-fluoropropan-2-yl)carbamoyl]pyridin-2-yl}carbamothioyl)carbamate (800 mg, 1.96 mmol) was added. The resulting mixture was stirred at 65° C. for 2 h. Subsequently, it was cooled to rt and concentrated under reduced pressure. The residue was diluted with water (100 ml). The precipitate was collected by suction filtration. It was triturated with satd. sodium bicarbonate solution (100 ml) and stirred for 4 h. The precipitate was collected by suction filtration, washed with water (20 ml) and dried in vacuo to yield 507 mg (96% purity, 78% yield) the title compound.

LC-MS (method 8): $R_t$=1.04 min; MS (ESIpos): m/z=316, 318 $[M+H]^+$ $^1$H-NMR (300 MHz, DMSO-$d_6$) δ [ppm]: 1.30 (d, 3H), 4.25-4.49 (m, 2H), 4.55-4.65 (m, 1H), 6.57 (s, 2H), 7.60 (s, 1H), 7.92 (s, 1H), 10.14 (d, 1H).

Intermediate I-44

4,4,4-Trifluoro-3-[4-(4,4,5,5-tetramethyl-1,3,2-dioxaborolan-2-yl)-1H-pyrazol-1-yl]butanenitrile (mixture of enantiomers)

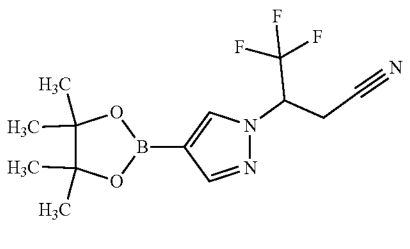 [SMILES: CC1(C)OB(c2cnn(C(CC#N)C(F)(F)F)c2)OC1(C)C]

A mixture of 4-(4,4,5,5-tetramethyl-1,3,2-dioxaborolan-2-yl)-1H-pyrazole (1.46 g, 7.51 mmol) and 4,4,4-trifluorobut-2-enenitrile (1.00 g, 8.26 mmol) in acetonitrile (20 ml) was cooled with an water ice bath and DBU (110 pl, 750 mol) was added dropwise. The mixture was warmed to rt and stirred overnight. The solvent was removed under reduced pressure and the residue was purified by column chromatography (Biotage® SNAP Ultra 50 g cartridge, eluent: cyclohexane/ethyl acetate gradient 1:0 to 1:1) to yield 490 mg (95% purity, 20% yield) of the title compound.

LC-MS (method 1): $R_t$=1.81 min; MS (ESIpos): m/z=316 $[M+H]^+$ $^1$H-NMR (400 MHz, DMSO-$d_6$) δ [ppm]: 1.27 (s, 12H), 3.56 (dd, 1H), 3.66 (dd, 1H), 5.90-6.01 (m, 1H), 7.80 (s, 1H), 8.25 (s, 1H).

Intermediate I-45

7-{[4-(4,4,5,5-Tetramethyl-1,3,2-dioxaborolan-2-yl)-1H-pyrazol-1-yl]methyl}-1H-indazole

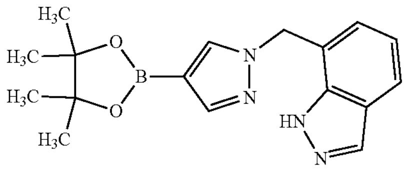 [SMILES: CC1(C)OB(c2cnn(Cc3cccc4cn[nH]c34)c2)OC1(C)C]

To a solution of 7-(bromomethyl)-1H-indazole hydrogen bromide [CAS-RN 1956306-65-2](1.30 g, 81% purity, 3.61 mmol) in DMF (15 ml) at −50° C. were added 4-(4,4,5,5-tetramethyl-1,3,2-dioxaborolan-2-yl)-1H-pyrazole (1.05 g, 5.41 mmol) and caesium carbonate (2.35 g, 7.21 mmol). The reaction mixture was stirred for 1.5 h and then filtered. The filtrate was diluted with water (20 ml) and extracted with ethyl acetate (3×20 ml). The combined organic layers were washed with brine (50 ml), dried over anhydrous sodium sulfate, and the solvent was evaporated under reduced pressure. The residue was purified by HPLC (column: C18, 120 g, 20*35 um; eluent: water (A), acetonitrile (B); gradient: 10% B to 70% B in 25 min; flow rate: 60 ml/min) to yield 290 mg (99% purity, 25% yield) of the title compound.

LC-MS (method 7): $R_t$=1.40 min; MS (ESIpos): m/z=325 $[M+H]^+$

Intermediate I-46

1-[(1S)-1-Phenylpropyl]-4-(4,4,5,5-tetramethyl-1,3,2-dioxaborolan-2-yl)-1H-pyrazole

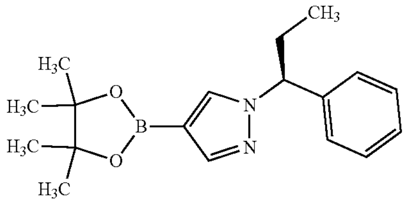 [SMILES: CC[C@@H](c1ccccc1)n1cc(B2OC(C)(C)C(C)(C)O2)cn1]

(4,4,5,5-Tetramethyl-1,3,2-dioxaborolan-2-yl)-1H-pyrazole (1.57 g, 8.08 mmol) was dissolved in THF (14 ml). (1R)-1-Phenylpropan-1-ol (1.00 g, 7.34 mmol) and triphenylphosphine (3.85 g, 14.7 mmol) were added to the solution. DBAD (3.38 g, 14.69 mmol) in THF (6 ml) was added to the mixture at rt. After stirring for 1 h under reflux the reaction mixture was cooled to rt and concentrated under reduced pressure. The residue was purified by flash column chromatography (C18, 330 g; eluent: water/acetonitrile gradient 70:30 to 40:60) to yield 800 mg (95% purity, 33% yield) of the title compound.

LC-MS (method 7): $R_t$=1.73 min; MS (ESIpos): m/z=313 $[M+H]^+$ $^1$H-NMR (300 MHz, DMSO-$d_6$) δ [ppm]: 0.77 (t, 3H), 1.24 (s, 12H), 2.12 (dquin, 1H), 2.28-2.45 (m, 1H), 5.34 (dd, 1H), 7.23-7.39 (m, 5H), 7.62 (s, 1H), 8.09 (s, 1H).

Intermediate I-47

1-[(2-Methyl-1-phenylpropyl]-4-(4,4,5,5-tetramethyl-1,3,2-dioxaborolan-2-yl)-1H-pyrazole (mixture of enantiomers)

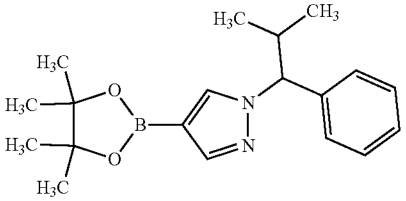 [SMILES: CC(C)C(c1ccccc1)n1cc(B2OC(C)(C)C(C)(C)O2)cn1]

DBAD (1.78 g, 7.73 mmol) and triphenylphospine (2.03 g, 7.73 mmol) were dissolved in THF (7.5 ml) and cooled to 0° C. 2-Methyl-1-phenylpropan-1-ol [CAS-RN 611-69-8] (1.16 g, 7.73 mmol) was added and subsequently a solution of 4-(4,4,5,5-tetramethyl-1,3,2-dioxaborolan-2-yl)-1H-pyrazole (1.00 g, 5.15 mmol) in THF (7.5 ml) was added dropwise. The mixture was stirred at rt for 6 h and left stand overnight. The solvent was removed in vacuo and the residue was purified by column chromatography (Biotage® SNAP Ultra 50 g cartridge, eluent: cyclohexane/ethyl acetate gradient). Further purification was achieved in a second chromatography (Biotage® SNAP Ultra C18 30 g cartridge, eluent: acetonitrile/water gradient 30:70 to 90:10) to yield 390 mg (90% 10 purity, 21% yield) of the title compound.

LC-MS (method 1): $R_t$=2.31 min; MS (ESIpos): m/z=327 $[M+H]^+$ $^1$H-NMR (400 MHz, DMSO-$d_6$) δ [ppm]: 0.70-0.77 (m, 6H), 1.23 (s, 12H), 2.69-2.82 (m, 1H), 4.97 (d, 1H), 7.23-7.37 (m, 3H), 7.49-7.55 (m, 2H), 7.60 (s, 1H), 8.10 (s, 1H).

Intermediate I-48

1-[Cyclobutyl(phenyl)methyl]-4-(4,4,5,5-tetramethyl-1,3,2-dioxaborolan-2-yl)-1H-pyrazole (mixture of enantiomers)

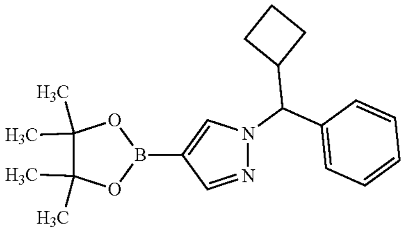 [SMILES: CC1(C)OB(c2cnn(C(c3ccccc3)C3CCC3)c2)OC1(C)C]

Di-tert-butylazodicarboxylate (356 mg, 1.55 mmol) and triphenylphosphine (406 mg, 1.55 mmol) were stirred at 0° C. in dry tetrahydrofuran (4.0 ml) for 15 min. Then 4-(4,4,5,5-tetramethyl-1,3,2-dioxaborolan-2-yl)-1H-pyrazole (200 mg, 1.03 mmol) and cyclobutyl(phenyl)methanol [CAS-RN 4397-00-6](251 mg, 1.55 mmol) as solution in dry tetrahydrofuran (4.0 ml) were slowly added. The reaction mixture was stirred at rt for 12 h and then concentrated. The crude product was purified directly by preparative HPLC to yield 16.0 mg (90% purity, 4% yield) of the title compound.

LC-MS (method 1): $R_t$=2.37 min; MS (ESIpos): m/z=339 $[M+H]^+$

Intermediate I-49

1-Methylcyclopropane-1-carbonyl chloride

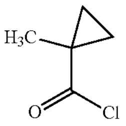

To a solution of 1-methylcyclopropane-1-carboxylic acid [CAS-RN 6914-76-7](5.00 g, 49.9 mmol) and a catalytic amount of dimethylformamide in dry dichloromethane (80 ml) at 0° C. was slowly added oxalyl chloride (4.2 ml, 50 mmol). The reaction was stirred for 3 h at rt. The reaction was concentrated under reduced pressure to give crude 1-methylcyclopropane-1-carbonyl chloride which was directly used in the next step.

Intermediate I-50

N-methoxy-N,1-dimethylcyclopropane-1-carboxamide

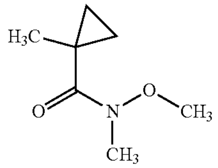

To a solution of N-methoxymethanamine hydrochloride [CAS-RN 6638-79-5](4.87 g, 49.9 mmol) and N,N-diisopropylethylamine (17 ml, 100 mmol) in dry dichloromethane (150 ml), was slowly added a solution of 1-methylcyclopropane-1-carbonyl chloride (5.92 g, 49.9 mmol) in dry dichloromethane (30 ml). The reaction mixture was stirred at rt for 12 h and then quenched with water (100 ml). The organic layer was separated and washed with IN hydrochloric acid and brine. Finally, the organic layer was dried over sodium sulfate and concentrated in vacuo. The residue was purified by silica gel column chromatography (eluent: cyclohexane/ethyl acetate 7:3) to yield 5.16 g (100% purity, 72% yield) of the title compound.

GC-MS (GC-MS method 1): $R_t$=2.62 min; MS (El pos): m/z=143 $[M]^+$ $^1$H-NMR (400 MHz, DMSO-$d_6$) δ [ppm]: 0.50-0.54 (q, 2H), 0.84-0.94 (q, 2H), 1.28 (s, 3H), 3.12 (s, 3H), 3.31 (s, 3H).

Intermediate I-51

(1-Methylcyclopropyl)(phenyl)methanone

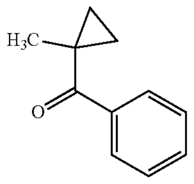

To a solution of N-methoxy-N,1-dimethylcyclopropane-1-carboxamide (1.03 g, 7.17 mmol) in dry diethyl ether (15 ml) at 0° C. was added dropwise a solution of phenylmagnesium bromide (7.2 ml, 1.0 M, 7.2 mmol) in THF. The reaction mixture was stirred at rt for 12 h and then quenched with water. The reaction mixture was extracted twice with ethyl acetate, and the organic layer was dried over sodium sulfate and concentrated in vacuo. The residue was purified by silica-gel chromatography (eluent: cyclohexane/ethyl acetate 95:5) to yield 1.18 g (95% purity, 97% yield) of the title compound.

GC-MS (GC-MS method 1): $R_t$=3.83 min; MS (El pos): m/z=160 $[M]^+$ $^1$H-NMR (400 MHz, DMSO-$d_6$) δ [ppm]: 0.83 (q, 2H), 1.14 (q, 2H), 1.37 (s, 3H), 7.45-7.59 (m, 3H), 7.74 (d, 2H).

Intermediate I-52

(1-Methylcyclopropyl)(phenyl)methanol (mixture of enantiomers)

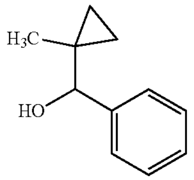

To a solution of (1-methylcyclopropyl)(phenyl)methanone (1.18 g, 95% purity, 6.96 mmol) in dry tetrahydrofuran (10 ml) was added portionwise sodium tetrahydroborate (132 mg, 3.48 mmol) and the reaction mixture was stirred at rt for 3 h. The reaction was quenched with acidified water (pH 5) and extracted three times with ethyl acetate. The organic layer was dried over sodium sulfate, filtered and concentrated. The residue was purified by silica gel column chromatography (eluent: cyclohexane/ethyl acetate 9:1) to yield 821 mg (100% purity, 73% yield) of the title compound.

LC-MS (method 1): $R_t$=1.63 min; MS (ESIneg): m/z=145 $[M-OH]^-$ $^1$H-NMR (400 MHz, DMSO-$d_6$) δ [ppm]: 0.19 (ddd, 1H), 0.25 (ddd, 1H), 0.58 (ddd, 1H), 0.67 (ddd, 1H), 0.82 (s, 3H), 1.40 (s, 1H), 4.05 (d, 1H), 5.09 (d, 1H), 7.19-7.36 (m, 5H).

Intermediate I-53

1-[(1-Methylcyclopropyl)(phenyl)methyl]-4-(4,4,5,5-tetramethyl-1,3,2-dioxaborolan-2-yl)-1H-pyrazole (mixture of enantiomers)

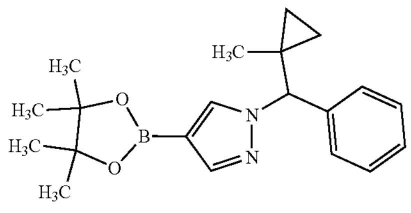 [SMILES: CC1(C(c2ccccc2)n2cc(B3OC(C)(C)C(C)(C)O3)cn2)CC1]

Di-tert-butylazodicarboxylate (1.09 g, 4.72 mmol) and triphenylphosphine (1.24 g, 4.72 mmol) were stirred in dry tetrahydrofuran (20 ml) at 0° C. for 15 min. Then 4-(4,4,5,5-tetramethyl-1,3,2-dioxaborolan-2-yl)-1H-pyrazole (610 mg, 3.14 mmol) and (1-methylcyclopropyl)(phenyl)methanol (765 mg, 4.72 mmol) as a solution in dry tetrahydrofuran (5 ml) were slowly added. The reaction mixture was stirred at rt for 12 h and was then concentrated in vacuo. The crude product was purified directly by HPLC to yield 309 mg (96% purity, 28% yield) of the title compound as a racemic mixture.

LC-MS (method 1): $R_t$=2.36 min; MS (ESIpos): m/z=339 $[M+H]^+$ $^1$H-NMR (400 MHz, DMSO-$d_6$) δ [ppm]: 0.40-0.52 (m, 3H), 0.63-0.70 (m, 1H), 1.07 (s, 3H), 1.26 (s, 12H), 5.27 (s, 1H), 7.19-7.35 (m, 5H), 7.65 (s, 1H), 8.01 (s, 1H).

Intermediate I-54

2,2-Dimethyl-1-phenylpropan-1-ol (mixture of enantiomers)

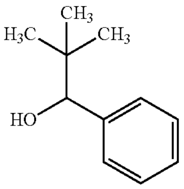

To a solution of pivalaldehyde (2.00 g, 23.22 mmol) in dry. tetrahydrofuran (25 ml) at 0° C. was added phenylmagnesium bromide (27.9 ml, 1 M in THF, 27.9 mmol). After stirring for 2 h at rt, the reaction mixture was quenched with water (60 ml) and extracted three times with ethyl acetate (80 ml each). The combined organic layers were washed with brine (120 ml), dried over anhydrous sodium sulfate and concentrated under reduced pressure. The crude product was purified by silica gel column chromatography (120 g, eluent: petroleum ether/ethyl acetate 5:1) to yield 3.90 g (90% purity, 92% yield) of the title compound.

$^1$H-NMR (300 MHz, DMSO-$d_6$) δ [ppm]: 0.83 (s, 9H), 4.22 (d, 1H), 5.15 (d, 1H), 7.18-7.32 (m, 5H).

Intermediate I-55

1-[2,2-Dimethyl--1-phenylpropyl]-4-(4,4,5,5-tetramethyl-1,3,2-dioxaborolan-2-yl)-1H-pyrazole (mixture of enantiomers)

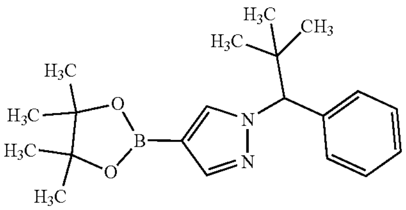 [SMILES: CC(C)(C)C(c1ccccc1)n1cc(B2OC(C)(C)C(C)(C)O2)cn1]

To a solution of 2,2-dimethyl-1-phenylpropan-1-ol (2.00 g, 90% purity, 11.0 mmol) in dry tetrahydrofuran (80 ml) were added 4-(4,4,5,5-tetramethyl-1,3,2-dioxaborolan-2-yl)-1H-pyrazole (2.39 g, 98% purity, 12.1 mmol) followed by triphenylphosphine (5.75 g, 21.9 mmol). A solution of DBAD (5.05 g, 21.92 mmol) in dry tetrahydrofuran (20 ml) was added to the reaction mixture within 10 min. After stirring for 2 h under reflux, the reaction mixture was cooled to rt and concentrated under reduced pressure. The crude product was purified by flash column chromatography (Column: C18, 330 g; Mobile Phase A: Water, Mobile Phase B: acetonitrile; Gradient: 50% B to 90% B in 25 min, 220/254 nm), to give 700 mg crude product which was further purified by column chromatography on silica gel (120 g, eluent: petroleum ether/ethyl acetate 2:1) to yield 450 mg (93% purity, 1 1% yield) of the title compound.

LC-MS (method 20): $R_t$=2.89 min; MS (ESIpos): m/z=341 $[M-H]^+$ $^1$H-NMR (400 MHz, DMSO-$d_6$) δ [ppm]: 0.91 (s, 9H), 1.23 (s, 12H), 5.30 (s, 1H), 7.25-7.34 (m, 3H), 7.60-7.63 (m, 2H), 7.69 (s, 1H), 8.04 (s, 1H).

Intermediate I-56

3,3-Difluorocyclobutane-1-carbonyl chloride

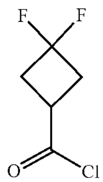

To a solution of 3,3-difluorocyclobutane-1-carboxylic acid [CAS-RN 107496-54-8](1.20 g, 8.82 mmol) in dry dichloromethane (15 ml) and a catalytic amount of dimethylformamide at 0° C., was slowly added oxalyl chloride (750 pl, 8.8 mmol). The reaction was stirred for 3 h at rt. The reaction was concentrated to give crude 3,3-difluorocyclobutane-1-carbonyl chloride which was directly used in the next step.

Intermediate I-57

3,3-Difluoro-N-methoxy-N-methylcyclobutane-1-carboxamide

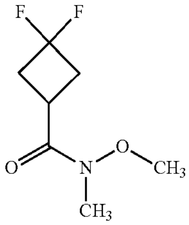

To a solution of N-methoxymethanamine hydrochloride (860 mg, 8.82 mmol) and N,N-diisopropylethylamine (3.1 ml, 18 mmol) in dry dichloromethane (25 ml) was slowly added a solution of 3,3-difluorocyclobutane-1-carbonyl chloride (1.36 g, 8.82 mmol) in dry dichloromethane (10 ml). The reaction mixture was stirred at rt for 12 h and then quenched with water (50 ml). The organic layer was separated and washed with 1N hydrochloric acid and brine. Finally, the organic layer was dried over sodium sulfate and concentrated in vacuo to yield 1.54 g (90% purity, 87% yield) of the title compound. The product was used without further purification in the next step.

LC-MS (method 2): $R_t$=0.67 min; MS (ESIpos): m/z=180 [M+H]J

Intermediate I-58

(3,3-Difluorocyclobutyl)(phenyl)methanone

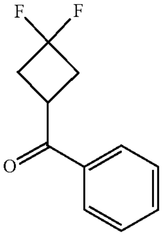 [SMILES: O=C(c1ccccc1)C1CC(F)(F)C1]

To a solution of 3,3-difluoro-N-methoxy-N-methylcyclobutane-1-carboxamide (1.54 g, 90% purity, 7.74 mmol) in dry diethyl ether (16 ml) at 0° C. was added dropwise a solution of phenylmagnesium bromide (7.7 ml, 1.0 M, 7.7 mmol) in tetrahydrofuran. The reaction mixture was stirred at rt for 12 h and then quenched with water. The aqueous layer was extracted twice with ethyl acetate, and the combined organic layers were dried over sodium sulfate and concentrated in vacuo. The residue was purified by silica gel column chromatography (eluent: cyclohexane/ethyl acetate 95:5) to yield 1.02 g (88% purity, 59% yield) of the title compound.

GC-MS (GC-MS method 1): $R_t$=4.05 min; MS (EIpos): m/z=196 $[M]^+$ $^1$H-NMR (400 MHz, DMSO-$d_6$) δ [ppm]: 2.77-3.00 (m, 4H), 3.98-4.10 (m, 1H), 7.55 (t, 2H), 7.67 (t, 1H), 7.97 (d, 2H).

Intermediate I-59

(3,3-Difluorocyclobutyl)(phenyl)methanol (mixture of enantiomers)

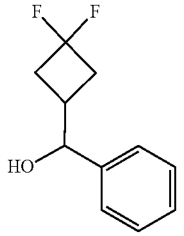 [SMILES: OC(c1ccccc1)C1CC(F)(F)C1]

To a solution of (3,3-difluorocyclobutyl)(phenyl)methanone (1.02 g, 88% purity, 4.57 mmol) was added portionwise sodium tetrahydroborate (86.5 mg, 2.29 mmol) and the reaction mixture was stirred at rt for 3 h. Subsequently, it was quenched with acidified water (pH 5) and extracted three times with ethyl acetate. The combined organic layers were dried over sodium sulfate, filtered and concentrated in vacuo. The residue was purified by silica-gel column chromatography (eluent: cyclohexane/ethyl acetate 9:1) to yield 796 mg (100% purity, 88% yield) of the title compound as a racemic mixture.

LC-MS (method 1): $R_t$=1.61 min; MS (ESIpos): m/z=181 $[M+H/-OH]^+$ $^1$H-NMR (400 MHz, DMSO-$d_6$) δ [ppm]: 2.32-2.48 (m, 4H), 2.48-2.62 (m, 1H), 4.52 (t, 1H), 5.50 (d, 1H), 7.22-7.27 (m, 1H), 7.27-7.35 (m, 4H).

Intermediate I-60

1-[(3,3-Difluorocyclobutyl)(phenyl)methyl]-4-(4,4,5,5-tetramethyl-1,3,2-dioxaborolan-2-yl)-1H-pyrazole (mixture of enantiomers)

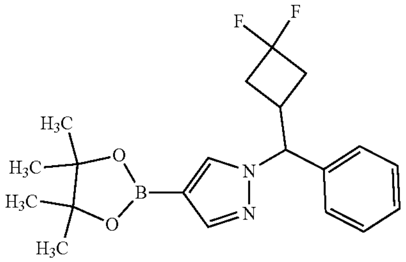 [SMILES: CC1(C)OB(c2cnn(C(c3ccccc3)C3CC(F)(F)C3)c2)OC1(C)C]

Di-tert-butylazodicarboxylate (863 mg, 3.75 mmol) and triphenylphosphine (983 mg, 3.75 mmol) were stirred at 0° C. in dry tetrahydrofuran (15 ml) for 15 min. Then 4-(4,4,5,5-tetramethyl-1,3,2-dioxaborolan-2-yl)-1H-pyrazole (485 mg, 2.50 mmol) and (3,3-difluorocyclobutyl)(phenyl)methanol (743 mg, 3.75 mmol) as a solution in dry THF (5 ml) were slowly added. The reaction mixture was stirred at rt for 12 h and then concentrated in vacuo. The crude product was purified directly by HPLC to yield 495 mg (83% purity, 44% yield) of the title compound.

LC-MS (method 1): $R_t$=2.26 min; MS (ESIpos): m/z=375 $[M+H]^+$ $^1$H-NMR (400 MHz, DMSO-$d_6$) δ [ppm]: 1.23 (s, 12H), 2.21-2.43 (m, 3H), 2.48-2.60 (m, 2H), 5.49 (d, 1H), 7.23-7.44 (m, 5H), 7.61 (s, 1H), 8.10 (s, 1H).

Intermediate I-61

4-(4,4,5,5-Tetramethyl-1,3,2-dioxaborolan-2-yl)-1-(3,3,3-trifluoro-1-phenylpropyl)-1H-pyrazole (mixture of enantiomers)

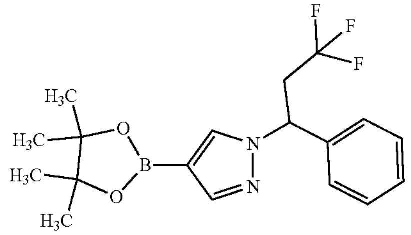 [SMILES: CC1(C)OB(c2cnn(C(CC(F)(F)F)c3ccccc3)c2)OC1(C)C]

Di-tert-butylazodicarboxylate (1.25 g, 5.41 mmol) and triphenylphosphine (1.42 g, 5.41 mmol) were stirred at 0° C. in dry tetrahydrofuran (7.5 ml) for 15 min. Then 4-(4,4,5,5-tetramethyl-1,3,2-dioxaborolan-2-yl)-1H-pyrazole (700 mg, 3.61 mmol) and 3,3,3-trifluoro-1-phenylpropan-1-ol [CAS-RN 2340-22-9](1.03 g, 5.41 mmol) as a solution in dry tetrahydrofuran (2.5 ml) were slowly added. The reaction mixture was stirred at rt for 12 h and then concentrated in vacuo. The crude product was purified directly by preparative HPLC to yield 516 mg (100% purity, 39% yield) of the title compound as a racemic mixture.

LC-MS (method 1): $R_t$=2.24 min; MS (ESIpos): m/z=367 $[M+H]^+$ $^1$H-NMR (400 MHz, DMSO-$d_6$) δ [ppm]: 1.24 (s, 12H), 3.31 (s, 2H), 3.51-3.71 (m, 1H), 5.67-5.98 (m, 1H), 7.21-7.39 (m, 3H), 7.41-7.48 (m, 2H), 7.63 (s, 1H), 7.62-8.15 (m, 11H), 8.22 (s, 1H).

Intermediate I-62

Ethyl (4-bromo-1H-pyrazol-1-yl)(phenyl)acetate (mixture of enantiomers)

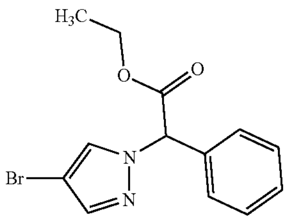 [SMILES: CCOC(=O)C(c1ccccc1)n1cc(Br)cn1]

Sodium hydride (136 mg, 60% purity in mineral oil, 3.40 mmol) in THF (5.0 ml) was cooled to −20° C. and a solution of 4-bromo-1H-pyrazole (500 mg, 3.40 mmol) in THF (5.0 ml) was added dropwise. The mixture was stirred for 30 min, then ethyl bromo(phenyl)acetate (827 mg, 3.40 mmol) was added as a solution in THF (5.0 ml). The mixture was slowly warmed to rt and stirred overnight. Water (20 ml) was added to the mixture and it was extracted twice with ethyl acetate (20 ml each). The combined organic layers were washed with brine and filtered through a hydrophobic phase separation filter. The solvent was removed in vacuo and the residue was purified by column chromatography (Biotage® SNAP Ultra 50 g cartridge, eluent: cyclohexane/ethyl acetate gradient 95:5 to 70:30) to yield 603 mg (100% purity, 57% yield) of the title compound.

LC-MS (method 1): $R_t$=1.99 min; MS (ESIpos): m/z=309, 311 $[M+H]^+$ $^1$H-NMR (400 MHz, DMSO-$d_6$) δ [ppm]: 1.15 (t, 3H), 4.19 (q, 2H), 6.48 (s, 1H), 7.39-7.47 (m, 5H), 7.62 (s, 1H), 7.93 (s, 1H).

Intermediate I-63

2-(4-Bromo-1H-pyrazol-1-yl)-2-phenylethan-1-ol (mixture of enantiomers)

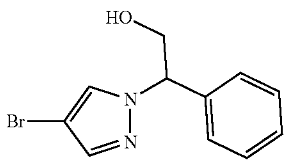 [SMILES: OCC(c1ccccc1)n1cc(Br)cn1]

A solution of ethyl (4-bromo-1H-pyrazol-1-yl)(phenyl) acetate (300 mg, 970 μmol) in THF (7.0 ml) was cooled to −15° C. and a solution of lithiumaluminium hydride in THF (970 pl, 1.0 M, 970 μmol) was added dropwise. Afterwards, water (50 μl) was added and stirred for 5 min, then 20% sodium 15 hydroxide solution (100 μl) and further water (100 μl) was added. The mixture was filtered through kieselgur which was rinsed with ethyl acetate (25 ml). The combined filtrates were concentrated in vacuo to yield 258 mg (90% purity, 90% yield) of the title compound which was used without further purification.

LC-MS (method 1): $R_t$=1.52 min; MS (ESIpos): m/z=267, 269 $[M+H]^+$ $^1$H-NMR (400 MHz, DMSO-$d_6$) δ [ppm]: 3.91 (dt, 1H), 4.20 (ddd, 1H), 5.14 (dd, 1H), 5.43 (dd, 1H), 7.24-7.37 (m, 5H), 7.57 (s, 1H), 8.16 (s, 1H).

Intermediate 1-64

4-Bromo-1-(2-methoxy-1-phenylethyl)-1H-pyrazole (mixture of enantiomers)

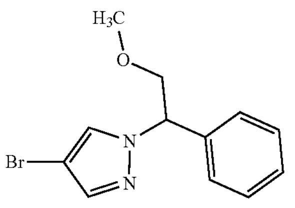 [SMILES: COCC(c1ccccc1)n1cc(Br)cn1]

A suspension of sodium hydride (394 mg, 60% purity in mineral oil, 9.85 mmol) in THE (30 ml) was cooled to 0° C. and a solution of 2-(4-bromo-1H-pyrazol-1-yl)-2-phenylethan-1-ol (1.95 g, 90% purity, 6.57 mmol) in THE (25 ml) was added dropwise. Stirring was continued at 0° C. for 1 h. Then iodomethane (490 pl, 7.9 mmol) was added. The mixture was warmed to rt and stirred for 1 h. Water (5 ml), ethyl acetate (20 ml) and brine (10 ml) were added. The separated aqueous layer was extracted with ethyl acetate (20 ml) and the combined organic layers were filtered through a hydrophobic phase separation filter. The solvent was removed in vacuo and the residue was purified by column chromatography (Biotage® SNAP Ultra 10 g cartridge, eluent: cyclohexane/ethyl acetate gradient 90:10 to 50:50) to yield 1.39 g (95% purity, 71% yield) of the title compound.

LC-MS (method 2): $R_t$=0.99 min; MS (ESIpos): m/z=281, 283 $[M+H]^+$ $^1$H-NMR (400 MHz, DMSO-$d_6$) δ [ppm]: 3.27 (s, 3H), 3.83 (dd, 1H), 4.20 (dd, 1H), 5.67 (dd, 1H), 7.27-7.37 (m, 5H), 7.58 (s, 1H), 8.18 (s, 1H).

Intermediate I-65

1-(2-Methoxy-1-phenylethyl)-4-(4,4,5,5-tetramethyl-1,3,2-dioxaborolan-2-yl)-1H-pyrazole (mixture of enantiomers)

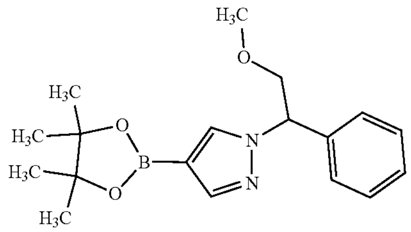 [SMILES: COCC(c1ccccc1)n1cc(B2OC(C)(C)C(C)(C)O2)cn1]

To 4-bromo-1-(2-methoxy-1-phenylethyl)-1H-pyrazole (1.27 g, 4.51 mmol), 4,4,4',4',5,5,5',5'-octamethyl-2,2'-bi-1,3,2-dioxaborolane (2.29 g, 9.03 mmol) and potassium acetate (1.33 g, 13.5 mmol) was added DMF (20 ml) and the mixture was degassed with argon. 1,1'-Bis(diphenylphosphino)ferrocene-palladium(II)dichloride dichloromethane complex (184 mg, 226 μmol) was added and the mixture was heated to 90° C. for 7 h. It was then cooled to rt and filtered through kieselgur which was rinsed with ethyl acetate (100 ml) and water (50 ml). The aqueous layer was separated from the combined filtrates and extracted with ethyl acetate (50 ml). The combined organic layers were filtered through a hydrophobic phase separation filter. The solvent was removed in vacuo and the residue was purified by column chromatography (Biotage® SNAP Ultra 50 g cartridge, eluent: cyclohexane/ethyl acetate gradient 100:0 to 75:25) to yield 1.14 g (95% purity, 73% yield) of the title compound.

LC-MS (method 1): $R_t$=2.02 min; MS (ESIpos): m/z=329 $[M+H]^+$ $^1$H-NMR (400 MHz, DMSO-$d_6$) δ [ppm]: 1.25 (s, 12H), 3.26 (s, 3H), 3.85 (dd, 1H), 4.23 (dd, 1H), 5.70 (dd, 1H), 7.26-7.36 (m, 5H), 7.62 (s, 1H), 8.12 (s, 1H).

Intermediate I-66

Phenyl(tetrahydro-2H-pyran-4-yl)methanol (mixture of enantiomers)

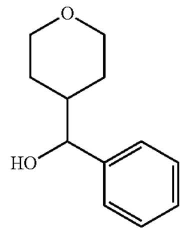 [SMILES: OC(c1ccccc1)C1CCOCC1]

A solution of phenylmagnesium bromide in diethyl ether (23 ml, 3.0 M, 70 mmol) was cooled with a water ice bath and a solution of tetrahydro-2H-pyran-4-carbaldehyde (4.00 g, 35.0 mmol) in diethyl ether (20 ml) was added dropwise (inner temperature was kept below 10° C.). The mixture was warmed to rt, THF (40 ml) was added and stirred for 30 min. Subsequently, satd. aqueous 20 ammonium chloride solution (40 ml) was added with cooling, After stirring for 5 min the aqueous layer was separated and extracted with diethyl ether. The combined organic layers were washed with satd. aqueous ammonium chloride solution (50 ml), water (50 ml) and brine (50 ml) and dried over anhydrous sodium sulfate. The solvent was removed under reduced pressure and the residue was purified by column chromatography (Biotage® SNAP Ultra 100 g cartridge, eluent: cyclohexane/ethyl acetate gradient 92:8 to 41:59) to yield 4.11 g (100% purity, 61% yield) of the title compound.

GC-MS (GC-MS method 1): $R_t$=5.46 min; MS (ESIpos): m/z=192 $[M]^+$ $^1$H-NMR (600 MHz, DMSO-$d_6$) δ [ppm]: 1.06-1.11 (m, 1H), 1.19-1.30 (m, 2H), 1.63-1.70 (m, 2H), 3.12-3.17 (m, 1H), 3.17-3.23 (m, 1H), 3.76 (br dd, 1H), 3.84 (br dd, 1H), 4.24 (dd, 1H), 5.17 (d, 1H), 7.22 (tt, 1H), 7.26-7.33 (m, 4H).

Intermediate I-67

1-[Phenyl(tetrahydro-2H-pyran-4-yl)methyl]-4-(4,4,5,5-tetramethyl-1,3,2-dioxaborolan-2-yl)-1H-pyrazole (mixture of enantiomers)

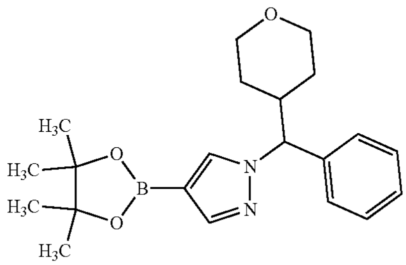 [SMILES: CC1(C)OB(c2cnn(C(c3ccccc3)C3CCOCC3)c2)OC1(C)C]

To a mixture of 4-(4,4,5,5-tetramethyl-1,3,2-dioxaborolan-2-yl)-1H-pyrazole (1.00 g, 5.15 mmol) and phenyl(tetrahydro-2H-pyran-4-yl)methanol (991 mg, 5.15 mmol) in toluene (10 ml) was added CMBP (1.24 g, 5.15 mmol) and the mixture was heated to 80° C. overnight. The solvent was then removed in vacuo and the residue was purified by column chromatography (Biotage® SNAP Ultra 25 g cartridge, eluent: cyclohexane/ethyl acetate gradient 95:5 to 80:20) to yield 1.60 g (57% purity, 48% yield) which was used without further purification.

LC-MS (method 1): $R_t$=2.08 min; MS (ESIpos): m/z=369 $[M+H]^+$

Intermediate I-68 tert-Butyl 4-[hydroxy(phenyl)methyl]piperidine-1-carboxylate (mixture of enantiomers)

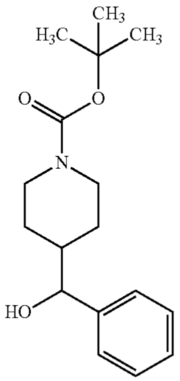 [SMILES: CC(C)(C)OC(=O)N1CCC(C(O)c2ccccc2)CC1]

A solution of tert-butyl 4-formylpiperidine-1-carboxylate (3.00 g, 14.1 mmol) in THF (30 ml) was cooled with an water ice bath and a solution of phenylmagnesium bromide in diethyl ether (9.4 ml, 3.0 M, 28 mmol) was added dropwise (inner temperature was kept below 10° C.). The reaction was then warmed to rt and stirring was continued for 1 h. The mixture was again cooled with water ice and satd. aqueous ammonium chloride solution (50 ml) was added. The aqueous layer was separated and the pH was adjusted to 6 by addition on 1N hydrochloric acid. It was extracted twice with ethyl acetate (50 ml each) and the combined organic layers were washed with brine and dried over anhydrous sodium sulfate. The solvent was evaporated under reduced pressure and the residue was purified by column chromatography (Biotage® SNAP Ultra 50 g cartridge, eluent: cyclohexane/ethyl acetate gradient 0:100 to 60:40) to yield 2.35 g (95% purity, 54% yield) of the title compound.

GC-MS (GC-MS method 1): $R_t$=7.34 min; MS (ESIpos): m/z=235 $[M-C(CH_3)_3+H]^+$ $^1$H-NMR (600 MHz, DMSO-$d_6$) δ [ppm]: 1.00-1.12 (m, 2H), 1.19-1.24 (m, 1H), 1.37 (s, 9H), 1.56-1.65 (m, 1H), 1.70-1.76 (m, 1H), 2.49-2.68 (m, 2H), 3.83-4.00 (m, 2H), 4.27 (dd, 1H), 5.19 (d, 1H), 7.20-7.24 (m, 1H), 7.26-7.33 (m, 4H).

Intermediate I-69 tert-Butyl 4-{phenyl[4-(4,4,5,5-tetramethyl-1,3,2-dioxaborolan-2-yl)-1H-pyrazol-1-yl]methyl}piperidine-1-carboxylate (mixture of enantiomers)

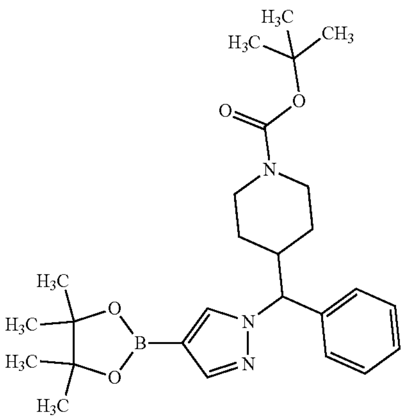 [SMILES: CC(C)(C)OC(=O)N1CCC(C(c2ccccc2)n2cc(B3OC(C)(C)C(C)(C)O3)cn2)CC1]

A solution of DIAD (1.7 ml, 8.6 mmol) and triphenylphosphine (2.25 g, 8.58 mmol) in THF (10 ml) was cooled to 0° C. and tert-butyl 4-[hydroxy(phenyl)methyl]piperidine-1-carboxylate (2.00 g, 6.86 mmol) was added as a solution in THF (10 ml). 4-(4,4,5,5-Tetramethyl-1,3,2-dioxaborolan-2-yl)-1H-pyrazole (1.11 g, 5.72 mmol) in THF (10 ml) was added dropwise. The reaction mixture was warmed to rt and stirred overnight. The solvent was then removed in vacuo. The crude product was purified by column chromatography (Biotage® SNAP Ultra 100 g cartridge, eluent: cyclohexane/ethyl acetate gradient 100:0 to 80:20, then ethyl acetate/2-propanol 10:1) to yield material which was further purified by chromatography (Biotage® SNAP Ultra C18 120 g cartridge, eluent: acetonitrile/water gradient 80:20 to 95:5) to yield 582 mg (80% purity, 17% yield) of the title compound.

LC-MS (method 1): $R_t$=2.49 min; MS (ESIpos): m/z=468 $[M+H]^+$ $^1$H-NMR (400 MHz, DMSO-$d_6$) δ [ppm]: 1.057 (0.52), 1.070 (0.60), 1.142 (0.60), 1.157 (1.35), 1.175 (2.23), 1.192 (1.28), 1.227 (11.16), 1.245 (0.80), 1.367 (16.00), 1.988 (3.37), 4.020 (0.91), 4.038 (0.82), 5.120 (0.62), 5.147 (0.59), 7.278 (0.71), 7.284 (0.45), 7.296 (0.71), 7.321 (0.87), 7.340 (1.23), 7.357 (0.50), 7.515 (1.16), 7.533 (0.93), 7.620 (1.52), 8.073 (1.59).

Intermediate I-70

1-[4-(Morpholin-4-yl)phenyl]propan-1-ol (mixture of enantiomers)

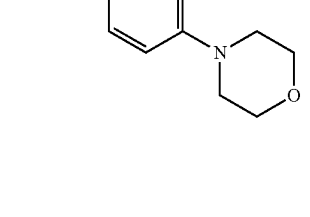

4-(Morpholin-4-yl)benzaldehyde (2.00 g, 10.5 mmol) was dissolved in diethyl ether (16 ml) and cooled to an inner temperature of −5° C. Within 30 min a solution of ethylmagnesium bromide in diethyl ether (4.2 ml, 3.0 M, 13 mmol) was added. Afterwards, the solution was warmed to rt. Water ice was added to the reaction mixture and after stirring for 5 min water was added. The mixture was acidified with 4N hydrochloric acid. The organic layer was separated and the aqueous layer was extracted twice with diethyl ether. The combined organic layers were washed with brine and dried over sodium sulfate. The solvent was then removed in vacuo to yield 2.41 g (96% purity, 100% yield) of the title compound.

LC-MS (method 1): $R_t$=1.24 min; MS (ESIpos): m/z=222 $[M+H]^+$ $^1$H-NMR (600 MHz, DMSO-$d_6$) δ [ppm]: 0.79 (t, 3H), 1.50-1.64 (m, 2H), 3.03-3.08 (m, 4H), 3.70-3.75 (m, 4H), 4.30-4.35 (m, 1H), 4.90 (d, 1H), 6.88 (d, 2H), 7.16 (d, 2H).

Intermediate I-71

4-(4-{1-[4-(4,4,5,5-Tetramethyl-1,3,2-dioxaborolan-2-yl)-1H-pyrazol-1-yl]propyl}phenyl)morpholine (mixture of enantiomers)

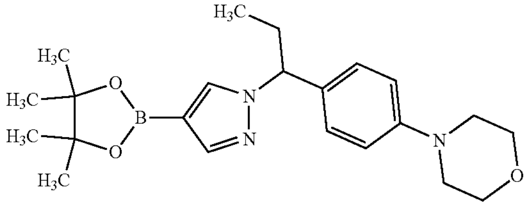 [SMILES: CCC(c1ccc(N2CCOCC2)cc1)n1cc(B2OC(C)(C)C(C)(C)O2)cn1]

DIAD (2.4 ml, 12 mmol) and triphenylphosphine (3.20 g, 12.2 mmol) were dissolved in THF (20 ml) and cooled to 0° C. 1-[4-(Morpholin-4-yl)phenyl]propan-1-ol (2.16 g, 9.76 mmol) was added and subsequently a solution of 4-(4,4,5,5-tetramethyl-1,3,2-dioxaborolan-2-yl)-1H-pyrazole (1.58 g, 8.13 mmol) in THE (20 ml) was added dropwise. The mixture was stirred at rt overnight. The solvent was removed in vacuo and the residue was purified by column chromatography (Biotage® SNAP Ultra C18 120 g cartridge, eluent: acetonitrile/water gradient 80:20 to 95:5) to yield 594 mg (70% purity, 13% yield) of the title compound.

LC-MS (method 1): $R_t$=2.11 min; MS (ESIpos): m/z=398 $[M+H]^+$ $^1$H-NMR (500 MHz, DMSO-$d_6$) δ [ppm]: 0.75 (t, 3H), 1.23 (s, 12H), 2.02-2.13 (m, 1H), 2.24-2.37 (m, 1H), 3.05-3.08 (m, 4H), 3.70-3.73 (m, 4H), 5.21 (dd, 1H), 6.86-6.90 (m, 2H), 7.21-7.25 (m, 2H), 7.58 (s, 1H), 8.00 (s, 1H).

Intermediate I-72

1-[(1S)-1-(4-Fluorophenyl)propyl]-4-(4,4,5,5-tetramethyl-1,3,2-dioxaborolan-2-yl)-1H-pyrazole

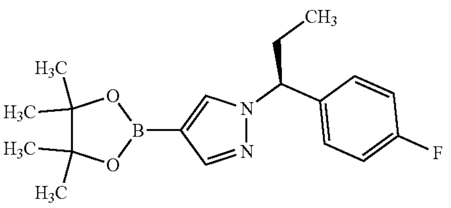 [SMILES: CC[C@@H](c1ccc(F)cc1)n1cc(B2OC(C)(C)C(C)(C)O2)cn1]

To a solution of 4-(4,4,5,5-tetramethyl-1,3,2-dioxaborolan-2-yl)-1H-pyrazole (2.77 g, 14.3 mmol), (1R)-1-(4-fluorophenyl)propan-1-ol (2.00 g. 13.0 mmol) and triphenylphosphine (6.81 g. 25.9 mmol) in THF (40 ml) was added dropwise DBAD (5.97 g. 25.9 mmol) in THE (10 ml). The 15 resulting mixture was stirred for 2 h at reflux. It was then cooled to rt and the reaction mixture was concentrated under reduced pressure. The residue was purified by flash column chromatography (C18, 25 g, eluent: water/acetonitrile gradient 85:15 to 50:50) to yield 1.94 g (98% purity, 44% yield) of the title compound.

LC-MS (method 21): $R_t$=2.53 min; MS (ESIpos): m/z=331 $[M+H]^+$ $^1$H-NMR (400 MHz, DMSO-$d_6$) δ [ppm]: 0.76 (t, 3H), 1.23 (s, 12H), 2.10 (m, 1H), 2.28-2.41 (m, 1H), 5.36 (dd, 1H), 7.11-7.19 (m, 2H), 7.39-7.45 (m, 2H), 7.64 (s, 1H), 8.11 (s, 1H).

$^{19}$F-NMR (376 MHz, DMSO-$d_6$) δ [ppm]: −114.90 (s, 1F).

Intermediate I-73

1-[1-(4-Fluorophenyl)-2-methylpropyl]-4-(4,4,5,5-tetramethyl-1,3,2-dioxaborolan-2-yl)-1H-pyrazole (mixture of enantiomers)

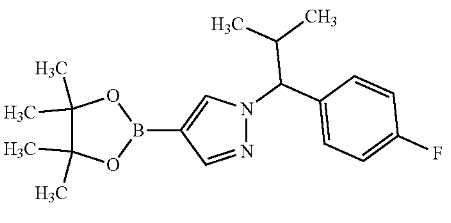 [SMILES: CC(C)C(c1ccc(F)cc1)n1cc(B2OC(C)(C)C(C)(C)O2)cn1]

Di-tert-butylazodicarboxylate (1.34 g, 5.80 mmol) and triphenylphosphine (1.52 g, 5.80 mmol) were stirred at 0° C. in dry tetrahydrofuran (10 ml) for 15 min. Then 4-(4,4,5,5-tetramethyl-1,3,2-dioxaborolan-2-yl)-1H-pyrazole (750 mg, 3.87 mmol) and 1-(4-fluorophenyl)-2-methylpropan-1-ol [CAS-RN 1766-28-5](975 mg, 5.80 mmol) as a solution in dry tetrahydrofuran (5 ml) were slowly added. The reaction mixture was stirred at rt for 4 days and was then concentrated. The crude product was purified directly by preparative HPLC to yield 516 mg 392 mg (100% purity, 29% yield) of the title compound as a racemic mixture.

LC-MS (method 1): $R_t$=2.35 min; MS (ESIpos): m/z=345 $[M+H]^+$ $^1$H-NMR (400 MHz, DMSO-$d_6$) δ [ppm]: 0.71 (d, 3H), 0.74 (d, 3H), 2.65-2.76 (m, 1H), 5.01 (d, 1H), 7.16 (t, 2H), 7.54-7.59 (m, 2H), 7.60 (s, 1H), 8.10 (s, 1H).

Intermediate I-74

4-(4,4,5,5-Tetramethyl-1,3,2-dioxaborolan-2-yl)-1-{1-[4-(trifluoromethyl)phenyl]propyl}-1H-pyrazole (mixture of enantiomers)

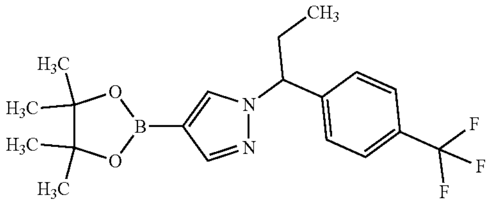 [SMILES: CCC(c1ccc(C(F)(F)F)cc1)n1cc(B2OC(C)(C)C(C)(C)O2)cn1]

To a solution of 1-[4-(trifluoromethyl)phenyl]propan-1-ol (3.00 g, 14.5 mmol), 4-(4,4,5,5-tetramethyl-1,3,2-dioxaborolan-2-yl)-1H-pyrazole (3.42 g, 17.5 mmol) and triphenylphosphine (7.63 g, 29.1 mmol) in THF (40 ml) at rt was added a solution of DBAD (6.70 g, 29.1 mmol) in THF (20 ml). The resulting mixture was stirred under reflux for 3 h. It was cooled to rt and the solvent was removed in vacuo. The residue was purified by column chromatography (C18, 40 g; eluent: water/acetonitrile gradient 80:20 to 40:60; flow rate: 50 ml/min) to yield 2.95 g (94% purity, 50% yield) of the title compound.

LC-MS (method 7): $R_t$=1.88 min; MS (ESIpos): m/z=381 $[M+H]^+$ $^1$H-NMR (300 MHz, DMSO-$d_6$) δ [ppm]: 0.79 (t, 3H), 1.25 (s, 12H), 2.07-2.23 (m, 1H), 2.30-2.48 (m, 1H), 5.49 (dd, 1H), 7.57 (d, 2H), 7.67 (s, 1H), 7.71 (d, 2H), 8.17 (s, 1H).

$^{19}$F-NMR (282 MHz, DMSO-$d_6$) δ [ppm]: −60.99 (s, 3F).

Intermediate I-75

1-(5-Fluoropyridin-2-yl)propan-1-ol (mixture of enantiomers)

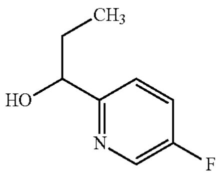

A solution of ethylmagnesium bromide (9.6 ml, 1.0 M, 9.6 mmol) in tetrahydrofuran was added dropwise to solution of 5-fluoropyridine-2-carbaldehyde [CAS-RN 31181-88-1] (1.00 g, 7.99 mmol) in dry tetrahydrofuran (20 ml) at 0° C. The reaction mixture was stirred and rt for 40 h and then quenched with water. The mixture was extracted twice with ethyl acetate, and the combined organic layers were washed with 1N hydrochloric acid and brine. It was dried over sodium sulfate and concentrated. The residue was purified by column chromatography (Biotage® SNAP Ultra 50 g cartridge, eluent: dichloromethane-methanol gradient 98:2 to 96:4) to yield 552 mg (96% purity, 43% yield) of the title compound as a racemic mixture.

LC-MS (method 1): $R_t$=0.97 min; MS (ESIpos): m/z=156 $[M+H]^+$ $^1$H-NMR (400 MHz, DMSO-$d_6$) δ [ppm]: 0.83 (t, 3H), 1.56-1.67 (m, 1H), 1.70-1.80 (m, 1H), 4.49-4.54 (m, 1H), 5.35 (d, 1H), 7.52 (dd, 1H), 7.69 (td, 1H), 8.46 (d, 1H).

Intermediate I-76

5-Fluoro-2-{1-[4-(4,4,5,5-tetramethyl-1,3,2-dioxaborolan-2-yl)-1H-pyrazol-1-yl]propyl}pyridine (mixture of enantiomers)

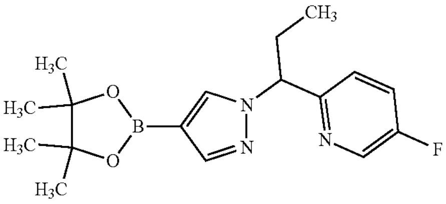 [SMILES: CCC(c1ccc(F)cn1)n1cc(B2OC(C)(C)C(C)(C)O2)cn1]

Under argon atmosphere di-tert-butylazodicarboxylate (816 mg, 3.54 mmol) and triphenylphosphine (930 mg, 3.54 mmol) were stirred at 0° C. in dry tetrahydrofuran (3.5 ml) for 15 min. Then 4-(4,4,5,5-tetramethyl-1,3,2-dioxaborolan-2-yl)-1H-pyrazole (459 mg, 2.36 mmol) and 1-(5-fluoropyridin-2-yl)propan-1-ol (550 mg, 3.54 mmol) as a solution in dry tetrahydrofuran (3.5 ml) were slowly added. The reaction mixture was stirred at rt for 12 h and then concentrated. The crude product was purified directly column chromatography (Biotage® SNAP Ultra 50 g cartridge, eluent: dichloromethane-methanol 98:2) to yield 737 mg (96% purity, 90% yield) of the title compound as a racemic mixture.

LC-MS (method 1): $R_t$=1.99 min; MS (ESIpos): m/z=332 $[M+H]^+$ $^1$H-NMR (400 MHz, DMSO-$d_6$) δ [ppm]: 0.77 (t, 3H), 1.25 (s, 12H), 2.17-2.40 (m, 2H), 5.40-5.54 (m, 1H), 7.26-7.37 (m, 1H), 7.62 (s, 1H), 7.65-7.74 (m, 1H), 8.07-8.17 (m, 1H), 8.51-8.66 (m, 1H).

Intermediate I-77

1-(5-Chloropyridin-3-yl)propan-1-ol (mixture of enantiomers)

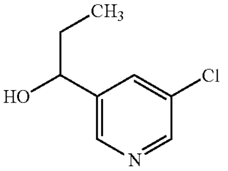

To a solution of 5-chloropyridine-3-carbaldehyde [CAS-RN 113118-82-4](3.95 g, 27.9 mmol) in dry tetrahydrofuran (100 ml) was added ethylmagnesium bromide (33 ml, 1.0 M in THF, 33 mmol) dropwise at 0° C. After stirring for 2 h at rt, the reaction was quenched with satd. aqueous solution of ammonium chloride. The mixture was extracted twice with ethyl acetate, and the combined organic layers were dried over anhydrous sodium sulfate and concentrated. The residue was purified by column chromatography (Biotage® SNAP Ultra 50 g cartridge, eluent: dichloromethane-methanol 98:2, 96:4) to yield 3.36 g (80% purity, 56% yield) of the title compound.

LC-MS (method 3): $R_t$=0.84 min; MS (ESIpos): m/z=172 $[M+H]^+$ $^1$H-NMR (400 MHz, DMSO-$d_6$) δ [ppm]: 0.83 (t, 3H), 1.65 (quin, 2H), 4.53-4.59 (m, 1H), 5.43 (d, 1H), 7.82 (s, 1H), 8.48 (br s, 2H).

Intermediate I-78

3-Chloro-5-{1-[4-(4,4,5,5-tetramethyl-1,3,2-dioxaborolan-2-yl)-1H-pyrazol-1-yl]propyl}pyridine (mixture of enantiomers)

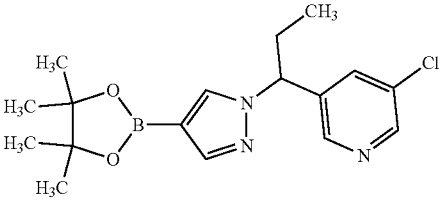 [SMILES: CCC(c1cncc(Cl)c1)n1cc(B2OC(C)(C)C(C)(C)O2)cn1]

Under argon atmosphere di-tert-butylazodicarboxylate (712 mg, 3.09 mmol) and triphenylphosphine (811 mg, 3.09 mmol) were stirred at 0° C. in dry tetrahydrofuran (8 ml) for 15 min. Then 4-(4,4,5,5-tetramethyl-1,3,2-dioxaborolan-2-yl)-1H-pyrazole (400 mg, 2.06 mmol) and 1-(5-chloropyridin-3-yl)propan-1-ol (531 mg, 3.09 mmol) as a solution in dry tetrahydrofuran (4 ml) were slowly added. The reaction mixture was stirred at rt for 12 h and then concentrated. The crude product was purified directly column chromatography (Biotage® SNAP Ultra 50 g cartridge, eluent: dichloromethane-methanol 98:2) to yield 582 mg (75% purity, 61% yield) of the title compound as a racemic mixture.

LC-MS (method 3): $R_t$=1.38 min; MS (ESIpos): m/z=348 $[M+H]^+$ $^1$H-NMR (400 MHz, DMSO-$d_6$) δ [ppm]: 0.77 (t, 3H), 1.25 (s, 12H), 2.10-2.21 (m, 1H), 2.31-2.43 (m, 1H), 5.44-5.51 (m, 1H), 7.66 (s, 1H), 7.94 (s, 1H), 8.19 (s, 1H), 8.49-8.62 (m, 2H).

Intermediate I-79

1-(5-Chloropyridin-3-yl)-2-methylpropan-1-ol (mixture of enantiomers)

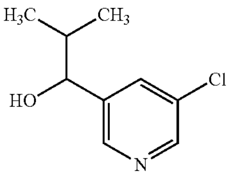

To a solution of 5-chloropyridine-3-carbaldehyde [CAS-RN 113118-82-4](3.00 g, 95% purity, 20.13 mmol) in dry tetrahydrofuran (30 ml) at 0° C. was added dropwise isopropylmagnesium bromide (24.2 ml, 1.0 M in tetrahydrofuran, 24.2 mmol). After stirring for 2 h at rt, water (150 ml)

was added and the reaction mixture was extracted three times with ethyl acetate (200 ml each). The combined organic layers were washed with brine (300 ml) and dried over anhydrous sodium sulfate. The solvent was evaporated under reduced pressure and the crude product was purified by column chromatography (silica gel 120 g; eluent: petroleum ether/ethyl acetate 9:1) to yield 2.20 g (96% purity, 57% yield) of the title compound.

LC-MS (method 5): $R_t$=0.81 min; MS (ESIpos): m/z=186 (M+H)+

$^1$H-NMR (300 MHz, DMSO-$d_6$) δ [ppm]: 0.72-0.83 (m, 6H), 1.97-2.04 (m, 1H), 4.32-4.35 (m, 1H), 5.35 (d, 1H), 7.45 (d, 1H), 7.86-7.90 (m, 1H), 8.51 (s, 1H).

Intermediate I-80

3-Chloro-5-{2-methyl-1-[4-(4,4,5,5-tetramethyl-1,3,2-dioxaborolan-2-yl)-1H-pyrazol-1-yl]propyl}pyridine (mixture of enantiomers)

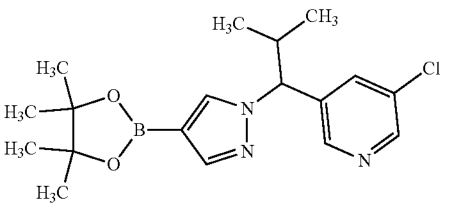 [SMILES: CC(C)C(c1cncc(Cl)c1)n1cc(B2OC(C)(C)C(C)(C)O2)cn1]

To 1-(5-Chloropyridin-2-yl)-2-methylpropan-1-ol (3.20 g, 96% purity, 16.6 mmol) in tetrahydrofuran (40 ml) were added 4-(4,4,5,5-tetramethyl-1,3,2-dioxaborolan-2-yl)-1H-pyrazole (3.85 g, 19.9 mmol) and triphenylphosphine (8.68 g. 33.09 mmol). A solution of DBAD (7.62 g, 33.1 mmol) in tetrahydrofuran (20 ml) was added within 3 min at rt. After stirring for 3 h under reflux, the reaction mixture was cooled to rt and concentrated in vacuo. The crude product was purified by flash column chromatography (Column: C18, 400 g; Mobile Phase A: Water, Mobile Phase B: Acetonitrile; Gradient: 40% B to 80% B in 25 min, 220 and 254 nm), to give 1.80 g (80% purity) of crude product which was further purified by column chromatography on silica gel (220 g, eluent: petroleum ether/ethyl acetate 10:1) to yield 600 mg (95% purity, 10% yield) of the title compound.

LC-MS (method 22): $R_t$=1.88 min; MS (ESIpos): m/z=362 $(M+H)^+$ $^1$H-NMR (300 MHz, DMSO-$d_6$) δ [ppm]: 0.73-0.77 (m, 6H), 1.24 (s, 12H), 2.72-2.80 (m, 1H), 5.19 (d, 1H), 7.59-7.64 (m, 2H), 7.92-7.96 (m, 1H), 8.13 (s, 1H1), 8.62 (s, 1H).

Intermediate I-81

1-[6-(Difluoromethyl)pyridin-3-yl]propan-1-ol (mixture of enantiomers)

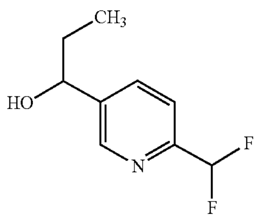

To a solution of 6-(difluoromethyl)pyridine-3-carbaldehyde (1.00 g, 6.36 mmol) at 0° C. in dry diethyl ether (20 ml) was added dropwise a solution of ethylmagnesium bromide (7.0 ml, 1.0 M in THF, 7.0 mmol). The reaction mixture was stirred at rt for 12 h and then quenched with water. The mixture was extracted three times with ethyl acetate, and the combined organic layers were washed with brine, dried over sodium sulfate and concentrated. The residue was purified by silica gel column chromatography (eluent: cyclohexane/ethyl acetate 7:3) to yield 872 mg (88% purity, 64% yield) of the title compound as a racemic mixture.

LC-MS (method 1): $R_t$=1.09 min; MS (ESIpos): m/z=188 $[M+H]^+$ $^1$H-NMR (500 MHz, DMSO-$d_6$) δ [ppm]: 0.84 (t, 3H), 1.61-1.71 (m, 2H), 4.57-4.63 (m, 1H), 5.41 (d, 1H), 6.93 (t, 1H), 7.65 (d, 1H), 7.91 (dd, 1H), 8.62 (d, 1H).

Intermediate I-82

2-(Difluoromethyl)-5-{1-[4-(4,4,5,5-tetramethyl-1,3,2-dioxaborolan-2-yl)-1H-pyrazol-1-yl]propyl}pyridine (mixture of enantiomers)

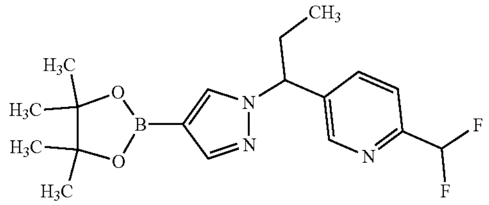

To a solution of 4-(4,4,5,5-tetramethyl-1,3,2-dioxaborolan-2-yl)-1H-pyrazole (1.80 g, 9.26 mmol) in tetrahydrofuran (50 ml) was added 1-[6-(trifluoromethoxy)pyridin-3-yl]propan-1-ol (1.80, 7.72 mmol, 95% purity) and triphenylphosphine (6.07 g, 23.14 mmol). DBAD (5.33 g, 23.14 mmol) in dry tetrahydrofuran (10 ml) was added at rt to the solution within 2 min. After stirring for 0.5 h under reflux the reaction mixture was cooled to rt and then concentrated under reduced pressure. Then the crude product was purified by preparative HPLC (Column: C18, 330 g; Mobile Phase A: Water, Mobile Phase B: acetonitrile; Gradient: 20% B to 60% B in 25 min, 220 and 254 nm), The fractions containing the desired product were combined and dried in vacuo to yield 1.60 g (92% purity, 48% yield) of the title compound.

LC-MS (method 22): $R_t$=2.09 min; MS (ESIpos): m/z=364 $(M+H)^+$ $^1$H-NMR (300 MHz, DMSO-$d_6$) δ [ppm]: 0.78 (t, 3H), 1.24 (s, 12H), 2.11-2.47 (m, 2H), 5.53 (dd, 1H), 6.93 (t, 1H), 7.62-7.77 (m, 2H), 7.94 (d, 1H), 8.19 (s, 1H), 8.68 (br s, 1H).

Intermediate I-83

1-[6-(Difluoromethyl)pyridin-3-yl]-2-methylpropan-1-ol (mixture of enantiomers)

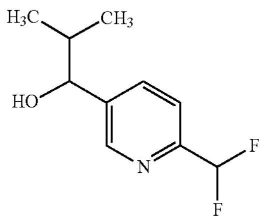

To a solution of 6-(difluoromethyl)pyridine-3-carbaldehyde [CAS-RN 946578-32-1](2.45 g, 15.6 mmol) at 0° C. in dry 2-methyltetrahydrofuran (50 ml) was added dropwise a solution of isopropylmagnesium bromide (5.7 ml, 3.0 M in 2-methyl tetrahydrofuran, 17 mmol). The reaction mixture was stirred at rt for 12 h and then quenched with water. The mixture was extracted three times with ethyl acetate, and the combined organic layers were washed with brine, dried over sodium sulfate and concentrated. The residue was purified by silica gel column chromatography (eluent: cyclohexane/ethyl acetate 7:3) to yield 991 mg (93% purity, 29% yield) of the title compound as a racemic mixture.

LC-MS (method 1): $R_t$=1.33 min; MS (ESIpos): m/z=202 $[M+H]^+$ $^1$H-NMR (400 MHz, DMSO-$d_6$) δ [ppm]: 0.77 (d, 6H), 0.84 (d, 6H), 1.87 (qd, 1H), 2.52-2.56 (m, 3H), 4.42 (t, 1H), 5.40 (d, 1H), 6.93 (t, 11H), 7.65 (d, 1H), 7.88 (dd, 1H), 8.58 (d, 1H).

Intermediate I-84

2-(Difluoromethyl)-5-{(2-methyl-1-[4-(4,4,5,5-tetramethyl-1,3,2-dioxaborolan-2-yl)-1H-pyrazol-1-yl]propyl}pyridine (mixture of enantiomers)

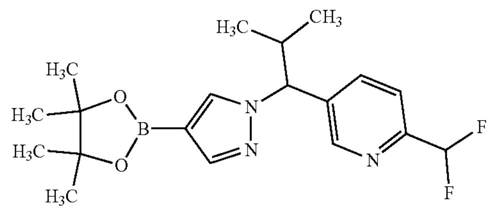

Di-isopropylbutylazodicarboxylate (1.7 ml, 8.5 mmol) and triphenylphosphine (2.23 g, 8.50 mmol) were stirred at 0° C. in dry tetrahydrofuran (30 ml) for 15 min. Then 4-(4,4,5,5-tetramethyl-1,3,2-dioxaborolan-2-yl)-1H-pyrazole (1.10 g, 5.67 mmol) and 1-[6-(difluoromethyl)pyridin-3-yl]-2-methylpropan-1-ol (1.39 g, 90% purity, 6.24 mmol) as a solution in dry THF (10 ml) were slowly added. The reaction mixture was stirred at rt for 12 h and then quenched with water. The reaction mixture was extracted twice with ethyl acetate, and the combined organic layers were washed with brine, dried over sodium sulfate and concentrated. The residue was purified by silica gel column chromatography (eluent: cyclohexane/ethyl acetate gradient 9:1 to 6:4) to yield 1.21 g (86% purity, 49% yield) of the title compound as a racemic mixture.

LC-MS (method 1): $R_t$=2.13 min; MS (ESIpos): m/z=378 $[M+H]^+$ $^1$H-NMR (400 MHz, DMSO-$d_6$) δ [ppm]: 0.76 (t, 6H), 1.20-1.26 (m, 12H), 2.80 (dq, 1H), 5.20 (d, 1H), 6.94 (t, 1H), 7.65 (s, 1H), 7.71 (d, 1H), 8.17 (s, 1H), 8.19 (dd, 1H), 8.82 (d, 1H).

Intermediate I-85

Cyclopropyl[6-(difluoromethyl)pyridin-3-yl]methanol (mixture of enantiomers)

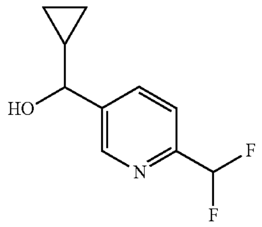 [SMILES: OC(c1ccc(C(F)F)nc1)C1CC1]

Under argon atmosphere, to a solution of 6-(difluoromethyl)pyridine-3-carbaldehyde [CAS-RN 946578-32-1] (1.00 g, 6.36 mmol) at 0° C. in dry diethyl ether (20 ml) was added dropwise a solution of cyclopropylmagnesium bromide (14 ml, 0.50 M in THF, 7.0 mmol). The reaction mixture was stirred at rt for 12 h and then quenched with water. The reaction mixture was extracted three times with ethyl acetate, and the combined organic layers were washed with brine, dried over sodium sulfate and concentrated. The residue was purified by silica gel column chromatography (eluent: cyclohexane/ethyl acetate 7:3) to yield 1.06 g (90% purity, 75% yield) of the title compound as a racemic mixture.

LC-MS (method 1): $R_t$=1.15 min; MS (ESIpos): m/z=200 $[M+H]^+$ $^1$H-NMR (600 MHz, DMSO-$d_6$) δ [ppm]: 0.38-0.52 (m, 4H), 1.00-1.13 (m, 1H), 4.11 (dd, 1H), 5.49 (d, 1H), 6.94 (t, 1H), 7.67 (d, 1H), 7.98 (dd, 1H), 8.68 (s, 1H).

Intermediate I-86

5-{Cyclopropyl[4-(4,4,5,5-tetramethyl-1,3,2-dioxaborolan-2-yl)-1H-pyrazol-1-yl]methyl}-2-(difluoromethyl)pyridine (mixture of enantiomers)

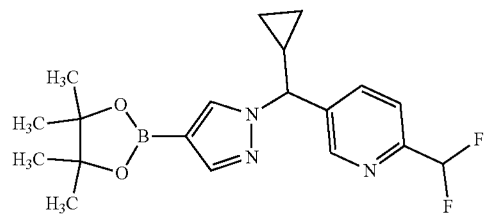

Di-isopropylazodicarboxylate (1.3 ml, 6.5 mmol) and triphenylphosphine (1.71 g, 6.51 mmol) were stirred at 0° C. in dry tetrahydrofuran (12 ml) for 15 min. Then 4-(4,4,5,5-tetramethyl-1,3,2-dioxaborolan-2-yl)-1H-pyrazole ((842 mg, 4.34 mmol) and cyclopropyl[6-(difluoromethyl)pyridin-3-yl]methanol (1.06 g, 90% purity, 4.78 mmol) as a solution in dry THF (6 ml) were slowly added. The reaction mixture was stirred at rt for 12 h and then quenched with water. The reaction mixture was extracted twice with ethyl acetate, and the combined organic layers were washed with brine, dried over sodium sulfate and concentrated. The residue was purified by silica gel column chromatography (eluent: cyclohexane/ethyl acetate gradient 9:1 to 6:4) to yield 15 469 mg (82% purity, 24% yield) of the title compound as a racemic mixture.

LC-MS (method 1): $R_t$=1.97 min; MS (ESIpos): m/z=376 $[M+H]^+$ $^1$H-NMR (600 MHz, DMSO-$d_6$) δ [ppm]: 0.42-0.50 (m, 1H), 0.50-0.57 (m, 1H), 0.65-0.72 (m, 2H), 1.26 (s, 12H), 1.76-1.91 (m, 1H), 4.88 (d, 1H), 6.94 (t, 1H), 7.64 (s, 1H), 7.69 (d, 1H), 7.91 (d, 1H), 8.25 (s, 1H), 8.65 (br s, 1H).

Intermediate I-87

1-[6-(Trifluoromethyl)pyridin-3-yl]propan-1-ol (mixture of enantiomers)

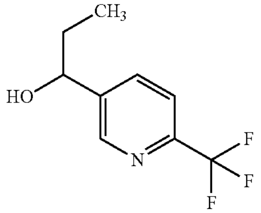

A solution of ethylmagnesium bromide in THF (40 ml, 1.0 M, 40 mmol) was added dropwise to a solution of 6-(trifluoromethyl)pyridine-3-carbaldehyde [CAS-RN 386704-12-7](5.80 g, 33.1 mmol) in dry tetrahydrofuran (100 ml) at 0° C. The reaction mixture was stirred and rt for 3 h and then quenched with water. The mixture was extracted twice with ethyl acetate, and the combined organic layers were washed with brine and dried over sodium sulfate. The solvent was removed in vacuo and the residue was purified by column chromatography (Biotage® SNAP Ultra 100 g cartridge, eluent: cyclohexane/ethyl acetate 8:2) to yield 3.65 g (99% purity, 53% yield) of the title compound as a racemic mixture.

LC-MS (method 1): $R_t$=1.38 min; MS (ESIpos): m/z=206 $[M+H]^+$ $^1$H-NMR (400 MHz, DMSO-$d_6$) δ [ppm]: 0.85 (t, 3H), 1.63-1.71 (m, 2H), 4.65 (q, 1H), 5.51 (d, 1H), 7.86 (d, 1H), 8.00 (d, 1H), 8.71 (s, 1H).

Intermediate I-88

5-{1-[4-(4,4,5,5-Tetramethyl-1,3,2-dioxaborolan-2-yl)-1H-pyrazol-1-yl]propyl}-2-(trifluoromethyl)pyridine (mixture of enantiomers)

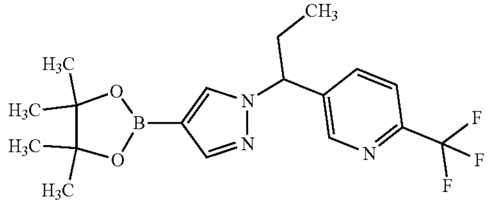

Di-isopropylazodicarboxylate (4.3 ml, 22 mmol) and triphenylposphine (5.73 g, 21.9 mmol) were stirred at 0° C. in dry tetrahydrofuran (100 ml) for 15 min. Then 4-(4,4,5,5-tetramethyl-1,3,2-dioxaborolan-2-yl)-1H-pyrazole (2.83 g, 14.6 mmol) and 1-[6-(trifluoromethyl)pyridin-3-yl]propan-1-ol (3.59 g, 17.5 mmol) as a solution in dry tetrahydrofuran (100 ml) (20 ml) were slowly added. The reaction mixture was stirred at rt for 12 h and then concentrated. The crude product was purified by column chromatography (Biotage® SNAP Ultra 100 g cartridge, eluent: cyclohexane/ethyl acetate gradient 100:0 to 85:15) to yield 5.29 g (78% purity, 74% yield) of the title compound as a racemic mixture.

LC-MS (method 3): $R_t$=1.45 min; MS (ESIpos): m/z=382 $[M+H]^+$ $^1$H-NMR (400 MHz, DMSO-$d_6$) δ [ppm]: 0.79 (t, 3H), 1.24 (m, 12H), 2.17-2.22 (m, 111), 2.32-2.47 (m, 1H), 5.59 (dd, 1H), 7.67 (s, 1H), 7.89 (d, 1H), 8.03 (dd, 1H), 8.20 (s, 1H), 8.77 (d, 1H).

Intermediate I-89

(1R)-1-[6-(Trifluoromethyl)pyridin-3-yl]propan-1-ol (enantioenriched)

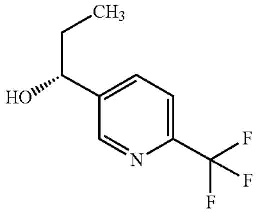

In a dry flask N,N'-[(1S,2S)-cyclohexane-1,2-diyl]bis(1,1,1-trifluoromethanesulfonamide) (216 mg, 571 μmol) [CAS-RN 153077-87-3] was dissolved in toluene (11 ml) and purged with dry argon for 5 min. Tetraisopropyl orthotitanate (10 ml, 34 mmol) was added at rt. The mixture was heated to 40° C. and stirred at this temperature for 20 min, then cooled to −78° C. Diethylzinc (36 ml, 1.1 M in toluene, 40 mmol) was added slowly to keep the temperature below −50° C. 6-(trifluoromethyl)pyridine-3-carbaldehyde (5.00 g, 28.6 mmol) was added dropwise as a solution in toluene (10 ml) and the mixture was warmed to −30° C. to −20° C. and stirred for 2 h. The mixture was poured into a mixture of satd. aq. ammonium chloride solution (50 ml), 1 N hydrochloric acid (20 ml), water (20 ml) and ethyl acetate (100 ml). The organic layer was separated. The aqueous layer was stirred twice with ethyl acetate (100 ml each) and the organic layers were combined and dried over sodium sulfate. The solvent was removed in vacuo and the residue was purified by column chromatography (Biotage® SNAP Ultra 100 g cartridge, eluent: cyclohexane/ethyl acetate gradient 1:0 to 3:2) to yield 4.07 g (100% purity, 69% yield) of the title compound. Analytical chiral chromatography revealed 60% ee.

LC-MS (method 1): $R_t$=1.41 min; MS (ESIpos): m/z=206 $[M+H]^+$

Analytical chiral HPLC. Column: Phenomenex cellulose-1, 3 μm, 50×4.6 mm; Eluent A: n-heptane; Eluent B: ethanol+0.2% diethylamine; isocratic: 95% A+5% B; flow: 1 ml/min; UV: 220 nm.

Stereoisomer 1: $R_t$=1.693 min (major enantiomer) and

Stereoisomer 2: $R_t$=1.874 min (minor enantiomer)

$^1$H-NMR (600 MHz, DMSO-$d_6$) δ [ppm]: 0.85 (t, 3H), 1.62-1.73 (m, 2H), 4.66 (q, 1H), 5.49 (d, 1H), 7.86 (d, 1H), 8.00 (dd, 1H), 8.71 (d, 1H).

Intermediate I-90

5-{(1S)-1-[4-(4,4,5,5-Tetramethyl-1,3,2-dioxaborolan-2-yl)-1H-pyrazol-1-yl]propyl}-2-(trifluoromethyl)pyridine (enantioenriched)

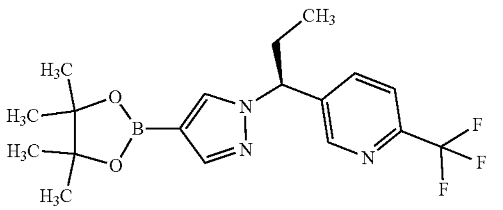

Triphenylposphine (6.50 g, 24.8 mmol) was dissolved in tetrahydrofuran (90 ml) and cooled to 0° C. Di-isopropylazodicarboxylate (4.9 ml, 25 mmol) was added dropwise. After 5 min a solution of (1R)-1-[6-(trifluoromethyl)pyridin-3-yl]propan-1-ol (enantioenriched with 60% ee) (4.07 g, 19.8 mmol) and 4-(4,4,5,5-tetramethyl-1,3,2-dioxaborolan-2-yl)-1H-pyrazole (3.21 g, 16.5 mmol) in tetrahydrofuran (30 ml) was added, and the mixture was warmed to rt and stirred for 2 d. Water (1 ml) was added and the mixture was concentrated in vacuo. The residue was purified by column chromatography (Biotage® SNAP Ultra 100 g cartridge, eluent: cyclohexane/ethyl acetate gradient 20 1:0 to 17:3) and then by preparative HPLC (Chromatorex C18, 10 μm, 125×30 mm; eluent: water (+0.1% formic acid)/acetonitrile gradient 9:1 to 1:19) to yield 1.94 g (37% yield) of the title compound as a 7:3 mixture of boronic acid and corresponding pinacole ester.

LC-MS (MCW-FT-MS-M1): $R_t$=1.28 min; MS (ESIpos): m/z=300 [M+H]$^+$ (boronic acid) and $R_t$=2.19 min; MS (ESIpos): m/z=382 [M+H]$^+$ (pinacole ester).

Intermediate I-91

2-Methyl-1-[6-(trifluoromethyl)pyridin-3-yl]propan-1-ol (mixture of enantiomers)

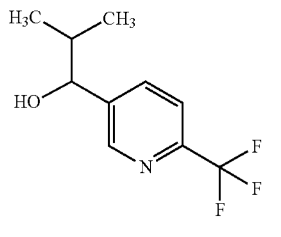

To a solution of isopropylmagnesium bromide in THF (252 ml, 1M, 250 mmol) at 0° C., was added within 15 min 6-(trifluoromethyl)nicotinaldehyde (20.0 g, 114 mmol) in diethyl ether (130 ml). After stirring for 1 h at rt, water (1.5 1) was added and the mixture was concentrated in vacuo. The solids were filtered off and the filtrate was extracted three times with ethyl acetate (200 ml each). The combined organic layers were washed with brine (400 ml) and dried over anhydrous sodium sulfate. The solvent was evaporated under reduced pressure and the crude product was purified by column chromatography (silica gel 330 g; eluent: petroleum ether/ethyl acetate 9:1) to give 10.8 g (98% purity, 42% yield) of the title compound.

LC-MS (method 23): $R_t$=0.89 min; MS (ESIpos): m/z=220 (M+H)$^+$ $^1$H-NMR (400 MHz, DMSO-$d_6$) δ [ppm]: 0.79 (d, 3H), 0.83 (d, 3H), 1.82-1.95 (m, 1H), 4.48 (t, 1H), 5.49 (d, 1H), 7.86 (d, 1H), 7.95-7.99 (m, 1H), 8.67-8.69 (m, 1H). $^{19}$F-NMR (376 MHz, DMSO-$d_6$) δ [ppm]: −66.33 (s, 3F).

Intermediate I-92

5-{2-Methyl-1-[4-(4,4,5,5-tetramethyl-1,3,2-dioxaborolan-2-yl)-1H-pyrazol-1-yl]propyl}-2-(trifluoromethyl)pyridine (mixture of enantiomers)

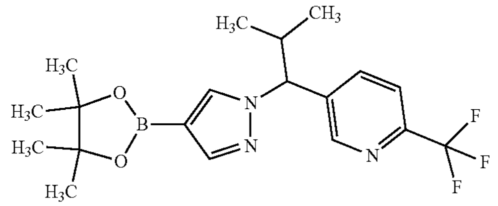

To a solution of 2-methyl-1-[6-(trifluoromethyl)pyridin-3-yl]propan-1-ol (31.0 g, 97% purity, 137 mmol) in THF (280 ml) were added 4-(4,4,5,5-tetramethyl-1,3,2-dioxaborolan-2-yl)-1H-pyrazole (47.9 g, 247 mmol) and triphenylphosphine (72.0 g, 274 mmol). A solution of DBAD (63.2 g, 274 mmol) in THE (100 ml) was added within 15 min at rt. After stirring for 2 h under reflux, the reaction mixture was cooled to rt and concentrated under reduced pressure. The crude product was purified by flash column chromatography (C18, 330 g; eluent: water/acetonitrile gradient 70:30 to 40:60; flow rate: 50 ml/min) to yield 23.5 g (97% purity, 42% yield) of the title compound containing 15% boronic acid.

LC-MS (method 16): $R_t$=1.36 min; MS (ESIpos): m/z=396 (M+H)$^+$ $^1$H-NMR (300 MHz, DMSO-$d_6$) δ [ppm]: 0.75-0.80 (m, 6H), 1.24 (s, 12H), 2.74-2.89 (m, 1H), 5.28 (d, 1H), 7.69 (s, 1H), 7.93 (d, 1H), 8.19 (s, 1H), 8.29 (dd, 1H), 8.93 (d, 1H). $^{19}$F-NMR (282 MHz, DMSO-$d_6$) δ [ppm]: −66.39 (s, 3F).

Intermediate I-93

Cyclopropyl[6-(trifluoromethyl)pyridin-3-yl]methanol (mixture of enantiomers)

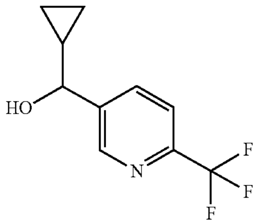 [SMILES: OC(c1ccc(C(F)(F)F)nc1)C1CC1]

A solution of cyclopropylmagnesium bromide in THE (25 ml, 0.50 M, 13 mmol) was added dropwise to solution of 6-(trifluoromethyl)pyridine-3-carbaldehyde [CAS-RN 386704-12-7](2.00 g, 11.4 mmol) in dry diethyl ether (35 ml) at 0° C. The reaction mixture was stirred and rt for 12 h and then quenched with water. The mixture was extracted twice with ethyl acetate. The combined organic layers were washed with brine, dried over sodium sulfate and concentrated. The residue was purified by silica gel column chromatography (eluent: cyclohexane/ethyl acetate 7:3) to yield 1.71 g (95% purity, 65% yield) of the title compound.

LC-MS (method 1): $R_t$=1.41 min; MS (ESIpos): m/z=218 $[M+H]^+$ $^1$H-NMR (600 MHz, DMSO-$d_6$) δ [ppm]: 0.39-0.57 (m, 4H), 1.01-1.12 (m, 1H), 4.16 (dd, 1H), 5.58 (d, 1H), 7.87 (d, 1H), 8.07 (dd, 1H), 8.78 (d, 1H).

Intermediate I-94

5-{Cyclopropyl[4-(4,4,5,5-tetramethyl-1,3,2-dioxaborolan-2-yl)-1H-pyrazol-1-yl]methyl}-2-(trifluoromethyl)pyridine (mixture of enantiomers)

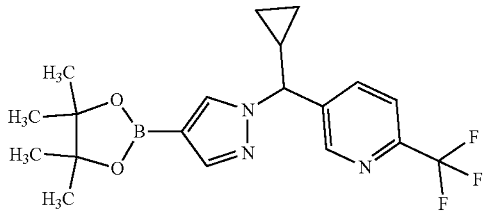

Di-tert-butylazodicarboxylate (2.34 g, 10.1 mmol) and triphenylphosphine (2.66 g, 10.1 mmol) were stirred at 0° C. in dry tetrahydrofuran (15 ml) for 15 min. Then 4-(4,4,5,5-tetramethyl-1,3,2-dioxaborolan-2-yl)-1H-pyrazole (1.31 g, 6.76 mmol) and cyclopropyl[6-(trifluoromethyl)pyridin-3-yl]methanol (1.70 g, 95% purity, 7.44 mmol) as a solution in dry tetrahydrofuran (5 ml) were slowly added. The reaction mixture was stirred at rt for 12 h and then quenched with brine. The reaction mixture was concentrated and purified directly by HPLC to yield 951 mg (94% purity, 33% yield) of the title compound.

LC-MS (method 1): $R_t$=2.12 min; MS (ESIpos): m/z=394 $[M+H]^+$ $^1$H-NMR (600 MHz, DMSO-$d_6$) δ [ppm]: 0.45-0.60 (m, 2H), 0.71 (br d, 2H), 1.16-1.31 (m, 12H), 1.82-1.95 (m, 1H), 4.94 (d, 1H), 7.65 (s, 1H), 7.90 (d, 1H), 7.95-8.02 (m, 1H), 8.28 (s, 1H), 8.74 (brs, 1H).

Intermediate I-95

Tetrahydro-2H-pyran-4-yl[6-(trifluoromethyl)pyridin-3-yl]methanol (mixture of enantiomers)

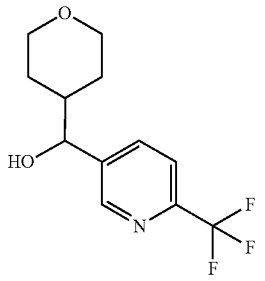 [SMILES: OC(c1ccc(C(F)(F)F)nc1)C1CCOCC1]

To 2-propylmagnesiumchloride (4.1 ml, 2.0 M in THF, 8.2 mmol) was added lithium chloride (366 mg, 8.63 mmol) and the suspension was stirred for 1 h at rt and then cooled to 0° C. 5-Bromo-2-(trifluoromethyl)pyridine (1.95 g, 8.63 mmol) was dissolved in THF (2.3 ml) and the solution was added dropwise, whilst the internal temperature was kept below 25° C. Subsequently, the mixture was stirred for 1 h at rt and then added dropwise to a solution of tetrahydro-2H-pyran-4-carbaldehyde (5.00 g, 43.8 mmol) in THF (90 ml) while cooling with ice. After addition was complete, the reaction mixture was warmed to rt and stirred for 1.5 h, then cooled with ice and satd. ammonium chloride solution (90 ml) was added. The mixture was diluted with water (30 ml) and ethyl acetate (30 ml). The aqeuous layer was extracted with ethyl acetate (100 ml). The combined organic layers were dried over sodium sulfate and the solvent was removed in vacuo. The residue was purified by column chromatography (in two portions; Biotage® SNAP Ultra 100 g cartridge, eluent: cyclohexane/ethyl acetate gradient 100:0 to 40:60) to yield 8.65 g (99% purity, 75% yield) of the title compound.

GC-MS (GC-MS method 2): $R_t$=6.39 min; MS (ESIpos): m/z=261 $[M]^+$ $^1$H-NMR (600 MHz, DMSO-$d_6$) δ [ppm]: 1.11-1.16 (m, 1H), 1.25-1.36 (m, 2H), 1.58-1.64 (m, 1H), 1.74-1.82 (m, 1H), 3.19 (td, 1H), 3.22 (td, 1H), 3.79 (dd, 1H), 3.85 (dd, 1H), 4.49 (dd, 1H), 5.57 (d, 1H), 7.86 (d, 1H), 7.98 (dd, 1H), 8.69 (s, 1H).

Intermediate I-96

5-{Tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (mixture of enantiomers)

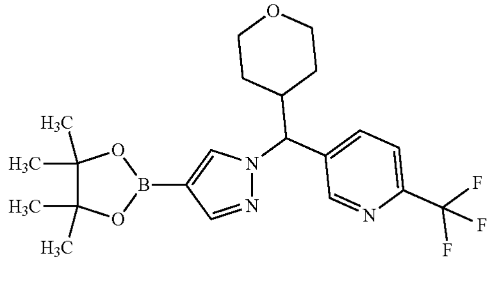 [SMILES: CC1(C)OB(c2cnn(C(c3ccc(C(F)(F)F)nc3)C3CCOCC3)c2)OC1(C)C]

DIAD (6.0 ml, 30 mmol) and triphenylphosphine (7.94 g, 30.3 mmol) were dissolved in THF (35 ml) and cooled to 0° C. A solution of tetrahydro-2H-pyran-4-yl[6-(trifluoromethyl)pyridin-3-yl]methanol (5.80 g, 22.2 mmol) in THF (35 ml) was added and subsequently a solution of 4-(4,4,5,5-tetramethyl-1,3,2-dioxaborolan-2-yl)-1H-pyrazole (3.92 g, 20.2 mmol) in THF (35 ml). The mixture was stirred at rt overnight. It was then diluted with ethyl acetate and washed with water and brine. The organic layer was dried over sodium sulfate and the solvent was removed in vacuo. Diethyl ether (100 ml) was added to the residue and the solids were removed by filtration. The filtrate was concentrated in vacuo, triturated with diisopropyl ether (70 ml), and the precipitate was removed by filtration. The filtrate was concentrated and purified by column chromatography (in 3 portions, Biotage® SNAP Ultra 50 g and 100 g cartridges, eluent: cyclohexane/ethyl acetate gradient 9:1 to 1:1) to yield 5.50 g (75% purity, 47% yield) of the title compound.

LC-MS (method 1): $R_t$=2.09 min; MS (ESIpos): m/z=438 $[M+H]^+$ $^1$H-NMR (400 MHz, DMSO-$d_6$) δ [ppm]: 0.98-1.29 (m, 4H), 1.23 (d, 12H), 2.69-2.81 (m, 1H), 3.24 (m, 2H), 3.75-3.85 (m, 2H), 5.42 (d, 1H), 7.68 (s, 1H), 7.93 (d, 1H), 8.16 (s, 1H), 8.28 (dd, 1H), 8.92 (d, 1H).

Intermediate I-97 tert-Butyl 4-{hydroxy[6-(trifluoromethyl)pyridin-3-yl]methyl}piperidine-1-carboxylate (mixture of enantiomers)

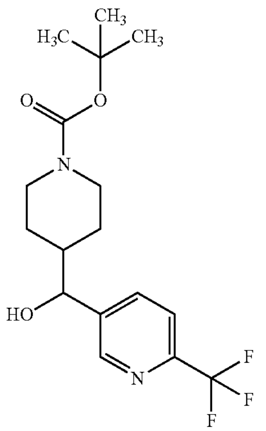 [SMILES: CC(C)(C)OC(=O)N1CCC(C(O)c2ccc(C(F)(F)F)nc2)CC1]

To a solution of isopropylmagnesium chloride in THF (4.1 ml, 2.0 M, 8.2 mmol) was added lithium chloride (366 mg, 8.63 mmol) and the suspension was stirred for 1 h at rt and then cooled with a water ice bath. 5-Bromo-2-(trifluoromethyl)pyridine (1.95 g, 8.63 mmol) was dissolved in THF (2.3 ml) and added dropwise (inner reaction temperature below 25° C.). Stirring was continued for 1 h at rt, the mixture was then added dropwise to an ice cold solution of tert-butyl 4-formylpiperidine-1-carboxylate (1.97 g, 9.23 mmol) in THF (20 ml). The reaction mixture was warmed to rt and stirred for 1.5 h. Satd. aqueous ammonium chloride solution (20 ml) was added under ice cooling, then it was extracted with ethyl acetate (100 ml). The organic layer was washed 10 with water (50 ml) and brine and filtered through a hydrophobic phase separation filter. The solvent was removed in vacuo and the residue was purified by column chromatography (Biotage® SNAP Ultra 50 g cartridge, eluent: cyclohexane/ethyl acetate gradient 1:0 to 1:1) to yield 1.72 g (100% purity, 52% yield) of the title compound.

LC-MS (method 2): $R_t$=0.98 min; MS (ESIpos): m/z=721 [2M+H].

$^1$H-NMR (600 MHz, $CDCl_3$) S [ppm]: 1.18-1.38 (m, 3H), 1.44 (s, 9H), 1.73-1.81 (m, 1H), 1.81-1.88 (m, 1H), 2.44 (d, 1H), 2.56-2.69 (m, 2H), 4.02-4.24 (m, 2H), 4.59 (dd, 1H), 7.68 (d, 1H), 7.85 (br dd, 1H), 8.64 (d, 1H).

Intermediate I-98 tert-Butyl 4-{[4-(4,4,5,5-tetramethyl-1,3,2-dioxaborolan-2-yl)-1H-pyrazol-1-yl][6-(trifluoromethyl)pyridin-3-yl]methyl}piperidine-1-carboxylate (mixture of enantiomers)

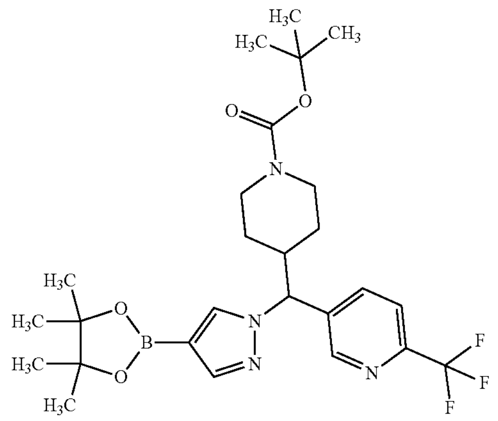 [SMILES: CC(C)(C)OC(=O)N1CCC(C(c2ccc(C(F)(F)F)nc2)n2cc(B3OC(C)(C)C(C)(C)O3)cn2)CC1]

A solution of DIAD (1.3 ml, 6.5 mmol) and triphenylphosphine (1.71 g, 6.51 mmol) in THF (7.6 ml) was cooled to 0° C. and a solution of tert-butyl 4-{hydroxy[6-(trifluoromethyl)pyridin-3-yl]methyl}piperidine-1-carboxylate (1.72 g, 4.77 mmol) in THF (7.6 ml) was added. 4-(4,4,5,5-tetramethyl-1,3,2-dioxaborolan-2-yl)-1H-pyrazole (842 mg, 4.34 mmol) was dissolved in THF (7.6 ml) and added to the reaction mixture which was then stirred at rt overnight. Water (2 ml) was added and the mixture was concentrated in vacuo. The residue was purified by column chromatography (Biotage® SNAP KP-NH 110 g cartridge, eluent: cyclohexane/ethyl acetate gradient 100:0 to 70:30, then ethyl acetate/methanol 90:10). The product was further purified by preparative HPLC (Chromatorex C18, 10 μm, 125×30 mm; eluent: water (0.1% formic acid)/acetonitrile gradient 90:10 to 5:95) to yield 792 mg (100% purity, 34% yield) of the title compound.

LC-MS (method 1): $R_t$=2.45 min; MS (ESIpos): m/z=537 $[M+H]^+$ $^1$H-NMR (400 MHz, DMSO-$d_6$) δ [ppm]: 1.00-1.20 (m, 3H), 1.23 (s, 12H), 1.37 (s, 9H), 2.58-2.76 (m, 4H), 3.81-3.96 (m, 2H), 5.43 (d, 1H), 7.69 (s, 1H), 7.93 (d, 1H), 8.14 (s, 1H), 8.27 (dd, 1H), 8.91 (d, 1H).

Intermediate I-99

1-[6-(Trifluoromethoxy)pyridin-3-yl]propan-1-ol (mixture of enantiomers)

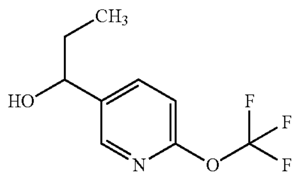

To a solution of 6-(trifluoromethoxy)nicotinaldehyde [CAS-RN 1361849-85-5](2.70 g, 13.6 mmol) in dry tetrahydrofuran (40 ml) was added at 0° C. ethyl magnesium bromide (9.04 ml, 27.1 mmol, 3 M in diethyl ether). After stirring at rt for 2 h, satd. aq. ammonium chloride solution (50 ml) was added to the reaction mixture and the solid was filtered off. The filtrate was extracted three times with ethyl acetate (80 ml each). The combined organic layers were washed with brine (120 ml) and dried over sodium sulfate. The solvent was evaporated under reduced pressure and the residue was purified by column chromatography on silica gel (120 g, eluent: petroleum ether/ethyl acetate 4:1) to give 2.40 g (98% purity, 78% yield) of the title compound.

LC-MS (method 16): $R_t$=1.05 min; MS (ESIpos): m/z=222 $(M+H)^+$ $^1$H-NMR (300 MHz, DMSO-$d_6$) δ [ppm]: 0.84 (t, 3H), 1.60-1.70 (m, 2H), 4.54-4.60 (m, 1H), 5.40 (d, 1H), 7.26 (d, 1H), 7.94-7.97 (m, 1H), 8.29 (s, 1H).

Intermediate I-100

5-{1-[4-(4,4,5,5-Tetramethyl-1,3,2-dioxaborolan-2-yl)-1H-pyrazol-1-yl]propyl}-2-(trifluoromethoxy) pyridine (mixture of enantiomers)

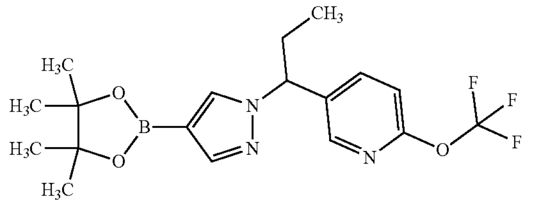 [SMILES: CCC(c1ccc(OC(F)(F)F)nc1)n1cc(B2OC(C)(C)C(C)(C)O2)cn1]

To a solution of 4-(4,4,5,5-tetramethyl-1,3,2-dioxaborolan-2-yl)-1H-pyrazole (2.48 g, 12.8 mmol) in tetrahydrofuran (60 ml) were added 1-[6-(trifluoromethoxy)pyridin-3-yl]propan-1-ol (2.40, 10.6 mmol) and triphenylphosphine (8.37 g, 31.9 mmol). A solution of DBAD (7.35 g, 31.9 mmol)-in tetrahydrofuran (20 ml) was added within 2 min at rt. After stirring for 30 min under reflux, the reaction mixture was cooled to rt and concentrated under reduced pressure. The crude product was purified by flash column chromatography (Column: C18, 330 g; eluent A: water, eluent B: acetonitrile; gradient: 20% B to 60% B in 30 min, 220/254 nm). The fractions containing the desired products were combined and concentrated to give 2.58 g (98% purity, 60% yield) of the title compound.

LC-MS (method 24): $R_t$=2.00 min; MS (ESIpos): m/z=398 $(M+H)^+$ $^1$H-NMR (400 MHz, DMSQ-$d_6$) δ [ppm]: 0.73-0.80 (m, 3H), 1.23 (s, 12H), 2.07-2.20 (m, 1H), 2.30-2.44 (m, 1H), 5.49 (dd, 1H), 7.27 (d, 1H), 7.65 (s, 1H), 8.02 (dd, 1H), 8.18 (s, 1H), 8.37 (d, 1H).

Intermediate I-101

6-(2,2,2-Trifluoroethoxy)pyridine-3-carbonyl chloride

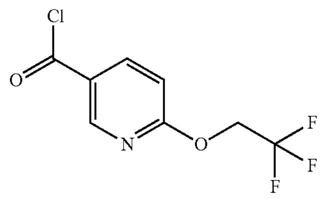 [SMILES: O=C(Cl)c1ccc(OCC(F)(F)F)nc1]

To a solution of 6-(2,2,2-trifluoroethoxy)pyridine-3-carboxylic acid [CAS-RN 175204-90-7](2.00 g, 9.04 mmol) in dry dichloromethane (20 ml) and a catalytic amount of dimethylformamid at 0° C. was slowly added dropwise oxalyl chloride (840 pl, 9.9 mmol). The reaction was stirred for 3 h at rt. The reaction was concentrated under reduced pressure to give the title compound which was directly used in the next step.

Intermediate I-102

N-Methoxy-N-methyl-6-(2,2,2-trifluoroethoxy)pyridine-3-carboxamide

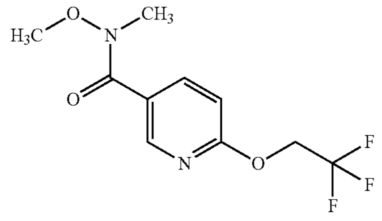 [SMILES: CON(C)C(=O)c1ccc(OCC(F)(F)F)nc1]

To a solution of 6-(2,2,2-trifluoroethoxy)pyridine-3-carbonyl (2.50 g, 9.06 mmol) and N-methoxymethanamine hydrochloride (1.33 g, 13.6 mmol) in dry tetrahydrofuran (30 ml), was slowly added N,N-diisopropylethylamine (7.9 ml, 45 mmol) and the reaction mixture was stirred at rt for 16 h. The reaction mixture was quenched with satd. aqueous solution of sodium bicarbonate and extracted three times with ethyl acetate. The combined organic layers were dried over sodium sulfate and concentrated to yield 1.87 g (95% purity, 74% yield) of the title compound. The product was used without further purification in the next step.

LC-MS (method 1): $R_t$=1.55 min; MS (ESIpos): m/z=265 $[M+H]^+$ $^1$H-NMR (600 MHz, DMSO-$d_6$) δ [ppm]: 3.28 (s, 3H), 3.57 (s, 3H), 5.06 (q, 2H), 7.06 (d, 1H), 8.06 (dd, 1H), 8.50 (d, 1H).

Intermediate I-103

1-[6-(2,2,2-Trifluoroethoxy)pyridin-3-yl]propan-1-one

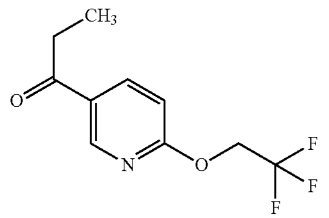 [SMILES: CCC(=O)c1ccc(OCC(F)(F)F)nc1]

To a solution of N-methoxy-N-methyl-6-(2,2,2-trifluoroethoxy)pyridine-3-carboxamide (6.06 g, 22.9 mmol) in dry diethyl ether (100 ml) at 0° C. was added dropwise a solution of ethylmagnesim bromide (9.2 ml, 3.0 M in diethyl ether, 28 mmol). The reaction mixture was stirred at rt for 12 h and then quenched with 1M hydrochloric acid. The reaction mixture was extracted twice with diethyl ether, and the combined organic layers were washed with brine, dried over sodium sulfate 20 and concentrated in vacuo. 5.28 g (100% purity, 99% yield) of the title compound was obtained and used without further purification.

LC-MS (method 1): $R_t$=1.88 min; MS (ESIpos): m/z=234 $[M+H]^+$ $^1$H-NMR (400 MHz, DMSO-$d_6$) δ [ppm]: 0.88 (t, 3H), 3.05 (q, 2H), 5.10 (q, 2H), 7.11 (d, 1H), 8.28 (dd, 1H), 8.85 (d, 1H).

Intermediate I-104

1-[6-(2,2,2-Trifluoroethoxy)pyridin-3-yl]propan-1-ol (mixture of enantiomers)

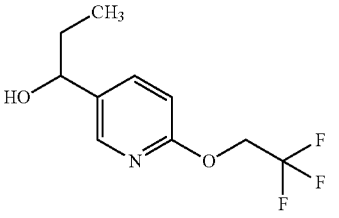 [SMILES: CCC(O)c1ccc(OCC(F)(F)F)nc1]

To a solution of 1-[6-(2,2,2-trifluoroethoxy)pyridin-3-yl]propan-1-one (5.28 g, 22.6 mmol) in dry tetrahydrofuran (98 ml) was added portionwise sodium tetrahydroborate (857 mg, 22.6 mmol) and the reaction mixture was stirred at rt for 5 h. The reaction mixture was quenched with satd. aqueous solution of ammonium chloride and extracted twice with ethyl acetate. The combined organic layers were dried over sodium sulfate and concentrated to yield 5.39 g (89% purity, 90% yield) of the title compound as a racemic mixture. The product was used without further purification in the next step.

LC-MS (method 1): $R_t$=1.64 min; MS (ESIpos): m/z=236 $[M+H]^+$ $^1$H-NMR (400 MHz, DMSO-$d_6$) δ [ppm]: 0.81 (t, 3H), 1.54-1.80 (m, 2H), 4.42-4.54 (m, 1H), 4.92-5.02 (m, 2H), 5.22 (d, 1H), 6.93 (d, 1H), 7.74 (dd, 1H), 8.10 (d, 1H).

Intermediate I-105

5-{1-[4-(4,4,5,5-tetramethyl-1,3,2-dioxaborolan-2-yl)-1H-pyrazol-1-yl]propyl}-2-(2,2,2-trifluoroethoxy)pyridine (mixture of enantiomers)

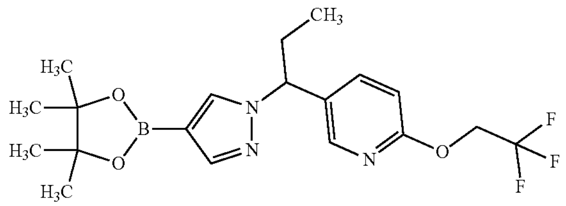 [SMILES: CCC(c1ccc(OCC(F)(F)F)nc1)n1cc(B2OC(C)(C)C(C)(C)O2)cn1]

DBAD (785 mg, 3.41 mmol) and triphenylphosphine (895 mg, 3.41 mmol) were stirred at 0° C. in dry tetrahydrofuran (4.5 ml) for 15 min. Then 4-(4,4,5,5-tetramethyl-1,3,2-dioxaborolan-2-yl)-1H-pyrazole (441 mg, 2.27 mmol) and 1-[6-(2,2,2-trifluoroethoxy)pyridin-3-yl]propan-1-ol (802 mg, 3.41 mmol) as a solution in dry tetrahydrofuran (4.5 ml) were slowly added. The reaction mixture was stirred at rt for 12 h and was then concentrated in vacuo. The crude product was purified directly by column chromatography (Biotage® SNAP Ultra 50 g cartridge, eluent: dichloromethane-methanol 98:2) and then by preparative HPLC to yield 326 mg (92% purity, 32% yield) of the title compound as a racemic mixture.

LC-MS (method 1): $R_t$=2.33 min; MS (ESIpos): m/z=412 $[M+H]^+$ $^1$H-NMR (600 MHz, DMSO-$d_6$) δ [ppm]: 0.76 (t, 3H), 1.24 (s, 12H), 2.11 (td, 1H), 2.35 (ddd, 1H), 4.91-5.01 (m, 2H), 5.39 (dd, 1H), 6.96 (d, 1H), 7.62 (s, 1H), 7.72-7.89 (m, 1H), 8.12 (s, 1H), 8.20 (s, 1H), 8.58 (s, 1H).

Intermediate I-106

2-Methyl-1-[6-(2,2,2-trifluoroethoxy)pyridin-3-yl]propan-1-one

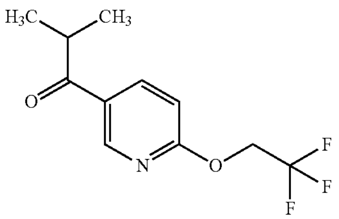 [SMILES: CC(C)C(=O)c1ccc(OCC(F)(F)F)nc1]

Under argon atmosphere, to a solution of N-methoxy-N-methyl-6-(2,2,2-trifluoroethoxy)pyridine-3-carboxamide (4.9 ml, 86% purity, 10 mmol) at 0° C. in dry diethyl ether (50 ml) was added dropwise a solution of isopropylmagnesium chloride (5.1 ml, 2.0 M in diethyl ether, 10 mmol). The reaction mixture was stirred at rt for 12 h. Isopropylmagnesium chloride (3.1 ml, 2.0 M in diethyl ether, 6.2 mmol) was further added and stirring was continued for 24 h. It was quenched with water and the mixture was extracted twice with ethyl acetate. The combined organic layers were washed with satd. aqueous solution of sodium bicarbonate, dried over sodium sulfate and concentrated in vacuo. The residue was purified by silica gel column chromatography (eluent: cyclohexane/ethyl acetate 9:1) to yield 1.14 g (96% purity, 43% yield) of the title compound.

LC-MS (method 1): $R_t$=2.01 min; MS (ESIpos): m/z=248 $[M+H]^+$ $^1$H-NMR (500 MHz, DMSO-$d_6$) δ [ppm]: 1.11 (d, 6H), 3.64 (hept, 1H), 5.10 (q, 2H), 7.12 (d, 1H), 8.30 (dd, 1H), 8.86 (d, 1H).

Intermediate I-107

2-Methyl-1-[6-(2,2,2-trifluoroethoxy)pyridin-3-yl]propan-1-ol (mixture of enantiomers)

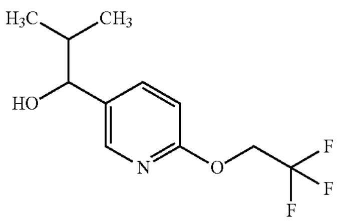 [SMILES: CC(C)C(O)c1ccc(OCC(F)(F)F)nc1]

To a solution of 2-methyl-1-[6-(2,2,2-trifluoroethoxy)pyridin-3-yl]propan-1-one (1.14 g, 96% purity, 4.42 mmol) in dry tetrahydrofuran (15 ml) was added portionwise sodium tetrahydroborate (83.6 mg, 2.21 mmol) and the reaction mixture was stirred at rt for 12 h. It was quenched with satd. aqueous ammonium chloride solution and extracted three times with ethyl acetate. The combined organic layers were dried over sodium sulfate and concentrated in vacuo. The residue was purified by silica gel column chromatography (eluent: cyclohexane/ethyl acetate 9:1) to yield 714 mg (98% purity, 64% yield) of the title compound as a racemic mixture.

LC-MS (method 1): $R_t$=1.84 min; MS (ESIpos): m/z=250 $[M+H]^+$ $^1$H-NMR (600 MHz, DMSO-$d_6$) δ [ppm]: 0.73 (d, 3H), 0.86 (d, 3H), 1.76-1.85 (m, 1H), 4.27 (dd, 1H), 4.92-5.02 (m, 2H), 5.21 (d, 1H), 6.93 (d, 1H), 7.71 (dd, 1H), 8.07 (d, 1H).

Intermediate I-108

5-{2-Methyl-1-[4-(4,4,5,5-tetramethyl-1,3,2-dioxaborolan-2-yl)-1H-pyrazol-1-yl]propyl}-2-(2,2,2-trifluoroethoxy)pyridine (mixture of enantiomers)

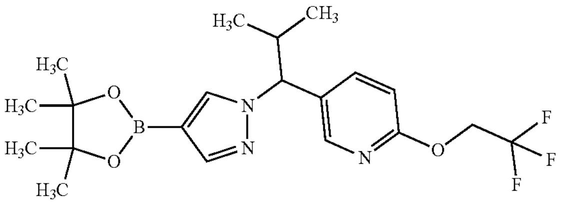 [SMILES: CC(C)C(c1ccc(OCC(F)(F)F)nc1)n1cc(B2OC(C)(C)C(C)(C)O2)cn1]

DBAD (878 mg, 3.81 mmol) and triphenylphosphine (1.00 g, 3.81 mmol) were stirred at 0° C. in dry tetrahydrofuran (6 ml) for 15 min. Then 4-(4,4,5,5-tetramethyl-1,3,2-dioxaborolan-2-yl)-1H-pyrazole (493 mg, 2.54 mmol) and 2-methyl-1-[6-(2,2,2-trifluoroethoxy)pyridin-3-yl]propan-1-ol (710 mg, 98% purity, 2.80 mmol) as a solution in dry THF (2 ml) were slowly added. The reaction mixture was stirred at rt for 12 h. The reaction mixture was then concentrated in vacuo and the residue was purified directly by preparative HPLC to yield 399 mg (91% purity, 33% yield) of the title compound as a racemic mixture.

LC-MS (method 1): $R_t$=2.41 min; MS (ESIpos): m/z=426 $[M+H]^+$ $^1$H-NMR (600 MHz, DMSO-$d_6$) δ [ppm]: 0.72 (d, 3H), 0.76 (d, 3H), 1.23 (s, 12H), 2.66-2.76 (m, 1H), 4.96 (q, 2H), 5.06 (d, 1H), 6.98 (d, 1H), 7.62 (s, 1H), 7.98-8.07 (m, 1H), 8.12 (s, 1H), 8.30 (d, 1H).

Intermediate I-109

Cyclopropyl[6-(2,2,2-trifluoroethoxy)pyridin-3-yl]methanone

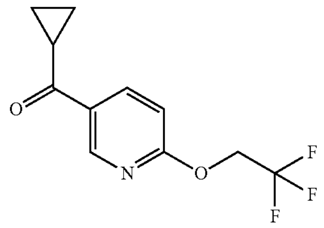 [SMILES: O=C(c1ccc(OCC(F)(F)F)nc1)C1CC1]

To a solution of N-methoxy-N-methyl-6-(2,2,2-trifluoroethoxy)pyridine-3-carboxamide (4.9 ml, 86% purity, 10 mmol) in dry diethyl ether (45 ml) at 0° C. was added dropwise a solution of cyclopropylmagnesium chloride in THF (21 ml, 0.50 M, 10 mmol). The reaction mixture was stirred at rt for 12 h. Further cyclopropylmagnesium chloride solution (8.2 ml, 0.50 M in THF, 4.1 mmol) was added and stirring was continued for 24 h. Then the reaction mixture was quenched with water and extracted twice with ethyl acetate. The combined organic layers were washed with satd. aqueous sodium bicarbonate solution, dried over sodium sulfate and concentrated in vacuo.

The residue was purified by silica gel column chromatography (eluent: cyclohexane/ethyl acetate 9:1) to yield 1.90 g (100% purity, 75% yield) of the title compound.

LC-MS (method 1): $R_t$=1.89 min; MS (ESIpos): m/z=246 $[M+H]^+$ $^1$H-NMR (500 MHz, DMSO-$d_6$) δ [ppm]: 1.06 (d, 4H), 2.89-2.95 (m, 1H), 5.11 (q, 2H), 7.13 (d, 1H), 8.35 (dd, 1H), 8.98 (d, 1H).

Intermediate I-110

Cyclopropyl[6-(2,2,2-trifluoroethoxy)pyridin-3-yl]methanol (mixture of enantiomers)

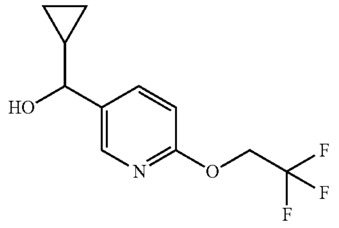 [SMILES: OC(c1ccc(OCC(F)(F)F)nc1)C1CC1]

To a solution of cyclopropyl[6-(2,2,2-trifluoroethoxy)pyridin-3-yl]methanone (1.89 g, 100% purity, 7.68 mmol) in dry tetrahydrofuran (20 ml) was added portionwise sodium tetrahydroborate (145 mg, 3.84 mmol) and the reaction mixture was stirred at rt for 12 h. Further sodium tetrahydroborate (145 mg, 3.84 mmol) was added and stirring was continued for 24 h. A third portion of sodium tetrahydroborate (145 mg, 3.84 mmol) was added followed by an additional 24 stirring period. The reaction mixture was quenched with satd. aqueous ammonium chloride solution and extracted three times with ethyl acetate. The combined organic layers were dried over sodium sulfate and concentrated in vacuo. The residue was purified by silica gel column chromatography (eluent: cyclohexane/ethyl acetate 7:3) to yield 691 mg (100% purity, 36% yield) of the title compound as a racemic mixture.

LC-MS (method 2): $R_t$=0.88 min; MS (ESIpos): m/z=248 $[M+H]^+$ $^1$H-NMR (600 MHz, DMSO-$d_6$) δ [ppm]: 0.29-0.34 (m, 1H), 0.37-0.44 (m, 2H), 0.44-0.50 (m, 1H), 1.01-1.07 (m, 1H), 2.54 (s, 2H), 3.98 (dd, 1H), 4.97 (q, 2H), 5.28 (d, 1H), 6.94 (d, 1H), 7.81 (dd, 1H), 8.15 (d, 1H).

Intermediate I-111

5-{Cyclopropyl[4-(4,4,5,5-tetramethyl-1,3,2-dioxaborolan-2-yl)-1H-pyrazol-1-yl]methyl}-2-(2,2,2-trifluoroethoxy)pyridine (mixture of enantiomers)

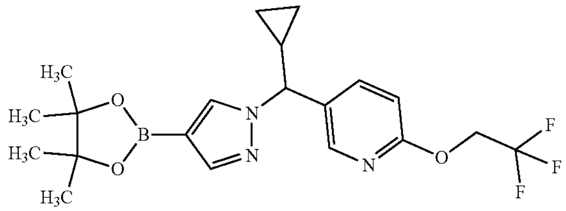 [SMILES: CC1(C)OB(c2cnn(C(c3ccc(OCC(F)(F)F)nc3)C3CC3)c2)OC1(C)C]

Di-isopropyl azodicarboxylate (640 1 μl, 3.2 mmol) and triphenylphosphine (977 mg, 3.73 mmol) were stirred at 0° C. in dry tetrahydrofuran (6 ml) for 15 min. Then 4-(4,4,5,5-tetramethyl-1,3,2-dioxaborolan-2-yl)-1H-pyrazole (482 mg, 2.48 mmol) and cyclopropyl[6-(2,2,2-trifluoroethoxy)pyridin-3-yl]methanol (676 mg, 2.73 mmol) as a solution in dry tetrahydrofuran (2 ml) were slowly added. The reaction mixture was stirred at rt for 12 h. The mixture was then concentrated in vacuo and the residue was directly purified by HPLC to yield 265 mg (89% purity, 22% yield) of the title compound. 15 LC-MS (method 1): $R_t$=2.27 min; MS (ESIpos): m/z=424 $[M+H]^+$ $^1$H-NMR (500 MHz, DMSO-$d_6$) δ [ppm]: 0.33-0.48 (m, 2H), 0.61-0.70 (m, 2H), 1.06-1.19 (m, 1H), 1.25 (m, 12H), 1.83-1.87 (m, 1H), 4.74 (d, 1H), 4.97 (q, 2H), 6.96 (d, 1H), 7.61 (s, 1H), 7.77 (dd, 1H), 8.19 (br s, 2H), Intermediate I-112

1-(3,5-Difluoropyridin-4-yl)-2-methylpropan-1-ol (mixture of enantiomers)

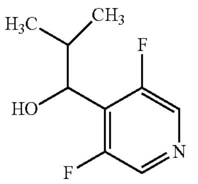

A solution of LDA in THF (9.1 ml, 2.0 M, 18 mmol) diluted with THF (30 ml) was cooled to −78° C. A solution of 3,5-difluoropyridine (1.50 g, 13.0 mmol) in THF (5 ml) was added dropwise and the mixture was stirred for 1 h at −78° C. Subsequently, 2-methylpropanal (1.8 ml, 20 mmol) was added and stirring was continued for 30 min. Then methanol and satd. aqueous ammonium chloride solution were added and the mixture was warmed to rt. It was diluted with dichloromethane and washed with satd. sodium bicarbonate solution. The organic layer was separated, concentrated in vacuo and purified by column chromatography (Biotage® SNAP Ultra 25 g cartridge, eluent: cyclohexane/ethyl acetate gradient 82:18 to 0:100) to yield 1.92 g (95% purity, 75% yield) of the title compound.

LC-MS (method 1): $R_t$=1.22 min; MS (ESIpos): m/z=188 $[M+H]^+$ $^1$H-NMR (500 MHz, DMSO-$d_6$) δ [ppm]: 0.69 (d, 3H), 1.04 (d, 3H), 2.03-2.13 (m, 1H), 4.51 (dd, 1H), 5.72 (d, 1H), 8.46 (s, 1H).

Intermediate I-113

3,5-Difluoro-4-{2-methyl-1-[4-(4,4,5,5-tetramethyl-1,3,2-dioxaborolan-2-yl)-1H-pyrazol-1-yl]propyl}pyridine (mixture of enantiomers)

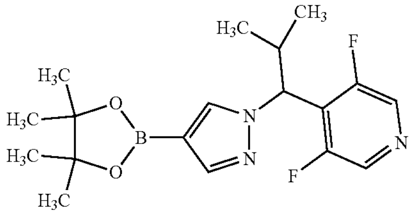 [SMILES: CC(C)C(c1c(F)cncc1F)n1cc(B2OC(C)(C)C(C)(C)O2)cn1]

A solution of 1-(3,5-difluoropyridin-4-yl)-2-methylpropan-1-ol (1.28 g, 95% purity, 6.49 mmol) and 2,6-dimethylpyridine (1.5 ml, 13 mmol) in dichloromethane (20 ml) was cooled to −10° C., 20 trifluoromethanesulfonic anhydride (1.2 ml, 7.1 mmol) was added dropwise and stirring was continued for 30 min. Then 4-(4;4,5,5-tetramethyl-1,3,2-dioxaborolan-2-yl)-1H-pyrazole (1.51 g, 7.79 mmol) was added. The mixture was heated to 40° C. and stirred for 2 h. It was the diluted with dichloromethane (10 ml) and water (10 ml). The aqueous layer was separated and extracted with dichloromethane (10 ml). The combined organic layers were filtered through a hydrophobic phase separation filter. The solvent was evaporated under reduced pressure and the residue was purified by column chromatography (Biotage®

SNAP Ultra 50 g cartridge, eluent: cyclohexane/ethyl acetate gradient 90:10 to 50:50) to yield 1.20 g (70% purity, 36% yield) of the title compound.

LC-MS (method 1): $R_t$=2.12 min; MS (ESIpos): m/z=364 $[M+H]^+$ $^1$H-NMR (400 MHz, DMSO-$d_6$) δ [ppm]: 0.82 (d, 3H), 0.88 (d, 3H), 1.24 (s, 12H), 2.95-3.09 (m, 1H), 5.48 (d, 1H), 7.61 (s, 1H), 8.15 (s, 1H), 8.54 (s, 2H).

Intermediate I-114

1-[2-(Trifluoromethyl)pyridin-4-yl]propan-1-ol (mixture of enantiomers)

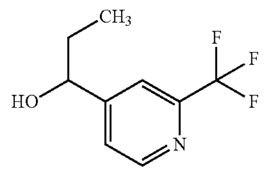

To a solution of a 4-bromo-2-(trifluoromethyl)pyridine [CAS-RN 887583-90-6](500 mg, 2.21 mmol) in freshly distilled tetrahydrofuran (5 ml) at 0° C. was added dropwise a solution of isopropylmagnesium chloride-lithium chloride complex (3.40 ml, 1.3 M in diethyl ether, 4.43 mmol). After stirring at 0° C. for 0.5 h, propionaldehyde (257 mg, 4.43 mmol) was added. The solution was warmed to rt and stirred for 2 h. Subsequently it was quenched with satd. ammonium chloride solution (20 ml) and extracted twice with ethyl acetate (50 ml each). The combined organic layers were washed twice with water (50 ml each) and dried over sodium sulfate. The solvent was evaporated under reduced pressure. The residue was purified by silica gel column chromatography (80 g, eluent: petroleum ether-ethyl acetate, 5:1) to yield 280 mg (90% purity, 56% yield) of the title compound.

$^1$H-NMR (400 MHz, DMSO-$d_6$) δ [ppm]: 0.85 (t, 3H), 1.53-1.75 (m, 2H), 4.64 (dt, 1H), 5.57 (d, 1H), 7.65 (d, 11H), 7.82 (s, 1H), 8.69 (d, 1H).

Intermediate I-115

4-{1-[4-(4,4,5,5-Tetramethyl-1,3,2-dioxaborolan-2-yl)-1H-pyrazol-1-yl]propyl}-2-(trifluoromethyl)pyridine (mixture of enantiomers)

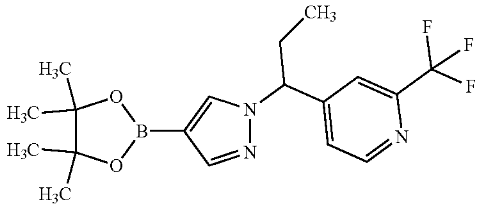 [SMILES: CCC(c1ccnc(C(F)(F)F)c1)n1cc(B2OC(C)(C)C(C)(C)O2)cn1]

Di-isopropylbutylazodicarboxylate (320 μl, 1.6 mmol) and triphenylphosphine (431 mg, 1.64 mmol) were stirred at 0° C. in dry tetrahydrofuran (5 ml) for 15 min. Then 4-(4,4,5,5-tetramethyl-1,3,2-dioxaborolan-2-yl)-1H-pyrazole (212 mg, 1.09 mmol) and 1-[2-(trifluoromethyl)pyridin-4-yl]propan-1-ol (337 mg, 1.64 mmol) as a solution in dry tetrahydrofuran (5 ml) were slowly added. The reaction mixture was stirred at rt for 12 h and was then concentrated. The residue was purified directly by column chromatography (Biotage® SNAP KP-NH 28 g cartridge, eluent: cyclohexane/ethyl acetate gradient 8:2 to 7:3) to yield 712 mg (46% purity, 78% yield) of the title compound as a racemic mixture which was used without further purification.

LC-MS (method 3): $R_t$=1.44 min; MS (ESIpos): m/z=382 $[M+H]^+$ $^1$H-NMR (600 MHz, DMSO-$d_6$) δ [ppm]: 0.776 (0.61), 0.778 (0.60), 0.788 (1.24), 0.790 (1.16), 0.799 (0.69), 0.841 (1.55), 0.844 (1.51), 0.853 (3.30), 0.856 (3.10), 0.866 (1.65), 0.868 (1.51), 1.079 (0.65), 1.082 (0.60), 1.158 (1.19), 1.165 (1.08), 1.185 (9.82), 1.195 (9.47), 1.226 (0.41), 1.257 (8.65), 1.280 (3.40), 1.283 (3.14), 1.369 (1.35), 1.372 (1.25), 1.380 (1.31), 1.383 (1.21), 1.397 (3.38), 1.400 (3.17), 1.612 (0.49), 1.622 (0.52), 1.624 (0.51), 1.686 (0.41), 1.698 (0.43), 3.345 (16.00), 3.348 (14.34), 4.647 (0.57), 4.652 (0.46), 4.657 (0.58), 4.773 (0.80), 4.783 (1.02), 4.792 (0.79), 5.577 (1.41), 5.580 (1.29), 5.585 (1.38), 5.587 (1.28), 7.613 (0.42), 7.656 (0.91), 7.665 (0.93), 7.717 (0.82), 7.719 (0.78), 7.826 (1.82), 7.834 (0.89), 8.220 (0.87), 8.222 (0.84), 8.697 (0.94), 8.705 (0.93), 8.735 (0.44), 8.743 (0.44), 8.882 (2.12).

Intermediate I-116

2-Methyl-1-[2-(trifluoromethyl)pyridin-4-yl]propan-1-ol (mixture of enantiomers)

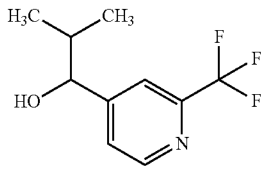

To a solution of 2-(trifluoromethyl)pyridine-4-carbaldehyde [CAS-RN 108338-20-1](756 mg, 4.32 mmol) in dry diethyl ether (12 ml) at 0° C. was slowly added a solution of isopropylmagnesium chloride in THF (2.6 ml, 2.0 M, 5.2 mmol). The reaction mixture was stirred at rt for 1 h. Satd. ammonium chloride solution was added and the mixture was diluted with water and ethyl acetate. The organic layer was separated and the aqueous layer was extracted with ethyl acetate. The combined organic layers were dried over sodium sulfate and concentrated. The residue was purified via column chromatography (Biotage® SNAP Ultra 25 g cartridge, eluent: cyclohexane/ethyl acetate gradient 8:2 to 7:3) to yield 215 mg (97% purity, 22% yield) of the title compound.

LC-MS (method 1): $R_t$=1.53 min; MS (ESIpos): m/z=220 $[M+H]^+$ $^1$H-NMR (600 MHz, DMSO-$d_6$) δ [ppm]: 0.77 (d, 3H), 0.84 (d, 3H), 1.89 (dd, 1H), 2.54 (s, 1H), 4.49 (t, 1H), 5.54 (d, 1H), 7.63 (d, 1H), 7.79 (s, 1H), 8.69 (d, 1H).

Intermediate 1-117

4-{2-Methyl-1-[4-(4,4,5,5-tetramethyl-1,3,2-dioxaborolan-2-yl)-1H-pyrazol-1-yl]propyl}-2-(trifluoromethyl)pyridine (mixture of enantiomers)

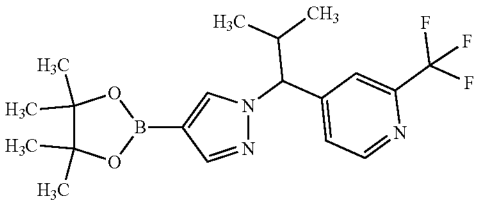 [SMILES: CC(C)C(c1ccnc(C(F)(F)F)c1)n1cc(B2OC(C)(C)C(C)(C)O2)cn1]

DBAD (226 mg, 981 mol) and triphenylphosphine (257 mg, 981 μmol) were stirred at 0° C. in dry tetrahydrofuran (4 ml) for 15 min. Then 4-(4,4,5,5-tetramethyl-1,3,2-dioxaborolan-2-yl)-1H-pyrazole (159 mg, 817 μmol) and 2-methyl-1-[2-(trifluoromethyl)pyridin-4-yl]propan-1-ol (215 mg, 981 μmol) as a solution in dry tetrahydrofuran (4 ml) were slowly added. The reaction mixture was stirred at rt for 12 h and then quenched with brine. The reaction mixture was concentrated in vacuo and the residue was purified directly by column chromatography (Biotage® SNAP KP-NH 28 g cartridge, eluent: cyclohexane/ethyl acetate gradient 8:2 to 7:3) to yield 286 mg (47% purity, 42% yield) of the title compound.

LC-MS (method 3): $R_t$=151.00 min; MS (ESIpos): m/z=396 $[M+H]^+$ $^1$H-NMR (500 MHz, DMSO-$d_6$) δ [ppm]: 0.749 (0.76), 0.756 (0.91), 0.765 (2.06), 0.779 (1.72), 0.833 (1.67), 0.847 (1.68), 1.235 (3.05), 1.275 (3.90), 1.390 (16.00), 1.398 (10.75), 1.580 (3.57), 4.494 (0.48), 5.531 (0.68), 5.540 (0.65), 7.687 (0.45), 7.785 (0.75), 8.166 (0.48), 8.574 (1.24), 8.687 (0.48), 8.696 (0.46).

Intermediate I-118

1-(2-Methoxypyridin-4-yl)-2-methylpropan-1-ol (mixture of enantiomers)

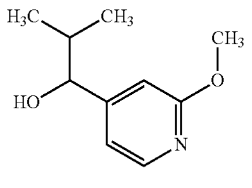

2-Methoxypyridine-4-carbaldehyde (6.00 g, 43.8 mmol) was dissolved in THF and cooled to 0° C.

A solution of isopropylmagnesium bromide in 2-methyltetrahydrofuran (18 ml, 2.9 M, 53 mmol) was added dropwise under cooling. After complete addition the mixture was further stirred at 0° C. for 1 h and subsequently warmed to rt. Stirring was continued for 3 h. Under cooling satd. aq. ammonium chloride solution (150 ml) was added, then diethyl ether (250 ml) and water (50 ml).

The organic layer was separated and washed with brine. It was dried over sodium sulfate and the solvent was evaporated. The residue was puried by column chromatography (Biotage® SNAP Ultra 50 g cartridge, eluent: cyclohexane/ethyl acetate gradient) to yield 1.93 g (96% purity, 23% yield) of the title compound.

GC-MS (GC-MS method 1): $R_t$=4.40 min; MS (ESIpos): m/z=181 $[M]^+$ $^1$H-NMR (500 MHz, DMSO-$d_6$) δ [ppm]: 0.79 (d, 3H), 0.81 (d, 3H), 1.77-1.87 (m, 1H), 3.83 (s, 3H), 4.27 (t, 1H), 5.28 (d, 1H), 6.70 (s, 1H), 6.90 (dd, 1H), 8.07 (d, 1H).

Intermediate I-119

2-Methoxy-4-{2-methyl-1-[4-(4,4,5,5-tetramethyl-1,3,2-dioxaborolan-2-yl)-1H-pyrazol-1-yl]propyl}pyridine (mixture of enantiomers)

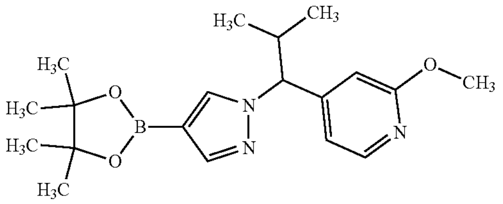

A solution of 4-(4,4,5,5-tetramethyl-1,3,2-dioxaborolan-2-yl)-1H-pyrazole (1.17 g, 6.03 mmol) and triphenyphosphine (2.06 g, 7.84 mmol) in 2-methyltetrahydrofuran (11 ml) was cooled to 0° C. DIAD (1.5 ml, 7.8 mmol) was added dropwise and the mixture was stirred for 15 min before 1-(2-methoxypyridin-4-yl)-2-methylpropan-1-ol (1.48 g, 96% purity, 7.84 mmol) was added dropwise as a solution in 2-methyltetrahydrofuran (6.0 ml). Stirring was continued for 30 min at 0° C., then at rt overnight. The solvent was evaporated in vacuo and the residue was purified by column chromatography (Biotage® SNAP Ultra 50 g cartridge, eluent: cyclohexane/ethyl acetate gradient) to yield 680 mg (88% purity, 28% yield) of the title compound.

LC-MS (method 2): $R_t$=1.13 min; MS (ESIpos): m/z=358 $[M+H]^+$ $^1$H-NMR (500 MHz, DMSO-$d_6$) δ [ppm]: 0.73 (d, 3H), 0.77 (d, 3H), 1.23 (s, 12H), 2.66-2.78 (m, 1H), 3.82 (s, 3H), 5.01 (d, 1H), 6.92 (s, 1H), 7.12 (dd, 111), 7.63 (s, 1H), 8.12 (d, 1H), 8.13 (s, 1H).

Intermediate I-120

1-(4,4-Difluorocyclohexyl)-4-(4,4,5,5-tetramethyl-1,3,2-dioxaborolan-2-yl)-1H-pyrazole

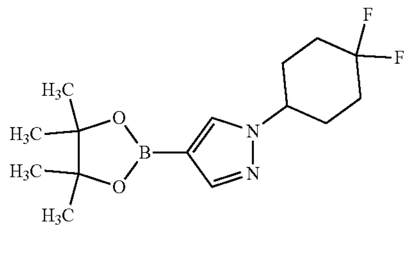 [SMILES: CC1(C)OB(c2cnn(C3CCC(F)(F)CC3)c2)OC1(C)C]

To a solution of 4-(4,4,5,5-tetramethyl-1,3,2-dioxaborolan-2-yl)-1H-pyrazole (8.55 g. 44.07 mmol) in toluene (60 ml) were added 4,4-difluorocyclohexanol [CAS-RN 22419-35-8](3.00 g, 22.04 mmol) and (tributylphosphoranylidene) acetonitrile (7.97 g, 33.05 mmol). The resulting mixture was irradiated for 3 h at 160° C. in a microwave reactor. After cooling down to rt, ethyl acetate (200 ml) was added. The mixture was washed twice with water (200 ml each) and brine (250 ml). The organic layer was dried over sodium sulfate and the solvent was evaporated under reduced pressure. The residue was purified by flash column (Column: C18,330 g; Mobile Phase A: Water, Mobile Phase B: Acetonitrile; Flow rate: 100 ml/min; Gradient: 30% B to 60% B in 25 min, 220/254 nm) to afford 2.20 g (99% purity, 31% yield) of the title compound.

LC-MS (method 25): $R_t$=1.72 min; MS (ESIpos): m/z=313 [M acid+H]$^+$ $^1$H-NMR (300 MHz, DMSO-$d_6$) δ [ppm]: 1.25 (s, 21H), 1.93-2.18 (m, 8H), 4.29-4.55 (m, 1H), 7.61 (s, 1H), 7.99 (s, 1H).

Intermediate I-121

4-[4-(4,4,5,5-Tetramethyl-1,3,2-dioxaborolan-2-yl)-1H-pyrazol-1-yl]piperidine hydrochloride

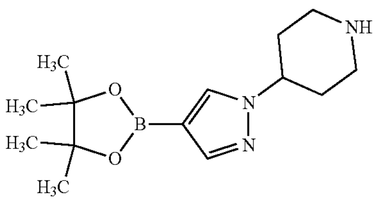

x HCl

To a solution of tert-butyl 4-[4-(4,4,5,5-tetramethyl-1,3,2-dioxaborolan-2-yl)-1H-pyrazol-1-yl]piperidine-1-carboxylate [CAS-RN 877399-74-1](1.00 g, 2.65 mmol) in 1,4-dioxane (8.0 ml) was added dropwise a solution of hydrochloric acid in 1,4-dioxane (10 ml, 4.0 M, 40 mmol), and the reaction mixture was stirred for 1 h at rt. The solution was concentrated under reduced pressure to yield 839 mg (100% purity, 100% yield) of the title compound.

LC-MS (method 4): $R_t$=1.56 min; MS (ESIpos): m/z=278 [M+H]$^+$ $^1$H-NMR (600 MHz, DMSO-$d_6$) δ [ppm]: 1.25 (s, 12H), 2.13-2.20 (m, 4H), 2.99-3.08 (m, 2H), 3.34-3.38 (m, 2H), 4.50-4.53 (m, 1H), 7.64 (s, 1H), 7.96 (s, 1H), 9.03 (br s, 2H).

Intermediate I-122

1-Ethyl-4-[4-(4,4,5,5-tetramethyl-1,3,2-dioxaborolan-2-yl)-1H-pyrazol-1-yl]piperidine

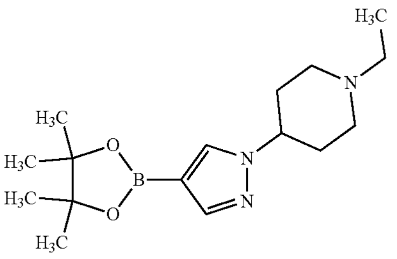 [SMILES: CCN1CCC(n2cc(B3OC(C)(C)C(C)(C)O3)cn2)CC1]

A solution of 4-[4-(4,4,5,5-tetramethyl-1,3,2-dioxaborolan-2-yl)-1H-pyrazol-1-yl]piperidine hydrochloride (150 mg, 478 μmol), acetaldehyde (40 μl, 720 μmol) and acetic acid (55 μl, 960 μmol) in methanol (5.0 ml) was stirred for 1 h at rt. Then sodium cyanoborohydride (21.0 mg, 335 μmol) was added and the reaction mixture was stirred at rt for 12 h. The reaction mixture was concentrated under reduced pressure and purified directly by HPLC to yield 37.5 mg (80% purity, 21% yield) of the title compound.

LC-MS (method 2): $R_t$=0.57 min; MS (ESIpos): m/z=306 [M+H]$^+$ $^1$H-NMR (500 MHz, DMSO-$d_6$) δ [ppm]: 1.25 (s, 12H), 2.15-2.37 (m, 5H), 2.94-3.15 (m, 4H), 3.25-3.42 (m, 2H), 3.46-3.60 (m, 2H), 4.38-4.60 (m, 1H), 7.64 (s, 1H), 7.76 (s, 1H).

Intermediate I-123

1-(Propan-2-yl)-4-[4-(4,4,5,5-tetramethyl-1,3,2-dioxaborolan-2-yl)-1H-pyrazol-1-yl]piperidine

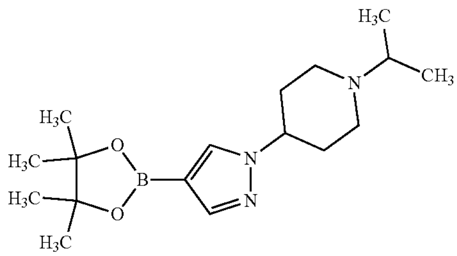 [SMILES: CC(C)N1CCC(n2cc(B3OC(C)(C)C(C)(C)O3)cn2)CC1]

A solution of 4-[4-(4,4,5,5-tetramethyl-1,3,2-dioxaborolan-2-yl)-1H-pyrazol-1-yl]piperidine hydrochloride (150 mg, 478 μmol), propan-2-one (53 sl, 720 mol) and acetic acid (55 1, 960 μmol) in methanol (5.0 ml) was stirred for 1 h at rt. Then sodium cyanoborohydride (21.0 mg, 335 μmol) was added and the reaction mixture was stirred at rt for 12 h. Further acetone (70 μl, 960 μmol) and sodium cyanoborohydride (9.02 mg, 143 μmol) were added, and the reaction mixture was stirred at rt for 19 h. Acetone (70 pl, 960 μmol) and sodium cyanoborohydride (9.02 mg, 143 μmol) were added a third time, and stirring was continued for 2 h at 50° C. The reaction mixture was quenched with water and extracted twice with ethyl acetate. The combined organic layers were washed with brine, and dried over sodium sulfate. The solvent was removed in vacuo. The residue was triturated with ethanol and the precipitate was filtered off. The filtrate was concentrated under reduced pressure to yield 125 mg (81% purity, 89% yield) of the title compound.

LC-MS (method 4): $R_t$=0.98 min; MS (ESIpos): m/z=238 [M+H]$^+$ $^1$H-NMR (500 MHz, DMSO-$d_6$) δ [ppm]: 1.013 (9.68), 1.025 (9.48), 1.244 (3.24), 1.365 (0.83), 1.869 (1.06), 1.907 (16.00), 1.956 (1.60), 2.006 (1.85), 2.028 (1.40), 2.071 (9.16), 2.361 (1.00), 2.784 (1.38), 2.825 (0.65), 2.944 (2.62), 3.333 (1.95), 4.117 (0.71), 6.220 (0.48), 7.417 (0.42), 7.619 (0.61), 7.651 (5.29), 7.679 (1.28), 7.746 (0.53), 7.750 (0.53), 7.860 (5.07), 7.870 (0.58).

Intermediate I-124

1-Benzyl-4-[4-(4,4,5,5-tetramethyl-1,3,2-dioxaborolan-2-yl)-1H-pyrazol-1-yl]piperidine

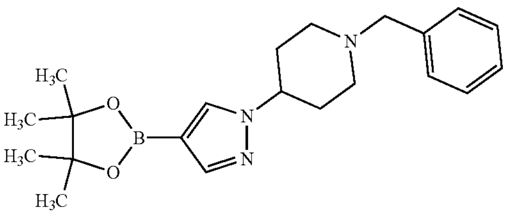 [SMILES: CC1(C)OB(c2cnn(C3CCN(Cc4ccccc4)CC3)c2)OC1(C)C]

DBAD (1.78 g, 7.73 mmol) and triphenylposphine (2.03 g, 7.73 mmol) were stirred at 0° C. in dry tetrahydrofuran (7.5 ml) for 15 min. Then 4-(4,4,5,5-tetramethyl-1,3,2-dioxaborolan-2-yl)-1H-pyrazole (1.00 g, 5.15 mmol) and 1-benzylpiperidin-4-ol (1.48 g, 7.73 mmol) as a solution in dry tetrahydrofuran (7.5 ml) were slowly added. The reaction mixture was stirred at rt for 12 h and then concentrated. The crude product was purified directly by preparative HPLC (gradient from 15% acetonitrile/85% water (+0.1% trifluoroacetic acid) to 55% acetonitrile/45% water (+0.1% trifluoroacetic acid) to yield 200 mg (48% purity, 6% yield) of the title compound.

LC-MS (method 1): $R_t$=0.54 min; MS (ESIpos): m/z=286 [M+H]J $^1$H-NMR (400 MHz, DMSO-$d_6$) δ [ppm]: 1.158 (2.13), 1.242 (16.00), 1.250 (6.57), 1.265 (4.35), 1.387 (1.68), 1.422 (0.50), 1.578 (2.08), 2.085 (12.96), 2.153 (0.86), 2.210 (1.50), 2.669 (0.55), 2.710 (0.47), 3.122 (0.80), 3.149 (0.92), 3.168 (2.34), 3.483 (1.22), 3.514 (1.14), 3.964 (0.45), 4.348 (1.82), 4.359 (1.71), 4.432 (0.71), 4.444 (0.67), 4.471 (0.58), 5.754 (0.46), 6.257 (0.40), 7.489 (2.07), 7.497 (2.63), 7.507 (3.81), 7.517 (3.37), 7.533 (1.86), 7.632 (1.28), 7.667 (0.45), 7.688 (1.16), 7.729 (0.58), 7.746 (1.11), 7.759 (0.75), 7.785 (0.80), 7.850 (1.19), 7.975 (1.35).

Intermediate I-125

1-(Oxetan-3-yl)-4-[4-(4,4,5,5-tetramethyl-1,3,2-dioxaborolan-2-yl)-1H-pyrazol-1-yl]piperidine

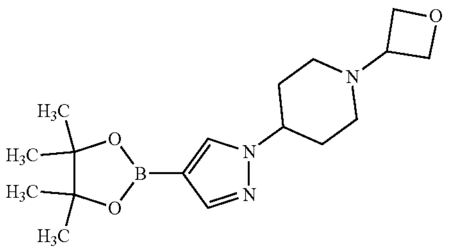

+

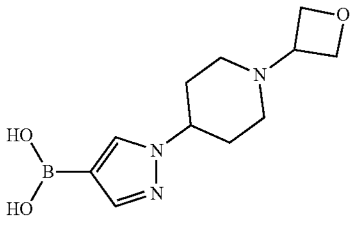

To a solution of 4-[4-(4,4,5,5-tetramethyl-1,3,2-dioxaborolan-2-yl)-1H-pyrazol-1-yl]piperidine hydrochloride (7.00 g. 20.76 mmol) in methanol (40 ml) was added oxetan-3-one [CAS-RN 6704-31-0](2.99 g, 41.51 mmol). The resulting mixture was stirred at rt for 0.5 h. Sodium cyanoborohydride (13.04 g. 207.56 mmol) was added in portions. After stirring at rt for 3 h, the reaction mixture was concentrated under reduced pressure. The residue was purified by preparative 15 HPLC (Column: C18, 330 g; Mobile Phase A: water, Mobile Phase B: acetonitrile; Gradient: 40% B to 80% B in 25 min, 220 and 254 nm). The fractions containing the desired product were combined and lyophilized to afford 2.10 g (95% purity, 29% yield) of the title compound (the ratio of pinacolate and boronic acid was 1:2).

LC-MS (method 25): $R_t$=0.55 min; MS (ESIpos): m/z=252 [M acid+H]$^+$

LC-MS (method 25): $R_t$=1.18 min; MS (ESIpos): m/z=334 [M ester+H]$^+$

Intermediate I-126

Oxetane-3-carbaldehyde

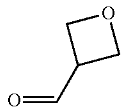

To a solution of oxetan-3-ylmethanol [CAS-RN 6246-06-6](0.70 g, 7.94 mmol) in dichloromethane (20 ml) at 0° C. was added Dess-Martin periodinane (2.97 g, 7.15 mmol). After stirring at rt for 2 h, the reaction mixture was quenched with satd. aq. sodium thiosulfate solution (50 ml). The solid was filtered off and the filtrate was extracted three times with dichloromethane (50 ml each). The combined organic layers were washed with brine (100 ml) and dried over anhydrous sodium sulfate. The solvent was evaporated under reduced pressure. The residue was purified by silica gel column chromatography (eluent: petroleum ether/ethyl acetate 1:3) to yield 0.50 g (90% purity, 66% yield) of the title compound.

$^1$H-NMR (300 MHz, DMSO-$d_6$) δ [ppm]: 3.82-3.93 (m, 1H), 4.64-4.73 (m, 4H), 9.83 (s, 1H).

Intermediate I-127

1-[(Oxetan-3-yl)methyl]-4-[4-(4,4,5,5-tetramethyl-1,3,2-dioxaborolan-2-yl)-1H-pyrazol-1-yl]piperidine

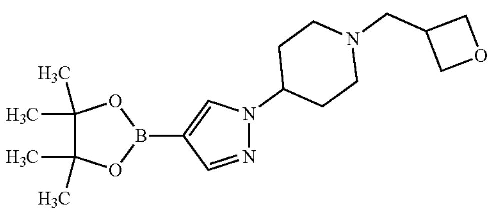

+

-continued

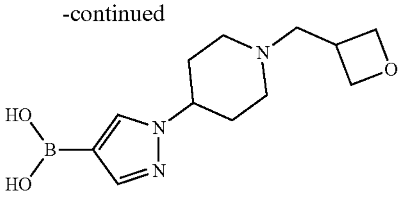

4-[4-(4,4,5,5-Tetramethyl-1,3,2-dioxaborolan-2-yl)-1H-pyrazol-1-yl]piperidine hydrochloride (137 mg, 0.39 mmol, 90% purity) was treated with 1 M potassium carbonate in methanol (5 ml). After stirring at rt for 3 h, water (15 ml) was added. The resulting solution was extracted three times with ethyl ether (15 ml each). The combined organic layers were dried over anhydrous sodium sulfate and the solvent was evaporated in vacuo. The residue was dissolved in methanol (5 ml) and oxetane-3-carbaldehyde (150 mg, 1.57 mmol, 90% purity) was added in two portions within 0.5 h. The reaction mixture was stirred at rt for 3 h. Then sodium cyanoborohydride (246 mg, 3.92 mmol) was added. The mixture was stirred for another 3 h, then quenched with satd. ammonium chloride solution (10 ml) and was then extracted three times with ethyl acetate (15 ml each). The organic layers were combined and dried over anhydrous sodium sulfate. The solvent was evaporated under reduced pressure. The residue was purified by preparative HPLC (Column: C18, 40 g; Mobile Phase A: water, Mobile Phase B: acetonitrile; Gradient: 40% B to 80% B in 25 min, 220 and 254 nm). The fractions containing the desired product were combined and lyophilized to afford 45 mg (80% purity, 26% yield) of the title compound. The ratio pinacol ester/boronic acid was 1:3).

LC-MS (method 25): $R_t$=0.20-0.36 min; MS (ESIpos): m/z=266 [M acid+H]$^+$

LC-MS (method 25): $R_t$=0.96 min; MS (ESIpos): m/z=348 [M ester+H]$^+$

Intermediate I-128 tert-Butyl 3-[(methanesulfonyl)oxy]azetidine-1-carboxylate

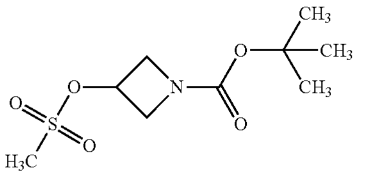 [SMILES: CC(C)(C)OC(=O)N1CC(OS(C)(=O)=O)C1]

To a solution of tert-butyl 3-hydroxyazetidine-1-carboxylate [CAS-RN 141699-55-0](1.00 g, 5.77 mmol) and N,N-diisopropylethylamine (1.5 ml, 8.7 mmol) in dry dichloromethane (29 ml) at 0° C. was added methanesulfonyl chloride (490 μl, 6.4 mmol) and the reaction mixture was stirred for 1 h at 0° C. Then it was quenched with water and extracted with dichloromethane. The combined organic layers were dried over sodium sulfate, filtered and concentrated under reduced pressure to yield 1.46 g (100% purity, 99% yield) of the title compound.

LC-MS (method 3): $R_t$=1.01 min; MS (ESIpos): m/z=196 [M+H-C4H8]$^+$ $^1$H-NMR (600 MHz, DMSO-$d_6$) δ [ppm]: 1.38 (s, 9H), 3.33 (s, 3H), 3.92 (br d, 2H), 4.17-4.27 (m, 2H), 5.25 (td, 1H).

Intermediate I-129 tert-Butyl 3-[4-(4,4,5,5-tetramethyl-1,3,2-dioxaborolan-2-yl)-1H-pyrazol-1-yl]azetidine-1-carboxylate

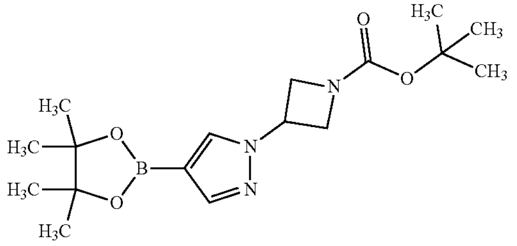 [SMILES: CC(C)(C)OC(=O)N1CC(n2cc(B3OC(C)(C)C(C)(C)O3)cn2)C1]

A solution of 4-(4,4,5,5-tetramethyl-1,3,2-dioxaborolan-2-yl)-1H-pyrazole (1.24 g, 6.37 mmol), tert-butyl 3-[(methanesulfonyl)oxy]azetidine-1-carboxylate (1.60 g, 6.37 mmol) and caesium carbonate (3.32 g, 10.2 mmol) in N,N-dimethylformamide (15 ml) was stirred at 100° C. under argon for 14 h. The reaction mixture is mixed with water and filtered. The filtrate was purified directly by HPLC to yield 513 mg (87% purity, 20% yield) of the title compound.

LC-MS (method 2): $R_t$=1.12 min; MS (ESIpos): m/z=350 [M+H]$^+$ $^1$H-NMR (600 MHz, DMSO-$d_6$) δ [ppm]: 1.25 (s, 12H), 1.40 (s, 9H), 4.06-4.15 (m, 2H), 4.22-4.31 (m, 2H), 5.19-5.25 (m, 1H), 7.71 (s, 1H), 8.07 (s, 1H).

Intermediate I-130

1-(1-Benzylazetidin-3-yl)-4-(4,4,5,5-tetramethyl-1,3,2-dioxaborolan-2-yl)-1H-pyrazole

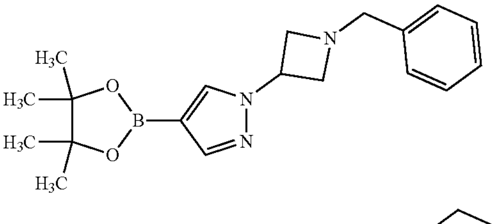

+

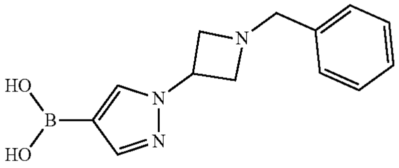

Triphenylphosphine (2.03 g, 7.73 mmol) and diisopropylazodicarboxylate (1.5 ml, 7.7 mmol) were stirred at 0° C. in dry tetrahydrofuran (7.5 ml) for 15 min. Then 4-(4,4,5,5-tetramethyl-1,3,2-dioxaborolan-2-yl)-1H-pyrazole (1.00 g, 5.15 mmol) and 1-benzylazetidin-3-ol (1.26 g, 7.73 mmol) as a solution in dry tetrahydrofuran (7.5 ml) were slowly added. The reaction mixture was stirred at rt for 12 h and was then concentrated under reduced pressure. The residue was purified directly by HPLC to yield 583 mg (14% yield) of the title compound as a mixture of 42.4% pinacol ester and 57.6% corresponding boronic acid.

LC-MS (method 1): $R_t$=1.29 min; MS (ESIpos): m/z=340 [M acid+H]$^+$ $^1$H-NMR (600 MHz, DMSO-$d_6$) δ [ppm]: 1.249 (16.00), 3.391 (1.15), 3.403 (1.95), 3.414 (1.21), 3.432 (0.68), 3.444 (0.41), 3.653 (0.64), 3.665 (2.25), 3.681 (7.55), 4.995 (0.92), 5.006 (1.38), 5.017 (1.11), 5.030 (0.64), 7.231 (0.56), 7.235 (0.76), 7.240 (0.97), 7.242 (0.98), 7.245 (1.31), 7.250 (1.07), 7.255 (1.05), 7.259 (0.63), 7.307 (3.56), 7.312 (10.55), 7.316 (4.07), 7.322 (3.55), 7.326 (0.83), 7.333 (0.41), 7.335 (0.53), 7.644 (1.28), 7.709 (4.51), 7.754 (10.94), 8.003 (4.67), 8.106 (1.36).

Intermediate I-131

1-(2,3-Dihydro-1H-inden-1-yl)-4-(4,4,5,5-tetramethyl-1,3,2-dioxaborolan-2-yl)-1H-pyrazole (mixture of enantiomers)

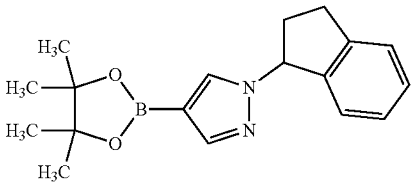 [SMILES: CC1(C)OB(c2cnn(C3CCc4ccccc43)c2)OC1(C)C]

To a mixture of 4-(4,4,5,5-tetramethyl-1,3,2-dioxaborolan-2-yl)-1H-pyrazole (1.00 g, 5.15 mmol) and 2,3-dihydro-1H-inden-1-ol (899 mg, 6.70 mmol) in toluene (10 ml) was added CMBP (1.62 g, 6.70 mmol) and it was heated to 80° C. overnight. The solvent was removed in vacuo and the residue was purified by column chromatography (Biotage® SNAP Ultra 50 g cartridge, eluent: cyclohexane/ethyl acetate gradient 96:4 to 80:20) and subsequently in a second chromatography (Biotage® SNAP Ultra C18 60 g cartridge, eluent: acetonitrile/water gradient 20:80 to 47:53) to yield 435 mg (100% purity, 27% yield) of the title compound.

LC-MS (method 2): $R_t$=1.11 min; MS (ESIpos): m/z=311 [M+H]$^+$ $^1$H-NMR (400 MHz, DMSO-$d_6$) δ [ppm]: 1.24 (s, 12H), 2.34-2.45 (m, 1H), 2.54-2.63 (m, 1H), 2.87-2.97 (m, 1H), 3.08-3.19 (m, 1H), 5.92 (dd, 1H), 7.05 (d, 1H), 7.14-7.20 (m, 1H), 7.27 (t, 1H), 7.31-7.36 (m, 1H), 7.59 (s, 1H), 7.89 (s, 1H).

Intermediate I-132

1-(3,4-Dihydro-2H-1-benzopyran-4-yl)-4-(4,4,5,5-tetramethyl-1,3,2-dioxaborolan-2-yl)-1H-pyrazole (mixture of enantiomers)

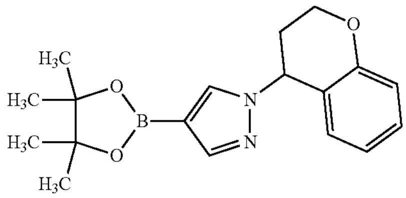 [SMILES: CC1(C)OB(c2cnn(C3CCOc4ccccc43)c2)OC1(C)C]

To a solution of 4-(4,4,5,5-tetramethyl-1,3,2-dioxaborolan-2-yl)-1H-pyrazole (100 mg, 515 mol) and 3,4-dihydro-2H-1-benzopyran-4-ol (101 mg, 670 mol) in toluene (1.0 ml) was added CMBP (180 µl, 670 µmol) and the mixture was stirred at rt for 2 h, then heated to 80° C. overnight. The solvent was removed in vacuo and the residue was purified by column chromatography (Biotage® SNAP Ultra 10 g cartridge, eluent: cyclohexane/ethyl acetate gradient 100:0 to 40:60) to yield 57.2 mg (90% purity, 31% yield) of the title compound.

LC-MS (method 1): $R_t$=2.06 min; MS (ESIpos): m/z=327 [M+H]$^+$ $^1$H-NMR (400 MHz, DMSO-$d_6$) δ [ppm]: 1.24 (s, 12H), 2.27-2.45 (m, 2H), 4.14-4.31 (m, 2H), 5.67 (t, 1H), 6.82-6.89 (m, 3H), 7.18-7.24 (m, 1H), 7.64 (s, 1H), 7.86 (s, 1H).

Intermediate I-133

[1-(5,6,7,8-Tetrahydroisoquinolin-8-yl)-1H-pyrazol-4-yl]boronic acid (mixture of enantiomers)

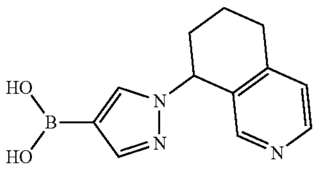 [SMILES: OB(O)c1cnn(C2CCCc3ccncc32)c1]

To a solution of 5,6,7,8-tetrahydroisoquinolin-8-ol [CAS-RN 139484-32-5](2.00 g, 97% purity, 13.0 mmol) in THF (50 ml) were added 4-(4,4,5,5-tetramethyl-1,3,2-dioxaborolan-2-yl)-1H-pyrazole (3.03 g, 15.6 mmol) and triphenylphosphine (6.82 g, 26.0 mmol). A solution of DBAD (5.99 g, 26.0 mmol) in THF (10 ml) was added within 2 min at rt. After stirring for 1 h under reflux, the reaction mixture was cooled to rt and concentrated under reduced pressure. The residue was purified by flash column chromatography (C18, 330 g; eluent: water/acetonitrile gradient 80:20 to 45:55) to yield 1.00 g crude product, which was purified by column chromatography (silica gel, 120 g; eluent: dichloromethane/methanol, 9:1) to yield 400 mg (97% purity, 12% yield) of the title compound.

LC-MS (method 17): $R_t$=0.75 min; MS (ESIpos): m/z=244 (M+H)$^+$ $^1$H-NMR (300 MHz, DMSO-$d_6$) δ [ppm]: 1.74-1.87 (m, 2H), 2.07-2.30 (m, 2H), 2.71-2.95 (m, 2H), 5.69 (t, 1H), 7.22 (d, 1H), 7.71 (s, 1H), 7.74 (s, 2H), 7.76 (s, 1H), 7.94 (s, 1H), 8.34 (d, 1H).

Intermediate I-134

[1-(5,6,7,8-Tetrahydroquinolin-5-yl)-1H-pyrazol-4-yl]boronic acid (mixture of enantiomers)

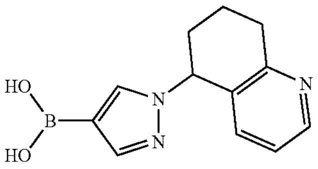 [SMILES: OB(O)c1cnn(C2CCCc3ncccc32)c1]

To a solution of 5,6,7,8-tetrahydroquinolin-5-ol [CAS-RN 194151-99-0](2.00 g, 98% purity, 13.1 mmol) in THF (50 m) were added 4-(4,4,5,5-tetramethyl-1,3,2-dioxaborolan-2-yl)-1H-pyrazole (3.06 g, 15.8 mmol) and triphenylphosphine (6.89 g, 26.3 mmol). A solution of DBAD (6.05 g, 26.3 mmol) in THF (10 ml) was added in 2 min at rt. After stirring for 1 h under reflux, the reaction mixture was cooled to rt and concentrated under reduced pressure. The residue was purified by flash column chromatography (C18, 330 g; eluent water/acetonitrile gradient 80:20 to 45:55) to give 1.00 g crude product, which was purified by column chromatography (silica gel, 120 g; eluent: dichloromethane/methanol, 9:1) to yield 410 mg (92% purity, 12% yield) the title compound.

LC-MS (method 17): $R_t$=0.59 min; MS (ESIpos): m/z=244 $(M+H)^+$ $^1$H-NMR (300 MHz, DMSO-$d_6$) δ [ppm]: 1.81-2.00 (m, 2H), 2.11-2.24 (m, 2H), 2.82-3.04 (m, 2H), 5.67 (t, 1H), 7.08 (dd, 1H), 7.16 (dd, 1H), 7.70 (s, 1H), 7.74 (s, 2H), 7.79 (s, 1H), 8.42 (dd, 1H).

Intermediate I-135

[1-(5,6,7,8-Tetrahydroisoquinolin-5-yl)-1H-pyrazol-4-yl]boronic acid (mixture of enantiomers)

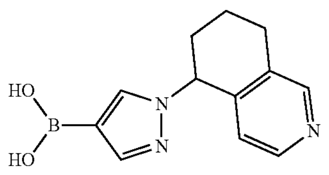 [SMILES: OB(O)c1cnn(C2CCCc3cnccc32)c1]

To a solution of 5,6,7,8-tetrahydroisoquinolin-5-ol [CAS-RN 97112-03-3](1.40 g, 98% purity, 9.20 mmol) in THE (25 ml) were added 4-(4,4,5,5-tetramethyl-1,3,2-dioxaborolan-2-yl)-1H-pyrazole (3.57 g, 18.4 mmol) and triphenylphosphine (4.82 g, 18.4 mmol). A solution of DBAD (4.24 g, 18.4 mmol) in THE (5 ml) was added within 3 min at rt. After stirring at 70° C. for 3 h, the reaction mixture was cooled to rt and concentrated under reduced pressure. The residue was purified by flash column chromatography (C18, 330 g; eluent water/acetonitrile gradient 80:20 to 45:55) to give 800 mg crude product, which was purified by column chromatography (silica gel 120 g; eluent: dichloromethane/methanol 9:1) to yield 224 mg (95% purity, 10% yield) of the title compound.

LC-MS (method 15): $R_t$=0.97 min; MS (ESIpos): m/z=244 $(M+H)^+$ $^1$H-NMR (300 MHz, DMSO-$d_6$) δ [ppm]: 1.82-2.04 (m, 2H), 2.16-2.28 (m, 2H), 2.78-2.93 (m, 2H), 5.64 (t, 1H), 6.57-6.61 (m, 1H), 7.64-7.76 (m, 2H), 7.82-7.88 (m, 1H), 8.26-8.29 (m, 1H), 8.44-8.46 (m, 1H).

Intermediate I-136

[1-(5,6,7,8-Tetrahydroquinolin-8-yl)-1H-pyrazol-4-yl]boronic acid (mixture of enantiomers)

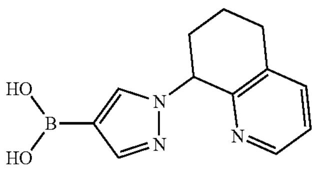 [SMILES: OB(O)c1cnn(C2CCCc3cccnc32)c1]

To a solution of 5,6,7,8-tetrahydroquinolin-8-ol [CAS-RN 14531-46-0](2.00 g, 97% purity, 13.0 mmol) in THE (40 ml) were added 4-(4,4,5,5-tetramethyl-1,3,2-dioxaborolan-2-yl)-1H-pyrazole (4.54 g, 23.4 mmol) and triphenylphosphine (6.82 g, 26.0 mmol). A solution of DBAD (5.99 g, 26.0 mmol) in THF (20 ml) was added within 3 min at rt. After stirring for 3 h under reflux, the reaction mixture was cooled to rt and concentrated under reduced pressure. The residue was purified by flash column chromatography (C18, 400 g; eluent: water/acetonitrile gradient 40:60 to 20:80) to give 1.50 g (60% purity) of crude product, which was purified by column chromatography (silica gel 220 g, eluent: dichloromethane/methanol 10:1) to yield 458 mg (90% purity, 13% yield) of the title compound.

LC-MS (method 8): $R_t$=0.65 min; MS (ESIpos): m/z=244 $(M+H)^+$ $^1$H-NMR (300 MHz, DMSO-$d_6$) δ [ppm]: 1.73-1.88 (m, 2H), 2.13-2138 (m, 2H), 2.72-2.98 (m, 2H), 5.54 (t, 1H), 7.27 (dd, 1H), 7.59-7.70 (m, 5H), 8.34 (dd, 1H).

Intermediate I-137

1-(5-Chlorothiophen-2-yl)propan-1-ol (mixture of enantiomers)

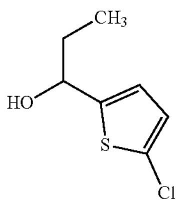

To a solution of 5-chlorothiophene-2-carbaldehyde [CAS-RN 7283-96-7](2.00 g, 13.6 mmol) in dry tetrahydrofuran (40 ml) at 0° C. was added dropwise a solution of ethylmagnesium bromide in THF (15 ml, 1.0 M, 15 mmol). The reaction mixture was stirred at rt for 12 h and was then quenched with 1M hydrochloric acid. The reaction mixture was extracted twice with ethyl acetate. The combined organic layers were washed with brine, dried over sodium sulfate and concentrated to yield 2.66 g (94% purity, 99% yield) of the title compound which was used without further purification in the next step.

LC-MS (method 2): $R_t$=0.87 min; MS (ESIpos): m/z=258 $[M-18/+H]^+$ $^1$H-NMR (600 MHz, DMSO-$d_6$) δ [ppm]: 0.86 (t, 3H), 1.65 (quin, 2H), 4.61 (br t, 1H), 5.66 (br s, 1H), 6.77 (br d, 1H), 6.93 (d, 11H).

Intermediate I-138

1-[1-(5-Chlorothiophen-2-yl)propyl]-4-(4,4,5,5-tetramethyl-1,3,2-dioxaborolan-2-yl)-1H-pyrazole (mixture of enantiomers)

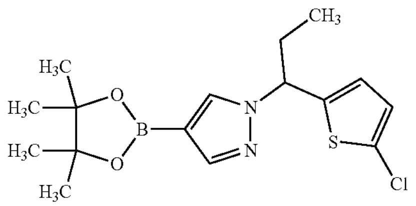 [SMILES: CCC(c1ccc(Cl)s1)n1cc(B2OC(C)(C)C(C)(C)O2)cn1]

Diisopropyl azodicarboxylate (3.1 ml, 16 mmol) and triphenylphosphine (4.83 g, 18.4 mmol) were 5 stirred at 0° C. in dry tetrahydrofuran (30 ml) for 15 min. Then 4-(4,4,5,5-tetramethyl-1,3,2-dioxaborolan-2-yl)-1H-pyrazole (2.38 g, 12.3 mmol) and 1-(5-chlorothiophen-2-yl)propan-1-ol (2.65 g, 90% purity, 13.5 mmol) as a solution in dry THF (10 ml) were slowly added. The reaction mixture was stirred at rt for 12 h. The reaction mixture was concentrated and purified directly by silica gel column chromatographie (eluent: cyclohexane/ethyl acetate gradient 9:1 to 3:2) to yield 1.93 g (73% purity, 32% yield) of the title compound.

LC-MS (method 1): $R_t$=2.38 min; MS (ESIpos): m/z=353 $[M+H]^+$ $^1$H-NMR (500 MHz, DMSO-$d_6$) δ [ppm]: 0.734 (1.03), 0.739 (0.43), 0.748 (2.27), 0.753 (0.72), 0.763 (1.07), 0.843 (1.07), 0.857 (2.30), 0.872 (1.14), 0.979 (0.42), 1.117 (0.54), 1.133 (0.44), 1.162 (0.44), 1.245 (16.00), 1.636.(0.66), 1.650 (0.80), 1.664 (0.62), 5.645 (0.88), 5.655 (0.85), 15 6.766 (0.56), 6.768 (0.59), 6.773 (0.62), 6.775 (0.66), 6.925 (1.00), 6.933 (0.97), 6.950 (0.46), 6.957 (1.51), 6.962 (1.90), 6.970 (0.53), 7.654 (1.48), 8.070 (1.58).

Intermediate I-139 tert-Butyl 3-[4-(2-amino-8-{[(2S)-butan-2-yl]carbamoyl}[1,2,4]triazolo[1,5-a]pyridin-6-yl)-1H-pyrazol-1-yl]azetidine-1-carboxylate

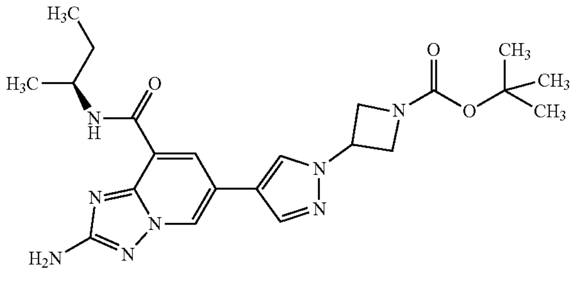 [SMILES: CC[C@H](C)NC(=O)c1cc(-c2cnn(C3CN(C(=O)OC(C)(C)C)C3)c2)cn2nc(N)nc12]

2-Amino-6-bromo-N-[(2S)-butan-2-yl][1,2,4]triazolo[1,5-a]pyridine-8-carboxamide (183 mg, 587 μmol), {1-[1-(tert-butoxycarbonyl)azetidin-3-yl]-1H-pyrazol-4-yl}boronic acid (188 mg, 704 μmol), sodium carbonate (311 mg, 2.93 mmol) and 1,1'-bis(diphenylphosphino)ferrocene-palladium(II)dichloride dichloromethane complex (24.0 mg, 29.3 μmol) were reacted according to procedure A in a mixture of 1,4-dioxane (6.0 ml) and water (2.0 ml). The residue was purified by column chromatography (Biotage® SNAP KP-NH 11 g cartridge, eluent: cyclohexane/ethyl acetate gradient 8:2 to 2:8) to yield 259 mg (97% purity, 94% yield) of the title compound.

LC-MS (method 2): $R_t$=0.96 min; MS (ESIpos): m/z=455 $[M+H]^+$ $^1$H-NMR (600 MHz, DMSO-$d_6$) δ [ppm]: 0.95 (t, 3H), 1.22 (d, 3H), 1.42 (s, 9H); 1.52-1.63 (m, 2H), 3.95-4.10 (m, 2H), 4.10-4.24 (m, 2H), 4.29-4.37 (m, 2H), 5.18-5.25 (m, 1H), 6.41 (s, 2H), 8.15 (s, 11H), 8.28 (d, 1H), 8.56 (s, 1H), 9.09 (d, 1H), 9.29 (d, 1H).

Intermediate I-140

2-Amino-6-[1-(azetidin-3-yl)-1H-pyrazol-4-yl]-N-[(2S)-butan-2-yl][1,2,4]triazolo[1,5-a]pyridine-8-carboxamide trifluoroacetic acid

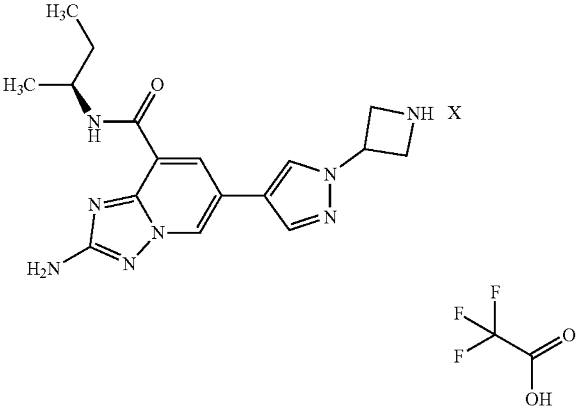

To a solution of tert-butyl-3-[4-(2-amino-8-{[(2S)-butan-2-yl]carbamoyl}[1,2,4]triazolo[1,5-a]pyridin-6-yl)-1H-pyrazol-1-yl]azetidine-1-carboxylate (183 mg, 403 μmol) in dichloromethane (2.0 ml, 31 mmol) was added trifluoroacetic acid (310 μl, 4.0 mmol) and the reaction mixture was stirred at rt for 12 h. Then the solution was concentrated under reduced pressure and the residue—was taken up in a minimum amount of ethyl acetate and crystallized by addition of tert-butyl methyl ether. The precipitate was collected by suction filtration and was washed with a mixture of tert-butyl methyl ether/ethyl acetate 1:1 to yield 143 mg (100% purity, 76% yield) of the title compound.

LC-MS (method 1): $R_t$=0.86 min; MS (ESIpos): m/z=355 $[M+H]^+$ $^1$H-NMR (400 MHz, DMSO-$d_6$) δ [ppm]: 0.94 (t, 3H), 1.22 (d, 3H), 1.53-1.64 (m, 2H), 3.98-4.05 (m, 1H), 4.32-4.54 (m, 4H), 5.41-5.43 (m, 1H), 6.43 (br s, 2H), 8.27 (s, 2H), 8.50 (s, 1H), 8.73-8.98 (m, 1H), 9.01-9.16 (m, 1H), 9.28 (br d, 1H).

EXAMPLES

Unless otherwise noted, when the structure of a compound depicted in Table 1A includes more stereochemical information than is included in its corresponding Example, the corresponding Example is understood to include that additional stereochemical information.

Example I-1

2-Amino-N-[(2S)-butan-2-yl]-6-[1-(cyclopropylmethyl)-1H-pyrazol-4-yl][1,2,4]triazolo[1,5-a]pyridine-8-carboxamide (single stereoisomer)

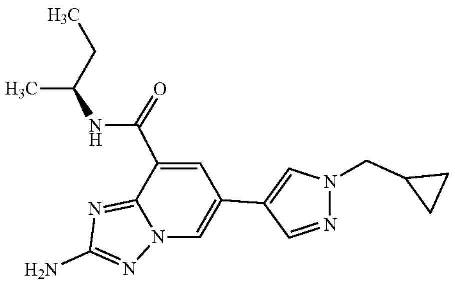 [SMILES: CC[C@H](C)NC(=O)c1cc(-c2cnn(CC3CC3)c2)cn2nc(N)nc12]

2-Amino-6-bromo-N-[(2S)-butan-2-yl][1,2,4]triazolo[1,5-a]pyridine-8-carboxamide (160 mg, 513 mol), 1-(cyclopropylmethyl)-4-(4,4,5,5-tetramethyl-1,3,2-dioxaborolan-2-yl)-1H-pyrazole (153 mg, 615 μmol), 1,1'-bis(diphenylphosphino)ferrocene-palladium(II)dichloride dichloromethane complex (20.9 mg, 25.6 μmol) and sodium carbonate (272 mg, 2.56 mmol) were reacted according to procedure A in a mixture of water (1.5 ml) and 1,4-dioxane (4.5 ml). After 3 h at 90° C., the reaction was quenched with water and extracted with dichloromethane. The organic layer was dried over sodium sulfate, filtered and concentrated under reduced pressure. The residue was purified by column chromatography (Biotage® SNAP KP-NH 11 g cartridge, eluent: cyclohexane/ethyl acetate gradient 8:2 to 0:10) to yield 122 mg (99% purity, 67% yield) of the title compound.

LC-MS (method 1): $R_t$=1.52 min; MS (ESIpos): m/z=354 $[M+H]^+$ $^1$H-NMR (400 MHz, DMSO-$d_6$) δ [ppm]: 0.37-0.44 (m, 2H), 0.52-0.58 (m, 2H), 0.95 (t, 3H), 1.22 (d, 3H), 1.24-1.31 (m, 1H), 1.53-1.64 (m, 2H), 3.99 (d, 2H), 4.01-4.06 (m, 1H), 6.39 (s, 2H), 7.99 (s, 1H), 8.25 (d, 1H), 8.38 (s, 1H), 9.06 (d, 1H), 9.29 (d, 1H).

Example I-2

2-Amino-N-[(2S)-butan-2-yl]-7-[1-(3-cyano-1,1,1-trifluoropropan-2-yl)-1H-pyrazol-4-yl][1,2,4]triazolo[1,5-a]pyridine-5-carboxamide (mixture of diastereomers)

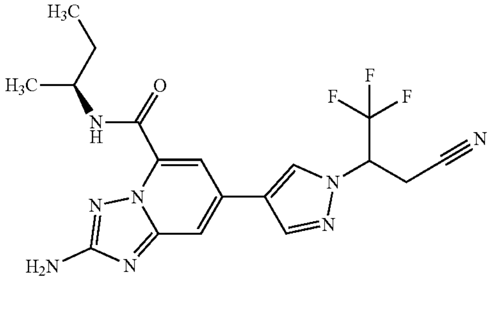 [SMILES: CC[C@H](C)NC(=O)c1cc(-c2cnn(C(CC#N)C(F)(F)F)c2)cc2nc(N)nn12]

2-Amino-N-[(2S)-butan-2-yl]-7-chloro[1,2,4]triazolo[1,5-a]pyridine-5-carboxamide (75.0 mg, 280 μmol) was reacted with 4,4,4-trifluoro-3-[4-(4,4,5,5-tetramethyl-1,3,2-dioxaborolan-2-yl)-1H-pyrazol-1-yl]butanenitrile (132 mg, 80% purity, 336 μmol) for 2 h at 90° C. following general procedure B using 0.1 eq. catalyst. The reaction mixture was diluted with ethyl acetate (5 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 80:20 to 0:100) to yield 97.7 mg (99% purity, 82% yield) of the title compound.

LC-MS (method 1): $R_t$=1.56 min; MS (ESIpos): m/z=421 $[M+H]^+$ $^1$H-NMR (400 MHz, DMSO-$d_6$) δ [ppm]: 0.96 (t, 3H), 1.25 (d, 3H), 1.62 (quin, 2H), 3.59 (dd, 1H), 3.71 (dd, 1H), 3.96-4.08 (m, 1H), 5.90-6.03 (m, 1H), 6.40 (s, 2H), 7.80 (d, 1H), 7.88 (d, 1H), 8.41 (s, 1H), 8.79 (s, 1H), 10.07 (d, 1H).

Example I-3

2-Amino-N-[(2S)-butan-2-yl]-6-[1-(4,4-difluorocyclohexyl)-1H-pyrazol-4-yl][1,2,4]triazolo[1,5-a]pyridine-8-carboxamide (single stereoisomer)

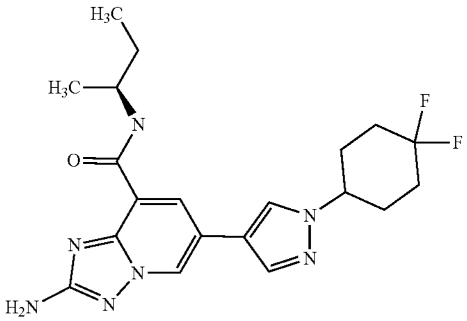

2-Amino-6-bromo-N-[(2S)-butan-2-yl][1,2,4]triazolo[1,5-a]pyridine-8-carboxamide (250 mg, 801 μmol), 1-(4,4-difluorocyclohexyl)-4-(4,4,5,5-tetramethyl-1,3,2-dioxaborolan-2-yl)-1H-pyrazole (300 mg, 961 mol), 1,1'-bis(diphenylphosphino)ferrocene-palladium(II)dichloride dichloromethane complex (32.7 mg, 40.0 mol) and caesium carbonate (783 mg, 2.40 mmol) were 15 reacted according to procedure A in a mixture of water (3.4 ml) and 1,4-dioxane (10 ml). After stirring for 12 h at 90° C., the reaction mixture was filtered through a short pad of Florisil. The organic layer was concentrated and the residue was purified by preparative HPLC to yield 257 mg (100% purity, 77% yield) of the title compound.

LC-MS (method 1): $R_t$=1.72 min; MS (ESIpos): m/z=418 $[M+H]^+$ $^1$H-NMR (600 MHz, DMSO-$d_6$) δ [ppm]: 0.94 (t, 3H), 1.22 (d, 3H), 1.54-1.62 (m, 2H), 2.02-2.18 (m, 8H), 4.02 (dt, 1H), 4.40-4.46 (m, 1H), 6.42 (s, 2H), 8.03 (s, 1H), 8.28 (d, 1H), 8.49 (s, 1H), 9.08 (d, 1H), 9.30 (d, 1H).

Example I-4

2-Amino-N-[(2S)-butan-2-yl]-6-[1-(1-methylazetidin-3-yl)-1H-pyrazol-4-yl][1,2,4]triazolo[1,5-a]pyridine-8-carboxamide (single stereoisomer)

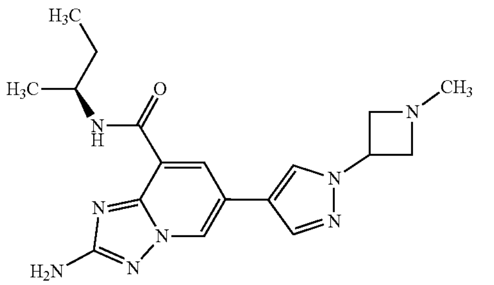 [SMILES: CC[C@H](C)NC(=O)c1cc(-c2cnn(C3CN(C)C3)c2)cn2nc(N)nc12]

Triethylamine (32 pl, 230 μmol) was added to a solution of 2-amino-6-[1-(azetidin-3-yl)-1H-pyrazol-4-yl]-N-[(2S)-butan-2-yl][1,2,4]triazolo[1,5-a]pyridine-8-carboxamide trifluoroacetic acid (106 mg, 226 mol) in dry methanol (4.0 ml, 99 mmol) and the reaction mixture was stirred at rt for 10 min. Acetic acid (13 μl, 230 μmol) followed by paraformaldehyde (7.47 mg, 249 μmol) were added and the reaction mixture was stirred for 1 h. Sodium cyanoborohydride (14.2 mg, 226 μmol) was added and the suspension was stirred overnight. The reaction mixture was quenched with water and extracted twice with ethyl acetate. The combined organic layers were washed with brine, then dried over anhydrous sodium sulfate and concentrated in vacuo. The residue was purified by preparative HPLC to yield 16.6 mg (100% purity, 20% yield) of the title compound.

LC-MS (method 1): $R_t$=0.88 min; MS (ESIpos): m/z=369 $[M+H]^+$ $^1$H-NMR (400 MHz, DMSO-$d_6$) δ [ppm]: 0.94 (t, 3H), 1.22 (d, 3H), 1.53-1.63 (m, 2H), 2.34 (s, 3H), 3.37-3.42 (m, 2H), 3.69-3.74 (m, 2H), 3.98-4.05 (dt, 1H), 4.95 (quin, 1H), 6.40 (s, 2H), 8.06 (s, 1H), 8.27 (d, 1H), 8.53 (s, 1H), 9.08 (d, 1H), 9.28 (d, 1H).

Example I-5

2-Amino-6-[1-(1-benzylazetidin-3-yl)-1H-pyrazol-4-yl]-N-[(2S)-butan-2-yl][1,2,4]triazolo[1,5-a]pyridine-8-carboxamide (single stereoisomer)

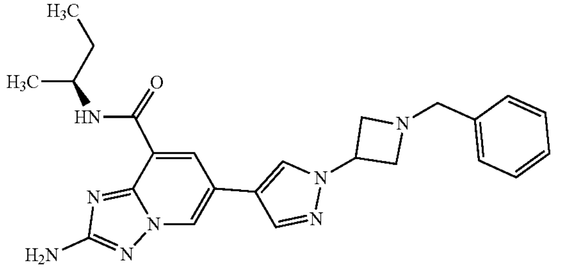 [SMILES: CC[C@H](C)NC(=O)c1cc(-c2cnn(C3CN(Cc4ccccc4)C3)c2)cn2nc(N)nc12]

2-Amino-6-bromo-N-[(2S)-butan-2-yl][1,2,4]triazolo[1,5-a]pyridine-8-carboxamide (75.0 mg, 240 μmol), 1-(1-benzylazetidin-3-yl)-4-(4,4,5,5-tetramethyl-1,3,2-dioxaborolan-2-yl)-1H-pyrazole (89.7 mg, 264 μmol), sodium carbonate(127 mg, 1.20 mmol) and 1,1'-bis(diphenylphosphino)ferrocene-palladium(II)dichloride dichloromethane complex (9.81 mg, 12.0 μmol) were reacted according to procedure A in a mixture of 1,4-dioxane (2.5 ml) and water (820 μl). The reaction mixture was stirred for 12 h at 90° C. The reaction was quenched with water, filtered through a hydrophobic phase separation filter, which was rinsed with ethyl acetate (15 ml). The solvent was removed in vacuo and the residue was purified by column chromatography (Biotage® SNAP KP-NH 11 g cartridge, eluent: cyclohexane/ethyl acetate gradient 8:2 to 2:8) to yield 91.0 mg (100% purity, 85% yield) of the title compound.

LC-MS (method 1): $R_t$=1.19 min; MS (ESIpos): m/z=445 $[M+H]^+$ $^1$H-NMR (600 MHz, DMSO-$d_6$) δ [ppm]: 0.95 (t, 3H), 1.22 (d, 3H), 1.53-1.64 (m, 2H), 3.48 (t, 2H), 3.68-3.74 (m, 4H), 3.99-4.05 (m, 1H), 5.00-5.05 (m, 1H), 6.41 (s, 2H), 7.21-7.30 (m, 1H), 7.31-7.35 (m, 4H), 8.08 (s, 1H), 8.29 (d, 1H), 8.56 (s, 1H), 9.09 (d, 1H), 9.29 (d, 1H).

Example I-6

2-Amino-N-[(2S)-butan-2-yl]-6-[1-(1-ethylpiperidin-4-yl)-1H-pyrazol-4-yl][1,2,4]triazolo[1,5-a]pyridine-8-carboxamide (single stereoisomer)

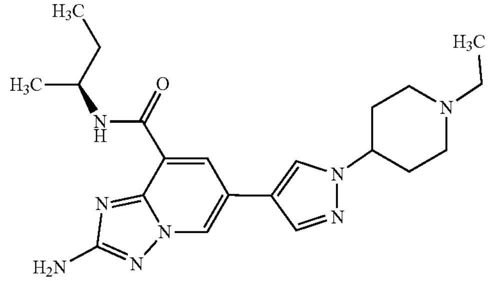 [SMILES: CC[C@H](C)NC(=O)c1cc(-c2cnn(C3CCN(CC)CC3)c2)cn2nc(N)nc12]

2-Amino-6-bromo-N-[(2S)-butan-2-yl][1,2,4]triazolo[1,5-a]pyridine-8-carboxamide (34.9 mg, 112 μmol), 1-ethyl-4-[4-(4,4,5,5-tetramethyl-1,3,2-dioxaborolan-2-yl)--1H-pyrazol-1-yl]piperidine (37.5 mg, 123 mol), sodium carbonate (59.2 mg, 558 μmol) and 1,1'-bis(diphenylphosphino)ferrocene-palladium(II)dichloride dichloromethane complex (4.56 mg, 5.58 μmol) were reacted according to procedure A in a mixture of 1,4-dioxane (1.0 ml) and water (340 μl). The reaction mixture was stirred for 4 h at 90° C., then quenched with water and extracted with dichloromethane. The combined organic layers were dried over anhydrous sodium sulfate and the solvent was removed in vacuo. The residue was purified by preparative HPLC to yield 8.70 mg (93% purity, 18% yield) of the title compound.

LC-MS (method 1): $R_t$=0.94 min; MS (ESIpos): m/z=411 $[M+H]^+$ $^1$H-NMR (500 MHz, DMSO-$d_6$) δ [ppm]: 0.94 (m, 3H), 1.02 (t, 3H), 1.21 (d, 3H), 1.54-1.62 (m, 2H), 1.91-2.07 (m, 6H), 2.37 (q, 2H), 2.96 (br d, 2H), 4.02 (dt, 1H), 4.00-4.03 (m, 1H), 6.38 (s, 2H), 7.99 (s, 1H), 8.26 (d, 1H), 8.42 (s, 1H), 9.04 (d, 1H), 9.28 (d, 1H).

Example I-7

2-Amino-N-[(2S)-butan-2-yl]-6-{1-[1-(propan-2-yl)piperidin-4-yl]-1H-pyrazol-4-yl}[1,2,4]triazolo[1,5-a]pyridine-8-carboxamide (single stereoisomer)

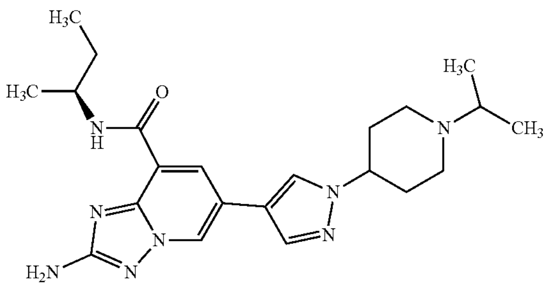 [SMILES: CC[C@H](C)NC(=O)c1cc(-c2cnn(C3CCN(C(C)C)CC3)c2)cn2nc(N)nc12]

2-Amino-6-bromo-N-[(2S)-butan-2-yl][1,2,4]triazolo[1,5-a]pyridine-8-carboxamide (102 mg, 326 mol), {1-[1-(propan-2-yl)piperidin-4-yl]-1H-pyrazol-4-yl}boronic acid (92.8 mg, 392 μmol), sodium carbonate (173 mg, 1.63 mmol) and 1,1'-bis(diphenylphosphino)ferrocene-palladium (II)dichloride dichloromethane complex (13.3 mg, 16.3 μmol) were reacted according to procedure A in a mixture of 1,4-dioxane (3.0 ml) and water (990 l). The reaction mixture was stirred for 4 h at 90° C. The residue was purified by column chromatography (Biotage® SNAP KP-NH 11 g cartridge, eluent: cyclohexane/ethyl acetate gradient 8:2 to 2:8) to yield 92.7 mg (100% purity, 67% yield) of the title compound.

LC-MS (method 1): $R_t$=0.97 min; MS (ESIpos): m/z=425 $[M+H]^+$ $^1$H-NMR (500 MHz, DMSO-$d_6$) δ [ppm]: 0.94 (t, 3H), 0.99 (d, 6H), 1.22 (d, 3H), 1.54-1.63 (m, 2H), 1.92 (qd, 2H), 2.01-2.08 (m, 2H), 2.23-2.30 (m, 2H), 2.72-2.77 (m, 1H), 2.88 (br d, 2H), 3.99-4.08 (m, 1H), 4.09-4.12 (m, 1H), 6.38 (s, 2H), 7.99 (s, 1H), 8.26 (d, 1H), 8.42 (s, 1H), 9.04 (d, 1H), 9.29 (d, 1H).

Example I-8

2-Amino-N-[(2S)-butan-2-yl]-6-{1-[1-(oxetan-3-yl)piperidin-4-yl]-1H-pyrazol-4-yl}[1,2,4]triazolo[1,5-a]pyridine-8-carboxamide (single stereoisomer)

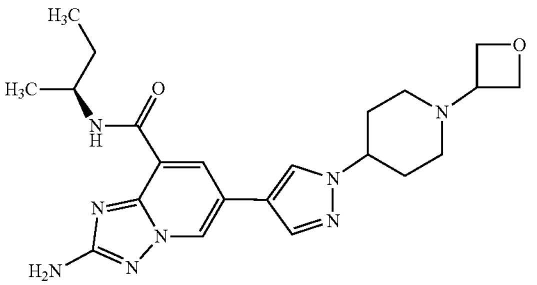 [SMILES: CC[C@H](C)NC(=O)c1cc(-c2cnn(C3CCN(C4COC4)CC3)c2)cn2nc(N)nc12]

2-Amino-6-bromo-N-[(2S)-butan-2-yl][1,2,4]triazolo[1,5-a]pyridine-8-carboxamide (75.0 mg, 240 μmol), 1-(oxetan-3-yl)-4-[4-(4,4,5,5-tetramethyl-1,3,2-dioxaborolan-2-yl)-1H-pyrazol-1-yl]piperidine (96.1 mg, 288 mol), sodium carbonate (127 mg, 1.20 mmol). and 1,1'-bis(diphenylphosphino)ferrocene-palladium(II)dichloride dichloromethane complex (9.81 mg, 12.0 μmol) were reacted according to procedure A in a mixture of 1,4-dioxane (2.5 ml) and water (820 l). The reaction mixture was stirred for 12 h at 90° C. The reaction mixture was quenched with water and filtered through a hydrophobic phase separation filter which was rinsed with ethyl acetate (15 ml). The solvent was removed in vacuo and the residue was purified by column chromatography (Biotage® SNAP KP-NH 11 g cartridge, eluent: cyclohexane/ethyl acetate gradient 8:2 to 2:8) to yield 60.0 mg (100% purity, 57% yield) of the title compound.

LC-MS (method 1): $R_t$=0.93 min; MS (ESIpos): m/z=439 $[M+H]^+$ $^1$H-NMR (600 MHz, DMSO-$d_6$) δ [ppm]: 0.95 (t, 3H), 1.22 (d, 3H), 1.54-1.63 (m, 2H), 1.93-2.08 (m, 6H), 2.79-2.83 (m, 2H), 3.45 (quin, 1H), 3.99-4.04 (m, 1H), 4.12-4.21 (m, 1H), 4.45 (t, 2H), 4.55 (t, 2H), 6.40 (s, 2H), 8.01 (s, 1H), 8.27 (d, 11H), 8.44 (s, 1H), 9.05 (d, 1H), 9.29 (d, 1H).

Example I-9

2-Amino-N-[(2S)-butan-2-yl]-6-(1-{1-[(oxetan-3-yl)methyl]piperidin-4-yl}-1H-pyrazol-4-yl)[1,2,4]triazolo[1,5-a]pyridine-8-carboxamide (single stereoisomer)

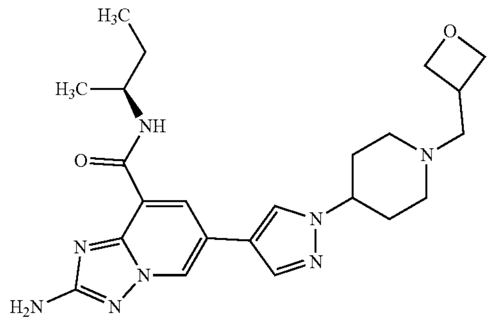 [SMILES: CC[C@H](C)NC(=O)c1cc(-c2cnn(C3CCN(CC4COC4)CC3)c2)cn2nc(N)nc12]

2-Amino-6-bromo-N-[(2S)-butan-2-yl][1,2,4]triazolo[1,5-a]pyridine-8-carboxamide (78.5 mg, 251 mol), 1-[(oxetan-3-yl)methyl]-4-[4-(4,4,5,5-tetramethyl-1,3,2-dioxaborolan-2-yl)-1H-pyrazol-1-yl]piperidine (131 mg, 80% purity, 302 mol), sodium carbonate (133 mg, 1.26 mmol) and 1,1'-bis(diphenylphosphino)ferrocene-palladium(II)dichloride dichloromethane complex (10 mg, 13 μmol) were reacted according to procedure A in a mixture of water (1.0 ml) and 1,4-dioxane (3.0 ml). The reaction mixture was stirred for 2.5 h at 90° C. The reaction mixture was quenched with water and filtered through a hydrophobic phase separation filter which was rinsed with ethyl acetate (15 ml). The filtrate was concentrated under reduced pressure. The residue was purified by preparative HPLC to yield 82.4 mg (100% purity, 72% yield) of the title compound.

LC-MS (method 2): $R_t$=0.59 min; MS (ESIpos): m/z=453 $[M+H]^+$ $^1$H-NMR (500 MHz, $CDCl_3$) δ [ppm]: 1.01 (t, 3H), 1.30 (d, 3H), 1.54-1.76 (m, 6H), 2.05-2.28 (m, 5H), 2.77-2.89 (m, 1H), 2.90-3.04 (m, 2H), 3.17-3.39 (m, 1H), 4.11-4.28 (m, 2H), 4.45 (br t, 2H), 4.57 (s, 2H), 4.84 (br t, 2H), 7.75 (s, 1H), 7.77 (s, 1H), 8.42 (d, 1H), 8.47 (d, 1H), 9.19 (br d, 1H).

Example I-10

2-Amino-6-[1-(1-benzylpiperidin-4-yl)-1H-pyrazol-4-yl]-N-[(2S)-butan-2-yl][1,2,4]triazolo[1,5-a]pyridine-8-carboxamide (single stereoisomer)

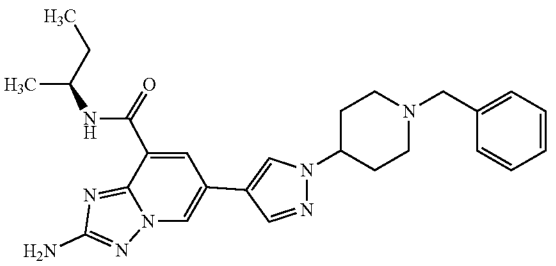 [SMILES: CC[C@H](C)NC(=O)c1cc(-c2cnn(C3CCN(Cc4ccccc4)CC3)c2)cn2nc(N)nc12]

2-Amino-6-bromo-N-[(2S)-butan-2-yl][1,2,4]triazolo[1,5-a]pyridine-8-carboxamide (70.0 mg, 224 µmol), 1-benzyl-4-[4-(4,4,5,5-tetramethyl-1,3,2-dioxaborolan-2-yl)-1H-pyrazol-1-yl]piperidine (98.8 mg, 269 µmol), sodium carbonate (119 mg, 1.12 mmol) and 1,1'-bis(diphenylphosphino)ferrocene-palladium(II)dichloride dichloromethane complex (9.16 mg, 11.2 mol) were reacted according to procedure A in a mixture of 1,4-dioxane (2.0 ml) and water (700 1). After 3 h at 90° C., the reaction mixture was quenched with water and filtered through a hydrophobic phase separation filter which was rinsed with ethyl acetate (15 ml). The filtrate was concentrated and dried under reduced pressure. The residue was purified by column chromatography (Biotage® SNAP KP-NH 11 g cartridge, eluent: cyclohexane/ethyl acetate gradient 8:2 to 0:10) to yield 20.6 mg (95% purity, 18% yield) of the title compound.

LC-MS (method 1): $R_t$=1.13 min; MS (ESIpos): m/z=473 $[M+H]^+$ $^1$H-NMR (400 MHz, DMSO-$d_6$) δ [ppm]: 0.94 (t, 3H), 1.22 (d, 3H), 1.55-1.62 (m, 2H), 1.94-2.07 (m, 4H), 2.15 (br t, 2H), 2.91 (br d, 2H), 3.53 (s, 2H), 3.98-4.03 (m, 11H), 4.14-4.20 (m, 11H), 6.38 (s, 2H), 7.23-7.31 (m, 1H), 7.31-7.36 (m, 3H), 7.51-7.65 (m, 1H), 7.99 (s, 1H), 8.26 (d, 1H), 8.44 (s, 1H), 9.04 (d, 1H), 9.28 (d, 111).

Example I-11

6-[1-(1-Acetylpiperidin-4-yl)-1H-pyrazol-4-yl]-2-amino-N-[(2S)-butan-2-yl][1,2,4]triazolo[1,5-a]pyridine-8-carboxamide (single stereoisomer)

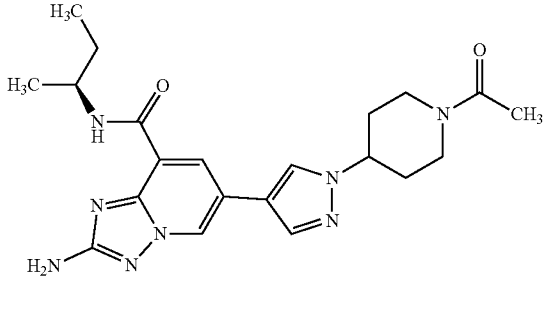 [SMILES: CC[C@H](C)NC(=O)c1cc(-c2cnn(C3CCN(C(C)=O)CC3)c2)cn2nc(N)nc12]

2-Amino-6-bromo-N-[(2S)-butan-2-yl][1,2,4]triazolo[1,5-a]pyridine-8-carboxamide (75.0 mg, 240 µmol), 1-{4-[4-(4,4,5,5-tetramethyl-1,3,2-dioxaborolan-2-yl)-1H-pyrazol-1-yl]piperidin-1-yl}ethan-1-one (92.0 mg, 288 µmol), sodium carbonate (127 mg, 1.20 mmol) and 1,1'-bis(diphenylphosphino)ferrocene-palladium(II)dichloride dichloromethane complex (9.81 mg, 12.0 µmol) were reacted according to procedure A in a mixture of 1,4-dioxane (2.5 ml) and water (820 µl). The reaction mixture was stirred for 12 h at 90° C. The reaction mixture was quenched with water and filtered through a hydrophobic phase separation filter, which was rinsed with ethyl acetate (15 ml). The filtrate was concentrated and dried under reduced pressure. The residue was purified by column chromatography (Biotage® SNAP KP-NH 11 g cartridge, eluent: cyclohexane/ethyl acetate gradient 4:1 to 1:4) to yield 84.0 mg (100% purity, 82% yield) of the title compound.

LC-MS (method 1): $R_t$=1.24 min; MS (ESIpos): m/z=425 $[M+H]^+$ $^1$H-NMR (500 MHz, DMSO-$d_6$) δ [ppm]: 0.94 (t, 3H), 1.22 (d, 3H), 1.52-1.64 (m, 2H), 1.78 (qd, 1H), 1.91 (qd, 1H), 2.02-2.11 (m, 5H), 2.68-2.79 (m, 1H), 3.18-3.29 (m, 1H), 3.93 (br d, 1H), 3.99-4.05 (m, 1H), 4.41-4.50 (m, 2H), 6.41 (s, 2H), 8.02 (s, 1H), 8.27 (d, 1H), 8.46 (s, 1H), 9.06 (d, 1H), 9.29 (d, 1H).

Example I-12

2-Amino-N-[(2S)-butan-2-yl]-7-(1-cyclopentyl-1H-pyrazol-4-yl)[1,2,4]triazolo[1,5-a]pyridine-5-carboxamide (single stereoisomer)

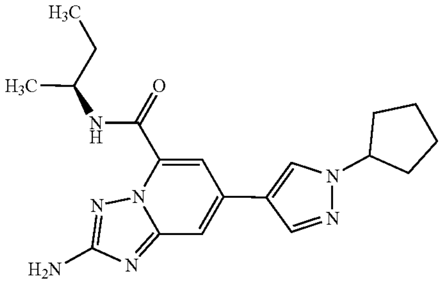 [SMILES: CC[C@H](C)NC(=O)c1cc(-c2cnn(C3CCCC3)c2)cc2nc(N)nn12]

2-Amino-N-[(2S)-butan-2-yl]-7-chloro[1,2,4]triazolo[1,5-a]pyridine-5-carboxamide (75.0 mg, 280 µmol) was reacted with 1-cyclopentyl-4-(4,4,5,5-tetramethyl-1,3,2-dioxaborolan-2-yl)-1H-pyrazole (95.5 mg, 364 mol) for 2 h at 90° C. following general procedure B using 0.1 eq. catalyst. The reaction mixture was diluted with ethyl acetate (5 ml) and filtered through a hydrophobic phase separation filter. The solvent was evaporated under reduced pressure and the residue purified by column chromatography (Biotage® SNAP KP-NH 28 g cartridge, eluent: cyclohexane/ethyl acetate gradient 9:1 to 1:4) to yield 70.2 mg (99% purity, 68% yield) of the title compound.

LC-MS (method 1): $R_t$=1.70 min; MS (ESIpos): m/z=368 $[M+H]^+$ $^1$H-NMR (400 MHz, DMSO-$d_6$) δ [ppm]: 0.96 (t, 3H), 1.24 (d, 3H), 1.56-1.71 (m, 4H), 1.76-1.87 (m, 2H), 1.92-2.02 (m, 2H), 2.06-2.16 (m, 2H), 3.96-4.07 (m, 1H), 4.68-4.76 (m, 1H), 6.33 (s, 2H), 7.77-7.80 (m, 2H), 8.10 (d, 1H), 8.54 (s, 1H), 10.09 (d, 1H).

Example I-13

2-Amino-N-[(2S)-butan-2-yl]-6-[1-(2,3-dihydro-1H-inden-1-yl)-1H-pyrazol-4-yl][1,2,4]triazolo[1,5-a]pyridine-8-carboxamide (mixture of diastereomers)

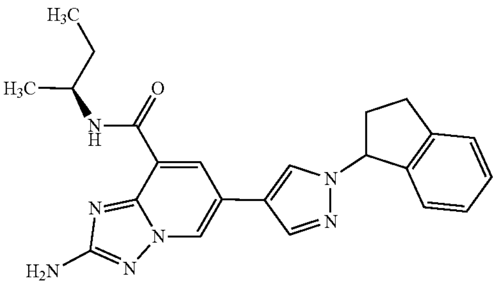 [SMILES: CC[C@H](C)NC(=O)c1cc(-c2cnn(C3CCc4ccccc43)c2)cn2nc(N)nc12]

2-Amino-6-bromo-N-[(2S)-butan-2-yl][1,2,4]triazolo[1,5-a]pyridine-8-carboxamide (175 mg, 561 μmol) was reacted with 1-(2,3-dihydro-1H-inden-1-yl)-4-(4,4,5,5-tetramethyl-1,3,2-dioxaborolan-2-yl)-1H-pyrazole (209 mg, 673 mol) for 1 h at 90° C. following general procedure B using 0.05 eq. catalyst and 4 eq. sodium carbonate. The reaction mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 75:25 to 15:85) to yield 190 mg (100% purity, 82% yield) of the title compound.

LC-MS (method 1): $R_t$=1.85 min; MS (ESIpos): m/z=416 $[M+H]^+$ $^1$H-NMR (400 MHz, DMSO-$d_6$) δ [ppm]: 0.94 (t, 3H), 1.21 (d, 3H), 1.50-1.66 (m, 2H), 2.42-2.49 (m, 1H), 2.60-2.72 (m, 1H), 2.92-3.02 (m, 1H), 3.16-3.25 (m, 1H), 3.96-4.07 (m, 1H), 5.89-5.95 (m, 1H), 6.38 (s, 2H), 7.10-7.15 (m, 1H), 7.16-7.21 (m, 1H), 7.29 (t, 1H), 7.33-7.38 (m, 1H), 8.03 (s, 1H), 8.25 (d, 1H), 8.39 (s, 1H), 9.07 (d, 1H), 9.28 (d, 1H).

Example I-14

2-Amino-N-[(2S)-butan-2-yl]-6-[1-(2,3-dihydro-1H-inden-1-yl)-1H-pyrazol-4-yl][1,2,4]triazolo[1,5-a]pyridine-8-carboxamide (stereoisomer 1, eutomer)

2-Amino-N-[(2S)-butan-2-yl]-6-[1-(2,3-dihydro-1H-inden-1-yl)-1H-pyrazol-4-yl][1,2,4]triazolo[1,5-a]pyridine-8-carboxamide (mixture of diastereomers) (160 mg, 100% purity) from the previous example was separated by chiral chromatography to yield stereoisomer 1 (68 mg, 99% purity) and stereoisomer 2 (70 mg, 98% purity).

Column: Daicel Chiralcel OJ-H, 5 μm, 250×20 mm; Eluent A: n-heptane; Eluent B: ethanol+0.2% diethylamine; isocratic: 50% A+50% B; flow: 15 ml/min; UV: 220 nm; temperature: 60° C.

Stereoisomer 1: $R_t$=5.59 min and

Stereoisomer 2: $R_t$=7.75 min (cf. next example)

Analytical chiral HPLC. Column: Daicel ChiralCel OJ-H, 5 Am, 250×4.6 mm; Eluent A: iso-hexane; Eluent B: ethanol; isocratic: 50% A+50% B; flow: 1 ml/min; UV: 220 nm; temperature: 70° C.

Stereoisomer 1: $R_t$=4.246 min and

Stereoisomer 2: $R_t$=5.701 min (cf. next example)

LC-MS (method 1): $R_t$=1.82 min; MS (ESIpos): m/z=416 $[M+H]^+$ $^1$H-NMR (500 MHz, DMSO-$d_6$) δ [ppm]: 0.94 (t, 3H), 1.21 (d, 3H), 1.53-1.63 (m, 2H), 2.43-2.48 (m, 1H), 2.61-2.69 (m, 11H), 2.93-3.01 (m, 1H), 3.16-3.24 (m, 1H), 3.96-4.06 (m, 1H), 5.92 (dd, 1H), 6.38 (s, 2H), 7.11-7.14 (m, 1H), 7.19 (t, 11H), 7.29 (t, 1H), 7.34-7.38 (m, 11H), 8.02 (s, 1H), 8.25 (d, 1H), 8.39 (s, 1H), 9.06 (d, 11H), 9.28 (d, 11H).

Example I-15

2-Amino-N-[(2S)-butan-2-yl]-6-[1-(2,3-dihydro-1H-inden-1-yl)-1H-pyrazol-4-yl][1,2,4]triazolo[1,5-a]pyridine-8-carboxamide (stereoisomer 2, distomer)

The product was isolated in the previous example as second stereoisomer.

LC-MS (method 1): $R_t$=1.82 min; MS (ESIpos): m/z=416 $[M+H]^+$ $^1$H-NMR (500 MHz, DMSO-$d_6$) δ [ppm]: 0.925 (7.40), 0.940 (16.00), 0.955 (7.73), 1.207 (15.56), 1.220 (15.27), 1.536 (0.40), 1.550 (1.10), 1.563 (2.71), 1.571 (2.60), 1.577 (3.73), 1.586 (2.97), 1.592 (2.53), 1.599 (2.34), 1.613 (0.92), 2.436 (0.62), 2.449 (1.24), 2.453 (0.99), 2.466 (1.72), 2.476 (2.12), 2.618 (0.70), 2.628 (0.95), 2.634 (1.65), 2.644 (2.16), 2.651 (1.17), 2.661 (1.94), 2.671 (1.17), 2.677 (0.66), 2.687 (0.59), 2.937 (0.99), 2.952 (1.39), 2.968 (1.87), 2.983 (1.76), 2.999 (1.03), 3.174 (1.32), 3.184 (1.46), 3.191 (1.39), 3.202 (1.61), 3.216 (1.14), 3.223 (1.06), 3.233 (0.92), 3.346 (0.59), 3.985 (0.84), 3.998 (1.79), 4.012 (2.23), 4.026 (1.72), 4.040 (0.73), 5.906 (2.20), 5.920 (3.00), 5.934 (2.01), 6.382 (11.20), 7.119 (3.11), 7.134 (4.91), 7.173 (2.42), 7.188 (4.10), 7.203 (1.90), 7.272 (2.12), 7.287 (4.21), 7.301 (2.31), 7.349 (4.65), 7.364 (3.00), 8.025 (10.43), 8.247 (7.29), 8.251 (7.14), 8.388 (10.22), 9.064 (7.51), 9.067 (7.18), 9.269 (3.55), 9.285 (3.41).

Example I-16

2-Amino-N-[(2S)-butan-2-yl]-7-[1-(3,4-dihydro-2H-chromen-4-yl)-1H-pyrazol-4-yl][1,2,4]triazolo[1,5-a]pyridine-5-carboxamide (mixture of diastereomers)

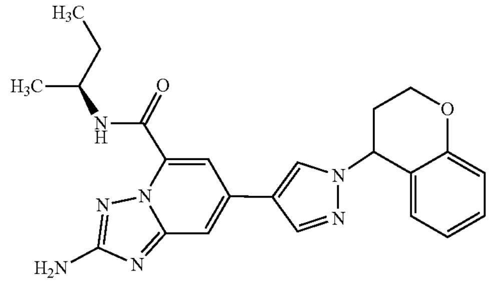 [SMILES: CC[C@H](C)NC(=O)c1cc(-c2cnn(C3CCOc4ccccc43)c2)cc2nc(N)nn12]

2-Amino-N-[(2S)-butan-2-yl]-7-chloro[1,2,4]triazolo[1,5-a]pyridine-5-carboxamide (100 mg, 374 μmol) was reacted with 1-(3,4-dihydro-2H-chromen-4-yl)-4-(4,4,5,5-tetramethyl-1,3,2-dioxaborolan-2-yl)-1H-pyrazole (146 mg, 448 μmol) for 1 h at 90° C. following general procedure B using 0.1 eq. catalyst. The reaction mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 65:35 to 10:90) to yield 105 mg (100% purity, 65% yield) of the title compound.

LC-MS (method 1): $R_t$=1.72 min; MS (ESIpos): m/z=432 $[M+H]^+$ $^1$H-NMR (400 MHz, DMSO-$d_6$) δ [ppm]: −0.008 (1.01), 0.008 (0.89), 0.933 (6.72), 0.952 (16.00), 0.970 (7.54), 1.070 (3.15), 1.226 (15.09), 1.242 (15.16), 1.397 (0.77), 1.569 (1.14), 1.587 (4.08), 1.605 (5.32), 1.623 (3.81), 1.641 (1.00), 1.989 (0.46), 2.367 (0.68), 2.382 (0.97), 2.402 (1.19), 2.430 (0.80), 2.440 (0.99), 2.447 (1.30), 2.456 (1.58), 2.465 (1.00), 2.472 (1.00), 3.920 (0.43), 3.969 (0.66), 3.986 (1.50), 4.003 (1.93), 4.021 (1.61), 4.038 (0.69), 4.291 (0.54), 4.309 (1.80), 4.325 (3.22), 4.334 (2.93), 4.343 (1.69), 4.352 (1.91), 4.371 (0.55), 5.682 (1.61), 5.697 (3.39), 5.711 (1.58), 6.342 (8.58), 6.836 (1.45), 6.854 (3.51), 6.869 (5.53), 6.888 (4.36), 6.908 (3.62), 6.924 (2.00), 7.194 (1.72), 7.199 (1.69), 7.215 (2.78), 7.233 (1.41), 7.237 (1.32), 7.777 (5.96), 7.782 (8.20), 7.802 (8.16), 7.807 (5.86), 8.190 (9.58), 8.549 (8.78), 10.062 (2.78), 10.082 (2.74).

Example I-17

2-Amino-N-[(2S)-butan-2-yl]-7-[1-(3,4-dihydro-2H-chromen-4-yl)-1H-pyrazol-4-yl][1,2,4]triazolo[1,5-a]pyridine-5-carboxamide (stereoisomer 1, eutomer)

2-Amino-N-[(2S)-butan-2-yl]-7-[1-(3,4-dihydro-2H-chromen-4-yl)-1H-pyrazol-4-yl][1,2,4]triazolo[1,5-a]pyridine-5-carboxamide (mixture of diastereomers) (85 mg, 100% purity) from the previous example was separated by chiral chromatography to yield stereoisomer 1 (39 mg, 100% purity) and stereoisomer 2 (41 mg, 100% purity).

Column: Daicel Chiralcel OJ-H, 5 μm, 250×20 mm; Eluent A: n-heptane; Eluent B: ethanol+0.04% diethylamine; isocratic: 50% A+50% B; flow: 20 ml/min; UV: 220 nm; temperature: 30° C.

Stereoisomer 1: $R_t$=6.600 min and

Stereoisomer 2: $R_t$=9.514 min (cf. next example)

Analytical chiral HPLC. Column: Daicel ChiralCel OJ-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R_t$=1.241 min and

Stereoisomer 2: $R_t$=1.577 min (cf. next example) LC-MS (method 1): $R_t$=1.75 min; MS (ESIpos): m/z=432 $[M+H]^+$ $^1$H-NMR (400 MHz, DMSO-$d_6$) δ [ppm]: 0.95 (t, 3H), 1.16 (t, 1H), 1.60 (quin, 2H), 2.31-2.49 (m, 4H), 3.95-4.06 (m, 1H), 4.27-4.39 (m, 2H), 5.70 (t, 1H), 6.34 (s, 2H), 6.83-6.94 (m, 3H), 7.18-7.25 (m, 1H), 7.79 (dd, 2H), 8.19 (s, 1H), 8.55 (s, 1H), 10.07 (d, 1H).

Example I-18

2-Amino-N-[(2S)-butan-2-yl]-7-[1-(3,4-dihydro-2H-chromen-4-yl)-1H-pyrazol-4-yl][1,2,4]triazolo[1,5-a]pyridine-5-carboxamide (stereoisomer 2, distomer)

The product was isolated in the previous example as second stereoisomer.

LC-MS (method 1): $R_t$=1.75 min; MS (ESIpos): m/z=432 $[M+H]^-$ $^1$H-NMR (400 MHz, DMSO-$d_6$) δ [ppm]: −0.008 (1.61), 0.803 (0.46), 0.858 (0.81), 0.933 (6.70), 0.951 (15.51), 0.970 (7.39), 1.105 (0.63), 1.120 (0.63), 1.141 (3.64), 1.159 (7.54), 1.177 (3.85), 1.225 (15.49), 1.242 (16.00), 1.326 (0.77), 1.569 (1.14), 1.587 (4.13), 1.605 (5.33), 1.622 (3.75), 1.641 (1.02), 2.328 (0.49), 2.366 (1.22), 2.381 (1.05), 2.401 (1.32), 2.430 (0.91), 2.447 (1.42), 2.455 (1.71), 2.472 (1.17), 2.671 (0.51), 2.711 (0.61), 2.933 (0.95), 3.969 (0.74), 3.986 (1.55), 4.004 (1.94), 4.021 (1.61), 4.038 (0.71), 4.292 (0.59), 4.309 (1.88), 4.325 (3.37), 4.333 (3.16), 4.343 (1.81), 4.352 (2.02), 4.371 (0.58), 5.682 (1.68), 5.696 (3.47), 5.711 (1.71), 6.341 (8.53), 6.836 (1.47), 6.854 (3.67), 6.869 (5.63), 6.888 (4.30), 6.908 (3.80), 6.924 (2.06), 7.194 (1.74), 7.198 (1.78), 7.215 (2.95), 7.233 (1.45), 7.237 (1.43), 7.775 (5.35), 7.780 (7.69), 7.801 (7.29), 7.806 (5.56), 8.190 (9.50), 8.549 (8.76), 10.060 (2.80), 10.080 (2.83).

Example I-19

2-Amino-N-[(2S)-butan-2-yl]-7-[1-(5,6,7,8-tetrahydroquinolin-5-yl)-1H-pyrazol-4-yl][1,2,4]triazolo[1,5-a]pyridine-5-carboxamide (mixture of diastereomers)

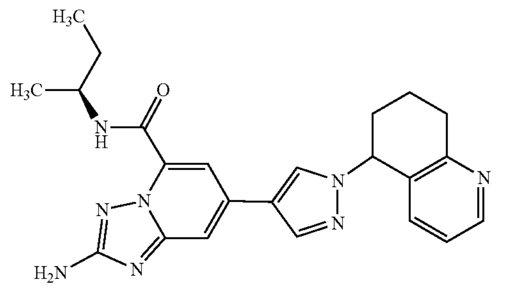 [SMILES: CC[C@H](C)NC(=O)c1cc(-c2cnn(C3CCCc4ncccc43)c2)cc2nc(N)nn12]

2-Amino-N-[(2S)-butan-2-yl]-7-chloro[1,2,4]triazolo[1,5-a]pyridine-5-carboxamide (75.0 mg, 280 μmol) was reacted with [1-(5,6,7,8-tetrahydroquinolin-5-yl)-1H-pyrazol-4-yl]boronic acid (81.7 mg, 336 mol) for 2 h at 80° C. following general procedure B using 0.1 eq. catalyst. The reaction mixture was diluted with ethyl acetate (5 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 60:40 to 0:100, then ethyl acetate/2-propanol gradient 100:0 to 90:10) to yield 42.8 mg (98% purity, 35% yield) of the title compound.

LC-MS (method 1): $R_t$=1.14 min; MS (ESIpos): m/z=431 $[M+H]^+$ $^1$H-NMR (600 MHz, DMSO-$d_6$) δ [ppm]: 0.95 (t, 3H), 1.23 (d, 3H), 1.60 (quin, 2H), 1.87-1.96 (m, 1H), 2.03-2.11 (m, 1H), 2.18-2.32 (m, 2H), 2.91 (dt, 1H), 2.97-3.04 (m, 1H), 3.96-4.04 (m, 1H), 5.68-5.73 (m, 1H), 6.35 (s, 2H), 7.14-7.19 (m, 2H), 7.76-7.81 (m, 2H), 8.18 (s, 1H), 8.41-8.44 (m, 111), 8.55 (s, 1H), 10.08 (d, 1H).

Example I-20

2-Amino-N-[(2S)-butan-2-yl]-7-[1-(5,6,7,8-tetrahydroisoquinolin-5-yl)-1H-pyrazol-4-yl][1,2,4]triazolo[1,5-a]pyridine-5-carboxamide (mixture of diastereomers)

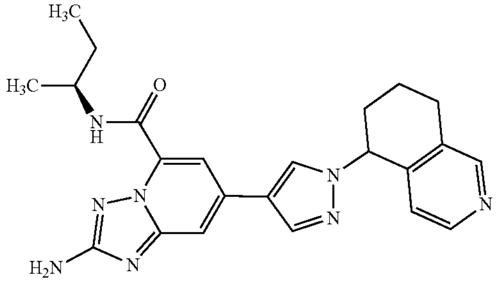 [SMILES: CC[C@H](C)NC(=O)c1cc(-c2cnn(C3CCCc4cnccc43)c2)cc2nc(N)nn12]

2-Amino-N-[(2S)-butan-2-yl]-7-chloro[1,2,4]triazolo[1,5-a]pyridine-5-carboxamide (75.0 mg, 280 μmol) was reacted with [1-(5,6,7,8-tetrahydroisoquinolin-5-yl)-1H-pyrazol-4-yl]boronic acid (102 mg, 420 mol) for 3 h at 90° C. following general procedure B using 0.1 eq. catalyst. The 10 reaction mixture was diluted with ethyl acetate (5 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 70:30 to 0:100) to yield 33.3 mg (99% purity, 27% yield) of the title compound.

LC-MS (method 1): $R_t$=1.17 min; MS (ESIpos): m/z=431 $[M+H]^+$ $^1$H-NMR (400 MHz, DMSO-$d_6$) δ [ppm]: 0.95 (t, 3H), 1.24 (d, 4H), 1.61 (quin, 2H), 1.81-1.94 (m, 1H), 2.00-2.12 (m, 1H), 2.21-2.34 (m, 2H), 2.78-2.95 (m, 2H), 3.95-4.06 (m, 111), 5.65 (t, 1H), 6.35 (s, 2H), 6.70 (d, 1H), 7.78-7.81 (m, 2H), 8.19 (s, 11H), 8.26 (d, 1H), 8.43 (s, 1H), 8.60 (s, 1H), 10.08 (d, 111).

Example I-21

2-Amino-N-[(2S)-butan-2-yl]-7-[1-(5,6,7,8-tetrahydroisoquinolin-8-yl)-1H-pyrazol-4-yl][1,2,4]triazolo[1,5-a]pyridine-5-carboxamide (mixture of diastereomers)

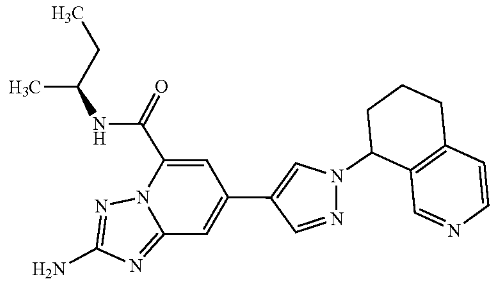 [SMILES: CC[C@H](C)NC(=O)c1cc(-c2cnn(C3CCCc4ccncc43)c2)cc2nc(N)nn12]

2-Amino-N-[(2S)-butan-2-yl]-7-chloro[1,2,4]triazolo[1,5-a]pyridine-5-carboxamide (75.0 mg, 280 μmol) was reacted with [1-(5,6,7,8-tetrahydroisoquinolin-8-yl)-1H-pyrazol-4-yl]boronic acid (81.7 mg, 336 μmol) for 2 h at 80° C. following general procedure B using 0.1 eq. catalyst. The reaction mixture was diluted with ethyl acetate (5 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 6:4 to 0:1, then ethyl acetate/2-propanol gradient 1:0 to 9:1) to yield 59.7 mg (98% purity, 49% yield) of the title compound.

LC-MS (method 1): $R_t$=1.18 min; MS (ESIpos): m/z=431 $[M+H]^+$ $^1$H-NMR (600 MHz, DMSO-$d_6$) δ [ppm]: 0.95 (t, 3H), 1.23 (d, 3H), 1.61 (quin, 2H), 1.80-1.88 (m, 1H), 1.92-2.01 (m, 1H), 2.19-2.32 (m, 2H), 2.81 (dt, 1H), 2.87-2.95 (m, 1H), 3.96-4.04 (m, 1H), 5.73 (t, 1H), 6.35 (s, 2H), 7.24 (d, 1H), 7.77-7.81 (m, 2H), 8.02 (s, 1H), 8.18 (s, 1H), 8.35 (d, 1H), 8.53 (s, 1H), 10.08 (d, 1H).

Example I-22

2-Amino-N-[(2S)-butan-2-yl]-7-[1-(5,6,7,8-tetrahydroquinolin-8-yl)-1H-pyrazol-4-yl][1,2,4]triazolo[1,5-a]pyridine-5-carboxamide (mixture of diastereomers)

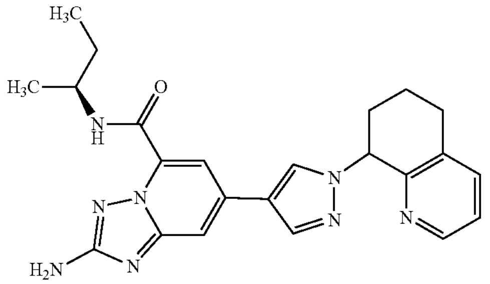 [SMILES: CC[C@H](C)NC(=O)c1cc(-c2cnn(C3CCCc4cccnc43)c2)cc2nc(N)nn12]

The reaction was run in two batches of equal size. 2-Amino-N-[(2S)-butan-2-yl]-7-chloro[1,2,4]triazolo[1,5-a]pyridine-5-carboxamide (75.0 mg, 280 μmol) was reacted with [1-(5,6,7,8-tetrahydroquinolin-8-yl)-1H-pyrazol-4-yl]boronic acid (95.3 mg, 392 mol) for 2 h at 90° C. following general procedure B using 0.1 eq. catalyst. The reaction mixture was diluted with ethyl acetate (5 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 7:3 to 0:1). The product was further purified by preparative HPLC (Chromatorex C18, 10 μm, 125×30 mm; eluent: water+0.1% formic acid/acetonitrile gradient) to yield 33.1 mg (100% purity, 14% yield) of the title compound.

LC-MS (method 1): $R_t$=1.48 min; MS (ESIpos): m/z=431 $[M+H]^+$ $^1$H-NMR (600 MHz, DMSO-$d_6$) δ [ppm]: 0.95 (t, 3H), 1.23 (d, 3H), 1.61 (quin, 2H), 1.79-1.88 (m, 1H), 1.96-2.05 (m, 1H), 2.25-2.39 (m, 2H), 2.83 (dt, 1H), 2.90-2.97 (m, 1H), 3.96-4.04 (m, 1H), 5.59 (t, 1H), 6.34 (s, 2H), 7.26 (dd, 1H), 7.63 (d, 1H), 7.76 (dd, 2H), 8.08 (s, 1H), 8.33 (d, 1H), 8.39 (s, 1H), 10.09 (d, 1H).

Example I-23

2-Amino-N-[(2S)-butan-2-yl]-6-{1-[(1H-indazol-7-yl)methyl]-1H-pyrazol-4-yl}[1,2,4]triazolo[1,5-a]pyridine-8-carboxamide (single stereoisomer)

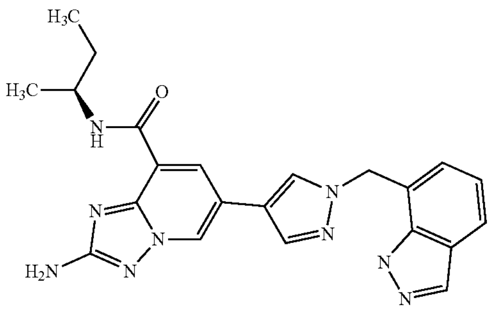

To a mixture of 2-amino-6-bromo-N-[(2S)-butan-2-yl][1,2,4]triazolo[1,5-a]pyridine-8-carboxamide (60.0 mg, 192 μmol), 7-{[4-(4,4,5,5-tetramethyl-1,3,2-dioxaborolan-2-yl)-1H-pyrazol-1-yl]methyl}-1H-indazole (74.8 mg, 231 mol), sodium carbonate (106 mg, 769 μmol), and 1,1'-bis(diphenylphosphino)ferrocene-palladium(II)dichloride dichloromethane complex [CAS-RN 95464-05-4](7.85 mg, 9.61 μmol) was added a degassed mixture of 1,4-dioxane (1.2 ml) and water (400 l). The reaction mixture was stirred at 90° C. for 1 h. The reaction mixture was then diluted with ethyl acetate and filtered through a hydrophobic phase separation filter which was rinsed with ethyl acetate. The filtrate was evaporated under reduced pressure. The residue was purified by column chromatography (Biotage® SNAP KP-NH 11 g cartridge, eluent: cyclohexane/ethyl acetate gradient 1:1 to 0:1, then ethyl acetate/2-propanol 1:0 to 8:2) and product fractions were collected. The compound was then further purified by HPLC (Chromatorex C18, 10 m, 125×30 mm; eluent: water/acetonitrile gradient 9:1 to 1:9) to yield 23.2 mg (100% purity, 28% yield) of the title compound.

LC-MS (method 1): $R_t$=1.49 min; MS (ESIpos): m/z=430 $[M+H]^+$ $^1$H-NMR (500 MHz, DMSO-$d_6$) δ [ppm]: 0.94 (t, 3H), 1.21 (d, 3H), 1.53-1.63 (m, 2H), 3.97-4.06 (m, 1H), 5.68 (s, 2H), 6.39 (s, 2H), 7.07-7.12 (m, 1H), 7.13-7.16 (m, 1H), 7.73 (dd, 1H), 8.05 (d, 1H), 8.14 (s, 1H), 8.24 (d, 1H), 8.55 (s, 1H), 9.05 (d, 1H), 9.28 (d, 1H), 13.22 (br s, 1H).

Example I-24

2-Amino-N-[(2S)-butan-2-yl]-7-{1-[2-methyl-1-phenylpropyl]-1H-pyrazol-4-yl}[1,2,4]triazolo[1,5-a]pyridine-5-carboxamide (mixture of diastereomers)

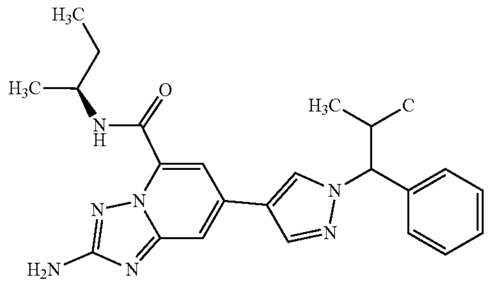

2-Amino-N-[(2S)-butan-2-yl]-7-chloro[1,2,4]triazolo[1,5-a]pyridine-5-carboxamide (150 mg, 92% purity, 515 μmol) was reacted with 1-[2-methyl-1-phenylpropyl]-4-(4,4,5,5-tetramethyl-1,3,2-dioxaborolan-2-yl)-1H-pyrazole (252 mg, 90% purity, 696 mol) for 90 min at 90° C. following general procedure C using 0.1 eq. catalyst. The reaction mixture was directly purified by chromatography (Biotage® SNAP Ultra 25 g cartridge, eluent: dichloromethane/methanol gradient 1:0 to 85:15). The product was further purified by HPLC (Chromatorex C18, 10 m, 125×30 mm; eluent: water (0.1% formic acid)/acetonitrile gradient 1:0 to 85:15) to yield 180 mg (99% purity, 80% yield) of the title compound.

LC-MS (method 2): $R_t$=1.14 min; MS (ESIpos): m/z=432 $[M+H]^+$ $^1$H-NMR (500 MHz, DMSO-$d_6$) δ [ppm]: 0.78 (d, 3H), 0.83 (d, 3H), 0.95 (t, 3H), 1.24 (d, 3H), 1.61 (quin, 2H), 2.72-2.84 (m, 1H), 3.97-4.06 (m, 1H), 4.95 (d, 1H), 6.33 (s, 2H), 7.27-7.32 (m, 1H), 7.34-7.39 (m, 2H), 7.54-7.58 (m, 2H), 7.74-7.79 (m, 2H), 8.13 (s, 1H), 8.70 (s, 1H), 10.08 (d, 1H).

Example I-25

2-Amino-N-[(2S)-butan-2-yl]-7-{1-[2-methyl-1-phenylpropyl]-1H-pyrazol-4-yl}[1,2,4]triazolo[1,5-a]pyridine-5-carboxamide (stereoisomer 1, distomer)

2-Amino-N-[(2S)-butan-2-yl]-7-{1-[2-methyl-1-phenylpropyl]-1H-pyrazol-4-yl}[1,2,4]triazolo[1,5-a]pyridine-5-carboxamide (mixture of diastereomers) (163 mg, 99% purity) from the previous example was separated by chiral chromatography to yield stereoisomer 1 (56 mg, 100% purity) and stereoisomer 2 (62 mg, 100% purity).

Column: Daicel Chiralpak IA 5 μm, 250×20 mm; Eluent A: iso-hexane; Eluent B: ethanol+0.2% diethylamine; isocratic: 50% A+50% B; flow: 35 ml/min; UV: 220 nm; temperature: 40° C.

Stereoisomer 1: $R_t$=6.40 min and

Stereoisomer 2: $R_t$=7.59 min (cf. next example)

Analytical chiral HPLC. Column: Daicel Chiralpak IA-3, 3 µm, 50×4.6 mm; Eluent A: n-heptane; Eluent B: 2-propanol+0.2% diethylamine; isocratic: 50% A+50% B; flow: 1 ml/min; UV: 220 nm.

Stereoisomer 1: $R_t$=1.225 min and

Stereoisomer 2: $R_t$=1.393 min (cf. next example) LC-MS (method 2): $R_t$=1.07 min; MS (ESIpos): m/z=432 $[M+H]^+$ $^1$H-NMR (600 MHz, DMSO-$d_6$) δ [ppm]: 0.78 (d, 3H), 0.83 (d, 3H), 0.95 (t, 3H), 1.24 (d, 3H), 1.61 (quin, 2H), 2.74-2.82 (m, 1H), 3.97-4.05 (m, 1H), 4.95 (d, 1H), 6.34 (s, 2H), 7.27-7.31 (m, 1H), 7.34-7.38 (m, 2H), 7.54-7.58 (m, 2H), 7.75-7.78 (m, 2H), 8.14 (s, 1H), 8.71 (s, 1H), 10.08 (d, 1H).

Example I-26

2-Amino-N-[(2S)-butan-2-yl]-7-{1-[2-methyl-1-phenylpropyl]-1H-pyrazol-4-yl}[1,2,4]triazolo[1,5-a]pyridine-5-carboxamide (stereoisomer 2, eutomer)

The product was isolated in the previous example as second stereoisomer.

LC-MS (method 2): $R_t$=1.07 min; MS (ESIpos): m/z=432 $[M+H]^+$ $^1$H-NMR (600 MHz, DMSO-$d_6$) δ [ppm]: 0.78 (d, 3H), 0.83 (d, 3H), 0.95 (t, 3H), 1.24 (d, 3H), 1.61 (quin, 2H), 2.73-2.82 (m, 1H), 3.97-4.05 (m, 1H), 4.95 (d, 1H), 6.35 (s, 2H), 7.27-7.31 (m, 1H), 7.34-7.38 (m, 2H), 7.54-7.58 (m, 2H), 7.75-7.78 (m, 2H), 8.14 (s, 1H), 8.71 (s, 1H), 10.08 (d, 1H).

Example I-27

2-Amino-N-[(2S)-butan-2-yl]-6-{1-[cyclobutyl(phenyl)methyl]-1H-pyrazol-4-yl}[1,2,4]triazolo[1,5-a]pyridine-8-carboxamide (mixture of diastereomers)

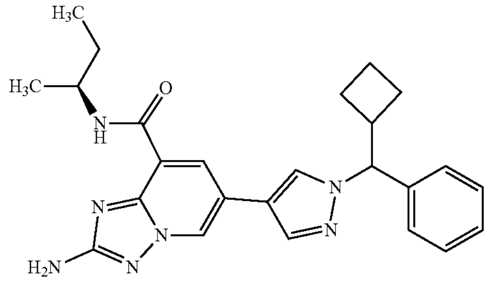 [SMILES: CC[C@H](C)NC(=O)c1cc(-c2cnn(C(c3ccccc3)C3CCC3)c2)cn2nc(N)nc12]

2-Amino-6-bromo-N-[(2S)-butan-2-yl][1,2,4]triazolo[1,5-a]pyridine-8-carboxamide (9.43 mg, 30.2 mol), 1-[cyclobutyl(phenyl)methyl]-4-(4,4,5,5-tetramethyl-1,3,2-dioxaborolan-2-yl)-1H-pyrazole (13.6 mg, 90% purity, 36.3 µmol), sodium carbonate (16.0 mg, 151 µmol) and 1,1'-bis(diphenylphosphino)ferrocene-palladium(II)dichloride dichloromethane complex (1.23 mg, 1.51 µmol) were reacted according to procedure A in a mixture of 1,4-dioxane (300 l) and water (100 µl). The residue was purified by preparative HPLC (neutral) to yield 9.00 mg (91% purity, 61% yield) of the title compound as a mixture of diastereoisomers.

LC-MS (method 1): $R_t$=2.05 min; MS (ESIpos): m/z=444 $[M+H]^+$ $^1$H-NMR (400 MHz, DMSO-$d_6$) δ [ppm]: 0.94 (t, 3H), 1.21 (d, 3H), 1.54-1.62 (m, 2H), 1.71-1.93 (m, 6H), 1.98-2.06 (m, 1H), 3.33-3.43 (m, 1H), 3.98-4.05 (m, 1H), 5.36 (d, 1H), 6.38 (s, 2H), 7.25-7.41 (m, 6H), 8.00 (s, 11H), 8.26 (d, 11H), 8.52 (s, 1H), 9.05 (d, 11H), 9.28 (d, 1H).

Example I-28

2-Amino-N-[(2S)-butan-2-yl]-6-{1[(1-methylcyclopropyl)(phenyl)methyl]-1H-pyrazol-4-yl}[1,2,4]triazolo[1,5-a]pyridine-8-carboxamide (mixture of diastereomers)

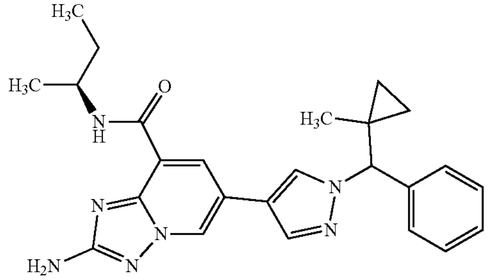 [SMILES: CC[C@H](C)NC(=O)c1cc(-c2cnn(C(c3ccccc3)C3(C)CC3)c2)cn2nc(N)nc12]

2-Amino-6-bromo-N-[(2S)-butan-2-yl][1,2,4]triazolo[1,5-a]pyridine-8-carboxamide (236 mg, 757 µmol), 1-[(1-methylcyclopropyl)(phenyl)methyl]-4-(4,4,5,5-tetramethyl-1,3,2-dioxaborolan-2-yl)-1H-pyrazole (320 mg, 96% purity, 908 µmol), sodium carbonate (401 mg, 3.78 mmol) and 1,1'-bis(diphenylphosphino)ferrocene-palladium(II)dichloride dichloromethane complex (30.9 mg, 37.8 µmol) were reacted according to procedure A in a mixture of 1,4-dioxane (8.0 ml) and water (1.5 ml). The reaction mixture was stirred at 90° C. for 2.5 h. The residue was purified by preparative HPLC to give a diastereomeric mixture of 267 mg (95% purity, 75% yield) of the title compound.

LC-MS (method 1): $R_t$=2.04 min; MS (ESIpos): m/z=444 $[M+H]^+$ $^1$H-NMR (400 MHz, DMSO-$d_6$) δ [ppm]: 0.41-0.55 (m, 3H), 0.71-0.77 (m, 1H), 0.94 (t, 3H), 1.13 (s, 3H), 1.22 (d, 3H), 1.53-1.63 (m, 2H), 3.98-4.06 (m, 1H), 5.24-5.28 (m, 1H), 6.39 (s, 2H), 7.22-7.38 (m, 5H), 8.07 (s, 1H), 8.29 (d, 1H), 8.49 (s, 11H), 9.13 (d, 11H), 9.29 (d, 1H).

Example I-29

2-Amino-N-[(2S)-butan-2-yl]-6-{1[(1-methylcyclopropyl)(phenyl)methyl]-1H-pyrazol-4-yl}[1,2,4]triazolo[1,5-a]pyridine-8-carboxamide (stereoisomer 1, eutomer)

2-Amino-N-[(2S)-butan-2-yl]-6-{1[(1-methylcyclopropyl)(phenyl)methyl]-1H-pyrazol-4-yl}[1,2,4]triazolo[1,5-a]pyridine-8-carboxamide (mixture of diastereomers) (267 mg, 95% purity) from the previous example was separated by chiral preparative SFC to yield 92 mg of stereoisomer 1 and 91 mg of stereoisomer 2.

Instrument: THAR SFC-Super Chrom Prep 200; Column: Daicel OJ-H, 5 m, 250×25 mm; Eluent A: $CO_2$; Eluent B: methanol; isocratic: 82% A+18% B; flow: 80 ml/min; UV: 210 nm; temperature: 40° C.

Stereoisomer 1: $R_t$=4.80 min and

Stereoisomer 2: $R_t$=8.23 min (see next example)

Analytical SFC-method: Column: Chiralcel AD, 3 μm, 4.6×100 mm; Eluent A: $CO_2$; Eluent B: methanol; isocratic: 80% A+20% B; flow: 3 ml/min; UV: 210 nm; temperature: 40° C.

Stereoisomer 1: $R_t$=1.89 min and

Stereoisomer 2: $R_t$=2.77 min (see next example)

LC-MS (method 1): $R_t$=2.04 min; MS (ESIpos): m/z=444 $[M+H]^+$ $^1$H-NMR (400 MHz, DMSO-$d_6$) δ [ppm]: 0.44-0.55 (m, 3H), 0.72-0.77 (m, 1H), 0.94 (t, 3H), 1.13 (s, 3H), 1.22 (d, 3H), 1.53-1.63 (m, 2H), 3.98-4.06 (m, 1H), 5.27 (s, 1H), 6.39 (s, 2H), 7.27-7.37 (m, 5H), 8.06 (s, 1H), 8.29 (d, 1H), 8.49 (s, 1H), 9.13 (d, 1H), 9.29 (d, 1H).

Example I-30

2-Amino-N-[(2S)-butan-2-yl]-6-{1[(1-methylcyclopropyl)(phenyl)methyl]-1H-pyrazol-4-yl}[1,2,4]triazolo[1,5-a]pyridine-8-carboxamide (sterioisomer 2, distomer)

The product was isolated in the previous example as second stereoisomer.

LC-MS (method 1): $R_t$=2.05 min; MS (ESIpos): m/z=444 $[M+H]^+$ $^1$H-NMR (400 MHz, DMSO-$d_6$) δ [ppm]: −0.008 (3.25), 0.006 (2.22), 0.008 (3.06), 0.445 (0.75), 0.459 (1.26), 0.472 (1.38), 0.493 (1.08), 0.503 (1.58), 0.516 (4.20), 0.530 (1.41), 0.539 (0.74), 0.729 (1.01), 0.742 (1.35), 0.756 (0.82), 0.925 (4.26), 0.944 (10.20), 0.962 (4.83), 1.129 (16.00), 1.212 (9.73), 1.228 (9.81), 1.547 (0.53), 1.565 (1.66), 1.572 (1.32), 1.583 (2.24), 1.601 (1.48), 1.606 (1.49), 1.625 (0.49), 2.367 (0.43), 2.524 (1.11), 2.710 (0.43), 3.982 (0.42), 3.999 (0.93), 4.017 (1.14), 4.035 (0.94), 4.051 (0.42), 5.266 (4.98), 6.386 (5.57), 7.269 (0.85), 7.279 (2.93), 7.286 (2.78), 7.299 (5.73), 7.333 (4.38), 7.351 (2.88), 7.365 (0.72), 7.370 (1.19), 8.065 (5.88), 8.284 (4.59), 8.288 (4.57), 8.486 (5.52), 9.131 (4.54), 9.136 (4.41), 9.276 (1.97), 9.296 (1.90).

Example I-31

2-Amino-N-[(2S)-butan-2-yl]-6-{1-[(3,3-difluorocyclobutyl)(phenyl)methyl]-1H-pyrazol-4-yl}[1,2,4]triazolo[1,5-a]pyridine-8-carboxamide (mixture of diastereomers)

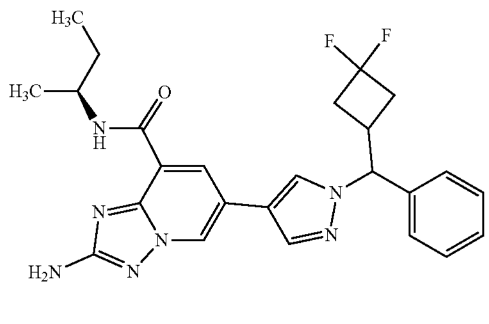 [SMILES: CC[C@H](C)NC(=O)c1cc(-c2cnn(C(c3ccccc3)C3CC(F)(F)C3)c2)cn2nc(N)nc12]

2-Amino-6-bromo-N-[(2S)-butan-2-yl][1,2,4]triazolo[1,5-a]pyridine-8-carboxamide (298 mg, 956 μmol), 1-[(3,3-difluorocyclobutyl)(phenyl)methyl]-4-(4,4,5,5-tetramethyl-1,3,2-dioxaborolan-2-yl)-1H-pyrazole (517 mg, 83% purity, 1.15 mmol), sodium carbonate (506 mg, 4.78 mmol) and 1,1'-bis(diphenylphosphino)ferrocene-palladium(II)dichloride dichloromethane complex (39.0 mg, 47.8 mol) were reacted according to procedure A in a mixture of 1,4-dioxane (8.0 ml) and water (1.5 ml). After 3 h at 90° C., the reaction mixture was quenched with water, filtered through a hydrophobic phase separation filter which was rinsed with ethyl acetate (15 ml). The solvent was removed in vacuo and the residue was purified by preparative HPLC to give a diasteromeric mixture of 352 mg (100% purity, 77% yield) of the title compound.

LC-MS (method 1): $R_t$=1.98 min; MS (ESIpos): m/z=480 $[M+H]^+$ $^1$H-NMR (400 MHz, DMSO-$d_6$) δ [ppm]: 0.94 (t, 3H), 1.21 (d, 3H), 1.56-1.61 (m, 2H), 2.33-2.47 (m, 2H), 2.63-2.75 (m, 1H), 3.98-4.05 (m, 1H), 5.48 (d, 1H), 6.39 (s, 2H), 7.28-7.39 (m, 3H), 7.44 (d, 2H), 8.05 (s, 1H), 8.27 (d, 1H), 8.57 (s, 1H), 9.06 (d, 1H), 9.27 (d, 1H).

Example I-32

2-Amino-N-[(2S)-butan-2-yl]-6-{1-[(3,3-difluorocyclobutyl)(phenyl)methyl]-1H-pyrazol-4-yl}[1,2,4]triazolo[1,5-a]pyridine-8-carboxamide (stereoisomer 1, distomer)

2-Amino-N-[(2S)-butan-2-yl]-6-{1-[(3,3--difluorocyclobutyl)(phenyl)methyl]-1H-pyrazol-4-yl}[1,2,4]triazolo[1,5-a]pyridine-8-carboxamide (352 mg, 100% purity) from the previous example was separated by chiral preparative SFC to yield 123 mg of stereoisomer 1 and 118 mg of stereoisomer 2.

Instrument: THAR SFC-Super Chrom Prep 200; Column: Daicel OJ-H, 5 μm, 250×25 mm; Eluent A: $CO_2$; Eluent B: methanol; isocratic: 80% A+20% B; flow: 80 ml/min; UV: 210 nm; temperature: 40° C.

Analytical SFC-method: Column: Chiralcel AD, 3 μm, 4.6×100 mm; Eluent A: $CO_2$; EluentB: methanol; isocratic: 80% A+20% B; flow: 3 ml/min; UV: 210 nm; temperature: 40° C.

Stereoisomer 1: $R_t$=1.44 min and

Stereoisomer 2: $R_t$=1.69 min (cf. next example)

LC-MS (method 1): $R_t$=1.99 min; MS (ESIpos): m/z=480 $[M+H]^+$ $^1$H-NMR (400 MHz, DMSO-$d_6$) δ [ppm]: −0.149 (0.69), −0.008 (6.36), 0.008 (5.82), 0.146 (0.71), 0.920 (6.71), 0.939 (16.00), 0.957 (7.56), 1.206 (15.23), 1.222 (15.38), 1.541 (0.81), 1.559 (2.54), 1.566 (2.08), 1.577 (3.47), 1.582 (2.74), 1.595 (2.26), 1.601 (2.33), 1.619 (0.79), 2.328 (0.48), 2.367 (1.08), 2.445 (1.39), 2.524 (2.41), 2.670 (1.08), 2.674 (1.10), 2.689 (0.87), 2.710 (1.56), 2.723 (0.71), 3.980 (0.67), 3.996 (1.48), 4.014 (1.81), 4.032 (1.47), 4.048 (0.66), 5.462 (3.18), 5.490 (3.08), 6.384 (8.91), 7.287 (0.91), 7.298 (0.67), 7.305 (3.39), 7.312 (1.10), 7.323 (3.24), 7.343 (4.32), 7.362 (7.09), 7.380 (3.26), 7.430 (7.36), 7.448 (4.93), 7.452 (3.49), 8.047 (9.25), 8.262 (6.86), 8.266 (6.88), 8.572 (8.79), 9.060 (6.73), 9.064 (6.67), 9.263 (3.20), 9.283 (3.12).

Example I-33

2-Amino-N-[(2S)-butan-2-yl]-6-{1-[(3,3-difluorocyclobutyl)(phenyl)methyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 1): $R_t$=1.99 min; MS (ESIpos): m/z=480 $[M+H]^+$ $^1$H-NMR (400 MHz, DMSO-$d_6$) δ [ppm]: 0.94 (t, 3H), 1.21 (d, 3H), 1.54-1.62 (m, 2H), 2.37-2.48 (m, 2H), 2.64-2.76 (m, 1H), 3.96-4.06 (m, 1H), 5.48 (d, 1H), 6.38 (s, 2H), 7.29-7.40 (m, 3H), 7.44 (d, 2H), 8.05 (s, 1H), 8.26 (d, 1H), 8.57 (s, 1H), 9.06 (d, 1H), 9.27 (d, 1H).

Example I-34

2-Amino-N-[(2S)-butan-2-yl]-6-{1-[2,2-dimethyl-1-phenylpropyl]-1H-pyrazol-4-yl}[1,2,4]triazolo[1,5-a]pyridine-8-carboxamide (mixture of diastereomers)

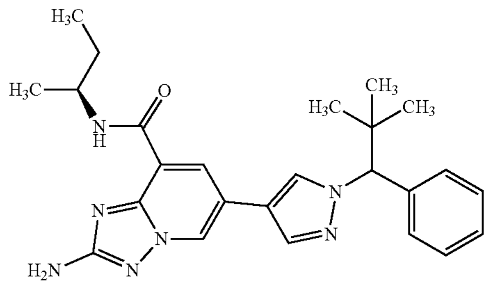 [SMILES: CC[C@H](C)NC(=O)c1cc(-c2cnn(C(c3ccccc3)C(C)(C)C)c2)cn2nc(N)nc12]

2-Amino-6-bromo-N-[(2S)-butan-2-yl][1,2,4]triazolo[1,5-a]pyridine-8-carboxamide (175 mg, 561 μmol), 1-[2,2-dimethyl-1-phenylpropyl]-4-(4,4,5,5-tetramethyl-1,3,2-dioxaborolan-2-yl)-1H-pyrazole (229 mg, 673 μmol), sodium carbonate (297 mg, 2.80 mmol) and 1,1'-bis(diphenylphosphino)ferrocene-palladium(II)dichloride dichloromethane complex (22.9 mg, 28.0 μmol) were reacted according to procedure A in a mixture of 1,4-dioxane (4.0 ml) and water (1.5 μl). After stirring for 2.5 h at 90° C., the reaction mixture was quenched with water and filtered through a hydrophobic phase separation filter which was rinsed with ethyl acetate (15 ml). The filtrate was concentrated in vacuo. The residue was purified by column chromatography (Biotage® SNAP KP-NH 11 g cartridge, eluent: cyclohexane/ethyl acetate gradient 9:1 to 1:1) to yield 134 mg (100% purity, 54% yield) of the title compound as a mixture of two diastereomers.

LC-MS (method 1): $R_t$=2.24 min; MS (ESIpos): m/z=446 $[M+H]^+$ $^1$H-NMR (400 MHz, DMSO-$d_6$) δ [ppm]: 0.94 (t, 3H), 0.99 (s, 9H), 1.21 (d, 3H), 1.54-1.63 (m, 2H), 3.92-4.05 (m, 1H), 5.25 (s, 1H), 6.38 (s, 2H), 7.28-7.38 (m, 3H), 7.67 (d, 2H), 8.10 (s, 1H), 8.23 (d, 1H), 8.48 (s, 1H), 9.06 (d, 1H), 9.27 (d, 1H).

Example I-35

2-Amino-N-[(2S)-butan-2-yl]-6-{1-[2,2-dimethyl-1-phenylpropyl]-1H-pyrazol-4-yl}[1,2,4]triazolo[1,5-a]pyridine-8-carboxamide (stereoisomer 1, distomer)

2-Amino-N-[(2S)-butan-2-yl]-6-{1-[2,2-dimethyl-1-phenylpropyl]-1H-pyrazol-4-yl}[1,2,4]triazolo[1,5-a]pyridine-8-carboxamide (134 mg, 100% purity) was separated by chiral preparative HPLC to yield stereoisomer 1 (33.7 mg, 100% purity) and stereoisomer 2 (35.2 mg, 100% purity).

Column: Daicel Chiralpak AD_H, 5 m, 250×20 mm; Eluent A: n-heptane; Eluent B: ethanol; isocratic: 30% A+70% B; flow: 20 ml/min; UV: 220 nm; temperature: 40° C.

Stereoisomer 1: $R_t$=2.56 min and

Stereoisomer 2: $R_t$=4.65 min (cf. next example)

Analytical chiral HPLC-method: Column: Daicel Chiralpak AD-3, 3 m, 50×4.6 mm; Eluent A: n-heptane; Eluent B: 2-propanol+0.2% diethylamine; isocratic: 50% A+50% B; flow: 1 ml/min; UV: 220 nm Stereoisomer 1: $R_t$=1.16 min and Stereoisomer 2: $R_t$=1.71 min (cf. next example)

LC-MS (method 1): $R_t$=2.24 min; MS (ESIpos): m/z=446 $[M+H]^+$ $^1$H-NMR (400 MHz, DMSO-$d_6$) δ [ppm]: 0.918 (1.82), 0.937 (4.37), 0.955 (2.14), 0.988 (16.00), 1.204 (4.12), 1.220 (4.16), 1.558 (0.74), 1.563 (0.59), 1.576 (0.99), 1.594 (0.64), 1.597 (0.68), 2.525 (0.42), 4.010 (0.47), 5.254 (2.04), 6.379 (2.31), 7.299 (0.92), 7.316 (0.86), 7.335 (1.33), 7.354 (1.74), 7.371 (0.66), 7.375 (0.43), 7.659 (1.68), 7.676 (1.54), 7.680 (1.13), 8.099 (2.32), 8.230 (1.94), 8.235 (1.97), 8.476 (2.14), 9.052 (1.95), 9.057 (1.94), 9.261 (0.82), 9.280 (0.80).

Example I-36

2-Amino-N-[(2S)-butan-2-yl]-6-{1-[2,2-dimethyl-1-phenylpropyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 1): $R_t$=2.23 min; MS (ESIpos): m/z=446 $[M+H]^+$ $^1$H-NMR (400 MHz, DMSO-$d_6$) δ [ppm]: 0.94 (t, 3H), 0.99 (s, 9H), 1.21 (d, 3H), 1.56-1.62 (m, 2H), 3.98-4.05 (m, 1H), 5.25 (s, 1H), 6.38 (s, 2H), 7.28-7.38 (m, 3H), 7.67 (d, 2H), 8.10 (s, 1H), 8.23 (d, 1H), 8.48 (s, 1H), 9.06 (d, 1H), 9.27 (d, 1H).

Example I-37

2-Amino-N-[(2S)-butan-2-yl]-6-{1-[3,3,3-trifluoro-1-phenylpropyl]-1H-pyrazol-4-yl}[1,2,4]triazolo[1,5-a]pyridine-8-carboxamide (mixture of diastereomers)

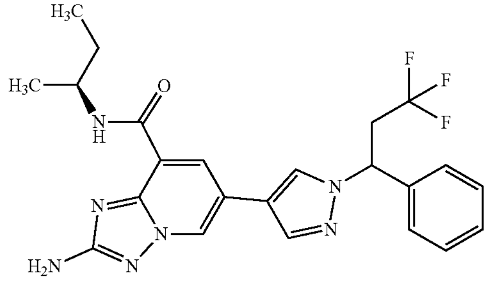 [SMILES: CC[C@H](C)NC(=O)c1cc(-c2cnn(C(CC(F)(F)F)c3ccccc3)c2)cn2nc(N)nc12]

2-Amino-6-bromo-N-[(2S)-butan-2-yl][1,2,4]triazolo[1,5-a]pyridine-8-carboxamide (364 mg, 1.17 mmol), 4-(4,4,5,5-tetramethyl-1,3,2-dioxaborolan-2-yl)-1-(3,3,3-trifluoro-1-phenylpropyl)-1H-pyrazole (513 mg, 1.40 mmol), sodium carbonate (619 mg, 5.84 mmol) and 1,1'-bis(diphenylphosphino)ferrocene-palladium(II)dichloride dichloromethane complex (47.7 mg, 58.4 μmol) were reacted according to procedure A in a mixture of 1,4-dioxane (10 ml) and water (2.0 ml). After 3 h at 90° C., the reaction mixture was quenched with water and filtered through a hydrophobic phase separation filter, which was rinsed with ethyl acetate (15 ml). The filtrate was concentrated and dried under reduced pressure. The residue was purified by preparative HPLC to give 188 mg (100% purity, 34% yield) of the title compound as a diastereomeric mixture.

LC-MS (method 1): $R_t$=1.95 min; MS (ESIpos): m/z=472 $[M+H]^+$ $^1$H-NMR (400 MHz, DMSO-$d_6$) δ [ppm]: 0.94 (t, 3H), 1.21 (d, 3H), 1.54-1.62 (m, 2H), 3.20-3.30 (m, 1H), 3.62-3.67 (m, 1H), 4.01 (dt, 1H), 5.85 (dd, 1H), 6.39 (s, 2H), 7.30-7.43 (m, 3H), 7.49 (d, 2H), 8.09 (s, 1H), 8.23 (d, 1H), 8.64 (s, 1H), 9.05 (d, 1H), 9.27 (d, 1H).

Example I-38

2-Amino-N-[(2S)-butan-2-yl]-6-[1-(3,3,3-trifluoro-1-phenylpropyl)-1H-pyrazol-4-yl][1,2,4]triazolo[1,5-a]pyridine-8-carboxamide (stereoisomer 1, eutomer)

2-Amino-N-[(2S)-butan-2-yl]-6-{1-[3,3,3-trifluoro-1-phenylpropyl]-1H-pyrazol-4-yl}[1,2,4]triazolo[1,5-a]pyridine-8-carboxamide (mixture of diastereomers) (188 mg, 100% purity) was separated by chiral preparative SFC to yield stereoisomer 1 (68 mg, 100% purity) and stereoisomer 2 (73 mg, 100% purity).

Instrument: THAR SFC-Super Chrom Prep 200; Column: Daicel Chiralpak AD-H, 5 μm, 250×20 mm; Eluent A: $CO_2$; Eluent B: ethanol; isocratic: 75% A+25% B; flow: 80 ml/min; UV: 210 nm; temperature: 40° C.

Analytical SFC-method: Column: Chiralcel AD, 3 μm, 4.6×100 mm; Eluent A: $CO_2$; Eluent B: ethanol; isocratic: 75% A+25% B; flow: 3 ml/min; UV: 210 nm; temperature: 40° C.

Stereoisomer 1: $R_t$=2.75 min and

Stereoisomer 2: $R_t$=3.40 (cf. next example)

LC-MS (method 1): $R_t$=1.95 min; MS (ESIpos): m/z=472 $[M+H]^+$ $^1$H-NMR (400 MHz, DMSO-$d_6$) δ [ppm]: 0.94 (t, 3H), 1.21 (d, 3H), 1.53-1.64 (m, 2H), 3.21-3.30 (m, 1H), 3.66 (dquin, 1H), 4.02 (dt, 1H), 5.85 (dd, 1H), 6.39 (s, 2H), 7.30-7.41 (m, 3H), 7.49 (d, 2H), 8.09 (s, 11H), 8.23 (d, 1H), 8.64 (s, 11H), 9.04 (d, 11H), 9.27 (d, 1H).

Example I-39

2-Amino-N-[(2S)-butan-2-yl]-6-[1-(3,3,3-trifluoro-1-phenylpropyl)-1H-pyrazol-4-yl][1,2,4]triazolo[1,5-a]pyridine-8-carboxamide (stereoisomer 2, distomer)

The product was isolated in the previous example as second stereoisomer.

LC-MS (method 1): $R_t$=1.95 min; MS (ESIpos): m/z=472 $[M+H]^+$ $^1$H-NMR (400 MHz, DMSO-$d_6$) δ [ppm]: −0.149 (0.47), −0.008 (4.15), 0.008 (3.81), 0.146 (0.42), 0.920 (6.82), 0.938 (16.00), 0.957 (7.76), 1.205 (15.15), 1.222 (15.30), 1.541 (0.90), 1.559 (2.63), 1.566 (2.22), 1.577 (3.62), 1.595 (2.35), 1.600 (2.44), 1.618 (0.81), 2.328 (0.58), 2.367 (0.57), 2.671 (0.55), 2.711 (0.52), 3.240 (0.71), 3.253 (1.07), 3.267 (0.86), 3.280 (1.67), 3.619 (0.93), 3.644 (1.40), 3.657 (0.97), 3.670 (1.04), 3.682 (1.18), 3.707 (0.83), 3.979 (0.72), 3.997 (1.56), 4.015 (1.98), 4.032 (1.64), 4.049 (0.72), 5.834 (1.86), 5.847 (1.91), 5.859 (1.93), 5.871 (1.66), 6.393 (9.27), 7.306 (0.98), 7.324 (3.57), 7.342 (3.49), 7.362 (5.03), 7.380 (7.55), 7.398 (3.12), 7.477 (7.53), 7.495 (5.55), 8.093 (9.94), 8.223 (7.20), 8.228 (7.20), 8.642 (9.07), 9.042 (7.06), 9.047 (7.09), 9.256 (3.17), 9.276 (3.16).

Example I-40

2-Amino-N-[(2S)-butan-2-yl]-6-[1-(2-methoxy-1-phenylethyl)-1H-pyrazol-4-yl][1,2,4]triazolo[1,5-a]pyridine-8-carboxamide (mixture of diastereomers)

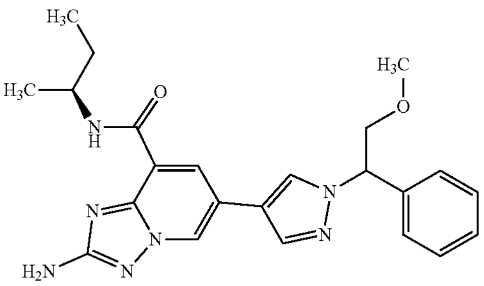 [SMILES: CC[C@H](C)NC(=O)c1cc(-c2cnn(C(COC)c3ccccc3)c2)cn2nc(N)nc12]

2-Amino-6-bromo-N-[(2S)-butan-2-yl][1,2,4]triazolo[1,5-a]pyridine-8-carboxamide (300 mg, 961 μmol) was reacted with 1-(2-methoxy-1-phenylethyl)-4-(4,4,5,5-tetramethyl-1,3,2-dioxaborolan-2-yl)-1H-pyrazole (386 mg, 90% purity, 1.06 mmol) for 1 h at 90° C. following general procedure B using 0.1 eq. catalyst. The reaction mixture was filtered through kieselgur which was rinsed with 15 ethyl acetate (50 ml) and water (50 ml). The filtrates were collected and the aqueous layer was extracted with ethyl acetate (50 ml). The combined organic layers were washed with brine and filtered through a hydrophobic phase separation filter. The solvent was evaporated under reduced pressure and the residue purified by column chromatography (Biotage® SNAP Ultra 25 g cartridge, eluent: cyclohexane/ethyl acetate gradient 80:20 to 0:100) to yield 297 mg (95% purity, 68% 20 yield) of the title compound.

LC-MS (method 1): $R_t$=1.71 min; MS (ESIpos): m/z=434 $[M+H]^+$ $^1$H-NMR (400 MHz, DMSO-$d_6$) δ [ppm]: 0.94 (t, 3H), 1.22 (d, 3H), 1.52-1.64 (m, 2H), 3.31 (s, 3H), 3.88 (dd, 1H), 3.96-4.08 (m, 1H), 4.27 (t, 1H), 5.69 (dd, 1H), 6.39 (s, 2H), 7.27-7.40 (m, 5H), 8.06 (s, 1H), 8.26 (d, 1H), 8.57 (s, 1H), 9.07 (d, 1H), 9.28 (d, 1H).

Example I-41

2-Amino-N-[(2S)-butan-2-yl]-6-[1-(2-methoxy-1-phenylethyl)-1H-pyrazol-4-yl][1,2,4]triazolo[1,5-a]pyridine-8-carboxamide (stereoisomer 1, eutomer)

2-Amino-N-[(2S)-butan-2-yl]-6-[1-(2-methoxy-1-phenylethyl)-1H-pyrazol-4-yl][1,2,4]triazolo[1,5-a]pyridine-8-carboxamide (mixture of diastereomers) (252 mg, 95% purity) from the previous example was separated by chiral chromatography to yield stereoisomer 1 (98 mg, 99% purity) and stereoisomer 2 (95 mg, 90% purity). Stereoisomer 2 was further purified by preparative HPLC (Chromatorex C18, 10 μm, 125×30 mm; eluent: water/acetonitrile gradient 90:10 to 5:95) to yield stereoisomer 2 (54 mg, 100% purity).

Column: Daicel Chiralpak AD-H 5, μm, 250×20 mm; Eluent A: n-heptane; Eluent B: 2-propanol; isocratic: 50% A+50% B; flow: 15 ml/min; UV: 210 nm; temperature: 50° C.

Stereoisomer 1: $R_t$=12.058 min and

Stereoisomer 2: $R_t$=15.976 min (cf. next example)

Analytical chiral HPLC. Column: Daicel AD-3, 3 m, 50×4.6 mm; Eluent A: n-heptane; Eluent B: 2-propanol; isocratic: 50% A+50% B; flow: 1 ml/min; UV: 220 nm.

Stereoisomer 1: $R_t$=3.550 min and

Stereoisomer 2: $R_t$=6.714 min (cf. next example)

LC-MS (method 1): $R_t$=1.71 min; MS (ESIpos): m/z=434 $[M+H]^+$ $^1$H-NMR (400 MHz, DMSO-$d_6$) δ [ppm]: 0.924 (0.75), 0.943 (1.80), 0.961 (0.85), 1.208 (1.70), 1.224 (1.71), 3.305 (5.14), 3.311 (16.00), 6.388 (1.00), 7.353 (1.01), 7.363 (1.08), 7.368 (1.82), 8.058 (1.13), 8.259 (0.82), 8.264 (0.80), 8.568 (1.02), 9.064 (0.84), 9.069 (0.79).

Example 1-42

2-Amino-N-[(2S)-butan-2-yl]-6-[1-(2-methoxy-1-phenylethyl)-1H-pyrazol-4-yl][1,2,4]triazolo[1,5-a]pyridine-8-carboxamide (stereoisomer 2, distomer)

The product was isolated in the previous example as second stereoisomer.

LC-MS (method 1): $R_t$=1.71 min; MS (ESIpos): m/z=434 $[M+H]^+$ $^1$H-NMR (400 MHz, DMSO-$d_6$) δ [ppm]: 0.923 (1.51), 0.942 (3.57), 0.961 (1.70), 1.209 (3.36), 1.225 (3.40), 1.563 (0.59), 1.569 (0.48), 1.581 (0.79), 1.599 (0.52), 1.603 (0.54), 3.305 (9.96), 3.310 (16.00), 3.863 (0.45), 3.875 (0.55), 3.889 (0.59), 3.901 (0.51), 4.017 (0.41), 4.241 (0.51), 4.265 (0.73), 4.290 (0.47), 5.668 (0.47), 5.680 (0.51), 5.692 (0.51), 5.704 (0.45), 6.388 (1.93), 7.302 (0.48), 7.311 (0.47), 7.318 (0.61), 7.324 (0.48), 7.333 (0.55), 7.353 (2.01), 7.363 (2.18), 7.368 (3.57), 8.058 (2.12), 8.259 (1.60), 8.264 (1.59), 8.568 (1.94), 9.064 (1.59), 9.069 (1.58), 9.271 (0.68), 9.290 (0.66).

Example I-43

2-Amino-N-[(2S)-butan-2-yl]-6-{1-[1-(4-fluorophenyl)-2-methylpropyl]-1H-pyrazol-4-yl}[1,2,4]triazolo[1,5-a]pyridine-8-carboxamide (mixture of diastereomers)

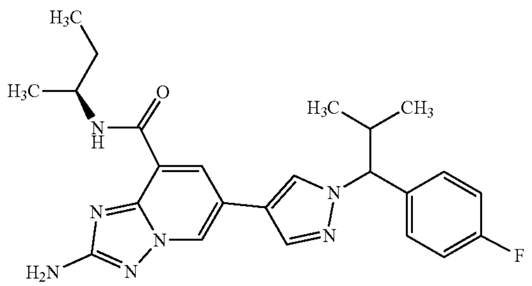 [SMILES: CC[C@H](C)NC(=O)c1cc(-c2cnn(C(c3ccc(F)cc3)C(C)C)c2)cn2nc(N)nc12]

2-Amino-6-bromo-N-[(2S)-butan-2-yl][1,2,4]triazolo[1,5-a]pyridine-8-carboxamide (295 mg, 944 μmol), 1-[1-(4-fluorophenyl)-2-methylpropyl]-4-(4,4,5,5-tetramethyl-1,3,2-dioxaborolan-2-yl)-1H-pyrazole (390 mg, 1.13 mmol), sodium carbonate (500 mg, 4.72 mmol) and 1,1'-bis(diphenylphosphino)ferrocene-palladium(II)dichloride dichloromethane complex (38.5 mg, 47.2 μmol) were reacted according to procedure A in a mixture of 1,4-dioxane (9 ml) and water (3 ml). After 3 h at 90° C., the reaction mixture was quenched with water and filtered through a hydrophobic phase separation filter which was rinsed with ethyl acetate (15 ml). The filtrate concentrated and dried under reduced pressure. The residue was purified by preparative HPLC to give 350 mg (100% purity, 82% yield) of the title compound as a diastereomeric mixture.

LC-MS (method 2): $R_t$=1.10 min; MS (ESIpos): m/z=450 $[M+H]^+$ $^1$H-NMR (400 MHz, DMSO-$d_6$) δ [ppm]: 0.78 (d, 2H), 0.81 (d, 1H), 0.94 (t, 3H), 1.21 (d, 3H), 1.56-1.62 (m, 2H), 2.66-2.78 (m, 1H), 3.96-4.06 (m, 1H), 4.98 (d, 1H), 6.38 (s, 2H), 7.18 (t, 2H), 7.60 (dd, 2H), 8.03 (s, 1H), 8.24 (d, 1H), 8.53 (s, 1H), 9.04 (d, 1H), 9.27 (d, 1H).

Example I-44

2-Amino-N-[(2S)-butan-2-yl]-6-{1-[1-(4-fluorophenyl)-2-methylpropyl]-1H-pyrazol-4-yl}[1,2,4]triazolo[1,5-a]pyridine-8-carboxamide (stereoisomer 1, distomer)

2-Amino-N-[(2S)-butan-2-yl]-6-{1-[1-(4-fluorophenyl)-2-methylpropyl]-1H-pyrazol-4-yl}[1,2,4]triazolo[1,5-a]pyridine-8-carboxamide (mixture of diastereomers) (350 mg 100% purity) was separated by chiral preparative SFC to yield stereoisomer 1 (166 mg, 95% purity) and stereoisomer 2 (166 mg, 95% purity).

Instrument: THAR SFC-Super Chrom Prep 200; Column: Daicel Chiralpak AD-H, 5 μm, 250×30 mm; Eluent A: $CO_2$; Eluent B: 2-propanol; isocratic: 65% A+35% B; flow: 115 ml/min; UV: 210 nm; temperature: 40° C.

Stereoisomer 1: $R_t$=5.32 min and

Stereoisomer 2: $R_t$=13.35 (cf. next example)

Analytical SFC-method: Column: Chiralcel AD, 3 μm, 4.6×50 mm; Eluent A: $CO_2$; Eluent B: 2-propanol; isocratic: 50% A+50% B; flow: 3 ml/min; UV: 220 nm; temperature: 40° C.

Stereoisomer 1: $R_t$=3.36 min and

Stereoisomer 2: $R_t$=4.36 (cf. next example)

LC-MS (method 1): $R_t$=2.05 min; MS (ESIpos): m/z=450 $[M+H]^+$ $^1$H-NMR (400 MHz, DMSO-$d_6$) δ [ppm]: −0.008 (2.83), 0.008 (2.19), 0.768 (10.93), 0.785 (11.13), 0.811 (11.94), 0.827 (12.05), 0.920 (6.77), 0.939 (16.00), 0.957 (7.60), 0.988 (0.63), 1.004 (0.62), 1.031 (9.42), 1.046 (9.58), 1.205 (15.46), 1.221 (15.70), 1.234 (1.74), 1.262 (0.53), 1.541 (0.88), 1.547 (0.74), 1.559 (2.65), 1.566 (2.13), 1.577 (3.59), 1.581 (2.90), 1.595 (2.39), 1.600 (2.40), 1.613 (0.75), 1.618 (0.85), 2.525 (1.26), 2.703 (0.94), 2.712 (0.85), 2.720 (1.31), 2.731 (1.13), 2.736 (1.11), 2.747 (1.31), 2.763 (0.88), 3.978 (0.68), 3.995 (1.46), 4.013 (1.77), 4.031 (1.47), 4.047 (0.66), 4.324 (1.46), 4.334 (1.41), 4.968 (3.87), 4.995 (3.76), 6.380 (8.65), 7.163 (3.82), 7.185 (7.88), 7.207 (4.21), 7.585 (4.07), 7.590 (2.03), 7.599 (4.70), 7.607 (4.51), 7.616 (1.95), 7.621 (3.87), 8.030 (8.74), 8.235 (7.02), 8.239 (6.98), 8.533 (8.34), 9.034 (6.99), 9.038 (6.87), 9.260 (3.08), 9.280 (3.04), 10.191 (0.90).

Example I-45

2-Amino-N-[(2S)-butan-2-yl]-6-{1-[1-(4-fluorophenyl)-2-methylpropyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 1): $R_t$=2.05 min; MS (ESIpos): m/z=450 $[M+H]^+$ $^1$H-NMR (400 MHz, DMSO-$d_6$) δ [ppm]: 0.78 (d, 3H), 0.82 (d, 3H), 0.94 (t, 3H), 1.21 (d, 3H), 1.54-1.62 (m, 2H), 2.66-2.79 (m, 1H), 3.96-4.06 (m, 1H), 4.98 (d, 1H), 6.38 (s, 2H), 7.18 (t, 2H), 7.54-7.67 (m, 2H), 8.03 (s, 1H), 8.24 (d, 1H), 8.53 (s, 1H), 9.04 (d, 1H), 9.27 (d, 1H).

Example I-46

2-Amino-N-[(2S)-butan-2-yl]-6-(1-{[4-(trifluoromethyl)phenyl]methyl}-1H-pyrazol-4-yl)[1,2,4]triazolo[1,5-a]pyridine-8-carboxamide (single stereoisomer)

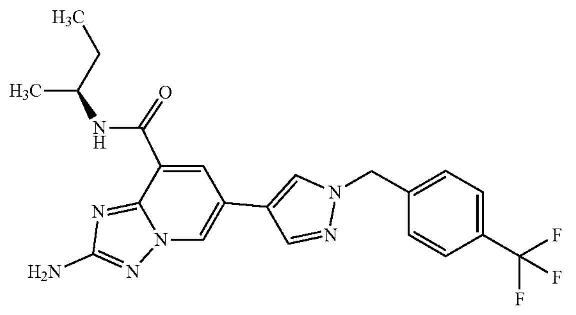 [SMILES: CC[C@H](C)NC(=O)c1cc(-c2cnn(Cc3ccc(C(F)(F)F)cc3)c2)cn2nc(N)nc12]

2-Amino-6-bromo-N-[(2S)-butan-2-yl][1,2,4]triazolo[1,5-a]pyridine-8-carboxamide (60.0 mg, 192 μmol) was reacted with 4-(4,4,5,5-tetramethyl-1,3,2-dioxaborolan-2-yl)-1-{[4-(trifluoromethyl)phenyl]methyl}-1H-pyrazole (90.2 mg, 90% purity, 231 μmol) for 2 h at 80° C. following general procedure B using 0.1 eq. catalyst. The mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 75:25 to 15:85) to yield 69.0 mg (99% purity, 77% yield) of the title compound.

LC-MS (method 2): $R_t$=0.99 min; MS (ESIpos): m/z=458 $[M+H]^+$ $^1$H-NMR (600 MHz, DMSO-$d_6$) δ [ppm]: 0.94 (t, 3H), 1.22 (d, 3H), 1.53-1.64 (m, 2H), 3.97-4.06 (m, 1H), 5.48 (s, 2H), 6.38 (s, 2H), 7.49 (d, 2H), 7.73 (d, 2H), 8.08 (s, 1H), 8.25 (d, 1H), 8.49 (s, 1H), 9.06 (d, 1H), 9.27 (d, 1H).

Example I-47

2-Amino-N-[(2S)-butan-2-yl]-6-(1-{1-[4-(morpholin-4-yl)phenyl]propyl}-1H-pyrazol-4-yl)[1,2,4]triazolo[1,5-a]pyridine-8-carboxamide (mixture of diastereomers)

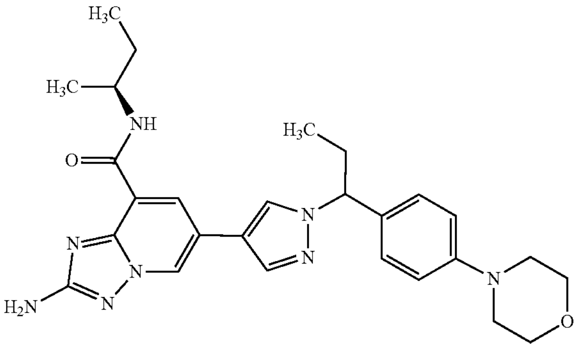 [SMILES: CCC(c1ccc(N2CCOCC2)cc1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (150 mg, 481 μmol) was reacted with 4-(4-{1-[4-(4,4,5,5-tetramethyl-1,3,2-dioxaborolan-2-yl)-1H-pyrazol-1-yl]propyl}phenyl)morpholine (300 mg, 70% purity, 529 μmol) for 2 h at 90° C. following general procedure B using 0.1 eq. catalyst. The reaction mixture was filtered through a hydrophobic phase separation filter which was washed with ethyl acetate. The filtrate was evaporated under reduced pressure. The residue was purified by column chromatography (Biotage® SNAP KP-NH 11 g cartridge, eluent: cyclohexane/ethyl acetate gradient 80: 20 to 0:100) to yield 166 mg (99% purity, 68% yield) of the title compound.

LC-MS (method 1): $R_t$=1.83 min; MS (ESIpos): m/z=503 $[M+H]^+$ $^1$H-NMR (600 MHz, DMSO-$d_6$) δ [ppm]: 0.813 (6.76), 0.825 (13.52), 0.837 (6.31), 0.926 (7.66), 0.939 (16.00), 0.951 (7.55), 1.069 (3.61), 1.162 (0.90), 1.174 (1.80), 1.207 (15.44), 1.218 (15.21), 1.562 (2.70), 1.574 (4.28), 1.586 (3.61), 1.595 (2.37), 1.989 (3.15), 2.110 (1.80), 2.122 (2.37), 2.133 (1.92), 2.335 (1.58), 2.349 (1.69), 2.360 (1.46), 2.384 (1.58), 2.425 (2.14), 2.614 (1.24), 2.653 (1.80), 3.059 (9.92), 3.066 (12.62), 3.074 (9.35), 3.701 (10.82), 3.709 (13.07), 3.717 (9.46), 3.927 (0.79), 4.000 (2.03), 4.011 (2.70), 4.023 (2.70), 4.035 (1.46), 5.183 (2.25), 5.194 (2.93), 5.209 (2.03), 6.382 (11.72), 6.892 (8.23), 6.907 (8.23), 7.257 (8.79), 7.271 (7.66), 8.000 (10.14), 8.242 (6.99), 8.485 (9.69), 9.043 (6.99), 9.269 (3.61), 9.282 (3.61).

Example I-48

2-Amino-N-[(2S)-butan-2-yl]-6-(1-{1-[4-(morpholin-4-yl)phenyl]propyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{1-[4-(morpholin-4-yl)phenyl]propyl}-1H-pyrazol-4-yl)[1,2,4]triazolo[1,5-a]pyridine-8-carboxamide (mixture of diastereomers) (128 mg, 99% purity) from the previous example was separated by chiral chromatography to yield stereoisomer 1 (36 mg, 98% purity) and stereoisomer 2 (34 mg, 95% purity).

Column: Daicel Chiralpak IC 5 μm, 250×20 mm; Eluent A: n-heptane; Eluent B: ethanol+0.2% diethylamine; isocratic: 80% A+20% B; flow: 35 ml/min; UV: 220 nm; temperature: 30° C.

Stereoisomer 1: $R_t$=20.517 min and

Stereoisomer 2: $R_t$=24.029 (cf. next example)

Analytical chiral HPLC. Column: Chiraltek IC-3, 3 μm; Eluent A: iso-hexane; Eluent B: ethanol+0.2% diethylamine; isocratic: 50% A+50% B; UV: 235 nm.

Stereoisomer 1: $R_t$=5.712 min and

Stereoisomer 2: $R_t$=6.467 min (cf. next example)

LC-MS (method 1): $R_t$=1.83 min; MS (ESIpos): m/z=503 $[M+H]^+$ $^1$H-NMR (600 MHz, DMSO-$d_6$) δ [ppm]: 0.814 (6.77), 0.825 (13.48), 0.838 (6.55), 0.858 (0.99), 0.927 (7.76), 0.939 (16.00), 0.951 (7.76), 1.101 (0.42), 1.146 (1.28), 1.158 (2.49), 1.170 (1.37), 1.208 (15.65), 1.219 (15.27), 1.552 (1.15), 1.563 (2.75), 1.575 (4.09), 1.587 (3.32), 1.596 (2.43), 1.608 (0.99), 2.100 (0.96), 2.110 (1.69), 2.122 (2.14), 2.134 (1.85), 2.146 (1.02), 2.324 (1.05), 2.336 (1.50), 2.350 (1.53), 2.362 (1.34), 2.374 (0.89), 2.386 (0.64), 2.426 (0.83), 2.615 (0.42), 2.655 (0.73), 2.925 (0.67), 2.934 (0.61), 3.059 (9.58), 3.067 (12.36), 3.075 (9.45), 3.702 (10.35), 3.710 (12.65), 3.718 (9.29), 3.990 (0.89), 4.001 (1.85), 4.013 (2.33), 4.024 (1.82), 4.035 (0.80), 5.184 (2.08), 5.195 (2.71), 5.209 (2.01), 6.383 (8.91), 6.893 (7.92), 6.907 (8.27), 7.257 (8.50), 7.272 (7.76), 8.001 (9.84), 8.244 (6.61), 8.246 (6.87), 8.485 (9.52), 9.044 (6.64), 9.047 (6.83), 9.270 (3.77), 9.283 (3.64).

Example I-49

2-Amino-N-[(2S)-butan-2-yl]-6-(1-{1-[4-(morpholin-4-yl)phenyl]propyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 1): $R_t$=1.83 min; MS (ESIpos): m/z=503 $[M+H]^+$ $^1$H-NMR (600 MHz, DMSO-$d_6$) δ [ppm]: 0.814 (7.60), 0.826 (13.80), 0.838 (6.55), 0.859 (1.20), 0.928 (8.17), 0.940 (15.56), 0.952 (7.36), 1.036 (0.46), 1.147 (1.72), 1.160 (3.04), 1.172 (1.72), 1.208 (16.00), 1.219 (14.69), 1.541 (0.73), 1.553 (1.48), 1.564 (3.14), 1.576 (4.62), 1.587 (3.76), 1.597 (2.46), 1.609 (0.92), 2.100 (1.20), 2.111 (1.86), 2.123 (2.31), 2.134 (1.98), 2.146 (1.08), 2.324 (1.27), 2.337 (1.78), 2.347 (1.73), 2.362 (1.41), 2.374 (0.92), 2.426 (0.52), 2.915 (0.56), 2.926 (0.84), 2.935 (0.84), 2.947 (0.55), 3.059 (12.05), 3.066 (14.01), 3.074 (9.28), 3.702 (12.79), 3.710 (14.28), 3.718 (9.13), 3.992 (1.08), 4.003 (2.10), 4.014 (2.50), 4.025 (1.82), 4.037 (0.78), 5.184 (2.38), 5.195 (3.15), 5.209 (1.97), 6.386 (6.54), 6.892 (8.38), 6.907 (8.09), 7.258 (8.95), 7.272 (7.59), 8.002 (9.77), 8.247 (7.19), 8.486 (9.48), 9.047 (7.16), 9.271 (3.97), 9.285 (3.70).

Example I-50

2-Amino-N-[(2S)-butan-2-yl]-7-{1-[(1H-indazol-7-yl)methyl]-1H-pyrazol-4-yl}[1,2,4]triazolo[1,5-a]pyridine-5-carboxamide (single stereoisomer)

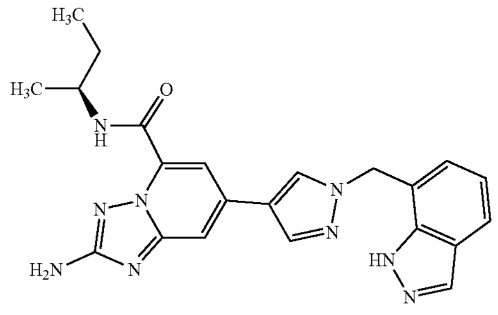 [SMILES: CC[C@H](C)NC(=O)c1cc(-c2cnn(Cc3cccc4cn[nH]c34)c2)cc2nc(N)nn12]

2-Amino-N-[(2S)-butan-2-yl]-7-chloro[1,2,4]triazolo[1,5-a]pyridine-5-carboxamide (60.0 mg, 224 μmol) was reacted with 7-{[4-(4,4,5,5-tetramethyl-1,3,2-dioxaborolan-2-yl)-1H-pyrazol-1-yl]methyl}-1H-indazole (87.2 mg, 269 mol) for 1 h at 90° C. following general procedure B using 0.1 eq. catalyst. The reaction mixture was diluted with ethyl acetate and filtered through a hydrophobic phase separation filter which was washed with ethyl acetate. The filtrate was evaporated under reduced pressure. The residue was purified by column chromatography (Biotage® SNAP KP-NH 11 g cartridge, eluent: cyclohexane/ethyl acetate gradient 50:50 to 0:100, then ethyl acetate/2-propanol 100:0 to 80:20) to yield 53.2 mg (95% purity, 53% yield) of the title compound.

LC-MS (method 1): $R_t$=1.49 min; MS (ESIpos): m/z=430 $[M+H]^+$ $^1$H-NMR (500 MHz, DMSO-$d_6$) δ [ppm]: 0.96 (t, 3H), 1.24 (d, 3H), 1.61 (quin, 2H), 3.96-4.07 (m, 1H), 5.69 (s, 2H), 6.35 (s, 2H), 7.07-7.13 (m, 1H), 7.13-7.19 (m, 1H), 7.74 (d, 1H), 7.77 (s, 2H), 8.14 (d, 1H), 8.17 (s, 1H), 8.71 (s, 1H), 10.09 (d, 1H), 13.30 (s, 1H).

Example I-51

2-Amino-N-[(2S)-butan-2-yl]-7-{1-[phenyl(tetrahydro-2H-pyran-4-yl)methyl]-1H-pyrazol-4-yl}[1,2,4]triazolo[1,5-a]pyridine-5-carboxamide (mixture of diastereomers)

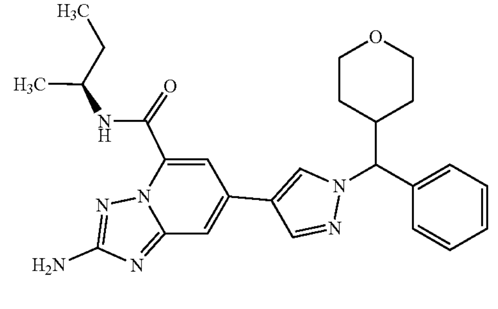 [SMILES: CC[C@H](C)NC(=O)c1cc(-c2cnn(C(c3ccccc3)C3CCOCC3)c2)cc2nc(N)nn12]

2-Amino-N-[(2S)-butan-2-yl]-7-chloro[1,2,4]triazolo[1,5-a]pyridine-5-carboxamide (100 mg, 374 μmol) was reacted with 1-[phenyl(tetrahydro-2H-pyran-4-yl)methyl]-

4-(4,4,5,5-tetramethyl-1,3,2-dioxaborolan-2-yl)-1H-pyrazole (516 mg, 40% purity, 560 μmol) for 2 h at 90° C. following 5 general procedure B using 0.1 eq. catalyst. The reaction mixture was diluted with ethyl acetate (5 ml) and filtered through a hydrophobic phase separation filter. The solvent was removed in vacuo and the residue purified by column chromatography (Biotageo SNAP KP-NH 28 g cartridge, eluent: cyclohexane/ethyl acetate gradient 80:20 to 0:100) to yield 150 mg (98% purity, 83% yield) of the title compound.

LC-MS (method 1): $R_t$=1.79 min; MS (ESIpos): m/z=474 $[M+H]^+$ $^1$H-NMR (500 MHz, DMSO-$d_6$) δ [ppm]: 0.95 (t, 3H), 1.08-1.22 (m, 3H), 1.24 (d, 3H), 1.25-1.35 (m, 1H), 1.61 (quin, 2H), 2.66-2.75 (m, 1H), 3.21-3.30 (m, 2H), 3.77-3.86 (m, 2H), 3.96-4.05 (m, 1H), 5.11 (d, 1H), 6.33 (s, 2H), 7.28-7.32 (m, 1H), 7.35-7.39 (m, 2H), 7.55-7.59 (m, 2H), 7.75-7.78 (m, 2H), 8.15 (s, 1H), 8.70 (s, 1H), 10.07 (d, 1H).

Example I-52

2-Amino-N-[(2S)-butan-2-yl]-7-{1-[phenyl(tetrahydro-2H-pyran-4-yl)methyl]-1H-pyrazol-4-yl}[1,2,4]triazolo[1,5-a]pyridine-5-carboxamide (stereoisomer 1, eutomer)

2-Amino-N-[(2S)-butan-2-yl]-7-{1-[phenyl(tetrahydro-2H-pyran-4-yl)methyl]-1H-pyrazol-4-yl}[1,2,4]triazolo[1,5-a]pyridine-5-carboxamide (mixture of diastereomers) (148 mg, 98% purity) from the previous example was separated by chiral chromatography to yield stereoisomer 1 (51 mg, 99% purity) and stereoisomer 2 (56 mg, 99% purity).

Column: Daicel Chiralcel OD-H, 5 m, 250×20 mm; Eluent A: n-heptane; Eluent B: ethanol+0.1% diethylamine; isocratic: 85% A+15% B; flow: 30 ml/min; UV: 220 nm; temperature: 30° C. Stereoisomer 1: $R_t$=7.468 min and Stereoisomer 2: $R_t$=8.881 min (cf. next example)

Analytical chiral HPLC. Column: Phenomenex cellulose, 3 μm, 50×4.6 mm; Eluent A: n-heptane;

Eluent B: ethanol+0.2% diethylamine; isocratic: 80% A+20% B; flow: 1 ml/min; UV: 220 nm.

Stereoisomer 1: $R_t$=1.590 min and

Stereoisomer 2: $R_t$=1.577 min (cf. next example)

Stereoisomer 1: The stereochemical configuration of the methine carbon atom bonded to the pyrazole was (S).

LC-MS (method 1): $R_t$=1.79 min; MS (ESIpos): m/z=474 $[M+H]^+$ $^1$H-NMR (500 MHz, DMSO-$d_6$) δ [ppm]: 0.95 (t, 3H), 1.09-1.35 (m, 7H), 1.57-1.64 (m, 2H), 2.66-2.75 (m, 1H), 3.21-3.32 (m, 2H), 3.77-3.86 (m, 2H), 3.97-4.06 (m, 1H), 5.11 (d, 1H), 6.36 (s, 2H), 7.28-7.33 (m, 1H), 7.35-7.40 (m, 2H), 7.55-7.59 (m, 2H), 7.76-7.78 (m, 2H), 8.16 (s, 1H), 8.71 (s, 1H), 10.08 (d, 1H).

Example I-53

2-Amino-N-[(2S)-butan-2-yl]-7-{1-[phenyl(tetrahydro-2H-pyran-4-yl)methyl]-1H-pyrazol-4-yl}[1,2,4]triazolo[1,5-a]pyridine-5-carboxamide (stereoisomer 2, distomer)

The product was isolated in the previous example as second stereoisomer.

LC-MS (method 1): $R_t$=1.79 min; MS (ESIpos): m/z=474 $[M+H]^+$ $^1$H-NMR (500 MHz, DMSO-$d_6$) δ [ppm]: −0.007 (0.61), 0.006 (0.53), 0.839 (0.46), 0.846 (0.59), 0.861 (0.61), 0.937 (6.82), 0.952 (15.82), 0.967 (7.45), 1.101 (1.32), 1.125 (1.53), 1.142 (0.74), 1.157 (1.30), 1.172 (1.58), 1.196 (2.06), 1.212 (1.45), 1.229 (15.67), 1.243 (16.00), 1.262 (1.14), 1.278 (1.30), 1.287 (1.32), 1.303 (1.04), 1.310 (1.04), 1.327 (0.51), 1.336 (0.51), 1.576 (1.12), 1.591 (3.97), 1.605 (5.09), 1.619 (3.76), 1.634 (0.99), 2.672 (0.43), 2.696 (1.68), 2.717 (1.14), 2.739 (0.41), 3.228 (0.94), 3.247 (1.96), 3.251 (1.83), 3.262 (1.37), 3.270 (1.32), 3.281 (2.01), 3.286 (2.14), 3.296 (0.66), 3.305 (1.50), 3.309 (1.42), 3.317 (1.04), 3.353 (1.20), 3.360 (0.81), 3.369 (0.53), 3.791 (1.35), 3.815 (2.26), 3.839 (1.25), 3.982 (0.76), 3.995 (1.60), 4.010 (1.86), 4.023 (1.63), 4.037 (0.74), 5.096 (3.54), 5.118 (3.41), 6.357 (8.55), 7.289 (1.17), 7.303 (3.64), 7.318 (2.62), 7.356 (4.43), 7.372 (7.07), 7.386 (3.10), 7.564 (6.36), 7.578 (5.65), 7.581 (4.17), 7.760 (3.89), 7.764 (11.34), 7.767 (11.19), 7.771 (3.82), 8.162 (9.08), 8.713 (8.06), 10.076 (2.95), 10.092 (2.87).

Example I-54

2-Amino-N-[(2S)-butan-2-yl]-7-{1-[(1S)-1-(4-fluorophenyl)propyl]-1H-pyrazol-4-yl}[1,2,4]triazolo[1,5-a]pyridine-5-carboxamide (single stereoisomer)

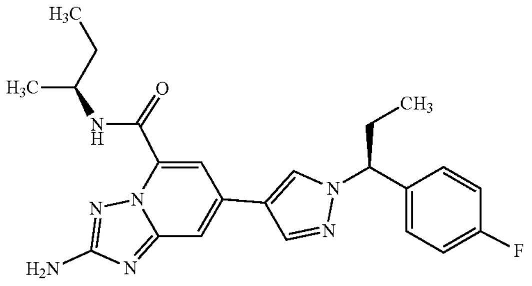 [SMILES: CC[C@H](C)NC(=O)c1cc(-c2cnn([C@@H](CC)c3ccc(F)cc3)c2)cc2nc(N)nn12]

2-Amino-N-[(2S)-butan-2-yl]-7-chloro[1,2,4]triazolo[1,5-a]pyridine-5-carboxamide (75.0 mg, 280 μmol) was reacted with 1-[(1S)-1-(4-fluorophenyl)propyl]-4-(4,4,5,5-tetramethyl-1,3,2-dioxaborolan-2-yl)-1H-pyrazole (111 mg, 336 μmol) for 1 h at 90° C. following general procedure B using [1,1'-Bis(di-tert-butylphosphino)ferrocene]dichloropalladium(II) [CAS-RN 95408-45-0](9.13 mg, 14.0 μmol) as catalyst. The reaction mixture was diluted with ethyl acetate and filtered through a hydrophobic phase separation filter. The solvent was removed in vacuo and the residue purified by column chromatography (Biotage® SNAP KP-NH 11 g cartridge, eluent: cyclohexane/ethyl acetate gradient 75:25 to 0:100) to yield 110 mg (100% purity, 90% yield) of the title compound.

LC-MS (method 1): $R_t$=1.92 min; MS (ESIpos): m/z=436 $[M+H]^+$ $^1$H-NMR (400 MHz, DMSO-$d_6$) δ [ppm]: 0.84 (t, 3H), 0.96 (t, 3H), 1.24 (d, 3H), 1.61 (quin, 2H), 2.15 (dquin, 1H), 2.31-2.45 (m, 1H), 3.96-4.07 (m, 1H), 5.36 (dd, 1H), 6.34 (s, 2H), 7.15-7.21 (m, 2H), 7.42-7.48 (m, 2H), 7.78 (q, 2H), 8.16 (s, 1H), 8.70 (s, 1H), 10.08 (d, 1H).

Example I-55

2-Amino-N-[(2S)-butan-2-yl]-6-{1-[1-(5-fluoropyridin-2-yl)propyl]-1H-pyrazol-4-yl}[1,2,4]triazolo[1,5-a]pyridine-8-carboxamide (mixture of diastereomers)

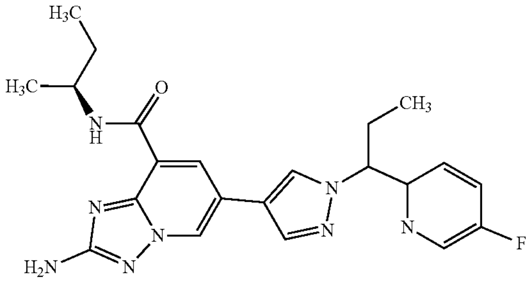

2-Amino-6-bromo-N-[(2S)-butan-2-yl][1,2,4]triazolo[1,5-a]pyridine-8-carboxamide (200 mg, 641 mol), 5-fluoro-2-{1-[4-(4,4,5,5-tetramethyl-1,3,2-dioxaborolan-2-yl)-1H-pyrazol-1-yl]propyl}pyridine (255 mg, 769 μmol), sodium carbonate (340 mg, 3.20 mmol) and 1,1'-bis(diphenylphosphino)ferrocene-palladium(II)dichloride dichloromethane complex (26.2 mg, 32.0 μmol) were reacted according to procedure A in a mixture of 1,4-dioxane (6.1 ml) and water (2.0 ml). 5-Fluoro-2-{1-[4-(4,4,5,5-tetramethyl-1,3,2-dioxaborolan-2-yl)-1H-pyrazol-1-yl]propyl}pyridine (318 mg, 961 μmol) and 1,1'-bis(diphenylphosphino)ferrocene-palladium(II)dichloride dichloromethane complex (26.2 mg, 32.0 μmol) were added and the reaction mixture was further stirred at 90° C. for 3 h. The reaction was quenched with water and filtered through a hydrophobic phase separation filter which was rinsed with ethyl acetate (15 ml). The filtrate was concentrated and dried under reduced pressure. The residue was purified by column chromatography (Biotage® SNAP KP-NH 11 g cartridge, eluent: cyclohexane/ethyl acetate gradient 8:2 to 2:8) to yield 182 mg (100% purity, 65% yield) of the title compound as a mixture of diastereomers.

LC-MS (method 2): $R_t$=0.94 min; MS (ESIpos): m/z=437 $[M+H]^+$ $^1$H-NMR (400 MHz, DMSO-$d_6$) δ [ppm]: 0.86 (t, 3H), 0.94 (t, 3H), 1.22 (d, 3H), 1.55-1.62 (m, 2H), 2.24-2.41 (m, 2H), 4.02 (sept, 1H), 5.45 (dd, 1H), 6.39 (s, 2H), 7.38 (dd, 1H), 7.72 (td, 1H), 8.05 (s, 1H), 8.27 (d, 1H), 8.56 (d, 2H), 8.56 (s, 1H), 9.08 (d, 1H), 9.28 (d, 1H).

Example I-56

2-Amino-N-[(2S)-butan-2-yl]-6-{1-[1-(5-fluoropyridin-2-yl)propyl]-1H-pyrazol-4-yl}[1,2,4]triazolo[1,5-a]pyridine-8-carboxamide (stereoisomer 1, eutomer)

2-Amino-N-[(2S)-butan-2-yl]-6-{1-[1-(5-fluoropyridin-2-yl)propyl]-1H-pyrazol-4-yl}[1,2,4]triazolo[1,5-a]pyridine-8-carboxamide was separated by chiral preparative SFC to yield stereoisomer 1 (63.8 mg, 100% purity) and stereoisomer 2 (62.6 mg, 100% purity).

Instrument: THAR SFC-Super Chrom Prep 200; Column: Daicel Chiralpak AD-H, 5 m, 250×20 mm; Eluent A: $CO_2$; Eluent B: methanol; isocratic: 70% A+30% B; flow: 80 ml/min; UV: 210 nm; temperature: 40° C.

Analytical SFC-method: Column: Chiralcel AY, 3 μm, 4.6×100 mm; Eluent A: $CO_2$; Eluent B: methanol; isocratic: 70% A+30% B; flow: 3 ml/min; UV: 210 nm; temperature: 40° C.

Stereoisomer 1: $R_t$=1.99 min and

Stereoisomer 2: $R_t$=3.81 min (cf. next example)

LC-MS (method 1): $R_t$=1.67 min; MS (ESIpos): m/z=437 $[M+H]^+$ $^1$H-NMR (500 MHz, DMSO-$d_6$) δ [ppm]: 0.86 (t, 3H), 0.94 (t, 3H), 1.22 (d, 3H), 1.54-1.63 (m, 2H), 2.25-2.47 (m, 2H), 4.02 (dt, 1H), 5.46 (dd, 1H), 6.39 (s, 2H), 7.38 (dd, 1H), 7.72 (td, 1H), 8.05 (s, 1H), 8.27 (d, 1H), 8.56 (d, 2H), 8.56 (s, 1H), 9.08 (d, 1H), 9.28 (d, 1H).

Example I-57

2-Amino-N-[(2S)-butan-2-yl]-6-{1-[1-(5-fluoropyridin-2-yl)propyl]-1H-pyrazol-4-yl}[1,2,4]triazolo[1,5-a]pyridine-8-carboxamide (stereoisomers 2, distomer)

The product was isolated in the previous example as second stereoisomer.

LC-MS (method 1): $R_t$=1.71 min; MS (ESIpos): m/z=437 $[M+H]^+$ $^1$H-NMR (600 MHz, DMSO-$d_6$) δ [ppm]: 0.848 (6.62), 0.860 (14.08), 0.872 (6.73), 0.932 (7.37), 0.944 (16.00), 0.956 (7.85), 1.213 (15.39), 1.224 (15.36), 1.546 (0.41), 1.557 (0.99), 1.569 (2.57), 1.580 (3.74), 1.590 (2.97), 1.601 (2.36), 1.613 (0.94), 2.272 (0.74), 2.283 (1.40), 2.295 (2.20), 2.307 (2.05), 2.319 (1.29), 2.329 (0.62), 2.341 (1.24), 2.353 (1.60), 2.368 (1.50), 2.379 (1.08), 2.391 (0.76), 3.996 (0.79), 4.008 (1.71), 4.019 (2.17), 4.031 (1.71), 4.042 (0.76), 5.444 (2.20), 5.454 (2.53), 5.459 (2.61), 5.469 (2.14), 6.399 (11.00), 7.373 (2.60), 7.381 (2.70), 7.388 (2.91), 7.395 (2.77), 7.707 (1.61), 7.712 (1.70), 7.721 (3.06), 7.726 (3.15), 7.736 (1.51), 7.741 (1.52), 8.058 (9.94), 8.273 (7.03), 8.276 (6.90), 8.557 (5.56), 8.561 (5.64), 8.569 (9.73), 9.085 (7.05), 9.088 (6.90), 9.277 (3.55), 9.290 (3.41).

Example I-58

2-Amino-N-[(2S)-butan-2-yl]-6-{1-[1-(5-chloropyridin-3-yl)propyl]-1H-pyrazol-4-yl}[1,2,4]triazolo[1,5-a]pyridine-8-carboxamide (mixture of diastereomers)

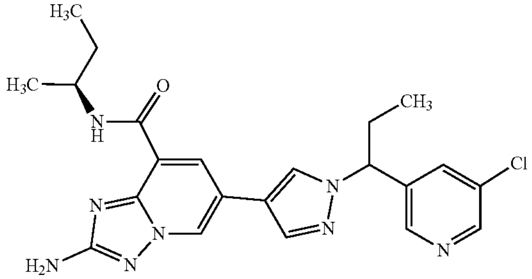 [SMILES: CCC(c1cncc(Cl)c1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (155 mg, 497 μmol), 3-chloro-5-{1-[4-(4,4,5,5-tetramethyl-1,3,2-dioxaborolan-2-yl)-1H-pyrazol-1-yl]propyl}pyridine (505 mg, 41% purity, 596 μmol), 1,1'-bis(diphenylphosphino)ferrocene-palladium(II) dichloride dichloromethane complex (20.3 mg, 24.8 μmol)

and sodium carbonate (263 mg, 2.48 mmol) were reacted according to procedure A in a mixture of water (1.5 ml) and 1,4-dioxane (4.5 ml). After 12 h at 90° C., the reaction was quenched with water and extracted with 20 dichloromethane. The organic layer was dried over sodium sulfate, filtered and concentrated under reduced pressure. The residue was purified by column chromatography (Biotagea SNAP KP-NH 11 g cartridge, gradient: cyclohexane/ethyl acetate gradient 8:2 to 0:10) to yield 87 mg (98% purity, 39% yield) of the title compound as a mixture of two diasteromers.

LC-MS (method 1): $R_t$=1.76 min; MS (ESIpos): m/z=453 $[M+H]^+$ $^1$H-NMR (400 MHz, DMSO-$d_6$) δ [ppm]: 0.86 (t, 3H), 0.94 (t, 3H), 1.22 (d, 3H), 1.55-1.60 (m, 2H), 2.18-2.21 (m, 1H), 2.33-2.46 (m, 1H), 4.02 (dt, 1H), 5.48 (dd, 1H), 6.40 (s, 2H), 7.97 (t, 1H), 8.10 (s, 1H), 8.27 (d, 1H), 8.58 (dd, 2H), 8.60 (s, 1H), 9.07 (d, 1H), 9.28 (d, 1H).

Example I-59

2-Amino-N-[(2S)-butan-2-yl]-6-{1-[1-(5-chloropyridin-3-yl)propyl]-1H-pyrazol-4-yl}[1,2,4]triazolo[1,5-a]pyridine-8-carboxamide (stereoisomer 1, distomer)

2-Amino-N-[(2S)-butan-2-yl]-6-{1-[1-(5-chloropyridin-3-yl)propyl]-1H-pyrazol-4-yl}[1,2,4]triazolo[1,5-a]pyridine-8-carboxamide (87 mg, 98% purity) was separated by chiral preparative HPLC to yield stereoisomer 1 (31 mg, 99% purity) and stereoisomer 2 (20 mg, 99% purity).

Column: Daicel Chiralpak AD_H, 5 μm, 250×20 mm; Eluent A: n-heptane; Eluent B: ethanol; isocratic: 20% A+80% B; flow: 20 ml/min; UV: 220 nm; temperature: 30° C.

Stereoisomer 1: $R_t$=13.14 min and

Stereoisomer 2: $R_t$=19.64 min (cf. next example)

Analytical chiral HPLC-method: Column: Daicel Chiralpak AD-H, 5 μm, 250×4.6 mm; Eluent A: iso-hexane; Eluent B: ethanol; isocratic: 20% A+80% B; flow: 1 ml/min; UV: 220 nm; temperature: 30° C.

Stereoisomer 1: $R_t$=14.75 min and

Stereoisomer 2: $R_t$=20.46 min (cf. next example)

LC-MS (method 2): $R_t$=0.92 min; MS (ESIpos): m/z=453 $[M+H]^+$ $^1$H-NMR (600 MHz, DMSO-$d_6$) δ [ppm]: 0.843 (7.20), 0.855 (14.33), 0.866 (6.85), 0.930 (7.71), 0.942 (16.00), 0.954 (7.86), 1.211 (15.85), 1.222 (15.47), 1.544 (0.56), 1.555 (1.21), 1.567 (2.88), 1.578 (4.27), 1.589 (3.56), 1.599 (2.50), 1.610 (0.96), 2.173 (1.04), 2.184 (1.79), 2.196 (2.33), 2.207 (1.95), 2.219 (1.14), 2.390 (1.44), 2.403 (1.62), 2.418 (1.54), 2.426 (1.79), 2.441 (1.04), 2.614 (0.43), 2.655 (0.58), 3.995 (0.94), 4.006 (2.00), 4.018 (2.53), 4.029 (1.90), 4.041 (0.81), 5.463 (2.27), 5.474 (2.63), 5.479 (2.55), 5.489 (2.25), 6.403 (12.11), 7.971 (6.34), 8.103 (10.36), 8.274 (7.38), 8.576 (6.42), 8.579 (6.17), 8.592 (7.25), 8.606 (10.21), 9.077 (7.46), 9.274 (3.92), 9.287 (3.77).

Example I-60

2-Amino-N-[(2S)-butan-2-yl]-6-{1-[1-(5-chloropyridin-3-yl)propyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 2): $R_t$=0.92 min; MS (ESIpos): m/z=453 $[M+H]^+$ $^1$H-NMR (600 MHz, DMSO-$d_6$) δ [ppm]: 0.86 (t, 3H), 0.94 (t, 3H), 1.22 (d, 3H), 1.53-1.63 (m, 2H), 2.18-2.22 (m, 1H), 2.38-2.48 (m, 1H), 4.02 (dt, 1H), 5.48 (dd, 1H), 6.40 (s, 2H), 7.97 (s, 1H), 8.10 (s, 1H), 8.28 (s, 1H), 8.58 (dd, 2H), 8.61 (s, 1H), 9.08 (s, 1H), 9.28 (d, 1H).

Example I-61

2-Amino-N-[(2S)-butan-2-yl]-6-{1-[1-(5-chloropyridin-3-yl)-2-methylpropyl]-1H-pyrazol-4-yl}[1,2,4]triazolo[1,5-a]pyridine-8-carboxamide (mixture of diastereomers)

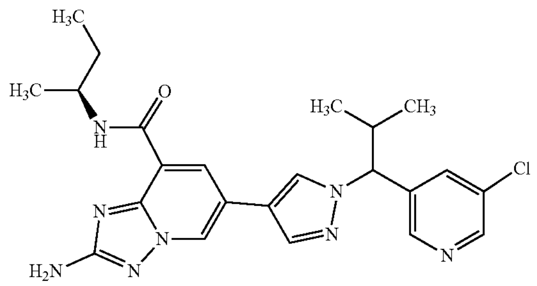 [SMILES: CC[C@H](C)NC(=O)c1cc(-c2cnn(C(c3cncc(Cl)c3)C(C)C)c2)cn2nc(N)nc12]

2-Amino-6-bromo-N-[(2S)-butan-2-yl][1,2,4]triazolo[1,5-a]pyridine-8-carboxamide (114 mg, 365 μmol), 3-chloro-5-{2-methyl-1-[4-(4,4,5,5-tetramethyl-1,3,2-dioxaborolan-2-yl)-1H-pyrazol-1-yl]propyl}pyridine (158 mg, 438 μmol), 1,1'-bis(diphenylphosphino)ferrocene-palladium(II)dichloride dichloromethane complex (14.9 mg, 18.3 μmol) and sodium carbonate (116 mg, 1.10 mmol) were reacted according to procedure A in a mixture of 1,4-dioxane (3.0 ml) and water (1.0 ml). After stirring for 3 h at 90° C., the reaction was quenched with water and extracted with dichloromethane. The organic layer was dried over anhydrous sodium sulfate, filtered and concentrated. The residue was purified via column chromatography (Biotage® SNAP KP-NH 11 g cartridge, eluent: cyclohexane/ethyl acetate gradient 8:2 to 2:8) to yield 132 mg (99% purity, 77% yield) of the title compound as a mixture of diasteromers.

LC-MS (method 1): $R_t$=1.88 min; MS (ESIpos): m/z=467 $[M+H]^+$ $^1$H-NMR (600 MHz, DMSO-$d_6$) δ [ppm]: 0.81 (d, 2H), 0.85 (d, 1H), 0.94 (t, 3H), 1.22 (d, 3H), 1.53-1.63 (m, 2H), 2.74-2.82 (m, 1H), 3.93-4.04 (m, 1H), 5.14 (d, 1H), 6.41 (s, 2H), 8.10 (s, 1H), 8.17 (t, 1H), 8.26 (d, 1H), 8.58 (s, 1H), 8.59 (d, 1H), 8.73 (d, 1H), 9.07 (d, 1H), 9.28 (d, 1H).

Example I-62

2-Amino-N-[(2S)-butan-2-yl]-6-{1-[1-(5-chloropyridin-3-yl)-2-methylpropyl]-1H-pyrazol-4-yl}[1,2,4]triazolo[1,5-a]pyridine-8-carboxamide (stereoisomer 1, distomer)

2-Amino-N-[(2S)-butan-2-yl]-6-{1-[1-(5-chloropyridin-3-yl)-2-methylpropyl]-1H-pyrazol-4-yl}[1,2,4]triazolo[1,5-a]pyridine-8-carboxamide (mixture of diastereomers) (97 mg, 99% purity) was separated by chiral preparative HPLC to yield stereoisomer 1 (23.6 mg, 99% purity) and stereoisomer 2 (27.2 mg, 99% purity).

Column: Daicel Chiralpak IE, 5 m, 250×20 mm; Eluent A: n-heptane; Eluent B: ethanol; isocratic: 40% A+60% B; flow: 20 ml/min; UV: 220 nm; temperature: 40° C.

Stereoisomer 1: $R_t$=7.82 min and

Stereoisomer 2: $R_t$=8.89 min (cf. next example)

Analytical chiral HPLC-method: Column: Daicel Chiralpak IE, 3 m, 50×4.6 mm; Eluent A: n-heptane; Eluent B: ethanol+0.2% diethylamine; isocratic: 50% A+50% B; flow: 1 ml/min; UV: 220 nm; temperature: 40° C.

Stereoisomer 1: $R_t$=1.98 min and

Stereoisomer 2: $R_t$=2.30 min (cf. next example)

LC-MS (method 1): $R_t$=1.89 min; MS (ESIpos): m/z=467 $[M+H]^+$ $^1$H-NMR (400 MHz, DMSO-$d_6$) δ [ppm]: 0.799 (10.35), 0.815 (10.81), 0.831 (11.30), 0.848 (11.47), 0.921 (6.64), 0.940 (16.00), 0.958 (7.49), 1.149 (0.92), 1.206 (15.28), 1.223 (15.15), 1.560 (2.46), 1.578 (3.19), 1.596 (2.37), 2.328 (0.92), 2.367 (1.12), 2.671 (0.85), 2.711 (0.92), 2.797 (1.22), 3.996 (1.38), 4.014 (1.74), 4.033 (1.45), 5.126 (3.98), 5.153 (3.84), 6.391 (8.15), 8.090 (9.20), 8.159 (3.48), 8.165 (5.72), 8.170 (3.58), 8.247 (7.46), 8.251 (7.59), 8.576 (8.08), 8.587 (7.49), 8.593 (7.33), 8.723 (6.05), 8.728 (6.14), 9.054 (7.59), 9.058 (7.72), 9.262 (3.12), 9.282 (2.92).

Example I-63

2-Amino-N-[(2S)-butan-2-yl]-6-{1-[1-(5-chloropyridin-3-yl)-2-methylpropyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 1): $R_t$=1.89 min; MS (ESIpos): m/z=467 $[M+H]^+$ $^1$H-NMR (400 MHz, DMSO-$d_6$) δ [ppm]: 0.82 (d, 2H), 0.85 (d, 1H), 0.94 (t, 3H), 1.21 (d, 3H), 1.53-1.64 (m, 2H), 2.71-2.83 (m, 1H), 3.98-4.05 (dt, 1H), 5.14 (d, 1H), 6.39 (s, 2H), 8.09 (s, 1H), 8.17 (t, 1H), 8.25 (d, 1H), 8.58 (s, 11H), 8.59 (d, 1H), 8.73 (d, 1H), 9.06 (d, 1H), 9.27 (d, 1H).

Example I-64

2-Amino-N-[(2S)-butan-2-yl]-6-(1-{1-[6-(difluoromethyl)pyridin-3-yl]propyl}-1H-pyrazol-4-yl)[1,2,4]triazolo[1,5-a]pyridine-8-carboxamide (mixture of diastereomers)

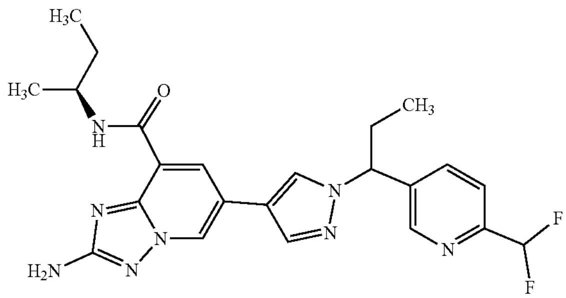 [SMILES: CCC(c1ccc(C(F)F)nc1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (175 mg, 561 μmol), 2-(difluoromethyl)-5-{1-[4-(4,4,5,5-tetramethyl-1,3,2-dioxaborolan-2-yl)-1H-pyrazol-1-yl]propyl}pyridine (257 mg, 95% purity, 673 μmol), sodium carbonate (297 mg, 2.80 mmol) and 1,1'-bis(diphenylphosphino)ferrocene-palladium(II)dichloride dichloromethane complex (22.9 mg, 28.0 μmol) were reacted according to procedure A in a mixture of 1,4-dioxane (7.0 ml) and water (1.0 ml). The reaction mixture was stirred for 2.5 h at 90° C. The residue was purified by preparative HPLC to give 184 mg (100% purity, 70% yield) of the title compound as a mixture of two diasteromers.

LC-MS (method 1): $R_t$=1.74 min; MS (ESIpos): m/z=469 $[M+H]^+$ $^1$H-NMR (500 MHz, DMSO-$d_6$) δ [ppm]: 0.87 (t, 3H), 0.94 (t, 3H), 1.22 (d, 3H), 1.53-1.63 (m, 2H), 2.17-2.26 (m, 1H), 2.39-2.49 (m, 1H), 3.98-4.05 (m, 1H), 5.53 (dd, 1H), 6.41 (s, 2H), 6.94 (t, 1H), 7.71 (d, 1H), 8.00 (dd, 1H), 8.11 (s, 1H), 8.28 (d, 1H), 8.62 (s, 1H), 8.74 (d, 1H), 9.08 (d, 1H), 9.26-9.31 (m, 11H).

Example I-65

2-Amino-N-[(2S)-butan-2-yl]-6-(1-{1-[6-(difluoromethyl)pyridin-3-yl]propyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{1-[6-(difluoromethyl)pyridin-3-yl]propyl}-1H-pyrazol-4-yl)[1,2,4]triazolo[1,5-a]pyridine-8-carboxamide (mixture of diastereomers) (184 mg, 100% pure) was separated by chiral preparative HPLC to yield stereoisomer 1 (70 mg, 100% purity) and stereoisomer 2 (38 mg, 100% purity).

Column: Daicel Chiralpak IE, 5 m 250×20 mm; Eluent A: n-heptane; Eluent B: ethanol+0.2% diethylamine; isocratic: 50% A+50% B; flow: 15 ml/min; UV: 210 nm; temperature: 40° C.

Stereoisomer 1: $R_t$=9.33 min and

Stereoisomer 2: $R_t$=10.75 min (cf. next example)

Analytical chiral HPLC-method: Column: Daicel Chiralpak IE-3, 3 m, 50×4.6 mm; Eluent A: n-heptane; Eluent B: ethanol+0.2% diethylamine; isocratic: 50% A+50% B; flow: 1 ml/min; UV: 220 nm; temperature: 40° C.

Stereoisomer 1: $R_t$=2.30 min and

Stereoisomer 2: $R_t$=2.70 min (cf. next example)

LC-MS (method 1): $R_t$=1.74 min; MS (ESIpos): m/z=469 $[M+H]^+$ $^1$H-NMR (500 MHz, DMSO-$d_6$) δ [ppm]: −0.007 (3.03), 0.007 (2.70), 0.856 (5.77), 0.871 (12.54), 0.885 (5.78), 0.927 (7.05), 0.942 (16.00), 0.956 (7.50), 1.210 (15.15), 1.223 (15.04), 1.550 (0.85), 1.564 (2.39), 1.573 (2.08), 1.579 (3.24), 1.585 (2.38), 1.593 (2.17), 1.600 (2.17), 1.615 (0.82), 2.183 (0.78), 2.196 (1.28), 2.210 (1.85), 2.225 (1.45), 2.238 (0.90), 2.409 (0.90), 2.424 (1.20), 2.428 (1.08), 2.437 (1.14), 2.443 (1.22), 2.451 (0.93), 2.456 (1.10), 2.470 (0.91), 3.990 (0.71), 4.004 (1.47), 4.018 (1.84), 4.032 (1.47), 4.045 (0.68), 5.512 (1.71), 5.524 (1.91), 5.530 (1.94), 5.542 (1.61), 6.412 (9.18), 6.834 (2.58), 6.944 (5.44), 7.054 (2.26), 7.699 (4.12), 7.715 (4.56), 7.984 (2.75), 7.988 (2.78), 8.000 (2.41), 8.005 (2.41), 8.106 (9.57), 8.273 (7.15), 8.277 (7.29), 8.620 (8.82), 8.733 (4.59), 8.736 (4.62), 9.080 (7.19), 9.084 (7.23), 9.275 (3.27), 9.291 (3.15).

Example I-66

2-Amino-N-[(2S)-butan-2-yl]-6-(1-{1-[6-(difluoromethyl)pyridin-3-yl]propyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 1): $R_t$=1.73 min; MS (ESIpos): m/z=469 [M+H]$^+$ $^1$H-NMR (500 MHz, DMSO-$d_6$) δ [ppm]: 0.87 (t, 3H), 0.94 (t, 3H), 1.22 (d, 3H), 1.53-1.63 (m, 2H), 2.18-2.22 (m, 1H), 2.39-2.49 (m, 1H), 3.99-4.05 (dt, 1H), 5.53 (dd, 1H), 6.41 (s, 2H), 6.94 (t, 1H), 7.71 (d, 11H), 7.99 (dd, 11H), 8.10 (s, 1H), 8.27 (d, 1H), 8.62 (s, 11H), 8.73 (d, 11H), 9.08 (d, 1H), 9.26-9.31 (m, 1H).

Example I-67

2-Amino-N-[(2S)-butan-2-yl]-6-(1-{1-[6-(difluoromethyl)pyridin-3-yl]-2-methylpropyl}-1H-pyrazol-4-yl)[1,2,4]triazolo[1,5-a]pyridine-8-carboxamide (mixture of diastereomers)

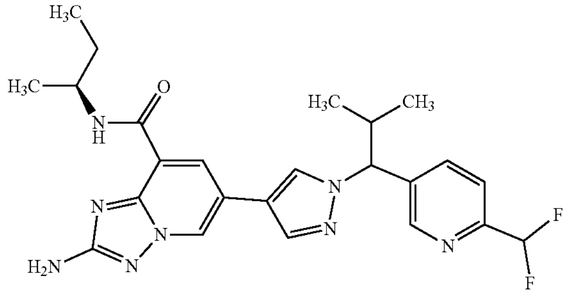 [SMILES: CC[C@H](C)NC(=O)c1cc(-c2cnn(C(c3ccc(C(F)F)nc3)C(C)C)c2)cn2nc(N)nc12]

2-Amino-6-bromo-N-[(2S)-butan-2-yl][1,2,4]triazolo[1,5-a]pyridine-8-carboxamide (38.0 mg, 122 μmol), 2-(difluoromethyl)-5-{2-methyl-1-[4-(4,4,5,5-tetramethyl-1,3,2-dioxaborolan-2-yl)-1H-pyrazol-1-yl]propyl}pyridine (55.1 mg, 146 μmol), sodium carbonate (64.5 mg, 609 μmol) and 1,1'-bis(diphenylphosphino)ferrocene-palladium(II)dichloride dichloromethane complex (4.97 mg, 6.09 μmol) were reacted according to procedure A in a mixture of 1,4-dioxane (1.5 ml) and water (200 μl). The reaction mixture was stirred for 2.5 h at 100° C. The residue was purified by preparative HPLC to yield 43.0 mg (100% purity, 73% yield) of the title compound as a mixture of two diasteromers.

LC-MS (method 1): $R_t$=1.80 min; MS (ESIpos): m/z=483 [M+H]$^+$ $^1$H-NMR (500 MHz, DMSO-$d_6$) δ [ppm]: 0.80 (d, 3H), 0.86 (d, 3H), 0.94 (t, 3H), 1.21 (d, 3H), 1.53-1.63 (m, 2H), 2.76-2.86 (m, 1H), 3.99-4.04 (m, 1H), 5.19 (d, 1H), 6.41 (s, 2H), 6.95 (t, 1H), 7.73 (d, 1H), 8.09 (s, 1H), 8.21 (d, 1H), 8.25 (s, 1H), 8.59 (s, 11H), 8.86 (d, 1H), 9.06 (d, 1H), 9.28 (d, 1H).

Example I-68

2-Amino-N-[(2S)-butan-2-yl]-6-(1-{1-[6-(difluoromethyl)pyridin-3-yl]-2-methylpropyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{1-[6-(difluoromethyl)pyridin-3-yl]-2-methylpropyl}-1H-pyrazol-4-yl)[1,2,4]triazolo[1,5-a]pyridine-8-carboxamide was separated by chiral preparative HPLC to yield stereoisomer 1 (11.6 mg, 100% purity) and stereoisomer 2 (15.8 mg, 100% purity).

Column: Daicel Chiralpak IG, 5 μm, 250×20 mm; Eluent A: n-heptane; Eluent B: 2-propanol; isocratic: 20% A+80% B; flow: 15 ml/min; UV: 220 nm; temperature: 70° C.

Stereoisomer 1: $R_t$=5.78 min and

Stereoisomer 2: $R_t$=8.07 min (cf. next example)

Analytical chiral HPLC-method: Column: Daicel Chiralpak IG, 5 μm, 250×4.6 mm; Eluent A: iso-hexane; Eluent B: 2-propanol; isocratic: 20% A+80% B; flow: 1 ml/min; UV: 220 nm, Temperature 70° C.

Stereoisomer 1: $R_t$=6.25 min and

Stereoisomer 2: $R_t$=8.68 min (cf. next example)

LC-MS (method 1): $R_t$=1.85 min; MS (ESIpos): m/z=483 [M+H]$^+$ $^1$H-NMR (500 MHz, DMSO-$d_6$) δ [ppm]: 0.006 (3.35), 0.795 (11.28), 0.808 (11.38), 0.855 (11.94), 0.868 (11.99), 0.924 (7.13), 0.939 (16.00), 0.954 (7.75), 1.207 (15.12), 1.220 (15.11), 1.262 (0.44), 1.548 (0.95), 1.562 (2.48), 1.570 (2.27), 1.576 (3.42), 1.583 (2.63), 1.590 (2.33), 1.598 (2.30), 1.612 (0.88), 2.733 (1.11), 2.793 (0.98), 2.806 (1.39), 2.818 (1.22), 2.827 (1.38), 2.840 (0.97), 2.893 (1.29), 3.987 (0.77), 4.001 (1.61), 4.015 (2.04), 4.029 (1.63), 4.043 (0.75), 5.174 (4.04), 5.196 (3.89), 6.408 (9.86), 6.837 (2.47), 6.947 (5.25), 7.057 (2.22), 7.720 (4.43), 7.737 (4.66), 8.092 (9.89), 8.203 (2.85), 8.207 (2.86), 8.220 (2.64), 8.224 (2.67), 8.246 (6.89), 8.250 (7.12), 8.586 (9.17), 8.861 (5.07), 8.864 (5.08), 9.060 (6.92), 9.064 (7.06), 9.268 (3.50), 9.284 (3.35).

Example I-69

2-Amino-N-[(2S)-butan-2-yl]-6-(1-{1-[6-(difluoromethyl)pyridin-3-yl]-2-methylpropyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 1): $R_t$=1.85 min; MS (ESIpos): m/z=483 [M+H]$^+$ $^1$H-NMR (500 MHz, DMSO-$d_6$) δ [ppm]: 0.80 (d, 3H), 0.86 (d, 3H), 0.94 (t, 3H), 1.21 (d, 3H), 1.53-1.63 (m, 2H), 2.78-2.85 (m, 1H), 3.99-4.04 (dt, 1H), 5.18 (d, 1H), 6.41 (s, 2H), 6.95 (t, 1H), 7.73 (d, 1H), 8.09 (s, 1H), 8.21 (d, 1H), 8.25 (s, 1H), 8.59 (s, 1H), 8.86 (d, 1H), 9.06 (d, 1H), 9.28 (d, 1H).

Example I-70

2-Amino-N-[(2S)-butan-2-yl]-6-(1-{1-[6-(trifluoromethyl)pyridin-3-yl]propyl}-1H-pyrazol-4-yl)[1,2,4]triazolo[1,5-a]pyridine-8-carboxamide (mixture of stereoisomers)

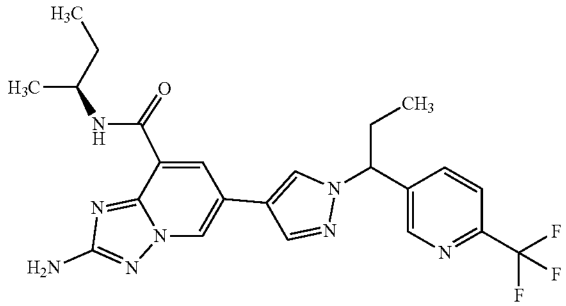 [SMILES: CCC(c1ccc(C(F)(F)F)nc1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (177 mg, 567 μmol), 5-{1-[4-(4,4,5,5-tetramethyl-1,3,2-dioxaborolan-2-yl)-1H-pyrazol-1-yl]propyl}-2-(trifluoromethyl)pyridine (355 mg, 73% purity, 680 μmol), 1,1'-bis(diphenylphosphino)ferrocene-palladium(II)dichloride dichloromethane complex (23.1 mg, 28.3 μmol) and water (1.5 ml) were reacted according to procedure A in a mixture of sodium carbonate (300 mg, 2.83 mmol) and 1,4-dioxane (4.5 ml). After 3 h at 90° C., the reaction was quenched with water and extracted with dichloromethane. The organic layer was dried over sodium sulfate, filtered and concentrated under reduced pressure. The residue was purified by column chromatography (Biotage® SNAP KP-NH 11 g cartridge, gradient: cyclohexane/ethyl acetate gradient 8:2 to 0:10) to yield 100 mg (98% purity, 36% yield) of the title compound as a mixture of two diastereomers.

LC-MS (method 1): $R_t$=1.86 min; MS (ESIpos): m/z=487 $[M+H]^+$ $^1$H-NMR (400 MHz, DMSO-$d_6$) δ [ppm]: 0.88 (t, 3H), 0.94 (t, 3H), 1.22 (d, 3H), 1.53-1.64 (m, 2H), 2.17-2.28 (m, 1H), 2.37-2.48 (m, 1H), 3.97-4.06 (m, 1H), 5.58 (dd, 1H), 6.40 (s, 2H), 7.92 (d, 11H), 8.06 (dd, 1H), 8.12 (s, 1H), 8.27 (d, 1H), 8.62 (s, 1H), 8.82 (d, 1H), 9.08 (d, 1H), 9.28 (d, 1H).

Example I-71

2-Amino-N-[(2S)-butan-2-yl]-6-(1-{(1S)-1-[6-(trifluoromethyl)pyridin-3-yl]propyl}-1H-pyrazol-4-yl)[1,2,4]triazolo[1,5-a]pyridine-8-carboxamide (single stereoisomer)

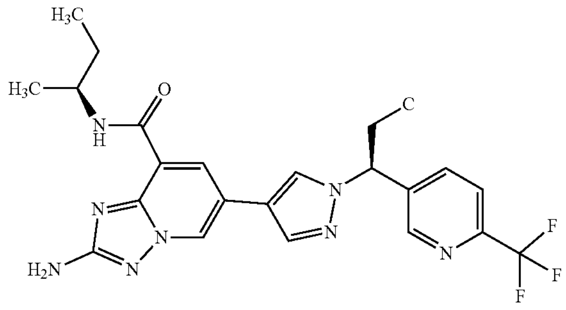

2-Amino-6-bromo-N-[(2S)-butan-2-yl][1,2,4]triazolo[1,5-a]pyridine-8-carboxamide (220 mg, 705 μmol), enantioenriched 5-{(1S)-1-[4-(4,4,5,5-tetramethyl-1,3,2-dioxaborolan-2-yl)-1H-pyrazol-1-yl]propyl}-2-(trifluoromethyl)pyridine (322 mg, 846 mol), sodium carbonate (373 mg, 3.52 mmol) and XPhos-Pd-G2 (55.4 mg, 70.5 μmol) were added to a mixture of dioxane (4.2 ml) and water (600 l). The mixture was degassed with argon and heated for 2 h to 90° C. It was cooled to rt and diluted with ethyl acetate (15 ml) and water (4 ml). The organic layer was separated and the aqueous layer was extracted twice with ethyl acetate (8 ml each). The combined organic layers were concentrated in vacuo and the residue was purified by column chromatography (Biotage® SNAP KP-NH 28 g cartridge, eluent: cyclohexane/ethyl acetate gradient 9:1 to 0:1). The product was then further purified by preparative HPLC (Chromatorex C18, 10 μm, 125×30 mm; eluent: water (0.1% formic acid)/acetonitrile gradient 9:1 to 0:1) to yield 274 mg (100% purity, 74% yield) of the enantioenrichted title compound. This was separated by chiral preparative SFC to yield 2-amino-N-[(2S)-butan-2-yl]-6-(1-{(1S)-1-[6-(trifluoromethyl)pyridin-3-yl]propyl}-1H-pyrazol-4-yl)[1,2,4]triazolo[1,5-a]pyridine-8-carboxamide (172 mg, 100% purity) and 2-amino-N-[(2S)-butan-2-yl]-6-(1-{(1R)-1-[6-(trifluoromethyl)pyridin-3-yl]propyl}-1H-pyrazol-4-yl)[1,2,4]triazolo[1,5-a]pyridine-8-carboxamide (52 mg, 100% purity).

Instrument: THAR SFC-Super Chrom Prep 200; Column: Daicel Chiralpak AD-H, 5 μm, 250×20 mm; Eluent A: $CO_2$; Eluent B: 2-propanol; isocratic: 60% A+40% B; flow: 100 ml/min; UV: 210 nm; temperature: 38° C.

(S,R)-Isomer: $R_t$=3.13 min and (cf. next example)

(S,S)-Isomer: $R_t$=6.80 min

Analytical SFC-method: Column: Chiralpak AD-H, 3 μm, 4.6×100 mm; Eluent A: $CO_2$; Eluent B: 2-propanol; isocratic: 70% A+30% B; flow: 3 ml/min; UV: 210 nm; temperature: 40° C.

(S,R)-Isomer: $R_t$=1.990 min (cf. next example)

(S,S)-Isomer: $R_t$=4.911 min

LC-MS (method 2): $R_t$=0.97 min; MS (ESIpos): m/z=487 $[M+H]^+$ $^1$H-NMR (400 MHz, DMSO-$d_6$) δ [ppm]: 0.88 (t, 3H), 0.94 (t, 3H), 1.22 (d, 3H), 1.52-1.65 (m, 2H), 2.16-2.29 (m, 1H), 2.39-2.49 (m, 1H), 3.96-4.08 (m, 1H), 5.59 (dd, 1H), 6.40 (s, 2H), 7.92 (d, 1H), 8.06 (dd, 1H), 8.12 (s, 1H), 8.28 (d, 1H), 8.62 (s, 1H), 8.82 (d, 1H), 9.08 (d, 1H), 9.28 (d, 1H).

Example I-72

2-Amino-N-[(2S)-butan-2-yl]-6-(1-{(1R)-1-[6-(trifluoromethyl)pyridin-3-yl]propyl}-1H-pyrazol-4-yl)[1,2,4]triazolo[1,5-a]pyridine-8-carboxamide (single stereoisomer)

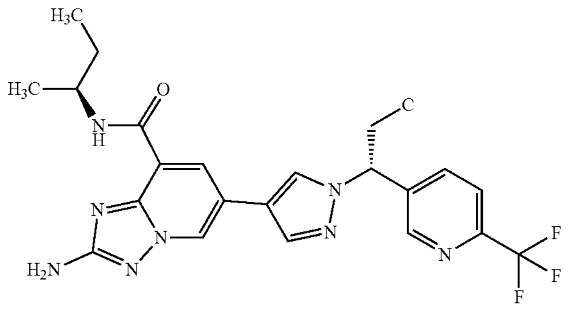

The product was isolated in the previous example as minor stereoisomer.

LC-MS (method 2): $R_t$=0.97 min; MS (ESIpos): m/z=487 $[M+H]^+$ $^1$H-NMR (400 MHz, DMSO-$d_6$) δ [ppm]: 0.860 (5.58), 0.878 (12.76), 0.896 (6.01), 0.923 (6.89), 0.941 (16.00), 0.960 (7.76), 0.989 (0.46), 1.004 (0.43), 1.208 (15.03), 1.225 (15.31), 1.545 (0.84), 1.562 (2.59), 1.568 (2.19), 1.580 (3.56), 1.598 (2.36), 1.603 (2.49), 1.621 (0.86), 2.191 (0.74), 2.208 (1.25), 2.225 (1.86), 2.243 (1.51), 2.259 (0.95), 2.368 (0.44), 2.411 (0.91), 2.429 (1.19), 2.434 (1.08), 2.446 (1.12), 2.453 (1.28), 2.470 (1.14), 2.672 (0.41), 2.712 (0.43), 3.983 (0.71), 3.999 (1.54), 4.017 (1.95), 4.035 (1.60), 4.051 (0.72), 5.565 (1.75), 5.580 (2.02), 5.589 (2.12), 5.604 (1.73), 6.397 (9.21), 7.907 (4.23), 7.928 (5.49), 8.052 (2.83), 8.056 (2.91), 8.076 (2.25), 8.118 (10.09), 8.272 (6.82), 8.276 (7.26), 8.620 (9.26), 8.820 (4.76), 8.824 (4.86), 9.077 (6.74), 9.081 (7.03), 9.267 (3.33), 9.287 (3.24).

Example I-73

2-Amino-N-[(2S)-butan-2-yl]-6-(1-{2-methyl-1-[6-(trifluoromethyl)pyridin-3-yl]propyl}-1H-pyrazol-4-yl)[1,2,4]triazolo[1,5-a]pyridine-8-carboxamide (mixture of diastereomers)

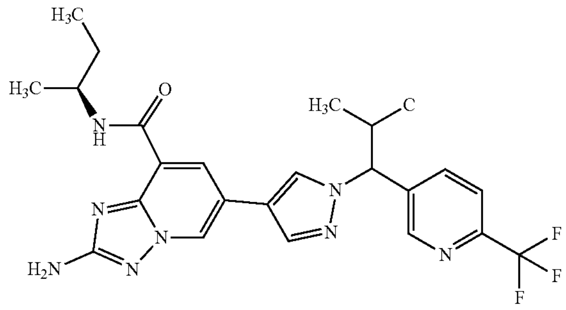

2-Amino-6-bromo-N-[(2S)-butan-2-yl][1,2,4]triazolo[1,5-a]pyridine-8-carboxamide (100 mg, 320 μmol), 5-{2-methyl-1-[4-(4,4,5,5-tetramethyl-1,3,2-dioxaborolan-2-yl)-1H-pyrazol-1-yl]propyl}-2-(trifluoromethyl)pyridine (159 mg, 95% purity, 384 μmol), sodium carbonate (170 mg, 1.60 mmol) and 1,1'-bis(diphenylphosphino)ferrocene-palladium (II)dichloride dichloromethane complex (13.1 mg, 16.0 mol) were reacted according to procedure A in a mixture of 1,4-dioxane (4.0 ml) and water (600 μl). The reaction mixture was stirred for 2.5 h at 90° C. The residue was purified by preparative HPLC to give 2-amino-N-[(2S)-butan-2-yl]-6-(1-{2-methyl-1-[6-(trifluoromethyl)pyridin-3-yl]propyl}-1H-pyrazol-4-yl)[1,2,4]triazolo[1,5-a]pyridine-8-carboxamide as a mixture of two diasteromers.

LC-MS (method 1): $R_t$=1.96 min; MS (ESIpos): m/z=501 $[M+H]^+$ $^1$H-NMR (500 MHz, DMSO-$d_6$) δ [ppm]: 0.81 (d, 3H), 0.87 (d, 3H), 0.94 (t, 3H), 1.22 (d, 3H), 1.53-1.63 (m, 2H), 2.80-2.85 (m, 1H), 3.99-4.04 (m, 1H), 5.25 (d, 1H), 6.39 (s, 2H), 7.94 (d, 1H), 8.10 (s, 1H), 8.25 (s, 1H), 8.30 (d, 1H), 8.58 (s, 1H), 8.96 (s, 1H), 9.06 (d, 1H), 9.27 (d, 1H).

Example I-74

2-Amino-N-[(2S)-butan-2-yl]-6-(1-{2-methyl-1-[6-(trifluoromethyl)pyridin-3-yl]propyl}-1H-pyrazol-4-yl)[1,2,4]triazolo[1,5-a]pyridine-8-carboxamide (stereoisomer 1, distomer)]

2-Amino-N-[(2S)-butan-2-yl]-6-(1-{2-methyl-1-[6-(trifluoromethyl)pyridin-3-yl]propyl}-1 H-pyrazol-4-yl)[1,2,4]triazolo[1,5-a]pyridine-8-carboxamide (mixture of diastereomers) (62 mg, 100% purity) was separated by chiral preparative HPLC to yield stereoisomer 1(14.6 mg, 100% purity) and stereoisomer 2 (16.6 mg, 100% purity).

Column: Daicel Chiralpak AD_H, 5 μm, 250×20 mm; Eluent A: n-heptane; Eluent B: ethanol; isocratic: 30% A+70% B; flow: 20 ml/min; UV: 220 nm; temperature: 40° C.

Stereoisomer 1: $R_t$=6.04 min and

Stereoisomer 2: $R_t$=8.48 min (cf. next example)

Analytical chiral HPLC-method: Column: Chiralteck AD-3, 3 m, 250×4.6 mm; Eluent A: n-heptane; Eluent B: ethanol; isocratic: 20% A+80% B; flow: 1 ml/min; UV: 220 nm Stereoisomer 1: $R_t$=3.30 min and Stereoisomer 2: $R_t$=5.46 min (cf. next example)

LC-MS (method 1): $R_t$=1.97 min; MS (ESIpos): m/z=501 $[M+H]^+$ $^1$H-NMR (500 MHz, DMSO-$d_6$) δ [ppm]: −0.007 (3.69), 0.006 (2.48), 0.801 (11.25), 0.815 (11.27), 0.864 (12.08), 0.877 (11.93), 0.924 (7.12), 0.939 (16.00), 0.954 (7.46), 1.160 (0.43), 1.207 (14.87), 1.220 (14.81), 1.234 (1.47), 1.549 (0.91), 1.563 (2.39), 1.570 (2.05), 1.577 (3.21), 1.583 (2.39), 1.591 (2.12), 1.598 (2.11), 1.612 (0.76), 2.363 (0.48), 2.636 (0.50), 2.696 (0.85), 2.804 (1.10), 2.817 (1.28), 2.825 (1.15), 2.830 (1.13), 2.838 (1.40), 2.852 (0.98), 3.986 (0.74), 4.000 (1.56), 4.014 (1.88), 4.028 (1.45), 4.042 (0.69), 5.243 (3.95), 5.264 (3.79), 6.385 (3.89), 7.931 (4.48), 7.948 (4.83), 8.101 (9.60), 8.244 (6.51), 8.248 (6.65), 8.286 (2.54), 8.290 (2.54), 8.303 (2.25), 8.579 (8.72), 8.954 (4.59), 9.053 (6.47), 9.057 (6.52), 9.259 (3.00), 9.274 (2.92).

Example I-75

2-Amino-N-[(2S)-butan-2-yl]-6-(1-{2-methyl–1-[6-(trifluoromethyl)pyridin-3-yl]propyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 1): $R_t$=1.96 min; MS (ESIpos): m/z=501 $[M+H]^+$ $^1$H-NMR (500 MHz, DMSO-$d_6$) δ [ppm]: 0.81 (d, 3H), 0.87 (d, 3H), 0.94 (t, 3H), 1.21 (d, 4H), 1.52-1.63 (m, 2H), 2.80-2.85 (m, 1H), 3.99-4.04 (m, 1H), 5.25 (d, 1H), 6.39 (br s, 2H), 7.94 (d, 1H), 8.10 (s, 1H), 8.25 (s, 1H), 8.30 (d, 1H), 8.58 (s, 1H), 8.96 (s, 1H), 9.06 (d, 1H), 9.27 (d, 1H).

Example I-76

2-Amino-N-[(2S)-butan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of stereoisomers)

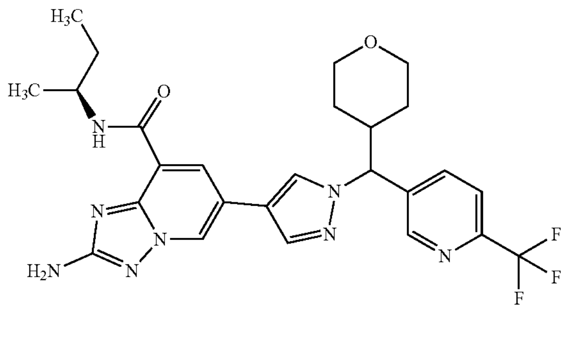 [SMILES: CC[C@H](C)NC(=O)c1cc(-c2cnn(C(c3ccc(C(F)(F)F)nc3)C3CCOCC3)c2)cn2nc(N)nc12]

2-Amino-6-bromo-N-[(2S)-butan-2-yl][1,2,4]triazolo[1,5-a]pyridine-8-carboxamide (100 mg, 320 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (182 mg, 416 μmol) for 2 h at 90° C. following general procedure B using 0.1 eq. XPhos-Pd-G2 as catalyst. The reaction mixture was diluted with ethyl acetate (15 ml) and washed with water (3 ml). The aqueous layer was extracted twice with ethyl acetate (8 ml each). The combined organic layers were concentrated in vacuo and the residue was purified by column chromatography (Biotage® SNAP KP-NH 110 g cartridge, eluent: cyclohexane/ethyl acetate gradient 90:10 to 0:100) to yield 140 mg (97% purity, 78% yield) of the title compound.

LC-MS (method 2): $R_t$=0.94 min; MS (ESIpos): m/z=543 $[M+H]^+$ $^1$H-NMR (500 MHz, DMSO-$d_6$) δ [ppm]: −0.007 (0.57), 0.006 (0.46), 0.925 (7.01), 0.940 (16.00), 0.955 (7.64), 1.072 (3.70), 1.101 (1.46), 1.208 (15.08), 1.221 (15.28), 1.261 (0.57), 1.270 (0.57), 1.285 (1.17), 1.294 (1.24), 1.309 (1.42), 1.317 (1.46), 1.333 (1.41), 1.340 (1.35), 1.356 (0.98), 1.363 (0.92), 1.380 (0.43), 1.549 (0.89), 1.563 (2.59), 1.572 (2.07), 1.578 (3.48), 1.584 (2.44), 1.592 (2.35), 1.599 (2.15), 1.607 (0.68), 1.614 (0.81), 2.738 (0.44), 2.760 (1.17), 2.782 (1.15), 2.804 (0.41), 3.245 (1.18), 3.265 (3.02), 3.269 (3.00), 3.288 (3.16), 3.292 (3.03), 3.799 (1.48), 3.828 (1.70), 3.860 (1.24), 3.989 (0.72), 4.002 (1.50), 4.017 (1.87), 4.030 (1.48), 4.044 (0.65), 5.391 (3.75), 5.413 (3.63), 6.396 (9.32), 7.942 (4.57), 7.958 (4.88), 8.124 (9.78), 8.246 (8.55), 8.250 (8.31), 8.305 (2.63), 8.309 (2.50), 8.322 (2.29), 8.325 (2.18), 8.581 (8.90), 8.969 (4.85), 8.972 (4.57), 9.060 (8.36), 9.064 (7.92), 9.262 (3.46), 9.278 (3.31).

Example I-77

2-Amino-N-[(2S)-butan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of stereoisomers) (126 mg, 97% purity) from the previous example was separated by chiral chromatography to yield stereoisomer 1 (35 mg, 98% purity) and stereoisomer 2 (36 mg, 98% purity).

Column: Daicel Chiralcel OZ-H, 5 μm, 250×20 mm; Eluent A: n-heptane; Eluent B: ethanol+0.2% diethylamine; isocratic: 50% A+50% B; flow: 15 ml/min; UV: 210 nm; temperature: 40° C.

Stereoisomer 1: $R_t$=8.668 min and

Stereoisomer 2: $R_t$=9.604 min (cf. next example)

Analytical chiral HPLC. Column: Chiraltek OZ-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R_t$=3.716 min and

Stereoisomer 2: $R_t$=4.799 min (cf. next example)

LC-MS (method 2): $R_t$=0.94 min; MS (ESIpos): m/z=543 $[M+H]^+$ $^1$H-NMR (600 MHz, DMSO-$d_6$) δ [ppm]: 0.858 (0.44), 0.927 (6.95), 0.940 (15.05), 0.952 (7.44), 1.083 (1.56), 1.103 (1.90), 1.210 (16.00), 1.221 (15.41), 1.267 (0.63), 1.275 (0.73), 1.288 (1.39), 1.295 (1.46), 1.308 (1.39), 1.316 (1.78), 1.336 (1.71), 1.342 (1.46), 1.356 (1.22), 1.376 (0.49), 1.543 (0.44), 1.555 (0.95), 1.566 (2.44), 1.578 (3.54), 1.586 (2.85), 1.597 (2.29), 1.610 (0.93), 2.426 (0.51), 2.654 (0.46), 2.743 (0.54), 2.761 (1.41), 2.780 (1.39), 2.799 (0.54), 3.250 (1.41), 3.270 (3.83), 3.800 (1.66), 3.816 (1.61), 3.835 (1.71), 3.854 (1.56), 3.992 (0.78), 4.004 (1.73), 4.015 (2.20), 4.027 (1.68), 4.038 (0.73), 5.391 (3.98), 5.409 (3.83), 6.375 (10.78), 7.938 (4.51), 7.952 (4.78), 8.117 (9.29), 8.244 (6.54), 8.246 (6.49), 8.304 (2.93), 8.318 (2.78), 8.573 (8.61), 8.967 (5.59), 9.053 (6.46), 9.257 (3.56), 9.270 (3.44).

Example I-78

2-Amino-N-[(2S)-butan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 2, eutomer)

The product was isolated in the previous example as second stereoisomer. The stereochemical configuration of the methine carbon atom bonded to the pyrazole was (S).

LC-MS (method 2): $R_t$=0.94 min; MS (ESIpos): m/z=543 $[M+H]^+$ $^1$H-NMR (600 MHz, DMSO-$d_6$) δ [ppm]: 0.94 (t, 3H), 1.07-1.12 (m, 1H), 1.20-1.25 (m, 4H), 1.26-1.39 (m, 2H), 1.58 (m, 2H), 2.73-2.82 (m, 1H), 3.24-3.29 (m, 2H), 3.78-3.87 (m, 2H), 4.02 (m, 1H), 5.40 (d, 1H), 6.38 (s, 2H), 7.95 (d, 1H), 8.12 (s, 1H), 8.25 (d, 1H), 8.31 (d, 1H), 8.57 (s, 1H), 8.97 (s, 1H), 9.05 (d, 1H), 9.26 (d, 1H).

Example I-79 tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (mixture of stereoisomers)

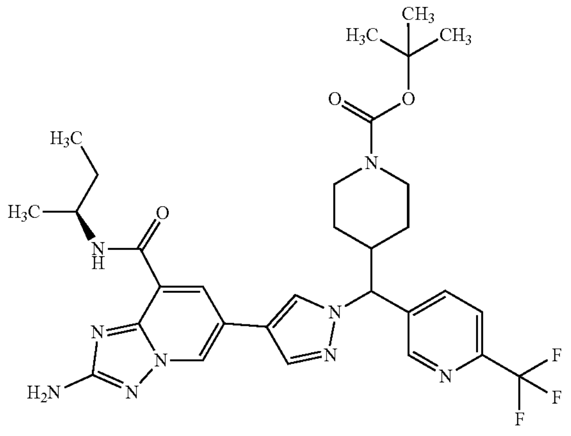 [SMILES: CC[C@H](C)NC(=O)c1cc(-c2cnn(C(c3ccc(C(F)(F)F)nc3)C3CCN(C(=O)OC(C)(C)C)CC3)c2)cn2nc(N)nc12]

2-Amino-6-bromo-N-[(2S)-butan-2-yl][1,2,4]triazolo[1,5-a]pyridine-8-carboxamide (150 mg, 481 mol) was reacted with tert-butyl 4-{[4-(4,4,5,5-tetramethyl-1,3,2-dioxaborolan-2-yl)-1H-pyrazol-1-yl][6-(trifluoromethyl)pyridin-3-yl]methyl}piperidine-1-carboxylate (309 mg, 576 μmol) for 2 h at 90° C. following general procedure B using 0.05 eq. catalyst. The reaction mixture was diluted with ethyl acetate (10 ml), filtered through a hydrophobic phase separation filter and concentrated in vacuo. The residue was purified by column chromatography (Biotage® SNAP KP-NH 28 g cartridge, eluent: cyclohexane/ethyl acetate gradient 80:20 to 0:100) to yield 241 mg (98% purity, 77% yield) of the title compound.

LC-MS (method 1): $R_t$=2.19 min; MS (ESIpos): m/z=642 $[M+H]^+$ $^1$H-NMR (600 MHz, DMSO-$d_6$) δ [ppm]: 0.929 (1.24), 0.941 (2.68), 0.954 (1.29), 1.074 (1.58), 1.166 (0.60), 1.177 (0.52), 1.189 (0.44), 1.210 (2.43), 1.221 (2.33), 1.372 (1.08), 1.379 (16.00), 1.568 (0.44), 1.580 (0.59), 1.592 (0.40), 1.989 (0.53), 5.400 (0.61), 5.418 (0.59), 6.376 (1.63), 7.940

(0.77), 7.954 (0.80), 8.122 (1.62), 8.245 (1.31), 8.248 (1.31), 8.545 (1.30), 8.963 (0.76), 8.965 (0.74), 9.052 (1.33), 9.055 (1.32), 9.259 (0.60), 9.272 (0.58).

Example I-80 tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (stereoisomer 1, distomer)

tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (193 mg, 98% purity) from the previous example was separated by chiral chromatography to yield stereoisomer 1 (72.8 mg, 99% purity) and stereoisomer 2 (74.3 mg, 99% purity).

Column: Daicel Chiralpak AD SFC, 250×20 mm; Eluent A: $CO_2$; Eluent B: 2-propanol; isocratic: 75% A+25% B; flow: 80 ml/min; UV: 210 nm; temperature: 40° C.

Stereoisomer 1: $R_t$=5.0 min and

Stereoisomer 2: $R_t$=9.3 min (cf. next example)

Analytical SFC-method: Column: Chiralpak AD, 4.6×100 mm; Eluent A: $CO_2$; Eluent B: 2-propanol; isocratic: 75% A+25% B; flow: 3 ml/min; UV: 210 nm.

Stereoisomer 1: $R_t$=2.920 min and

Stereoisomer 2: $R_t$=6.250 min (cf. next example)

LC-MS (method 1): $R_t$=1.27 min; MS (ESIpos): m/z=542 $[M+H]^+$ $^1$H-NMR (600 MHz, DMSO-$d_6$) δ [ppm]: 0.005 (0.44), 0.928 (7.01), 0.940 (16.00), 0.953 (7.37), 1.073 (0.79), 1.137 (2.48), 1.142 (2.45), 1.185 (0.87), 1.210 (15.34), 1.221 (15.38), 1.245 (1.38), 1.262 (0.72), 1.555 (0.75), 1.567 (2.21), 1.575 (1.91), 1.579 (3.03), 1.585 (2.12), 1.587 (2.03), 1.591 (2.05), 1.597 (2.07), 1.610 (0.79), 2.426 (0.58), 2.439 (0.62), 2.460 (1.59), 2.477 (2.12), 2.481 (2.08), 2.518 (0.77), 2.521 (0.76), 2.524 (0.61), 2.573 (0.63), 2.577 (0.55), 2.609 (0.83), 2.615 (1.00), 2.655 (0.48), 2.915 (1.25), 2.936 (1.28), 2.941 (1.29), 2.947 (1.29), 2.968 (1.08), 3.992 (0.66), 4.003 (1.34), 4.015 (1.62), 4.027 (1.34), 4.038 (0.63), 5.345 (2.79), 5.363 (2.72), 6.375 (8.40), 7.933 (3.83), 7.947 (4.05), 8.108 (7.92), 8.241 (6.81), 8.244 (6.71), 8.296 (2.12), 8.300 (2.10), 8.310 (1.93), 8.313 (1.90), 8.566 (7.33), 8.958 (3.95), 8.961 (3.87), 9.046 (6.67), 9.049 (6.63), 9.259 (2.93), 9.272 (2.81).

Example I-81 tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (stereoisomer 2, eutomer)

The product was isolated in the previous example as second stereoisomer.

LC-MS (method 1): $R_t$=1.28 min; MS (ESIpos): m/z=542 $[M+H]^+$ $^1$H-NMR (400 MHz, DMSO-$d_6$) δ [ppm]: 0.94 (t, 3H), 1.10-1.30 (m, 4H), 1.21 (d, 3H), 1.38 (s, 9H), 1.48-1.66 (m, 2H), 2.61-2.82 (m, 311), 3.83-3.97 (m, 2H), 3.97-4.06 (m, 1H), 5.41 (d, 1H), 6.40 (s, 2H), 7.95 (d, 11H), 8.13 (s, 1H), 8.24 (d, 11H), 8.31 (dd, 11H), 8.55 (s, 1H), 8.96 (d, 1H), 9.06 (d, 1H), 9.27 (d, 1H).

Example I-82

2-Amino-N-[(2S)-butan-2-yl]-6-(1-{piperidin-4-yl[6-(trifluoromethyl)pyridin-3-yl]methyl}-1H-pyrazol-4-yl)[1,2,4]triazolo[1,5-a]pyridine-8-carboxamide (stereoisomer 1, distomer)

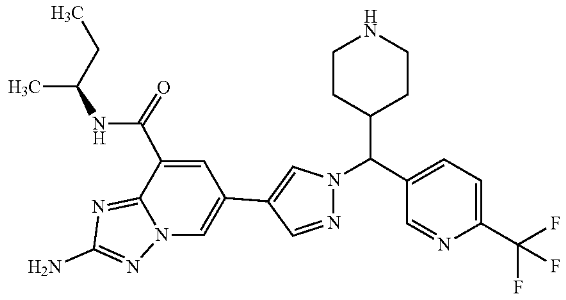 [SMILES: CC[C@H](C)NC(=O)c1cc(-c2cnn(C(c3ccc(C(F)(F)F)nc3)C3CCNCC3)c2)cn2nc(N)nc12]

tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (stereoisomer 1) (71.0 mg, 111 mol) was dissolved in dichloromethane (2.0 ml), trifluoroacetic acid (430 pl, 5.5 mmol) was added and the mixture was stirred for 30 min at rt. The reaction mixture was concentrated in vacuo and the residue was dissolved in acetonitrile (4 ml). The solution was filtered through a SPE-cartridge (Agilent, PL-HCO3 MP SPE 500 mg) which was rinsed with acetonitrile (12 ml) and evaporated to yield 38.6 mg (99% purity, 64% yield) of the title compound.

LC-MS (method 1): $R_t$=1.27 min; MS (ESIpos): m/z=542 $[M+H]^+$ $^1$H-NMR (600 MHz, DMSO-$d_6$) δ [ppm]: 0.94 (t, 3H), 1.10-1.28 (m, 7H), 1.52-1.64 (m, 2H), 2.43-2.49 (m, 2H), 2.57-2.64 (m, 1H), 2.90-3.00 (m, 2H), 3.98-4.05 (m, 1H), 5.35 (d, 1H), 6.37 (s, 2H), 7.94 (d, 1H), 8.11 (s, 1H), 8.24 (d, 1H), 8.31 (dd, 1H), 8.57 (s, 1H), 8.96 (d, 1H), 9.05 (d, 1H), 9.27 (d, 1H).

Example I-83

2-Amino-N-[(2S)-butan-2-yl]-6-(1-{piperidin-4-yl[6-(trifluoromethyl)pyridin-3-yl]methyl}-1H-pyrazol-4-yl)[1,2,4]triazolo[1,5-a]pyridine-8-carboxamide (stereoisomer 2, eutomer)

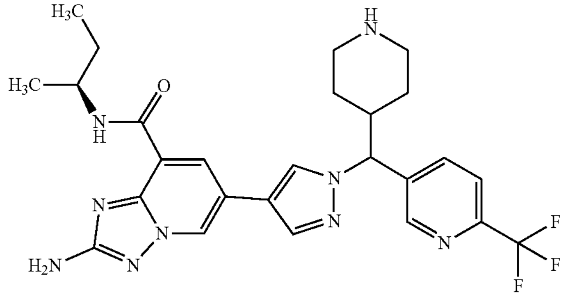 [SMILES: CC[C@H](C)NC(=O)c1cc(-c2cnn(C(c3ccc(C(F)(F)F)nc3)C3CCNCC3)c2)cn2nc(N)nc12]

tert-Butyl 4-{(4-{2-amino-8-[(2S)-butan-2-ylcarbamoyl][1,2,4]triazolo[1,5-a]pyridin-6-yl}-1H-pyrazol-1-yl)[6-(trifluoromethyl)pyridin-3-yl]methyl}piperidine-1-carboxylate (stereoisomer 2) (72.5 mg, 113 mol) was dissolved in dichloromethane (2.0 ml), trifluoroacetic acid (440 pl, 5.6 mmol) was added and the mixture was stirred for 30 min at rt. The reaction mixture was concentrated in vacuo and the residue was dissolved in acetonitrile (4 ml). The solution was filtered through a SPE-cartridge (Agilent, PL-HCO3 MP SPE 500 mg) which was rinsed with acetonitrile 15 (12 ml) and evaporated to yield 38.6 mg (99% purity, 64% yield) of the title compound.

LC-MS (method 1): $R_t$=1.28 min; MS (ESIpos): m/z=542 $[M+H]^+$ $^1$H-NMR (600 MHz, DMSO-$d_6$) δ [ppm]: 0.94 (t, 3H), 1.09-1.26 (m, 7H), 1.54-1.63 (m, 2H), 2.37-2.62 (m, 4H), 2.87-2.95 (m, 2H), 3.98-4.05 (m, 1H), 5.34 (d, 1H), 6.37 (s, 2H), 7.94 (d, 1H), 8.10 (s, 1H), 8.24 (d, 1H), 8.30 (dd, 1H), 8.57 (s, 1H), 8.96 (d, 1H), 9.05 (d, 1H), 9.26 (d, 1H).

Example I-84

6-(1-{(1-Acetylpiperidin-4-yl)[6-(trifluoromethyl)pyridin-3-yl]methyl}-1 H-pyrazol-4-yl)-2-amino-N-[(2S)-butan-2-yl][1,2,4]triazolo[1,5-a]pyridine-8-carboxamide (single stereoisomer)

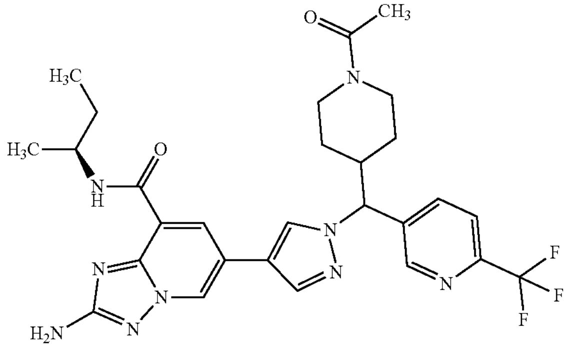 [SMILES: CC[C@H](C)NC(=O)c1cc(-c2cnn(C(c3ccc(C(F)(F)F)nc3)C3CCN(C(C)=O)CC3)c2)cn2nc(N)nc12]

2-Amino-N-[(2S)-butan-2-yl]-6-(1-{piperidin-4-yl[6-(trifluoromethyl)pyridin-3-yl]methyl}-1H-pyrazol-4-yl)[1,2,4]triazolo[1,5-a]pyridine-8-carboxamide (single stereoisomer, eutomer) (73.0 mg, 135 μmol) from the previous example was dissolved in THF (2.5 ml) and cooled to 0° C. Acetic anhydride (13 1d, 130 μmol) and pyridine (11 1) were added dropwise and the reaction mixture was stirred for 5 min at 0° C. While cooling, satd. sodium bicarbonate solution (2 ml) was added. The mixture was extracted three times with ethyl acetate (2 ml each) and the combined organic layers where washed with satd. sodium bicarbonate solution and brine. The organic layer was filtered through a hydrophobic phase separation filter and the filtrate was concentrated in vacuo. The residue was purified by preparative HPLC (Chromatorex C18, 10 μm, 125×30 mm; eluent: water/acetonitrile gradient 9:1 to 5:95) to yield 45.6 mg (100% purity, 58% yield) of the title compound.

An overall scheme for the preparation of this compound from Example I-81 is depicted below:

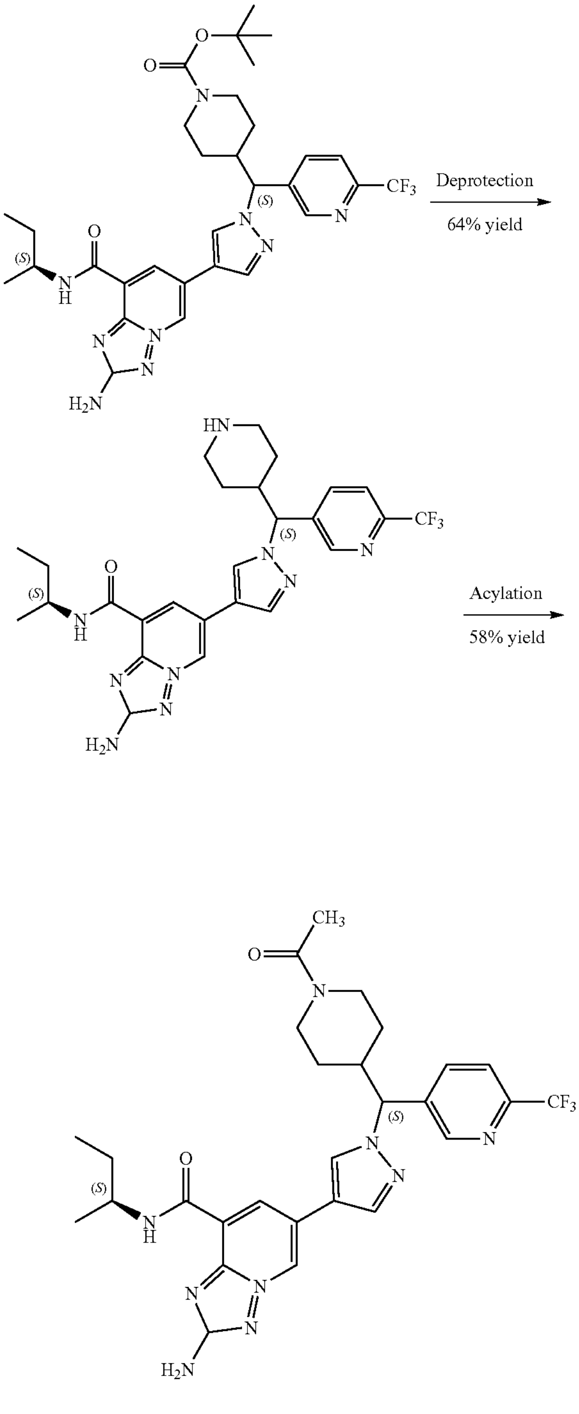

LC-MS (method 1): $R_t$=1.67 min; MS (ESIpos): m/z=584 $[M+H]^+$ H-NMR (500 MHz, $CDCl_3$) 5 [ppm]: 1.00 (t, 3H), 1.14-1.31 (m, 5H), 1.36-1.44 (m, 1H), 1.47-1.53 (m, 1H), 1.62-1.70 (m, 2H), 2.08 (d, 3H), 2.46-2.59 (m, 1H), 2.72-2.83 (m, 1H), 2.98-3.12 (m, 1H), 3.79-3.86 (m, 1H), 4.13-4.22 (m, 1H), 4.55-4.59 (m, 2H), 4.63-4.70 (m, 1H), 4.88 (d, 1H), 7.72 (d, 1H), 7.77 (s, 1H), 7.86 (d, 1H), 8.15-8.20 (m, 1H), 8.38 (d, 1H), 8.44-8.47 (m, 1H), 8.81-8.83 (m, 1H), 9.16 (br d, 1H).

Example I-85

2-Amino-N-[(2S)-butan-2-yl]-6-(1-{1-[6-(2,2,2-trifluoroethoxy)pyridin-3-yl]propyl}-1H-pyrazol-4-yl)[1,2,4]triazolo[1,5-a]pyridine-8-carboxamide (mixture of diastereomers)

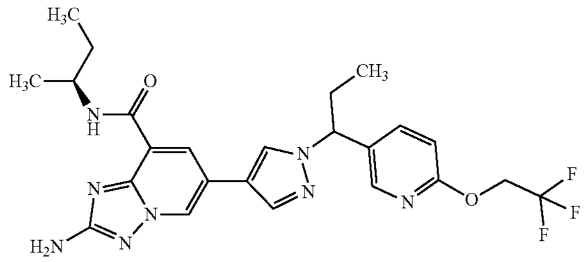 [SMILES: CCC(c1ccc(OCC(F)(F)F)nc1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (94.0 mg, 301 μmol), 5-{1-[4-(4,4,5,5-tetramethyl-1,3,2-dioxaborolan-2-yl)-1H-pyrazol-1-yl]propyl}-2-(2,2,2-trifluoroethoxy)pyridine (161 mg, 92% purity, 361 μmol), sodium carbonate (160 mg, 1.51 mmol) and 1,1'-bis(diphenylphosphino)ferrocene-palladium (II)dichloride dichloromethane complex (12.3 mg, 15.1 μmol) were reacted according to procedure A in a mixture of 1,4-dioxane (4.0 ml) and water (600 1). The reaction mixture was stirred for 2.5 h at 100° C. The residue was purified by column chromatography (Biotage® SNAP KP-NH 11 g cartridge, eluent: cyclohexane 15/ethyl acetate gradient 8:2 to 2:8) to yield 110 mg (99% purity, 70% yield) of the title compound as a mixture of two diastereomers.

LC-MS (method 1): $R_t$=2.01 min; MS (ESIpos): m/z=517 $[M+H]^+$ $^1$H-NMR (500 MHz, DMSO-$d_6$) δ [ppm]: 0.84 (t, 3H), 0.94 (t, 3H), 1.22 (d, 3H), 1.55-1.62 (m, 2H), 2.13-2.17 (m, 1H), 2.35-2.48 (m, 1H), 3.99-4.04 (m, 1H), 4.97 (q, 2H), 5.38 (dd, 1H), 6.38 (s, 2H), 6.98 (d, 1H), 7.87 (dd, 1H), 8.05 (s, 1H), 8.26 (dd, 2H), 8.55 (s, 1H), 9.06 (d, 1H), 9.27 (d, 1H). 1

Example I-86

2-Amino-N-[(2S)-butan-2-yl]-6-(1-{1-[6-(2,2,2-trifluoroethoxy)pyridin-3-yl]propyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{1-[6-(2,2,2-trifluoroethoxy)pyridin-3-yl]propyl}-1H-pyrazol-4-yl)[1,2,4]triazolo[1,5-a]pyridine-8-carboxamide (mixture of diastereoisomers) (110 mg, 99% purity) was separated by chiral preparative HPLC to yield stereoisomer 1 (24 mg, 100% purity) and stereoisomer 2 (27 mg, 100% purity).

Column: Daicel Chiralpak IA, 5 μm, 250×30 mm; Eluent A: n-heptane; Eluent B: 2-propanol+0.2% diethylamine; isocratic: 55% A+45% B; flow: 50 ml/min; UV: 210 nm; temperature: 40° C.

Stereoisomer 1: $R_t$=7.95 min and

Stereoisomer 2: $R_t$=12.62 min (cf. next example)

Analytical chiral HPLC-method: Column: Daicel Chiralpack IA-3, 3 μm, 50×4.6 mm; Eluent A: n-heptan; Eluent B: 2-propanol+0.2% diethylamine; isocratic: 50% A+50% B; flow: 1 ml/min; UV: 220 nm Stereoisomer 1: $R_t$=1.64 min and Stereoisomer 2: $R_t$=2.51 min (cf. next example)

LC-MS (method 1): $R_t$=2.01 min; MS (ESIpos): m/z=517 $[M+H]^+$ $^1$H-NMR (500 MHz, DMSO-$d_6$) δ [ppm]: 0.828 (5.48), 0.842 (11.88), 0.857 (5.42), 0.926 (7.03), 0.941 (16.00), 0.956 (7.49), 1.032 (0.50), 1.045 (0.50), 1.208 (15.00), 1.221 (14.87), 1.549 (0.86), 1.563 (2.34), 1.572 (2.03), 1.577 (3.14), 1.584 (2.30), 1.592 (2.09), 1.599 (2.09), 1.614 (0.75), 2.128 (0.75), 2.141 (1.32), 2.155 (1.84), 2.170 (1.51), 2.183 (0.86), 2.365 (1.02), 2.379 (1.13), 2.392 (1.07), 2.397 (1.15), 2.410 (0.98), 2.425 (0.71), 3.293 (0.46), 3.988 (0.71), 4.001 (1.44), 4.016 (1.80), 4.030 (1.44), 4.043 (0.65), 4.946 (2.70), 4.964 (7.72), 4.982 (7.30), 5.000 (2.26), 5.368 (1.74), 5.381 (2.05), 5.386 (2.07), 5.399 (1.67), 6.406 (8.87), 6.980 (5.00), 6.997 (5.10), 7.862 (3.16), 7.866 (3.16), 7.879 (2.95), 7.884 (3.03), 8.060 (9.43), 8.252 (5.27), 8.259 (9.06), 8.263 (7.55), 8.565 (8.62), 9.063 (7.13), 9.067 (7.13), 9.273 (3.26), 9.289 (3.12).

Example I-87

2-Amino-N-[(2S)-butan-2-yl]-6-(1-{1-[6-(2,2,2-trifluoroethoxy)pyridin-3-yl]propyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 1): $R_t$=2.01 min; MS (ESIpos): m/z=517 $[M+H]^+$ $^1$H-NMR (500 MHz, DMSO-$d_6$) δ [ppm]: 0.84 (t, 3H), 0.94 (t, 3H), 1.21 (d, 3H), 1.53-1.62 (m, 2H), 2.13-2.17 (m, 1H), 2.35-2.48 (m, 1H), 3.99-4.04 (dt, 1H), 4.97 (q, 2H), 5.38 (dd, 1H), 6.41 (s, 2H), 6.99 (d, 1H), 7.87 (dd, 1H), 8.06 (s, 1H), 8.26 (s, 2H), 8.56 (s, 1H), 9.06 (d, 1H), 9.28 (d, 1H).

Example I-88

2-Amino-N-[(2S)-butan-2-yl]-6-(1-{2-methyl-1-[6-(2,2,2-trifluoroethoxy)pyridin-3-yl]propyl}-1H-pyrazol-4-yl)[1,2,4]triazolo[1,5-a]pyridine-8-carboxamide (mixture of diastereomers)

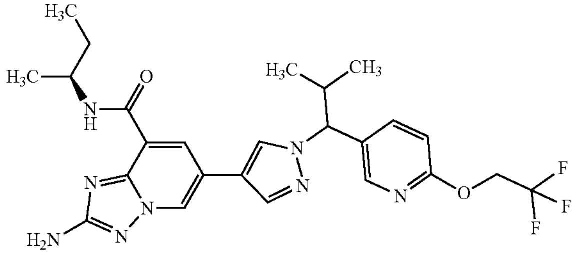 [SMILES: CC[C@H](C)NC(=O)c1cc(-c2cnn(C(c3ccc(OCC(F)(F)F)nc3)C(C)C)c2)cn2nc(N)nc12]

2-Amino-6-bromo-N-[(2S)-butan-2-yl][1,2,4]triazolo[1,5-a]pyridine-8-carboxamide (105 mg, 336 mol), 5-{2-methyl-1-[4-(4,4,5,5-tetramethyl-1,3,2-dioxaborolan-2-yl)-1H-pyrazol-1-yl]propyl}-2-(2,2,2-trifluoroethoxy)pyridine (189 mg, 91% purity, 404 mol), sodium carbonate (178 mg, 1.68 mmol) and 1,1'-bis(diphenylphosphino)ferrocene-palladium(II)dichloride dichloromethane complex (13.7 mg, 16.8 mol) were reacted according to procedure A in a mixture of 1,4-dioxane (4.0 ml) and water (600 μl). The reaction mixture was stirred for 2.5 h at 90° C. The residue was purified by preparative HPLC to yield 110 mg (96% purity, 59% yield) of the title compound as a mixture of two diastereomers.

LC-MS (method 1): $R_t$=2.14 min; MS (ESIpos): m/z=531 $[M+H]^+$ $^1$H-NMR (500 MHz, DMSO-$d_6$) δ [ppm]: 0.80 (d, 3H), 0.83 (d, 3H), 0.94 (t, 3H), 1.21 (d, 3H), 1.53-1.63 (m, 2H), 2.72-2.77 (m, 1H), 3.99-4.04 (m, 1H), 4.93-5.01 (m, 2H), 5.04 (d, 1H), 6.38 (s, 2H), 7.00 (d, 1H), 8.03-8.07 (m, 2H), 8.24 (d, 1H), 8.35 (d, 1H), 8.54 (s, 1H), 9.04 (d, 1H), 9.27 (d, 1H).

Example I-89

2-Amino-N-[(2S)-butan-2-yl]-6-(1-{2-methyl-1-[6-(2,2,2-trifluoroethoxy)pyridin-3-yl]propyl}-1H-pyrazol-4-yl)[1,2,4]triazolo[1,5-a]pyridine-8-carboxamide (stereoisomer 1, distomer)

2-Amino-N-[(2S)-butan-2-yl]-6-(1-{2-methyl-1-[6-(2,2,2-trifluoroethoxy)pyridin-3-yl]propyl}-1H-pyrazol-4-yl)[1,2,4]triazolo[1,5-a]pyridine-8-carboxamide (mixture of diastereomers) (110 mg, 96% purity) was separated by chiral preparative SFC to yield stereoisomer 1 (30.6 mg, 100% purity) and stereoisomer 2 (40.5 mg, 100% purity).

Instrument: THAR SFC-Super Chrom Prep 200; Column: Daicel Chiralpak AD-H, 5 µm, 250×20 mm; Eluent A: $CO_2$; Eluent B: 2-propanol; isocratic: 70% A+30% B; flow: 80 ml/min; UV: 210 nm; temperature: 40° C.

Analytical SFC-method: Column: Chiralcel AD, 3 µm, 4.6×100 mm; Eluent A: $CO_2$; Eluent B: 2-propanol; isocratic: 70% A+30% B; flow: 3 ml/min; UV: 210 nm; temperature: 40° C.

Stereoisomer 1: $R_t$=1.72 min and

Stereoisomer 2: $R_t$=4.39 min (cf. next example)

LC-MS (method 2): $R_t$=1.13 min; MS (ESIpos): m/z=531 $[M+H]^+$ $^1$H-NMR (500 MHz, DMSO-$d_6$) δ [ppm]: 0.790 (10.86), 0.803 (11.13), 0.817 (11.47), 0.830 (11.28), 0.924 (7.10), 0.939 (16.00), 0.954 (7.67), 1.206 (15.00), 1.220 (14.89), 1.548 (0.88), 1.561 (2.42), 1.570 (2.15), 1.576 (3.30), 1.583 (2.46), 1.590 (2.23), 1.597 (2.19), 1.612 (0.81), 2.723 (0.92), 2.737 (1.34), 2.745 (1.11), 2.749 (1.15), 2.759 (1.30), 2.772 (0.92), 3.296 (0.54), 3.305 (0.92), 3.354 (1.53), 3.373 (0.42), 3.986 (0.77), 4.000 (1.57), 4.014 (1.96), 4.028 (1.57), 4.041 (0.73), 4.946 (2.42), 4.964 (6.91), 4.982 (6.60), 5.000 (2.11), 5.026 (3.99), 5.048 (3.84), 6.403 (9.40), 6.999 (5.14), 7.016 (5.18), 8.041 (3.26), 8.046 (3.57), 8.052 (10.13), 8.058 (3.15), 8.063 (3.11), 8.239 (6.91), 8.243 (7.02), 8.347 (5.26), 8.352 (5.10), 8.547 (8.94), 9.048 (6.91), 9.052 (6.98), 9.269 (3.45), 9.284 (3.34).

Example I-90

2-Amino-N-[(2S)-butan-2-yl]-6-(1-{2-methyl-1-[6-(2,2,2-trifluoroethoxy)pyridin-3-yl]propyl}-1H-pyrazol-4-yl)[1,2,4]triazolo[1,5-a]pyridine-8-carboxamide (stereoisomer 2, eutomer)

The product was isolated in the previous example as second stereoisomer.

LC-MS (method 2): $R_t$=1.13 min; MS (ESIpos): m/z=531 $[M+H]^+$ $^1$H-NMR (500 MHz, DMSO-$d_6$) δ [ppm]: 0.79 (d, 1H), 0.83 (d, 1H), 0.94 (t, 3H), 1.21 (d, 3H), 1.53-1.63 (m, 2H), 2.70-2.79 (m, 1H), 3.24-3.32 (m, 1H), 3.35-3.54 (m, 1H), 3.97-4.06 (m, 1H), 4.94-5.05 (m, 3H), 6.40 (s, 2H), 7.01 (d, 1H), 8.03-8.07 (m, 2H), 8.24 (d, 1H), 8.35 (d, 1H), 8.55 (s, 1H), 9.05 (d, 1H), 9.28 (d, 1H).

Example I-91

2-Amino-N-[(2S)-butan-2-yl]-6-(1-{2-methyl-1-[2-(trifluoromethyl)pyridin-4-yl]propyl}-1H-pyrazol-4-yl)[1,2,4]triazolo[1,5-a]pyridine-8-carboxamide (mixture of diastereomers)

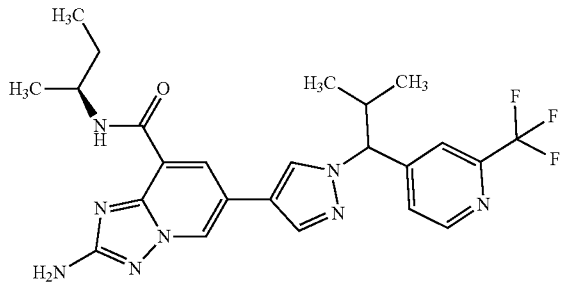 [SMILES: CC[C@H](C)NC(=O)c1cc(-c2cnn(C(c3ccnc(C(F)(F)F)c3)C(C)C)c2)cn2nc(N)nc12]

2-Amino-N-[(2S)-butan-2-yl]-6-chloro[1,2,4]triazolo[1,5-a]pyridine-8-carboxamide (161 mg, 603 µmol), 4-{2-methyl-1-[4-(4,4,5,5-tetramethyl-1,3,2-dioxaborolan-2-yl)-1H-pyrazol-1-yl]propyl}-2-(trifluoromethyl)pyridine (286 mg, 724 µmol), 1,1'-bis(diphenylphosphino)ferrocene-palladium(II)dichloride dichloromethane complex (24.6 mg, 30.2 µmol) and sodium carbonate (192 mg, 1.81 mmol) were reacted according to procedure A in a mixture of 1,4-dioxane (3.0 ml) and water (1.0 ml). After 3 h stirring at 90° C., the reaction was quenched with water and extracted with dichloromethane. The combined organic layers were dried over anhydrous sodium sulfate, filtered and concentrated. The residue was purified by column chromatography (Biotage® SNAP KP-NH 11 g cartridge, eluent: cyclohexane/ethyl acetate gradient 4:1 to 1:4) to yield 38.0 mg (96% purity, 12% yield) of the title compound as a mixture of two diastereomers.

LC-MS (method 1): $R_t$=1.99 min; MS (ESIpos): m/z=501 $[M+H]^+$ $^1$H-NMR (500 MHz, DMSO-$d_6$) δ [ppm]: 0.80 (d, 3H), 0.86 (d, 3H), 0.94 (t, 3H), 1.21 (d, 4H), 1.50-1.65 (m, 2H), 2.73-2.85 (m, 1H), 3.95-4.07 (m, 1H), 5.26 (d, 1H), 6.39 (s, 2H), 7.89 (d, 1H), 8.07 (s, 1H), 8.12 (s, 1H), 8.22-8.27 (m, 1H), 8.58 (s, 1H), 8.78 (d, 1H), 9.06 (d, 1H), 9.27 (d, 1H).

Example I-92

2-Amino-N-[(2S)-butan-2-yl]-7-(1-{1-[6-(difluoromethyl)pyridin-3-yl]propyl}-1H-pyrazol-4-yl)[1,2,4]triazolo[1,5-a]pyridine-5-carboxamide (mixture of diastereomers)

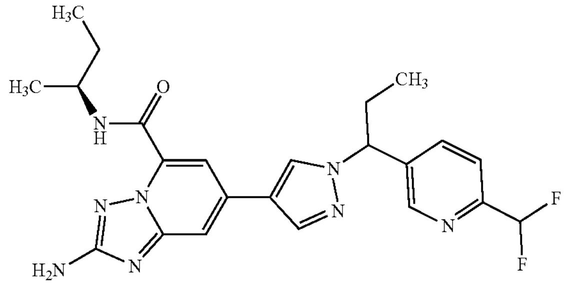 [SMILES: CCC(c1ccc(C(F)F)nc1)n1cc(-c2cc(C(=O)N[C@@H](C)CC)n3nc(N)nc3c2)cn1]

2-Amino-N-[(2S)-butan-2-yl]-7-chloro[1,2,4]triazolo[1,5-a]pyridine-5-carboxamide (153 mg, 571 μmol), 2-(difluoromethyl)-5-{1-[4-(4,4,5,5-tetramethyl-1,3,2-dioxaborolan-2-yl)-1H-pyrazol-1-yl]propyl}pyridine (262 mg, 95% purity, 686 mol), 1,1'-bis(diphenylphosphino)ferrocene-palladium(II)dichloride dichloromethane complex (23.3 mg, 28.6 μmol) and sodium carbonate (303 mg, 2.86 mmol) were reacted according to procedure A in a mixture of 1,4-dioxane (7.0 ml) and water (1.0 ml). The reaction mixture was stirred for 2.5 h at 90° C. The residue was purified by preparative HPLC to yield 211 mg (100% purity, 79% yield) of the title compound.

LC-MS (method 1): $R_t$=1.73 min; MS (ESIpos): m/z=469 $[M+H]^+$ $^1$H-NMR (500 MHz, DMSO-$d_6$) δ [ppm]: 0.87 (t, 3H), 0.96 (t, 3H), 1.24 (d, 3H), 1.61 (quin, 2H), 2.22 (hept, 1H), 2.40-2.49 (m, 1H), 3.97-4.06 (m, 1H), 5.54 (dd, 1H), 6.37 (s, 2H), 6.95 (t, 1H), 7.71 (d, 1H), 7.80 (s, 2H), 8.00 (dd, 1H), 8.22 (s, 1H), 8.74 (d, 1H), 8.77 (s, 1H), 10.09 (d, 1H).

Example I-93

2-Amino-N-[(2S)-butan-2-yl]-7-(1-{1-[6-(difluoromethyl)pyridin-3-yl]propyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{1-[6-(difluoromethyl)pyridin-3-yl]propyl}-1H-pyrazol-4-yl)[1,2,4]triazolo[1,5-a]pyridine-5-carboxamide (mixture of diastereomers) (211 mg, 100% purity) was separated by chiral preparative HPLC to yield stereoisomer 1 (89 mg, 100% purity) and stereoisomer 2 (91 mg, 100% purity).

Column: YMC Chiralart Amylose SA, 5 μm 250×20 mm; Eluent A: n-heptane; Eluent B: ethanol+0.2% diethylamine; isocratic: 25% A+75% B; flow: 15 ml/min; UV: 220 nm; temperature 60° C.

Stereoisomer 1: $R_t$=7.39 min and

Stereoisomer 2: $R_t$=8.85 min (cf. next example)

Analytical chiral HPLC-method: Column: Daicel Chiralpak IA, 5 μm, 250×4.6 mim; Eluent A: iso-hexane; Eluent B: ethanol; isocratic: 25% A+75% B; flow: 1 ml/min; UV: 220 nm, temperature 70° C.

Stereoisomer 1: $R_t$=6.83 min and

Stereoisomer 2: $R_t$=9.57 min (cf. next example)

LC-MS (method 1): $R_t$=1.73 min; MS (ESIpos): m/z=469 $[M+H]^+$ $^1$H-NMR (600 MHz, DMSO-$d_6$) δ [ppm]: 0.856 (3.97), 0.868 (8.25), 0.880 (3.81), 0.943 (4.72), 0.956 (10.11), 0.968 (4.84), 1.233 (9.82), 1.244 (9.57), 1.585 (0.84), 1.597 (2.77), 1.609 (3.58), 1.620 (2.52), 1.633 (0.65), 2.198 (0.60), 2.209 (0.89), 2.220 (1.22), 2.232 (0.98), 2.243 (0.59), 2.424 (0.72), 2.436 (0.93), 2.440 (0.86), 2.447 (0.95), 2.452 (1.02), 2.459 (0.90), 2.463 (1.04), 2.475 (1.08), 2.519 (0.58), 2.522 (0.58), 3.990 (0.50), 4.001 (1.11), 4.013 (1.31), 4.024 (1.06), 4.035 (0.45), 5.527 (1.17), 5.537 (1.29), 5.543 (1.26), 5.553 (1.08), 6.359 (6.27), 6.851 (1.53), 6.942 (3.19), 7.033 (1.34), 7.703 (2.67), 7.716 (2.87), 7.799 (16.00), 7.992 (1.78), 7.996 (1.73), 8.006 (1.60), 8.009 (1.53), 8.216 (5.93), 8.740 (3.07), 8.743 (2.96), 8.766 (5.66), 10.076 (1.98), 10.089 (1.89).

Example I-94

2-Amino-N-[(2S)-butan-2-yl]-7-(1-{1-[6-(difluoromethyl)pyridin-3-yl]propyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.73 min; MS (ESIpos): m/z=469 $[M+H]^+$ $^1$H-NMR (500 MHz, DMSO-$d_6$) δ [ppm]: 0.87 (t, 3H), 0.96 (t, 3H), 1.24 (d, 3H), 1.61 (quin, 2H), 2.18-2.26 (m, 1H), 2.40-2.49 (m, 1H), 3.99-4.04 (m, 1H), 5.54 (dd, 1H), 6.37 (s, 2H), 6.95 (t, 1H), 7.71 (d, 1H), 7.80 (s, 2H), 8.00 (dd, 1H), 8.22 (s, 1H), 8.74 (s, 1H), 8.77 (s, 1H), 10.09 (d, 1H).

Example I-95

2-Amino-N-[(2S)-butan-2-yl]-7-(1-{1-[6-(difluoromethyl)pyridin-3-yl]-2-methylpropyl}-1H-pyrazol-4-yl)[1,2,4]triazolo[1,5-a]pyridine-5-carboxamide (mixture of diastereomers)

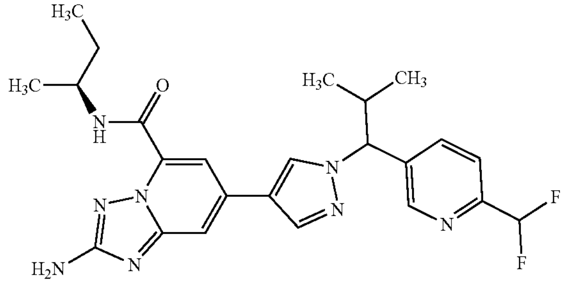 [SMILES: CC[C@H](C)NC(=O)c1cc(-c2cnn(C(c3ccc(C(F)F)nc3)C(C)C)c2)cc2nc(N)nn12]

2-Amino-N-[(2S)-butan-2-yl]-7-chloro[1,2,4]triazolo[1,5-a]pyridine-5-carboxamide (32.0 mg, 120 μmol), 2-(difluoromethyl)-5-{(2-methyl-1-[4-(4,4,5,5-tetramethyl-1,3,2-dioxaborolan-2-yl)-1H-pyrazol-1-yl]propyl}pyridine (54.1 mg, 143 μmol), 1,1'-bis(diphenylphosphino)ferrocene-palladium(II)dichloride dichloromethane complex (4.88 mg, 5.98 μmol) and sodium carbonate (63.3 mg, 598 μmol) were reacted according to procedure A in a mixture of 1,4-dioxane (1.5 ml) and water (200 μl). The reaction mixture was stirred for 2.5 h at 100° C. The residue was purified by preparative HPLC to yield 44.0 mg (100% purity, 76% yield) of the title compound as a mixture of two diastereomers.

LC-MS (method 1): $R_t$=1.81 min; MS (ESIpos): m/z=483 $[M+H]^+$ $^1$H-NMR (500 MHz, DMSO-$d_6$) δ [ppm]: 0.80 (d, 3H), 0.86 (d, 3H), 0.95 (t, 3H), 1.24 (d, 3H), 1.58-1.64 (m, 2H), 2.78-2.88 (m, 1H), 3.99-4.04 (dt, 1H), 5.20 (d, 1H), 6.37 (s, 2H), 1H), 6.95 (t, 1H), 7.74 (d, 1H), 7.78 (d, 2H), 8.19-8.24 (m, 2H), 8.74 (s, 1H), 8.87 (s, 1H), 10.09 (d, 1H).

Example I-96

2-Amino-N-[(2S)-butan-2-yl]-7-(1-{1-[6-(difluoromethyl)pyridin-3-yl]-2-methylpropyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-f{1-[6-(difluoromethyl)pyridin-3-yl]-2-methylpropyl}-1H-pyrazol-4-yl)[1,2,4]triazolo[1,5-a]pyridine-5-carboxamide (mixture of diastereomers) (44.0 mg, 100% purity) was separated by chiral preparative HPLC to yield stereoisomer 1 (15.0 mg, 100% purity) and stereoisomer 2 (15.0 mg, 100% purity).

Column: Daicel Chiralpak IA, 5 μm, 250×20 mm; Eluent A: iso-heptane; Eluent B: ethanol; isocratic: 25% A+75% B; flow: 15 ml/min; UV: 210 nm; temperature 50° C.

Stereoisomer 1: $R_t$=5.06 min and

Stereoisomer 2: $R_t$=9.48 min (cf. next example)

Analytical chiral HPLC-method: Column: Daicel Chiralpak IA, 3 μm, 50×4.6 mm; Eluent A: iso-heptane; Eluent B: ethanol; isocratic: 25% A+75% B; flow: 1 ml/min; UV: 220 nm; temperature 60° C.

Stereoisomer 1: $R_t$=7.12 min and

Stereoisomer 2: $R_t$=10.24 min (cf. next example)

LC-MS (method 1): $R_t$=1.84 min; MS (ESIpos): m/z=483 $[M+H]^+$ $^1$H-NMR (500 MHz, DMSO-$d_6$) δ [ppm]: −0.120 (0.45), −0.006 (4.34), 0.006 (3.81), 0.117 (0.46), 0.797 (10.93), 0.811 (11.02), 0.851 (11.53), 0.864 (11.54), 0.938 (7.16), 0.953 (16.00), 0.968 (7.62), 1.230 (15.39), 1.243 (15.18), 1.577 (1.23), 1.592 (4.26), 1.606 (5.56), 1.620 (3.92), 1.635 (1.03), 2.804 (0.96), 2.817 (1.32), 2.826 (1.14), 2.839 (1.31), 2.852 (0.90), 3.983 (0.80), 3.996 (1.69), 4.011 (2.08), 4.024 (1.71), 4.038 (0.77), 5.189 (3.91), 5.210 (3.74), 6.366 (9.41), 6.839 (2.44), 6.948 (5.21), 7.058 (2.13), 7.726 (4.29), 7.742 (4.52), 7.771 (3.81), 7.775 (11.26), 7.777 (11.70), 7.781 (4.20), 8.209 (11.92), 8.226 (2.54), 8.230 (2.59), 8.736 (8.83), 8.866 (4.83), 8.869 (4.91), 10.074 (3.15), 10.090 (3.07).

Example I-97

2-Amino-N-[(2S)-butan-2-yl]-7-(1-{1-[6-(difluoromethyl)pyridin-3-yl]-2-methylpropyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.84 min; MS (ESIpos): m/z=483 $[M+H]^+$ $^1$H-NMR (500 MHz, DMSO-$d_6$) δ [ppm]: 0.80 (d, 3H), 0.86 (d, 3H), 0.95 (t, 3H), 1.24 (d, 3H), 1.58-1.64 (m, 2H), 2.80-2.85 (m, 1H), 3.98-4.04 (m, 1H), 5.20 (d, 1H), 6.37 (s, 2H), 6.95 (t, 1H), 7.73 (d, 11H), 7.78 (s, 2H), 8.21 (s, 11H), 8.22 (d, 2H), 8.74 (s, 1H), 8.87 (s, 1H), 10.08 (d, 1H).

Example I-98

2-Amino-N-[(2S)-butan-2-yl]-7-(1-{cyclopropyl[6-(difluoromethyl)pyridin-3-yl]methyl}-1H-pyrazol-4-yl)[1,2,4]triazolo[1,5-a]pyridine-5-carboxamide (mixture of diastereomers)

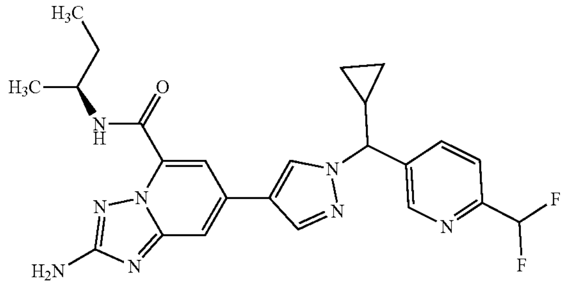 [SMILES: CC[C@H](C)NC(=O)c1cc(-c2cnn(C(c3ccc(C(F)F)nc3)C3CC3)c2)cc2nc(N)nn12]

2-Amino-N-[(2S)-butan-2-yl]-7-chloro[1,2,4]triazolo[1,5-a]pyridine-5-carboxamide (75.0 mg, 280 μmol), 5-{cyclopropyl[4-(4,4,5,5-tetramethyl-1,3,2-dioxaborolan-2-yl)-1H-pyrazol-1-yl]methyl}-2-(difluoromethyl)pyridine (153 mg, 82% purity, 336 μmol), 1,1'-bis(diphenylphosphino)ferrocene-palladium(II)dichloride dichloromethane complex (11.4 mg, 14.0 μmol) and sodium carbonate (148 mg, 1.40 mmol) were reacted according to procedure A in a mixture of 1,4-dioxane (3.5 ml) and water (500 μl). The reaction mixture was stirred for 3 h at 100° C. The residue was purified by preparative HPLC to yield 57.0 mg (100% purity, 42% yield) of the title compound as a mixture of two diastereomers.

LC-MS (method 1): $R_t$=1.73 min; MS (ESIpos): m/z=481 $[M+H]^+$ $^1$H-NMR (400 MHz, DMSO-$d_6$) δ [ppm]: 0.51-0.65 (m, 2H), 0.70-0.79 (m, 2H), 0.96 (t, 3H), 1.24 (d, 3H), 1.58-1.63 (m, 2H), 1.88-1.92 (m, 1H), 4.02 (dt, 1H), 4.91 (d, 1H), 6.36 (s, 2H), 6.95 (t, 1H), 7.72 (d, 1H), 7.82 (s, 2H), 7.97 (dd, 1H), 8.19 (s, 1H), 8.72 (d, 1H), 8.82 (s, 1H), 10.09 (d, 1H).

Example I-99

2-Amino-N-[(2S)-butan-2-yl]-7-(1-{cyclopropyl[6-(difluoromethyl)pyridin-3-yl]methyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{cyclopropyl[6-(difluoromethyl)pyridin-3-yl]methyl}-1H-pyrazol-4-yl)[1,2,4]triazolo[1,5-a]pyridine-5-carboxamide (mixture of diastereomers) 57.0 mg (100% purity, 42% yield) was separated by chiral preparative HPLC to yield stereoisomer 1 (20.0 mg 100% purity) and stereoisomer 2 (20.0 mg, 100% purity).

Column: Daicel Chiralpak IF-5, 5 μm, 250×20 mm; Eluent A: n-heptane; Eluent B: ethanol; isocratic: 30% A+70% B; flow: 25 ml/min; UV: 220 nm; temperature 60° C.

Stereoisomer 1: $R_t$=5.68 min and

Stereoisomer 2: $R_t$=7.75 min (cf. next example)

Analytical chiral HPLC-method: Column: Daicel Chiralpak IF-3, 3 μm, 50×4.6 mm; Eluent A: iso-heptane; Eluent B: ethanol+0.2% diethylamine; isocratic: 0% A+100% B; flow: 1 ml/min;

UV: 220 nm; temperature 60° C.

Stereoisomer 1: $R_t$=2.61 min and

Stereoisomer 2: $R_t$=4.01 min (cf. next example)

LC-MS (method 1): $R_t$=1.72 min; MS (ESIpos): m/z=481 $[M+H]^+$ $^1$H-NMR (400 MHz, DMSO-$d_6$) δ [ppm]: −0.008 (0.64), 0.008 (0.57), 0.523 (0.53), 0.536 (0.75), 0.549 (0.98), 0.597 (1.02), 0.609 (0.81), 0.623 (0.53), 0.735 (2.57), 0.747 (1.24), 0.755 (2.54), 0.939 (4.12), 0.958 (9.70), 0.976 (4.60), 1.109 (0.70), 1.126 (1.38), 1.145 (0.71), 1.233 (9.59), 1.249 (9.46), 1.384 (1.14), 1.576 (0.71), 1.594 (2.53), 1.612 (3.26), 1.629 (2.35), 1.648 (0.61), 1.879 (0.70), 1.892 (0.75), 1.904 (0.70), 2.328 (0.47), 2.367 (0.42), 2.524 (1.65), 2.559 (0.43), 2.670 (0.50), 2.710 (0.42), 3.980 (0.43), 3.996 (0.96), 4.015 (1.13), 4.032 (0.97), 4.048 (0.42), 4.892 (2.11), 4.917 (2.08), 6.355 (5.30), 6.812 (1.63), 6.949 (3.18), 7.086 (1.42), 7.706 (2.31), 7.727 (2.74), 7.820 (16.00), 7.952 (1.70), 7.957 (1.67), 7.972 (1.40), 7.977 (1.40), 8.189 (5.54), 8.715 (2.59), 8.719 (2.54), 8.821 (5.24), 10.079 (1.80), 10.099 (1.76).

Example I-100

2-Amino-N-[(2S)-butan-2-yl]-7-(1-{cyclopropyl[6-(difluoromethyl)pyridin-3-yl]methyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.73 min; MS (ESIpos): m/z=481 $[M+H]^+$ $^1$H-NMR (400 MHz, DMSO-$d_6$) δ [ppm]: 0.51-0.64 (m, 2H), 0.70-0.79 (m, 2H), 0.96 (t, 3H), 1.24 (d, 3H), 1.58-1.65 (m, 2H), 1.85-1.94 (m, 1H), 4.02 (dt, 1H), 4.90 (d, 1H), 6.36 (s, 2H), 6.95 (t, 1H), 7.72 (d, 1H), 7.82 (s, 2H), 7.96 (dd, 1H), 8.19 (s, 1H), 8.72 (d, 1H), 8.82 (s, 11H), 10.09 (d, 1H).

Example 1-101

2-Amino-N-[(2S)-butan-2-yl]-7-(1-{1-[6-(trifluoromethyl)pyridin-3-yl]propyl}-1H-pyrazol-4-yl)[1,2,4]triazolo[1,5-a]pyridine-5-carboxamide (mixture of diastereomers)

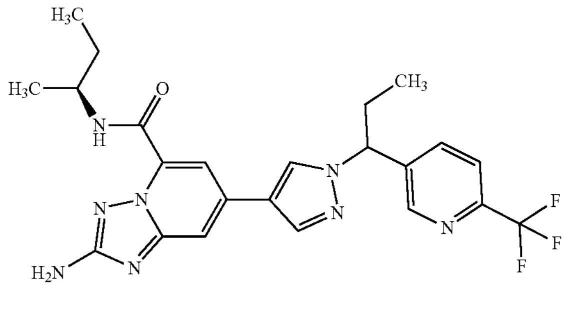 [SMILES: CCC(c1ccc(C(F)(F)F)nc1)n1cc(-c2cc(C(=O)N[C@@H](C)CC)n3nc(N)nc3c2)cn1]

2-Amino-N-[(2S)-butan-2-yl]-7-chloro[1,2,4]triazolo[1,5-a]pyridine-5-carboxamide (75.0 mg, 280 μmol), 5-{1-[4-(4,4,5,5-tetramethyl-1,3,2-dioxaborolan-2-yl)-1H-pyrazol-1-yl]propyl}-2-(trifluoromethyl)pyridine (190 mg, 73% purity, 364 μmol), 1,1'-bis(diphenylphosphino)ferrocene-palladium(II)dichloride dichloromethane complex (34.3 mg, 42.0 μmol) and sodium carbonate (148 mg, 1.40 mmol) were reacted according to procedure A in a mixture of water (500 μl) and 1,4-dioxane (3.0 ml). The reaction was quenched with water and extracted with dichloromethane.

The combined organic layers were dried over anhydrous sodium sulfate, filtered and concentrated. The residue was purified by preparative HPLC to yield 39.0 mg (97% purity, 28% yield) of the title compound as a mixture of two diastereomers.

LC-MS (method 1): $R_t$=1.88 min; MS (ESIpos): m/z=487 $[M+H]^+$ $^1$H-NMR (500 MHz, DMSO-$d_6$) δ [ppm]: 0.88 (t, 3H), 0.96 (t, 3H), 1.24 (d, 3H), 1.61 (quin, 2H), 2.22-2.26 (m, 1H), 2.36-2.48 (m, 1H), 3.97-4.06 (m, 1H), 5.60 (dd, 1H), 6.35 (s, 2H), 7.80 (s, 2H), 7.92 (d, 1H), 8.07 (d, 1H), 8.23 (s, 1H), 8.77 (s, 1H), 8.83 (s, 1H), 10.08 (br d, 1H).

Example I-102

2-Amino-N-[(2S)-butan-2-yl]-7-(1-{1-[6-(trifluoromethyl)pyridin-3-yl]propyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{.1-[6-(trifluoromethyl)pyridin-3-yl]propyl}-1H-pyrazol-4-yl)[1,2,4]triazolo[1,5-a]pyridine-5-carboxamide (mixture of diastereomers) (39.0 mg, 97% purity) was separated by chiral preparative SFC to yield 10.6 mg of stereoisomer 1 and 9.8 mg of stereoisomer 2.

Instrument: THAR SFC-Super Chrom Prep 200; Column: Daicel Chiralpak AD-H, 5 m, 250×20 mm; Eluent A: $CO_2$; Eluent B: 2-propanol; isocratic: 68% A+32% B; flow: 80 ml/min; UV: 210 nm; temperature: 40° C.

Analytical SFC-method: Column: Chiralcel AD, 3 μm, 4.6×100 mm; Eluent A: $CO_2$; Eluent B: 2-propanol; isocratic: 70% A+30% B; flow: 3 ml/min; UV: 210 nm; temperature: 40° C.

Stereoisomer 1: $R_t$=1.89 min and

Stereoisomer 2: $R_t$=4.52 min (cf. next example)

LC-MS (method 1): $R_t$=1.85 min; MS (ESIpos): m/z=487 $[M+H]^+$ $^1$H-NMR (500 MHz, DMSO-$d_6$) δ [ppm]: 0.858 (3.67), 0.872 (7.81), 0.887 (3.64), 0.937 (4.45), 0.952 (9.98), 0.967 (4.71), 1.229 (9.95), 1.243 (9.60), 1.577 (0.78), 1.592 (2.64), 1.606 (3.42), 1.620 (2.42), 1.635 (0.63), 2.205 (0.47), 2.217 (0.82), 2.232 (1.13), 2.246 (0.91), 2.259 (0.56), 2.425 (0.60), 2.440 (0.82), 2.444 (0.75), 2.453 (0.85), 2.458 (0.88), 2.472 (0.88), 3.269 (0.72), 3.279 (0.63), 3.287 (0.88), 3.344 (0.82), 3.353 (0.44), 3.982 (0.50), 3.995 (1.07), 4.010 (1.25), 4.024 (1.07), 4.037 (0.47), 5.580 (1.07), 5.592 (1.22), 5.599 (1.25), 5.610 (1.04), 6.346 (5.84), 7.797 (16.00), 7.909 (2.60), 7.925 (3.17), 8.059 (1.66), 8.062 (1.66), 8.075 (1.35), 8.078 (1.35), 8.225 (5.93), 8.763 (5.49), 8.825 (2.89), 8.829 (2.85), 10.067 (1.88), 10.083 (1.82).

Example I-103

2-Amino-N-[(2S)-butan-2-yl]-7-(1-{1-[6-(trifluoromethyl)pyridin-3-yl]propyl}-1 H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.85 min; MS (ESIpos): m/z=487 $[M+H]^+$ $^1$H-NMR (500 MHz, DMSO-$d_6$) δ [ppm]: 0.87 (br t, 3H), 0.95 (t, 3H), 1.23 (d, 3H), 1.61 (quin, 2H), 2.22-2.25 (m, 1H), 2.36-2.48 (m, 1H), 3.98-4.04 (m, 1H), 5.59 (br dd, 1H), 6.35 (s, 2H), 7.80 (s, 2H), 7.92 (d, 1H), 8.07 (br d, 1H), 8.23 (s, 1H), 8.76 (s, 1H), 8.83 (s, 1H), 10.07 (br d, 1H).

Example I-104

2-Amino-N-[(2S)-butan-2-yl]-7-(1-{2-methyl-1-[6-(trifluoromethyl)pyridin-3-yl]propyl}-1H-pyrazol-4-yl)[1,2,4]triazolo[1,5-a]pyridine-5-carboxamide (mixture of diastereomers)

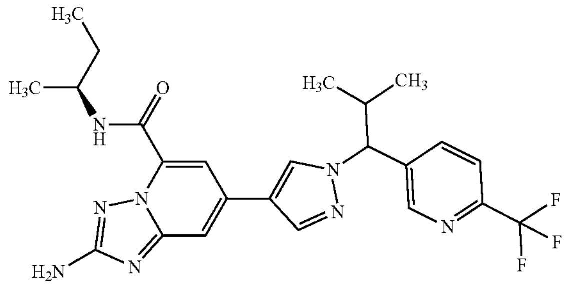 [SMILES: CC[C@H](C)NC(=O)c1cc(-c2cnn(C(c3ccc(C(F)(F)F)nc3)C(C)C)c2)cc2nc(N)nn12]

2-Amino-N-[(2S)-butan-2-yl]-7-chloro[1,2,4]triazolo[1,5-a]pyridine-5-carboxamide (110 mg, 411 μmol), 5-{2-methyl-1-[4-(4,4,5,5-tetramethyl-1,3,2-dioxaborolan-2-yl)-1H-pyrazol-1-yl]propyl}-2-(trifluoromethyl)pyridine (204 mg, 95% purity, 493 μmol), 1,1'-bis(diphenylphosphino) ferrocene-palladium(II)dichloride dichloromethane complex (16.8 mg, 20.5 μmol) and sodium carbonate (218 mg, 2.05 mmol) were reacted according to procedure A in a mixture of 1,4-dioxane (4.0 ml) and water (600 μl). After stirring at 90° C. for 2.5 h, the reaction was quenched with water and the mixture was filtered through a hydrophobic phase separation filter which was rinsed with ethyl acetate (15 ml). The filtrate was concentrated and dried under reduced pressure. The residue was purified by preparative HPLC to yield 173 mg (96% purity, 81% yield) of the title compound as a mixture of two diasteromers.

LC-MS (method 1): $R_t$=1.96 min; MS (ESIpos): m/z=501 $[M+H]^+$ $^1$H-NMR (500 MHz, DMSO-$d_6$) δ [ppm]: 0.81 (d, 3H), 0.87 (d, 3H), 0.96 (t, 3H), 1.24 (d, 3H), 1.61 (quin, 2H), 2.74-2.88 (m, 1H), 4.01 (dt, 1H), 5.27 (d, 1H), 6.35 (s, 2H), 7.78 (s, 2H), 7.95 (d, 1H), 8.22 (s, 1H), 8.31 (d, 1H), 8.73 (s, 1H), 8.96 (s, 1H), 10.08 (d, 1H).

Example I-105

2-Amino-N-[(2S)-butan-2-yl]-7-(1-{2-methyl-1-[6-(trifluoromethyl)pyridin-3-yl]propyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{2-methyl-1-[6-(trifluoromethyl)pyridin-3-yl]propyl}-1H-pyrazol-4-yl)[1,2,4]triazolo[1,5-a]pyridine-5-carboxamide (mixture of diastereoisomers) (173 mg 96% purity) was separated by chiral preparative SFC to yield stereoisomer 1 (63.4 mg, 100% purity) and stereoisomer 2 (62.6 mg, 100% purity).

Instrument: THAR SFC-Super Chrom Prep 200; Column: Daicel Chiralpak IA, 5 μm, 250×20 mm; Eluent A: $CO_2$; Eluent B: 2-propanol; isocratic: 75% A+25% B; flow: 80 ml/min; UV: 210 run; temperature: 40° C.

Analytical SFC-method: Column: Chiralcel IA, 3 μm, 4.6×100 mm; Eluent A: $CO_2$; Eluent B: 2-propanol; isocratic: 70% A+30% B; flow: 3 ml/min; UV: 210 nm; temperature: 40° C.

Stereoisomer 1: $R_t$=2.17 min and

Stereoisomer 2: $R_t$=3.53 min (cf. next example)

LC-MS (method 1): $R_t$=1.96 min; MS (ESIpos): m/z=501 $[M+H]^+$ $^1$H-NMR (500 MHz, DMSO-$d_6$) δ [ppm]: −0.006 (3.92), 0.007 (2.66), 0.804 (10.42), 0.817 (10.44), 0.860 (11.03), 0.873 (11.03), 0.938 (7.06), 0.953 (16.00), 0.968 (7.50), 1.230 (15.26), 1.243 (15.15), 1.578 (1.18), 1.593 (4.05), 1.607 (5.12), 1.621 (3.77), 1.636 (0.98), 2.363 (0.46), 2.636 (0.46), 2.815 (0.89), 2.829 (1.24), 2.837 (1.07), 2.842 (1.02), 2.850 (1.22), 2.863 (0.87), 3.982 (0.74), 3.996 (1.61), 4.009 (1.85), 4.024 (1.57), 4.037 (0.70), 5.257 (3.68), 5.279 (3.55), 6.345 (7.89), 7.769 (3.44), 7.773 (13.95), 7.775 (13.38), 7.779 (2.92), 7.937 (4.21), 7.953 (4.49), 8.217 (8.98), 8.293 (2.40), 8.296 (2.31), 8.309 (2.14), 8.313 (2.05), 8.728 (8.22), 8.959 (4.36), 8.962 (4.21), 10.064 (2.83), 10.080 (2.75).

Example I-106

2-Amino-N-[(2S)-butan-2-yl]-7-(1-{2-methyl-1-[6-(trifluoromethyl)pyridin-3-yl]propyl}-1H-pyrazol-4-yl)[1,2,4]triazolo[1,5-a]pyridine-5-carboxamide (stereoisomers 2, eutomer)

The product was isolated in the previous example as second stereoisomer.

LC-MS (method 1): $R_t$=1.96 min; MS (ESIpos): m/z=501 $[M+H]^+$ $^1$H-NMR (500 MHz, DMSO-$d_6$) δ [ppm]: 0.81 (d, 3H), 0.87 (d, 3H), 0.95 (t, 3H), 1.24 (d, 3H), 1.61 (quin, 2H), 2.79-2.88 (m, 1H), 3.97-4.05 (m, 1H), 5.27 (d, 1H), 6.35 (s, 2H), 7.78 (s, 2H), 7.95 (d, 11H), 8.22 (s, 11H), 8.30 (dd, 11H), 8.73 (s, 1H), 8.96 (d, 11H), 10.07 (d, 1H).

Example I-107

2-Amino-N-[(2S)-butan-2-yl]-7-(1-{cyclopropyl[6-(trifluoromethyl)pyridin-3-yl]methyl}-1H-pyrazol-4-yl)[1,2,4]triazolo[1,5-a]pyridine-5-carboxamide (mixture of diastereomers)

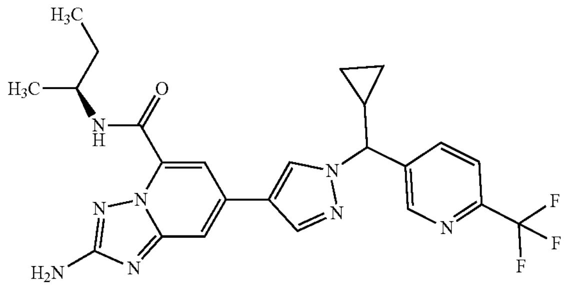 [SMILES: CC[C@H](C)NC(=O)c1cc(-c2cnn(C(c3ccc(C(F)(F)F)nc3)C3CC3)c2)cc2nc(N)nn12]

2-Amino-N-[(2S)-butan-2-yl]-7-chloro[1,2,4]triazolo[1,5-a]pyridine-5-carboxamide (100 mg, 374 μmol), 5-{cyclopropyl[4-(4,4,5,5-tetramethyl-1,3,2-dioxaborolan-2-yl)-1H-pyrazol-1-yl]methyl}2-(trifluoromethyl)pyridine (188 mg, 94% purity, 448 μmol), 1,1'-bis(diphenylphosphino)ferrocene-palladium(II)dichloride dichloromethane complex (15.3 mg, 18.7 μmol) and sodium carbonate (198 mg, 1.87 mmol) were reacted according to procedure A in a mixture of 1,4-dioxane (4.0 ml) and water (600 μl). After stirring at 90° C. for 2.5 h, the reaction was quenched with water and the mixture was filtered through a hydrophobic phase separation filter which was rinsed with ethyl acetate (15 ml). The filtrate was concentrated and dried under reduced pressure. The residue was purified by preparative HPLC to yield 136 mg (100% purity, 73% yield) of the title compound as a mixture of two diastereomers.

LC-MS (method 1): $R_t$=1.84 min; MS (ESIpos): m/z=499 $[M+H]^+$ $^1$H-NMR (500 MHz, DMSO-$d_6$) δ [ppm]: 0.52-0.61 (m, 1H), 0.61-0.67 (m, 1H), 0.72-0.80 (m, 2H), 0.96 (t, 3H), 1.24 (d, 3H), 1.62 (quin, 2H), 1.86-1.95 (m, 1H), 3.98-4.06 (m, 1H), 4.97 (d, 1H), 6.36 (s, 2H), 7.83 (s, 2H), 7.93 (d, 1H), 8.04 (dd, 1H), 8.21 (s, 1H), 8.81 (s, 1H), 8.83 (s, 1H), 10.09 (d, 1H).

Example I-108

2-Amino-N-[(2S)-butan-2-yl]-7-(1-{cyclopropyl[6-(trifluoromethyl)pyridin-3-yl]methyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{cyclopropyl[6-(trifluoromethyl)pyridin-3-yl]methyl}-1H-pyrazol-4-yl)[1,2,4]triazolo[1,5-a]pyridine-5-carboxamide (mixture of diastereoisomers) (136 mg; 100% purity) was separated by chiral preparative HPLC to yield stereoisomer 1 (37 mg, 95% purity) and stereoisomer 2 (10 mg, 100% purity).

Column: Daicel Chiralpak IA, 5 μm, 250×30 mm; Eluent A: n-heptane; Eluent B: 2-propanol+0.2% diethylamine; isocratic: 55% A+45% B; flow: 35 ml/min; UV: 220 nm, Temperature: 40° C.

Stereoisomer 1: $R_t$=8.63 min and

Stereoisomer 2: $R_t$=12.69 min (cf. next example)

Analytical chiral HPLC-method: Column: Daicel Chiralpack IA; 3 μm; 50×4.6 mm; Eluent A: n-heptane; Eluent B: 2-propanol+0.2% diethylamine; isocratic: 50% A+50% B; flow: 1 ml/min; UV: 220 nm Stereoisomer 1: $R_t$=1.79 min and Stereoisomer 2: $R_t$=2.75 min (cf. next example)

LC-MS (method 1): $R_t$=1.84 min; MS (ESIpos): m/z=499 $[M+H]^+$ $^1$H-NMR (500 MHz, DMSO-$d_6$) δ [ppm]: 0.546 (0.81), 0.558 (1.30), 0.567 (1.56), 0.574 (1.36), 0.611 (0.64), 0.620 (1.32), 0.627 (1.65), 0.637 (1.34), 0.739 (1.14), 0.751 (3.60), 0.767 (3.54), 0.778 (0.99), 0.944 (7.38), 0.959 (16.00), 0.974 (7.38), 1.211 (0.66), 1.225 (1.01), 1.235 (15.08), 1.249 (14.92), 1.261 (0.44), 1.584 (1.23), 1.598 (4.04), 1.612 (5.10), 1.627 (3.71), 1.641 (0.97), 1.874 (0.64), 1.884 (0.75), 1.889 (1.16), 1.894 (0.97), 1.900 (1.16), 1.905 (0.95), 1.910 (1.14), 1.925 (0.53), 3.297 (0.48), 3.988 (0.75), 4.001 (1.60), 4.016 (1.93), 4.030 (1.60), 4.043 (0.70), 4.955 (3.60), 4.975 (3.63), 6.378 (8.68), 6.409 (0.40), 7.825 (4.02), 7.829 (11.12), 7.832 (11.05), 7.836 (3.78), 7.930 (3.85), 7.946 (5.03), 8.032 (2.64), 8.036 (2.62), 8.049 (1.93), 8.212 (9.25), 8.812 (4.37), 8.816 (4.31), 8.840 (8.42), 10.091 (2.97), 10.107 (2.86).

Example I-109

2-Amino-N-[(2S)-butan-2-yl]-7-(1-{cyclopropyl[6-(trifluoromethyl)pyridin-3-yl]methyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.84 min; MS (ESIpos): m/z=499 $[M+H]^+$ $^1$H-NMR (500 MHz, DMSO-$d_6$) δ [ppm]: 0.53-0.60 (m, 1H), 0.60-0.67 (m, 1H), 0.72-0.81 (m, 2H), 0.96 (t, 3H), 1.24 (d, 3H), 1.61 (quin, 2H), 1.86-1.94 (m, 1H), 3.98-4.06 (m, 1H), 4.97 (d, 1H), 6.38 (s, 2H), 7.83 (q, 2H), 7.94 (d, 1H), 8.04 (dd, 1H), 8.21 (s, 1H), 8.82 (s, 1H), 8.84 (s, 1H), 10.10 (d, 1H).

Example I-110

2-Amino-N-[(2S)-butan-2-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (mixture of diastereomers)

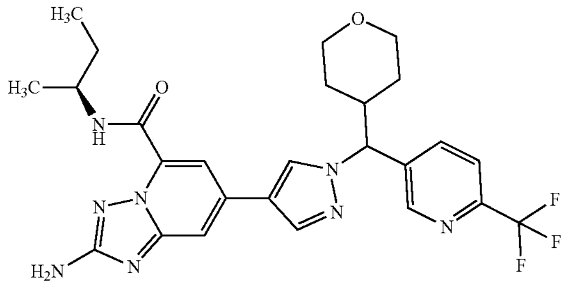 [SMILES: CC[C@H](C)NC(=O)c1cc(-c2cnn(C(c3ccc(C(F)(F)F)nc3)C3CCOCC3)c2)cc2nc(N)nn12]

2-Amino-N-[(2S)-butan-2-yl]-7-chloro[1,2,4]triazolo[1,5-a]pyridine-5-carboxamide (150 mg, 560 mol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (309 mg, 87% purity, 616 μmol), XPhos-Pd-G2 (22.0 mg, 28.0 μmol) and caesium carbonate (548 mg, 1.68 mmol) were reacted according to procedure A in a mixture of 1,4-dioxane (6.0 ml) and water (600 μl). The reaction mixture was stirred for 4 h at 90° C. The reaction was quenched with water and the mixture was filtered through a hydrophobic phase separation filter which was rinsed with ethyl acetate (15 ml). The filtrate was concentrated under reduced pressure. The residue was purified by preparative HPLC to yield 210 mg (100% purity, 69% yield) of the title compound as a mixture of diastereomers.

LC-MS (method 1): $R_t$=1.80 min; MS (ESIpos): m/z=543 $[M+H]^+$ $^1$H-NMR (400 MHz, DMSO-$d_6$) δ [ppm]: 0.95 (t, 3H), 1.08-1.26 (m, 2H), 1.24 (d, 3H), 1.27-1.37 (m, 2H), 1.61 (quin, 2H), 2.76-2.80 (m, 1H), 3.23-3.30 (m, 2H), 3.77-3.88 (m, 2H), 3.98-4.04 (m, 11H), 5.41 (d, 1H), 6.35 (s, 2H), 7.77 (d, 1H), 7.79 (d, 1H), 7.95 (d, 1H), 8.24 (s, 11H), 8.32 (dd, 1H), 8.73 (s, 1H), 8.97 (s, 1H), 10.08 (d, 1H).

Example I-111

2-Amino-N-[(2S)-butan-2-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (mixture of diastereomers) (210 mg, 100% purity) was separated by chiral preparative HPLC to yield stereoisomer 1 (89 mg, 100% purity) and stereoisomer 2 (86 mg, 100% purity).

Column: Daicel Chiralpak IC, 5 μm, 250×20 mm; Eluent A: n-heptane; Eluent B: ethanol+0.2% diethylamine; isocratic: 80% A+20% B; flow: 20 ml/min; UV: 220 nm; temperature: 50° C.

Stereoisomer 1: $R_t$=14.83 min and

Stereoisomer 2: $R_t$=17.08 min (cf. next example)

Analytical chiral HPLC-method: Column: Daicel Chiralpak IC, 5 μm, 250×4.6 mm; Eluent A: n-heptane; Eluent B: ethanol+0.2% diethylamine; isocratic: 80% A+20% B; flow: 1 ml/min; UV: 220 nm; temperature: 50° C.

Stereoisomer 1: $R_t$=14.33 min and

Stereoisomer 2: $R_t$=16.40 min (cf. next example)

Stereoisomer 1: The stereochemical configuration of the methine carbon atom bonded to the pyrazole was (S).

LC-MS (method 1): $R_t$=1.81 min; MS (ESIpos): m/z=543 $[M+H]^+$ $^1$H-NMR (600 MHz, DMSO-$d_6$) δ [ppm]: 0.861 (0.46), 0.942 (7.03), 0.955 (16.00), 0.967 (7.54), 1.076 (1.14), 1.100 (1.53), 1.184 (1.12), 1.204 (1.43), 1.230 (15.04), 1.241 (15.08), 1.266 (0.59), 1.275 (0.60), 1.287 (1.12), 1.294 (1.23), 1.308 (1.18), 1.314 (1.29), 1.333 (1.26), 1.339 (1.15), 1.353 (0.95), 1.360 (0.91), 1.374 (0.43), 1.582 (1.11), 1.595 (3.90), 1.606 (5.24), 1.618 (3.82), 1.630 (1.00), 2.756 (0.42), 2.775 (1.11), 2.794 (1.11), 3.248 (1.06), 3.268 (2.77), 3.287 (2.74), 3.306 (1.10), 3.801 (1.27), 3.816 (1.18), 3.838 (1.29), 3.854 (1.15), 3.989 (0.75), 4.000 (1.61), 4.012 (1.91), 4.024 (1.61), 4.035 (0.72), 5.409 (3.55), 5.427 (3.39), 6.391 (8.89), 7.775 (5.45), 7.778 (7.77), 7.792 (7.67), 7.795 (5.42), 7.958 (4.36), 7.972 (4.61), 8.253 (9.17), 8.318 (2.41), 8.320 (2.36), 8.331 (2.17), 8.334 (2.14), 8.746 (8.39), 8.978 (4.46), 8.981 (4.38), 10.084 (3.20), 10.098 (3.05).

Example I-112

2-Amino-N-[(2S)-butan-2-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=1.81 min; MS (ESIpos): m/z=543 $[M+H]^+$ $^1$H-NMR (600 MHz, DMSO-$d_6$) δ [ppm]: 0.95 (t, 3H), 1.07-1.10 (m, 1H), 1.19 (br d, 1H), 1.24 (d, 3H), 1.28-1.36 (m, 2H), 1.60 (quin, 2H), 2.71-2.86 (m, 1H), 3.28 (br d, 2H), 3.79-3.86 (m, 2H), 4.00-4.02 (m, 1H), 5.41 (s, 1H), 5.43 (s, 1H), 6.39 (s, 2H), 7.77 (d, 1H), 7.79 (d, 1H), 7.96 (d, 1H), 8.25 (s, 1H), 8.32 (dd, 1H), 8.74 (s, 1H), 8.98 (s, 1H), 10.09 (d, 1H).

Example I-113

2-Amino-N-[(2S)-butan-2-yl]-7-(1-{1-[6-(2,2,2-trifluoroethoxy)pyridin-3-yl]propyl}-1H-pyrazol-4-yl)[1,2,4]triazolo[1,5-a]pyridine-5-carboxamide (mixture of diastereomers)

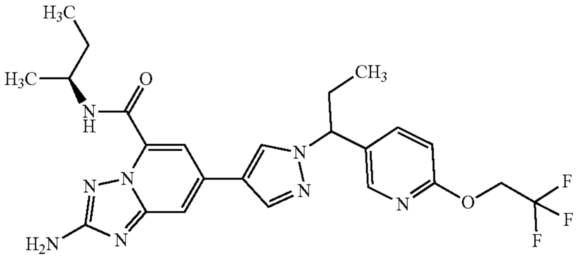 [SMILES: CCC(c1ccc(OCC(F)(F)F)nc1)n1cc(-c2cc(C(=O)N[C@@H](C)CC)n3nc(N)nc3c2)cn1]

2-Amino-N-[(2S)-butan-2-yl]-7-chloro[1,2,4]triazolo[1,5-a]pyridine-5-carboxamide (81.0 mg, 303 μmol), 5-{1-[4-(4,4,5,5-tetramethyl-1,3,2-dioxaborolan-2-yl)-1H-pyrazol-1-yl]propyl}-2-(2,2,2-trifluoroethoxy)pyridine (162 mg, 92% purity, 363 mol), sodium carbonate (160 mg, 1.51 mmol) and 1,1'-bis(diphenylphosphino)ferrocene-palladium (II)dichloride dichloromethane complex (12.4 mg, 15.1 μmol) were reacted according to procedure A in a mixture of 1,4-dioxane (3.5 ml) and water (500 μl). The reaction mixture was stirred for 2.5 h at 100° C. The residue was purified by preparative HPLC to yield 87.0 mg (98% purity, 55% yield) of the title compound as a mixture of two diastereomers.

LC-MS (method 1): $R_t$=2.00 min; MS (ESIpos): m/z=517 $[M+H]^+$ $^1$H-NMR (500 MHz, DMSO-$d_6$) δ [ppm]: 0.84 (t, 3H), 0.96 (t, 311), 1.24 (d, 3H), 1.58-1.64 (m, 2H), 2.15-2.19 (m, 1H), 2.34-2.48 (m, 1H), 3.99-4.04 (m, 1H), 4.94-5.00 (q, 2H), 5.40 (dd, 1H), 6.34 (s, 2H), 6.99 (d, 1H), 7.78 (q, 2H), 7.88 (dd, 1H), 8.17 (s, 1H), 8.26 (d, 1H), 8.71 (s, 1H), 10.08 (d, 1H).

Example I-114

2-Amino-N-[(2S)-butan-2-yl]-7-(1-{1-[6-(2,2,2-trifluoroethoxy)pyridin-3-yl]propyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{1-[6-(2,2,2-trifluoroethoxy)pyridin-3-yl]propyl}-1H-pyrazol-4-yl)[1,2,4]triazolo[1,5-a]pyridine-5-carboxamide (mixture of diastereoisomers) (87 mg, 100% purity) was separated by chiral preparative HPLC to yield stereoisomer 1 (29 mg, 100% purity) and stereoisomer 2 (32 mg, 100% purity).

Column: Daicel Chiralpak IA, 5 m, 250×30 mm; Eluent A: n-heptane; Eluent B: 2-propanol+0.2% diethylamine; isocratic: 55% A+45% B; flow: 35 ml/min; UV: 220 nm; temperature: 40° C.

Stereoisomer 1: $R_t$=7.36 min and

Stereoisomer 2: $R_t$=11.58 min (cf. next example)

Analytical chiral HPLC-method: Column: Daicel Chiralpack IA-3, 3 m, 50×4.6 mm; Eluent A: n-heptan; Eluent B: 2-propanol+0.2% diethylamine; isocratic: 50% A+50% B; flow: 1 ml/min; UV: 220 nm Stereoisomer 1: $R_t$=1.47 min and Stereoisomer 2: $R_t$=2.44 min (cf. next example)

LC-MS (method 1): $R_t$=2.00 min; MS (ESIpos): m/z=517 $[M+H]^+$ $^1$H-NMR (500 MHz, DMSO-$d_6$) δ [ppm]: 0.826 (3.96), 0.840 (8.38), 0.854 (3.91), 0.940 (4.99), 0.955 (11.31), 0.970 (5.36), 1.231 (10.74), 1.244 (10.61), 1.579 (0.89), 1.594 (2.96), 1.608 (3.85), 1.622 (2.71), 1.637 (0.71), 2.138 (0.54), 2.151 (0.95), 2.165 (1.29), 2.179 (1.08), 2.193 (0.64), 2.375 (0.62), 2.389 (0.82), 2.403 (0.78), 2.408 (0.84), 2.421 (0.74), 2.435 (0.51), 3.984 (0.54), 3.997 (1.18), 4.011 (1.42), 4.025 (1.18), 4.038 (0.51), 4.946 (1.87), 4.965 (5.40), 4.983 (5.08), 5.001 (1.58), 5.383 (1.27), 5.396 (1.51), 5.401 (1.51), 5.414 (1.18), 6.364 (6.42), 6.984 (3.58), 7.001 (3.63), 7.786 (16.00), 7.870 (2.18), 7.875 (2.21), 7.887 (2.06), 7.892 (2.11), 8.175 (6.72), 8.261 (3.61), 8.266 (3.51), 8.718 (6.12), 10.079 (2.24), 10.095 (2.15).

Example I-115

2-Amino-N-[(2S)-butan-2-yl]-7-(1-{1-[6-(2,2,2-trifluoroethoxy)pyridin-3-yl]propyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=2.00 min; MS (ESIpos): m/z=517 [M+H]J $^1$H-NMR (500 MHz, DMSO-$d_6$) δ [ppm]: 0.84 (t, 3H), 0.95 (t, 3H), 1.24 (d, 3H), 1.58-1.64 (m, 2H), 2.15-2.19 (m, 1H), 2.36-2.48 (m, 1H), 4.01 (dt, 1H), 4.97 (q, 2H), 5.40 (dd, 1H), 6.36 (s, 2H), 6.99 (d, 1H), 7.79 (s, 2H), 7.88 (dd, 1H), 8.17 (s, 1H), 8.26 (d, 1H), 8.72 (s, 1H), 10.09 (d, 11H).

Example I-116

2-Amino-N-[(2S)-butan-2-yl]-7-(1-{2-methyl-1-[6-(2,2,2-trifluoroethoxy)pyridin-3-yl]propyl}-1H-pyrazol-4-yl)[1,2,4]triazolo[1,5-a]pyridine-5-carboxamide (mixture of diastereomers)

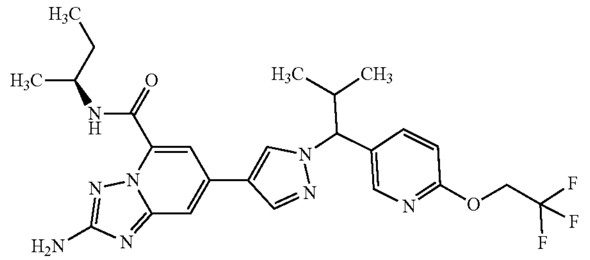 [SMILES: CC[C@H](C)NC(=O)c1cc(-c2cnn(C(c3ccc(OCC(F)(F)F)nc3)C(C)C)c2)cc2nc(N)nn12]

2-Amino-N-[(2S)-butan-2-yl]-7-chloro[1,2,4]triazolo[1,5-a]pyridine-5-carboxamide (100 mg, 374 μmol), 5-{2-methyl-1-[4-(4,4,5,5-tetramethyl-1,3,2-dioxaborolan-2-yl)-1H-pyrazol-1-yl]propyl}-2-(2,2,2-trifluoroethoxy)pyridine (210 mg, 91% purity, 448 μmol), 1,1'-bis(diphenylphosphino)ferrocene-palladium(II)dichloride dichloromethane complex (15.3 mg, 18.7 μmol) and sodium carbonate (198 mg, 1.87 mmol) were reacted according to procedure A in a mixture of 1,4-dioxane (4.0 ml) and water (600 μl). The residue was purified by preparative HPLC to give 111.0 mg (97% purity, 47% yield) of the title compound as a mixture of two diastereomers.

LC-MS (method 1): $R_t$=2.11 min; MS (ESIpos): m/z=531 $[M+H]^+$ $^1$H-NMR (500 MHz, DMSO-$d_6$) δ [ppm]: 0.80 (d, 3H), 0.82 (d, 3H), 0.95 (t, 3H), 1.24 (d, 3H), 1.58-1.64 (m, 2H), 2.78-2.74 (m, 1H), 3.98-4.04 (m, 1H), 4.94-5.01 (m, 2H), 5.05 (d, 1H), 6.34 (s, 2H), 7.01 (d, 11H), 7.77 (q, 2H), 8.06 (dd, 1H), 8.16 (s, 11H), 8.35 (d, 11H), 8.69 (s, 11H), 10.08 (d, 1H).

Example I-117

2-Amino-N-[(2S)-butan-2-yl]-7-(1-{2-methyl-1-[6-(2,2,2-trifluoroethoxy)pyridin-3-yl]propyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{2-methyl-1-[6-(2,2,2-trifluoroethoxy)pyridin-3-yl]propyl}-1H-pyrazol-4-yl)[1,2,4]triazolo[1,5-a]pyridine-5-carboxamide (mixture of diastereomers) (90 mg, 97% pure) was separated by chiral preparative HPLC to yield stereoisomer 1 (43 mg, 100% purity) and stereoisomer 2 (40 mg, 100% purity).

Column: Daicel Chiralpak IA, 5 μm, 250×30 mm; Eluent A: n-heptane; Eluent B: 2-propanol+0.2% diethylamine; isocratic: 55% A+45% B; flow: 35 ml/min; UV: 210 in, temperature: 40° C.

Stereoisomer 1: $R_t$=7.43 min and

Stereoisomer 2: $R_t$=10.78 min (cf. next example)

Analytical chiral HPLC-method: Column: Daicel Chiralpack IA-3 3ym 50×4.6 mm; EluentA: n-heptan; Eluent B: 2-propanol+0.2% diethylamine; isocratic: 50% A+50% B; flow: 1 ml/min; UV: 220 nm, temperature: 40° C.

Stereoisomer 1: $R_t$=1.30 min and

Stereoisomer 2: $R_t$=2.01 min (cf. next example)

LC-MS (method 1): $R_t$=2.11 min; MS (ESIpos): m/z=531 $[M+H]^+$ $^1$H-NMR (500 MHz, DMSO-$d_6$) δ [ppm]: 0.793 (6.17), 0.807 (6.63), 0.815 (6.81), 0.828 (6.53), 0.939 (4.22), 0.954 (9.63), 0.969 (4.55), 1.230 (9.06), 1.243 (9.04), 1.262 (0.45), 1.578 (0.69), 1.592 (2.42), 1.607 (3.14), 1.621 (2.26), 1.636 (0.62), 2.736 (0.55), 2.749 (0.75), 2.758 (0.65), 2.762 (0.65), 2.771 (0.75), 2.784 (0.52), 3.983 (0.45), 3.996 (1.00), 4.011 (1.17), 4.024 (0.97), 4.038 (0.44), 4.947 (1.42), 4.965 (4.05), 4.984 (3.85), 5.002 (1.21), 5.042 (2.26), 5.064 (2.16), 6.364 (5.26), 7.005 (2.97), 7.022 (2.98), 7.768 (16.00), 8.048 (1.79), 8.053 (1.80), 8.065 (1.69), 8.070 (1.72), 8.170 (5.55), 8.353 (3.03), 8.358 (2.89), 8.699 (4.96), 10.077 (1.89), 10.093 (1.80).

Example I-118

2-Amino-N-[(2S)-butan-2-yl]-7-(1-{2-methyl-1-[6-(2,2,2-trifluoroethoxy)pyridin-3-yl]propyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=2.11 min; MS (ESIpos): m/z=531 $[M+H]^+$ $^1$H-NMR (500 MHz, DMSO-$d_6$) δ [ppm]: 0.80 (d, 3H), 0.82 (d, 3H), 0.95 (t, 3H), 1.24 (d, 3H), 1.58-1.64 (m, 2H), 2.70-2.80 (m, 11H), 3.97-4.05 (m, 1H), 4.97 (q, 2H), 5.05 (d, 1H), 6.36 (s, 2H), 7.01 (d, 1H), 7.77 (s, 2H), 8.06 (dd, 1H), 8.17 (s, 1H), 8.36 (d, 1H), 8.70 (s, 1H), 10.09 (d, 1H).

Example I-119

2-Amino-N-[(2S)-butan-2-yl]-7-(1-{cyclopropyl[6-(2,2,2-trifluoroethoxy)pyridin-3-yl]methyl}-1H-pyrazol-4-yl)[1,2,4]triazolo[1,5-a]pyridine-5-carboxamide (mixture of diastereomers)

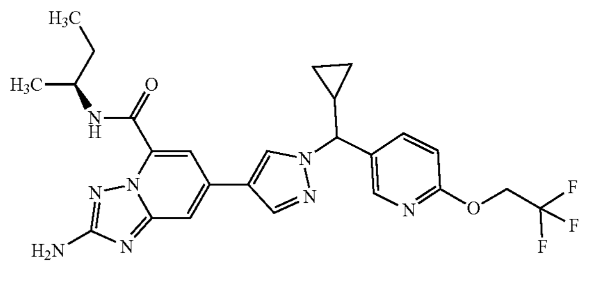 [SMILES: CC[C@H](C)NC(=O)c1cc(-c2cnn(C(c3ccc(OCC(F)(F)F)nc3)C3CC3)c2)cc2nc(N)nn12]

2-Amino-N-[(2S)-butan-2-yl]-7-chloro[1,2,4]triazolo[1,5-a]pyridine-5-carboxamide (62.0 mg, 232 mol), 5-{cyclopropyl[4-(4,4,5,5-tetramethyl-1,3,2-dioxaborolan-2-yl)-1H-pyrazol-1-yl]methyl}-2-(2,2,2-trifluoroethoxy)pyridine (132 mg, 89% purity, 278 μmol), 1,1'-bis(diphenylphosphino)ferrocene-palladium(II)dichloride dichloromethane complex (9.46 mg, 11.6 μmol) and sodium carbonate (123 mg, 1.16 mmol) were reacted according to procedure A in a mixture of 1,4-dioxane (2.5 ml) and water (370 μl). The reaction mixture was stirred for 2.5 h at 90° C. 1,1'-Bis(diphenylphosphino)ferrocene-palladium(II)dichloride dichloromethane complex (9.46 mg, 11.6 mol) were added and the reaction was further stirred for 3 h at 110° C. The residue was purified by preparative HPLC to yield 55.0 mg (100% purity, 44% yield) of the title compound as a mixture of two diastereomers.

LC-MS (method 1): $R_t$=1.99 min; MS (ESIpos): m/z=529 $[M+H]^+$ $^1$H-NMR (500 MHz, DMSO-$d_6$) δ [ppm]: 0.47-0.55 (m, 2H), 0.67-0.75 (m, 2H), 0.96 (t, 3H), 1.24 (d, 3H), 1.58-1.64 (m, 2H), 1.83-1.91 (m, 1H), 3.99-4.04 (m, 1H), 4.76 (d, 1H), 4.98 (q, 2H), 6.35 (s, 211), 6.99 (d, 1H), 7.80 (q, 2H), 7.83 (dd, 1H), 8.15 (s, 1H), 8.25 (d, 1H), 8.76 (s, 1H), 10.09 (d, 1H).

Example I-120

2-Amino-N-[(2S)-butan-2-yl]-7-(1-{cyclopropyl[6-(2,2,2-trifluoroethoxy)pyridin-3-yl]methyl}-1H-pyrazol-4-yl)[1,2,4]triazolo[1,5-a]pyridine-5-carboxamide (stereoisomer 1, distomer)

2-Amino-N-[(2S)-butan-2-yl]-7-(1-{cyclopropyl[6-(2,2,2-trifluoroethoxy)pyridin-3-yl]methyl}-1H-pyrazol-4-yl)[1,2,4]triazolo[1,5-a]pyridine-5-carboxamide (mixture of diastereoisomers) (55.0 mg, 100% purity) was separated by chiral preparative HPLC to yield stereoisomer 1 (17.5 mg, 100% purity) and stereoisomer 2 (19.6 mg, 100% purity).

Column: Daicel Chiralpak AD_H, 5 μm, 250×20 mm; Eluent A: n-heptane; Eluent B: 2-propanol; isocratic: 60% A+40% B; flow: 15 ml/min; UV: 210 nm; temperature: 40° C.

Stereoisomer 1: $R_t$=9.13 min and

Stereoisomer 2: $R_t$=12.80 min (cf. next example)

Analytical chiral HPLC-method: Column: Chiralpak AD-3, 3 μm, 250×4.6 mm; Eluent A: n-heptane; Eluent B: 2-propanol; isocratic: 50% A+50% B; flow: 1 ml/min; UV: 220 nm Stereoisomer 1: $R_t$=2.89 min and Stereoisomer 2: $R_t$=4.54 min (cf. next example)

LC-MS (method 1): $R_t$=2.02 min; MS (ESIpos): m/z=529 $[M+H]^+$ $^1$H-NMR (500 MHz, DMSO-$d_6$) δ [ppm]: −0.007 (2.87), 0.006 (2.22), 0.497 (1.43), 0.510 (1.89), 0.523 (1.39), 0.701 (2.86), 0.717 (2.90), 0.943 (4.36), 0.958 (9.96), 0.973 (4.68), 1.234 (9.50), 1.247 (9.40), 1.582 (0.73), 1.597 (2.55), 1.611 (3.28), 1.625 (2.35), 1.640 (0.62), 1.859 (0.48), 1.865 (0.74), 1.875 (0.75), 1.885 (0.73), 3.986 (0.47), 3.999 (1.02), 4.014 (1.22), 4.028 (1.00), 4.041 (0.44), 4.748 (2.44), 4.768 (2.36), 4.956 (1.71), 4.975 (4.93), 4.993 (4.66), 5.011 (1.46), 6.367 (5.49), 6.987 (3.12), 7.004 (3.22), 7.808 (16.00), 7.823 (2.04), 7.828 (2.02), 7.841 (1.84), 7.846 (1.89), 8.158 (5.90), 8.249 (3.13), 8.253 (3.08), 8.772 (5.32), 10.090 (1.90), 10.105 (1.83).

Example I-121

2-Amino-N-[(2S)-butan-2-yl]-7-(1-{cyclopropyl[6-(2,2,2-trifluoroethoxy)pyridin-3-yl]methyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R_t$=2.02 min; MS (ESIpos): m/z=529 $[M+H]^+$ $^1$H-NMR (500 MHz, DMSO-$d_6$) δ [ppm]: 0.47-0.55 (m, 2H), 0.68-0.74 (m, 2H), 0.96 (t, 3H), 1.24 (d, 3H), 1.58-1.63 (m, 2H), 1.84-1.91 (m, 1H), 3.97-4.05 (m, 1H), 4.76 (d, 1H), 4.98 (q, 10 2H), 6.37 (s, 2H), 6.99 (d, 1H), 7.81 (s, 2H), 7.83 (dd, 1H), 8.16 (s, 1H), 8.25 (d, 1H), 8.77 (s, 1H), 10.10 (d, 1H).

Example I-122

2-Amino-N-[(2S)-butan-2-yl]-7-(1-{1-[2-(trifluoromethyl)pyridin-4-yl]propyl}-1H-pyrazol-4-yl)[1,2,4]triazolo[1,5-a]pyridine-5-carboxamide (mixture of diastereomers)

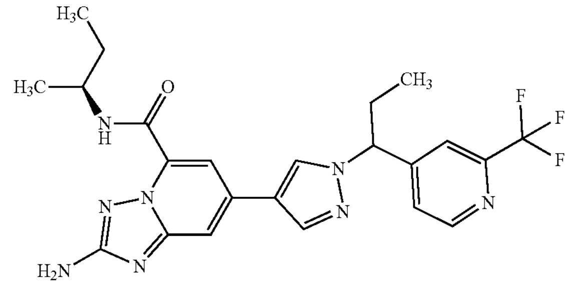 [SMILES: CCC(c1ccnc(C(F)(F)F)c1)n1cc(-c2cc(C(=O)N[C@@H](C)CC)n3nc(N)nc3c2)cn1]

2-Amino-N-[(2S)-butan-2-yl]-7-chloro[1,2,4]triazolo[1,5-a]pyridine-5-carboxamide (89.6 mg, 335 μmol), 4-{1-[4-(4,4,5,5-tetramethyl-1,3,2-dioxaborolan-2-yl)-1H-pyrazol-1-yl]propyl}-2-(trifluoromethyl)pyridine (356 mg, 43% purity, 402 μmol), 1,1'-bis(diphenylphosphino)ferrocene-palladium(II)dichloride dichloromethane complex (41.0 mg, 50.2 mol) and sodium carbonate (106 mg, 1.00 mmol) were reacted according to procedure A in a mixture of 1,4-dioxane (3.0 ml) and water (1.0 ml). After stirring for 3 h at 90° C., the reaction was quenched with water and the mixture was extracted with dichloromethane. The combined organic layers were dried over anhydrous sodium sulfate, filtered and concentrated. The residue was purified via column chromatography (Biotage® SNAP KP-NH 11 g cartridge, eluent: cyclohexane/ethyl acetate gradient 9:1, 1:4) to yield 78.0 mg (99% purity, 47% yield) of the title compound as a mixture of two diasteromers.

LC-MS (method 1): $R_t$=1.86 min; MS (ESIpos): m/z=487 $[M+H]^+$ $^1$H-NMR (600 MHz, DMSO-$d_6$) δ [ppm]: 0.87 (t, 3H), 0.96 (t, 3H), 1.24 (d, 3H), 1.59-1.63 (m, 2H), 2.19-2.27 (m, 1H), 2.38-2.48 (m, 1H), 3.99-4.04 (m, 1H), 5.60 (dd, 1H), 7.65 (dd, 1H), 7.82 (s, 2H), 7.88 (s, 1H), 8.28 (s, 1H), 8.76 (d, 1H), 8.79 (s, 1H), 10.04 (d, 1H).

Example I-123

2-Amino-N-[(2S)-butan-2-yl]-7-{1-[1-(3,5-difluoro-pyridin-4-yl)-2-methylpropyl]-1H-pyrazol-4-yl}[1,2,4]triazolo[1,5-a]pyridine-5-carboxamide (mixture of diastereomers)

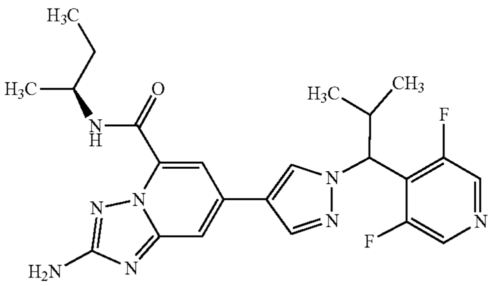 [SMILES: CC[C@H](C)NC(=O)c1cc(-c2cnn(C(c3c(F)cncc3F)C(C)C)c2)cc2nc(N)nn12]

2-Amino-N-[(2S)-butan-2-yl]-7-chloro[1,2,4]triazolo[1,5-a]pyridine-5-carboxamide (150 mg, 560 μmol) was reacted with 3,5-difluoro-4-{2-methyl-1-[4-(4,4,5,5-tetramethyl-1,3,2-dioxaborolan-2-yl)-1H-pyrazol-1-yl]propyl}pyridine (349 mg, 70% purity, 672 μmol) for 2 h at 80° C. following general procedure B using 0.1 eq. catalyst. The reaction mixture was then diluted with ethyl acetate (20 ml) and filtered through a hydrophobic phase separation filter which was rinsed with ethyl acetate. The solvent was evaporated under reduced pressure. The residue was purified by column chromatography (Biotage® SNAP KP-NH 28 g cartridge, eluent: cyclohexane/ethyl acetate gradient 80:20 to 0:100) to yield product which was further purified by preparative HPLC (Chromatorex C18, 10 μm, 125×30 mm; eluent: water (0.1% formic acid)/acetonitrile gradient) to yield 136 mg (100% purity, 52% yield) of the title compound.

LC-MS (method 1): $R_t$=1.79 min; MS (ESIpos): m/z=469 $[M+H]^+$ $^1$H-NMR (600 MHz, DMSO-$d_6$) δ [ppm]: 0.92 (d, 3H), 0.94-0.98 (m, 6H), 1.24 (d, 3H), 1.61 (quin, 2H), 3.05-3.13 (m, 1H), 3.98-4.05 (m, 1H), 5.46 (d, 1H), 6.37 (s, 2H), 7.80-7.83 (m, 2H), 8.17 (s, 1H), 8.58 (s, 2H), 8.81 (s, 1H), 10.07 (br d, 1H).

Example I-124

2-Amino-N-[(2S)-butan-2-yl]-7-{1-[1-(3,5-difluoro-pyridin-4-yl)-2-methylpropyl]-1H-pyrazol-4-yl}[1,2,4]triazolo[1,5-a]pyridine-5-carboxamide (single stereoisomer, distomer)

2-Amino-N-[(2S)-butan-2-yl]-7--{1-[1-(3,5-difluoropyridin-4-yl)-2-methylpropyl]-1H-pyrazol-4-yl}[1,2,4]triazolo[1,5-a]pyridine-5-carboxamide (mixture of diastereomers) (120 mg, 100% purity) from the previous example was separated by chiral chromatography to yield stereoisomer 1 (24 mg, 99% purity) and stereoisomer 2 (29 mg, 97% purity).

Column: Daicel Chiralpak IE 5 μm, 250×20 mm; Eluent A: n-heptane; Eluent B: ethanol; isocratic: 50% A+50% B; flow: 20 ml/min; UV: 220 nm; temperature: 40° C.

Stereoisomer 1: $R_t$=11.549 min and

Stereoisomer 2: $R_t$=12.658 min (cf. next example)

Analytical chiral HPLC. Column: Daicel Chiralpak IE-3, 3 sm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R_t$=1.948 min and

Stereoisomer 2: $R_t$=2.145 min (cf. next example)

LC-MS (method 1): $R_t$=1.78 min; MS (ESIpos): m/z=469 $[M+H]^+$ $^1$H-NMR (400 MHz, DMSO-$d_6$) δ [ppm]: −0.008 (0.54), 0.008 (0.59), 0.911 (5.79), 0.928 (6.31), 0.937 (9.74), 0.955 (16.00), 0.973 (4.85), 1.231 (9.77), 1.247 (9.80), 1.573 (0.73), 1.591 (2.54), 1.609 (3.23), 1.626 (2.37), 1.645 (0.62), 2.524 (1.38), 3.075 (0.55), 3.091 (0.58), 3.104 (0.55), 3.976 (0.44), 3.993 (0.98), 4.010 (1.11), 4.029 (0.95), 4.045 (0.40), 5.440 (2.18), 5.468 (2.10), 6.352 (5.25), 7.801 (3.00), 7.806 (5.78), 7.814 (5.75), 7.819 (2.88), 8.167 (5.77), 8.571 (11.02), 8.799 (4.35), 10.056 (1.74), 10.075 (1.70).

Example I-125

2-Amino-N-[(2S)-butan-2-yl]-7-{1-[1-(3,5-difluoro-pyridin-4-yl)-2-methylpropyl]-1H-pyrazol-4-yl}[1;2,4]triazolo[1,5-a]pyridine-5-carboxamide (single stereoisomer, eutomer)

The product was isolated in the previous example as second stereoisomer.

LC-MS (method 1): $R_t$=1.79 min; MS (ESIpos): m/z=469 $[M+H]^+$ $^1$H-NMR (400 MHz, DMSO-$d_6$) δ [ppm]: −0.008 (0.82), 0.008 (0.80), 0.846 (0.43), 0.861 (0.46), 0.911 (6.30), 0.928 (6.85), 0.938 (11.70), 0.956 (16.00), 0.975 (5.35), 1.087 (0.41), 1.102 (0.41), 10 1.154 (0.44), 1.230 (10.61), 1.247 (10.72), 1.574 (0.79), 1.592 (2.78), 1.609 (3.48), 1.627 (2.58), 1.646 (0.68), 2.328 (0.58), 2.367 (0.48), 2.671 (0.59), 2.711 (0.51), 3.075 (0.62), 3.091 (0.62), 3.104 (0.61), 3.976 (0.50), 3.993 (1.09), 4.010 (1.24), 4.029 (1.05), 4.045 (0.48), 5.440 (2.36), 5.468 (2.28), 6.352 (5.86), 7.801 (3.47), 7.805 (6.72), 7.814 (6.69), 7.819 (3.48), 8.168 (6.54), 8.557 (0.61), 8.571 (13.35), 8.800 (4.73), 10.056 (1.89), 10.075 (1.88).

Example I-126

2-Amino-N-[(2S)-butan-2-yl]-7-{1-[1-(2-methoxy-pyridin-4-yl)-2-methylpropyl]-1H-pyrazol-4-yl}[1,2,4]triazolo[1,5-a]pyridine-5-carboxamide (mixture of diastereomers)

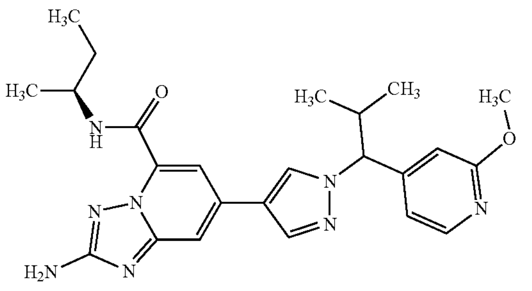 [SMILES: CC[C@H](C)NC(=O)c1cc(-c2cnn(C(c3ccnc(OC)c3)C(C)C)c2)cc2nc(N)nn12]

2-Amino-N-[(2S)-butan-2-yl]-7-chloro[1,2,4]triazolo[1,5-a]pyridine-5-carboxamide (160 mg, 96% purity, 574.mol) was reacted with 2-methoxy-4-{2-methyl-1-[4-(4,4,5,5-tetramethyl-1,3,2-dioxaborolan-2-yl)-1H-pyrazol-1-yl]propyl}pyridine (314 mg, 88% purity, 775 µmol) for 90 min at 80° C. following general procedure C using 0.1 eq. catalyst. The reaction mixture was directly purified by chromatography (Biotage® SNAP Ultra 25 g cartridge, eluent: dichloromethane/methanol gradient 100:0 to 85:15). The resulting product was further purified by preparative HPLC (Chromatorex C18, 10 m, 125×30 mm; eluent: water (0.1% formic acid)/acetonitrile gradient) to yield 170 mg (91% purity, 58% yield) of the title compound.

LC-MS (method 2): $R_t$=0.99 min; MS (ESIpos): m/z=463 $[M+H]^+$ $^1$H-NMR (600 MHz, DMSO-$d_6$) δ [ppm]: 0.81 (d, 3H), 0.84 (d, 3H), 0.96 (t, 3H), 1.24 (d, 3H), 1.61 (quin, 2H), 2.70-2.79 (m, 1H), 3.83 (s, 3H), 3.97-4.05 (m, 1H), 5.00 (d, 1H), 6.36 (s, 2H), 6.97 (s, 1H), 7.16 (dd, 1H), 7.78 (s, 2H), 8.15 (d, 1H), 8.18 (s, 1H), 8.72 (s, 1H), 10.08 (d, 1H).

Example I-127

2-Amino-N-[(2S)-butan-2-yl]-7-{1-[1-(2-methoxy-pyridin-4-yl)-2-methylpropyl]-1H-pyrazol-4-yl}[1,2,4]triazolo[1,5-a]pyridine-5-carboxamide (stereoisomer 1, distomer)

2-Amino-N-[(2S)-butan-2-yl]-7-{1-[1-(2-methoxypyridin-4-yl)-2-methylpropyl]-1H-pyrazol-4-yl}[1,2,4]triazolo[1,5-a]pyridine-5-carboxamide (mixture of diastereomers) (170 mg, 91% purity) from the previous example was separated by chiral chromatography to yield stereoisomer 1 (65 mg, 100% purity) and stereoisomer 2 (66 mg, 100% purity).

Column: Daicel Chiralcel OJ-H, 5 µm, 250×20 mm; Eluent A: n-heptane; Eluent B: ethanol+0.2% diethylamine; isocratic: 85% A+15% B; flow: 35 ml/min; UV: 220 nm; temperature: 40° C.

Stereoisomer 1: $R_t$=6.675 min and

Stereoisomer 2: $R_t$=10.718 min (cf. next example)

Analytical chiral HPLC. Column: Daicel ChiralCel OJ-3, 3 m, 50×4.6 mm; Eluent A: n-heptane; Eluent B: ethanol+0.2% diethylamine; isocratic: 80% A+20% B; flow: 1 ml/min; UV: 220 nm.

Stereoisomer 1: $R_t$=2.232 min and

Stereoisomer 2: $R_t$=3.686 min (cf. next example)

LC-MS (method 2): $R_t$=0.96 min; MS (ESIpos): m/z=463 [M+H]J $^1$H-NMR (400 MHz, DMSO-$d_6$) δ [ppm]: 0.81 (d, 3H), 0.84 (d, 3H), 0.95 (t, 3H), 1.24 (d, 3H), 1.61 (quin, 2H), 2.69-2.80 (m, 1H), 4.01 (spt, 1H), 5.00 (d, 1H), 6.35 (s, 2H), 6.97 (s, 1H), 7.15 (dd, 1H), 7.77 (s, 2H), 8.14 (d, 1H), 8.18 (s, 1H), 8.72 (s, 1H), 10.07 (d, 1H).

Example I-128

2-Amino-N-[(2S)-butan-2-yl]-7-{1-[1-(2-methoxy-pyridin-4-yl)-2-methylpropyl]-1H-pyrazol-4-yl}[1,2,4]triazolo[1,5-a]pyridine-5-carboxamide (stereoisomer 2, eutomer)

The product was isolated in the previous example as second stereoisomer.

LC-MS (method 2): $R_t$=0.96 min; MS (ESIpos): m/z=463 $[M+H]^+$ $^1$H-NMR (400 MHz, DMSO-$d_6$) δ [ppm]: 0.81 (d, 3H), 0.84 (d, 3H), 0.95 (t, 3H), 1.24 (d, 4H), 1.56-1.66 (m, 2H), 2.69-2.80 (m, 1H), 3.95-4.07 (m, 1H), 5.00 (d, 1H), 6.35 (s, 2H), 6.97 (s, 1H), 7.15 (dd, 11H), 7.77 (s, 2H), 8.14 (d, 1H), 8.18 (s, 1H), 8.72 (s, 1H), 10.07 (d, 11H).

Example I-129

2-Amino-N-[(2S)-butan-2-yl]-6-{1-[1-(5-chloro-2-thienyl)propyl]-1H-pyrazol-4-yl}[1,2,4]triazolo[1,5-a]pyridine-8-carboxamide (mixture of diastereomers)

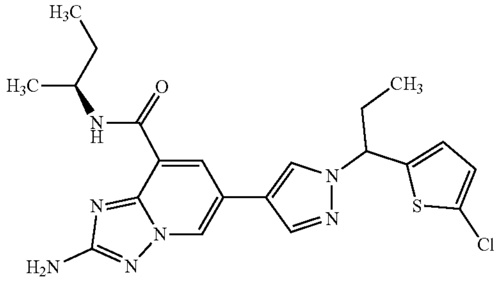 [SMILES: CCC(c1ccc(Cl)s1)n1cc(-c2cc(C(=O)N[C@@H](C)CC)c3nc(N)nn3c2)cn1]

2-Amino-6-bromo-N-[(2S)-butan-2-yl][1,2,4]triazolo[1,5-a]pyridine-8-carboxamide (120 mg, 384 µmol), 1-[l-(5-chloro-2-thienyl)propyl]-4-(4,4,5,5-tetramethyl-1,3,2-dioxaborolan-2-yl)-1H-pyrazole (223 mg, 73% purity, 461 µmol), sodium carbonate (204 mg, 1.92 mmol) and 1,1'-bis(diphenylphosphino)ferrocene-palladium(II)dichloride dichloromethane complex (15.7 mg, 19.2 µmol) were reacted according to procedure A in a mixture of 1,4-dioxane (4.5 ml) and water (700 µl). The reaction mixture was stirred for 4.5 h at 100° C. The residue was purified by preparative HPLC to yield 106 mg (96% purity, 58% yield) of the title compound as a mixture of two diastereomers.

LC-MS (method 1): $R^t$=2.03 min; MS (ESIpos): m/z=458 $[M+H]^+$ $^1$H-NMR (500 MHz, DMSO-$d_6$) δ [ppm]: 0.83 (t, 3H), 0.94 (t, 3H), 1.22 (d, 3H), 1.54-1.63 (m, 2H), 2.09-2.24 (m, 1H), 2.16-2.33 (m, 1H), 3.98-4.06 (m, 1H), 5.58 (dd, 1H), 6.39 (s, 2H), 6.98-7.02 (m, 2H), 8.09 (s, 1H), 8.25 (d, 1H), 8.50 (s, 1H), 9.07 (d, 1H), 9.27 (d, 1H).

Example I-130

2-Amino-N-[(2S)-butan-2-yl]-6-{1-[1-(5-chloro-2-thienyl)propyl]-1H-pyrazol-4-yl}[1,2,4]triazolo[1,5-a]pyridine-8-carboxamide (stereoisomer 1, distomer 2-Amino-N-[(2S)-butan-2-yl]-6-{1-[1-(5-chloro-2-thienyl)propyl]-1H-pyrazol-4-yl}[1,2,4]triazolo[1,5-a]pyridine-8-carboxamide (mixture of diastereomers) (106 mg, 96% purity) was separated by chiral preparative HPLC to yield stereoisomer 1 (41 mg, 100% purity) and stereoisomer 2 (42 mg, 100% purity).

Column: Chiralpak IF-H, 5 μm, 250×20 mm; Eluen tA: n-heptane; Eluent B: ethanol; isocratic: 50% A+50% B; flow: 15 ml/min; UV: 210 nm; temperature 40° C.

Stereoisomer 1: $R^t$=10.95 min and

Stereoisomer 2: $R^t$=13.84 min (cf. next example)

Analytical chiral HPLC-method: Column: Chiralteck IF-3, 3 μm, 250×4.6 mm; Eluent A: n-heptane; Eluent B: ethanol; isocratic: 50% A+50% B; flow: 1 ml/min; UV: 220 nm Stereoisomer 1: $R^t$=4.97 min and Stereoisomer 2: $R^t$=6.44 min (cf. next example)

LC-MS (method 1): $R^t$=2.07 min; MS (ESIpos): m/z=458 [M+H]+

$^1$H-NMR (500 MHz, DMSO-$d_6$) δ [ppm]: 0.83 (t, 3H), 0.94 (t, 3H), 1.22 (d, 3H), 1.53-1.63 (m, 2H), 2.12-2.21 (m, 1H), 2.30-2.52 (m, 1H), 3.99-4.04 (m, 1H), 5.58 (dd, 1H), 6.41 (s, 2H), 6.98-7.02 (m, 2H), 8.10 (s, 1H), 8.25 (d, 1H), 8.51 (s, 1H), 9.08 (d, 1H), 9.28 (d, 1H).

Example I-131

2-Amino-N-[(2S)-butan-2-yl]-6-{1-[1-(5-chloro-2-thienyl)propyl]-1H-pyrazol-4-yl}[1,2,4]triazolo[1,5-a]pyridine-8-carboxamide (stereoisomer 2, eutomer)

The product was isolated in the previous example as second stereoisomer.

LC-MS (method 1): $R^t$=2.07 min; MS (ESIpos): m/z=458-[M+H]$^+$ $^1$H-NMR (500 MHz, DMSO-$d_6$) δ [ppm]: 0.83 (t, 3H), 0.94 (t, 3H), 1.22 (d, 3H), 1.54-1.63 (m, 2H), 2.12-2.21 (m, 1H), 2.28-2.34 (m, 1H), 3.99-4.04 (m, 1H), 5.59 (dd, 1H), 6.41 (s, 2H), 6.98-7.02 (m, 2H), 8.10 (s, 1H), 8.25 (d, 1H), 8.51 (s, 1H), 9.08 (d, 1H), 9.28 (d, 1H).

Example I-132

2-Amino-N-cyclobutyl-6-{1-[(4-fluorophenyl)methyl]-1H-pyrazol-4-yl}[1,2,4]triazolo[1,5-a]pyridine-8-carboxamide

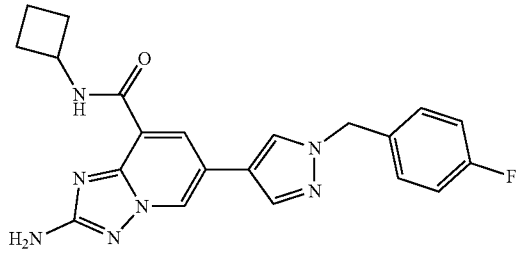 [SMILES: Nc1nc2c(C(=O)NC3CCC3)cc(-c3cnn(Cc4ccc(F)cc4)c3)cn2n1]

2-Amino-6-bromo-N-cyclobutyl[1,2,4]triazolo[1,5-a]pyridine-8-carboxamide (50.0 mg, 161 μmol) was reacted with 1-[(4-fluorophenyl)methyl]-4-(4,4,5,5-tetramethyl-1,3,2-dioxaborolan-2-yl)-1H-pyrazole (58.5 mg, 193 μmol) for 1 h at 90° C. following general procedure B using 0.05 eq. catalyst. The mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 65:35 to 0:100) to yield 48.8 mg (100% purity, 75% yield) of the title compound.

LC-MS (method 2): $R^t$=0.87 min; MS (ESIpos): m/z=406 [M+H]$^+$ $^1$H-NMR (500 MHz, DMSO-$d_6$) δ [ppm]: 1.71-1.80 (m, 2H), 1.96-2.06 (m, 2H), 2.31-2.39 (m, 2H), 4.44-4.53 (m, 1H), 5.34 (s, 2H), 6.43 (s, 2H), 7.16-7.22 (m, 2H), 7.33-7.39 (m, 2H), 8.04 (s, 1H), 8.21 (d, 1H), 8.45 (s, 1H), 9.06 (d, 1H), 9.59 (d, 1H).

Example I-133

2-Amino-6-(1-benzyl-1H-pyrazol-4-yl)-N-[(2S)-1,1,1-trifluorobutan-2-yl][1,2,4]triazolo[1,5-a]pyridine-8-carboxamide (single stereoisomer)

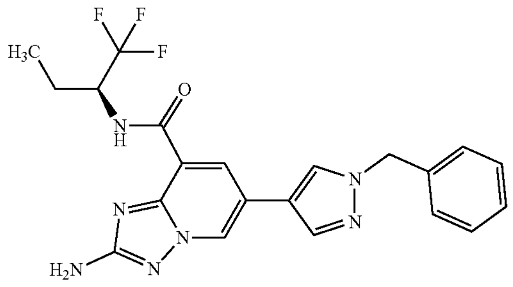 [SMILES: CC[C@H](NC(=O)c1cc(-c2cnn(Cc3ccccc3)c2)cn2nc(N)nc12)C(F)(F)F]

2-Amino-6-bromo-N-[(2S)-1,1,1-trifluorobutan-2-yl][1,2,4]triazolo[1,5-a]pyridine-8-carboxamide (60.0 mg, 164 μmol) was reacted with 1-benzyl-4-(4,4,5,5-tetramethyl-1,3,2-dioxaborolan-2-yl)-1H-pyrazole (46.6 mg, 164 μmol) for 2 h at 110° C. following general procedure B using 0.05 eq. catalyst, then further 0.05 eq. catalyst was added and heating was continued for 1.5 h. The reaction mixture was filtered through a hydrophobic phase separation filter which was rinsed with ethyl acetate (15 ml). The solvent was removed in vacuo and the residue was purified by column chromatography (Biotage® SNAP KP-NH 11 g cartridge, eluent: cyclohexane/ethyl 15 acetate gradient 80:20 to 0:100) and additionally via preparative HPLC (Chromatorex C18, 10 μm, 125×30 mm; eluent: water/acetonitrile gradient 90:10 to 5:95) to yield 33.6 mg (100% purity, 46% yield) of the title compound.

LC-MS (method 1): $R^t$=1.84 min; MS (ESIpos): m/z=444 [M+H]$^+$ $^1$H-NMR (400 MHz, DMSO-$d_6$) δ [ppm]: 1.00 (t, 3H), 1.60-1.74 (m, 1H), 1.89-2.01 (m, 1H), 4.75-4.89 (m, 1H), 5.36 (s, 2H), 6.48 (s, 2H), 7.27-7.40 (m, 5H), 8.06 (s, 1H), 8.29 (d, 1H), 8.48 (s, 1H), 9.13 (d, 1H), 9.70 (d, 1H).

Example I-134

2-Amino-6-(1-benzyl-1H-pyrazol-4-yl)-N-[(2R)-1,1,1-trifluorobutan-2-yl][1,2,4]triazolo[1,5-a]pyridine-8-carboxamide (single stereoisomer)

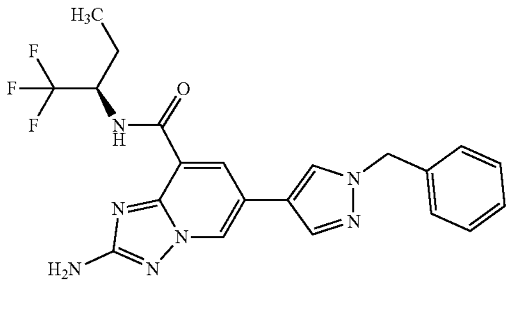 [SMILES: CC[C@@H](NC(=O)c1cc(-c2cnn(Cc3ccccc3)c2)cn2nc(N)nc12)C(F)(F)F]

2-Amino-6-bromo-N-[(2R)-1,1,1-trifluorobutan-2-yl][1,2,4]triazolo[1,5-a]pyridine-8-carboxamide (65.0 mg, 178 μmol) was reacted with 1-benzyl-4-(4,4,5,5-tetramethyl-1,3,2-dioxaborolan-2-yl)-1H-pyrazole (61.7 mg, 90% purity, 195 μmol) for 1 h at 90° C. following general procedure B using 0.05 eq. catalyst. The reaction mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 85:15 to 8:92) to yield 62.3 mg (95% purity, 75% yield) of the title compound.

LC-MS (method 1): $R^t$=1.84 min; MS (ESIpos): m/z=444 $[M+H]^+$ $^1$H-NMR (500 MHz, DMSO-$d_6$) δ [ppm]: 1.01 (t, 3H), 1.63-1.73 (m, 1H), 1.90-2.00 (m, 1H), 4.88 (s, 1H), 5.36 (s, 2H), 6.48 (s, 2H), 7.27-7.39 (m, 5H), 8.07 (d, 1H), 8.29 (d, 1H), 8.49 (d, 1H), 9.13 (d, 1H), 9.70 (d, 1H).

Example I-135

2-Amino-6-{1-[(4-fluorophenyl)methyl]-1H-pyrazol-4-yl}-N-[(2S)-1-methoxypropan-2-yl][1,2,4]triazolo[1,5-a]pyridine-8-carboxamide (single stereoisomer)

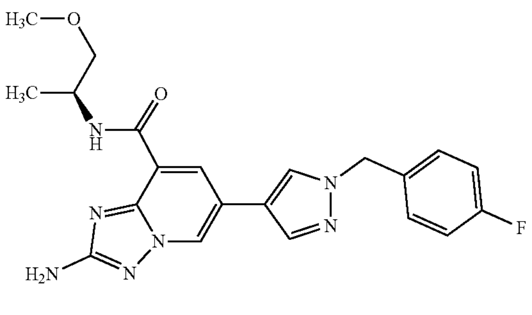 [SMILES: COC[C@H](C)NC(=O)c1cc(-c2cnn(Cc3ccc(F)cc3)c2)cn2nc(N)nc12]

2-Amino-6-bromo-N-[(2S)-1-methoxypropan-2-yl][1,2,4]triazolo[1,5-a]pyridine-8-carboxamide (60.0 mg, 183 μmol) was reacted with 1-[(4-fluorophenyl)methyl]-4-(4,4,5,5-tetramethyl-1,3,2-dioxaborolan-2-yl)-1H-pyrazole (58.2 mg, 95% purity, 183 μmol) for 1 h at 110° C. following general procedure B using 0.05 eq. catalyst. The reaction mixture was filtered through a hydrophobic phase separation filter which was rinsed with ethyl acetate (15 ml). The filtrate was concentrated in vacuo and the residue was purified by column chromatography (Biotage® SNAP KP-NH 11 g cartridge, eluent: cyclohexane/ethyl acetate gradient 85:15 to 30:70) to yield 22.6 mg (100% purity, 29% yield) of the title compound.

LC-MS (method 1): $R^t$=1.53 min; MS (ESIpos): m/z=424 $[M+H]^+$ $^1$H-NMR (400 MHz, DMSO-$d_6$): δ [ppm]=1.23 (d, 3H), 3.31 (s, 3H, under water), 3.38-3.42 (m, 1H), 3.43-3.48 (m, 1H), 4.19-4.31 (m, 1H), 5.34 (s, 2H), 6.38 (s, 2H), 7.15-7.23 (m, 2H), 7.33-7.39 (m, 2H), 8.04 (s, 1H), 8.24 (d, 1H), 8.45 (s, 1H), 9.06 (d, 1H), 9.38 (d, 1H).

Example I-136

2-Amino-6-[1-(4-fluorobenzyl)-1H-pyrazol-4-yl]-N-(5-oxopyrrolidin-3-yl)[1,2,4]triazolo[1,5-a]pyridine-8-carboxamide (mixture of enantiomers)

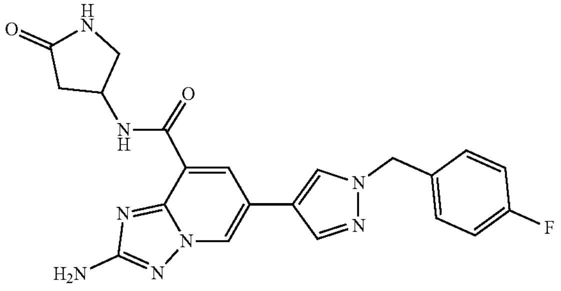 [SMILES: Nc1nc2c(C(=O)NC3CNC(=O)C3)cc(-c3cnn(Cc4ccc(F)cc4)c3)cn2n1]

2-Amino-6-bromo-N-(5-oxopyrrolidin-3-yl)[1,2,4]triazolo[1,5-a]pyridine-8-carboxamide (100 mg, 295 μmol) was reacted with 1-[(4-fluorophenyl)methyl]-4-(4,4,5,5-tetramethyl-1,3,2-dioxaborolan-2-yl)-1H-pyrazole (109 mg, 90% purity, 324 μmol) for 1 h at 90° C. following general procedure B using 0.05 eq. catalyst. The reaction mixture was diluted with ethyl acetate and filtered through a hydrophobic phase separation filter which was rinsed with ethyl acetate. The combined filtrates were concentrated in vacuo and the residue was purified by preparative HPLC (Chromatorex C18, 10 μm, 125×30 mm; eluent: water/acetonitrile gradient 95:5 to 50:50) to yield 45.3 mg (100% purity, 35% yield) of the title compound.

LC-MS (method 2): $R^t$=0.65 min; MS (ESIpos): m/z=435 $[M+H]^+$

LC-MS (method 1): $R^t$=1.15 min; MS (ESIpos): m/z=435 $[M+H]^+$ $^1$H-NMR (500 MHz, DMSO-$d_6$) δ [ppm]: 2.20 (dd, 1H), 2.68 (dd, 1H), 3.21 (dd, 1H), 3.69 (dd, 1H), 4.63-4.71 (m, 1H), 5.34 (s, 2H), 6.42 (s, 2H), 7.16-7.22 (m, 2H), 7.33-7.39 (m, 2H), 7.75 (s, 1H), 8.04 (s, 1H), 8.23 (d, 1H), 8.45 (s, 1H), 9.08 (d, 1H), 9.62 (d, 1H).

Example I-137

2-Amino-6-[1-(cyclopropylmethyl)-1H-pyrazol-4-yl]-N-[1-fluoropropan-2-yl][1,2,4]triazolo[1,5-a]pyridine-8-carboxamide (mixture of enantiomers)

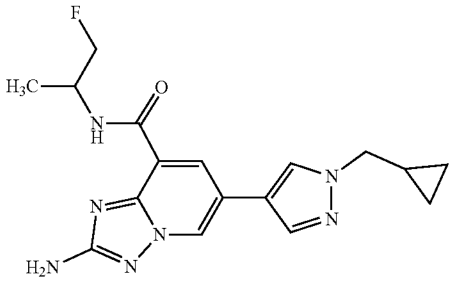 [SMILES: CC(CF)NC(=O)c1cc(-c2cnn(CC3CC3)c2)cn2nc(N)nc12]

2-amino-6-bromo-N-[1-fluoropropan-2-yl][1,2,4]triazolo[1,5-a]pyridine-8-carboxamide (159 mg, 503 μmol), 1-(cyclopropylmethyl)-4-(4,4,5,5-tetramethyl-1,3,2-dioxaborolan-2-yl)-1H-pyrazole (150 mg, 604 μmol), 1,1'-bis(diphenylphosphino)ferrocene-palladium(II)dichloride dichloromethane complex (20.5 mg, 25.1 μmol) and water (1.5 ml) were reacted according to procedure A in a mixture of sodium carbonate (267 mg, 2.51 mmol) and 1,4-dioxane (4.5 ml). After 3 h at 90° C., the reaction was quenched with water and extracted with dichloromethane. The organic layer was dried over sodium sulfate, filtered and concentrated under reduced pressure. The residue was purified by column chromatography (Biotage® SNAP KP-NH 11 g cartridge, eluent: cyclohexane/ethyl acetate gradient 8:2 to 0:10) to yield 123 mg (99% purity, 68% yield) of the title compound as a racemic mixture.

LC-MS (method 1): $R^t$=1.34 min; MS (ESIpos): m/z=358 $[M+H]^+$ $^1$H-NMR (400 MHz, DMSO-$d_6$) δ [ppm]: 0.38-0.43 (m, 2H), 0.53-0.58 (m, 2H), 1.24-1.32 (m, 2H), 1.30 (d, 1H), 3.99 (d, 2H), 4.31-4.50 (m, 2H), 4.55-4.62 (m, 1H), 6.41 (s, 2H), 8.00 (s, 1H), 8.27 (d, 1H), 8.39 (s, 1H), 9.08 (d, 1H), 9.48 (d, 1H).

Example I-138

2-Amino-N-(1-fluoropropan-2-yl)-6-{1-[(1H-indazol-7-yl)methyl]-1H-pyrazol-4-yl}[1,2,4]triazolo[1,5-a]pyridine-8-carboxamide (mixture of enantiomers)

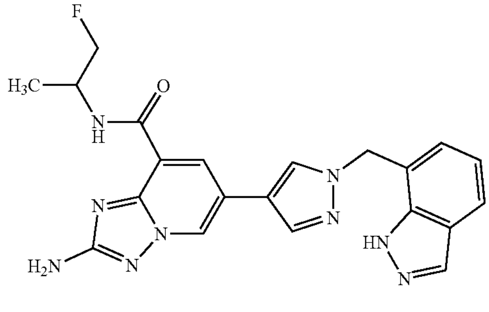 [SMILES: CC(CF)NC(=O)c1cc(-c2cnn(Cc3cccc4cn[nH]c34)c2)cn2nc(N)nc12]

2-Amino-6-bromo-N-[1-fluoropropan-2-yl][1,2,4]triazolo[1,5-a]pyridine-8-carboxamide (250 mg, 791 μmol), 7-{[4-(4,4,5,5-tetramethyl-1,3,2-dioxaborolan-2-yl)-1H-pyrazol-1-yl]methyl}-1H-indazole (256 mg, 791 μmol), sodium carbonate (419 mg, 3.95 mmol) and 1,1'-bis(diphenylphosphino)ferrocene-palladium(II)dichloride dichloromethane complex (32.3 mg, 39.5 μmol) were reacted according to procedure A in a mixture of 1,4-dioxane (7.5 ml) and water (2.5 ml). The residue was purified by column chromatography (Biotage® SNAP KP-NH 11 g cartridge, eluent: cyclohexane/ethyl acetate gradient 1:1 to 0:1) to yield 34.0 mg (94% purity, 9% yield) of the title compound as racemic mixture.

LC-MS (method 1): $R^t$=1.37 min; MS (ESIpos): m/z=434 $[M+H]^+$ $^1$H-NMR (400 MHz, DMSO-$d_6$) δ [ppm]: 1.29 (d, 3H), 4.29-4.42 (m, 1H), 4.42-4.49 (m, 1H), 4.54-4.61 (m, 1H), 5.68 (s, 2H), 6.41 (br s, 2H), 7.04-7.16 (m, 2H), 7.73 (d, 1H), 8.06 (s, 1H), 8.26 (d, 1H), 8.56 (s, 1H), 9.08 (d, 1H), 9.47 (d, 1H), 13.29 (br s, 1H).

Example I-139

2-Amino-N-(1-fluoropropan-2-yl)-6-{1-[2-methyl-1-phenylpropyl]-1H-pyrazol-4-yl}[1,2,4]triazolo[1,5-a]pyridine-8-carboxamide (mixture of diastereomers 1)

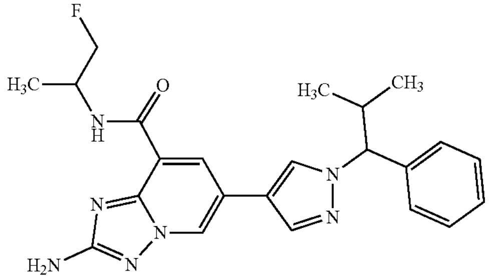 [SMILES: CC(CF)NC(=O)c1cc(-c2cnn(C(c3ccccc3)C(C)C)c2)cn2nc(N)nc12]

2-Amino-6-bromo-N-[1-fluoropropan-2-yl][1,2,4]triazolo[1,5-a]pyridine-8-carboxamide stereoisomer 1 (150 mg, 474 μmol), 1-[2-methyl-1-phenylpropyl]-4-(4,4,5,5-tetramethyl-1,3,2-dioxaborolan-2-yl)-1H-pyrazole (186 mg, 569 μmol), sodium carbonate (251 mg, 2.37 mmol) and 1,1'-bis(diphenylphosphino)ferrocene-palladium(II)dichloride dichloromethane complex (19.4 mg, 23.7 μmol) were reacted according to procedure A in a mixture of 1,4-dioxane (4.5 ml) and water (1.5 ml). The residue was purified by column chromatography (Biotage® SNAP KP-NH 11 g cartridge, eluent: cyclohexane/ethyl acetate gradient 8:2 to 0:10) to yield 155 mg (100% purity, 75% yield) of the title compound as a mixture of diastereomers.

LC-MS (method 1): $R^t$=1.86 min; MS (ESIpos): m/z=436 $[M+H]^+$ $^1$H-NMR (400 MHz, DMSO-$d_6$) δ [ppm]: 0.78 (d, 3H), 0.83 (d, 3H), 1.29 (d, 3H), 2.71-2.81 (m, 1H), 4.30-4.49 (m, 2H), 4.54-4.61 (m, 1H), 4.94 (d, 1H), 6.40 (s, 2H), 7.27-7.32 (m, 1H), 7.32-7.38 (m, 2H), 7.55 (d, 2H), 8.03 (s, 1H), 8.26 (d, 1H), 8.56 (s, 1H), 9.06 (d, 1H), 9.47 (d, 1H).

Example I-140

2-Amino-N-(1-fluoropropan-2-yl)-6-[1-(2-methyl-1-phenylpropyl)-1H-pyrazol-4-yl][1,2,4]triazolo[1,5-a]pyridine-8-carboxamide (stereoisomer 1-1, eutomer) 2-Amino-N-(1-fluoropropan-2-yl)-6-{1-[2-methyl-1-phenylpropyl]-1H-pyrazol-4-yl}[1,2,4]triazolo[1,5-a]pyridine-8-carboxamide (mixture of diastereomers) (155 mg, 100% purity) from the previous example was separated by chiral SFC chromatography to yield stereoisomer 1 (44.7 mg, 100% purity) and stereoisomer 2 (44.3 mg, 100% purity).

Instrument: THAR SFC-Super Chrom Prep 200; Column: Daicel OJ-H, 5 μm, 250×25 mm; Eluent A: $CO_2$; Eluent B: methanol; isocratic: 82% A+18% B; flow: 80 ml/min; UV: 210 nm; temperature: 40° C.

Stereoisomer 1: $R^t$=5.00 min and

Stereoisomer 2: $R^t$=12.20 min (cf. next example)

Analytical SFC-method: Column: Chiralcel OJ, 3 μm, 4.6×100 mm; Eluent A: $CO_2$; Eluent B: methanol; isocratic: 80% A+20% B; flow: 3 ml/min; UV: 210 nm; temperature: 40° C.

Stereoisomer 1: $R^t$=2.52 min and

Stereoisomer 2: $R^t$=4.24 min (cf. next example)

LC-MS (method 1): $R^t$=1.86 min; MS (ESIpos): m/z=436 $[M+H]^+$ $^1$H-NMR (400 MHz, DMSO-$d_6$) δ [ppm]: 0.78 (d, 3H), 0.83 (d, 3H), 1.29 (d, 3H), 2.74-2.80 (m, 1H), 4.30-4.43 (m, 1H), 4.43-4.49 (m, 1H), 4.54-4.61 (m, 1H), 4.94 (d, 1H), 6.40 (s, 2H), 7.27-7.32 (m, 1H), 7.32-7.38 (m, 2H), 7.55 (d, 2H), 8.03 (s, 1H), 8.26 (d, 1H), 8.56 (s, 1H), 9.06 (d, 1H), 9.47 (d, 1H).

Example I-141

2-Amino-N-(1-fluoropropan-2-yl)-6-[1-(2-methyl-1-phenylpropyl)-1H-pyrazol-4-yl][1,2,4]triazolo[1,5-a]pyridine-8-carboxamide (stereoisomer 1-2, distomer)

The product was isolated in the previous example as second stereoisomer.

LC-MS (method 1): $R^t$=1.86 min; MS (ESIpos): m/z=436 $[M+H]^+$ $^1$H-NMR (400 MHz, DMSO-$d_6$) δ [ppm]: 0.78 (d, 3H), 0.83 (d, 3H), 1.29 (d, 3H), 2.71-2.82 (m, 1H), 4.29-4.42 (m, 1H), 4.43-4.49 (m, 1H), 4.54-4.61 (m, 1H), 4.94 (d, 1H), 6.40 (s, 2H), 7.27-7.32 (m, 1H), 7.32-7.38 (m, 2H), 7.55 (d, 2H), 8.03 (s, 1H), 8.26 (d, 1H), 8.56 (s, 1H), 9.06 (d, 1H), 9.47 (d, 1H).

Example I-142

2-Amino-N-[1-fluoropropan-2-yl]-6-{1-[2-methyl-1-phenylpropyl]-1H-pyrazol-4-yl}[1,2,4]triazolo[1,5-a]pyridine-8-carboxamide (mixture of diastereomers 2)

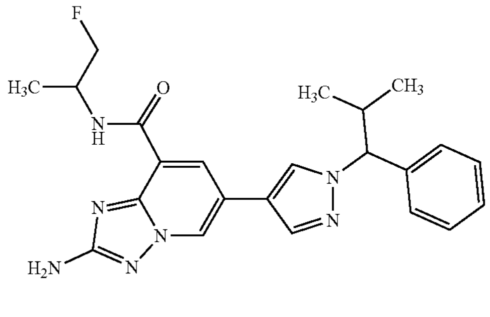 [SMILES: CC(CF)NC(=O)c1cc(-c2cnn(C(c3ccccc3)C(C)C)c2)cn2nc(N)nc12]

2-Amino-6-bromo-N-[1-fluoropropan-2-yl][1,2,4]triazolo[1,5-a]pyridine-8-carboxamide stereoisomer 2 (150 mg, 474 μmol), 1-[2-methyl-1-phenylpropyl]-4-(4,4,5,5-tetramethyl-1,3,2-dioxaborolan-2-yl)-1H-pyrazole (186 mg, 569 μmol), sodium carbonate (251 mg, 2.37 mmol) and 1,1'-bis(diphenylphosphino)ferrocene-palladium(II)dichloride dichloromethane complex (19.4 mg, 23.7 μmol) were reacted according to procedure A in a mixture of 1,4-dioxane (4.5 ml) and water (1.5 ml). The residue was purified by column chromatography (Biotage® SNAP KP-NH 11 g cartridge, eluent: cyclohexane/ethyl acetate gradient 8:2 to 0:10) to yield 158 mg (100% purity, 76% yield) of the title compound as a mixture of diastereomers.

LC-MS (method 1): $R^t$=1.88 min; MS (ESIpos): m/z=436 $[M+H]^+$ $^1$H-NMR (400 MHz, DMSO-$d_6$) δ [ppm]: 0.78 (d, 3H), 0.83 (d, 3H), 1.29 (d, 3H), 2.71-2.81 (m, 1H), 4.30-4.42 (m, 1H), 4.42-4.49 (m, 1H), 4.54-4.61 (m, 1H), 4.94 (d, 1H), 6.40 (s, 2H), 7.27-7.32 (m, 1H), 7.32-7.38 (m, 2H), 7.55 (d, 2H), 8.03 (s, 1H), 8.26 (d, 1H), 8.56 (s, 1H), 9.06 (d, 1H), 9.47 (d, 1H).

Example I-143

2-Amino-6-{1-[3,4-dihydro-2H-1-benzopyran-4-yl]-1H-pyrazol-4-yl}-N-[1-fluoropropan-2-yl][1,2,4]triazolo[1,5-a]pyridine-8-carboxamide (mixture of diastereomers)

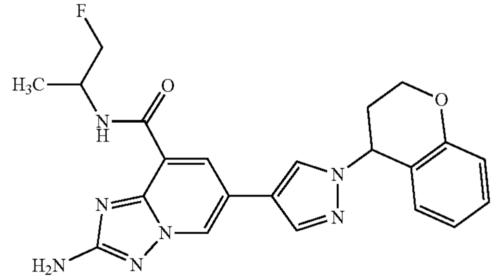 [SMILES: CC(CF)NC(=O)c1cc(-c2cnn(C3CCOc4ccccc43)c2)cn2nc(N)nc12]

2-Amino-6-bromo-N-[(2S)-1-fluoropropan-2-yl][1,2,4]triazolo[1,5-a]pyridine-8-carboxamide stereoisomer 1 (100 mg, 316 μmol), 1-[3,4-dihydro-2H-1-benzopyran-4-yl]-4-(4,4,5,5-tetramethyl-1,3,2-dioxaborolan-2-yl)-1H-pyrazole mixture of enantiomers (112 mg, 345 μmol), sodium carbonate (168 mg, 1.58 mmol) and 1,1'-bis(diphenylphosphino)ferrocene-palladium(II)dichloride dichloromethane complex (12.9 mg, 15.8 μmol) were reacted according to procedure A in a mixture of 1,4-dioxane (3.0 ml) and water (1.0 ml). The reaction was quenched with water and the mixture was filtered through a hydrophobic phase separation filter which was rinsed with ethyl acetate (15 ml). The filtrate was concentrated under reduced pressure. The residue was purified by silica-gel chromatography (Biotage® SNAP KP-NH 11 g cartridge, eluent: cyclohexane/ethyl acetate gradient 4:1 to 1:4) to yield 61.9 mg (100% purity, 45% yield) of the title compound as mixture of diasteromers.

LC-MS (method 1): $R^t$=1.58 min; MS (ESIpos): m/z=436 $[M+H]^+$ $^1$H-NMR (400 MHz, DMSO-$d_6$) δ [ppm]: 1.29 (d, 3H), 2.34-2.48 (m, 2H), 4.28-4.41 (m, 3H), 4.42-4.48 (m, 1H), 4.54-4.61 (m, 1H), 5.68 (t, 1H), 6.41 (s, 2H), 6.83-6.94 (m, 3H), 7.21 (t, 1H), 8.09 (s, 1H), 8.28 (d, 1H), 8.40 (s, 1H), 9.11 (d, 1H), 9.47 (d, 1H).

Example I-144

2-Amino-6-{1-(3,4-dihydro-2H-1-benzopyran-4-yl)-1H-pyrazol-4-yl}-N-[1-fluoropropan-2-yl][1,2,4]triazolo[1,5-a]pyridine-8-carboxamide (mixture of diastereomers)

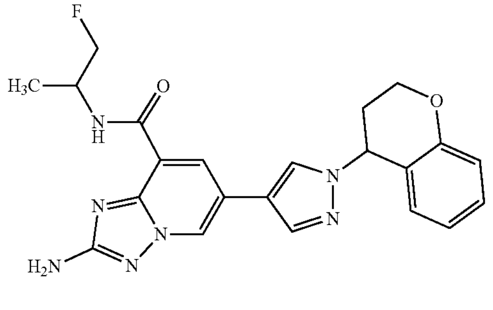 [SMILES: CC(CF)NC(=O)c1cc(-c2cnn(C3CCOc4ccccc43)c2)cn2nc(N)nc12]

2-Amino-6-bromo-N-[1-fluoropropan-2-yl][1,2,4]triazolo[1,5-a]pyridine-8-carboxamide stereoisomer 2 (100 mg, 316 μmol), 1-[3,4-dihydro-2H-1-benzopyran-4-yl]-4-(4,4,5,5-tetramethyl-1,3,2-dioxaborolan-2-yl)-1H-pyrazole (112 mg, 345 μmol), sodium carbonate (168 mg, 1.58 mmol) and 1,1'-bis(diphenylphosphino)ferrocene-palladium(II)dichloride dichloromethane complex (12.9 mg, 15.8 μmol) were reacted according to procedure A in a mixture of 1,4-dioxane (3.0 ml) and water (1.0 ml). The residue was purified by silica gel chromatography (Biotage® SNAP KP-NH 11 g cartridge, eluent: cyclohexane/ethyl acetate gradient:2, 0:10) to yield 69.1 mg (100% purity, 50% yield) of the title compound as a mixture of diastereoisomers.

LC-MS (method 1): $R^t$=1.58 min; MS (ESIpos): m/z=436 $[M+H]^+$ $^1$H-NMR (400 MHz, DMSO-$d_6$) δ [ppm]: 1.29 (d, 3H), 2.33-2.48 (m, 2H), 4.29-4.42 (m, 3H), 4.42-4.49 (m, 1H), 4.52-4.60 (m, 1H), 5.68 (t, 1H), 6.41 (s, 2H), 6.83-6.90 (m, 2H), 6.90-6.94 (m, 1H), 7.21 (t, 1H), 8.09 (s, 1H), 8.28 (d, 1H), 8.40 (s, 1H), 9.11 (d, 1H), 9.47 (d, 1H).

Example I-145

2-Amino-6-[1-(3,4-dihydro-2H-chromen-4-yl)-1H-pyrazol-4-yl]-N-(1-fluoropropan-2-yl)[1,2,4]triazolo[1,5-a]pyridine-8-carboxamide (stereoisomer 1, eutomer)

2-Amino-6-{1-[3,4-dihydro-2H-1-benzopyran-4-yl]-1H-pyrazol-4-yl}-N-[1-fluoropropan-2-yl][1,2,4]triazolo[1,5-a]pyridine-8-carboxamide (69.1 mg, 100% purity) as a mixture of diastereoisomers from the previous example was separated by chiral SFC chromatography to yield stereoisomer 1 (20.0 mg, 100% purity) and stereoisomer 2 (18.8 mg, 100% purity).

Instrument: THAR SFC-Super Chrom Prep 200; Column: Daicel OJ-H, 5 μm, 250×25 mm; Eluent A: $CO_2$; Eluent B: methanol; isocratic: 80% A+20% B; flow: 80 ml/min; UV: 210 nm; temperature: 40° C.

Analytical SFC-method: Column: Chiralcel OJ, 3 m, 4.6×100 mm; Eluent A: $CO_2$; Eluent B: methanol; isocratic: 80% A+20% B; flow: 3 ml/min; UV: 210 nm; temperature: 40° C.

Stereoisomer 1: $R^t$=1.88 min and

Stereoisomer 2: $R^t$=2.18 min (cf. next example)

LC-MS (method 2): $R^t$=0.89 min; MS (ESIpos): m/z=436 $[M+H]^+$ $^1$H-NMR (400 MHz, DMSO-$d_6$) δ [ppm]: 1.29 (d, 3H), 2.32-2.48 (m, 2H), 4.28-4.41 (m, 3H), 4.41-4.49 (m, 1H), 4.54-4.61 (m, 1H), 5.68 (t, 1H), 6.40 (s, 2H), 6.83-6.94 (m, 3H), 7.21 (t, 1H), 8.08 (s, 1H), 8.27 (d, 1H), 8.40 (s, 1H), 9.11 (d, 1H), 9.47 (d, 1H).

Example I-146

2-Amino-6-[1-(3,4-dihydro-2H-chromen-4-yl)-1H-pyrazol-4-yl]-N-(1-fluoropropan-2-yl)[1,2,4]triazolo[1,5-a]pyridine-8-carboxamide (stereoisomer 2, distomer) The product was isolated in the previous example as second stereoisomer.

LC-MS (method 2): $R^t$=0.88 min; MS (ESIpos): m/z=436 $[M+H]^+$ $^1$H-NMR (400 MHz, DMSO-$d_6$) δ [ppm]: 1.29 (d, 3H), 2.33-2.48 (m, 2H), 4.28-4.42 (m, 3H), 4.42-4.49 (m, 1H), 4.54-4.61 (m, 1H), 5.68 (t, 1H), 6.40 (s, 2H), 6.83-6.94 (m, 3H), 7.21 (t, 1H), 8.09 (s, 1H), 8.27 (d, 1H), 8.40 (s, 1H), 9.11 (d, 1H), 9.47 (d, 1H).

Example I-147

2-Amino-N-[1-fluoropropan-2-yl]-6-(1-{(1-[6-(trifluoromethyl)pyridin-3-yl]propyl}-1H-pyrazol-4-yl)[1,2,4]triazolo[1,5-a]pyridine-8-carboxamide (mixture of stereoisomers)

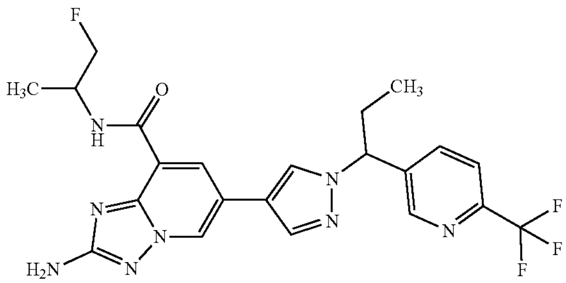 [SMILES: CCC(c1ccc(C(F)(F)F)nc1)n1cc(-c2cc(C(=O)NC(C)CF)c3nc(N)nn3c2)cn1]

2-Amino-6-bromo-N-(1-fluoropropan-2-yl)[1,2,4]triazolo[1,5-a]pyridine-8-carboxamide (153 mg, 484 μmol), 5-{1-[4-(4,4,5,5-tetramethyl-1,3,2-dioxaborolan-2-yl)-1H-pyrazol-1-yl]propyl}-2-(trifluoromethyl)pyridine (303 mg, 73% purity, 580 μmol), 1,1'-bis(diphenylphosphino)ferrocene-palladium(II)dichloride dichloromethane complex (19.7 mg, 24.2 μmol) and water (1.5 ml) were reacted according to procedure A in a mixture of sodium carbonate (256 mg, 2.42 mmol) and 1,4-dioxane (4.5 ml). After 3 h at 90° C., the reaction was quenched with water and the mixture was filtered through a hydrophobic phase separation filter which was rinsed with ethyl acetate (15 ml). The filtrate was concentrated under reduced pressure. The residue was purified by column chromatography (Biotage® SNAP KP-NH 11 g cartridge, eluent: cyclohexane/ethyl acetate gradient 8:2 to 0:10) to yield 92.0 mg (99% purity, 38% yield) of the title compound.

LC-MS (method 1): $R^t$=1.71 min; MS (ESIpos): m/z=491 $[M+H]^+$ $^1$H-NMR (400 MHz, DMSO-$d_6$) δ [ppm]: 0.88 (t, 3H), 1.29 (d, 3H), 2.22 (m, 1H), 2.32-2.47 (m, 1H), 4.30-4.41 (m, 1H), 4.41-4.51 (m, 1H), 4.52-4.63 (m, 1H), 5.58 (dd, 1H), 6.42 (s, 2H), 7.92 (d, 1H), 8.06 (dd, 1H), 8.12 (s, 1H), 8.29 (d, 1H), 8.63 (s, 1H), 8.82 (d, 1H), 9.10 (d, 1H), 9.47 (d, 1H).

Example I-148

2-Amino-7-{1-[(1S)-1-(4-fluorophenyl)propyl]-1H-pyrazol-4-yl}-N-(1-fluoropropan-2-yl)[1,2,4]triazolo[1,5-a]pyridine-5-carboxamide (mixture of diastereomers)

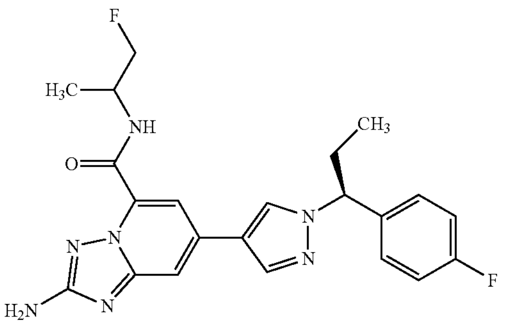 [SMILES: CC[C@@H](c1ccc(F)cc1)n1cc(-c2cc(C(=O)NC(C)CF)n3nc(N)nc3c2)cn1]

2-Amino-7-bromo-N-(1-fluoropropan-2-yl)[1,2,4]triazolo[1,5-a]pyridine-5-carboxamide (200 mg, 633 μmol) was reacted with 1-[(1S)-1-(4-fluorophenyl)propyl]-4-(4,4,5,5-tetramethyl-1,3,2-dioxaborolan-2-yl)-1H-pyrazole (230 mg, 696 μmol) for 1.5 h at 90° C. following general procedure B using 0.1 eq. catalyst. Additional 0.1 eq. catalyst was added and heating continued for 4 h, then further 1-[(1S)-1-(4-fluorophenyl)propyl]-4-(4,4,5,5-tetramethyl-1,3,2-dioxaborolan-2-yl)-1H-pyrazole (42.0 mg, 127 μmol) and 0.1 eq. catalyst was added and heating was continued for 1 h. The reaction mixture was combined with a second one (50 mg starting material), diluted with ethyl acetate (30 ml) and washed with water (20 ml). The aqueous layer was separated and extracted with ethyl acetate (20 ml). The combined organic layers were washed with brine and filtered through a hydrophobic phase separation filter. The solvent was removed in vacuo and the residue purified by column chromatography (Biotage® SNAP KP-NH 28 g cartridge, eluent: cyclohexane/ethyl acetate gradient 80:20 to 0:100). The product was further purified by preparative HPLC (Chromatorex C18, 10 μm, 125×30 mm; eluent: water/acetonitrile gradient 90:10 to 5:95) to yield 185 mg (100% purity, 53% yield) of the title compound.

LC-MS (method 1): $R^t$=1.75 min; MS (ESIpos): m/z=440 $[M+H]^+$ $^1$H-NMR (400 MHz, DMSO-$d_6$) δ [ppm]: 0.818 (7.08), 0.836 (16.00), 0.854 (7.45), 1.303 (14.42), 1.320 (14.54), 2.074 (0.57), 2.115 (0.99), 2.131 (1.73), 2.149 (2.47), 2.167 (2.10), 2.184 (1.22), 2.329 (0.62), 2.349 (1.20), 2.367 (2.04), 2.383 (1.49), 2.389 (1.62), 2.406 (1.37), 2.424 (0.92), 2.711 (0.47), 4.310 (0.73), 4.328 (1.04), 4.338 (0.83), 4.345 (0.80), 4.357 (0.82), 4.368 (0.82), 4.376 (0.77), 4.386 (1.08), 4.397 (0.76), 4.404 (0.76), 4.442 (0.66), 4.454 (0.57), 4.466 (2.88), 4.476 (4.64), 4.486 (2.53), 4.499 (0.70), 4.509 (0.45), 4.560 (0.65), 4.572 (0.63), 4.583 (2.64), 4.595 (4.73), 4.605 (2.55), 4.618 (0.67), 4.628 (0.50), 5.339 (2.28), 5.355 (2.76), 5.362 (2.80), 5.378 (2.25), 6.355 (11.89), 7.156 (4.73), 7.178 (10.05), 7.201 (5.59), 7.432 (5.49), 7.445 (6.25), 7.453 (5.62), 7.467 (4.80), 7.803 (15.00), 7.806 (14.54), 7.811 (4.70), 8.166 (11.76), 8.711 (11.30), 10.285 (3.92), 10.304 (3.86).

Example I-149

2-Amino-7-{1-[(IS)-1-(4-fluorophenyl)propyl]-1H-pyrazol-4-yl}-N-(1-fluoropropan-2-yl)[1,2,4]triazolo[1,5-a]pyridine-5-carboxamide (stereoisomer 1, eutomer)

2-Amino-7-{1-[(1S)-1-(4-fluorophenyl)propyl]-1H-pyrazol-4-yl}-N-(1-fluoropropan-2-yl)[1,2,4]triazolo[1,5-a]pyridine-5-carboxamide (mixture of diastereomers) (146 mg, 100% purity) from the previous example was separated by chiral chromatography to yield stereoisomer 1 (68 mg, 99% purity) and stereoisomer 2 (64 mg, 99 purity).

Column: Daicel Chiralpak IG, 5 μm, 250×20 mm; Eluent A: n-heptane; Eluent B: ethanol+0.2% diethylamine; isocratic: 50% A+50% B; flow: 15 ml/min; UV: 220 nm; temperature: 50° C.

Stereoisomer 1: $R^t$=14.55 min and

Stereoisomer 2: $R^t$=15.55 min (cf. next example)

Analytical chiral HPLC. Column: Daicel Chiralpak ID, 5 μm, 250×4.6 mm; Eluent A: iso-hexane; Eluent B: 2-propanol; isocratic: 50% A+50% B; flow: 1 ml/min; UV: 220 nm; temperature: 60° C.

Stereoisomer 1: $R^t$=9.998 min and

Stereoisomer 2: $R^t$=10.643 min (cf. next example)

LC-MS (method 1): $R^t$=1.78 min; MS (ESIpos): m/z=440 $[M+H]^+$ $^1$H-NMR (500 MHz, DMSO-$d_6$) δ [ppm]: 0.84 (t, 3H), 1.31 (d, 3H), 2.10-2.20 (m, 1H), 2.33-2.44 (m, 1H), 4.29-4.42 (m, 1H), 4.46-4.52 (m, 1H), 4.55-4.62 (m, 1H), 5.36 (dd, 1H), 6.35 (s, 2H), 7.15-7.20 (m, 2H), 7.43-7.47 (m, 2H), 7.80-7.82 (m, 2H), 8.17 (s, 1H), 8.71 (s, 1H), 10.29 (d, 1H).

Example I-150

2-Amino-7-{1-[(1S)-1-(4-fluorophenyl)propyl]-1H-pyrazol-4-yl}-N-(1-fluoropropan-2-yl)[1,2,4]triazolo[1,5-a]pyridine-5-carboxamide (stereoisomer 2, distomer)

The product was isolated in the previous example as second stereoisomer.

LC-MS (method 1): $R^t$=1.78 min; MS (ESIpos): m/z=440 $[M+H]^+$ $^1$H-NMR (500 MHz, DMSO-$d_6$) δ [ppm]: 0.824 (7.46), 0.839 (16.00), 0.853 (7.39), 1.153 (0.55), 1.232 (0.41), 1.308 (13.99), 1.322 (13.87), 2.124 (1.05), 2.137 (1.78), 2.151 (2.42), 2.165 (2.00), 2.179 (1.16), 2.359 (1.23), 2.373 (1.60), 2.377 (1.36), 2.419 (0.92), 4.324 (0.75), 4.332 (0.71), 4.338 (1.04), 4.347 (0.82), 4.353 (0.80), 4.362 (0.79), 4.371 (0.80), 4.376 (0.74), 4.385 (1.02), 4.393 (0.71), 4.399 (0.70), 4.462 (0.79), 4.471 (0.71), 4.481 (2.63), 4.491 (3.40), 4.501 (2.28), 4.511 (0.73), 4.519 (0.54), 4.557 (0.76), 4.566 (0.75), 4.575 (2.39), 4.585 (2.79), 4.587 (2.75), 4.596 (2.32), 4.606 (0.71), 4.615 (0.55), 5.345 (2.29), 5.358 (2.69), 5.364 (2.68), 5.376 (2.18), 6.354 (11.57), 7.161 (5.06), 7.179 (10.33), 7.197 (5.49), 7.437 (5.40), 7.441 (2.54), 7.448 (6.06), 7.454 (5.40), 7.465 (4.69), 7.802 (5.90), 7.806 (11.20), 7.812 (11.49), 7.816 (5.44), 8.167 (11.84), 8.709 (11.05), 10.290 (3.72), 10.306 (3.62).

Example I-151

2-Amino-N-[(2S)-1-hydroxypropan-2-yl]-6-(1-{1-[6-(trifluoromethyl)pyridin-3-yl]propyl}-1H-pyrazol-4-yl)[1,2,4]triazolo[1,5-a]pyridine-8-carboxamide (mixture of diastereomers)

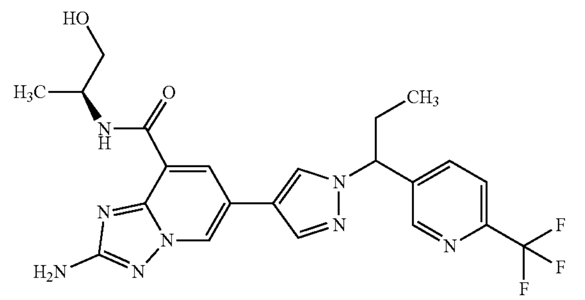 [SMILES: CCC(c1ccc(C(F)(F)F)nc1)n1cc(-c2cc(C(=O)N[C@@H](C)CO)c3nc(N)nn3c2)cn1]

2-Amino-6-bromo-N-[(2S)-1-hydroxypropan-2-yl][1,2,4]triazolo[1,5-a]pyridine-8-carboxamide (150 mg, 477 μmol), 5-{1-[4-(4,4,5,5-tetramethyl-1,3,2-dioxaborolan-2-yl)-1H-pyrazol-1-yl]propyl}-2-(trifluoromethyl)pyridine (237 mg, 621 μmol), sodium carbonate (253 mg, 2.39 mmol) and XPhos-Pd-G2 (37.6 mg, 47.7 μmol) were added to a mixture of dioxane (2.8 ml) and water (400 μl). The mixture was degassed with argon and heated for 2 h to 80° C. It was cooled to rt, diluted with ethyl acetate and filtered through a hydrophobic phase separation filter. The filtrate was concentrated in vacuo and the residue was purified by column chromatography (Biotage® SNAP KP-NH 28 g cartridge, eluent: cyclohexane/ethyl acetate gradient 9:1 to 0:1) to yield 170 mg (100% purity, 73% yield) of the title compound.

LC-MS (method 2): $R^t$=0.80 min; MS (ESIpos): m/z=489 $[M+H]^+$ $^1$H-NMR (600 MHz, DMSO-$d_6$) δ [ppm]: 0.869 (6.69), 0.881 (14.97), 0.893 (6.97), 1.073 (1.58), 1.217 (15.97), 1.228 (16.00), 2.205 (0.87), 2.216 (1.41), 2.228 (2.10), 2.240 (1.58), 2.251 (1.03), 2.425 (1.39), 2.437 (1.28), 2.441 (1.14), 2.448 (1.25), 2.453 (1.36), 2.460 (1.01), 2.464 (1.22), 2.476 (0.68), 2.517 (0.73), 2.520 (0.71), 2.654 (0.41), 3.271 (0.68), 3.334 (1.20), 3.338 (0.60), 3.436 (0.98), 3.445 (1.96), 3.454 (2.78), 3.463 (3.18), 3.473 (1.63), 3.497 (1.52), 3.506 (3.02), 3.514 (2.50), 3.523 (1.77), 3.531 (0.98), 4.089 (0.65), 4.098 (1.28), 4.110 (1.66), 4.121 (1.28), 4.130 (0.65), 4.867 (2.78), 4.876 (5.69), 4.885 (2.78), 5.571 (1.99), 5.581 (2.18), 5.587 (2.20), 5.597 (1.93), 6.358 (10.59), 7.906 (4.65), 7.920 (5.52), 8.057 (2.80), 8.060 (2.83), 8.070 (2.31), 8.074 (2.37), 8.113 (10.50), 8.281 (7.81), 8.284 (8.00), 8.611 (9.96), 8.819 (4.93), 8.822 (4.93), 9.071 (7.76), 9.074 (7.78), 9.309 (3.46), 9.322 (3.37).

Example I-152

2-Amino-N-[(2S)-1-hydroxypropan-2-yl]-6-(1-{1-[6-(trifluoromethyl)pyridin-3-yl]propyl}-1H-pyrazol-4-yl)[1,2,4]triazolo[1,5-a]pyridine-8-carboxamide (stereoisomer 1, eutomer)

2-Amino-N-[(2S)-1-hydroxypropan-2-yl]-6-(1-{1-[6-(trifluoromethyl)pyridin-3-yl]propyl}-1H-pyrazol-4-yl)[1,2,4]triazolo[1,5-a]pyridine-8-carboxamide (mixture of diastereomers) (160 mg, 100% purity) from the previous example was separated by chiral chromatography to yield stereoisomer 1 (39 mg, 100% purity) and stereoisomer 2 (39 mg, 100% purity).

Column: Daicel Chiralpak IC-H, 5 μm, 250×20 mm; Eluent A: n-heptane; Eluent B: ethanol+0.2% diethylamine; isocratic: 50% A+50% B; flow: 20 ml/min; UV: 210 nm; temperature: 40° C.

Stereoisomer 1: $R^t$=4.865 min and

Stereoisomer 2: $R^t$=7.207 min (cf. next example)

Analytical chiral HPLC. Column: Chiraltek IC-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=2.827 min and

Stereoisomer 2: $R^t$=5.279 min (cf. next example)

Stereoisomer 1: The stereochemical configuration of the methine carbon atom bonded to the pyrazole was (S).

LC-MS (method 2): $R^t$=0.82 min; MS (ESIpos): m/z=489 $[M+H]^+$ $^1$H-NMR (600 MHz, DMSO-$d_6$) δ [ppm]: 0.88 (t, 3H), 1.22 (d, 3H), 2.19-2.27 (m, 1H), 2.41-2.48 (m, 1H), 3.43-3.48 (m, 1H), 3.49-3.54 (m, 1H), 4.08-4.14 (m, 1H), 4.87 (t, 1H), 5.58 (dd, 1H), 6.36 (s, 2H), 7.91 (d, 1H), 8.06 (dd, 1H), 8.11 (s, 1H), 8.28 (d, 1H), 8.61 (s, 1H), 8.82 (d, 1H), 9.07 (d, 1H), 9.31 (d, 1H).

Example I-153

2-Amino-N-[(2S)-1-hydroxypropan-2-yl]-6-(1-{1-[6-(trifluoromethyl)pyridin-3-yl]propyl}-1H-pyrazol-4-yl)[1,2,4]triazolo[1,5-a]pyridine-8-carboxamide (stereoisomer 2, distomer)

The product was isolated in the previous example as second stereoisomer.

LC-MS (method 2): $R^t$=0.82 min; MS (ESIpos): m/z=489 $[M+H]^+$ $^1$H-NMR (600 MHz, DMSO-$d_6$) δ [ppm]: 0.858 (0.53), 0.869 (6.61), 0.882 (14.25), 0.894 (6.67), 1.086 (0.53), 1.098 (1.01), 1.110 (0.59), 1.218 (15.78), 1.229 (16.00), 2.206 (0.85), 2.216 (1.37), 2.229 (2.00), 2.241 (1.55), 2.252 (1.00), 2.426 (1.29), 2.437 (1.31), 2.441 (1.16), 2.449 (1.30), 2.453 (1.39), 2.461 (1.08), 2.465 (1.26), 2.476 (0.92), 2.524 (0.49), 3.269 (0.57), 3.436 (0.88), 3.446 (1.71), 3.455 (2.41), 3.464 (2.81), 3.473 (1.45), 3.498 (1.51), 3.506 (2.89), 3.515 (2.31), 3.523 (1.71), 3.532 (0.89), 4.090 (0.67), 4.099 (1.23), 4.111 (1.67), 4.122 (1.24), 4.131 (0.65), 4.865 (2.28), 4.874 (4.62), 4.883 (2.30), 5.572 (1.93), 5.582 (2.13), 5.588 (2.13), 5.597 (1.84), 6.358 (10.03), 7.907 (4.47), 7.920 (5.36), 8.057 (2.79), 8.060 (2.77), 8.071 (2.33), 8.074 (2.31), 8.114 (10.01), 8.282 (7.40), 8.285 (7.52), 8.612 (9.36), 8.820 (4.84), 8.823 (4.82), 9.072 (7.23), 9.075 (7.25), 9.310 (3.47), 9.323 (3.39).

Example I-154

2-Amino-N-[(2S)-1-hydroxypropan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of diastereomers)

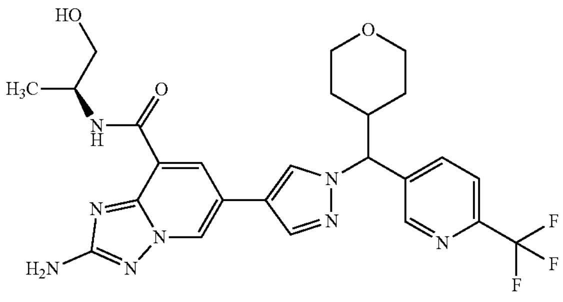 [SMILES: C[C@@H](CO)NC(=O)c1cc(-c2cnn(C(c3ccc(C(F)(F)F)nc3)C3CCOCC3)c2)cn2nc(N)nc12]

2-Amino-6-bromo-N-[(2S)-1-hydroxypropan-2-yl][1,2,4]triazolo[1,5-a]pyridine-8-carboxamide (250 mg, 796 µmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (418 mg, 955 µmol), sodium carbonate (422 mg, 3.98 mmol), and XPhos-Pd-G2 (62.6 mg, 79.6 µmol) were added to a mixture of dioxane (4.5 ml) and water (1.5 ml). It was degassed with argon and the mixture was heated for 2.5 h to 90° C. It was cooled to rt, diluted with ethyl acetate (20 ml) and filtered through a hydrophobic phase separation filter. The filtrate was concentrated in vacuo and the residue was purified by column chromatography (Biotage® SNAP KP-NH 55 g cartridge, eluent: cyclohexane/ethyl acetate/2-propanol gradient 7:3:0 to 0:1:0 to 0:4:1) to yield 341 mg (99% purity, 78% yield) of the title compound.

LC-MS (method 1): $R^t$=1.42 min; MS (ESIpos): m/z=545 $[M+H]^+$ $^1$H-NMR (500 MHz, DMSO-$d_6$) δ [ppm]: −0.007 (1.62), 0.006 (1.37), 1.071 (3.11), 1.101 (1.47), 1.212 (15.21), 1.225 (16.00), 1.260 (0.55), 1.269 (0.58), 1.284 (1.14), 1.293 (1.23), 1.309 (1.46), 1.317 (1.49), 1.333 (1.41), 1.340 (1.40), 1.356 (0.98), 1.363 (0.92), 1.381 (0.41), 2.403 (0.44), 2.521 (0.73), 2.678 (0.47), 2.739 (0.44), 2.761 (1.21), 2.776 (0.82), 2.783 (1.18), 2.806 (0.42), 3.245 (1.14), 3.265 (3.00), 3.269 (3.02), 3.288 (3.16), 3.292 (3.03), 3.427 (0.92), 3.438 (1.75), 3.449 (2.61), 3.460 (3.02), 3.471 (1.56), 3.489 (1.43), 3.499 (2.73), 3.510 (2.25), 3.521 (1.46), 3.531 (0.79), 3.799 (1.40), 3.828 (1.65), 3.837 (1.46), 3.860 (1.25), 4.082 (0.66), 4.093 (1.23), 4.108 (1.59), 4.122 (1.21), 4.132 (0.61), 4.879 (2.71), 4.889 (5.60), 4.900 (2.65), 5.391 (3.82), 5.412 (3.69), 6.377 (9.28), 7.942 (4.73), 7.958 (5.06), 8.125 (10.14), 8.253 (8.53), 8.257 (8.59), 8.305 (2.68), 8.308 (2.64), 8.321 (2.38), 8.325 (2.33), 8.582 (9.09), 8.969 (4.87), 8.972 (4.77), 9.063 (8.43), 9.067 (8.27), 9.304 (3.33), 9.320 (3.22).

Example I-155

2-Amino-N-[(2S)-1-hydroxypropan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 1, eutomer)

2-Amino-N-[(2S)-1-hydroxypropan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of diastereomers) (305 mg, 99% purity) from the previous example was separated by chiral chromatography to yield stereoisomer 1 (141 mg, 100% purity) and stereoisomer 2 (141 mg, 100% purity).

Column: Daicel Chiralcel OD-H, 5 µm, 250×20 mm; Eluent A: n-heptane; Eluent B: ethanol+0.2% diethylamine; isocratic: 30% A+70% B; flow: 20 ml/min; UV: 210-400 nm; temperature: 30° C.

Stereoisomer 1: $R^t$=5.79 min and

Stereoisomer 2: $R^t$=7.89 min (cf. next example)

Analytical chiral HPLC. Column: Chiraltek OZ-3, 3 µm, 50×4.6 mm; Eluent A: n-heptane; Eluent B: ethanol+0.2% diethylamine; isocratic: 20% A+80% B; flow: 1 ml/min; UV: 220 nm.

Stereoisomer 1: $R^t$=2.312 min and

Stereoisomer 2: $R^t$=3.503 min (cf. next example)

LC-MS (method 1): $R^t$=1.43 min; MS (ESIpos): m/z=545 $[M+H]^+$ $^1$H-NMR (400 MHz, DMSO-$d_6$) δ [ppm]: 1.03-1.14 (m, 1H), 1.18-1.41 (m, 6H), 2.71-2.84 (m, 1H), 3.22-3.31 (m, 2H), 3.40-3.56 (m, 2H), 3.83 (br t, 2H), 4.04-4.17 (m, 1H), 4.89 (t, 1H), 5.40 (d, 1H), 6.38 (s, 2H), 7.95 (d, 1H), 8.12 (s, 1H), 8.25 (d, 1H), 8.31 (dd, 1H), 8.58 (s, 1H), 8.97 (d, 1H), 9.06 (d, 1H), 9.31 (d, 1H).

Example I-156

2-Amino-N-[(2S)-1-hydroxypropan-2-yl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 2, distomer)

The product was isolated in the previous example as second stereoisomer.

LC-MS (method 1): $R^t$=1.42 min; MS (ESIpos): m/z=545 $[M+H]^+$ $^1$H-NMR (400 MHz, DMSO-$d_6$) δ [ppm]: −0.008 (2.42), 0.008 (3.23), 1.072 (1.31), 1.102 (1.67), 1.209 (14.81), 1.226 (16.00), 1.260 (0.85), 1.279 (1.24), 1.290 (1.41), 1.310 (1.61), 1.324 (1.73), 1.338 (1.52), 1.355 (1.22), 1.388 (0.43), 2.329 (0.41), 2.367 (0.49), 2.671 (0.52), 2.711 (0.56), 2.757 (1.20), 2.785 (1.20), 2.812 (0.46), 3.239 (1.16), 3.263 (2.99), 3.292 (3.43), 3.418 (0.75), 3.432 (1.47), 3.445 (2.41), 3.459 (3.02), 3.473 (1.69), 3.482 (1.73), 3.495 (3.09), 3.508 (2.46), 3.521 (1.47), 3.534 (0.79), 3.734 (0.54), 3.796 (1.58), 3.827 (2.60), 3.862 (1.43), 4.073 (0.62), 4.088 (1.21), 4.105 (1.68), 4.122 (1.25), 4.136 (0.64), 4.874 (2.49), 4.888 (5.27), 4.901 (2.52), 5.387 (3.70), 5.414 (3.57), 6.376 (9.01), 7.939 (4.43), 7.960 (4.97), 8.124 (9.51), 8.251 (6.44), 8.255 (6.89), 8.301 (2.73), 8.305 (2.74), 8.325 (2.49), 8.582 (8.93), 8.971 (5.01), 9.061 (6.48), 9.065 (6.78), 9.301 (3.57), 9.320 (3.50).

Example I-157

2-Amino-N-[(2S)-1-hydroxypropan-2-yl]-6-(1-{1-[6-(trifluoromethoxy)pyridin-3-yl]propyl}-1H-pyrazol-4-yl)[1,2,4]triazolo[1,5-a]pyridine-8-carboxamide (mixture of diastereomers)

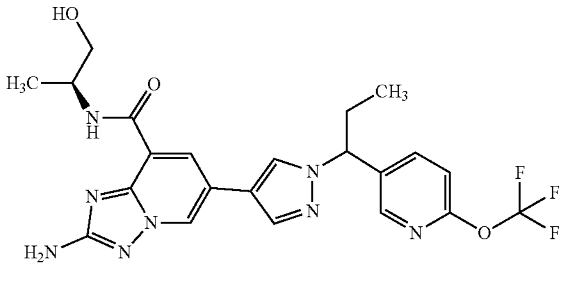 [SMILES: CCC(c1ccc(OC(F)(F)F)nc1)n1cc(-c2cc(C(=O)N[C@@H](C)CO)c3nc(N)nn3c2)cn1]

2-Amino-6-bromo-N-[(2S)-1-hydroxypropan-2-yl][1,2,4]triazolo[1,5-a]pyridine-8-carboxamide (220 mg, 700 μmol), 5-{1-[4-(4,4,5,5-tetramethyl-1,3,2-dioxaborolan-2-yl)-1H-pyrazol-1-yl]propyl}-2-(trifluoromethoxy)pyridine (362 mg, 910 μmol), sodium carbonate (371 mg, 3.50 mmol) and XPhos-Pd-G2 (55.1 mg, 70.0 μmol) were added to a mixture of dioxane (4.1 ml) and water (590 μl). The mixture was degassed with argon and heated for 2 h to 80° C. It was cooled to rt and diluted with ethyl acetate (15 ml) and water (2 ml). The organic layer was separated and the aqueous layer was extracted with ethyl acetate (10 ml). The combined organic layers were concentrated in vacuo and the residue was purified by column chromatography (Biotage® SNAP KP-NH 28 g cartridge, eluent: cyclohexane/ethyl acetate gradient 9:1 to 0:1, then ethyl acetate/2-propanol 5:1) to yield 273 mg (96% purity, 74% yield) of the title compound.

LC-MS (method 2): $R^t$=0.84 min; MS (ESIpos): m/z=505 $[M+H]^+$ $^1$H-NMR (600 MHz, DMSO-$d_6$) δ [ppm]: 0.86 (t, 3H), 1.22 (d, 3H), 2.14-2.23 (m, 1H), 2.37-2.46 (m, 1H), 3.42-3.48 (m, 1H), 3.49-3.54 (m, 1H), 4.07-4.15 (m, 1H), 4.90 (t, 1H), 5.49 (dd, 1H), 6.38 (s, 2H), 7.30 (d, 1H), 8.05 (dd, 1H), 8.09 (s, 1H), 8.28 (d, 1H), 8.43 (d, 1H), 8.59 (s, 1H), 9.08 (d, 1H), 9.32 (d, 1H).

Example I-158

2-Amino-N-[(2S)-1-hydroxypropan-2-yl]-6-(1-{1-[6-(trifluoromethoxy)pyridin-3-yl]propyl}-1H-pyrazol-4-yl)[1,2,4]triazolo[1,5-a]pyridine-8-carboxamide (stereoisomer 1, eutomer)

2-Amino-N-[(2S)-1-hydroxypropan-2-yl]-6-(1-{1-[6-(trifluoromethoxy)pyridin-3-yl]propyl}-1H-pyrazol-4-yl)[1,2,4]triazolo[1,5-a]pyridine-8-carboxamide (mixture of diastereomers) (310 mg, 96% purity) was separated by chiral chromatography to yield stereoisomer 1 (117 mg, 100% purity) and stereoisomer 2 (110 mg, 100% purity).

Instrument: THAR SFC-Super Chrom Prep 200; Column: Daicel Chiralpak AD-H, 5 m, 250×20 mm; Eluent A: $CO_2$; Eluent B: 2-propanol; isocratic: 65% A+35% B; flow: 100 ml/min; UV: 210 nm; temperature: 40° C.

Stereoisomer 1: $R^t$=2.54 min and

Stereoisomer 2: $R^t$=4.54 min (cf. next example)

Analytical chiral HPLC. Column: Chiraltek IC-3, 3 m, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=3.561 min and

Stereoisomer 2: $R^t$=2.248 min (cf. next example)

LC-MS (method 1): $R^t$=1.61 min; MS (ESIpos): m/z=505 $[M+H]^+$ $^1$H-NMR (400 MHz, DMSO-$d_6$) δ [ppm]: 0.86 (t, 3H), 1.22 (d, 3H), 2.12-2.25 (m, 1H), 2.36-2.46 (m, 1H), 3.40-3.55 (m, 2H), 4.06-4.16 (m, 1H), 4.89 (t, 1H), 5.49 (dd, 1H), 6.37 (s, 2H), 7.30 (d, 1H), 8.05 (dd, 1H), 8.09 (s, 1H), 8.28 (d, 1H), 8.42 (d, 1H), 8.59 (s, 1H), 9.07 (d, 1H), 9.32 (d, 1H).

Example I-159

2-Amino-N-[(2S)-1-hydroxypropan-2-yl]-6-(1-{1-[6-(trifluoromethoxy)pyridin-3-yl]propyl}-1H-pyrazol-4-yl)[1,2,4]triazolo[1,5-a]pyridine-8-carboxamide (stereoisomer 2, distomer)

The product was isolated in the previous example as second stereoisomer.

LC-MS (method 1): $R^t$=1.61 min; MS (ESIpos): m/z=505 $[M+H]^+$ $^1$H-NMR (400 MHz, DMSO-$d_6$) δ [ppm]: −0.149 (0.56), −0.008 (4.53), 0.008 (5.56), 0.146 (0.54), 0.838 (5.94), 0.856 (13.56), 0.874 (6.23), 1.211 (15.78), 1.227 (16.00), 2.150 (0.83), 2.167 (1.39), 2.185 (2.06), 2.202 (1.66), 2.219 (1.01), 2.328 (0.43), 2.367 (0.58), 2.380 (0.96), 2.398 (1.28), 2.403 (1.17), 2.415 (1.21), 2.421 (1.34), 2.433 (0.94), 2.438 (1.17), 2.456 (0.83), 2.671 (0.40), 2.711 (0.43), 3.420 (0.83), 3.434 (1.59), 3.447 (2.60), 3.461 (3.23), 3.475 (1.79), 3.486 (1.82), 3.498 (3.32), 3.511 (2.62), 3.525 (1.59), 3.537 (0.87), 4.076 (0.65), 4.089 (1.23), 4.107 (1.68), 4.124 (1.25), 4.138 (0.63), 4.877 (2.82), 4.890 (6.03), 4.904 (2.82), 5.468 (1.90), 5.484 (2.22), 5.491 (2.33), 5.507 (1.90), 6.374 (9.43), 7.286 (5.24), 7.308 (5.60), 8.033 (3.41), 8.040 (3.54), 8.055 (3.27), 8.061 (3.43), 8.091 (9.99), 8.273 (7.62), 8.277 (7.82), 8.421 (5.36), 8.427 (5.36), 8.587 (9.59), 9.069 (7.60), 9.073 (7.64), 9.307 (3.70), 9.327 (3.59).

Example 1-160

2-Amino-6-{1-[1-(4-fluorophenyl)-2-methylpropyl]-1H-pyrazol-4-yl}-N-[(2S)-1-hydroxypropan-2-yl][1,2,4]triazolo[1,5-a]pyridine-8-carboxamide (mixture of diastereomers)

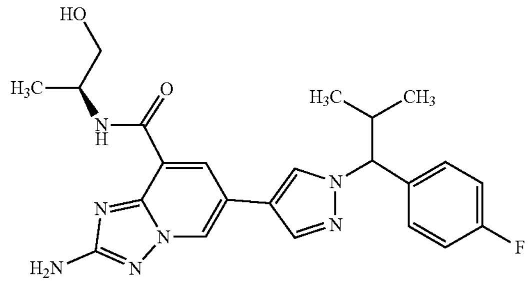 [SMILES: CC(C)C(c1ccc(F)cc1)n1cc(-c2cc(C(=O)N[C@@H](C)CO)c3nc(N)nn3c2)cn1]

2-Amino-6-bromo-N-[(2S)-1-hydroxypropan-2-yl][1,2,4]triazolo[1,5-a]pyridine-8-carboxamide (344 mg, 1.09 mmol) was reacted with 1-[1-(4-fluorophenyl)-2-methylpropyl]-4-(4,4,5,5-tetramethyl-1,3,2-dioxaborolan-2-yl)-1H-pyrazole (490 mg, 1.42 μmol) for 2.5 h at 90° C. following general procedure B using 0.1 eq. catalyst. The reaction mixture was cooled to rt and filtered through a hydrophobic phase separation filter. The filtrate was concentrated in vacuo and purified by column chromatography (Biotage® SNAP KP-NH 55 g cartridge, eluent: cyclohexane/ethyl acetate gradient 3:7 to 0:1) to yield 457 mg (98% purity, 90% yield) of the title compound.

LC-MS (method 1): $R^t$=1.64 min; MS (ESIpos): m/z=452 $[M+H]^+$ $^1$H-NMR (600 MHz, DMSO-$d_6$) δ [ppm]: −0.008 (1.59), 0.008 (1.64), 0.768 (8.32), 0.785 (8.46), 0.812 (9.14), 0.828 (9.28), 1.070 (3.25), 1.157 (4.25), 1.175 (8.62), 1.193 (4.43), 1.209 (11.48), 1.226 (11.59), 1.989 (16.00), 2.705 (0.68), 2.721 (0.96), 2.732 (0.84), 2.737 (0.82), 2.748 (0.98), 2.765 (0.68), 3.419 (0.59), 3.433 (1.15), 3.446 (1.88), 3.460 (2.33), 3.474 (1.27), 3.484 (1.23), 3.497 (2.30), 3.509 (1.80), 3.523 (1.10), 3.536 (0.59), 3.919 (0.51), 4.003 (1.21), 4.021 (3.69), 4.039 (3.65), 4.057 (1.28), 4.074 (0.46), 4.087 (0.89), 4.106 (1.14), 4.123 (0.89), 4.136 (0.44), 4.875 (2.11), 4.889 (4.46), 4.902 (2.11), 4.969 (3.04), 4.996 (2.96), 6.363 (6.53), 7.163 (3.21), 7.185 (6.49), 7.207 (3.49), 7.586 (3.22), 7.591 (1.51), 7.599 (3.60), 7.607 (3.55), 7.616 (1.38), 7.621 (3.09), 8.033 (7.65), 8.244 (6.30), 8.248 (6.45), 8.535 (6.72), 9.038 (6.14), 9.042 (6.13), 9.304 (2.31), 9.323 (2.25).

Example I-161

2-Amino-6-{1-[1-(4-fluorophenyl)-2-methylpropyl]-1H-pyrazol-4-yl}-N-[(2S)-1-hydroxypropan-2-yl][1,2,4]triazolo[1,5-a]pyridine-8-carboxamide (stereoisomer 1, distomer)

2-Amino-6-{1-[1-(4-fluorophenyl)-2-methylpropyl]-1H-pyrazol-4-yl}-N-[(2S)-1-hydroxypropan-2-yl][1,2,4]triazolo[1,5-a]pyridine-8-carboxamide (mixture of diastereomers) (455 mg, 98% purity) from the previous example was separated by chiral chromatography to yield stereoisomer 1 (162 mg, 93% purity) and stereoisomer 2 (149 mg, 100% purity).

Instrument: THAR SFC-Super Chrom Prep 200; Column: Chiralpak IA, 5 μm, 250×30 mm; Eluent A: $CO_2$; Eluent B: 2-propanol; isocratic: 50% A+50% B; flow: 90 ml/min; UV: 210 nm; temperature: 40° C.

Stereoisomer 1: $R^t$=5.0 min and

Stereoisomer 2: $R^t$=9.5 min (cf. next example)

Analytical chiral HPLC. Column: Daicel Chiralpak IA-3, 3 μm, 4.6×100 mm; Eluent A: n-heptane;

Eluent B: 2-propanol+0.2% diethylamine; isocratic: 50% A+50% B; flow: 1 ml/min; UV: 220 nm.

Stereoisomer 1: $R^t$=1.366 min and

Stereoisomer 2: $R^t$=2.409 min (cf. next example)

LC-MS (method 1): $R^t$=1.65 min; MS (ESIpos): m/z=452 $[M+H]^+$ $^1$H-NMR (500 MHz, DMSO-$d_6$) δ [ppm]: −0.007 (0.81), 0.006 (0.72), 0.770 (11.73), 0.784 (11.88), 0.814 (12.77), 0.827 (12.88), 0.992 (2.24), 1.004 (2.27), 1.117 (0.75), 1.130 (0.75), 1.212 (15.85), 1.226 (16.00), 1.285 (0.93), 2.075 (2.27), 2.521 (0.70), 2.525 (0.66), 2.566 (0.43), 2.677 (0.52), 2.697 (0.43), 2.710 (1.03), 2.723 (1.44), 2.732 (1.21), 2.737 (1.19), 2.745 (1.42), 2.758 (1.00), 3.427 (0.77), 3.438 (1.47), 3.449 (2.19), 3.459 (2.56), 3.470 (1.36), 3.489 (1.41), 3.499 (2.63), 3.509 (2.07), 3.520 (1.49), 3.530 (0.83), 4.081 (0.69), 4.092 (1.21), 4.107 (1.53), 4.121 (1.16), 4.131 (0.61), 4.878 (1.91), 4.888 (3.87), 4.899 (2.04), 4.972 (4.13), 4.993 (4.03), 6.363 (8.48), 7.168 (4.53), 7.172 (1.78), 7.185 (8.99), 7.199 (1.68), 7.203 (4.65), 7.264 (0.78), 7.281 (0.92), 7.470 (0.95), 7.487 (0.81), 7.589 (4.32), 7.594 (2.10), 7.600 (4.85), 7.607 (4.76), 7.614 (1.94), 7.618 (4.15), 8.033 (9.39), 8.245 (8.79), 8.249 (8.79), 8.534 (8.65), 9.039 (8.77), 9.043 (8.57), 9.308 (3.34), 9.324 (3.23), 10.193 (2.04).

Example I-162

2-Amino-6-{1-[1-(4-fluorophenyl)-2-methylpropyl]-1H-pyrazol-4-yl}-N-[(2S)-1-hydroxypropan-2-yl][1,2,4]triazolo[1,5-a]pyridine-8-carboxamide (stereoisomer 2, eutomer)

The product was isolated in the previous example as second stereoisomer.

LC-MS (method 1): $R^t$=1.65 min; MS (ESIpos): m/z=452 $[M+H]^+$ $^1$H-NMR (400 MHz, DMSO-$d_6$) δ [ppm]: 0.78 (d, 3H), 0.82 (d, 3H), 1.22 (d, 3H), 2.68-2.79 (m, 1H), 3.41-3.55 (m, 2H), 4.04-4.17 (m, 1H), 4.89 (t, 1H), 4.98 (d, 1H), 6.36 (s, 2H), 7.14-7.22 (m, 2H), 7.57-7.64 (m, 2H), 8.03 (s, 1H), 8.25 (d, 1H), 8.54 (s, 1H), 9.04 (d, 1H), 9.31 (d, 1H).

Example I-163

2-Amino-N-(1-hydroxy-2-methylpropan-2-yl)-6-(1-{1-[6-(trifluoromethyl)pyridin-3-yl]propyl}-1H-pyrazol-4-yl)[1,2,4]triazolo[1,5-a]pyridine-8-carboxamide (mixture of stereoisomers)

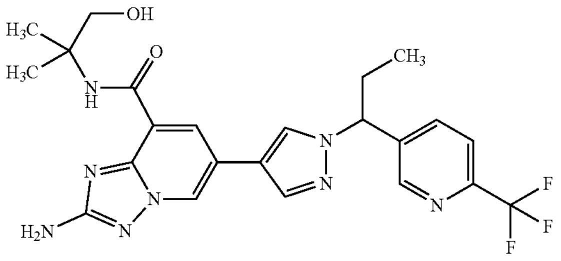 [SMILES: CCC(c1ccc(C(F)(F)F)nc1)n1cc(-c2cc(C(=O)NC(C)(C)CO)c3nc(N)nn3c2)cn1]

2-Amino-6-bromo-N-(1-hydroxy-2-methylpropan-2-yl)[1,2,4]triazolo[1,5-a]pyridine-8-carboxamide (150 mg, 457 μmol) was reacted with 5-{1-[4-(4,4,5,5-tetramethyl-1,3,2-dioxaborolan-2-yl)-1H-pyrazol-1-yl]propyl}-2-(trifluoromethyl)pyridine (227 mg, 594 μmol) for 2 h at 90° C. following general procedure B using 0.1 eq. XPhos-Pd-G2 as catalyst. The reaction mixture was diluted with ethyl acetate (15 ml) and washed with water (3 ml). The aqueous layer was separated and extracted twice with ethyl acetate (8 ml each). The combined organic layers were concentrated in vacuo and the residue was purified by column chromatography (Biotageo SNAP KP-NH 28 g cartridge, eluent: cyclohexane/ethyl acetate gradient 90:10 to 0:100) to yield 156 mg (100% purity, 68% yield) of the title compound.

LC-MS (method 2): $R^t$=0.83 min; MS (ESIpos): m/z=503 $[M+H]^+$ $^1$H-NMR (400 MHz, DMSO-$d_6$) δ [ppm]: 0.861 (1.66), 0.879 (3.79), 0.897 (1.77), 1.378 (16.00), 2.224 (0.56), 2.242 (0.46), 3.572 (2.15), 3.586 (2.17), 4.922 (0.74), 4.936 (1.68), 4.951 (0.70), 5.562 (0.53), 5.578 (0.60), 5.586 (0.62), 5.601 (0.52), 6.333 (2.69), 7.907 (1.28), 7.928 (1.68), 8.050 (0.88), 8.055 (0.88), 8.071 (0.66), 8.107 (3.12), 8.258 (2.10), 8.263 (2.19), 8.610 (2.84), 8.819 (1.45), 8.823 (1.45), 9.060 (2.08), 9.064 (2.11), 9.344 (2.09).

Example I-164

2-Amino-N-(1-hydroxy-2-methylpropan-2-yl)-6-(1-{1-[6-(trifluoromethyl)pyridin-3-yl]propyl}-1H-pyrazol-4-yl)[1,2,4]triazolo[1,5-a]pyridine-8-carboxamide (stereoisomer 1, eutomer)

2-Amino-N-(1-hydroxy-2-methylpropan-2-yl)-6-(1-{1-[6-(trifluoromethyl)pyridin-3-yl]propyl}-1H-pyrazol-4-yl)[1,2,4]triazolo[1,5-a]pyridine-8-carboxamide (mixture of stereoisomers) (142 mg, 100% purity) from the previous example was separated by chiral chromatography to yield stereoisomer 1 (46 mg, 100% purity) and stereoisomer 2 (48 mg, 98% purity).

Column: Daicel Chiralpak IE, 5 m, 250×20 mm; Eluent A: n-heptane; Eluent B: ethanol+0.2% diethylamine; isocratic: 50% A+50% B; flow: 20 ml/min; UV: 210 nm; temperature: 50° C.

Stereoisomer 1: $R^t$=10.725 min and

Stereoisomer 2: $R^t$=12.565 min (cf. next example)

Analytical chiral HPLC. Column: Daicel Chiralpak IE-3, 3 μm, 50×4.6 mm; Eluent A: n-heptane;

Eluent B: ethanol+0.2% diethylamine; isocratic: 50% A+50% B; flow: 1 ml/min; UV: 220 nm.

Stereoisomer 1: $R^t$=2.806 min and

Stereoisomer 2: $R^t$=3.385 min (cf. next example)

LC-MS (method 2): $R^t$=0.85 min; MS (ESIpos): m/z=503 $[M+H]^+$ $^1$H-NMR (600 MHz, DMSO-$d_6$) δ [ppm]: 0.88 (t, 3H), 1.38 (s, 6H), 2.18-2.28 (m, 1H), 2.40-2.48 (m, 1H), 3.58 (d, 2H), 4.93 (t, 1H), 5.58 (dd, 1H), 6.31 (s, 2H), 7.91 (d, 1H), 8.06 (br d, 1H), 8.10 (s, 1H), 8.26 (s, 1H), 8.60 (s, 1H), 8.82 (s, 1H), 9.05 (s, 1H), 9.34 (s, 1H).

Example I-165

2-Amino-N-(1-hydroxy-2-methylpropan-2-yl)-6-(1-{1-[6-(trifluoromethyl)pyridin-3-yl]propyl}-1H-pyrazol-4-yl)[1,2,4]triazolo[1,5-a]pyridine-8-carboxamide (stereoisomer 2, distomer)

The product was isolated in the previous example as second stereoisomer.

LC-MS (method 2): $R^t$=0.85 min; MS (ESIpos): m/z=503 $[M+H]^+$ $^1$H-NMR (600 MHz, DMSO-$d_6$) δ [ppm]: 0.868 (1.88), 0.881 (3.95), 0.893 (1.86), 1.379 (16.00), 2.214 (0.42), 2.226 (0.58), 2.238 (0.47), 3.575 (2.25), 3.584 (2.25), 4.915 (0.63), 4.924 (1.33), 4.933 (0.61), 5.567 (0.57), 5.577 (0.62), 5.583 (0.62), 5.593 (0.55), 6.312 (2.98), 7.906 (1.28), 7.920 (1.51), 8.054 (0.84), 8.068 (0.70), 8.101 (2.79), 8.259 (1.91), 8.261 (1.95), 8.600 (2.52), 8.817 (1.46), 9.052 (1.83), 9.055 (1.87), 9.342 (2.06).

Example I-166

2-Amino-N-(1-hydroxy-2-methylpropan-2-yl)-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of stereoisomers)

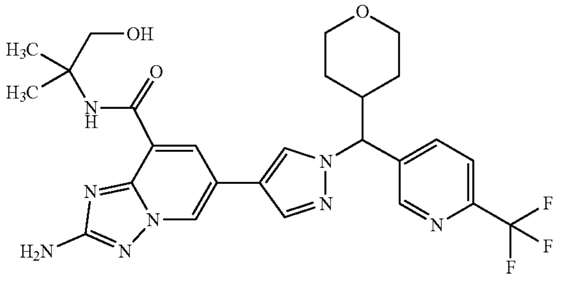 [SMILES: CC(C)(CO)NC(=O)c1cc(-c2cnn(C(c3ccc(C(F)(F)F)nc3)C3CCOCC3)c2)cn2nc(N)nc12]

2-Amino-6-bromo-N-(1-hydroxy-2-methylpropan-2-yl)[1,2,4]triazolo[1,5-a]pyridine-8-carboxamide (150 mg, 457 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (260 mg, 594 μmol) for 2 h at 90° C. following general procedure B using 0.1 eq. XPhos-Pd-G2 as catalyst. The reaction mixture was diluted with ethyl acetate (15 ml) and washed with water (3 ml). The aqueous layer was separated and extracted twice with ethyl acetate (8 ml each). The combined organic layers were concentrated in vacuo and the residue was purified by column chromatography (Biotage© SNAP KP-NH 28 g cartridge, eluent: cyclohexane/ethyl acetate gradient 90:10 to 0:100, then ethyl acetate/2-propanol 5:1) to yield 207 mg (100% purity, 81% yield) of the title compound.

LC-MS (method 2): $R^t$=0.80 min; MS (ESIpos): m/z=559 $[M+H]^+$ $^1$H-NMR (400 MHz, DMSO-$d_6$) δ [ppm]: 1.070 (0.58), 1.100 (0.43), 1.230 (0.48), 1.295 (0.45), 1.325 (0.59), 1.374 (16.00), 3.262 (0.86), 3.291 (0.95), 3.568 (2.06), 3.583 (2.09), 3.797 (0.42), 3.827 (0.71), 4.918 (0.73), 4.932 (1.74), 4.947 (0.72), 5.383 (1.06), 5.410 (1.02), 6.330 (2.52), 7.939 (1.34), 7.960 (1.47), 8.111 (2.97), 8.229 (2.18), 8.234 (2.28), 8.300 (0.76), 8.305 (0.76), 8.325 (0.69), 8.573 (2.62), 8.966 (1.41), 8.970 (1.41), 9.041 (2.16), 9.045 (2.21), 9.336 (2.07).

Example I-167

2-Amino-N-(1-hydroxy-2-methylpropan-2-yl)-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 1, distomer)

2-Amino-N-(1-hydroxy-2-methylpropan-2-yl)-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (mixture of stereoisomers) (190 mg, 100% purity) from the previous example was separated by chiral chromatography to yield stereoisomer 1 (54 mg, 98% purity) and stereoisomer 2 (56 mg, 98% purity).

Column: Daicel Chiralcel OZ-H, 5 μm, 250×20 mm; Eluent A: n-heptane; Eluent B: ethanol+0.2% diethylamine; isocratic: 65% A+35% B; flow: 20 ml/min; UV: 210 nm.

Stereoisomer 1: $R^t$=7.780 min and

Stereoisomer 2: $R^t$=9.958 min (cf. next example)

Analytical chiral HPLC. Column: Chiraltek OZ-3, 3 µm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=3.095 min and

Stereoisomer 2: $R^t$=4.375 min (cf. next example)

LC-MS (method 2): $R^t$=0.82 min; MS (ESIpos): m/z=559 $[M+H]^+$ $^1$H-NMR (600 MHz, DMSO-$d_6$) δ [ppm]: 1.082 (0.44), 1.102 (0.57), 1.210 (0.43), 1.232 (0.62), 1.292 (0.41), 1.298 (0.43), 1.319 (0.47), 1.342 (0.50), 1.357 (0.45), 1.378 (16.00), 2.758 (0.40), 2.776 (0.40), 3.270 (0.98), 3.290 (1.24), 3.574 (2.27), 3.583 (2.27), 3.801 (0.48), 3.816 (0.45), 3.839 (0.48), 3.858 (0.44), 4.912 (0.74), 4.922 (1.60), 4.932 (0.73), 5.388 (1.17), 5.406 (1.14), 6.312 (3.08), 7.938 (1.35), 7.952 (1.44), 8.107 (2.79), 8.232 (1.89), 8.235 (1.95), 8.307 (0.84), 8.318 (0.78), 8.566 (2.48), 8.967 (1.61), 9.035 (1.83), 9.037 (1.92), 9.337 (2.21).

Example I-168

2-Amino-N-(1-hydroxy-2-methylpropan-2-yl)-6-(1-{tetrahydro-2H-pyran-4-yl[6-(trifluoromethyl)pyridin-3-yl]methyl}-1H-pyrazol-4-yl)[1,2,4]triazolo[1,5-a]pyridine-8-carboxamide (stereoisomer 2, eutomer)

The product was isolated in the previous example as second stereoisomer.

The stereochemical configuration of the methine carbon atom bonded to the pyrazole was (S).

LC-MS (method 2): Rc=0.82 min; MS (ESIpos): m/z=559 $[M+H]^+$ $^1$H-NMR (600 MHz, DMSO-$d_6$) δ [ppm]: 1.06-1.11 (m, 1H), 1.19-1.25 (m, 1H), 1.26-1.37 (m, 2H), 1.38 (s, 6H), 2.72-2.81 (m, 1H), 3.24-3.29 (m, 2H), 3.58 (d, 2H), 3.79-3.87 (m, 2H), 4.92 (t, 1H), 5.40 (d, 1H), 6.31 (s, 2H), 7.94 (d, 1H), 8.11 (s, 1H), 8.23 (d, 1H), 8.31 (dd, 1H), 8.57 (s, 1H), 8.97 (d, 1H), 9.04 (d, 1H), 9.34 (s, 1H).

Example I-169

2-Amino-N-(1-hydroxy-2-methylpropan-2-yl)-6-(1-{1-[6-(trifluoromethoxy)pyridin-3-yl]propyl}-1H-pyrazol-4-yl)[1,2,4]triazolo[1,5-a]pyridine-8-carboxamide (mixture of enantiomers)

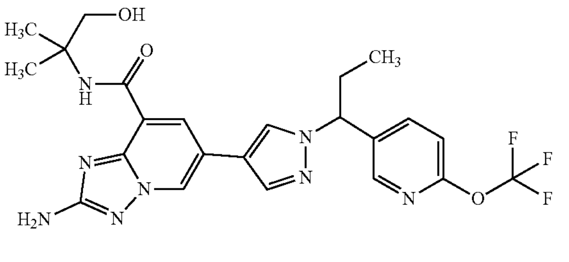 [SMILES: CCC(c1ccc(OC(F)(F)F)nc1)n1cc(-c2cc(C(=O)NC(C)(C)CO)c3nc(N)nn3c2)cn1]

2-Amino-6-bromo-N-(1-hydroxy-2-methylpropan-2-yl)[1,2,4]triazolo[1,5-a]pyridine-8-carboxamide (250 mg, 762 µmol), 5-{1-[4-(4,4,5,5-tetramethyl-1,3,2-dioxaborolan-2-yl)-1H-pyrazol-1-yl]propyl}-2-(trifluoromethoxy)pyridine (393 mg, 990 µmol), sodium carbonate (404 mg, 3.81 mmol) and XPhos-Pd-G2 (59.9 mg, 76.2 µmol) were added to a mixture of dioxane (4.4 ml) and water (630 µl). The mixture was degassed with argon and heated for 2 h to 90° C. It was cooled to rt and diluted with ethyl acetate (15 ml) and water (2 ml). The organic layer was separated and the aqueous layer was extracted with ethyl acetate (10 ml). The combined organic layers were concentrated in vacuo and the residue was purified by column chromatography (Biotage© SNAP KP-NH 28 g cartridge, eluent: cyclohexane/ethyl acetate gradient 9:1 to 0:1) to yield 303 mg (100% purity, 77% yield) of the title compound.

LC-MS (method 2): $R^t$=0.88 min; MS (ESIpos): m/z=519 $[M+H]^+$ $^1$H-NMR (500 MHz, DMSO-$d_6$) δ [ppm]: 0.842 (1.69), 0.857 (3.76), 0.871 (1.72), 1.377 (16.00), 2.184 (0.56), 2.198 (0.43), 2.403 (0.43), 3.573 (2.15), 3.584 (2.15), 4.924 (0.77), 4.935 (1.81), 4.947 (0.74), 5.469 (0.54), 5.481 (0.62), 5.487 (0.62), 5.500 (0.52), 6.328 (2.62), 7.289 (1.53), 7.306 (1.58), 8.035 (0.97), 8.040 (0.96), 8.052 (0.91), 8.057 (0.92), 8.079 (2.82), 8.253 (2.28), 8.256 (2.23), 8.421 (1.57), 8.426 (1.50), 8.577 (2.61), 9.051 (2.28), 9.054 (2.19), 9.344 (1.98).

Example I-170

2-Amino-N-(1-hydroxy-2-methylpropan-2-yl)-6-(1-{1-[6-(trifluoromethoxy)pyridin-3-yl]propyl}-1H-pyrazol-4-yl)[1,2,4]triazolo[1,5-a]pyridine-8-carboxamide (stereoisomer 1, eutomer)

2-Amino-N-(1-hydroxy-2-methylpropan-2-yl)-6-(1-{1-[6-(trifluoromethoxy)pyridin-3-yl]propyl}-1H-pyrazol-4-yl)[1,2,4]triazolo[1,5-a]pyridine-8-carboxamide (mixture of enantiomers) (300 mg, 100% purity) from the previous example was separated by chiral chromatography to yield stereoisomer 1 (120 mg, 100% purity) and stereoisomer 2 (128 mg, 100% purity).

Instrument: THAR SFC-Super Chrom Prep 200; Column: Chiralpak IC-H, 5 m, 250×20 mm;

Eluent A: $CO_2$; Eluent B: 2-propanol; isocratic: 65% A+35% B; flow: 100 ml/min; UV: 210 nm; temperature: 40° C.

Stereoisomer 1: $R^t$=2.05 min and

Stereoisomer 2: $R^t$=3.28 min (cf. next example)

Analytical SFC-method: Column: Chiralcel IC, 3 m, 4.6×100 mm; Eluent A: $CO_2$; Eluent B: ethanol; isocratic: 70% A+30% B; flow: 3 ml/min; UV: 210 nm.

Stereoisomer 1: $R^t$=1.629 min and

Stereoisomer 2: $R^t$=2.802 min (cf. next example)

LC-MS (method 1): $R^t$=1.72 min; MS (ESIpos): m/z=519 $[M+H]^+$ $^1$H-NMR (400 MHz, DMSO-$d_6$) δ [ppm]: 0.86 (t, 3H), 1.38 (s, 6H), 2.12-2.24 (m, 1H), 2.35-2.46 (m, 1H), 3.58 (d, 2H), 4.93 (t, 1H), 5.48 (dd, 1H), 6.33 (s, 2H), 7.30 (d, 1H), 8.04 (dd, 1H), 8.08 (s, 1H), 8.25 (d, 1H), 8.42 (d, 1H), 8.58 (s, 1H), 9.05 (d, 1H), 9.34 (s, 1H).

Example I-171

2-Amino-N-(1-hydroxy-2-methylpropan-2-yl)-6-(1-{1-[6-(trifluoromethoxy)pyridin-3-yl]propyl}-1H-pyrazol-4-yl)[1,2,4]triazolo[1,5-a]pyridine-8-carboxamide (stereoisomer 2, distomer)

The product was isolated in the previous example as second stereoisomer.

LC-MS (method 1): $R^t$=1.72 min; MS (ESIpos): m/z=519 $[M+H]^+$ $^1$H-NMR (400 MHz, DMSO-$d_6$) δ [ppm]: −0.008 (0.54), 0.008 (0.70), 0.838 (1.64), 0.856 (3.76), 0.874 (1.75), 1.376 (16.00), 2.183 (0.57), 2.201 (0.47), 3.571 (2.13), 3.585 (2.19), 4.920 (0.74), 4.934 (1.77), 4.949 (0.73), 5.464 (0.55), 5.480 (0.63), 5.487 (0.66), 5.503 (0.53), 6.328 (2.65), 7.287 (1.45), 7.308 (1.54), 8.032 (0.94), 8.038 (0.97), 8.053 (0.91), 8.059 (0.95), 8.079 (2.82), 8.251 (2.05), 8.256 (2.10), 8.420 (1.50), 8.425 (1.48), 8.577 (2.72), 9.050 (2.04), 9.054 (2.04), 9.342 (2.06).

Example I-172

2-Amino-6-{1-[1-(5-chloropyridin-3-yl)-2-methylpropyl]-1H-pyrazol-4-yl}-N-(1-hydroxy-2-methylpropan-2-yl)[1,2,4]triazolo[1,5-a]pyridine-8-carboxamide (mixture of enantiomers)

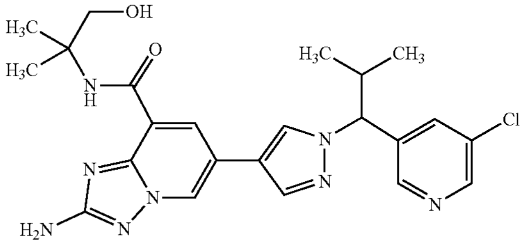 [SMILES: CC(C)C(c1cncc(Cl)c1)n1cc(-c2cc(C(=O)NC(C)(C)CO)c3nc(N)nn3c2)cn1]

2-Amino-6-bromo-N-(1-hydroxy-2-methylpropan-2-yl)[1,2,4]triazolo[1,5-a]pyridine-8-carboxamide (120 mg, 366 μmol), 3-chloro-5-{2-methyl-1-[4-(4,4,5,5-tetramethyl-1,3,2-dioxaborolan-2-yl)-1H-pyrazol-1-yl]propyl}pyridine (145 mg, 402 μmol), caesium carbonate (357 mg, 1.10 mmol) and XPhos-Pd-G2 (14.4 mg, 18.3 μmol) were heated in a mixture of 1,4-dioxane (4.0 ml) and water (400 μl) for 4 h to 90° C. It was then cooled to rt and purified by preparative HPLC to give 73.0 mg (100% purity, 41% yield) of the title compound.

LC-MS (method 1): $R^t$=1.63 min; MS (ESIpos): m/z=483 $[M+H]^+$ $^1$H-NMR (400 MHz, DMSO-$d_6$) δ [ppm]: −0.008 (0.61), 0.008 (0.73), 0.800 (3.22), 0.816 (3.36), 0.832 (3.58), 0.848 (3.58), 1.376 (16.00), 3.571 (2.10), 3.585 (2.14), 4.919 (0.73), 4.933 (1.80), 4.948 (0.73), 5.123 (1.23), 5.150 (1.18), 6.327 (2.58), 8.080 (2.91), 8.161 (1.05), 8.166 (1.77), 8.171 (1.11), 8.235 (2.14), 8.240 (2.20), 8.570 (2.67), 8.588 (1.84), 8.594 (1.81), 8.723 (1.89), 8.728 (1.89), 9.038 (2.14), 9.043 (2.16), 9.341 (2.04).

Example I-173

2-Amino-6-{1-[1-(5-chloropyridin-3-yl)-2-methylpropyl]-1H-pyrazol-4-yl}-N-(1-hydroxy-2-methylpropan-2-yl)[1,2,4]triazolo[1,5-a]pyridine-8-carboxamide (stereoisomer 1, eutomer)

2-Amino-6-{1-[1-(5-chloropyridin-3-yl)-2-methylpropyl]-1H-pyrazol-4-yl}-N-(1-hydroxy-2-methylpropan-2-yl)[1,2,4]triazolo[1,5-a]pyridine-8-carboxamide (mixture of enantiomers) (60 mg, 100% purity) from the previous example was separated by chiral chromatography to yield stereoisomer 1 (29 mg, 100% purity) and stereoisomer 2 (28 mg, 100% purity).

Column: Daicel Chiralcel OZ-H, 5 μm, 250×20 mm; Eluent A: n-heptane; Eluent B: ethanol+0.2% diethylamine; isocratic: 75% A+25% B; flow: 20 ml/min; UV: 235 nm; temperature: 40° C.

Stereoisomer 1: $R^t$=7.691 min and

Stereoisomer 2: $R^t$=9.384 min (cf. next example)

Analytical chiral HPLC. Column: Daicel Chiralcel OZ-H, 5 μm, 250×4.6 mm; Eluent A: n-heptane; Eluent B: ethanol+0.2% diethylamine; isocratic: 75% A+25% B; flow: 1 ml/min; UV: 235 nm; temperature: 70° C.

Stereoisomer 1: $R^t$=7.994 min and

Stereoisomer 2: $R^t$=9.686 min (cf. next example)

LC-MS (method 1): $R^t$=1.63 min; MS (ESIpos): m/z=483 $[M+H]^+$ $^1$H-NMR (400 MHz, DMSO-$d_6$) δ [ppm]: 0.81 (d, 3H), 0.84 (d, 3H), 1.38 (s, 6H), 2.72-2.83 (m, 1H), 3.58 (d, 2H), 4.93 (t, 1H), 5.14 (d, 1H), 6.33 (s, 2H), 8.08 (s, 1H), 8.17 (t, 1H), 8.24 (d, 1H), 8.57 (s, 1H), 8.59 (d, 1H), 8.73 (d, 1H), 9.04 (d, 1H), 9.34 (s, 1H).

Example I-174

2-Amino-6-{1-[1-(5-chloropyridin-3-yl)-2-methylpropyl]-1H-pyrazol-4-yl}-N-(1-hydroxy-2-methylpropan-2-yl)[1,2,4]triazolo[1,5-a]pyridine-8-carboxamide (stereoisomer 2, distomer)

The product was isolated in the previous example as second stereoisomer.

LC-MS (method 1): $R^t$=1.63 min; MS (ESIpos): m/z=483 $[M+H]^+$ $^1$H-NMR (400 MHz, DMSO-$d_6$) δ [ppm]: 0.799 (3.27), 0.816 (3.41), 0.831 (3.64), 0.847 (3.65), 1.376 (16.00), 2.765 (0.41), 3.570 (2.13), 3.585 (2.18), 4.919 (0.72), 4.933 (1.73), 4.948 (0.73), 5.122 (1.25), 5.150 (1.20), 6.327 (2.64), 8.079 (2.89), 8.161 (1.03), 8.166 (1.76), 8.171 (1.09), 8.234 (2.05), 8.239 (2.12), 8.569 (2.72), 8.588 (1.46), 8.594 (1.42), 8.723 (1.88), 8.727 (1.87), 9.038 (2.03), 9.042 (2.07), 9.340 (2.07).

Example I-175

2-Amino-6-{1-[(1H-indazol-7-yl)methyl]-1H-pyrazol-4-yl}-N-[(3S)-tetrahydrofuran-3-yl][1,2,4]triazolo[1,5-a]pyridine-8-carboxamide (single stereoisomer)

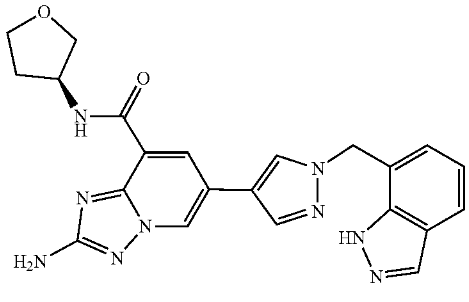 [SMILES: Nc1nc2c(C(=O)N[C@H]3CCOC3)cc(-c3cnn(Cc4cccc5cn[nH]c45)c3)cn2n1]

2-Amino-6-bromo-N-[(3S)-tetrahydrofuran-3-yl][1,2,4]triazolo[1,5-a]pyridine-8-carboxamide (60.0 mg, 184 μmol) was reacted with 7-{[4-(4,4,5,5-tetramethyl-1,3,2-dioxaborolan-2-yl)-1H-pyrazol-1-yl]methyl}-1H-indazole (71.6 mg, 221 μmol) for 1 h at 90° C. following general 10 procedure B using 0.05 eq. catalyst. The reaction mixture was diluted with ethyl acetate and filtered through a hydrophobic phase separation filter which was rinsed with ethyl acetate. The combined filtrates were concentrated in vacuo and the residue was purified by preparative HPLC (Chromatorex C18, 10 μm, 125×30 mm; eluent: water/acetonitrile gradient 90:10 to 10:90) to yield 16.2 mg (100% purity, 20% yield) of the title compound.

LC-MS (method 1): $R^t$=1.23 min; MS (ESIpos): m/z=444 $[M+H]^+$ $^1$H-NMR (400 MHz, DMSO-$d_6$) δ [ppm]: 1.82-1.91 (m, 1H), 2.24-2.38 (m, 1H), 3.65 (dd, 1H), 3.77 (td, 1H), 3.86-3.96 (m, 2H), 4.54-4.62 (m, 1H), 5.67 (s, 2H), 6.42 (s, 2H), 7.07-7.17 (m, 2H), 7.73 (d, 1H), 8.06 (s, 1H), 8.14 (d, 1H), 8.23 (d, 1H), 8.56 (s, 1H), 9.07 (d, 1H), 9.60 (d, 1H), 13.29 (s, 1H).

Example I-176

2-Amino-N-[(3S)-tetrahydrofuran-3-yl]-7-[1-(tetrahydro-2H-pyran-4-yl)-1H-pyrazol-4-yl][1,2,4]triazolo[1,5-a]pyridine-5-carboxamide (single stereoisomer)

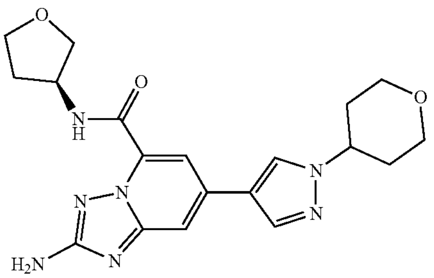

2-Amino-7-chloro-N-[(3S)-tetrahydrofuran-3-yl][1,2,4]triazolo[1,5-a]pyridine-5-carboxamide (50.4 mg, 100% purity, 179 μmol) was reacted with 1-(tetrahydro-2H-pyran-4-yl)-4-(4,4,5,5-tetramethyl-1,3,2-dioxaborolan-2-yl)-1H-pyrazole (70.0 mg, 96% purity, 242 μmol) for 1.5 h at 80° C. following general procedure C using 0.1 eq. catalyst. The reaction mixture was directly purified by column chromatography (Biotage® SNAP Ultra 10 g cartridge, eluent: dichloromethane/methanol gradient 100:0 to 85:15). The obtained material was further purified by preparative HPLC (Chromatorex C18, 10 μm, 125×30 mm; eluent: water (0.1% formic acid)/acetonitrile gradient 90:10 to 5:95) to yield 37.0 mg (100% purity, 52% yield) of the title compound.

LC-MS (method 2): $R^t$=0.73 min; MS (ESIpos): m/z=398 $[M+H]^+$ $^1$H-NMR (500 MHz, DMSO-$d_6$) δ [ppm]: 1.90-2.07 (m, 5H), 2.30 (dq, 1H), 3.46-3.52 (m, 2H), 3.70 (dd, 1H), 3.79 (td, 1H), 3.90-3.94 (m, 2H), 3.95-4.00 (m, 2H), 4.39-4.47 (m, 1H), 4.54-4.60 (m, 1H), 6.37 (s, 2H), 7.79 (s, 2H), 8.13 (s, 1H), 8.59 (s, 1H), 10.38 (d, 1H).

Example I-177

2-Amino-N-[(3S)-tetrahydrofuran-3-yl]-7-(1-{1-[6-(trifluoromethyl)pyridin-3-yl]propyl}-1H-pyrazol-4-yl)[1,2,4]triazolo[1,5-a]pyridine-5-carboxamide (mixture of diastereomers)

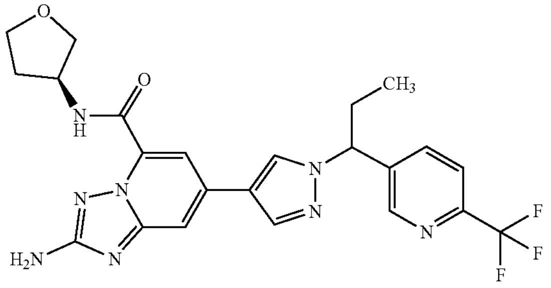 [SMILES: CCC(c1ccc(C(F)(F)F)nc1)n1cc(-c2cc(C(=O)N[C@H]3CCOC3)n3nc(N)nc3c2)cn1]

2-Amino-7-chloro-N-[(3S)-tetrahydrofuran-3-yl][1,2,4]triazolo[1,5-a]pyridine-5-carboxamide (75.0 mg, 266 μmol), 5-1-[4-(4,4,5,5-tetramethyl-1,3,2-dioxaborolan-2-yl)-1H-pyrazol-1-yl]propyl}-2-(trifluoromethyl)pyridine (181 mg, 73% purity, 346 μmol), 1,1'-bis(diphenylphosphino)ferrocene-palladium(II)dichloride dichloromethane complex (32.6 mg, 39.9 μmol) and water (500 μl) were reacted according to procedure A in a mixture of sodium carbonate (141 mg, 1.33 mmol) and 1,4-dioxane (3.0 ml). After 2.5 h at 90° C., the reaction was quenched with water and the mixture was extracted with dichloromethane. The combined organic layers were dried over anhydrous sodium sulfate, filtered and concentrated. The residue was purified by preparative HPLC to yield 56.0 mg (100% purity, 42% yield) of the title compound as a mixture of two diastereomers.

LC-MS (method 1): $R^t$=1.60 min; MS (ESIpos): m/z=501 $[M+H]^+$ $^1$H-NMR (500 MHz, DMSO-$d_6$) δ [ppm]: 0.88 (t, 3H), 1.22-1.33 (m, 1H), 1.39 (s, 13H), 1.90-1.96 (m, 1H), 2.19-2.37 (m, 2H), 2.40-2.48 (m, 1H), 3.70 (dd, 1H), 3.78 (td, 1H), 3.88-3.95 (m, 2H), 4.54-4.59 (m, 1H), 5.60 (dd, 1H), 6.38 (s, 2H), 7.79 (d, 1H), 7.81 (d, 1H), 7.92 (d, 1H), 8.07 (dd, 1H), 8.13 (br s, 1H), 8.23 (s, 1H), 8.58 (br s, 1H), 8.77 (s, 1H), 8.83 (d, 1H), 10.37 (d, 1H).

Example I-178

2-Amino-N-[(3S)-tetrahydrofuran-3-yl]-7-(1-{1-[6-(trifluoromethyl)pyridin-3-yl]propyl}-1H-pyrazol-4-yl)[1,2,4]triazolo[1,5-a]pyridine-5-carboxamide (stereoisomer 1, distomer)

2-Amino-N-[(3S)-tetrahydrofuran-3-yl]-7-(1-{1-[6-(trifluoromethyl)pyridin-3-yl]propyl}-1H-pyrazol-4-yl)[1,2,4]triazolo[1,5-a]pyridine-5-carboxamide to give was separated by chiral preparative SFC to yield stereoisomer 1 (15.4 mg, 100% purity) and stereoisomer 2 (15.1 mg, 100% purity).

Instrument: THAR SFC-Super Chrom Prep 200; Column: Daicel Chiralpak AD-H, 5 μm, 250×20 mm; Eluent A: $CO_2$; Eluent B: 2-propanol; isocratic: 70% A+30% B; flow: 80 ml/min; UV: 210 nm; temperature: 40° C.

Analytical SFC-method: Column: Chiralcel AD, 3 μm, 4.6×100 mm; Eluent A: $CO_2$; Eluent B: 2-propanol; isocratic: 70% A+30% B; flow: 3 ml/min; UV: 210 nm; temperature: 40° C.

Stereoisomer 1: R, =3.22 min and

Stereoisomer 2: $R^t$=5.84 min (cf. next example)

LC-MS (method 1): $R^t$=1.56 min; MS (ESIpos): m/z=501 $[M+H]^+$ $^1$H-NMR (500 MHz, DMSO-$d_6$) δ [ppm]: 0.862 (7.39), 0.876 (16.00), 0.891 (7.25), 1.034 (0.54), 1.046 (0.58), 1.901 (0.78), 1.912 (1.02), 1.916 (1.12), 1.926 (1.73), 1.934 (1.76), 1.941 (1.19), 1.945 (1.19), 1.949 (1.08), 1.960 (0.81), 2.208 (1.02), 2.221 (1.59), 2.235 (2.34), 2.249 (1.83), 2.264 (1.69), 2.280 (2.37), 2.290 (1.29), 2.295 (2.37), 2.305 (2.07), 2.310 (1.25), 2.321 (2.03), 2.336 (0.81), 2.414 (0.41), 2.428 (1.22), 2.442 (1.69), 2.446 (1.49), 2.455 (1.73), 2.461 (1.80), 2.470 (1.49), 2.475 (1.83), 3.270 (0.92), 3.331 (1.32), 3.683 (2.95), 3.690 (3.02), 3.701 (3.49), 3.708 (3.32), 3.762 (1.63), 3.773 (1.83), 3.779 (3.53), 3.790 (3.46), 3.795 (2.10), 3.806 (1.90), 3.896 (3.83), 3.908 (4.81), 3.915 (4.20), 3.919 (4.47), 3.926 (3.66), 3.936 (3.42), 3.951 (1.42), 4.539 (0.51), 4.547 (0.95), 4.554 (1.39), 4.560 (1.80), 4.567 (1.76), 4.573 (1.69), 4.580 (1.25), 4.586 (0.85), 5.582 (2.24), 5.594 (2.47), 5.601 (2.54), 5.613 (2.10), 6.376 (11.73), 7.786 (7.59), 7.790 (10.37), 7.806 (10.37), 7.810 (7.32), 7.912 (5.25), 7.928 (6.41), 8.059 (3.36), 8.063 (3.32), 8.075 (2.71), 8.079 (2.64), 8.233 (12.00), 8.769 (11.15), 8.827 (5.80), 8.831 (5.69), 10.363 (4.00), 10.377 (3.83).

Example I-179

2-Amino-N-[(3S)-tetrahydrofuran-3-yl]-7-(1-{1-[6-(trifluoromethyl)pyridin-3-yl]propyl}-1H-pyrazol-4-yl)[1,2,4]triazolo[1,5-a]pyridine-5-carboxamide (stereoisomer 2, eutomer)

The product was isolated in the previous example as second stereoisomer.

LC-MS (method 1): $R^t$=1.56 min; MS (ESIpos): m/z=501 $[M+H]^+$ $^1$H-NMR (500 MHz, DMSO-$d_6$) δ [ppm]: 0.88 (t, 3H), 1.90-1.96 (m, 1H), 2.20-2.34 (m, 2H), 2.41-2.48 (m, 1H), 3.70 (dd, 1H), 3.78 (td, 1H), 3.89-3.95 (m, 2H), 4.54-4.59 (m, 1H), 5.60 (dd, 1H), 6.38 (s, 2H), 7.79 (d, 1H), 7.81 (d, 1H), 7.92 (d, 1H), 8.07 (dd, 1H), 8.23 (s, 1H), 8.77 (s, 1H), 8.83 (s, 1H), 10.37 (d, 1H).

Example I-180

2-Amino-7-(1-{2-methyl-1-[6-(trifluoromethyl)pyridin-3-yl]propyl}-1H-pyrazol-4-yl)-N-[(3S)-tetrahydrofuran-3-yl][1,2,4]triazolo[1,5-a]pyridine-5-carboxamide (mixture of diastereomers)

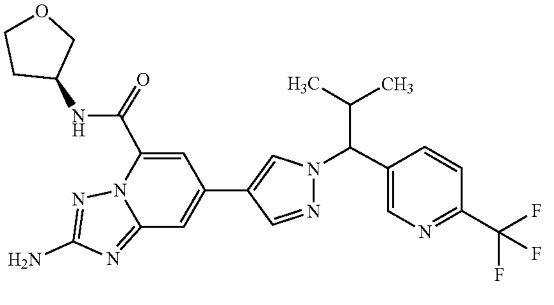 [SMILES: CC(C)C(c1ccc(C(F)(F)F)nc1)n1cc(-c2cc(C(=O)N[C@H]3CCOC3)n3nc(N)nc3c2)cn1]

2-Amino-7-chloro-N-[(3S)-tetrahydrofuran-3-yl][1,2,4]triazolo[1,5-a]pyridine-5-carboxamide (110 mg, 390 μmol), 5-{2-methyl-1-[4-(4,4,5,5-tetramethyl-1,3,2-dioxaborolan-2-yl)-1H-pyrazol-1-yl]propyl}-2-(trifluoromethyl)pyridine (194 mg, 95% purity, 469 μmol), 1,1'-bis(diphenylphosphino)ferrocene-palladium(II)dichloride dichloromethane complex (15.9 mg, 19.5 μmol) and sodium carbonate (207 mg, 1.95 mmol) were reacted according to procedure A in a mixture of 1,4-dioxane (4.0 ml) and water (600 μl). After stirring at 90° C. for 2.5 h, the reaction was quenched with water and the mixture was filtered through a hydrophobic phase separation filter which was rinsed with ethyl acetate (15 ml). The filtrate was concentrated and dried under reduced pressure. The residue was purified by preparative HPLC to yield 132 mg (100% purity, 66% yield) of the title compound as a mixture of two diastereomers.

LC-MS (method 1): $R^t$=1.69 min; MS (ESIpos): m/z=515 $[M+H]^+$ $^1$H-NMR (500 MHz, DMSO-$d_6$) δ [ppm]: 0.81 (d, 3H), 0.87 (d, 3H), 1.89-1.99 (m, 2H), 2.25-2.34 (m, 1H), 2.81-2.87 (m, 1H), 3.69 (dd, 1H), 3.78 (td, 1H), 3.89-3.96 (m, 2H), 4.54-4.59 (m, 1H), 5.27 (d, 1H), 6.38 (s, 2H), 7.76 (d, 1H), 7.79 (d, 1H), 7.95 (d, 1H), 8.22 (s, 1H), 8.30 (dd, 1H), 8.73 (s, 1H), 8.96 (s, 1H), 10.37 (d, 1H).

Example I-181

2-Amino-7-(1-{2-methyl-1-[6-(trifluoromethyl)pyridin-3-yl]propyl}-1H-pyrazol-4-yl)-N-[(3S)-tetrahydrofuran-3-yl][1,2,4]triazolo[1,5-a]pyridine-5-carboxamide (stereoisomer 1, distomer)

2-Amino-7-(1-{2-methyl-1-[6-(trifluoromethyl)pyridin-3-yl]propyl}-1H-pyrazol-4-yl)-N-[(3S)-tetrahydrofuran-3-yl][1,2,4]triazolo[1,5-a]pyridine-5-carboxamide 132 mg (100% purity) was separated by chiral preparative SFC to yield stereoisomer 1 (47.9 mg, 100% purity) and stereoisomer 2 (44.4 mg, 100% purity).

Instrument: THAR SFC-Super Chrom Prep 200; Column: Daicel Chiralpak AD-H, 5 μm, 250×20 mm; Eluent A: $CO_2$; Eluent B: 2-propanol; isocratic: 68% A+32% B; flow: 80 ml/min; UV: 210 nm; temperature: 40° C.

Analytical SFC-method: Column: Chiralcel AD, 3 m, 4.6×100 mm; Eluent A: $CO_2$; Eluent B: 2-propanol; isocratic: 75% A+25% B; flow: 3 ml/min; UV: 210 nm; temperature: 40° C.

Stereoisomer 1: $R^t$=4.24 min and

Stereoisomer 2: $R^t$=7.51 min (cf. next example)

LC-MS (method 1): $R^t$=1.69 min; MS (ESIpos): m/z=515 $[M+H]^+$ $^1$H-NMR (500 MHz, DMSO-$d_6$) δ [ppm]: −0.007 (3.02), 0.006 (2.52), 0.804 (15.15), 0.817 (15.20), 0.860 (15.98), 0.873 (16.00), 1.897 (0.82), 1.905 (1.01), 1.908 (1.08), 1.912 (1.16), 1.916 (1.18), 1.923 (1.88), 1.931 (1.90), 1.938 (1.29), 1.941 (1.27), 1.945 (1.20), 1.956 (0.89), 2.262 (0.93), 2.277 (2.41), 2.288 (1.29), 2.293 (2.56), 2.303 (2.26), 2.308 (1.37), 2.318 (2.18), 2.334 (0.85), 2.637 (0.42), 2.801 (0.51), 2.814 (1.31), 2.827 (1.82), 2.836 (1.54), 2.840 (1.54), 2.849 (1.82), 2.862 (1.27), 2.875 (0.49), 3.334 (0.46), 3.680 (3.23), 3.687 (3.34), 3.698 (3.80), 3.705 (3.66), 3.760 (1.80), 3.771 (1.99), 3.777 (3.89), 3.788 (3.83), 3.793 (2.37), 3.805 (2.11), 3.894 (4.21), 3.902 (2.71), 3.906 (5.16), 3.913 (4.73), 3.916 (5.05), 3.924 (4.02), 3.933 (3.87), 3.948 (1.61), 4.537 (0.51), 4.544 (1.04), 4.551 (1.52), 4.558 (1.97), 4.564 (2.01), 4.571 (1.90), 4.577 (1.44), 4.584 (0.93), 4.591 (0.46), 5.256 (5.39), 5.278 (5.20), 6.375 (12.87), 7.758 (8.50), 7.762 (10.95), 7.783 (10.99), 7.787 (8.31), 7.937 (6.13), 7.954 (6.59), 8.222 (13.10), 8.291 (3.53), 8.295 (3.47), 8.308 (3.15), 8.311 (3.09), 8.732 (12.05), 8.959 (6.47), 8.962 (6.36), 10.359 (4.46), 10.372 (4.29).

Example I-182

2-Amino-7-(1-{2-methyl-1-[6-(trifluoromethyl)pyridin-3-yl]propyl}-1H-pyrazol-4-yl)-N-[(3S)-tetrahydrofuran-3-yl][1,2,4]triazolo[1,5-a]pyridine-5-carboxamide (stereoisomer 2, eutomer)

The product was isolated in the previous example as second stereoisomer. The stereochemical configuration of the methine carbon atom bonded to the pyrazole was (R).

LC-MS (method 1): $R^t$=1.69 min; MS (ESIpos): m/z=515 $[M+H]^+$ $^1$H-NMR (500 MHz, DMSO-$d_6$) δ [ppm]: 0.81 (d, 3H), 0.87 (d, 3H), 1.90-1.96 (m, 1H), 2.28-2.32 (dq, 1H), 2.84 (dq, 1H), 3.70 (dd, 1H), 3.79 (td, 1H), 3.90-3.95 (m, 2H), 4.54-4.59 (m, 1H), 5.27 (d, 1H), 6.37 (s, 2H), 7.76 (d, 1H), 7.79 (d, 1H), 7.94 (d, 1H), 8.22 (s, 1H), 8.30 (dd, 1H), 8.73 (s, 1H), 8.96 (d, 1H), 10.37 (d, 1H).

Example I-183

2-Amino-N-[(3S)-tetrahydrofuran-3-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (mixture of stereoisomers)

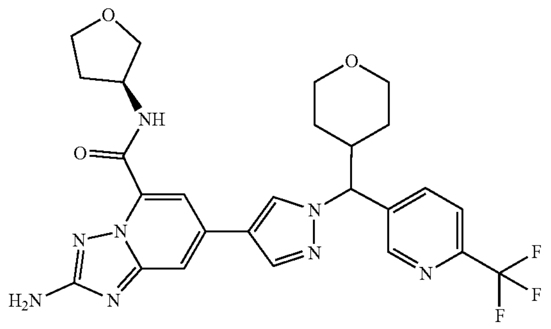 [SMILES: Nc1nc2cc(-c3cnn(C(c4ccc(C(F)(F)F)nc4)C4CCOCC4)c3)cc(C(=O)N[C@H]3CCOC3)n2n1]

2-Amino-7-chloro-N-[(3S)-tetrahydrofuran-3-yl][1,2,4]triazolo[1,5-a]pyridine-5-carboxamide (250 mg, 887 μmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (466 mg, 1.06 mmol) and sodium carbonate (470 mg, 4.44 mmol) were added to a mixture of dioxane (11 ml) and water (3.7 ml). It was degassed with argon, XPhos-Pd-G2 (69.8 mg, 88.7 μmol) was added and the mixture was heated for 2 h to 90° C. It was cooled to rt, diluted with ethyl acetate and filtered through a hydrophobic phase separation filter. The filtrate was concentrated in vacuo and the residue was purified by column chromatography (Biotage® SNAP KP-NH 11 g cartridge, eluent: cyclohexane/ethyl acetate/2-propanol gradient 7:3:0 to 0:1:0 to 0:4:1) to yield 385 mg (100% purity, 78% yield) of the title compound.

LC-MS (method 1): $R^t$=1.52 min; MS (ESIpos): m/z=557 $[M+H]^+$ $^1$H-NMR (600 MHz, DMSO-$d_6$) δ [ppm]: 0.005 (0.43), 1.077 (10.71), 1.092 (2.02), 1.112 (2.39), 1.197 (1.91), 1.217 (2.43), 1.271 (0.77), 1.278 (0.87), 1.291 (1.82), 1.298 (1.98), 1.312 (1.81), 1.320 (2.04), 1.330 (1.24), 1.341 (2.10), 1.348 (1.88), 1.362 (1.61), 1.368 (1.50), 1.382 (0.70), 1.390 (0.62), 1.909 (0.90), 1.918 (1.24), 1.921 (1.32), 1.924 (1.32), 1.930 (2.11), 1.937 (2.14), 1.943 (1.47), 1.946 (1.44), 1.949 (1.37), 1.958 (1.00), 2.274 (0.97), 2.286 (2.67), 2.299 (2.85), 2.308 (2.63), 2.320 (2.45), 2.333 (0.89), 2.758 (0.74), 2.770 (1.23), 2.776 (1.98), 2.782 (1.26), 2.789 (1.28), 2.795 (1.94), 2.801 (1.16), 2.814 (0.70), 3.252 (1.72), 3.256 (1.88), 3.275 (4.85), 3.293 (5.30), 3.689 (3.58), 3.695 (3.68), 3.704 (4.17), 3.710 (3.98), 3.769 (2.17), 3.778 (2.39), 3.783 (4.67), 3.792 (4.92), 3.797 (4.32), 3.806 (4.68), 3.820 (2.14), 3.824 (2.09), 3.836 (2.26), 3.841 (2.26), 3.856 (2.03), 3.903 (4.27), 3.912 (6.47), 3.918 (4.24), 3.924 (5.80), 3.927 (4.57), 3.938 (4.59), 3.950 (1.98), 4.548 (0.59), 4.554 (1.17), 4.560 (1.75), 4.566 (2.27), 4.571 (2.34), 4.576 (2.23), 4.582 (1.68), 4.587 (1.13), 4.593 (0.54), 5.408 (6.20), 5.426 (5.98), 6.373 (16.00), 7.766 (10.07), 7.769 (12.85), 7.789 (13.06), 7.792 (9.99), 7.946 (7.37), 7.960 (7.79), 8.243 (15.45), 8.313 (4.16), 8.316 (4.02), 8.327 (3.77), 8.330 (3.67), 8.731 (14.25), 8.975 (7.72), 8.978 (7.49), 10.365 (5.36), 10.376 (5.15).

Example I-184

2-Amino-N-[(3S)-tetrahydrofuran-3-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (stereoisomer 1, distomer)

2-Amino-N-[(3S)-tetrahydrofuran-3-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (mixture of stereoisomers) (333 mg, 100% purity) from the previous example was separated by chiral chromatography to yield stereoisomer 1 (156 mg, 98% purity) and stereoisomer 2 (160 mg, 98% purity).

Column: Daicel Chiralcel OZ-H, 5 μm, 250×20 mm; Eluent: ethanol+0.2% diethylamine; flow: 15 ml/min; UV: 220 num; temperature: 70° C.

Stereoisomer 1: $R^t$=7.71 min and

Stereoisomer 2: $R^t$=9.00 min (cf. next example)

Analytical chiral HPLC. Column: Daicel Chiralcel OZ-H, 5 μm, 250×4.6 mm; Eluent: ethanol+0.2% diethylamine; flow: 1 ml/min; UV: 220 nm; temperature: 70° C.

Stereoisomer 1: $R^t$=6.556 min and

Stereoisomer 2: $R^t$=8.824 min (cf. next example)

LC-MS (method 1): $R^t$=1.52 min; MS (ESIpos): m/z=557 $[M+H]^+$ $^1$H-NMR (600 MHz, DMSO-$d_6$) δ [ppm]: 1.068 (2.26), 1.088 (2.44), 1.176 (2.03), 1.196 (2.50), 1.259 (0.76), 1.267 (0.85), 1.280 (1.85), 1.287 (2.00), 1.301 (2.06), 1.306 (2.15), 1.325 (2.09), 1.331 (2.15), 1.345 (1.74), 1.352 (1.56), 1.365 (0.68), 1.373 (0.59), 1.895 (1.03), 1.902 (1.26), 1.904 (1.32), 1.908 (1.47), 1.910 (1.47), 1.917 (2.32), 1.923 (2.32), 1.929 (1.56), 1.932 (1.56), 1.935 (1.44), 1.938 (1.38), 1.944 (1.09), 2.261 (1.09), 2.274 (2.94), 2.283 (1.65), 2.287 (3.12), 2.295 (2.85), 2.299 (1.71), 2.308 (2.74), 2.321 (1.06), 2.423 (0.41), 2.652 (0.41), 2.746 (0.76), 2.759 (1.32), 2.765 (2.06), 2.771 (1.32), 2.778 (1.32), 2.784 (2.00), 2.790 (1.24), 2.802 (0.68), 3.240 (1.85), 3.259 (4.91), 3.279 (4.88), 3.298 (1.97), 3.678 (4.00), 3.683 (4.15), 3.693 (4.65), 3.699 (4.41), 3.726 (0.79), 3.757 (2.29), 3.766 (2.44), 3.771 (4.88), 3.780 (5.15), 3.785 (4.50), 3.794 (4.85), 3.808 (2.21), 3.825 (2.32), 3.829 (2.35), 3.848 (2.12), 3.886 (5.32), 3.896 (6.24), 3.902 (5.94), 3.911 (9.91), 3.926 (4.74), 3.938 (2.03), 4.536 (0.68), 4.541 (1.26), 4.547 (1.85), 4.553 (2.38), 4.558 (2.41), 4.564 (2.32), 4.569 (1.74), 4.574 (1.15), 4.580 (0.56), 5.399 (6.21), 5.418 (5.97), 6.413 (15.56), 7.756 (11.00), 7.759 (12.79), 7.792 (12.97), 7.795 (10.79), 7.950 (7.68), 7.963 (8.03), 8.250 (16.00), 8.308 (4.35), 8.311 (4.21), 8.322 (3.91), 8.324 (3.79), 8.740 (14.53), 8.970 (8.06), 8.973 (7.79), 10.373 (6.00), 10.384 (5.71).

Example I-185

2-Amino-N-[(3S)-tetrahydrofuran-3-yl]-7-(1-{tetrahydro-2H-pyran-4-yl[6-(trifluoromethyl)pyridin-3-yl]methyl}-1H-pyrazol-4-yl)[1,2,4]triazolo[1,5-a]pyridine-5-carboxamide (stereoisomer 2, eutomer)

The product was isolated in the previous example as second stereoisomer. Stereoisomer 1: The stereochemical configuration of the methine carbon atom bonded to the pyrazole was (S).

LC-MS (method 1): $R^t$=1.52 min; MS (ESIpos): m/z=557 $[M+H]^+$ $^1$H-NMR (600 MHz, DMSO-$d_6$) δ [ppm]: 1.06-1.11 (m, 1H), 1.16-1.22 (m, 1H), 1.26-1.39 (m, 2H), 1.90-1.96 (m, 1H), 2.30 (dq, 1H), 2.74-2.82 (m, 1H), 3.24-3.32 (m, 2H), 3.70 (dd, 1H), 3.73-3.87 (m, 3H), 3.89-3.95 (m, 2H), 4.54-4.59 (m, 1H), 5.42 (d, 1H), 6.42 (s, 2H), 7.76 (d, 1H), 7.80 (d, 1H), 7.97 (d, 1H), 8.26 (s, 1H), 8.32 (dd, 1H), 8.75 (s, 1H), 8.98 (d, 1H), 10.38 (d, 1H).

Example I-186

2-amino-N-[(3S)-tetrahydrofuran-3-yl]-7-(1-{(1-[6-(2,2,2-trifluoroethoxy)pyridin-3-yl]propyl}-1H-pyrazol-4-yl)[1,2,4]triazolo[1,5-a]pyridine-5-carboxamide (mixture of diastereoisomers)

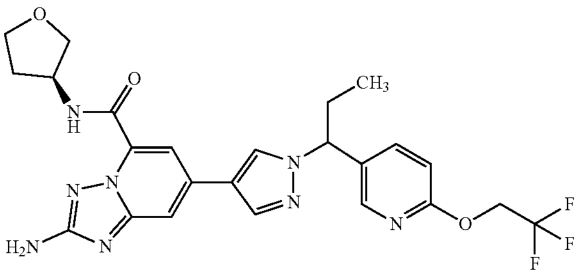 [SMILES: CCC(c1ccc(OCC(F)(F)F)nc1)n1cc(-c2cc(C(=O)N[C@H]3CCOC3)n3nc(N)nc3c2)cn1]

2-Amino-7-chloro-N-[(3S)-tetrahydrofuran-3-yl][1,2,4]triazolo[1,5-a]pyridine-5-carboxamide (150 mg, 532 μmol), 5-{1-[4-(4,4,5,5-tetramethyl-1,3,2-dioxaborolan-2-yl)-1H-pyrazol-1-yl]propyl}-2-(2,2,2-trifluoroethoxy)pyridine (279 mg, 86% purity, 586 μmol), XPhos-Pd-G2 (20.9 mg, 26.6 μmol) and caesium carbonate (520 mg, 1.60 mmol) were reacted according to procedure A in a mixture of 1,4-dioxane (4.5 ml) and water (500 l). The reaction mixture was stirred for 2.5 h at 90° C. The residue was purified by preparative HPLC to yield 127 mg (100% purity, 45% yield) of the title compound as a mixture of two diastereomers.

LC-MS (method 1): $R^t$=1.76 min; MS (ESIpos): m/z=531 $[M+H]^+$ $^1$H-NMR (400 MHz, DMSO-$d_6$) δ [ppm]: 0.84 (t, 3H), 1.89-1.97 (m, 1H), 2.16 (dt, 1H), 2.25-2.34 (m, 1H), 2.37-2.44 (m, 1H), 3.69 (dd, 1H), 3.78 (td, 1H), 3.89-3.96 (m, 2H), 4.53-4.60 (m, 1H), 4.97 (q, 2H), 5.40 (dd, 1H), 6.37 (s, 2H), 6.99 (d, 1H), 7.78 (d, 2H), 7.87 (dd, 1H), 8.17 (s, 1H), 8.26 (d, 1H), 8.71 (s, 1H), 10.37 (d, 1H).

Example I-187

2-Amino-N-[(3S)-tetrahydrofuran-3-yl]-7-(1-{(1-[6-(2,2,2-trifluoroethoxy)pyridin-3-yl]propyl}-1H-pyrazol-4-yl)[1,2,4]triazolo[1,5-a]pyridine-5-carboxamide (stereoisomer 1, eutomer)

2-Amino-N-[(3S)-tetrahydrofuran-3-yl]-7-(1-{(1-[6-(2,2,2-trifluoroethoxy)pyridin-3-yl]propyl}-1H-pyrazol-4-yl)[1,2,4]triazolo[1,5-a]pyridine-5-carboxamide (mixture of diastereoisomers) (127 mg, 100% purity) was separated by chiral preparative HPLC to yield stereoisomer 1 (33.7 mg, 100% purity) and stereoisomer 2 (33.1 mg, 100% purity).

Column: Daicel Chiralpak OX-H, 5 μm, 250×20 mm; Eluent A: n-heptane; Eluent B: 2-propanol+0.2% diethylamine; isocratic: 50% A+50% B; flow: 20 ml/min; UV: 220 nm; temperature: 40° C.

Stereoisomer 1: $R^t$=6.21 min and

Stereoisomer 2: $R^t$=7.48 min (cf. next example)

Analytical chiral HPLC-method: Column: Chiralpak AD-3, 3 μm, 250×4.6 mm; Eluent A: n-heptane; Eluent B: 2-propanol+0.2% diethylamine; isocratic: 50% A+50% B; flow: 1 ml/min;

UV: 220 nm; temperature: 30° C.

Stereoisomer 1: $R^t$=1.54 min and

Stereoisomer 2: $R^t$=2.00 min (cf. next example)

LC-MS (method 1): $R^t$=1.78 min; MS (ESIpos): m/z=531 $[M+H]^+$ $^1$H-NMR (400 MHz, DMSO-$d_6$) δ [ppm]: 0.84 (t, 3H), 1.89-1.97 (m, 1H), 2.13-2.20 (m, 1H), 2.25-2.34 (m, 1H), 2.35-2.45 (m, 1H), 3.69 (dd, 1H), 3.78 (td, 1H), 3.89-3.96 (m, 2H), 4.53-4.60 (m, 1H), 4.97 (q, 2H), 5.40 (dd, 1H), 6.37 (s, 2H), 6.99 (d, 1H), 7.78 (d, 2H), 7.87 (dd, 1H), 8.17 (s, 1H), 8.26 (d, 1H), 8.71 (s, 1H), 10.37 (d, 1H).

Example I-188

2-Amino-N-[(3S)-tetrahydrofuran-3-yl]-7-(1-{(1-[6-(2,2,2-trifluoroethoxy)pyridin-3-yl]propyl}-1H-pyrazol-4-yl)[1,2,4]triazolo[1,5-a]pyridine-5-carboxamide (stereoisomer 2, distomer)

The product was isolated in the previous example as second stereoisomer.

LC-MS (method 1): $R^t$=1.78 min; MS (ESIpos): m/z=531 $[M+H]^+$ $^1$H-NMR (400 MHz, DMSO-$d_6$) δ [ppm]: 0.84 (t, 3H), 1.89-1.97 (m, 1H), 2.13-2.20 (m, 1H), 2.25-2.34 (m, 1H), 2.35-2.45 (m, 1H), 3.69 (dd, 1H), 3.78 (td, 1H), 3.89-3.96 (m, 2H), 4.53-4.60 (m, 1H), 4.97 (q, 2H), 5.40 (dd, 1H), 6.37 (s, 2H), 6.99 (d, 1H), 7.78 (d, 2H), 7.87 (dd, 1H), 8.17 (s, 1H), 8.26 (d, 1H), 8.71 (s, 1H), 10.37 (d, 1H).

Assessment of pharmacological efficacy

The pharmacological activity of Compounds of Formula (A), (AI), (I), (I-A), (I-B), (I-C), or (I-D) can be demonstrated by in vitro and in vivo studies, as known to the person skilled in the art. The application examples which follow describe the biological action of Compounds of Formula (A), (AI), (I), (I-A), (I-B), (I-C), (I-D), without restricting the disclosure to these examples.

DLK biochemical assay

DLK assay is a biochemical assay format designed to screen for inhibitors of DLK. Enzymatic activity of DLK is measured by monitoring phosphorylation of the physiological substrate MKK7 (MAP2K7, Dual specificity mitogen-activated protein kinase kinase 7). Phosphorylation is detected by a TR-FRET system whereby His-tagged MKK7 is labeled by a XL665-labeled anti-His antibody (FRET acceptor, emission 665 nm). DLK phosphorylates MKK7 at T275/S277, which is detected by an Eu-labeled anti-phospho-MKK7 (T275/S277) antibody (FRET donor, excitation 340 nm). Phosphorylation of MKK7 results in an increased TR-FRET signal (Ratio XL665-channel/Eu-channel) and inhibition of enzymatic activity of DLK decreases the TR-FRET signal.

Assay Protocol for 1536 MTP format: test compounds are predispensed (60 nl) in test plates; +3 μl DLK solution (10 nM DLK, catalytic domain, Cama Biosiences, 0.6 mM DTT in assay buffer); +21 substrate solution (15 nM MKK7, LDB; 60 μM ATP; 0.4 mM DTT in assay buffer); 90 min incubation at RT; +2 μl detection mix (5 nM XL665-labeled anti-His antibody, Cisbio; 0.1 nM Eu-labeled anti-phospho-MKK7 (T275/S277), Cisbio/Millipore in detection buffer); 16 h incubation at 37° C.; endpoint measurement BMG (HTRF).

Assay Protocol for 384 low volume MTP format: 1 μl of test compounds is pipetted into test plate; +5 μl DLK solution (10 nM DLK, catalytic domain, Carna Biosiences in assay buffer); +5 μl substrate solution (15 nM MKK7, LDB; 60 M ATP, in assay buffer); 90 min incubation at RT; +9 μl detection mix (20 nM XL665-labeled anti-His antibody, Cisbio; 0.4 nM Eu-labeled anti-phospho-MKK7 (T275/S277), Cisbio/Millipore in detection buffer); 16 h incubation at 4° C.; endpoint measurement BMG (HTRF).

All indicated concentrations are final concentrations.

Assay buffer (1536 format): 50 mM Hepes pH 7.5, 10 mM MgCl2, 1 mM EGTA, 0.01% Triton X-100, 0.01% BSA, 1:500 Smart Block.

Assay buffer (384 format): 50 mM Hepes pH 7.5, 10 mM MgCl2, 1 mM EGTA, 1 mM DTT, 0.01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

LZK biochemical assay

LZK assay is a biochemical assay format designed to screen for inhibitors of LZK. Enzymatic activity of LZK is measured by monitoring phosphorylation of the physiological substrate MKK7 (MAP2K7, Dual specificity mitogen-activated protein kinase kinase 7). Phosphorylation is detected by a TR-FRET system whereby His-tagged MKK7 is labeled by a XL665-labeled anti-His antibody (FRET acceptor, emission 665 nm). LZK phosphorylates MKK7 at T275/S277 which is detected by an Eu-labeled anti-phospho-MKK7 (T275/S277) antibody (FRET donor, excitation 340 nm). Phosphorylation of MKK7 results in an increased TR-FRET signal (Ratio XL665-channel/Eu-channel) and inhibition of enzymatic activity of LZK decreases the TR-FRET signal.

Assay Protocol for 384 low volume MTP format: 1 1 of test compound is pipetted into test plate; +5 μl LZK solution (10 nM LZK, catalytic domain, Carna Biosiences in assay buffer); +5 μl substrate solution (15 nM MKK7, LDB; 15 μM ATP, in assay buffer); 90 min incubation at RT; +5 μl detection mix (20 nM XL665-labeled anti-His antibody, Cisbio; 0.4 nM Eu-labeled anti-phospho-MKK7 (T275/S277), Cisbio/Millipore in detection buffer); 16 h incubation at 32° C.; endpoint measurement BMG (HTRF).

All indicated concentrations final concentrations.

Assay buffer (384 format): 50 mM Hepes pH 7.5, 10 mM MgCl2, 1 mM EGTA, 1 mM DTT, 0.01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

Biochemical results

| Expl.* | DLK $IC_{50}$ [nM] | LZK $IC_{50}$ [nM] |
|---|---|---|
| 1 | 97 | 83 |
| 2 | 36 | 74 |
| 3 | 66 | 12 |
| 4 | 84 | 26 |
| 5 | 55 | 15 |
| 6 | 17 | 6.7 |
| 7 | 32 | 3.8 |
| 8 | 68 | 9.4 |
| 9 | 80 | 6.9 |
| 10 | 24 | 9.0 |
| 11 | 82 | 14 |
| 12 | 120 | 70 |
| 13 | 68 | 7.7 |
| 14 | 12 | 4.7 |
| 15 | 31 | 7.8 |
| 16 | 22 | 3.3 |
| 17 | 22 | 4.7 |
| 18 | 47 | 6.0 |
| 19 | 21 | 3.9 |
| 20 | 11 | 4.4 |
| 21 | 33 | 5.1 |
| 22 | 27 | 13 |
| 23 | 2.7 | 56 |
| 24 | 2.7 | 23 |
| 25 | 23 | 140 |
| 26 | 1.1 | 18 |
| 27 | 7.7 | 390 |
| 28 | 9.2 | 380 |
| 29 | 2.3 | 170 |
| 30 | 140 | 310 |
| 31 | 3.8 | 150 |
| 32 | 56 | 180 |
| 33 | 2.2 | 59 |
| 34 | 9.5 | 520 |
| 35 | 410 | 990 |
| 36 | 25 | 180 |
| 37 | 3.6 | 240 |
| 38 | 1.3 | 91 |
| 39 | 24 | 230 |
| 40 | 4.5 | 67 |
| 41 | 2.8 | 26 |
| 42 | 9.8 | 37 |
| 43 | 2.9 | 66 |
| 44 | 33 | 160 |
| 45 | 1.3 | 32 |
| 46 | 25 | 40 |
| 47 | 3.8 | 40 |
| 48 | 25 | 120 |
| 49 | 1.5 | 17 |
| 50 | 1.6 | 25 |
| 51 | 1.8 | 8.7 |
| 52 | 0.7 | 5.6 |
| 53 | 11 | 24 |
| 54 | 1.9 | 8.5 |
| 55 | 6.7 | 49 |
| 56 | 2.7 | 19 |
| 57 | 59 | 61 |
| 58 | 1.6 | 16 |
| 59 | 20 | 58 |
| 60 | 3.7 | 8.9 |
| 61 | 0.6 | 3.3 |
| 62 | 8.8 | 74 |
| 63 | 0.4 | 5.2 |
| 64 | 1.7 | 7.0 |
| 65 | 25 | 33 |
| 66 | 0.8 | 4.1 |
| 67 | 1.1 | 5.6 |
| 68 | 14 | 43 |
| 69 | 1.0 | 3.9 |
| 70 | 2.1 | 6.5 |
| 71 | 1.4 | 4.5 |

-continued

| Biochemical results | | |
|---|---|---|
| Expl.* | DLK $IC_{50}$ [nM] | LZK $IC_{50}$ [nM] |
| 72 | 10 | 16 |
| 73 | 1.6 | 5.8 |
| 74 | 10 | 16 |
| 75 | 1.1 | 2.4 |
| 76 | 0.5 | 1.1 |
| 77 | 5.9 | 6.9 |
| 78 | 0.7 | 1.7 |
| 79 | 0.8 | 1.4 |
| 80 | 45 | 40 |
| 81 | 6.6 | 8.5 |
| 82 | 0.9 | 0.5 |
| 83 | 0.3 | 0.7 |
| 84 | 0.5 | 1.2 |
| 85 | 4.7 | 38 |
| 86 | 100 | 160 |
| 87 | 1.3 | 16 |
| 88 | 7.5 | 120 |
| 89 | 230 | 2000 |
| 90 | 3.0 | 34 |
| 91 | 2.9 | 15 |
| 92 | 2.0 | 3.9 |
| 93 | 6.5 | 6.3 |
| 94 | 1.0 | 1.9 |
| 95 | 1.5 | 4.7 |
| 96 | 14 | 17 |
| 97 | 0.9 | 2.1 |
| 98 | 8.6 | 7.3 |
| 99 | 31 | 14 |
| 100 | 2.8 | 4.3 |
| 101 | 1.2 | 2.8 |
| 102 | 7.0 | 11 |
| 103 | 0.8 | 2.4 |
| 104 | 1.3 | 2.9 |
| 105 | 13 | 14 |
| 106 | 1.0 | 1.6 |
| 107 | 1.7 | 3.5 |
| 108 | 28 | 17 |
| 109 | 1.8 | 3.5 |
| 110 | 1.6 | 2.3 |
| 111 | 0.5 | 1.4 |
| 112 | 8.0 | 7.0 |
| 113 | 5.4 | 12 |
| 114 | 49 | 130 |
| 115 | 4.2 | 20 |
| 116 | 8.2 | 68 |
| 117 | 73 | 250 |
| 118 | 8.6 | 29 |
| 119 | 6.5 | 36 |
| 120 | 44 | 140 |
| 121 | 1.9 | 30 |
| 122 | 3.5 | 7.4 |
| 123 | 5.9 | 170 |
| 124 | 60 | 270 |
| 125 | 5.4 | 66 |
| 126 | 0.2 | 1.3 |
| 127 | 17 | 52 |
| 128 | 0.5 | 3.3 |
| 129 | 3.4 | 39 |
| 130 | 53 | 100 |
| 131 | 1.5 | 33 |
| 132 | 85 | 240 |
| 133 | 110 | 330 |
| 134 | 230 | 970 |
| 135 | 190 | 550 |
| 136 | 23 | 210 |
| 137 | 140 | 150 |
| 138 | 3.0 | 190 |
| 139 | 1.7 | 64 |
| 140 | 0.5 | 32 |
| 141 | 26 | 355 |
| 142 | 4.2 | 240 |
| 143 | 33 | 15 |
| 144 | 84 | 79 |
| 145 | 110 | 110 |

-continued

| Biochemical results | | |
|---|---|---|
| Expl.* | DLK $IC_{50}$ [nM] | LZK $IC_{50}$ [nM] |
| 146 | 130 | 85 |
| 147 | 3.9 | 25 |
| 148 | 1.6 | 32 |
| 149 | 1.7 | 13 |
| 150 | 6.5 | 60 |
| 151 | 6.9 | 9.8 |
| 152 | 0.7 | 3.9 |
| 153 | 6.2 | 29 |
| 154 | 1.1 | 4.6 |
| 155 | 0.7 | 3.9 |
| 156 | 13 | 23 |
| 157 | 5.7 | 13 |
| 158 | 0.6 | 3.4 |
| 159 | 6.7 | 30 |
| 160 | 4.3 | 130 |
| 161 | 51 | 540 |
| 162 | 1.3 | 83 |
| 163 | 7.6 | 30 |
| 164 | 6.3 | 52 |
| 165 | 64 | 190 |
| 166 | 4.2 | 20 |
| 167 | 22 | 85 |
| 168 | 1.5 | 8.9 |
| 169 | 26 | 71 |
| 170 | 5.5 | 18 |
| 171 | 85 | 150 |
| 172 | 4.0 | 76 |
| 173 | 2.0 | 49 |
| 174 | 62 | 690 |
| 175 | 3.8 | 150 |
| 176 | 220 | 210 |
| 177 | 2.6 | 18 |
| 178 | 17 | 64 |
| 179 | 1.8 | 7.9 |
| 180 | 1.6 | 6.1 |
| 181 | 2.1 | 14 |
| 182 | 0.3 | 1.2 |
| 183 | 1.7 | 6.0 |
| 184 | 13 | 22 |
| 185 | 0.8 | 2.3 |
| 186 | 6.2 | 16 |
| 187 | 0.8 | 18 |
| 188 | 16 | 190 |

*Example numbers I-# where # is the number listed in the column.

Preparation of human stem cell-derived RGCs (hRGCs)

H7 or H9 human embryonic stem cells or patient-derived induced pluripotent stem cells were modified to express mouse Thy1.2 and tdTomato from the BRN3B locus (Sluch et al., 2017). To produce RGCs, stem cells were dissociated to single cells and plated on Matrigel (Coming, USA) coated plates at a density of 52.6 K/cm$^2$ in mTeSRI with 5 mM blebbistatin, a time point designated as day minus 1 (d-1). One day after plating, mTeSR1 was completely exchanged for N2B27 media [1:1 mix of DMEM/F12 and Neurobasal with GlutaMAX Supplement, antibiotic-antimycotic, 1% N2 Supplement, and 2% B27 Supplement (all from ThermoFisher Scientific)] to start differentiation; this day was designated as day 0 (d0). Small molecules were added to the cells on day 1 (d1), 24 hours after d0. Small molecule addition was done in fresh N2B27 media. Cells were fed with a full exchange of N2B27 media every other day unless a small molecule was to be removed or added on that day of differentiation, requiring daily feeding. The following small molecules were aliquoted as 1,000× stocks in dimethyl sulfoxide (DMSO) and used at the working concentration noted in parentheses: Forskolin (FSK; 25 mM-Cell Signaling Technology, Danvers, MA), Dorsomorphin (1 mM-R&D Systems, Minneapolis, MN), IDE2 (2.5 mM-R&D Systems), DAPT (10 mM-Cell Signaling Technology). Nicotinamide (NIC; Sigma-Aldrich) was resuspended in water at 100× and used at a 10 mM working concentration. Dorsomorphin and IDE2 (DID) were added from day 1 to 6, NIC from day 1 to 10, FSK from day 1 to 30, and DAPT from day 18 to 30. Differentiation was carried out at 37° C. in 5% CO2/20% O2. After 35 days in culture, when abundant RGCs have appeared (indicated by red fluorescence), cultures were dissociated into a single cell suspension. Cultures were washed with phosphate buffered saline (PBS, pH 7.4), incubated with TrypLE Express for 15 minutes at 37° C., and then further incubated with Accumax (Sigma-Aldrich) for an additional 45 minutes. Cells were then purified using the anti-Thy1.2 MACS system (Miltenyi Biotec) or EasySep™ Mouse CD90.2 Positive Selection Kit II (Stemcell Technologies), per the manufacturer's protocol, and seeded into multiwell dishes at 10,000-30,000 cells/cm$^2$.

Preparation ofprimary mouse RGCs (mRGCs)

Retinas were isolated from postnatal day 0-3 mice and the tissue dissociated into a single cell suspension with papain. Microglia were immunodepleted with CELLection Dynabeads (Invitrogen) conjugated to anti-CD11b (BD Pharmingen, 554859). The suspension of remaining retinal cells was immunopanned on plates pre-conjugated with goat anti-mouse IgM (Jackson Immunoresearch, 115-001-020) and mouse anti-Thy1.2 antibodies (BioRad, MCA02R) at room temperature After washing the retinal cells that did not bind Thy1.2 from the plates, the bound retinal ganglion cells (RGCs) were released with trypsin (Sigma T9201). The enriched mRGC population was counted, and seeded into multiwell dishes at 10,000-30,000 cells/cm$^2$.

Determination of survival by CellTiter-Glo

In order to test compounds, RGCs were plated in 96- or 384-well Nunclon or Falcon dishes. Growth media consists of Neurobasal (Life Technologies) supplemented with NS21, Sato, L-glutamine and penicillin/streptomycin with N-acetyl-cysteine, insulin, sodium pyruvate, triiodothyronine (T3), and forskolin (Chen et al., 2008) for the mRGCs or in N2/B27 media without additional components for the hRGCs. For mRGCs, cells were plated in poly-D-lysine-coated wells and no additional injury was induced (i.e. cells die after 72 hours from isolation and plating). For hRGCs, cells were injured with the addition of 10-1000 nM colchicine. For both sets of RGCs, increasing doses of the kinase inhibitors was added at the time of injury and survival was quantitated after 72 hours using CellTiter-Glo (Promega, Madison) and measuring relative light units (RLU) or by staining cultures with conventional viability dyes (i.e. ethidium homodimer exclusion, calcein AM uptake) and measuring survival by automated image analysis.

Part II. Materials, Methods, Synthetic Procedures, and Biological Data for Compounds of Formula (H)

GC-MS methods

GC-MS method 1: Instrument: Thermo Scientific DSQII, Thermo Scientific Trace GC Ultra; Column: Restek RTX-35MS, 15 m×200 μm×0.33 μm; constant flow rate with He: 1.20 ml/min; Oven: 60° C.; Inlet: 220° C.; Gradient: 60° C., 30° C./min to 300° C. (then hold for 3.33 min).

GC-MS method 2: Instrument: Waters MS SQ Detector 2, GC Agilent A7890; Column: Restek RTX-35MS, 15 m×200 μm×0.33 μm; constant flow rate with He: 1.20 ml/min; Oven: 60° C.; Inlet: 240° C.; Gradient: 60° C., 30° C./min to 300° C. (then hold for 3.33 min).

LC-MS methods

LC-MS method 1: Instrument MS: Thermo Scientific FT-MS; Instrument UHPLC+: Thermo Scientific UltiMate 3000; Column: Waters, HSS T3, C18 1.8 μm, 2.1×75 mm; Eluent A: water+0.01% formic acid; Eluent B: acetonitrile+0.01% formic acid; Gradient: 0.0 min 10% B to 2.5 min 95% B to 3.5 min 95% B; Oven: 50° C.; Flow rate: 0.90 ml/min; UV-Detection: 210 nm/Optimum Integration Path 210-300 nm LC-MS method 2: Instrument: Waters ACQUITY SQD UPLC System; Column: Waters Acquity UPLC HSS T3, 1.8 μm, 50×1 mm; Eluent A: 1 1 water+0.25 ml formic acid, Eluent B: 1 1 acetonitrile+0.25 ml formic acid; Gradient: 0.0 min 90% A to 1.2 min 5% A to 2.0 min 5% A; Oven: 50° C.; Flow rate: 0.40 ml/min; UV-Detection: 210 nm.

LC-MS method 3: Instrument: Agilent MS Quad 6150; HPLC: Agilent 1290; Column: Waters Acquity UPLC HSS T3, 1.8 μm, 50×2.1 mm; Eluent A: 11 water+0.25 ml formic acid, Eluent B: 11 acetonitrile+0.25 ml formic acid; Gradient: 0.0 min 90% A to 0.3 min 90% A to 1.7 min 5% A to 3.0 min 5% A; Oven: 50° C.; Flow rate: 1.20 ml/min; UV-Detection: 205-305 nm.

LC-MS method 4: Instrument: Waters Single Quad MS System; Instrument Waters UPLC Acquity; Column: Waters BEH C18, 1.7 μm; 50×2.1 mm; Eluent A: 1 1 water+1.0 ml 25% aq. ammonia; Eluent B: acetonitrile; Gradient: 0.0 min 92% A to 0.1 min 92% A to 1.8 min 5% A to 3.5 min 5% A; Oven: 50° C.; Flow rate: 0.45 ml/min; UV-Detection: 210 nm.

LC-MS method 5: Column: Ascentis Express C18, 2.7 μm, 3.0×50 mm. A linear gradient was applied, starting at 95% A (A: 0.05% TFA in water) and ending at 95% B (B: 0.05% TFA in acetonitrile) over 1.7 min with a total run time of 3.0 min. Oven: 40° C.; Flow rate: 1.5 ml/min.

LC-MS method 6: Column: Kinetex EVO-C18, 2.6 μm, 3.0×50 mm. A linear gradient was applied, starting at 90% A (A: 5 mM ammonium bicarbonate in water) and ending at 95% B (B: acetonitrile) over 2.1 min with a total run time of 3.0 min. Oven: 40° C.; Flow rate: 1.3 ml/min.

LC-MS method 7: Column: Kinetex EVO-C18 100A, 2.6 μm, 2.1×50 mm. A linear gradient was applied, starting at 90% A (A: 5 mM ammonium bicarbonate in water) and ending at 95% B (B: acetonitrile) over 2.0 min with a total run time of 3.0 min. Oven: 40° C.; Flow rate: 1.2 ml/min.

LC-MS method 8: Column: Shim-pack XR-ODS, 2.2 μm, 3.0×50 mm. A linear gradient was applied, starting at 95% A (A: 0.05% TFA in water) and ending at 95% B (B: 0.05% TFA in acetonitrile) over 1.2 min with a total run time of 2.0 min. Oven: 40° C.; Flow rate: 1.5 ml/min.

LC-MS method 9: Column: Ascentis Express C18, 2.7 μm, 2.1×50 mm. A linear gradient was applied, starting at 60% A (A: 0.05% TFA in water) and ending at 95% B (B: 0.05% TFA in acetonitrile) over 3.0 min with a total run time of 4.5 min. Oven: 40° C.; Flow rate: 1.5 ml/min.

LC-MS method 10: Column: Ascentis Express C18, 2.7 μm, 2.1×50 mm. A linear gradient was applied, starting at 95% A (A: 0.05% TFA in water) and ending at 100% B (B: 0.05% TFA in acetonitrile) over 1.2 min with a total run time of 2.0 min. Oven: 40° C.; Flow rate: 1.5 ml/min.

LC-MS method 11: Column: Ascentis Express C18, 2.7 μm, 2.1×50 mm. A linear gradient was applied, starting at 95% A (A: 0.05% TFA in water) and ending at 95% B (B: 0.05% TFA in acetonitrile) over 3.2 min with a total run time of 4.5 min. Oven: 40° C.; Flow rate: of 1.5 ml/min.

Intermediates

Intermediate II-1

Ethyl [(5-bromo-3-chloropyridin-2-yl)carbamothioyl]carbamate

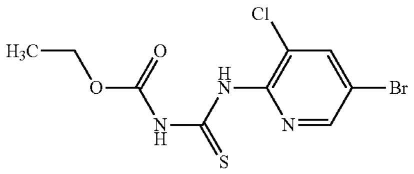 [SMILES: CCOC(=O)NC(=S)Nc1ncc(Br)cc1Cl]

To a solution of 5-bromo-3-chloropyridin-2-amine [CAS-RN 38185-55-6](4.50 g, 21.7 mmol) in 1,4-dioxane (67 ml), ethyl carbonisothiocyanatidate (2.6 ml, 22 mmol) was added dropwise and the reaction was stirred at rt for 12 h. The reaction mixture was concentrated and the residue was taken up in 2 ml tert-butyl methyl ether and 1 ml cyclohexane and filtered by suction filtration. The solid was further washed with 3 ml tert-butyl methyl ether dried under high vacuum to give 6.50 g (100% purity, 88% yield) of the title compound.

LC-MS (method 1): $R^t$=1.75 min; MS (ESIpos): m/z=338 $[M+H]^+$ $^1$H-NMR (400 MHz, DMSO-$d_6$) δ [ppm]: 1.27 (t, 3H), 4.23 (d, 1H), 4.23 (q, 1H), 8.44 (d, 1H), 8.61 (d, 1H), 11.41 (s, 1H), 11.52 (s, 1H).

Intermediate II-2

6-Bromo-8-chloro[1,2,4]triazolo[1,5-a]pyridin-2-amine

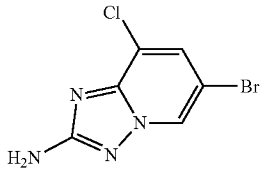 [SMILES: Nc1nc2c(Cl)cc(Br)cn2n1]

To a solution of hydroxylamine hydrochloride (8.96 g, 129 mmol) and N,N-diisopropylethylamine (21 ml, 120 mmol) in a mixture of methanol/ethanol 1:1 (120 ml) heated to 60° C. was added ethyl [(5-bromo-3-chloropyridin-2-yl)carbamothioyl]carbamate (8.08 g, 23.9 mmol) dissolved in THF. The resulting hydrogen sulfide gas was trapped into a sodium hypochlorite/sodium hydroxyde solution. The reaction was stirred at 60° C. for 1 h. The reaction mixture was allowed to cool down to rt and quenched with 10% aq. sodium bicarbonate solution (25 ml) to achieve pH=7-8. The reaction was further diluted with water (120 ml), and stirred for 10 min. The resulting precipitate collected by suction filtration and washed with water (250 ml) and diethylether (120 ml), then dried in vacuum to give 5.62 g (100% purity, 95% yield) of the title compound.

LC-MS (method 1): $R^t$=1.04 min; MS (ESIpos): m/z=246 $[M+H]^+$ $^1$H-NMR (500 MHz, DMSO-$d_6$) δ [ppm]: 6.36 (s, 2H), 7.86 (d, 1H), 8.94 (d, 1H).

Intermediate II-3

Ethyl [(4,6-dichloropyridin-2-yl)carbamothioyl]carbamate

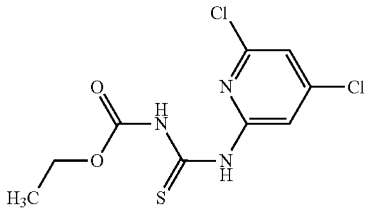 [SMILES: CCOC(=O)NC(=S)Nc1cc(Cl)cc(Cl)n1]

To a solution of 4,6-dichloropyridin-2-amine [CAS-RN 116632-24-7](141 g, 866 mmol) in 1,4-dioxane (1.8 1), ethyl carbonisothiocyanatidate (110 ml, 950 mmol) was slowly added dropwise and the reaction was stirred at rt for 31 h. The reaction mixture was concentrated in vacuo and the residue was taken up in petroleum ether (2 1) and collected by suction filtration. The solid was further dried under high vacuum to give 278 g of the title compound which was used without further purification in the next step.

Intermediate II-4

5,7-Dichloro[1,2,4]triazolo[1,5-a]pyridin-2-amine

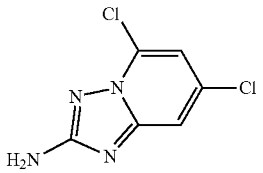 [SMILES: Nc1nc2cc(Cl)cc(Cl)n2n1]

To a solution of hydroxylamine hydrochloride (135 g, 1.95 μmol) and N,N-diisopropylethylamine (310 ml, 1.8 μmol) in a 1:1 mixture of methanol and ethanol (2.71) heated to 60° C. was added ethyl [(4,6-dichloropyridin-2-yl)carbamothioyl]carbamate (106 g, 360 mmol) as a solution in THF. The resulting hydrogen sulfide gas was trapped with a sodium hypochlorite/sodium hydroxyde solution. The reaction was stirred at 60° C. for 1 h. The reaction mixture was allowed to cool down to rt and quenched with 10% aq. sodium bicarbonate solution (2.7 1). The reaction was further diluted with water (5.5 1) and stirred for 10 min. The resulting precipitate was collected by suction filtration. The solid was dried in vacuo over phosphorus pentoxide to give 52.9 g (100% purity, 72% yield) of the title compound.

LC-MS (method 1): $R^t$=1.04 min; MS (ESIpos): m/z=202 $[M+H]^+$ $^1$H-NMR (500 MHz, DMSO-$d_6$) δ [ppm]: 6.44 (s, 2H), 7.35 (d, 1H), 7.57 (d, 1H).

Intermediate II-5

7-{[4-(4,4,5,5-Tetramethyl-1,3,2-dioxaborolan-2-yl)-1H-pyrazol-1-yl]methyl}-1H-indazole

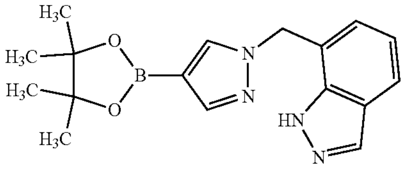 [SMILES: CC1(C)OB(c2cnn(Cc3cccc4cn[nH]c34)c2)OC1(C)C]

To a solution of 7-(bromomethyl)-1H-indazole hydrobromide [CAS-RN 1956306-65-2](1.30 g, 81% purity, 3.61 mmol) in DMF (15 ml) at −50° C. were added 4-(4,4,5,5-tetramethyl-1,3,2-dioxaborolan-2-yl)-1H-pyrazole (1.05 g, 5.41 mmol) and caesium carbonate (2.35 g, 7.21 mmol). The reaction was stirred for 1.5 h and then filtered. The filtrate was diluted with water (20 ml) and extracted with ethyl acetate (3×20 ml). The combined organic layers were washed with brine (50 ml), dried over anhydrous sodium sulfate, and the solvent was evaporated under reduced pressure. The residue was purified by chromatography (column: C18, 120 g, eluent: water (A), acetonitrile (B); gradient: 10% B to 70% B in 25 min; flow rate: 60 ml/min) to yield 290 mg (99% purity, 25% yield) of the title compound.

LC-MS (method 5): $R^t$=1.40 min; MS (ESIpos): m/z=325 $[M+H]^+$

Intermediate II-6

1-[(IS)-1-Phenylpropyl]-4-(4,4,5,5-tetramethyl-1,3,2-dioxaborolan-2-yl)-1H-pyrazole

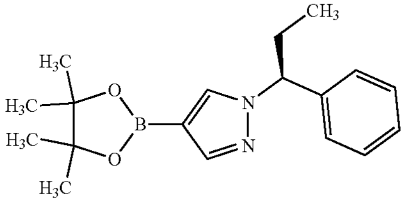 [SMILES: CC[C@@H](c1ccccc1)n1cc(B2OC(C)(C)C(C)(C)O2)cn1]

(4,4,5,5-Tetramethyl-1,3,2-dioxaborolan-2-yl)-1H-pyrazole (1.57 g, 8.08 mmol) was dissolved in THF (14 ml). (1R)-1-Phenylpropan-1-ol (1.00 g, 7.34 mmol) and triphenylphosphine (3.85 g, 14.7 mmol) were added to the solution. DBAD (3.38 g, 14.69 mmol) in THF (6 ml) was added to the mixture at rt. After stirring for 1 h under reflux the reaction mixture was cooled to rt and concentrated under reduced pressure. The residue was purified by flash column chromatography (C18, 330 g; eluent: water/acetonitrile gradient 70:30 to 40:60; flow rate: 80 ml/min) to yield 800 mg (95% purity, 33% yield) of the title compound.

LC-MS (method 5): $R^t$=1.73 min; MS (ESIpos): m/z=313 $[M+H]^+$ $^1$H-NMR (300 MHz, DMSO-$d_6$) δ [ppm]: 0.77 (t, 3H), 1.24 (s, 12H), 2.12 (dquin, 1H), 2.28-2.45 (m, 1H), 5.34 (dd, 1H), 7.23-7.39 (m, 5H), 7.62 (s, 1H), 8.09 (s, 1H).

Intermediate II-7

1-[(1S)-1-(4-Fluorophenyl)propyl]-4-(4,4,5,5-tetramethyl-1,3,2-dioxaborolan-2-yl)-1H-pyrazole

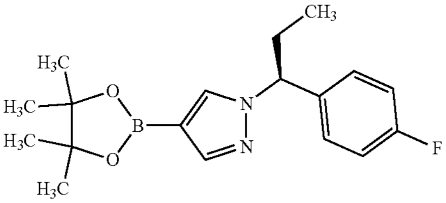 [SMILES: CC[C@@H](c1ccc(F)cc1)n1cc(B2OC(C)(C)C(C)(C)O2)cn1]

To a solution of 4-(4,4,5,5-tetramethyl-1,3,2-dioxaborolan-2-yl)-1H-pyrazole (2.77 g, 14.3 mmol), (1R)-1-(4-fluorophenyl)propan-1-ol (2.00 g. 13.0 mmol) and triphenylphosphine (6.81 g. 25.9 mmol) in THF (40 ml) was added dropwise DBAD (5.97 g. 25.9 mmol) in THF (10 ml). The resulting mixture was stirred for 2 h at reflux. It was then cooled to rt and the reaction mixture was concentrated under reduced pressure. The residue was purified by flash column chromatography (C18, 25 g, eluent: water/acetonitrile gradient 85:15 to 50:50; flow rate: 80 ml/min to yield 1.94 g (98% purity, 44% yield) of the title compound.

LC-MS (method 9): $R^t$=2.53 min; MS (ESIpos): m/z=331 $[M+H]^+$ $^1$H-NMR (400 MHz, DMSO-$d_6$) δ [ppm]: 0.76 (t, 3H), 1.23 (s, 12H), 2.10 (m, 1H), 2.28-2.41 (m, 1H), 5.36 (dd, 1H), 7.11-7.19 (m, 2H), 7.39-7.45 (m, 2H), 7.64 (s, 1H), 8.11 (s, 1H).

$^{19}$F-NMR (376 MHz, DMSO-$d_6$) δ [ppm]: −114.90 (s, 1F).

Intermediate II-8

4-(4,4,5,5-Tetramethyl-1,3,2-dioxaborolan-2-yl)-1-{1-[4-(trifluoromethyl)phenyl]propyl}-1H-pyrazole (mixture of enantiomers)

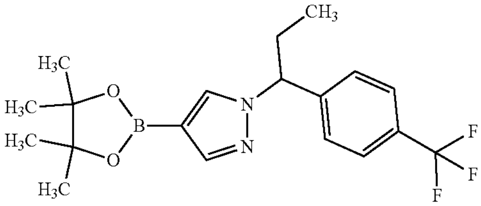 [SMILES: CCC(c1ccc(C(F)(F)F)cc1)n1cc(B2OC(C)(C)C(C)(C)O2)cn1]

To a solution of 1-[4-(trifluoromethyl)phenyl]propan-1-ol (3.00 g, 14.5 mmol), 4-(4,4,5,5-tetramethyl-1,3,2-dioxaborolan-2-yl)-1H-pyrazole (3.42 g, 17.5 mmol) and triphenylphosphine (7.63 g, 29.1 mmol) in THF (40 ml) at rt was added a solution of DBAD (6.70 g, 29.1 mmol) in THF (20 ml). The resulting mixture was stirred under reflux for 3 h. It was cooled to rt and the solvent was removed in vacuo. The residue was purified by column chromatography (C18, 40 g; eluent: water/acetonitrile gradient 80:20 to 40:60; flow rate: 50 ml/min) to yield 2.95 g (94% purity, 50% yield) the title compound.

LC-MS (method 5): Rc=1.88 min; MS (ESIpos): m/z=381 $[M+H]^+$ $^1$H-NMR (300 MHz, DMSO-$d_6$) δ [ppm]: 0.79 (t, 3H), 1.25 (s, 12H), 2.07-2.23 (m, 1H), 2.30-2.48 (m, 1H), 5.49 (dd, 1H), 7.57 (d, 2H), 7.67 (s, 1H), 7.71 (d, 2H), 8.17 (s, 1H).

$^{19}$F-NMR (282 MHz, DMSO-$d_6$) δ [ppm]: −60.99 (s, 3F).

Intermediate 11-9

Phenyl(tetrahydro-2H-pyran-4-yl)methanol (mixture of enantiomers)

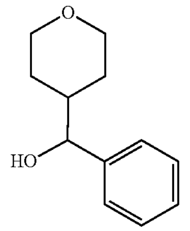 [SMILES: OC(c1ccccc1)C1CCOCC1]

A solution of phenylmagnesium bromide in diethyl ether (23 ml, 3.0 M, 70 mmol) was cooled with a water ice bath and a solution of tetrahydro-2H-pyran-4-carbaldehyde (4.00 g, 35.0 mmol) in diethyl ether (20 ml) was added dropwise (inner temperature was kept<10° C.). The mixture was warmed to rt, THF (40 ml) was added and stirred for 30 min. Subsequently, satd. aqueous ammonium chloride solution (40 ml) was added with cooling. The mixture was stirred for 5 min. Subsequently, the aqueous layer was separated and extracted with diethyl ether. The combined organic layers were washed with satd. aqueous ammonium chloride solution (50 ml), water (50 ml) and brine (50 ml) and dried over anhydrous sodium sulfate. The solvent was removed under reduced pressure and the residue was purified by column chromatography (Biotage® SNAP Ultra 100 g cartridge, eluent: cyclohexane/ethyl acetate gradient 92:8 to 41:59) to yield 4.11 g (100% purity, 61% yield) of the title compound.

GC-MS (GC-MS method 1): $R^t$=5.46 min; MS (ESIpos): m/z=192 [M]$^+$ $^1$H-NMR (600 MHz, DMSO-$d_6$) δ [ppm]: 1.06-1.11 (m, 1H), 1.19-1.30 (m, 2H), 1.63-1.70 (m, 2H), 3.12-3.17 (m, 1H), 3.17-3.23 (m, 1H), 3.76 (br dd, 1H), 3.84 (br dd, 1H), 4.24 (dd, 1H), 5.17 (d, 1H), 7.22 (tt, 1H), 7.26-7.33 (m, 4H).

Intermediate II-10

1-[Phenyl(tetrahydro-2H-pyran-4-yl)methyl]-4-(4,4,5,5-tetramethyl-1,3,2-dioxaborolan-2-yl)-1H-pyrazole (mixture of enantiomers)

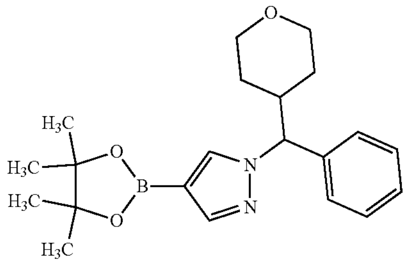 [SMILES: CC1(C)OB(c2cnn(C(c3ccccc3)C3CCOCC3)c2)OC1(C)C]

To a mixture of 4-(4,4,5,5-tetramethyl-1,3,2-dioxaborolan-2-yl)-1H-pyrazole (1.00 g, 5.15 mmol) and phenyl(tetrahydro-2H-pyran-4-yl)methanol (991 mg, 5.15 mmol) in toluene (10 ml) was added CMBP (1.24 g, 5.15 mmol) and the mixture was heated to 80° C. overnight. The solvent was then removed in vacuo and the residue was purified by column chromatography (Biotage® SNAP Ultra 25 g cartridge, eluent: cyclohexane/ethyl acetate gradient 95:5 to 80:20) to yield 1.60 g (57% purity, 48% yield) of the title compound which was used without further purification.

LC-MS (method 1): $R^t$=2.08 min; MS (ESIpos): m/z=369 [M+H]$^+$

Intermediate II-11

1-[4-(Morpholin-4-yl)phenyl]propan-1-ol (mixture of enantiomers)

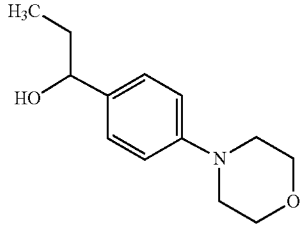 [SMILES: CCC(O)c1ccc(N2CCOCC2)cc1]

4-(Morpholin-4-yl)benzaldehyde (2.00 g, 10.5 mmol) was dissolved in diethyl ether (16 ml) and cooled to an inner temperature of −5° C. Within 30 min a solution of ethylmagnesium bromide in diethyl ether (4.2 ml, 3.0 M, 13 mmol) was added dropwise. Afterwards, the solution was warmed to rt. Water ice was added to the reaction mixture and after stirring for 5 min water was added. The mixture was acidified with 4N hydrochloric acid. The organic layer was separated and the aqueous layer was extracted twice with diethyl ether. The combined organic layers were washed with brine and dried over anhydrous sodium sulfate. The solvent was then removed in vacuo to yield 2.41 g (96% purity, 100% yield) of the title compound.

LC-MS (method 1): $R^t$=1.24 min; MS (ESIpos): m/z=222 [M+H]$^+$ $^1$H-NMR (600 MHz, DMSO-$d_6$) δ [ppm]: 0.79 (t, 3H), 1.50-1.64 (m, 2H), 3.03-3.08 (m, 4H), 3.70-3.75 (m, 4H), 4.30-4.35 (m, 1H), 4.90 (d, 1H), 6.88 (d, 2H), 7.16 (d, 2H).

Intermediate II-12

4-(4-{1-[4-(4,4,5,5-Tetramethyl-1,3,2-dioxaborolan-2-yl)-1H-pyrazol-1-yl]propyl}phenyl)morpholine (mixture of enantiomers)

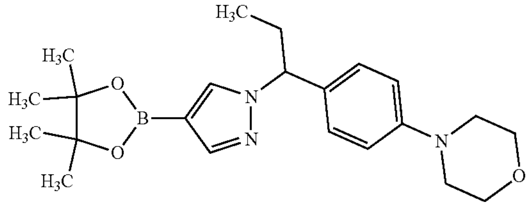 [SMILES: CCC(c1ccc(N2CCOCC2)cc1)n1cc(B2OC(C)(C)C(C)(C)O2)cn1]

DIAD (2.4 ml, 12 mmol) and triphenylphosphine (3.20 g, 12.2 mmol) were dissolved in THE (20 ml) and cooled to 0° C. 1-[4-(Morpholin-4-yl)phenyl]propan-1-ol (2.16 g, 9.76 mmol) was added and subsequently a solution of 4-(4,4,5,5-tetramethyl-1,3,2-dioxaborolan-2-yl)-1H-pyrazole (1.58 g, 8.13 mmol) in THF (20 ml) was added dropwise. The mixture was stirred at rt overnight. The solvent was removed in vacuo and the residue was purified by column chromatography (Biotage® SNAP Ultra C18 120 g cartridge, eluent: acetonitrile/water gradient 80:20 to 95:5) to yield 594 mg (70% purity, 13% yield) of the title compound.

LC-MS (method 1): $R^t$=2.11 min; MS (ESIpos): m/z=398 $[M+H]^+$ $^1$H-NMR (500 MHz, DMSO-$d_6$) δ [ppm]: 0.75 (t, 3H), 1.23 (s, 12H), 2.02-2.13 (m, 1H), 2.24-2.37 (m, 1H), 3.05-3.08 (m, 4H), 3.70-3.73 (m, 4H), 5.21 (dd, 1H), 6.86-6.90 (m, 2H), 7.21-7.25 (m, 2H), 7.58 (s, 1H), 8.00 (s, 1H).

Intermediate II-13 tert-Butyl 4-[hydroxy(phenyl)methyl]piperidine-1-carboxylate (mixture of enantiomers)

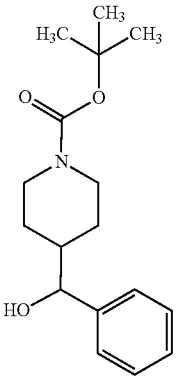

A solution of tert-butyl 4-formylpiperidine-1-carboxylate (3.00 g, 14.1 mmol) in THE (30 ml) was cooled with a water ice bath and a solution of phenylmagnesium bromide in diethyl ether (9.4 ml, 3.0 M, 28 mmol) was added dropwise (inner temperature was kept<10° C.). The reaction was then warmed to rt and stirring was continued for 1 h. The mixture was again cooled with water ice and satd. aqueous ammonium chloride solution (50 ml) was added. The aqueous layer was separated and the pH was adjusted to 6 by addition on 1N hydrochloric acid. It was extracted twice with ethyl acetate (50 ml each) and the combined organic layers were washed with brine and dried over anhydrous anhydrous sodium sulfate. The solvent was evaporated under reduced pressure and the residue was purified by column chromatography (Biotage® SNAP Ultra 50 g cartridge, eluent: cyclohexane/ethyl acetate gradient 0:100 to 60:40) to yield 2.35 g (95% purity, 54% yield) of the title compound.

GC-MS (GC-MS method 1): $R^t$=7.34 min; MS (ESIpos): m/z=235 $[M-C(CH_3)_3+H]^+$ $^1$H-NMR (600 MHz, DMSO-$d_6$) δ [ppm]: 1.00-1.12 (m, 2H), 1.19-1.24 (m, 1H), 1.37 (s, 9H), 1.56-1.65 (m, 1H), 1.70-1.76 (m, 1H), 2.49-2.68 (m, 2H), 3.83-4.00 (m, 2H), 4.27 (dd, 1H), 5.19 (d, 1H), 7.20-7.24 (m, 1H), 7.26-7.33 (m, 4H).

Intermediate II-14 tert-Butyl 4-{phenyl[4-(4,4,5,5-tetramethyl-1,3,2-dioxaborolan-2-yl)-1H-pyrazol-1-yl]methyl}piperidine-1-carboxylate (mixture of enantiomers)

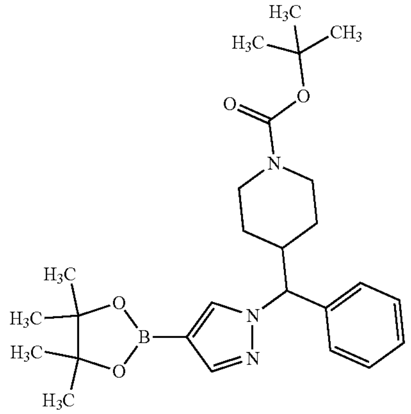 [SMILES: CC(C)(C)OC(=O)N1CCC(C(c2ccccc2)n2cc(B3OC(C)(C)C(C)(C)O3)cn2)CC1]

A solution of DIAD (1.7 ml, 8.6 mmol) and triphenylphosphine (2.25 g, 8.58 mmol) in THF (10 ml) was cooled to 0° C. and tert-butyl 4-[hydroxy(phenyl)methyl]piperidine-1-carboxylate (2.00 g, 6.86 mmol) was added as a solution in THF (10 ml). 4-(4,4,5,5-Tetramethyl-1,3,2-dioxaborolan-2-yl)-1H-pyrazole (1.11 g, 5.72 mmol) in THE (10 ml) was added dropwise. The reaction mixture was warmed to rt and stirred overnight. The solvent was then removed in vacuo. The crude product was purified by column chromatography (Biotage® SNAP Ultra 100 g cartridge, eluent: cyclohexane/ethyl acetate gradient 100:0 to 80:20, then ethyl acetate/2-propanol 10:1) to yield material which was further purified by chromatography (Biotage® SNAP Ultra C18 120 g cartridge, eluent: acetonitrile/water gradient 80:20 to 95:5) to yield 582 mg (80% purity, 17% yield) of the title compound.

LC-MS (method 1): $R^t$=2.49 min; MS (ESIpos): m/z=468 $[M+H]^+$ $^1$H-NMR (400 MHz, DMSO-$d_6$) δ [ppm]: 1.057 (0.52), 1.070 (0.60), 1.142 (0.60), 1.157 (1.35), 1.175 (2.23), 1.192 (1.28), 1:227 (11.16), 1.245 (0.80), 1.367 (16.00), 1.988 (3.37), 4.020 (0.91), 4.038 (0.82), 5.120 (0.62), 5.147 (0.59), 7.278 (0.71), 7.284 (0.45), 7.296 (0.71), 7.321 (0.87), 7.340 (1.23), 7.357 (0.50), 7.515 (1.16), 7.533 (0.93), 7.620 (1.52), 8.073 (1.59).

Intermediate II-15

1-(2-Methoxypyridin-4-yl)-2-methylpropan-1-ol (mixture of enantiomers)

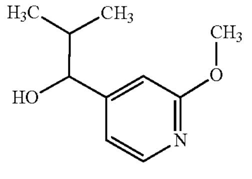

2-Methoxypyridine-4-carbaldehyde (6.00 g, 43.8 mmol) was dissolved in THF and cooled to 0° C. A solution of isopropylmagnesium bromide in 2-methyltetrahydrofuran (18 ml, 2.9 M, 53 mmol) was added dropwise with cooling. After complete addition the mixture was further stirred at 0° C. for 1 h and subsequently warmed to rt. Stirring was continued for 3 h. While cooling, satd. aq. ammonium chloride solution (150 ml) was added, then diethyl ether (250 ml) and water (50 ml). The organic layer was separated and washed with brine. It was dried over anhydrous sodium sulfate and the solvent was evaporated. The residue was puried by column chromatography (Biotage® SNAP Ultra 50 g cartridge, eluent: cyclohexane/ethyl acetate gradient) to yield 1.93 g (96% purity, 23% yield) of the title compound.

GC-MS (GC-MS method 1): $R^t$=4.40 min; MS (ESIpos): m/z=181 $[M]^+$ $^1$H-NMR (500 MHz, DMSO-$d_6$) δ [ppm]: 0.79 (d, 3H), 0.81 (d, 3H), 1.77-1.87 (m, 1H), 3.83 (s, 3H), 4.27 (t, 1H), 5.28 (d, 1H), 6.70 (s, 1H), 6.90 (dd, 1H), 8.07 (d, 1H).

Intermediate II-16

2-Methoxy-4-{2-methyl-1-[4-(4,4,5,5-tetramethyl-1,3,2-dioxaborolan-2-yl)-1H-pyrazol-1-yl]propyl}pyridine (mixture of enantiomers)

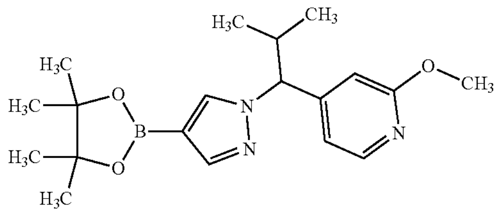

A solution of 4-(4,4,5,5-tetramethyl-1,3,2-dioxaborolan-2-yl)-1H-pyrazole (1.17 g, 6.03 mmol) and triphenyphosphine (2.06 g, 7.84 mmol) in 2-methyltetrahydrofuran (11 ml) was cooled to 0° C. DIAD (1.5 ml, 7.8 mmol) was added dropwise and the mixture was stirred for 15 min before 1-(2-methoxypyridin-4-yl)-2-methylpropan-1-ol (1.48 g, 96% purity, 7.84 mmol) was added dropwise as a solution in 2-methyltetrahydrofuran (6.0 ml). Stirring was continued for 30 min at 0° C., then at rt overnight. The solvent was evaporated in vacuo and the residue was purified by column chromatography (Biotage® SNAP Ultra 50 g cartridge, eluent: cyclohexane/ethyl acetate gradient) to yield 680 mg (88% purity, 28% yield) of the title compound.

LC-MS (method 2): Rc=1.13 min; MS (ESIpos): m/z=358 $[M+H]^+$ $^1$H-NMR (500 MHz, DMSO-$d_6$) δ [ppm]: 0.73 (d, 3H), 0.77 (d, 3H), 1.23 (s, 12H), 2.66-2.78 (m, 1H), 3.82 (s, 3H), 5.01 (d, 1H), 6.92 (s, 1H), 7.12 (dd, 1H), 7.63 (s, 1H), 8.12 (d, 1H), 8.13 (s, 1H).

Intermediate II-17

1-[6-(Difluoromethyl)pyridin-3-yl]propan-1-ol (mixture of enantiomers)

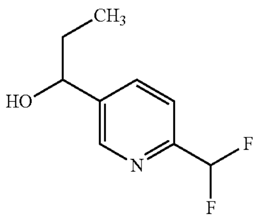

Under argon atmosphere, to a solution of 6-(difluoromethyl)pyridine-3-carbaldehyde (1.00 g, 6.36 mmol) at 0° C. in dry diethyl ether (20 ml) was added dropwise a solution of ethylmagnesium bromide (7.0 ml, 1.0 M in THF, 7.0 mmol). The reaction was stirred at rt for 12 h and then quenched with water. The reaction mixture was extracted three times with ethyl acetate, and the combined organic layers were washed with brine, dried over anhydrous sodium sulfate and concentrated. The residue was purified by column chromatography (eluent: cyclohexane/ethyl acetate 7:3) to yield 872 mg (88% purity, 64% yield) of the title compound.

LC-MS (method 1): $R^t$=1.09 min; MS (ESIpos): m/z=188 $[M+H]^+$ $^1$H-NMR (500 MHz, DMSO-$d_6$) δ [ppm]: 0.84 (t, 3H), 1.61-1.71 (m, 2H), 4.57-4.63 (m, 1H), 5.41 (d, 1H), 6.93 (t, 1H), 7.65 (d, 1H), 7.91 (dd, 1H), 8.62 (d, 1H).

Intermediate II-18

2-(Difluoromethyl)-5-{1-[4-(4,4,5,5-tetramethyl-1,3,2-dioxaborolan-2-yl)-1H-pyrazol-1-yl]propyl}pyridine (mixture of enantiomers)

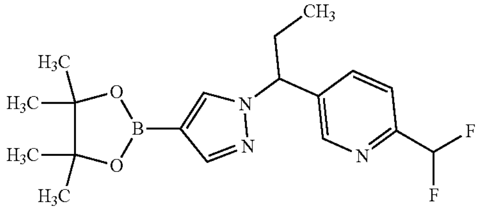 [SMILES: CCC(c1ccc(C(F)F)nc1)n1cc(B2OC(C)(C)C(C)(C)O2)cn1]

To a solution of 4-(4,4,5,5-tetramethyl-1,3,2-dioxaborolan-2-yl)-1H-pyrazole (1.80 g, 9.26 mmol) in THF (50 ml) was added 1-[6-(trifluoromethoxy)pyridin-3-yl]propan-1-ol (1.80, 7.72 mmol, 94.8% purity) and triphenylphosphine (6.07 g, 23.1 mmol). The di-tert-butyl azodicarboxylate (5.33 g, 23.14 mmol) in dry THF (10 ml) was added to the solution within 2 min at rt. After stirring for 0.5 h under reflux the reaction mixture was cooled to rt, then concentrated under reduced pressure. The crude product was purified by preparative HPLC (Column: C18, 330 g; Eluent A: Water, Eluent B: acetonitrile; Flow rate: 50 ml/min; Gradient: 20% B to 60% B in 25 min, 220/254 nm) The fractions containing the desired products were combined and concentrated in vacuo to yield 1.60 g (92% purity, 48% yield) of the title compound.

LC-MS (method 7): $R^t$=2.09 min; MS (ESIpos): m/z=364 $(M+H)^+$ $^1$H-NMR (300 MHz, DMSO-$d_6$) δ [ppm]: 0.78 (t, 3H), 1.24 (s, 12H), 2.11-2.47 (m, 2H), 5.53 (dd, 1H), 6.93 (t, 1H), 7.62-7.77 (m, 2H), 7.94 (d, 1H), 8.19 (s, 1H), 8.68 (br s, 1H).

Intermediate II-19

1-[6-(Difluoromethyl)pyridin-3-yl]-2-methylpropan-1-ol (mixture of enantiomers)

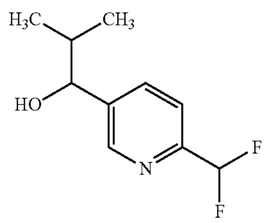

Under argon atmosphere, to a solution of 6-(difluoromethyl)pyridine-3-carbaldehyde [CAS-RN 946578-32-1] (2.45 g, 15.6 mmol) at 0° C. in dry 2-methyltetrahydrofuran (50 ml) was added dropwise a solution of isopropylmagnesium bromide (5.7 ml, 3.0 M in 2-methyltetrahydrofuran, 17 mmol). The reaction was stirred at rt for 12 h and then quenched with water. The reaction mixture was extracted three times with ethyl acetate, and the combined organic layers were washed with brine, dried over anhydrous sodium sulfate and concentrated. The residue was purified by column chromatography (silica gel, eluent: cyclohexane/ethyl acetate 7:3) to yield 991 mg (93% purity, 29% yield) of the title compound.

LC-MS (method 1): $R^t$=1.33 min; MS (ESIpos): m/z=202 $[M+H]^+$ $^1$H-NMR (400 MHz, DMSO-$d_6$) δ [ppm]: 0.77 (d, 6H), 0.84 (d, 6H), 1.87 (qd, 1H), 2.52-2.56 (m, 3H), 4.42 (t, 1H), 5.40 (d, 1H), 6.93 (t, 1H), 7.65 (d, 1H), 7.88 (dd, 1H), 8.58 (d, 1H).

Intermediate II-20

2-(Difluoromethyl)-5-{(2-methyl-1-[4-(4,4,5,5-tetramethyl-1,3,2-dioxaborolan-2-yl)-1H-pyrazol-1-yl]propyl}pyridine (mixture of enantiomers)

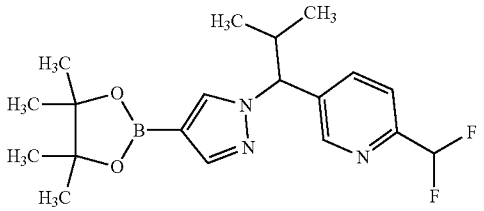 [SMILES: CC(C)C(c1ccc(C(F)F)nc1)n1cc(B2OC(C)(C)C(C)(C)O2)cn1]

Under argon atmosphere DIAD (1.7 ml, 8.5 mmol) and triphenylphosphine (2.23 g, 8.50 mmol) were stirred at 0° C. in dry THE (30 ml) for 15 min. Then 4-(4,4,5,5-tetramethyl-1,3,2-dioxaborolan-2-yl)-1H-pyrazole (1.10 g, 5.67 mmol) and 1-[6-(difluoromethyl)pyridin-3-yl]-2-methylpropan-1-ol (1.39 g, 90% purity, 6.24 mmol) in a solution of dry THE (10 ml) were slowly added. The reaction was stirred at rt for 12 h, then quenched with water. The reaction mixture was extracted two times with ethyl acetate, and the combined organic layers were washed with brine, dried over anhydrous sodium sulfate and concentrated. The residue was purified by column chromatography (silica gel, eluent: cyclohexane/ethyl acetate gradient 9:1 to 6:4) to yield 1.21 g (86% purity, 49% yield) of the title compound.

LC-MS (method 1): $R^t$=2.13 min; MS (ESIpos): m/z=378 $[M+H]^+$ $^1$H-NMR (400 MHz, DMSO-$d_6$) δ [ppm]: 0.76 (t, 6H), 1.20-1.26 (m, 12H), 2.80 (dq, 1H), 5.20 (d, 1H), 6.94 (t, 1H), 7.65 (s, 1H), 7.71 (d, 1H), 8.17 (s, 1H), 8.19 (dd, 1H), 8.82 (d, 1H).

Intermediate II-21

[6-(Difluoromethyl)pyridin-3-yl](tetrahydro-2H-pyran-4-yl)methanol (mixture of enantiomers)

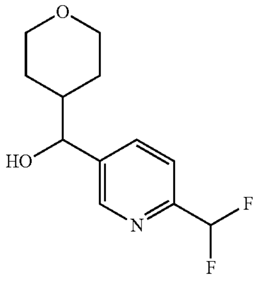 [SMILES: OC(c1ccc(C(F)F)nc1)C1CCOCC1]

To a solution of 5-bromo-2-(difluoromethyl)pyridine [CAS-RN 845827-13-6](2.00 g, 9.42 mmol) in freshly distilled THF (30 ml) was added a solution of isopropylmagnesium chloride-lithium chloride complex (14.5 ml, 18.9 mmol, 1.3 M in THF) dropwise at 0° C. under argon atmosphere. After stirring at 0° C. for 1.5 h, tetrahydro-2H-pyran-4-carbaldehyde [CAS-RN 50675-18-8](2.20 g, 18.9 mmol) was added at 0° C. under argon atmosphere. The solution was stirred at rt for 1.5 h and quenched with saturated ammonium chloride solution (60 ml) and extracted with ethyl acetate (40 ml×2). The combined organic layers were dried over anhydrous sodium sulfate, filtered and concentrated under reduced pressure. The residue was purified by column chromatography 120 g (eluent: petroleum ether/ethyl acetate, 85:15) to yield 1.72 g (95% purity, 71% yield) of the title compound.

LC-MS (method 7): $R^t$=0.71 min; MS (ESIpos): m/z=244 $[M+H]^+$ $^1$H-NMR (400 MHz, DMSO-$d_6$) δ [ppm]: 1.09-1.35 (m, 3H), 1.53-1.69 (m, 1H), 1.70-1.82 (m, 1H), 3.14-3.29 (m, 2H), 3.74-3.89 (m, 2H), 4.44 (dd, 1H), 5.52 (d, 1H), 6.94 (t, 1H), 7.67 (d, 1H), 7.91 (dd, 1H), 8.59-8.62 (m, 1H).

Intermediate II-22

2-(Difluoromethyl)-5-{tetrahydro-2H-pyran-4-yl[4-(4,4,5,5-tetramethyl-1,3,2-dioxaborolan-2-yl)-1H-pyrazol-1-yl]methyl}pyridine (mixture of enantiomers)

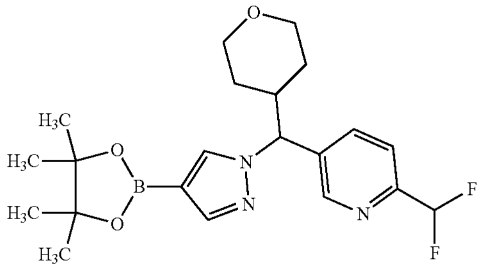 [SMILES: CC1(C)OB(c2cnn(C(c3ccc(C(F)F)nc3)C3CCOCC3)c2)OC1(C)C]

To a solution of [6-(difluoromethyl)pyridin-3-yl](tetrahydro-2H-pyran-4-yl)methanol (2.20 g, 8.59 mmol, 95% purity) in toluene (30 ml) was added 4-(4,4,5,5-tetramethyl-1,3,2-dioxaborolan-2-yl)-1H-pyrazole (3.33 g, 17.2 mmol) and cyanomethylenetributylphosphorane (2.70 g, 11.2 mmol) at rt. The resulting mixture was irradiated for 3 h at 160° C. in a microwave reactor. The reaction mixture was cooled down to rt, then concentrated under reduced pressure. The crude mixture was purified by preparative HPLC (Column: C18, 330 g; Eluent A: Water, Eluent B: acetonitrile; Flow rate: 100 ml/min; Gradient: 10% B to 60% B in 40 min, 220/254 nm), to afford 840 mg (98% purity, 23% yield) of the title compound.

LC-MS (method 7): $R^t$=1.32 min; MS (ESIpos): m/z=420 $(M+H)^+$ $^1$H-NMR (300 MHz, DMSO-$d_6$) δ [ppm]: 0.68-1.12 (m, 3H), 1.16-1.51 (m, 13H), 2.56-2.82 (m, 1H), 3.24 (br t, 2H), 3.72-3.88 (m, 2H), 5.36 (d, 1H), 6.94 (t, 1H), 7.65-7.78 (m, 2H), 8.16 (s, 1H), 8.20 (dd, 1H), 8.83 (br s, 1H).

Intermediate II-23

1-[6-(Trifluoromethyl)pyridin-3-yl]propan-1-ol (mixture of enantiomers)

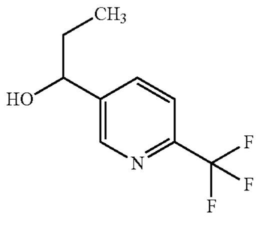

Under argon, a solution of ethylmagnesium bromide in THF (40 ml, 1.0 M, 40 mmol) was added dropwise at 0° C. to a solution of 6-(trifluoromethyl)pyridine-3-carbaldehyde [CAS-RN 386704-12-7](5.80 g, 33.1 mmol) in dry THF (100 ml). The reaction was stirred and rt for 3 h and quenched with water. The reaction mixture was extracted two times with ethyl acetate, and the organic layer was washed with brine, then dried over anhydrous sodium sulfate and concentrated. The residue was purified by column chromatography (Biotage® SNAP Ultra 100 g cartridge, eluent: cyclohexane/ethyl acetate 8:2) to yield 3.65 g (99% purity, 53% yield) of the title compound.

LC-MS (method 1): $R^t$=1.38 min; MS (ESIpos): m/z=206 $[M+H]^+$ $^1$H-NMR (400 MHz, DMSO-$d_6$) δ [ppm]: 0.85 (t, 3H), 1.63-1.71 (m, 2H), 4.65 (q, 1H), 5.51 (d, 1H), 7.86 (d, 11H), 8.00 (d, 1H), 8.71 (s, 1H).

Intermediate II-24

5-{1-[4-(4,4,5,5-Tetramethyl-1,3,2-dioxaborolan-2-yl)-1H-pyrazol-1-yl]propyl}-2-(trifluoromethyl)pyridine (mixture of enantiomers)

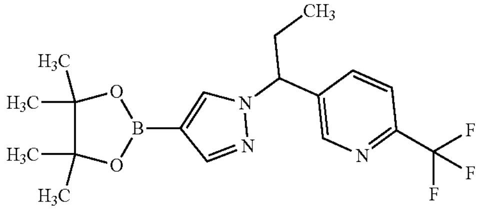 [SMILES: CCC(c1ccc(C(F)(F)F)nc1)n1cc(B2OC(C)(C)C(C)(C)O2)cn1]

Under argon atmosphere DIAD (4.3 ml, 22 mmol) and triphenylposphine (5.73 g, 21.9 mmol) were stirred at 0° C. in dry THF (100 ml) for 15 min. Then 4-(4,4,5,5-tetramethyl-1,3,2-dioxaborolan-2-yl)-1H-pyrazole (2.83 g, 14.6 mmol) and 1-[6-(trifluoromethyl)pyridin-3-yl]propan-1-ol (3.59 g, 17.5 mmol) in a solution of dry THF (100 ml) (20 ml) were slowly added. The reaction was stirred at rt for 12 h and then concentrated. The crude product was purified by column chromatography (Biotage® SNAP Ultra 100 g cartridge, eluent: cyclohexane/ethyl acetate gradient 100:0 to 85:15) to yield 5.29 g (78% purity, 74% yield) of the title compound.

LC-MS (method 3): $R_t$=1.45 min; MS (ESIpos): m/z=382 $[M+H]^+$ $^1$H-NMR (400 MHz, DMSO-$d_6$) δ [ppm]: 0.79 (t, 3H), 1.24 (m, 12H), 2.17-2.22 (m, 1H), 2.32-2.47 (m, 1H), 5.59 (dd, 1H), 7.67 (s, 1H), 7.89 (d, 1H), 8.03 (dd, 1H), 8.20 (s, 1H), 8.77 (d, 1H).

Intermediate II-25

2-Methyl-1-[6-(trifluoromethyl)pyridin-3-yl]propan-1-ol (mixture of enantiomers)

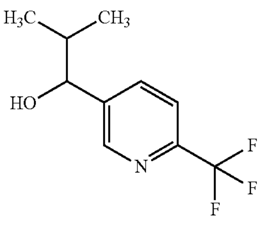

To a solution of isopropylmagnesium bromide in THF (252 ml, IM, 250 mmol) at 0° C. was added 6-(trifluoromethyl)nicotinaldehyde (20.0 g, 114 mmol) in diethyl ether (130 ml) dropwise within 15 min. After stirring for 1 h at rt water (1.5 1) was added and the mixture was concentrated in vacuo. The solids were filtered off and the filtrate was extracted three times with ethyl acetate (200 ml each). The combined organic layers were washed with brine (400 ml) and dried over anhydrous anhydrous sodium sulfate. The solvent was evaporated under reduced pressure and the crude product was purified by column chromatography (silica gel 330 g; eluent: petroleum ether/ethyl acetate 9:1) to give 10.8 g (98% purity, 42% yield) of the title compound.

LC-MS (method 10): $R^t$=0.89 min; MS (ESIpos): m/z=220 $(M+H)^+$ $^1$H-NMR (400 MHz, DMSO-$d_6$) δ [ppm]: 0.79 (d, 3H), 0.83 (d, 3H), 1.82-1.95 (m, 1H), 4.48 (t, 1H), 5.49 (d, 1H), 7.86 (d, 1H), 7.95-7.99 (m, 1H), 8.67-8.69 (m, 1H).

$^{19}$F-NMR (376 MHz, DMSO-$d_6$) δ [ppm]: −66.33 (s, 3F).

Intermediate II-26

5-{2-Methyl-1-[4-(4,4,5,5-tetramethyl-1,3,2-dioxaborolan-2-yl)-1H-pyrazol-1-yl]propyl}-2-(trifluoromethyl)pyridine (mixture of enantiomers)

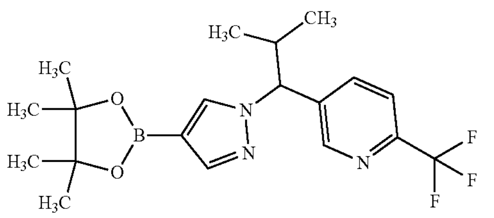 [SMILES: CC(C)C(c1ccc(C(F)(F)F)nc1)n1cc(B2OC(C)(C)C(C)(C)O2)cn1]

To a solution of 2-methyl-1-[6-(trifluoromethyl)pyridin-3-yl]propan-1-ol (31.0 g, 97% purity, 137 mmol) in THF (280 ml) were added 4-(4,4,5,5-tetramethyl-1,3,2-dioxaborolan-2-yl)-1H-pyrazole (47.9 g, 247 mmol) and triphenylphosphine (72.0 g, 274 mmol). A solution of DBAD (63.2 g, 274 mmol) in THE (100 ml) was added within 15 min at rt. After stirring for 2 h under reflux, the reaction mixture was cooled to rt and concentrated under reduced pressure. The crude product was purified by flash column chromatography (C18, 330 g; eluent: water/acetonitrile gradient 70:30 to 40:60; flow rate: 50 ml/min) to yield 23.5 g (97% purity, 42% yield) of the title compound containing 15% boronic acid.

LC-MS (method 8): $R^t$=1.36 min; MS (ESIpos): m/z=396 $(M+H)^+$ $^1$H-NMR (300 MHz, DMSO-$d_6$) δ [ppm]: 0.73-0.79 (m, 6H), 1.22 (s, 12H), 2.70-2.87 (m, 1H), 5.27 (d, 1H), 7.67 (s, 1H), 7.91 (d, 1H), 8.17 (s, 1H), 8.27 (br d, 1H), 8.89-8.94 (m, 1H).

$^{19}$F-NMR (282 MHz, DMSO-$d_6$) δ [ppm]: −66.39 (s, 3F).

Intermediate II-27

Tetrahydro-2H-pyran-4-yl[6-(trifluoromethyl)pyridin-3-yl]methanol (mixture of enantiomers)

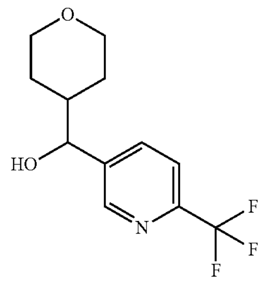 [SMILES: OC(c1ccc(C(F)(F)F)nc1)C1CCOCC1]

To 2-propylmagnesiumchloride (4.1 ml, 2.0 M in THF, 8.2 mmol) was added lithium chloride (366 mg, 8.63 mmol) and the suspension was stirred for 1 h at rt and then cooled to 0° C. 5-Bromo-2-(trifluoromethyl)pyridine (1.95 g, 8.63 mmol) was dissolved in THF (2.3 ml) and the solution was added dropwise, whilst the internal temperature was kept<25° C. The mixture was stirred for 1 h at rt and then added dropwise to a solution of tetrahydro-2H-pyran-4-carbaldehyde (5.00 g, 43.8 mmol) in THF (90 ml) while cooling with ice. After addition was complete, the reaction was warmed to rt and stirred for 1.5 h, then cooled with ice and saturated ammonium chloride solution (90 ml) was added. The mixture was diluted with water (30 ml) and ethyl acetate (30 ml). The aqeuous layer was extracted with ethyl acetate (100 ml). The combined organic layers were dried over anhydrous sodium sulfate and the solvent was removed in vacuo. The residue was purified by column chromatography (in two portions; Biotage® SNAP Ultra 100 g cartridge, eluent: cyclohexane/ethyl acetate gradient 100:0 to 40:60) to yield 8.65 g (99% purity, 75% yield) of the title compound.

LC-MS (GC-MS method 2): $R^t$=6.39 min; MS (ESIpos): m/z=261 $[M]^+$ $^1$H-NMR (600 MHz, DMSO-$d_6$) δ [ppm]: 1.11-1.16 (m, 1H), 1.25-1.36 (m, 2H), 1.58-1.64 (m, 1H), 1.74-1.82 (m, 1H), 3.19 (td, 1H), 3.22 (td, 1H), 3.79 (dd, 1H), 3.85 (dd, 1H), 4.49 (dd, 1H), 5.57 (d, 1H), 7.86 (d, 1H), 7.98 (dd, 1H), 8.69 (s, 1H).

Intermediate II-28

5-{Tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (mixture of enantiomers)

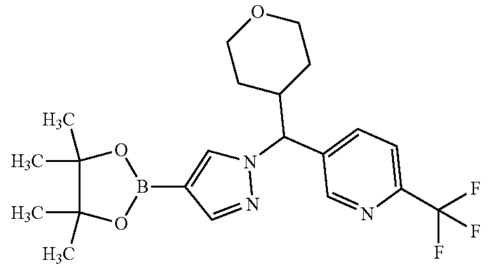 [SMILES: CC1(C)OB(c2cnn(C(c3ccc(C(F)(F)F)nc3)C3CCOCC3)c2)OC1(C)C]

DIAD (6.0 ml, 30 mmol) and triphenylphosphine (7.94 g, 30.3 mmol) were dissolved in THF (35 ml) and cooled to 0° C. A solution of tetrahydro-2H-pyran-4-yl[6-(trifluoromethyl)pyridin-3-yl]methanol (5.80 g, 22.2 mmol) in THE (35 ml) was added and subsequently a solution of 4-(4,4,5,5-tetramethyl-1,3,2-dioxaborolan-2-yl)-1H-pyrazole (3.92 g, 20.2 mmol) in THF (35 ml). The mixture was stirred at rt overnight. It was then diluted with ethyl acetate and washed with water and brine. The organic layer was dried over anhydrous sodium sulfate and the solvent was removed in vacuo. Diethyl ether (100 ml) was added to the residue and the residue was removed by filtration. The filtrate was concentrated in vacuo, triturated with diisopropyl ether (70 ml), and the precipitate was removed by filtration. The filtrate was concentrated and purified by column chromatography (in 3 portions, Biotage® SNAP Ultra 50 g and 100 g cartridges, eluent: cyclohexane/ethyl acetate gradient 90:10 to 50:50) to yield 5.50 g (75% purity, 47% yield) of the title compound.

LC-MS (method 1): $R^t$=2.09 min; MS (ESIpos): m/z=438 $[M+H]^+$ $^1$H-NMR (400 MHz, DMSO-$d_6$) δ [ppm]: 0.98-1.29 (m, 4H), 1.23 (d, 12H), 2.69-2.81 (m, 1H), 3.24 (m, 2H), 3.75-3.85 (m, 2H), 5.42 (d, 1H), 7.68 (s, 1H), 7.93 (d, 1H), 8.16 (s, 1H), 8.28 (dd, 1H), 8.92 (d, 1H).

Intermediate II-29

4,4,4-Trifluoro-3-[4-(4,4,5,5-tetramethyl-1,3,2-dioxaborolan-2-yl)-1H-pyrazol-1-yl]butanenitrile (mixture of enantiomers)

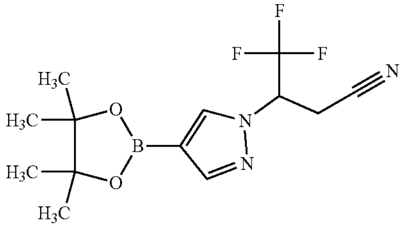 [SMILES: CC1(C)OB(c2cnn(C(CC#N)C(F)(F)F)c2)OC1(C)C]

A mixture of 4-(4,4,5,5-tetramethyl-1,3,2-dioxaborolan-2-yl)-1H-pyrazole (1.46 g, 7.51 mmol) and 4,4,4-trifluorobut-2-enenitrile (1.00 g, 8.26 mmol) in acetonitrile (20 ml) was cooled with an water ice bath and DBU (110 1, 750 μmol) was added dropwise. It was warmed to rt and stirred overnight. The solvent was removed under reduced pressure and the residue was purified by column chromatography (Biotage® SNAP Ultra 50 g cartridge, eluent: cyclohexane/ethyl acetate gradient 100:0 to 50:50) to yield 490 mg (95% purity, 20% yield) of the title compound.

LC-MS (method 1): $R^t$=1.81 min; MS (ESIpos): m/z=316 $[M+H]^+$ $^1$H-NMR (400 MHz, DMSO-$d_6$) δ [ppm]: 1.27 (s, 12H), 3.56 (dd, 1H), 3.66 (dd, 1H), 5.90-6.01 (m, 1H), 7.80 (s, 1H), 8.25 (s, 1H).

Intermediate II-30

4-[4-(4,4,5,5-tetramethyl-1,3,2-dioxaborolan-2-yl)-1H-pyrazol-1-yl]piperidine hydrochloride

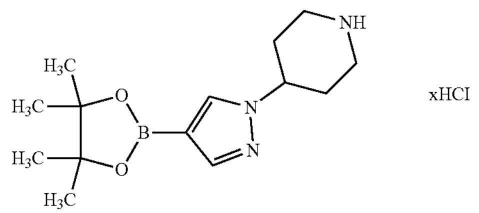 [SMILES: CC1(C)OB(c2cnn(C3CCNCC3)c2)OC1(C)C]

To a solution of tert-butyl 4-[4-(4,4,5,5-tetramethyl-1,3,2-dioxaborolan-2-yl)-1H-pyrazol-1-yl]piperidine-1-carboxylate [CAS-RN 877399-74-1](1.00 g, 2.65 mmol) in 1,4-dioxane (8.0 ml) was added dropwise a solution of hydrochloric acid in 1,4-dioxane (10 ml, 4.0 M, 40 mmol), and the reaction was stirred for 1 h at rt. The solution was concentrated under reduced pressure to yield 839 mg (100% purity, 100% yield) of the title compound.

LC-MS (method 4): $R^t$=1.56 min; MS (ESIpos): m/z=278 $[M+H]^+$ $^1$H-NMR (600 MHz, DMSO-$d_6$) δ [ppm]: 1.25 (s, 12H), 2.13-2.20 (m, 4H), 2.99-3.08 (m, 2H), 3.34-3.38 (m, 2H), 4.50-4.53 (m, 1H), 7.64 (s, 1H), 7.96 (s, 1H), 9.03 (br s, 2H).

Intermediate 11-31

1-(Oxetan-3-yl)-4-[4-(4,4,5,5-tetramethyl-1,3,2-dioxaborolan-2-yl)-1H-pyrazol-1-yl]piperidine

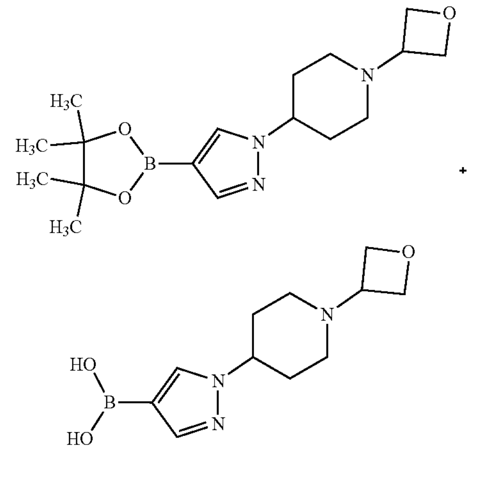

To a solution 4-[4-(4,4,5,5-tetramethyl-1,3,2-dioxaborolan-2-yl)-1H-pyrazol-1-yl]piperidine hydrochloride (7.00 g. 20.76 mmol) in methanol (40 ml) was added oxetan-3-one [CAS-RN 6704-31-0](2.99 g, 41.5 mmol). The resulting mixture was stirred at rt for 0.5 h. Sodium cyanoborohydride (13.0 g. 208 mmol) was added in portions. After stirring at rt for 3 h, the reaction mixture was concentrated under reduced pressure. The residue was purified by preparative HPLC (Column: C18, 330 g; eluent A: water, eluent B: acetonitrile; flow rate: 70 ml/min; gradient: 40% B to 80% B in 25 min, 220 and 254 nm). The fractions containing the desired product were 15 combined and lyophilized to afford 2.10 g (95% purity, 29% yield) of a mixture of 1-(oxetan-3-yl)-4-(4-(4,4,5,5-tetramethyl-1,3,2-dioxaborolan-2-yl)-1H-pyrazol-1-yl)piperidine and 1-(1-(oxetan-3-yl)piperidin-4-yl)-1H-pyrazol-4-ylboronic acid (ester/acid-ratio 1:2).

LC-MS (method 6): $R^t$=0.55 min; MS (ESIpos): m/z=252 [M acid+H]$^+$

LC-MS (method 6): $R^t$=1.18 min; MS (ESIpos): m/z=334 [M ester+H]$^+$ $^1$H-NMR (300 MHz, DMSO-$d_6$) δ [ppm]: 1.29 (s, 4H), 1.85-2.00 (m, 6H), 2.70-2.80 (m, 2H), 3.35-3.44 (m, 1H), 4.10-4.20 (m, 1H), 4.45-4.57 (m, 4H), 7.58 (s, 0.3H), 7.66 (s, 0.6H), 7.70-7.74 (m, 1.3H), 7.90 (s, 0.6H), 7.95 (s, 0.3H).

Intermediate II-32

6-(1-Benzyl-1H-pyrazol-4-yl)-8-chloro[1,2,4]triazolo[1,5-a]pyridin-2-amine

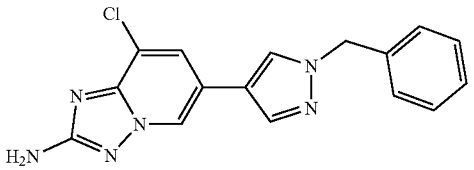 [SMILES: Nc1nc2c(Cl)cc(-c3cnn(Cc4ccccc4)c3)cn2n1]

6-Bromo-8-chloro[1,2,4]triazolo[1,5-a]pyridin-2-amine (4.30 g, 17.4 mmol) was reacted with 1-benzyl-4-(4,4,5,5-tetramethyl-1,3,2-dioxaborolan-2-yl)-1H-pyrazole (4.94 g, 17.4 mmol) for 2 h at 90° C. following general procedure B using 0.05 eq. catalyst. Subsequently, water (150 ml) was added and the precipitate was collected by suction filtration and washed twice with water (200 ml each, discarded) and ethyl acetate (200 ml each) to yield 3.50 g (98% purity, 61% yield) of the title compound. The organic filtrate was dried over anhydrous sodium sulfate and the solvent was evaporated under reduced pressure. The residue was triturated with acetonitrile/methanol (1:1, 50 ml) and the precipitate was collected by suction filtration and washed three times with acetonitrile (20 ml each) to yield 478 mg (98% purity, 8% yield) of the title compound. The filtrate was concentrated in vacuo and purified by column chromatography (Biotage® SNAP Ultra C18 30 g cartridge, eluent: acetonitrile/water gradient 5:95 to 50:50, then to 95:5) to yield a third batch of 88.0 mg (95% purity, 1% yield). The total yield was 70%.

LC-MS (method 2): $R^t$=0.76 min; MS (ESIpos): m/z=325 [M+H]$^+$

LC-MS (method 1): $R^t$=1.40 min; MS (ESIpos): m/z=325 [M+H]$^+$ $^1$H-NMR (400 MHz, DMSO-$d_6$) δ [ppm]: 5.34 (s, 2H), 6.23 (s, 2H), 7.25-7.39 (m, 5H), 7.93 (d, 1H), 8.05 (s, 1H), 8.40 (s, 1H), 8.88 (d, 1H).

Intermediate II-33

8-Chloro-6-(1-{1-[6-(trifluoromethyl)pyridin-3-yl]propyl}-1H-pyrazol-4-yl)[1,2,4]triazolo[1,5-a]pyridin-2-amine (mixture of enantiomers)

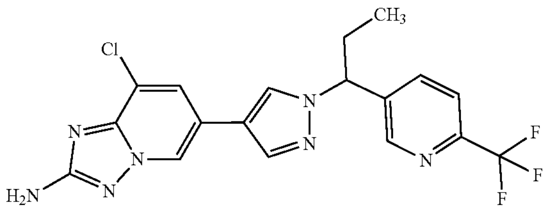 [SMILES: CCC(c1ccc(C(F)(F)F)nc1)n1cc(-c2cc(Cl)c3nc(N)nn3c2)cn1]

6-Bromo-8-chloro[1,2,4]triazolo[1,5-a]pyridin-2-amine (1.00 g, 4.04 mmol), 5-{1-[4-(4,4,5,5-tetramethyl-1,3,2-dioxaborolan-2-yl)-1H-pyrazol-1-yl]propyl}-2-(trifluoromethyl)pyridine (2.37 g, 78% purity, 4.85 mmol) and sodium carbonate (2.14 g, 20.2 mmol) were suspended under argon in a mixture of 1,4-dioxane (40 ml) and water (6.6 ml). Then 1,1'-Bis(diphenylphosphino)ferrocene-palladium(II)dichloride dichloromethane complex (165 mg, 202 μmol) was added, and the reaction was stirred for 2.5 h at 90° C. 1,1'-bis(diphenylphosphino)ferrocene-palladium(II)dichloride dichloromethane complex (165 mg, 202 μmol) was added and the reaction was stirred for 3 h at 90° C. The reaction mixture was filtered through a hydrophobic phase separation filter, washed with 15 ml of ethyl acetate, concentrated and dried under high vacuum. The residue was purified by column chromatography (Biotage® SNAP KP-NH 55 g cartridge, eluent: cyclohexane/ethyl acetate gradient 4:1 to 1:4) to yield 708 mg (95% purity, 39% yield) of the title compound.

LC-MS (method 1): $R^t$=1.73 min; MS (ESIpos): m/z=422 [M+H]$^+$ $^1$H-NMR (400 MHz, DMSO-$d_6$) δ [ppm]: 0.88 (t, 3H), 2.16-2.27 (m, 1H), 2.33-2.48 (m, 1H), 5.56 (dd, 1H), 6.24 (s, 2H), 7.92 (d, 1H), 7.95 (s, 1H), 8.03 (dd, 1H), 8.12 (s, 1H), 8.56 (s, 1H), 8.80 (d, 1H), 8.90 (d, 1H).

Intermediate 11-34

8-Chloro-6-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

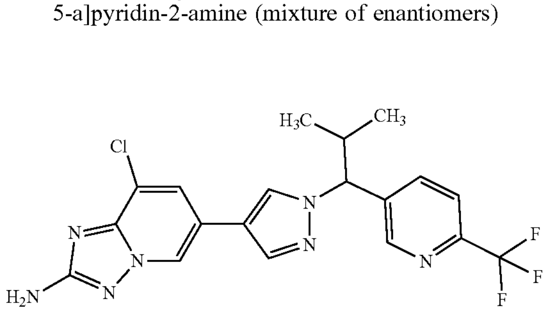

6-Bromo-8-chloro[1,2,4]triazolo[1,5-a]pyridin-2-amine (886 mg, 3.58 mmol), 5-{2-methyl-1-[4-(4,4,5,5-tetramethyl-1,3,2-dioxaborolan-2-yl)-1H-pyrazol-1-yl]propyl}-2-(trifluoromethyl)pyridine (1.81 g, 86% purity, 3.94 mmol), sodium carbonate (1.90 g, 17.9 mmol) and 1,1'-bis(diphenylphosphino)ferrocene-palladium(II)dichloride dichloromethane complex (146 mg, 179 μmol) were reacted according to procedure A in a mixture of 1,4-dioxane (18 ml) and water (5.8 ml). The reaction mixture was quenched with water, filtered through a hydrophobic phase separation filter, washed with ethyl acetate (15 ml) and concentrated in vacuo. The residue was purified by column chromatography (Biotage® SNAP KP-NH 55 g cartridge, eluent: cyclohexane/ethyl acetate gradient 4:1 to 1:4) to yield 900 mg (100% purity, 58% yield) of the title compound.

LC-MS (method 2): $R^t$=0.91 min; MS (ESIpos): m/z=436 $[M+H]^+$ $^1$H-NMR (600 MHz, DMSO-$d_6$) δ [ppm]: 0.81 (d, 3H), 0.87 (d, 3H), 2.79 (dq, 1H), 5.23 (d, 1H), 6.25 (s, 2H), 7.93 (s, 1H), 7.94 (d, 1H), 8.10 (s, 1H), 8.27 (dd, 1H), 8.52 (s, 1H), 8.88 (d, 1H), 8.95 (d, 1H).

Intermediate II-35

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers)

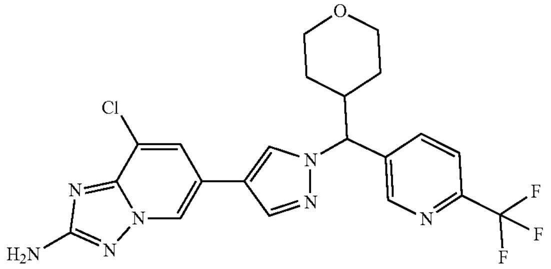 [SMILES: Nc1nc2c(Cl)cc(-c3cnn(C(c4ccc(C(F)(F)F)nc4)C4CCOCC4)c3)cn2n1]

6-Bromo-8-chloro[1,2,4]triazolo[1,5-a]pyridin-2-amine (1.00 g, 4.04 mmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (2.50 g, 85% purity, 4.85 mmol), caesium carbonate (3.95 g, 12.1 mmol) and 1,1'-bis(diphenylphosphino)ferrocene-palladium(II)dichloride dichloromethane complex (165 mg, 202 μmol) were reacted according to procedure A in a mixture of 1,4-dioxane (40 ml) and water (6.6 ml). The reaction mixture was quenched with water and filtered through a hydrophobic phase separation filter, washed with ethyl acetate (30 ml) and concentrated in vacuo. The residue was suspended triturated in tert-butyl methyl ether (15 ml) and collected by suction filtration. The resulting powder was washed with tert-butyl methyl ether (15 ml) and dried under reduced pressure to yield 1.77 g (95% purity, 87% yield) of the title compound.

LC-MS (method 1): $R^t$=1.55 min; MS (ESIpos): m/z=478 $[M+H]^+$ $^1$H-NMR (600 MHz, DMSO-$d_6$) δ [ppm]: 1.05-1.12 (m, 1H), 1.21-1.27 (m, 1H), 1.27-1.40 (m, 2H), 2.66-2.78 (m, 1H), 3.23-3.30 (m, 2H), 3.78-3.87 (m, 2H), 5.38 (d, 1H), 6.23 (s, 2H), 7.92 (s, 1H), 7.95 (d, 1H), 8.12 (s, 1H), 8.29 (d, 1H), 8.52 (s, 1H), 8.88 (s, 1H), 8.96 (s, 1H).

Intermediate II-36

8-Chloro-6-{1-[1-(oxetan-3-yl)piperidin-4-yl]-1H-pyrazol-4-yl}[1,2,4]triazolo[1,5-a]pyridin-2-amine

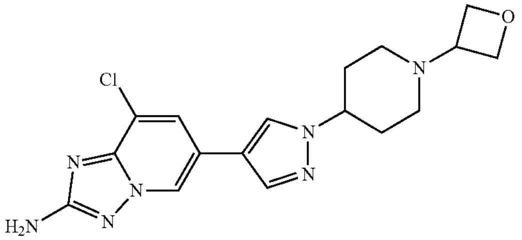 [SMILES: Nc1nc2c(Cl)cc(-c3cnn(C4CCN(C5COC5)CC4)c3)cn2n1]

6-Bromo-8-chloro[1,2,4]triazolo[1,5-a]pyridin-2-amine (300 mg, 1.21 mmol), 1-(oxetan-3-yl)-4-[4-(4,4,5,5-tetramethyl-1,3,2-dioxaborolan-2-yl)-1H-pyrazol-1-yl]piperidine (485 mg, 1.45 mmol), sodium carbonate (642 mg, 6.06 mmol) and 1,1'-bis(diphenylphosphino)ferrocene-palladium(II)dichloride dichloromethane complex (49.5 mg, 60.6 μmol) were reacted according to procedure A in a mixture of 1,4-dioxane (6.0 ml) and water (2.0 ml). The reaction mixture is filtered through a hydrophobic phase separation filter, washed with ethyl acetate (15 ml), concentrated and dried in vacuo. The residue was purified by preparative HPLC with 0.05% ammonia to yield 156 mg (100% purity, 34% yield) of the title compound.

LC-MS (method 1): $R^t$=0.61 min; MS (ESIpos): m/z=374 $[M+H]^+$ $^1$H-NMR (400 MHz, DMSO-$d_6$) δ [ppm]: 1.90-2.09 (m, 6H), 2.75-2.83 (m, 2H), 3.45 (quin, 1H), 4.11-4.19 (m, 1H), 4.45 (t, 2H), 4.55 (t, 2H), 6.22 (s, 2H), 7.94 (d, 1H), 8.01 (s, 1H), 8.41 (s, 1H), 8.87 (d, 1H).

Intermediate II-37

4-(1-Benzyl-1H-pyrazol-4-yl)-2,6-dichloropyridine

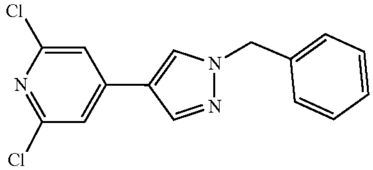 [SMILES: Clc1cc(-c2cnn(Cc3ccccc3)c2)cc(Cl)n1]

To a solution of 2,6-dichloro-4-iodopyridine (20.0 g, 73.0 mmol) and 1-benzyl-4-(4,4,5,5-tetramethyl-1,3,2-dioxaborolan-2-yl)-1H-pyrazole (24.90 g, 87.6 mmol) in 1,4-dioxane (120 ml) were added sodium carbonate (31.0 g, 292 mmol) in water (40 ml) and 1,1'-bis(diphenylphosphino)ferrocene-palladium(II)dichloride dichloromethane complex [CAS-RN 95464-05-4](2.67 g, 3.65 mmol) under nitrogen atmosphere. The resulting mixture was stirred at 90° C. for 1 h. After cooling to rt, the reaction mixture was diluted with ethyl acetate (50 ml) and filtered. The filtrate was concentrated under reduced pressure. The residue was purified by flash chromatography (silica gel; eluent: petroleum ether/ethyl acetate, 3:1) to yield 18.0 g (98% purity, 79% yield) of the title compound.

LC-MS (method 8): $R^t$=1.27 min; MS (ESIpos): m/z=304 $[M+H]^+$ $^1$H-NMR (300 MHz, DMSO-$d_6$) δ [ppm]: 6.37 (s, 2H), 7.27-7.40 (m, 5H), 7.84 (s, 2H), 8.27 (s, 1H), 8.70 (s, 1H).

Intermediate II-38

4-(1-Benzyl-1H-pyrazol-4-yl)-6-chloropyridin-2-amine

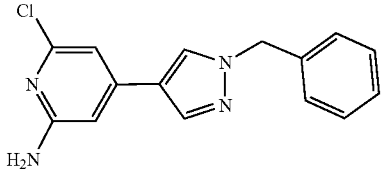 [SMILES: Nc1cc(-c2cnn(Cc3ccccc3)c2)cc(Cl)n1]

To a solution of 4-(1-benzyl-1H-pyrazol-4-yl)-2,6-dichloropyridine (21.0 g, 69.0 mmol) in 1,4-dioxane (300 ml) was added aq. ammonia (30%, 900 ml). The resulting mixture was stirred overnight at 150° C. in an autoclave. It was cooled to rt, diluted with ethyl acetate (800 ml) and water (800 ml). The aqueous layer was separated and extracted twice with ethyl acetate (800 ml each). The combined organic layers were dried over anhydrous sodium sulfate the solvend was evaporated under reduced pressure. The crude product crystallized overnight. It was triturated with cyclohexane (200 ml) and tert-butyl methyl ether (30 ml). The precipitate was collected by suction filtration to give 17.0 g (95% purity, 82% yield) the title compound.

LC-MS (method 8): $R^t$=0.98 min; MS (ESIpos): m/z=285 $[M+H]^+$ $^1$H-NMR (300 MHz, DMSO-$d_6$) δ [ppm]: 5.35 (s, 2H), 6.31 (br s, 2H), 6.51 (d, 1H), 6.78 (d, 1H), 7.28-7.39 (m, 5H), 7.94 (s, 1H), 8.39 (s, 1H).

Intermediate II-39

Ethyl {[4-(1-benzyl-1H-pyrazol-4-yl)-6-chloropyridin-2-yl]carbamothioyl}carbamate

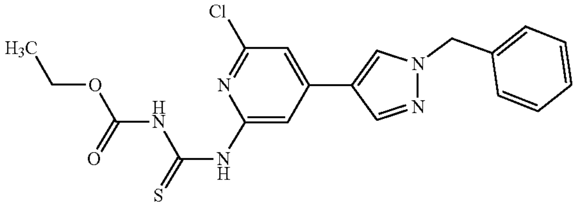 [SMILES: CCOC(=O)NC(=S)Nc1cc(-c2cnn(Cc3ccccc3)c2)cc(Cl)n1]

To a solution of 4-(1-benzyl-1H-pyrazol-4-yl)-6-chloropyridin-2-amine (17.0 g, 59.7 mmol) in 1,4-dioxane (300 ml) at rt was added dropwise ethyl carbonisothiocyanatidate (23.5 g, 179 mmol). The resulting mixture was stirred overnight at rt and then diluted with hexane (700 ml). The precipitate was collected by suction filtration, washed twice with hexane (100 ml each) and dried in vacuo to yield 16.5 g (97% purity, 64% yield) the title compound.

LC-MS (method 8): $R^t$=1.30 min; MS (ESIpos): m/z=479 $[M+ACN+Na]^+$ $^1$H-NMR (400 MHz, DMSO-$d_6$) δ [ppm]: 1.27 (t, 3H), 4.24 (q, 2H), 5.40 (s, 2H), 7.29-7.39 (m, 5H), 7.63 (d, 1H), 8.10 (s, 1H), 8.57 (s, 1H), 8.80 (s, 1H), 11.63 (s, 1H), 12.11 (s, 1H).

Intermediate II-40

7-(1-Benzyl-1H-pyrazol-4-yl)-5-chloro[1,2,4]triazolo[1,5-a]pyridin-2-amine

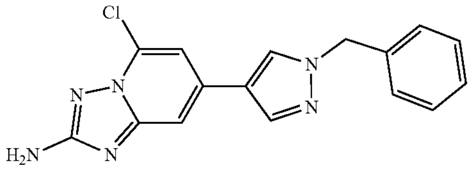 [SMILES: Nc1nc2cc(-c3cnn(Cc4ccccc4)c3)cc(Cl)n2n1]

To a solution of hydroxylamine hydrochloride (5.01 g, 72.1 mmol) in methanol (250 ml) at rt were added N,N-diisopropylethylamine (19 ml, 110 mmol) and the resulting mixture was heated to 60° C. Ethyl {[4-(1-benzyl-1H-pyrazol-4-yl)-6-chloropyridin-2-yl] carbamothioyl}carbamate (15.0 g, 36.1 mmol) was added. After stirring at 65° C. for 3 h the reaction mixture was cooled to rt and diluted with water (500 ml). The precipitate was collected by suction filtration. The filter cake was triturated with saturated sodium bicarbonate solution (200 ml) and stirred overnight. The precipitate was collected by suction filtration, washed with water (50 ml) and dried in vacuo to give 10.4 g (99% purity, 88% yield) of the title compound.

LC-MS (method 5): $R^t$=1.09 min; MS (ESIpos): m/z=325 $[M+H]^+$ $^1$H-NMR (300 MHz, DMSO-$d_6$) δ [ppm]: 5.36 (s, 2H), 6.26 (s, 2H), 7.20-7.46 (m, 6H), 7.60 (s, 1H), 8.17 (s, 1H), 8.56 (s, 1H).

Intermediate II-41

2,6-Dichloro-4-(1-{2-methyl-1-[6-(trifluoromethyl)pyridin-3-yl]propyl}-1H-pyrazol-4-yl)pyridine (mixture of enantiomers)

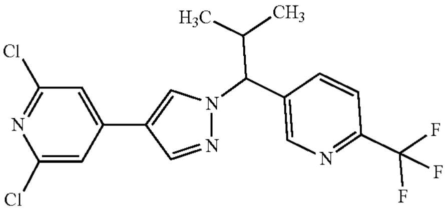 [SMILES: CC(C)C(c1ccc(C(F)(F)F)nc1)n1cc(-c2cc(Cl)nc(Cl)c2)cn1]

To a solution of 5-{2-methyl-1-[4-(4,4,5,5-tetramethyl-1,3,2-dioxaborolan-2-yl)-1H-pyrazol-1-yl]propyl}-2-(trifluoromethyl)pyridine (27.0 g, 97% purity, 66.3 mmol) and 2,6-dichloro-4-iodopyridine (20.0 g, 72.9 mmol) in 1,4-dioxane (300 ml) were added a solution of sodium carbonate (21.1 g, 199 mmol) in water (120 ml) and 1,1'-bis(diphenylphosphino)ferrocenepalladium(II) chloride (5.41 g, 6.63 mmol) under nitrogen atmosphere. After stirring at 90° C. for 2 h, the reaction mixture was cooled to rt, diluted with water (1.0 1) and the solid was filtered off. The filtrate was extracted three times with ethyl acetate (300 ml each). The combined organic layers were washed with brine (500 ml) and dried over anhydrous anhydrous sodium sulfate. The solvent was evaporated under reduced pressure and the crude product was purified by column chromatography (silica gel 330 g; eluent: petroleum ether/ethyl acetate 10:1) to yield 20.2 g (98% purity, 72% yield) of the title compound.

LC-MS (method 10): $R^t$=1.33 min; MS (ESIpos): m/z=416 $(M+H)^+$ $^1$H-NMR (300 MHz, DMSO-$d_6$) δ [ppm]: 0.80 (d, 3H), 0.85 (d, 3H), 2.70-2.88 (m, 1H), 5.27 (d, 1H), 7.82 (s, 2H), 7.94 (d, 1H), 8.27 (dd, 1H), 8.32 (s, 1H), 8.82 (s, 1H), 8.95 (d, 1H). $^{19}$F-NMR (282 MHz, DMSO-$d_6$) δ [ppm]: −66.48 (s, 3F).

Intermediate II-42

6-Chloro-4-(1-{2-methyl-1-[6-(trifluoromethyl)pyridin-3-yl]propyl}-1H-pyrazol-4-yl)pyridin-2-amine (mixture of enantiomers)

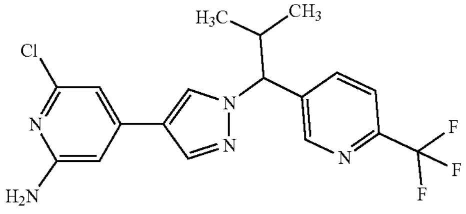 [SMILES: CC(C)C(c1ccc(C(F)(F)F)nc1)n1cc(-c2cc(N)nc(Cl)c2)cn1]

A solution of 2,6-dichloro-4-(1-{2-methyl-1-[6-(trifluoromethyl)pyridin-3-yl]propyl}-1H-pyrazol-4-yl)pyridine (23.0 g, 98% purity, 54.3 mmol) in 1,4-dioxane (300 ml) was treated with aq. ammonia (30%, 1000 ml). After stirring at 150° C. for 26 h in an autoclave reactor, the reaction mixture was cooled to rt, diluted with ethyl acetate (400 ml) and water (1.0 1). The aqueous layer was separated and extracted twice with ethyl acetate (400 ml each). The combined organic layers were dried over anhydrous sodium sulfate and the solvent was evaporated under reduced pressure. The crude product was purified by column chromatography (silica gel 330 g; eluent: petroleum ether/ethyl acetate 3:1) to yield 11.3 g (99% purity, 52% yield) of the title compound.

LC-MS (method 11): $R^t$=2.05 min; MS (ESIpos): m/z=396 $(M+H)^+$ $^1$H-NMR (400 MHz, DMSO-$d_6$) δ [ppm]: 0.79 (d, 3H), 0.83 (d, 3H), 2.74-2.87 (m, 1H), 5.26 (d, 1H), 6.32 (s, 2H), 6.51-6.53 (m, 1H), 6.78 (s, 1H), 7.94 (d, 1H), 7.99 (s, 1H), 8.28 (dd, 1H), 8.51 (s, 1H), 8.95 (d, 1H).

$^{19}$F-NMR (376 MHz, DMSO-$d_6$) δ [ppm]: −66.43 (s, 3F).

Intermediate II-43

Ethyl {[6-chloro-4-(1-{2-methyl-1-[6-(trifluoromethyl)pyridin-3-yl]propyl}-1H-pyrazol-4-yl)pyridin-2-yl]carbamothioyl}carbamate (mixture of enantiomers)

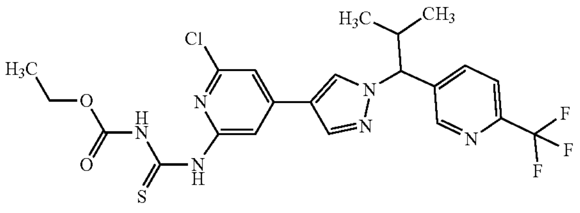

To a stirred solution of 6-chloro-4-(1-{2-methyl-1-[6-(trifluoromethyl)pyridin-3-yl]propyl}-1H-pyrazol-4-yl) pyridin-2-amine (11.6 g, 29.0 mmol) in 1,4-dioxane (110 ml) was added ethyl carbonisothiocyanatidate (11.4 g, 87.0 mmol) dropwise at rt. The resulting mixture was stirred overnight at rt. Then hexane (220 ml) was added. The precipitate was collected by suction filtration, washed twice with hexane (50 ml each) and dried in vacuo to yield 12.8 g (98% purity, 82% yield) the title compound.

$^1$H-NMR (300 MHz, DMSO-$d_6$) δ [ppm]: 0.80 (d, 3H), 0.84 (d, 3H), 1.27 (t, 3H), 2.72-2.90 (m, 1H), 4.24 (q, 2H), 5.35 (d, 1H), 7.64 (d, 1H), 7.95 (d, 1H), 8.19 (s, 1H), 8.30 (dd, 1H), 8.67 (s, 1H), 8.81 (s, 1H), 8.96 (d, 1H), 11.67 (s, 1H), 12.14 (s, 1H).

$^{19}$F-NMR (282 MHz, DMSO-$d_6$) δ [ppm]: −66.44 (s, 3F).

Intermediate 11-44

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

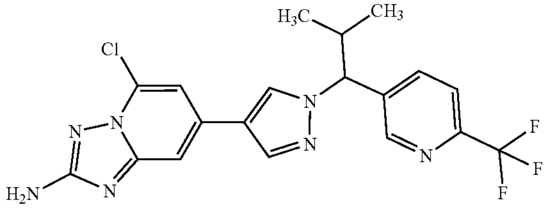 [SMILES: CC(C)C(c1ccc(C(F)(F)F)nc1)n1cc(-c2cc(Cl)n3nc(N)nc3c2)cn1]

To a solution of hydroxylamine hydrochloride (2.44 g, 35.1 mmol, dried) in dry methanol (70 ml) was added N,N-diisopropylethylamine (6.06 g, 46.9 mmol) at rt. After stirring at 60° C. for 10 min, ethyl {[6-chloro-4-(1-{2-methyl-1-[6-(trifluoromethyl)pyridin-3-yl]propyl}-1H-pyrazol-4-yl)pyridin-2-yl]carbamothioyl}carbamate (6.30 g, 11.7 mmol) was added. The resulting mixture was stirred at 65° C. for 3 h. It was then cooled to rt and water (100 ml) was added. The precipitate was collected by suction filtration. It was stirred in satd. sodium carbonate solution (100 ml) overnight, collected by suction filtration and dried in vacuo to yield 4.25 g (96% purity, 80% yield) the title compound.

LC-MS (method 5): $R^t$=1.37 min; MS (ESIpos): m/z=436 $(M+H)^+$ $^1$H-NMR (300 MHz, DMSO-$d_6$) δ [ppm]: 0.82 (d, 3H), 0.88 (d, 3H), 2.71-2.92 (m, 1H), 5.26 (d, 1H), 6.28 (s, 2H), 7.47 (s, 1H), 7.62 (s, 1H), 7.97 (d, 1H), 8.24 (s, 1H), 8.30 (d, 1H), 8.70 (s, 1H), 8.98 (s, 1H).

$^{19}$F-NMR (282 MHz, DMSO-$d_6$) δ [ppm]: −66.41 (s, 3F).

Intermediate II-45

6-Bromo-8-(1-methyl-1H-pyrazol-4-yl)[1,2,4]triazolo[1,5-a]pyridin-2-amine

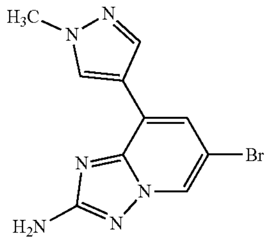 [SMILES: Cn1cc(-c2cc(Br)cn3nc(N)nc23)cn1]

6-Bromo-8-iodo[1,2,4]triazolo[1,5-a]pyridin-2-amine [CAS-RN 1883816-46-3](250 mg, 738 μmol) was reacted with 1-methyl-4-(4,4,5,5-tetramethyl-1,3,2-dioxaborolan-2-yl)-1H-pyrazole (153 mg, 738 μmol) for 2 h at 90° C. following general procedure B using 0.05 eq. catalyst. Thereafter, another batch 1-methyl-4-(4,4,5,5-tetramethyl-1,3,2-dioxaborolan-2-yl)-1H-pyrazole (153 mg, 738 μmol) and further 0.05 eq. catalyst were added and heating was continued for further 2 h. The reaction mixture was diluted with ethyl acetate (20 ml) and filtered through a hydrophobic phase separation filter which was rinsed with ethyl acetae (15 ml). Volatiles were removed in vacuo and the residue was triturated with methanol/acetonitrile (1:1, 5 ml). The precipitate was collected by suction filtration and washed twice with methanol (2 ml each) to yield 130 mg (100% purity, 60% yield) of the title compound.

LC-MS (method 2): $R^t$=0.63 min; MS (ESIpos): m/z=293, 295 [M+H]$^+$ $^1$H-NMR (400 MHz, DMSO-$d_6$) δ [ppm]: 3.91 (s, 3H), 6.18 (s, 2H), 7.91 (d, 1H), 8.30 (s, 1H), 8.55 (s, 1H), 8.75 (d, 1H).

Intermediate II-46

6-Bromo-8-(1-ethyl-1H-pyrazol-4-yl)[1,2,4]triazolo[1,5-a]pyridin-2-amine

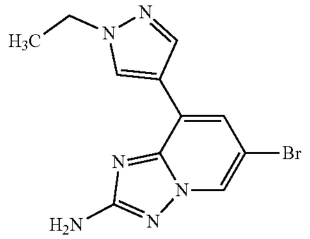 [SMILES: CCn1cc(-c2cc(Br)cn3nc(N)nc23)cn1]

6-Bromo-8-iodo[1,2,4]triazolo[1,5-a]pyridin-2-amine (694 mg, 2.05 mmol) was reacted with 1-ethyl-4-(4,4,5,5-tetramethyl-1,3,2-dioxaborolan-2-yl)-1H-pyrazole (500 mg, 2.25 mmol) for 2 h at 90° C. following general procedure B using 0.05 eq. catalyst. Subsequently, additional 0.05 eq. catalyst was added and heating was continued for 2 h. The reaction mixture was diluted with ethyl acetate (80 ml) and water (40 ml). The aqueous layer was separated and extracted twice with ethyl acetate (60 ml each). The combined organic layers were washed with brine and filtered through a hydrophobic phase separation filter. The solvent was evaporated under reduced pressure and the residue was purified by column chromatography (Biotage® SNAP Ultra 25 g cartridge, eluent: cyclohexane/ethyl acetate gradient 80:20 to 0:100) to yield 476 mg (95% purity, 72% yield) of the title compound.

LC-MS (method 1): $R^t$=1.27 min; MS (ESIpos): m/z=307, 309 [M+H]$^+$ $^1$H-NMR (400 MHz, DMSO-$d_6$) δ [ppm]: 1.42 (t, 3H), 4.20 (q, 2H), 6.18 (s, 2H), 7.91 (d, 1H), 8.32 (s, 1H), 8.59 (s, 1H), 8.75 (d, 1H).

Intermediate HI-47

6-Bromo-8-[1-(2,2,2-trifluoroethyl)-1H-pyrazol-4-yl][1,2,4]triazolo[1,5-a]pyridin-2-amine

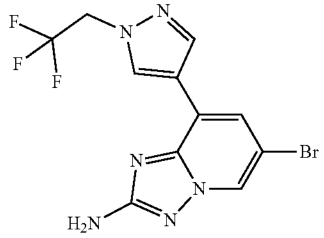 [SMILES: Nc1nc2c(-c3cnn(CC(F)(F)F)c3)cc(Br)cn2n1]

6-Bromo-8-iodo[1,2,4]triazolo[1,5-a]pyridin-2-amine (3.50 g, 10.3 mmol) was reacted with 4-(4,4,5,5-tetramethyl-1,3,2-dioxaborolan-2-yl)-1-(2,2,2-trifluoroethyl)-1H-pyrazole [CAS-RN 1883816-46-3](3.42 g, 12.4 mmol) for 2 h at 90° C. following general procedure B using 0.06 eq. catalyst. The reaction mixture was diluted with ethyl acetate (400 ml) and water (50 ml). The precipitate was collected by suction filtration and washed with water and acetonitrile to yield 440 mg (100% purity, 12% yield) of the title compound. The organic layer of the filtrate was separated and washed with water and brine and dried over anhydrous sodium sulfate. The solvent was concentrated under reduced pressure to a volume of 15 ml and the precipitate was collected by suction filtration and washed with acetonitrile to yield a second batch of 2.70 g (100% purity, 72% yield) of the title compound. The mother liquor was concentrated and purified by column chromatography (Biotage® SNAP Ultra 50 g cartridge, eluent: cyclohexane/ethyl acetate gradient 90:10 to 10:90) which resulted in a third batch of 230 mg (92% purity, 6% yield) of the title compound. The total yield was 90%.

LC-MS (method 2): $R^t$=0.78 min; MS (ESIpos): m/z=361 [M+H]$^+$ $^1$H-NMR (500 MHz, DMSO-$d_6$) δ [ppm]: 5.28 (q, 2H), 6.21 (s, 2H), 8.02 (d, 1H), 8.46 (s, 1H), 8.74 (s, 1H), 8.81 (d, 1H).

Intermediate I-48

4-(4,4,5,5-Tetramethyl-1,3,2-dioxaborolan-2-yl)-1-(1,1,1-trifluoropropan-2-yl)-1H-pyrazole (mixture of enantiomers)

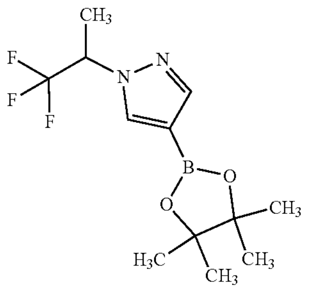 [SMILES: CC(n1cc(B2OC(C)(C)C(C)(C)O2)cn1)C(F)(F)F]

4-(4,4,5,5-Tetramethyl-1,3,2-dioxaborolan-2-yl)-1H-pyrazole (2.76 g, 14.2 mmol) was dissolved in dimethylformamide (50 ml) and 1,1,1-trifluoropropan-2-yl nonafluorobutane-1-sulfonate (7.32 g, 100% purity, 18.5 mmol) and caesium carbonate (11.7 g, 35.8 mmol) were added. The suspension was stirred at rt overnight. The mixture was filtered and the filter was rinsed with ethyl acetate (50 ml). The combined filtrates were concentrated and the residue was purified by column chromatography (Biotage® SNAP Ultra 100 g cartridge, eluent: cyclohexane/ethyl acetate gradient 95:5 to 50:50) to yield 2.24 g (98% purity, 53% yield) of the title compound.

LC-MS (GC-MS method 1): $R^t$=4.24 min; MS (ESIpos): m/z=290 $[M]^+$ $^{1}H$-NMR (400 MHz, DMSO-$d_6$) δ [ppm]: 1.26 (s, 12H), 1.67 (d, 3H), 5.36-5.48 (m, 1H), 7.70 (s, 1H), 8.14 (s, 1H).

Intermediate 11-49

6-Bromo-8-[1-(1,1,1-trifluoropropan-2-yl)-1H-pyrazol-4-yl][1,2,4]triazolo[1,5-a]pyridin-2-amine (mixture of enantiomers)

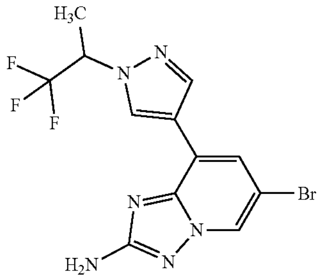 [SMILES: CC(n1cc(-c2cc(Br)cn3nc(N)nc23)cn1)C(F)(F)F]

6-Bromo-8-iodo[1,2,4]triazolo[1,5-a]pyridin-2-amine (2.38 g, 7.01 mmol) was reacted with 4-(4,4,5,5-tetramethyl-1,3,2-dioxaborolan-2-yl)-1-(1,1,1-trifluoropropan-2-yl)-1H-pyrazole (2.44 g, 8.41 mmol) for 1.5 h at 90° C. following general procedure B using 0.05 eq. catalyst. Ethyl acetate (50 ml) and water (30 ml) were added to the reaction mixture. The organic layer was separated and washed with water (30 ml) and brine (20 ml) and filtered through a hydrophobic phase separation filter. The solvent was removed in vacuo. The crude product was purified by column chromatography (Biotage® SNAP KP-NH 110 g cartridge, eluent: cyclohexane/ethyl acetate gradient 90:10 to 20:80) to yield 1.70 g (98% purity, 63% yield) of the title compound.

LC-MS (method 1): $R^t$=1.58 min; MS (ESIpos): m/z=375 $[M+H]^+$ $^{1}H$-NMR (600 MHz, DMSO-$d_6$) δ [ppm]: 1.72 (d, 3H), 5.51-5.60 (m, 1H), 6.21 (s, 2H), 8.01 (d, 1H), 8.47 (s, 1H), 8.78 (s, 1H), 8.81 (d, 1H).

Intermediate II-50

6-Bromo-8-(1-cyclopropyl-1H-pyrazol-4-yl)[1,2,4]triazolo[1,5-a]pyridin-2-amine

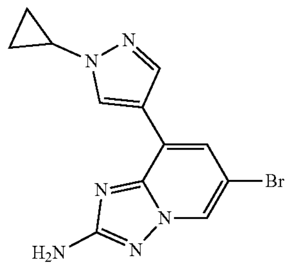 [SMILES: Nc1nc2c(-c3cnn(C4CC4)c3)cc(Br)cn2n1]

6-Bromo-8-iodo[1,2,4]triazolo[1,5-a]pyridin-2-amine (658 mg, 1.94 mmol) was reacted with 1-cyclopropyl-4-(4,4,5,5-tetramethyl-1,3,2-dioxaborolan-2-yl)-1H-pyrazole (500 mg, 2.14 mmol) for 2 h at 90° C. following general procedure B using 0.05 eq. catalyst. Subsequently, additional 0.05 eq. catalyst was added and heating was continued for 3 h. The reaction mixture was diluted with ethyl acetate (80 ml) and water (40 ml). The aqueous layer was separated and extracted with ethyl acetate (60 ml). The combined organic layers were washed with brine and filtered through a hydrophobic phase separation filter. The solvent was evaporated under reduced pressure and the residue was purified by column chromatography (Biotage® SNAP Ultra 25 g cartridge, eluent: cyclohexane/ethyl acetate gradient 80:20 to 0:100) to yield 325 mg (95% purity, 50% yield) of the title compound.

LC-MS (method 1): $R^t$=1.35 min; MS (ESIpos): m/z=319, 321 $[M+H]^+$ $^{1}H$-NMR (400 MHz, DMSO-$d_6$) δ [ppm]: 0.98-1.11 (m, 4H), 3.76-3.83 (m, 1H), 6.21 (s, 2H), 7.93 (d, 1H), 8.31 (s, 1H), 8.64 (s, 1H), 8.75 (d, 1H).

Intermediate II-51

2-[4-(2-Amino-6-bromo[1,2,4]triazolo[1,5-a]pyridin-8-yl)-1H-pyrazol-1-yl]ethan-1-ol

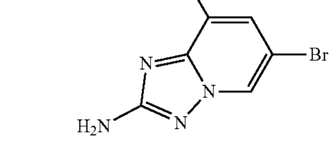

6-Bromo-8-iodo[1,2,4]triazolo[1,5-a]pyridin-2-amine (906 mg, 2.67 mmol) was reacted with 2-[4-(4,4,5,5-tetramethyl-1,3,2-dioxaborolan-2-yl)-1H-pyrazol-1-yl]ethan-1-ol [CAS-RN 1040377-08-9](700 mg, 2.94 mmol) for 2 h at 90° C. following general procedure B using 0.05 eq. catalyst. Ethyl acetate (40 ml) and water (80 ml) were added and the precipitate was collected by suction filtration and washed with dimethylsulfoxide/acetonitrile. It was purified by preparative HPLC (Chromatorex C18, 10 μm, 125×30 mm; eluent: water/acetonitrile gradient 95:5 to 50:50). The title compound precipitated from the product fractions and was collected by suction filtration to yield 256 mg (100% purity, 30% yield). The mother liquor was evaporated to yield another fraction of 55.0 mg (90% purity, 6% yield). The mother liquor aqueous layer from the reaction mixture was acidified with 1N hydrochloric acid and extracted twice with ethyl acetate (40 ml each). The combined organic layers were washed with brine and filtered through a hydrophobic phase separation filter. The solvent was evaporated under reduced pressure and the remainder purified by column chromatography (Biotage® SNAP Ultra 25 g cartridge, eluent: cyclohexane/ethyl acetate gradient 60:40 to 0:100 then ethylacetate/2-propanol 95:5) to yield 144 mg (100% purity, 17% yield) of the title compound. The total yield was 53%.

LC-MS (method 1): $R^t$=0.96 min; MS (ESIpos): m/z=323, 325 $[M+H]^+$ $^1$H-NMR (400 MHz, DMSO-$d_6$) δ [ppm]: 3.76 (q, 2H), 4.20 (t, 2H), 4.94 (t, 1H), 6.19 (s, 2H), 7.93 (d, 1H), 8.33 (s, 1H), 8.60 (s, 1H), 8.74 (d, 1H).

Intermediate II-52

6-Bromo-8-[3-(methanesulfonyl)phenyl][1,2,4]triazolo[1,5-a]pyridin-2-amine

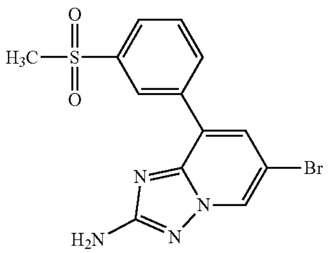 [SMILES: CS(=O)(=O)c1cccc(-c2cc(Br)cn3nc(N)nc23)c1]

6-Bromo-8-iodo[1,2,4]triazolo[1,5-a]pyridin-2-amine (500 mg, 1.48 mmol) was reacted with [3-(methanesulfonyl)phenyl]boronic acid (354 mg, 1.77 mmol) for 2.5 h at 90° C. following general procedure B using 0.05 eq. catalyst. The reaction mixture was diluted with ethyl acetate (20 ml) and washed with water (20 ml). The aqueous layer was extracted once with ethyl acetate (20 ml) and the combined organic layers were washed with brine and filtered through a hydrophobic phase separation filter. The solvent was removed in vacuo and the residue was purified by column chromatography (Biotage® SNAP KP-NH 55 g cartridge, eluent: cyclohexane/ethyl acetate gradient 90:10 to 20:80) to yield 326 mg (99% purity, 59% yield) of the title compound.

LC-MS (method 1): $R^t$=1.29 min; MS (ESIpos): m/z=367 $[M+H]^+$ $^1$H-NMR (600 MHz, DMSO-$d_6$) δ [ppm]: 3.30 (s, 3H), 6.31 (s, 2H), 7.78 (t, 1H), 7.98 (dt, 1H), 8.03 (d, 1H), 8.51 (dt, 1H), 8.59 (t, 1H), 9.00 (d, 1H).

Intermediate II-53

6-Bromo-8-[3-(ethanesulfonyl)phenyl][1,2,4]triazolo[1,5-a]pyridin-2-amine

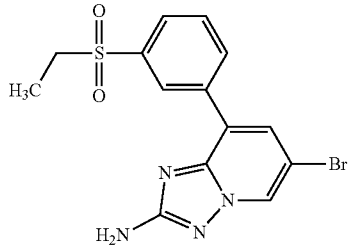 [SMILES: CCS(=O)(=O)c1cccc(-c2cc(Br)cn3nc(N)nc23)c1]

6-Bromo-8-iodo[1,2,4]triazolo[1,5-a]pyridin-2-amine [CAS-RN 1883816-46-3](750 mg, 2.21 mmol) was reacted [3-(ethanesulfonyl)phenyl]boronic acid (568 mg, 2.66 mmol) for 2.5 h at 90° C. following general procedure B using 0.05 eq. catalyst. The reaction mixture was extracted twice with ethyl acetate (50 ml each). The combined organic layers were washed with brine and filtered through a hydrophobic phase separation filter. The solvent was removed in vacuo and the residue was purified by column chromatography (Biotage® SNAP KP-NH 28 g cartridge, eluent: cyclohexane/ethyl acetate gradient 4:1 to 0:1). A mixed fraction required a second chromatography. The combined yield was 513 mg (99% purity, 60% yield) of the title compound.

LC-MS (method 1): $R^t$=1.35 min; MS (ESIpos): m/z=381 $[M+H]^+$ $^1$H-NMR (600 MHz, DMSO-$d_6$) δ [ppm]: 1.15 (t, 3H), 3.38 (q, 2H), 6.29 (s, 2H), 7.79 (t, 1H), 7.93 (d, 1H), 8.02 (d, 1H), 8.51 (d, 1H), 8.56 (s, 1H), 9.00 (d, 1H).

Intermediate II-54

1-Bromo-3-(trifluoromethanesulfonyl)benzene

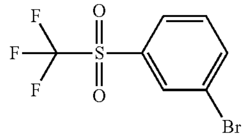 [SMILES: O=S(=O)(c1cccc(Br)c1)C(F)(F)F]

To 1-bromo-3-[(trifluoromethyl)sulfanyl]benzene (2.00 g, 7.78 mmol) in a solvent mixture (water/dichloromethane/acetonitrile 2:1:1, 60 ml) was added ruthenium(III) chloride (80.7 mg, 389 μmol). Under rigorous stirring sodium periodate (4.99 g, 23.3 mmol) was added portionwise within 5 min. The mixture was slightly cooled with cold water and stirring was continued for 1 h. Ethyl acetate (100 ml) was added and the mixture was filtered through kieselguhr which was rinsed with ethyl acetate. The organic layer was separated from the filtrate and washed with water and brine and dried over anhydrous sodium sulfate. The solvent was removed in vacuo and the residue was purified by column chromatography (Biotage® SNAP Ultra 25 g cartridge, eluent: cyclohexane/ethyl acetate gradient 100:0 to 85:15) to yield 1.90 g (100% purity, 84% yield) of the title compound.

LC-MS (§ OA-APGC-MS-1): $R^t$=4.16 min; MS (APGC/MS): m/z=288, 290 $[M]^+$ $^1$H-NMR (500 MHz, $CDCl_3$) S [ppm]: 7.57 (t, 1H), 7.95-8.01 (m, 2H), 8.17-8.19 (m, 1H).

Intermediate II-55

5 4,4,5,5-Tetramethyl-2-[3-(trifluoromethanesulfonyl)phenyl]-1,3,2-dioxaborolane

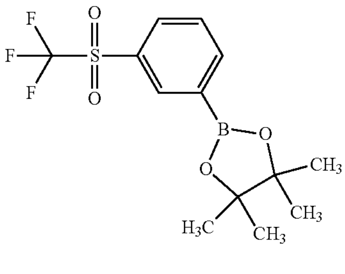 [SMILES: CC1(C)OB(c2cccc(S(=O)(=O)C(F)(F)F)c2)OC1(C)C]

A mixture of 1-bromo-3-(trifluoromethanesulfonyl)benzene (1.90 g, 6.57 mmol), 4,4,4',4',5,5,5',5'-octamethyl-2,2'-bi-1,3,2-dioxaborolane (2.50 g, 9.86 mmol), potassium acetate (1.94 g, 19.7 mmol) and 1,1'-bis(diphenylphosphino) ferrocene-palladium(II)dichloride dichloromethane complex [CAS-RN 95464-05-4](537 mg, 657 μmol) in degassed dioxane (29 ml) was heated to 90° C. for 5 h. The reaction mixture was filtered through kieselguhr, which was rinsed with ethyl acetate. The filtrate was concentrated in vacuo and the residue was purified by column chromatography (Biotage® SNAP Ultra 50 g cartridge, eluent: cyclohexane/ethyl acetate gradient 100:0 to 50:50) to yield 2.30 g (85% purity, 88% yield) of the title compound.

LC-MS (method 1): $R^t$=1.46 min; MS (ESIpos): m/z=508 $[M+H]^+$ $^1$H-NMR (600 MHz, DMSO-$d_6$) δ [ppm]: 1.34 (s, 12H), 7.90 (t, 1H), 8.22 (s, 1H), 8.28 (dd, 2H).

Intermediate II-56

6-Bromo-8-[3-(trifluoromethanesulfonyl)phenyl][1,2,4]triazolo[1,5-a]pyridin-2-amine

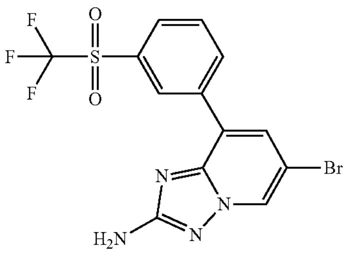 [SMILES: Nc1nc2c(-c3cccc(S(=O)(=O)C(F)(F)F)c3)cc(Br)cn2n1]

6-Bromo-8-iodo[1,2,4]triazolo[1,5-a]pyridin-2-amine (400 mg, 1.18 mmol) was reacted with 4,4,5,5-tetramethyl-2-[3-(trifluoromethanesulfonyl)phenyl]-1,3,2-dioxaborolane (513 mg, 85% purity, 1.30 mmol) for 2 h at 90° C. following general procedure B using 0.1 eq. catalyst. Ethyl acetate (20 ml) was added and the mixture was washed with water (5 ml). The aqeuous layer was separated and extracted with ethyl acetate. The combined organic layers were dried over anhydrous sodium sulfate and the solvent was removed in vacuo. The residue was purified by column chromatography (Biotage® SNAP Ultra 25 g cartridge, eluent: cyclohexane/ethyl acetate gradient 100:0 to 20:80) to yield 330 mg (90% purity, 60% yield) of the title compound.

LC-MS (method 2): $R^t$=0.97 min; MS (ESIpos): m/z=423 $[M+H]^+$ $^1$H-NMR (600 MHz, DMSO-$d_6$) δ [ppm]: 6.31 (s, 2H), 7.98 (t, 1H), 8.10 (d, 1H), 8.19 (d, 1H), 8.73 (d, 1H), 8.95 (s, 1H), 9.03 (d, 1H).

Intermediate II-57

2-[3-(2-Amino-6-bromo[1,2,4]triazolo[1,5-a]pyridin-8-yl)phenyl]propan-2-ol

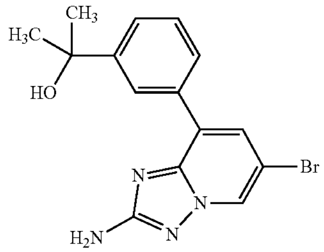 [SMILES: CC(C)(O)c1cccc(-c2cc(Br)cn3nc(N)nc23)c1]

6-Bromo-8-iodo[1,2,4]triazolo[1,5-a]pyridin-2-amine (500 mg, 1.48 mmol) was reacted with [3-(2-hydroxypropan-2-yl)phenyl]boronic acid (319 mg, 1.77 mmol) for 2.5 h at 90° C. following general procedure B using 0.05 eq. catalyst. The reaction mixture was diluted with ethyl acetate (20 ml) and washed with water (20 ml). The aqueous layer was extracted once with ethyl acetate (20 ml) and the combined organic layers were washed with brine and filtered through a hydrophobic phase separation filter. The solvent was removed in vacuo and the residue was purified by column chromatography (Biotage® SNAP KP-NH 28 g cartridge, eluent: cyclohexane/ethyl acetate gradient 80:20 to 0:100) to yield 345 mg (93% purity, 63% yield) of the title compound.

LC-MS (method 1): $R^t$=1.49 min; MS (ESIpos): m/z=347 $[M+H]^+$ $^1$H-NMR (600 MHz, DMSO-$d_6$) δ [ppm]: 1.49 (s, 6H), 5.06 (s, 1H), 6.19 (br s, 2H), 7.41 (t, 1H), 7.53 (d, 1H), 7.79 (s, 1H), 8.00 (d, 1H), 8.03 (s, 1H), 8.90 (s, 1H).

Intermediate II-58

[3-(2-Amino-6-bromo[1,2,4]triazolo[1,5-a]pyridin-8-yl)-4-chlorophenyl]methanol

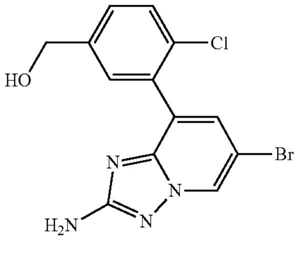 [SMILES: Nc1nc2c(-c3cc(CO)ccc3Cl)cc(Br)cn2n1]

6-Bromo-8-iodo[1,2,4]triazolo[1,5-a]pyridin-2-amine (500 mg, 1.48 mmol) was reacted with [2-chloro-5-(hydroxymethyl)phenyl]boronic acid (330 mg, 1.77 mmol) for 2.5 h at 90° C. following general procedure B using 0.05 eq. catalyst. The reaction mixture was diluted with ethyl acetate (20 ml) and water (10 ml) was added. The precipitate was collected by suction filtration and washed 20 with ethyl acetate to yield 397 mg (99% purity, 75% yield) of the title compound. From the filtrate the aqueous layer was separated and extracted with ethyl acetate (20 ml). The combined organic layers were filtered through a hydrophobic phase separation filter and the solvent was removed in vacuo. The residue was purified by column chromatography (Biotage® SNAP KP-NH 28 g cartridge, eluent: cyclohexane/ethyl acetate/2-propanol gradient 80:20:0 to 0:100:0 to 0:80:20) to yield another batch 57.3 mg (99% purity, 11% yield) of the title compound.

LC-MS (method 1): $R^t$=1.36 min; MS (ESIpos): m/z=353 $[M+H]^+$ $^1$H-NMR (400 MHz, DMSO-$d_6$) δ [ppm]: 4.53 (s, 2H), 5.34 (br s, 1H), 6.19 (s, 2H), 7.39-7.45 (m, 3H), 7.52-7.56 (m, 2H), 8.99 (d, 1H).

Intermediate II-59

6-Bromo-8-[3-(dimethylamino)phenyl][1,2,4]triazolo[1,5-a]pyridin-2-amine

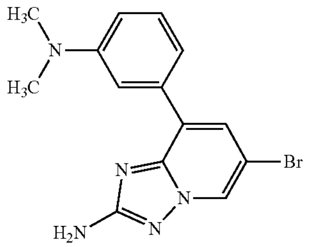 [SMILES: CN(C)c1cccc(-c2cc(Br)cn3nc(N)nc23)c1]

6-Bromo-8-iodo[1,2,4]triazolo[1,5-a]pyridin-2-amine (500 mg, 1.48 mmol) was reacted with [3-(dimethylamino) phenyl]boronic acid (292 mg, 1.77 mmol) for 2 h at 90° C. following general procedure B using 0.05 eq. catalyst. The mixture was diluted with ethyl acetate (20 ml) and washed with water (20 ml). The aqueous layer was extracted three times with ethyl acetate (20 ml each) and the combined organic layers were filtered through a hydrophobic phase separation filter. The solvent was removed in vacuo and the residue was purified by column chromatography (Biotage® SNAP KP-NH 55 g cartridge, eluent: cyclohexane/ethyl acetate gradient 90:10 to 20:80). The product was further purified by preparative HPLC (Chromatorex C18, 10 μm, 125×30 mm; eluent: water/acetonitrile gradient 90:10 to 5:95) to yield 175 mg (99% purity, 35% yield) of the title compound.

LC-MS (method 1): $R^t$=1.60 min; MS (ESIpos): m/z=332 $[M+H]^+$ $^1$H-NMR (600 MHz, DMSO-$d_6$) δ [ppm]: 2.96 (s, 6H), 6.17 (s, 2H), 6.79 (dd, 1H), 7.28 (t, 1H), 7.35-7.38 (m, 2H), 7.78 (d, 1H), 8.88 (d, 1H).

Intermediate II-60

7-Chloro-5-[6-(cyclopropyloxy)pyridin-3-yl][1,2,4]triazolo[1,5-a]pyridin-2-amine

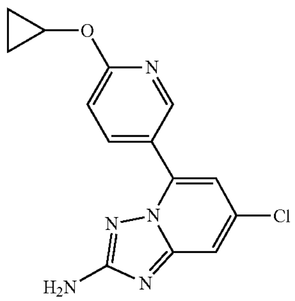 [SMILES: Nc1nc2cc(Cl)cc(-c3ccc(OC4CC4)nc3)n2n1]

5,7-Dichloro[1,2,4]triazolo[1,5-a]pyridin-2-amine (355 mg, 1.75 mmol), 2-(cyclopropyloxy)-5-(4,4,5,5-tetramethyl-1,3,2-dioxaborolan-2-yl)pyridine (502 mg, 1.92 mmol), 1,1'-bis(diphenylphosphino)ferrocene-palladium(II) dichloride dichloromethane complex (143 mg, 175 mol) and sodium carbonate (556 mg, 5.25 mmol) were reacted according to procedure A in a mixture of water (1.5 ml) and 1,4-dioxane (4.5 ml). The reaction was stirred at 100° C. for 20 h. 10 The reaction was quenched with water and extracted with dichloromethane. The combined organic layers were dried over anhydrous sodium sulfate, filtered and concentrated. The residue was purified by column chromatography (Biotage® SNAP KP-NH 11 g cartridge, eluent: cyclohexane/ethyl acetate gradient 4:1 to 1:4) to yield 345 mg (85% purity, 56% yield) of the title compound.

LC-MS (method 1): $R^t$=1.53 min; MS (ESIpos): m/z=302 $[M+H]^+$ $^1$H-NMR (600 MHz, DMSO-$d_6$) δ [ppm]: 4.60 (d, 2H), 5.19 (dd, 1H), 5.24 (dd, 1H), 5.92-6.09 (m, 1H), 6.24 (s, 2H), 6.55 (d, 1H), 7.16 (d, 1H), 7.48 (d, 1H), 8.15 (dd, 1H), 8.58 (d, 1H).

Intermediate II-61

7-Chloro-5-(6-cyclopropylpyridin-3-yl)[1,2,4]triazolo[1,5-a]pyridin-2-amine

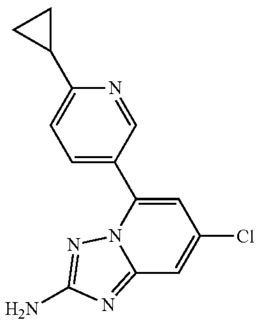 [SMILES: Nc1nc2cc(Cl)cc(-c3ccc(C4CC4)nc3)n2n1]

5,7-Dichloro[1,2,4]triazolo[1,5-a]pyridin-2-amine (375 mg, 1.85 mmol), 2-cyclopropyl-5-(4,4,5,5-tetramethyl-1,3,2-dioxaborolan-2-yl)pyridine (498 mg, 2.03 mmol), 1,1'-bis (diphenylphosphino)ferrocene-palladium(II)dichloride dichloromethane complex (151 mg, 185 mol) and sodium carbonate (587 mg, 5.54 mmol) were reacted according to procedure A in a mixture of water (1.5 ml) and 1,4-dioxane (4.5 ml). The reaction was stirred at 100° C. for 20 h. The reaction mixture was quenched with water and extracted with dichloromethane. The combined organic layers were dried over anhydrous sodium sulfate, filtered and concentrated. The residue was purified by column chromatography (Biotage® SNAP KP-NH 11 g cartridge, eluent: cyclohexane/ethyl acetate gradient 4:1 to 1:4) to yield 235 mg (100% purity, 45% yield) of the title compound and a fraction of lower purity, 184 mg (84% purity, 29% yield).

LC-MS (method 1): $R^t$=1.43 min; MS (ESIpos): m/z=286 $[M+H]^+$ $^1$H-NMR (400 MHz, DMSO-$d_6$) δ [ppm]: 0.98-1.06 (m, 4H), 2.17-2.24 (m, 1H), 6.21 (s, 2H), 7.21 (d, 1H), 7.47 (d, 1H), 7.54 (d, 1H), 8.25 (dd, 1H), 8.96 (d, 1H).

Intermediate II-62

7-Chloro-5-[6-(difluoromethoxy)pyridin-3-yl][1,2,4]triazolo[1,5-a]pyridin-2-amine

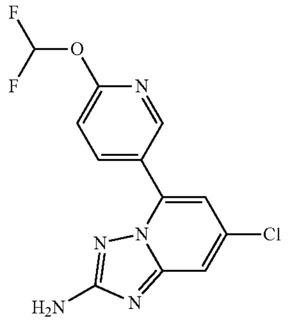 [SMILES: Nc1nc2cc(Cl)cc(-c3ccc(OC(F)F)nc3)n2n1]

5,7-Dichloro[1,2,4]triazolo[1,5-a]pyridin-2-amine (345 mg, 1.70 mmol), 2-(difluoromethoxy)-5-(4,4,5,5-tetramethyl-1,3,2-dioxaborolan-2-yl)pyridine (507 mg, 1.87 mmol), 1,1'-bis(diphenylphosphino)ferrocene-palladium(II) dichloride dichloromethane complex (139 mg, 170 μmol) and sodium carbonate (540 mg, 5.10 mmol) were reacted according to procedure A in a mixture of water (1.5 ml) and 1,4-dioxane (4.5 ml). The reaction was stirred at 100° C. for 20 h. The reaction was quenched with water and extracted with dichloromethane. The combined organic layers were dried over anhydrous sodium sulfate, filtered and concentrated. The residue was purified by column chromatography (Biotage® SNAP KP-NH 11 g cartridge, gradient: cyclohexane/ethyl acetate gradient 4:1 to 1:4) to yield 244 mg (100% purity, 46% yield) of the title compound.

LC-MS (method 1): $R^t$=1.62 min; MS (ESIpos): m/z=312 $[M+H]^+$ $^1$H-NMR (400 MHz, DMSO-$d_6$) δ [ppm]: 6.25 (s, 2H), 7.28 (s, 1H), 7.29 (d, 1H), 7.58 (d, 1H), 7.81 (t, 1H), 8.54 (dd, 1H), 8.87 (d, 1H).

Intermediate II-63

7-Chloro-5-[6-(trifluoromethyl)pyridin-3-yl][1,2,4]triazolo[1,5-a]pyridin-2-amine

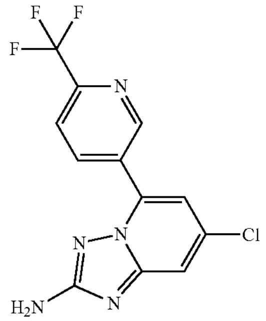 [SMILES: Nc1nc2cc(Cl)cc(-c3ccc(C(F)(F)F)nc3)n2n1]

5,7-Dichloro[1,2,4]triazolo[1,5-a]pyridin-2-amine (1.00 g, 4.93 mmol), [6-(trifluoromethyl)pyridin-3-yl]boronic acid (1.03 g, 5.42 mmol), 1,1'-bis(diphenylphosphino)ferrocene-palladium(II)dichloride dichloromethane complex (402 mg, 493 μmol) and sodium carbonate (1.57 g, 14.8 mmol) were reacted according to procedure A in a mixture of water (4.0 ml) and 1,4-dioxane (12 ml). The reaction was stirred at 100° C. for 20 h. The reaction was quenched with water and extracted with dichloromethane. The combined organic layers were dried over anhydrous sodium sulfate, filtered and concentrated. The residue was purified by column chromatography (Biotage® SNAP KP-NH 11 g cartridge, eluent: cyclohexane/ethyl acetate gradient 4:1 to 1:4) to yield 1.28 g (98% purity, 81% yield) of the title compound.

LC-MS (method 1): $R^t$=1.57 min; MS (ESIpos): m/z=314 $[M+H]^+$ $^1$H-NMR (400 MHz, DMSO-$d_6$) δ [ppm]: 6.29 (s, 2H), 7.40 (d, 1H), 7.66 (d, 1H), 8.13 (d, 1H), 8.71 (dd, 1H), 9.31 (d, 1H).

Intermediate II-64

1-Fluorocyclopropane-1-carbonyl chloride

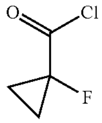

To a solution of 1-fluorocyclopropanecarboxylic acid [CAS-RN 137081-41-5](3 g, 28.8 mmol) in dry dichloromethane (60 ml) and a catalytic amount of dimethylformamid at 0° C. was slowly added oxalyl chloride (2.51 ml, 28.8 mmol). The reaction was strired for 3 h at rt. The reaction was concentrated under reduced pressure to give crude 1-fluorocyclopropane-1-carbonyl chloride which was directly used in the next step.

Intermediate II-65

1-(1-Fluorocyclopropyl)-1-hydroxy-5-methoxy-penta-1,4-dien-3-one (mixture of diastereomers)

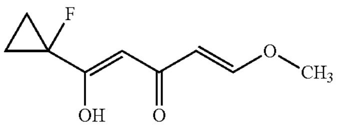

Under argon atmosphere, a solution of lithium 1,1,1-trimethyl-N-(trimethylsilyl)silanaminide (58 ml, 1.0 M in THF, 58 mmol) was added dropwise at −70° C. to a solution of (3E)-4-methoxybut-3-en-2-one [CAS-RN 4652-27-1] (6.41 g, 90% purity, 57.7 mmol) in 80 ml of dry THF. The mixture was stirred for 30 min before a solution of 1-fluorocyclopropane-1-carbonyl chloride (3.53 g, 28.8 mmol) in 60 ml dry dichloromethane was added dropwise over 30 min at −70° C. The mixture was stirred for 1 h at this temperature, before warming up to rt. The reaction mixture was quenched with a saturated solution of ammonium chloride. The reaction mixture was concentrated under reduced pressure and the residue was diluted with water and extracted twice with ethyl acetate. The organic layer was dried over anhydrous sodium sulfate, filtered and concentrated to give crude 1-(1-fluorocyclopropyl)-1-hydroxy-5-methoxypenta-1,4-dien-3-one which was directly used in the next step.

Intermediate II-66

2-(1-Fluorocyclopropyl)-4H-pyran-4-one

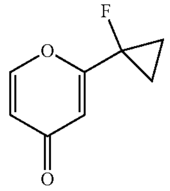 [SMILES: O=c1ccoc(C2(F)CC2)c1]

Trifluoroacetic acid (6.5 ml, 85 mmol) was added dropwise to a solution of starting material 1-(1-fluorocyclopropyl)-1-hydroxy-5-methoxypenta-1,4-dien-3-one (7.87 g, 42.3 mmol) in dichloromethane (60 ml), and the reaction mixture was stirred at rt for 2 h. The solvent was removed under reduce pressure and the residue was purified by column chromatography (Biotage® KP-NH 110 g cartridge, eluent: cyclohexane/ethyl acetate gradient 9:1 to 1:4) to yield 1.90 g (86% purity, 25% yield) of the title compound.

LC-MS (method 2): $R^t$=0.48 min; MS (ESIpos): m/z=155 $[M+H]^+$ $^1$H-NMR (400 MHz, DMSO-$d_6$) δ [ppm]: 1.36 (m, 2H), 1.56 (dq, 2H), 6.29 (dd, 1H), 6.40 (br s, 1H), 8.10 (d, 1H).

Intermediate II-67

2-(1-Fluorocyclopropyl)pyridin-4(1H)-one

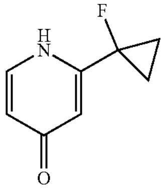 [SMILES: O=c1cc[nH]c(C2(F)CC2)c1]

A solution of 2-(1-fluorocyclopropyl)-4H-pyran-4-one (440 mg, 2.85 mmol) in aq. ammonia (7.0 ml, 25% in water) was stirred under reflux for 1 h. The reaction mixture was concentrated and the oily residue was further dried in vacuo to give 508 mg (100% purity, quant. yield) of the title compound which was used directly in the next step.

LC-MS (method 1): $R^t$=0.40 min; MS (ESIpos): m/z=154 $[M+H]^+$ $^1$H-NMR (600 MHz, DMSO-$d_6$) δ [ppm]: 1.20-1.35 (m, 2H), 1.43 (dq, 2H), 6.64 (br s, 1H), 6.96 (br s, 1H), 8.16 (br d, 1H).

Intermediate II-68

4-Bromo-2-(1-fluorocyclopropyl)pyridine

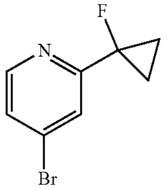 [SMILES: FC1(c2cc(Br)ccn2)CC1]

2-(1-Fluorocyclopropyl)pyridin-4(1H)-one (1.89 g, 85% purity, 10.5 mmol) was mixed with phosphoric tribromide [CAS-RN 7789-59-5](3.30 g, 11.5 mmol) at rt (caution, exothermic reaction) and the mixture was heated to 120° C. for 15 min. Subsequently, further phosphoric 10 tribromide (3.00 g, 10.5 mmol) was added and stirring at 120° C. was continued for 1 h. The reaction mixture was allowed to cool to rt, then washed with saturated aq. sodium bicarbonate solution. The aqueous phase was extracted twice with ethyl acetate. The combined organic layers were dried over anhydrous sodium sulfate, filtered and concentrated (maximum 40° C., minimum 50 mbar) to yield 1.60 g (97% purity, 68% yield) of the title compound.

LC-MS (method 1): R, =1.94 min; MS (ESIpos): m/z=215 $[M+H]^+$ $^1$H-NMR (400 MHz, DMSO-$d_6$) δ [ppm]: 1.27-1.44 (m, 2H), 1.46-1.59 (m, 2H), 7.59 (dd, 1H), 7.77 (t, 1H), 8.40 (d, 1H).

Intermediate II-69

2-(1-Fluorocyclopropyl)-4-(4,4,5,5-tetramethyl-1,3,2-dioxaborolan-2-yl)pyridine

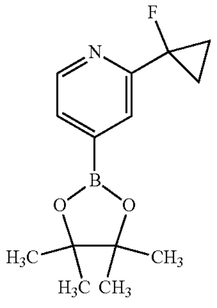 [SMILES: CC1(C)OB(c2ccnc(C3(F)CC3)c2)OC1(C)C]

4-Bromo-2-(1-fluorocyclopropyl)pyridine (125 mg, 97% purity, 558 µmol), 4,4,4',4',5,5,5',5'-octamethyl-2,2'-bi-1,3,2-dioxaborolane [CAS-RN 73183-34-3](170 mg, 670 µmol) and potassium acetate (164 mg, 1.67 mmol) were suspended under argon in 1,4-dioxane (2.5 ml). The mixture was degassed and purged with argon several times. Then 1,1'-bis(diphenylphosphino)ferrocene-palladium(II)dichloride dichloromethane complex (170 mg, 670 µmol) was added, and the reaction was stirred for 12 h at 90° C. The reaction mixture was filtered through a pad of silica gel and washed with cyclohexane. The filtrate was concentrated under reduced pressure to yield the title compound which was directly used in the next step.

Intermediate II-70

7-Chloro-5-[2-(1-fluorocyclopropyl)pyridin-4-yl][1,2,4]triazolo[1,5-a]pyridin-2-amine

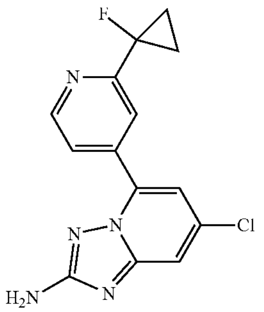 [SMILES: Nc1nc2cc(Cl)cc(-c3ccnc(C4(F)CC4)c3)n2n1]

5,7-Dichloro[1,2,4]triazolo[1,5-a]pyridin-2-amine (103 mg, 507 µmol), [2-(1-fluorocyclopropyl)pyridin-4-yl]boronic acid (101 mg, 558 µmol), 1,1'-bis(diphenylphosphino)ferrocene-palladium(II)dichloride dichloromethane complex (41.4 mg, 50.7 µmol) and caesium carbonate (496 mg, 1.52 mmol) were reacted according to procedure A in a mixture of water (500 1) and 1,4-dioxane (12 ml). The reaction was stirred at 90° C. for 4 h. The reaction was quenched with water and extracted with dichloromethane. The combined organic layers were dried over anhydrous sodium sulfate, filtered and concentrated. The residue was purified by HPLC to yield 78.0 mg (87% purity, 44% yield) of the title compound.

LC-MS (method 2): $R^t$=0.86 min; MS (ESIpos): m/z=304 $[M+H]^+$ $^1$H-NMR (600 MHz, DMSO-$d_6$) δ [ppm]: 1.42 (br d, 2H), 1.50-1.64 (m, 2H), 6.28 (br s, 2H), 7.33 (br s, 1H), 7.64 (br s, 2H), 7.78-7.89 (m, 1H), 8.17 (br s, 1H), 8.62-8.74 (m, 1H).

Intermediate II-71 tert-Butyl 3,3-difluorocyclobutane-1-carboxylate

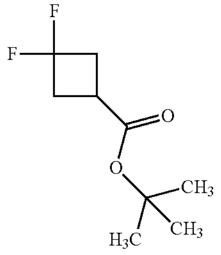

To a solution of 3,3-difluorocyclobutane-1-carboxylic acid [CAS-RN 107496-54-8](10.0 g, 73.5 mmol) under argon in dry dichloromethane (100 ml) at 0° C., was added 2-methylpropan-2-ol (14 ml, 150 mmol) followed by 4-dimethylaminopyridine (898 mg, 7.35 mmol) and N,N'-dicyclohexylmethanediimine (16.7 g, 80.8 mmol). The suspension is stirred at rt for 12 h and filtered. The solid was washed with dichloromethane and the filtrate was washed twice with 1M aqueous hydrochloric acid solution, once with saturated solution of sodium bicarbonate and with brine. The organic layer was dried over anhydrous sodium sulfate, filtered and concentrated. The residue was taken up in cyclohexane, passed through a silica gel pad, and washed with cyclohexane.

The filtrate was concentrated under reduced pressure to yield 8.86 g (100% purity, 63% yield) of the title compound.

$^1$H-NMR (400 MHz, DMSO-$d_6$) δ [ppm]: 1.42 (s, 9H), 2.62-2.87 (m, 4H), 2.90-2.99 (m, 1H).

Intermediate II-72 tert-Butyl 1-(5-bromopyridin-2-yl)-3,3-difluorocyclobutane-1-carboxylate

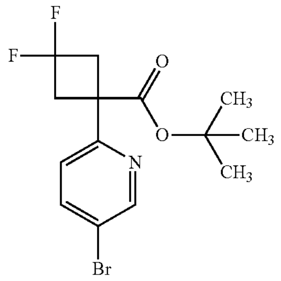 [SMILES: CC(C)(C)OC(=O)C1(c2ccc(Br)cn2)CC(F)(F)C1]

To a solution under argon of tert-butyl 3,3-difluorocyclobutane-1-carboxylate (8.86 g, 46.1 mmol) and 5-bromo-2-fluoropyridine [CAS-RN 107496-54-8](4.7 ml, 46 mmol) in toluene (130 ml) at 0° C., was added dropwise a solution of sodium hexamethyldisilazane (55 ml, 1.0 M in THF, 55 mmol) and the reaction was stirred for 30 min at 0° C. then overnight at rt. The reaction mixture was quenched with water, and the aqueous phase was extracted once with ethyl acetate. The organic layer was washed with brine, dried over anhydrous sodium sulfate and concentrated. The residue was purified by column chromatography (Biotage® SNAP Ultra 100 g cartridge, eluent: cyclohexane/ethyl acetate gradient 100:0 to 93:7) to yield 4.00 g (95% purity, 24% yield) of the title compound.

LC-MS (method 2): Rc=1.22 min; MS (ESIpos): m/z=348 $[M+H]^+$ $^1$H-NMR (600 MHz, DMSO-$d_6$) δ [ppm]: 1.35 (s, 9H), 2.66-2.85 (m, 1H), 2.91-3.18 (m, 1H), 7.43 (d, 1H), 8.10 (dd, 1H), 8.70 (d, 1H).

Intermediate II-73

5-Bromo-2-(3,3-difluorocyclobutyl)pyridine

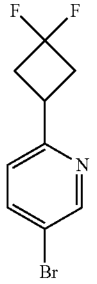

A solution of tert-butyl 1-(5-bromopyridin-2-yl)-3,3-difluorocyclobutane-1-carboxylate (4.00 g, 11.5 mmol) and trifluoroacetic acid (3.5 ml, 46 mmol) in dichloromethane (40 ml) was stirred at rt for 12 h. Trifluoroacetic acid (3.5 ml, 46 mmol) was further added and the reaction mixture was allowed to stir at rt for 24 h. The reaction mixture was concentrated and the residue was dissolved in toluene (40 ml). The solution was stirred for 8 h at 100° C., then cool down to rt and concentrated.

The residue was partitioned between ethyl acetate and a saturated aqueous solution of sodium bicarbonate. The layers were separated and the aqueous layer was extracted once more with ethyl acetate. The combined organic layers were dried over anhydrous sodium sulfate and concentrated to yield 2.79 g (95% purity, 93% yield) of the title compound.

LC-MS (method 1): $R^t$=1.99 min; MS (ESIpos): m/z=248 $[M+H]^+$ $^1$H-NMR (600 MHz, DMSO-$d_6$) δ [ppm]: 2.80-2.97 (m, 4H), 3.52-3.55 (m, 1H), 7.36 (d, 1H), 8.00 (dd, 1H), 8.70 (d, 1H).

Intermediate 1I-74

2-(3,3-Difluorocyclobutyl)-5-(4,4,5,5-tetramethyl-1,3,2-dioxaborolan-2-yl)pyridine

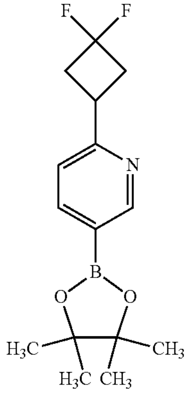

5-Bromo-2-(3,3-difluorocyclobutyl)pyridine (2.74 g, 11.0 mmol), 4,4,4',4', 5,5,5',5'-octamethyl-2,2'-bi-1,3,2-dioxaborolane [CAS-RN 73183-34-3](4.21 g, 16.6 mmol) and potassium acetate (3.25 g, 33.1 mmol) were suspended under argon in dry 1,4-dioxane (120 ml). Then 1,1'-bis(diphenylphosphino)ferrocene-palladium(II)dichloride dichloromethane complex (451 mg, 552 mol) was added, and the reaction was stirred for 16 h at 90° C. The reaction mixture was filtered and the solid was washed with ethyl acetate (15 ml). The filtrate was evaporated and the residue was suspended in a minimum of acetonitrile and water. A brown solid precipitated, which was filtered through kieselguhr and discarded. The filtrate was concentrated and the residue was stirred for 1 h in petroleum ether and allowed to stand overnight in the freezer. At rt, the suspension was filtered and the solid washed 3 times with petroleum ether and dried under high vacuum. The filtrate was concentrated in a rotary evaporator, taken up in methanol and purified by preparative HPLC to yield 1.65 g (86% purity, 43% yield) of the title compound.

LC-MS (method 1): $R^t$=0.70 min; MS (ESIpos): m/z=214 $[M+H]^+$ $^1$H-NMR (400 MHz, DMSO-$d_6$) δ [ppm]: 1.31 (s, 12H), 2.74-2.99 (m, 4H), 3.36-3.59 (m, 1H), 7.37 (d, 1H), 7.94 (d, 1H), 8.77 (s, 1H).

Intermediate 11-75

2-(Difluoromethyl)-5-(4,4,5,5-tetramethyl-1,3,2-dioxaborolan-2-yl)pyridine

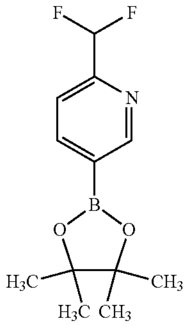

5-Bromo-2-(difluoromethyl)pyridine [CAS-RN 845827-13-6](950 mg, 4.57 mmol), 4,4,4',4',5,5,5',5'-octamethyl-2,2'-bi-1,3,2-dioxaborolane [CAS-RN 73183-34-3](1.74 g, 6.85 mmol) and potassium acetate (1.34 g, 13.7 mmol) were suspended under argon in 1,4-dioxane (40 ml). The mixture was degassed and purged with argon several times. Then 1,1'-bis(diphenylphosphino)ferrocene-palladium(II)dichloride dichloromethane complex (186 mg, 228 μmol) was added, and the reaction was stirred for 8 h at 90° C. The reaction mixture was filtered through a pad of silica gel and washed with cyclohexane. The filtrate was concentrated under reduced pressure and the residue directly purified by preparative HPLC to yield 980 mg (80% purity, 99% yield) of the title compound.

LC-MS (method 2): $R^t$=0.49 min; MS (ESIpos): m/z=174 $[M+H]^+$ $^1$H-NMR (500 MHz, CHLOROFORM-d) 8 [ppm]: 1.36 (s, 12H), 6.64 (t, 1H), 7.62 (d, 1H), 8.16-8.24 (d, 1H), 8.97 (s, 1H).

Intermediate II-76

1-(5-Bromopyridin-2-yl)cyclobutan-1-ol

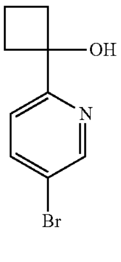 [SMILES: OC1(c2ccc(Br)cn2)CCC1]

In a reaction flask under argon, 2-propylmagnesium chloride (7.0 ml, 2.0 M in THF, 14 mmol) was added dropwise to a solution of 5-bromo-2-iodopyridine [CAS-RN 223463-13-6](4.00 g, 14.1 mmol) in dry THF (50 ml) at −20° C., then the mixture was stirred at 0° C. for 1 h. The reaction mixture was cooled back down to −15° C., cyclobutanone [CAS-RN 1191-95-3](1.2 ml, 17 mmol) was slowly added and the reaction mixture was stirred at rt for 12 h. The solution was cooled again to −15° C. and further 2-propylmagnesium chloride (5.0 ml, 2.0 M in THF, 10 mmol) was added, followed by stirring for 2 h at rt. Cyclobutanone (1.2 ml, 17 mmol) was added and the reaction mixture was stirred for 1 h. The reaction mixture was quenched with water and acidified with 1 N hydrochloric acid. The aqueous layer was extracted three times with ethyl acetate, and the combined organic layers were dried over anhydrous sodium sulfate and were concentrated in vacuo.

The residue was purified by column chromatography (Biotage® SNAP Ultra 340 g cartridge, eluent: cyclohexane/ethyl acetate gradient 95:5 to 90:10) to yield 1.27 g (100% purity, 40% yield) of the title compound.

LC-MS (method 1): $R^t$=1.45 min; MS (ESIpos): m/z=228 $[M+H]^+$ $^1$H-NMR (400 MHz, DMSO-$d_6$) δ [ppm]: 1.73-1.95 (m, 2H), 2.17-2.25 (m, 2H), 2.53-2.56 (m, 2H), 5.83 (s, 1H), 7.52 (dd, 1H), 7.99 (dd, 1H), 8.65-8.67 (m, 1H).

Intermediate II-77

1-[5-(4,4,5,5-Tetramethyl-1,3,2-dioxaborolan-2-yl)pyridin-2-yl]cyclobutan-1-ol

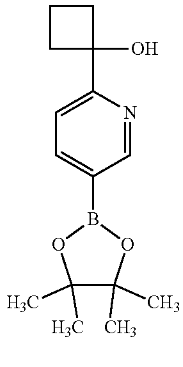

1-(5-Bromopyridin-2-yl)cyclobutan-1-ol (250 mg, 1.10 mmol), 4,4,4',4',5,5,5',5'-octamethyl-2,2'-bi-1,3,2-dioxaborolane [CAS-RN 73183-34-3](418 mg, 1.64 mmol) and potassium acetate (323 mg, 3.29 mmol) were suspended under argon in 1,4-dioxane (6.0 ml). The mixture was degassed and purged with argon several times. Then 1,1'-bis(diphenylphosphino)ferrocene-palladium(II)dichloride dichloromethane complex (44.8 mg, 54.8 μmol) was added, and the reaction was stirred for 2.5 h at 90° C. The reaction mixture was filtered through a pad of silica gel and washed with cyclohexane. The filtrate was concentrated under reduced pressure to give the title compound which was used without further purification in the next step.

Intermediate II-78

5-(2-Amino-7-chloro[1,2,4]triazolo[1,5-a]pyridin-5-yl)pyridin-2(1H)-one

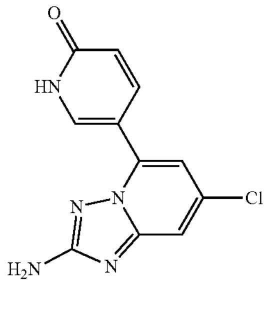 [SMILES: Nc1nc2cc(Cl)cc(-c3ccc(=O)[nH]c3)n2n1]

5,7-Dichloro[1,2,4]triazolo[1,5-a]pyridin-2-amine (300 mg, 94% purity, 1.39 mmol) was reacted with 5-(4,4,5,5-tetramethyl-1,3,2-dioxaborolan-2-yl)pyridin-2(11H)-one (384 mg, 1.74 mmol) for 2.5 h at 90° C. following general procedure B using 0.1 eq. catalyst. The mixture was concentrated in vacuum and the crude product purified by preparative HPLC (Chromatorex C18, 10 m, 125×30 mm; eluent: water/acetonitrile gradient 95:5 to 50:50) to yield 40.0 mg (99% purity, 11% yield) of the title compound.

LC-MS (method 1): $R^t$=0.86 min; MS (ESIpos): m/z=262 $[M+H]^+$ $^1$H-NMR (400 MHz, DMSO-$d_6$) δ [ppm]: 6.23 (s, 2H), 6.46 (d, 1H), 7.20 (d, 1H), 7.44 (d, 1H), 8.09 (dd, 1H), 8.49 (d, 1H), 12.15 (br s, 1H).

Intermediate II-79

N-[5-bromo-1-(difluoromethyl)pyridin-2(1H)-ylidene]acetamide

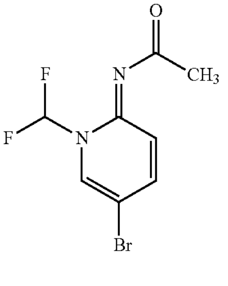

A suspension of N-(5-bromopyridin-2-yl)acetamide [7169-97-3](6.00 g, 27.9 mmol) and sodium chloro(difluoro)acetate [1895-39-2](5.10 g, 33.5 mmol) was stirred at reflux in acetonitrile (61 ml) for 12 h. Upon reaction a solid was formed which was filtered off and the reaction mixture was further stirred at reflux for two days. The suspension was filtered and the solid washed with acetonitrile. The filtrate was concentrated under reduced pressure to yield 7.71 g (92% purity, 96% yield) of the title compound.

LC-MS (method 2): $R^t$=0.64 min; MS (ESIpos): m/z=265 $[M+H]^+$

Intermediate II-80

5-Bromo-1-(difluoromethyl)pyridin-2(11)-one

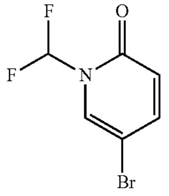 [SMILES: O=c1ccc(Br)cn1C(F)F]

A suspension of N-[5-bromo-1-(difluoromethyl)pyridin-2(1H)-ylidene]acetamide (7.71 g, 29.1 mmol) and potassium hydrogen sulfate (400 mg, 2.94 mmol) in acetonitrile (25 ml) and water (40 ml) was stirred at reflux for two h. The reaction mixture was allowed to cool down to rt, then extracted three times with ethyl acetate. The combined organic layers were washed with brine, dried over anhydrous sodium sulfate, filtered and concentrated. The residue was purified by column chromatography (Biotage® SNAP Ultra 100 g cartridge, eluent: cyclohexane/ethyl acetate gradient 95:5 to 80:20) to yield 5.24 g (97% purity, 78% yield) of the title compound.

LC-MS (method 1): $R^t$=1.27 min; MS (ESIpos): m/z=224 $[M+H]^+$ $^1$H-NMR (600 MHz, DMSO-$d_6$) δ [ppm]: 6.52 (d, 1H), 7.66 (dd, 1H), 7.78 (t, 1H), 8.08 (d, 1H).

Intermediate II-81

1-(Difluoromethyl)-5-(4,4,5,5-tetramethyl-1,3,2-dioxaborolan-2-yl)pyridin-2(H)-one

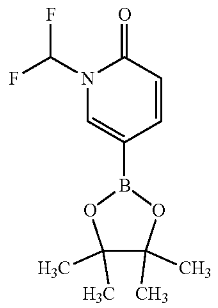 [SMILES: CC1(C)OB(c2ccc(=O)n(C(F)F)c2)OC1(C)C]

5-Bromo-1-(difluoromethyl)pyridin-2(1H)-one (3.00 g, 13.4 mmol), 4,4,4',4',5,5,5',5'-octamethyl-2,2'-bi-1,3,2-dioxaborolane [CAS-RN 73183-34-3](4.08 g, 16.1 mmol) and potassium acetate (3.94 g, 40.2 mmol) were suspended under argon in 1,4-dioxane (41 ml). The mixture was degassed and purged with argon several times. Then 1,1'-bis(diphenylphosphino)ferrocene-palladium(II)dichloride dichloromethane complex (547 mg, 670 μmol) was added, and the reaction was stirred for 2.5 h at 90° C. The reaction mixture was filtered through a pad of silica gel and washed with ethyl acetate. The filtrate was concentrated and the residue is purified by column chromatography (Biotage® SNAP Ultra 100 g cartridge, eluent: cyclohexane/ethyl acetate gradient 1:0 to 9:1) to yield 2.64 g (71% purity, 51% yield) of the title compound.

LC-MS (method 1): $R^t$=1.84 min; MS (ESIpos): m/z=272 $[M+H]^+$ $^1$H-NMR (600 MHz, DMSO-$d_6$) δ [ppm]: 1.28 (s, 12H), 6.51 (d, 1H), 7.59 (dd, 1H), 7.80 (d, 1H), 7.84 (t, 1H).

Intermediate II-82

5-(2-Amino-7-chloro[1,2,4]triazolo[1,5-a]pyridin-5-yl)-1-(difluoromethyl)pyridin-2(11H)-one

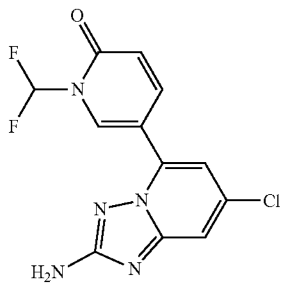 [SMILES: Nc1nc2cc(Cl)cc(-c3ccc(=O)n(C(F)F)c3)n2n1]

5,7-Dichloro[1,2,4]triazolo[1,5-a]pyridin-2-amine (160 mg, 788 µmol), 1-(difluoromethyl)-5-(4,4,5,5-tetramethyl-1,3,2-dioxaborolan-2-yl)pyridin-2(1H)-one (164 mg, 867 µmol), caesium carbonate (770 mg, 2.36 mmol) and 1,1'-bis(diphenylphosphino)ferrocene-palladium(II)dichloride dichloromethane complex (64.4 mg, 78.8 µmol) were reacted according to procedure A in a mixture of 1,4-dioxane (4.0 ml) and water (500 µl). The reaction mixture was stirred for 4 h at 90° C., then 10 filtered through a hydrophobic phase separation filter, washed with ethyl acetate, concentrated and dried in vacuo. The residue was used in the next step without further purification.

Intermediate II-83

5-Bromo-1-(2,2-difluoroethyl)pyridin-2(1H)-one

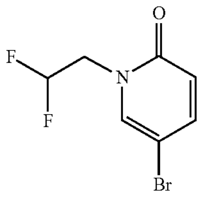 [SMILES: O=c1ccc(Br)cn1CC(F)F]

5-Bromopyridin-2(1H)-one [CAS-RN 13466-38-1](2.00 g, 11.5 mmol) and N,N-diisopropylethylamine (2.2 ml, 13 mmol) were stirred in dry dimethylformamide (20 ml) for 30 min, then 2,2-difluoroethyl trifluoromethanesulfonate [CAS RN 74427-22-8](2.95 g, 13.8 mmol) was added dropwise and the reaction mixture was allowed to stir at rt for 12 h. The reaction mixture was quenched with saturated aqueous ammonium chloride solution and extracted three times with tert-butyl methyl ether. The combined organic layers were dried over anhydrous sodium sulfate, filtered and the solvent removed under reduced pressure. The residue was purified by column chromatography (Biotage® SNAP Ultra 50 g cartridge, eluent: cyclohexane/ethyl acetate 1:1) to yield 1.24 g (100% purity, 45% yield) of the title compound.

LC-MS (method 2): $R^t$=0.58 min; MS (ESIpos): m/z=238 $[M+H]^+$ $^1$H-NMR (600 MHz, DMSO-$d_6$) δ [ppm]: 4.35 (td, 2H), 6.30 (tt, 1H), 6.45 (d, 1H), 7.59 (dd, 1H), 8.01 (d, 1H).

Intermediate II-84

1-(2,2-Difluoroethyl)-5-(4,4,5,5-tetramethyl-1,3,2-dioxaborolan-2-yl)pyridin-2(1H)-one

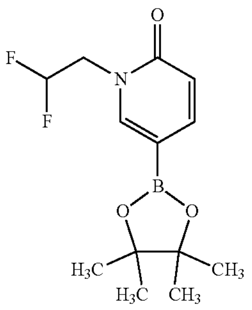 [SMILES: CC1(C)OB(c2ccc(=O)n(CC(F)F)c2)OC1(C)C]

5-Bromo-1-(2,2-difluoroethyl)pyridin-2(1H)-one (1.24 g, 5.21 mmol), 4,4,4',4',5,5,5',5'-octamethyl-2,2'-bi-1,3,2-dioxaborolane [CAS-RN 73183-34-3](1.59 g, 6.25 mmol) and potassium acetate (1.53 g, 15.6 mmol) were suspended under argon in 1,4-dioxane (16 ml). The mixture was degassed and purged with argon several times. Then 1,1'-bis(diphenylphosphino)ferrocene-palladium(II)dichloride dichloromethane complex (213 mg, 260 µmol) was added, and the reaction was stirred for 2.5 h at 90° C. The reaction mixture was filtered through a pad of silica gel and washed with ethyl acetate. The filtrate was concentrated and the residue is purified by column chromatography (Biotage® SNAP Ultra 50 g cartridge, eluent: cyclohexane/ethyl acetate gradient 95:5 to 80:20) to yield 1.20 g (100% purity, 81% yield) of the title compound.

LC-MS (method 1): $R^t$=1.65 min; MS (ESIpos): m/z=286 $[M+H]^+$ $^1$H-NMR (600 MHz, DMSO-$d_6$) δ [ppm]: 1.27 (s, 12H), 4.45 (td, 2H), 6.29 (tt, 1H), 6.42 (d, 1H), 7.53 (dd, 1H), 7.97 (br s, 1H).

Intermediate II-85

5-(2-Amino-7-chloro[1,2,4]triazolo[1,5-a]pyridin-5-yl)-1-(2,2-difluoroethyl)pyridin-2(11H)-one

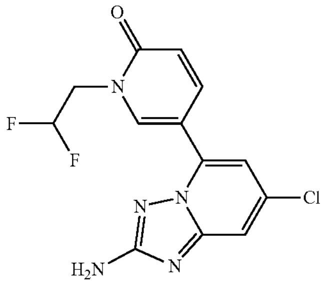 [SMILES: Nc1nc2cc(Cl)cc(-c3ccc(=O)n(CC(F)F)c3)n2n1]

5,7-Dichloro[1,2,4]triazolo[1,5-a]pyridin-2-amine (150 mg, 739 µmol), 1-(2,2-difluoroethyl)-5-(4,4,5,5-tetramethyl-1,3,2-dioxaborolan-2-yl)pyridin-2(1H)-one (232 mg, 813 μmol), caesium carbonate (722 mg, 2.22 mmol) and 1,1'-bis(diphenylphosphino)ferrocene-palladium(II)dichloride dichloromethane complex (60.3 mg, 73.9 μmol) were reacted according to procedure A in a mixture of 1,4-dioxane (4.0 ml) and water (500 μl). The reaction mixture was stirred for 4 h at 90° C., then filtered through a short pad of Florisil and washed with ethyl acetate. The filtrate was concentrated and the residue was triturated in a mixture of methanol and tert-butylmethylether to give a solid. The solid was collected by suction filtration and washed with tert-butylmethylether to yield the title compound. The filtrate was concentrated in vacuo and the residue was purified by preparative HPLC to yield the title compound. The two fractions were combined to give 129 mg (94% purity, 20 51% yield) of the title compound.

LC-MS (method 1): $R^t$=1.13 min; MS (ESIpos): m/z=326 $[M+H]^+$ $^1$H-NMR (600 MHz, DMSO-$d_6$) δ [ppm]: 4.46 (td, 2H), 6.20 (s, 2H), 6.40 (tt, 1H), 6.60 (d, 1H), 7.13 (d, 1H1), 7.50 (d, 1H), 8.18 (dd, 1H), 8.56 (d, 1H).

Intermediate II-86

5-Bromo-1-(2,2,2-trifluoroethyl)pyridin-2(li)-one

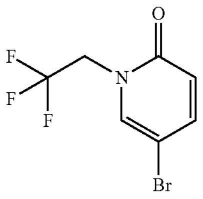 [SMILES: O=c1ccc(Br)cn1CC(F)(F)F]

In a flask under argon atmosphere, a solution of 5-bromopyridin-2(1H)-one [CAS-RN 13466-38-1](2.00 g, 11.5 mmol) and N,N-diisopropylethylamine (2.2 ml, 13 mmol) was stirred in dry dimethylformamide (20 ml) for 30 min, then 2,2,2-trifluoroethyl trifluoromethanesulfonate [CAS-RN 6226-25-1](75 1, 14 mmol) was added dropwise and the reaction mixture was allowed to stir at rt for two days. The reaction mixture was quenched with saturated aqueous ammonium chloride solution, then extracted twice with ethyl acetate. The combined organic layers were dried over anhydrous sodium sulfate, filtered and the solvent removed under reduced pressure. The residue was purified by column chromatography (Biotage® SNAP Ultra 100 g cartridge, eluent: cyclohexane/ethyl acetate gradient 90:10 to 40:60) to yield 1.97 g (100% purity, 67% yield) of the title compound.

LC-MS (method 1): $R^t$=1.29 min; MS (ESIpos): m/z=256 $[M+H]^+$ $^1$H-NMR (600 MHz, DMSO-$d_6$) δ [ppm]: 4.81 (q, 2H), 6.49 (d, 1H), 7.61 (dd, 1H), 8.02 (d, 1H).

Intermediate II-87

5-(4,4,5,5-Tetramethyl-1,3,2-dioxaborolan-2-yl)-1-(2,2,2-trifluoroethyl)pyridin-2(1H)-one

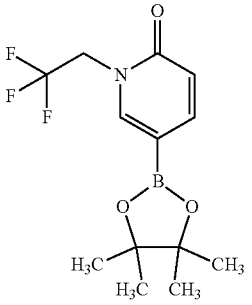 [SMILES: CC1(C)OB(c2ccc(=O)n(CC(F)(F)F)c2)OC1(C)C]

5-Bromo-1-(2,2,2-trifluoroethyl)pyridin-2(1H)-one [CAS-RN 1114563-10-8](8.30 g, 32.4 mmol), 4,4,4',4',5,5,5',5'-octamethyl-2,2'-bi-1,3,2-dioxaborolane (9.88 g, 38.9 mmol) and potassium acetate (9.54 g, 97.3 mmol) were suspended under argon in 1,4-dioxane (90 ml). The mixture was degassed and purged with argon three times. 1,1'-Bis(diphenylphosphino)ferrocene-palladium(II)dichloride dichloromethane complex (1.32 g, 1.62 mmol) was added, and the reaction was stirred for 3 h at 90° C. The reaction mixture was filtered through Celite® which was rinsed with ethyl acetate (50 ml). The filtrate was concentrated under reduced pressure. The residue was purified by column chromatography (Biotage® SNAP Ultra 340 g cartridge, eluent: cyclohexane/ethyl acetate gradient 9:1 to 1:4) to yield 8.24 g (95% purity, 80% yield) of the title compound.

LC-MS (method 1): $R^t$=1.78 min; MS (ESIpos): m/z=304 $[M+H]^+$ $^1$H-NMR (400 MHz, DMSO-$d_6$) δ [ppm]: 1.28 (s, 12H), 4.94 (q, 2H), 6.46 (d, 1H), 7.54 (dd, 1H), 8.00 (s, 1H).

Intermediate II-88

5-(2-Amino-6-bromo[1,2,4]triazolo[1,5-a]pyridin-8-yl)-1-(2,2,2-trifluoroethyl)pyridin-2(1H)-one

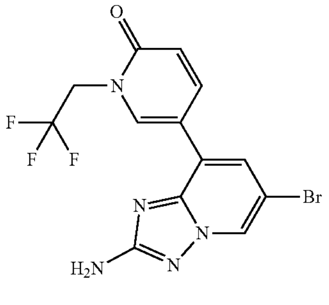 [SMILES: Nc1nc2c(-c3ccc(=O)n(CC(F)(F)F)c3)cc(Br)cn2n1]

6-Bromo-8-iodo[1,2,4]triazolo[1,5-a]pyridin-2-amine (3.39 g, 10.0 mmol), 5-(4,4,5,5-tetramethyl-1,3,2-dioxaborolan-2-yl)-1-(2,2,2-trifluoroethyl)pyridin-2(1H)-one (3.18 g, 10.5 mmol), and caesium carbonate (9.77 g, 30.0 mmol) were added to a mixture of 1,4-dioxane (63 ml) and water (6.3 ml) which was degassed with argon before 1,1'-bis(diphenylphosphino)ferrocene-palladium(II)dichloride dichloromethane complex (817 mg, 1.00 mmol) was added. The mixture was stirred at 80° C. for 3 h. The aqueous layer was then separated and extracted with ethyl acetate (10 ml). The combined organic layers were concentrated in vacuo. The residue was triturated with dichloromethane (30 ml) and THE (8 ml) and the precipitate was collected by suction filtration and washed with dichloromethane to yield 3.41 g (92% purity, 81% yield) of the title compound.

LC-MS (method 1): $R^t$=1.33 min; MS (ESIpos): m/z=388 $[M+H]^+$ $^1$H-NMR (400 MHz, DMSO-$d_6$) δ [ppm]: 4.92 (q, 2H), 6.24 (s, 2H), 6.63 (d, 1H), 7.80 (d, 1H), 8.35 (dd, 1H), 8.71 (d, 1H), 8.90 (d, 1H).

Intermediate II-89

5-(2-Amino-7-chloro[1,2,4]triazolo[1,5-a]pyridin-5-yl)-1-(2,2,2-trifluoroethyl)pyridin-2(1H)-one

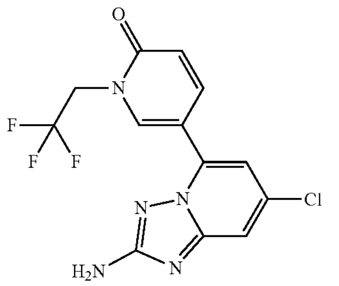 [SMILES: Nc1nc2cc(Cl)cc(-c3ccc(=O)n(CC(F)(F)F)c3)n2n1]

5,7-Dichloro[1,2,4]triazolo[1,5-a]pyridin-2-amine (160 mg, 788 μmol), 5-(4,4,5,5-tetramethyl-1,3,2-dioxaborolan-2-yl)-1-(2,2,2-trifluoroethyl)pyridin-2(11H)-one (192 mg, 867 μmol), caesium carbonate (770 mg, 2.36 mmol) and 1,1'-bis(diphenylphosphino)ferrocene-palladium(II)dichloride dichloromethane complex (64.4 mg, 78.8 μmol) were reacted according to procedure A in a mixture of 1,4-dioxane (4.0 ml) and water (500 μl). The reaction mixture was stirred for 4 h at 90° C., then filtered through a hydrophobic phase separation filter, washed with ethyl acetate, concentrated and dried under high vacuum. The residue was used in the next step without further purification.

Intermediate II-90

5-Bromo-1-(2,2,2-trifluoroethyl)pyrazin-2(1H)-one

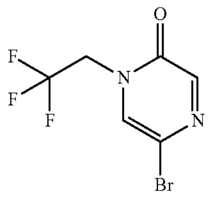 [SMILES: O=c1cnc(Br)cn1CC(F)(F)F]

5-Bromopyrazin-2-ol [CAS-RN 374063-92-0](5.00 g, 28.6 mmol) and N,N-diisopropylethylamine (5.5 ml, 31 mmol) were stirred in dry dimethylformamide (50 ml) for 10 min, then 2,2-difluoroethyl trifluoromethanesulfonate [CAS RN 74427-22-8](9.95 g, 42.9 mmol) was added dropwise and the 15 reaction mixture was allowed to stir at rt for 12 h. The reaction mixture was quenched with saturated aqueous ammonium chloride solution, then extracted three times with ethyl acetate. The combined organic layers were dried over anhydrous sodium sulfate, filtered and the solvent was removed under reduced pressure. The residue is purified by column chromatography (Biotage® SNAP Ultra 100 g cartridge, eluent: cyclohexane/ethyl acetate gradient 9:1 to 3:7) to yield 2.41 g 20 (100% purity, 33% yield) of the title compound.

LC-MS (method 1): $R^t$=1.20 min; MS (ESIpos): m/z=257 $[M+H]^+$ $^1$H-NMR (600 MHz, DMSO-$d_6$) δ [ppm]: 4.81 (q, 2H), 8.03 (s, 1H), 8.07 (s, 1H).

Intermediate II-91

5-(4,4,5,5-Tetramethyl-1,3,2-dioxaborolan-2-yl)-1-(2,2,2-trifluoroethyl)pyrazin-2(1H)-one

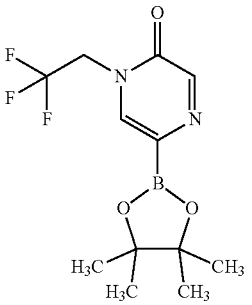 [SMILES: CC1(C)OB(c2cn(CC(F)(F)F)c(=O)cn2)OC1(C)C]

5-Bromo-1-(2,2,2-trifluoroethyl)pyrazin-2(1H)-one (1.31 g, 5.10 mmol), 4,4,4',4',5,5,5',5'-octamethyl-2,2'-bi-1,3,2-dioxaborolane [CAS-RN 73183-34-3](1.55 g, 6.12 mmol) and potassium acetate (1.50 g, 15.3 mmol) were suspended under argon in 1,4-dioxane (15.0 ml). The mixture was degassed and purged with argon several times. Then 1,1'-bis(diphenylphosphino)ferrocene-palladium(II)dichloride dichloromethane complex (208 mg, 255 μmol) was added, and the reaction was stirred for 3 h at 90° C. The reaction mixture was filtered through a pad of silica gel and washed with cyclohexane. The filtrate was concentrated in vacuo to give the title compound which was used in the next step without further purification.

Intermediate II-92

5-(2-Amino-7-chloro[1,2,4]triazolo[1,5-a]pyridin-5-yl)-1-(2,2,2-trifluoroethyl)pyrazin-2(1H)-one

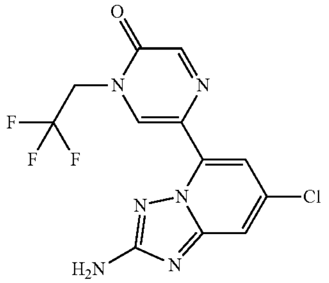

In a flask under argon atmosphere, 5,7-dichloro[1,2,4]triazolo[1,5-a]pyridin-2-amine (180 mg, 884 μmol), [5-oxo-4-(2,2,2-trifluoroethyl)-4,5-dihydropyrazin-2-yl]boronic acid (216 mg, 973 μmol), caesium carbonate (864 mg, 2.65-mmol) and 1,1'-bis(diphenylphosphino)ferrocene-palladium(II)dichloride dichloromethane complex (72.2 mg, 88.4 μmol) were reacted according to procedure A in a mixture of 1,4-dioxane (7.0 ml) and water (3.0 ml). After stirring for 4 h at 90° C., the reaction mixture was filtered through a short pad of Florisil and washed with ethyl acetate. The organic layer was concentrated and the residue was purified via preparative HPLC to yield 109 mg (100% purity, 36% yield) of the title compound.

LC-MS (method 1): $R^t$=1.49 min; MS (ESIpos): m/z=345 $[M+H]^+$ $^1$H-NMR (400 MHz, DMSO-$d_6$) 5.01 (q, 2H), 6.29 (s, 2H), 7.58 (d, 1H), 7.60 (d, 1H), 8.37 (d, 1H), 9.56 (s, 1H).

Intermediate II-93

4-Bromo-1-(2,2-difluoroethyl)pyridin-2(1H)-one

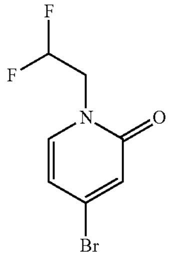

4-Bromopyridin-2(1H)-one [CAS RN 36953-37-4](1.50 g, 8.62 mmol) and N,N-diisopropylethylamine (1.7 ml, 9.5 mmol) were stirred in dry dimethylformamide (15 ml) for 30 min, then 2,2-difluoroethyl trifluoromethanesulfonate [CAS RN 74427-22-8](2.21 g, 10.3 mmol) was added dropwise and the reaction mixture was allowed to stir at rt for 12 h. The reaction mixture 20 was quenched with saturated aqueous ammonium chloride solution, then extracted three times with tert-butylmethylether. The combined organic layers were dried over anhydrous anhydrous sodium sulfate, filtered and the solvent removed under reduced pressure. The residue was purified by column chromatography (Biotage® SNAP Ultra 50 g cartridge, eluent: cyclohexane/ethyl acetate gradient 1:0 to 1:1) to yield 760 mg (100% purity, 37% yield) of the title compound.

LC-MS (method 1): $R^t$=1.15 min; MS (ESIpos): m/z=238 $[M+H]^+$ $^1$H-NMR (400 MHz, DMSO-$d_6$) δ [ppm]: 4.37 (td, 2H), 6.29 (tt, 1H), 6.54 (dd, 1H), 6.80 (d, 1H), 7.66 (d, 1H).

Intermediate II-94

1-(2,2-Difluoroethyl)-4-(4,4,5,5-tetramethyl-1,3,2-dioxaborolan-2-yl)pyridin-2(1H)-one

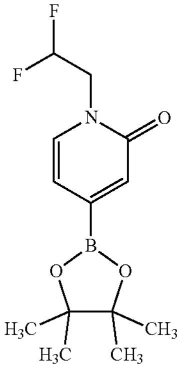 [SMILES: CC1(C)OB(c2ccn(CC(F)F)c(=O)c2)OC1(C)C]

4-Bromo-1-(2,2-difluoroethyl)pyridin-2(1H)-one (710 mg, 2.98 mmol), 4,4,4',4',5,5,5',5'-octamethyl-2,2'-bi-1,3,2-dioxaborolane [CAS-RN 73183-34-3](909 mg, 3.58 mmol) and potassium acetate (878 mg, 8.95 mmol) were suspended under argon in 1,4-dioxane (28.0 ml). The mixture was degassed and purged with argon several times. Then 1,1'-bis(diphenylphosphino)ferrocene-palladium(II)dichloride dichloromethane complex (122 mg, 149 μmol) was added, and the reaction was stirred for 2 h at 90° C. The reaction mixture was diluted in ethyl acetate and filtered through a pad of silica gel. The filtrate was concentrated in vacuo and the residue was purified by column chromatography (Biotage® SNAP Ultra 50 g cartridge, eluent: cyclohexane/ethyl acetate gradient 9:1 to 1:1) to yield 526 mg (100% purity, 62% yield) of the title compound.

$^1$H-NMR (500 MHz, DMSO-$d_6$) δ [ppm]: 1.29 (s, 12H), 4.37 (td, 2H), 6.28 (tt, 1H), 6.32 (dd, 1H), 6.66 (s, 1H), 7.63 (d, 1H).

Intermediate II-95

4-Bromo-1-(2,2,2-trifluoroethyl)pyridin-2(H)-one

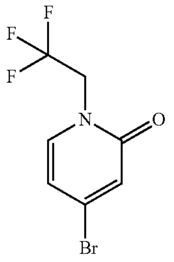

4-Bromopyridin-2(1H)-one [CAS RN 36953-37-4](1.50 g, 8.62 mmol) and N,N-diisopropylethylamine (1.7 ml, 9.5 mmol) were stirred in dry dimethylformamide (15 ml) for 30 min, then 2,2-trifluoroethyl trifluoromethanesulfonate [CAS RN 74427-22-8](2.40 g, 10.3 mmol) 10 was added dropwise and the reaction mixture was allowed to stir at rt for 24 h. The reaction mixture was quenched with saturated aqueous ammonium chloride solution, then extracted three times with tert-butylmethylether. The combined organic layers were dried over anhydrous anhydrous sodium sulfate, filtered and the solvent removed under reduced pressure. The residue was purified by column chromatography (Biotage® SNAP Ultra 50 g cartridge, eluent: cyclohexane/ethyl acetate 15 gradient 1:0 to 1:1) to yield 1.47 g (100% purity, 66% yield) of the title compound.

LC-MS (method 2): $R^t$=0.67 min; MS (ESIpos): m/z=256 $[M+H]^+$ $^1$H-NMR (400 MHz, DMSO-$d_6$) δ [ppm]: 4.84 (q, 2H), 6.58 (dd, 1H), 6.86 (d, 1H), 7.67 (d, 1H).

Intermediate II-96

4-(4,4,5,5-Tetramethyl-1,3,2-dioxaborolan-2-yl)-1-(2,2,2-trifluoroethyl)pyridin-2(1H)-one

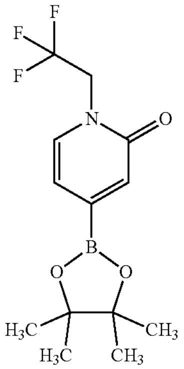 [SMILES: CC1(C)OB(c2ccn(CC(F)(F)F)c(=O)c2)OC1(C)C]

4-Bromo-1-(2,2,2-trifluoroethyl)pyridin-2(1H)-one (1.42 g, 5.55 mmol), 4,4,4',4',5,5,5',5'-octamethyl-2,2'-bi-1,3,2-dioxaborolane [CAS-RN 73183-34-3](1.69 g, 6.66 mmol) and potassium acetate (1.63 g, 16.6 mmol) were suspended under argon in 1,4-dioxane (53.0 ml). The mixture was degassed and purged with argon several times. Then 1,1'-bis(diphenylphosphino)ferrocene-palladium(II)dichloride dichloromethane complex (226 mg, 277 µmol) was added, and the reaction was stirred for 2 h at 90° C. The reaction mixture was diluted in ethyl acetate and filtered through a pad of silica gel. The filtrate was concentrated under reduced pressure and the residue was purified by column chromatography (Biotage® SNAP Ultra 100 g cartridge, eluent: cyclohexane/ethyl acetate gradient 9:1 to 1:1) to yield 1.27 g (91% purity, 69% yield) of the title compound. $^1$H-NMR (500 MHz, DMSO-$d_6$) δ [ppm]: 1.29 (s, 12H), 4.86 (q, 2H), 6.36 (dd, 1H), 6.68 (s, 1H), 7.63 (d, 1H).

Intermediate II-97

7-Chloro-5-[1-(2,2,2-trifluoroethyl)-1H-pyrazol-4-yl][1,2,4]triazolo[1,5-a]pyridin-2-amine

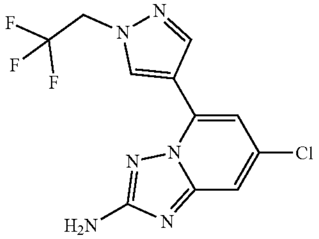 [SMILES: Nc1nc2cc(Cl)cc(-c3cnn(CC(F)(F)F)c3)n2n1]

5,7-Dichloro[1,2,4]triazolo[1,5-a]pyridin-2-amine [CAS-RN 1233526-60-7](300 mg, 90% purity, 1.33 mmol) was reacted with 4-(4,4,5,5-tetramethyl-1,3,2-dioxaborolan-2-yl)-1-(2,2,2-trifluoroethyl)-1H-pyrazole [CAS-RN 1049730-42-8](511 mg, 97% purity, 1.80 mmol) for 1.5 h at 90° C. following general procedure C using 0.1 eq. catalyst. The reaction mixture was directly purified by column chromatography (Biotage® SNAP Ultra 50 g cartridge, eluent: dichloromethane/methanol gradient 100:0 to 85:15). The isolated material was triturated with THF (3.0 ml), collected by suction filtration and washed with THF (1.0 ml) to yield 260 mg (97% purity, 60% yield) of the title compound. The mother liquor was purified by column chromatography (Biotage® SNAP KP-NH 28 g cartridge, eluent: cyclohexane/ethyl acetate gradient 100:0 to 10:90) to give a second batch of 40.0 mg (100% purity, 9% yield). The total yield was 69%.

LC-MS (method 2): $R^t$=0.77 min; MS (ESIpos): m/z=317 $[M+H]^+$ $^1$H-NMR (500 MHz, DMSO-$d_6$) δ [ppm]: 5.34 (q, 2H), 6.23 (s, 2H), 7.41 (d, 1H), 7.55 (d, 1H), 8.62 (s, 1H), 9.01 (s, 1H).

Intermediate II-98

7-Chloro-5-(1-cyclopentyl-1H-pyrazol-4-yl)[1,2,4]triazolo[1,5-a]pyridin-2-amine

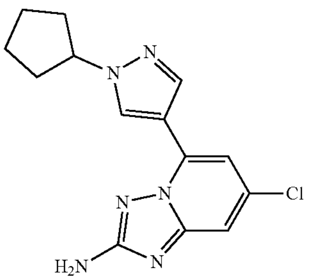 [SMILES: Nc1nc2cc(Cl)cc(-c3cnn(C4CCCC4)c3)n2n1]

5,7-Dichloro[1,2,4]triazolo[1,5-a]pyridin-2-amine (526 mg, 90% purity, 2.33 mmol) was reacted with 1-cyclopentyl-4-(4,4,5,5-tetramethyl-1,3,2-dioxaborolan-2-yl)-1H-pyrazole (850 mg, 97% purity, 3.14 mmol) for 2 h at 90° C. following general procedure C using 0.1 eq. catalyst. The reaction mixture was directly purified by column chromatography (Biotage® SNAP Ultra 50 g cartridge, eluent: dichloromethane/methanol gradient 0:100 to 85:15). The product required a second purification by column chromatography (Biotage® SNAP Ultra 50 g cartridge, eluent: cyclohexane/ethyl acetate gradient 100:0 to 5:95) to yield 580 mg (100% purity, 82% yield) of the title compound.

LC-MS (method 2): $R^t$=0.86 min; MS (ESIpos): m/z=303 $[M+H]^+$ $^1$H-NMR (500 MHz, DMSO-$d_6$) δ [ppm]: 1.64-1.73 (m, 2H), 1.78-1.88 (m, 2H), 1.93-2.02 (m, 2H), 2.10-2.19 (m, 2H), 4.80 (quin, 1H), 6.23 (s, 2H), 7.34 (d, 1H), 7.48 (d, 1H), 8.51 (s, 1H), 8.88 (s, 1H).

Intermediate II-99

2-Amino-5-bromo-N-propanoylpyridine-3-carbohydrazide

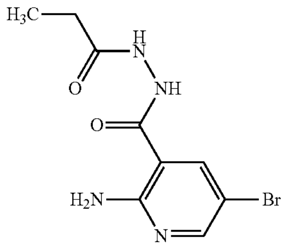 [SMILES: CCC(=O)NNC(=O)c1cc(Br)cnc1N]

To a mixture of 2-amino-5-bromopyridine-3-carboxylic acid (8.21 g, 37.8 mmol), propanehydrazide (4.00 g, 45.4 mmol), and triethylamine (21 ml, 150 mmol) in DMF (28 ml) at rt was added dropwise a solution of T3P (66 ml, 50% in DMF, 113 mmol. The reaction was then stirred at rt for 5 h. Subsequently, it was diluted with water and ethyl acetate and the aqueous layer was separated and extracted twice with ethyl acetate. The combined organic layers were dried over anhydrous anhydrous sodium sulfate and the solvent was evaporated under reduced pressure. The residue was triturated with ethyl acetate/tert-butyl methyl ether and the precipitate was collected by suction filtration to yield 3.90 g (75% purity, 27% yield) of the title compound.

LC-MS (method 2): $R^t$=0.40 min; MS (ESIpos): m/z=287, 289 $[M+H]^+$ $^1$H-NMR (500 MHz, DMSO-$d_6$) δ [ppm]: 1.06 (t, 3H), 2.19 (q, 2H), 7.21 (s, 2H), 8.11 (d, 1H), 8.20 (d, 1H), 9.83 (s, 1H), 10.29 (s, 1H).

Intermediate II-100

5-Bromo-3-(5-ethyl-1,3,4-thiadiazol-2-yl)pyridin-2-amine

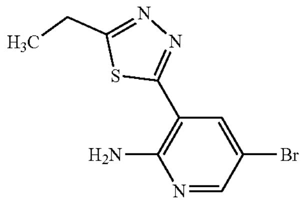

2-Amino-5-bromo-N'-propanoylpyridine-3-carbohydrazide (1.50 g, 75% purity, 3.92 mmol) was dissolved in THF (30 ml) and Lawesson's reagent (1.90 g, 4.70 mmol) was added. The mixture was heated under reflux for 3 h. Solid material was then removed by filtration and the filter was rinsed with ethyl acetate. Water was added to the filtrate and the aqueous layer was separated and extracted twice with ethyl acetate. The combined organic layers were filtered through a hydrophobic phase separation filter and the solvent was removed in vacuo. The residue was purified by column chromatography (Biotage® SNAP KP-NH 110 g cartridge, eluent: cyclohexane/ethyl acetate gradient 90:10 to 15:85) to yield 829 mg (100% purity, 74% yield) of the title compound.

LC-MS (method 1): $R^t$=1.65 min; MS (ESIpos): m/z=285, 287 $[M+H]^+$ $^1$H-NMR (500 MHz, DMSO-$d_6$) δ [ppm]: 1.36 (t, 3H), 3.15 (q, 2H), 7.73 (br s, 2H), 8.06 (d, 1H), 8.21 (d, 1H).

Intermediate II-101

Ethyl {[5-bromo-3-(5-ethyl-1,3,4-thiadiazol-2-yl)pyridin-2-yl]carbamothioyl}carbamate

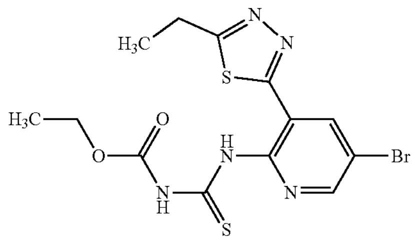 [SMILES: CCOC(=O)NC(=S)Nc1ncc(Br)cc1-c1nnc(CC)s1]

5-Bromo-3-(5-ethyl-1,3,4-thiadiazol-2-yl)pyridin-2-amine (850 mg, 2.98 mmol) was dissolved in 1,4-dioxane (15 ml) and ethyl carbonisothiocyanatidate (390 μl, 3.3 mmol) was added dropwise. The mixture was heated to 50° C. overnight. Subsequently, the mixture was concentrated in vacuo and the residue was triturated with cyclohexane/tert-butyl methyl ether. The precipitate was collected by suction filtration to yield 972 mg (93% purity, 73% yield) of the title compound.

LC-MS (method 1): $R^t$=1.81 min; MS (ESIpos): m/z=416, 418 $[M+H]^+$ $^1$H-NMR (500 MHz, DMSO-$d_6$) δ [ppm]: 1.28 (t, 3H), 1.34 (t, 3H), 3.17 (q, 2H), 4.25 (q, 2H), 8.73 (d, 1H), 8.80 (d, 1H), 11.60-11.74 (m, 2H).

Intermediate II-102

6-Bromo-8-(5-ethyl-1,3,4-thiadiazol-2-yl)[1,2,4]triazolo[1,5-a]pyridin-2-amine

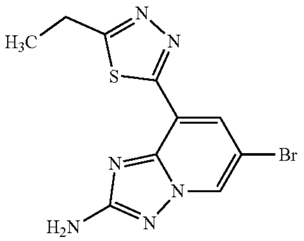 [SMILES: CCc1nnc(-c2cc(Br)cn3nc(N)nc23)s1]

A solution of hydroxylamine hydrochloride (771 mg, 11.1 mmol) and N,N-diisopropylethylamine (1.8 ml, 10 mmol) in methanol/ethanol (1:1, 15 ml) was heated to 60° C. and ethyl {[5-bromo-3-(5-ethyl-1,3,4-thiadiazol-2-yl)pyridin-2-yl]carbamothioyl}carbamate (920 mg, 93% purity, 2.06 mmol) was added. The mixture was stirred at 60° C. for 1 h and then cooled to rt. The pH was adjusted to 6-7 by addition of satd. sodium bicarbonate solution and the mixture was poured into water (100 ml). It was stirred for 10 min and the precipitate was collected by suction filtration and washed with water (5 ml) and dried in vacuo to yield 658 mg (90% purity, 89% yield) of the title compound.

LC-MS (method 1): $R^t$=1.28 min; MS (ESIpos): m/z=325, 327 $[M+H]^+$ $^1$H-NMR (500 MHz, DMSO-$d_6$) δ [ppm]: 1.40 (t, 3H), 3.20 (q, 2H), 6.56 (s, 2H), 8.36 (s, 1H), 9.16 (s, 1H).

Intermediate II-103

2-Amino-5-bromo-N-(2-methylpropanoyl)pyridine-3-carbohydrazide

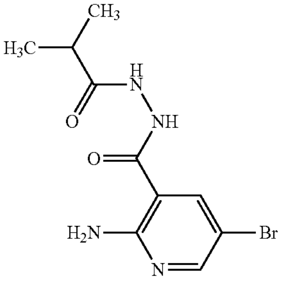 [SMILES: CC(C)C(=O)NNC(=O)c1cc(Br)cnc1N]

To a mixture of 2-amino-5-bromopyridine-3-carboxylic acid (8.85 g, 40.8 mmol), 2-methylpropanehydrazide (5.00 g, 49.0 mmol), and triethylamine (23 ml, 160 mmol) in DMF (30 ml) at rt was added dropwise a solution of T3P (71 ml, 50% purity, 120 mmol). The reaction was then stirred at rt for 5 h. Subsequently, it was diluted with water and ethyl acetate and the aqueous layer was separated and extracted twice with ethyl acetate. The combined organic layers were dried over anhydrous anhydrous sodium sulfate and the solvent was evaporated under reduced pressure. The residue was triturated with ethyl acetate/tert-butyl methyl ether and the precipitate was collected by suction filtration to yield 7.87 g (99% purity, 63% yield) of the title compound. LC-MS (method 1): $R^t$=0.85 min; MS (ESIpos): m/z=301, 303 $[M+H]^+$ $^1$H-NMR (400 MHz, DMSO-$d_6$) δ [ppm]: 1.07 (d, 6H), 7.21 (s, 2H), 8.12 (d, 1H), 8.20 (d, 1H), 9.84 (s, 1H), 10.29 (br s, 1H).

Intermediate II-104

5-Bromo-3-[5-(propan-2-yl)-1,3,4-thiadiazol-2-yl] pyridin-2-amine

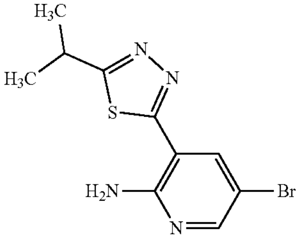 [SMILES: CC(C)c1nnc(-c2cc(Br)cnc2N)s1]

2-Amino-5-bromo-N'-(2-methylpropanoyl)pyridine-3-carbohydrazide (3.00 g, 9.96 mmol) was dissolved in THF (60 ml) and Lawesson's reagent (4.84 g, 12.0 mmol) was added. The mixture was heated under reflux for 3 h. The reaction mixture was combined with an experient using 500 mg starting material. Solid material was then removed by filtration and the filter was rinsed with ethyl acetate. The solvent was removed in vacuo. The residue was purified by column chromatography (Biotage® SNAP Ultra C18 60 g cartridge, eluent: acetonitrile/water gradient 25:75 to 77:23, then to 95:5). The product fractions were concentrated in vacuo and the remaining aqueous solution was extracted three times with ethyl acetate. The combined organic layers were washed with brine, filtered through a hydrophobic phase separation filter and the solvent was removed in vacuo to yield 1.86 g (80% purity, 43% yield) of the title compound which was used without further purification.

LC-MS (method 1): $R^t$=1.84 min; MS (ESIpos): m/z=299, 301 $[M+H]^+$ $^1$H-NMR (400 MHz, DMSO-$d_6$) δ [ppm]: 1.41 (d, 6H), 3.49 (spt, 1H), 7.73 (br s, 2H), 8.07 (d, 1H), 8.21 (d, 1H).

Intermediate II-105

Ethyl({5-bromo-3-[5-(propan-2-yl)-1,3,4-thiadiazol-2-yl]pyridin-2-yl}carbamothioyl)carbamate

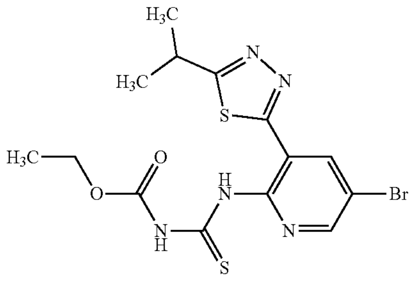 [SMILES: CCOC(=O)NC(=S)Nc1ncc(Br)cc1-c1nnc(C(C)C)s1]

5-Bromo-3-[5-(propan-2-yl)-1,3,4-thiadiazol-2-yl]pyridin-2-amine (1.80 g, 80% purity, 4.81 mmol) was dissolved in 1,4-dioxane (20 ml) and ethyl carbonisothiocyanatidate (620 μl, 5.3 mmol) was added dropwise. The mixture was stirred at rt overnight and then heated to 60° C. for 6 h. Subsequently, the mixture was concentrated in vacuo and the residue was triturated with tert-butyl methyl ether. The precipitate was collected by suction filtration and purified by column chromatography (Biotage® SNAP Ultra 25 g cartridge, eluent: cyclohexane/ethyl acetate gradient 90:10 to 46:54) to yield 1.15 g (80% purity, 44% yield) of the title compound.

LC-MS (method 1): R, =1.98 min; MS (ESIpos): m/z=430, 432 $[M+H]^+$ $^1$H-NMR (400 MHz, DMSO-$d_6$) δ [ppm]: 1.28 (t, 3H), 1.39 (d, 6H), 3.53 (spt, 1H), 4.25 (q, 2H), 8.72 (d, 1H), 8.80 (d, 1H), 11.66 (s, 1H), 11.73 (s, 1H).

Intermediate II-106

6-Bromo-8-[5-(propan-2-yl)-1,3,4-thiadiazol-2-yl][1,2,4]triazolo[1,5-a]pyridin-2-amine

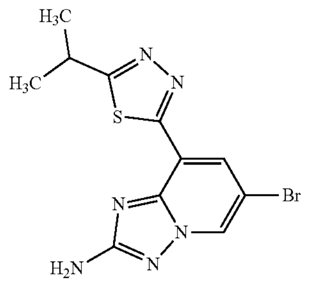 [SMILES: CC(C)c1nnc(-c2cc(Br)cn3nc(N)nc23)s1]

A solution of hydroxylamine hydrochloride (698 mg, 10.0 mmol) and N,N-diisopropylethylamine (1.6 ml, 9.3 mmol) in methanol/ethanol (1:1, 25 ml) was heated to 60° C. and ethyl ({5-bromo-3-[5-(propan-2-yl)-1,3,4-thiadiazol-2-yl]pyridin-2-yl}carbamothioyl)carbamate (1.00 g, 80% purity, 1.86 mmol) was added. The mixture was stirred at 60° C. for 1 h and then cooled to rt. The pH was adjusted to 6-7 by addition of satd. sodium bicarbonate solution and the mixture was poured into water (100 ml). It was stirred for 10 min and the precipitate was collected by suction filtration and washed with water (5 ml) and dried in vacuo to yield 630 mg (98% purity, 97% yield) of the title compound.

LC-MS (method 2): $R^t$=0.78 min; MS (ESIpos): m/z=338, 340 $[M+H]^+$ $^1$H-NMR (400 MHz, DMSO-$d_6$) δ [ppm]: 1.43 (d, 6H), 3.55 (spt, 1H), 6.57 (s, 2H), 8.38 (d, 1H), 9.17 (d, 1H).

Intermediate II-107

2-Amino-5-bromo-N-[(2S)-3-hydroxy-2-methylpropanoyl]pyridine-3-carbohydrazide

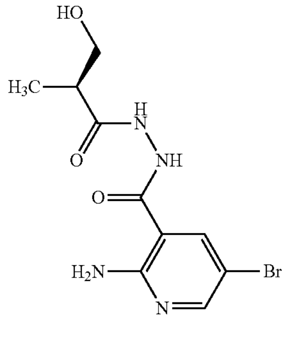 [SMILES: C[C@@H](CO)C(=O)NNC(=O)c1cc(Br)cnc1N]

To a mixture of 2-amino-5-bromopyridine-3-carboxylic acid (500 mg, 2.30 mmol) and (2S)-3-hydroxy-2-methylpropanehydrazide [CAS-RN 26543-06-6](354 mg, 3.00 mmol) in DMF (4.0 ml) were added N,N-diisopropylamine (13.6 ml, 78 mmol and HATU (1.31 g, 3.46 mmol) and the reaction was stirred at rt overnight. Water and ethyl acetate were added. The aqueous layer was separated and extracted twice with ethyl acetate. The combined organic layers were filtered through a hydrophobic phase separation filter and the solvent was evaporated under reduced pressure. The residue was triturated with dichloromethane/tert-butyl methyl ether and the precipitate was collected by suction filtration to yield 256 mg (85% purity, 30% yield) of the title compound.

LC-MS (method 2): R, =0.36 min; MS (ESIpos): m/z=317, 319 $[M+H]^+$ $^1$H-NMR (500 MHz, DMSO-$d_6$) δ [ppm]: 1.03 (d, 3H), 2.47-2.56 (m, 1H), 3.32-3.37 (m, 1H), 3.58 (ddd, 1H), 4.68 (t, 1H), 7.20 (s, 2H), 8.13 (d, 1H), 8.19 (d, 1H), 9.85 (s, 1H), 10.35 (s, 1H).

Intermediate 11-108

2-Amino-5-bromo-N-[(2S)-3-{[tert-butyl(dimethyl)silyl]oxy}-2-methylpropanoyl]pyridine-3-carbohydrazide

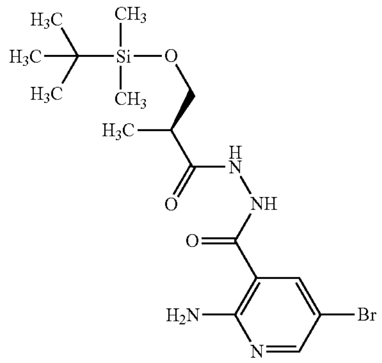 [SMILES: C[C@@H](CO[Si](C)(C)C(C)(C)C)C(=O)NNC(=O)c1cc(Br)cnc1N]

2-Amino-5-bromo-N'-[(2S)-3-hydroxy-2-methylpropanoyl]pyridine-3-carbohydrazide (2.00 g, 80% purity, 5.05 mmol) was dissolved in THF (37 ml) and imidazole (515 mg, 7.57 mmol), DMAP (30.8 mg, 252 μmol), and tert-butyl (chloro)dimethylsilane (912 mg, 6.05 mmol) were added. The mixture was stirred at rt for 3 h and then diluted with water/dichloromethane. The aqueous phase was separated and extracted twice with dichloromethane. The combined organic layers were filtered through a hydrophobic phase separation filter and the solvent was evaporated under reduced pressure. The crude product was purified by column chromatography (Biotage® SNAP Ultra 50 g cartridge, eluent: cyclohexane/ethyl acetate gradient 95:5 to 35:65) to yield 1.01 g (100% purity, 46% yield) of the title compound.

LC-MS (method 1): $R^t$=1.98 min; MS (ESIpos): m/z=431, 433 $[M+H]^+$ $^1$H-NMR (500 MHz, DMSO-$d_6$) δ [ppm]: 0.04 (s, 3H), 0.05 (s, 3H), 0.87 (s, 9H), 1.04 (d, 3H), 2.52-2.61 (m, 1H), 3.49 (dd, 1H), 3.76 (dd, 1H), 7.19 (br s, 2H), 8.12 (d, 1H), 8.19 (d, 1H), 9.88 (s, 1H), 10.33 (s, 1H).

Intermediate II-109

5-Bromo-3-{5-[(2S)-1-{[tert-butyl(dimethyl)silyl]oxy}propan-2-yl]-1,3,4-thiadiazol-2-yl}pyridin-2-amine

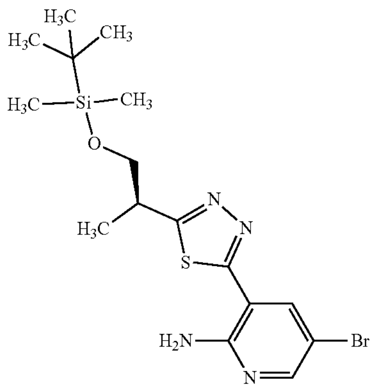 [SMILES: C[C@@H](CO[Si](C)(C)C(C)(C)C)c1nnc(-c2cc(Br)cnc2N)s1]

2-Amino-5-bromo-N'-[(2S)-3-{[tert-butyl(dimethyl)silyl]oxy}-2-methylpropanoyl]pyridine-3-carbohydrazide (900 mg, 2.09 mmol) was dissolved in THF (27 ml) and Lawesson's reagent (1.01 g, 2.50 mmol) was added. The mixture was heated under reflux for 3 h. The reaction mixture was combined with an experiment of 0.10 g starting material. Water and ethyl acetate were added, the aqueous layer was separated and extracted twice with ethyl acetate. The combined organic layers were filtered through a hydrophobic phase separation filter and the solvent was removed in vacuo. 15 The residue was purified by column chromatography (Biotage® SNAP KP-NH 55 g cartridge, eluent: cyclohexane/ethyl acetate gradient 100:0 to 35:65) to yield 829 mg (100% purity, 71% yield) of the title compound.

LC-MS (method 1): $R^t$=2.75 min; MS (ESIpos): m/z=429, 431 $[M+H]^+$ $^1$H-NMR (500 MHz, DMSO-$d_6$) δ [ppm]: 0.03 (s, 6H), 0.85 (s, 9H), 1.39 (d, 3H), 3.50-3.57 (m, 20 1H), 3.82 (dd, 1H), 3.87 (dd, 1H), 7.73 (s, 2H), 8.02 (d, 1H), 8.22 (d, 1H).

Intermediate II-110

Ethyl [(5-bromo-3-{5-[(2S)-1-{[tert-butyl(dimethyl)silyl]oxy}propan-2-yl]-1,3,4-thiadiazol-2-yl}pyridin-2-yl)carbamothioyl]carbamate

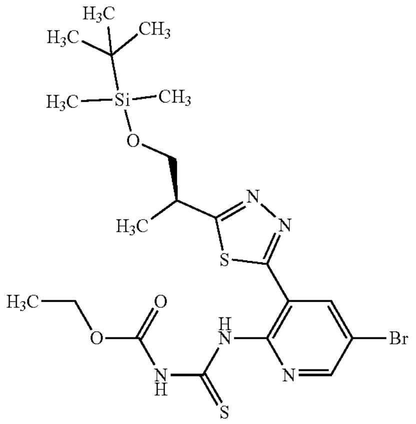 [SMILES: CCOC(=O)NC(=S)Nc1ncc(Br)cc1-c1nnc([C@@H](C)CO[Si](C)(C)C(C)(C)C)s1]

5-Bromo-3-{5-[(2S)-1-{[tert-butyl(dimethyl)silyl]oxy}propan-2-yl]-1,3,4-thiadiazol-2-yl}pyridin-2-amine (700 mg, 1.63 mmol) was dissolved in 1,4-dioxane (9.0 ml) and ethyl carbonisothiocyanatidate (210 µl, 1.8 mmol) was added dropwise. The mixture was stirred at rt overnight and then heated to 50° C. for 2 h. Subsequently, the mixture was concentrated in vacuo and the residue was purified by column chromatography (Biotage® SNAP Ultra 50 g cartridge, eluent: cyclohexane/ethyl acetate gradient 95:5 to 57:43) to yield 797 mg (90% purity, 79% yield) of the title compound.

LC-MS (method 1): $R^t$=2.74 min; MS (ESIpos): m/z=560, 562 $[M+H]^+$

Intermediate II-111

6-Bromo-8-{5-[(2S)-1-{[tert-butyl(dimethyl)silyl]oxy}propan-2-yl]-1,3,4-thiadiazol-2-yl}[1,2,4]triazolo[1,5-a]pyridin-2-amine

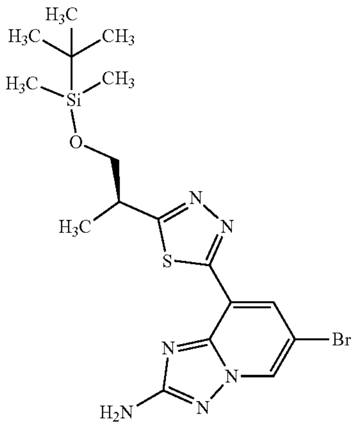 [SMILES: C[C@@H](CO[Si](C)(C)C(C)(C)C)c1nnc(-c2cc(Br)cn3nc(N)nc23)s1]

A solution of hydroxylamine hydrochloride (480 mg, 6.91 mmol) and N,N-diisopropylethylamine (1.1 ml, 6.4 mmol)

in methanol/ethanol (1:1, 11 ml) was heated to 60° C. and ethyl [(5-bromo-3-{5-[(2S)-1-{[tert-butyl(dimethyl)silyl]oxy}propan-2-yl]-1,3,4-thiadiazol-2-yl}pyridin-2-yl)carbamothioyl]carbamate (797 mg, 90% purity, 1.28 mmol) was added. The mixture was stirred at 60° C. for 1 h and then cooled to rt. The pH was adjusted to 6-7 by addition of satd. sodium bicarbonate solution and the mixture was poured into water (100 ml). It was stirred for 10 min and the precipitate was collected by suction filtration and washed with water (5 ml) and dried in vacuo to yield 537 mg (95% purity, 85% yield) of the title compound.

LC-MS (method 1): $R^t$=0.46 min; MS (ESIpos): m/z=469, 471 $[M+H]^+$ $^1$H-NMR (500 MHz, DMSO-$d_6$) δ [ppm]: 0.01 (s, 6H), 0.83 (s, 9H), 1.41 (d, 3H), 3.55-3.63 (m, 1H), 3.83-3.92 (m, 2H), 6.49 (br s, 2H), 8.39 (d, 1H), 9.17 (d, 1H).

Intermediate II-112 tert-Butyl 4-[(4-{2-amino-5-[1-(2,2,2-trifluoroethyl)-1H-pyrazol-4-yl][1,2,4]triazolo[1,5-a]pyridin-7-yl}-1H-pyrazol-1-yl)(phenyl)methyl]piperidine-1-carboxylate (mixture of enantiomers)

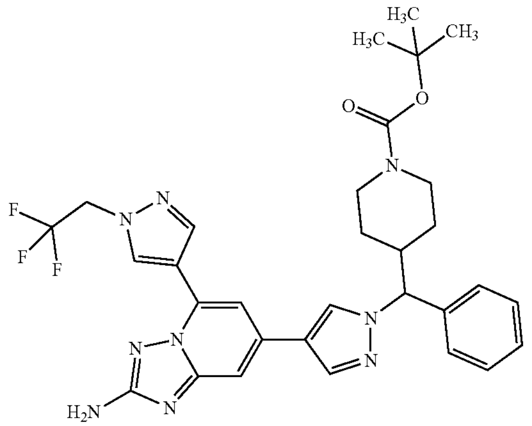 [SMILES: CC(C)(C)OC(=O)N1CCC(C(c2ccccc2)n2cc(-c3cc(-c4cnn(CC(F)(F)F)c4)n4nc(N)nc4c3)cn2)CC1]

7-Chloro-5-[1-(2,2,2-trifluoroethyl)-1H-pyrazol-4-yl][1,2,4]triazolo[1,5-a]pyridin-2-amine (150 mg, 474 μmol) was reacted with tert-butyl 4-{phenyl[4-(4,4,5,5-tetramethyl-1,3,2-dioxaborolan-2-yl)-1H-pyrazol-1-yl]methyl}piperidine-1-carboxylate (332 mg, 80% purity, 568 μmol) for 2 h at 90° C. following general procedure B using 0.1 eq. catalyst. The reaction mixture was diluted with ethyl acetate (5 ml) and filtered through a hydrophobic phase separation filter. The solvent was removed in vacuo and the residue was purified by column chromatography (Biotage® SNAP KP-NH 110 g cartridge, eluent: cyclohexane/ethyl acetate gradient 80:20 to 0:100) and preparative HPLC preparative HPLC (Chromatorex C18, 10 m, 125×30 mm; eluent: water/acetonitrile gradient 90:10 to 5:95) to yield 101 mg (99% purity, 34% yield) of the title compound.

LC-MS (method 1): $R^t$=2.06 min; MS (ESIpos): m/z=622 $[M+H]^+$ $^1$H-NMR (400 MHz, DMSO-$d_6$) δ [ppm]: 1.03-1.33 (m, 4H), 1.38 (s, 9H), 2.56-2.77 (m, 3H), 3.85-3.99 (m, 2H), 5.11 (d, 1H), 5.34 (q, 2H), 6.02 (s, 2H), 7.28-7.34 (m, 1H), 7.35-7.41 (m, 2H), 7.48 (d, 1H), 7.55-7.59 (m, 2H), 7.62 (d, 1H), 8.21 (s, 1H), 8.62 (s, 1H), 8.63 (s, 1H), 8.97 (s, 1H).

Intermediate II-113 tert-Butyl 4-[(4-{2-amino-5-[1-(2,2,2-trifluoroethyl)-1H-pyrazol-4-yl][1,2,4]triazolo[1,5-a]pyridin-7-yl}-1H-pyrazol-1-yl)(phenyl)methyl]piperidine-1-carboxylate (stereoisomer 1) tert-Butyl 4-[(4-{2-amino-5-[1-(2,2,2-trifluoroethyl)-1H-pyrazol-4-yl][1,2,4]triazolo[1,5-a]pyridin-7-yl}-1H-pyrazol-1-yl)(phenyl)methyl]piperidine-1-carboxylate (mixture of enantiomers) (100 mg, 99% purity) from the previous example was separated by chiral chromatography to yield stereoisomer 1 (30 mg, 99% purity) and stereoisomer 2 (28 mg, 99% purity.

Column: Daicel Chiralpak OX-H 5, 5 μm, 250×20 mm; Eluent A: n-heptane; Eluent B: ethanol (+0.2% diethylamine); isocratic: 65% A+35% B; flow: 25 ml/min; UV: 220 nm; temperature: 50° C.

Stereoisomer 1: $R^t$=4.5 min and

Stereoisomer 2: $R^t$=5.0 min (cf. next example)

Analytical chiral HPLC method: Column: Daicel Chiralpak AD-3, 3 μm, 50×4.6 mm; Eluent A: n-heptane; Eluent B: 2-propanol+0.2% diethylamine; isocratic: 50% A+50% B; flow: 1 ml/min; UV: 220 nm.

Stereoisomer 1: $R^t$=1.117 min and

Stereoisomer 2: $R^t$=1.203 min (cf. next example)

LC-MS (method 1): $R^t$=2.10 min; MS (ESIpos): m/z=622 $[M+H]^+$ $^1$H-NMR (600 MHz, DMSO-$d_6$) δ [ppm]: 1.04-1.31 (m, 4H), 1.38 (s, 9H), 2.56-2.77 (m, 3H), 3.86-3.98 (m, 2H), 5.11 (d, 1H), 5.34 (q, 2H), 6.02 (s, 2H), 7.29-7.33 (m, 1H), 7.36-7.40 (m, 2H), 7.48 (d, 1H), 7.55-7.59 (m, 2H), 7.62 (d, 1H), 8.22 (s, 1H), 8.62 (s, 1H), 8.63 (s, 1H), 8.94-8.99 (m, 1H).

Intermediate II-114 tert-Butyl 4-[(4-{2-amino-5-[1-(2,2,2-trifluoroethyl)-1H-pyrazol-4-yl][1,2,4]triazolo[1,5-a]pyridin-7-yl}-1H-pyrazol-1-yl)(phenyl)methyl]piperidine-1-carboxylate (stereoisomer 2)

The product was isolated in the previous example as second stereoisomer.

LC-MS (method 1): $R^t$=2.10 min; MS (ESIpos): m/z=622 $[M+H]^+$ $^1$H-NMR (600 MHz, DMSO-$d_6$) δ [ppm]: 1.05-1.31 (m, 4H), 1.38 (s, 9H), 2.56-2.77 (m, 3H), 3.86-3.98 (m, 2H), 5.11 (d, 1H), 5.34 (q, 2H), 6.02 (s, 2H), 7.29-7.33 (m, 1H), 7.36-7.40 (m, 2H), 7.48 (d, 1H), 7.55-7.58 (m, 2H), 7.62 (d, 1H), 8.22 (s, 1H), 8.62 (s, 1H), 8.63 (s, 1H), 8.97 (s, 1H).

Intermediate II-115

8-{5-[(2S)-1-{[tert-Butyl(dimethyl)silyl]oxy}propan-2-yl]-1,3,4-thiadiazol-2-yl}-6-{1-[(1H-indazol-7-yl)methyl]-1H-pyrazol-4-yl}[1,2,4]triazolo[1,5-a]pyridin-2-amine

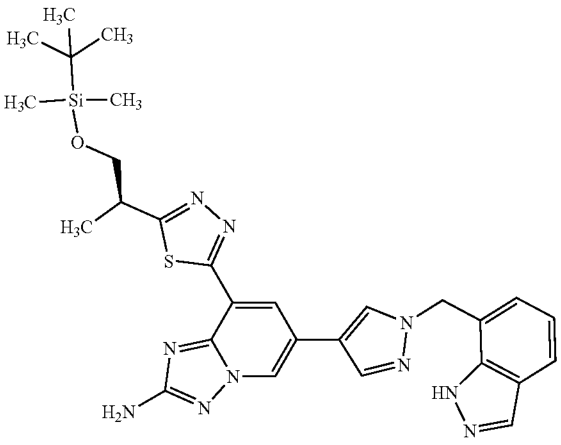 [SMILES: C[C@@H](CO[Si](C)(C)C(C)(C)C)c1nnc(-c2cc(-c3cnn(Cc4cccc5cn[nH]c45)c3)cn3nc(N)nc23)s1]

6-Bromo-8-{5-[(2S)-1-{[tert-butyl(dimethyl)silyl]oxy}propan-2-yl]-1,3,4-thiadiazol-2-yl}[1,2,4]triazolo[1,5-a]pyridin-2-amine (100 mg, 213 μmol) was reacted with 7-{[4-(4,4,5,5-tetramethyl-1,3,2-dioxaborolan-2-yl)-1H-pyrazol-1-yl]methyl}-1H-indazole (82.9 mg, 256 μmol) for 1 h at 90° C. following general procedure B using 0.1 eq. catalyst. The reaction mixture was diluted with ethyl acetate and filtered through a hydrophobic phase separation filter which was rinsed with ethyl acetate. The combined filtrates were concentrated in vacuo and the residue was purified by column chromatography (Biotage® KP-SIL 10 g cartridge, eluent: cyclohexane/ethyl acetate gradient 80:20 to 0:100) to yield 101 mg (100% purity, 81% yield) of the title compound.

LC-MS (method 2): $R^t$=1.20 min; MS (ESIpos): m/z=587 $[M+H]^+$ $^1$H-NMR (400 MHz, DMSO-$d_6$) δ [ppm]: 0.01 (s, 6H), 0.84 (s, 9H), 1.42 (d, 3H), 3.54-3.64 (m, 1H), 3.86-3.91 (m, 2H), 5.69 (s, 2H), 6.34 (br s, 2H), 7.07-7.13 (m, 1H), 7.13-7.18 (m, 1H), 7.74 (d, 1H), 8.11 (s, 1H), 8.14 (d, 1H), 8.55 (d, 1H), 8.62 (s, 1H), 9.09 (d, 1H), 13.30 (s, 1H).

EXAMPLES

Unless otherwise noted, when the structure of a compound depicted in Table 2A includes more stereochemical information than is included in its corresponding Example, the corresponding Example is understood to include that additional stereochemical information.

Example II-1

{3-[2-Amino-6-(1-{1-[6-(trifluoromethyl)pyridin-3-yl]propyl}-1H-pyrazol-4-yl)[1,2,4]triazolo[1,5-a]pyridin-8-yl]-4-chlorophenyl}methanol (mixture of enantiomers)

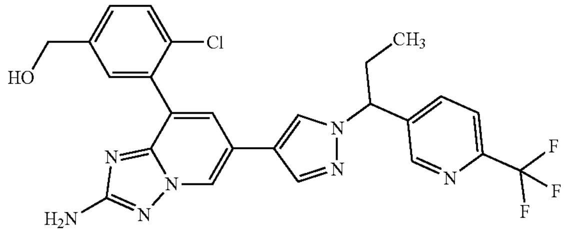 [SMILES: CCC(c1ccc(C(F)(F)F)nc1)n1cc(-c2cc(-c3cc(CO)ccc3Cl)c3nc(N)nn3c2)cn1]

[3-(2-Amino-6-bromo[1,2,4]triazolo[1,5-a]pyridin-8-yl)-4-chlorophenyl]methanol (125 mg, 353 μmol) was reacted with 5-{1-[4-(4,4,5,5-tetramethyl-1,3,2-dioxaborolan-2-yl)-1H-pyrazol-1-yl]propyl}-2-(trifluoromethyl)pyridine (162 mg, 424 μmol) for 2 h at 90° C. following general 15 procedure B using 0.05 eq. catalyst. The reaction mixture was diluted with dichloromethane/methanol (4:1) and filtered. The filtrate was concentrated in vacuo and the residue was purified by column chromatography (Biotage® SNAP KP-NH 11 g cartridge, eluent: cyclohexane/ethyl acetate/2-propanol gradient 80:20:0 to 0:100:0 to 0:80:20). The product was further purified by preparative HPLC (Chromatorex C18, 10 μm, 125×30 mm; eluent: water (0.1% formic acid)/20 acetonitrile gradient 90:10 to 5:95) to yield 95.0 mg (98% purity, 50% yield) of the title compound.

LC-MS (method 1): $R^t$=1.70 min; MS (ESIpos): m/z=528 $[M+H]^+$ $^1$H-NMR (600 MHz, DMSO-$d_6$) δ [ppm]: 0.869 (7.23), 0.881 (16.00), 0.893 (7.29), 2.187 (0.96), 2.198 (1.48), 2.210 (2.17), 2.222 (1.64), 2.233 (1.07), 2.386 (0.55), 2.398 (1.12), 2.410 (1.41), 2.414 (1.23), 2.422 (1.39), 2.426 (1.55), 2.433 (1.05), 2.437 (1.30), 2.449 (0.93), 2.469 (0.62), 2.516 (0.59), 2.520 (0.57), 3.269 (1.91), 4.537 (9.19), 4.546 (9.34), 5.306 (3.72), 5.315 (8.00), 5.325 (3.53), 5.495 (0.59), 5.537 (2.10), 5.547 (2.26), 5.553 (2.30), 5.563 (2.01), 6.009 (11.08), 7.401 (2.64), 7.405 (3.01), 7.415 (3.17), 7.418 (3.81), 7.450 (6.02), 7.453 (5.26), 7.527 (7.70), 7.541 (6.22), 7.680 (8.80), 7.683 (8.96), 7.900 (4.76), 7.913 (5.83), 8.023 (2.99), 8.027 (3.01), 8.037 (2.44), 8.040 (2.44), 8.117 (11.03), 8.556 (10.46), 8.798 (5.13), 8.801 (5.20), 8.930 (8.82), 8.933 (8.82).

Example II-2

{3-[2-Amino-6-(1-{1-[6-(trifluoromethyl)pyridin-3-yl]propyl}-1H-pyrazol-4-yl)[1,2,4]triazolo[1,5-a]pyridin-8-yl]-4-chlorophenyl}methanol (stereoisomer 1, distomer)

{3-[2-Amino-6-(1-{1-[6-(trifluoromethyl)pyridin-3-yl]propyl}-1H-pyrazol-4-yl)[1,2,4]triazolo[1,5-a]pyridin-8-yl]-4-chlorophenyl}methanol (mixture of enantiomers) (85 mg, 98% purity) from the previous example was separated by chiral chromatography to yield stereoisomer 1 (29 mg, 97% purity) and stereoisomer 2 (30 mg, 95% purity).

Column: Daicel Chiralpak IF, 5 μm, 250×20 mm; Eluent A: n-heptane; Eluent B: ethanol+0.2% diethylamine; isocratic: 50% A+50% B; flow: 20 ml/min; UV: 210 nm; temperature: 40° C.

Stereoisomer 1: $R^t$=5.706 min and

Stereoisomer 2: $R^t$=8.015 min (cf. next example)

Analytical chiral HPLC method: Column: Daicel Chiralpak IF-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.643 min and

Stereoisomer 2: $R^t$=2.671 min (cf. next example)

LC-MS (method 1): $R^t$=1.71 min; MS (ESIpos): m/z=528 $[M+H]^+$ $^1$H-NMR (600 MHz, DMSO-$d_6$) δ [ppm]: −0.100 (0.61), 0.005 (3.44), 0.034 (0.81), 0.097 (0.41), 0.847 (1.22), 0.859 (2.23), 0.867 (7.70), 0.879 (16.00), 0.891 (7.29), 1.124 (1.01), 1.234 (0.81), 2.185 (1.01), 2.196 (1.62), 2.208 (2.23), 2.220 (1.62), 2.231 (1.22), 2.384 (1.82), 2.396 (1.22), 2.408 (1.62), 2.423 (3.65), 2.435 (1.42), 2.447 (0.81), 2.515 (2.63), 2.518 (2.43), 2.521 (2.03), 2.569 (1.82), 2.573 (4.25), 2.577 (0.61), 2.612 (1.42), 2.652 (2.03), 3.222 (0.61), 3.233 (1.01), 3.260 (0.61), 3.266 (0.81), 3.332 (7.49), 3.335 (15.19), 3.339 (3.44), 3.360 (2.23), 3.365 (1.42), 3.373 (0.61), 3.733 (0.41), 4.533 (9.11), 4.543 (9.52), 5.305 (4.05), 5.314 (8.30), 5.324 (3.85), 5.535 (2.03), 5.545 (2.23), 5.551 (2.43), 5.561 (2.23), 6.004 (10.73), 7.399 (2.63), 7.402 (2.84), 7.412 (3.04), 7.416 (3.65), 7.446 (5.87), 7.449 (5.27), 7.525 (7.70), 7.539 (6.28), 7.676 (8.51), 7.679 (8.71), 7.898 (4.66), 7.912 (5.67), 8.021 (3.04), 8.024 (3.04), 8.038 (2.43), 8.114 (10.94), 8.553 (10.33), 8.798 (5.27), 8.926 (8.51), 8.929 (8.71).

Example II-3

{3-[2-Amino-6-(1-{1-[6-(trifluoromethyl)pyridin-3-yl]propyl}-1H-pyrazol-4-yl)[1,2,4]triazolo[1,5-a]pyridin-8-yl]-4-chlorophenyl}methanol (stereoisomer 2, eutomer)

The product was isolated in the previous example as second stereoisomer. The stereochemical configuration of the methine carbon atom bonded to the pyrazole was (S).

LC-MS (method 1): $R^t$=1.71 min; MS (ESIpos): m/z=528 $[M+H]^+$ $^1$H-NMR (600 MHz, DMSO-$d_6$) δ [ppm]: 0.88 (t, 3H), 2.17-2.25 (m, 1H), 2.37-2.47 (m, 1H), 4.54 (d, 2H), 5.32 (t, 1H), 5.55 (dd, 1H), 6.01 (s, 2H), 7.41 (dd, 1H), 7.45 (d, 1H), 7.53 (d, 1H), 7.68 (d, 1H), 7.91 (d, 1H), 8.03 (dd, 1H), 8.12 (s, 1H), 8.56 (s, 1H), 8.80 (d, 1H), 8.93 (d, 1H).

Example II-4

{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-4-chlorophenyl}methanol (mixture of enantiomers)

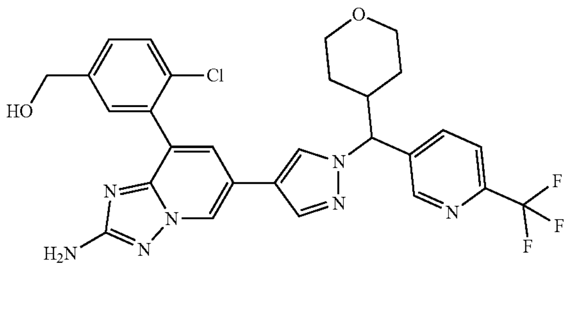 [SMILES: Nc1nc2c(-c3cc(CO)ccc3Cl)cc(-c3cnn(C(c4ccc(C(F)(F)F)nc4)C4CCOCC4)c3)cn2n1]

[3-(2-Amino-6-bromo[1,2,4]triazolo[1,5-a]pyridin-8-yl)-4-chlorophenyl]methanol (200 mg, 566 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (297 mg, 679 μmol) for 2 h at 90° C. following general procedure B using 0.05 eq. catalyst. The reaction mixture was diluted with ethyl acetate and filtered through a hydrophobic phase separation filter. The filtrate was concentrated in vacuo and the residue purified by column chromatography (Biotage® SNAP KP-NH 11 g cartridge, eluent: cyclohexane/ethyl acetate/2-propanol gradient 70:30:0 to 0:100:0 to 0:80:20) to yield 210 mg (99% purity, 63% yield) of the title compound.

LC-MS (method 1): $R^t$=1.63 min; MS (ESIpos): m/z=584 $[M+H]^+$ $^1$H-NMR (600 MHz, DMSO-$d_6$) δ [ppm]: 1.069 (2.55), 1.089 (2.77), 1.232 (2.17), 1.251 (3.10), 1.273 (0.92), 1.280 (0.97), 1.294 (2.12), 1.300 (2.27), 1.314 (2.77), 1.336 (2.72), 1.350 (1.90), 1.369 (0.67), 2.425 (0.55), 2.654 (0.57), 2.729 (2.20), 2.747 (2.12), 2.766 (0.82), 3.239 (2.12), 3.257 (4.32), 3.794 (2.75), 3.810 (2.55), 3.837 (2.72), 3.853 (2.50), 4.535 (13.07), 4.545 (13.00), 5.306 (4.25), 5.315 (8.00), 5.325 (3.90), 5.349 (5.92), 5.367 (5.60), 6.009 (16.00), 7.404 (4.05), 7.417 (4.92), 7.445 (9.00), 7.526 (8.10), 7.540 (6.50), 7.648 (10.22), 7.931 (6.65), 7.944 (6.90), 8.118 (13.37), 8.279 (4.62), 8.293 (4.20), 8.519 (13.07), 8.909 (10.25), 8.950 (8.57).

Example II-5

{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-4-chlorophenyl}methanol (stereoisomer 1, eutomer)

{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-4-chlorophenyl}methanol (mixture of enantiomers) (192 mg, 99% purity) from the previous example was separated by chiral chromatography to yield stereoisomer 1 (89 mg, 97% purity) and stereoisomer 2 (87 mg, 97% purity).

Column: Daicel Chiralpak IA, 5 m, 250×20 mm; Eluent: ethanol+0.2% diethylamine; flow: 15 ml/min; UV: 220 nm; temperature: 50° C.

Stereoisomer 1: $R^t$=7.85 min and

Stereoisomer 2: $R^t$=11.18 min (cf. next example)

Analytical chiral HPLC method: Column: Daicel Chiralpak IA, 5 m, 250×4.6 mm; Eluent: ethanol+0.2% diethylamine; flow: 1 ml/min; UV: 235 nm; temperature: 60° C.

Stereoisomer 1: $R^t$=5.655 min and

Stereoisomer 2: $R^t$=7.182 min (cf. next example)

Stereoisomer 1: The stereochemical configuration of the methine carbon atom bonded to the pyrazole was (S).

LC-MS (method 1): $R^t$=1.64 min; MS (ESIpos): m/z=584 $[M+H]^+$ $^1$H-NMR (600 MHz, DMSO-$d_6$) δ [ppm]: 1.04-1.09 (m, 1H), 1.21-1.26 (m, 1H), 1.27-1.38 (m, 2H), 2.69-2.78 (m, 1H), 3.22-3.31 (m, 2H), 3.77-3.87 (m, 2H), 4.54 (d, 2H), 5.34-5.38 (m, 2H), 6.07 (s, 2H), 7.40-7.43 (m, 1H), 7.44-7.46 (m, 1H), 7.54 (d, 1H), 7.66 (s, 1H), 7.95 (d, 1H), 8.13 (s, 1H), 8.29 (br d, 1H), 8.51-8.56 (m, 1H), 8.92-8.94 (m, 1H), 8.96 (s, 1H).

Example II-6

{3-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-4-chlorophenyl}methanol (stereoisomer 2, distomer)

The product was isolated in the previous example as second stereoisomer.

LC-MS (method 1): $R^t$=1.63 min; MS (ESIpos): m/z=584 $[M+H]^+$ $^1$H-NMR (600 MHz, DMSO-$d_6$) δ [ppm]: 0.717 (0.56), 0.729 (0.57), 0.845 (1.06), 0.857 (1.16), 1.055 (2.44), 1.076 (2.85), 1.113 (0.65), 1.124 (0.58), 1.223 (2.32), 1.244 (3.29), 1.276 (0.91), 1.283 (0.97), 1.296 (2.22), 1.303 (2.96), 1.323 (3.87), 1.344 (2.59), 1.365 (0.78), 1.806 (0.74), 1.817 (0.68), 2.163 (0.49), 2.429 (0.43), 2.618 (0.44), 2.658 (0.55), 2.708 (0.83), 2.727 (2.24), 2.746 (2.23), 2.764 (0.83), 3.234 (2.00), 3.252 (3.99), 3.262 (2.47), 3.272 (2.51), 3.281 (4.01), 3.301 (2.08), 3.326 (0.44), 3.383 (0.46), 3.734 (2.01), 3.795 (2.74), 3.809 (2.54), 3.838 (2.76), 3.856 (2.52), 3.896 (0.94), 4.536 (13.77), 4.545 (14.00), 5.355 (10.06), 5.365 (9.57), 5.373 (8.54), 6.067 (16.00), 6.855 (0.51), 6.870 (0.50), 7.290 (0.48), 7.304 (0.43), 7.407 (4.28), 7.421 (5.27), 7.447 (9.75), 7.533 (9.12), 7.547 (7.33), 7.664 (11.28), 7.945 (7.36), 7.959 (7.78), 8.136 (15.23), 8.285 (4.88), 8.299 (4.45), 8.539 (14.36), 8.933 (11.61), 8.958 (9.25).

Example II-7

2-{3-[2-Amino-6-(1-{1-[6-(trifluoromethyl)pyridin-3-yl]propyl}-1H-pyrazol-4-yl)[1,2,4]triazolo[1,5-a]pyridin-8-yl]phenyl}propan-2-ol (mixture of enantiomers)

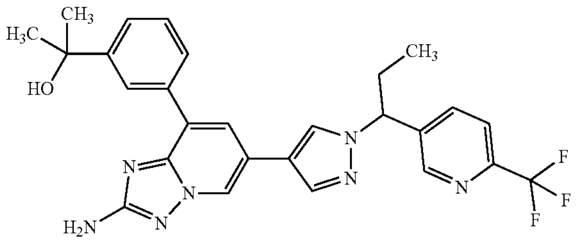 [SMILES: CCC(c1ccc(C(F)(F)F)nc1)n1cc(-c2cc(-c3cccc(C(C)(C)O)c3)c3nc(N)nn3c2)cn1]

2-[3-(2-Amino-6-bromo[1,2,4]triazolo[1,5-a]pyridin-8-yl)phenyl]propan-2-ol (125 mg, 360 μmol) was reacted with 5-{1-[4-(4,4,5,5-tetramethyl-1,3,2-dioxaborolan-2-yl)-1H-pyrazol-1-yl]propyl}-2-(trifluoromethyl)pyridine (165 mg, 432 μmol) for 2 h at 90° C. following general procedure B using 0.05 eq. catalyst. The reaction mixture was diluted with ethyl acetate (20 ml) and filtered through a hydrophobic phase separation filter. The filtrate was concentrated and purified by column chromatography (Biotage® SNAP KP-NH 11 g cartridge, eluent: cyclohexane/ethyl acetate/2-propanol gradient 80:20:0 to 0:100:0 to 0:80:20). The product was further purified by preparative HPLC (Chromatorex C18, 10 μm, 125×30 mm; eluent: water (0.1% formic acid)/acetonitrile gradient 90:10 to 5:95) to yield 67.0 mg (100% purity, 36% yield) of the title compound.

LC-MS (method 1): $R^t$=1.81 min; MS (ESIpos): m/z=522 $[M+H]^+$ $^1$H-NMR (600 MHz, DMSO-$d_6$) δ [ppm]: 0.882 (1.73), 0.895 (3.85), 0.907 (1.78), 1.505 (16.00), 2.231 (0.53), 5.044 (2.51), 5.577 (0.50), 5.587 (0.54), 5.593 (0.55), 5.603 (0.48), 6.033 (2.55), 7.407 (0.72), 7.420 (1.60), 7.433 (0.95), 7.514 (0.88), 7.527 (0.70), 7.849 (1.90), 7.851 (1.97), 7.910 (1.18), 7.923 (1.42), 7.944 (0.79), 7.957 (0.75), 8.046 (0.71), 8.050 (0.71), 8.060 (0.58), 8.063 (0.60), 8.097 (0.91), 8.100 (1.65), 8.103 (0.94), 8.154 (2.68), 8.571 (2.52), 8.817 (1.21), 8.820 (1.24), 8.859 (1.91), 8.862 (1.94).

Example II-8

2-{3-[2-Amino-6-(1-{1-[6-(trifluoromethyl)pyridin-3-yl]propyl}-1H-pyrazol-4-yl)[1,2,4]triazolo[1,5-a]pyridin-8-yl]phenyl}propan-2-ol (stereoisomer 1, distomer)

2-{3-[2-Amino-6-(1-{1-[6-(trifluoromethyl)pyridin-3-yl]propyl}-1H-pyrazol-4-yl)[1,2,4]triazolo[1,5-a]pyridin-8-yl]phenyl}propan-2-ol (mixture of enantiomers) (120 mg, 99% purity) from the previous example was separated by chiral chromatography to yield stereoisomer 1 (40 mg, 97% purity) and stereoisomer 2 (43 mg, 95% purity).

Column: Daicel Chiralcel OD-H, 5 μm, 250×20 mm; Eluent A: n-heptane; Eluent B: ethanol+0.2% diethylamine; isocratic: 50% A+50% B; flow: 15 ml/min; UV: 210 nm; temperature: 40° C.

Stereoisomer 1: $R^t$=5.231 min and

Stereoisomer 2: $R^t$=8.021 min (cf. next example)

Analytical chiral HPLC method: Column: Phenomenex cellulose-1, 3 μm, 50×4.6 mm; Eluent A: n-heptane; Eluent B: ethanol+0.2% diethylamine; isocratic: 50% A+50% B; flow: 1 ml/min; 25 UV: 220 nm.

Stereoisomer 1: $R^t$=0.978 min and

Stereoisomer 2: $R^t$=1.730 min (cf. next example)

LC-MS (method 1): $R^t$=1.80 min; MS (ESIpos): m/z=522 $[M+H]^+$ $^1$H-NMR (600 MHz, DMSO-$d_6$) δ [ppm]: 0.883 (1.80), 0.895 (3.84), 0.907 (1.80), 1.133 (0.49), 1.145 (0.99), 1.157 (0.50), 1.506 (16.00), 2.232 (0.54), 2.244 (0.42), 5.046 (2.46), 5.579 (0.52), 5.589 (0.57), 5.595 (0.56), 5.604 (0.48), 6.035 (2.32), 7.408 (0.72), 7.421 (1.55), 7.434 (0.90), 7.515 (0.94), 7.528 (0.71), 7.851 (1.48), 7.853 (1.61), 7.910 (1.22), 7.924 (1.43), 7.946 (0.85), 7.959 (0.78), 8.048 (0.79), 8.051 (0.74), 8.061 (0.63), 8.065 (0.58), 8.099 (1.06), 8.102 (1.65), 8.104 (0.89), 8.155 (2.55), 8.573 (2.30), 8.818 (1.34), 8.821 (1.25), 8.862 (1.41), 8.864 (1.33).

Example II-9

2-{3-[2-Amino-6-(1-{1-[6-(trifluoromethyl)pyridin-3-yl]propyl}-1H-pyrazol-4-yl)[1,2,4]triazolo[1,5-a]pyridin-8-yl]phenyl}propan-2-ol (stereoisomer 2, eutomer)

The product was isolated in the previous example as second stereoisomer.

LC-MS (method 1): $R^t$=1.80 min; MS (ESIpos): m/z=522 $[M+H]^+$ $^1$H-NMR (600 MHz, DMSO-$d_6$) δ [ppm]: 0.89 (t, 3H), 1.50 (s, 6H), 2.19-2.27 (m, 1H), 2.41-2.47 (m, 1H), 5.04 (s, 1H), 5.59 (dd, 1H), 6.03 (s, 2H), 7.42 (t, 1H), 7.51-7.53 (m, 1H), 7.85 (d, 1H), 7.92 (d, 1H), 7.94-7.96 (m, 1H), 8.05 (dd, 1H), 8.10 (t, 1H), 8.15 (s, 1H), 8.57 (s, 1H), 8.82 (d, 1H), 8.86 (d, 1H).

Example II-10

2-{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]phenyl}propan-2-ol (mixture of enantiomers)

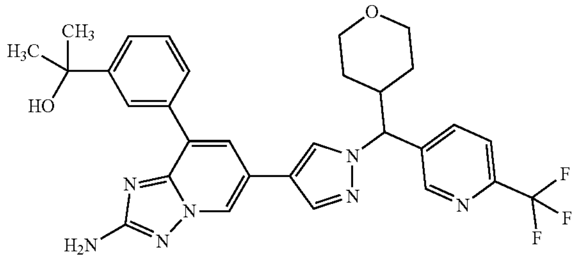 [SMILES: CC(C)(O)c1cccc(-c2cc(-c3cnn(C(c4ccc(C(F)(F)F)nc4)C4CCOCC4)c3)cn3nc(N)nc23)c1]

2-[3-(2-Amino-6-bromo[1,2,4]triazolo[1,5-a]pyridin-8-yl)phenyl]propan-2-ol (125 mg, 360 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (189 mg, 432 μmol) for 2 h at 90° C. following general procedure B using 0.05 eq. catalyst. The reaction mixture was diluted with ethyl acetate (20 ml) and filtered through a hydrophobic phase separation filter. The solvent was removed in vacuo and the residue was purified by column chromatography (Biotage® SNAP KP-NH 11 g cartridge, eluent: cyclohexane/ethyl acetate/2-propanol gradient 80:20:0 to 0:100:0 to 0:80:20) to yield 143 mg (95% purity, 65% yield) of the title compound.

LC-MS (method 1): $R^t$=1.73 min; MS (ESIpos): m/z=578 $[M+H]^+$ $^1$H-NMR (600 MHz, DMSO-$d_6$) δ [ppm]: 1.084 (0.72), 1.105 (0.83), 1.232 (0.69), 1.251 (0.89), 1.310 (0.64), 1.330 (0.80), 1.351 (0.79), 1.369 (0.59), 1.505 (16.00), 2.750 (0.63), 2.767 (0.62), 3.254 (0.81), 3.272 (1.96), 3.803 (0.85), 3.821 (0.79), 3.843 (0.85), 3.861 (0.77), 5.046 (3.09), 5.393 (1.33), 5.411 (1.27), 6.035 (3.84), 7.407 (0.75), 7.419 (1.52), 7.432 (0.93), 7.514 (1.48), 7.526 (1.19), 7.816 (2.47), 7.942 (2.66), 7.955 (2.70), 8.089 (2.25), 8.159 (2.75), 8.310 (1.24), 8.323 (1.12), 8.522 (2.73), 8.842 (2.42), 8.976 (2.19).

Example II-11

2-{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]phenyl}propan-2-ol (stereoisomer 1, distomer)

2-{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]phenyl}propan-2-ol (mixture of enantiomers) (110 mg, 95% purity) from the previous example was separated by chiral chromatography to yield stereoisomer 1 (41 mg, 99% purity) and stereoisomer 2 (39 mg, 99% purity).

Column: Daicel Chiralcel OZ-H, 5 m, 250×20 mm; Eluent A: n-heptane; Eluent B: ethanol+0.2% diethylamine; isocratic: 60% A+40% B; flow: 20 ml/min; UV: 220 nm; temperature: 30° C.

Stereoisomer 1: $R^t$=9.874 min and

Stereoisomer 2: $R^t$=13.464 (cf. next example)

Analytical chiral HPLC method: Column: Chiraltek OZ-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=3.399 min and

Stereoisomer 2: $R^t$=4.763 min (cf. next example)

LC-MS (method 1): $R^t$=1.72 min; MS (ESIpos): m/z=578 $[M+H]^+$ $^1$H-NMR (600 MHz, DMSO-$d_6$) δ [ppm]: 1.101 (0.49), 1.251 (0.53), 1.309 (0.41), 1.329 (0.43), 1.353 (0.41), 1.504 (16.00), 3.272 (1.08), 3.309 (0.47), 3.802 (0.45), 3.817 (0.41), 3.844 (0.44), 5.042 (3.71), 5.392 (1.14), 5.410 (1.10), 6.033 (2.87), 7.405 (0.71), 7.418 (1.55), 7.431 (0.91), 7.513 (1.02), 7.526 (0.78), 7.813 (1.88), 7.816 (1.86), 7.941 (2.25), 7.954 (2.29), 8.087 (1.73), 8.157 (2.85), 8.307 (0.79), 8.320 (0.71), 8.520 (2.70), 8.839 (1.91), 8.841 (1.86), 8.974 (1.48).

Example II-12

2-{3-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]phenyl}propan-2-ol (stereoisomer 2, eutomer)

The product was isolated in the previous example as second stereoisomer. The stereochemical configuration of the methine carbon atom bonded to the pyrazole was (S).

LC-MS (method 1): $R^t$=1.72 min; MS (ESIpos): m/z=578 $[M+H]^+$ $^1$H-NMR (600 MHz, DMSO-$d_6$) δ [ppm]: 1.07-1.12 (m, 1H), 1.21-1.27 (m, 1H), 1.27-1.40 (m, 2H), 1.50 (s, 6H), 2.72-2.80 (m, 1H), 3.23-3.32 (m, 2H), 3.79-3.87 (m, 2H), 5.04 (s, 1H), 5.40 (d, 1H), 6.03 (s, 2H), 7.42 (t, 1H), 7.50-7.54 (m, 1H), 7.81 (d, 1H), 7.95 (d, 2H), 8.09 (t, 1H), 8.16 (s, 1H), 8.31 (dd, 1H), 8.52 (s, 1H), 8.84 (d, 1H), 8.98 (d, 1H).

Example II-13

8-[3-(Methylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers)

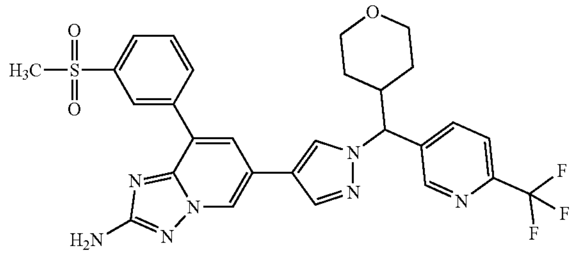 [SMILES: CS(=O)(=O)c1cccc(-c2cc(-c3cnn(C(c4ccc(C(F)(F)F)nc4)C4CCOCC4)c3)cn3nc(N)nc23)c1]

6-Bromo-8-[3-(methanesulfonyl)phenyl][1,2,4]triazolo[1,5-a]pyridin-2-amine (100 mg, 99% purity, 270 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (141 mg, 324 μmol) for 2 h at 90° C. following general procedure B using 0.05 eq. catalyst. The reaction mixture was diluted with ethyl acetate (20 ml) and filtered through a hydrophobic phase separation filter. The filtrate was concentrated in vacuo and purified by column chromatography (Biotage® SNAP KP-NH 11 g cartridge, eluent: cyclohexane/ethyl acetate/2-propanol gradient 80:20:0 to 0:100:0 to 0:80:20) to yield 107 mg (99% purity, 66% yield) of the title compound.

LC-MS (method 1): $R^t$=1.63 min; MS (ESIpos): m/z=598 $[M+H]^+$ $^1$H-NMR (500 MHz, $CDCl_3$) δ [ppm]: −0.007 (0.53), 0.007 (0.45), 1.241 (0.98), 1.259 (0.49), 1.268 (0.71), 1.359 (0.56), 1.368 (0.59), 1.384 (0.58), 1.393 (0.69), 1.409 (1.01), 1.417 (1.28), 1.429 (0.87), 1.437 (0.66), 1.602 (10.42), 2.803 (0.44), 2.825 (0.43), 3.118 (16.00), 3.341 (0.46), 3.345 (0.49), 3.365 (0.96), 3.369 (0.92), 3.388 (0.54), 3.392 (0.45), 3.412 (0.44), 3.435 (0.81), 3.441 (0.70), 3.457 (0.46), 3.464 (0.40), 3.704 (0.58), 3.951 (0.58), 3.957 (0.61), 3.980 (1.07), 4.006 (0.62), 4.564 (1.93), 4.906 (1.61), 4.928 (1.56), 7.634 (2.78), 7.637 (2.76), 7.714 (2.63), 7.729 (3.21), 7.745 (1.24), 7.791 (3.60), 7.854 (3.71), 7.988 (1.24), 8.004 (1.09), 8.204 (1.05), 8.208 (1.02), 8.221 (0.97), 8.224 (0.94), 8.398 (1.22), 8.413 (1.22), 8.425 (2.44), 8.428 (2.35), 8.448 (1.55), 8.451 (2.40), 8.845 (1.91), 8.848 (1.84).

Example II-14

8-[3-(Methylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomer 1, eutomer)

8-[3-(Methylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers) (90 mg, 99% purity) from the previous example was separated by chiral chromatography to yield stereoisomer 1 (29 mg, 100% purity) and stereoisomer 2 (30 mg, 100% purity).

Column: Daicel Chiralpak IG, 5 μm, 250×20 mm; Eluent ethanol 100%; flow: 20 ml/min; UV: 210 nm; temperature: 60° C.

Stereoisomer 1: $R^t$=9.5 min and

Stereoisomer 2: $R^t$=13.4 min (cf. next example)

Analytical chiral HPLC method: Column: Daicel Chiralpak IG, 5 m, 250×4.6 mm; Eluent ethanol 100%; flow: 1 ml/min; UV: 220 nm; temperature: 70° C.

Stereoisomer 1: $R^t$=9.411 min and

Stereoisomer 2: $R^t$=13.187 min (cf. next example)

LC-MS (method 1): $R^t$=1.63 min; MS (ESIpos): m/z=598 $[M+H]^+$ $^1$H-NMR (400 MHz, DMSO-$d_6$) δ [ppm]: 1.05-1.14 (m, 1H), 1.20-1.40 (m, 3H), 2.71-2.82 (m, 1H), 3.23-3.29 (m, 2H), 3.30 (s, 3H), 3.84 (br t, 2H), 5.41 (d, 1H), 6.18 (s, 2H), 7.80 (t, 1H), 7.94-8.00 (m, 2H), 8.02 (d, 1H), 8.20 (s, 1H), 8.32 (dd, 1H), 8.50 (dt, 1H), 8.56 (s, 1H), 8.66 (t, 1H), 8.94 (d, 1H), 8.98 (d, 1H).

Example II-15

8-[3-(Methylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomer 2, distomer)

The product was isolated in the previous example as second stereoisomer.

LC-MS (method 1): $R^t$=1.63 min; MS (ESIpos): m/z=598 $[M+H]^+$ $^1$H-NMR (400 MHz, DMSO-$d_6$) δ [ppm]: 3.300 (2.93), 3.312 (16.00), 6.178 (0.63), 7.798 (0.44), 7.967 (0.44), 8.018 (0.51), 8.022 (0.53), 8.196 (0.76), 8.555 (0.68), 8.657 (0.48), 8.936 (0.54), 8.940 (0.55).

Example II-16

8-[3-(Ethylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers)

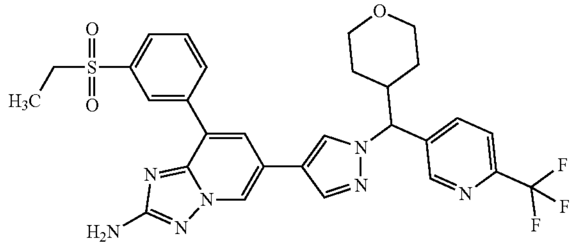 [SMILES: CCS(=O)(=O)c1cccc(-c2cc(-c3cnn(C(c4ccc(C(F)(F)F)nc4)C4CCOCC4)c3)cn3nc(N)nc23)c1]

6-Bromo-8-[3-(ethanesulfonyl)phenyl][1,2,4]triazolo[1,5-a]pyridin-2-amine (125 mg, 328 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (186 mg, 426 μmol) for 3 h at 90° C. following general procedure B using 0.1 eq. catalyst. The reaction mixture was diluted with ethyl acetate (20 ml) and filtered through a hydrophobic phase separation filter. The solvent was removed in vacuo and the residue was purified by column chromatography (Biotage® SNAP KP-NH 11 g cartridge, eluent: cyclohexane/ethyl acetate gradient 70:30 to 0:100) to yield 147 mg (99% purity, 73% yield) of the title compound.

LC-MS (method 1): $R^t$=1.70 min; MS (ESIpos): m/z=612 $[M+H]^+$

Example II-17

8-[3-(Ethylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomer 1, distomer)

8-[3-(Ethylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers) (114 mg, 99% purity) from the previous example was separated by chiral chromatography to yield stereoisomer 1 (52 mg, 99% purity) and stereoisomer 2 (54 mg, 98% purity).

Column: Daicel Chiralcel OZ-H, 5 m, 250×20 mm; Eluent A: n-heptane; Eluent B: ethanol+0.2% diethylamine; isocratic: 30% A+70% B; flow: 20 ml/min; UV: 235 nm; temperature: 40° C.

Stereoisomer 1: $R^t$=9.004 min and

Stereoisomer 2: $R^t$=12.371 min (cf. next example)

Analytical chiral HPLC method: Column: Daicel Chiralcel OZ-H, 5 μm, 250×4.6 mm; Eluent A: n-heptane; Eluent B: ethanol+0.2% diethylamine; isocratic: 30% A+70% B; flow: 1 ml/min; UV: 235 nm; temperature 40° C.

Stereoisomer 1: $R^t$=9.390 min and

Stereoisomer 2: $R^t$=13.463 min (cf. next example)

LC-MS (method 1): $R^t$=1.70 min; MS (ESIpos): m/z=612 $[M+H]^+$ $^1$H-NMR (600 MHz, DMSO-$d_6$) δ [ppm]: 1.071 (1.20), 1.092 (1.39), 1.141 (7.16), 1.153 (16.00), 1.165 (7.19), 1.226 (1.16), 1.246 (1.51), 1.292 (0.48), 1.300 (0.51), 1.313 (1.07), 1.321 (1.21), 1.333 (1.32), 1.342 (1.58), 1.352 (1.24), 1.363 (1.04), 2.429 (0.67), 2.520 (0.65), 2.658 (0.56), 2.730 (0.41), 2.748 (1.08), 2.767 (1.04), 3.251 (1.05), 3.270 (2.71), 3.290 (2.69), 3.310 (1.20), 3.368 (2.06), 3.380 (6.80), 3.392 (6.50), 3.405 (1.83), 3.733 (0.51), 3.804 (1.26), 3.820 (1.15), 3.846 (1.26), 3.862 (1.12), 5.401 (3.31), 5.419 (3.17), 6.204 (7.84), 7.798 (2.36), 7.811 (4.99), 7.824 (2.80), 7.933 (2.93), 7.946 (2.44), 7.959 (4.14), 7.972 (4.27), 8.024 (5.91), 8.027 (5.96), 8.208 (8.69), 8.313 (2.34), 8.316 (2.28), 8.327 (2.10), 8.498 (2.71), 8.511 (2.60), 8.569 (7.92), 8.626 (3.28), 8.628 (5.59), 8.952 (6.17), 8.954 (6.18), 8.985 (4.33).

Example II-18

8-[3-(Ethylsulfonyl)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomer 2, eutomer)

The product was isolated in the previous example as second stereoisomer. The stereochemical configuration of the methine carbon atom bonded to the pyrazole was (S).

LC-MS (method 1): $R^t$=1.69 min; MS (ESIpos): m/z=612 $[M+H]^+$ $^1$H-NMR (600 MHz, DMSO-$d_6$) δ [ppm]: 1.05-1.11 (m, 1H), 1.15 (t, 3H), 1.21-1.27 (m, 1H), 1.28-1.40 (m, 2H), 2.71-2.80 (m, 1H), 3.23-3.32 (m, 2H), 3.39 (q, 2H), 3.79-3.88 (m, 2H), 5.41 (d, 1H), 6.21 (s, 2H), 7.81 (t, 1H), 7.93-7.95 (m, 1H), 7.97 (d, 1H), 8.03 (d, 1H), 8.21 (s, 1H), 8.32 (dd, 1H), 8.49-8.52 (m, 1H), 8.57 (s, 1H), 8.63 (t, 1H), 8.95 (d, 1H), 8.99 (d, 1H).

Example II-19

6-(1-{Tetrahydro-2H-pyran-4-yl[6-(trifluoromethyl)pyridin-3-yl]methyl}-1H-pyrazol-4-yl)-8-{3-[(trifluoromethyl)sulfonyl]phenyl}[1,2,4]triazolo[1,5-a]pyridin-2-amine (mixture of enantiomers)

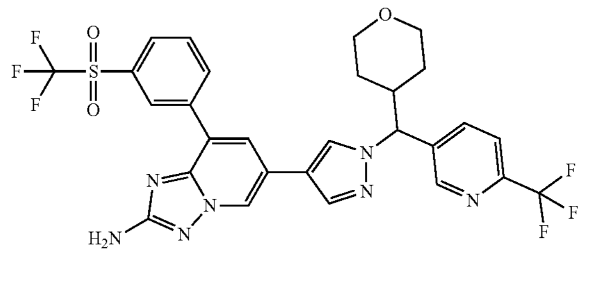 [SMILES: Nc1nc2c(-c3cccc(S(=O)(=O)C(F)(F)F)c3)cc(-c3cnn(C(c4ccc(C(F)(F)F)nc4)C4CCOCC4)c3)cn2n1]

6-Bromo-8-[3-(trifluoromethanesulfonyl)phenyl][1,2,4]triazolo[1,5-a]pyridin-2-amine (160 mg, 90% purity, 342 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (194 mg, 444 μmol) for 2 h at 90° C. following general procedure B using 0.1 eq. XPhos-Pd-G2 as catalyst. The reaction mixture was diluted with ethyl acetate (15 ml) and washed with water (3 ml). The aqueous layer was separated and extracted twice with ethyl acetate (8 ml each). The combined organic layers were concentrated in vacuo and the residue was purified by column chromatography (Biotage® SNAP KP-NH 28 g cartridge, eluent: cyclohexane/ethyl acetate gradient 90:10 to 0:100) to yield 170 mg (98% purity, 75% yield) of the title compound.

LC-MS (method 2): $R^t$=1.03 min; MS (ESIpos): m/z=652 $[M+H]^+$ $^1$H-NMR (400 MHz, DMSO-$d_6$) δ [ppm]: −0.008 (0.88), 0.008 (0.88), 1.071 (4.14), 1.106 (2.19), 1.231 (1.71), 1.258 (2.40), 1.292 (0.80), 1.312 (2.08), 1.323 (2.27), 1.343 (2.96), 1.353 (3.02), 1.373 (1.84), 1.384 (1.74), 1.404 (0.56), 1.415 (0.48), 1.989 (0.40), 2.075 (0.61), 2.329 (0.45), 2.369 (0.51), 2.525 (1.63), 2.672 (0.45), 2.712 (1.02), 2.742 (1.68), 2.770 (1.63), 2.797 (0.59), 3.245 (1.71), 3.269 (4.17), 3.298 (5.18), 3.803 (2.16), 3.834 (3.45), 3.871 (1.87), 5.394 (5.34), 5.420 (5.08), 6.195 (12.45), 7.947 (6.49), 7.967 (7.24), 7.986 (4.06), 8.006 (8.60), 8.026 (4.99), 8.110 (10.04), 8.114 (10.26), 8.181 (4.11), 8.209 (14.64), 8.303 (3.87), 8.308 (3.77), 8.324 (3.45), 8.328 (3.39), 8.565 (13.14), 8.754 (4.38), 8.774 (4.27), 8.974 (11.41), 8.978 (16.00), 9.009 (7.56).

Example II-20

6-(1-{Tetrahydro-2H-pyran-4-yl[6-(trifluoromethyl)pyridin-3-yl]methyl}-1H-pyrazol-4-yl)-8-{3-[(trifluoromethyl)sulfonyl]phenyl}[1,2,4]triazolo[1,5-a]pyridin-2-amine (stereoisomer 1, distomer)

6-(1-{Tetrahydro-2H-pyran-4-yl[6-(trifluoromethyl)pyridin-3-yl]methyl}-1H-pyrazol-4-yl)-8-{3-[(trifluoromethyl)sulfonyl]phenyl}[1,2,4]triazolo[1,5-a]pyridin-2-amine (mixture of enantiomers) (152 mg, 98% purity) from the previous example was separated by chiral chromatography to yield stereoisomer 1 (68 mg, 99% purity) and stereoisomer 2 (73 mg, 96% purity).

Column: Daicel Chiralcel OZ-H, 5 μm, 250×20 mm; Eluent A: n-heptane; Eluent B: ethanol+0.2% diethylamine; isocratic: 50% A+50% B; flow: 15 ml/min; UV: 220 nm; temperature: 50° C.

Stereoisomer 1: $R^t$=9.03 min and

Stereoisomer 2: $R^t$=12.85 min (cf. next example)

Analytical chiral HPLC method: Column: Daicel Chiralcel OZ-H, 5 μm, 250×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=7.003 min and

Stereoisomer 2: $R^t$=10.581 min (cf. next example)

LC-MS (method 1): $R^t$=2.05 min; MS (ESIpos): m/z=652 $[M+H]^+$ $^1$H-NMR (600 MHz, DMSO-$d_6$) δ [ppm]: 0.858 (0.53), 1.088 (2.21), 1.108 (2.62), 1.237 (2.37), 1.258 (2.91), 1.297 (0.94), 1.305 (0.99), 1.317 (2.07), 1.324 (2.30), 1.339 (2.89), 1.345 (2.36), 1.351 (2.34), 1.359 (2.76), 1.372 (1.84), 1.379 (1.74), 1.393 (0.76), 1.400 (0.66), 2.425 (0.51), 2.614 (0.43), 2.654 (0.57), 2.729 (0.82), 2.748 (2.13), 2.766 (2.07), 2.785 (0.78), 3.237 (0.69), 3.257 (1.95), 3.276 (5.76), 3.314 (2.53), 3.735 (0.60), 3.808 (2.50), 3.823 (2.30), 3.846 (2.46), 3.865 (2.25), 5.397 (6.25), 5.415 (6.02), 6.174 (16.00), 7.945 (7.30), 7.959 (7.71), 7.991 (4.20), 8.005 (8.61), 8.018 (4.70), 8.106 (10.29), 8.108 (10.31), 8.180 (4.85), 8.193 (4.47), 8.203 (15.38), 8.306 (4.36), 8.319 (4.04), 8.559 (14.56), 8.755 (5.00), 8.768 (4.75), 8.967 (10.72), 8.970 (10.93), 8.979 (8.27), 9.007 (8.74).

Example 1H-21

6-(1-{Tetrahydro-2H-pyran-4-yl[6-(trifluoromethyl)pyridin-3-yl]methyl}-1H-pyrazol-4-yl)-8-{3-[(trifluoromethyl)sulfonyl]phenyl}[1,2,4]triazolo[1,5-a]pyridin-2-amine (stereoisomer 2, eutomer)

The product was isolated in the previous example as second stereoisomer.

LC-MS (method 1): $R^t$=2.05 min; MS (ESIpos): m/z=652 $[M+H]^+$ $^1$H-NMR (600 MHz, DMSO-$d_6$) δ [ppm]: 1.07-1.12 (m, 1H), 1.22-1.27 (m, 1H), 1.29-1.41 (m, 2H), 2.72-2.80 (m, 1H), 3.25-3.33 (m, 2H), 3.79-3.88 (m, 2H), 5.41 (d, 1H), 6.17 (s, 2H), 7.95 (d, 1H), 8.00 (t, 1H), 8.11 (d, 1H), 8.17-8.20 (m, 1H), 8.20 (s, 1H), 8.31 (dd, 1H), 8.56 (s, 1H), 8.75-8.78 (m, 1H), 8.97 (d, 1H), 8.98 (d, 1H), 9.01 (t, 1H).

Example II-22

8-[3-(Dimethylamino)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers)

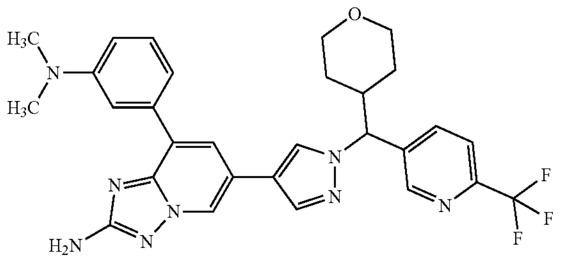 [SMILES: CN(C)c1cccc(-c2cc(-c3cnn(C(c4ccc(C(F)(F)F)nc4)C4CCOCC4)c3)cn3nc(N)nc23)c1]

6-Bromo-8-[3-(dimethylamino)phenyl][1,2,4]triazolo[1,5-a]pyridin-2-amine (100 mg, 301 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (158 mg, 361 μmol) for 2 h at 90° C. following general procedure B using 0.05 eq. catalyst. The reaction mixture was diluted with dichloromethane/water (4:1) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate/2-propanol gradient 70:30:0 to 0:100:0 to 0:80:20) to yield 112 mg (100% purity, 66% yield) of the title compound.

LC-MS (method 1): $R^t$=1.81 min; MS (ESIpos): m/z=563 $[M+H]^+$ $^1$H-NMR (600 MHz, DMSO-$d_6$) δ [ppm]: 1.073 (0.65), 2.967 (16.00), 3.272 (0.76), 3.292 (1.26), 5.376 (0.91), 5.394 (0.88), 6.017 (2.35), 6.783 (0.56), 6.786 (0.56), 6.797 (0.58), 6.800 (0.58), 7.274 (0.64), 7.287 (1.20), 7.300 (0.81), 7.356 (0.87), 7.369 (0.63), 7.445 (0.85), 7.449 (1.09), 7.452 (0.78), 7.839 (1.67), 7.841 (1.65), 7.940 (1.07), 7.954 (1.13), 8.161 (2.26), 8.304 (0.63), 8.307 (0.61), 8.318 (0.57), 8.320 (0.55), 8.535 (2.12), 8.823 (1.69), 8.825 (1.70), 8.972 (1.14), 8.974 (1.12).

Example II-23

8-[3-(Dimethylamino)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomers 1, distomer)

8-[3-(Dimethylamino)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (mixture of enantiomers) (98 mg, 100% purity) from the previous example was separated by chiral chromatography to yield stereoisomer 1 (33 mg, 98% purity) and stereoisomer 2 (34 mg, 96% purity).

Column: Daicel Chiralpak IE-H, 5 μm, 250×20 mm; Eluent A: n-heptane; Eluent B: ethanol+0.2% diethylamine; isocratic: 50% A+50% B; flow: 20 ml/min; UV: 210 nm; temperature: 60° C.

Stereoisomer 1: $R^t$=9.453 min and

Stereoisomer 2: $R^t$=11.720 min (cf. next example)

Analytical chiral HPL. Daicel Chiralpak IE-3, 3 μm, 50×4.6 mm; Eluent A: n-heptane; Eluent B: ethanol+0.2% diethylamine; isocratic: 30% A+70% B; flow: 1 ml/min; UV: 220 nm.

Stereoisomer 1: $R^t$=6.652 min and

Stereoisomer 2: $R^t$=11.052 min (cf. next example)

LC-MS (method 1): $R^t$=1.81 min; MS (ESIpos): m/z=563 $[M+H]^+$ $^1$H-NMR (600 MHz, DMSO-$d_6$) δ [ppm]: 1.069 (0.41), 1.082 (0.48), 1.231 (0.50), 1.247 (0.58), 1.327 (0.46), 1.336 (0.49), 1.346 (0.42), 2.967 (16.00), 3.266 (0.75), 3.287 (0.75), 3.801 (0.41), 3.842 (0.41), 5.379 (0.99), 5.397 (0.94), 6.073 (2.45), 6.784 (0.62), 6.788 (0.63), 6.797 (0.63), 6.801 (0.66), 7.276 (0.64), 7.289 (1.29), 7.302 (0.84), 7.359 (0.99), 7.372 (0.72), 7.438 (1.23), 7.847 (1.66), 7.850 (1.66), 7.954 (1.19), 7.967 (1.25), 8.175 (2.47), 8.308 (0.71), 8.322 (0.65), 8.551 (2.29), 8.842 (1.75), 8.844 (1.71), 8.977 (1.34).

Example II-24

8-[3-(Dimethylamino)phenyl]-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (stereoisomers 2, eutomer)

The product was isolated in the previous example as second stereoisomer.

LC-MS (method 1): $R^t$=1.81 min; MS (ESIpos): m/z=563 $[M+H]^+$ $^1$H-NMR (600 MHz, DMSO-$d_6$) δ [ppm]: 1.05-1.10 (m, 1H), 1.21-1.40 (m, 3H), 2.71-2.80 (m, 1H), 2.97 (s, 6H), 3.23-3.32 (m, 2H), 3.78-3.87 (m, 2H), 5.39.(d, 1H), 6.07 (s, 2H), 6.79 (dd, 1H), 7.29 (t, 1H), 7.37 (d, 1H), 7.42-7.45 (m, 1H), 7.85 (d, 1H), 7.96 (d, 1H), 8.18 (s, 1H), 8.32 (br dd, 1H), 8.55 (s, 1H), 8.84 (d, 1H), 8.98 (s, 1H).

Example II-25

8-[2-(Difluoromethoxy)pyridin-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers)

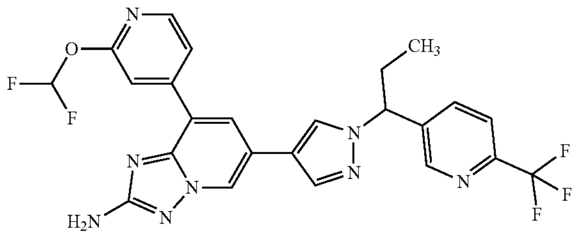 [SMILES: CCC(c1ccc(C(F)(F)F)nc1)n1cc(-c2cc(-c3ccnc(OC(F)F)c3)c3nc(N)nn3c2)cn1]

8-Chloro-6-(1-{1-[6-(trifluoromethyl)pyridin-3-yl]propyl}-1H-pyrazol-4-yl)[1,2,4]triazolo[1,5-a]pyridin-2-amine (145 mg, 344 μmol), [2-(difluoromethoxy)pyridin-4-yl]boronic acid (78.0 mg, 413 μmol), caesium carbonate (336 mg, 1.03 mmol) and XPhos-Pd-G2 (13.5 mg, 17.2 μmol) were reacted according to procedure A in a mixture of 1,4-dioxane (2.9 ml) and water (970 μl). After 12 h at 90° C., the reaction mixture was quenched with water filtered through a hydrophobic phase separation filter, washed with 15 ml of ethyl acetate and concentrated. The residue was purified via column chromatography (Biotage® SNAP KP-NH 11 g cartridge, eluent: cyclohexane/ethyl acetate gradient 4:1 to 1:4) to give 97.0 mg (100% purity, 53% yield) of the title compound as a mixture of enantiomers.

LC-MS (method 2): $R^t$=1.04 min; MS (ESIpos): m/z=531 [M+H]$^+$ $^1$H-NMR (600 MHz, DMSO-$d_6$) δ [ppm]: 0.91 (t, 3H), 2.23-2.28 (m, 1H), 2.39-2.48 (m, 1H), 5.59 (dd, 1H), 6.31 (br s, 2H), 7.79 (t, 1H), 7.93 (d, 1H), 8.05 (br d, 1H), 8.11 (s, 1H), 8.21 (d, 1H), 8.23 (s, 1H), 8.28 (s, 1H), 8.40 (d, 1H), 8.66 (s, 1H), 8.82 (s, 1H), 9.04 (s, 1H).

Example II-26

8-[2-(Difluoromethoxy)pyridin-4-yl]-6-(1-{1-[6-(trifluoromethyl)pyridin-3-yl]propyl}-1H-pyrazol-4-yl)[1,2,4]triazolo[1,5-a]pyridin-2-amine (stereoisomer 1, distomer)

8-[2-(difluoromethoxy)pyridin-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers) (97 mg, 100% purity) was separated by chiral preparative HPLC to yield stereoisomer 1 (30.8 mg, 100% purity) and stereoisomer 2 (33.5 mg, 100% purity).

Column: Chiralpak IE, 5 μm, 250×20 mm; Eluent A: n-heptane; Eluent B: ethanol+0.2% diethylamine; isocratic: 70% A+30% B; flow: 15 ml/min; UV: 210 nm; temperature: 40° C.

Stereoisomer 1: $R^t$=10.33 min and

Stereoisomer 2: $R^t$=13.37 min (cf. next example)

Analytical chiral HPLC method: Column: Daicel Chiralpak IE 3.3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=4.44 min and

Stereoisomer 2: $R^t$=5.94 min (cf. next example)

LC-MS (method 1): $R^t$=1.99 min; MS (ESIpos): m/z=531 [M+H]$^+$

Example II-27

8-[2-(Difluoromethoxy)pyridin-4-yl]-6-(1-f{1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.99 min; MS (ESIpos): m/z=531 [M+H]$^+$ $^1$H-NMR (400 MHz, DMSO-$d_6$) δ [ppm]: 0.91 (t, 3H), 2.19-2.29 (m, 1H), 2.37-2.47 (m, 1H), 5.59 (dd, 1H), 6.31 (s, 2H), 7.79 (t, 1H), 7.93 (d, 1H), 8.04 (dd, 1H), 8.11 (s, 1H), 8.19-8.26 (m, 2H), 8.28 (d, 1H), 8.40 (d, 1H), 8.65 (s, 1H), 8.82 (s, 1H), 9.04 (d, 1H).

Example II-28

7-(1-{2-Methyl-1-[6-(trifluoromethyl)pyridin-3-yl]propyl}-1H-pyrazol-4-yl)-5-[2-(trifluoromethyl)pyridin-4-yl][1,2,4]triazolo[1,5-a]pyridin-2-amine (mixture of enantiomers)

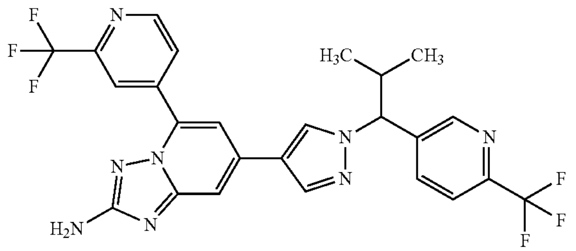 [SMILES: CC(C)C(c1ccc(C(F)(F)F)nc1)n1cc(-c2cc(-c3ccnc(C(F)(F)F)c3)n3nc(N)nc3c2)cn1]

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (210 mg, 482 μmol), [2-(trifluoromethyl)pyridin-4-yl]boronic acid (120 mg, 626 μmol), XPhos-Pd-G2 (28.4 mg, 36.1 μmol) and sodium carbonate (255 mg, 2.41 mmol) were reacted according to procedure A in a mixture of water (1.0 ml) and 1,4-dioxane (3.0 ml). After stirring 3 h at 90° C., the reaction was quenched with water and extracted with dichloromethane. The organic layer was dried over anhydrous sodium sulfate, filtered and concentrated. The residue was purified via column chromatography (Biotage® SNAP KP-NH 11 g cartridge, eluent: cyclohexane/ethyl acetate gradient 4:1 to 1:4) to yield 124 mg (99% purity, 47% yield) of the title compound as a mixture of enantiomers.

LC-MS (method 1): $R^t$=2.01 min; MS (ESIpos): m/z=547 [M+H]$^+$ $^1$H-NMR (400 MHz, DMSO-$d_6$) δ [ppm]: 0.82 (d, 3H), 0.88 (d, 3H), 2.77-2.88 (m, 1H), 5.27 (d, 1H), 6.15 (s, 2H), 7.57 (d, 1H), 7.73 (d, 1H), 7.95 (d, 1H), 8.28 (s, 1H), 8.30 (d, 1H), 8.40 (d, 1H), 8.59 (s, 1H), 8.70 (s, 1H), 8.96 (br s, 1H), 8.99 (d, 1H).

Example II-29

7-(1-{2-Methyl-1-[6-(trifluoromethyl)pyridin-3-yl]propyl}-1H-pyrazol-4-yl)-5-[2-(trifluoromethyl)pyridin-4-yl][1,2,4]triazolo[1,5-a]pyridin-2-amine (stereoisomer 1, distomer)

7-(1-{2-Methyl-1-[6-(trifluoromethyl)pyridin-3-yl]propyl}-1H-pyrazol-4-yl)-5-[2-(trifluoromethyl)pyridin-4-yl][1,2,4]triazolo[1,5-a]pyridin-2-amine (mixture of enantiomers) (124 mg, 99% purity) was separated by chiral preparative HPLC to yield stereoisomer 1 (45.6 mg, 100% purity) and stereoisomer 2 (45.3 mg, 99% purity).

Column: Chiralcel OZ-H, 5 μm, 250×20 mm; Eluent A: n-heptane; Eluent B: ethanol+0.2% diethylamine; isocratic: 70% A+30% B; flow: 20 ml/min; UV: 210 nm; temperature: 40° C.

Stereoisomer 1: $R^t$=5.90 min and

Stereoisomer 2: $R^t$=10.07 min (cf. next example)

Analytical chiral HPLC method: Column: Daicel Chiralpak OZ-3, 3 μm, 50×4.6 mm; Eluent A: 20 n-heptane; Eluent B: ethanol+0.2% diethylamine; isocratic: 50% A+50% B; flow: 1 ml/min; UV: 220 nm.

Stereoisomer 1: $R^t$=2.05 min and

Stereoisomer 2: $R^t$=3.44 min (cf. next example)

LC-MS (method 1): $R^t$=2.00 min; MS (ESIpos): m/z=547 $[M+H]^+$

Example II-30

7-(1-{2-Methyl-1-[6-(trifluoromethyl)pyridin-3-yl]propyl}-1H-pyrazol-4-yl)-5-[2-(trifluoromethyl)pyridin-4-yl][1,2,4]triazolo[1,5-a]pyridin-2-amine (stereoisomer 2, eutomer)

The product was isolated in the previous example as second stereoisomer.

LC-MS (method 1): $R^t$=2.00 min; MS (ESIpos): m/z=547 $[M+H]^+$ $^1$H-NMR (400 MHz, DMSO-$d_6$) δ [ppm]: 0.82 (d, 3H), 0.88 (d, 3H), 2.74-2.89 (m, 1H), 5.26 (d, 1H), 6.15 (s, 2H), 7.57 (d, 1H), 7.72 (d, 1H), 7.95 (d, 1H), 8.28 (s, 1H), 8.29 (d, 1H), 8.39 (dd, 1H), 8.58 (s, 1H), 8.70 (s, 1H), 8.96 (br s, 1H), 8.98 (d, 1H).

Example II-31

5-[2-(1-Fluorocyclopropyl)pyridin-4-yl]-7-(1-{1-[6-(trifluoromethyl)pyridin-3-yl]propyl}-1H-pyrazol-4-yl)[1,2,4]triazolo[1,5-a]pyridin-2-amine (mixture of enantiomers)

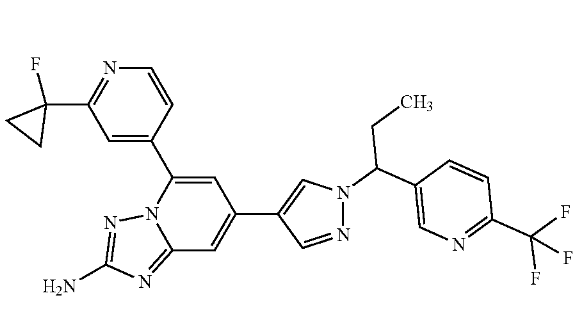 [SMILES: CCC(c1ccc(C(F)(F)F)nc1)n1cc(-c2cc(-c3ccnc(C4(F)CC4)c3)n3nc(N)nc3c2)cn1]

7-Chloro-5-[2-(1-fluorocyclopropyl)pyridin-4-yl][1,2,4]triazolo[1,5-a]pyridin-2-amine (203 mg, 668 μmol), 5-{1-[4-(4,4,5,5-tetramethyl-1,3,2-dioxaborolan-2-yl)-1H-pyrazol-1-yl]propyl}-2-(trifluoromethyl)pyridine (289 mg, 97% purity, 735 μmol), caesium carbonate (653 mg, 2.01 mmol) and XPhos-Pd-G2 (26.3 mg, 33.4 μmol) were reacted according to procedure A in a mixture of 1,4-dioxane (6.0 ml) and water (750 μl). After 2 h at 90° C., the reaction mixture was quenched with water filtered through a hydrophobic phase separation filter, washed with 15 ml of ethyl acetate and concentrated. The residue was purified via column chromatography (Biotage® SNAP KP-NH 55 g cartridge, eluent: cyclohexane/ethyl acetate gradient 9:1 to 1:9) to yield 167 mg (97% purity, 47% yield) of the title compound as a mixture of enantiomers.

LC-MS (method 1): $R^t$=1.90 min; MS (ESIpos): m/z=523 $[M+H]^+$ $^1$H-NMR (600 MHz, DMSO-$d_6$) δ [ppm]: 0.89 (t, 3H), 1.40-1.47 (m, 2H), 1.55-1.62 (m, 2H), 2.20-2.27 (m, 1H), 2.41-2.49 (m, 1H), 5.59 (dd, 1H), 6.09 (s, 2H), 7.48 (d, 1H), 7.70 (d, 1H), 7.88 (d, 1H), 7.92 (d, 1H), 8.05 (d, 1H), 8.20 (s, 1H), 8.28 (s, 1H), 8.69 (d, 1H), 8.75 (s, 1H), 8.82 (s, 1H).

Example II-32

5-[2-(1-Fluorocyclopropyl)pyridin-4-yl]-7-(1-{1-[6-(trifluoromethyl)pyridin-3-yl]propyl}-1H-pyrazol-4-yl)[1,2,4]triazolo[1,5-a]pyridin-2-amine (stereoisomer 1, distomer)

5-[2-(1-Fluorocyclopropyl)pyridin-4-yl]-7-(1-{1-[6-(trifluoromethyl)pyridin-3-yl]propyl}-1H-pyrazol-4-yl)[1,2,4]triazolo[1,5-a]pyridin-2-amine 167 mg (97% purity, 47% yield) was separated by chiral preparative HPLC to yield stereoisomer 1 (62.2 mg, 100% purity) and stereoisomer 2 (66.9 mg, 98% purity).

Column: Chiralpak IE, 5 μm, 250×20 mm; Eluent A: n-heptane; Eluent B: ethanol; isocratic: 50% A+50% B; flow: 25 ml/min; UV: 210 nm; temperature: 40° C.

Stereoisomer 1: $R^t$=9.01 min and

Stereoisomer 2: $R^t$=11.05 min (cf. next example)

Analytical chiral HPLC method: Column: Daicel Chiralpak IE-3, 3 μm, 50×4.6 mm; Eluent A: n-heptane; Eluent B: ethanol; isocratic: 50% A+50% B; flow: 1 ml/min; UV: 220 nm.

Stereoisomer 1: $R^t$=1.73 min and

Stereoisomer 2: $R^t$=1.99 min (cf. next example)

LC-MS (method 1): $R^t$=1.88 min; MS (ESIpos): m/z=523 $[M+H]^+$

Example II-33

5-[2-(1-Fluorocyclopropyl)pyridin-4-yl]-7-(1-f{1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer. The stereochemical configuration of the methine carbon atom bonded to the pyrazole was (R).

LC-MS (method 1): $R^t$=1.89 min; MS (ESIpos): m/z=523 $[M+H]^+$ $^1$H-NMR (400 MHz, DMSO-$d_6$) δ [ppm]: 0.89 (t, 3H), 1.36-1.50 (m, 2H), 1.58 (dq, 2H), 2.18-2.29 (m, 1H), 2.37-2.50 (m, 1H), 5.59 (dd, 1H), 6.11 (s, 2H), 7.49 (d, 1H), 7.71 (d, 1H), 7.88 (d, 1H), 7.92 (d, 1H), 8.05 (dd, 1H), 8.20 (s, 1H), 8.29 (s, 1H), 8.70 (d, 1H), 8.76 (s, 1H), 8.82 (d, 1H).

Example II-34

7-(1-{Tetrahydro-2H-pyran-4-yl[6-(trifluoromethyl)pyridin-3-yl]methyl}-1H-pyrazol-4-yl)-5-[2-(trifluoromethyl)pyridin-4-yl][1,2,4]triazolo[1,5-a]pyridin-2-amine (mixture of enantiomers)

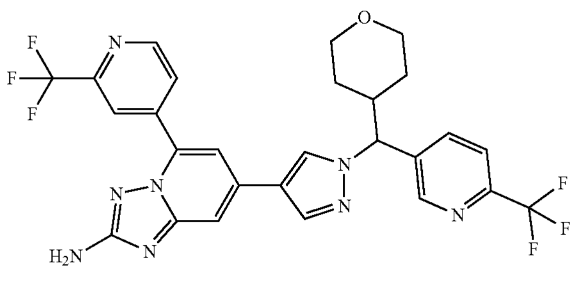 [SMILES: Nc1nc2cc(-c3cnn(C(c4ccc(C(F)(F)F)nc4)C4CCOCC4)c3)cc(-c3ccnc(C(F)(F)F)c3)n2n1]

7-Chloro-5-[2-(trifluoromethyl)pyridin-4-yl][1,2,4]triazolo[1,5-a]pyridin-2-amine (155 mg, 493 μmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (237 mg, 542 μmol), XPhos-Pd-G2 (19.4 mg, 24.6 μmol) and caesium carbonate (481 mg, 1.48 mmol) were reacted according to procedure A in a mixture of 1,4-dioxane (4 ml) and water (500 μl). The reaction was stirred for 3 h at 90° C. The residue was purified by preparative HPLC to yield 55.0 mg (100% purity, 19% yield) of the title compound as a mixture of enantiomers.

LC-MS (method 1): $R^t$=1.83 min; MS (ESIpos): m/z=589 $[M+H]^+$ $^1$H-NMR (400 MHz, DMSO-$d_6$) δ [ppm]: 1.09 (br d, 1H), 1.19-1.26 (m, 1H), 1.27-1.41 (m, 2H), 2.71-2.81 (m, 1H), 3.23-3.30 (m, 2H), 3.78-3.88 (m, 2H), 5.41 (d, 1H), 6.15 (s, 2H), 7.57 (d, 1H), 7.72 (d, 1H), 7.96 (d, 1H), 8.30 (s, 1H), 8.31 (d, 1H), 8.39 (d, 1H), 8.58 (s, 1H), 8.70 (s, 1H), 8.98 (s, 1H), 8.98 (s, 1H).

Example II-35

7-(1-{Tetrahydro-2H-pyran-4-yl[6-(trifluoromethyl)pyridin-3-yl]methyl}-1H-pyrazol-4-yl)-5-[2-(trifluoromethyl)pyridin-4-yl][1,2,4]triazolo[1,5-a]pyridin-2-amine (stereoisomer 1, distomer)

7-(1-{Tetrahydro-2H-pyran-4-yl[6-(trifluoromethyl)pyridin-3-yl]methyl}-1H-pyrazol-4-yl)-5-[2-(trifluoromethyl)pyridin-4-yl][1,2,4]triazolo[1,5-a]pyridin-2-amine (55 mg, 100% purity) was separated by chiral preparative HPLC to yield stereoisomer 1 (21.5 mg, 100% purity) and stereoisomer 2 (24.2 mg, 100% purity).

Column: Chiralpak IE, 5 m, 250×20 mm; Eluent A: n-heptane; Eluent B: ethanol+0.2% diethylamine; isocratic: 50% A+50% B; flow: 20 ml/min; UV: 210 nm; temperature: 40° C.

Stereoisomer 1: $R^t$=8.41 and

Stereoisomer 2: $R^t$=10.33 min (cf. next example)

Analytical chiral HPLC method: Column: Daicel Chiralpak IE-3, 3 m, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.84 min and

Stereoisomer 2: $R^t$=2.47 min (cf. next example)

LC-MS (method 1): $R^t$=1.84 min; MS (ESIpos): m/z=589 $[M+H]^+$

Example II-36

7-(1-{Tetrahydro-2H-pyran-4-yl[6-(trifluoromethyl)pyridin-3-yl]methyl}-1H-pyrazol-4-yl)-5-[2-(trifluoromethyl)pyridin-4-yl][1,2,4]triazolo[1,5-a]pyridin-2-amine (stereoisomer 2, eutomer)

The product was isolated in the previous example as second stereoisomer. The stereochemical configuration of the methine carbon atom bonded to the pyrazole was (S).

LC-MS (method 1): $R^t$=1.84 min; MS (ESIpos): m/z=589 $[M+H]^+$ $^1$H-NMR (400 MHz, DMSO-$d_6$) δ [ppm]: 1.06-1.15 (m, 2H), 1.17-1.29 (m, 2H), 1.29-1.40 (m, 2H), 2.66-2.91 (m, 2H), 3.23-3.30 (m, 2H), 3.77-3.90 (m, 2H), 5.41 (d, 1H), 6.15 (s, 2H), 7.56 (d, 1H), 7.72 (d, 1H), 7.96 (d, 1H), 8.32 (br d, 1H), 8.39 (d, 1H), 8.58 (s, 1H), 8.70 (s, 1H), 8.99 (d, 2H).

Example II-37

8-[6-(Trifluoromethyl)pyridin-3-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers)

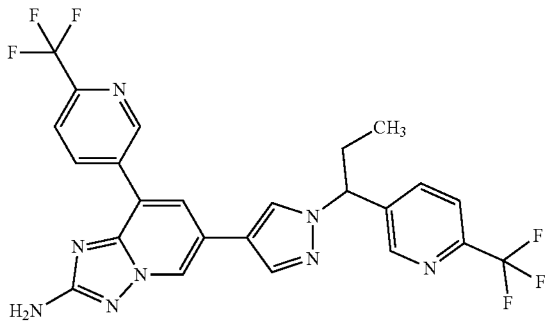 [SMILES: CCC(c1ccc(C(F)(F)F)nc1)n1cc(-c2cc(-c3ccc(C(F)(F)F)nc3)c3nc(N)nn3c2)cn1]

8-Chloro-6-(1-{1-[6-(trifluoromethyl)pyridin-3-yl]propyl}-1H-pyrazol-4-yl)[1,2,4]triazolo[1,5-a]pyridin-2-amine (1545.0 mg, 2527.3 mol, 69% purity), [6-(trifluoromethyl)pyridin-3-yl]boronic acid (579.0 mg, 3032.7 μmol), caesium carbonate (2470 mg, 7581 μmol) and XPhos-Pd-G2 (99.4 mg, 126.3 μmol) were reacted according to procedure A in a mixture of 1,4-dioxane (20.0 ml) and water (3.0 ml). The reaction was stirred for 3 h at 90° C. The reaction mixture was quenched with water, filtered through a hydrophobic phase separation filter, washed with ethyl acetate (15 ml) and concentrated under reduced pressure. The residue was purified by preparative HPLC to yield 1.13 g (91% purity, 76% yield) of the title compound as a mixture of enantiomers.

LC-MS (method 1): $R^t$=1.97 min; MS (ESIpos): m/z=533 $[M+H]^+$ $^1$H-NMR (400 MHz, DMSO-$d_6$) δ [ppm]: 0.90 (t, 4H), 2.18-2.30 (m, 1H), 2.33-2.48 (m, 1H), 5.60 (dd, 1H), 6.25 (s, 2H), 7.93 (d, 1H), 8.02-8.12 (m, 2H), 8.21 (s, 1H), 8.24 (d, 1H), 8.63 (s, 1H), 8.82 (d, 1H), 8.91 (dd, 1H), 9.02 (d, 1H), 9.54 (d, 1H).

Example II-38

8-[6-(Trifluoromethyl)pyridin-3-yl]-6-(1-{1-[6-(trifluoromethyl)pyridin-3-yl]propyl}-1H-pyrazol-4-yl)[1,2,4]triazolo[1,5-a]pyridin-2-amine (stereoisomer 1, distomer)

8-[6-(Trifluoromethyl)pyridin-3-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers) (1128 mg, 91% purity) was separated by chiral preparative SFC to yield stereoisomer 1 (274 mg, 95% purity) and stereoisomer 2 (419 mg, 100% purity).

Instrument: THAR SFC-Super Chrom Prep 200; Column: Daicel Chiralpak OZ, 20 μm, 450×50 mm; Eluent A: $CO_2$; Eluent B: methanol; isocratic: 60% A+40% B; flow: 400 ml/min; UV: 210 nm; temperature: 35° C.

Analytical chiral SFC-method: Column: Daicel Chiralpak OZ, 3 m, 100×4.6 mm; Eluent A: $CO_2$;

Eluent B: methanol; isocratic: 70% A+30% B; flow: 3 ml/min; UV: 210 nm; temperature: 30° C.

Stereoisomer 1: $R^t$=3.66 min and

Stereoisomer 2: $R^t$=5.84 min (cf. next example)

LC-MS (method 1): $R^t$=1.96 min; MS (ESIpos): m/z=533 $[M+H]^+$

Example II-39

8-[6-(Trifluoromethyl)pyridin-3-yl]-6-(1-{1-[6-(trifluoromethyl)pyridin-3-yl]propyl}-1 H-pyrazol-4-yl)[1,2,4]triazolo[1,5-a]pyridin-2-amine (stereoisomer 2, eutomer)

The product was isolated in the previous example as second stereoisomer. The stereochemical configuration of the methine carbon atom bonded to the pyrazole was (R).

LC-MS (method 1): $R^t$=1.96 min; MS (ESIpos): m/z=533 $[M+H]^+$ $^1$H-NMR (400 MHz, DMSO-$d_6$) δ [ppm]: 0.90 (t, 3H), 2.18-2.29 (m, 1H), 2.37-2.48 (m, 1H), 5.60 (dd, 1H), 6.25 (s, 2H), 7.93 (d, 1H), 8.05 (dd, 1H), 8.08 (d, 1H), 8.21 (s, 1H), 8.24 (s, 1H), 8.63 (s, 1H), 8.82 (d, 1H), 8.91 (dd, 1H), 9.02 (d, 1H), 9.54 (d, 1H).

Example II-40

6-(1-{2-Methyl-1-[6-(trifluoromethyl)pyridin-3-yl]propyl}-1H-pyrazol-4-yl)-8-[6-(trifluoromethyl)pyridin-3-yl][1,2,4]triazolo[1,5-a]pyridin-2-amine (mixture of enantiomers)

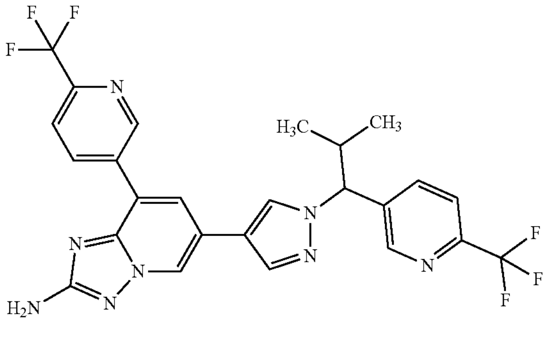 [SMILES: CC(C)C(c1ccc(C(F)(F)F)nc1)n1cc(-c2cc(-c3ccc(C(F)(F)F)nc3)c3nc(N)nn3c2)cn1]

8-Chloro-6-(1-{2-methyl-1-[6-(trifluoromethyl)pyridin-3-yl]propyl}-1H-pyrazol-4-yl)[1,2,4]triazolo[1,5-a]pyridin-2-amine (68.0 mg, 156 μmol), [6-(trifluoromethyl)pyridin-3-yl]boronic acid (35.7 mg, 187 μmol), caesium carbonate (153 mg, 468 μmol) and XPhos-Pd-G2 (6.14 mg, 7.80 μmol) were reacted according to procedure A in a mixture of 1,4-dioxane (3.8 ml) and water (1.3 ml). The reaction was stirred for 3 h at 90° C. The reaction mixture was quenched with water filtered through a hydrophobic phase separation filter, washed with 15 ml of ethyl acetate and concentrated.

A second batch of the same reaction was prepared using 8-chloro-6-(1-{2-methyl-1-[6-(trifluoromethyl)pyridin-3-yl]propyl}-1H-pyrazol-4-yl)[1,2,4]triazolo[1,5-a]pyridin-2-amine (20.0 mg, 46 μmol), [6-(trifluoromethyl)pyridin-3-yl]boronic acid (10 mg, 55 μmol), caesium carbonate (44 mg, 137 μmol) and XPhos-Pd-G2 (1.8 mg, 2.3 μmol) in a mixture of 1,4-dioxane (2.0 ml) and water (0.33 ml). The residues of the two batches were combined and purified by preparative HPLC to yield 88.7 mg (100% purity, 80% yield) of the title compound as a racemic mixture.

LC-MS (method 1): $R^t$=2.07 min; MS (ESIpos): m/z=547 $[M+H]^+$ $^1$H-NMR (600 MHz, DMSO-$d_6$) δ [ppm]: 0.83 (d, 3H), 0.90 (d, 3H), 2.78-2.85 (m, 1H), 5.26 (d, 1H), 6.25 (br s, 2H), 7.95 (d, 1H), 8.08 (d, 1H), 8.20 (d, 2H), 8.29 (br d, 1H), 8.59 (s, 1H), 8.90 (br d, 1H), 8.97 (s, 1H), 9.00 (s, 1H), 9.53 (s, 1H).

Example II-41

6-(1-{2-Methyl-1-[6-(trifluoromethyl)pyridin-3-yl]propyl}-1H-pyrazol-4-yl)-8-[6-(trifluoromethyl)pyridin-3-yl][1,2,4]triazolo[1,5-a]pyridin-2-amine (stereoisomer 1, distomer)

6-(1-{2-Methyl-1-[6-(trifluoromethyl)pyridin-3-yl]propyl}-1H-pyrazol-4-yl)-8-[6-(trifluoromethyl)pyridin-3-yl][1,2,4]triazolo[1,5-a]pyridin-2-amine (mixture of enantiomers) (88.7 mg, 100% purity) was separated by chiral preparative HPLC to yield stereoisomer 1 (29.2 mg, 100% purity) and stereoisomer 2 (26.6 mg, 100% purity).

Column: Daicel Chiralpak IG, 5 μm, 250×20 mm; Eluent A: n-heptane; Eluent B: ethanol; isocratic: 40% A+60% B; flow: 15 ml/min; UV: 220 nm; temperature: 60° C.

Stereoisomer 1: $R^t$=10.25 min and

Stereoisomer 2: $R^t$=13.52 min (cf. next example)

Analytical chiral HPLC method: Column: Daicel Chiralpak IG, 5 m, 250×4.6 mm; Eluent A: n-heptane; Eluent B: ethanol+0.2% diethylamine; isocratic: 40% A+60% B; flow: 1 ml/min; UV: 235 nm; temperature: 70° C.

Stereoisomer 1: $R^t$=7.19 min and

Stereoisomer 2: $R^t$=9.86 min (cf. next example)

LC-MS (method 1): $R^t$=2.07 min; MS (ESIpos): m/z=547 $[M+H]^+$

Example II-42

6-(1-{2-Methyl-1-[6-(trifluoromethyl)pyridin-3-yl]propyl}-1H-pyrazol-4-yl)-8-[6-(trifluoromethyl)pyridin-3-yl][1,2,4]triazolo[1,5-a]pyridin-2-amine (stereoisomer 2, eutomer)

The product was isolated in the previous example as second stereoisomer.

LC-MS (method 1): $R^t$=2.07 min; MS (ESIpos): m/z=547 $[M+H]^+$ $^1$H-NMR (400 MHz, DMSO-$d_6$) δ [ppm]: 0.82 (d, 3H), 0.90 (d, 3H), 2.76-2.87 (m, 1H), 5.26 (d, 1H), 6.24 (s, 2H), 7.95 (d, 1H), 8.07 (d, 1H), 8.19 (s, 1H), 8.20 (d, 1H), 8.29 (dd, 1H), 8.59 (s, 1H), 8.90 (dd, 1H), 8.96 (d, 1H), 9.00 (d, 1H), 9.53 (d, 1H).

Example II-43

8-(6-Cyclopropylpyridin-3-yl)-6-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

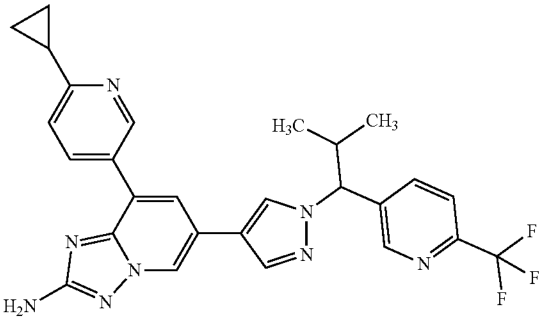 [SMILES: CC(C)C(c1ccc(C(F)(F)F)nc1)n1cc(-c2cc(-c3ccc(C4CC4)nc3)c3nc(N)nn3c2)cn1]

8-Chloro-6-(1-{2-methyl-1-[6-(trifluoromethyl)pyridin-3-yl]propyl}-1H-pyrazol-4-yl)[1,2,4]triazolo[1,5-a]pyridin-2-amine (88.3 mg, 202 μmol), 2-cyclopropyl-5-(4,4,5,5-tetramethyl-1,3,2-dioxaborolan-2-yl)pyridine (59.6 mg, 243 μmol), sodium carbonate (107 mg, 1.01 mmol) and 1,1'-bis(diphenylphosphino)ferrocene-palladium(II)dichloride dichloromethane complex (8.27 mg, 10.1 μmol) were reacted according to procedure A in a mixture of 1,4-dioxane (4.0 ml) and water (1.3 ml). The reaction was stirred for 12 h at 90° C. As the reaction was not completed, 2-cyclopropyl-5-(4,4,5,5-tetramethyl-1,3,2-dioxaborolan-2-yl)pyridine (59.6 mg, 243 μmol), XPhos-Pd-G2 (7.97 mg, 10.1 μmol) and caesium carbonate (132 mg, 405 μmol) were added and the mixture was stirred for 3 h at 90° C. The reaction mixture was quenched with water filtered through a hydrophobic phase separation filter, washed with ethyl acetate (15 ml) and concentrated. The residue was purified by preparative HPLC to yield 84.9 mg (94% purity, 76% yield) of the title compound as a racemic mixture.

LC-MS (method 1): $R^t$=1.86 min; MS (ESIpos): m/z=519 $[M+H]^+$ $^1$H-NMR (400 MHz, DMSO-$d_6$) δ [ppm]: 0.82 (d, 3H), 0.89 (d, 3H), 0.93-1.03 (m, 4H), 2.12-2.20 (m, 1H), 2.78-2.84 (m, 1H), 5.24 (d, 1H), 6.13 (s, 2H), 7.43 (d, 1H), 7.93-7.96 (m, 1H), 8.01 (s, 1H), 8.16 (s, 1H), 8.28 (dd, 1H), 8.43 (dd, 1H), 8.58 (s, 1H), 8.71 (d, 1H), 8.88 (d, 1H), 8.96 (s, 1H), 9.17 (d, 1H).

Example II-44

8-(6-Cyclopropylpyridin-3-yl)-6-(1-{(2-methyl-1-[6-(trifluoromethyl)pyridin-3-yl]propyl}-1H-pyrazol-4-yl)[1,2,4]triazolo[1,5-a]pyridin-2-amine (stereoisomer 1, distomer)

8-(6-Cyclopropylpyridin-3-yl)-6-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers) (84.9 mg, 94% purity) was separated by chiral preparative HPLC to yield stereoisomer 1 (18.5 mg, 100% purity) and stereoisomer 2 (20.8 mg, 100% purity).

Column: Daicel ChiralpakOX H 250×20 mm; Eluent A: n-heptane; Eluent B: ethanol; isocratic: 45% A+55% B; flow: 25 ml/min; UV: 220 nm; temperature: 40° C.

Stereoisomer 1: $R^t$=3.22 min and

Stereoisomer 2: $R^t$=4.34 min (cf. next example)

Analytical chiral HPLC method: Column: Daicel Chiralpak OX-3, 3 μm, 50×4.6 mm; Eluent A: n-heptane; Eluent B: ethanol+0.2% diethylamine; isocratic: 50% A+50% B; flow: 1 ml/min; UV: 220 nm Stereoisomer 1: $R^t$=1.53 min and Stereoisomer 2: $R^t$=1.96 min (cf. next example)

LC-MS (method 1): $R^t$=1.86 min; MS (ESIpos): m/z=519 $[M+H]^+$

Example II-45

8-(6-Cyclopropylpyridin-3-yl)-6-(1-{2-methyl-1-[6-(trifluoromethyl)pyridin-3-yl]propyl}-1H-pyrazol-4-yl)[1,2,4]triazolo[1,5-a]pyridin-2-amine (sterioisomer 2, eutomer)

The product was isolated in the previous example as second stereoisomer.

LC-MS (method 1): $R^t$=1.86 min; MS (ESIpos): m/z=519 $[M+H]^+$ $^1$H-NMR (400 MHz, DMSO-$d_6$): 0.82 (d, 3H), 0.89 (d, 3H), 0.96-1.04 (m, 4H), 2.13-2.20 (m, 1H), 2.78-2.84 (m, 1H), 5.24 (d, 1H), 6.13 (s, 2H), 7.43 (d, 11H), 7.95 (d, 1H), 8.01 (d, 1H), 8.16 (s, 1H), 8.28 (dd, 1H), 8.43 (dd, 1H), 8.58 (s, 1H), 8.88 (d, 1H), 8.96 (s, 1H), 9.17 (d, 1H).

Example II-46

6-{1-[1-(Oxetan-3-yl)piperidin-4-yl]-1H-pyrazol-4-yl}-8-[6-(trifluoromethyl)pyridin-3-yl][1,2,4]triazolo[1,5-a]pyridin-2-amine

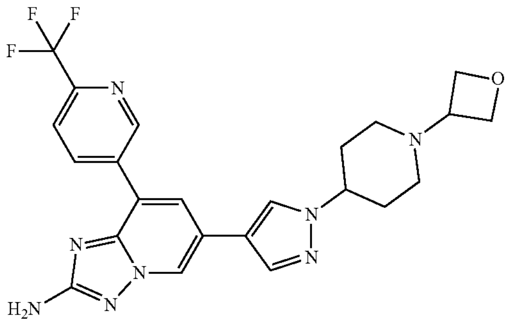 [SMILES: Nc1nc2c(-c3ccc(C(F)(F)F)nc3)cc(-c3cnn(C4CCN(C5COC5)CC4)c3)cn2n1]

8-Chloro-6-{1-[1-(oxetan-3-yl)piperidin-4-yl]-1H-pyrazol-4-yl}[1,2,4]triazolo[1,5-a]pyridin-2-amine (39.0 mg, 104 μmol), [6-(trifluoromethyl)pyridin-3-yl]boronic acid (23.9 mg, 125 μmol), caesium carbonate (102 mg, 313 μmol) and XPhos-Pd-G2 (4.10 mg, 5.22 μmol) were reacted according to procedure A in a mixture of 1,4-dioxane (2.0 ml) and water (670 μl). The reaction was stirred for 2 min at 120° C. under microwave irradiation. The reaction mixture was quenched with water filtered through a hydrophobic phase separation filter, washed with 15 ml of ethyl acetate and concentrated under reduced pressure. The residue was purified by preparative HPLC to yield 35.6 mg (100% purity, 70% yield) of the title compound.

LC-MS (method 1): $R^t$=0.99 min; MS (ESIpos): m/z=485 $[M+H]^+$ $^1$H-NMR (400 MHz, DMSO-$d_6$) δ [ppm]: 1.94-2.07 (m, 4H), 2.07-2.12 (m, 2H), 2.76-2.86 (m, 2H), 3.42-3.50 (m, 1H), 4.14-4.23 (m, 1H), 4.46 (br d, 2H), 4.56 (br t, 2H), 6.23 (s, 2H), 8.06-8.14 (m, 2H), 8.24 (d, 1H), 8.47-8.53 (m, 1H), 8.92 (dd, 1H), 8.99 (s, 1H), 9.54 (s, 1H).

Example II-47

7-(1-Benzyl-1H-pyrazol-4-yl)-5-(6-cyclopropylpyridin-3-yl)[1,2,4]triazolo[1,5-a]pyridin-2-amine

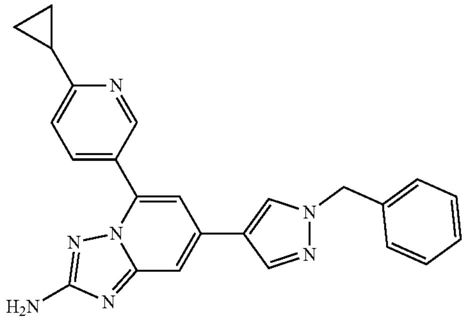 [SMILES: Nc1nc2cc(-c3cnn(Cc4ccccc4)c3)cc(-c3ccc(C4CC4)nc3)n2n1]

7-(1-Benzyl-1H-pyrazol-4-yl)-5-chloro[1,2,4]triazolo[1,5-a]pyridin-2-amine (147 mg, 453 μmol), 2-cyclopropyl-5-(4,4,5,5-tetramethyl-1,3,2-dioxaborolan-2-yl)pyridine (144 mg, 588 μmol), 1,1'-bis(diphenylphosphino)ferrocene-palladium(II)dichloride dichloromethane complex (55.4 mg, 67.9 μmol) and sodium carbonate (144 mg, 1.36 mmol) were reacted according to procedure A in a mixture of 1,4-dioxane (3.0 ml) and water (1.0 ml). After stirring 3 h at 90° C., the reaction was quenched with water and extracted with dichloromethane. The combined organic layers were dried over anhydrous sodium sulfate, filtered and concentrated. The residue was purified via column chromatography (Biotage® SNAP KP-NH 11 g cartridge, eluent: cyclohexane/ethyl acetate gradient 9:1 to 1:4) to yield 153 mg (99% purity, 82% yield) of the title compound.

LC-MS (method 2): $R^t$=0.85 min; MS (ESIpos): m/z=408 $[M+H]^+$ $^1$H-NMR (500 MHz, DMSO-$d_6$) δ [ppm]: 0.98-1.06 (m, 4H), 2.18-2.24 (m, 1H), 5.37 (s, 2H), 6.04 (s, 2H), 7.28-7.34 (m, 3H), 7.34-7.40 (m, 3H), 7.48 (d, 1H), 7.60 (d, 1H), 8.20 (s, 1H), 8.31 (dd, 1H), 8.59 (s, 1H), 9.00 (d, 1H).

Example II-48

5-[6-(Cyclopropyloxy)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

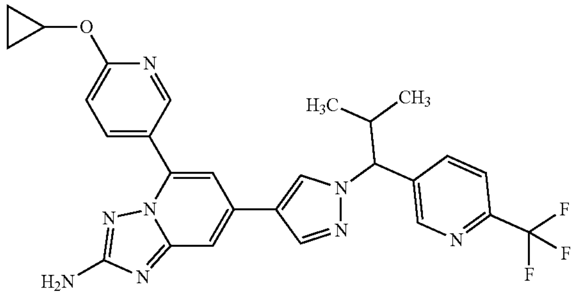 [SMILES: CC(C)C(c1ccc(C(F)(F)F)nc1)n1cc(-c2cc(-c3ccc(OC4CC4)nc3)n3nc(N)nc3c2)cn1]

7-Chloro-5-[6-(cyclopropyloxy)pyridin-3-yl][1,2,4]triazolo[1,5-a]pyridin-2-amine (65.0 mg, 95% purity, 205 μmol), 5-{2-methyl-1-[4-(4,4,5,5-tetramethyl-1,3,2-dioxaborolan-2-yl)-1H-pyrazol-1-yl]propyl}-2-(trifluoromethyl)pyridine (115 mg, 77% purity, 225 μmol), 1,1'-bis(diphenylphosphino)ferrocene-palladium(II)dichloride dichloromethane complex (25.1 mg, 30.7 μmol) and sodium carbonate (108 mg, 1.02 mmol) were reacted according to procedure A in a mixture of 1,4-dioxane (2.5 ml) and water (500 l). The reaction was stirred for 3 h at 100° C. The residue was purified by preparative HPLC to yield 6.30 mg (100% purity, 6% yield) of the title compound as a mixture of enantiomers.

LC-MS (method 1): $R^t$=1.68 min; MS (ESIpos): m/z=535 $[M+H]^+$ $^1$H-NMR (500 MHz, DMSO-$d_6$) δ [ppm]: 0.81 (d, 3H), 0.87 (d, 3H), 2.79-2.86 (m, 1H), 4.61 (br d, 2H), 5.19 (dd, 1H), 5.25 (t, 2H), 5.98-6.10 (m, 3H), 6.57 (d, 1H), 7.27 (d, 1H), 7.54 (d, 1H), 7.96 (d, 1H), 8.14 (dd, 1H), 8.23 (s, 1H), 8.30 (d, 1H), 8.61 (d, 1H), 8.65 (s, 1H), 8.96 (s, 1H).

Example II-49

5-[6-(Difluoromethoxy)pyridin-3-yl]-7-(1-{1-[6-(difluoromethyl)pyridin-3-yl]-2-methylpropyl}-1H-pyrazol-4-yl)[1,2,4]triazolo[1,5-a]pyridin-2-amine (mixture of enantiomers)

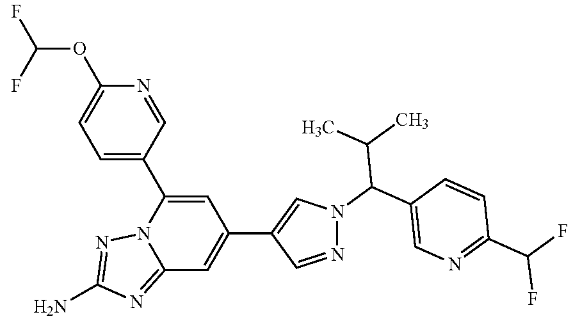 [SMILES: CC(C)C(c1ccc(C(F)F)nc1)n1cc(-c2cc(-c3ccc(OC(F)F)nc3)n3nc(N)nc3c2)cn1]

7-Chloro-5-[6-(difluoromethoxy)pyridin-3-yl][1,2,4]triazolo[1,5-a]pyridin-2-amine (90.0 mg, 289 μmol), 2-(difluoromethyl)-5-{2-methyl-1-[4-(4,4,5,5-tetramethyl-1,3,2-dioxaborolan-2-yl)-1H-pyrazol-1-yl]propyl}pyridine (140 mg, 86% purity, 318 μmol), 1,1'-bis(diphenylphosphino) ferrocene-palladium(II)dichloride dichloromethane complex (35.4 mg, 43.3 μmol) and sodium carbonate (153 mg, 1.44 mmol) were reacted according to procedure A in a mixture of water (500 μl) and 1,4-dioxane (3.0 ml). The reaction was stirred for 3 h at 90° C. The residue was purified by preparative HPLC to yield 90.0 mg (100% purity, 59% yield) of the title compound as a mixture of enantiomers.

LC-MS (method 1): $R^t$=1.89 min; MS (ESIpos): m/z=527 $[M+H]^+$ $^1$H-NMR (600 MHz, DMSO-$d_6$) δ [ppm]: 0.81 (d, 3H), 0.88 (d, 3H), 2.79-2.84 (m, 1H), 5.18 (d, 1H), 6.07 (s, 2H), 6.95 (t, 1H), 7.30 (d, 1H), 7.41 (d, 1H), 7.62 (s, 1H), 7.73 (d, 1H), 7.82 (t, 1H), 8.20 (d, 1H), 8.24 (s, 1H), 8.59 (dd, 1H), 8.69 (s, 1H), 8.86 (s, 1H), 8.90 (d, 1H).

Example II-50

5-[6-(Difluoromethoxy)pyridin-3-yl]-7-(1-f{1-[6-(difluoromethyl)pyridin-3-yl]-2-methylpropyl}-1H-pyrazol-4-yl)[1,2,4]triazolo[1,5-a]pyridin-2-amine (stereoisomer 1, distomer)

5-[6-(Difluoromethoxy)pyridin-3-yl]-7-(1-{1-[6-(difluoromethyl)pyridin-3-yl]-2-methylpropyl}-1H-pyrazol-4-yl)[1,2,4]triazolo[1,5-a]pyridin-2-amine (mixture of enantiomers) (90.0 mg, 100% 20 purity) was separated by chiral preparative HPLC to yield stereoisomer 1 (28 mg, 100% purity) and stereoisomer 2 (29 mg, 100% purity).

Column: Daicel Chiralpak IE, 5 m, 250×20 mm; Eluent A: n-heptane; Eluent B: ethanol; isocratic: 50% A+50% B; flow: 20 ml/min; UV: 220 nm; temperature: 50° C.

Stereoisomer 1: $R^t$=7.15 min and

Stereoisomer 2: $R^t$=13.28 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.88 min and

Stereoisomer 2: $R^t$=3.03 min (cf. next example)

LC-MS (method 1): $R^t$=1.89 min; MS (ESIpos): m/z=527 $[M+H]^+$

Example II-51

5-[6-(Difluoromethoxy)pyridin-3-yl]-7-(1-{1-[6-(difluoromethyl)pyridin-3-yl]-2-methylpropyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.90 min; MS (ESIpos): m/z=527 $[M+H]^+$ $^1$H-NMR (400 MHz, DMSO-$d_6$) δ [ppm]: 0.81 (d, 3H), 0.88 (d, 3H), 2.78-2.84 (m, 1H), 5.18 (d, 1H), 6.06 (s, 2H), 6.95 (t, 1H), 7.30 (d, 1H), 7.41 (d, 1H), 7.62 (d, 1H), 7.73 (d, 1H), 7.82 (t, 1H), 8.20 (dd, 1H), 8.23 (s, 1H), 8.58 (dd, 1H), 8.69 (s, 1H), 8.86 (d, 1H), 8.90 (d, 1H).

Example II-52

5-(6-Cyclopropylpyridin-3-yl)-7-(1-{1-[6-(difluoromethyl)pyridin-3-yl]-2-methylpropyl}-1H-pyrazol-4-yl)[1,2,4]triazolo[1,5-a]pyridin-2-amine (mixture of enantiomers)

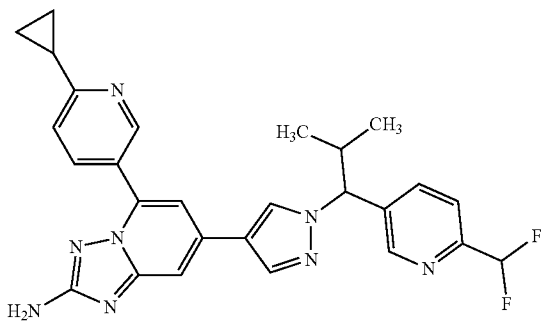 [SMILES: CC(C)C(c1ccc(C(F)F)nc1)n1cc(-c2cc(-c3ccc(C4CC4)nc3)n3nc(N)nc3c2)cn1]

7-Chloro-5-(6-cyclopropylpyridin-3-yl)[1,2,4]triazolo[1,5-a]pyridin-2-amine (90.0 mg, 84% purity, 266 μmol), 2-(difluoromethyl)-5-{2-methyl-1-[4-(4,4,5,5-tetramethyl-1,3,2-dioxaborolan-2-yl)-1H-pyrazol-1-yl]propyl}pyridine (129 mg, 86% purity, 292 μmol), 1,1'-bis(diphenylphosphino) ferrocene-palladium(II)dichloride dichloromethane complex (32.5 mg, 39.8 μmol) and sodium carbonate (141 mg, 1.33 mmol) were reacted according to procedure A in a mixture of 1,4-dioxane (3.0 ml) and water (500 1). The reaction was stirred for 3 h at 90° C. The residue was purified by column chromatography (Biotage® SNAP KP-NH 11 g cartridge, eluent: cyclohexane/ethyl acetate gradient 4:1 to 1:4) to yield 68.0 mg (100% purity, 51% yield) of the title compound as a mixture of enantiomers.

LC-MS (method 2): $R^t$=0.94 min; MS (ESIpos): m/z=501 $[M+H]^+$ $^1$H-NMR (600 MHz, DMSO-$d_6$) δ [ppm]: 0.81 (d, 3H), 0.87 (d, 3H), 0.99-1.06 (m, 4H), 2.16-2.25 (m, 1H), 2.78-2.82 (m, 1H), 5.18 (d, 1H), 6.02 (s, 2H), 6.95 (t, 1H), 7.36 (d, 1H), 7.48 (d, 1H), 7.59 (d, 1H), 7.73 (d, 1H), 8.20 (d, 1H), 8.22 (s, 1H), 8.30 (dd, 1H), 8.69 (s, 1H), 8.86 (s, 1H), 8.99 (d, 1H).

Example II-53

5-(6-Cyclopropylpyridin-3-yl)-7-(1-{1-[6-(difluoromethyl)pyridin-3-yl]-2-methylpropyl}-1H-pyrazol-4-yl)[1,2,4]triazolo[1,5-a]pyridin-2-amine (stereoisomer 1, distomer)

5-(6-Cyclopropylpyridin-3-yl)-7-(1-{1-[6-(difluoromethyl)pyridin-3-yl]-2-methylpropyl}-1H-pyrazol-4-yl)[1,2,4]triazolo[1,5-a]pyridin-2-amine (mixture of enantiomers) (68 mg, 100% purity) was separated by chiral preparative HPLC to yield stereoisomer 1 (15.2 mg, 100% purity) and stereoisomer 2 (14.5 mg, 100% purity).

Column: Chiralpak IE, 5 m, 250×20 mm; Eluent A: iso-hexane; Eluent B: ethanol+0.2% diethylamine; isocratic: 30% A+70% B; flow: 20 ml/min; UV: 220 nm; temperature: 40° C.

Stereoisomer 1: $R^t$=9.85 min and

Stereoisomer 2: $R^t$=13.45 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 20% A+80% B; flow: 1 ml/min; UV: 220 nm.

Stereoisomer 1: $R^t$=1.83 min and

Stereoisomer 2: $R^t$=2.28 min (cf. next example)

LC-MS (method 2): $R^t$=0.95 min; MS (ESIpos): m/z=501 $[M+H]^+$

Example II-54

5-(6-Cyclopropylpyridin-3-yl)-7-(1-{1-[6-(difluoromethyl)pyridin-3-yl]-2-methylpropyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 2): $R^t$=0.95 min; MS (ESIpos): m/z=501 $[M+H]^+$ $^1$H-NMR (400 MHz, DMSO-$d_6$) δ [ppm]: 0.81 (d, 3H), 0.87 (d, 3H), 0.98-1.07 (m, 4H), 2.16-2.24 (m, 1H), 2.74-2.87 (m, 1H), 5.17 (d, 1H), 6.01 (s, 2H), 6.94 (t, 1H), 7.36 (d, 1H), 7.48 (d, 1H), 7.58 (d, 1H), 7.73 (d, 1H), 8.19 (d, 1H), 8.22 (s, 1H), 8.30 (dd, 1H), 8.69 (s, 1H), 8.86 (d, 1H), 8.92-9.06 (m, 1H).

Example II-55

5-(6-Cyclopropylpyridin-3-yl)-7-(1-{1-[6-(trifluoromethyl)pyridin-3-yl]propyl}-1H-pyrazol-4-yl)[1,2,4]triazolo[1,5-a]pyridin-2-amine (mixture of enantiomers)

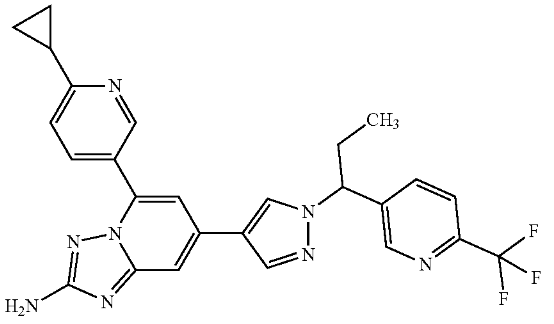 [SMILES: CCC(c1ccc(C(F)(F)F)nc1)n1cc(-c2cc(-c3ccc(C4CC4)nc3)n3nc(N)nc3c2)cn1]

7-Chloro-5-(6-cyclopropylpyridin-3-yl)[1,2,4]triazolo[1,5-a]pyridin-2-amine (75.0 mg, 262 μmol), 5-{1-[4-(4,4,5,5-tetramethyl-1,3,2-dioxaborolan-2-yl)-1H-pyrazol-1-yl]propyl}-2-(trifluoromethyl)pyridine (164 mg, 67% purity, 289 μmol), 1,1'-bis(diphenylphosphino)ferrocene-palladium(II) dichloride dichloromethane complex (32.2 mg, 39.4 μmol) and sodium carbonate (139 mg, 1.31 mmol) were reacted according to procedure A in a mixture of 1,4-dioxane (3.0 ml) and water (500 μl). The reaction was stirred for 3 h at 90° C. The reaction mixture was quenched with water filtered through a hydrophobic phase separation filter, washed with 15 ml of ethyl acetate and concentrated under reduced pressure. The residue was purified by preparative HPLC to yield 73.0 mg (94% purity, 52% yield) of the title compound as a racemic mixture.

LC-MS (method 1): $R^t$=1.81 min; MS (ESIpos): m/z=505 $[M+H]^+$ $^1$H-NMR (400 MHz, DMSO-$d_6$) δ [ppm]: 0.89 (t, 3H), 0.99-1.06 (m, 4H), 2.15-2.27 (m, 2H), 2.36-2.48 (m, 1H), 5.59 (dd, 1H), 6.04 (s, 2H), 7.40 (d, 1H), 7.48 (d, 1H), 7.62 (d, 1H), 7.93 (d, 1H), 8.04 (br d, 1H), 8.27 (s, 1H), 8.31 (dd, 1H), 8.74 (s, 1H), 8.82 (s, 1H), 9.00 (d, 1H).

Example II-56

5-(6-Cyclopropylpyridin-3-yl)-7-(1-{1-[6-(trifluoromethyl)pyridin-3-yl]propyl}-1H-pyrazol-4-yl)[1,2,4]triazolo[1,5-a]pyridin-2-amine (stereoisomer 1, distomer)

5-(6-Cyclopropylpyridin-3-yl)-7-(1-{1-[6-(trifluoromethyl)pyridin-3-yl]propyl}-1H-pyrazol-4-yl)[1,2,4]triazolo[1,5-a]pyridin-2-amine (mixture of enantiomers) (73 mg, 94% purity) was separated by chiral preparative HPLC to yield stereoisomer 1 (28 mg, 100% purity) and stereoisomer 2 (27.3 mg, 100% purity).

Column: Chiraltek OX-H, 5 μm, 250×20 mm; Eluent A: iso-hexane; Eluent B: ethanol+0.2% diethylamine; isocratic: 30% A+70% B; flow: 20 ml/min; UV: 210 nm; temperature: 50° C.

Stereoisomer 1: $R^t$=4.57 min and

Stereoisomer 2: $R^t$=6.44 min (cf. next example)

Analytical chiral HPLC method: Column: Daicel Chiraltek OX-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=3.65 min and

Stereoisomer 2: $R^t$=8.31 min (cf. next example)

LC-MS (method 1): $R^t$=1.81 min; MS (ESIpos): m/z=505 $[M+H]^+$

Example II-57

5-(6-Cyclopropylpyridin-3-yl)-7-(1-{1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.81 min; MS (ESIpos): m/z=505 $[M+H]^+$ $^1$H-NMR (400 MHz, DMSO-$d_6$) δ [ppm]: 0.89 (t, 3H), 0.99-1.07 (m, 4H), 2.17-2.27 (m, 2H), 2.37-2.48 (m, 1H), 5.58 (dd, 1H), 6.02 (s, 2H), 7.40 (d, 1H), 7.48 (d, 1H), 7.61 (d, 1H), 7.92 (d, 1H), 8.04 (dd, 1H), 8.26 (s, 1H), 8.31 (dd, 1H), 8.74 (s, 1H), 8.82 (d, 1H), 9.00 (d, 1H).

Example II-58

5-(6-Cyclopropylpyridin-3-yl)-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

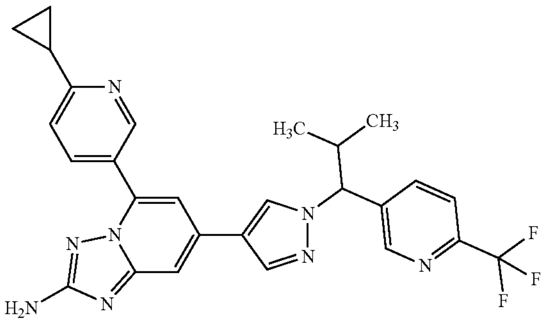 [SMILES: CC(C)C(c1ccc(C(F)(F)F)nc1)n1cc(-c2cc(-c3ccc(C4CC4)nc3)n3nc(N)nc3c2)cn1]

7-Chloro-5-(6-cyclopropylpyridin-3-yl)[1,2,4]triazolo[1,5-a]pyridin-2-amine (75.0 mg, 262 mol), 5-{2-methyl-1-[4-(4,4,5,5-tetramethyl-1,3,2-dioxaborolan-2-yl)-1H-pyrazol-1-yl]propyl}-2-(trifluoromethyl)pyridine (148 mg, 77% purity, 289 μmol), 1,1'-bis(diphenylphosphino)ferrocene-palladium(II)dichloride dichloromethane complex (32.2 mg, 39.4 μmol) and sodium carbonate (139 mg, 1.31 mmol) were reacted according to procedure A in a mixture of 1,4-dioxane (3.0 ml) and water (500 μl). The reaction was stirred for 3 h at 90° C. The residue was purified by preparative HPLC to yield 82.0 mg (91% purity, 55% yield) of the title compound as a mixture of enantiomers.

LC-MS (method 1): $R^t$=1.93 min; MS (ESIpos): m/z=519 $[M+H]^+$ $^1$H-NMR (600 MHz, DMSO-$d_6$) δ [ppm]: 0.82 (d, 3H), 0.88 (d, 3H), 0.99-1.06 (m, 4H), 2.18-2.24 (m, 1H), 2.80-2.84 (m, 1H), 5.25 (d, 1H), 6.03 (s, 2H), 7.37 (d, 1H), 7.48 (d, 1H), 7.60 (d, 1H), 7.95 (d, 1H), 8.25 (s, 1H), 8.26-8.32 (m, 2H), 8.70 (s, 1H), 8.96 (s, 1H), 8.99 (d, 1H).

Example II-59

5-(6-Cyclopropylpyridin-3-yl)-7-(1-{2-methyl-1-[6-(trifluoromethyl)pyridin-3-yl]propyl}-1H-pyrazol-4-yl)[1,2,4]triazolo[1,5-a]pyridin-2-amine (stereoisomers 1, distomer)

5-(6-Cyclopropylpyridin-3-yl)-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers) (82 mg, 91% purity) was separated by chiral preparative HPLC to yield stereoisomer 1 (28.5 mg, 100% purity) and stereoisomer 2 (28.2 mg, 100% purity).

Column: Chiraltek OX-H, 5 μm, 250×20 mm; Eluent A: iso-hexane; Eluent B: ethanol+0.2% diethylamine; isocratic: 30% A+70% B; flow: 20 ml/min; UV: 210 nm; temperature: 50° C.

Stereoisomer 1: $R^t$=7.04 min and

Stereoisomer 2: $R^t$=9.18 min (cf. next example)

Analytical chiral HPLC method: Column: Daicel Chiraltek OX-3, 3 m, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=2.58 min and

Stereoisomer 2: $R^t$=3.47 min (cf. next example)

LC-MS (method 1): $R^t$=1.98 min; MS (ESIpos): m/z=519 $[M+H]^+$

Example II-60

5-(6-Cyclopropylpyridin-3-yl)-7-(1-{2-methyl-1-[6-(trifluoromethyl)pyridin-3-yl]propyl}-1 H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.98 min; MS (ESIpos): m/z=519 $[M+H]^+$ $^1$H-NMR (400 MHz, DMSO-$d_6$) δ [ppm]: 0.82 (d, 3H), 0.88 (d, 3H), 0.97-1.08 (m, 4H), 2.17-2.24 (m, 1H), 2.79-2.85 (m, 1H), 5.25 (d, 1H), 6.02 (s, 2H), 7.36 (d, 1H), 7.48 (d, 1H), 7.59 (d, 1H), 7.95 (d, 1H), 8.24 (s, 1H), 8.27-8.32 (m, 2H), 8.70 (s, 1H), 8.95 (d, 1H), 8.99 (d, 1H).

Example II-61

7-(1-{1-[6-(Difluoromethyl)pyridin-3-yl]propyl}-1H-pyrazol-4-yl)-5-[6-(trifluoromethyl)pyridin-3-yl][1,2,4]triazolo[1,5-a]pyridin-2-amine (mixture of enantiomers)

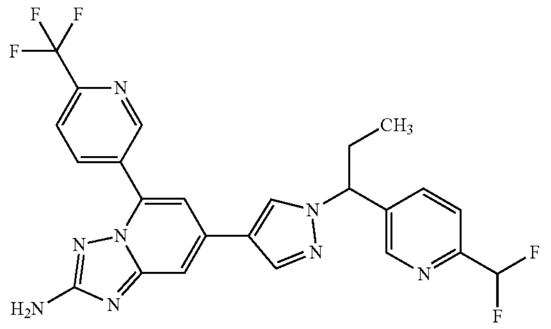 [SMILES: CCC(c1ccc(C(F)F)nc1)n1cc(-c2cc(-c3ccc(C(F)(F)F)nc3)n3nc(N)nc3c2)cn1]

7-Chloro-5-[6-(trifluoromethyl)pyridin-3-yl][1,2,4]triazolo[1,5-a]pyridin-2-amine (90.0 mg, 91% purity, 260 μmol), 2-(difluoromethyl)-5-{1-[4-(4,4,5,5-tetramethyl-1,3,2-dioxaborolan-2-yl)-1H-pyrazol-1-yl]propyl}pyridine (116 mg, 90% purity, 286 μmol), 1,1'-bis(diphenylphosphino)ferrocene-palladium(II)dichloride dichloromethane complex (31.9 mg, 39.0 μmol) and sodium carbonate (138 mg, 1.30 mmol) were reacted according to procedure A in a mixture of 1,4-dioxane (3.0 ml) and water (500 μl). The reaction was stirred for 3 h at 90° C. 2-(Difluoromethyl)-5-{1-[4-(4,4,5,5-tetramethyl-1,3,2-dioxaborolan-2-yl)-1H-pyrazol-1-yl]propyl}pyridine (50.0 mg) and 1,1'-bis(diphenylphosphino)ferrocene-palladium(II)dichloride dichloromethane complex (15.0 mg) were added and the reaction was further stirred for 1 h at 90° C. The residue was purified via column chromatography (Biotage® SNAP KP-NH 11 g cartridge, eluent: cyclohexane/ethyl acetate gradient 4:1 to 1:4) to yield 64.0 mg (100% purity, 48% yield) of the title compound as a mixture of enantiomers.

LC-MS (method 2): $R^t$=0.97 min; MS (ESIpos): m/z=515 $[M+H]^+$ $^1$H-NMR (600 MHz, DMSO-$d_6$) δ [ppm]: 0.88 (t, 3H), 2.21-2.24 (m, 1H), 2.39-2.44 (m, 1H), 5.54 (dd, 1H), 6.11 (s, 2H), 6.94 (t, 1H), 7.56 (d, 1H), 7.72 (dd, 2H), 7.97 (dd, 1H), 8.13 (d, 1H), 8.27 (s, 1H), 8.71-8.74 (m, 2H), 8.76 (dd, 1H), 9.36 (s, 1H).

Example II-62

7-(1-{1-[6-(Difluoromethyl)pyridin-3-yl]propyl}-1H-pyrazol-4-yl)-5-[6-(trifluoromethyl)pyridin-3-yl][1,2,4]triazolo[1,5-a]pyridin-2-amine (stereoisomer 1, distomer)

7-(1-{1-[6-(Difluoromethyl)pyridin-3-yl]propyl}-1H-pyrazol-4-yl)-5-[6-(trifluoromethyl)pyridin-3-yl][1,2,4]triazolo[1,5-a]pyridin-2-amine (mixture of enantiomers) (64 mg, 100% purity) was separated by chiral preparative HPLC to yield stereoisomer 1 (18 mg, 100% purity) and stereoisomer 2 (17.6 mg, 100% purity)., Column: Daicel Chiralcel OX-H, 5 μm, 250×20 mm; Eluent A: n-heptane; Eluent B:

ethanol+0.2% diethylamine; isocratic: 50% A+50% B; flow: 30 ml/min; UV: 220 nm; temperature: 40° C.

Stereoisomer 1: $R^t$=8.79 min and

Stereoisomer 2: $R^t$=11.80 min (cf. next example)

Analytical chiral HPLC method: Column: Daicel Chiraltek OX-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=1.48 min and

Stereoisomer 2: $R^t$=2.16 min (cf. next example)

Example II-63

7-(1-{1-[6-(Difluoromethyl)pyridin-3-yl]propyl}-1H-pyrazol-4-yl)-5-[6-(trifluoromethyl)pyridin-3-yl][1,2,4]triazolo[1,5-a]pyridin-2-amine (stereoisomer 2, eutomer)

The product was isolated in the previous example as second stereoisomer.

LC-MS (method 1): $R^t$=1.79 min; MS (ESIpos): m/z=515 $[M+H]^+$ $^1$H-NMR (400 MHz, DMSO-$d_6$) δ [ppm]: 0.88 (t, 3H), 2.16-2.27 (m, 1H), 2.37-2.48 (m, 1H), 5.54 (dd, 1H), 6.11 (s, 2H), 6.94 (t, 1H), 7.56 (d, 1H), 7.69-7.73 (m, 2H), 7.97 (dd, 1H), 8.13 (d, 1H), 8.26 (s, 1H), 8.71-8.78 (m, 3H), 9.36 (d, 1H).

Example 1H-64

7-(1-{1-[6-(Difluoromethyl)pyridin-3-yl]-2-methylpropyl}-1H-pyrazol-4-yl)-5-[6-(trifluoromethyl)pyridin-3-yl][1,2,4]triazolo[1,5-a]pyridin-2-amine (mixture of enantiomers)

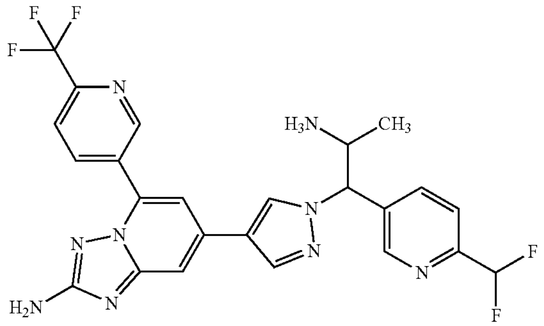 [SMILES: CC(N)C(c1ccc(C(F)F)nc1)n1cc(-c2cc(-c3ccc(C(F)(F)F)nc3)n3nc(N)nc3c2)cn1]

7-Chloro-5-[6-(trifluoromethyl)pyridin-3-yl][1,2,4]triazolo[1,5-a]pyridin-2-amine (90.0 mg, 98% purity, 280 μmol), 2-(difluoromethyl)-5-{2-methyl-1-[4-(4,4,5,5-tetramethyl-1,3,2-dioxaborolan-2-yl)-1H-pyrazol-1-yl]propyl}pyridine (136 mg, 86% purity, 308 μmol), 1,1'-bis(diphenylphosphino)ferrocene-palladium(II)dichloride dichloromethane complex (34.3 mg, 42.0 μmol) and sodium carbonate (149 mg, 1.40 mmol) were reacted according to procedure A in a mixture of 1,4-dioxane (3.0 ml) and water (500 μl). The reaction was stirred for 3 h at 90° C. The residue was purified by preparative HPLC to yield 88.0 mg (100% purity, 59% yield) of the title compound as a mixture of enantiomers.

LC-MS (method 1): $R^t$=1.90 min; MS (ESIpos): m/z=529 $[M+H]^+$ $^1$H-NMR (400 MHz, DMSO-$d_6$) δ [ppm]: 0.82 (d, 3H), 0.88 (d, 3H), 2.78-2.84 (m, 1H), 5.20 (d, 1H), 6.11 (s, 2H), 6.95 (t, 1H), 7.58 (d, 1H), 7.71 (s, 1H), 7.74 (d, 1H), 8.14 (d, 1H), 8.20 (dd, 1H), 8.26 (s, 1H), 8.72 (s, 1H), 8.75 (d, 1H), 8.86 (d, 1H), 9.35 (d, 1H).

Example II-65

7-(1-{1-[6-(Difluoromethyl)pyridin-3-yl]-2-methylpropyl}-1H-pyrazol-4-yl)-5-[6-(trifluoromethyl)pyridin-3-yl][1,2,4]triazolo[1,5-a]pyridin-2-amine (stereoisomer 1, distomer)

7-(1-{1-[6-(Difluoromethyl)pyridin-3-yl]-2-methylpropyl}-1H-pyrazol-4-yl)-5-[6-(trifluoromethyl)pyridin-3-yl][1,2,4]triazolo[1,5-a]pyridin-2-amine (mixture of enantiomers) (88.0 mg, 100% purity) was separated by chiral preparative HPLC to yield stereoisomer 1 (19.6 mg, 100% purity) and stereoisomer 2 (20.5 mg, 100% purity).

Column: Daicel Chiralcel OZ-H, 5 μm, 250×20 mm; Eluent A: n-heptane; Eluent B: ethanol+0.2% diethylamine; isocratic: 20% A+80% B; flow: 20 ml/min; UV: 220 nm; temperature: 40° C.

Stereoisomer 1: $R^t$=4.37 min and

Stereoisomer 2: $R^t$=6.13 min (cf. next example)

Analytical chiral HPLC method: Column: Daicel Chiralpak OZ-3, 3 μm, 50×4.6 mm; Eluent A: n-heptane; Eluent B: ethanol+0.2% diethylamine; isocratic: 20% A+80% B; flow: 1 ml/min; UV: 220 nm.

Stereoisomer 1: $R^t$=0.98 min and

Stereoisomer 2: $R^t$=1.42 min (cf. next example)

LC-MS (method 1): $R^t$=1.89 min; MS (ESIpos): m/z=529 $[M+H]^+$

Example II-66

7-(1-{1-[6-(Difluoromethyl)pyridin-3-yl]-2-methylpropyl}-1 H-pyrazol-4-yl)-5-[6-(trifluoromethyl)pyridin-3-yl][1,2,4]triazolo[1,5-a]pyridin-2-amine (stereoisomer 2, eutomer)

The product was isolated in the previous example as second stereoisomer.

LC-MS (method 1): $R^t$=1.89 min; MS (ESIpos): m/z=529 $[M+H]^+$ $^1$H-NMR (400 MHz, DMSO-$d_6$) δ [ppm]: 0.81 (d, 3H), 0.88 (d, 3H), 2.78-2.84 (m, 1H), 5.19 (d, 1H), 6.10 (s, 2H), 6.95 (s, 1H), 7.53 (d, 1H), 7.69 (s, 1H), 7.73 (d, 1H), 8.13 (d, 1H), 8.20 (dd, 1H), 8.25 (s, 1H), 8.70 (s, 1H), 8.75 (d, 1H), 8.86 (d, 1H), 9.35 (d, 1H).

Example II-67

5-(6-Cyclopropylpyridin-3-yl)-7-(1-{1-[6-(difluoromethyl)pyridin-3-yl]propyl}-1H-pyrazol-4-yl)[1,2,4]triazolo[1,5-a]pyridin-2-amine (mixture of enantiomers)

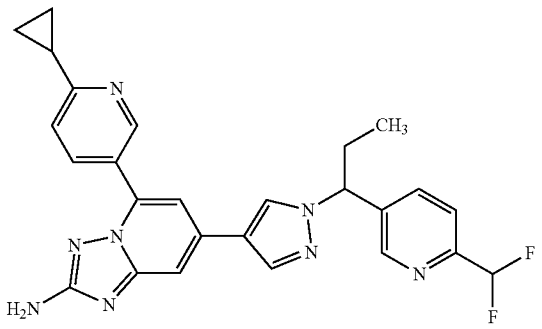 [SMILES: CCC(c1ccc(C(F)F)nc1)n1cc(-c2cc(-c3ccc(C4CC4)nc3)n3nc(N)nc3c2)cn1]

7-Chloro-5-(6-cyclopropylpyridin-3-yl)[1,2,4]triazolo[1,5-a]pyridin-2-amine (90.0 mg, 84% purity, 266 μmol), 2-(difluoromethyl)-5-{1-[4-(4,4,5,5-tetramethyl-1,3,2-dioxaborolan-2-yl)-1H-pyrazol-1-yl]propyl}pyridine (118 mg, 90% purity, 292 μmol), 1,1'-bis(diphenylphosphino)ferrocene-palladium(II)dichloride dichloromethane complex (32.5 mg, 39.8 μmol) and sodium carbonate (141 mg, 1.33 mmol) were reacted according to procedure A in a mixture of 1,4-dioxane (3.0 ml) and water (500 μl). The reaction was stirred for 3 h at 90° C. The residue was purified by preparative HPLC to yield 76.0 mg (100% purity, 59% yield) of the title compound as a mixture of enantiomers.

LC-MS (method 1): $R^t$=1.65 min; MS (ESIpos): m/z=487 $[M+H]^+$ $^1$H-NMR (400 MHz, DMSO-$d_6$) δ [ppm]: 0.88 (t, 3H), 0.99-1.07 (m, 4H), 2.16-2.26 (m, 2H), 2.37-2.48 (m, 1H), 5.53 (dd, 1H), 6.10 (s, 2H), 6.94 (t, 1H), 7.46 (d, 1H), 7.49 (d, 1H), 7.63 (d, 1H), 7.71 (d, 1H), 7.97 (dd, 1H), 8.26 (s, 1H), 8.31 (dd, 1H), 8.72 (s, 1H), 8.75 (s, 1H), 9.00 (d, 1H).

Example II-68

5-(6-Cyclopropylpyridin-3-yl)-7-(1-{1-[6-(difluoromethyl)pyridin-3-yl]propyl}-1H-pyrazol-4-yl)[1,2,4]triazolo[1,5-a]pyridin-2-amine (stereoisomer 1, distomer)

5-(6-Cyclopropylpyridin-3-yl)-7-(1-{1-[6-(difluoromethyl)pyridin-3-yl]propyl}-1H-pyrazol-4-yl)[1,2,4]triazolo[1,5-a]pyridin-2-amine (mixture of enantiomers) (76 mg, 100% purity) was separated by chiral preparative HPLC to yield stereoisomer 1 (15.7 mg, 98% purity) and stereoisomer 2 (15.5 mg, 98% purity).

Column: Daicel Chiralpak OX, 5 μm, 250×20 mm; Eluent A: n-heptane; Eluent B: ethanol+0.2% diethylamine; isocratic: 0% A+100% B; flow: 25 ml/min; UV: 220 nm; temperature: 40° C.

Stereoisomer 1: $R^t$=10.72 min and

Stereoisomer 2: $R^t$=14.27 min (cf. next example)

Analytical chiral HPLC method: Column: Daicel Chiralpak OX-3, 3 μm, 50×4.6 mm; Eluent A: n-heptane; Eluent B: ethanol; isocratic: 0% A+100% B; flow: 1 ml/min; UV: 220 nm.

Stereoisomer 1: $R^t$=1.29 min and

Stereoisomer 2: $R^t$=1.70 min (cf. next example)

LC-MS (method 1): $R^t$=1.73 min; MS (ESIpos): m/z=487 $[M+H]^+$

Example II-69

5-(6-Cyclopropylpyridin-3-yl)-7-(1-{1-[6-(difluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.73 min; MS (ESIpos): m/z=487 $[M+H]^+$ $^1$H-NMR (400 MHz, DMSO-$d_6$) δ [ppm]: 0.82-0.93 (m, 3H), 0.95-1.13 (m, 4H), 2.16-2.27 (m, 2H), 2.37-2.48 (m, 1H), 5.52 (dd, 1H), 6.02 (s, 2H), 6.94 (t, 1H), 7.39 (d, 1H), 7.48 (d, 1H), 7.61 (d, 1H), 7.71 (d, 1H), 7.97 (dd, 1H), 8.24 (s, 1H), 8.31 (dd, 1H), 8.73 (br s, 2H), 9.00 (s, 1H).

Example II-70

5-[6-(Difluoromethyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

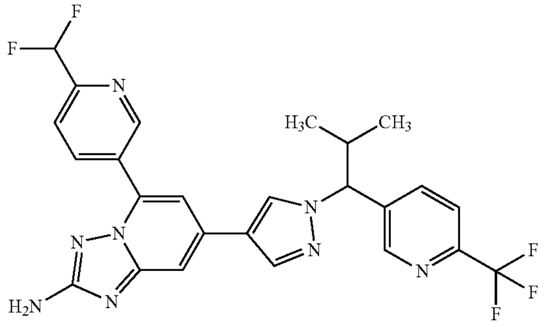 [SMILES: CC(C)C(c1ccc(C(F)(F)F)nc1)n1cc(-c2cc(-c3ccc(C(F)F)nc3)n3nc(N)nc3c2)cn1]

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (100 mg, 96% purity, 220 μmol), 2-(difluoromethyl)-5-(4,4,5,5-tetramethyl-1,3,2-dioxaborolan-2-yl)pyridine (84.3 mg, 80% purity, 264 μmol), XPhos-Pd-G2 (13.0 mg, 16.5 μmol) and caesium carbonate (359 mg, 1.10 mmol) were reacted according to procedure A in a mixture of 1,4-dioxane (3.5 ml) and water (500 μl). The reaction was stirred for 3 h at 90° C. The residue was purified by preparative HPLC to yield 98.0 mg (100% purity, 84% yield) of the title compound as a mixture of enantiomers.

LC-MS (method 1): $R^t$=1.99 min; MS (ESIpos): m/z=529 $[M+H]^+$ $^1$H-NMR (400 MHz, DMSO-$d_6$) δ [ppm]: 0.82 (d, 3H), 0.89 (d, 3H), 2.79-2.85 (m, 1H), 5.26 (d, 1H), 6.08 (s, 2H), 7.07 (t, 1H), 7.49 (d, 1H), 7.67 (d, 1H), 7.90 (d, 1H), 7.95 (d, 1H), 8.26 (s, 1H), 8.29 (d, 1H), 8.65 (dd, 1H), 8.71 (s, 1H), 8.96 (s, 1H), 9.26 (d, 1H).

Example II-71

5-[6-(Difluoromethyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (stereoisomers 1, distomer)

5-[6-(Difluoromethyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers) (98.0 mg, 100% purity) was separated by chiral preparative HPLC to yield stereoisomer 1 (26.6 mg, 100% purity) and stereoisomer 2 (27.1 mg, 100% purity).

Column: Chriralcel OZ-H, 5 μm, 250×20 mm; Eluent A: n-heptane; Eluent B: ethanol+0.2% diethylamine; isocratic: 50% A+50% B; flow: 20 ml/min; UV: 210 nm; temperature: 40° C.

Stereoisomer 1: $R^t$=5.00 min and

Stereoisomer 2: $R^t$=9.31 min (cf. next example)

Analytical chiral HPLC method: Column: Daicel Chiralpak OZ-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.22 min and

Stereoisomer 2: $R^t$=2.61 min (cf. next example)

LC-MS (method 2): $R^t$=1.00 min; MS (ESIpos): m/z=529 $[M+H]^+$

Example II-72

5-[6-(Difluoromethyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 2): $R^t$=1.00 min; MS (ESIpos): m/z=529 $[M+H]^+$ $^1$H-NMR (400 MHz, DMSO-$d_6$) δ [ppm]: 0.82 (d, 3H), 0.88 (d, 3H), 2.80-2.85 (m, 2H), 5.26 (d, 1H), 6.08 (s, 2H), 7.07 (t, 1H), 7.49 (d, 1H), 7.67 (d, 1H), 7.90 (d, 1H), 7.95 (d, 1H), 8.26 (s, 1H), 8.29 (d, 1H), 8.65 (dd, 1H), 8.70 (s, 1H), 8.96 (s, 1H), 9.26 (d, 1H).

Example II-73

5-[6-(3,3-Difluorocyclobutyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

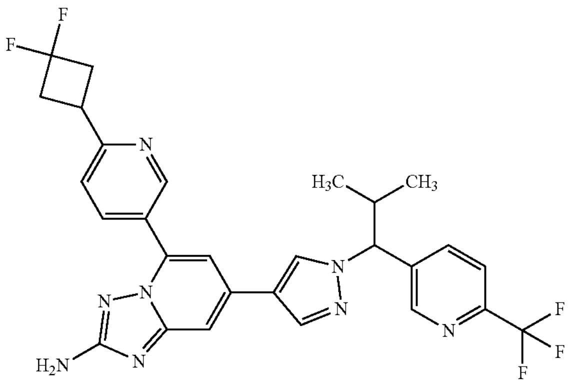 [SMILES: CC(C)C(c1ccc(C(F)(F)F)nc1)n1cc(-c2cc(-c3ccc(C4CC(F)(F)C4)nc3)n3nc(N)nc3c2)cn1]

4-yl)[1,2,4]triazolo[1,5-a]pyridin-2-amine (150 mg, 96% purity, 330 μmol), 2-(3,3-difluorocyclobutyl)-5-(4,4,5,5-tetramethyl-1,3,2-dioxaborolan-2-yl)pyridine (117 mg, 396 μmol), XPhos-Pd-G2 (13.0 mg, 16.5 μmol) and caesium carbonate (323 mg, 991 μmol) were reacted according to procedure A in a mixture of 1,4-dioxane (4.5 ml) and water (1.5 ml). The reaction was stirred for 3 h at 90° C. The residue was purified by preparative HPLC to yield 164 mg (94% purity, 82% yield) of the title compound as a mixture of enantiomers.

LC-MS (method 2): $R^t$=1.04 min; MS (ESIpos): m/z=569 $[M+H]^+$ $^1$H-NMR (400 MHz, DMSO-$d_6$) δ [ppm]: 0.82 (d, 3H), 0.89 (d, 3H), 2.80-2.91 (m, 1H), 2.88-3.05 (m, 4H), 3.65 (quind, 1H), 5.25 (d, 1H), 6.04 (s, 2H), 7.41 (d, 1H), 7.55 (d, 1H), 7.62 (d, 1H), 7.95 (d, 1H), 8.25 (s, 1H), 8.29 (d, 1H), 8.40 (dd, 1H), 8.70 (s, 1H), 8.96 (s, 1H), 9.16 (d, 1H).

Example II-74

5-[6-(3,3-Difluorocyclobutyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (stereoisomer 1, distomer)

5-[6-(3,3-Difluorocyclobutyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (134 mg, 94% purity) was separated by chiral preparative HPLC to yield stereoisomer 1 (47.5 mg, 100% purity) and stereoisomer 2 (47.4 mg, 100% purity).

Column: Daicel Chiralcel OZ-H, 5 μm, 250×20 mm; Eluent A: n-heptane; Eluent B: ethanol+0.2% diethylamine; isocratic: 50% A+50% B; flow: 20 ml/min; UV: 220 nm; temperature: 40° C.

Stereoisomer 1: $R^t$=5.96 min and

Stereoisomer 2: $R^t$=11.19 min (cf. next example)

Analytical chiral HPLC method: Column: Daicel Chiralpak OX-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.20 min and

Stereoisomer 2: $R^t$=1.51 min (cf. next example)

LC-MS (method 1): $R^t$=2.03 min; MS (ESIpos): m/z=569 $[M+H]^+$

Example 1-75

5-[6-(3,3-Difluorocyclobutyl)pyridin-3-yl]-7-(1-{2-methyl-1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=2.03 min; MS (ESIpos): m/z=569 $[M+H]^+$ $^1$H-NMR (400 MHz, DMSO-$d_6$) δ [ppm]: 0.82 (d, 3H), 0.88 (d, 3H), 2.79-2.84 (m, 1H), 2.88-3.05 (m, 4H), 3.65 (quind, 1H), 5.25 (d, 1H), 6.03 (s, 2H), 7.41 (d, 1H), 7.55 (d, 1H), 7.62 (d, 1H), 7.95 (d, 1H), 8.25 (s, 1H), 8.29 (d, 1H), 8.40 (dd, 1H), 8.70 (s, 1H), 8.96 (s, 1H), 9.16 (d, 1H).

Example II-76

7-(1-{[6-(Difluoromethyl)pyridin-3-yl](tetrahydro-2H-pyran-4-yl)methyl}-1H-pyrazol-4-yl)-5-[6-(trifluoromethyl)pyridin-3-yl][1,2,4]triazolo[1,5-a]pyridin-2-amine (mixture of enantiomers)

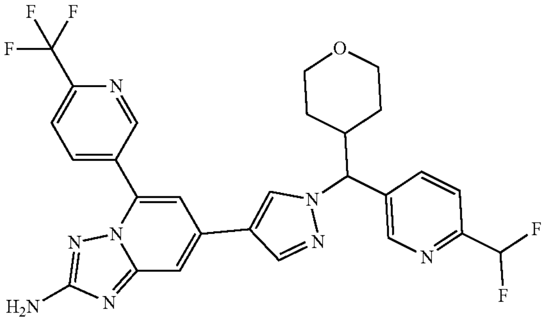 [SMILES: Nc1nc2cc(-c3cnn(C(c4ccc(C(F)F)nc4)C4CCOCC4)c3)cc(-c3ccc(C(F)(F)F)nc3)n2n1]

7-Chloro-5-[6-(trifluoromethyl)pyridin-3-yl][1,2,4]triazolo[1,5-a]pyridin-2-amine (153 mg, 488 μmol), 2-(difluoromethyl)-5-{tetrahydro-2H-pyran-4-yl[4-(4,4,5,5-tetramethyl-1,3,2-dioxaborolan-2-yl)-1H-pyrazol-1-yl] methyl}pyridine (225 mg, 537 μmol), 1,1'-bis (diphenylphosphino)ferrocene-palladium(II)dichloride dichloromethane complex (39.8 mg, 48.8 μmol) and sodium carbonate (258 mg, 2.44 mmol) were reacted according to procedure A in a mixture of 1,4-dioxane (6.0 ml) and water (2.0 ml). After stirring for 3 h at 90° C., the reaction was quenched with water and extracted with dichloromethane. The organic layer was dried over anhydrous anhydrous sodium sulfate, filtered and concentrated. The residue was purified via column chromatography (Biotage® SNAP KP-NH 11 g cartridge, eluent cyclohexane/ethyl acetate gradient 4:1 to 1:4) to yield 197 mg (99% purity, 70% yield) of the title compound as a mixture of enantiomers.

LC-MS (method 1): $R^t$=1.70 min; MS (ESIpos): m/z=571 $[M+H]^+$ $^1$H-NMR (400 MHz, DMSO-$d_6$) δ [ppm]: 1.00-1.40 (m, 4H), 2.67-2.79 (m, 1H), 3.23-3.30 (m, 2H), 3.78-3.88 (m, 2H), 5.34 (d, 1H), 6.11 (s, 2H), 6.95 (t, 1H), 7.53 (d, 1H), 7.69 (d, 1H), 7.74 (d, 1H), 8.13 (d, 1H), 8.22 (dd, 1H), 8.27 (s, 1H), 8.70 (s, 1H), 8.75 (dd, 1H), 8.88 (br s, 1H), 9.35 (br s, 1H).

Example II-77 7-(1-{[6-(Difluoromethyl)pyridin-3-yl](tetrahydro-2H-pyran-4-yl)methyl}-1H-pyrazol-4-yl)-5-[6-(trifluoromethyl)pyridin-3-yl][1,2,4]triazolo [1,5-a]pyridin-2-amine (stereoisomer 1, distomer)

7-(1-{[6-(Difluoromethyl)pyridin-3-yl](tetrahydro-2H-pyran-4-yl)methyl}-1H-pyrazol-4-yl)-5-[6-(trifluoromethyl)pyridin-3-yl][1,2,4]triazolo[1,5-a]pyridin-2-amine (mixture of enantiomers) (197 mg, 99% purity) was separated by chiral preparative SFC to yield enantiomer 1 (64.9 mg, 99% purity) and stereoisomer 2 (65.7 mg, 99% purity).

Instrument: THAR SFC-Super Chrom Prep 200; Column: Daicel Chiralcel OZ-H, 5 m, 250×20 mm; Eluent A: $CO_2$; Eluent B: methanol; isocratic: 65% A+35% B; flow: 80 ml/min; UV: 210 nm, temperature: 40° C.

Analytical SFC-method: Column: Daicel OZ-H, 5 m 50×4.6 mm; Eluent A: $CO_2$; Eluent B: methanol; isocratic: 70% A+30% B; flow: 3 ml/min; UV: 210 nm; temperature 40° C.

Stereoisomer 1: $R^t$=3.62 min and

Stereoisomer 2: $R^t$=5.98 min (cf. next example)

LC-MS (method 1): $R^t$=1.69 min; MS (ESIpos): m/z=571 $[M+H]^+$

Example II-78

7-(1-{[6-(Difluoromethyl)pyridin-3-yl](tetrahydro-2H-pyran-4-yl)methyl}-1H-pyrazol-4-yl)-5-[6-(trifluoromethyl)pyridin-3-yl][1,2,4]triazolo[1,5-a]pyridin-2-amine (stereoisomer 2, eutomer)

The product was isolated in the previous example as second stereoisomer. Stereoisomer 1: The stereochemical configuration of the methine carbon atom bonded to the pyrazole was (R).

LC-MS (method 1): $R^t$=1.69 min; MS (ESIpos): m/z=571 $[M+H]^+$ $^1$H-NMR (400 MHz, DMSO-$d_6$) δ [ppm]: 0.96-1.40 (m, 4H), 2.68-2.79 (m, 1H), 3.23-3.30 (m, 2H), 3.78-3.88 (m, 2H), 5.34 (d, 1H), 6.11 (s, 2H), 6.95 (t, 1H), 7.16-7.27 (m, 1H), 7.53 (d, 1H), 7.69 (d, 1H), 7.74 (d, 1H), 8.13 (d, 1H), 8.22 (dd, 1H), 8.27 (s, 1H), 8.69 (s, 1H), 8.75 (dd, 1H), 8.87 (br s, 1H), 9.35 (br s, 1H).

Example II-79

7-(1-{2-Methyl-1-[6-(trifluoromethyl)pyridin-3-yl] propyl}-1H-pyrazol-4-yl)-5-[6-(pyrrolidin-1-yl)pyridin-3-yl][1,2,4]triazolo[1,5-a]pyridin-2-amine (mixture of enantiomers)

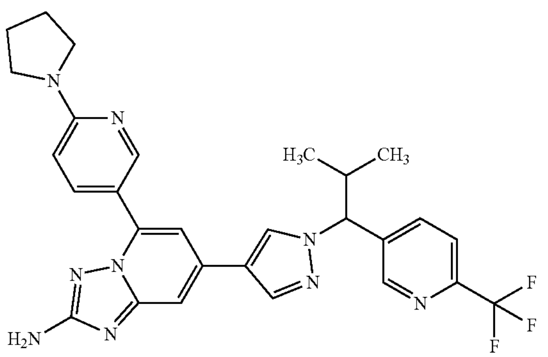 [SMILES: CC(C)C(c1ccc(C(F)(F)F)nc1)n1cc(-c2cc(-c3ccc(N4CCCC4)nc3)n3nc(N)nc3c2)cn1]

5-Chloro-7-(1-{2-methyl-1-[6-(trifluoromethyl)pyridin-3-yl]propyl}-1 H-pyrazol-4-yl)[1,2,4]triazolo[1,5-a]pyridin-2-amine (168 mg, 385 μmol), 2-(pyrrolidin-1-yl)-5-(4,4,5,5-tetramethyl-1,3,2-dioxaborolan-2-yl)pyridine (137 mg, 501 μmol), XPhos-Pd-G2 (22.7 mg, 28.9 μmol) and sodium carbonate (204 mg, 1.93 mmol) were reacted according to procedure A in a mixture of water (800 1) and 1,4-dioxane (2.4 ml). After stirring for 3 h at 90° C., the reaction was quenched with water and extracted with dichloromethane. The organic layer was dried over anhydrous sodium sulfate, filtered and concentrated. The residue was purified via column chromatography (Biotage® SNAP KP-NH 11 g cartridge, eluent: cyclohexane/ethyl acetate gradient 4:1 to 1:4) to yield 40.0 mg (99% purity, 19% yield) of the title compound as a mixture of enantiomers.

LC-MS (method 2): $R^t$=0.79 min; MS (ESIpos): m/z=548 $[M+H]^+$ $^1$H-NMR (600 MHz, DMSO-$d_6$) δ [ppm]: 0.82 (d, 3H), 0.88 (d, 3H), 2.00-2.07 (m, 4H), 2.86 (dq, 1H), 5.29 (d, 1H), 6.51 (s, 2H), 6.86-7.04 (m, 1H), 7.55 (s, 1H), 7.62 (s, 1H), 7.96 (d, 1H), 8.30 (s, 1H), 8.31 (d, 2H), 8.41 (br d, 1H), 8.77 (s, 1H), 8.82 (d, 1H), 8.97 (s, 1H).

Example II-80

1-{5-[2-Amino-7-(1-{2-methyl-1-[6-(trifluoromethyl)pyridin-3-yl]propyl}-1 H-pyrazol-4-yl)[1,2,4]triazolo[1,5-a]pyridin-5-yl]pyridin-2-yl}cyclobutan-1-ol (mixture of enantiomers)

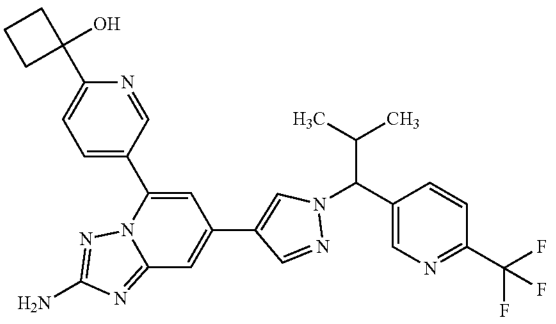 [SMILES: CC(C)C(c1ccc(C(F)(F)F)nc1)n1cc(-c2cc(-c3ccc(C4(O)CCC4)nc3)n3nc(N)nc3c2)cn1]

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (318 mg, 729 μmol)), 1-[5-(4,4,5,5-tetramethyl-1,3,2-dioxaborolan-2-yl)pyridin-2-yl]cyclobutan-1-ol (301 mg, 1.09 mmol), XPhos-Pd-G2 (28.7 mg, 36.5 μmol) and caesium carbonate (713 mg, 2.19 mmol) were reacted according to procedure A in a mixture of water (1.0 ml) and 1,4-dioxane (3.0 ml). After stirring for 2.5 h at 90° C., XPhos-Pd-G2 (57.4 mg, 72.9 μmol) were added and the reaction was further stirred for 2.5 h at 90° C. The reaction was quenched with water and extracted with dichloromethane. The organic layer was dried over anhydrous sodium sulfate, filtered and concentrated. The residue was purified by column chromatography (Biotage® SNAP KP-NH 28 g cartridge, eluent: cyclohexane/ethyl acetate gradient 1:1 to 0:1) to yield 290 mg (100% purity, 73% yield) of the title compound as a mixture of enantiomers.

LC-MS (method 1): $R^t$=1.79 min; MS (ESIpos): m/z=549 $[M+H]^+$ $^1$H-NMR (500 MHz, $CDCl_3$) S [ppm]: 0.91 (d, 3H), 0.97 (d, 3H), 1.86-2.05 (m, 2H), 2.05-2.21 (m, 2H), 2.28 (br d, 1H), 2.52-2.65 (m, 4H), 2.87 (dt, 1H), 4.73-4.93 (m, 3H), 7.05 (d, 1H), 7.49 (s, 1H), 7.71 (d, 1H), 7.77 (d, 1H), 7.88 (s, 1H), 7.94 (s, 1H), 8.18 (br d, 1H), 8.41 (dd, 1H), 8.82 (s, 1H), 8.99 (s, 1H).

Example II-81

1-{5-[2-Amino-7-(1-{2-methyl-1-[6-(trifluoromethyl)pyridin-3-yl]propyl}-1H-pyrazol-4-yl)[1,2,4]triazolo[1,5-a]pyridin-5-yl]pyridin-2-yl}cyclobutan-1-ol (stereoisomer 1, eutomer)

1-{5-[2-Amino-7-(1-{2-methyl-1-[6-(trifluoromethyl)pyridin-3-yl]propyl}-1H-pyrazol-4-yl)[1,2,4]triazolo[1,5-a]pyridin-5-yl]pyridin-2-yl}cyclobutan-1-ol (237 mg, 100% purity) was separated by chiral preparative HPLC to yield stereoisomer 1 (98.0 mg, 100% purity) and stereoisomer 2 (99.0 mg, 100% purity).

Instrument: Agilent Prep 100; Column: Chiralpak IE, 5 μm, 250×20 mm; Eluent A: n-heptane;

Eluent B: ethanol+0.2% diethylamine; isocratic: 0% A+100% B; flow: 15 ml/min; UV: 220 nm; temperature: 50° C.

Stereoisomer 1: $R^t$=8.58 min and

Stereoisomer 2: $R^t$=10.21 min (cf. next example)

Analytical chiral HPLC method: Column: Daicel Chiralpak IG, 5 μm, 250×4.6 mm; Eluent A: n-heptane; Eluent B: ethanol+0.2% diethylamine; isocratic: 0% A+100% B; flow: 1 ml/min; UV: 220 nm, temperature: 50° C.

Stereoisomer 1: $R^t$=7.04 min and

Stereoisomer 2: $R^t$=8.71 min (cf. next example)

Stereoisomer 1: The stereochemical configuration of the methine carbon atom bonded to the pyrazole was (R).

LC-MS (method 1): $R^t$=1.79 min; MS (ESIpos): m/z=549 $[M+H]^+$ $^1$H-NMR (400 MHz, DMSO-$d_6$) δ [ppm]: 0.82 (d, 3H), 0.89 (d, 3H), 1.84-2.00 (m, 2H), 2.25-2.34 (m, 2H), 2.53-2.64 (m, 2H), 2.79-2.85 (m, 1H), 5.25 (d, 1H), 5.87 (s, 1H), 6.04 (s, 2H), 7.42 (d, 1H), 7.62 (d, 1H), 7.72 (d, 1H), 7.95 (d, 1H), 8.26 (s, 1H), 8.29 (d, 1H), 8.40 (dd, 1H), 8.72 (s, 1H), 8.96 (s, 1H), 9.13 (d, 1H).

Example II-82

1-{5-[2-Amino-7-(1-{2-methyl-1-[6-(trifluoromethyl)pyridin-3-yl]propyl}-1H-pyrazol-4-yl)[1,2,4]triazolo[1,5-a]pyridin-5-yl]pyridin-2-yl}cyclobutan-1-ol (stereoisomer 2, distomer)

The product was isolated in the previous example as second stereoisomer.

LC-MS (method 1): $R^t$=1.79 min; MS (ESIpos): m/z=549 $[M+H]^+$

Example II-83

5-(6-Cyclopropylpyridin-3-yl)-7-{1-[1-(oxetan-3-yl)piperidin-4-yl]-1H-pyrazol-4-yl}[1,2,4]triazolo[1,5-a]pyridin-2-amine

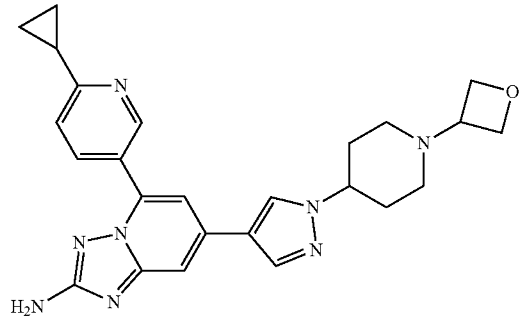 [SMILES: Nc1nc2cc(-c3cnn(C4CCN(C5COC5)CC4)c3)cc(-c3ccc(C4CC4)nc3)n2n1]

7-Chloro-5-(6-cyclopropylpyridin-3-yl)[1,2,4]triazolo[1,5-a]pyridin-2-amine (75.0 mg, 262 μmol), 1-(oxetan-3-yl)-4-[4-(4,4,5,5-tetramethyl-1,3,2-dioxaborolan-2-yl)-1H-pyrazol-1-yl]piperidine (96.2 mg, 289 μmol), 1,1'-bis(diphenylphosphino)ferrocene-palladium(II)dichloride dichloromethane complex (32.2 mg, 39.4 μmol) and water (500 1) were reacted according to procedure A in a mixture of sodium carbonate (139 mg, 1.31 mmol) and 1,4-dioxane (3.0 ml). The reaction was stirred for 3 h at 90° C. The reaction mixture was quenched with water filtered through a hydrophobic phase separation filter, washed with 15 ml of ethyl acetate and concentrated under reduced pressure. The residue was purified by preparative HPLC to yield 81.0 mg (100% purity, 68% yield) of the title compound.

LC-MS (method 1): $R^t$=0.84 min; MS (ESIpos): m/z=457 $[M+H]^+$ $^1$H-NMR (600 MHz, DMSO-$d_6$) δ [ppm]: 0.99-1.06 (m, 4H), 1.92-2.04 (m, 4H), 2.06-2.10 (m, 2H), 2.18-2.24 (m, 1H), 2.76-2.84 (m, 2H), 3.43-3.47 (m, 1H), 4.14-4.21 (m, 1H), 4.45 (t, 2H), 4.55 (t, 2H), 6.01 (s, 2H), 7.40 (d, 1H), 7.49 (d, 1H), 7.59 (d, 1H), 8.15 (s, 1H), 8.33 (dd, 1H), 8.60 (s, 1H), 9.01 (d, 1H).

Example II-84

7-(1-Benzyl-1H-pyrazol-4-yl)-5-(2-cyclopropylpyrimidin-5-yl)[1,2,4]triazolo[1,5-a]pyridin-2-amine

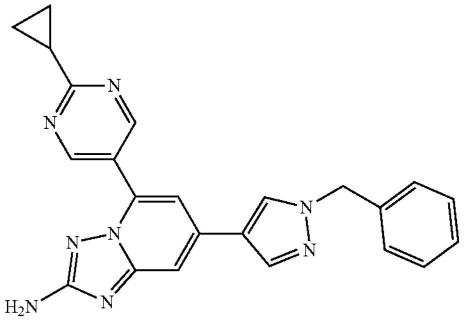 [SMILES: Nc1nc2cc(-c3cnn(Cc4ccccc4)c3)cc(-c3cnc(C4CC4)nc3)n2n1]

7-(1-Benzyl-1H-pyrazol-4-yl)-5-chloro[1,2,4]triazolo[1,5-a]pyridin-2-amine (200 mg, 616 μmol), 2-cyclopropyl-5-(4,4,5,5-tetramethyl-1,3,2-dioxaborolan-2-yl)pyrimidine (197 mg, 801 μmol), 1,1'-bis(diphenylphosphino)ferrocene-palladium(II)dichloride dichloromethane complex (75.4 mg, 92.4 μmol) and water (1.2 ml) were reacted according to procedure A in a mixture of sodium carbonate (326 mg, 3.08 mmol) and 1,4-dioxane (6.0 ml). After 2.5 h at 90° C., the reaction was quenched with water and extracted with dichloromethane. The combined organic layers were dried over anhydrous anhydrous sodium sulfate, filtered and concentrated. The residue was purified by preparative HPLC to yield 193 mg (100% purity, 77% yield) of the title compound.

LC-MS (method 1): $R^t$=1.58 min; MS (ESIpos): m/z=409 $[M+H]^+$ $^1$H-NMR (500 MHz, DMSO-$d_6$) δ [ppm]: 1.04-1.16 (m, 4H), 2.24-2.34 (m, 1H), 5.37 (s, 2H), 6.06 (s, 2H), 7.27-7.39 (m, 5H), 7.50 (d, 1H), 7.63 (d, 1H), 8.20 (s, 1H), 8.57 (s, 1H), 9.28 (s, 2H).

Example II-85

7-(1-{2-Methyl-1-[6-(trifluoromethyl)pyridin-3-yl]propyl}-1H-pyrazol-4-yl)-5-[2-(2,2,2-trifluoroethoxy)pyrimidin-5-yl][1,2,4]triazolo[1,5-a]pyridin-2-amine (mixture of enantiomers)

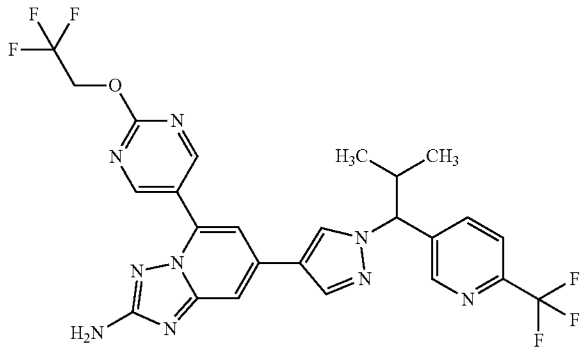 [SMILES: CC(C)C(c1ccc(C(F)(F)F)nc1)n1cc(-c2cc(-c3cnc(OCC(F)(F)F)nc3)n3nc(N)nc3c2)cn1]

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (188 mg, 431 μmol), [2-(2,2,2-trifluoroethoxy)pyrimidin-5-yl]boronic acid (124 mg, 561 μmol), XPhos-Pd-G2 (25.5 mg, 32.4 μmol) and sodium carbonate (229 mg, 2.16 mmol) were reacted according to procedure A in a mixture of water (1.0 ml) and 1,4-dioxane (3.0 ml). After stirring for 3 h at 90° C., the reaction was quenched with water and extracted with dichloromethane. The organic layer was dried over anhydrous sodium sulfate, filtered and concentrated. The residue was purified via silicagel column chromatography (Biotage® SNAP KP-NH 11 g cartridge, eluent: cyclohexane/ethyl acetate gradien 4:1 to 1:4) to yield 25.0 mg (99% purity, 10% yield) of the title compound as a mixture of enantiomers.

LC-MS (method 2): $R^t$=1.03 min; MS (ESIpos): m/z=578 $[M+H]^+$ $^1$H-NMR (400 MHz, DMSO-$d_6$) δ [ppm]: 0.82 (d, 3H), 0.89 (d, 3H), 2.79-2.85 (m, 1H), 5.17 (q, 2H), 5.26 (d, 1H), 6.11 (s, 2H), 7.52 (d, 1H), 7.64 (d, 1H), 7.95 (d, 1H), 8.26 (s, 1H), 8.29 (d, 1H), 8.69 (s, 1H), 8.96 (s, 1H), 9.38 (s, 2H).

Example II-86

7-(1-Benzyl-1H-pyrazol-4-yl)-5-(pyrazin-2-yl)[1,2,4]triazolo[1,5-a]pyridin-2-amine

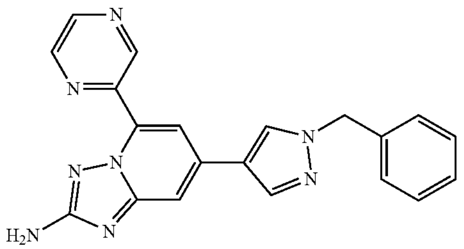 [SMILES: Nc1nc2cc(-c3cnn(Cc4ccccc4)c3)cc(-c3cnccn3)n2n1]

A solution of 7-(1-benzyl-1H-pyrazol-4-yl)-5-chloro[1,2,4]triazolo[1,5-a]pyridin-2-amine (100 mg, 308 μmol), 2-(tributylstannyl)pyrazine (125 mg, 339 μmol) and tetrakis(triphenylphosphine)palladium(0) (10.7 mg, 9.24 μmol) in dry DMF (2.0 ml) was stirred under argon at 100° C. for 2.5 h. 2-(Tri-n-butylstannyl)pyrazine (56.8 mg, 154 μmol) were added and the reaction mixture was further stirred at 110° C. for 3 h. The reaction was directly purified by preparative HPLC to yield 12.0 mg (100% purity, 11% yield) of the title compound.

LC-MS (method 1): $R^t$=1.35 min; MS (ESIpos): m/z=369 $[M+H]^+$ $^1$H-NMR (500 MHz, DMSO-$d_6$) δ [ppm]: 5.37 (s, 2H), 6.18 (s, 2H), 7.29-7.34 (m, 3H), 7.34-7.39 (m, 2H), 7.74 (d, 1H), 7.80 (d, 1H), 8.17 (s, 1H), 8.61 (s, 1H), 8.79 (d, 1H), 8.88 (dd, 1H), 9.95 (d, 1H).

Example II-87

7-(1-Benzyl-1H-pyrazol-4-yl)-5-(5-ethylpyrazin-2-yl)[1,2,4]triazolo[1,5-a]pyridin-2-amine

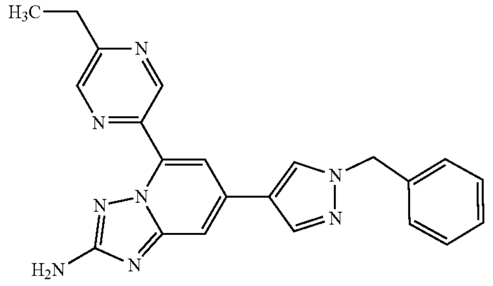 [SMILES: CCc1cnc(-c2cc(-c3cnn(Cc4ccccc4)c3)cc3nc(N)nn23)cn1]

7-(1-Benzyl-1H-pyrazol-4-yl)-5-chloro[1,2,4]triazolo[1,5-a]pyridin-2-amine (100 mg, 308 μmol), 2-ethyl-5-(4,4,5,5-tetramethyl-1,3,2-dioxaborolan-2-yl)pyrazine (93.7 mg, 400 μmol), 1,1'-bis(diphenylphosphino)ferrocene-palladium (II)dichloride dichloromethane complex (12.6 mg, 15.4 μmol) and sodium carbonate (163 mg, 1.54 mmol) were reacted according to procedure A in a mixture of 1,4-dioxane (3.0 ml) and water (600 μl). The reaction was stirred for 2.5 h at 100° C. 1,1'-Bis(diphenylphosphino)ferrocene-palladium(II)dichloride dichloromethane complex (12.6 mg, 15.4 μmol) were further added and the reaction was stirred for 6 h at 100° C. The residue was purified by preparative HPLC to give 7-(1-benzyl-1H-pyrazol-4-yl)-5-(5-ethylpyrazin-2-yl)[1,2,4]triazolo[1,5-a]pyridin-2-amine 14.0 mg (97% purity, 11% yield).

LC-MS (method 1): $R_t$=1.58 min; MS (ESIpos): m/z=397 $[M+H]^+$ $^1$H-NMR (500 MHz, DMSO-$d_6$) δ [ppm]: 1.32 (t, 4H), 2.92 (q, 2H), 5.37 (s, 2H), 6.14 (s, 2H), 7.27-7.39 (m, 5H), 7.71 (d, 1H), 7.75 (d, 1H), 8.16 (s, 1H), 8.60 (s, 1H), 8.78 (d, 1H), 9.82 (d, 1H).

Example II-88

7-(1-Benzyl-1H-pyrazol-4-yl)-5-(6-methylpyridazin-4-yl)[1,2,4]triazolo[1,5-a]pyridin-2-amine

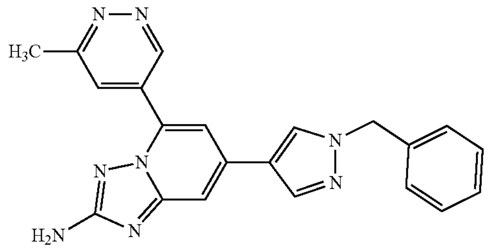 [SMILES: Cc1cc(-c2cc(-c3cnn(Cc4ccccc4)c3)cc3nc(N)nn23)cnn1]

7-(1-Benzyl-1H-pyrazol-4-yl)-5-chloro[1,2,4]triazolo[1,5-a]pyridin-2-amine (205 mg, 632 μmol), 3-methyl-5-(4,4,5,5-tetramethyl-1,3,2-dioxaborolan-2-yl)pyridazine (167 mg, 759 μmol), 1,1'-bis(diphenylphosphino)ferrocene-palladium(II)dichloride dichloromethane complex (25.8 mg, 31.6 μmol) and sodium carbonate(159 mg, 1.90 mmol) were reacted according to procedure A in a mixture of 1,4-dioxane (3.0 ml) and water (1.0 ml). The reaction was stirred for 3 h at 90° C. The reaction was quenched with water and extracted with dicloromethane. The organic layer was dried over anhydrous sodium sulfate, filtered and concentrated. The residue was purified via column chromatography (Biotage® SNAP KP-NH 11 g cartridge, eluent: cyclohexane/ethyl acetate gradient 4:1 to 1:4) to yield 168 mg (98% purity, 68% yield) of the title compound.

LC-MS (method 1): $R^t$=1.26 min; MS (ESIpos): m/z=383 $[M+H]^+$ $^1$H-NMR (400 MHz, DMSO-$d_6$) δ [ppm]: 2.74 (s, 3H), 5.38 (s, 2H), 6.16 (s, 2H), 7.27-7.40 (m, 5H), 7.63 (s, 1H), 7.72 (s, 1H), 8.23 (s, 1H), 8.29 (d, 1H), 8.60 (s, 1H), 9.76 (d, 1H).

Example II-89

6-(1-Benzyl-1H-pyrazol-4-yl)-8-{1-[(2,2-difluorocyclopropyl)methyl]-1H-pyrazol-4-yl}[1,2,4]triazolo[1,5-a]pyridin-2-amine (mixture of enantiomers)

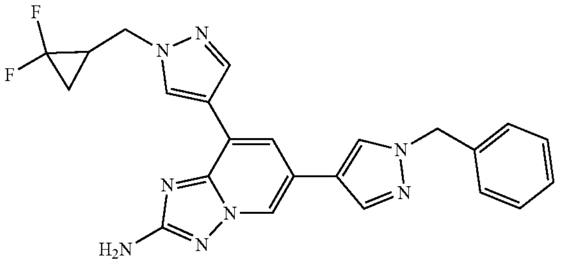 [SMILES: Nc1nc2c(-c3cnn(CC4CC4(F)F)c3)cc(-c3cnn(Cc4ccccc4)c3)cn2n1]

6-(1-Benzyl-1H-pyrazol-4-yl)-8-chloro[1,2,4]triazolo[1,5-a]pyridin-2-amine (100 mg, 95% purity, 293 μmol) was reacted with 1-[(2,2-difluorocyclopropyl)methyl]-4-(4,4,5,5-tetramethyl-1,3,2-dioxaborolan-2-yl)-1H-pyrazole [CAS-RN 2101930-90-7](132 mg, 85% purity, 395 μmol) for 2 h at 80° C. following general procedure C using 0.15 eq. catalyst. The reaction mixture was directly purified by column chromatography (Biotage® SNAP Ultra 10 g cartridge, eluent: dichloromethane/methanol gradient 100:0 to 85:15). The product was further purified by preparative HPLC (Chromatorex C18, 10 m, 125×30 mm; eluent: water (0.1% formic acid)/acetonitrile gradient 90:10 to 5:95) to yield 64.0 mg (100% purity, 49% yield) of the title compound.

LC-MS (method 2): $R^t$=0.89 min; MS (ESIpos): m/z=447 $[M+H]^+$ $^1$H-NMR (400 MHz, DMSO-$d_6$) δ [ppm]: 1.47-1.58 (m, 1H), 1.66-1.78 (m, 1H), 2.23-2.37 (m, 1H), 4.34 (d, 2H), 5.37 (s, 2H), 6.02 (s, 2H), 7.26-7.34 (m, 3H), 7.34-7.40 (m, 2H), 8.01 (s, 1H), 8.09 (s, 1H), 8.39 (s, 1H), 8.41 (s, 1H), 8.62 (s, 1H), 8.73 (s, 1H).

Example II-90

8-(1-Methyl-1H-pyrazol-4-yl)-6-{1-[(1S)-1-phenylpropyl]-1H-pyrazol-4-yl}[1,2,4]triazolo[1,5-a]pyridin-2-amine

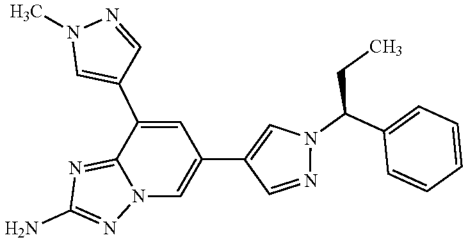 [SMILES: CC[C@@H](c1ccccc1)n1cc(-c2cc(-c3cnn(C)c3)c3nc(N)nn3c2)cn1]

6-Bromo-8-(1-methyl-1H-pyrazol-4-yl)[1,2,4]triazolo[1,5-a]pyridin-2-amine (100 mg, 341 μmol) was reacted with 1-[(1S)-1-phenylpropyl]-4-(4,4,5,5-tetramethyl-1,3,2-dioxaborolan-2-yl)-1H-pyrazole (107 mg, 341 μmol) for 2 h at 90° C. following general procedure B using 0.05 eq. catalyst.

The reaction mixture was diluted with ethyl acetate (10 ml) and washed with water (10 ml). The aqueous layer was extracted with ethyl acetate (10 ml) and the combined organic layers were washed with brine (10 ml) and filtered through a hydrophobic phase separation filter. The solvent was removed in vacuo and the residue was purified by column chromatography (Biotage® SNAP KP-NH 11 g cartridge, eluent: cyclohexane/ethyl acetate gradient 80:20 to 0:100) to yield 78.3 mg (99% purity, 57% yield) of the title compound.

LC-MS (method 1): $R^t$=1.60 min; MS (ESIpos): m/z=399 $[M+H]^+$ $^1$H-NMR (400 MHz, DMSO-$d_6$) δ [ppm]: 0.87 (t, 3H), 2.10-2.23 (m, 1H), 2.31-2.45 (m, 1H), 3.93 (s, 3H), 5.31 (dd, 1H), 6.02 (s, 2H), 7.25-7.39 (m, 5H), 8.00 (d, 1H), 8.08 (s, 1H), 8.32 (s, 1H), 8.50 (s, 1H), 8.54 (s, 1H), 8.72 (d, 1H).

Example II-91

8-(1-Ethyl-1H-pyrazol-4-yl)-6-{1-[(1S)-1-phenylpropyl]-1H-pyrazol-4-yl}[1,2,4]triazolo[1,5-a]pyridin-2-amine

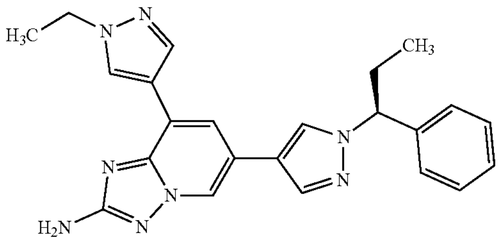 [SMILES: CC[C@@H](c1ccccc1)n1cc(-c2cc(-c3cnn(CC)c3)c3nc(N)nn3c2)cn1]

6-Bromo-8-(1-ethyl-1H-pyrazol-4-yl)[1,2,4]triazolo[1,5-a]pyridin-2-amine (75.0 mg, 95% purity, 232 μmol) was reacted with 1-[(1S)-1-phenylpropyl]-4-(4,4,5,5-tetramethyl-1,3,2-dioxaborolan-2-yl)-1H-pyrazole (72.4 mg, 232 μmol) for 3 h at 90° C. following general procedure B using 0.05 eq. catalyst. The reaction mixture was diluted with ethyl acetate (10 ml) and filtered through a hydrophobic phase separation filter. The filtrate was concentrated in vacuo and the residue was purified by column chromatography (Biotage® SNAP KP-NH 11 g cartridge, eluent: cyclohexane 15/ethyl acetate gradient 4:1 to 0:1) to yield 67.8 mg (95% purity, 67% yield) of the title compound.

LC-MS (method 1): $R^t$=1.70 min; MS (ESIpos): m/z=413 $[M+H]^+$ $^1$H-NMR (400 MHz, DMSO-$d_6$) δ [ppm]: 0.87 (t, 3H), 1.43 (t, 3H), 2.11-2.23 (m, 1H), 2.31-2.45 (m, 1H), 4.22 (q, 2H), 5.31 (dd, 1H), 6.02 (s, 2H), 7.25-7.39 (m, 5H), 8.00 (d, 1H), 8.08 (s, 1H), 8.34 (s, 1H), 8.50 (s, 1H), 8.57 (s, 1H), 8.72 (d, 1H).

Example II-92

8-(1-Cyclopropyl-1H-pyrazol-4-yl)-6-{1-[(IS)-1-phenylpropyl]-1H-pyrazol-4-yl}[1,2,4]triazolo[1,5-a]pyridin-2-amine

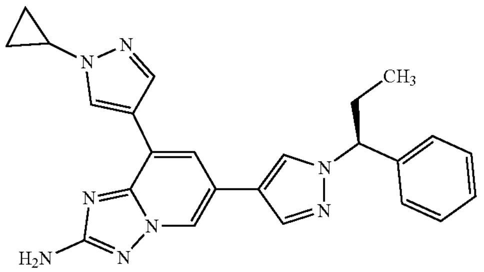 [SMILES: CC[C@@H](c1ccccc1)n1cc(-c2cc(-c3cnn(C4CC4)c3)c3nc(N)nn3c2)cn1]

6-Bromo-8-(1-cyclopropyl-1H-pyrazol-4-yl)[1,2,4]triazolo[1,5-a]pyridin-2-amine (100 mg, 95% purity, 298 μmol) was reacted with 1-[(1S)-1-phenylpropyl]-4-(4,4,5,5-tetramethyl-1,3,2-dioxaborolan-2-yl)-1H-pyrazole (92.9 mg, 298 μmol) for 2 h at 90° C. following general procedure B using 0.05 eq. catalyst. The reaction mixture was diluted with ethyl acetate (10 ml) and filtered through a hydrophobic phase separation filter. The filtrate was concentrated in vacuo and the residue was purified by column chromatography (Biotage® SNAP KP-NH 11 g cartridge, eluent: cyclohexane/ethyl acetate gradient 4:1 to 0:1) to yield 86.4 mg (95% purity, 65% yield) of the title compound.

LC-MS (method 1): $R^t$=1.74 min; MS (ESIpos): m/z=425 $[M+H]^+$ $^1$H-NMR (400 MHz, DMSO-$d_6$) δ [ppm]: 0.87 (t, 3H), 0.99-1.12 (m, 4H), 2.11-2.23 (m, 1H), 2.32-2.46 (m, 1H), 3.80 (tt, 1H), 5.31 (dd, 1H), 6.05 (s, 2H), 7.25-7.39 (m, 5H), 8.00 (d, 1H), 8.08 (s, 1H), 8.33 (s, 1H), 8.49 (s, 1H), 8.63 (s, 1H), 8.72 (d, 1H).

Example II-93

6-{1-[(1S)-1-Phenylpropyl]-1H-pyrazol-4-yl}-8-[1-(2,2,2-trifluoroethyl)-1H-pyrazol-4-yl][1,2,4]triazolo[1,5-a]pyridin-2-amine

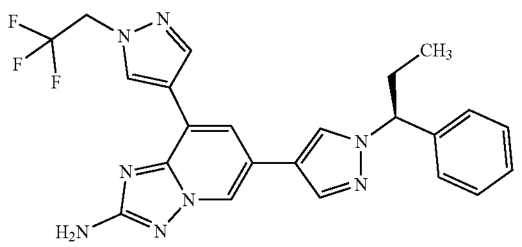 [SMILES: CC[C@@H](c1ccccc1)n1cc(-c2cc(-c3cnn(CC(F)(F)F)c3)c3nc(N)nn3c2)cn1]

6-Bromo-8-[1-(2,2,2-trifluoroethyl)-1H-pyrazol-4-yl][1,2,4]triazolo[1,5-a]pyridin-2-amine (75.0 mg, 208 μmol) was reacted with 1-[(1S)-1-phenylpropyl]-4-(4,4,5,5-tetramethyl-1,3,2-dioxaborolan-2-yl)-1H-pyrazole (84.3 mg, 270 μmol) for 2 h at 80° C. following general procedure C using 0.15 eq. catalyst. The reaction mixture was then diluted with ethyl acetate and filtered through a hydrophobic phase separation filter. The solvent was evaporated under reduced pressure. The residue was purified by column chromatography (Biotage® SNAP KP-NH 11 g cartridge, eluent: cyclohexane/ethyl acetate gradient 90: 10 to 20:80) to yield 68.5 mg (98% purity, 69% yield) of the title compound.

LC-MS (method 1): $R^t$=1.83 min; MS (ESIpos): m/z=467 $[M+H]^+$ $^1$H-NMR (400 MHz, DMSO-$d_6$) δ [ppm]: 0.87 (t, 3H), 2.11-2.23 (m, 1H), 2.31-2.45 (m, 1H), 5.24-5.35 (m, 3H), 6.05 (s, 2H), 7.26-7.39 (m, 5H), 8.08 (d, 1H), 8.10 (s, 1H), 8.49 (s, 1H), 8.51 (s, 1H), 8.72 (s, 1H), 8.77 (d, 1H).

Example II-94

6-{1-[(1S)-1-Phenylpropyl]-1H-pyrazol-4-yl}-8-[1-(1,1,1-trifluoropropan-2-yl)-1H-pyrazol-4-yl][1,2,4]triazolo[1,5-a]pyridin-2-amine (mixture of stereoisomers)

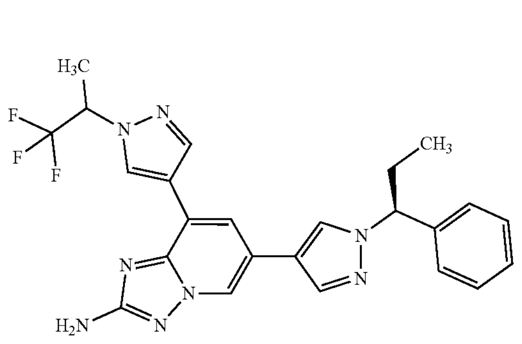 [SMILES: CC[C@@H](c1ccccc1)n1cc(-c2cc(-c3cnn(C(C)C(F)(F)F)c3)c3nc(N)nn3c2)cn1]

6-Bromo-8-[1-(1,1,1-trifluoropropan-2-yl)-1H-pyrazol-4-yl][1,2,4]triazolo[1,5-a]pyridin-2-amine (196 mg, 83% purity, 433 μmol) was reacted with 1-[(1S)-1-phenylpropyl]-4-(4,4,5,5-tetramethyl-1,3,2-dioxaborolan-2-yl)-1H-pyrazole (162 mg, 520 μmol) for 1.5 h at 90° C. following general procedure B using 0.1 eq. catalyst. The reaction mixture was diluted with ethyl acetate and washed with water. The organic layer was filtered through a hydrophobic phase separation filter and concentrated in vacuo. The crude product was purified by column chromatography (Biotage® SNAP KP-NH 28 g cartridge, eluent: dichloromethane/methanol gradient 80:20 to 0:100). The product was further purified by preparative HPLC (Chromatorex C18, 10 μm, 125×30 mm; eluent: water (0.1% formic acid)/acetonitrile gradient 9:1 to 1:19) to yield 137 mg (99% purity, 65% yield) of the title compound.

LC-MS (method 1): $R^t$=1.92 min; MS (ESIpos): m/z=481 $[M+H]^+$ $^1$H-NMR (600 MHz, DMSO-$d_6$) δ [ppm]: 0.87 (t, 3H), 1.73 (d, 3H), 2.13-2.21 (m, 1H), 2.34-2.43 (m, 1H), 5.32 (dd, 1H), 5.56 (dt, 1H), 6.06 (s, 2H), 7.27-7.30 (m, 1H), 7.33-7.38 (m, 4H), 8.07 (d, 1H), 8.10 (s, 1H), 8.48-8.50 (m, 1H), 8.50 (s, 1H), 8.75 (s, 1H), 8.77 (d, 1H).

Example II-95

6-{1-[(1S)-1-Phenylpropyl]-1H-pyrazol-4-yl}-8-[1-(1,1,1-trifluoropropan-2-yl)-1H-pyrazol-4-yl][1,2,4]triazolo[1,5-a]pyridin-2-amine (stereoisomer 1, eutomer)

6-{1-[(1S)-1-Phenylpropyl]-1H-pyrazol-4-yl}-8-[1-(1,1,1-trifluoropropan-2-yl)-1H-pyrazol-4-yl][1,2,4]triazolo[1,5-a]pyridin-2-amine (mixture of stereoisomers) (100 mg, 99% purity) from the previous example was separated by chiral chromatography to yield stereoisomer 1 (43 mg, 100% purity) and stereoisomer 2 (40 mg, 100% purity).

Column: Daicel Chiralcel OX-H, 5 μm, 250×30 mm; Eluent A: n-heptane; Eluent B: ethanol+0.2% diethylamine; isocratic: 50% A+50% B; flow: 25 ml/min; UV: 220 nim; temperature: 40° C.

Stereoisomer 1: $R^t$=4.65 min and

Stereoisomer 2: $R^t$=5.65 min (cf. next example)

Analytical chiral HPLC method: Column: Daicel Chiralpak OX-3, 3 m, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.490 min and

Stereoisomer 2: $R^t$=1.925 min (cf. next example)

LC-MS (method 2): $R^t$=1.01 min; MS (ESIpos): m/z=481 $[M+H]^+$ $^1$H-NMR (400 MHz, DMSO-$d_6$) δ [ppm]: 0.87 (t, 3H), 1.73 (d, 3H), 2.11-2.23 (m, 1H), 2.32-2.45 (m, 1H), 5.32 (dd, 1H), 5.50-5.62 (m, 1H), 6.05 (s, 2H), 7.26-7.32 (m, 1H), 7.33-7.39 (m, 4H), 8.06 (d, 1H), 8.10 (s, 1H), 8.49 (s, 1H), 8.50 (s, 1H), 8.75 (s, 1H), 8.76 (d, 1H).

Example II-96

6-{1-[(1S)-1-Phenylpropyl]-1H-pyrazol-4-yl}-8-[1-(1,1,1-trifluoropropan-2-yl)-1H-pyrazol-4-yl][1,2,4]triazolo[1,5-a]pyridin-2-amine (stereoisomer 2, distomer)

The product was isolated in the previous example as second stereoisomer.

LC-MS (method 2): $R^t$=1.01 min; MS (ESIpos): m/z=481 $[M+H]^+$ $^1$H-NMR (400 MHz, DMSO-$d_6$) δ [ppm]: 0.007 (0.81), 0.855 (4.95), 0.874 (11.13), 0.892 (5.19), 1.724 (9.43), 1.742 (9.50), 2.134 (0.65), 2.150 (1.13), 2.168 (1.67), 2.186 (1.39), 2.203 (0.84), 2.350 (0.81), 2.368 (1.42), 2.373 (1.01), 2.384 (0.97), 2.391 (1.08), 2.402 (0.75), 2.408 (0.90), 2.425 (0.62), 2.524 (1.00), 5.303 (1.65), 5.319 (1.92), 5.326 (2.00), 5.342 (1.63), 5.521 (0.53), 5.539 (1.31), 5.558 (1.72), 5.576 (1.23), 5.594 (0.47), 6.050 (7.46), 7.266 (0.72), 7.272 (0.83), 7.281 (1.69), 7.289 (1.51), 7.297 (1.80), 7.303 (1.21), 7.331 (1.51), 7.352 (7.04), 7.361 (8.09), 7.366 (16.00), 7.381 (1.43), 8.061 (5.80), 8.065 (5.93), 8.096 (8.20), 8.489 (9.07), 8.500 (8.06), 8.746 (8.20), 8.762 (5.95), 8.766 (5.96).

Example II-97

2-[4-(2-Amino-6-{1-[(15)-1-phenylpropyl]-1H-pyrazol-4-yl}[1,2,4]triazolo[1,5-a]pyridin-8-yl)-1H-pyrazol-1-yl]ethan-1-ol

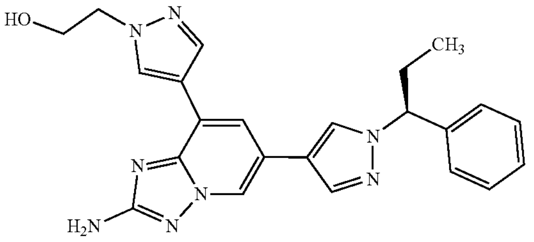 [SMILES: CC[C@@H](c1ccccc1)n1cc(-c2cc(-c3cnn(CCO)c3)c3nc(N)nn3c2)cn1]

2-[4-(2-Amino-6-bromo[1,2,4]triazolo[1,5-a]pyridin-8-yl)-1H-pyrazol-1-yl]ethan-1-ol (75.0 mg, 232 μmol) was reacted with 1-[(1S)-1-phenylpropyl]-4-(4,4,5,5-tetramethyl-1,3,2-dioxaborolan-2-yl)-1H-pyrazole (72.5 mg, 232 μmol) for 2 h at 90° C. following general procedure B using 0.05 eq. catalyst. The reaction mixture was diluted with ethyl acetate (30 ml) and washed with water (20 ml). The aqueous layer was extracted with ethyl acetate and the combined organic layers were filtered through a hydrophobic phase separation filter. The solvent was evaporated and the residue was purified by column chromatography (Biotage® SNAP KP-NH 11 g cartridge, eluent: cyclohexane/ethyl acetate/2-propanol gradient 50:50:0 to 0:100:0 to 0:90:10) to yield 56.7 mg (98% purity, 56% yield) of the title compound.

LC-MS (method 1): R, =1.45 min; MS (ESIpos): m/z=429 $[M+H]^+$ $^1$H-NMR (400 MHz, DMSO-$d_6$) δ [ppm]: 0.87 (t, 3H), 2.11-2.23 (m, 1H), 2.31-2.45 (m, 1H), 3.78 (q, 2H), 4.21 (t, 2H), 4.96 (t, 1H), 5.31 (dd, 1H), 6.03 (s, 2H), 7.25-7.31 (m, 1H), 7.32-7.39 (m, 4H), 8.01 (d, 1H), 8.09 (s, 1H), 8.36 (s, 1H), 8.51 (s, 1H), 8.59 (s, 1H), 8.71 (d, 1H).

Example II-98

6-{1-[(1S)-1-(4-fluorophenyl)propyl]-1H-pyrazol-4-yl}-8-[1-(2,2,2-trifluoroethyl)-1H-pyrazol-4-yl][1,2,4]triazolo[1,5-a]pyridin-2-amine

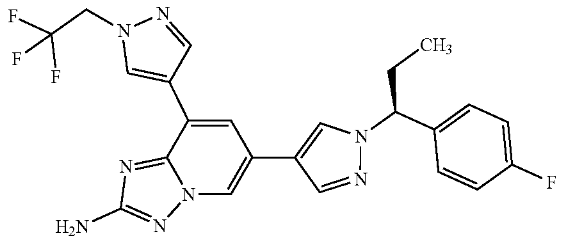 [SMILES: CC[C@@H](c1ccc(F)cc1)n1cc(-c2cc(-c3cnn(CC(F)(F)F)c3)c3nc(N)nn3c2)cn1]

6-Bromo-8-[1-(2,2,2-trifluoroethyl)-1H-pyrazol-4-yl][1,2,4]triazolo[1,5-a]pyridin-2-amine (75.0 mg, 208 μmol) was reacted with 1-[(IS)-1-(4-fluorophenyl)propyl]-4-(4,4,5,5-tetramethyl-1,3,2-dioxaborolan-2-yl)-1H-pyrazole (89.2 mg, 270 μmol) for 2 h at 80° C. following general procedure C using 0.15 eq. catalyst. The reaction mixture was then diluted with ethyl acetate and filtered through a hydrophobic phase separation filter. The solvent was evaporated under reduced pressure.

The residue was purified by column chromatography (Biotage® SNAP KP-NH 11 g cartridge, eluent: cyclohexane/ethyl acetate gradient 90:10 to 20:80) to yield 54.3 mg (95% purity, 51% yield) of the title compound.

LC-MS (method 1): $R^t$=1.85 min; MS (ESIpos): m/z=485 $[M+H]^+$ $^1$H-NMR (400 MHz, DMSO-$d_6$) δ [ppm]: 0.86 (t, 3H), 2.09-2.21 (m, 1H), 2.30-2.44 (m, 1H), 5.28 (q, 2H), 5.35 (dd, 1H), 6.05 (s, 2H), 7.15-7.22 (m, 2H), 7.39-7.46 (m, 2H), 8.07 (d, 1H), 8.10 (s, 1H), 8.48-8.51 (m, 2H), 8.72 (s, 1H), 8.76 (d, 1H).

Example II-99

8-(1-Methyl-1H-pyrazol-4-yl)-6-(1-{1-[4-(trifluoromethyl)phenyl]propyl}-1H-pyrazol-4-yl)[1,2,4]triazolo[1,5-a]pyridin-2-amine (mixture of enantiomers)

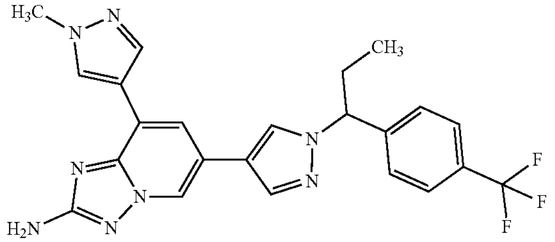 [SMILES: CCC(c1ccc(C(F)(F)F)cc1)n1cc(-c2cc(-c3cnn(C)c3)c3nc(N)nn3c2)cn1]

6-Bromo-8-(1-methyl-1H-pyrazol-4-yl)[1,2,4]triazolo[1,5-a]pyridin-2-amine (150 mg, 92% purity, 471 μmol) was reacted with 4-(4,4,5,5-tetramethyl-1,3,2-dioxaborolan-2-yl)-1-{1-[4-(trifluoromethyl)phenyl]propyl}-1H-pyrazole (242 mg, 636 μmol) for 1.5 h at 80° C. following general procedure C using 0.1 eq. catalyst. The reaction mixture was directly purified by column chromatography ((Biotage® SNAP Ultra 25 g cartridge, eluent: dichloromethane/methanol gradient 100:0 to 85:15). The product was further purified by preparative HPLC (Chromatorex C18, 10 m, 125×30 mm; eluent: water/acetonitrile gradient 90:10 to 5:95) to yield 130 mg (95% purity, 56% yield) of the title compound.

LC-MS (method 2): $R^t$=0.97 min; MS (ESIpos): m/z=467 $[M+H]^+$ $^1$H-NMR (600 MHz, DMSO-$d_6$) δ [ppm]: 0.005 (0.44), 0.880 (3.32), 0.892 (7.08), 0.904 (3.24), 2.169 (0.44), 2.179 (0.71), 2.192 (1.01), 2.204 (0.77), 2.215 (0.50), 2.380 (0.55), 2.392 (0.73), 2.403 (0.65), 2.407 (0.67), 2.415 (0.51), 2.418 (0.60), 2.430 (0.42), 2.518 (0.54), 2.521 (0.53), 2.524 (0.52), 3.930 (16.00), 5.458 (0.95), 5.468 (1.06), 5.474 (1.05), 5.484 (0.89), 6.037 (5.08), 7.565 (3.09), 7.579 (3.42), 7.728 (3.71), 7.742 (3.06), 8.005 (3.60), 8.008 (3.50), 8.127 (5.12), 8.324 (5.54), 8.539 (5.15), 8.543 (5.33), 8.734 (3.63), 8.737 (3.45).

Example II-100

8-(1-Methyl-1H-pyrazol-4-yl)-6-(1-{1-[4-(trifluoromethyl)phenyl]propyl}-1H-pyrazol-4-yl)[1,2,4]triazolo[1,5-a]pyridin-2-amine (stereoisomer 1, distomer)

8-(1-Methyl-1H-pyrazol-4-yl)-6-(1-{1-[4-(trifluoromethyl)phenyl]propyl}-1H-pyrazol-4-yl)[1,2,4]triazolo[1,5-a]pyridin-2-amine (mixture of enantiomers) (115 mg, 95% purity) from the previous example was separated by chiral chromatography to yield stereoisomer 1 (36 mg, 99% purity) and stereoisomer 2 (37 mg, 99% purity).

Column: Daicel Chiralpak OX-H, 5 μm, 250×30 mm; Eluent A: n-heptane; Eluent B: ethanol+0.2% diethylamine; isocratic: 60% A+40% B; flow: 40 ml/min; UV: 220 nm; temperature: 40° C.

Stereoisomer 1: $R^t$=8.312 min and

Stereoisomer 2: $R^t$=11.359 min (cf. next example)

Analytical chiral HPLC method: Column: Daicel Chiralpak OX-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: Rc=1.470 min and

Stereoisomer 2: $R^t$=2.183 min (cf. next example)

LC-MS (method 2): $R^t$=0.96 min; MS (ESIpos): m/z=467 $[M+H]^+$ $^1$H-NMR (500 MHz, DMSO-$d_6$) δ [ppm]: 0.878 (3.02), 0.893 (6.77), 0.907 (3.11), 1.145 (0.45), 2.179 (0.66), 2.193 (0.97), 2.208 (0.74), 2.221 (0.47), 2.376 (0.46), 2.391 (0.61), 2.395 (0.53), 2.404 (0.57), 2.409 (0.62), 2.419 (0.44), 2.423 (0.53), 3.931 (16.00), 5.454 (0.87), 5.467 (0.99), 5.473 (1.01), 5.485 (0.85), 6.025 (4.78), 7.565 (2.82), 7.581 (3.35), 7.726 (3.60), 7.742 (2.94), 8.002 (3.63), 8.006 (3.63), 8.125 (5.13), 8.323 (5.54), 8.534 (4.83), 8.543 (5.30), 8.729 (3.85), 8.733 (3.81).

Example II-101

8-(1-Methyl-1H-pyrazol-4-yl)-6-(1-{1-[4-(trifluoromethyl)phenyl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 2): $R^t$=0.96 min; MS (ESIpos): m/z=467 $[M+H]^+$ $^1$H-NMR (500 MHz, DMSO-$d_6$) δ [ppm]: 0.89 (t, 3H), 2.14-2.25 (m, 1H), 2.35-2.46 (m, 1H), 3.93 (s, 3H), 5.47 (dd, 1H), 6.02 (s, 2H), 7.57 (d, 2H), 7.73 (d, 2H), 8.00 (d, 1H), 8.12 (s, 1H), 8.32 (s, 1H), 8.53 (s, 1H), 8.54 (s, 1H), 8.73 (d, 1H).

Example II-102

6-(1-{1-[4-(Morpholin-4-yl)phenyl]propyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers)

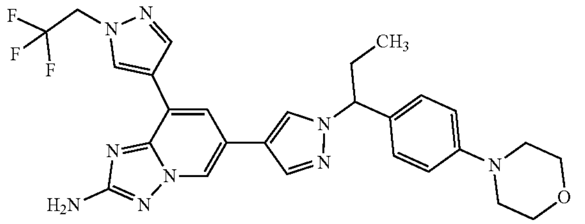 [SMILES: CCC(c1ccc(N2CCOCC2)cc1)n1cc(-c2cc(-c3cnn(CC(F)(F)F)c3)c3nc(N)nn3c2)cn1]

6-Bromo-8-[1-(2,2,2-trifluoroethyl)-1H-pyrazol-4-yl][1,2,4]triazolo[1,5-a]pyridin-2-amine (143 mg, 396 μmol) was reacted with 4-(4-{1-[4-(4,4,5,5-tetramethyl-1,3,2-dioxaborolan-2-yl)-1H-pyrazol-1-yl]propyl}phenyl)morpholine (270 mg, 70% purity, 476 μmol) for 2 h at 80° C. following general procedure C using 0.1 eq. catalyst. The reaction mixture was diluted with ethyl acetate and filtered through a hydrophobic phase separation filter. The filtrate was concentrated in vacuo. The residue was purified by column chromatography (Biotage® SNAP KP-NH 11 g cartridge, eluent: cyclohexane/ethyl acetate gradient 90:10 to 25:75) and then by preparative HPLC (Chromatorex C18, 10 μm, 125×30 mm; eluent: water/acetonitrile gradient) to yield 188 mg (97% purity, 83% yield) of the title compound.

LC-MS (method 1): $R^t$=1.75 min; MS (ESIpos): m/z=552 $[M+H]^+$ $^1$H-NMR (600 MHz, DMSO-$d_6$) δ [ppm]: 0.837 (6.09), 0.850 (12.96), 0.862 (6.11), 1.071 (5.33), 2.076 (2.04), 2.112 (0.83), 2.123 (1.52), 2.135 (2.03), 2.147 (1.73), 2.158 (0.99), 2.319 (0.95), 2.331 (1.37), 2.343 (1.33), 2.346 (1.34), 2.357 (1.20), 2.369 (0.76), 3.059 (8.95), 3.067 (11.65), 3.076 (9.07), 3.703 (9.85), 3.711 (11.97), 3.719 (8.95), 3.929 (0.85), 5.186 (2.00), 5.197 (2.51), 5.201 (2.45), 5.212 (1.91), 5.262 (1.56), 5.277 (4.35), 5.293 (4.14), 5.308 (1.32), 6.051 (10.15), 6.900 (7.74), 6.915 (8.16), 7.238 (8.32), 7.253 (7.49), 8.066 (16.00), 8.458 (9.21), 8.500 (10.32), 8.724 (9.72), 8.756 (7.04), 8.759 (7.19).

Example II-103

6-(1-{1-[4-(Morpholin-4-yl)phenyl]propyl}-1H-pyrazol-4-yl)-8-[1-(2,2,2-trifluoroethyl)-1H-pyrazol-4-yl][1,2,4]triazolo[1,5-a]pyridin-2-amine (stereoisomer 1, distomer)

6-(1-{1-[4-(Morpholin-4-yl)phenyl]propyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers) (151 mg, 97% purity) from the previous example was separated by chiral chromatography to yield stereoisomer 1 (73 mg, 98% purity) and stereoisomer 2 (68 mg, 98% purity).

Column: Daicel Chiralcel OD-H, 5 μm, 250×20 mm; Eluent A: n-heptane; Eluent B: ethanol+0.2% diethylamine; isocratic: 50% A+50% B; flow: 25 ml/min; UV: 220 nm; temperature: 40° C.

Stereoisomer 1: $R^t$=7.00 min and

Stereoisomer 2: $R^t$=9.25 min (cf. next example)

Analytical chiral HPLC method: Column: Phenomenex cellulose, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.627 min and

Stereoisomer 2: $R^t$=2.184 min (cf. next example)

LC-MS (method 1): $R^t$=1.73 min; MS (ESIpos): m/z=552 $[M+H]^+$ $^1$H-NMR (600 MHz, DMSO-$d_6$) δ [ppm]: 0.838 (6.08), 0.850 (13.11), 0.862 (6.72), 1.123 (0.99), 1.135 (1.99), 1.147 (1.07), 1.234 (0.45), 2.113 (0.85), 2.124 (1.56), 2.136 (1.99), 2.147 (1.79), 2.159 (1.00), 2.319 (0.93), 2.332 (1.36), 2.345 (1.40), 2.357 (1.21), 2.369 (0.83), 2.381 (0.49), 2.423 (0.81), 2.570 (1.40), 2.652 (0.73), 2.863 (0.64), 2.875 (0.64), 3.061 (8.52), 3.069 (11.52), 3.077 (9.17), 3.259 (0.49), 3.327 (1.74), 3.703 (9.30), 3.710 (11.77), 3.718 (8.97), 5.184 (1.95), 5.198 (2.49), 5.209 (1.93), 5.249 (1.55), 5.264 (4.45), 5.280 (4.28), 5.295 (1.47), 6.018 (10.29), 6.897 (7.34), 6.912 (7.80), 7.237 (8.04), 7.252 (7.34), 8.055 (16.00), 8.443 (9.22), 8.490 (10.05), 8.718 (9.40), 8.744 (6.99).

Example II-104

6-(1-{1-[4-(Morpholin-4-yl)phenyl]propyl}-1H-pyrazol-4-yl)-8-[1-(2,2,2-trifluoroethyl)-1H-pyrazol-4-yl][1,2,4]triazolo[1,5-a]pyridin-2-amine (stereoisomer 2, eutomer)

The product was isolated in the previous example as second stereoisomer.

LC-MS (method 1): $R^t$=1.73 min; MS (ESIpos): m/z=552 $[M+H]^+$ $^1$H-NMR (600 MHz, DMSO-$d_6$) δ [ppm]: 0.85 (t, 3H), 2.10-2.18 (m, 1H), 2.30-2.39 (m, 1H), 3.05-3.09 (m, 4H), 3.69-3.73 (m, 4H), 5.20 (dd, 1H), 5.27 (q, 2H), 6.02 (s, 2H), 6.90 (d, 2H), 7.25 (d, 2H), 8.06 (s, 2H), 8.44 (s, 1H), 8.49 (s, 1H), 8.72 (s, 1H), 8.74 (s, 1H).

Example II-105

6-(1-{1-[6-(Difluoromethyl)pyridin-3-yl]propyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers)

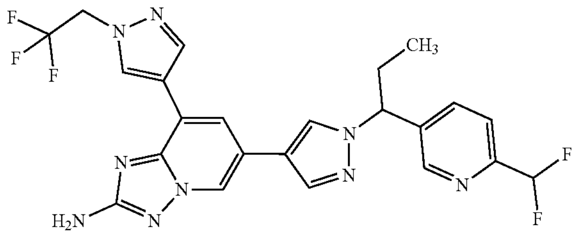 [SMILES: CCC(c1ccc(C(F)F)nc1)n1cc(-c2cc(-c3cnn(CC(F)(F)F)c3)c3nc(N)nn3c2)cn1]

6-Bromo-8-[1-(2,2,2-trifluoroethyl)-1H-pyrazol-4-yl][1,2,4]triazolo[1,5-a]pyridin-2-amine (100 mg, 277 μmol) was reacted with 2-(difluoromethyl)-5-{1-[4-(4,4,5,5-tetramethyl-1,3,2-dioxaborolan-2-yl)-1H-pyrazol-1-yl]propyl}pyridine (121 mg, 90% purity, 333 μmol) for 2 h at 80° C. following general procedure C using 0.1 eq. catalyst. Then further 0.1 eq. catalyst was added and heating was continued for another 3 h. The reaction mixture was diluted with dichloromethane (2 ml) and purified by column chromatography (Biotage® SNAP Ultra 25 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 45.0 mg (97% purity, 30% yield) of the title compound.

LC-MS (method 2): $R^t$=0.86 min; MS (ESIpos): m/z=518 $[M+H]^+$ $^1$H-NMR (600 MHz, DMSO-$d_6$) δ [ppm]: 0.884 (7.40), 0.896 (16.00), 0.908 (7.49), 2.200 (0.97), 2.211 (1.61), 2.223 (2.29), 2.234 (1.83), 2.245 (1.10), 2.410 (1.11), 2.422 (1.48), 2.426 (1.52), 2.433 (1.39), 2.438 (1.47), 2.445 (1.06), 2.449 (1.30), 2.461 (0.91), 2.472 (0.43), 2.522 (0.59), 2.656 (0.40), 3.295 (0.62), 5.264 (1.78), 5.280 (4.91), 5.295 (4.60), 5.310 (1.43), 5.520 (2.15), 5.530 (2.39), 5.536 (2.39), 5.546 (2.09), 6.067 (11.46), 6.856 (3.01), 6.948 (6.33), 7.039 (2.63), 7.709 (5.15), 7.722 (5.63), 7.963 (3.36), 7.967 (3.33), 7.977 (2.95), 7.980 (2.96), 8.079 (7.93), 8.082 (7.97), 8.155 (11.86), 8.491 (12.97), 8.558 (11.21), 8.724 (13.06), 8.730 (6.02), 8.781 (8.29), 8.783 (8.32).

Example II-106

6-(1-{1-[6-(Difluoromethyl)pyridin-3-yl]propyl}-1H-pyrazol-4-yl)-8-[1-(2,2,2-trifluoroethyl)-1H-pyrazol-4-yl][1,2,4]triazolo[1,5-a]pyridin-2-amine (stereoisomer 1, distomer)

6-(1-{1-[6-(Difluoromethyl)pyridin-3-yl]propyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers) (61 mg, 98% purity) from the previous example was separated by chiral chromatography to yield stereoisomer 1 (22 mg, 99% purity) and stereoisomer 2 (23 mg, 99% purity).

Column: Daicel Chiralpak IB, 5 μm, 250×20 mm; Eluent A: n-heptane; Eluent B: ethanol+0.2% diethylamine; isocratic: 50% A+50% B; flow: 20 ml/min; UV: 210 nm; temperature: 40° C.

Stereoisomer 1: $R^t$=4.892 min and

Stereoisomer 2: $R^t$=7.181 min (cf. next example)

Analytical chiral HPLC method: Column: Daicel Chiralpak IB-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.311 min and

Stereoisomer 2: $R^t$=2.032 min (cf. next example)

LC-MS (method 2): $R^t$=0.89 min; MS (ESIpos): m/z=518 $[M+H]^+$ $^1$H-NMR (400 MHz, DMSO-$d_6$) δ [ppm]: −0.149 (0.93), −0.008 (8.13), 0.008 (8.05), 0.146 (0.86), 0.840 (0.61), 0.858 (1.37), 0.876 (7.30), 0.894 (16.00), 0.912 (7.23), 1.115 (0.90), 1.133 (0.54), 1.242 (0.93), 2.186 (0.97), 2.202 (1.55), 2.220 (2.34), 2.238 (1.83), 2.254 (1.19), 2.323 (1.01), 2.328 (1.40), 2.332 (1.04), 2.366 (1.04), 2.396 (1.22), 2.414 (1.55), 2.419 (1.51), 2.430 (1.51), 2.437 (1.69), 2.454 (1.51), 2.523 (5.07), 2.665 (1.01), 2.670 (1.40), 2.710 (1.01), 5.248 (1.87), 5.271 (5.39), 5.294 (5.11), 5.316 (1.62), 5.510 (2.01), 5.526 (2.37), 5.534 (2.48), 5.549 (1.98), 6.057 (10.43), 6.807 (3.56), 6.943 (7.23), 7.081 (3.13), 7.702 (4.96), 7.722 (5.86), 7.956 (3.52), 7.962 (3.52), 7.977 (2.91), 7.982 (3.02), 8.073

(8.41), 8.077 (8.63), 8.151 (12.19), 8.486 (13.48), 8.553 (11.25), 8.720 (14.24), 8.728 (6.15), 8.774 (9.02), 8.778 (9.10).

Example II-107

6-(1-{1-[6-(Difluoromethyl)pyridin-3-yl]propyl}-1H-pyrazol-4-yl)-8-[1-(2,2,2-trifluoroethyl)-1H-pyrazol-4-yl][1,2,4]triazolo[1,5-a]pyridin-2-amine (stereoisomer 2, eutomer)

The product was isolated in the previous example as second stereoisomer.

LC-MS (method 2): $R^t$=0.89 min; MS (ESIpos): m/z=518 $[M+H]^+$ $^1$H-NMR (400 MHz, DMSO-$d_6$) δ [ppm]: 0.89 (t, 3H), 2.16-2.28 (m, 1H), 2.36-2.48 (m, 1H), 5.28 (q, 2H), 5.53 (dd, 1H), 6.06 (s, 2H), 6.94 (t, 1H), 7.71 (d, 1H), 7.97 (dd, 1H), 8.08 (d, 1H), 8.15 (s, 1H), 8.49 (s, 1H), 8.55 (s, 1H), 8.70-8.74 (m, 2H), 8.78 (d, 1H).

Example II-108

8-[1-(2,2-Difluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers)

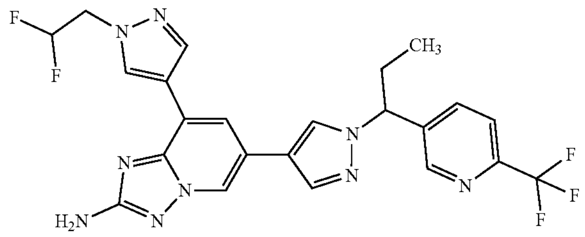 [SMILES: CCC(c1ccc(C(F)(F)F)nc1)n1cc(-c2cc(-c3cnn(CC(F)F)c3)c3nc(N)nn3c2)cn1]

8-Chloro-6-(1-{1-[6-(trifluoromethyl)pyridin-3-yl]propyl}-1H-pyrazol-4-yl)[1,2,4]triazolo[1,5-a]pyridin-2-amine (170 mg, 93% purity, 375 μmol) was reacted with 1-(2,2-difluoroethyl)-4-(4,4,5,5-tetramethyl-1,3,2-dioxaborolan-2-yl)-1H-pyrazole [CAS-RN 1049730-40-6](126 mg, 487 μmol) for 2 h at 90° C. following general procedure B using 0.1 eq. XPhos-Pd-G2 as catalyst.

The reaction mixture was diluted with ethyl acetate (8 ml) and washed with water (2 ml). The aqueous layer was extracted twice with ethyl acetate (8 ml each). The combined organic layers were concentrated in vacuo and the residue purified by column chromatography (Biotage® SNAP KP-NH 28 g cartridge, eluent: cyclohexane/ethyl acetate gradient 90:10 to 0:100) to yield 130 mg (97% purity, 65% yield) of the title compound.

LC-MS (method 2): $R^t$=0.89 min; MS (ESIpos): m/z=518 $[M+H]^+$ $^1$H-NMR (400 MHz, DMSO-$d_6$) δ [ppm]: −0.008 (1.52), 0.008 (1.59), 0.883 (7.05), 0.901 (16.00), 0.919 (7.37), 1.069 (3.49), 2.200 (0.90), 2.217 (1.54), 2.235 (2.31), 2.252 (1.86), 2.269 (1.18), 2.328 (0.88), 2.367 (0.86), 2.405 (1.18), 2.423 (1.56), 2.429 (1.41), 2.440 (1.41), 2.447 (1.63), 2.458 (1.20), 2.464 (1.50), 2.670 (0.94), 2.711 (0.84), 3.918 (0.45), 4.699 (2.12), 4.708 (2.33), 4.738 (4.37), 4.747 (4.50), 4.776 (2.21), 4.785 (1.99), 5.570 (2.21), 5.585 (2.46), 5.594 (2.59), 5.609 (2.12), 6.055 (11.16), 6.272 (0.77), 6.281 (1.56), 6.290 (0.71), 6.409 (1.50), 6.418 (3.08), 6.427 (1.50), 6.547 (0.66), 6.555 (1.37), 6.564 (0.71), 7.915 (4.84), 7.936 (6.90), 8.027 (3.60), 8.032 (3.66), 8.048 (10.65), 8.052 (11.14), 8.164 (12.34), 8.329 (0.47), 8.437 (13.30), 8.561 (11.72), 8.616 (0.45), 8.656 (12.25), 8.762 (8.16), 8.766 (8.57), 8.815 (5.57), 8.820 (5.61).

Example II-109

8-[1-(2,2-Difluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (stereoisomers 1, distomer)

8-[1-(2,2-Difluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers) (115 mg, 97% purity) from the previous example was separated by chiral chromatography to yield stereoisomer 1 (46 mg, 98% purity) and stereoisomer 2 (45 mg, 98% purity).

Column: Daicel Chiralcel OZ-H, 5 μm, 250×20 mm; Eluent A: n-heptane; Eluent B: ethanol+0.2% diethylamine; isocratic: 70% A+30% B; flow: 20 ml/min; UV: 220 nm; temperature: 50° C.

Stereoisomer 1: $R^t$=10.386 min and

Stereoisomer 2: $R^t$=14.515 min (cf. next example)

Analytical chiral HPLC method: Column: Chiraltek OZ-3, 3 μm, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=3.688 min and

Stereoisomer 2: $R^t$=5.413 min (cf. next example)

LC-MS (method 2): $R^t$=0.89 min; MS (ESIpos): m/z=518 $[M+H]^+$ $^1$H-NMR (600 MHz, DMSO-$d_6$) δ [ppm]: 0.892 (7.69), 0.904 (16.00), 0.916 (7.53), 1.161 (0.67), 2.215 (1.06), 2.226 (1.79), 2.238 (2.43), 2.250 (1.97), 2.261 (1.22), 2.420 (1.22), 2.432 (1.66), 2.443 (1.58), 2.447 (1.61), 2.459 (1.45), 2.471 (1.01), 2.654 (0.44), 4.711 (2.20), 4.717 (2.30), 4.737 (4.50), 4.743 (4.45), 4.762 (2.25), 4.768 (1.99), 5.575 (2.38), 5.585 (2.72), 5.591 (2.67), 5.601 (2.25), 6.035 (12.82), 6.325 (1.27), 6.410 (1.45), 6.416 (2.64), 6.422 (1.37), 6.507 (1.17), 20 7.914 (5.13), 7.928 (6.29), 8.034 (4.06), 8.045 (10.67), 8.047 (10.72), 8.158 (11.60), 8.435 (12.25), 8.554 (11.26), 8.656 (11.62), 8.756 (8.75), 8.759 (7.82), 8.815 (6.63).

Example II-110

8-[1-(2,2-Difluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (stereoisomers 2, eutomer)

The product was isolated in the previous example as second stereoisomer.

LC-MS (method 2): $R^t$=0.89 min; MS (ESIpos): m/z=518 $[M+H]^+$ $^1$H-NMR (600 MHz, DMSO-$d_6$) δ [ppm]: 0.90 (t, 3H), 2.20-2.28 (m, 1H), 2.40-2.48 (m, 1H), 4.74 (td, 2H), 5.59 (dd, 1H), 6.04 (s, 2H), 6.42 (tt, 1H), 7.92 (d, 1H), 8.03-8.06 (m, 2H), 8.16 (s, 1H), 8.43 (s, 1H), 8.55 (s, 1H), 8.66 (s, 1H), 8.76 (d, 1H), 8.82 (d, 1H).

Example II-111

8-[1-(2,2,2-trifluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers)

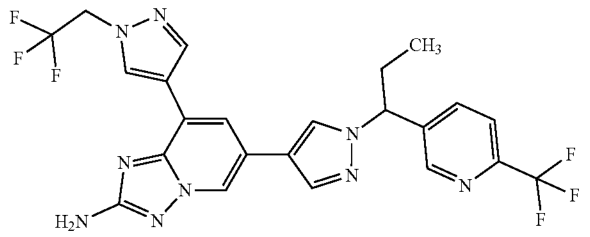 [SMILES: CCC(c1ccc(C(F)(F)F)nc1)n1cc(-c2cc(-c3cnn(CC(F)(F)F)c3)c3nc(N)nn3c2)cn1]

6-Bromo-8-[1-(2,2,2-trifluoroethyl)-1H-pyrazol-4-yl][1,2,4]triazolo[1,5-a]pyridin-2-amine (200 mg, 554 μmol) was reacted with 5-{1-[4-(4,4,5,5-tetramethyl-1,3,2-dioxaborolan-2-yl)-1H-pyrazol-1-yl]propyl}-2-(trifluoromethyl)pyridine (261 mg, 97% purity, 665 μmol) for 2 h at 90° C. following general procedure C using 0.1 eq. catalyst. The reaction mixture was diluted with ethyl acetate and filtered through a hydrophobic phase separation filter. The solvents were removed in vacuo and the residue purified by column chromatography (Biotage® SNAP KP-NH 28 g cartridge, eluent: cyclohexane/ethyl acetate gradient 90:10 to 0:100) to yield 200 mg (97% purity, 65% yield) of the title compound.

LC-MS (method 2): $R^t$=0.96 min; MS (ESIpos): m/z=536 $[M+H]^+$ $^1$H-NMR (400 MHz, DMSO-$d_6$) δ [ppm]: −0.008 (2.05), 0.008 (1.98), 0.883 (6.99), 0.902 (16.00), 0.920 (7.28), 1.069 (9.51), 2.201 (0.88), 2.217 (1.51), 2.235 (2.33), 2.253 (1.86), 2.269 (1.23), 2.323 (1.04), 2.328 (1.35), 2.333 (1.01), 2.367 (1.20), 2.405 (1.23), 2.423 (1.57), 2.440 (1.51), 2.447 (1.76), 2.464 (1.67), 2.670 (1.32), 2.710 (1.13), 3.917 (1.39), 5.249 (2.08), 5.272 (5.70), 5.295 (5.32), 5.318 (1.70), 5.572 (2.14), 5.587 (2.49), 5.595 (2.55), 5.610 (2.05), 6.061 (11.09), 6.905 (0.66), 6.923 (0.88), 6.940 (0.69), 7.787 (0.79), 7.803 (0.76), 7.915 (4.88), 7.936 (6.90), 8.028 (3.53), 8.032 (3.59), 8.053 (2.58), 8.076 (8.57), 8.080 (8.69), 8.169 (12.44), 8.375 (1.92), 8.428 (0.76), 8.444 (0.79), 8.484 (13.70), 8.562 (11.46), 8.685 (1.80), 8.720 (12.41), 8.780 (9.10), 8.784 (9.17), 8.816 (5.73), 8.820 (5.76).

Example II-112

8-[1-(2,2,2-trifluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (stereoisomer 1, distomer)

8-[1-(2,2,2-trifluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (mixture of enantiomers) (200 mg, 97% purity) of the previous example was separated by chiral chromatography to yield stereoisomer 1 (96 mg, 90% purity) and stereoisomer 2 (86 mg, 100% purity).

Column: Chiralart Cellulose SB, 5 μm, 250×20 mm; Eluent A: n-heptane; Eluent B: ethanol+0.2% diethylamine; isocratic: 50% A+50% B; flow: 15 ml/min; UV: 220 nm; temperature: 40° C.

Stereoisomer 1: $R^t$=8.75 min and

Stereoisomer 2: $R^t$=13.5 min (cf. next example)

Analytical chiral HPLC method: Column: Phenomenex cellulose, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.164 min and

Stereoisomer 2: $R^t$=2.745 min (cf. next example)

LC-MS (method 1): $R^t$=1.81 min; MS (ESIpos): m/z=536 $[M+H]^+$ $^1$H-NMR (400 MHz, DMSO-$d_6$) δ [ppm]: 0.008 (0.65), 0.884 (6.98), 0.902 (16.00), 0.920 (7.33), 1.157 (0.65), 2.202 (0.90), 2.218 (1.45), 2.236 (2.24), 2.253 (1.74), 2.270 (1.15), 2.329 (0.75), 2.368 (0.45), 2.407 (1.10), 2.424 (1.50), 2.430 (1.35), 2.441 (1.35), 2.447 (1.55), 2.459 (1.10), 2.465 (1.35), 2.671 (0.80), 2.712 (0.45), 5.250 (1.89), 5.273 (5.48), 5.296 (5.18), 5.318 (1.64), 5.572 (2.09), 5.587 (2.44), 5.596 (2.49), 5.611 (2.09), 6.062 (10.57), 7.916 (4.98), 7.937 (7.03), 8.029 (3.54), 8.034 (3.59), 8.049 (2.54), 8.054 (2.59), 8.077 (8.67), 8.081 (8.97), 8.170 (12.86), 8.486 (14.26), 8.563 (11.61), 8.721 (12.76), 8.781 (9.42), 8.785 (9.57), 8.817 (5.78), 8.821 (5.78).

Example II-113

8-[1-(2,2,2-trifluoroethyl)-1H-pyrazol-4-yl]-6-(1-{1-[6-(trifluoromethyl)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 1): $R^t$=1.81 min; MS (ESIpos): m/z=536 $[M+H]^+$ $^1$H-NMR (400 MHz, DMSO-$d_6$) δ [ppm]: 0.90 (t, 3H), 2.18-2.29 (m, 1H), 2.38-2.48 (m, 1H), 5.28 (q, 2H), 5.59 (dd, 1H), 6.06 (s, 2H), 7.93 (d, 1H), 8.04 (dd, 1H), 8.08 (d, 1H), 8.17 (s, 1H), 8.49 (s, 1H), 8.56 (s, 1H), 8.72 (s, 1H), 8.78 (d, 1H), 8.82 (d, 1H).

Example II-114

5-[1-(2,2,2-Trifluoroethyl)-1H-pyrazol-4-yl]-7-(1-{1-[6-(trifluoromethoxy)pyridin-3-yl]propyl}-1H-pyrazol-4-yl)[1,2,4]triazolo[1,5-a]pyridin-2-amine (mixture of enantiomers)

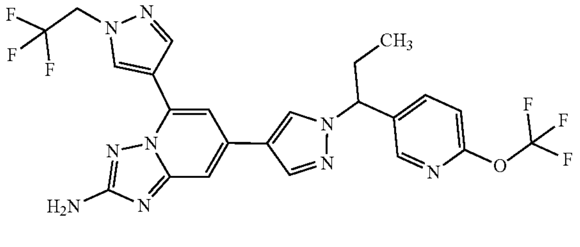 [SMILES: CCC(c1ccc(OC(F)(F)F)nc1)n1cc(-c2cc(-c3cnn(CC(F)(F)F)c3)n3nc(N)nc3c2)cn1]

7-Chloro-5-[1-(2,2,2-trifluoroethyl)-1H-pyrazol-4-yl][1,2,4]triazolo[1,5-a]pyridin-2-amine (110 mg, 347 μmol) was reacted with 5-{1-[4-(4,4,5,5-tetramethyl-1,3,2-dioxaborolan-2-yl)-1H-pyrazol-1-yl]propyl}-2-(trifluoromethoxy)pyridine (179 mg, 452 μmol) for 2 h at 80° C. following general procedure C using 0.10 eq. catalyst. The reaction mixture was directly purified by column chromatography (Biotage® SNAP Ultra 25 g cartridge, eluent: dichloromethane/methanol gradient 100:0 to 85:15). The product was further purified by preparative HPLC (Chromatorex C18, 10 m, 125×30 mm; eluent: water (0.1% formic acid)/acetonitrile gradient 90:10 to 5:95) to yield 77.0 mg (100% purity, 40% yield) of the title compound.

LC-MS (method 2): $R^t$=0.96 min; MS (ESIpos): m/z=552 $[M+H]^+$ $^1$H-NMR (400 MHz, DMSO-$d_6$) δ [ppm]: −0.008 (2.31), 0.008 (2.61), 0.804 (0.46), 0.822 (0.95), 0.840 (0.57), 0.861 (7.02), 0.879 (16.00), 0.897 (7.38), 2.174 (1.00), 2.190 (1.68), 2.208 (2.44), 2.225 (1.97), 2.242 (1.20), 2.369 (0.59), 2.390 (1.22), 2.408 (1.63), 2.413 (1.42), 2.425 (1.51), 2.431 (1.61), 2.443 (1.21), 2.448 (1.38), 2.466 (0.97), 5.304 (2.04), 5.327 (5.86), 5.350 (5.55), 5.372 (1.76), 5.489 (2.22), 5.505 (2.61), 5.513 (2.81), 5.528 (2.21), 6.027 (10.52), 7.301 (6.47), 7.323 (6.75), 7.508 (8.80), 7.513 (9.08), 7.648 (9.05), 7.652 (8.49), 7.669 (0.52), 8.019 (4.10), 8.025 (4.38), 8.040 (3.85), 8.046 (4.15), 8.070 (0.74), 8.235 (0.77), 8.256 (12.39), 8.409 (0.42), 8.415 (0.48), 8.428 (6.49), 8.435 (6.45), 8.514 (0.67), 8.634 (14.14), 8.681 (11.27), 8.977 (12.92).

Example II-115

5-[1-(2,2,2-Trifluoroethyl)-1H-pyrazol-4-yl]-7-(1-{1-[6-(trifluoromethoxy)pyridin-3-yl]propyl}-1H-pyrazol-4-yl)[1,2,4]triazolo[1,5-a]pyridin-2-amine (stereoisomer 1, distomer)

5-[1-(2,2,2-Trifluoroethyl)-1H-pyrazol-4-yl]-7-(1-{1-[6-(trifluoromethoxy)pyridin-3-yl]propyl}-1H-pyrazol-4-yl)[1,2,4]triazolo[1,5-a]pyridin-2-amine (mixture of enantiomers) (66 mg, 100% purity) from the previous example was separated by chiral chromatography to yield stereoisomer 1 25 (42 mg, 100% purity) and stereoisomer 2 (37 mg, 99% purity).

Column: Daicel Chiralcel OD-H, 5 μm, 250×20 mm; Eluent A: n-heptane; Eluent B: ethanol+0.2% diethylamine; isocratic: 80% A+20% B; flow: 20 ml/min; UV: 220 nm; temperature: 40° C.

Stereoisomer 1: $R^t$=10.70 min and

Stereoisomer 2: $R^t$=14.25 min (cf. next example)

Analytical chiral HPLC method: Column: Phenomenex cellulose, 3 μm, 50×4.6 mm; Eluent A: n-heptane; Eluent B: ethanol+0.2% diethylamine; isocratic: 80% A+20% B; flow: 1 ml/min; UV: 220 nm.

Stereoisomer 1: $R^t$=2.363 min and

Stereoisomer 2: $R^t$=3.205 min (cf. next example)

Stereoisomer 1: The stereochemical configuration of the methine carbon atom bonded to the pyrazole was (S).

LC-MS (method 2): $R^t$=0.98 min; MS (ESIpos): m/z=552 $[M+H]^+$ $^1$H-NMR (400 MHz, DMSO-$d_6$) δ [ppm]: −0.149 (0.75), −0.008 (5.71), 0.008 (6.13), 0.146 (0.65), 0.860 (7.16), 0.878 (16.00), 0.896 (7.30), 1.087 (0.42), 1.102 (0.47), 1.140 (0.47), 1.158 (0.94), 1.177 (0.51), 1.235 (0.56), 2.172 (0.89), 2.188 (1.54), 2.206 (2.29), 2.224 (1.87), 2.240 (1.12), 2.324 (0.89), 2.328 (1.31), 2.333 (1.03), 2.367 (1.87), 2.388 (1.08), 2.406 (1.40), 2.411 (1.31), 2.422 (1.31), 2.429 (1.50), 2.441 (1.12), 2.446 (1.36), 2.464 (1.08), 2.524 (5.47), 2.561 (1.82), 2.666 (1.12), 2.671 (1.50), 2.675 (1.08), 2.711 (1.68), 5.302 (1.96), 5.325 (5.61), 5.348 (5.33), 5.370 (1.68), 5.487 (2.20), 5.503 (2.57), 5.511 (2.67), 5.526 (2.15), 6.026 (8.37), 7.300 (6.22), 7.322 (6.55), 7.506 (8.51), 7.510 (8.98), 7.646 (8.47), 7.650 (8.09), 8.016 (4.07), 8.023 (4.21), 8.038 (3.84), 8.044 (4.07), 8.254 (12.12), 8.426 (6.22), 8.432 (6.27), 8.631 (13.47), 8.679 (11.32), 8.974 (12.35).

Example II-116

5-[1-(2,2,2-Trifluoroethyl)-1H-pyrazol-4-yl]-7-(1-{1-[6-(trifluoromethoxy)pyridin-3-yl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 2): $R^t$=0.98 min; MS (ESIpos): m/z=552 $[M+H]^+$ $^1$H-NMR (400 MHz, DMSO-$d_6$) δ [ppm]: 0.88 (t, 3H), 2.14-2.27 (m, 1H), 2.38-2.47 (m, 1H), 5.34 (q, 2H), 5.51 (dd, 1H), 6.03 (s, 2H), 7.31 (d, 1H), 7.51 (d, 1H), 7.65 (d, 1H), 8.03 (dd, 1H), 8.25 (s, 1H), 8.43 (d, 1H), 8.63 (s, 1H), 8.68 (s, 1H), 8.97 (s, 1H).

Example II-117

6-(1-{Tetrahydro-2H-pyran-4-yl[6-(trifluoromethyl)pyridin-3-yl]methyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers)

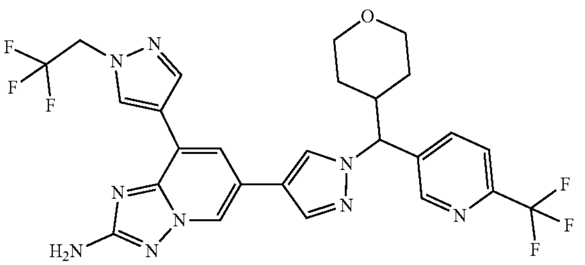 [SMILES: Nc1nc2c(-c3cnn(CC(F)(F)F)c3)cc(-c3cnn(C(c4ccc(C(F)(F)F)nc4)C4CCOCC4)c3)cn2n1]

6-Bromo-8-[1-(2,2,2-trifluoroethyl)-1H-pyrazol-4-yl][1,2,4]triazolo[1,5-a]pyridin-2-amine (150 mg, 415 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (236 mg, 540 μmol) for 2 h at 80° C. following general procedure B using 0.1 eq. XPhos-Pd-G2 as catalyst. The reaction mixture was diluted with ethyl acetate and filtered through a hydrophobic phase separation filter. The filtrate was concentrated in vacuo and the residue purified by column chromatography (Biotage® SNAP KP-NH 28 g cartridge, eluent: cyclohexane/ethyl acetate gradient 90:10 to 0:100) to yield 220 mg (97% purity, 87% yield) of the title compound.

LC-MS (method 1): $R^t$=1.72 min; MS (ESIpos): m/z=592 $[M+H]^+$ $^1$H-NMR (600 MHz, DMSO-$d_6$) δ [ppm]: 0.005 (0.79), 1.074 (0.63), 1.088 (1.68), 1.108 (1.91), 1.177 (0.70), 1.243 (1.54), 1.262 (2.04), 1.301 (0.67), 1.309 (0.74), 1.322 (1.55), 1.329 (1.75), 1.343 (2.24), 1.351 (1.89), 1.362 (1.96), 1.376 (1.34), 1.382 (1.22), 1.396 (0.58), 1.403 (0.47), 1.989 (1.22), 2.426 (0.45), 2.474 (0.46), 2.521 (0.50), 2.524 (0.49), 2.575 (1.01), 2.655 (0.41), 2.730 (0.64), 2.742 (1.03), 2.748 (1.67), 2.755 (1.03), 2.761 (1.04), 2.767 (1.63), 2.773 (0.93), 2.785 (0.62), 3.256 (1.41), 3.259 (1.58), 3.266 (1.58), 3.275 (3.53), 3.278 (4.50), 3.318 (1.51), 3.321 (1.22), 3.332 (1.12), 3.810 (1.86), 3.826 (1.71), 3.846 (1.80), 3.850 (1.82), 3.869 (1.62), 5.254 (2.16), 5.270 (5.80), 5.285 (5.37), 5.300 (1.62), 5.384 (5.47), 5.401 (5.25), 6.042 (13.13), 7.947 (6.51), 7.961 (6.84), 8.038 (10.51), 8.041 (10.45), 8.164 (14.05), 8.305

(3.55), 8.308 (3.49), 8.318 (3.24), 8.321 (3.11), 8.474 (16.00), 8.507 (12.87), 8.716 (14.45), 8.751 (11.42), 8.754 (11.21), 8.980 (6.49), 8.982 (6.33).

Example II-118

6-(1-{Tetrahydro-2H-pyran-4-yl[6-(trifluoromethyl) pyridin-3-yl]methyl}-1H-pyrazol-4-yl)-8-[1-(2,2,2-trifluoroethyl)-1H-pyrazol-4-yl][1,2,4]triazolo[1,5-a] pyridin-2-amine (stereoisomer 1, eutomer)

6-(1-{Tetrahydro-2H-pyran-4-yl[6-(trifluoromethyl)pyridin-3-yl]methyl}-1H-pyrazol-4-yl)-8-[1-(2,2,2-trifluoroethyl)-1H-pyrazol-4-yl][1,2,4]triazolo[1,5-a]pyridin-2-amine (mixture of enantiomers) (218 mg, 97% purity) from the previous example was separated by chiral chromatography to yield stereoisomer 1 (65 mg, 99% purity) and stereoisomer 2 (67 mg, 99% purity).

Column: Daicel Chiralpak IB, 5 µm, 250×20 mm; Eluent A: n-heptane; Eluent B: ethanol+0.2% diethylamine; isocratic: 60% A+40% B; flow: 20 ml/min; UV: 210 nm; temperature: 40° C.

Stereoisomer 1: $R^t$=6.831 min and

Stereoisomer 2: $R^t$=9.354 min (cf. next example)

Analytical chiral HPLC method: Column: Daicel Chiralpak IB-3, 3 µm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.479 min and

Stereoisomer 2: $R^t$=1.893 min (cf. next example)

Stereoisomer 1: The stereochemical configuration of the methine carbon atom bonded to the pyrazole was (S).

LC-MS (method 2): $R^t$=0.93 min; MS (ESIpos): m/z=592 $[M+H]^+$ $^1$H-NMR (600 MHz, DMSO-$d_6$) δ [ppm]: 1.07-1.12 (m, 1H), 1.25 (m, 1H), 1.29-1.41 (m, 2H), 2.72-2.79 (m, 1H), 3.25-3.33 (m, 2H), 3.79-3.88 (m, 2H), 5.27 (d, 2H), 5.39 (d, 1H), 6.04 (s, 2H), 7.95 (d, 1H), 8.04 (d, 1H), 8.16 (s, 1H), 8.31 (dd, 1H), 8.47 (s, 1H), 8.50 (s, 1H), 8.71 (s, 1H), 8.75 (d, 1H), 8.98 (d, 1H).

Example II-119

6-(1-{Tetrahydro-2H-pyran-4-yl[6-(trifluoromethyl) pyridin-3-yl]methyl}-1H-pyrazol-4-yl)-8-[1-(2,2,2-trifluoroethyl)-1H-pyrazol-4-yl][1,2,4]triazolo[1,5-a] pyridin-2-amine (stereoisomer 2, distomer)

The product was isolated in the previous example as second stereoisomer.

LC-MS (method 2): $R^t$=0.93 min; MS (ESIpos): m/z=592 $[M+H]^+$ $^1$H-NMR (600 MHz, DMSO-$d_6$) δ [ppm]: 0.846 (0.50), 0.858 (0.71), 1.087 (1.89), 1.107 (2.20), 1.137 (0.71), 1.239 (2.08), 1.260 (2.51), 1.300 (0.76), 1.307 (0.78), 1.320 (1.70), 1.328 (1.91), 1.341 (2.48), 1.350 (2.15), 1.361 (2.27), 1.37-3 (1.56), 1.380 (1.42), 1.394 (0.69), 2.386 (0.47), 2.424 (0.73), 2.571 (1.28), 2.613 (0.50), 2.653 (0.73), 2.728 (0.69), 2.747 (1.84), 2.766 (1.80), 2.784 (0.64), 3.257 (1.89), 3.263 (1.70), 3.277 (4.80), 3.317 (2.51), 3.328 (2.10), 3.734 (0.73), 3.810 (2.08), 3.825 (1.94), 3.850 (2.08), 3.868 (1.91), 3.896 (0.50), 5.252 (2.15), 5.267 (6.17), 5.283 (5.91), 5.298 (1.89), 5.382 (5.65), 5.400 (5.53), 6.038 (14.04), 7.946 (6.78), 7.960 (7.18), 8.036 (9.74), 8.039 (10.00), 8.161 (14.39), 8.303 (3.78), 8.306 (3.78), 8.316 (3.57), 8.472 (16.00), 8.505 (13.42), 8.713 (14.53), 8.748 (10.30), 8.751 (10.47), 8.978 (7.04), 8.981 (7.07).

Example II-120

6-{1-[1-(Oxetan-3-yl)piperidin-4-yl]-1H-pyrazol-4-yl}-8-[1-(2,2,2-trifluoroethyl)-1H-pyrazol-4-yl][1,2,4]triazolo[1,5-a]pyridin-2-amine

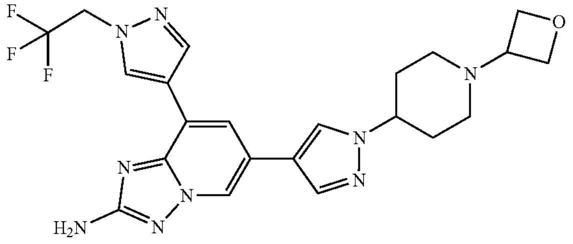 [SMILES: Nc1nc2c(-c3cnn(CC(F)(F)F)c3)cc(-c3cnn(C4CCN(C5COC5)CC4)c3)cn2n1]

6-Bromo-8-[1-(2,2,2-trifluoroethyl)-1H-pyrazol-4-yl][1,2,4]triazolo[1,5-a]pyridin-2-amine (60.0 5 mg, 166 µmol) was reacted with 1-(oxetan-3-yl)-4-[4-(4,4,5,5-tetramethyl-1,3,2-dioxaborolan-2-yl)-1H-pyrazol-1-yl]piperidine (74.7 mg, 224 µmol) for 2 h at 80° C. following general procedure C using 0.15 eq. catalyst. The reaction mixture was directly purified by column chromatography (Biotage® SNAP Ultra 10 g cartridge, eluent: dichloromethane/methanol gradient 100:0 to 85:15). The product was further purified by preparative HPLC (Chromatorex C18, 10 µm, 125×30 mm; eluent: water (0.1% formic acid)/acetonitrile gradient 90:10 to 5:95) to yield 68.0 mg (97% purity, 81% yield) of the title compound.

LC-MS (method 2): $R^t$=0.49 min; MS (ESIpos): m/z=488 $[M+H]^+$ $^1$H-NMR (400 MHz, DMSO-$d_6$) δ [ppm]: 1.92-2.13 (m, 6H), 2.76-2.86 (m, 2H), 3.42-3.50 (m, 1H), 4.13-4.23 (m, 1H), 4.46 (t, 2H), 4.56 (t, 2H), 5.29 (q, 2H), 6.05 (s, 2H), 8.06 (s, 1H), 8.08 (d, 1H), 8.44 (s, 1H), 8.49 (s, 1H), 8.72 (s, 1H), 8.75 (d, 1H).

Example II-121

7-(1-Benzyl-1H-pyrazol-4-yl)-5-[1-(difluoromethyl)-1H-pyrazol-4-yl][1,2,4]triazolo[1,5-a]pyridin-2-amine

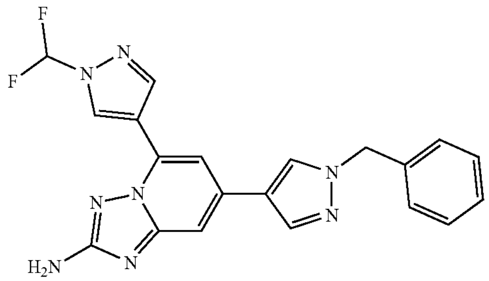 [SMILES: Nc1nc2cc(-c3cnn(Cc4ccccc4)c3)cc(-c3cnn(C(F)F)c3)n2n1]

7-(1-Benzyl-1H-pyrazol-4-yl)-5-chloro[1,2,4]triazolo[1,5-a]pyridin-2-. amine (75.0 mg, 231 µmol) was reacted with 1-(difluoromethyl)-4-(4,4,5,5-tetramethyl-1,3,2-dioxaborolan-2-yl)-1H-pyrazole [CAS-RN 1206640-82-5](73.3 mg, 300 µmol) for 2 h at 80° C. following general procedure C using 0.1 eq. catalyst. Additional 0.1 eq. catalyst was added and stirring was continued for 2 h at 90° C. The reaction mixture was diluted with ethyl acetate (5 ml) and filtered through a hydrophobic phase separation filter which was rinsed with ethyl acetate (20 ml). The combined filtrates were concentrated in vacuo. The residue was purified by column chromatography (Biotage® SNAP KP-NH 11 g cartridge, eluent: cyclohexane/ethyl acetate gradient 50:50 to 0:100) and then by preparative HPLC (Chromatorex C18, 10 μm, 125×30 mm; eluent: water/acetonitrile gradient 90:10 to 5:95) to yield 34.2 mg (100% purity, 36% yield) of the title compound.

LC-MS (method 1): $R^t$=1.57 min; MS (ESIpos): m/z=407 $[M+H]^+$ $^1$H-NMR (500 MHz, DMSO-$d_6$) δ [ppm]: 5.40 (s, 2H), 6.12 (s, 2H), 7.27-7.41 (m, 5H), 7.56 (d, 1H), 7.75 (d, 1H), 8.01 (t, 1H), 8.24 (s, 1H), 8.58 (s, 1H), 8.84 (s, 1H), 9.30 (s, 1H).

Example II-122

7-(1-Benzyl-1H-pyrazol-4-yl)-5-[1-(1,1,1-trifluoropropan-2-yl)-1H-pyrazol-4-yl][1,2,4]triazolo[1,5-a]pyridin-2-amine (mixture of enantiomers)

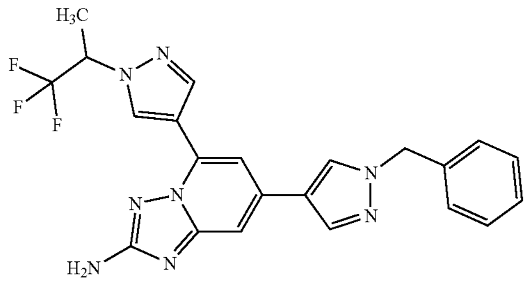 [SMILES: CC(n1cc(-c2cc(-c3cnn(Cc4ccccc4)c3)cc3nc(N)nn23)cn1)C(F)(F)F]

7-(1-Benzyl-1H-pyrazol-4-yl)-5-chloro[1,2,4]triazolo[1,5-a]pyridin-2-amine (100 mg, 100% purity, 308 μmol) was reacted with 4-(4,4,5,5-tetramethyl-1,3,2-dioxaborolan-2-yl)-1-(1,1,1-trifluoropropan-2-yl)-1H-pyrazole (232 mg, 52% purity, 416 μmol) for 2 h at 80° C. following general procedure C using 0.15 eq. catalyst. The reaction mixture was directly purified by column chromatography (Biotage® SNAP Ultra 10 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 105 mg (100% purity, 75% yield) of the title compound.

LC-MS (method 2): $R^t$=0.86 min; MS (ESIpos): m/z=453 $[M+H]^+$ $^1$H-NMR (600 MHz, DMSO-$d_6$) δ [ppm]: 1.76 (d, 3H), 5.39 (s, 2H), 5.57-5.66 (m, 1H), 6.02 (br s, 2H), 7.26-7.34 (m, 3H), 7.35-7.40 (m, 2H), 7.48 (br s, 1H), 7.64 (s, 1H), 8.21 (s, 1H), 8.57 (s, 1H), 8.64 (s, 1H), 9.01 (s, 1H).

Example II-123

3-{4-[2-Amino-7-(1-benzyl-1H-pyrazol-4-yl)[1,2,4]triazolo[1,5-a]pyridin-5-yl]-1H-pyrazol-1-yl}-4,4,4-trifluorobutanenitrile (mixture of enantiomers)

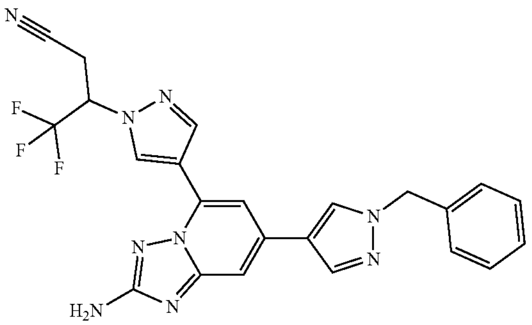 [SMILES: N#CCC(n1cc(-c2cc(-c3cnn(Cc4ccccc4)c3)cc3nc(N)nn23)cn1)C(F)(F)F]

7-(1-Benzyl-1H-pyrazol-4-yl)-5-chloro[1,2,4]triazolo[1,5-a]pyridin-2-amine (105 mg, 325 μmol) was reacted with 4,4,4-trifluoro-3-[4-(4,4,5,5-tetramethyl-1,3,2-dioxaborolan-2-yl)-1H-pyrazol-1-yl]butanenitrile (140 mg, 95% purity, 422 μmol) for 3 h at 80° C. following general procedure C using 0.15 eq. catalyst. The reaction mixture was diluted with ethyl acetate (10 ml) and filtered. The filter was rinsed with ethyl acetate (10 ml) and the combined organic layers were filtered through a hydrophobic phase separation filter. The solution was concentrated in vacuo and the crude product was purified by column chromatography (Biotage® SNAP KP-NH 11 g cartridge, eluent: cyclohexane/ethyl acetate gradient 80:20 to 0:100, then ethyl acetate/2-propanol 80:20). The product was further purified by preparative HPLC (Chromatorex C18, 10 μm, 125×30 mm; eluent: water (0.5% formic acid)/acetonitrile gradient 95:5 to 50:50) to yield 43.2 mg (96% purity, 27% yield) of the title compound.

LC-MS (method 1): $R^t$=1.63 min; MS (ESIpos): m/z=478 $[M+H]^+$ $^1$H-NMR (400 MHz, DMSO-$d_6$) δ [ppm]: 3.62 (dd, 1H), 3.71 (dd, 1H), 5.39 (s, 2H), 6.02 (s, 2H), 6.17-6.25 (m, 1H), 7.27-7.34 (m, 3H), 7.34-7.40 (m, 2H), 7.52 (d, 1H), 7.67 (d, 1H), 8.22 (s, 1H), 8.57 (s, 1H), 8.72 (s, 1H), 9.11 (s, 1H).

Example II-124

7-(1-Benzyl-1H-pyrazol-4-yl)-5-{1-[(2,2-difluorocyclopropyl)methyl]-1H-pyrazol-4-yl}[1,2,4]triazolo[1,5-a]pyridin-2-amine (mixture of enantiomers)

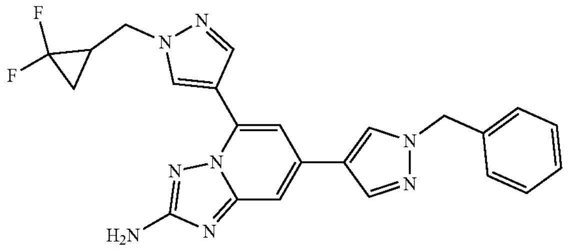 [SMILES: Nc1nc2cc(-c3cnn(Cc4ccccc4)c3)cc(-c3cnn(CC4CC4(F)F)c3)n2n1]

7-(1-Benzyl-1H-pyrazol-4-yl)-5-chloro[1,2,4]triazolo[1,5-a]pyridin-2-amine (80.0 mg, 100% purity, 246 μmol) was reacted with 1-[(2,2-difluorocyclopropyl)methyl]-4-(4,4,5,5-tetramethyl-1,3,2-dioxaborolan-2-yl)-1H-pyrazole [CAS-RN 2101930-90-7](111 mg, 85% purity, 333 μmol) 5 for 2 h at 80° C. following general procedure C using 0.15 eq. catalyst. The reaction mixture was directly purified by column chromatography (Biotage® SNAP Ultra 10 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 48.0 mg (100% purity, 44% yield) of the title compound.

LC-MS (method 2): $R^t$=0.83 min; MS (ESIpos): m/z=447 $[M+H]^+$ $^1$H-NMR (400 MHz, DMSO-$d_6$) δ [ppm]: 1.50-1.60 (m, 1H), 1.69-1.79 (m, 1H), 2.25-2.39 (m, 1H), 4.32-4.43 (m, 2H), 5.39 (s, 2H), 5.98 (s, 2H), 7.27-7.34 (m, 3H), 7.35-7.40 (m, 2H), 7.45 (d, 1H), 7.58 (d, 1H), 8.20 (s, 1H), 8.55 (s, 1H), 8.56 (s, 1H), 8.87 (s, 1H).

Example II-125

7-(1-Benzyl-1H-pyrazol-4-yl)-5-[1-(tetrahydrofuran-3-yl)-1H-pyrazol-4-yl][1,2,4]triazolo[1,5-a]pyridin-2-amine (mixture of enantiomers)

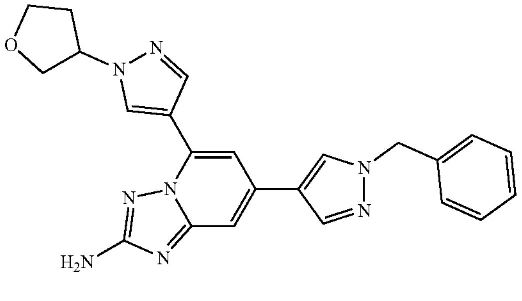 [SMILES: Nc1nc2cc(-c3cnn(Cc4ccccc4)c3)cc(-c3cnn(C4CCOC4)c3)n2n1]

7-(1-Benzyl-1H-pyrazol-4-yl)-5-chloro[1,2,4]triazolo[1,5-a]pyridin-2-amine (70.0 mg, 100% purity, 216 μmol) was reacted with 1-(tetrahydrofuran-3-yl)-4-(4,4,5,5-tetramethyl-1,3,2-dioxaborolan-2-yl)-1H-pyrazole [CAS-RN 1029715-63-6](80.9 mg, 291 μmol) for 2 h at 80° C. following general procedure C using 0.15 eq. catalyst. The reaction mixture was directly purified by column chromatography (Biotage® SNAP Ultra 10 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 46.0 mg (100% purity, 50% yield) of the title compound.

LC-MS (method 2): R, =0.74 min; MS (ESIpos): m/z=427 $[M+H]^+$ $^1$H-NMR (600 MHz, DMSO-$d_6$) δ [ppm]: 2.29-2.35 (m, 1H), 2.42-2.49 (m, 1H), 3.86 (td, 1H), 3.98 (dd, 1H), 4.02-4.07 (m, 2H), 5.13-5.18 (m, 1H), 5.39 (s, 2H), 6.02 (s, 2H), 7.28-7.33 (m, 3H), 7.35-7.39 (m, 2H), 7.45 (d, 1H), 7.59 (d, 1H), 8.21 (s, 1H), 8.55 (s, 1H), 8.56 (s, 1H), 8.87 (s, 1H).

Example II-126

7-(1-Benzyl-1H-pyrazol-4-yl)-5-[1-(tetrahydro-2H-pyran-4-yl)-1H-pyrazol-4-yl][1,2,4]triazolo[1,5-a]pyridin-2-amine

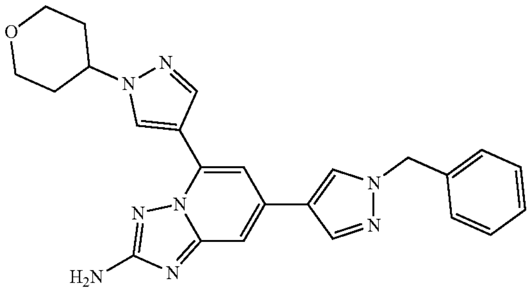 [SMILES: Nc1nc2cc(-c3cnn(Cc4ccccc4)c3)cc(-c3cnn(C4CCOCC4)c3)n2n1]

7-(1-Benzyl-1H-pyrazol-4-yl)-5-chloro[1,2,4]triazolo[1,5-a]pyridin-2-amine (75.0 mg, 231 μmol) was reacted with 1-(tetrahydro-2H-pyran-4-yl)-4-(4,4,5,5-tetramethyl-1,3,2-dioxaborolan-2-yl)-1H-pyrazole [CAS-RN 1040377-03-4] (83.5 mg, 300 μmol) for 2.5 h at 90° C. following general procedure C using 0.15 eq. catalyst. The reaction mixture was diluted with ethyl acetate and filtered through a hydrophobic phase separation filter. The filtrate was concentrated in vacuo and the residue was purified by column chromatography (Biotage® SNAP KP-NH 11 g cartridge, eluent: cyclohexane/ethyl acetate/2-propanol gradient 70:30:0 to 0:100:0 to 0:80:20). The product was further purified by preparative HPLC (Chromatorex C18, 10 μm, 125×30 mm; eluent: water/acetonitrile gradient 95:5 to 50:50) to yield 44.5 mg (100% purity, 44% yield) of the title compound.

LC-MS (method 1): $R^t$=1.41 min; MS (ESIpos): m/z=441 $[M+H]^+$ $^1$H-NMR (400 MHz, DMSO-$d_6$) δ [ppm]: 1.94-2.11 (m, 4H), 3.51 (td, 2H), 3.97-4.04 (m, 2H), 4.48-4.58 (m, 1H), 5.39 (s, 2H), 6.00 (s, 2H), 7.27-7.40 (m, 5H), 7.44 (d, 1H), 7.58 (d, 1H), 8.20 (d, 1H), 8.54 (s, 1H), 8.55 (s, 1H), 8.89 (s, 1H).

Example II-127

7-{1-[(1S)-1-Phenylpropyl]-1H-pyrazol-4-yl}-5-[1-(2,2,2-trifluoroethyl)-1H-pyrazol-4-yl][1,2,4]triazolo[1,5-a]pyridin-2-amine

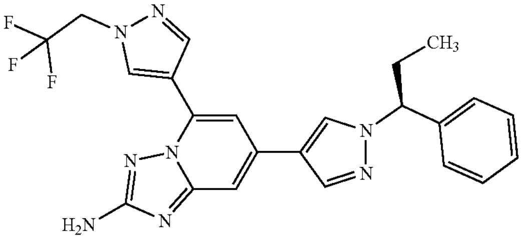 [SMILES: CC[C@@H](c1ccccc1)n1cc(-c2cc(-c3cnn(CC(F)(F)F)c3)n3nc(N)nc3c2)cn1]

7-Chloro-5-[1-(2,2,2-trifluoroethyl)-1H-pyrazol-4-yl][1,2,4]triazolo[1,5-a]pyridin-2-amine (60.0 mg, 84% purity, 159 μmol) was reacted with 1-[(1S)-1-phenylpropyl]-4-(4,4,5,5-tetramethyl-1,3,2-dioxaborolan-2-yl)-1H-pyrazole (67.1 mg, 215 μmol) for 1 h at 80° C. following general procedure C using 0.10 eq. catalyst. The reaction mixture was directly purified by column chromatography (Biotage® SNAP Ultra 10 g cartridge, eluent: dichloromethane/methanol gradient 100:0 to 85:15) and in a second step by preparative HPLC (Chromatorex C18, 10 μm, 125×30 mm; eluent: water (0.1% formic acid)/acetonitrile gradient 90:10 to 5:95 to yield 18.0 mg (98% purity, 24% yield) of the title compound.

LC-MS (method 2): $R^t$=1.05 min; MS (ESIpos): m/z=467 $[M+H]^+$ $^1$H-NMR (500 MHz, DMSO-$d_6$) δ [ppm]: 0.88 (t, 3H), 2.13-2.23 (m, 1H), 2.35-2.44 (m, 1H), 5.29-5.37 (m, 3H), 6.00 (s, 2H), 7.26-7.31 (m, 1H), 7.33-7.40 (m, 4H), 7.50 (d, 1H), 7.65 (d, 1H), 8.21 (s, 1H), 8.64 (s, 1H), 8.66 (s, 1H), 8.97 (s, 1H).

Example II-128

7-{1-[(1S)-1-(4-Fluorophenyl)propyl]-1H-pyrazol-4-yl}-5-[1-(2,2,2-trifluoroethyl)-1H-pyrazol-4-yl][1,2,4]triazolo[1,5-a]pyridin-2-amine

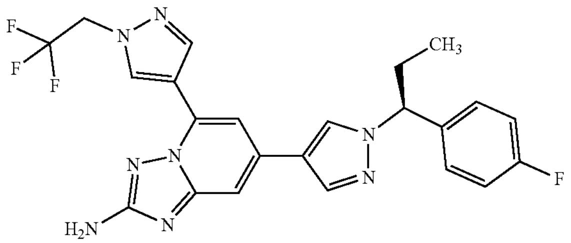 [SMILES: CC[C@@H](c1ccc(F)cc1)n1cc(-c2cc(-c3cnn(CC(F)(F)F)c3)n3nc(N)nc3c2)cn1]

7-Chloro-5-[1-(2,2,2-trifluoroethyl)-1H-pyrazol-4-yl][1,2,4]triazolo[1,5-a]pyridin-2-amine (60.0 mg, 95% purity, 180 μmol) was reacted with 1-[(1S)-1-(4-fluorophenyl)propyl]-4-(4,4,5,5-tetramethyl-1,3,2-dioxaborolan-2-yl)-1H-pyrazole (80.2 mg, 243 μmol) for 1 h at 80° C. following general procedure C using 0.10 eq. catalyst. The reaction mixture was directly purified by column 5 chromatography (Biotage® SNAP Ultra 10 g cartridge, eluent: dichloromethane/methanol gradient 100:0 to 85:15) and in a second step by preparative HPLC (Chromatorex C18, 10 μm, 125×30 mm; eluent: water (0.1% formic acid)/acetonitrile gradient 90:10 to 5:95 to yield 20.0 mg (98% purity, 22% yield) of the title compound.

LC-MS (method 2): $R^t$=1.07 min; MS (ESIpos): m/z=485 $[M+H]^+$ $^1$H-NMR (500 MHz, DMSO-$d_6$) δ [ppm]: 0.86 (t, 3H), 2.12-2.21 (m, 1H), 2.34-2.44 (m, 1H), 5.30-5.39 (m, 3H), 6.01 (s, 2H), 7.16-7.22 (m, 2H), 7.41-7.46 (m, 2H), 7.50 (d, 1H), 7.64 (d, 1H), 8.21 (s, 1H), 8.64 (s, 1H), 8.65 (s, 1H), 8.98 (s, 1H).

Example II-129

5-[1-(2,2,2-Trifluoroethyl)-1H-pyrazol-4-yl]-7-(1-{1-[4-(trifluoromethyl)phenyl]propyl}-1H-pyrazol-4-yl)[1,2,4]triazolo[1,5-a]pyridin-2-amine (mixture of enantiomers)

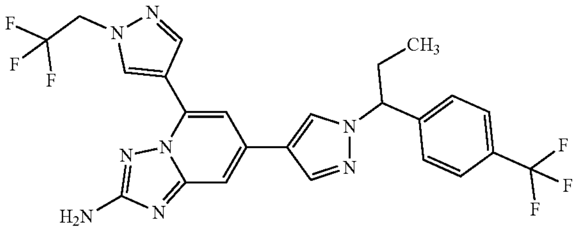 [SMILES: CCC(c1ccc(C(F)(F)F)cc1)n1cc(-c2cc(-c3cnn(CC(F)(F)F)c3)n3nc(N)nc3c2)cn1]

7-Chloro-5-[1-(2,2,2-trifluoroethyl)-1H-pyrazol-4-yl][1,2,4]triazolo[1,5-a]pyridin-2-amine (190 mg, 80% purity, 480 μmol) was reacted with 4-(4,4,5,5-tetramethyl-1,3,2-dioxaborolan-2-yl)-1-{1-[4-(trifluoromethyl)phenyl]propyl}-1H-pyrazole (246 mg, 648 μmol) for 1.5 h at 80° C. following general procedure C using 0.10 eq. catalyst. After the addition of further 0.10 eq. catalyst, heating was continued for another 1.5 h. The reaction mixture was directly purified by column chromatography (Biotage® SNAP Ultra 10 g cartridge, eluent: dichloromethane/methanol gradient 100:0 to 85:15) and in a second step by preparative HPLC (Chromatorex C18, 10 μm, 125×30 mm; eluent: water (0.1% formic acid)/acetonitrile gradient 90:10 to 5:95 to yield 119 mg (100% purity, 46% yield) of the title compound.

LC-MS (method 2): $R^t$=1.02 min; MS (ESIpos): m/z=535 $[M+H]^+$ $^1$H-NMR (500 MHz, DMSO-$d_6$) δ [ppm]: 0.89 (t, 3H), 2.16-2.26 (m, 1H), 2.35-2.47 (m, 1H), 5.34 (q, 2H), 5.50 (dd, 1H), 6.04 (s, 2H), 7.52 (s, 1H), 7.58 (d, 2H), 7.67 (s, 1H), 7.74 (d, 2H), 8.26 (s, 1H), 8.64 (s, 1H), 8.70 (s, 1H), 8.98 (s, 1H).

Example II-130

5-[1-(2,2,2-Trifluoroethyl)-1H-pyrazol-4-yl]-7-(1-{1-[4-(trifluoromethyl)phenyl]propyl}-1H-pyrazol-4-yl)[1,2,4]triazolo[1,5-a]pyridin-2-amine (stereoisomer 1, distomer)

5-[1-(2,2,2-Trifluoroethyl)-1H-pyrazol-4-yl]-7-(1-{1-[4-(trifluoromethyl)phenyl]propyl}-1H-pyrazol-4-yl)[1,2,4]triazolo[1,5-a]pyridin-2-amine (mixture of enantiomers) (110 mg, 100% purity, 206 μmol) from the previous example was separated by chiral chromatography to yield stereoisomer 1 (36 mg, 96% purity) and stereoisomer 2 (39 mg, 97% purity).

Column: Daicel Chiralcel OD-H, 5 μm, 250×20 mm; Eluent A: n-heptane; Eluent B: ethanol+0.2% diethylamine; isocratic: 85% A+15% B; flow: 20 ml/min; UV: 220 nm; temperature: 40° C.

Stereoisomer 1: $R^t$=12.796 min and

Stereoisomer 2: $R^t$=16.552 min (cf. next example)

Analytical chiral HPLC method: Column: Phenomenex cellulose, 3 μm, 50×4.6 mm; Eluent A: n-heptane; Eluent B: ethanol+0.2% diethylamine; isocratic: 80% A+20% B; flow: 1 ml/min; UV: 220 nm.

Stereoisomer 1: $R^t$=1.931 min and

Stereoisomer 2: $R^t$=2.406 min (cf. next example)

LC-MS (method 2): $R^t$=1.03 min; MS (ESIpos): m/z=535 $[M+H]^+$ $^1$H-NMR (400 MHz, DMSO-$d_6$) δ [ppm]: 0.875 (7.25), 0.893 (16.00), 0.911 (7.36), 1.140 (0.67), 1.158 (1.41), 1.176 (0.74), 2.171 (0.94), 2.187 (1.68), 2.205 (2.33), 2.222 (1.88), 2.239 (1.27), 2.328 (0.61), 2.366 (0.92), 2.382 (1.12), 2.400 (1.52), 2.417 (1.41), 2.424 (1.54), 2.440 (1.43), 2.458 (0.94), 2.671 (0.60), 2.710 (0.69), 5.302 (1.99), 5.325 (5.77), 5.347 (5.50), 5.370 (1.72), 5.473 (2.13), 5.488 (2.49), 5.496 (2.57), 5.511 (2.10), 6.030 (5.80), 7.516 (8.26), 7.520 (8.52), 7.569 (7.12), 7.590 (8.82), 7.658 (8.08), 7.662 (7.63), 7.730 (9.24), 7.750 (7.30), 8.254 (12.35), 8.638 (13.54), 8.695 (11.37), 8.976 (12.51).

Example II-131

5-[1-(2,2,2-Trifluoroethyl)-1H-pyrazol-4-yl]-7-(1-{1-[4-(trifluoromethyl)phenyl]propyl}-1H-pyrazol-4-yl)[1,2,4]triazolo[1,5-a]pyridin-2-amine (stereoisomer 2, eutomer)

The product was isolated in the previous example as second stereoisomer.

LC-MS (method 2): $R^t$=1.02 min; MS (ESIpos): m/z=535 $[M+H]^+$ $^1$H-NMR (400 MHz, DMSO-$d_6$) δ [ppm]: 0.89 (t, 3H), 2.15-2.27 (m, 1H), 2.36-2.47 (m, 1H), 5.34 (q, 2H), 5.49 (dd, 1H), 6.03 (br s, 2H), 7.52 (d, 1H), 7.58 (d, 2H), 7.66 (d, 1H), 7.74 (d, 2H), 8.25 (s, 1H), 8.64 (s, 1H), 8.70 (s, 1H), 8.98 (s, 1H).

Example II-132

5-(1-Cyclopentyl-1H-pyrazol-4-yl)-7-(1-{1-[4-(trifluoromethyl)phenyl]propyl}-1H-pyrazol-4-yl)[1,2,4]triazolo[1,5-a]pyridin-2-amine (mixture of enantiomers)

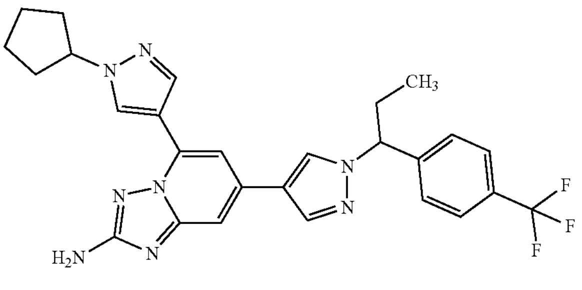 [SMILES: CCC(c1ccc(C(F)(F)F)cc1)n1cc(-c2cc(-c3cnn(C4CCCC4)c3)n3nc(N)nc3c2)cn1]

7-Chloro-5-(1-cyclopentyl-1H-pyrazol-4-yl)[1,2,4]triazolo[1,5-a]pyridin-2-amine (180 mg, 595 μmol) was reacted with 4-(4,4,5,5-tetramethyl-1,3,2-dioxaborolan-2-yl)-1-{1-[4-(trifluoromethyl)phenyl]propyl}-1H-pyrazole (305 mg, 803 μmol) for 2 h at 90° C. following general procedure C using 0.15 eq. catalyst. The reaction mixture was directly purified by column chromatography (Biotage® SNAP Ultra 25 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 130 mg (96% purity, 40% yield) of the title compound.

LC-MS (method 2): $R^t$=1.10 min; MS (ESIpos): m/z=521 $[M+H]^+$ $^1$H-NMR (600 MHz, DMSO-$d_6$) δ [ppm]: 0.879 (8.66), 0.891 (15.96), 0.903 (8.05), 1.686 (5.07), 1.693 (5.26), 1.842 (5.38), 1.976 (3.46), 1.987 (4.57), 1.997 (4.85), 2.008 (3.62), 2.147 (4.19), 2.156 (5.05), 2.168 (4.78), 2.179 (3.94), 2.191 (3.23), 2.203 (2.89), 2.215 (2.45), 2.226 (1.47), 2.395 (1.67), 2.409 (2.31), 2.422 (2.32), 2.430 (2.06), 2.446 (1.40), 2.618 (0.41), 4.790 (0.99), 4.801 (2.85), 4.813 (4.00), 4.825 (2.71), 4.837 (0.85), 5.480 (2.75), 5.490 (3.47), 5.505 (2.53), 6.016 (12.38), 7.462 (8.01), 7.576 (10.30), 7.587 (16.00), 7.733 (10.43), 7.747 (8.76), 8.241 (10.38), 8.508 (10.84), 8.673 (10.14), 8.843 (10.89).

Example II-133

5-(1-Cyclopentyl-1H-pyrazol-4-yl)-7-(1-{1-[4-(trifluoromethyl)phenyl]propyl}-1H-pyrazol-4-yl)[1,2,4]triazolo[1,5-a]pyridin-2-amine (single enantiomer, distomer)

5-(1-Cyclopentyl-1H-pyrazol-4-yl)-7-(1-{1-[4-(trifluoromethyl)phenyl]propyl}-1H-pyrazol-4-yl)[1,2,4]triazolo[1,5-a]pyridin-2-amine (mixture of enantiomers) (110 mg, 96% purity) from the previous example was separated by chiral chromatography to yield stereoisomer 1 (32 mg, 98% purity) and stereoisomer 2 (39 mg, 100% purity).

Column: Daicel Chiralpak ID, 5 m, 250×20 mm; Eluent A: n-heptane; Eluent B: 2-propanol+0.2% diethylamine; isocratic: 30% A+70% B; flow: 15 ml/min; UV: 220 nm; temperature: 60° C.

Stereoisomer 1: $R^t$=11.42 min and

Stereoisomer 2: $R^t$=12.95 min (cf. next example)

Analytical chiral HPLC method: Column: Chiralpak ID-3, 3 μm, 50×4.6 mm; Eluent A: n-heptane;

Eluent B: 2-propanol+0.2% diethylamine; isocratic: 20% A+80% B; flow: 1 ml/min; UV: 220 nm.

Stereoisomer 1: $R^t$=1.935 min and

Stereoisomer 2: $R^t$=2.507 min (cf. next example)

LC-MS (method 2): $R^t$=1.09 min; MS (ESIpos): m/z=521 $[M+H]^+$ $^1$H-NMR (600 MHz, DMSO-$d_6$) δ [ppm]: 0.878 (7.80), 0.890 (16.00), 0.902 (7.51), 1.082 (0.77), 1.092 (0.77), 1.159 (0.60), 1.263 (1.39), 1.678 (2.16), 1.686 (3.39), 1.693 (3.52), 1.704 (2.35), 1.718 (0.75), 1.724 (0.64), 1.811 (0.81), 1.830 (2.50), 1.842 (3.43), 1.846 (3.25), 1.856 (2.18), 1.869 (0.73), 1.878 (0.48), 1.962 (1.17), 1.975 (2.16), 1.986 (2.91), 1.996 (3.14), 2.007 (2.37), 2.018 (0.92), 2.135 (1.39), 2.146 (2.70), 2.155 (3.29), 2.168 (3.12), 2.178 (2.58), 2.191 (2.41), 2.203 (2.39), 2.214 (1.89), 2.225 (1.19), 2.394 (1.25), 2.406 (1.64), 2.417 (1.62), 2.422 (1.66), 2.429 (1.44), 2.433 (1.50), 2.445 (1.08), 2.457 (0.54), 2.656 (0.46), 4.788 (0.77), 4.800 (2.31), 4.812 (3.41), 4.824 (2.21), 4.836 (0.69), 5.479 (2.21), 5.488 (2.52), 5.494 (2.54), 5.504 (2.08), 6.013 (10.94), 7.458 (7.39), 7.460 (7.55), 7.574 (7.84), 7.580 (9.34), 7.583 (9.82), 7.588 (8.86), 7.636 (0.44), 7.733 (8.97), 7.746 (7.43), 8.238 (11.15), 8.252 (0.58), 8.505 (11.84), 8.671 (10.38), 8.840 (11.69).

Example II-134

5-(1-Cyclopentyl-1H-pyrazol-4-yl)-7-(1-{1-[4-(trifluoromethyl)phenyl]propyl}-1H-pyrazol-4-yl)[1,2,4]triazolo[1,5-a]pyridin-2-amine (single enantiomer, eutomer)

The product was isolated in the previous example as second stereoisomer.

LC-MS (method 2): $R^t$=1.09 min; MS (ESIpos): m/z=521 $[M+H]^+$ $^1$H-NMR (600 MHz, DMSO-$d_6$) δ [ppm]: 0.89 (t, 3H), 1.64-1.74 (m, 2H), 1.80-1.88 (m, 2H), 1.95-2.03 (m, 2H), 2.11-2.24 (m, 3H), 2.37-2.46 (m, 1H), 4.81 (quin, 1H), 5.49 (dd, 1H), 6.01 (s, 2H), 7.46 (d, 1H), 7.58 (dd, 3H), 7.73 (s, 1H), 7.75 (s, 1H), 8.24 (s, 1H), 8.50 (s, 1H), 8.67 (s, 1H1), 8.84 (s, 1H).

Example II-135

5-[1-(2,2,2-Trifluoroethyl)-1H-pyrazol-4-yl]-7-(1-{[2-(trifluoromethoxy)pyridin-4-yl]methyl}-1H-pyrazol-4-yl)[1,2,4]triazolo[1,5-a]pyridin-2-amine

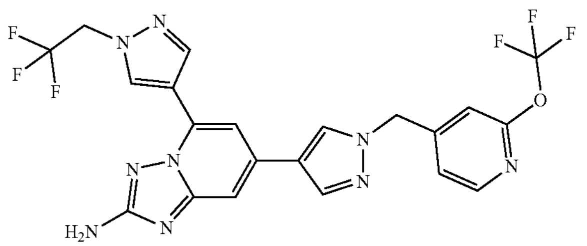 [SMILES: Nc1nc2cc(-c3cnn(Cc4ccnc(OC(F)(F)F)c4)c3)cc(-c3cnn(CC(F)(F)F)c3)n2n1]

7-Chloro-5-[1-(2,2,2-trifluoroethyl)-1H-pyrazol-4-yl][1,2,4]triazolo[1,5-a]pyridin-2-amine (50.0 mg, 96% purity, 152 μmol) was reacted with (1-{[2-(trifluoromethoxy)pyridin-4-yl]methyl}-1H-pyrazol-4-yl)boronic acid (61.2 mg, 96% purity, 205 μmol) for 1.5 h at 80° C. following general procedure C using 0.1 eq. catalyst. The crude reaction mixture was purified by column chromatography (Biotage® SNAP Ultra 10 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 38.0 mg (94% purity, 45% yield) of the title compound.

LC-MS (method 2): $R^t$=0.88 min; MS (ESIpos): m/z=524 $[M+H]^+$ $^1$H-NMR (500 MHz, DMSO-$d_6$) δ [ppm]: 5.34 (q, 2H), 5.56 (s, 2H), 6.05 (s, 2H), 7.09 (s, 1H), 7.23 (d, 1H), 7.53 (s, 1H), 7.68 (s, 1H), 8.31 (s, 1H), 8.36 (d, 1H), 8.62 (s, 1H), 8.64 (s, 1H), 8.99 (s, 1H).

Example II-136

7-{1-[1-(2-Methoxypyridin-4-yl)-2-methylpropyl]-1H-pyrazol-4-yl}-5-[1-(2,2,2-trifluoroethyl)-1H-pyrazol-4-yl][1,2,4]triazolo[1,5-a]pyridin-2-amine (mixture of enantiomers)

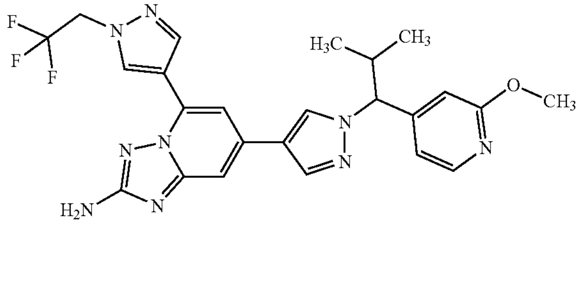 [SMILES: COc1cc(C(C(C)C)n2cc(-c3cc(-c4cnn(CC(F)(F)F)c4)n4nc(N)nc4c3)cn2)ccn1]

7-Chloro-5-[1-(2,2,2-trifluoroethyl)-1H-pyrazol-4-yl][1,2,4]triazolo[1,5-a]pyridin-2-amine (180 mg, 96% purity, 546 μmol) was reacted with 2-methoxy-4-{2-methyl-1-[4-(4,4,5,5-tetramethyl-1,3,2-dioxaborolan-2-yl)-1H-pyrazol-1-yl]propyl}pyridine (299 mg, 88% purity, 737)μmol) for 1.5 h at 80° C. following general procedure C using 0.1 eq. catalyst. The reaction mixture was directly purified by column chromatography (Biotage® SNAP Ultra 25 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 140 mg (95% purity, 48% yield) of the title compound.

LC-MS (method 2): $R^t$=0.90 min; MS (ESIpos): m/z=512 $[M+H]^+$ $^1$H-NMR (600 MHz, DMSO-$d_6$) δ [ppm]: 0.731 (0.79), 0.742 (0.76), 0.764 (0.80), 0.775 (0.79), 0.823 (5.21), 0.835 (5.18), 0.861 (5.63), 0.872 (5.51), 2.518 (0.54), 2.521 (0.55), 2.524 (0.51), 2.711 (0.46), 2.722 (0.63), 2.729 (0.54), 2.733 (0.51), 2.740 (0.62), 2.751 (0.44), 3.820 (2.26), 3.834 (16.00), 4.994 (1.90), 5.012 (1.80), 5.317 (0.71), 5.332 (1.90), 5.347 (1.77), 5.362 (0.56), 6.029 (4.23), 6.958 (3.09), 7.143 (1.67), 7.145 (1.61), 7.152 (1.66), 7.154 (1.57), 7.493 (3.00), 7.496 (2.99), 7.631 (3.02), 7.633 (2.80), 8.149 (2.42), 8.158 (2.32), 8.228 (4.35), 8.633 (4.91), 8.653 (4.05), 8.974 (4.51).

Example II-137

7-{1-[1-(2-Methoxypyridin-4-yl)-2-methylpropyl]-1H-pyrazol-4-yl}-5-[l-(2,2,2-trifluoroethyl)-1H-pyrazol-4-yl][1,2,4]triazolo[1,5-a]pyridin-2-amine (stereoisomer 1, distomer)

7-{1-[1-(2-Methoxypyridin-4-yl)-2-methylpropyl]-1H-pyrazol-4-yl}-5-[1-(2,2,2-trifluoroethyl)-1H-pyrazol-4-yl][1,2,4]triazolo[1,5-a]pyridin-2-amine (mixture of enantiomers) (130 mg, 95% purity) from the previous example was separated by chiral chromatography to yield stereoisomer 1 (50 mg, 100% purity) and stereoisomer 2 (51 mg, 99% purity).

Column: Daicel Chiralcel OD-H, 5 μm, 250×20 mm; Eluent A: n-heptane; Eluent B: ethanol+0.2% diethylamine; isocratic: 80% A+20% B; flow: 25 ml/min; UV: 220 nm; temperature: 40° C.

Stereoisomer 1: $R^t$=12.570 min and

Stereoisomer 2: $R^t$=17.695 min (cf. next example)

Analytical chiral HPLC method: Column: Phenomenex cellulose, 3 m, 50×4.6 mm; Eluent A: n-heptane; Eluent B: ethanol+0.2% diethylamine; isocratic: 80% A+20% B; flow: 1 ml/min; UV: 220 nm.

Stereoisomer 1: $R^t$=2.227 min and

Stereoisomer 2: $R^t$=3.115 min (cf. next example)

LC-MS (method 2): $R^t$=0.91 min; MS (ESIpos): m/z=512 $[M+H]^+$ $^1$H-NMR (400 MHz, DMSO-$d_6$) δ [ppm]: 0.821 (5.35), 0.837 (5.54), 0.858 (5.98), 0.874 (5.93), 1.158 (0.41), 2.701 (0.46), 2.711 (0.50), 2.717 (0.67), 2.727 (0.56), 2.733 (0.56), 2.744 (0.64), 2.760 (0.44), 3.833 (16.00), 4.989 (2.02), 5.016 (1.95), 5.302 (0.79), 5.325 (2.29), 5.347 (2.16), 5.370 (0.68), 6.029 (2.51), 6.956 (3.46), 7.138 (1.76), 7.141 (1.77), 7.152 (1.84), 7.154 (1.84), 7.490 (3.28), 7.494 (3.46), 7.628 (3.30), 7.632 (3.12), 8.145 (2.53), 8.158 (2.47), 8.225 (4.79), 8.630 (5.27), 8.649 (4.47), 8.971 (4.87).

Example II-138

7-{1-[1-(2-Methoxypyridin-4-yl)-2-methylpropyl]-1H-pyrazol-4-yl}-5-[1-(2,2,2-trifluoroethyl)-1H-pyrazol-4-yl][1,2,4]triazolo[1,5-a]pyridin-2-amine (stereoisomer 2, eutomer)

The product was isolated in the previous example as second stereoisomer.

LC-MS (method 2): $R^t$=0.91 min; MS (ESIpos): m/z=512 $[M+H]^+$ $^1$H-NMR (400 MHz, DMSO-$d_6$) δ [ppm]: 0.83 (d, 3H), 0.87 (d, 3H), 2.68-2.80 (m, 1H), 3.83 (s, 3H), 5.00 (d, 1H), 5.34 (q, 2H), 6.03 (br s, 2H), 6.96 (s, 1H), 7.15 (dd, 1H), 7.49 (d, 1H), 7.63 (d, 1H), 8.15 (d, 1H), 8.23 (s, 1H), 8.63 (s, 1H), 8.65 (s, 1H), 8.97 (s, 1H).

Example II-139

7-(1-{2-Methyl-1-[6-(trifluoromethyl)pyridin-3-yl]propyl}-1H-pyrazol-4-yl)-5-[1-(2,2,2-trifluoroethyl)-1H-pyrazol-4-yl][1,2,4]triazolo[1,5-a]pyridin-2-amine (mixture of enantiomers)

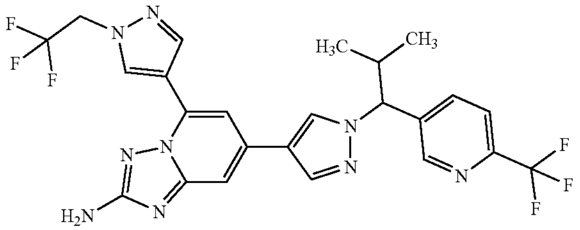 [SMILES: CC(C)C(c1ccc(C(F)(F)F)nc1)n1cc(-c2cc(-c3cnn(CC(F)(F)F)c3)n3nc(N)nc3c2)cn1]

7-Chloro-5-[1-(2,2,2-trifluoroethyl)-1H-pyrazol-4-yl][1,2,4]triazolo[1,5-a]pyridin-2-amine (180 mg, 96% purity, 546 μmol) was reacted with 5-{2-methyl-1-[4-(4,4,5,5-tetramethyl-1,3,2-dioxaborolan-2-yl)-1H-pyrazol-1-yl]propyl}-2-(trifluoromethyl)pyridine (388 mg, 75% purity, 737 μmol) for 1.5 hat 80° C. following general procedure C using 0.1 eq. catalyst. After the addition of further 0.1 eq. catalyst heating was continued for another 1.5 h. The reaction mixture was then purified by column chromatography (Biotage® SNAP Ultra 10 g cartridge, eluent: dichloromethane/methanol gradient 100:0 to 85:15). The product was then further purified by preparative HPLC (Chromatorex C18, 10 μm, 125×30 mm; eluent: water (0.1% formic acid)/acetonitrile gradient 90:10 to 5:95 to yield 95.0 mg (91% purity, 29% yield) of the title compound.

LC-MS (method 2): $R^t$=1.00 min; MS (ESIpos): m/z=550 $[M+H]^+$ $^1$H-NMR (600 MHz, DMSO-$d_6$) δ [ppm]: 0.823 (12.78), 0.834 (12.55), 0.891 (13.34), 0.901 (13.02), 2.803 (0.48), 2.814 (1.15), 2.825 (1.62), 2.832 (1.40), 2.836 (1.40), 2.843 (1.58), 2.854 (1.07), 4.094 (0.44), 5.260 (4.45), 5.277 (4.26), 5.320 (1.83), 5.335 (4.86), 5.351 (4.55), 5.365 (1.47), 6.040 (10.64), 7.497 (7.15), 7.500 (7.29), 7.635 (7.13), 7.638 (6.87), 7.953 (4.95), 7.967 (5.20), 8.270 (10.15), 8.295 (3.17), 8.309 (2.88), 8.634 (11.07), 8.676 (9.63), 8.979 (16.00).

Example II-140

7-(1-{2-Methyl-1-[6-(trifluoromethyl)pyridin-3-yl]propyl}-1H-pyrazol-4-yl)-5-[1-(2,2,2-trifluoroethyl)-1H-pyrazol-4-yl][1,2,4]triazolo[1,5-a]pyridin-2-amine (single enantiomer, distomer)

7-(1-{2-Methyl-1-[6-(trifluoromethyl)pyridin-3-yl]propyl}-1H-pyrazol-4-yl)-5-[1-(2,2,2-trifluoroethyl)-1H-pyrazol-4-yl][1,2,4]triazolo[1,5-a]pyridin-2-amine (mixture of enantiomers) (85 mg, 91% purity) from the previous example was separated by chiral chromatography to yield stereoisomer 1 (34 mg, 99% purity) and stereoisomer 2 (32 mg, 99% purity).

Column: Daicel Chiralcel OD-H, 5 μm, 250×20 mm; Eluent A: n-heptane; Eluent B: 2-propanol+0.2% diethylamine; isocratic: 70% A+30% B; flow: 20 ml/min; UV: 210 nm; temperature: 50° C.

Stereoisomer 1: $R^t$=6.547 min and

Stereoisomer 2: $R^t$=10.505 min (cf. next example)

Analytical chiral HPLC method: Column: Chiraltek IE-3, 3 μm, 50×4.6 mm; Eluent A: iso-hexane;

Eluent B: 2-propanol+0.2% diethylamine; isocratic: 50% A+50% B; flow: 1 ml/min; UV: 220 nm.

Stereoisomer 1: $R^t$=3.183 min and

Stereoisomer 2: $R^t$=3.954 min (cf. next example)

LC-MS (method 2): $R^t$=0.97 min; MS (ESIpos): m/z=550 $[M+H]^+$ $^1$H-NMR (400 MHz, DMSO-$d_6$) δ [ppm]: −0.008 (2.72), 0.008 (2.53), 0.818 (11.59), 0.834 (11.84), 0.885 (12.28), 0.901 (12.48), 1.030 (0.54), 1.136 (1.34), 1.154 (2.92), 1.172 (1.44), 1.266 (0.54), 1.388 (0.50), 1.781 (0.45), 2.328 (1.44), 2.367 (1.59), 2.524 (5.89), 2.670 (1.39), 2.710 (1.63), 2.801 (1.04), 2.817 (1.49), 2.844 (1.49), 2.907 (0.79), 5.251 (4.16), 5.277 (4.01), 5.300 (1.68), 5.323 (4.85), 5.346 (4.56), 5.368 (1.54), 6.024 (8.92), 7.487 (7.58), 7.491 (8.12), 7.624 (7.33), 7.628 (6.98), 7.945 (4.80), 7.965 (5.50), 8.261 (10.70), 8.285 (2.82), 8.305 (2.63), 8.624 (11.79), 8.668 (9.51), 8.969 (16.00).

Example II-141

7-(1-{2-Methyl-1-[6-(trifluoromethyl)pyridin-3-yl]propyl}-1H-pyrazol-4-yl)-5-[1-(2,2,2-trifluoroethyl)-1H-pyrazol-4-yl][1,2,4]triazolo[1,5-a]pyridin-2-amine (single enantiomer, eutomer)

The product was isolated in the previous example as second stereoisomer.

LC-MS (method 2): $R^t$=0.98 min; MS (ESIpos): m/z=550 $[M+H]^+$ $^1$H-NMR (400 MHz, DMSO-$d_6$) δ [ppm]: 0.83 (d, 3H), 0.89 (d, 3H), 2.78-2.88 (m, 1H), 5.26 (d, 1H), 5.34 (q, 2H), 6.03 (s, 2H), 7.49 (d, 1H), 7.63 (d, 1H), 7.96 (d, 1H), 8.26 (s, 1H), 8.30 (dd, 1H), 8.62 (s, 1H), 8.67 (s, 1H), 8.97 (s, 2H).

Example II-142

5-{1-[(2,2-Difluorocyclopropyl)methyl]-1H-pyrazol-4-yl}-7-(1-{2-methyl-1-[6-(trifluoromethyl)pyridin-3-yl]propyl}-1H-pyrazol-4-yl)[1,2,4]triazolo[1,5-a]pyridin-2-amine (mixture of stereoisomers)

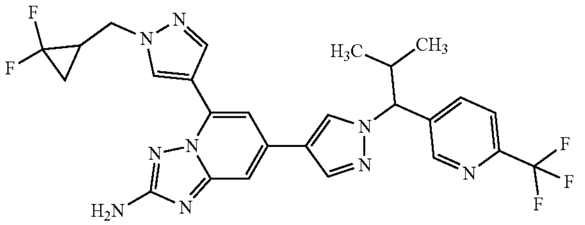 [SMILES: CC(C)C(c1ccc(C(F)(F)F)nc1)n1cc(-c2cc(-c3cnn(CC4CC4(F)F)c3)n3nc(N)nc3c2)cn1]

5-Chloro-7-(1-{2-methyl-1-[6-(trifluoromethyl)pyridin-3-yl]propyl}-1H-pyrazol-4-yl)[1,2,4]triazolo[1,5-a]pyridin-2-amine (75.0 mg, 96% purity, 165 μmol) was reacted with 1-[(2,2-difluorocyclopropyl)methyl]-4-(4,4,5,5-tetramethyl-1,3,2-dioxaborolan-2-yl)-1H-pyrazole [CAS-RN 2101930-90-7](61.0 mg, 215 μmol) for 4 h at 80° C. following general procedure C using 0.15 eq. catalyst. The reaction mixture was diluted with ethyl acetate (10 ml) and filtered.

The filter was rinsed with ethyl acetate (10 ml) and the combined filtrates were filtered through a hydrophobic phase separation filter. The mixture was concentrated in vacuo and the residue was purified by column chromatography (Biotage® SNAP KP-NH 11 g cartridge, eluent: cyclohexane/ethyl acetate gradient 70:30 to 0:100). The product was further purified by preparative HPLC (Chromatorex C18, 10 μm, 125×30 mm; eluent: water (0.5% formic acid)/acetonitrile gradient 50:50 to 5:95 to yield 32.3 mg (99% purity, 35% yield) of the title compound.

LC-MS (method 1): $R^t$=1.88 min; MS (ESIpos): m/z=558 $[M+H]^+$ $^1$H-NMR (400 MHz, DMSO-$d_6$) δ [ppm]: 0.83 (d, 3H), 0.89 (d, 3H), 1.49-1.60 (m, 1H), 1.68-1.80 (m, 1H), 2.25-2.39 (m, 1H), 2.76-2.90 (m, 1H), 4.38 (br d, 2H), 5.27 (d, 1H), 5.99 (s, 2H), 7.45 (d, 1H), 7.56 (d, 1H), 7.95 (d, 1H), 8.25 (s, 1H), 8.30 (dd, 1H), 8.53 (s, 1H), 8.65 (s, 1H), 8.86 (s, 1H), 8.97 (d, 1H).

Example II-143

5-(1-Cyclopentyl-1H-pyrazol-4-yl)-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers)

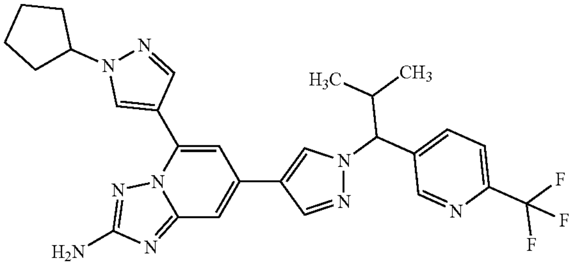 [SMILES: CC(C)C(c1ccc(C(F)(F)F)nc1)n1cc(-c2cc(-c3cnn(C4CCCC4)c3)n3nc(N)nc3c2)cn1]

7-Chloro-5-(1-cyclopentyl-1H-pyrazol-4-yl)[1,2,4]triazolo[1,5-a]pyridin-2-amine (180 mg, 595 μmol) was reacted with 5-{2-methyl-1-[4-(4,4,5,5-tetramethyl-1,3,2-dioxaborolan-2-yl)-1H-pyrazol-1-yl]propyl}-2-(trifluoromethyl)pyridine (423 mg, 75% purity, 803 μmol) for 2 h at 90° C. following general procedure C using 0.15 eq. catalyst. Further 0.15 eq. catalyst was then added and heating was continued for another 2 h. The reaction mixture was directly purified by column chromatography (Biotage® SNAP Ultra 25 g cartridge, eluent: dichloromethane/methanol gradient 10 100:0 to 85:15). The product was further purified by preparative HPLC (Chromatorex C18, 10 μm, 125×30 mm; eluent: water (0.1% formic acid)/acetonitrile gradient 90:10 to 5:95) to yield 124 mg (96% purity, 37% yield) of the title compound.

LC-MS (method 2): $R^t$=1.03 min; MS (ESIpos): m/z=536 $[M+H]^+$ $^1$H-NMR (400 MHz, DMSO-$d_6$) δ [ppm]: −0.008 (2.62), 0.008 (2.56), 0.755 (0.61), 0.760 (0.62), 0.771 (0.65), 0.777 (0.64), 0.816 (14.81), 0.833 (15.10), 0.882 (15.75), 0.898 (16.00), 1.672 (2.05), 1.682 (3.70), 1.694 (4.16), 1.699 (3.35), 1.710 (2.98), 1.730 (0.91), 1.740 (0.92), 1.797 (0.84), 1.825 (2.71), 1.830 (2.45), 1.841 (3.86), 1.850 (3.55), 1.862 (2.45), 1.881 (0.87), 1.895 (0.53), 1.947 (1.16), 1.968 (2.23), 1.984 (3.26), 1.998 (3.78), 2.015 (2.91), 2.034 (1.16), 2.123 (1.51), 2.139 (3.09), 2.153 (3.80), 2.172 (3.20), 2.185 (2.13), 2.202 (0.85), 2.785 (0.51), 2.801 (1.29), 2.818 (1.81), 2.828 (1.57), 2.834 (1.57), 2.845 (1.85), 2.861 (1.26), 2.878 (0.47), 4.093 (0.80), 4.777 (0.87), 4.795 (2.70), 4.812 (4.19), 4.830 (2.70), 4.847 (0.83), 5.251 (5.30), 5.277 (5.16), 6.008 (9.49), 7.428 (6.43), 7.547 (9.57), 7.551 (9.08), 7.944 (6.19), 7.964 (6.91), 8.244 (12.78), 8.288 (3.79), 8.292 (3.77), 8.308 (3.40), 8.312 (3.38), 8.491 (15.16), 8.644 (11.89), 8.834 (15.06), 8.971 (6.98), 8.975 (6.93).

Example II-144

5-(1-Cyclopentyl-1H-pyrazol-4-yl)-7-(1-{2-methyl-1-[6-(trifluoromethyl)pyridin-3-yl]propyl}-1H-pyrazol-4-yl)[1,2,4]triazolo[1,5-a]pyridin-2-amine (single enantiomer, distomer)

5-(1-Cyclopentyl-1H-pyrazol-4-yl)-7-(1-{2-methyl-1-[6-(trifluoromethyl)pyridin-3-yl]propyl}-1H-pyrazol-4-yl)[1,2,4]triazolo[1,5-a]pyridin-2-amine (mixture of enantiomers) (112 mg, 96% purity) from the previous example was separated by chiral chromatography to yield stereoisomer 1 (39 mg, 100% purity) and stereoisomer 2 (35 mg, 98% purity).

Column: Daicel Chiralpak IE, 5 m, 250×20 mm; Eluent A: n-heptane; Eluent B: ethanol; isocratic: 50% A+50% B; flow: 20 ml/min; UV: 220 nm; temperature: 30° C.

Stereoisomer 1: $R^t$=8.563 min and

Stereoisomer 2: $R^t$=11.112 min (cf. next example)

Analytical chiral HPLC method: Column: Daicel Chiralpak IE-3, 3 μm, 50×4.6 mm; Eluent A: n-heptane; Eluent B: ethanol; isocratic: 50% A+50% B; flow: 1 ml/min; UV: 220 nm.

Stereoisomer 1: $R^t$=1.910 min and

Stereoisomer 2: $R^t$=2.446 min (cf. next example)

LC-MS (method 2): $R^t$=1.06 min; MS (ESIpos): m/z=536 $[M+H]^+$ $^1$H-NMR (600 MHz, DMSO-$d_6$) δ [ppm]: 0.818 (15.71), 0.829 (15.02), 0.884 (16.00), 0.894 (15.09), 1.104 (0.52), 1.160 (0.89), 1.172 (0.62), 1.232 (1.61), 1.624 (1.38), 1.686 (4.39), 1.694 (4.42), 1.705 (2.94), 1.841 (4.50), 1.973 (3.62), 1.984 (4.53), 1.994 (4.74), 2.005 (3.42), 2.135 (1.93), 2.146

(3.49), 2.156 (4.17), 2.167 (3.54), 2.176 (2.45), 2.388 (0.54), 2.427 (0.91), 2.656 (0.43), 2.811 (1.49), 2.822 (2.01), 2.832 (1.80), 2.840 (1.91), 2.851 (1.24), 3.509 (0.95), 4.790 (0.92), 4.802 (2.80), 4.813 (3.95), 4.825 (2.61), 4.838 (0.71), 5.257 (5.32), 5.275 (5.05), 6.066 (2.40), 7.434 (8.68), 7.566 (8.20), 7.950 (5.94), 7.963 (6.11), 8.251 (11.61), 8.294 (4.10), 8.307 (3.70), 8.494 (12.47), 8.652 (10.92), 8.835 (12.55), 8.973 (7.60).

Example II-145

5-(1-Cyclopentyl-1H-pyrazol-4-yl)-7-(1-{2-methyl-1-[6-(trifluoromethyl)pyridin-3-yl]propyl}-1H-pyrazol-4-yl)[1,2,4]triazolo[1,5-a]pyridin-2-amine (single enantiomer, eutomer)

The product was isolated in the previous example as second stereoisomer.

LC-MS (method 2): $R^t$=1.06 min; MS (ESIpos): m/z=536 $[M+H]^+$ $^1$H-NMR (600 MHz, DMSO-$d_6$) δ [ppm]: 0.82 (d, 3H), 0.89 (d, 3H), 1.64-1.75 (m, 2H), 1.78-1.89 (m, 2H), 1.92-2.04 (m, 2H), 2.10-2.21 (m, 2H), 2.78-2.87 (m, 1H), 4.81 (quin, 1H), 5.27 (d, 1H), 6.04 (br s, 2H), 7.43 (d, 1H), 7.56 (d, 1H), 7.96 (d, 1H), 8.25 (s, 1H), 8.30 (br dd, 1H), 8.49 (s, 1H), 8.65 (s, 1H), 8.84 (s, 1H), 8.98 (d, 1H).

Example II-146

7-{1-[Phenyl(tetrahydro-2H-pyran-4-yl)methyl]-1H-pyrazol-4-yl}-5-[1-(2,2,2-trifluoroethyl)-1H-pyrazol-4-yl][1,2,4]triazolo[1,5-a]pyridin-2-amine (mixture of enantiomers)

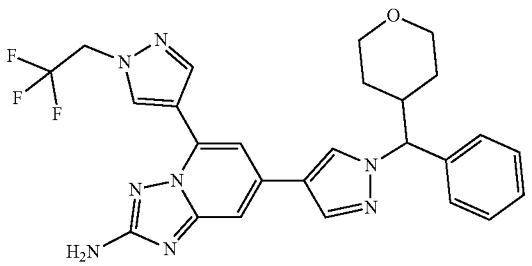 [SMILES: Nc1nc2cc(-c3cnn(C(c4ccccc4)C4CCOCC4)c3)cc(-c3cnn(CC(F)(F)F)c3)n2n1]

7-Chloro-5-[1-(2,2,2-trifluoroethyl)-1H-pyrazol-4-yl][1,2,4]triazolo[1,5-a]pyridin-2-amine (100 mg, 316 μmol) was reacted with 1-[phenyl(tetrahydro-2H-pyran-4-yl)methyl]-4-(4,4,5,5-tetramethyl-1,3,2-dioxaborolan-2-yl)-1H-pyrazole (436 mg, 40% purity, 474 μmol) for 2 h at 80° C. following general procedure B using 0.1 eq. [1,1'-bis(di-tert-butylphosphino)ferrocene]dichloropalladium(II) as catalyst. The reaction mixture was diluted with ethyl acetate (5 ml) and filtered through a hydrophobic phase separation filter. The solvents were removed in vacuo and the residue was purified by column chromatography (Biotage® SNAP KP-NH 10 g cartridge, eluent: cyclohexane/ethyl acetate gradient 80:20 to 0:100) to yield 87.5 mg (97% purity, 51% yield) of the title compound.

LC-MS (method 1): $R^t$=1.68 min; MS (ESIpos): m/z=523 $[M+H]^+$ $^1$H-NMR (400 MHz, DMSO-$d_6$) δ [ppm]: 1.070 (8.02), 1.105 (1.91), 1.134 (2.79), 1.157 (1.31), 1.175 (1.81), 1.193 (1.18), 1.228 (3.61), 1.245 (4.63), 1.285 (2.46), 1.310 (2.43), 1.334 (1.61), 1.363 (0.66), 1.474 (0.43), 1.836 (0.43), 1.989 (2.69), 2.074 (3.38), 2.329 (0.49), 2.367 (0.53), 2.459 (0.46), 2.672 (2.33), 2.701 (1.94), 2.710 (1.74), 3.231 (1.84), 3.261 (4.47), 3.291 (5.26), 3.799 (2.56), 3.823 (4.44), 3.858 (2.30), 3.919 (1.15), 4.021 (0.66), 4.039 (0.69), 5.078 (5.55), 5.104 (5.45), 5.299 (2.40), 5.322 (6.93), 5.345 (6.74), 5.369 (2.20), 6.012 (13.21), 7.290 (2.00), 7.309 (5.75), 7.327 (4.63), 7.362 (7.26), 7.381 (11.17), 7.398 (4.76), 7.474 (10.02), 7.478 (10.32), 7.561 (10.84), 7.579 (9.17), 7.616 (9.89), 7.620 (9.23), 8.207 (14.32), 8.630 (16.00), 8.645 (13.27), 8.968 (14.65).

Example II-147

7-{1-[Phenyl(tetrahydro-2H-pyran-4-yl)methyl]-1H-pyrazol-4-yl}-5-[1-(2,2,2-trifluoroethyl)-1H-pyrazol-4-yl][1,2,4]triazolo[1,5-a]pyridin-2-amine (stereoisomer 1, eutomer)

7-{1-[Phenyl(tetrahydro-2H-pyran-4-yl)methyl]-1H-pyrazol-4-yl}-5-[1-(2,2,2-trifluoroethyl)-1H-pyrazol-4-yl][1,2,4]triazolo[1,5-a]pyridin-2-amine (mixture of enantiomers) (78 mg, 97% purity) from the previous example was separated by chiral chromatography to yield stereoisomer 1 (29 mg, 99% purity) and stereoisomer 2 (29 mg, 99% purity).

Column: Daicel Chiralcel OD-H, 5 μm, 250×20 mm; Eluent A: n-heptane; Eluent B: ethanol+0.2% diethylamine; isocratic: 80% A+20% B; flow: 35 ml/min; UV: 220 nm; temperature: 50° C.

Stereoisomer 1: $R^t$=8.760 min and

Stereoisomer 2: $R^t$=11.767 min (cf. next example)

Analytical chiral HPLC method: Column: Chiraltek OD-3, 3 m, 50×4.6 mm; Eluent A: iso-hexane; Eluent B: ethanol+0.2% diethylamine; isocratic: 50% A+50% B; flow: 1 ml/min; UV: 220 nm.

Stereoisomer 1: $R^t$=2.358 min and

Stereoisomer 2: $R^t$=3.034 min (cf. next example)

LC-MS (method 1): $R^t$=1.68 min; MS (ESIpos): m/z=523 $[M+H]^+$ $^1$H-NMR (400 MHz, DMSO-$d_6$) δ [ppm]: 1.08-1.38 (m, 5H), 3.22-3.28 (m, 2H), 3.78-3.88 (m, 2H), 5.09 (d, 1H), 5.33 (q, 2H), 6.02 (br s, 2H), 7.28-7.34 (m, 1H), 7.35-7.41 (m, 2H), 7.48 (d, 1H), 7.55-7.59 (m, 2H), 7.62 (d, 1H), 8.21 (s, 1H), 8.63 (s, 1H), 8.65 (s, 1H), 8.97 (s, 1H).

Example II-148

7-{1-[Phenyl(tetrahydro-2H-pyran-4-yl)methyl]-1H-pyrazol-4-yl}-5-[1-(2,2,2-trifluoroethyl)-1H-pyrazol-4-yl][1,2,4]triazolo[1,5-a]pyridin-2-amine (stereoisomer 2, distomer)

The product was isolated in the previous example as second stereoisomer.

LC-MS (method 1): $R^t$=1.69 min; MS (ESIpos): m/z=523 $[M+H]^+$ $^1$H-NMR (400 MHz, DMSO-$d_6$) δ [ppm]: 0.844 (0.63), 0.857 (1.04), 1.031 (0.65), 1.048 (0.65), 1.104 (2.01), 1.140 (4.55), 1.158 (5.69), 1.176 (2.93), 1.215 (2.03), 1.245 (4.26), 1.278 (2.25), 1.310 (2.18), 1.332 (1.40), 2.328 (0.82), 2.367 (0.92), 2.671 (2.15), 2.701 (1.60), 2.710 (1.89), 2.905 (0.75), 2.923 (1.02), 2.936 (0.92), 2.954 (0.75), 3.231 (1.96), 3.261 (4.94), 3.799 (2.13), 3.828 (3.68), 3.858 (1.91), 5.078 (5.16), 5.105 (4.94), 5.299 (2.15), 5.323 (6.25), 5.345 (5.93), 5.368 (1.84), 6.026 (5.08), 7.290 (1.62), 7.308 (5.47), 7.327 (4.19), 7.361 (6.61), 7.381 (10.53), 7.398 (4.43), 7.475 (9.68), 7.479 (10.19), 7.561 (9.78), 7.579 (8.52), 7.620 (9.13), 7.624 (8.76), 8.208 (13.99), 8.630 (16.00), 8.646 (12.54), 8.968 (14.40).

Example II-149

7-(1-{Tetrahydro-2H-pyran-4-yl[6-(trifluoromethyl)pyridin-3-yl]methyl}-1H-pyrazol-4-yl)-5-[1-(2,2,2-trifluoroethyl)-1H-pyrazol-4-yl][1,2,4]triazolo[1,5-a]pyridin-2-amine (mixture of enantiomers)

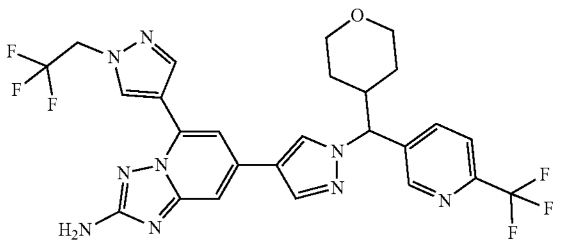 [SMILES: Nc1nc2cc(-c3cnn(C(c4ccc(C(F)(F)F)nc4)C4CCOCC4)c3)cc(-c3cnn(CC(F)(F)F)c3)n2n1]

7-Chloro-5-[1-(2,2,2-trifluoroethyl)-1H-pyrazol-4-yl][1,2,4]triazolo[1,5-a]pyridin-2-amine (150 mg, 474 μmol) was reacted with 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (259 mg, 592 μmol) for 2 h at 90° C. following general procedure B using 0.1 eq. XPhos-Pd-G2 as catalyst. The mixture was diluted with ethyl acetate (15 ml) and washed with water (2 ml). The aqueous phase was extracted twice with ethyl acetate (8 ml each). The combined organic layers were concentrated in vacuo and the residue was purified by column chromatography (Biotage® SNAP KP-NH 28 g cartridge, eluent: cyclohexane/ethyl acetate gradient 90:10 to 0:100) to yield 220 mg (100% purity, 79% yield) of the title compound.

LC-MS (method 2): $R^t$=0.91 min; MS (ESIpos): m/z=592 $[M+H]^+$ $^1$H-NMR (400 MHz, DMSO-$d_6$) δ [ppm]: 1.05-1.14 (m, 1H), 1.20-1.27 (m, 1H), 1.27-1.43 (m, 2H), 2.71-2.83 (m, 1H), 3.23-3.31 (m, 2H), 3.78-3.89 (m, 2H), 5.34 (q, 2H), 5.41 (d, 1H), 6.03 (s, 2H), 7.49 (d, 1H), 7.62 (d, 1H), 7.96 (d, 1H), 8.28 (s, 1H), 8.32 (dd, 1H), 8.62 (s, 1H), 8.66 (s, 1H), 8.97 (s, 1H), 8.99 (d, 1H).

Example II-150 7-(1-{Tetrahydro-2H-pyran-4-yl[6-(trifluoromethyl)pyridin-3-yl]methyl}-1H-pyrazol-4-yl)-5-[1-(2,2,2-trifluoroethyl)-1H-pyrazol-4-yl][1,2,4]triazolo[1,5-a]pyridin-2-amine (stereoisomer 1, eutomer)

7-(1-{Tetrahydro-2H-pyran-4-yl[6-(trifluoromethyl)pyridin-3-yl]methyl}-1H-pyrazol-4-yl)-5-[1-(2,2,2-trifluoroethyl)-1H-pyrazol-4-yl][1,2,4]triazolo[1,5-a]pyridin-2-amine (mixture of enantiomers) (220 mg, 100% purity) from the previous example was separated by chiral chromatography to yield stereoisomer 1 (88 mg, 100% purity) and stereoisomer 2 (94 mg, 100% purity).

Column: Daicel Chiralpak IB, 5 μm, 250×20 mm; Eluent A: n-heptane; Eluent B: ethanol+0.2% diethylamine; isocratic: 60% A+40% B; flow: 20 ml/min; UV: 220 nm; temperature: 40° C.

Stereoisomer 1: $R^t$=5.415 min and

Stereoisomer 2: $R^t$=6.546 min (cf. next example)

Analytical chiral HPLC method: Column: Daicel Chiralpak IB-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=1.298 min and

Stereoisomer 2: $R^t$=1.482 min (cf. next example)

LC-MS (method 2): $R^t$=0.88 min; MS (ESIpos): m/z=592 $[M+H]^+$ $^1$H-NMR (400 MHz, DMSO-$d_6$) δ [ppm]: 1.10 (br d, 1H), 1.19-1.27 (m, 1H), 1.27-1.43 (m, 2H), 2.71-2.83 (m, 1H), 3.23-3.30 (m, 2H), 3.78-3.89 (m, 2H), 5.34 (q, 2H), 5.41 (d, 1H), 6.03 (s, 2H), 7.49 (d, 1H), 7.62 (d, 1H), 7.96 (d, 1H), 8.28 (s, 1H), 8.32 (dd, 1H), 8.62 (s, 1H), 8.66 (s, 1H), 8.97 (s, 1H), 8.99 (d, 1H).

Example II-151

7-(1-{Tetrahydro-2H-pyran-4-yl[6-(trifluoromethyl)pyridin-3-yl]methyl}-1H-pyrazol-4-yl)-5-[1-(2,2,2-trifluoroethyl)-1H-pyrazol-4-yl][1,2,4]triazolo[1,5-a]pyridin-2-amine (stereoisomer 2, distomer)

The product was isolated in the previous example as second stereoisomer.

LC-MS (method 2): $R^t$=0.88 min; MS (ESIpos): m/z=592 $[M+H]^+$ $^1$H-NMR (400 MHz, DMSO-$d_6$) δ [ppm]: 1.090 (2.29), 1.109 (2.63), 1.217 (1.60), 1.247 (2.40), 1.297 (0.80), 1.316 (2.00), 1.326 (2.23), 1.347 (2.91), 1.358 (2.91), 1.378 (1.89), 1.389 (1.77), 2.328-(1.43), 2.333 (1.14), 2.367 (1.09), 2.524 (5.89), 2.671 (1.60), 2.711 (1.20), 2.756 (1.83), 2.784 (1.71), 3.248 (1.66), 3.272 (4.51), 3.805 (2.06), 3.836 (3.54), 3.871 (1.89), 5.301 (2.17), 5.324 (6.34), 5.347 (5.94), 5.369 (2.00), 5.393 (5.26), 5.419 (5.03), 6.028 (12.06), 7.488 (9.66), 7.492 (10.51), 7.621 (9.37), 7.625 (9.20), 7.953 (6.40), 7.974 (7.14), 8.281 (14.17), 8.308 (3.77), 8.312 (3.89), 8.329 (3.37), 8.623 (16.00), 8.660 (12.86), 8.969 (14.51), 8.990 (7.03).

Example II-152

7-{1-[Phenyl(piperidin-4-yl)methyl]-1H-pyrazol-4-yl}-5-[1-(2,2,2-trifluoroethyl)-1H-pyrazol-4-yl][1,2,4]triazolo[1,5-a]pyridin-2-amine (single stereoisomer)

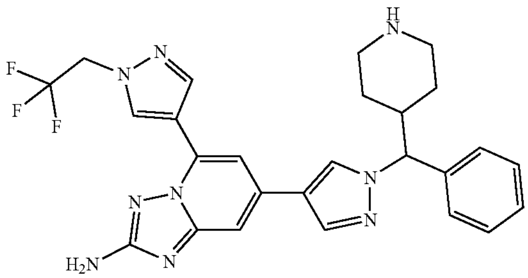 [SMILES: Nc1nc2cc(-c3cnn(C(c4ccccc4)C4CCNCC4)c3)cc(-c3cnn(CC(F)(F)F)c3)n2n1]

tert-Butyl 4-[(4-{2-amino-5-[1-(2,2,2-trifluoroethyl)-1H-pyrazol-4-yl][1,2,4]triazolo[1,5-a]pyridin-7-yl}-1H-pyrazol-1-yl)(phenyl)methyl]piperidine-1-carboxylate (stereoisomer 2) was dissolved in dichloromethane (1.0 ml). Trifluoroacetic acid (100 μl, 1.3 mmol) was added. The reaction was stirred overnight at rt. The mixture was concentrated in vacuo. The residue was dissolved in methanol (2 ml) and filtered through a basic cartridge (Agilent PL-HCO3 MP SPE, 500 mg) and eluted with dichloromethane/methanol 1:1. The solvents were removed in vacuo to 20 yield 23.3 mg (95% purity, 98% yield) of the title compound.

LC-MS (method 1): $R^t$=1.19 min; MS (ESIneg): m/z=566 $[M-H+HCOOH]^-$ $^1$H-NMR (400 MHz, DMSO-$d_6$) δ [ppm]: 1.01-1.29 (m, 4H), 2.36-2.48 (m, 2H), 2.90 (br t, 2H), 5.03 (d, 1H), 5.33 (q, 2H), 6.01 (s, 2H), 7.27-7.33 (m, 1H), 7.34-7.40 (m, 2H), 7.47 (d, 1H), 7.54-7.58 (m, 2H), 7.62 (d, 1H), 8.19 (s, 1H), 8.63 (s, 1H), 8.64 (s, 1H), 8.92-9.01 (m, 1H).

Example II-153

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(difluoromethyl)pyridin-2(1H)-one (mixture of enantiomers)

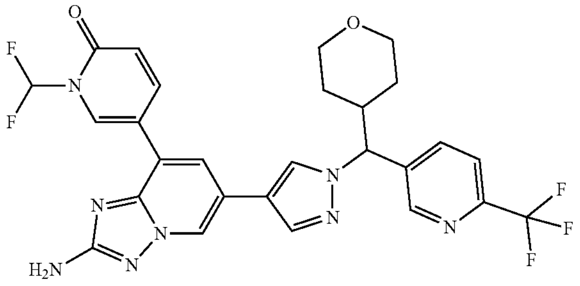 [SMILES: Nc1nc2c(-c3ccc(=O)n(C(F)F)c3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (186 mg, 389 μmol), 1-(difluoromethyl)-5-(4,4,5,5-tetramethyl-1,3,2-dioxaborolan-2-yl)pyridin-2(1H)-one (127 mg, 467 μmol), XPhos-Pd-G2 (15.3 mg, 19.5 μmol) and caesium carbonate (380 mg, 1.17 mmol) were reacted according to procedure A in a mixture of water (1.6 ml) and 1,4-dioxane (4.9 ml). After stirring for 12 h at 90° C., the reaction mixture was filtered through a Chromabond XTR/SiOH 3 ml 550/500 mg cartridge. The organic layer was concentrated and the residue was purified by preparative HPLC to yield 120 mg (100% purity, 53% yield) of the title compound as a mixture of enantiomers.

LC-MS (method 1): $R^t$=1.64 min; MS (ESIpos): m/z=587 $[M+H]^+$ $^1$H-NMR (600 MHz, DMSO-$d_6$) δ [ppm]: 1.10 (br d, 1H), 1.25 (br d, 1H), 1.29-1.41 (m, 2H), 2.72-2.79 (m, 1H), 3.24-3.29 (m, 2H), 3.79-3.88 (m, 2H), 5.39 (d, 1H), 6.16 (s, 2H), 6.73 (d, 1H), 7.94 (d, 1H), 7.95 (t, 1H), 8.01 (s, 1H), 8.19 (s, 1H), 8.31 (br d, 1H), 8.46 (dd, 1H), 8.55 (s, 1H), 8.86 (s, 1H), 8.98 (s, 1H), 9.12 (d, 1H).

Example II-154

5-[2-Amino-6-(1-{tetrahydro-2H-pyran-4-yl[6-(trifluoromethyl)pyridin-3-yl]methyl}-1H.-pyrazol-4-yl)[1,2,4]triazolo[1,5-a]pyridin-8-yl]-1-(difluoromethyl)pyridin-2(H)-one (stereoisomer 1, distomer)

5-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(difluoromethyl)pyridin-2(1H)-one (120 mg, 100% purity) was separated by chiral preparative HPLC to yield stereoisomer 1 (33 mg, 100% purity) and stereoisomer 2 (32 mg, 100% purity).

Column: Chiralpak OZ-H, 5 μm, 250×20 mm; Eluent A: n-heptane; Eluent B: ethanol+0.2% diethylamine; isocratic: 20% A+80% B; flow: 20 ml/min; UV: 210 nm; temperature: 50° C.

Stereoisomer 1: $R^t$=5.63 min and

Stereoisomer 2: $R^t$=7.73 min (cf. next example)

Analytical chiral HPLC method: Column: Daicel Chiralpak OZ-3, 3 μm, 50×4.6 mm; Eluent A: n-heptane; Eluent B: ethanol+0.2% diethylamine; isocratic: 20% A+80% B; flow: 1 ml/min;

UV: 220 nm, temperature: 40° C.

Stereoisomer 1: $R^t$=3.72 min and

Stereoisomer 2: $R^t$=6.59 min (cf. next example)

LC-MS (method 1): $R^t$=1.64 min; MS (ESIpos): m/z=587 $[M+H]^+$ $^1$H-NMR (400 MHz, DMSO-$d_6$) δ [ppm]: −0.149 (0.55), 0.146 (0.48), 0.859 (0.45), 1.073 (2.28), 1.104 (2.82), 1.141 (0.61), 1.159 (0.99), 1.177 (0.55), 1.232 (2.66), 1.256 (3.21), 1.282 (1.06), 1.294 (1.09), 1.312 (2.63), 1.323 (2.98), 1.344 (3.56), 1.352 (3.53), 1.373 (2.28), 2.329 (0.67), 2.367 (0.61), 2.671 (0.77), 2.711 (1.38), 2.739 (2.02), 2.767 (1.99), 3.244 (1.96), 3.269 (5.16), 3.733 (0.74), 3.804 (2.66), 3.835 (4.36), 3.870 (2.37), 3.895 (0.51), 5.374 (6.00), 5.401 (5.87), 6.180 (14.78), 6.719 (6.89), 6.744 (7.09), 7.823 (3.33), 7.947 (7.41), 7.968 (9.62), 7.972 (8.69), 8.007 (10.36), 8.010 (10.68), 8.122 (2.89), 8.195 (16.00), 8.301 (4.55), 8.321 (4.07), 8.445 (4.87), 8.451 (5.03), 8.470 (4.78), 8.476 (5.00), 8.551 (14.81), 8.862 (11.03), 8.865 (11.32), 8.979 (8.37), 9.115 (8.43), 9.121 (8.53).

Example II-155

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(difluoromethyl)pyridin-2(1H)-one (stereoisomer 2, eutomer)

The product was isolated in the previous example as second stereoisomer. The stereochemical configuration of the methine carbon atom bonded to the pyrazole was (S).

LC-MS (method 1): $R^t$=1.65 min; MS (ESIpos): m/z=587 $[M+H]^+$ $^1$H-NMR (400 MHz, DMSO-$d_6$) δ [ppm]: 1.02-1.17 (m, 1H), 1.18-1.41 (m, 3H), 2.66-2.81 (m, 1H), 3.23-3.30 (m, 2H), 3.73-3.89 (m, 2H), 5.39 (d, 1H), 6.18 (s, 2H), 6.73 (d, 1H), 7.96 (d, 1H), 7.97 (t, 1H), 8.01 (d, 1H), 8.19 (s, 1H), 8.31 (dd, 1H), 8.46 (dd, 1H), 8.55 (s, 1H), 8.86 (d, 1H), 8.98 (s, 1H), 9.12 (d, 1H).

Example II-156

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (mixture of enantiomers)

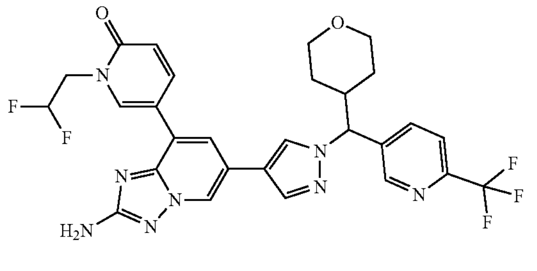 [SMILES: Nc1nc2c(-c3ccc(=O)n(CC(F)F)c3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (200 mg, 419 μmol), 1-(2,2-difluoroethyl)-5-(4,4,5,5-tetramethyl-1,3,2-dioxaborolan-2-yl)pyridin-2(1H)-one (143 mg, 502 μmol), XPhos-Pd-G2 (16.5 mg, 20.9 μmol) and caesium carbonate (409 mg, 1.26 mmol) were reacted according to procedure A in a mixture of water (2.6 ml) and 1,4-dioxane (7.9 ml). After stirring for 3 h at 90° C., the reaction mixture was filtered through a short pad of Florisil. The organic layer was concentrated and the residue was purified via preparative HPLC to yield 182 mg (100% purity, 72% yield) of the title compound as a mixture of enantiomers.

LC-MS (method 1): $R^t$=1.55 min; MS (ESIpos): m/z=601 $[M+H]^+$ $^1$H-NMR (600 MHz, DMSO-$d_6$) δ [ppm]: 1.10 (br d, 1H), 1.24 (br d, 1H), 1.29-1.40 (m, 2H), 2.72-2.79 (m, 1H), 3.25-3.28 (m, 1H), 3.79-3.88 (m, 2H), 4.45 (td, 2H), 5.40 (d, 1H), 6.09 (s, 2H), 6.41 (tt, 1H6.63 (d, 1H), 7.86 (d, 1H), 7.95 (d, 1H), 8.15 (s, 1H), 8.31 (dd, 1H), 8.38 (dd, 1H), 8.50 (s, 1H), 8.75 (d, 1H), 8.82 (d, 1H), 8.98 (br s, 1H).

Example II-157

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (stereoisomer 1, distomer)

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (182 mg, 100% purity) was separated by chiral preparative HPLC to yield stereoisomer 1 (73 mg, 100% purity) and stereoisomer 2 (74 mg, 100% purity).

Column: Chiralpak OZ-H, 5 μm, 250×20 mm; Eluent A: n-heptane; Eluent B: ethanol+0.2% diethylamine; isocratic: 30% A+70% B; flow: 20 ml/min; UV: 210 nm; temperature: 50° C.

Stereoisomer 1: $R^t$=5.97 min and

Stereoisomer 2: $R^t$=8.23 min (cf. next example)

Analytical chiral HPLC method: Column: Daicel Chiralpak OZ-H, 5 μm, 250×4.6 mm; Eluent A: n-heptane; Eluent B: ethanol+0.2% diethylamine; isocratic: 30% A+70% B; flow: 1 ml/min; UV: 220 nm, temperature: 50° C.

Stereoisomer 1: $R^t$=6.65 min and

Stereoisomer 2: $R^t$=9.66 min (cf. next example)

LC-MS (method 1): $R^t$=1.57 min; MS (ESIpos): m/z=601 $[M+H]^+$ $^1$H-NMR (600 MHz, DMSO-$d_6$) δ [ppm]: 1.072 (3.34), 1.093 (3.73), 1.221 (3.13), 1.241 (4.10), 1.324 (3.82), 1.344 (5.07), 1.362 (3.40), 2.429 (0.52), 2.659 (0.59), 2.747 (2.85), 2.765 (2.81), 3.251 (2.65), 3.272 (6.56), 3.291 (6.70), 3.312 (3.05), 3.807 (3.74), 3.823 (3.68), 3.847 (3.87), 3.865 (3.52), 4.434 (3.59), 4.457 (6.52), 4.477 (3.60), 5.395 (5.54), 5.413 (5.51), 6.152 (16.00), 6.325 (1.74), 6.418 (3.31), 6.510 (1.60), 6.633 (6.16), 6.649 (6.33), 7.868 (10.50), 7.960 (6.10), 7.974 (6.50), 8.170 (11.85), 8.309 (5.40), 8.323 (5.12), 8.379 (4.80), 8.392 (4.71), 8.517 (11.67), 8.761 (8.89), 8.840 (10.72), 8.983 (9.66).

Example II-158

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (stereoisomer 2, eutomer)

The product was isolated in the previous example as second stereoisomer. The stereochemical configuration of the methine carbon atom bonded to the pyrazole was (S).

LC-MS (method 1): $R^t$=1.57 min; MS (ESIpos): m/z=601 $[M+H]^+$ $^1$H-NMR (600 MHz, DMSO-$d_6$) δ [ppm]: 1.09 (br d, 1H), 1.23 (br d, 1H), 1.28-1.40 (m, 2H), 2.73-2.80 (m, 1H), 3.28 (q, 2H), 3.73-3.89 (m, 2H), 4.46 (td, 2H), 5.41 (d, 1H), 6.16 (s, 2H), 6.42 (tt, 1H), 6.64 (d, 1H), 7.87 (s, 1H), 7.97 (d, 1H), 8.17 (s, 1H), 8.32 (br d, 1H), 8.39 (dd, 1H), 8.52 (s, 1H), 8.77 (d, 1H), 8.84 (s, 1H), 8.99 (s, 1H).

Example 1-159

5-[2-Amino-6-(1-{(1lS)-1-[6-(trifluoromethyl)pyridin-3-yl]propyl}-1H-pyrazol-4-yl)[1,2,4]triazolo[1,5-a]pyridin-8-yl]-1-(2,2,2-trifluoroethyl)pyridin-2(1H)-one

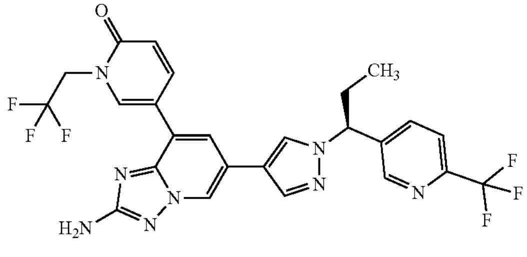 [SMILES: CC[C@@H](c1ccc(C(F)(F)F)nc1)n1cc(-c2cc(-c3ccc(=O)n(CC(F)(F)F)c3)c3nc(N)nn3c2)cn1]

5-(2-Amino-6-bromo[1,2,4]triazolo[1,5-a]pyridin-8-yl)-1-(2,2,2-trifluoroethyl)pyridin-2(1H)-one (1.00 g, 2.58 mmol) was reacted with enantioenriched (ee ca. 64%): 5-{(1S)-1-[4-(4,4,5,5-tetramethyl-1,3,2-dioxaborolan-2-yl)-1H-pyrazol-1-yl]propyl}-2-(trifluoromethyl)pyridine (1.18 g, 3.09 mmol) for 2.5 h at 90° C. following general procedure B using 0.1 eq. XPhos-Pd-G2 as catalyst. The reaction mixture was diluted with ethyl acetate (50 ml) and washed with water (50 ml). The aqueous layer was separated and extracted twice with ethyl acetate (50 ml each). The combined organic layers were washed with brine and filtered through a hydrophobic phase separation filter. The solvent was evaporated and the residue purified by column chromatography (Biotage® SNAP KP-NH 110 g cartridge, eluent:

cyclohexane/ethyl acetate/2-propanol gradient 7:3:0 to 0:1:0 to 0:9:1) to yield 691 mg (100% purity, 48% yield) of the enantioenriched compound.

The material was further purified by chiral preparative SFC to yield 0.76 g of the enantiopure title compound.

Instrument: SFC SCPA; Column: Daicel Chiralpak ID-H, 5 μm, 250×20 mm; Eluent A: $CO_2$; Eluent B: methanol; 0-3.19 min.: 60% A+40% B; 3.20-5.18 min.: 40% A+60% B; flow: 100 ml/min; UV: 210 nm; temperature: 40° C.

Stereoisomer 1: $R^t$=2.50 min (minor isomer, discarded) and

Stereoisomer 2: $R^t$=4.00 min (title compound)

Analytical chiral SFC-method: Column: Chiralpak ID-3, 3 μm, 100×4.6 mm; Eluent A: $CO_2$;

Eluent B: methanol; isocratic: 70% A+30% B; flow: 3 ml/min; UV: 210 nm; temperature: 30° C.

Stereoisomer 1: $R^t$=2.199 min (minor isomer, discarded) and

Stereoisomer 2: $R^t$=4.099 min (title compound).

The material was further purified by trituration with acetonitrile and suction filtration. The filtrate was purified by preparative HPLC (Chromatorex C18, 10 μm, 125×30 mm; eluent: water+0.1% formic acid/acetonitrile gradient 90:10 to 5:95) to afford a combined yield of 691 mg (100% purity, 48% yield) of the title compound.

LC-MS (method 1): $R^t$=1.73 min; MS (ESIpos): m/z=563 $[M+H]^+$ $^1$H-NMR (600 MHz, DMSO-$d_6$) δ [ppm]: 0.90 (t, 3H), 2.19-2.27 (m, 1H), 2.38-2.49 (m, 1H), 4.94 (q, 2H), 5.60 (dd, 1H), 6.10 (s, 2H), 6.67 (d, 1H), 7.89 (s, 1H), 7.93 (d, 1H), 8.04 (br dd, 1H), 8.16 (s, 1H), 8.38 (dd, 1H), 8.55-8.57 (m, 1H), 8.81 (s, 2H), 8.86 (s, 1H).

Example II-160

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (mixture of enantiomers)

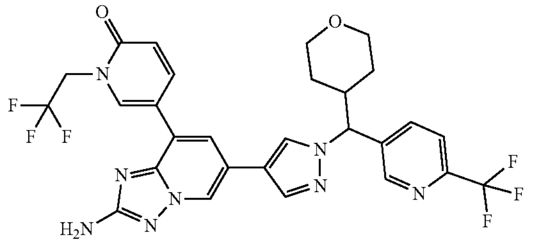 [SMILES: Nc1nc2c(-c3ccc(=O)n(CC(F)(F)F)c3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (186 mg, 389 μmol), 5-(4,4,5,5-tetramethyl-1,3,2-dioxaborolan-2-yl)-1-(2,2,2-trifluoroethyl)pyridin-2(1H)-one (142 mg, 467 μmol), caesium carbonate (380 mg, 1.17 mmol) and XPhos-Pd-G2 (15.3 mg, 19.5 μmol) were reacted according to procedure A in a mixture of 1,4-dioxane (4.9 ml) and water (1.6 ml). After 12 h at 90° C., the reaction mixture was quenched with water filtered through a hydrophobic phase separation filter, washed with of ethyl acetate and concentrated under reduced pressure. The residue was purified by preparative HPLC to yield 154 mg (100% purity, 64% yield) of the title compound as a mixture of enantiomers.

LC-MS (method 1): $R^t$=1.65 min; MS (ESIpos): m/z=619 $[M+H]^+$ $^1$H-NMR (600 MHz, DMSO-$d_6$) δ [ppm]: 1.10 (br d, 1H), 1.24 (br d, 1H), 1.29-1.40 (m, 2H), 2.72-2.79 (m, 1H), 3.24-3.28 (m, 2H), 3.79-3.87 (m, 2H), 4.93 (q, 2H), 5.40 (d, 1H), 6.07 (s, 2H), 6.67 (d, 1H), 7.85 (s, 1H), 7.95 (d, 1H), 8.15 (s, 1H), 8.31 (br d, 1H), 8.36 (dd, 1H), 8.50 (s, 1H), 8.79 (s, 1H), 8.83 (d, 1H), 8.97 (s, 1H).

Example II-161

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (stereoisomer 1, distomer)

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (mixture of enantiomers) (154 mg, 100% purity) was separated by chiral preparative HPLC to yield stereoisomer 1 (57.9 mg, 100% purity) and stereoisomer 2 (61.5 mg, 100% purity).

Column: Daicel Chiralcel OZ-H, 5 μm, 250×20 mm; Eluent A: n-heptane; Eluent B: ethanol+0.2% diethylamine; isocratic: 0% A+100% B; flow: 18 ml/min; UV: 210 nm; temperature: 50° C.

Stereoisomer 1: $R^t$=4.88 min and

Stereoisomer 2: $R^t$=6.05 min (cf. next example)

Analytical chiral HPLC method: Column: Daicel Chiralcel OZ-H, 5 μm, 250×4.6 mm; Eluent A: n-heptane; Eluent B: ethanol+0.2% diethylamine; isocratic: 0% A+100% B; flow: 1 ml/min; UV: 220 nm; temperature: 50° C.

Stereoisomer 1: $R^t$=4.80 min and

Stereoisomer 2: $R^t$=6.11 min (cf. next example)

LC-MS (method 1): $R^t$=1.64 min; MS (ESIpos): m/z=619 $[M+H]^+$

Example II-162

5-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(2,2,2-trifluoroethyl)pyridin-2(1H)-one (stereoisomer 2, eutomer)

The product was isolated in the previous example as second stereoisomer.

LC-MS (method 1): $R^t$=1.64 min; MS (ESIpos): m/z=619 $[M+H]^+$ $^1$H-NMR (600 MHz, DMSO-$d_6$) δ [ppm]: 1.08 (br d, 1H), 1.19-1.27 (m, 1H), 1.29-1.39 (m, 2H), 2.70-2.80 (m, 1H), 3.24-3.33 (m, 2H), 3.78-3.90 (m, 2H), 4.94 (q, 2H), 5.40 (d, 1H), 6.13 (s, 2H), 6.68 (d, 1H), 7.86 (d, 1H), 7.97 (d, 1H), 8.17 (s, 1H), 8.31 (dd, 1H), 8.37 (dd, 1H), 8.52 (s, 1H), 8.80 (d, 1H), 8.85 (d, 1H), 8.98 (s, 1H).

Example II-163

5-[2-Amino-6-(1-{1-[6-(trifluoromethoxy)pyridin-3-yl]propyl}-1H-pyrazol-4-yl)[1,2,4]triazolo[1,5-a]pyridin-8-yl]-1-(2,2,2-trifluoroethyl)pyridin-2(1H)-one (mixture of enantiomers)

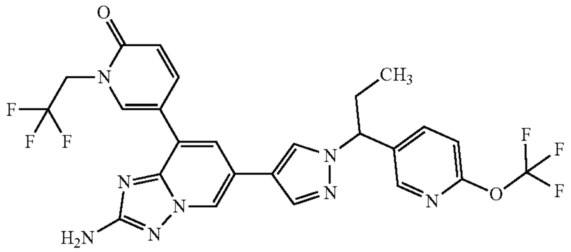 [SMILES: CCC(c1ccc(OC(F)(F)F)nc1)n1cc(-c2cc(-c3ccc(=O)n(CC(F)(F)F)c3)c3nc(N)nn3c2)cn1]

5-(2-Amino-6-bromo[1,2,4]triazolo[1,5-a]pyridin-8-yl)-1-(2,2,2-trifluoroethyl)pyridin-2(1H)-one (270 mg, 93% purity, 647 μmol) was reacted with 5-{1-[4-(4,4,5,5-tetramethyl-1,3,2-dioxaborolan-2-yl)-1H-pyrazol-1-yl]propyl}-2-(trifluoromethoxy)pyridine (334 mg, 841 μmol) for 2 h at 90° C. following general procedure B using 0.1 eq. XPhos-Pd-G2 as catalyst. The reaction mixture was diluted with ethyl acetate (15 ml) and washed with water (3 ml). The aqueous layer was separated and extracted twice with ethyl acetate (8 ml each). The combined organic layers were concentrated in vacuo and the residue was purified by column chromatography (Biotageo SNAP KP-NH 28 g cartridge, eluent: cyclohexane/ethyl acetate gradient 90:10 to 0:100) to yield 282 mg (98% purity, 74% yield) of the title compound.

LC-MS (method 2): $R^t$=0.92 min; MS (ESIpos): m/z=579 $[M+H]^+$ $^1$H-NMR (600 MHz, DMSO-$d_6$) δ [ppm]: 0.863 (7.61), 0.876 (16.00), 0.887 (7.48), 1.073 (0.49), 1.991 (0.50), 2.170 (1.02), 2.181 (1.71), 2.193 (2.41), 2.205 (1.94), 2.216 (1.18), 2.386 (1.22), 2.398 (1.56), 2.401 (1.39), 2.409 (1.52), 2.413 (1.59), 2.421 (1.20), 2.425 (1.42), 2.436 (0.94), 4.916 (1.93), 4.932 (5.44), 4.947 (5.17), 4.962 (1.62), 5.485 (2.37), 5.495 (2.69), 5.500 (2.67), 5.510 (2.26), 6.100 (11.97), 6.666 (6.15), 6.682 (6.15), 7.301 (6.03), 7.315 (6.21), 7.887 (7.99), 7.889 (8.06), 8.017 (3.80), 8.021 (3.84), 8.031 (3.60), 8.035 (3.60), 8.133 (11.42), 8.368 (3.74), 8.372 (3.81), 8.384 (3.61), 8.389 (3.68), 8.413 (6.43), 8.417 (6.33), 8.532 (10.97), 8.810 (5.40), 8.813 (5.23), 8.851 (8.51), 8.853 (8.51).

Example II-164

5-[2-Amino-6-(1-{1-[6-(trifluoromethoxy)pyridin-3-yl]propyl}-1H-pyrazol-4-yl)[1,2,4]triazolo[1,5-a]pyridin-8-yl]-1-(2,2,2-trifluoroethyl)pyridin-2(1H)-one (stereoisomer 1, eutomer)

5-[2-Amino-6-(1-{1-[6-(trifluoromethoxy)pyridin-3-yl]propyl}-1H-pyrazol-4-yl)[1,2,4]triazolo[1,5-a]pyridin-8-yl]-1-(2,2,2-trifluoroethyl)pyridin-2(1H)-one (mixture of enantiomers) (269 mg, 99% purity) from the previous example was separated by chiral preparative SFC to yield stereoisomer 1 (121 mg, 100% purity) and stereoisomer 2 (115 mg, 100% purity).

Column: Daicel Chiralpak IC-H, 5 m, 250×20 mm; 250×25 mm; Eluent A: $CO_2$; Eluent B: 2-propanol; isocratic: 65% A+35% B; flow: 100 ml/min; UV: 210 nm; temperature: 40° C.

Stereoisomer 1: $R^t$=2.75 min and

Stereoisomer 2: $R^t$=4.00 min (cf. next example)

Analytical chiral SFC-method: Column: Daicel Chiralpak IC, 3 m, 100×4.6 mm; Eluent A: $CO_2$;

Eluent B: 2-propanol; isocratic: 70% A+30% B; flow: 3 ml/min; UV: 210 nm.

Stereoisomer 1: $R^t$=2.699 min and

Stereoisomer 2: $R^t$=4.111 min (cf. next example)

LC-MS (method 1): $R^t$=1.84 min; MS (ESIpos): m/z=579 $[M+H]^+$ $^1$H-NMR (400 MHz, DMSO-$d_6$) δ [ppm]: 0.87 (t, 3H), 2.13-2.25 (m, 1H), 2.35-2.47 (m, 1H), 4.94 (q, 2H), 5.49 (dd, 1H), 6.09 (s, 2H), 6.67 (d, 1H), 7.31 (d, 1H), 7.88 (d, 1H), 8.02 (dd, 1H), 8.13 (s, 1H), 8.37 (dd, 1H), 8.41 (d, 1H), 8.53 (s, 1H), 8.81 (d, 1H), 8.85 (d, 1H).

Example II-165

5-[2-Amino-6-(1-{1-[6-(trifluoromethoxy)pyridin-3-yl]propyl}-1H-pyrazol-4-yl)[1,2,4]triazolo[1,5-a]pyridin-8-yl]-1-(2,2,2-trifluoroethyl)pyridin-2(1H)-one (stereoisomer 2, distomer)

The product was isolated in the previous example as second stereoisomer.

LC-MS (method 1): $R^t$=1.83 min; MS (ESIpos): m/z=579 $[M+H]^+$ $^1$H-NMR (400 MHz, DMSO-$d_6$) δ [ppm]: −0.150 (0.41), −0.008 (3.36), 0.008 (4.36), 0.146 (0.41), 0.855 (7.00), 0.873 (16.00), 0.891 (7.36), 2.156 (1.00), 2.172 (1.59), 2.190 (2.45), 2.208 (1.91), 2.224 (1.18), 2.328 (0.64), 2.369 (1.36), 2.389 (1.45), 2.411 (1.64), 2.428 (1.36), 2.446 (0.91), 2.671 (0.59), 2.711 (0.68), 4.901 (1.95), 4.924 (5.68), 4.947 (5.45), 4.970 (1.77), 5.475 (2.27), 5.490 (2.59), 5.498 (2.82), 5.513 (2.23), 6.091 (10.86), 6.658 (6.95), 6.682 (7.14), 7.295 (6.73), 7.317 (7.05), 7.881 (8.23), 7.885 (8.50), 8.009 (4.09), 8.015 (4.23), 8.030 (3.86), 8.036 (4.09), 8.129 (12.86), 8.358 (4.09), 8.365 (4.18), 8.383 (3.91), 8.389 (4.18), 8.408 (6.82), 8.414 (6.77), 8.527 (11.59), 8.803 (5.32), 8.809 (5.23), 8.844 (9.09), 8.848 (9.41).

Example II-166

5-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(2,2,2-trifluoroethyl)pyrazin-2(1H)-one (mixture of enantiomers)

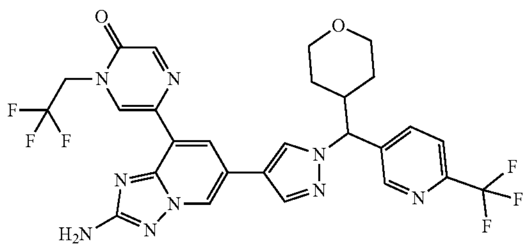 [SMILES: Nc1nc2c(-c3cn(CC(F)(F)F)c(=O)cn3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo

[1,5-a]pyridin-2-amine (291 mg, 608 μmol), [5-oxo-4-(2,2,2-trifluoroethyl)-4,5-dihydropyrazin-2-yl]boronic acid (216 mg, 973 μmol), XPhos-Pd-G2 (23.9 mg, 30.4 μmol) and caesium carbonate (594 mg, 1.82 mmol) were reacted according to procedure A in a mixture of water (7.0 ml) and 1,4-dioxane (3.0 ml). After stirring for 3 h at 90° C., the reaction mixture was filtered through a short pad of Florisil. The organic layer was concentrated and the residue was purified via preparative HPLC to yield 170 mg (100% purity, 45% yield) of the title compound as a mixture of enantiomers.

LC-MS (method 1): $R^t$=1.75 min; MS (ESIpos): m/z=620 $[M+H]^+$ $^1$H-NMR (400 MHz, DMSO-$d_6$) δ [ppm]: 1.10 (br d, 1H), 1.18-1.25 (m, 1H), 1.25-1.41 (m, 2H), 2.71-2.84 (m, 1H), 3.23-3.30 (m, 2H), 3.78-3.88 (m, 2H), 5.00 (q, 2H), 5.42 (d, 1H), 6.14 (s, 2H), 7.95 (d, 1H), 8.11 (s, 1H), 8.30-8.34 (m, 2H), 8.38 (d, 1H), 8.56 (s, 1H), 8.89 (d, 1H), 8.98 (s, 1H), 9.23 (s, 1H).

Example II-167

5-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(2,2,2-trifluoroethyl)pyrazin-2(1H)-one (stereoisomer 1, eutomer)

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyrazin-2(1H)-one (mixture of enantiomers) (170 mg, 100% purity) was separated by chiral preparative SFC to yield stereoisomer 1 (71 mg, 100% purity) and stereoisomer 2 (68 mg, 100% purity).

Column: YMC Chiralart Amylose SA, 5 μm, 250×25 mm; Eluent A: $CO_2$; Eluent B: methanol; isocratic: 60% A+40% B; flow: 22 ml/min; UV: 220 nm; temperature: 70° C.

Stereoisomer 1: $R^t$=7.45 min and

Stereoisomer 2: $R_t$=11.82 min (cf. next example)

Analytical chiral HPLC method: Column: Daicel Chiralpak AD-3, 3 m, 50×4.6 mm; Eluent A: n-heptane; Eluent B: ethanol+0.2% diethylamine; isocratic: 0% A+100% B; flow: 1 ml/min;

UV: 220 nm.

Stereoisomer 1: $R^t$=1.49 min and

Stereoisomer 2: $R^t$=3.37 min (cf. next example)

LC-MS (method 1): $R^t$=1.75 min; MS (ESIpos): m/z=620 $[M+H]^+$ $^1$H-NMR (600 MHz, DMSO-$d_6$) δ [ppm]: 1.10 (br d, 1H), 1.22 (br d, 1H), 1.26-1.39 (m, 2H), 2.76-2.83 (m, 1H), 3.25-3.32 (m, 2H), 3.79-3.87 (m, 2H), 5.01 (q, 2H), 5.42 (d, 1H), 6.15 (s, 2H), 7.96 (d, 1H), 8.12 (s, 1H), 8.32 (m, 2H), 8.39 (s, 1H), 8.56 (s, 1H), 8.89 (d, 1H), 8.98 (s, 1H), 9.23 (s, 1H).

Example II-168

5-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyrazin-2(1H)-one (stereoisomer 2, distomer)

The product was isolated in the previous example as second stereoisomer.

LC-MS (method 1): $R^t$=1.75 min; MS (ESIpos): m/z=620 $[M+H]^+$

Example II-169

4-[2-Amino-6-(1-{1-[6-(trifluoromethyl)pyridin-3-yl]propyl}-1H-pyrazol-4-yl)[1,2,4]triazolo[1,5-a]pyridin-8-yl]-1-methylpyridin-2(1H)-one (mixture of enantiomers)

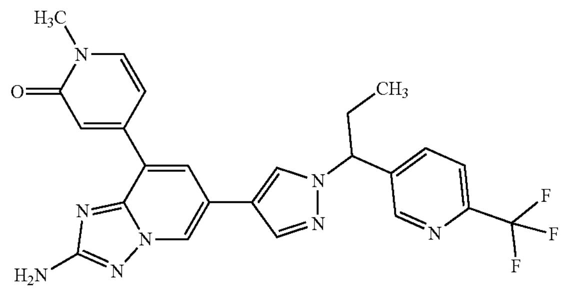 [SMILES: CCC(c1ccc(C(F)(F)F)nc1)n1cc(-c2cc(-c3ccn(C)c(=O)c3)c3nc(N)nn3c2)cn1]

8-Chloro-6-(1-{1-[6-(trifluoromethyl)pyridin-3-yl]propyl}-1H-pyrazol-4-yl)[1,2,4]triazolo[1,5-a]pyridin-2-amine (200 mg, 474 μmol), 1-methyl-4-(4,4,5,5-tetramethyl-1,3,2-dioxaborolan-2-yl)pyridin-2(1H)-one (134 mg, 569 μmol), caesium carbonate (463 mg, 1.42 mmol) and XPhos-Pd-G2 (18.7 mg, 23.7 μmol) were reacted according to procedure A in a mixture of 1,4-dioxane (9 ml) and water (1 ml). After 3 h at 90° C., the reaction mixture was quenched with water filtered through a hydrophobic phase separation filter, washed with of ethyl acetate and concentrated under reduced pressure. The residue was purified by preparative HPLC to yield 135 mg (100% purity, 58% yield) of the title compound as a mixture of enantiomers.

LC-MS (method 2): $R^t$=0.77 min; MS (ESIpos): m/z=495 $[M+H]^+$ $^1$H-NMR (600 MHz, DMSO-$d_6$) δ [ppm]: 0.90 (t, 3H), 2.19-2.29 (m, 1H), 2.39-2.48 (m, 1H), 3.48 (s, 3H), 5.58 (dd, 1H), 6.29 (s, 2H), 7.07 (dd, 1H), 7.57 (d, 1H), 7.79 (d, 1H), 7.92 (d, 1H), 8.04 (d, 1H), 8.09 (d, 1H), 8.20 (s, 1H), 8.64 (s, 1H), 8.81 (s, 1H), 8.97 (d, 1H).

Example II-170

4-[2-Amino-6-(1-{1-[6-(trifluoromethyl)pyridin-3-yl]propyl}-1H-pyrazol-4-yl)[1,2,4]triazolo[1,5-a]pyridin-8-yl]-1-methylpyridin-2(1H)-one (stereoisomer 1, distomer)

4-[2-Amino-6-(1-{1-[6-(trifluoromethyl)pyridin-3-yl]propyl}-1H-pyrazol-4-yl)[1,2,4]triazolo[1,5-a]pyridin-8-yl]-1-methylpyridin-2(1H)-one (mixture of enantiomers) (135 mg, 100% purity) was separated by chiral preparative HPLC to yield stereoisomer 1 (47.6 mg, 100% purity) and stereoisomer 2 (30.3 mg, 100% purity).

Column: Daicel Chiralpak IE, 5 μm, 250×20 mm; Eluent A: n-heptane; Eluent B: ethanol+0.2% diethylamine; isocratic: 20% A+80% B; flow: 15 ml/min; UV: 220 nm; temperature: 60° C.

Stereoisomer 1: $R^t$=10.25 min and

Stereoisomer 2: $R^t$=13.52 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 20% A+80% B; flow: 1 ml/min; UV: 220 nm.

Stereoisomer 1: $R^t$=3.20 min and

Stereoisomer 2: $R^t$=3.89 min (cf. next example)

LC-MS (method 1): $R^t$=1.44 min; MS (ESIpos): m/z=495 $[M+H]^+$

Example II-171

4-[2-Amino-6-(1-{1-[6-(trifluoromethyl)pyridin-3-yl]propyl}-1H-pyrazol-4-yl)[1,2,4]triazolo[1,5-a]pyridin-8-yl]-1-methylpyridin-2(1H)-one (stereoisomer 2, eutomer)

The product was isolated in the previous example as second stereoisomer.

LC-MS (method 1): $R^t$=1.44 min; MS (ESIpos): m/z=495 $[M+H]^+$ $^1$H-NMR (600 MHz, DMSO-$d_6$) δ [ppm]: 0.90 (t, 3H), 2.21-2.26 (m, 1H), 2.39-2.49 (m, 1H), 3.48 (s, 3H), 5.58 (dd, 1H), 6.29 (s, 2H), 7.09 (dd, 1H), 7.59 (brs, 1H), 7.81 (d, 1H), 7.93 (d, 1H), 8.04 (d, 1H), 8.11 (d, 1H), 8.21 (s, 1H), 8.67 (s, 1H), 8.82 (s, 1H), 9.00 (d, 1H).

Example II-172

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (mixture of enantiomers)

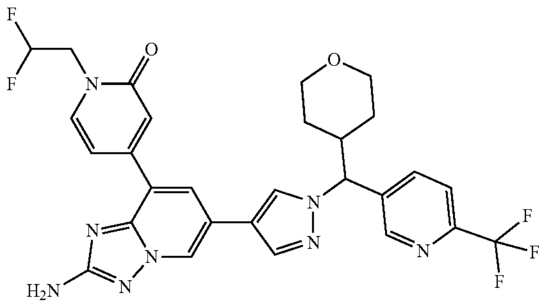 [SMILES: Nc1nc2c(-c3ccn(CC(F)F)c(=O)c3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (250 mg, 523 µmol), 1-(2,2-difluoroethyl)-4-(4,4,5,5-tetramethyl-1,3,2-dioxaborolan-2-yl)pyridin-2(1H)-one (179 mg, 628 µmol), XPhos-Pd-G2 (20.6 mg, 26.2 µmol) and caesium carbonate (511 mg, 1.57 mmol) were reacted according to procedure A in a mixture of water (9.9 ml) and 1,4-dioxane (3.3 ml). After stirring for 4 h at 90° C., the reaction mixture was filtered through a short pad of Florisil. The organic layer was concentrated and the residue was purified via preparative HPLC to yield 173 mg (100% purity, 55% yield) of the title compound as a mixture of enantiomers.

LC-MS (method 1): $R^t$=1.57 min; MS (ESIpos): m/z=601 $[M+H]^+$ $^1$H-NMR (400 MHz, DMSO-$d_6$) δ [ppm]: 1.08 (br d, 1H), 1.25 (br d, 1H), 1.29-1.42 (m, 2H), 2.68-2.80 (m, 1H), 3.23-3.29 (m, 1H), 3.78-3.89 (m, 2H), 4.43 (td, 2H), 5.38 (d, 1H), 6.26 (s, 2H), 6.35 (tt, 1H), 7.11 (dd, 1H), 7.59 (d, 1H), 7.79 (d, 1H), 7.96 (d, 1H), 8.08 (d, 1H), 8.20 (s, 1H), 8.31 (dd, 1H), 8.60 (s, 1H), 8.97 (br s, 2H).

Example II-173

4-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(2,2-difluoroethyl)pyridin-2(1H)-one (stereoisomer 1, distomer)

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (mixture of enantiomers) (173 mg, 100% purity) was separated by chiral preparative SFC to yield stereoisomer 1 (70 mg, 100% purity) and stereoisomer 2 (67 mg, 100% purity).

Column: Daicel Chiralcel OZ-H, 5 µm, 250×20 mm; Eluent A: $CO_2$; Eluent B: methanol; isocratic: 60% A+40% B; flow: 20 ml/min; UV: 220 nm; temperature: 40° C.

Stereoisomer 1: $R^t$=7.12 min and

Stereoisomer 2: $R^t$=10.05 min (cf. next example)

Analytical chiral HPLC method: Column: Daicel Chiraltek OZ-3, 3 m, 50×4.6 mm; Eluent A: n-heptane; Eluent B: ethanol+0.2% diethylamine; isocratic: 20% A+80% B; flow: 1 ml/min;

UV: 220 nm; temperature: 40° C.

Stereoisomer 1: $R^t$=4.03 min and

Stereoisomer 2: $R^t$=6.58 min (cf. next example)

LC-MS (method 2): $R^t$=0.83 min; MS (ESIpos): m/z=601 $[M+H]^+$

Example II-174

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2-difluoroethyl)pyridin-2(1H)-one (stereoisomer 2, eutomer)

The product was isolated in the previous example as second stereoisomer.

LC-MS (method 2): $R^t$=0.83 min; MS (ESIpos): m/z=601 $[M+H]^+$ $^1$H-NMR (600 MHz, DMSO-$d_6$) δ [ppm]: 1.10 (br d, 1H), 1.25 (br d, 1H), 1.29-1.40 (m, 2H), 2.71-2.81 (m, 1H), 3.24-3.31 (m, 2H), 3.73-3.88 (m, 2H), 4.44 (td, 2H), 5.38 (d, 1H), 6.27 (s, 2H), 6.35 (tt, 1H), 7.11 (dd, 1H), 7.60 (d, 1H), 7.79 (d, 1H), 7.96 (d, 1H), 8.07-8.10 (m, 1H), 8.20 (s, 1H), 8.31 (d, 1H), 8.60 (s, 1H), 8.98 (s, 2H).

Example II-175

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (mixture of enantiomers)

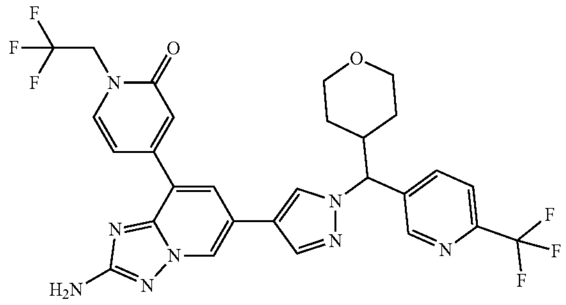 [SMILES: Nc1nc2c(-c3ccn(CC(F)(F)F)c(=O)c3)cc(-c3cnn(C(c4ccc(C(F)(F)F)nc4)C4CCOCC4)c3)cn2n1]

8-Chloro-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-2-amine (250 mg, 523 μmol), 4-(4,4,5,5-tetramethyl-1,3,2-dioxaborolan-2-yl)-1-(2,2,2-trifluoroethyl)pyridin-2(1H)-one (190 mg, 628 μmol), XPhos-Pd-G2 (20.6 mg, 26.2 μmol) and caesium carbonate (511 mg, 1.57 mmol) were reacted according to procedure A in a mixture of water (9.9 ml) and 1,4-dioxane (3.3 ml). After stirring for 4 h at 90° C., the reaction mixture was filtered through a short pad of Florisil. The organic layer was concentrated and the residue was purified via preparative HPLC to yield 125 mg (100% purity, 39% yield) of the title compound as a mixture of enantiomers.

LC-MS (method 1): $R^t$=1.65 min; MS (ESIpos): m/z=619 $[M+H]^+$ $^1$H-NMR (400 MHz, DMSO-$d_6$) δ [ppm]: 1.10 (br s, 1H), 1.31 (m, 1H), 1.30-1.42 (m, 2H), 2.67-2.80 (m, 1H), 3.21-3.34 (m, 2H), 3.77-3.90 (m, 2H), 4.91 (q, 2H), 5.38 (d, 1H), 6.28 (s, 2H), 7.14 (dd, 1H), 7.62 (d, 1H), 7.80 (d, 1H), 7.96 (d, 1H), 8.10 (d, 1H), 8.20 (s, 1H), 8.31 (dd, 1H), 8.60 (s, 1H), 8.98 (dd, 2H).

Example II-176

4-[2-Amino-6-(1-{tetrahydro-2H-pyran-4-yl[6-(trifluoromethyl)pyridin-3-yl]methyl}-1 H-pyrazol-4-yl)[1,2,4]triazolo[1,5-a]pyridin-8-yl]-1-(2,2,2-trifluoroethyl)pyridin-2(1H)-one (stereoisomer 1, eutomer)

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (mixture of enantiomers) (125 mg, 100% purity) was separated by chiral preparative SFC to yield stereoisomer 1 (50 mg, 100% purity) and stereoisomer 2 (52 mg, 100% purity).

Column: YMC Chiralart Amylose SA, 5 μm, 250×25 mm; Eluent A: $CO_2$; Eluent B: methanol; isocratic: 60% A+40% B; flow: 22 ml/min; UV: 220 nm; temperature: 70° C.

Stereoisomer 1: $R^t$=8.29 min and

Stereoisomer 2: $R^t$=11.70 min (cf. next example)

Analytical chiral HPLC method: Column: Daicel Chiralpak AD-3, 3 μm, 50×4.6 mm; Eluent A: n-heptane; Eluent B: ethanol+0.2% diethylamine; isocratic: 0% A+100% B; flow: 1 ml/min; UV: 220 nm; temperature: 55° C.

Stereoisomer 1: $R^t$=3.02 min and

Stereoisomer 2: $R^t$=4.77 min (cf. next example)

LC-MS (method 1): $R^t$=1.65 min; MS (ESIpos): m/z=619 $[M+H]^+$ $^1$H-NMR (600 MHz, DMSO-$d_6$) δ [ppm]: 1.09 (br d, 1H), 1.26 (br d, 1H), 1.31-1.40 (m, 2H), 2.71-2.79 (m, 1H), 3.24-3.31 (m, 2H), 3.79-3.88 (m, 2H), 4.92 (q, 2H), 5.38 (d, 1H), 6.28 (s, 2H), 7.14 (dd, 1H), 7.63 (d, 1H), 7.80 (d, 1H), 7.96 (d, 1H), 8.10 (s, 1H), 8.21 (s, 1H), 8.31 (br d, 1H), 8.60 (s, 1H), 8.98 (s, 1H), 8.99 (s, 1H).

Example II-177

4-[2-Amino-6-(1-{tetrahydro-2H-pyran-4-yl[6-(trifluoromethyl)pyridin-3-yl]methyl}-1H-pyrazol-4-yl)[1,2,4]triazolo[1,5-a]pyridin-8-yl]-1-(2,2,2-trifluoroethyl)pyridin-2(1H)-one (stereoisomer 2, distomer)

The product was isolated in the previous example as second stereoisomer.

LC-MS (method 1): $R^t$=1.65 min; MS (ESIpos): m/z=619 $[M+H]^+$ Pyridones (Reversed Core)

Example II-178

5-(2-Amino-7-{1-[(1S)-1-phenylpropyl]-1H-pyrazol-4-yl}[1,2,4]triazolo[1,5-a]pyridin-5-yl)pyridin-2(1H)-one

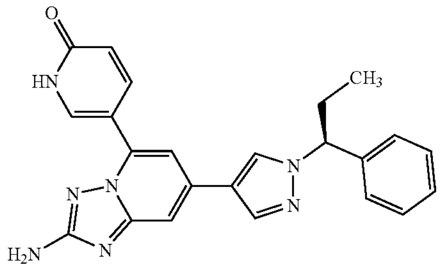 [SMILES: CC[C@@H](c1ccccc1)n1cc(-c2cc(-c3ccc(=O)[nH]c3)n3nc(N)nc3c2)cn1]

5-(2-Amino-7-chloro[1,2,4]triazolo[1,5-a]pyridin-5-yl)pyridin-2(1H)-one (38.8 mg, 148 μmol) was reacted with 1-[(1S)-.1-phenylpropyl]-4-(4,4,5,5-tetramethyl-1,3,2-dioxaborolan-2-yl)-1H-pyrazole (69.4 mg, 222 μmol) for 3 h at 100° C. following general procedure B using 0.15 eq. catalyst. Thereafter more catalyst (0.15 eq.) was added and heating was continued for another 4 h. The reaction mixture was diluted with dichloromethane (5 ml) and methanol (1 ml) and filtered. The solids were washed with dichloromethane and the combined filtrates were filtered through a hydrophobic phase separation filter. After concentration in vacuo the residue was purified by column chromatography (Biotage® SNAP Ultra 10 g cartridge, eluent: dichloromethane/methanol gradient 100:0 to 85:15). The product was further purified by preparative HPLC (Chromatorex C18, 10 μm, 125×30 mm; eluent: water (0.1% formic acid)/acetonitrile gradient 90:10 to 5:95) to yield 6.80 mg (99% purity, 11% yield) of the title compound.

LC-MS (method 1): $R^t$=1.41 min; MS (ESIpos): m/z=412 $[M+H]^+$ $^1$H-NMR (400 MHz, DMSO-$d_6$) δ [ppm]: 0.86 (t, 3H), 2.11-2.23 (m, 1H), 2.31-2.45 (m, 1H), 5.31 (dd, 1H), 6.02 (s, 2H), 6.49 (d, 1H), 7.25-7.40 (m, 6H), 7.52 (d, 1H), 8.12-8.20 (m, 2H), 8.49 (br s, 1H), 8.67 (s, 1H), 12.11 (br s, 1H).

Example II-179

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(difluoromethyl)pyridin-2(1H)-one (mixture of enantiomers)

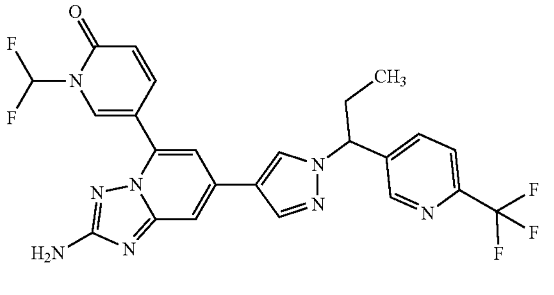 [SMILES: CCC(c1ccc(C(F)(F)F)nc1)n1cc(-c2cc(-c3ccc(=O)n(C(F)F)c3)n3nc(N)nc3c2)cn1]

5-(2-Amino-7-chloro[1,2,4]triazolo[1,5-a]pyridin-5-yl)-1-(difluoromethyl)pyridin-2(1H)-one (246 mg, 788 µmol), 5-{1-[4-(4,4,5,5-tetramethyl-1,3,2-dioxaborolan-2-yl)-1H-pyrazol-1-yl]propyl}-2-(trifluoromethyl)pyridine (330 mg, 867 µmol), XPhos-Pd-G2 (31.0 mg, 39.4 µmol) and caesium carbonate (770 mg, 2.36 mmol) were reacted according to procedure A in a mixture of water (500 1) and 1,4-dioxane (5.0 ml). After stirring for 4 h at 90° C., the reaction mixture was filtered through a Chromabond XTR/SiOH 3 ml 550/500 mg cartridge. The organic layer was concentrated and the residue was purified via preparative HPLC to yield 121 mg (96% purity, 28% yield) of the title compound as a mixture of enantiomers.

LC-MS (method 1): $R^t$=1.67 min; MS (ESIpos): m/z=531 $[M+H]^+$ $^1$H-NMR (400 MHz, DMSO-$d_6$) δ [ppm]: 0.89 (t, 3H), 2.19-2.27 (m, 1H), 2.36-2.47 (m, 1H), 5.60 (dd, 1H), 6.09 (s, 2H), 6.72 (d, 1H), 7.42 (s, 1H), 7.62 (s, 1H), 7.93 (d, 1H), 7.95 (t, 1H), 8.04 (d, 1H), 8.25 (d, 1H), 8.27 (s, 1H), 8.72 (s, 1H), 8.82 (s, 1H), 8.86 (s, 1H).

Example II-180

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(difluoromethyl)pyridin-2(1H)-one (stereoisomer 1, distomer)

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(difluoromethyl)pyridin-2(1H)-one (115 mg, 100% purity) was separated by chiral preparative HPLC to yield stereoisomer 1 (39 mg, 99% purity) and stereoisomer 2 (40 mg, 99% purity).

Column: Chiralpak IE-H, 5 µm, 250×20 mm; Eluent A: n-heptane; Eluent B: ethanol+0.2% diethylamine; isocratic: 60% A+40% B; flow: 20 ml/min; UV: 210 nm; temperature: 40° C.

Stereoisomer 1: $R^t$=11.12 min and

Stereoisomer 2: $R^t$=13.43 min (cf. next example)

Analytical chiral HPLC method: Column: Daicel Chiralpak IE-3, 3 µm, 50×4.6 mm; Eluent A: n-heptane; Eluent B: ethanol+0.2% diethylamine; isocratic: 50% A+50% B; flow: 1 ml/min; UV: 220 nm, temperature: 40° C.

Stereoisomer 1: $R^t$=2.39 min and

Stereoisomer 2: $R^t$=2.82 min (cf. next example)

LC-MS (method 1): $R^t$=1.67 min; MS (ESIpos): m/z=531 $[M+H]^+$ $^1$H-NMR (600 MHz, DMSO-$d_6$) δ [ppm]: 0.89 (t, 3H), 2.20-2.27 (m, 1H), 2.41-2.48 (m, 1H), 5.60 (dd, 1H), 6.07 (s, 2H), 6.72 (d, 1H), 7.42 (d, 1H), 7.62 (s, 1H), 7.93 (d, 1H), 7.95 (t, 1H), 8.04 (d, 1H), 8.25 (d, 1H), 8.27 (s, 1H), 8.71 (s, 1H), 8.81 (s, 1H), 8.86 (d, 1H).

Example II-181

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(difluoromethyl)pyridin-2(1H)-one (stereoisomer 2, eutomer)

The product was isolated in the previous example as second stereoisomer. The stereochemical configuration of the methine carbon atom bonded to the pyrazole was (S).

LC-MS (method 1): $R^t$=1.67 min; MS (ESIpos): m/z=531 $[M+H]^+$ $^1$H-NMR (600 MHz, DMSO-$d_6$) δ [ppm]: 0.89 (t, 3H), 2.20-2.27 (m, 1H), 2.41-2.48 (m, 1H), 5.60 (dd, 1H), 6.07 (s, 2H), 6.72 (d, 1H), 7.42 (d, 1H), 7.61 (s, 1H), 7.93 (d, 1H), 7.95 (t, 1H), 8.04 (d, 1H), 8.25 (d, 1H), 8.27 (s, 1H), 8.71 (s, 1H), 8.81 (s, 1H), 8.85 (d, 1H).

Example II-182

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(difluoromethyl)pyridin-2(1H)-one (mixture of enantiomers)

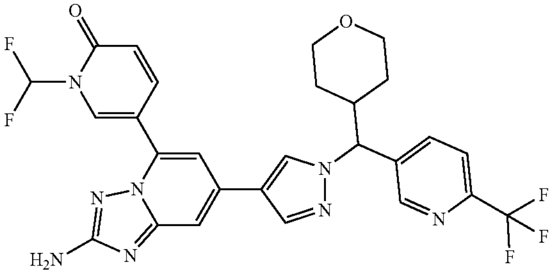 [SMILES: Nc1nc2cc(-c3cnn(C(c4ccc(C(F)(F)F)nc4)C4CCOCC4)c3)cc(-c3ccc(=O)n(C(F)F)c3)n2n1]

5-(2-Amino-7-chloro[1,2,4]triazolo[1,5-a]pyridin-5-yl)-1-(difluoromethyl)pyridin-2(1H)-one (192 mg, 616 µmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (349 mg, 85% purity, 677 µmol), 10 XPhos-Pd-G2 (24.2 mg, 30.8 µmol) and caesium carbonate (602 mg, 1.85 mmol) were reacted according to procedure A in a mixture of water (5 ml) and 1,4-dioxane (500 µl). After stirring for 4 h at 90° C., the reaction mixture was filtered through a short pad of Florisil. The organic layer was concentrated and the residue was purified via preparative HPLC to yield 103 mg (100% purity, 29% yield) of the title compound as a mixture of enantiomers.

LC-MS (method 1): $R^t$=1.60 min; MS (ESIpos): m/z=587 $[M+H]^+$ $^1$H-NMR (400 MHz, DMSO-de) S [ppm]: 1.09 (br d, 1H), 1.21 (br d, 1H), 1.27-1.43 (m, 2H), 2.70-2.82 (m, 1H), 3.23-3.30 (m, 2H), 3.77-3.89 (m, 2H), 5.40 (d, 1H), 6.09 (s, 2H), 6.72 (d, 1H), 7.39 (d, 1H), 7.59 (d, 1H), 7.95 (d, 1H), 7.97 (t, 1H), 8.25 (dd, 1H), 8.27 (s, 1H), 8.31 (dd, 1H), 8.67 (s, 1H), 8.84 (d, 1H), 8.98 (s, 1H).

Example II-183

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(difluoromethyl)pyridin-2(11H)-one (stereoisomer 1, distomer)

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(difluoromethyl)pyridin-2(1H)-one (mixture of enantiomers) (103 mg, 100% purity) was separated by chiral preparative HPLC to yield stereoisomer 1 (30.5 mg, 95% purity) and stereoisomer 2 (32.5 mg, 100% purity).

Column: Daicel Chiralpak IE-H, 5 μm, 250×20 mm; Eluent A: n-heptane; Eluent B: ethanol+0.2% diethylamine; isocratic: 60% A+40% B; flow: 20 ml/min; UV: 210 nm; temperature: 60° C.

Stereoisomer 1: $R^t$=13.55 min and

Stereoisomer 2: $R^t$=16.45 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=3.53 min and

Stereoisomer 2: $R^t$=5.19 min (cf. next example)

LC-MS (method 1): $R^t$=1.60 min; MS (ESIpos): m/z=587 $[M+H]^+$

Example II-184

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(difluoromethyl)pyridin-2(1H)-one (stereoisomer 2, eutomer)

The product was isolated in the previous example as second stereoisomer.

LC-MS (method 1): $R^t$=1.59 min; MS (ESIpos): m/z=587 $[M+H]^+$ $^1$H-NMR (400 MHz, DMSO-$d_6$) δ [ppm]: 1.09 (br d, 1H), 1.21 (br d, 1H), 1.27-1.43 (m, 2H), 2.70-2.82 (m, 1H), 3.23-3.30 (m, 2H), 3.77-3.93 (m, 2H), 5.40 (d, 1H), 6.09 (s, 2H), 6.72 (d, 1H), 7.38 (d, 1H), 7.59 (d, 1H), 7.95 (d, 1H), 7.97 (t, 1H), 8.25 (dd, 1H), 8.27 (s, 1H), 8.31 (dd, 1H), 8.67 (s, 1H), 8.84 (d, 1H), 8.96-9.01 (m, 1H).

Example II-185

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2-difluoroethyl)pyridin-2(1H)-one (mixture of enantiomers)

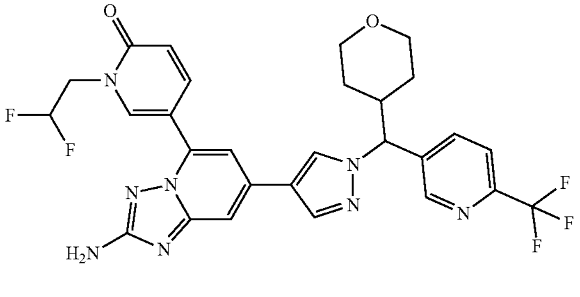 [SMILES: Nc1nc2cc(-c3cnn(C(c4ccc(C(F)(F)F)nc4)C4CCOCC4)c3)cc(-c3ccc(=O)n(CC(F)F)c3)n2n1]

5-(2-Amino-7-chloro[1,2,4]triazolo[1,5-a]pyridin-5-yl)-1-(2,2-difluoroethyl)pyridin-2(1H)-one (129 mg, 93% purity, 368 μmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (209 mg, 85% purity, 405 μmol), caesium carbonate (360 mg, 1.11 mmol) and XPhos-Pd-G2 (14.5 mg, 18.4 μmol) were 15 reacted according to procedure A in a mixture of 1,4-dioxane (4.0 ml) and water (400 μl). After 4 h at 90° C., the reaction mixture was quenched with water filtered through a hydrophobic phase separation filter, washed with of ethyl acetate and concentrated under reduced pressure. The residue was purified by preparative HPLC to yield 130 mg (100% purity, 59% yield) of the title compound as a mixture of enantiomers.

LC-MS (method 1): $R^t$=1.51 min; MS (ESIpos): m/z=601 $[M+H]^+$ $^1$H-NMR (400 MHz, DMSO-$d_6$) δ [ppm]: 1.09 (br d, 1H), 1.21 (br d, 1H), 1.27-1.40 (m, 2H), 2.71-2.81 (m, 1H), 3.23-3.28 (m, 2H), 3.79-3.88 (m, 2H), 4.43-4.52 (m, 2H), 5.41 (d, 1H), 6.03 (s, 2H), 6.42 (tt, 1H), 6.62 (d, 1H), 7.24 (d, 1H), 7.56 (d, 1H), 7.96 (d, 1H), 8.17 (dd, 1H), 8.23 (s, 1H), 8.31 (dd, 1H), 8.59 (d, 1H), 8.63 (s, 1H), 8.98 (s, 1H).

Example II-186

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2-difluoroethyl)pyridin-2(1H)-one (stereoisomer 1, distomer)

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(2,2-difluoroethyl)pyridin-2(1H)-one (130 mg, 100% purity) was separated by chiral preparative HPLC to yield stereoisomer 1 (41.1 mg, 100% purity) and stereoisomer 2 (39.1 mg, 100% purity).

Column: Daicel Chiralpak IE, 5 μm, 250×20 mm; Eluent A: n-heptane; Eluent B: ethanol+0.2% diethylamine; isocratic: 50% A+50% B; flow: 30 ml/min; UV: 220 nm; temperature: 50° C.

Stereoisomer 1: $R^t$=10.24 min and

Stereoisomer 2: $R^t$=12.33 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 50% A+50% B; flow: 1 ml/min; UV: 220 nm.

Stereoisomer 1: $R^t$=4.12 min and

Stereoisomer 2: $R^t$=5.74 min (cf next example)

LC-MS (method 1): $R^t$=1.53 min; MS (ESIpos): m/z=601 $[M+H]^+$

Example II-187

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2-difluoroethyl)pyridin-2(1H)-one (stereoisomer 2, eutomer)

The product was isolated in the previous example as second stereoisomer. The stereochemical configuration of the methine carbon atom bonded to the pyrazole was (S).

LC-MS (method 1): $R^t$=1.53 min; MS (ESIpos): m/z=601 $[M+H]^+$ $^1$H-NMR (600 MHz, DMSO-$d_6$) δ [ppm]: 1.05-1.12 (m, 1H), 1.20 (br d, 1H), 1.28-1.37 (m, 2H), 2.73-2.80 (m, 1H), 3.23-3.34 (m, 2H), 3.78-3.88 (m, 2H), 4.47 (td, 2H), 5.42 (d, 1H), 6.06 (s, 2H), 6.42 (tt, 1H), 6.63 (d, 1H), 7.25 (s, 1H), 7.57 (s, 1H), 7.97 (d, 1H), 8.17 (dd, 1H), 8.25 (s, 1H), 8.32 (dd, 1H), 8.59 (d, 1H), 8.64 (s, 1H), 8.98 (s, 1H).

Example 1H-188

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(2,2,2-trifluoroethyl)pyridin-2(1H)-one (mixture of enantiomers)

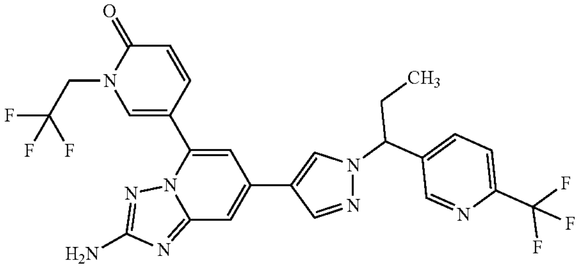 [SMILES: CCC(c1ccc(C(F)(F)F)nc1)n1cc(-c2cc(-c3ccc(=O)n(CC(F)(F)F)c3)n3nc(N)nc3c2)cn1]

5-(2-Amino-7-chloro[1,2,4]triazolo[1,5-a]pyridin-5-yl)-1-(2,2,2-trifluoroethyl)pyridin-2(1H)-one (271 mg, 788 μmol), 5-{1-[4-(4,4,5,5-tetramethyl-1,3,2-dioxaborolan-2-yl)-1H-pyrazol-1-yl]propyl}-2-(trifluoromethyl)pyridine (331 mg, 867 μmol), XPhos-Pd-G2 (31.0 mg, 39.4 μmol) and caesium carbonate (770 mg, 2.36 mmol) were reacted according to procedure A in a mixture of water (500 μl) and 1,4-dioxane (5.0 ml). After stirring for 4 h at 90° C., the reaction was quenched with water and extracted with dichloromethane. The organic layer was dried over anhydrous sodium sulfate, filtered and concentrated. The residue was purified via silicagel column chromatography (Biotage® SNAP KP-NH 28 g cartridge, eluent: cyclohexane/ethyl acetate gradient 1:1 to 0:1) to yield 114 mg (100% purity, 26% yield) of the title compound as a mixture of enantiomers.

LC-MS (method 2): $R^t$=0.87 min; MS (ESIpos): m/z=563 $[M+H]^+$ $^1$H-NMR (400 MHz, DMSO-$d_6$) δ [ppm]: 0.88 (t, 3H), 2.19-2.27 (m, 1H), 2.37-2.48 (m, 1H), 4.94 (q, 2H), 5.60 (dd, 1H), 6.02 (s, 2H), 6.66 (d, 1H), 7.27 (s, 1H), 7.60 (s, 1H), 7.93 (d, 1H), 8.05 (br d, 1H), 8.17 (dd, 1H), 8.23 (s, 1H), 8.63 (s, 1H), 8.68 (s, 1H), 8.82 (s, 1H).

Example II-189

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(2,2,2-trifluoroethyl)pyridin-2(1H)-one (stereoisomer 1, distomer)

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(2,2,2-trifluoroethyl)pyridin-2(1H)-one (107 mg, 100% purity) was separated by chiral preparative HPLC to yield stereoisomer 1 (37 mg, 99% purity) and stereoisomer 2 (36 mg, 99% purity).

Column: Chiralpak IE-H, 5 μm, 250×20 mm; Eluent A: n-heptane; Eluent B: ethanol+0.2% diethylamine; isocratic: 60% A+40% B; flow: 20 ml/min; UV: 210 nm; temperature: 40° C.

Stereoisomer 1: $R^t$=11.25 min and

Stereoisomer 2: $R^t$=13.67 min (cf. next example)

Analytical chiral HPLC method: Column: Daicel Chiralpak IE-3, 3 m, 50×4.6 mm; Eluent A: n-heptane; Eluent B: ethanol+0.2% diethylamine; isocratic: 50% A+50% B; flow: 1 ml/min; UV: 220 nm, temperature: 40° C.

Stereoisomer 1: $R^t$=1.3 min and

Stereoisomer 2: $R^t$=2.10 min (cf. next example)

LC-MS (method 1): $R^t$=1.68 min; MS (ESIpos): m/z=563 $[M+H]^+$ $^1$H-NMR (400 MHz, DMSO-$d_6$) δ [ppm]: 0.88 (t, 3H), 2.18-2.29 (m, 1H), 2.37-2.47 (m, 1H), 4.94 (q, 2H), 5.60 (dd, 1H), 6.02 (s, 2H), 6.66 (d, 1H), 7.27 (d, 1H), 7.59 (d, 1H), 7.93 (d, 1H), 8.05 (dd, 1H), 8.17 (dd, 1H), 8.23 (s, 1H), 8.62 (br s, 1H), 8.68 (s, 1H), 8.82 (br s, 1H).

Example II-190

5-[2-Amino-7-(1-{1-[6-(trifluoromethyl)pyridin-3-yl]propyl}-1H-pyrazol-4-yl)[1,2,4]triazolo[1,5-a]pyridin-5-yl]-1-(2,2,2-trifluoroethyl)pyridin-2(1H)-one (stereoisomer 2, eutomer)

The product was isolated in the previous example as second stereoisomer.

LC-MS (method 1): $R^t$=1.68 min; MS (ESIpos): m/z=563 $[M+H]^+$ $^1$H-NMR (400 MHz, DMSO-$d_6$) δ [ppm]: 0.88 (t, 3H), 2.17-2.32 (m, 1H), 2.35-2.47 (m, 1H), 3.18-3.28 (m, 1H), 4.94 (q, 2H), 5.60 (dd, 1H), 6.02 (s, 2H), 6.66 (d, 1H), 7.27 (d, 1H), 7.59 (d, 1H), 7.93 (d, 1H), 8.04 (d, 1H), 8.17 (dd, 1H), 8.23 (s, 1H), 8.62 (d, 1H), 8.68 (s, 1H), 8.82 (s, 1H).

Example II-191

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(2,2,2-trifluoroethyl)pyridin-2(1H)-one (mixture of enantiomers)

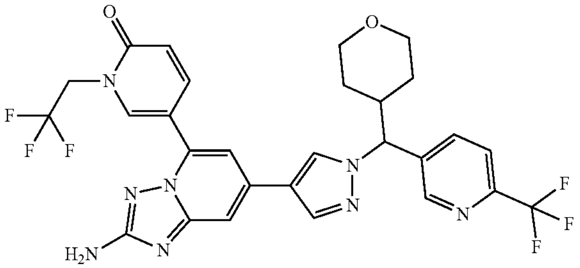

5-(2-Amino-7-chloro[1,2,4]triazolo[1,5-a]pyridin-5-yl)-1-(2,2,2-trifluoroethyl)pyridin-2(1H)-one (112 mg, 293 μmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (166 mg, 85% purity, 323 μmol), XPhos-Pd-G2 (11 mg, 15 μmol) and caesium carbonate (286 mg, 880 μmol) were reacted according to procedure A in a mixture of water (3 ml) and 1,4-dioxane (300 l). After stirring for 4 h at 90° C., the reaction mixture was filtered through a short pad of Florisil. The organic layer was concentrated and the residue was purified via preparative HPLC to yield 132 mg (100% purity, 72% yield) of the title compound as a mixture of enantiomers.

LC-MS (method 1): $R^t$=1.61 min; MS (ESIpos): m/z=619 $[M+H]^+$ $^1$H-NMR (400 MHz, DMSO-$d_6$) δ [ppm]: 1.10 (br d, 1H), 1.21 (br d, 1H), 1.28-1.39 (m, 2H), 2.73-2.80 (m, 1H), 3.24-3.33 (m, 2H), 3.79-3.87 (m, 2H), 4.93 (q, 2H), 5.41 (d, 1H), 6.00 (s, 2H), 6.66 (d, 1H), 7.23 (d, 1H), 7.56 (d, 1H), 7.95 (d, 1H), 8.16 (dd, 1H), 8.23 (s, 1H), 8.31 (dd, 1H), 8.61 (s, 1H), 8.63 (s, 1H), 8.97 (d, 1H).

Example II-192

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(2,2,2-trifluoroethyl)pyridin-2(1H)-one (stereoisomer 1, eutomer)

4-[2-Amino-6-(1-{1-[6-(trifluoromethyl)pyridin-3-yl]propyl}-1H-pyrazol-4-yl)[1,2,4]triazolo[1,5-a]pyridin-8-yl]-1-methylpyridin-2(1H)-one (mixture of enantiomers) (162 mg, 100% purity) was separated by chiral preparative HPLC to yield stereoisomer 1 (79 mg, 100% purity) and stereoisomer 2 (83 mg, 100% purity).

Column: Daicel Chiralpak IA, 5 m, 250×20 mm; Eluent A: n-heptane; Eluent B: ethanol+0.2% diethylamine; isocratic: 0% A+100% B; flow: 15 ml/min; UV: 220 nm; temperature: 70° C.

Stereoisomer 1: $R^t$=6.27 min and

Stereoisomer 2: $R^t$=8.58 min (cf. next example)

Analytical chiral HPLC method: Column: Daicel Chiralpak IA, 5 μm, 250×4.6 mm; Eluent A: n-heptane; Eluent B: ethanol+0.2% diethylamine; isocratic: 0% A+100% B; flow: 1 ml/min; UV: 220 nm; temperature: 70° C.

Stereoisomer 1: $R^t$=4.77 min and

Stereoisomer 2: $R^t$=7.11 min (cf. next example)

LC-MS (method 1): $R^t$=1.61 min; MS (ESIpos): m/z=619 $[M+H]^+$ $^1$H-NMR (600 MHz, DMSO-$d_6$) δ [ppm]: 1.06-1.14 (m, 1H), 1.16-1.26 (m, 1H), 1.28-1.39 (m, 2H), 2.73-2.80 (m, 1H), 3.24-3.33 (m, 2H), 3.79-3.90 (m, 2H), 4.94 (q, 2H), 5.42 (d, 1H), 6.06 (s, 2H), 6.67 (d, 1H), 7.23 (d, 1H), 7.58 (d, 1H), 7.97 (d, 1H), 8.16 (dd, 1H), 8.24 (s, 1H), 8.31 (dd, 1H), 8.61 (s, 1H), 8.64 (s, 1H), 8.98 (s, 1H).

Example II-193

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2,2-trifluoroethyl)pyridin-2(1H)-one (stereoisomer 2, distomer)

The product was isolated in the previous example as second stereoisomer.

LC-MS (method 1): $R^t$=1.61 min; MS (ESIpos): m/z=619 $[M+H]^+$

Example II-194

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2,2-trifluoroethyl)pyrazin-2(1H)-one (mixture of enantiomers)

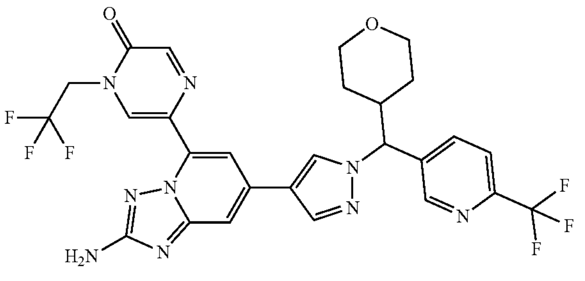

5-(2-Amino-7-chloro[1,2,4]triazolo[1,5-a]pyridin-5-yl)-1-(2,2,2-trifluoroethyl)pyrazin-2(1H)-one (109 mg, 316 μmol), 5-{tetrahydro-2H-pyran-4-yl[4-(4,4,5,5-tetramethyl-1,3,2-dioxaborolan-2-yl)-1H-pyrazol-1-yl]methyl}-2-(trifluoromethyl)pyridine (179 mg, 85% purity, 348 μmol), caesium carbonate (309 mg, 949 μmol) and XPhos-Pd-G2 (12.4 mg, 16 μmol) were reacted 10 according to procedure A in a mixture of 1,4-dioxane (4.5 ml) and water (1.5 ml). After 4 h at 90° C., the reaction mixture was quenched with water filtered through a hydrophobic phase separation filter, washed with of ethyl acetate and concentrated under reduced pressure. The residue was purified by preparative HPLC to yield 125 mg (92% purity, 59% yield) of the title compound as a mixture of enantiomers.

LC-MS (method 1): $R^t$=1.72 min; MS (ESIpos): m/z=620 $[M+H]^+$ $^1$H-NMR (600 MHz, DMSO-$d_6$) δ [ppm]: 1.10 (br d, 1H), 1.19 (br d, 1H), 1.25-1.39 (m, 2H), 2.77-2.83 (m, 1H), 3.25-3.34 (m, 2H), 3.79-3.87 (m, 2H), 5.02 (q, 2H), 5.44 (d, 1H), 6.12 (s, 2H), 7.64 (d, 1H), 7.82 (d, 1H), 7.97 (d, 1H), 8.23 (s, 1H), 8.34 (dd, 1H), 8.40 (d, 1H), 8.71 (s, 1H), 8.99 (s, 1H), 9.56 (s, 1H).

Example II-195

5-[2-Amino-7-(1-{tetrahydro-2H-pyran-4-yl[6-(trifluoromethyl)pyridin-3-yl]methyl}-1 H-pyrazol-4-yl)[1,2,4]triazolo[1,5-a]pyridin-5-yl]-1-(2,2,2-trifluoroethyl)pyrazin-2(1H)-one (stereoisomer 1, eutomer)

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2,2-trifluoroethyl)pyrazin-2(1H)-one (mixture of enantiomers) (124 mg, 92% purity) was separated by chiral preparative SFC to yield stereoisomer 1 (54 mg, 95% purity) and stereoisomer 2 (54 mg, 100% purity).

Column: YMC Chiralart Amylose SA, 5 μm, 250×25 mm; Eluent A: $CO_2$; Eluent B: methanol; isocratic: 60% A+40% B; flow: 22 ml/min; UV: 220 nm; temperature: 70° C.

Stereoisomer 1: $R^t$=6.92 min and

Stereoisomer 2: $R^t$=9.59 min (cf. next example)

Analytical chiral HPLC method: Column: Daicel Chiralpak IE-3, 3 μm, 50×4.6 mm; Eluent A: n-heptane; Eluent B: ethanol+0.2% diethylamine; isocratic: 100% A+0% B; flow: 1 ml/min; UV: 220 nm; temperature: 55° C.

Stereoisomer 1: $R^t$=3.38 min and

Stereoisomer 2: $R^t$=3.65 min (cf. next example)

LC-MS (method 2): $R^t$=0.89 min; MS (ESIpos): m/z=620 $[M+H]^+$ $^1$H-NMR (600 MHz, DMSO-$d_6$) δ [ppm]: 1.11 (br d, 1H), 1.20 (br d, 1H), 1.24-1.39 (m, 2H), 2.76-2.84 (m, 1H), 3.25-3.31 (m, 2H), 3.78-3.88 (m, 2H), 5.01 (q, 2H), 5.44 (d, 1H), 6.09 (s, 2H), 7.64 (d, 1H), 7.82 (d, 1H), 7.96 (d, 1H), 8.22 (s, 1H), 8.33 (dd, 1H), 8.40 (s, 1H), 8.69 (s, 1H), 8.99 (s, 1H), 9.56 (s, 1H).

Example II-196

5-[2-Amino-7-(1-{tetrahydro-2H-pyran-4-yl[6-(trifluoromethyl)pyridin-3-yl]methyl}-1H-pyrazol-4-yl)[1,2,4]triazolo[1,5-a]pyridin-5-yl]-1-(2,2,2-trifluoroethyl)pyrazin-2(1H)-one (stereoisomer 2, distomer)

The product was isolated in the previous example as second stereoisomer.

LC-MS (method 2): $R^t$=0.89 min; MS (ESIpos): m/z=620 $[M+H]^+$

Example II-197

6-(1-Benzyl-1H-pyrazol-4-yl)-8-(5-ethyl-1,3,4-thiadiazol-2-yl)[1,2,4]triazolo[1,5-a]pyridin-2-amine

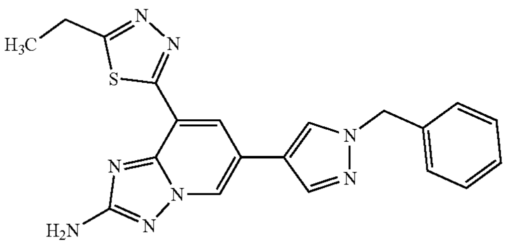 [SMILES: CCc1nnc(-c2cc(-c3cnn(Cc4ccccc4)c3)cn3nc(N)nc23)s1]

6-Bromo-8-(5-ethyl-1,3,4-thiadiazol-2-yl)[1,2,4]triazolo[1,5-a]pyridin-2-amine (70.0 mg, 93% purity, 200 μmol) was reacted with 1-benzyl-4-(4,4,5,5-tetramethyl-1,3,2-dioxaborolan-2-yl)-1H-pyrazole (68.3 mg, 240 μmol) for 1 h at 90° C. following general procedure B using 0.05 eq. catalyst. The mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 70:30 to 0:100, then ethyl acetate/2-propanol gradient 100:0 to 80:20). Final purification by preparative HPLC yielded 62.8 mg (100% purity, 78% yield) of the title compound.

LC-MS (method 1): $R^t$=1.52 min; MS (ESIpos): m/z=403 $[M+H]^+$ $^1$H-NMR (500 MHz, DMSO-$d_6$) δ [ppm]: 1.40 (t, 3H), 3.20 (q, 2H), 5.37 (s, 2H), 6.40 (s, 2H), 7.29-7.33 (m, 3H), 7.35-7.39 (m, 2H), 8.53 (s, 1H), 8.55 (d, 1H), 9.09 (d, 1H).

Example II-198

6-(1-Benzyl-1H-pyrazol-4-yl)-8-[5-(propan-2-yl)-1,3,4-thiadiazol-2-yl][1,2,4]triazolo[1,5-a]pyridin-2-amine

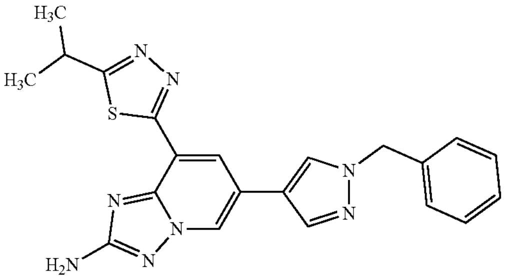 [SMILES: CC(C)c1nnc(-c2cc(-c3cnn(Cc4ccccc4)c3)cn3nc(N)nc23)s1]

6-Bromo-8-[5-(propan-2-yl)-1,3,4-thiadiazol-2-yl][1,2,4]triazolo[1,5-a]pyridin-2-amine (60.0 mg, 177 μmol) was reacted with 1-benzyl-4-(4,4,5,5-tetramethyl-1,3,2-dioxaborolan-2-yl)-1H-pyrazole (60.3 mg, 212 μmol) for 2 h at 90° C. following general procedure B using 0.05 eq. catalyst. The mixture was diluted with ethyl acetate and filtered through a hydrophobic phase separation filter which was rinsed with ethyl acetate. The combined filtrates were concentrated in vacuo and the residue was purified by column chromatography (Biotage® SNAP KP-NH 11 g cartridge, eluent: cyclohexane/ethyl acetate gradient 75:25 to 10:90) to yield 47.2 mg (95% purity, 61% yield) of the title compound.

LC-MS (method 1): $R^t$=1.66 min; MS (ESIpos): m/z=417 $[M+H]^+$ $^1$H-NMR (400 MHz, DMSO-$d_6$) δ [ppm]: 1.44 (d, 6H), 3.55 (spt, 1H), 5.37 (s, 2H), 6.41 (s, 2H), 7.28-7.33 (m, 3H), 7.34-7.40 (m, 2H), 8.10 (s, 1H), 8.53 (s, 1H), 8.54 (d, 1H), 9.10 (d, 1H).

Example II-199

(2S)-2-(5-{2-Amino-6-[1-(1H-indazol-7-ylmethyl)-1H-pyrazol-4-yl][1,2,4]triazolo[1,5-a]pyridin-8-yl}-1,3,4-thiadiazol-2-yl)propan-1-ol

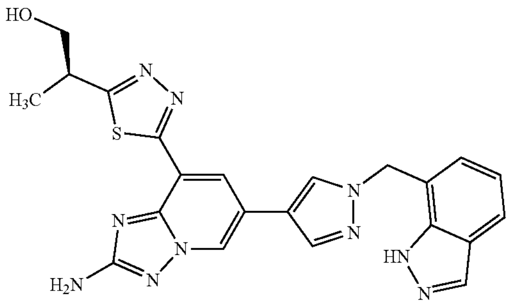 [SMILES: C[C@@H](CO)c1nnc(-c2cc(-c3cnn(Cc4cccc5cn[nH]c45)c3)cn3nc(N)nc23)s1]

8-{5-[1-{[tert-Butyl(dimethyl)silyl]oxy}propan-2-yl]-1,3,4-thiadiazol-2-yl}-6-{1-[(1H-indazol-7-yl)methyl]-1H-pyrazol-4-yl}[1,2,4]triazolo[1,5-a]pyridin-2-amine (100 mg, 170 μmol) was dissolved in THE (2.0 ml) and TBAF (260 1, 1.0 M in THF, 260 μmol) was added. The mixture was stirred at rt for 1 h. It was then diluted with ethyl acetate and washed with water. The aqueous layer was extracted twice with ethyl acetate. The combined organic layers were washed with brine and filtered through a hydrophobic phase separation filter. The solvent was removed in vacuo and the residue purified by preparative HPLC (Chromatorex C18, 10 m, 125×30 mm; eluent: water/acetonitrile gradient 90:10 to 10:90) to yield 35.2 mg (95% purity, 42% yield) of the title compound.

LC-MS (method 1): $R^t$=1.19 min; MS (ESIpos): m/z=473 $[M+H]^+$ $^1$H-NMR (400 MHz, DMSO-$d_6$) δ [ppm]: 1.40 (d;3H), 3.46-3.55 (m, 1H), 3.63-3.74 (m, 2H), 5.17 (br s, 1H), 5.69 (s, 2H), 6.43 (s, 2H), 7.07-7.18 (m, 2H), 7.74 (dd, 1H), 8.11 (s, 1H), 8.14 (s, 1H), 8.55 (d, 1H), 8.61 (s, 1H), 9.08 (d, 1H), 13.31 (br s, 1H).

Assessment of pharmacological efficacy

The pharmacological activity of Compounds of Formula (B), (BII), (II), (II-A), (II-B), (II-C), (II-D), (II-E), (II-F), (II-G), or (II-H) can be demonstrated by in vitro and in vivo studies, as known to the person skilled in the art. The application examples which follow describe the biological action of Compounds of Formula (B), (BII), (II), (II-A), (II-B), (II-C), (II-D), (II-E), (II-F), (II-G), or (II-H), without restricting the disclosure to these examples.

DLK biochemical assay

DLK assay is a biochemical assay format designed to screen for inhibitors of DLK. Enzymatic activity of DLK is measured by monitoring phosphorylation of the physiological substrate MKK7 (MAP2K7, Dual specificity mitogen-activated protein kinase kinase 7). Phosphorylation is detected by a TR-FRET system whereby His-tagged MKK7 is labeled by a XL665-labeled anti-His antibody (FRET acceptor, emission 665 nm). DLK phosphorylates MKK7 at T275/S277, which is detected by an Eu-labeled anti-phospho-MKK7 (T275/S277) antibody (FRET donor, excitation 340 nm). Phosphorylation of MKK7 results in an increased TR-FRET signal (Ratio XL665-channel/Eu-channel) and inhibition of enzymatic activity of DLK decreases the TR-FRET signal.

Assay Protocol for 1536 MTP format: test compounds are predispensed (60 nl) in test plates; +3 μl DLK solution (10 nM DLK, catalytic domain, Carna Biosiences, 0.6 mM DTT in assay buffer); +2 μl substrate solution (15 nM MKK7, LDB; 60 μM ATP; 0.4 mM DTT in assay buffer); 90 min incubation at RT; +2 μl detection mix (5 nM XL665-labeled anti-His antibody, Cisbio; 0.1 nM Eu-labeled anti-phospho-MKK7 (T275/S277), Cisbio/Millipore in detection buffer); 16 h incubation at 37° C.; endpoint measurement BMG (HTRF).

Assay Protocol for 384 low volume MTP format: 1 μl of test compounds is pipetted into test plate; +5 μl DLK solution (10 nM DLK, catalytic domain, Carna Biosiences in assay buffer); +5 μl substrate solution (15 nM MKK7, LDB; 60 M ATP, in assay buffer); 90 min incubation at RT; +9 μl detection mix (20 nM XL665-labeled anti-His antibody, Cisbio; 0.4 nM Eu-labeled anti-phospho-MKK7 (T275/S277), Cisbio/Millipore in detection buffer); 16 h incubation at 4° C.; endpoint measurement BMG (HTRF).

All indicated concentrations final concentrations.

Assay buffer (1536 format): 50 mM Hepes pH 7.5, 10 mM MgCl2, 1 mM EGTA, 0.01% Triton X-100, 0.01% BSA, 1:500 Smart Block.

Assay buffer (384 format): 50 mM Hepes pH 7.5, 10 mM MgCl2, 1 mM EGTA, 1 mM DTT, 0.01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

LZK biochemical assay

LZK assay is a biochemical assay format designed to screen for inhibitors of LZK. Enzymatic activity of LZK is measured by monitoring phosphorylation of the physiological substrate MKK7 (MAP2K7, Dual specificity mitogen-activated protein kinase kinase 7).

Phosphorylation is detected by a TR-FRET system whereby His-tagged MKK7 is labeled by a XL665-labeled anti-His antibody (FRET acceptor, emission 665 nm). LZK phosphorylates MKK7 at T275/S277 which is detected by an Eu-labeled anti-phospho-MKK7 (T275/S277) antibody (FRET donor, excitation 340 nm). Phosphorylation of MKK7 results in an increased TR-FRET signal (Ratio XL665-channel/Eu-channel) and inhibition of enzymatic activity of LZK decreases the TR-FRET signal.

Assay Protocol for 384 low volume MTP format: 1 μl of test compound is pipetted into test plate; +5 μl LZK solution (10 nM LZK, catalytic domain, Carna Biosiences in assay buffer); +5 μl substrate solution (15 nM MKK7, LDB; 15 μM ATP, in assay buffer); 90 min incubation at RT; +5 μl detection mix (20 nM XL665-labeled anti-His antibody, Cisbio; 0.4 nM Eu-labeled anti-phospho-MKK7 (T275/S277), Cisbio/Millipore in detection buffer); 16 h incubation at 32° C.; endpoint measurement BMG (HTRF).

All indicated concentrations final concentrations.

Assay buffer (384 format): 50 mM Hepes pH 7.5, 10 mM MgCl2, 1 mM EGTA, 1 mM DTT, 0.01% Triton X-100, 0.01% BSA, 1:500 Smart Block.

Detection buffer: 25 mM Tris/HCl pH 7.5, 100 mM EDTA, 100 mM NaCl, 200 mM KF, 0.01% Tween 20, 1:500 Smart Block.

Biochemical results

| Expl.* | DLK $IC_{50}$ [nM] | LZK $IC_{50}$ [nM] |
|---|---|---|
| 1 | 6.3 | 2.3 |
| 2 | 170 | 30 |
| 3 | 12 | 6.4 |
| 4 | 7.0 | 5.9 |
| 5 | 2.3 | 1.7 |
| 6 | 46 | 6.7 |
| 7 | 0.8 | 3.3 |
| 8 | 3.7 | 7.9 |
| 9 | 1.0 | 2.3 |
| 10 | 0.7 | 0.9 |
| 11 | 1.4 | 3.0 |
| 12 | 0.6 | 1.2 |
| 13 | 0.7 | 1.8 |
| 14 | 0.6 | 1.3 |
| 15 | 0.9 | 2.7 |
| 16 | 1.1 | 3.5 |
| 17 | 2.1 | 11 |
| 18 | 0.3 | 1.5 |
| 19 | 17 | 45 |
| 20 | 71 | 140 |
| 21 | 7.6 | 14 |
| 22 | 2.2 | 6.6 |
| 23 | 4.5 | 9.2 |
| 24 | 0.5 | 2.3 |
| 25 | 130 | 82 |
| 26 | 210 | 150 |
| 27 | 30 | 55 |
| 28 | 28 | 27 |
| 29 | 120 | 97 |
| 30 | 8.7 | 6.7 |
| 31 | 26 | 6.1 |
| 32 | 66 | 16 |

-continued

| Biochemical results | | |
|---|---|---|
| Expl.* | DLK $IC_{50}$ [nM] | LZK $IC_{50}$ [nM] |
| 33 | 17 | 7.6 |
| 34 | 15 | 7.1 |
| 35 | 63 | 44 |
| 36 | 6.3 | 7.9 |
| 37 | 46 | 74 |
| 38 | 56 | 120 |
| 39 | 24 | 52 |
| 40 | 44 | 120 |
| 41 | 380 | 770 |
| 42 | 18 | 52 |
| 43 | 4.2 | 26 |
| 44 | 60 | 100 |
| 45 | 9.5 | 10 |
| 46 | 750 | 380 |
| 47 | 33 | 120 |
| 48 | 7.5 | 11 |
| 49 | 31 | 84 |
| 50 | 280 | 270 |
| 51 | 13 | 25 |
| 52 | 6.0 | 19 |
| 53 | 33 | 48 |
| 54 | 4.0 | 8.9 |
| 55 | 21 | 24 |
| 56 | 37 | 56 |
| 57 | 18 | 14 |
| 58 | 21 | 22 |
| 59 | 92 | 190 |
| 60 | 11 | 7.9 |
| 61 | 65 | 62 |
| 62 | 440 | 220 |
| 63 | 97 | 51 |
| 64 | 40 | 59 |
| 65 | 440 | 210 |
| 66 | 45 | 43 |
| 67 | 12 | 15 |
| 68 | 36 | 86 |
| 69 | 4.8 | 9.4 |
| 70 | 26 | 15 |
| 71 | 160 | 74 |
| 72 | 16 | 17 |
| 73 | 44 | 44 |
| 74 | 510 | 170 |
| 75 | 27 | 15 |
| 76 | 21 | 16 |
| 77 | 160 | 61 |
| 78 | 5.2 | 5.3 |
| 79 | 46 | 27 |
| 80 | 21 | 17 |
| 81 | 4.0 | 2.4 |
| 82 | 42 | 42 |
| 83 | 210 | 110 |
| 84 | 55 | 290 |
| 85 | 230 | 320 |
| 86 | 54 | 900 |
| 87 | 42 | 530 |
| 88 | 480 | 620 |
| 89 | 12 | 39 |
| 90 | 6.5 | 230 |
| 91 | 5.2 | 115 |
| 92 | 6.7 | 150 |
| 93 | 19 | 68 |
| 94 | 22 | 200 |
| 95 | 5.6 | 40 |
| 96 | 17 | 60 |
| 97 | 8.1 | 380 |
| 98 | 14 | 56 |
| 99 | 9.2 | 150 |
| 100 | 58 | 500 |
| 101 | 6.8 | 110 |
| 102 | 5.7 | 140 |
| 103 | 64 | 160 |
| 104 | 6.0 | 51 |
| 105 | 9.4 | 42 |
| 106 | 40 | 47 |

-continued

| Biochemical results | | |
|---|---|---|
| Expl.* | DLK $IC_{50}$ [nM] | LZK $IC_{50}$ [nM] |
| 107 | 4.0 | 10 |
| 108 | 6.3 | 37 |
| 109 | 16 | 57 |
| 110 | 2.2 | 9.7 |
| 111 | 14 | 34 |
| 112 | 4.7 | 17 |
| 113 | 23 | 59 |
| 114 | 46 | 42 |
| 115 | 67 | 138 |
| 116 | 9.7 | 22 |
| 117 | 3.8 | 29 |
| 118 | 0.6 | 2.6 |
| 119 | 4.7 | 16 |
| 120 | 240 | 140 |
| 121 | 32 | 150 |
| 122 | 39 | 37 |
| 123 | 53 | 150 |
| 124 | 7.1 | 73 |
| 125 | 17 | 160 |
| 126 | 60 | 220 |
| 127 | 8.4 | 99 |
| 128 | 15 | 160 |
| 129 | 69 | 170 |
| 130 | 120 | 670 |
| 131 | 25 | 165 |
| 132 | 71 | 120 |
| 133 | 45 | 130 |
| 134 | 32 | 44 |
| 135 | 19 | 70 |
| 136 | 3.4 | 48 |
| 137 | 40 | 720 |
| 138 | 1.7 | 29 |
| 139 | 11 | 27 |
| 140 | 3.0 | 13 |
| 141 | 23 | 140 |
| 142 | 8.4 | 12 |
| 143 | 2.5 | 15 |
| 144 | 27 | 57 |
| 145 | 3.3 | 9.9 |
| 146 | 3.6 | 200 |
| 147 | 2.3 | 73 |
| 148 | 22 | 170 |
| 149 | 2.9 | 4.7 |
| 150 | 1.4 | 4.9 |
| 151 | 11 | 11 |
| 152 | 1.4 | 16 |
| 153 | 1.4 | 3.5 |
| 154 | 6.2 | 15 |
| 155 | 1.0 | 3.1 |
| 156 | 1.1 | 3.3 |
| 157 | 5.9 | 12 |
| 158 | 0.4 | 1.2 |
| 159 | 2.4 | 6.2 |
| 160 | 1.5 | 5.9 |
| 161 | 8.5 | 12 |
| 162 | 0.8 | 2.0 |
| 163 | 4.9 | 25 |
| 164 | 3.5 | 17 |
| 165 | 26 | 57 |
| 166 | 4.0 | 27 |
| 167 | 1.3 | 9.9 |
| 168 | 17 | 77 |
| 169 | 20 | 60 |
| 170 | 73 | 220 |
| 171 | 9.3 | 41 |
| 172 | 2.2 | 11 |
| 173 | 11 | 25 |
| 174 | 1.0 | 4.3 |
| 175 | 2.7 | 13 |
| 176 | 1.6 | 5.6 |
| 177 | 10 | 33 |
| 178 | 15 | 74 |
| 179 | 12 | 8.0 |
| 180 | 34 | 79 |

-continued

| Biochemical results | | |
|---|---|---|
| Expl.* | DLK $IC_{50}$ [nM] | LZK $IC_{50}$ [nM] |
| 181 | 2.7 | 5.4 |
| 182 | 4.0 | 6.5 |
| 183 | 22 | 19 |
| 184 | 1.2 | 2.4 |
| 185 | 1.3 | 2.0 |
| 186 | 4.1 | 4.5 |
| 187 | 0.2 | 0.5 |
| 188 | 7.1 | 10 |
| 189 | 15 | 32 |
| 190 | 2.9 | 5.4 |
| 191 | 3.2 | 6.3 |
| 192 | 1.3 | 2.2 |
| 193 | 15 | 12 |
| 194 | 3.6 | 17 |
| 195 | 1.1 | 5.2 |
| 196 | 16 | 50 |
| 197 | 240 | 690 |
| 198 | 150 | 260 |
| 199 | 12 | 410 |

*Example numbers II-# where # is listed in the column.

Preparation of human stem cell-derived RGCs (hRGCs)

H7 or H9 human embryonic stem cells or patient-derived induced pluripotent stem cells were modified to express mouse Thy1.2 and tdTomato from the BRN3B locus (Sluch et al., 2017). To produce RGCs, stem cells were dissociated to single cells and plated on Matrigel (Corning, USA) coated plates at a density of 52.6 K/$cm^2$ in mTeSR1 with 5 mM blebbistatin, a time point designated as day minus 1 (d-1). One day after plating, mTeSR1 was completely exchanged for N2B27 media [1:1 mix of DMEM/F12 and Neurobasal with GlutaMAX Supplement, antibiotic-antimycotic, 1% N2 Supplement, and 2% B27 Supplement (all from ThermoFisher Scientific)] to start differentiation; this day was designated as day 0 (d0). Small molecules were added to the cells on day 1 (d1), 24 hours after do. Small molecule addition was done in fresh N2B27 media. Cells were fed with a full exchange of N2B27 media every other day unless a small molecule was to be removed or added on that day of differentiation, requiring daily feeding. The following small molecules were aliquoted as 1,000× stocks in dimethyl sulfoxide (DMSO) and used at the working concentration noted in parentheses: Forskolin (FSK; 25 mM-Cell Signaling Technology, Danvers, MA), Dorsomorphin (1 mM-R&D Systems, Minneapolis, MN), IDE2 (2.5 mM-R&D Systems), DAPT (10 mM-Cell Signaling Technology). Nicotinamide (NIC; Sigma-Aldrich) was resuspended in water at 100× and used at a 10 mM working concentration. Dorsomorphin and IDE2 (DID) were added from day 1 to 6, NIC from day 1 to 10, FSK from day 1 to 30, and DAPT from day 18 to 30. Differentiation was carried out at 37° C. in 5% CO2/20% O2. After 35 days in culture, when abundant RGCs have appeared (indicated by red fluorescence), cultures were dissociated into a single cell suspension. Cultures were washed with phosphate buffered saline (PBS, pH 7.4), incubated with TrypLE Express for 15 minutes at 37C, and then further incubated with Accumax (Sigma-Aldrich) for an additional 45 minutes. Cells were then purified using the anti-Thy1.2 MACS system (Miltenyi Biotec) or EasySep™ Mouse CD90.2 Positive Selection Kit II (Stemcell Technologies), per the manufacturer's protocol, and seeded into multiwell dishes at 10,000-30,000 cells/$cm^2$.

Preparation of primary mouse RGCs (mRGCs)

Retinas were isolated from postnatal day 0-3 mice and the tissue dissociated into a single cell suspension with papain. Microglia were immunodepleted with CELLection Dynabeads (Invitrogen) conjugated to anti-CD11b (BD Pharmingen, 554859). The suspension of remaining retinal cells was immunopanned on plates pre-conjugated with goat anti-mouse IgM (Jackson Immunoresearch, 115-001-020) and mouse anti-Thy1.2 antibodies (BioRad, MCA02R) at room temperature After washing the retinal cells that did not bind Thy1.2 from the plates, the bound retinal ganglion cells (RGCs) were released with trypsin (Sigma T9201). The enriched mRGC population was counted, and seeded into multiwell dishes at 10,000-30,000 cells/$cm^2$.

Determination of survival by CellTiter-Glo

In order to test compounds, RGCs were plated in 96- or 384-well Nunclon or Falcon dishes.

Growth media consists of Neurobasal (Life Technologies) supplemented with NS21, Sato, L-glutamine and penicillin/streptomycin with N-acetyl-cysteine, insulin, sodium pyruvate, triiodothyronine (T3), and forskolin (Chen et al., 2008) for the mRGCs or in N2/B27 media without additional components for the hRGCs. For mRGCs, cells were plated in poly-D-lysine-coated wells and no additional injury was induced (i.e. cells die after 72 hours from isolation and plating). For hRGCs, cells were injured with the addition of 10-1000 nM colchicine. For both sets of RGCs, increasing doses of the kinase inhibitors was added at the time of injury and survival was quantitated after 72 hours using CellTiter-Glo (Promega, Madison) and measuring relative light units (RLU) or by staining cultures with conventional viability dyes (i.e. ethidium homodimer exclusion, calcein AM uptake) and measuring survival by automated image analysis.

Part III. Examples of Pharmaceutical Compositions for Compounds of Formula (I) and Formula (II)

Compounds of Formula (A), (Al), (I), (I-A), (I-B), (I-C), (I-D), (B), (BII), (II), (II-A), (II-B), (II-C), (II-D), (II-E), (II-F), (II-G), or (II-H) can be converted to pharmaceutical formulations as follows:

Tablet:

Composition:

100 mg of the compound of Formula (A), (Al), (I), (I-A), (I-B), (I-C), (I-D), (B), (BII), (II), (II-A), (II-B), (II-C), (II-D), (II-E), (II-F), (II-G), or (II-H), 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of Formula (A), (AI), (I), (I-A), (I-B), (I-C), (I-D), (B), (BII), (II), (II-A), (II-B), (II-C), (II-D), (II-E), (II-F), (II-G), or (II-H), lactose and starch is granulated with a 5% solution (w/w) of the PVP in water. The granules are dried and then mixed with the magnesium stearate for 5 minutes. This mixture is compressed in a conventional tabletting press (see above for format of the tablet). The guide value used for the pressing is a pressing force of 15 kN.

Suspension for oral administration:

Composition:

1000 mg of the compound of Formula (A), (AI), (I), (I-A), (I-B), (I-C), (I-D), (B), (BII), (II), (II-A), (II-B), (II-C), (II-D), (II-E), (II-F), (II-G), or (II-H), 1000 mg of ethanol (96%), 400 mg of Rhodigel® (xanthan gum from FMC, Pennsylvania, USA) and 99 g of water.

10 ml of oral suspension correspond to a single dose of 100 mg of the compound of Formula (A), (AI), (I), (I-A), (I-B), (I-C), (I-D), (B), (BII), (II), (II-A), (II-B), (II-C), (II-D), (II-E), (II-F), (II-G), or (II-H).

Production:

The Rhodigel is suspended in ethanol; the compound of Formula (A), (AI), (I), (I-A), (I-B), (I-C), (I-D), (B), (BII), (II), (II-A), (II-B), (II-C), (II-D), (II-E), (II-F), (II-G), or (II-H) is added to the suspension. The water is added while stirring. The mixture is stirred for about 6 h before swelling of the Rhodigel is complete.

Solution for oral administration:

Composition:

500 mg of the compound of Formula (A), (AI), (I), (I-A), (I-B), (I-C), (I-D), (B), (BII), (II), (II-A), (II-B), (II-C), (II-D), (II-E), (II-F), (II-G), or (II-H), 2.5 g of polysorbate and 97 g of polyethylene glycol 400. 20 g of oral solution correspond to a single dose of 100 mg of the compound of Formula (A), (AI), (I), (I-A), (I-B), (I-C), (I-D), (B), (BII), (II), (II-A), (II-B), (II-C), (II-D), (II-E), (II-F), (II-G), or (II-H).

Production:

The compound of Formula (A), (AI), (I), (I-A), (I-B), (I-C), (I-D), (B), (BII), (II), (II-A), (II-B), (II-C), (II-D), (II-E), (II-F), (II-G), or (11-H) is suspended in the mixture of polyethylene glycol and polysorbate with stirring. The stirring operation is continued until dissolution of the compound of Formula® (A), (AI), (I), (I-A), (I-3), (I-C), (I-D), (B), (BII), (II), (II-A), (II-B), (II-C), (II-D), (II-E), (II-F), (II-G), or (II-H) is complete.

Intravenous (i.v.) solution:

The compound of Formula (A), (Al), (I), (I-A), (I-B), (I-C), (I-D), (B), (BII), (II), (II-A), (II-B), (II-C), (II-D), (II-E), (II-F), (II-G), or (II-H) is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

Solution or suspension for topical administration to the eve (eye drops):

A sterile pharmaceutical preparation for topical administration to the eye can be prepared by reconstituting a lyophilizate of the compound of Formula (A), (Al), (I), (I-A), (I-B), (I-C), (I-D), (B), (BII), (II), (II-A), (II-B3), (II-C), (II-D), (II-E), (II-F), (II-G), or (II-H) in sterile saline. Suitable preservatives for such a solution or suspension are, for example, benzalkonium chloride, thiomersal or phenylmercury nitrate in a concentration range of from 0.001 to 1 percent by weight.

Part IV. Biological Examples

Inhibition of DLK and LZK can reduce the neuronal injury response and result in the protection of various neuronal populations from degeneration. Cells can be immunostained for p-Jun S73 (p-JUN), which is an indicator of DLK pathway activation. Accordingly, decreased p-JUN staining compared to a control can be indicative of inhibition of DLK pathway activation. RBPMS can be used to mark retinal ganglion cells (RGCs) and show changes in cell survival (e.g., increased RBPMS staining compared to a control can indicate increased cell survival).

Target Engagement Assay and Optic Nerve Crush

Unilateral optic nerve crush was performed on C57B6/J animals between 6 and 8 weeks of age, followed by intravitreal injection of 8 mM of the indicated compound of Formula (A), (AI), (I), (I-A), (I-B), (I-C), (I-D), (B), (BII), (II), (II-A), (II-B), (II-C), (II-D), (II-E), (II-F), (II-G), or (II-H). After 24 hours, animals were sacrificed and retinas were immunostained for p-cJun S73, an indicator of DLK pathway activation. Confocal microscopy was used to image retinal ganglion cells (RGCs) and ImageJ was used to quantify p-cJun intensity in 4000-6000 cells per retina (n=4). Compounds with the (SD) notation were tested at UCSD and images were analyzed. See FIG. 1. The decreased p-cJun intensity in the RGCs treated with the compound of Formula (I) indicated that the DLK pathway activation was inhibited compared to RGCs treated with the vehicle.

Figure 2:
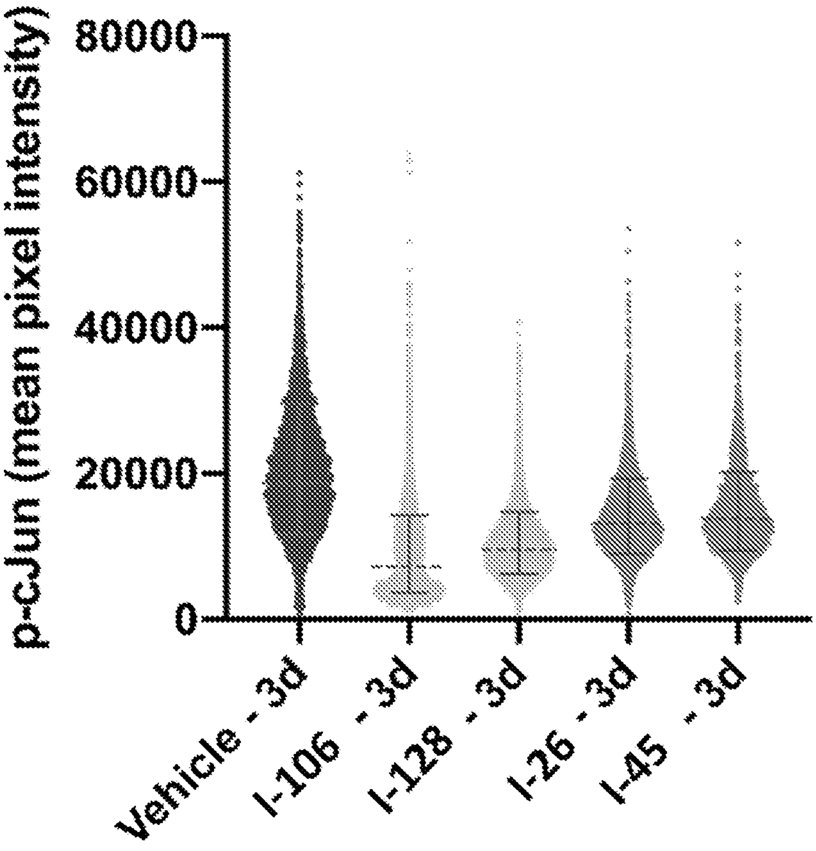
FIG. 2 is a plot showing the duration of action of compounds of Formula (I) and (II) in a three day target engagement assay.

Unilateral optic nerve crush was performed on C57B6/J animals between 6 and 8 weeks of age, followed by intravitreal injection of 8 mM of the indicated compound of Formula (A), (AI), (I), (I-A), (I-B), (I-C), (I-D), (B), (BII), (II), (II-A), (II-B3), (II-C), (II-D), (II-E), (II-F), (II-G), or (II-H). After 72 hours, animals were sacrificed and retinas were immunostained for p-cJun S73, an indicator of DLK pathway activation. Confocal microscopy was used to image RGCs and ImageJ was used to quantify p-cJun intensity in 4000-6000 cells per retina (n=4). See FIG. 2. The decreased p-cJun intensity in the RGCs treated with the compound of Formula (A), (AI), (I), (I-A), (I-B), (I-C), (I-D), (B), (BII), (II), (II-A), (II-B), (II-C), (II-D), (II-E), (II-F), (II-G), or (II-H) indicated that the DLK pathway activation was inhibited compared to RGCs treated with the vehicle.

Figure 3:
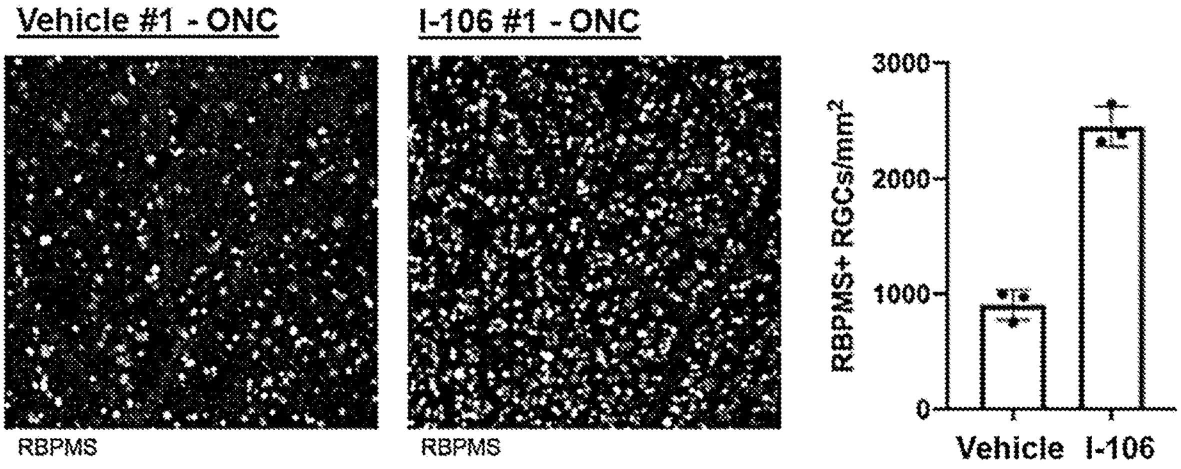
FIG. 3 has plots showing that compounds Formula (I) and (II) promote survival of retinal ganglion cells (RGCs) following optic nerve crush.

Unilateral optic nerve crush was performed on C57B6/J animals between 6 and 8 weeks of age, followed by intravitreal injection of 8 mM of I-106. A second injection was performed 4 days later. Two weeks after optic nerve crush, animals were sacrificed and retinas were immunostained for RBPMS. Confocal microscopy was used to image RGCs and ImageJ was used to quantify the density of RGCs. See FIG. 3. The compounds of Formula (A), (AI), (I), (I-A), (I-B), (I-C), (I-D), (B), (BII), (II), (II-A), (II-B), (II-C), (II-D), (II-E), (II-F), (II-G), or (II-H)promoted survival of RGCs following optic nerve crush as indicated by the increased density of RBPMS in cells treated with the compound of Formula (I) compared to the RGCs treated with the vehicle.

Studies with Rotenone

Figure 4:
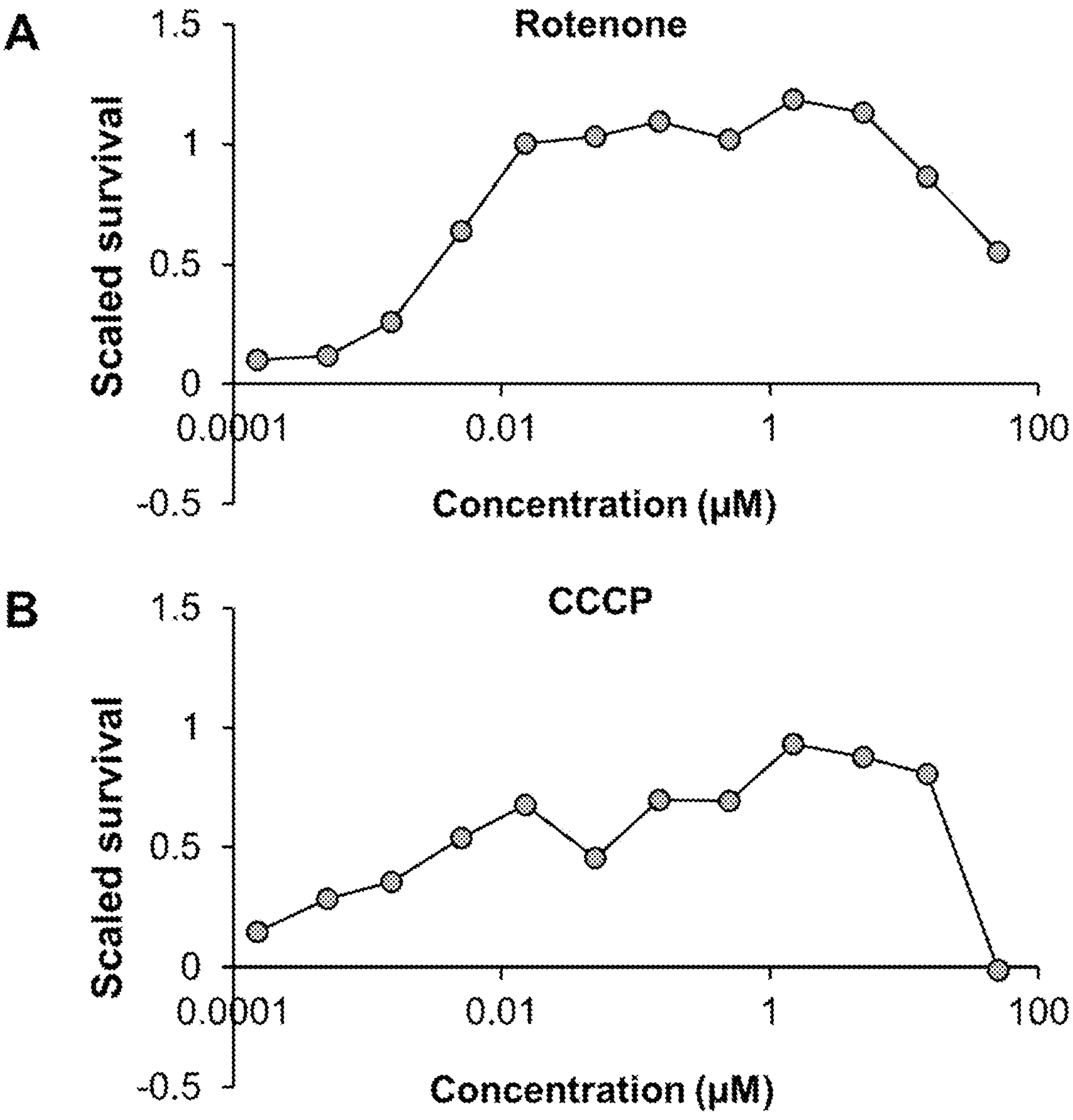
FIG. 4 is a plot showing that compound 1-84 is protective to human stem cell derived RGCs in models of mitochondrial injury.

Many neurodegenerative diseases, including glaucoma, are thought to invoke mitochondrial dysfunction. Rotenone is an inhibitor of mitochondrial complex 1 and can be used to study neurodegenerative diseases. For example, direct intravitreous injections of rotenone can induce rapid loss of RGCs followed by a reduced retinal nerve fiber layer (RNFL) thickness. The ocular changes induced by rotenone can also recapitulate Leber's hereditary optic neuropathy (LHON), which is caused by mutations in mitochondrial complex I.

hRGCs were challenged with (A) 1 uM rotenone or (B) 30 uM CCCP in the presence of increasing doses of 1-84 for 72 hours. Cell survival was quantified using Cell Titer Glo, an ATP-based luminescent assay. I-84 was protective to human stem cell derived RGCs in models of mitochondrial injury (FIG. 4).

Figure 5:
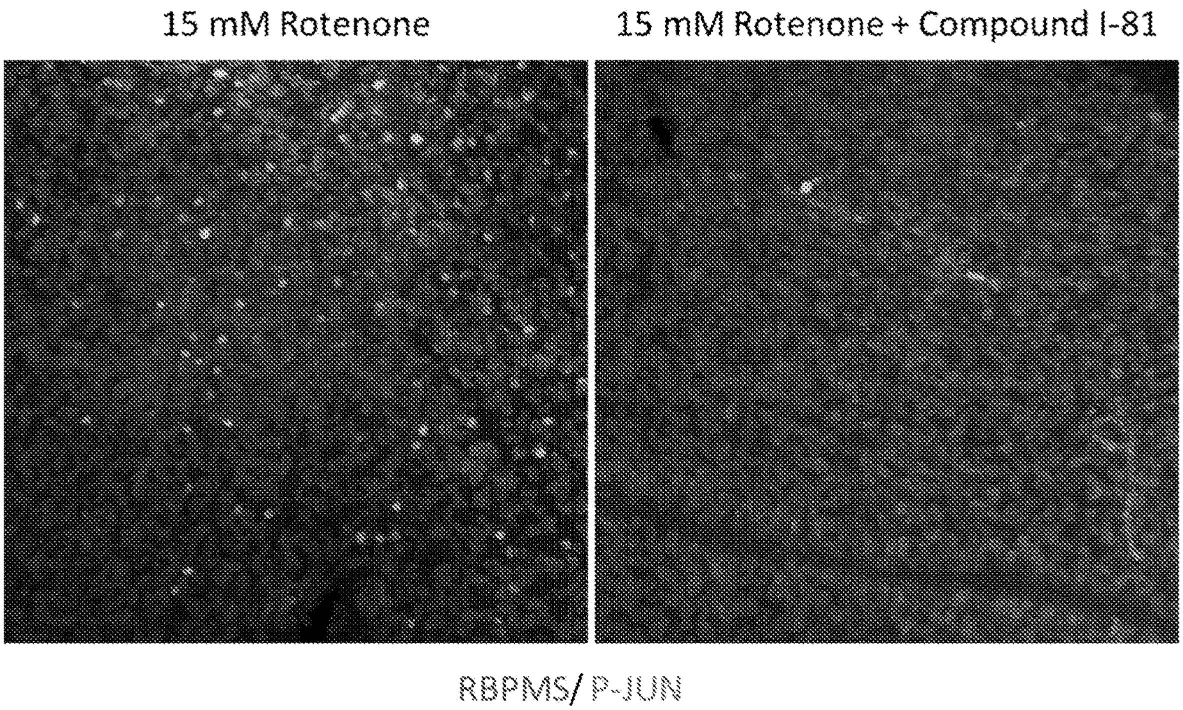
FIG. 5 has representative images of mice intravitreally injected with 15 mM rotenone in the presence or absence 1-81. Twenty-four hours following injection, retinas were extracted and immunofluorescently labelled with anti-RBPMS to mark RGCs and anti-phosphorlylated JUN (P-JUN) to examine DLK/JNK pathway induction. The white spots indicate P-JUN labelling.

Mice were intravitreally injected with 15 mM rotenone in the presence or absence I-81. 24 hrs following injection, retinas were extracted and immunofluorescently labelled with anti-RBPMS to mark RGCs and anti-phosphorlylated JUN (P-JUN) to examine DLK/JNK pathway induction. 1-81 inhibited mitochondrial toxicity induced DLK pathway upregulation in RGCs (FIG. 5) as indicated by the decreased p-cJun staining in the RGCs treated with the compound of Formula (A), (AI), (I), (I-A), (I-B), (I-C), (I-D), (B), (BII), (II), (II-A), (II-B), (II-C), (II-D), (II-E), (II-F), (II-G), or (II-H) and rotenone compared to RGCs treated with rotenone.

Figure 6:
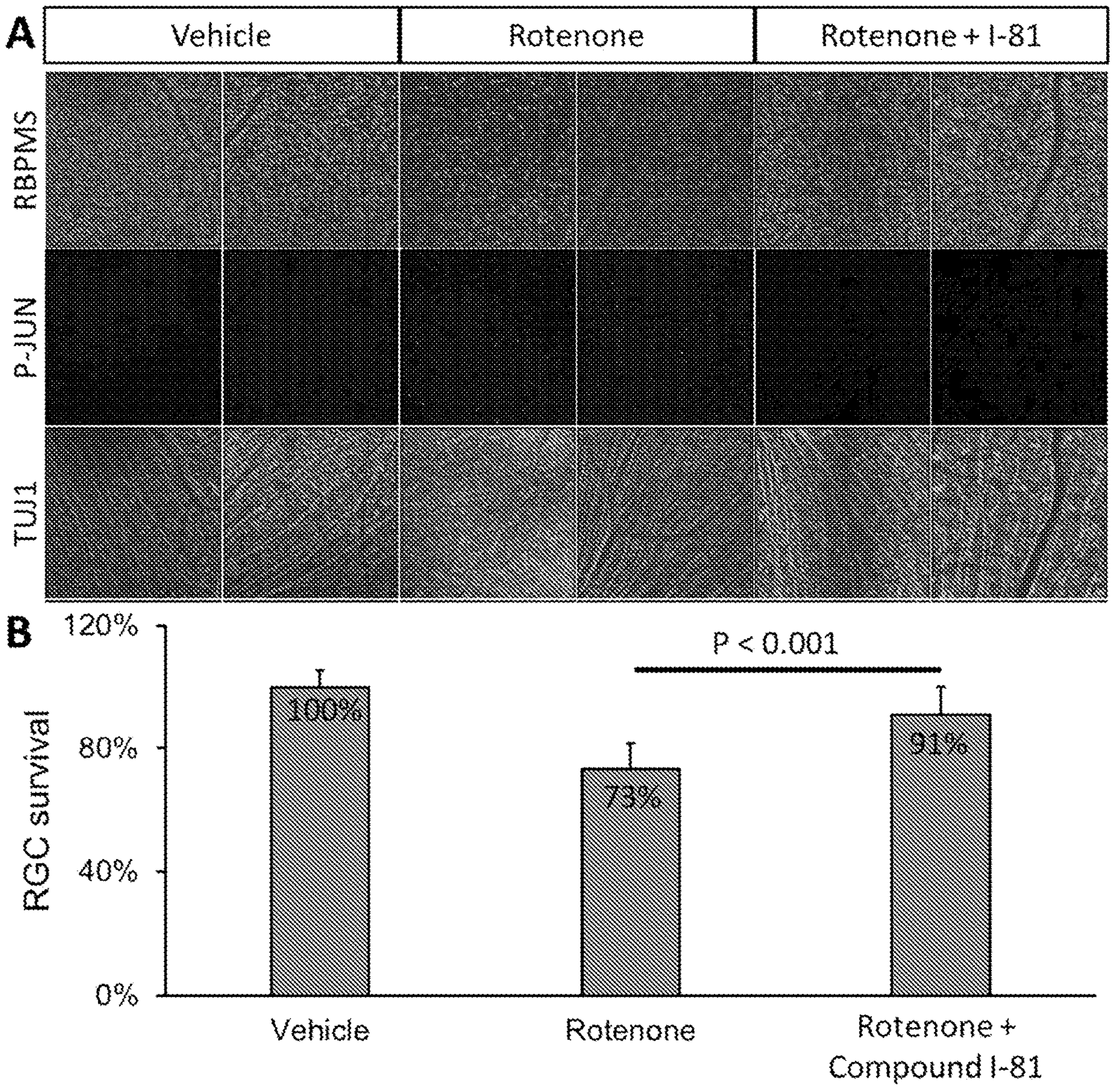
FIG. 6A is a representative image of mice intravitreally injected with either 1 μL of vehicle (DMSO), 15 mM rotenone, or 15 mM rotenone and 100 mM I-81. Three weeks following injection, retinas were extracted and immunofluorescently labelled with anti-RBPMS to mark RGCs, anti-phosphorylated JUN (P-JUN) to examine DLK/JNK pathway induction, and Tuj1 to visualize axons.
FIG. 6B is a plot showing quantification of RBPMS labelled RGCs using an automated image analysis software. Error bars are stdev, n=8.

Mice were intravitreally injected with either 1 μL of vehicle (DMSO), 15 mM rotenone, or 15 mM rotenone and 100 mM I-81. Three weeks following injection, retinas were extracted and immunofluorescently labelled with anti-RBPMS to mark RGCs, anti-phosphorylated JUN (P-JUN) to examine DLK/JNK pathway induction, and Tuj1 to visualize axons (FIG. 6A). RBPMS labelled RGCs were quantified using an automated image analysis software (FIG. 6B). I-81 protected against mitochondrial toxicity induced RGC death (see, for example, the top panel in FIG. 6A) and axon degeneration (see, for example, the bottom panel in FIG. 6A) in vivo.

Figure 7:
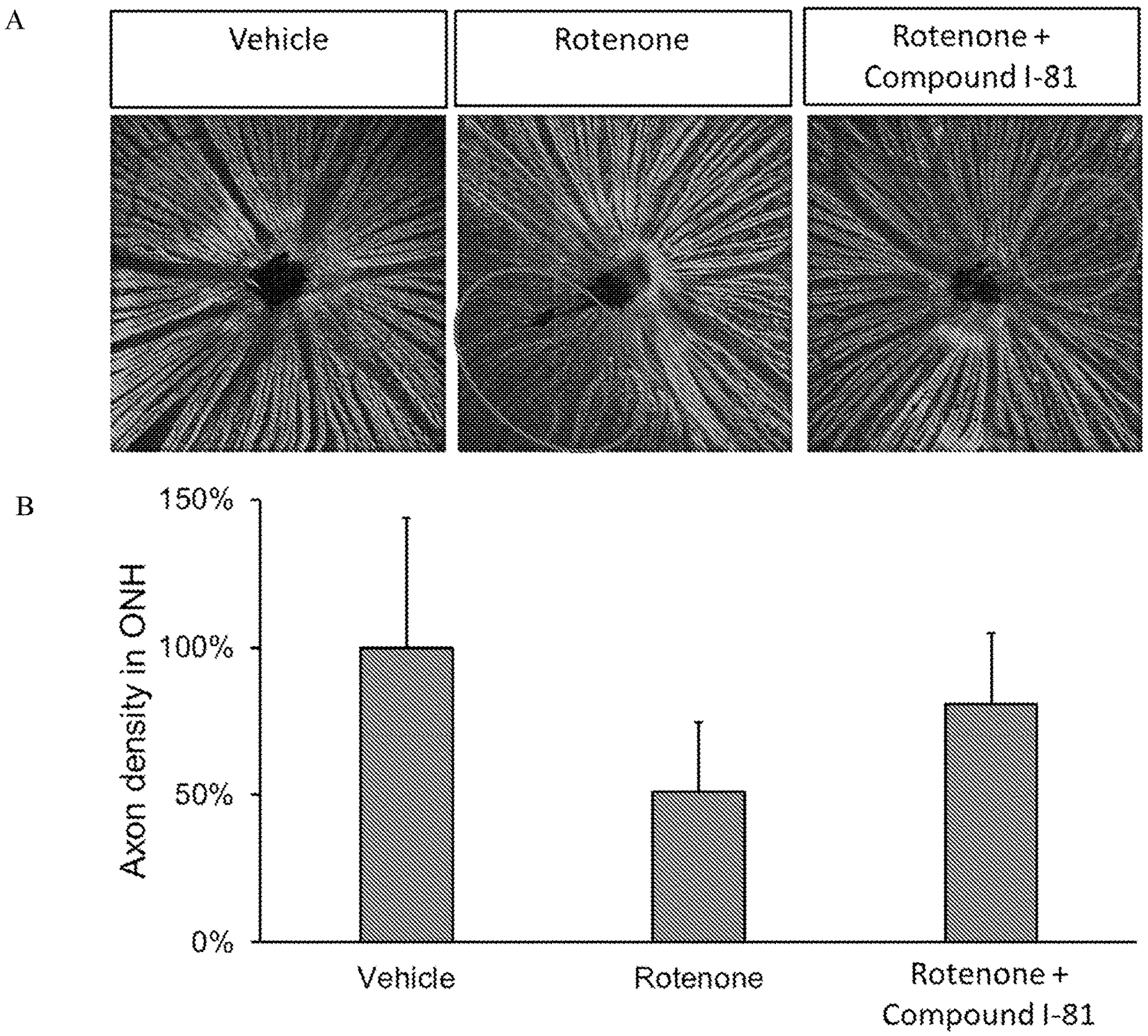
FIG. 7A are representative optic nerve head images of mouse eyes challenged with vehicle, 15 mM rotenone, or 15 mM rotenone with 100 mM I-81. Three weeks following injection, retinas were extracted and immunofluorescently labelled with Tuj1 to visualize axons. Circles indicate areas of axonal degeneration.
FIG. 7B is a plot showing the quantification of Tuj1 immunofluorescence using an automated image analysis software. Error bars are stdev, n=8.

Mouse eyes were challenged with vehicle, 15 mM rotenone, or 15 mM rotenone with 100 mM I-81 (FIG. 7A). Three weeks following injection, retinas were extracted and immunofluorescently labelled with Tuj1 to visualize axons. Tuj1 immunofluorescence was quantified using an automated image analysis software (FIG. 7B). I-81 protected against mitochondrial toxicity-induced axonal degeneration as indicated by the increased axon density in optic nerve head (ONH) treated with the compound of Formula (A), (AI), (I), (I-A), (I-B), (I-C), (I-D), (B), (BII), (II), (II-A), (II-B), (II-C), (II-D), (II-E), (II-F), (II-G), or (II-H) compared to optic nerve head (ONH) treated with rotenone and the compound of Formula (A), (AI), (I), (I-A), (I-B), (I-C), (I-D), (B), (BII), (II), (II-A), (II-B), (II-C), (II-D), (II-E), (II-F), (II-G), or (II-H).

Studies with colchicine

Colchicine inhibits microtubule polymerization and can disrupt axon function. Many neurodegenerative diseases exhibit axonal injury. Additionally, colchicine can cause peripheral neuropathy.

Figure 8:
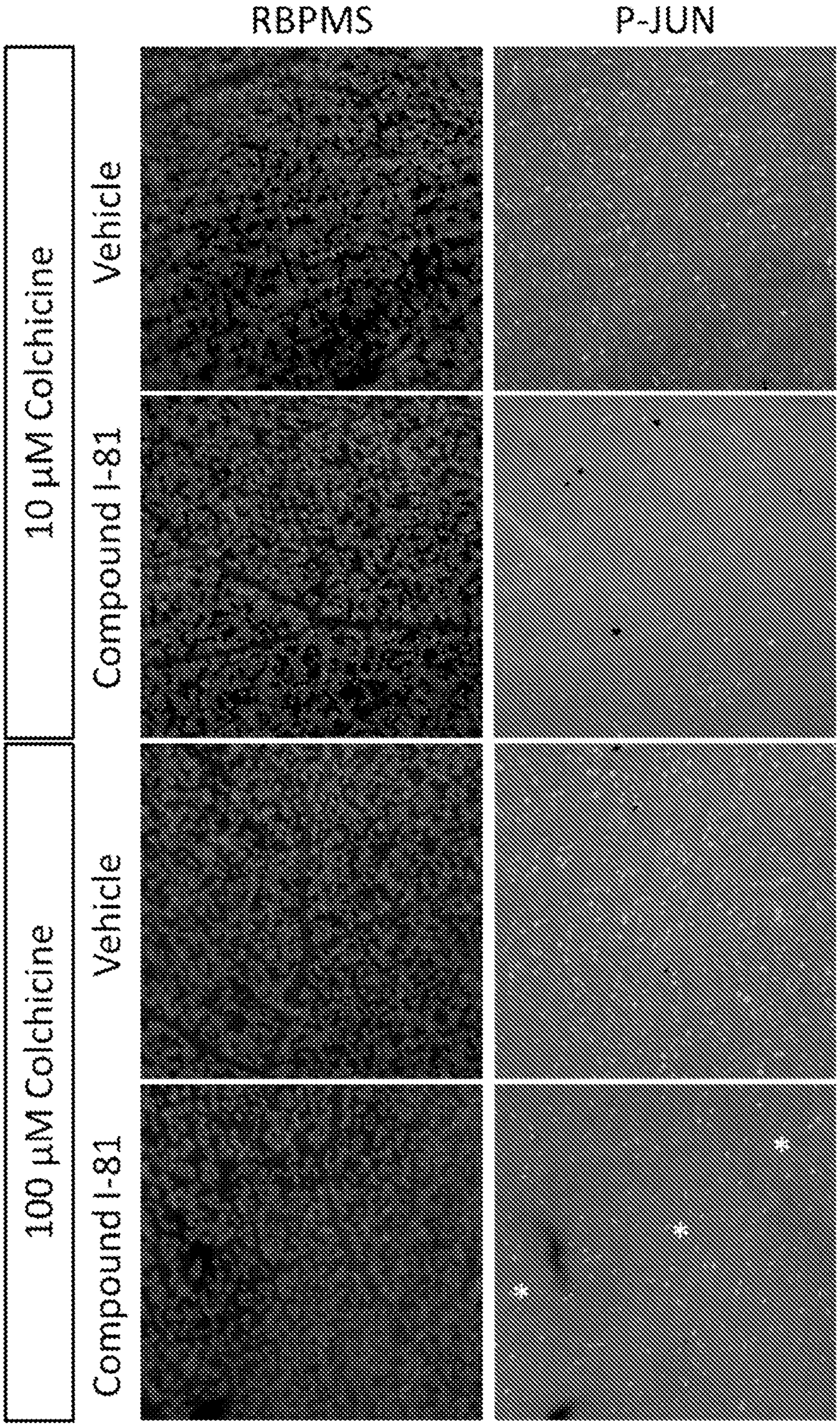
FIG. 8 are representative images of mice injected with 1 μL of either 10 μM or 100 μM colchicine and 1 μL of vehicle (DMSO) or 4 mM I-81 into the vitreous of the eye. Twenty-four hrs following injection, retinas were extracted and immunofluorescently labelled with anti-RBPMS to mark RGCs and anti-phosphorlylated JUN (P-JUN) to examine DLK/JNK pathway induction. * indicates P-JUN positive cells that are not RGCs.

Mice were injected with 1 μL of either 10 M or 100 μM colchicine and 1 μL of vehicle (DMSO) or 4 mM I-81 into the vitreous of the eye. 24 hrs following injection, retinas were extracted and immunofluorescently labelled with anti-RBPMS to mark RGCs and anti-phosphorlylated JUN (P-JUN) to examine DLK/JNK (see FIG. 8). 1-81 inhibited colchicine induced DLK pathway upregulation in RGCs as indicated by the decreased p-JUN intensity in the colchicine and I-81 treated RGCs compared the colchicine treated RGCs.

Figure 9:
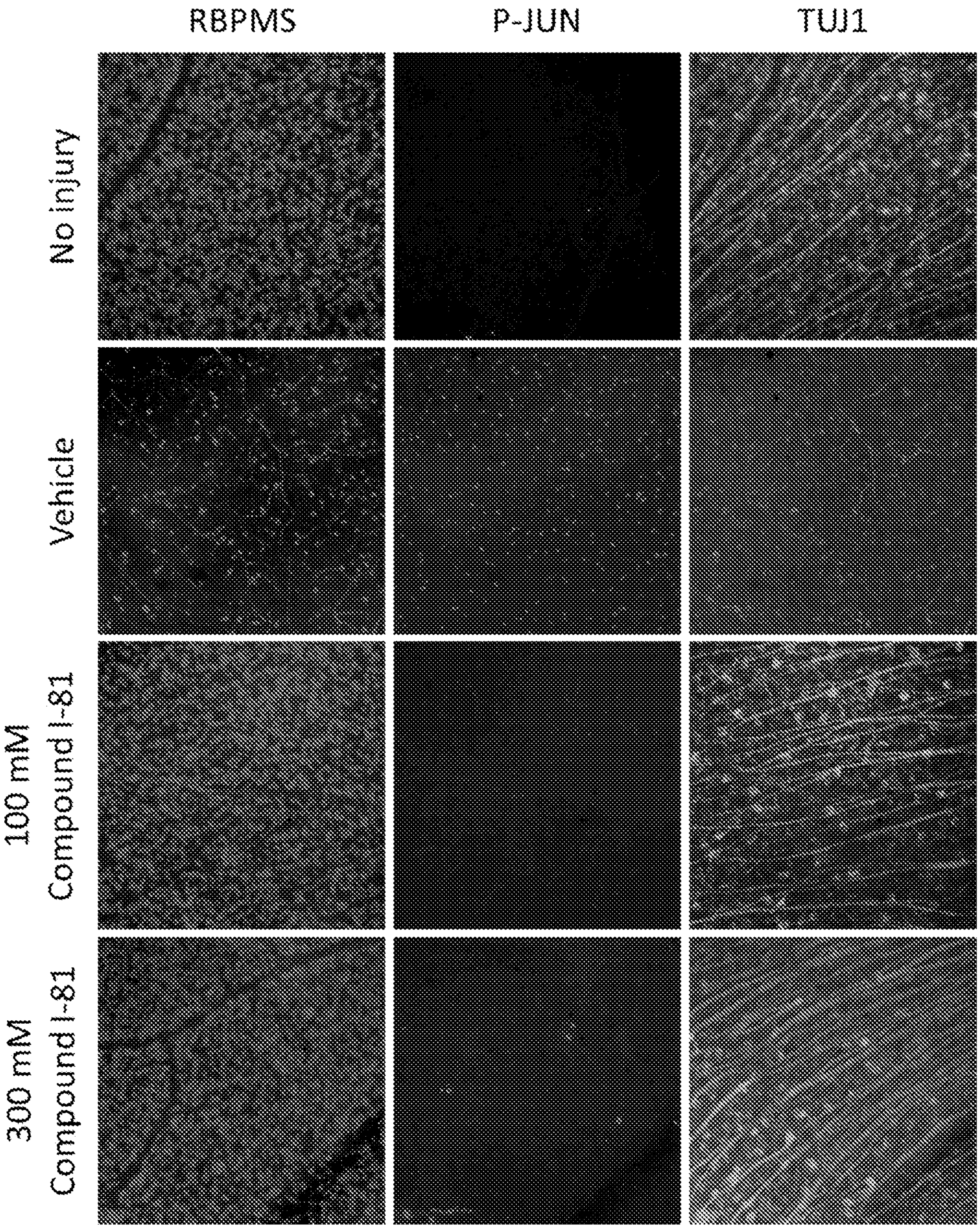
FIG. 9 has representative retinal flatmount images of mice intravitreally injected with 1 μL of vehicle (DMSO), 100 mM I-81, or 300 mM I-81 immediately following optic nerve crush injury. Retinas were extracted 1 month later and immunofluorescently labelled with anti-RBPMS to mark RGCs, anti-phosphorylated JUN (P-JUN) to examine DLK/JNK pathway induction, and Tuj1 to visualize axons.

Mice were intravitreally injected with 1 μL of vehicle (DMSO), 100 mM I-81, or 300 mM I-81 immediately following optic nerve crush injury. Retinas were extracted 1 month later and immunofluorescently labelled with anti-RBPMS to mark RGCs, anti-phosphorylated JUN (P-JUN) to examine DLK/JNK pathway induction, and Tuj1 to visualize axons (see FIG. 9). I-81 was protective to RGCs for at least 1 month after optic nerve crush injury as indicated by the increased density of RBPMS staining, decreased p-JUN intensity, and increased TUJ1 intensity in the I-81 treated RGCs compared to the vehicle treated RGCs.

Structural and Functional Studies

Figure 10:
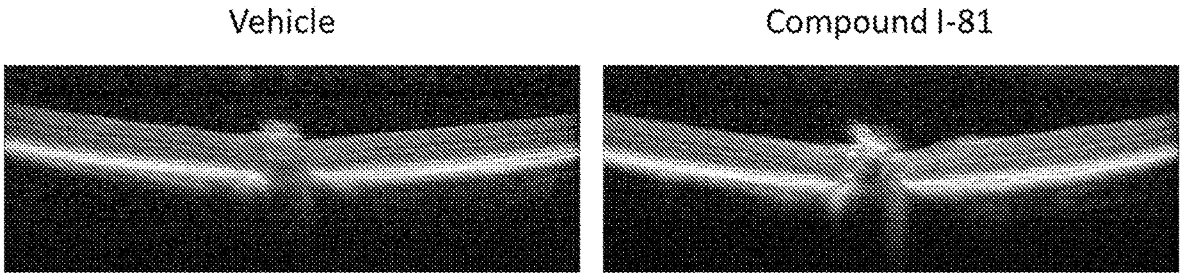
FIG. 10 are representative optical coherence tomography images of mice 7 days following intravitreal injections of either vehicle (DMSO) or 10 mM I-81.
Figure 11A:
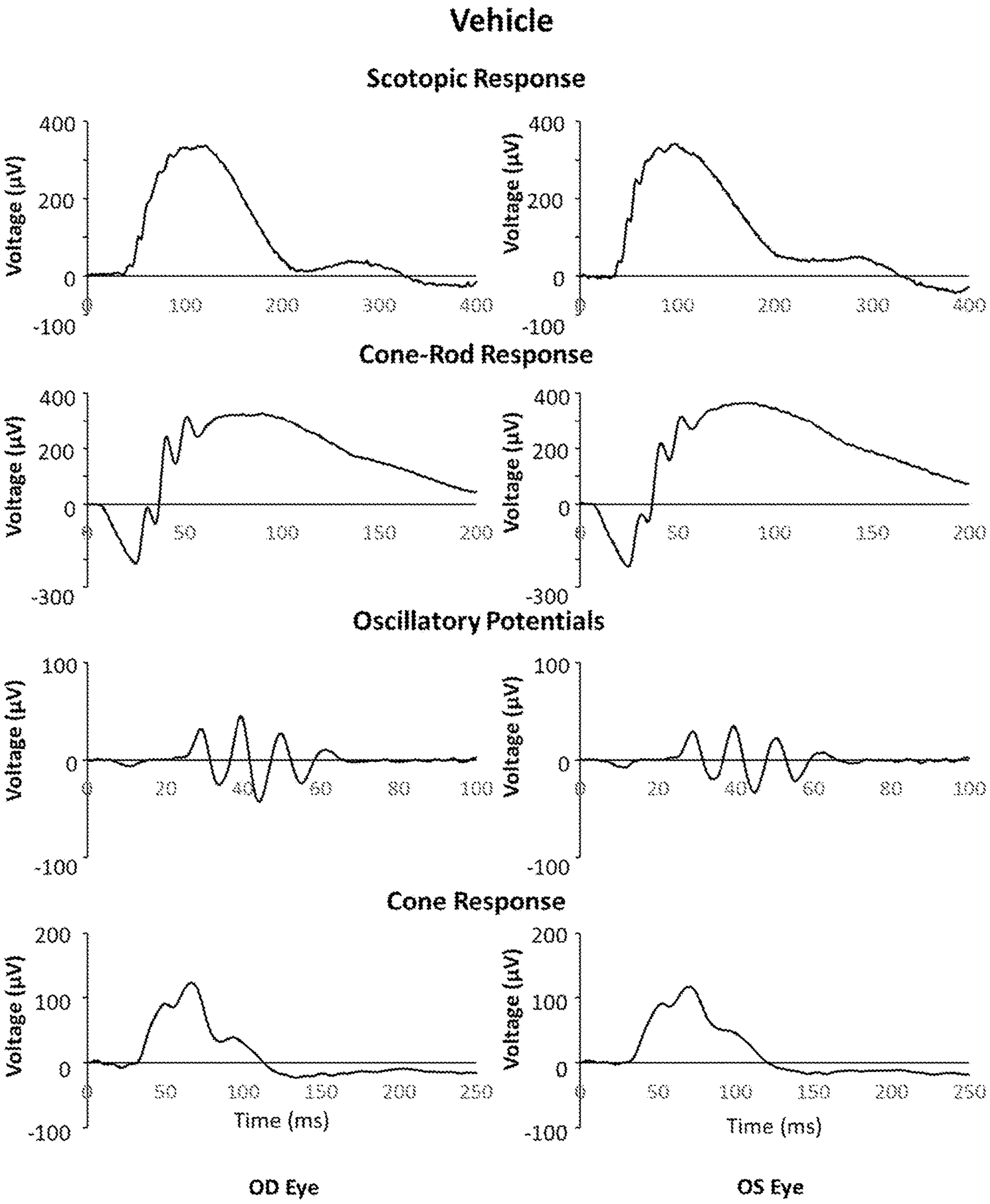
FIGS. 11A and 11B are representative retinal electroretinographs of mice 7 days following intravitreal injections of either vehicle (DMSO) or 10 mM I-81.
Figure 11B:
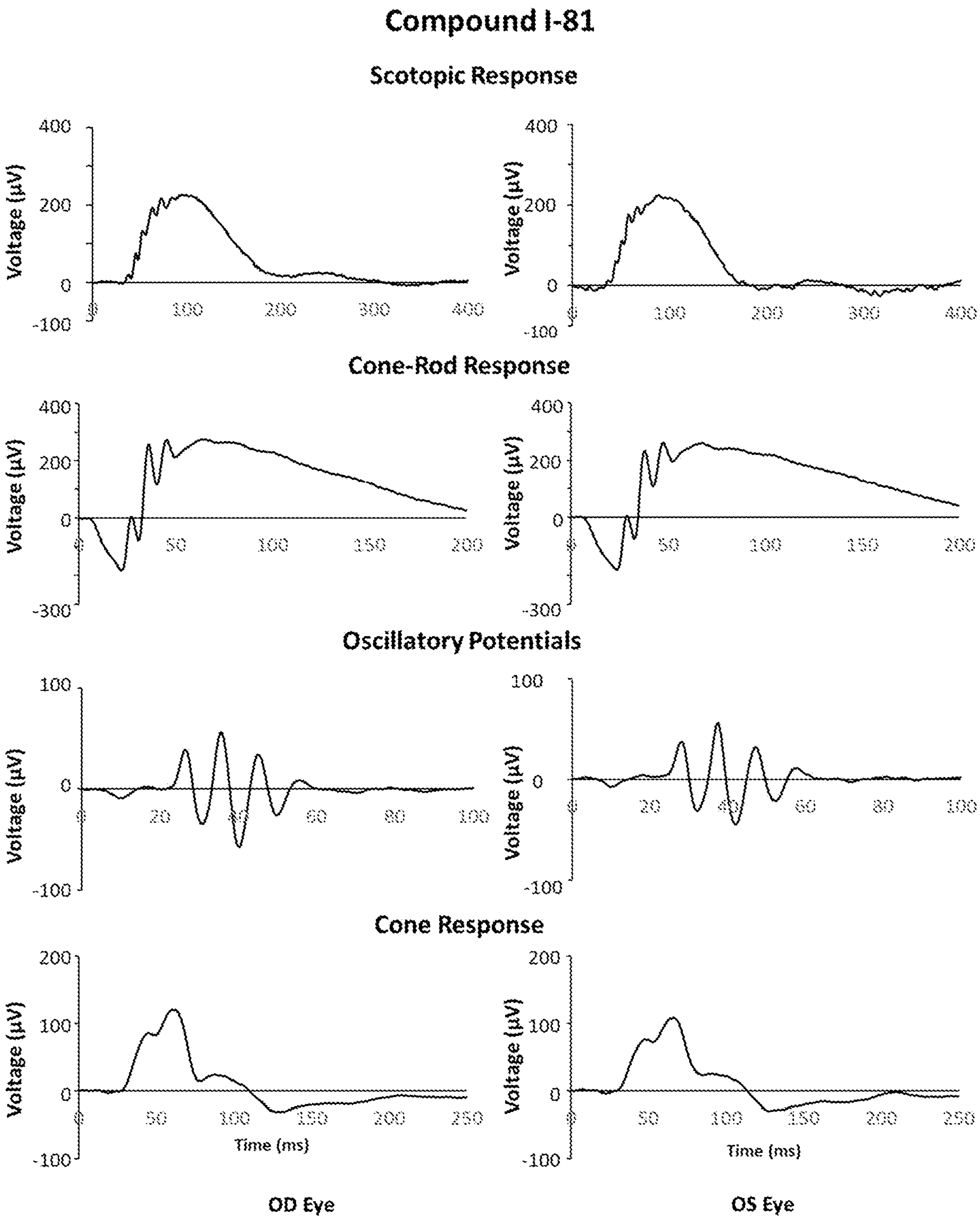

Optical coherence tomography images of mice 7 days following intravitreal injections of either vehicle (DMSO) or 10 mM I-81 were obtained (FIG. 10). Retinal electroretinographs were also acquired (FIGS. 11A and 11B). I-81 did not induce structural or functional toxicity to the retina.

Mice were injected with 1 μL of I-81 at various concentrations. Retinas were harvested at various timepoints and the relative amount of precipitated I-81 was assessed (FIG. 12).

OTHER EMBODIMENTS

Exemplary Embodiments

1. A compound of formula (A)

(A)

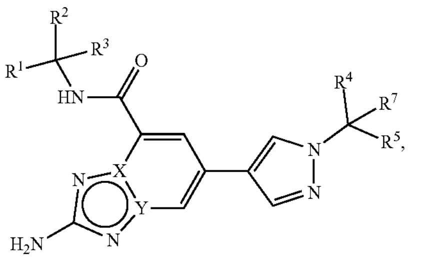

in which

X is nitrogen and Y is carbon, or

X is carbon and Y is nitrogen, $R^1$ and $R^2$ are each independently hydrogen or $(C_1$-$C_3)$-alkyl, $R^3$ is $(C_1$-$C_6)$-alkyl, $(C_3$-$C_7)$-cycloalkyl or $(C_3$-$C_7)$-cycloalkyl-$(C_1$-$C_3)$-alkyl wherein the $(C_1$-$C_6)$-alkyl, $(C_3$-$C_7)$-cycloalkyl, or $(C_3$-$C_7)$-cycloalkyl-$(C_1$-$C_3)$-alkyl may be substituted by hydroxyl, $(C_1$-$C_4)$-alkoxy, oxo, cyano, chlorine, bromine, or up to three times by fluorine, where $(C_1$-$C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, $(C_1$-$C_4)$-alkoxy, $(C_1$-$C_4)$-alkyl, oxo, cyano, chlorine, bromine, or fluorine, where $(C_1$-$C_4)$-alkoxy and $(C_1$-$C_4)$-alkyl may be substituted up to three times by fluorine, $R^4$ is hydrogen, $(C_1$-$C_6)$-alkyl, $(C_3$-$C_7)$-cycloalkyl or 4- to 7-membered heterocyclyl wherein the $(C_1$-$C_6)$-alkyl, $(C_3$-$C_7)$-cycloalkyl or 4- to 7-membered heterocyclyl may be substituted by $(C_1$-$C_4)$-alkyl, $(C_1$-$C_4)$-alkoxy, oxo, cyano, chlorine, bromine or up to three times by fluorine, where $(C_1$-$C_4)$-alkoxy and $(C_1$-$C_4)$-alkyl may be substituted up to three times by fluorine, and the nitrogen of a 4- to 7-membered heterocyclyl may be substituted by $C(O)OR^6$ or $C(O)R^6$, $R^5$ is $(C_3$-$C_7)$-cycloalkyl, cyanomethyl, phenyl, or heteroaryl wherein the $(C_3$-$C_7)$-cycloalkyl, phenyl or heteroaryl may be substituted by one or more $(C_1$-$C_4)$-alkyl, $(C_1$-$C_4)$-alkoxy, cyano, 4- to 7-membered heterocyclyl, chlorine, bromine or up to three times by fluorine where $(C_1$-$C_4)$-alkyl and $(C_1$-$C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, $(C_1$-$C_4)$-alkyl, $(C_1$-$C_4)$-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, and the nitrogen of each of the 4- to 7-membered heterocyclyl may independently be substituted by C(O)OR$^6$ or C(O)R$^6$, $R^6$ is ($C_1$-$C_4$)-alkyl, $R^7$ is hydrogen, ($C_1$-$C_5$)-alkyl, ($C_3$-$C_7$)-cycloalkyl or 4- to 7-membered heterocyclyl wherein the ($C_1$-$C_5$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, and the salts, solvates and solvates of the salts thereof.

2. A compound of formula (AI)

(AI)

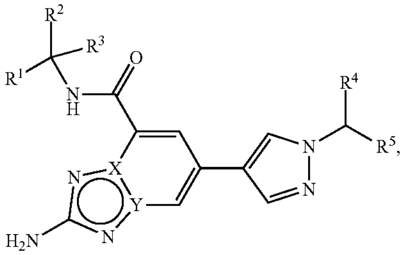

in which

X is nitrogen and Y is carbon, or

X is carbon and Y is nitrogen, $R^1$ and $R^2$ are each independently hydrogen or ($C_1$-$C_3$)-alkyl, $R^3$ is ($C_1$-$C_6$)-alkyl, ($C_3$-$C_7$)-cycloalkyl or ($C_3$-$C_7$)-cycloalkyl-($C_1$-$C_3$)-alkyl wherein the ($C_1$-$C_6$)-alkyl, ($C_3$-$C_7$)-cycloalkyl, or (C3-$C_7$)-cycloalkyl-($C_1$-$C_3$)-alkyl may be substituted by hydroxyl, ($C_1$-$C_4$)-alkoxy, oxo, cyano, chlorine, bromine, or up to three times by fluorine, where ($C_1$-$C_4$)-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, ($C_1$-$C_4$)-alkoxy, ($C_1$-$C_4$)-alkyl, oxo, cyano, chlorine, bromine, or fluorine, where ($C_1$-$C_4$)-alkoxy and ($C_1$-$C_4$)-alkyl may be substituted up to three times by fluorine, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, $R^5$ is ($C_3$-$C_7$)-cycloalkyl, cyanomethyl, phenyl, or heteroaryl wherein the ($C_3$-$C_7$)-cycloalkyl, phenyl or heteroaryl may be substituted by one or more ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, and the nitrogen of each of the 4- to 7-membered heterocyclyl may independently be substituted by C(O)OR$^6$ or C(O)R$^6$, $R^6$ is ($C_1$-$C_4$)-alkyl and the salts, solvates and solvates of the salts thereof.

3. A compound of formula (I)

(I)

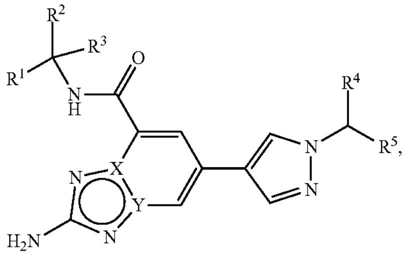

in which

X is nitrogen and Y is carbon, or

X is carbon and Y is nitrogen, $R^1$ and $R^2$ are each independently hydrogen or ($C_1$-$C_3$)-alkyl, $R^3$ is ($C_1$-$C_6$)-alkyl, ($C_3$-$C_7$)-cycloalkyl or ($C_3$-$C_7$)-cycloalkyl-($C_1$-$C_3$)-alkyl wherein the ($C_1$-$C_6$)-alkyl, ($C_3$-$C_7$)-cycloalkyl, or ($C_3$-$C_7$)-cycloalkyl-($C_1$-$C_3$)-alkyl may be substituted by hydroxyl, ($C_1$-$C_4$)-alkoxy, oxo, cyano, chlorine, bromine, or up to three times by fluorine, where ($C_1$-$C_4$)-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two heteratoms selected from the group consisting of O or N, wherein the ring may be substituted by hydroxyl, ($C_1$-$C_4$)-alkoxy, ($C_1$-$C_4$)-alkyl, oxo, cyano, chlorine, bromine, or fluorine, where ($C_1$-$C_4$)-alkoxy and ($C_1$-$C_4$)-alkyl may be substituted up to three times by fluorine, $R^4$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, $R^5$ is $(C_3-C_7)$-cycloalkyl, phenyl or heteroaryl wherein the $(C_3-C_7)$-cycloalkyl, phenyl or heteroaryl may be substituted by $(C_1-C_4)$-alkyl, $(C_1-C_4)$-alkoxy, cyano, 4- to 7-membered heterocyclyl, chlorine, bromine or up to three times by fluorine where $(C_1-C_4)$-alkyl and $(C_1-C_4)$-alkoxy may be substituted up to three times by fluorine, or $R^4$ and $R^5$ are joined to one another and, taken together with the carbon atom to which they are attached, form a 4- to 7-membered ring containing up to two heteratoms selected from the group consisting of O or N, wherein the ring may be substituted by benzyl, 4- to 7-membered heterocyclyl, $(C_1-C_4)$-alkyl, $(C_1-C_4)$-alkoxy, oxo, cyano, chlorine, bromine or up to three times by fluorine, or may be annellated with phenyl or heteroaryl where $(C_1-C_4)$-alkyl is optionally substituted by 4- to 7-membered heterocyclyl or up to three times by fluorine, and the nitrogen of each of the 4- to 7-membered heterocyclyls may independently be substituted by $C(O)OR^6$ or $C(O)R^6$, $R^6$ is $(C_1-C_4)$-alkyl and the salts, solvates and solvates of the salts thereof.

4. The compound of any one of Embodiments 1-3 in which X is nitrogen and Y is carbon, $R^1$ and $R^2$ are each independently hydrogen or methyl, $R^3$ is $(C_1-C_6)$-alkyl which may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two O atoms, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is $(C_1-C_6)$-alkyl, $(C_3-C_7)$-cycloalkyl, or 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

5. The compound of any one of Embodiments 1-4 in which

X is nitrogen and Y is carbon, $R^1$ is hydrogen, $R^2$ is methyl, $R^3$ is $(C_1-C_4)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, wherein the ring may be substituted by hydroxyl, $(C_1-C_4)$-alkoxy, chlorine, bromine, or fluorine where $(C_1-C_4)$-alkoxy may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

6. The compound of any one of Embodiments 1-3, wherein the compound is a compound of formula (I-A)

(I-A)

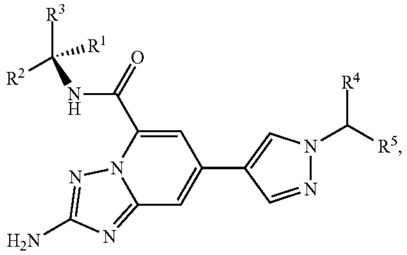

in which $R^1$ is hydrogen, $R^2$ is methyl, $R^3$ is $(C_1-C_3)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, $R^4$ is $(C_1-C_6)$-alkyl, $(C_3-C_7)$-cycloalkyl, 4- to 7-membered heterocyclyl wherein the $(C_1-C_5)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

7. The compound of any one of Embodiments 1-3, wherein the compound is a compound of formula (I-B)

(I-B)

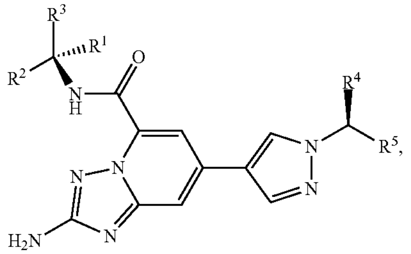

in which $R^1$ is hydrogen, $R^2$ is methyl, $R^3$ is methyl or ethyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a furanyl ring, $R^4$ is $(C_1-C_6)$-alkyl, cyclopropyl, cyclobutyl, cyclopentyl, 4- to 7-membered heterocyclyl, each of which may be substituted by chlorine, bromine or up to three times by fluorine and the nitrogen of a 4- to 7-membered heterocyclyl may be substituted by $C(O)OR^6$ or $C(O)R^6$, $R^5$ is phenyl, 3-pyridinyl or 4-pyridinyl, each of which may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

8. The compound of any one of Embodiments 1-3, wherein

X is carbon and Y is nitrogen, $R^1$ and $R^2$ are each independently hydrogen or methyl, $R^3$ is $(C_1-C_6)$-alkyl which may be substituted by hydroxyl, $(C_1-C_4)$-alkoxy, oxo, cyano, chlorine, bromine, or up to three times by fluorine, where $(C_1-C_4)$-alkoxy may be substituted up to three times by fluorine, or $R^1$ is hydrogen and $R^2$ and $R^3$ are joined to one another and, taken together with the carbon atom to which they are attached, form a 4- to 7-membered ring containing up to two O atoms, wherein the ring may be substituted by hydroxyl, $(C_1-C_4)$-alkoxy, $(C_1-C_4)$-alkyl, oxo, cyano, chlorine, bromine, or fluorine, where $(C_1-C_4)$-alkoxy and $(C_1-C_4)$-alkyl may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

9. The compound of any one of Embodiments 1-3 and 8, wherein

X is carbon and Y is nitrogen, $R^1$ is hydrogen, $R^2$ is methyl, $R^3$ is $(C_1-C_4)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, wherein the ring may be substituted by hydroxyl, $(C_1-C_4)$-alkoxy, chlorine, bromine, or fluorine where $(C_1-C_4)$-alkoxy may be substituted up to three times by fluorine, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where $(C_1-C_4)$-alkyl and $(C_1-C_4)$-alkoxy may be substituted up to three times by fluorine, $R^6$ is $(C_1-C_4)$-alkyl and the salts, solvates and solvates of the salts thereof.

10. The compound of any one of Embodiments 1-3, wherein the compound is a compound of formula (I-C)

(I-C)

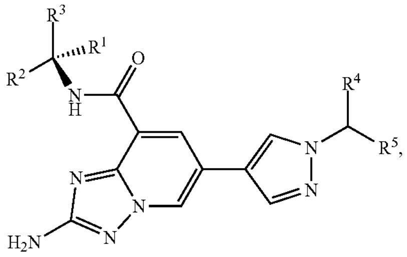

in which $R^1$ is hydrogen, $R^2$ is methyl, $R^3$ is $(C_1-C_3)$-alkyl which may be substituted by hydroxyl, $(C_1-C_4)$-alkoxy, chlorine or up to three times by fluorine, where $(C_1-C_4)$-alkoxy may be substituted up to three times by fluorine, or $R^2$ and $R^3$ are joined to one another and, taken together with the carbon atom to which they are attached, form a 4- to 7-membered ring containing up to one O atom, $R^4$ is $(C_1-C_6)$-alkyl, $(C_3-C_7)$-cycloalkyl, 4- to 7-membered heterocyclyl wherein the $(C_1-C_6)$-alkyl, $(C_3-C_7)$-cycloalkyl, or 4- to 7-membered heterocyclyl may be substituted by chlorine, bromine or up to three times by fluorine and the nitrogen of a 4- to 7-membered heterocyclyl may be substituted by $C(O)OR^6$ or $C(O)R^6$, $R^5$ is phenyl or pyridinyl wherein the phenyl or pyridinyl may be substituted by $(C_1-C_4)$-alkyl, $(C_1-C_4)$-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl and the salts, solvates and solvates of the salts thereof.

11. The compound of any one of Embodiments 1-3, wherein the compound is a compound of formula (I-D)

(I-D)

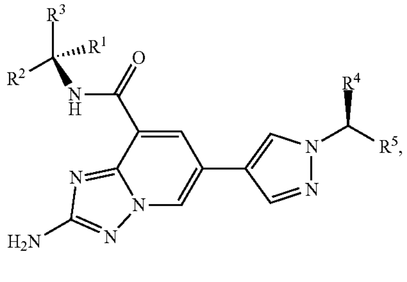

in which $R^1$ is hydrogen, $R^2$ is methyl, $R^3$ is methyl or ethyl which may be substituted by hydroxyl, ($C_1$-$C_4$)-alkoxy, chlorine or up to three times by fluorine, where ($C_1$-$C_4$)-alkoxy may be substituted up to three times by fluorine, or $R^2$ and $R^3$ are joined to one another and, taken together with the carbon atom to which they are attached, form a furanyl ring, $R^4$ is ($C_1$-$C_6$)-alkyl, cyclopropyl, cyclobutyl, cyclopentyl, 4- to 7-membered heterocyclyl, each of which may be substituted by chlorine, bromine or up to three times by fluorine and the nitrogen of a 4- to 7-membered heterocyclyl may be substituted by C(O)OR$^6$ or C(O)R$^6$, $R^5$ is phenyl, 3-pyridinyl or 4-pyridinyl, each of which may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl and the salts, solvates and solvates of the salts thereof.

12. The compound of any one of any one of Embodiments 1-5 and 7-11 in which $R^3$ is ethyl which may be substituted by hydroxyl, ($C_1$-$C_4$)-alkoxy, chlorine or up to three times by fluorine, where ($C_1$-$C_4$)-alkoxy may be substituted up to three times by fluorine.

13. The compound of any one of Embodiments 1-5 and 8-11 in which $R^4$ is 5- to 6-membered heterocyclyl which may be substituted by chlorine, bromine, or up to three times by fluorine and the nitrogen of the 5- to 6-membered heterocyclyl may be substituted by C(O)OR$^6$ or C(O)R$^6$.

14. The compound of any one of Embodiments 1-5 and 7-11 in which $R^5$ is phenyl, 3-pyridinyl, or 4-pyridinyl, each of which may be substituted by ($C_1$-$C_4$)-alkyl or ($C_1$-$C_4$)-alkoxy; where ($C_1$-$C_4$)-alkyl and ($C_1$-$C_4$)-alkoxy may be substituted up to three times by fluorine.

15. A compound of formula (B)

(B)

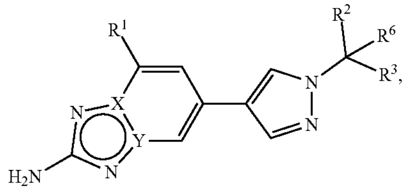

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —SO$_2$R$^4$, —NR$^4$R$^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^5$ are each independently ($C_1$-$C_4$)-alkyl optionally substituted up to three times by fluorine, $R^6$ is hydrogen, ($C_1$-$C_6$)-alkyl, ($C_3$-$C_7$)-cycloalkyl or 4- to 7-membered heterocyclyl wherein the ($C_1$-$C_6$)-alkyl, ($C_3$-$C_7$)-cycloalkyl or 4- to 7-membered heterocyclyl may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, and the nitrogen of a 4- to 7-membered heterocyclyl may be substituted by C(O)OR$^6$ or C(O)R$^6$, and the salts, solvates and solvates of the salts thereof.

16. A compound of formula (BII)

(BII)

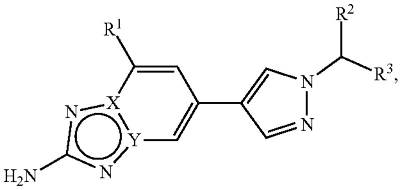

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered ring containing up to two heteratoms selected from the group consisting of O or N, which ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^5$ are each independently ($C_1$-$C_4$)-alkyl optionally substituted up to three times by fluorine and the salts, solvates and solvates of the salts thereof.

17. A compound of Formula (II)

(II)

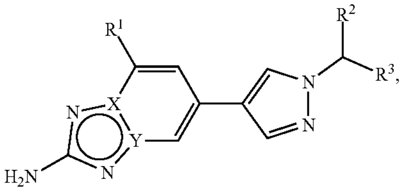

in which

X is nitrogen and Y is carbon, or

X is carbon and Y is nitrogen, $R^1$ is phenyl or heteroaryl, each of which may be substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl and ($C_3$-$C_7$)-cycloalkoxy may be substituted by hydroxyl, cyano and up to three times by fluorine $R^2$ is hydrogen, ($C_1$-$C_6$)-alkyl, ($C_3$-$C_7$)-cycloalkyl or 4- to 7-membered heterocyclyl, each of which may be substituted by ($C_1$-$C_4$)-alkyl, ($C_1$-$C_4$)-alkoxy, oxo, cyano, chlorine, bromine or up to three times by fluorine, where ($C_1$-$C_4$)-alkoxy and ($C_1$-$C_4$)-alkyl may be substituted up to three times by fluorine, $R^3$ is ($C_3$-$C_7$)-cycloalkyl, phenyl or heteroaryl wherein the ($C_3$-$C_7$)-cycloalkyl, phenyl or heteroaryl may be substituted by ($C_1$-$C_4$)-alkyl, ($C_1$-$C_4$)-alkoxy, cyano, 4- to 7-membered heterocyclyl, chlorine, bromine or up to three times by fluorine where ($C_1$-$C_4$)-alkyl and ($C_1$-$C_4$)-alkoxy may be substituted up to three times by fluorine, or $R^2$ and $R^3$ are joined to one another and, taken together with the carbon atom to which they are attached, form a 4- to 7-membered fused ring containing up to two heteratoms selected from the group consisting of O or N, which fused ring may be substituted by benzyl, 4- to 7-membered heterocyclyl, ($C_1$-$C_4$)-alkyl, ($C_1$-$C_4$)-alkoxy, oxo, cyano, chlorine, bromine or up to three times by fluorine, or may be annellated with phenyl or heteroaryl where ($C_1$-$C_4$)-alkyl is optionally substituted by 4- to 7-membered heterocyclyl or up to three times by fluorine, $R^4$ and $R^5$ are each independently ($C_1$-$C_4$)-alkyl optionally substituted up to three times by fluorine and the salts, solvates and solvates of the salts thereof.

18. The compound of any one of Embodiments 15-17 in which

X is nitrogen and Y is carbon, $R^1$ is phenyl or heteroaryl, each of which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl, 4- to 7-membered heterocyclyl wherein the ($C_1$-$C_6$)-alkyl, ($C_3$-$C_7$)-cycloalkyl, or 4- to 7-membered heterocyclyl may be substituted by chlorine, bromine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

19. The compound of any one of Embodiments 15-18 in which

X is nitrogen and Y is carbon, $R^1$ is phenyl, pyridonyl, pyrimidyl, pyridazinyl, pyrazinyl, pyrazolyl or thiadiazolyl, each of which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

20. The compound of any of Embodiments 15-18 in which

X is nitrogen and Y is carbon, $R^1$ is phenyl pyridonyl or pyrazolyl, each of which may be substituted by ($C_1$-$C_4$)-alkyl, ($C_3$-$C_7$)-cycloalkyl, ($C_1$-$C_4$)-alkoxy or —$SO_2R^4$ and in addition may be substituted by cyano, fluorine, chlorine or bromine, and where ($C_1$-$C_4$)-alkyl, ($C_3$-$C_7$)-cycloalkyl and ($C_1$-$C_4$)-alkoxy may be substituted by hydroxyl, cyano and up to three times by fluorine $R^2$ is ($C_1$—C)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ is ($C_1$-$C_4$)-alkyl optionally substituted up to three times by fluorine and the salts, solvates and solvates of the salts thereof.

21. The compound of any one of Embodiments 15-17, wherein the compound is a compound of formula (II-B)

(II-B)

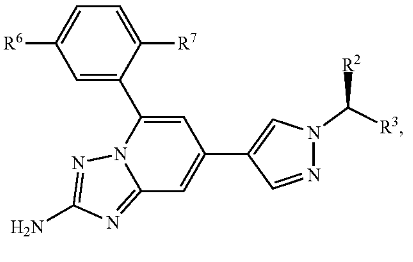

$R^2$ is ($C_1$-$C_5$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl which is substituted by hydroxyl, cyano or up to three times by fluorine $R^7$ is ($C_1$-$C_4$)-alkyl, chlorine, bromine or fluorine where ($C_1$-$C_4$)-alkyl is optionally substituted up to three times by fluorine and the salts, solvates and solvates of the salts thereof.

22. The compound of any one of Embodiments 15-17, wherein the compound is a compound of formula (II-C)

(II-C)

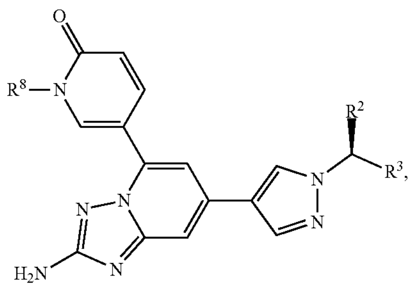

$R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^8$ is ($C_1$-$C_4$)-alkyl which is optionally substituted by hydroxyl, cyano or up to three times by fluorine and the salts, solvates and solvates of the salts thereof.

23. The compound of any one of Embodiments 15-17, wherein the compound is a compound of formula (II-D)

(II-D)

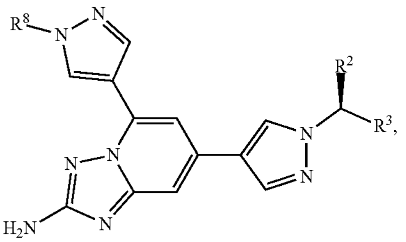

$R^2$ is ($C_1$-$C_5$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^8$ is ($C_1$-$C_4$)-alkyl which is optionally substituted by hydroxyl, cyano or up to three times by fluorine and the salts, solvates and solvates of the salts thereof.

24. The compound of any one of Embodiments 15-17 in which

X is carbon and Y is nitrogen, $R^1$ is phenyl or heteroaryl, each of which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-

$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl, 4- to 7-membered heterocyclyl wherein the ($C_1$-$C_6$)-alkyl, ($C_3$-$C_7$)-cycloalkyl, or 4- to 7-membered heterocyclyl may be substituted by chlorine, bromine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

25. The compound of any one of Embodiments 15-17 and 24 in which

X is carbon and Y is nitrogen, $R^1$ is phenyl, pyridonyl, pyrimidyl, pyridazinyl, pyrazinyl, pyrazolyl or thiadiazolyl, each of which may be substituted by ($C_1$-$C_4$)-alkyl, ($C_3$-$C_7$)-cycloalkyl, ($C_1$-$C_4$)-alkoxy, —$SO_2R^4$, —$NR^4R^5$, cyano, up to three times by hydroxyl, fluorine, chlorine or bromine, where ($C_1$-$C_4$)-alkyl, ($C_3$-$C_7$)-cycloalkyl, ($C_1$-$C_4$)-alkoxy and ($C_3$-$C_7$)-cycloalkoxy may be substituted by hydroxyl, cyano and up to three times by fluorine $R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ and $R^5$ are each independently ($C_1$-$C_4$)-alkyl optionally substituted up to three times by fluorine and the salts, solvates and solvates of the salts thereof.

26. The compound of any one of Embodiments 15-17, 24, or 25 in which

X is carbon and Y is nitrogen, $R^1$ is phenyl, pyridonyl or pyrazolyl, each of which may be substituted by ($C_1$-$C_4$)-alkyl, ($C_3$-$C_7$)-cycloalkyl, ($C_1$-$C_4$)-alkoxy or —$SO_2R^4$ and in addition may be substituted by cyano, fluorine, chlorine or bromine, and where ($C_1$-$C_4$)-alkyl, ($C_3$-$C_7$)-cycloalkyl and ($C_1$-$C_4$)-alkoxy may be substituted by hydroxyl, cyano and up to three times by fluorine $R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^4$ is ($C_1$-$C_4$)-alkyl optionally substituted up to three times by fluorine and the salts, solvates and solvates of the salts thereof.

27. The compound of any one of Embodiments 15-17, wherein the compound is a compound of formula (II-E)

(II-E)

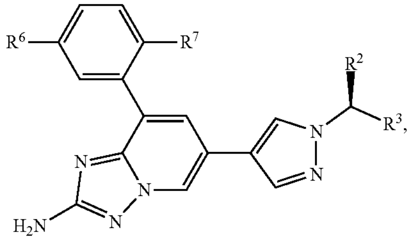

$R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^6$ is ($C_1$-$C_4$)-alkyl which is substituted by hydroxyl, cyano or up to three times by fluorine $R^7$ is ($C_1$-$C_4$)-alkyl, chlorine, bromine or fluorine where ($C_1$-$C_4$)-alkyl is optionally substituted up to three times by fluorine and the salts, solvates and solvates of the salts thereof.

28. The compound of any one of Embodiments 15-17, wherein the compound is a compound of formula (II-F)

(II-F)

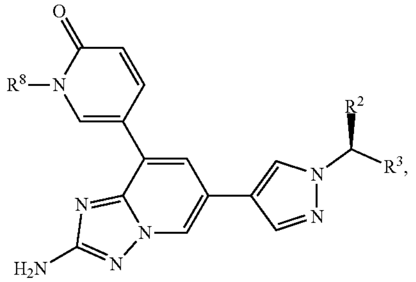

$R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^8$ is ($C_1$-$C_4$)-alkyl which is optionally substituted by hydroxyl, cyano or up to three times by fluorine and the salts, solvates and solvates of the salts thereof.

29. The compound of any one of Embodiments 15-17, wherein the compound is a compound of formula (II-G)

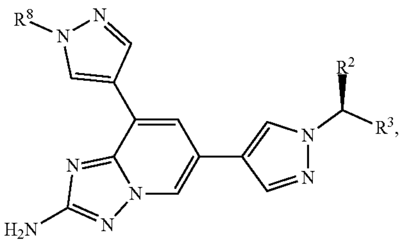

(II-G)

$R^2$ is ($C_1$-$C_6$)-alkyl, ($C_3$-$C_7$)-cycloalkyl, 4- to 7-membered heterocyclyl, each of which may be substituted by chlorine or up to three times by fluorine, $R^3$ is phenyl or pyridinyl wherein the phenyl or pyridinyl may be substituted by ($C_1$-$C_4$)-alkyl, ($C_1$-$C_4$)-alkoxy, cyano, chlorine, bromine or up to three times by fluorine where ($C_1$-$C_4$)-alkyl and ($C_1$-$C_4$)-alkoxy may be substituted up to three times by fluorine, $R^8$ is ($C_1$-$C_4$)-alkyl which is optionally substituted by hydroxyl, cyano or up to three times by fluorine and the salts, solvates and solvates of the salts thereof.

30. A pharmaceutical composition, the pharmaceutical composition comprising a compound according to any one of embodiments 1-29, or a pharmaceutically acceptable salt thereof, and a pharmaceutically acceptable excipient.

31. The pharmaceutical composition of embodiment 30, wherein the pharmaceutical composition is formulated for ocular administration.

32. The pharmaceutical composition of any one of embodiments 30-31, wherein the pharmaceutical composition is formulated as an eye drop, an ocular ointment, an ocular gel, an ocular coil, a contact lens, or an opthalmic insert.

33. The pharmaceutical composition of any one of embodiments 30-32, wherein pharmaceutical composition is formulated for intravitreal administration.

34. The pharmaceutical composition of embodiment 33, wherein the pharmaceutical 10-composition forms a depot at the site of injection.

35. The pharmaceutical composition of embodiment 30, wherein the pharmaceutical composition is formulated for systemic delivery.

36. The pharmaceutical composition of embodiment 30 or 35, wherein the pharmaceutical composition is formulated for delivery to the central nervous system.

37. A method for treating a neurodegenerative disease in a subject, the method comprising administering to the subject an effective amount of a compound of any one of embodiments 1-29, or a pharmaceutical composition according to any one of embodiments 29-36.

38. The method of embodiment 37, wherein the neurodegenerative disease is a neurodegenerative ophthalmological disorder.

39. The method of embodiment 38, wherein the neurodegenerative ophthalmological disorder is selected from age-related macular degeneration (AMD), choroidal neovascularization (CNV), choroidal neovascular membranes (CNVM), cystoid macular oedema (CME), epiretinal membranes (ERM) and macular perforations, myopia-associated choroidal neovascularization, angioid and vascular streaks, retinal detachment, diabetic retinopathy, diabetic macular oedema (DME), atrophic and hypertrophic lesions in the retinal pigment epithelium, retinal vein occlusion, choroidal retinal vein occlusion, macular oedema, macular oedema associated with renal vein occlusion, retinitis pigmentosa and other inherited retinal degenerations, retinopathy of prematurity, glaucoma, other optic neuropathies including toxic optic neuropathy, nonarteritic ischemic optic neuropathy, arteritic ischemic optic neuropathy/giant cell arteritis, traumatic optic, idiopathic intracranial hypertension/pseudotumor cerebri, inflammatory optic neuropathies, compressive optic neuropathies, infiltrative optic neuropathies, autoimmune optic neuropathies, lipid storage diseases, nutritional optic neuropathies, Leber's hereditary optic neuropathy, dominant optic atrophy, Friedrich's ataxia, radiation-induced optic neuropathy, iatrogenic optic neuropathies, space flight-associated neuro-ocular syndrome (SANS), inflammation disorders of the eye, refraction anomalies, neurotrophic keratopathy, corneal dennervation, and diabetic keratopathy.

40. The method of embodiment 39, wherein the inflammatory optic neuropathy is optic neuritis. 41. The method of embodiment 39, wherein the neurodegenerative ophthalmological disorder is selected from glaucoma, age-related macular degeneration (AMD), choroidal neovascularization (CNV), myopia-associated choroidal neovascularization, diabetic retinopathy, macular oedema, and retinal vein occlusion.

42. The method of any one of embodiments 37-41, wherein the compound of any one of embodiments 1-25 or the pharmaceutical composition according to any one of embodiments 26-32 is formulated for ocular administration.

43. The method of any one of embodiments 37-42, wherein the compound of any one of embodiments 1-25 is formulated as an eye drop, an ocular ointment, an ocular gel, an ocular coil, a contact lens, or an opthalamic insert.

44. The method of any one of embodiments 37-3439, wherein the compound of any one of embodiments 1-25 is formulated for intravitreal administration.

45. The method of any embodiment 44, wherein the compound of any one of embodiments 1-25 forms a depot at the site of injection.

46. The method of embodiment 37, wherein the neurodegenerative disease is selected from Amyotrophic lateral sclerosis (ALS), Alzheimer's disease, Parkinson's disease, Parkinson's-plus disease, Huntington's disease, peripheral neuropathies, ischemia, stroke, intracranial haemorrhage, cerebral haemorrhage, nerve damage caused by exposure to toxic compounds, injury to the nervous system, trigeminal neuralgia, glossopharyngeal neuralgia, Bell's Palsy, myasthenia gravis, muscular dystrophy, progressive muscular atrophy, primary lateral sclerosis (PLS), spinal muscular atrophy, inherited muscular atrophy, invertebrate disk syndromes, cervical spondylosis, plexus disorders, thoracic outlet destruction syndromes, *porphyria*, pseudobulbar palsy, progressive bulbar palsy, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie-Tooth disease, prion disease, Creutzfeldt-Jakob disease, Gerstmann-Striussler-Scheinker syndrome (GSS), fatal familial insomnia (FFI), bovine spongiform encephalopathy, Pick's disease, epilepsy, sensorineural hearing loss, traumatic brain injury, and AIDS demential complex.

47. The method of embodiment 46, wherein the compound of any one of embodiments 1-25 s formulated for delivery to the central nervous system of the subject.

48. A method for treating an optic neuropathy in a subject, the method comprising administering to the subject an effective amount of a compound of any one of embodiments 1-29, or a pharmaceutical composition according to any one of embodiments 30-36.

49. The method of embodiment 48, wherein the optic neuropathy is selected from glaucoma, inherited retinal degenerations, non-exudative AMD/geographic atrophy, retinal vascular diseases that produce ischemia, retinal detachments, and edema-producing diseases.

50. The method of any one of embodiments 48-49, wherein the compound of any one of embodiments 1-25 is formulated for ocular administration.

51. The method of any one of embodiments 48-50, wherein the compound of any one of embodiments 1-25 is formulated as an eye drop, an ocular ointment, an ocular gel, an ocular coil, a contact lens, or an opthalmic insert.

52. The method of any one of embodiments 37-51, further comprising administering an additional therapy or therapeutic agent to the subject.

53. Use of a compound of any one of embodiments 1-29, or a pharmaceutically acceptable salt thereof, for the manufacture of a medicament of treating a neurodegenerative disease in a subject.

54. A compound of any one of embodiments 1-29, or a pharmaceutically acceptable salt thereof, for use in treating a subject identified or diagnosed as having a neurodegenerative disease.

55. A method of inhibiting DLK and/or LZK activity in a mammalian cell, the method comprising contacting the mammalian cell with a compound of any one of embodiments 1-29, or a pharmaceutically acceptable salt thereof.

56. The method of embodiment 55, wherein the cell is a neuronal cell.

57. The method of any one of embodiments 55-56, wherein the contacting occurs in vivo.

58. The method of any one of embodiments 55-56, wherein the contacting occurs in vitro.

It is to be understood that while the invention has been described in conjunction with the detailed description thereof, the foregoing description is intended to illustrate and not limit the scope of the invention which is defined by the scope of the appended claims. Other aspects, advantages, and modification are within the scope of the following claims.

What is claimed is:

1. A compound of Formula (I)

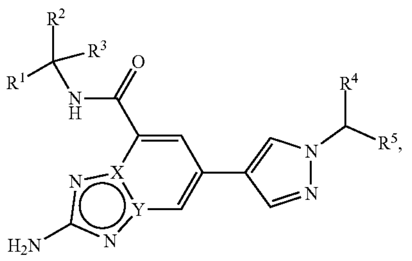

(I)

wherein

X is nitrogen and Y is carbon;

or

X is carbon and Y is nitrogen;

$R^1$ and $R^2$ each independently is hydrogen or $(C_1\text{-}C_3)$-alkyl;

$R^3$ is $(C_1\text{-}C_6)$-alkyl, $(C_3\text{-}C_7)$-cycloalkyl, or $(C_3\text{-}C_7)$-cycloalkyl-$(C_1\text{-}C_3)$-alkyl;

wherein;

the $(C_1\text{-}C_6)$-alkyl, $(C_3\text{-}C_7)$-cycloalkyl, or $(C_3\text{-}C_7)$-cycloalkyl-$(C_1\text{-}C_3)$-alkyl optionally is substituted by hydroxyl, $(C_1\text{-}C_4)$-alkoxy, oxo, cyano, chlorine, bromine, or up to three fluorine(s);

wherein;

$(C_1\text{-}C_4)$-alkoxy optionally is substituted by up to three fluorine(s) or $R^1$ is hydrogen; and $R^2$ and $R^3$ taken together with the carbon atom to which they are attached, form a 4- to 7-membered ring containing up to two heteroatoms selected from the group consisting of O and N;

wherein:

the 4- to 7-membered ring optionally is substituted by hydroxyl, $(C_1\text{-}C_4)$-alkoxy, $(C_1\text{-}C_4)$-alkyl, oxo, cyano, chlorine, bromine, or fluorine;

wherein:

$(C_1\text{-}C_4)$-alkoxy and $(C_1\text{-}C_4)$-alkyl optionally is substituted with up to three fluorine(s);

$R^4$ is hydrogen, $(C_1\text{-}C_6)$-alkyl, $(C_3\text{-}C_7)$-cycloalkyl, or 4- to 7-membered heterocyclyl;

wherein:

$(C_1\text{-}C_6)$-alkyl, $(C_3\text{-}C_7)$-cycloalkyl, or 4- to 7-membered heterocyclyl optionally is substituted by $(C_1\text{-}C_4)$-alkyl, $(C_1\text{-}C_4)$-alkoxy, oxo, cyano, chlorine, bromine or with up to three fluorine(s);

wherein:

$(C_1\text{-}C_4)$-alkoxy and $(C_1\text{-}C_4)$-alkyl optionally is substituted with up to three fluorine(s), and the nitrogen of the 4- to 7-membered heterocyclyl optionally is substituted by $C(O)OR^6$ or $C(O)R^6$;

$R^5$ is $(C_3\text{-}C_7)$-cycloalkyl, phenyl, or heteroaryl;

wherein:

$(C_3\text{-}C_7)$-cycloalkyl, phenyl, or heteroaryl optionally is substituted by $(C_1\text{-}C_4)$-alkyl, $(C_1\text{-}C_4)$-alkoxy, cyano, 4- to 7-membered heterocyclyl, chlorine, bromine or with up to three fluorine(s);

wherein:

$(C_1-C_4)$-alkyl and $(C_1-C_4)$-alkoxy optionally is substituted with up to three fluorine(s);

or $R^4$ and $R^5$, taken together with the carbon atom to which they are attached, form a 4- to 7-membered ring containing up to two heteroatoms selected from the group consisting of O and N;

wherein:

the 4- to 7-membered ring optionally is substituted by benzyl, 4- to 7-membered heterocyclyl, $(C_1-C_4)$-alkyl, $(C_1-C_4)$-alkoxy, oxo, cyano, chlorine, bromine, or up to three fluorine(s), or is annellated with phenyl or heteroaryl;

wherein:

$(C_1-C_4)$-alkyl optionally is substituted by a 4- to 7-membered heterocyclyl or up to three fluorine(s);

wherein:

the nitrogen of the 4- to 7-membered heterocyclyl optionally is substituted by $C(O)OR^6$ or $C(O)R^6$; and $R^6$ is $(C_1-C_4)$-alkyl; or a pharmaceutically acceptable salt thereof.

2. The compound of claim 1, wherein

X is carbon and Y is nitrogen;

$R^1$ and $R^2$ each independently is hydrogen or methyl;

$R^3$ is $(C_1-C_6)$-alkyl optionally substituted by hydroxyl, $(C_1-C_4)$-alkoxy, oxo, cyano, chlorine, bromine, or up to three fluorine(s);

wherein:

$(C_1-C_4)$-alkoxy optionally is substituted by up to three fluorine(s);

or $R^1$ is hydrogen and $R^2$ and $R^3$, taken together with the carbon atom to which they are attached, form a 4- to 7-membered ring containing up to two O atoms;

wherein:

the 4- to 7-membered ring optionally is substituted by hydroxyl, $(C_1-C_4)$-alkoxy, $(C_1-C_4)$-alkyl, oxo, cyano, chlorine, bromine, or fluorine;

wherein:

$(C_1-C_4)$-alkoxy and $(C_1-C_4)$-alkyl optionally is substituted with up to three fluorine(s);

$R^4$ is $(C_1-C_6)$-alkyl, $(C_3-C_7)$-cycloalkyl, or 4- to 7-membered heterocyclyl;

wherein:

$(C_1-C_6)$-alkyl, $(C_3-C_7)$-cycloalkyl, or 4- to 7-membered heterocyclyl optionally is substituted by chlorine, bromine, or up to three fluorine(s), and the nitrogen of the 4- to 7-membered heterocyclyl optionally is substituted by $C(O)OR^6$ or $C(O)R^6$;

$R^5$ is phenyl or pyridinyl;

wherein:

phenyl or pyridinyl optionally is substituted by $(C_1-C_4)$-alkyl, $(C_1-C_4)$-alkoxy, cyano, chlorine, bromine, or up to three fluorine(s);

wherein:

$(C_1-C_4)$-alkyl and $(C_1-C_4)$-alkoxy optionally is substituted by up to three fluorine(s);

$R^6$ is $(C_1-C_4)$-alkyl; or a pharmaceutically acceptable salt thereof.

3. The compound of claim 1, wherein

X is carbon and Y is nitrogen;

$R^1$ is hydrogen;

$R^2$ is methyl;

$R^3$ is $(C_1-C_4)$-alkyl optionally substituted by hydroxyl, $(C_1-C_4)$-alkoxy, chlorine or up to three fluorine(s);

wherein:

$(C_1-C_4)$-alkoxy optionally is substituted by up to three fluorine(s);

or $R^2$ and $R^3$, taken together with the carbon atom to which they are attached, form a 4- to 7-membered ring containing up to one O atom;

wherein:

the 4- to 7-membered ring optionally is substituted by hydroxyl, $(C_1-C_4)$-alkoxy, chlorine, bromine, or fluorine;

wherein:

$(C_1-C_4)$-alkoxy optionally is substituted with up to three fluorine(s);

$R^4$ is $(C_1-C_6)$-alkyl, $(C_3-C_7)$-cycloalkyl, or 4- to 7-membered heterocyclyl;

wherein:

$(C_1-C_6)$-alkyl, $(C_3-C_7)$-cycloalkyl, or 4- to 7-membered heterocyclyl optionally is substituted by chlorine, bromine, or with up to three fluorine(s), and the nitrogen of the 4- to 7-membered heterocyclyl optionally is substituted by $C(O)OR^6$ or $C(O)R^6$;

$R^5$ is phenyl or pyridinyl;

wherein:

phenyl or pyridinyl optionally is substituted by $(C_1-C_4)$-alkyl, $(C_1-C_4)$-alkoxy, cyano, chlorine, bromine, or with up to three fluorine(s);

wherein:

$(C_1-C_4)$-alkyl and $(C_1-C_4)$-alkoxy optionally is substituted with up to three fluorine(s); and $R^6$ is $(C_1-C_4)$-alkyl; or a pharmaceutically acceptable salt thereof.

4. The compound of claim 1, wherein the compound is a compound of Formula (I-C)

(I-C)

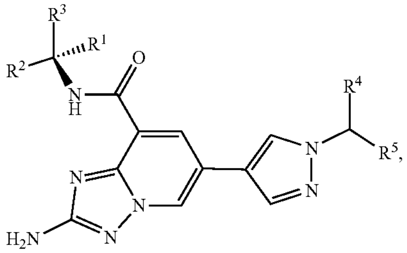

wherein $R^1$ is hydrogen;

$R^2$ is methyl;

$R^3$ is $(C_1-C_3)$-alkyl optionally substituted by hydroxyl, $(C_1-C_4)$-alkoxy, chlorine or up to three fluorine(s);

wherein:

$(C_1-C_4)$-alkoxy optionally is substituted by up to three fluorine(s);

or $R^2$ and $R^3$, taken together with the carbon atom to which they are attached, form a 4- to 7-membered ring containing up to one O atom;

$R^4$ is $(C_1-C_6)$-alkyl, $(C_3-C_7)$-cycloalkyl, or 4- to 7-membered heterocyclyl;

wherein:

$(C_1-C_6)$-alkyl, $(C_3-C_7)$-cycloalkyl, or 4- to 7-membered heterocyclyl optionally is substituted by chlorine, bromine, or up to three fluorine(s); and the nitrogen of the 4- to 7-membered heterocyclyl optionally is substituted by C(O)OR$^6$ or C(O)R$^6$;

R$^5$ is phenyl or pyridinyl;

wherein:

phenyl or pyridinyl optionally is substituted by ($C_1$-$C_4$)-alkyl, ($C_1$-$C_4$)-alkoxy, cyano, chlorine, bromine, or up to three fluorine(s);

wherein:

($C_1$-$C_4$)-alkyl and ($C_1$-$C_4$)-alkoxy optionally is substituted with up to three fluorine(s);

R$^6$ is ($C_1$-$C_4$)-alkyl; or a pharmaceutically acceptable salt thereof.

5. The compound of claim 1, wherein the compound is a compound of Formula (I-D)

(I-D)

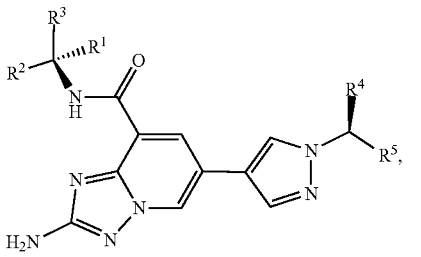

wherein

R$^1$ is hydrogen;

R$^2$ is methyl;

R$^3$ is methyl or ethyl optionally substituted by hydroxyl, ($C_1$-$C_4$)-alkoxy, chlorine, or up to three fluorine(s);

wherein:

($C_1$-$C_4$)-alkoxy optionally is substituted by up to three fluorine(s); or

R$^2$ and R$^3$, taken together with the carbon atom to which they are attached, form a furanyl ring;

R$^4$ is ($C_1$-$C_6$)-alkyl, cyclopropyl, cyclobutyl, cyclopentyl, or 4- to 7-membered heterocyclyl;

wherein:

($C_1$-$C_6$)-alkyl, cyclopropyl, cyclobutyl, cyclopentyl, or 4- to 7-membered heterocyclyl optionally is substituted by chlorine, bromine or up to three fluorine(s), and the nitrogen of the 4- to 7-membered heterocyclyl optionally is substituted by C(O)OR$^6$ or C(O)R$^6$;

R$^5$ is phenyl, 3-pyridinyl, or 4-pyridinyl;

wherein:

phenyl, 3-pyridinyl, or 4-pyridinyl optionally is substituted by ($C_1$-$C_4$)-alkyl, ($C_1$-$C_4$)-alkoxy, cyano, chlorine, bromine, or up to three fluorine(s);

wherein:

($C_1$-$C_4$)-alkyl and ($C_1$-$C_4$)-alkoxy optionally is substituted by up to three fluorine(s);

R$^6$ is ($C_1$-$C_4$)-alkyl; or a pharmaceutically acceptable salt thereof.

6. The compound of claim 1, wherein:

R$^3$ is ethyl optionally substituted by hydroxyl, ($C_1$-$C_4$)-alkoxy, chlorine, or up to three fluorine(s);

wherein:

($C_1$-$C_4$)-alkoxy optionally is substituted by up to three fluorine(s), or a pharmaceutically acceptable salt thereof.

7. The compound of claim 1, wherein:

R$^4$ is 5- to 6-membered heterocyclyl optionally substituted by chlorine, bromine, or up to three fluorine(s); and the nitrogen of the 5- to 6-membered heterocyclyl optionally is substituted by C(O)OR$^6$ or C(O)R$^6$ or a pharmaceutically acceptable salt thereof.

8. The compound of claim 1, wherein:

R$^5$ is phenyl, 3-pyridinyl, or 4-pyridinyl optionally substituted by ($C_1$-$C_4$)-alkyl or ($C_1$-$C_4$)-alkoxy;

wherein:

($C_1$-$C_4$)-alkyl and ($C_1$-$C_4$)-alkoxy optionally is substituted by up to three fluorine(s) or a pharmaceutically acceptable salt thereof.

9. A compound of Formula (II)

(II)

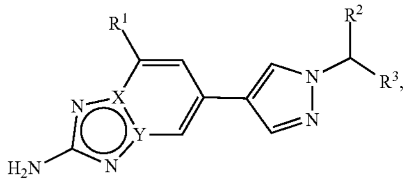

wherein

X is nitrogen and Y is carbon;

or

X is carbon and Y is nitrogen;

R$^1$ is phenyl or heteroaryl;

wherein:

the phenyl or heteroaryl optionally is substituted by ($C_1$-$C_4$)-alkyl, ($C_3$-$C_7$)-cycloalkyl, ($C_3$-$C_7$)-cycloalkyl-($C_1$-$C_3$)-alkyl, 4- to 7-membered heterocyclyl, ($C_1$-$C_4$)-alkoxy, ($C_3$-$C_7$)-cycloalkoxy, —$SO_2R^4$, —NR$^4$R$^5$, or cyano; or up to three hydroxyl, fluorine, chlorine, or bromine;

wherein:

($C_1$-$C_4$)-alkyl, ($C_3$-$C_7$)-cycloalkyl, ($C_1$-$C_4$)-alkoxy, ($C_3$-$C_7$)-cycloalkyl-($C_1$-$C_3$)-alkyl, and ($C_3$-$C_7$)-cycloalkoxy optionally is substituted by hydroxyl, cyano and up to three fluorine(s);

R$^2$ is hydrogen, ($C_1$-$C_6$)-alkyl, ($C_3$-$C_7$)-cycloalkyl, or 4- to 7-membered heterocyclyl;

wherein:

($C_1$-$C_6$)-alkyl, ($C_3$-$C_7$)-cycloalkyl, or 4- to 7-membered heterocyclyl optionally is substituted by ($C_1$-$C_4$)-alkyl, ($C_1$-$C_4$)-alkoxy, oxo, cyano, chlorine, bromine, or up to three fluorine(s);

wherein:

($C_1$-$C_4$)-alkoxy and ($C_1$-$C_4$)-alkyl optionally is substituted by up to three fluorine(s);

R$^3$ is ($C_3$-$C_7$)-cycloalkyl, phenyl, or heteroaryl;

wherein the ($C_3$-$C_7$)-cycloalkyl, phenyl, or heteroaryl optionally is substituted by ($C_1$-$C_4$)-alkyl, ($C_1$-$C_4$)-alkoxy, cyano, 4- to 7-membered heterocyclyl, chlorine, bromine, or up to three fluorine(s) wherein:

($C_1$-$C_4$)-alkyl and ($C_1$-$C_4$)-alkoxy optionally is substituted by up to three fluorine(s); or R$^2$ and R$^3$, taken together with the carbon atom to which they are attached, form a 4- to 7-membered fused ring containing up to two heteroatoms selected from the group consisting of O and N;

wherein:

the 4- to 7-membered ring optionally is substituted by benzyl, 4- to 7-membered heterocyclyl, ($C_1$-$C_4$)-alkyl, ($C_1$-$C_4$)-alkoxy, oxo, cyano, chlorine, bromine, or up to three fluorine(s), or is annellated with phenyl or heteroaryl;

wherein:

$(C_1-C_4)$-alkyl optionally is substituted by a 4- to 7-membered heterocyclyl or up to three fluorine(s);

$R^4$ and $R^5$ each independently is $(C_1-C_4)$-alkyl optionally substituted by up to three fluorine(s); or a pharmaceutically acceptable salt thereof.

10. The compound of claim 9, wherein:

X is carbon and Y is nitrogen;

$R^1$ is phenyl or heteroaryl;

wherein:

phenyl or heteroaryl optionally is substituted by $(C_1-C_4)$-alkyl, $(C_3-C_7)$-cycloalkyl, $(C_1-C_4)$-alkoxy, —$SO_2R^4$, —$NR^4R^5$, or cyano; or up to three hydroxyl, fluorine, chlorine, or bromine;

wherein:

$(C_1-C_4)$-alkyl, $(C_3-C_7)$-cycloalkyl, $(C_1-C_4)$-alkoxy, and $(C_3-C_7)$-cycloalkoxy optionally is substituted by hydroxyl, cyano, and up to three fluorine(s);

$R^2$ is $(C_1-C_6)$-alkyl, $(C_3-C_7)$-cycloalkyl, or 4- to 7-membered heterocyclyl;

wherein:

the $(C_1-C_6)$-alkyl, $(C_3-C_7)$-cycloalkyl, or 4- to 7-membered heterocyclyl optionally is substituted by chlorine, bromine, or up to three fluorine(s);

$R^3$ is phenyl or pyridinyl;

wherein:

the phenyl or pyridinyl optionally is substituted by $(C_1-C_4)$-alkyl, $(C_1-C_4)$-alkoxy, cyano, chlorine, bromine, or up to three fluorine(s);

wherein:

$(C_1-C_4)$-alkyl and $(C_1-C_4)$-alkoxy optionally is substituted by up to three fluorine(s);

$R^4$ and $R^5$ each independently is $(C_1-C_4)$-alkyl optionally substituted by up to three fluorine(s); or a pharmaceutically acceptable salt thereof.

11. The compound of claim 9, wherein X is carbon and Y is nitrogen;

$R^1$ is phenyl, pyridonyl, pyrimidyl, pyridazinyl, pyrazinyl, pyrazolyl, or thiadiazolyl;

wherein:

phenyl, pyridonyl, pyrimidyl, pyridazinyl, pyrazinyl, pyrazolyl, or thiadiazolyl optionally is substituted by $(C_1-C_4)$-alkyl, $(C_3-C_7)$-cycloalkyl, $(C_1-C_4)$-alkoxy, —$SO_2R^4$, —$NR^4R^5$, or cyano; or up to three hydroxyl, fluorine, chlorine, or bromine;

wherein:

$(C_1-C_4)$-alkyl, $(C_3-C_7)$-cycloalkyl, $(C_1-C_4)$-alkoxy, and $(C_3-C_7)$-cycloalkoxy optionally is substituted by hydroxyl, cyano, and up to three fluorine(s);

$R^2$ is $(C_1-C_6)$-alkyl, $(C_3-C_7)$-cycloalkyl, or 4- to 7-membered heterocyclyl;

wherein:

the $(C_1-C_6)$-alkyl, $(C_3-C_7)$-cycloalkyl, or 4- to 7-membered heterocyclyl optionally is substituted by chlorine or up to three times by fluorine(s);

$R^3$ is phenyl or pyridinyl;

wherein:

the phenyl or pyridinyl optionally is substituted by $(C_1-C_4)$-alkyl, $(C_1-C_4)$-alkoxy, cyano, chlorine, bromine, or up to three fluorine(s);

wherein:

$(C_1-C_4)$-alkyl and $(C_1-C_4)$-alkoxy optionally is substituted by up to three fluorine(s);

$R^4$ and $R^5$ each independently is $(C_1-C_4)$-alkyl optionally substituted by up to three fluorine(s); or a pharmaceutically acceptable salt thereof.

12. The compound of claim 9, wherein X is carbon and Y is nitrogen;

$R^1$ is phenyl, pyridonyl, or pyrazolyl;

wherein:

phenyl, pyridonyl, or pyrazolyl optionally is substituted by $(C_1-C_4)$-alkyl, $(C_3-C_7)$-cycloalkyl, $(C_1-C_4)$-alkoxy, —$SO_2R^4$, cyano, fluorine, chlorine, or bromine; and wherein:

$(C_1-C_4)$-alkyl, $(C_3-C_7)$-cycloalkyl, and $(C_1-C_4)$-alkoxy optionally is substituted by hydroxyl, cyano, and up to three fluorine(s);

$R^2$ is $(C_1-C_6)$-alkyl, $(C_3-C_7)$-cycloalkyl, 4- to 7-membered heterocyclyl;

wherein:

the $(C_1-C_6)$-alkyl, $(C_3-C_7)$-cycloalkyl, or 4- to 7-membered heterocyclyl optionally is substituted by chlorine or up to three times by fluorine(s);

$R^3$ is phenyl or pyridinyl;

wherein:

the phenyl or pyridinyl optionally is substituted by $(C_1-C_4)$-alkyl, $(C_1-C_4)$-alkoxy, cyano, chlorine, bromine, or up to three fluorine(s);

wherein:

$(C_1-C_4)$-alkyl and $(C_1-C_4)$-alkoxy optionally is substituted by up to three fluorine(s);

$R^4$ is $(C_1-C_4)$-alkyl optionally substituted by up to three fluorine(s); or a pharmaceutically acceptable salt thereof.

13. The compound of claim 9, wherein the compound is a compound of Formula (II-E)

(II-E)

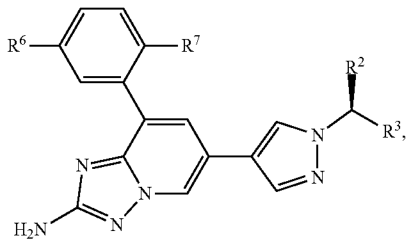

wherein $R^2$ is $(C_1-C_6)$-alkyl, $(C_3-C_7)$-cycloalkyl, or 4- to 7-membered heterocyclyl;

wherein:

$(C_1-C_6)$-alkyl, $(C_3-C_7)$-cycloalkyl, or 4- to 7-membered heterocyclyl optionally is substituted by chlorine or up to three fluorine(s);

$R^3$ is phenyl or pyridinyl;

wherein:

the phenyl or pyridinyl optionally is substituted by $(C_1-C_4)$-alkyl, $(C_1-C_4)$-alkoxy, cyano, chlorine, bromine, or up to three fluorine;

wherein:

$(C_1-C_4)$-alkyl and $(C_1-C_4)$-alkoxy optionally is substituted by up to three fluorine;

$R^6$ is $(C_1-C_4)$-alkyl optionally substituted by hydroxyl, cyano, or up to three fluorine(s);

$R^7$ is $(C_1-C_4)$-alkyl, chlorine, bromine, or fluorine;

wherein:

$(C_1-C_4)$-alkyl is optionally substituted by up to three fluorine(s); or a pharmaceutically acceptable salt thereof.

14. The compound of claim 9, wherein the compound is a compound of Formula (II-F)

(II-F)

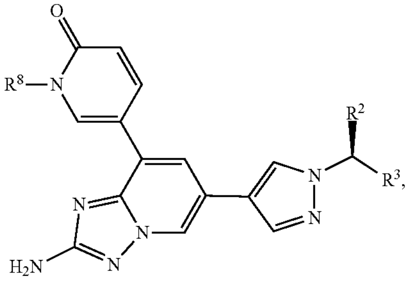

wherein:

$R^2$ is $(C_1\text{-}C_6)$-alkyl, $(C_3\text{-}C_7)$-cycloalkyl, or 4- to 7-membered heterocyclyl;

wherein:

$(C_1\text{-}C_6)$-alkyl, $(C_3\text{-}C_7)$-cycloalkyl, or 4- to 7-membered heterocyclyl optionally is substituted by chlorine or up to three fluorine(s);

$R^3$ is phenyl or pyridinyl;

wherein the phenyl or pyridinyl optionally is substituted by $(C_1\text{-}C_4)$-alkyl, $(C_1\text{-}C_4)$-alkoxy, cyano, chlorine, bromine or up to three fluorine(s);

wherein:

$(C_1\text{-}C_4)$-alkyl and $(C_1\text{-}C_4)$-alkoxy optionally is substituted by up to three fluorine;

$R^8$ is $(C_1\text{-}C_4)$-alkyl optionally substituted by hydroxyl, cyano, or up to three fluorine; or a pharmaceutically acceptable salt thereof.

15. The compound of claim 9, wherein the compound is a compound of Formula (II-G)

(II-G)

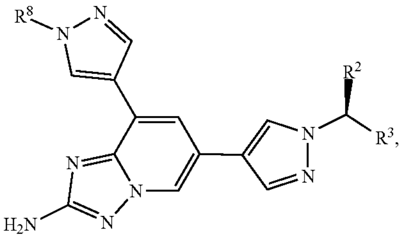

wherein:

$R^2$ is $(C_1\text{-}C_6)$-alkyl, $(C_3\text{-}C_7)$-cycloalkyl, or 4- to 7-membered heterocyclyl;

wherein:

$(C_1\text{-}C_6)$-alkyl, $(C_3\text{-}C_7)$-cycloalkyl, or 4- to 7-membered heterocyclyl optionally is substituted by chlorine or up to three fluorine;

$R^3$ is phenyl or pyridinyl;

wherein the phenyl or pyridinyl optionally is substituted by $(C_1\text{-}C_4)$-alkyl, $(C_1\text{-}C_4)$-alkoxy, cyano, chlorine, bromine, or up to three fluorine(s);

wherein:

$(C_1\text{-}C_4)$-alkyl and $(C_1\text{-}C_4)$-alkoxy optionally is substituted by up to three fluorine;

$R^8$ is $(C_1\text{-}C_4)$-alkyl optionally substituted by hydroxyl, cyano, or up to three fluorine; or a pharmaceutically acceptable salt thereof.

16. A pharmaceutical composition, the pharmaceutical composition comprising a compound according to claim 1, or a pharmaceutically acceptable salt thereof, and a pharmaceutically acceptable excipient.

17. The pharmaceutical composition of claim 16, wherein the pharmaceutical composition is formulated for ocular administration.

18. The pharmaceutical composition of claim 16, wherein the pharmaceutical composition is formulated as an eye drop, an ocular ointment, an ocular gel, an ocular coil, a contact lens, or an ophthalmic insert.

19. A method for treating a neurodegenerative disease in a subject, the method comprising administering to the subject an effective amount of a pharmaceutical composition according to claim 16: wherein the neurodegenerative disease is glaucoma or optic nerve injury.

20. The method of claim 19, wherein the pharmaceutical composition is formulated for delivery to the central nervous system of the subject.

21. The method of claim 19, wherein the pharmaceutical composition is formulated for ocular administration.

22. The method of claim 19, wherein the pharmaceutical composition is formulated as an eye drop, an ocular ointment, an ocular gel, an ocular coil, a contact lens, or an ophthalmic insert.

23. The method of claim 19, wherein the neurodegenerative disease is glaucoma.

24. The method of claim 19, wherein the neurodegenerative disease is optic nerve injury.

* * * * *